US010239843B2

(12) United States Patent
McGonagle et al.

(10) Patent No.: US 10,239,843 B2
(45) Date of Patent: Mar. 26, 2019

(54) 2,4-DIOXO-QUINAZOLINE-6-SULFONAMIDE DERIVATIVES AS INHIBITORS OF PARG

(71) Applicant: CANCER RESEARCH TECHNOLOGY LIMITED, London (GB)

(72) Inventors: Alison E. McGonagle, Manchester (GB); Allan Jordan, Manchester (GB); Bohdan Waszkowycz, Manchester (GB); Colin Hutton, Manchester (GB); Ian Waddell, Manchester (GB); James R. Hitchin, Manchester (GB); Kate Mary Smith, Manchester (GB); Niall M. Hamilton, Manchester (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/533,804

(22) PCT Filed: Dec. 11, 2015

(86) PCT No.: PCT/GB2015/053883
§ 371 (c)(1),
(2) Date: Jun. 7, 2017

(87) PCT Pub. No.: WO2016/092326
PCT Pub. Date: Jun. 16, 2016

(65) Prior Publication Data
US 2018/0016242 A1   Jan. 18, 2018

(30) Foreign Application Priority Data
Dec. 12, 2014   (GB) .................................. 1422098.2

(51) Int. Cl.
| | | |
|---|---|---|
| *A61K 31/517* | (2006.01) |
| *C07D 239/96* | (2006.01) |
| *C07D 401/14* | (2006.01) |
| *C07D 405/14* | (2006.01) |
| *C07D 413/14* | (2006.01) |
| *C07D 215/227* | (2006.01) |

(Continued)

(52) U.S. Cl.
CPC .......... *C07D 239/96* (2013.01); *A61K 31/517* (2013.01); *C07D 215/227* (2013.01); *C07D 217/22* (2013.01); *C07D 217/24* (2013.01); *C07D 237/32* (2013.01); *C07D 239/88* (2013.01); *C07D 239/90* (2013.01); *C07D 239/91* (2013.01); *C07D 241/44* (2013.01); *C07D 401/06* (2013.01); *C07D 401/14* (2013.01); *C07D 403/06* (2013.01); *C07D 403/14* (2013.01); *C07D 405/06* (2013.01); *C07D 405/14* (2013.01); *C07D 409/14* (2013.01); *C07D 413/06* (2013.01); *C07D 413/14* (2013.01); *C07D 417/06* (2013.01); *C07D 417/14* (2013.01); *C07D 471/04* (2013.01)

(58) Field of Classification Search
CPC .......................... C07D 413/06; A61K 31/517
USPC ......................................... 514/266.2; 544/285
See application file for complete search history.

(56) References Cited

U.S. PATENT DOCUMENTS

| | | |
|---|---|---|
| 4,429,126 A | 1/1984 | Ueda et al. |
| 7,994,202 B2 | 8/2011 | Atobe et al. |

(Continued)

FOREIGN PATENT DOCUMENTS

| | | |
|---|---|---|
| CN | 101429191 A | 5/2009 |
| DE | 19927415 A1 | 12/2000 |

(Continued)

OTHER PUBLICATIONS

International Search Report dated Feb. 23, 2016 corresponding to International Patent Application No. PCT/GB2015/053883 filed on Dec. 11, 2015, 17 pages.
UK Search Report dated Oct. 5, 2015 corresponding to priority application, GB1422098.2 filed on Dec. 12, 2014, 6 pages.
Chang, Yu Mi et al., "Petasis reaction of activated quinolone and isoquinoline with various boronic acids," *Tetrahedron Letters* (Mar. 2, 2005); 46:3053-3056.
Osmialowski, Borys et al., "2-Acylamino- and 2,4-Bis(acylamino)pyrimidines as Supramolecular Synthons Analyzed by Multiple Noncovalent Interactions. DFT, X-ray Diffraction, and NMR Spectral Studies," *The Journal of Organic Chemistry* (Nov. 2, 2012); 77:9609-9619.
Peng, Chin-Tzu et al., "The Synthesis of Some 6-N-Substituted Amido Derivatives of 4,6-Diaminquinaldine and a Study of their in vitro Antibacterial Activity," *Journal of the American Chemical Society* (Jan. 1, 1956); 78:3703-3708.

(Continued)

Primary Examiner — Jeffrey H Murray
(74) Attorney, Agent, or Firm — Mintz, Levin, Cohn, Ferris, Glovsky and Popeo, P.C.

(57) ABSTRACT

The present invention relates to compounds of formula I that function as inhibitors of PARG (Poly ADP-ribose glycohydrolase) enzyme activity wherein $R_{1a}$, $R_{1b}$, $R_{1c}$, $R_{1d}$, $R_{1e}$, W, $X_1$, $X_2$, $X_3$, $X_4$, $X_5$, $X_6$, $X_7$, c are each as defined herein. The present invention also relates to processes for the preparation of these compounds, to pharmaceutical compositions comprising them, and to their use in the treatment of proliferative disorders, such as cancer, as well as other diseases or conditions in which PARG activity is implicated.

(I)

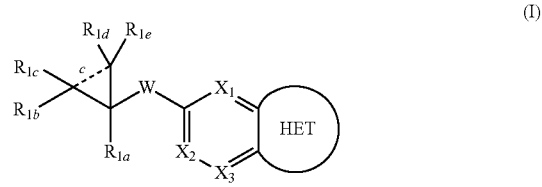

18 Claims, No Drawings

(51) Int. Cl.
| | |
|---|---|
| C07D 217/22 | (2006.01) |
| C07D 217/24 | (2006.01) |
| C07D 401/06 | (2006.01) |
| C07D 403/06 | (2006.01) |
| C07D 403/14 | (2006.01) |
| C07D 405/06 | (2006.01) |
| C07D 409/14 | (2006.01) |
| C07D 239/88 | (2006.01) |
| C07D 239/90 | (2006.01) |
| C07D 239/91 | (2006.01) |
| C07D 413/06 | (2006.01) |
| C07D 417/06 | (2006.01) |
| C07D 241/44 | (2006.01) |
| C07D 417/14 | (2006.01) |
| C07D 237/32 | (2006.01) |
| C07D 471/04 | (2006.01) |

(56) References Cited

U.S. PATENT DOCUMENTS

| | | |
|---|---|---|
| 2007/0049593 A1 | 3/2007 | Oka et al. |
| 2007/0219195 A1 | 9/2007 | Goldstein et al. |
| 2018/0194738 A1 | 7/2018 | McGonagle et al. |

FOREIGN PATENT DOCUMENTS

| | | | |
|---|---|---|---|
| EP | 1719773 A1 | 11/2006 | |
| JP | 2014/106019 A3 | 7/2014 | |
| WO | 00/76966 A2 | 12/2000 | |
| WO | 00/76966 A3 | 12/2000 | |
| WO | 01/02369 A2 | 1/2001 | |
| WO | 01/02369 A3 | 1/2001 | |
| WO | 01/16108 A2 | 3/2001 | |
| WO | 01/16108 A3 | 3/2001 | |
| WO | WO2003068743 * | 8/2003 | ........... C07D 211/52 |
| WO | 2004/083204 A1 | 9/2004 | |
| WO | 2005/030212 A1 | 4/2005 | |
| WO | 2007/014226 A2 | 2/2007 | |
| WO | 2007/014226 A3 | 2/2007 | |
| WO | 2007/087488 A2 | 8/2007 | |
| WO | 2007/087488 A3 | 8/2007 | |
| WO | 2009/047255 A1 | 4/2009 | |
| WO | 2011/140325 A1 | 11/2011 | |
| WO | 2011/140442 A1 | 11/2011 | |
| WO | 2012/035078 A1 | 3/2012 | |
| WO | 2012/080284 A2 | 6/2012 | |
| WO | 2012/080284 A3 | 6/2012 | |
| WO | 2013/027168 A1 | 2/2013 | |
| WO | 2013/067300 A1 | 5/2013 | |
| WO | 2014/106019 A2 | 7/2014 | |

OTHER PUBLICATIONS

Rörsch, Florian et al., Structure-Activity Relationship of Nonacidic Quinazolinone Inhibitors of Human Microsomal Prostaglandin Synthase 1 (mPGES 1); *Journal of Medicinal Chemistry* (Apr. 26, 2012); 55(8):3792-3803.

Tani, Junichi et al., "Studies on biologically Active Halogenated Compounds. II. Chemical Modifications of 6-Amino-2-fluoromethyl-3-(o-tolyl)-4(3H)-quinazolinone and the CNS Depressant Activities of Related Compounds," *Chem. Pharm. Bull.* (Nov. 1, 1979); 27(11):2675-2687.

Amé, Jean-Christophe, "Radiation-induced mitotic catastrophe in PARG-deficient cells," *Journal of Cell Science* (Accepted Feb. 24, 2009); 122:1990-2002.

Barber, Louise J. et al., "Secondary mutations in BRCA2 associated with clinical resistance to a PARP inhibitor," *J Pathol* (2013; accepted Oct. 24, 2012); 229:442-429.

Blen, Christian et al., "The Ups and Downs of Tannins as Inhibitors of Poly(ADP-Ribose)glycohydrolase," *Molecules* (Feb. 22, 2011) 16:1854-1877.

Caiafa, Paola et al., "Epigenetics: poly(ADP-ribosyl)ation of PARP-1 regulates genomic methylation patterns," *The FASEB Journal* (Mar. 2009; accepted for publication Oct. 23, 2008); 23:672-678.

Curtin, Nicola et al., "Therapeutic Applications of PARP Inhibitors: Anticancer Therapy and Beyond," *Mol Aspects Med.* (Dec. 2013; available in PMC Dec. 1, 2014); 34(6): .doi:10.106/j.mam.2013.01. 006 (71 pages).

Dahl, Markus et al., "Fine-Tuning of Smad Protein Function by Poly(ADP-Ribose) Polymerases and Poly(ADP-Ribose) Glycohydrolase during Transforming Growth Factor β Signaling," *PLOS One* (Aug. 18, 2014); 9(8):e103651 (19 pages).

Drost, R. et al., "Opportunities and hurdles in the treatment of BRCA1-related breast cancer," *Oncogene* (2014; published online Aug. 19, 2013) 33:3753-3763.

Erdélyi, Katalin et al., "Dual role of poly(ADP-ribose) glycohydrolase in the regulation of cell death in oxidatively stressed A549 cells," *FASEB J.* (Oct. 2009; accepted Jun. 4, 2009); 23(10):3553-3563.

Fathers, Catherine et al., "Inhibition of poly(ADP-ribose) glycohydrolase (PARG) specifically kills BRCA2-deficient tumor cells," *Cell Cycle* (Mar. 1, 2012); 11(5):990-997.

Fisher, Anna E. O. et al., "Poly(ADP-Ribose) Polymerase 1 Accelerates Single-Strand Break Repair in Concert with Poly(ADP-Ribose) Glycohydrolase," *Molecular and Cellular Biology* (Aug. 2007; published ahead of print Jun. 4, 2007); 27(15):5597-5604.

Frizzell, Kristine M. et al., "Global Analysis of Transcriptional Regulation by Poly(ADP-ribose) Polymerase-1 and Poly(ADP-ribose) Glycohydrolase in MCF-7 Human Breast Cancer Cells," *Journal of Biological Chemistry* (Dec. 4, 2009); 284(49):33926-33938.

Fujihara, H. et al., "Poly(ADP-ribose) Glycohydrolase Deficiency Sensitizes Mouse ES Cells to DNA Damaging Agents," *Current Cancer Drug Targets* (Accepted Sep. 17, 2009); 9:953-962.

Guastafierro, Tiziana et al., "ADP-ribose polymer depletion leads to nuclear Ctcf re-localization and chromatin rearrangement," *Biochem J.* (2013; published as BJ Immediate publication Nov. 2, 2012); 449:623-630.

Ji, Y et al., "Poly(ADP-ribosyl)ation of heterogeneous nuclear ribonucleaoproteins modulates splicing," *Nucleic Acids Research* (published online Apr. 3, 2009); 37(11):3501-3513.

Le May, Nicolas et al., "Poly(ADP-Ribose) Glycohydrolase Regulates Retinoic Acid Receptor-Mediated Gene Expression," *Molecular Cell* (Dec. 14, 2012); 48:785-798.

Mashimo, Masato et al., "Structure and function of the ARH family of ADP-ribose-acceptor hydrolases," *DNA Repair (Mast).* (Nov. 2014; available in PMC Nov. 1, 2015); 0:88-94. Doi:10.1016/j. dnarep.2014.03.005; 19 pages.

Mortusewicz, Oliver et al., "PARG is recruited to DNA damage sites through poly(ADP-ribose)- and PCNA-dependent mechanisms," *Nucleic Acids Research* (Mar. 11, 2011); 39(12):5045-5056.

Nakadate, Yusuke et al., "Silencing of poly(ADP-ribose) glycohydrolase sensitizes lung cancer cells to radiation through the abrogation of DNA damage checkpoint," *Biochemical and Biophysical Research Communications* (available online Nov. 6, 2013); 441:793-798.

Shirai, Hidenori et al., "Parg deficiency confers radio-sensitization through enhanced cell death in mouse ES cells exposed to various forms of ionizing radiation," *Biochemical and Biophysical Research Communications* (available online Apr. 23, 2013); 435:100-106.

Shirai, H. et al., "PARG dysfunction enhances DNA double strand break formation in S-phase after alkylation DNA damage and augments different cell death pathways," *Cell Death and Disease* (accepted Mar. 1, 2013); 4:e656; doi:10.1038/cddis.2013.133; 10 pages.

Zhou, Yiran et al., "Enhanced DNA Accessibility and Increased DNA Damage Induced by the Absence of Poly(ADP-ribose) Hydrolysis," *Biochemistry* (published on Web Jul. 23, 2010); 49(34):7360-7366.

Zhou, Yiran et al., "Synergistic cytotoxicity of N-methyl-N'-nitro-N-nitrosoguanidine and absence of poly(ADP-ribose) glycohydrolase involves chromatin decondensation," *International Journal of Oncology* (accepted Feb. 11, 2011); 39:121-127.

Substance Record for SID 105027706 Pubchem (Feb. 22, 2011) NCBI XP55244192; 6 pages.

(56) References Cited

OTHER PUBLICATIONS

Sun, Yanyan et al., "Tannic acid, an inhibitor of poly(ADP-ribose) glycohydrolase, sensitizes ovarian carcinoma cells to cisplatin," *Anti-Cancer Drugs* (Revised form accepted May 23, 2012) 23(9):979-990.
International Search Report dated Feb. 4, 2016 corresponding to International Patent Application No. PCT/GB2015/054064 filed on Dec. 17, 2015, 17 pages.
UK Search Report dated Oct. 1, 2015 corresponding to priority application, GB1422771.4 filed on Dec. 19, 2014, 5 pages.
Aldlab Chemicals Building Blocks (Nov. 2, 2014), Order No. Cat. AX103678857, see CHEMCATS Acc. No. 2132286836 for the compound having CAS Reg. No. 1411077-15-0; 18 pages.
Substance Record for SID 49925576 *Pubchem*(Jul. 10, 2008) NCBI XP55244188; 6 pages.

\* cited by examiner

2,4-DIOXO-QUINAZOLINE-6-SULFONAMIDE DERIVATIVES AS INHIBITORS OF PARG

FIELD OF THE INVENTION

The present invention relates to certain compounds that function as inhibitors of PARG (Poly ADP-ribose glycohydrolase) enzyme activity. The present invention also relates to processes for the preparation of these compounds, to pharmaceutical compositions comprising them, and to their use in the treatment of proliferative disorders, such as cancer, as well as other diseases or conditions in which PARG activity is implicated.

BACKGROUND OF THE INVENTION

Cancer is caused by uncontrolled and unregulated cellular proliferation. The consequence of this often rapid proliferation is a high level of oxidative stress within the tumour which damages DNA and leads to a much-increased mutation rate. Tumour cells therefore engage and rely heavily upon DNA damage repair mechanisms.

Single-strand breaks (SSBs) are the commonest type of lesion arising in cells and PARG (Poly ADP-ribose glycohydrolase) together with PARP is involved along with a number of other proteins in single strand break repair (SSBR) and another repair mechanism called base excision repair (BER).

One of the earliest events during single strand DNA repair is the binding of PARP (poly ADP-ribose polymerase) to the break and the rapid synthesis of poly ADP-ribose (PAR) on PARP itself. This molecular structure serves as a signal to recruit other DNA repair proteins, initially XRCC1, which will then repair the break (Mortusewicz, Fouquerel et al. 2011). The signal initiated by these PAR chains is short-lived as they are rapidly degraded by the enzyme PAR glycohydrolase (PARG). When PARP is bound to PAR, its catalytic activity is reduced and therefore PARG activity helps to restore PARP to its catalytically active form (Curtin and Szabo 2013).

PARG exists as a single gene with isoforms that reside in the nucleus, mitochondria and cytosol. The only other known protein with glycohydrolase activity is ARH3 which is localised to the mitochondria (Mashimo, Kato et al. 2014). Although, known primarily for its direct role in DNA repair, PARG impacts PAR signalling in splicing, transcriptional and epigenetic pathways (Ji and Tulin 2009) (Le May, Iltis et al. 2012) (Dahl, Maturi et al. 2014) (Guastafierro, Catizone et al. 2013) (Caiafa, Guastafierro et al. 2009).

Cancer cells may become addicted to a specific DNA repair pathway when other mechanisms of DNA repair are non-functional. Tumours carrying mutations in proteins involved in double strand break repair are often more sensitive to PARP inhibitors of SSBR. There is already some evidence that PARG depletion inhibits SSBR and reduces survival of BRCA2-deficient cells (Fathers, Drayton et al. 2012). However, other tumour mutations may give rise to deficiencies in double strand DNA repair mechanisms (so-called "BRCA-ness") thereby sensitising tumour cells to PARG inhibition.

PARG depletion has been studied in a number of murine and human model systems. Murine cells that are null or depleted for PARG display an increased sensitivity to experimental and clinical DNA damaging agents. However, as deficiency in PARG doesn't sensitise to all agents (e.g. gemcitabine, camptothecin) this suggests a specificity for PARG function with certain pathways of DNA damage repair and chemo- and radiotherapies (Fujihara, Ogino et al. 2009) (Shirai, Fujimori et al. 2013) (Zhou, Feng et al. 2010) (Zhou, Feng et al. 2011).

In humans PARG depletion sensitises lung, cervical and pancreatic cancer cells to γ-irradiation or experimental DNA damaging agents (e.g. hydrogen peroxide, Methylmethanesulfonate) (Ame, Fouquerel et al. 2009) (Nakadate, Kodera et al. 2013) (Shirai, Poetsch et al. 2013).

PARP inhibitors are currently undergoing a raft of clinical trials where the concept of synthetic lethality or chemo-sensitisation is being explored. Clinical resistance to PARP inhibitors has already been described (Drost and Jonkers 2014) (Barber, Sandhu et al. 2013) and therefore there is a requirement that alternative inhibitors targeting the DNA damage repair machinery are found. As PARG depletion leads to reduced rates of SSBR to the same extent as depletion of PARP1, PARG inhibition may provide a therapeutic advantage in PARP inhibitor resistant cells (Fisher, Hochegger et al. 2007). Furthermore, depletion of PARG has been reported to lead to a markedly different gene expression pattern to that of PARP depletion in breast cancer cells (Frizzell, Gamble et al. 2009).

Although current models show that PARG depletion leads to PARP-dependent effects on DNA repair, recent research has shown a mechanistic differentiation from PARP inhibition. Following a genotoxic stimulus depletion of PARG, in contrast to PARP depletion, leads to a drop in NAD levels. This leads to lung cancer cell death that may be as a result of energy failure (Erdelyi, Bai et al. 2009).

Cell permeable PARG inhibitors have been limited to compounds such as Tannic acid or Gallotannin which have questionable specificity for PARG and limited bioavailability (Sun, Zhang et al. 2012) (Fathers, Drayton et al. 2012) (Blenn, Wyrsch et al. 2011).

An object of this invention is to provide specific cell permeable inhibitors of PARG.

SUMMARY OF THE INVENTION

In one aspect, the present invention provides a compound as defined herein, or a pharmaceutically acceptable salt or solvate thereof.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a PARG inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of a PARG inhibitory effect.

In another aspect, the present invention provides a method of inhibiting PARG in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound, or a pharmaceutically acceptable salt or solvate thereof, as defined herein.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a benzene ring fused to a 5- or 6-membered ring containing 1, 2 or 3 ring heteroatoms;

a pyridine ring fused to a 5- or 6-membered ring containing 1, 2 or 3 ring heteroatoms;

a pyrimidine ring fused to a 5- or 6-membered ring containing 1 or 2 ring heteroatoms;

a pyrrole ring fused to a 5- or 6-membered ring containing 1, 2 or 3 ring heteroatoms;

a pyrazole ring fused to a 5- or 6-membered ring containing 1 or 2 ring heteroatoms;

a pyrazine ring fused to a 5- or 6-membered ring containing 1 or 2 ring heteroatoms;

an imidazole ring fused to a 5- or 6-membered ring containing 1 or 2 ring heteroatoms;

an oxazole ring fused to a 5- or 6-membered ring containing 1 or 2 ring heteroatoms;

an isoxazole ring fused to a 5- or 6-membered ring containing 1 or 2 ring heteroatoms;

a thiazole ring fused to a 5- or 6-membered ring containing 1 or 2 ring heteroatoms;

an isothiazole ring fused to a 5- or 6-membered ring containing 1 or 2 ring heteroatoms;

a thiophene ring fused to a 5- or 6-membered ring containing 1, 2 or 3 ring heteroatoms;

a furan ring fused to a 5- or 6-membered ring containing 1, 2 or 3 ring heteroatoms;

a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of formula (I) shown below, or a pharmaceutically acceptable salt thereof:

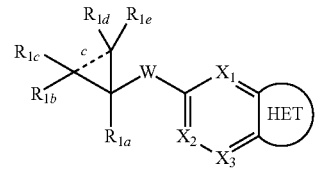

wherein:

bond c is absent or a single bond;

$R_{1a}$ is selected from hydrogen, fluoro, chloro, cyano, formyl, (1-2C)alkyl, (1-2C)haloalkyl, (2C)alkenyl, or (2C)alkynyl;

$R_{1b}$, $R_{1c}$, $R_{1d}$, and $R_{1e}$ are each independently selected from H, fluoro or methyl;

W is selected from $-NH-S(O)_y-$, $-S(O)_y-NH-$, $-C(O)NH-$, $-NHC(O)-$, $-NH-S(O)(NH)-$, $-S(O)(NH)-NH-$, wherein y is 0, 1 or 2;

$X_1$ is selected from $CR_2$ or N; wherein $R_2$ is H or fluoro;

$X_2$ is selected from $CR_3$ or N; wherein $R_3$ is H or fluoro;

$X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

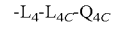

wherein $L_4$ is absent or a (1-3C)alkylene, (2-4C)alkenylene, or (2-4C)alkynylene, each of which is optionally substituted by (1-2C)alkyl or oxo;

$L_{4C}$ is absent or selected from O, S, SO, $SO_2$, $N(R_{4b})$, C(O), C(O)O, OC(O), $C(O)N(R_{4b})$, $N(R_{4b})C(O)$, $N(R_{4b})C(O)O$, $C(O)N(R_{4b})O$, $N(R_{4b})C(O)N(R_{4c})$, $S(O)_2N(R_{4b})$, or $N(R_{4b})SO_2$, wherein $R_{4b}$ and $R_{4c}$ are each independently selected from hydrogen or (1-2C) alkyl; and $Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_{4d}R_{4e}$, $OR_{4d}$, $C(O)R_{4d}$, $C(O)OR_{4d}$, $OC(O)R_{4d}$, $C(O)N(R_{4e})R_{4d}$, $N(R_{4e})C(O)R_{4d}$, $S(O)_yR_{4d}$ (where y is 0, 1 or 2), $SO_2N(R_{4e})R_{4d}$, $N(R_{4e})SO_2R_{4d}$ or $(CH_2)_zNR_{4e}R_{4d}$ (where z is 1, 2 or 3), wherein $R_{4d}$ and $R_{4e}$ are each independently selected from H or (1-4C) alkyl;

HET is a fused 6-membered saturated, partially saturated or fully unsaturated heterocyclic ring of formula:

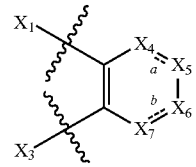

wherein bond a and bond b are single bonds, or one or both of bond a or bond b is optionally a double bond;

$X_4$ is selected from C(=O), C(=NH), C(=S), $CHR_{5c}$ or $N-R_{5N}$ when bond a is a single bond, or $CR_{5c}$ or N when bond a is a double bond;

wherein $R_{5c}$ is selected from H, halo, (1-2C)alkyl, (1-2C)alkoxy, amino, (1-2C)alkylamino, (1-2C)dialkylamino, cyano or (2C)alkynyl, wherein said (1-2C)alkyl is optionally substituted by one or more substituents selected from amino or halo;

$R_{5N}$ is selected from H, (1-2C)alkyl or (1-2C)haloalkyl;

$X_5$ is selected from C(=O), C(=NH), C(=S), $CHR_{6c}$ or N—$R_{6N}$ when a is a single bond, or $CR_{6c}$ or N when a is a double bond;

wherein $R_{6c}$ is selected from hydrogen, cyano, halo or a group of the formula:

-$L_6$-$L_{6C}$-$Q_{6C}$ wherein $L_6$ is absent or (1-3C)alkylene optionally substituted by (1-2C)alkyl or oxo;

$L_{6C}$ is absent or selected from O, S, SO, $SO_2$, $N(R_b)$, C(O), C(O)O, OC(O), C(O)N($R_b$), N($R_b$)C(O), N($R_b$)C(O)N($R_c$), S(O)$_2$N($R_b$), or N($R_b$)SO$_2$, wherein $R_b$ and $R_c$ are each independently selected from hydrogen or (1-2C)alkyl; and $Q_{6C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_dR_e$, $OR_d$, C(O)$R_d$, C(O)O$R_d$, OC(O)$R_d$, C(O)N($R_e$)$R_d$, N($R_e$)C(O)$R_d$, S(O)$_y$$R_d$ (where y is 0, 1 or 2), SO$_2$N($R_e$)$R_d$, N($R_e$)SO$_2$$R_d$ or (CH$_2$)$_z$N$R_e$$R_d$ (where z is 1, 2 or 3), wherein $R_d$ and $R_e$ are each independently selected from H or (1-4C)alkyl;

$R_{6N}$ is selected from hydrogen, or a group of the formula:

-$L_6$-$L_{6N}$-$Q_{6N}$ wherein $L_6$ is absent or (1-3C)alkylene optionally substituted by (1-2C)alkyl or oxo;

$L_{6N}$ is absent or selected from O, S, SO, $SO_2$, $N(R_f)$, C(O), C(O)O, OC(O), C(O)N($R_g$), N($R_f$)C(O), N($R_f$)C(O)N($R_g$), S(O)$_2$N($R_f$), or N($R_f$)SO$_2$, wherein $R_f$ and $R_g$ are each independently selected from hydrogen or (1-2C)alkyl; and $Q_{6N}$ is hydrogen, cyano, (1-6C)alkyl, (2C)alkynyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_hR_i$, $OR_h$, C(O)$R_h$, C(O)O$R_h$, OC(O)$R_h$, C(O)N($R_h$)$R_i$, N($R_h$)C(O)$R_i$, N($R_h$)C(O)O$R_i$, S(O)$_y$$R_h$ (where y is 0, 1 or 2), SO$_2$N($R_h$)$R_i$, N($R_h$)SO$_2$$R_i$ or (CH$_2$)$_z$N$R_h$$R_i$ (where z is 1, 2 or 3), wherein $R_h$ and $R_i$ are each independently selected from H or (1-4C)alkyl; or $Q_{6N}$ is optionally substituted by a group of formula:

—$W_{6N}$—$Z_{6N}$ wherein $W_{6N}$ is absent or (1-3C)alkylene optionally substituted by (1-2C)alkyl or oxo;

$Z_{6N}$ is selected from (3-5C)cycloalkyl, (3-6C)heterocycyl, (2C)alkynyl, phenyl, 5 or 6 membered heteroaryl, carboxy, carbamoyl or cyano, wherein $Z_{6N}$ is substituted by one or more substituents selected from (1-2C)alkyl, (1-2C)alkoxy or halo;

$X_6$ is selected from C(=O), C(=NH), C(=S), $CHR_{7c}$ or N—$R_{7N}$ when bond b is a single bond, or $CR_{7c}$ or N when bond b is a double bond;

wherein $R_{7c}$ is selected from hydrogen, cyano, halo or a group of the formula:

-$L_7$-$L_{7C}$-$Q_{7C}$ wherein $L_7$ is absent or (1-3C)alkylene optionally substituted by (1-2C)alkyl or oxo;

$L_{7C}$ is absent or selected from O, S, SO, $SO_2$, $N(R_j)$, C(O), C(O)O, OC(O), C(O)N($R_j$), N($R_j$)C(O), N($R_j$)C(O)N($R_k$), S(O)$_2$N($R_j$), or N($R_j$)SO$_2$, wherein $R_j$ and $R_k$ are each independently selected from hydrogen or (1-2C)alkyl; and $Q_{7C}$ is hydrogen, (1-6C)alkyl, (3-6C)cycloalkyl, aryl, aryl(1-2C)alkyl, heterocyclyl, heterocyclyl-(1-2C)alkyl, heteroaryl or heteroaryl-(1-2C)alkyl; and wherein $Q_{7C}$ is optionally substituted by one or more substituents selected from (1-4C)alkyl, halo, trifluoromethyl, trifluoromethoxy, amino, cyano, hydroxy, amino, carboxy, carbamoyl, sulphamoyl, $NR_lR_m$, $OR_l$, C(O)$R_m$, C(O)O$R_l$, OC(O)$R_m$, C(O)N($R_l$)$R_m$, N($R_l$)C(O)$R_m$, S(O)$_y$$R_l$ (where y is 0, 1 or 2), SO$_2$N($R_l$)$R_m$, N($R_l$)SO$_2$$R_m$ or (CH$_2$)$_z$N$R_l$$R_m$ (where z is 1, 2 or 3), wherein $R_l$ and $R_m$ are each independently selected from H or (1-4C)alkyl;

$R_{7N}$ is selected from hydrogen or a group of the formula:

-$L_7$-$L_{7N}$-$Q_{7N}$ wherein $L_7$ is absent or (1-3C)alkylene optionally substituted by (1-2C)alkyl or oxo;

$L_{7N}$ is selected from O, S, SO, $SO_2$, $N(R_n)$, C(O), C(O)O, OC(O), C(O)N($R_n$), N($R_n$)C(O), N($R_n$)C(O)N($R_o$), S(O)$_2$N($R_n$), or N($R_n$)SO$_2$, wherein $R_n$ and $R_o$ are each independently selected from hydrogen or (1-2C)alkyl; and $Q_{7N}$ is hydrogen, cyano, (1-6C)alkyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_pR_q$, $OR_p$, C(O)$R_p$, C(O)O$R_p$, OC(O)$R_p$, C(O)N($R_p$)$R_q$, N($R_r$)C(O)$R_p$, S(O)$_y$$R_p$ (where y is 0, 1 or 2), SO$_2$N($R_p$)$R_q$, N($R_r$)SO$_2$$R_p$ or (CH$_2$)$_z$N$R_p$$R_q$ (where z is 1, 2 or 3), wherein $R_p$ and $R_q$ are each independently selected from H or (1-4C)alkyl;

$X_7$ is selected from C(=O), C(=NH), C(=S), $CHR_{8c}$ or N—$R_{8N}$ when bond b is a single bond, or $CR_{8c}$ or N when bond b is a double bond;

wherein $R_{8c}$ is selected from hydrogen, cyano, halo or a group of the formula:

-$L_8$-$L_{8C}$-$Q_{8C}$ wherein $L_8$ is absent or (1-3C)alkylene, (3-4C)cycloalkylene, optionally substituted by one or more substituents selected from (1-2C)alkyl, halo, or oxo;

$L_{8C}$ is absent or selected from O, S, SO, $SO_2$, $N(R_r)$, C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or (1-2C)alkyl; and $Q_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein $Q_{8C}$ is optionally substituted by one or more substituents selected from (1-4C) alkyl, halo, trifluoromethyl, trifluoromethoxy, amino, cyano, hydroxy, amino, carboxy, carbamoyl, sulphamoyl, $NR_tR_u$, $OR_t$, $C(O)R_t$, $C(O)OR_t$, $OC(O)R_t$, $C(O)N(R_t)R_u$, $N(R_t)C(O)R_u$, $S(O)_yR_t$ (where y is 0, 1 or 2), $SO_2N(R_t)R_u$, $N(R_t)SO_2R_u$ or $(CH_2)_zNR_tR_u$ (where z is 1, 2 or 3), wherein $R_t$ and $R_u$ are each independently selected from H or (1-4C)alkyl; or $Q_{8C}$ is optionally substituted by a group of the formula:

—$W_{8C}$-$L_{8'}$-$Z_{8C}$ wherein
$W_{8C}$ is absent or (1-3C)alkylene optionally substituted by (1-2C)alkyl or oxo;
$L_{8'}$ is absent or selected from C(O), C(O)O, OC(O), $C(O)N(R_v)$, $N(R_v)C(O)$, $N(R_v)C(O)N(R_w)$, $S(O)_2N(R_v)$, or $N(R_v)SO_2$, wherein $R_v$ and $R_w$ are each independently selected from hydrogen or (1-2C)alkyl; and
$Z_{8C}$ is phenyl or 5-6 membered heteroaryl; wherein $Z_{8C}$ is optionally substituted by one or more substituents selected from (1-4C)alkyl, halo, (1-4C) haloalkyl, (1-4C)haloalkoxy, (1-4C)alkoxy, (1-4C)alkylamino, amino, cyano, hydroxyl, carboxy, carbamoyl or sulphamoyl; or $Q_{8c}$ and $R_4$ are linked, such that, together with the carbon atom to which they are attached, they form a group of the formula;

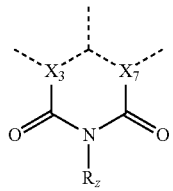

wherein $R_z$ is selected from (1-4C)alkyl, (1-4C)haloalkyl or a group of the formula:

-$L_{Rz}$-$Z_{Rz}$ wherein:
$L_{Rz}$ is absent or (1-3C)alkylene, optionally substituted by one or more substituents selected from (1-2C) alkyl, halo or oxo; and
$Z_{Rz}$ is aryl, carbocyclyl, heterocyclyl or heteroaryl, each of which is optionally substituted by one or more substituents selected from (1-4C)alkyl, halo, trifluoromethyl, trifluoromethoxy, haloalkyl, amino, cyano, hydroxyl, carboxy, carbamoyl or sulphamoyl;

$R_{8N}$ is selected from hydrogen or a group of the formula:

-$L_8$-$L_{8N}$-$Q_{8N}$ wherein
$L_8$ is absent or (1-3C)alkylene, (3-4C)cycloalkyl optionally substituted by one or more substituents selected from (1-2C)alkyl, halo or oxo;
$L_{8N}$ is absent or selected from O, S, SO, $SO_2$, $N(R_x)$, C(O), C(O)O, OC(O), $C(O)N(R_x)$, $N(R_x)C(O)$, $N(R_x)C(O)N(R_y)$, $N(R_x)C(O)O$, $S(O)_2N(R_x)$, or $N(R_x)SO_2$, wherein $R_x$ and $R_y$ are each independently selected from hydrogen or (1-2C)alkyl;

$Q_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, $NR_zR_{a'}$, $OR_z$, $C(O)R_z$, $C(O)OR_z$, $OC(O)R_z$, $C(O)N(Rz)R_{a'}$, $N(Rz)C(O)R_{a'}$, $S(O)_yRz$ (where y is 0, 1 or 2), $SO_2N(Rz)R_{a'}$, $N(Rz)SO_2R_{a'}$ or $(CH_2)_zNR_zR_{a'}$ (where z is 1, 2 or 3), wherein $R_z$ and $R_{a'}$ are each independently selected from H or (1-4C)alkyl; or $Q_{8N}$ is optionally substituted by a group of the formula:

—$W_{8N}$-$L_{8'}$-$Z_{8N}$ wherein
$W_{8N}$ is absent or (1-3C)alkylene optionally substituted by (1-2C)alkyl or oxo;
$L_{8'}$ is absent or selected C(O), C(O)O, OC(O), $C(O)N(R_b')$, $N(R_b')C(O)$, $N(R_b')C(O)N(R_c')$, $S(O)_2N(R_b')$, or $N(R_b')SO_2$, wherein $R_b'$ and $R_{c'}$ are each independently selected from hydrogen or (1-2C)alkyl; and
$Z_{8N}$ is phenyl, (1-4C)alkyl, (4-6C)heterocycyl or a 5-6 membered heteroaryl; wherein $Z_{8N}$ is optionally substituted by one or more substituents selected from (1-4C)alkyl, halo, (1-4C) haloalkyl, (1-4C)haloalkoxy, (1-4C)alkoxy, (1-4C)alkylamino, amino, cyano, hydroxyl, carboxy, carbamoyl or sulphamoyl;

with the proviso that:
one or two of $R_{1b-e}$ can be selected from a substituent other than H;
only one or two of $X_1$, $X_2$ or $X_3$ can be N;
Het may only comprise up to two ring nitrogen atoms; and
only one or two of $X_4$, $X_5$, $X_6$ or $X_7$ can be selected from C(=O), C(=NH) or C(=S).

In another aspect, the present invention relates to compounds of formula (I) shown above, or a pharmaceutically acceptable salt thereof, wherein:
bond c, $R_{1a}$, $R_{1b}$, $R_{1c}$, $R_{1d}$, $R_{1e}$, W, $X_1$, $X_2$, $X_3$, are all as defined above;
$R_4$ is selected from a group of the formula:

-$L_4$-$L_{4C}$-$Q_{4C}$ wherein
$L_4$ is absent or (1-3C)alkylene optionally substituted by (1-2C)alkyl or oxo;
$L_{4C}$ is absent or selected from O, S, SO, $SO_2$, $N(R_{4b})$, C(O), C(O)O, OC(O), $C(O)N(R_{4b})$, $N(R_{4b})C(O)$, $N(R_{4b})C(O)N(R_{4c})$, $S(O)_2N(R_{4b})$, or $N(R_{4b})SO_2$, wherein $R_{4b}$ and $R_{4c}$ are each independently selected from hydrogen or (1-2C)alkyl; and
$Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_{4d}R_{4e}$, $OR_{4d}$, $C(O)R_{4d}$, $C(O)OR_{4d}$, $OC(O)R_{4d}$, $C(O)N(R_{4e})R_{4d}$, $N(R_{4e})C(O)R_{4d}$, $S(O)_yR_{4d}$ (where y is 0, 1 or 2), $SO_2N(R_{4e})R_{4d}$, $N(R_{4e})SO_2R_{4d}$ or $(CH_2)_zNR_{4e}R_{4d}$ (where z is 1, 2 or 3), wherein $R_{4d}$ and $R_{4e}$ are each independently selected from H or (1-4C) alkyl;

HET, bond a, bond b, $X_4$, $X_5$ are as defined above;

13

$X_6$ is selected from C(=O), C(=NH), C(=S), CHR$_{7c}$ or N—R$_{7N}$ when bond b is a single bond, or CR$_{7c}$ or N when bond b is a double bond;
  wherein
    R$_{7c}$ is selected from hydrogen, cyano, halo or a group of the formula:

-L$_7$-L$_{7C}$-Q$_{7C}$ wherein
      L$_7$ is absent or (1-3C)alkylene optionally substituted by (1-2C)alkyl or oxo;
      L$_{7C}$ is absent or selected from O, S, SO, SO$_2$, N(R$_j$), C(O), C(O)O, OC(O), C(O)N(R$_j$), N(R$_j$)C(O), N(R$_j$)C(O)N(R$_k$), S(O)$_2$N(R$_j$), or N(R$_j$)SO$_2$, wherein R$_j$ and R$_k$ are each independently selected from hydrogen or (1-2C)alkyl; and
      Q$_{7C}$ is hydrogen, (1-6C)alkyl, (3-6C)cycloalkyl, aryl, heterocyclyl or heteroaryl; and wherein Q$_{7C}$ is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_l$R$_m$, OR$_l$, C(O)R$_m$, C(O)OR$_l$, OC(O)R$_m$, C(O)N(R$_l$)R$_m$, N(R$_l$)C(O)R$_m$, S(O)$_y$R$_l$ (where y is 0, 1 or 2), SO$_2$N(R$_l$)R$_m$, N(R$_l$)SO$_2$R$_m$ or (CH$_2$)$_z$NR$_l$R$_m$ (where z is 1, 2 or 3), wherein R$_l$ and R$_m$ are each independently selected from H or (1-4C)alkyl;
    R$_{7N}$ is selected from hydrogen or a group of the formula:

-L$_7$-L$_{7N}$-Q$_{7N}$ wherein
      L$_7$ is absent or (1-3C)alkylene optionally substituted by (1-2C)alkyl or oxo;
      L$_{7N}$ is selected from O, S, SO, SO$_2$, N(R$_n$), C(O), C(O)O, OC(O), C(O)N(R$_n$), N(R$_n$)C(O), N(R$_n$)C(O)N(R$_o$), S(O)$_2$N(R$_n$), or N(R$_n$)SO$_2$, wherein R$_n$ and R$_o$ are each independently selected from hydrogen or (1-2C)alkyl; and
      Q$_{7N}$ is hydrogen, cyano, (1-6C)alkyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_p$R$_q$, OR$_p$, C(O)R$_p$, C(O)OR$_p$, OC(O)R$_p$, C(O)N(R$_p$)R$_q$, N(R$_r$)C(O)R$_p$, S(O)$_y$R$_p$ (where y is 0, 1 or 2), SO$_2$N(R$_p$)R$_q$, N(R$_r$)SO$_2$R$_p$ or (CH$_2$)$_z$NR$_p$R$_q$ (where z is 1, 2 or 3), wherein R$_p$ and R$_q$ are each independently selected from H or (1-4C)alkyl;
$X_7$ is selected from C(=O), C(=NH), C(=S), CHR$_{8c}$ or N—R$_{8N}$ when bond b is a single bond, or CR$_{8c}$ or N when bond b is a double bond;
  wherein
    R$_{8c}$ is selected from hydrogen, cyano, halo or a group of the formula:

-L$_8$-L$_{8C}$-Q$_{8C}$ wherein
      L$_8$ is absent or (1-3C)alkylene, (3-4C)cycloalkylene, optionally substituted by one or more substituents selected from (1-2C)alkyl, halo, or oxo;
      L$_{8C}$ is absent or selected from O, S, SO, SO$_2$, N(R$_r$), C(O), C(O)O, OC(O), C(O)N(R$_r$), N(R$_r$)C(O), N(R$_r$)C(O)N(R$_s$), S(O)$_2$N(R$_r$), or N(R$_r$)SO$_2$, wherein R$_r$ and R$_s$ are each independently selected from hydrogen or (1-2C)alkyl; and

14

Q$_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein Q$_{8C}$ is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R$_u$ or (CH$_2$)$_z$NR$_t$R$_u$ (where z is 1, 2 or 3), wherein R$_t$ and R$_u$ are each independently selected from H or (1-4C)alkyl; or
    Q$_{8C}$ is optionally substituted by a group of the formula:

—W$_{8C}$-L$_{8'}$-Z$_{8C}$ wherein
      W$_{8C}$ is absent or (1-3C)alkylene optionally substituted by (1-2C)alkyl or oxo;
      L$_{8'}$ is absent or selected from C(O), C(O)O, OC(O), C(O)N(R$_v$), N(R$_v$)C(O), N(R$_v$)C(O)N(R$_w$), S(O)$_2$N(R$_v$), or N(R$_v$)SO$_2$, wherein R$_v$ and R$_w$ are each independently selected from hydrogen or (1-2C)alkyl; and
      Z$_{8C}$ is phenyl or 5-6 membered heteroaryl; wherein Z$_{8C}$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;
    R$_{8N}$ is selected from hydrogen or a group of the formula:

-L$_8$-L$_{8N}$-Q$_{8N}$ wherein
      L$_8$ is absent or (1-3C)alkylene, (3-4C)cycloalkyl optionally substituted by one or more substituents selected from (1-2C)alkyl, halo or oxo;
      L$_{8N}$ is absent or selected from O, S, SO, SO$_2$, N(R$_x$), C(O), C(O)O, OC(O), C(O)N(R$_x$), N(R$_x$)C(O), N(R$_x$)C(O)N(R$_y$), N(R$_x$)C(O)O, S(O)$_2$N(R$_x$), or N(R$_x$)SO$_2$, wherein R$_x$ and R$_y$ are each independently selected from hydrogen or (1-2C)alkyl;
      Q$_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_{a'}$, OR$_z$, C(O)R$_z$, C(O)OR$_z$, OC(O)R$_z$, C(O)N(Rz)R$_{a'}$, N(Rz)C(O)R$_{a'}$, S(O)$_y$Rz (where y is 0, 1 or 2), SO$_2$N(Rz)R$_{a'}$, N(Rz)SO$_2$R$_{a'}$ or (CH$_2$)$_z$NR$_z$R$_{a'}$ (where z is 1, 2 or 3), wherein R$_z$ and R$_{a'}$ are each independently selected from H or (1-4C)alkyl; or
    Q$_{8N}$ is optionally substituted by a group of the formula:

—W$_{8N}$-L$_{8'}$-Z$_{8N}$ wherein
      W$_{8N}$ is absent or (1-3C)alkylene optionally substituted by (1-2C)alkyl or oxo;
      L$_{8'}$ is absent or selected C(O), C(O)O, OC(O), C(O)N(R$_{b'}$), N(R$_{b'}$)C(O), N(R$_{b'}$)C(O)N(R$_{c'}$), S(O)$_2$N(R$_{b'}$), or N(R$_{b'}$)SO$_2$, wherein R$_{b'}$ and R$_{c'}$ are each independently selected from hydrogen or (1-2C)alkyl; and
      Z$_{8N}$ is phenyl, (1-4C)alkyl, (4-6C)heterocyclyl or a 5-6 membered heteroaryl; wherein Z$_{8N}$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

with the proviso that:

one or two of $R_{1b-e}$ can be selected from a substituent other than H;

only one or two of $X_1$, $X_2$ or $X_3$ can be N;

Het may only comprise up to two ring nitrogen atoms; and only one or two of $X_4$, $X_5$, $X_6$ or $X_7$ can be selected from C(=O), C(=NH) or C(=S).

Particular compounds of the invention include, for example, compounds of the formula I, or pharmaceutically acceptable salts and/or solvates thereof, wherein, unless otherwise stated, each of bond a, bond b, $R_{1a}$, $R_{1b}$, $R_{1c}$, $R_{1d}$, $R_{1e}$, W, $X_1$, $X_2$, $X_3$, $X_4$, $X_5$, $X_6$, $X_7$, c and any associated substitutent groups has any of the meanings defined hereinbefore or in any of paragraphs (1) to (53) hereinafter:—

(1) bond a and bond b are single bonds, or one of bond a or bond b is optionally a double bond;

(2) bond a and bond b are single bonds, or bond b is optionally a double bond;

(3) $R_{1a}$ is selected from hydrogen, fluoro, cyano, formyl, (1-2C)alkyl, (1-2C)haloalkyl or (2C)alkynyl;

(4) $R_{1a}$ is selected from hydrogen, cyano, formyl, (1-2C)alkyl or (1-2C)haloalkyl;

(5) $R_{1a}$ is selected from hydrogen, cyano, methyl or (1-2C)haloalkyl;

(6) $R_{1a}$ is selected from hydrogen, cyano, methyl or fluoromethyl;

(7) $R_{1a}$ is selected from cyano, methyl or fluoromethyl;

(8) $R_{1a}$ is selected from methyl or fluoromethyl;

(9) $R_{1a}$ is methyl;

(10) $R_{1b}$, $R_{1c}$, $R_{1d}$ and $R_{1e}$ are independently selected from H or fluoro;

(11) $R_{1b}$, $R_{1c}$, $R_{1d}$ and $R_{1e}$ are H;

(12) W is selected from —NH—S(O)$_y$—, —S(O)$_y$—NH—, —C(O)NH— or —NHC(O)—, wherein y is 0, 1 or 2;

(13) W is selected from —NH—S(O)$_2$—, —S(O)$_2$—NH—, —C(O)NH— or —NHC(O)—;

(14) W is selected from —NH—S(O)$_2$— or —S(O)$_2$—NH—;

(15) W is —NH—S(O)$_2$—;

(16) $X_1$ is N or CR$_2$, wherein $R_2$ is H or fluoro;

(17) $X_1$ is N or CH;

(18) $X_1$ is CH;

(19) $X_2$ is N or CR$_3$, wherein $R_3$ is H or fluoro;

(20) $X_2$ is N or CH;

(21) $X_2$ is CH or CF;

(22) $X_2$ is CH;

(23) $X_3$ is selected form CR$_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-L$_4$-L$_{4C}$-Q$_{4C}$ wherein

L$_4$ is absent or a (1-3C)alkylene, (2C)alkenylene or (2C)alkynylene, each of which is optionally substituted by (1-2C)alkyl or oxo;

L$_{4C}$ is absent or selected from O, S, SO, SO$_2$, N(R$_{4b}$), C(O), C(O)O, OC(O), C(O)N(R$_{4b}$), N(R$_{4b}$)C(O), C(O)N(R$_{4b}$)O, N(R$_{4b}$)C(O)N(R$_{4c}$), S(O)$_2$N(R$_{4b}$), or N(R$_{4b}$)SO$_2$, wherein R$_{4b}$ and R$_{4c}$ are each independently selected from hydrogen or (1-2C)alkyl; and Q$_{4C}$ is hydrogen, (1-6C)alkyl, (3-6C)cycloalkyl, aryl, heterocyclyl or heteroaryl; and wherein Q$_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_{4d}$R$_{4e}$, OR$_{4d}$, C(O)R$_{4d}$, C(O)OR$_{4d}$, OC(O)R$_{4d}$, C(O)N(R$_{4e}$)R$_{4d}$, N(R$_{4e}$)C(O)R$_{4d}$, S(O)$_y$R$_{4d}$ (where y is 0, 1 or 2), SO$_2$N(R$_{4e}$)R$_{4d}$, N(R$_{4e}$)SO$_2$R$_{4d}$ or (CH$_2$)$_z$NR$_{4e}$R$_{4d}$ (where z is 1, 2 or 3), wherein R$_{4d}$ and R$_{4e}$ are each independently selected from H or (1-4C)alkyl;

(24) $X_3$ is selected form CR$_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-L$_4$-L$_{4C}$-Q$_{4C}$ wherein

L$_4$ is absent or a (1-3C)alkylene, (2C)alkenylene, or (2C)alkynylene, each of which is optionally substituted by (1-2C)alkyl or oxo;

L$_{4C}$ is absent or selected from O, S, SO, SO$_2$, N(R$_{4b}$), C(O), C(O)O, OC(O), C(O)N(R$_{4b}$), N(R$_{4b}$)C(O), C(O)N(R$_{4b}$)O, N(R$_{4b}$)C(O)N(R$_{4c}$), S(O)$_2$N(R$_{4b}$), or N(R$_{4b}$)SO$_2$, wherein R$_{4b}$ and R$_{4c}$ are each independently selected from hydrogen or (1-2C)alkyl; and Q$_{4C}$ is hydrogen, (1-6C)alkyl, (3-6C)cycloalkyl, aryl, heterocyclyl or heteroaryl; and wherein Q$_{6C}$ is optionally substituted by one or more substituents selected from halo, trifluoromethyl, trifluoromethoxy, amino, cyano, hydroxy, amino, carboxy, carbamoyl or sulphamoyl;

(25) $X_3$ is selected form CR$_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-L$_4$-L$_{4C}$-Q$_{4C}$ wherein

L$_4$ is absent or (1-3C)alkylene or (2C)alkynylene, each of which is optionally substituted by (1-2C)alkyl or oxo;

L$_{4C}$ is absent or selected from SO$_2$, N(R$_{4b}$), C(O), C(O)O, OC(O), C(O)N(R$_{4b}$), N(R$_{4b}$)C(O) or C(O)N(R$_{4b}$)O, wherein R$_{4b}$ is selected from hydrogen or (1-2C)alkyl; and Q$_{4C}$ is hydrogen, (1-6C)alkyl, (3-6C)cycloalkyl, aryl, heterocyclyl or heteroaryl; and wherein Q$_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_{4d}$R$_{4e}$, OR$_{4d}$, C(O)R$_{4d}$, C(O)OR$_{4d}$, OC(O)R$_{4d}$, C(O)N(R$_{4e}$)R$_{4d}$, N(R$_{4e}$)C(O)R$_{4d}$, S(O)$_y$R$_{4d}$ (where y is 0, 1 or 2), SO$_2$N(R$_{4e}$)R$_{4d}$, N(R$_{4e}$)SO$_2$R$_{4d}$ or (CH$_2$)$_z$NR$_{4e}$R$_{4d}$ (where z is 1, 2 or 3), wherein R$_{4d}$ and R$_{4e}$ are each independently selected from H or (1-4C)alkyl;

(26) $X_3$ is selected form CR$_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-L$_4$-L$_{4C}$-Q$_{4C}$ wherein

L$_4$ is absent or a (1-3C)alkylene or (2C)alkynylene, each of which is optionally substituted by (1-2C)alkyl or oxo;

$L_{4C}$ is absent or selected from $SO_2$, $N(R_{4b})$, $C(O)$, $C(O)O$, $OC(O)$, $C(O)N(R_{4b})$, $N(R_{4b})C(O)$ or $C(O)N(R_{4b})O$, wherein $R_{4b}$ is selected from hydrogen or (1-2C)alkyl; and $Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(27) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-$L_4$-$L_{4C}$-$Q_{4C}$ wherein
$L_4$ is absent or (1-2C)alkylene optionally substituted by (1-2C)alkyl or oxo;
$L_{4C}$ is absent or selected from C(O)O, OC(O), C(O)N($R_{4b}$), N($R_{4b}$)C(O), wherein $R_{4b}$ is selected from hydrogen or (1-2C)alkyl; and
$Q_{4C}$ is hydrogen, (1-4C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(28) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-$L_{4C}$-$Q_{4C}$ wherein
$L_{4C}$ is absent or selected from C(O)N($R_{4b}$), wherein $R_{4b}$ is selected from hydrogen or (1-2C)alkyl; and
$Q_{4C}$ is hydrogen, (1-4C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(29) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-$L_{4C}$-$Q_{4C}$ wherein
$L_4$ is absent or selected from C(O)N($R_{4b}$), wherein $R_{4b}$ is selected from hydrogen or (1-2C)alkyl; and
$Q_{4C}$ is hydrogen, (1-4C)alkyl, (3-6C)cycloalkyl, phenyl, 5- or 6-membered heterocyclyl or 5- or 6-membered heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(30) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

-$L_{4C}$-$Q_{4C}$ wherein
$L_{4C}$ is absent or selected from C(O)N($R_{4b}$), wherein $R_{4b}$ is selected from hydrogen or (1-2C)alkyl; and
$Q_{4C}$ is hydrogen, (1-4C)alkyl, (3-6C)cycloalkyl, phenyl, or 5-membered heteroaryl; and wherein $Q_{6C}$ is optionally substituted by one or more substituents selected from halo, trifluoromethyl, trifluoromethoxy, amino, cyano, hydroxy or amino;

(31) $X_3$ is selected form $CR_4$ or N; wherein $R_4$ is H, halo, cyano, (1-2C)alkyl, (1-2C)haloalkyl, or (2C)alkynyl;

(32) $X_3$ is selected form $CR_4$ or N; wherein $R_4$ is H, halo, cyano or (1-2C)alkyl;

(33) $X_3$ is selected form $CR_4$ or N; wherein $R_4$ is H, fluoro, cyano or methyl;

(34) $X_3$ is selected form $CR_4$ or N; wherein $R_4$ is H or fluoro;

(35) $X_3$ is CH or CF;

(36) $X_4$ is selected from C(=O), C(=NH), C(=S), CHR$_{5c}$ or N—R$_{5N}$ when bond a is a single bond, or CR$_{5c}$ or N when bond a is a double bond;
wherein
R$_{5c}$ is selected from H, fluoro, (1-2C)alkyl, cyano or (2C)alkynyl;
R$_{5N}$ is selected from H, (1-2C)alkyl or CF$_3$;

(37) $X_4$ is selected from C(=O) or N—R$_{5N}$ when bond a is a single bond, or CR$_{5c}$ or N when bond a is a double bond;
wherein
R$_{5c}$ is selected from H, halo, (1-2C)alkyl, cyano or (2C)alkynyl;
R$_{5N}$ is selected from H, (1-2C)alkyl or CF$_3$;

(38) $X_4$ is selected from C(=O) or N—R$_{5N}$ when bond a is a single bond, or CR$_{5c}$ or N when bond a is a double bond;
wherein
R$_{5c}$ is selected from H, fluoro or (1-2C)alkyl;
R$_{5N}$ is selected from H, (1-2C)alkyl or CF$_3$;

(39) $X_4$ is C(=O) and bond a is a single bond;

(40) $X_5$ is selected is selected from C(=O), C(=NH), C(=S), N—R$_{6N}$ when a is a single bond;
wherein
R$_{6N}$ is selected from hydrogen, or a group of the formula:

-$L_6$-$L_{6N}$-$Q_{6N}$ wherein
$L_6$ is absent or (1-3C)alkylene optionally substituted by (1-2C)alkyl or oxo;
$L_{6N}$ is absent or selected from O, S, SO, SO$_2$, N(R$_f$), C(O), C(O)O, OC(O), C(O)N(R$_g$), N(R$_f$)C(O), N(R$_f$)C(O)N(R$_g$), S(O)$_2$N(R$_f$), or N(R$_f$)SO$_2$, wherein R$_f$ and R$_g$ are each independently selected from hydrogen or (1-2C)alkyl; and
$Q_{6N}$ is hydrogen, cyano, (1-6C)alkyl, (2C)alkynyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_h$R$_i$, OR$_h$, C(O)R$_h$, C(O)OR$_h$, OC(O)R$_h$, C(O)N(R$_h$)R$_i$, N(R$_h$)C(O)R$_i$, N(R$_h$)C(O)OR$_i$, S(O)$_y$R$_h$ (where y is 0, 1 or 2), SO$_2$N(R$_h$)R$_i$, N(R$_h$)SO$_2$R$_i$ or (CH$_2$)$_z$NR$_h$R$_i$ (where z is 1, 2 or 3), wherein R$_h$ and R$_i$ are each independently selected from H or (1-4C)alkyl; or $Q_{6N}$ is optionally substituted by a group of formula:

—W$_{6N}$—Z$_{6N}$ wherein
W$_{6N}$ is absent or (1-3C)alkylene optionally substituted by (1-2C)alkyl or oxo;

$Z_{6N}$ is selected from (3-5C)cycloalkyl, (3-6C)heterocycyl, (2C)alkynyl, phenyl, 5 or 6 membered heteroaryl, carboxy, carbamoyl or cyano, wherein $Z_{6N}$ is substituted by one or more substituents selected from (1-2C)alkyl, (1-2C)alkoxy or halo;

(41) $X_5$ is selected is selected from C(=O) or N—$R_{6N}$ when a is a single bond;
wherein
$R_{6N}$ is selected from hydrogen, or a group of the formula:

-$L_6$-$L_{6N}$-$Q_{6N}$ wherein
$L_6$ is absent or (1-3C)alkylene optionally substituted by (1-2C)alkyl or oxo;
$L_{6N}$ is absent or selected from O, S, SO, $SO_2$, $N(R_f)$, C(O), C(O)O, OC(O), $C(O)N(R_g)$, $N(R_f)C(O)$, or $N(R_f)SO_2$, wherein $R_f$ and $R_g$ are each independently selected from hydrogen or (1-2C)alkyl; and
$Q_{6N}$ is hydrogen, cyano, (1-6C)alkyl, (2C)alkynyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C) alkyl, $NR_hR_i$, $OR_h$, $C(O)R_h$, $C(O)OR_h$, $OC(O)R_h$, $C(O)N(R_h)R_i$, $N(R_h)C(O)R_i$, $N(R_h)C(O)OR_i$, $S(O)_yR_h$ (where y is 0, 1 or 2), wherein $R_h$ and $R_i$ are each independently selected from H or (1-4C)alkyl; or
$Q_{6N}$ is optionally substituted by a group of formula:

—$W_{6N}$—$Z_{6N}$ wherein
$W_{6N}$ is absent or (1-3C)alkylene optionally substituted by (1-2C)alkyl or oxo;
$Z_{6N}$ is selected from (3-5C)cycloalkyl, (3-6C)heterocycyl, (2C)alkynyl, phenyl, 5 or 6 membered heteroaryl, carboxy, carbamoyl or cyano, wherein $Z_{6N}$ is substituted by one or more substituents selected from (1-2C)alkyl, (1-2C)alkoxy or halo;

(42) $X_5$ is N—$R_{6N}$ and bond a is a single bond;
wherein
$R_{6N}$ is selected from a group of the formula:

-$L_6$-$Q_{6N}$ wherein
$L_6$ is (1-3C)alkylene;
$Q_{6N}$ is hydrogen, cyano or 5- or 6-membered heteroaryl, wherein said heteroaryl is optionally substituted by one or more substituents selected from halo, trifluoromethyl, hydroxy, amino, $N(R_h)C(O)OR_i$, or (1-4C)alkyl, wherein $R_h$ and $R_i$ are each independently selected from H or (1-4C)alkyl; or
$Q_{6N}$ is optionally substituted by a group of formula:

—$W_{6N}$—$Z_{6N}$ wherein
$W_{6N}$ is absent or (1-3C)alkylene optionally substituted by (1-2C)alkyl or oxo;
$Z_{6N}$ is selected from (3-5C)cycloalkyl, (2C)alkynyl, phenyl, 5 or 6 membered heteroaryl or cyano, wherein $Z_{6N}$ is substituted by one or more substituents selected from (1-2C)alkyl, (1-2C)alkoxy or halo;

(43) $X_5$ is N—$R_{6N}$ and bond a is a single bond;
wherein
$R_{6N}$ is selected from a group of the formula:

-$L_6$-$Q_{6N}$ wherein
$L_6$ is (1-2C)alkylene;
$Q_{6N}$ is 5- or 6-membered heteroaryl, wherein said heteroaryl is optionally substituted by one or more substituents selected from halo, trifluoromethyl, hydroxy, amino, $N(R_h)C(O)OR_i$, or (1-4C)alkyl, wherein $R_h$ and $R_i$ are each independently selected from H or (1-4C)alkyl;

(44) $X_6$ is selected from C(=O), C(=NH), C(=S), $CHR_7$ or N—$R_{7N}$ when bond b is a single bond, or $CR_7$, or N when bond b is a double bond;
wherein
$R_{7C}$ is selected from hydrogen, cyano, halo or a group of the formula:

-$L_7$-$L_{7C}$-$Q_{7C}$ wherein
$L_7$ is absent or (1-3C)alkylene optionally substituted by (1-2C)alkyl or oxo;
$L_{7C}$ is absent or selected from O, S, SO, $SO_2$, $N(R_j)$, C(O), C(O)O, OC(O), $C(O)N(R_j)$ or $N(R_j)C(O)$, wherein $R_j$ is selected from hydrogen or (1-2C)alkyl; and
$Q_{7C}$ is hydrogen, (1-6C)alkyl, (3-6C)cycloalkyl, aryl, heterocyclyl or heteroaryl; and wherein $Q_{7C}$ is optionally substituted by one or more substituents selected from (1-4C)alkyl, halo, trifluoromethyl, trifluoromethoxy, amino, cyano, hydroxy, amino, carboxy, carbamoyl or sulphamoyl;
$R_{7N}$ is selected from hydrogen or a group of the formula:

-$L_7$-$L_{7N}$-$Q_{7N}$ wherein
$L_7$ is absent or (1-3C)alkylene optionally substituted by (1-2C)alkyl or oxo;
$L_{7N}$ is absent or selected from O, S, SO, $SO_2$, $N(R_n)$, C(O), C(O)O, OC(O), $C(O)N(R_n)$ or $N(R_n)C(O)$, wherein $R_n$ is selected from hydrogen or (1-2C) alkyl; and
$Q_{7N}$ is hydrogen, cyano, (1-6C)alkyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl;

(45) $X_6$ is selected from C(=O) when bond b is a single bond, or $CR_{7O}$ or N when bond b is a double bond;
wherein
$R_{7C}$ is selected from hydrogen, cyano, halo or a group of the formula:

-$L_7$-$Q_{7C}$ wherein
$L_7$ is (1-3C)alkylene optionally substituted by (1-2C) alkyl or oxo; and
$Q_{7C}$ is hydrogen or (1-6C)alkyl, (3-6C)cycloalkyl, aryl, (3-6C)heterocyclyl or 5- or 6-membered heteroaryl; and wherein $Q_{7C}$ is optionally substituted by one or more substituents selected from (1-4C)alkyl or halo;

(46) $X_6$ is selected from C(=O) when bond b is a single bond, or $CR_{7c}$ or N when bond b is a double bond wherein $R_{7c}$ is selected from hydrogen or a group of the formula:

-$L_7$-$Q_{7C}$ wherein $L_7$ is (1-3C)alkylene optionally substituted by (1-2C) alkyl or oxo; and $Q_{7C}$ is hydrogen or (1-4C)alkyl, (3-6C)cycloalkyl, aryl, (3-6C)heterocyclyl or 5- or 6-membered heteroaryl; and wherein $Q_{7C}$ is optionally substituted by one or more substituents selected from (1-2C)alkyl or fluoro;

(47) $X_6$ is C(=O);

(48) $X_7$ is selected from C(=O) or N—$R_{8N}$ when bond b is a single bond, or $CR_{8c}$ or N when bond b is a double bond; wherein $R_{8c}$ is selected from hydrogen, cyano, halo or a group of the formula:

-$L_8$-$L_{8C}$-$Q_{8C}$ wherein $L_8$ is absent or (1-3C)alkylene, optionally substituted by or oxo;

$L_{8C}$ is absent or selected from O, S, SO, $SO_2$, N($R_r$), C(O), C(O)O, OC(O), C(O)N($R_r$) or N($R_r$)C(O), wherein $R_r$ is selected from hydrogen or (1-2C)alkyl; and $Q_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein $Q_{8C}$ is optionally substituted by one or more substituents selected from (1-4C) alkyl, halo, $NR_tR_u$, $OR_t$, C(O)$R_t$, C(O)O$R_t$, OC(O) $R_t$, wherein $R_t$ and $R_u$ are each independently selected from H or (1-2C)alkyl; or $Q_{8c}$ and $R_4$ are linked, such that, together with the carbon atom to which they are attached, they form a group of the formula;

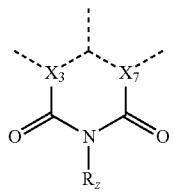

wherein $R_z$ is selected from (1-4C)alkyl, (1-4C)haloalkyl, or a group of the formula:

-$L_{Rz}$-$Z_{Rz}$ wherein:

$L_{Rz}$ is absent or (1-3C)alkylene; and $Z_{Rz}$ is aryl or heteroaryl, each of which is optionally substituted by one or more substituents selected from (1-4C)alkyl, halo, trifluoromethyl, amino, cyano or hydroxyl;

$R_{8N}$ is selected from hydrogen or a group of the formula:

-$L_8$-$L_{8N}$-$Q_{8N}$ wherein $L_8$ is absent or (1-3C)alkylene optionally substituted by one or more substituents selected from (1-2C) alkyl;

$L_{8N}$ is absent or selected from O, S, SO, $SO_2$, N($R_x$), C(O), C(O)O, OC(O), C(O)N($R_x$), N($R_x$)C(O), N($R_x$)C(O)O, wherein $R_x$ is selected from hydrogen or (1-2C)alkyl;

$Q_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, $NR_zR_{a'}$, $OR_z$, C(O)$R_z$, C(O)O$R_z$, OC(O)$R_z$, C(O)N(Rz)$R_{a'}$, N(Rz)C(O)$R_{a'}$ or S(O)$_y$Rz (where y is 0, 1 or 2), wherein $R_z$ and $R_{a'}$ are each independently selected from H or (1-2C)alkyl; or $Q_{8N}$ is optionally substituted by a group of the formula:

-$L_{8'}$-$Z_{8N}$ wherein $L_{8'}$ is absent or selected C(O), C(O)O, OC(O) or C(O)N($R_{b'}$), wherein $R_{b'}$ and $R_{c'}$ are each independently selected from hydrogen or (1-2C) alkyl; and $Z_{8N}$ is phenyl, (1-4C)alkyl, (4-6C)heterocycyl or a 5-6 membered heteroaryl; wherein $Z_{8N}$ is optionally substituted by one or more substituents selected from (1-2C)alkyl, halo, (1-2C) haloalkyl, (1-2C)haloalkoxy, (1-2C)alkoxy, (1-2C)alkylamino, amino, cyano, hydroxyl, carboxy, carbamoyl or sulphamoyl;

(49) $X_7$ is selected from C(=O) or N—$R_{8N}$ when bond b is a single bond, or $CR_{8c}$ or N when bond b is a double bond; wherein $R_{8c}$ is selected from hydrogen, cyano, halo or a group of the formula:

-$L_8$-$L_{8C}$-$Q_{8C}$ wherein $L_8$ is absent or (1-3C)alkylene, optionally substituted by or oxo;

$L_{8C}$ is absent or selected from O, S, SO, $SO_2$, N($R_r$), C(O), C(O)O, OC(O), C(O)N($R_r$) or N($R_r$)C(O), wherein $R_r$ is selected from hydrogen or (1-2C)alkyl; and $Q_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein $Q_{8C}$ is optionally substituted by one or more substituents selected from (1-4C) alkyl, halo, $NR_tR_u$, $OR_t$, C(O)$R_t$, C(O)O$R_t$, OC(O) $R_t$, wherein $R_t$ and $R_u$ are each independently selected from H or (1-2C)alkyl; or $Q_{8c}$ and $R_4$ are linked, such that, together with the carbon atom to which they are attached, they form a group of the formula;

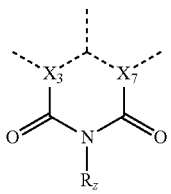

wherein $R_z$ is selected from (1-4C)alkyl or a group of the formula:

-$L_{Rz}$-$Z_{Rz}$ wherein:
L$_{Rz}$ is absent or (1-2C)alkylene; and
Z$_{Rz}$ is 5- or 6-membered heteroaryl, each of which is optionally substituted by one or more substituents selected from (1-4C)alkyl, halo, amino or hydroxyl;
R$_{8N}$ is selected from hydrogen or a group of the formula:

-L$_8$-L$_{8N}$-Q$_{8N}$ wherein
L$_8$ is absent or (1-3C)alkylene optionally substituted by one or more substituents selected from (1-2C)alkyl;
L$_{8N}$ is absent or selected from O, S, SO, SO$_2$, N(R$_x$), C(O), C(O)O, OC(O), C(O)N(R$_x$), N(R$_x$)C(O), N(R$_x$)C(O)O, wherein R$_x$ is selected from hydrogen or (1-2C)alkyl;
Q$_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_a$,, OR$_z$, C(O)R$_z$, C(O)OR$_z$, OC(O)R$_z$, C(O)N(Rz)R$_a$,, N(Rz)C(O)R$_a$, or S(O)$_y$Rz (where y is 0, 1 or 2), wherein R$_z$ and R$_a$, are each independently selected from H or (1-2C)alkyl; or
Q$_{8N}$ is optionally substituted by a group of the formula:

-L$_{8'}$-Z$_{8N}$ wherein
L$_{8'}$ is absent or selected C(O), C(O)O, OC(O) or C(O)N(R$_b$,), wherein R$_b$, and R$_c$, are each independently selected from hydrogen or (1-2C)alkyl; and
Z$_{8N}$ is phenyl, (1-4C)alkyl, (4-6C)heterocycyl or a 5-6 membered heteroaryl; wherein Z$_{8N}$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, hydroxyl, carboxy, carbamoyl or sulphamoyl;

(50) X$_7$ is selected from C(=O) or N—R$_{8N}$ when bond b is a single bond, or CR$_{8c}$ or N when bond b is a double bond;
wherein
R$_{8c}$ is selected from hydrogen, cyano, halo or a group of the formula:

-L$_8$-L$_{8C}$-Q$_{8C}$ wherein
L$_8$ is absent or (1-3C)alkylene, optionally substituted by or oxo;
L$_{8C}$ is absent or selected from O, S, SO, SO$_2$, N(R$_r$), C(O), C(O)O, OC(O), C(O)N(R$_r$) or N(R$_r$)C(O), wherein R$_r$ is selected from hydrogen or (1-2C)alkyl; and
Q$_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein Q$_{8C}$ is optionally substituted by one or more substituents selected from (1-4C)alkyl, halo, NR$_t$R$_u$, OR$_t$, C(O)R$_t$, C(O)OR$_t$, OC(O)R$_t$, wherein R$_t$ and R$_u$ are each independently selected from H or (1-2C)alkyl; or
R$_{8N}$ is selected from hydrogen or a group of the formula:

-L$_8$-L$_{8N}$-Q$_{8N}$ wherein
L$_8$ is absent or (1-3C)alkylene optionally substituted by one or more substituents selected from (1-2C)alkyl;
L$_{8N}$ is absent or selected from O, S, SO, SO$_2$, N(R$_x$), C(O), C(O)O, OC(O), C(O)N(R$_x$), N(R$_x$)C(O), N(R$_x$)C(O)O, wherein R$_x$ is selected from hydrogen or (1-2C)alkyl;
Q$_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_a$,, OR$_z$, C(O)R$_z$, C(O)OR$_z$, OC(O)R$_z$, C(O)N(Rz)R$_a$,, N(Rz)C(O)R$_a$, or S(O)$_y$Rz (where y is 0, 1 or 2), wherein R$_z$ and R$_a$, are each independently selected from H or (1-2C)alkyl; or
Q$_{8N}$ is optionally substituted by a group of the formula:

-L$_{8'}$-Z$_{8N}$ wherein
L$_{8'}$ is absent or selected C(O), C(O)O, OC(O) or C(O)N(R$_b$,), wherein R$_b$, and R$_c$, are each independently selected from hydrogen or (1-2C)alkyl; and
Z$_{8N}$ is phenyl, (1-4C)alkyl, (4-6C)heterocycyl or a 5-6 membered heteroaryl; wherein Z$_{8N}$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, hydroxyl, carboxy, carbamoyl or sulphamoyl;

(51) X$_7$ is selected from N—R$_{8N}$ when bond b is a single bond, or CR$_{8c}$ or N when bond b is a double bond;
wherein
R$_{8c}$ is selected from hydrogen, halo or a group of the formula:

-L$_8$-L$_{8C}$-Q$_{8C}$ wherein
L$_8$ is absent or (1-3C)alkylene, optionally substituted by or oxo;
L$_{8C}$ is absent or selected from O, N(R$_r$), C(O), C(O)O or C(O)N(R$_r$) wherein R$_r$ is selected from hydrogen or (1-2C)alkyl; and
Q$_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein Q$_{8C}$ is optionally substituted by one or more substituents selected from (1-4C)alkyl, halo, NR$_t$R$_u$, OR$_t$, wherein R$_t$ and R$_u$ are each independently selected from H or (1-2C)alkyl; or
R$_{8N}$ is selected from hydrogen or a group of the formula:

-L$_8$-L$_{8N}$-Q$_{8N}$ wherein
L$_8$ is absent or (1-3C)alkylene optionally substituted by one or more substituents selected from (1-2C)alkyl;
L$_{8N}$ is absent or selected from C(O)N(R$_x$) or N(R$_x$)C(O)O, wherein R$_x$ is selected from hydrogen or (1-2C)alkyl;
Q$_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, $NR_zR_{a'}$, $OR_E$, $C(O)N(R_z)R_{a'}$, $N(R_z)C(O)R_{a'}$ or $S(O)_yR_z$ (where y is 0, 1 or 2), wherein $R_z$ and $R_{a'}$ are each independently selected from H or (1-2C)alkyl; or $Q_{8N}$ is optionally substituted by a group of the formula:

-L$_{8'}$-Z$_{8N}$ wherein
L$_{8'}$ is absent or selected C(O) or C(O)N(R$_{b'}$), wherein R$_{b'}$ and R$_{c'}$ are each independently selected from hydrogen or (1-2C)alkyl; and
Z$_{8N}$ is phenyl, (1-4C)alkyl, (4-6C)heterocycyl or a 5-6 membered heteroaryl; wherein Z$_{8N}$ is optionally substituted by one or more substituents selected from (1-2C)alkyl, halo or hydroxyl;

(52) X$_7$ is selected from N—R$_{8N}$ when bond b is a single bond, or CR$_{8c}$ or N when bond b is a double bond; wherein
R$_{8c}$ is selected from hydrogen, halo or a group of the formula:

-L$_8$-L$_{8C}$-Q$_{8C}$ wherein
L$_8$ is absent or (1-3C)alkylene, optionally substituted by or oxo;
L$_{8C}$ is absent or selected from O, N(R$_r$), C(O), C(O)O or C(O)N(R$_r$) wherein R$_r$ is selected from hydrogen or (1-2C)alkyl; and
Q$_{8C}$ is hydrogen, cyano, (1-6C)alkyl, (3-6C)cycloalkyl, (2-3C)alkenyl, (2-3C)alkynyl, phenyl, 5- or 6-membered heterocyclyl or 5- or 6-membered heteroaryl; and wherein Q$_{8C}$ is optionally substituted by one or more substituents selected from (1-4C)alkyl, halo, NR$_t$R$_u$, OR$_t$, wherein R$_t$ and R$_u$ are each independently selected from H or (1-2C)alkyl; or R$_{8N}$ is selected from hydrogen or a group of the formula:

-L$_8$-L$_{8N}$-Q$_{8N}$ wherein
L$_8$ is absent or (1-3C)alkylene optionally substituted by one or more substituents selected from (1-2C)alkyl;
L$_{8N}$ is absent or selected from C(O)N(R$_x$) or N(R$_x$)C(O)O, wherein R$_x$ is selected from hydrogen or (1-2C)alkyl;
Q$_{8N}$ is hydrogen, cyano, (1-6C)alkyl, (3-6C)cycloalkyl, (2-3C)alkenyl, (2-3C)alkynyl, phenyl, 5- or 6-membered heterocyclyl or 5- or 6-membered heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_{a'}$, OR$_z$, C(O)N(R$_z$)R$_{a'}$, N(R$_z$)C(O)R$_{a'}$ or S(O)$_y$R$_z$ (where y is 0, 1 or 2), wherein R$_z$ and R$_{a'}$ are each independently selected from H or (1-2C)alkyl;

(53) c is a single bond.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.

Suitably, bond a and bond b are as defined in any one of paragraphs (1) to (2) above. Suitably, bond a and bond b are as defined in paragraph (2) above.

Suitably, R$_{1a}$ is as defined in any one of paragraphs (3) to (9) above. Most suitably, R$_{1a}$ is cyano, methyl or fluoromethyl.

Suitably, R$_{1b}$, R$_{1c}$, R$_{1d}$ and R$_{1e}$ are as defined in paragraphs (10) and (11) above. Most suitably, R$_{1b}$, R$_{1c}$, R$_{1d}$ and R$_{1e}$ are H.

Suitably, W is as defined in any one of paragraphs (12) to (15) above. Most preferably, W is as defined in paragraph (15), i.e. it is a —NH—SO$_2$— group whereby the NH group is linked to the carbon atom linked to R$_{1a}$.

Suitably, X$_1$ is as defined in any one of paragraphs (16) to (18) above. Most preferably, X$_1$ is as defined in paragraph (18).

Suitably, X$_2$ is as defined in any one of paragraphs (19) to (22) above. Most preferably, X$_2$ is as defined in paragraph (22).

Suitably, X$_3$ is as defined in any one of paragraphs (23) to (35) above. Most preferably, X$_3$ is as defined in paragraph (35).

Suitably, X$_4$ is as defined in any one of paragraphs (36) to (39) above. Most preferably, X$_4$ is as defined in paragraph (39).

Suitably, X$_5$ is as defined in any one of paragraphs (40) to (43) above. Most preferably, X$_5$ is as defined in paragraph (43).

Suitably, X$_6$ is as defined in any one of paragraphs (44) to (47) above. Most preferably, X$_6$ is as defined in paragraph (46).

Suitably, X$_7$ is as defined in any one of paragraphs (48) to (52) above. Most preferably, X$_7$ is as defined in paragraph (52).

In an embodiment of the compounds of the invention, Het must contain at least one C(=O), C(=NH) or C(=S). Suitably, Het must contain at least one C(=O).

In an embodiment, the compound of the present invention is not one of the following compounds:

(R)—N-(sec-butyl)-1-oxo-1,2,3,4-tetrahydroisoquinoline-7-sulfonamide;

(R)—N-(sec-butyl)-2-(3,4-difluorophenyl)-1-oxo-1,2,3,4-tetrahydroisoquinoline-7-sulfonamide;

4-chloro-N-(1-methylethyl)-6-quinoline sulphonamide;

4-chloro-N-methyl-N-(1-methylethyl)-6-quinoline sulphonamide;

4-chloro-6-(4-(cyclopropylamino)sulphonyl)-3-quinolinecarboxamide;

2-oxo-4-trifluoromethyl-1,2-dihydroquinoline-sulfonic acid isopropylmethylamide;

2-oxo-4-trifluoromethyl-1,2-dihydroquinoline-sulfonic acid isopropylamide;

3-[[(2S)-2-cyano-1-pyrrolidinyl]carbonyl]-1,2,3,4-tetrahydro-N-(1-methylethyl)-7-isoquinolinesulfonamide;

2-acetyl-1,2,3,4-tetrahydro-7-[[(1-methylethyl)amino]sulfonyl]-(methylester)-3(3S)-isoquinolinecarboxylic acid;

1,2,3,4-tetrahydro-7-[[(1-methylethyl)amino]sulfonyl]-3 (3S)-isoquinolinecarboxylic acid hydrochloride;

3,4-dihydro-7-[[(1-methylethyl)amino]sulphonyl]-2-(1,1-dimethylethyl)ester-(3S)-2,3(1H)-isoquinolinedicaboxylic acid;

3-[[(2S)-2-(aminocarbonyl)-1-pyrrolidinyl]carbonyl]-7-[[(1-3-methylethyl)amino]sulfonyl]-3,4-dihydro-(1-1-dimethylethyl)ester-(3S)-2(1H)-isoquinolinecarboxylic acid; or 3-[[(2S)-2-cyano-1-pyrrolidinyl]carbonyl]-3,4-dihydro-7-[[1-methylethyl)amino]sulfonyl]-(1,1-dimethylethyl)ester-(3S)-2(1H)-isoquinolinecarboxylic acid.

In a particular group of compounds of the invention, c is a single bond, i.e. the compounds have the structural formula Ia (a sub-definition of formula I) shown below:

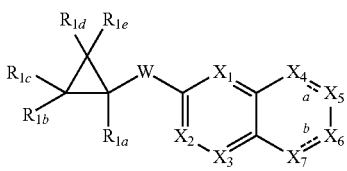

Ia wherein a, b, $X_1$, $X_2$, $X_3$, $X_4$, $X_5$, $X_6$, $X_7$, W, $R_{1a}$, $R_{1b}$, $R_{1c}$, $R_{1d}$, and $R_{1e}$ each have any one of the meanings defined herein; or a pharmaceutically acceptable salt, hydrate and/or solvate thereof.

In an embodiment of the compounds of formula Ia:
bond a and bond b are as defined in any one of paragraphs (1) to (2) above;
$R_{1a}$ is as defined in any one of paragraphs (3) to (9) above;
$R_{1b}$, $R_{1c}$, $R_{1d}$ and $R_{1e}$ are as defined in any one of paragraphs (10) and (11) above;
W is as defined in any one of paragraphs (12) to (15) above;
$X_1$ is as defined in any one of paragraphs (16) to (18) above;
$X_2$ is as defined in any one of paragraphs (19) to (22) above;
$X_3$ is as defined in any one of paragraphs (23) to (35) above;
$X_4$ is as defined in any one of paragraphs (36) to (39) above;
$X_5$ is as defined in any one of paragraphs (40) to (43) above;
$X_6$ is as defined in any one of paragraphs (44) to (47) above; and
$X_7$ is as defined in any one of paragraphs (48) and (52) above.

In an embodiment of the compounds of formula Ia:
bond a and bond b are as defined in paragraph (2) above
$R_{1a}$ is as defined in paragraph (9) above;
$R_{1b}$, $R_{1c}$, $R_{1d}$ and $R_{1e}$ are as defined in paragraph (11) above;
W is as defined in paragraph (15) above;
$X_1$ is as defined in paragraph (18) above;
$X_2$ is as defined in paragraph (22) above;
$X_3$ is as defined in paragraph (35) above;
$X_4$ is as defined in paragraph (39) above;
$X_5$ is as defined in paragraph (43) above;
$X_6$ is as defined in paragraph (46) above; and
$X_7$ is as defined in paragraph (52) above.

In a particular group of compounds of the invention, c is a single bond and W is —NH—S(O)$_2$—, i.e. the compounds have the structural formula IIa (a sub-definition of formula I) shown below:

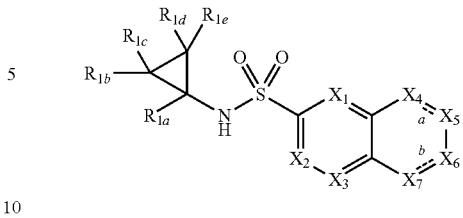

IIa wherein a, b, $X_1$, $X_2$, $X_3$, $X_4$, $X_5$, $X_6$, $X_7$, $R_{1a}$, $R_{1b}$, $R_{1c}$, $R_{1d}$, and $R_{1e}$ each have any one of the meanings defined herein; or a pharmaceutically acceptable salt, hydrate and/or solvate thereof.

In an embodiment of the compounds of formula IIa:
bond a and bond b are as defined in any one of paragraphs (1) to (2) above;
$R_{1a}$ is as defined in any one of paragraphs (3) to (9) above;
$R_{1b}$, $R_{1c}$, $R_{1d}$ and $R_{1e}$ are as defined in any one of paragraphs (10) and (11) above;
$X_1$ is as defined in any one of paragraphs (16) to (18) above;
$X_2$ is as defined in any one of paragraphs (19) to (22) above;
$X_3$ is as defined in any one of paragraphs (23) to (35) above;
$X_4$ is as defined in any one of paragraphs (36) to (39) above;
$X_5$ is as defined in any one of paragraphs (40) to (43) above;
$X_6$ is as defined in any one of paragraphs (44) to (47) above; and
$X_7$ is as defined in any one of paragraphs (48) and (52) above.

In an embodiment of the compounds of formula IIa:
bond a and bond b are as defined in paragraph (2) above
$R_{1a}$ is as defined in paragraph (9) above;
$R_{1b}$, $R_{1c}$, $R_{1d}$ and $R_{1e}$ are as defined in paragraph (11) above;
$X_1$ is as defined in paragraph (18) above;
$X_2$ is as defined in paragraph (22) above;
$X_3$ is as defined in paragraph (35) above;
$X_4$ is as defined in paragraph (39) above;
$X_5$ is as defined in paragraph (43) above;
$X_6$ is as defined in paragraph (46) above; and
$X_7$ is as defined in paragraph (52) above.

In a particular group of compounds of the invention, c is a single bond, W is —NH—S(O)$_2$— and $R_{1b}$, $R_{1c}$, $R_{1d}$ and $R_{1e}$ are H, i.e. the compounds have the structural formula IIb (a sub-definition of formula I) shown below:

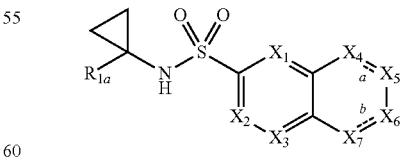

IIb wherein a, b, $X_1$, $X_2$, $X_3$, $X_4$, $X_5$, $X_6$, $X_7$ and $R_{1a}$ each have any one of the meanings defined herein; or a pharmaceutically acceptable salt, hydrate and/or solvate thereof.

In an embodiment of the compounds of formula IIb:
bond a and bond b are as defined in any one of paragraphs (1) to (2) above;

$R_{1a}$ is as defined in any one of paragraphs (3) to (9) above;
$X_1$ is as defined in any one of paragraphs (16) to (18) above;
$X_2$ is as defined in any one of paragraphs (19) to (22) above;
$X_3$ is as defined in any one of paragraphs (23) to (35) above;
$X_4$ is as defined in any one of paragraphs (36) to (39) above;
$X_5$ is as defined in any one of paragraphs (40) to (43) above;
$X_6$ is as defined in any one of paragraphs (44) to (47) above; and
$X_7$ is as defined in any one of paragraphs (48) and (52) above.

In an embodiment of the compounds of formula IIb:
bond a and bond b are as defined in paragraph (2) above;
$R_{1a}$ is as defined in paragraph (9) above;
$X_1$ is as defined in paragraph (18) above;
$X_2$ is as defined in paragraph (22) above;
$X_3$ is as defined in paragraph (35) above;
$X_4$ is as defined in paragraph (39) above;
$X_5$ is as defined in paragraph (43) above;
$X_6$ is as defined in paragraph (46) above; and
$X_7$ is as defined in paragraph (52) above.

In a particular group of compounds of the invention, c is a single bond, W is —NH—S(O)$_2$—, $R_{1b}$, $R_{1c}$, $R_{1d}$ and $R_{1e}$ are H, and $X_1$, is CH, i.e. the compounds have the structural formula IIc (a sub-definition of formula I) shown below:

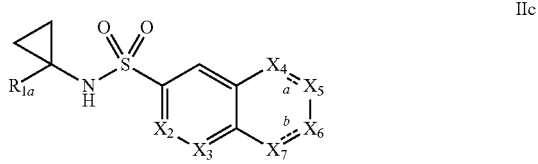

IIc wherein a, b, $X_2$, $X_3$, $X_4$, $X_5$, $X_6$, $X_7$ and $R_{1a}$ each have any one of the meanings defined herein; or a pharmaceutically acceptable salt, hydrate and/or solvate thereof.

In an embodiment of the compounds of formula IIc:
bond a and bond b are as defined in any one of paragraphs (1) to (2) above;
$R_{1a}$ is as defined in any one of paragraphs (3) to (9);
$X_2$ is as defined in any one of paragraphs (19) to (22) above;
$X_3$ is as defined in any one of paragraphs (23) to (35) above;
$X_4$ is as defined in any one of paragraphs (36) to (39) above;
$X_5$ is as defined in any one of paragraphs (40) to (43) above;
$X_6$ is as defined in any one of paragraphs (44) to (47) above; and
$X_7$ is as defined in any one of paragraphs (48) and (52).

In an embodiment of the compounds of formula IIc:
bond a and bond b are as defined in paragraph (2) above;
$R_{1a}$ is as defined in paragraph (9) above;
$X_2$ is as defined in paragraph (22) above;
$X_3$ is as defined in paragraph (35) above;
$X_4$ is as defined in paragraph (39) above;
$X_5$ is as defined in paragraph (43) above;
$X_6$ is as defined in paragraph (46) above; and
$X_7$ is as defined in paragraph (52).

In a particular group of compounds of the invention, W is —NH—S(O)$_2$—, $R_{1b}$, $R_{1c}$, $R_{1d}$ and $R_{1e}$ are H, $X_1$ is CH, $X_2$ is CH, $X_4$ is C=O and bond a is a single bond, i.e. the compounds have the structural formula IId (a sub-definition of formula I) shown below:

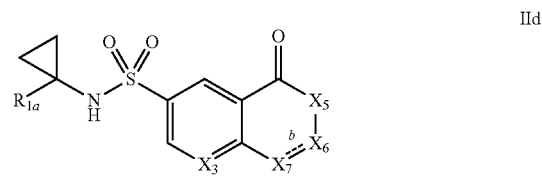

IId wherein b, $X_3$, $X_5$, $X_6$, $X_7$ and $R_{1a}$ each have any one of the meanings defined herein; or a pharmaceutically acceptable salt, hydrate and/or solvate thereof.

In an embodiment of the compounds of formula IId:
$R_{1a}$ is as defined in any one of paragraphs (3) to (9);
$X_3$ is as defined in any one of paragraphs (23) to (35) above;
$X_5$ is as defined in any one of paragraphs (40) to (43) above;
$X_6$ is as defined in any one of paragraphs (44) to (47) above; and
$X_7$ is as defined in any one of paragraphs (48) and (52).

In an embodiment of the compounds of formula IId:
$R_{1a}$ is as defined in paragraph (9) above;
$X_3$ is as defined in paragraph (35) above;
$X_5$ is as defined in paragraph (43) above;
$X_6$ is as defined in paragraph (46) above; and
$X_7$ is as defined in paragraph (52).

In a particular group of compounds of the invention compound, HET is a compound of Formula (III), (IV), (V), (VI), (VII), (VIII) or (IX):

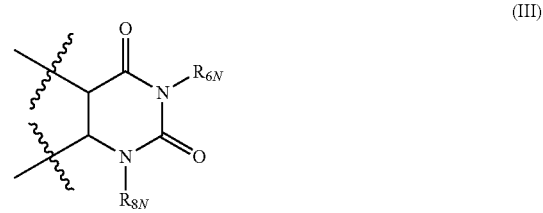

(III)

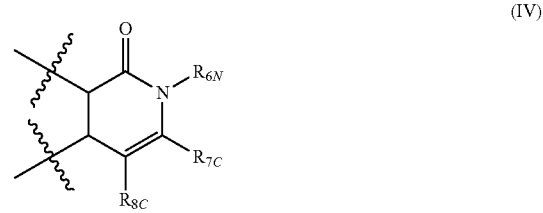

(IV)

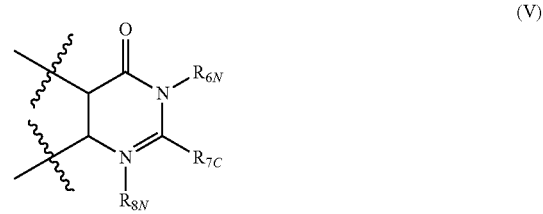

(V)

-continued (VI)
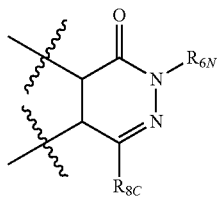

(VII)
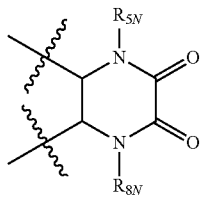

(VIII)
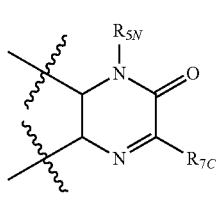

(IX)
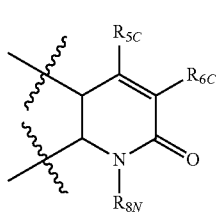

wherein $R_{5C}$, $R_{6C}$, $R_{5N}$, $R_{7C}$, $R_{6N}$ and $R_{8N}$ are as defined herein.

In another particular group of compounds of the invention compound, HET is a compound of Formula (III), (IV), (V), (VI), (VII) or (VIII):

(III)
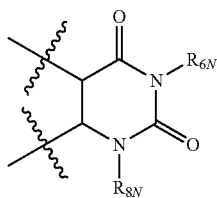

(IV)
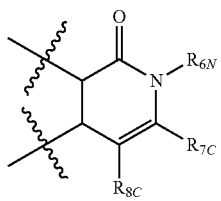

(V)
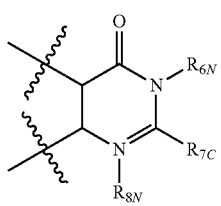

-continued (VI)
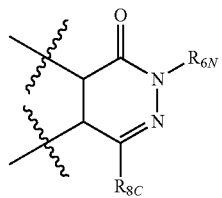

(VII)
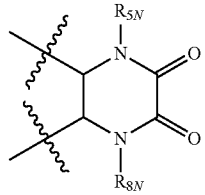

(VIII)
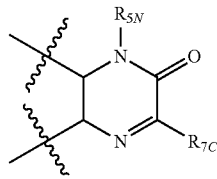

wherein $R_{5N}$, $R_{7C}$, $R_{6N}$ and $R_{8N}$ are as defined herein.

In another particular group of compounds of the invention compound, HET is a compound of Formula (III) or (V):

(III)
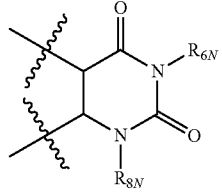

(V)
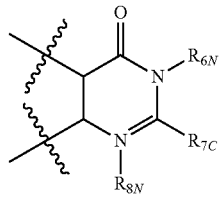

wherein $R_{7C}$, $R_{6N}$ and $R_{8N}$ are as defined herein.

In another particular group of compounds of the invention compound, HET is a compound of Formula (III):

(III)
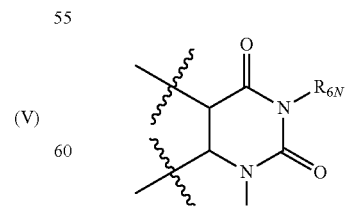

wherein $R_{6N}$ and $R_{8N}$ are as defined herein.

Particular compounds of the present invention include any of the compounds exemplified in the present application, or a pharmaceutically acceptable salt or solvate thereof, and, in particular, any of the following:

N-(1-methylcyclopropyl)-2,4-dioxo-1H-quinazoline-6-sulfonamide;
1,3-dimethyl-N-(1-methylcyclopropyl)-2,4-dioxo-quinazoline-6-sulfonamide;
N-(1-cyanocyclopropyl)-1,3-dimethyl-2,4-dioxo-quinazoline-6-sulfonamide;
1,3-diethyl-N-(1-methylcyclopropyl)-2,4-dioxo-quinazoline-6-sulfonamide;
N-(1-cyanocyclopropyl)-1,3-diethyl-2,4-dioxo-quinazoline-6-sulfonamide;
3-ethyl-N-(1-methylcyclopropyl)-2,4-dioxo-1H-quinazoline-6-sulfonamide;
3-methyl-N-(1-methylcyclopropyl)-2,4-dioxo-1H-quinazoline-6-sulfonamide;
1-benzyl-3-methyl-N-(1-methylcyclopropyl)-2,4-dioxo-quinazoline-6-sulfonamide;
1-ethyl-3-methyl-N-(1-methylcyclopropyl)-2,4-dioxo-quinazoline-6-sulfonamide;
1-benzyl-3-ethyl-N-(1-methylcyclopropyl)-2,4-dioxo-quinazoline-6-sulfonamide;
1-[(2,6-dichlorophenyl)methyl]-3-ethyl-N-(1-methylcyclopropyl)-2,4-dioxo-quinazoline-6-sulfonamide;
3-ethyl-1-methyl-N-(1-methylcyclopropyl)-2,4-dioxo-quinazoline-6-sulfonamide;
1-(cyclohexylmethyl)-3-ethyl-N-(1-methylcyclopropyl)-2,4-dioxo-quinazoline-6-sulfonamide;
1-(cyclopropylmethyl)-3-ethyl-N-(1-methylcyclopropyl)-2,4-dioxo-quinazoline-6-sulfonamide;
3-ethyl-N-(1-methylcyclopropyl)-2,4-dioxo-1-(2-pyrrolidin-1-ylethyl)quinazoline-6-sulfonamide;
3-ethyl-1-(3-methoxypropyl)-N-(1-methylcyclopropyl)-2,4-dioxo-quinazoline-6-sulfonamide;
3-ethyl-1-(2-methoxyethyl)-N-(1-methylcyclopropyl)-2,4-dioxo-quinazoline-6-sulfonamide;
3-ethyl-N-(1-methylcyclopropyl)-1-(2-morpholinoethyl)-2,4-dioxo-quinazoline-6-sulfonamide;
1-methyl-N-(1-methylcyclopropyl)-2,4-dioxo-quinazoline-6-sulfonamide;
3-(cyclopropylmethyl)-1-methyl-N-(1-methylcyclopropyl)-2,4-dioxo-quinazoline-6-sulfonamide;
4-methyl-N-(1-methylcyclopropyl)-2,3-dioxo-1H-quinoxaline-6-sulfonamide;
1-(cyclopropylmethyl)-4-methyl-N-(1-methylcyclopropyl)-2,3-dioxo-quinoxaline-6-sulfonamide;
1-(cyclopropylmethyl)-3-methyl-N-(1-methylcyclopropyl)-2,4-dioxo-quinazoline-6-sulfonamide;
3-ethyl-1-isobutyl-N-(1-methylcyclopropyl)-2,4-dioxo-quinazoline-6-sulfonamide;
1-(2-methoxyethyl)-3-methyl-N-(1-methylcyclopropyl)-2,4-dioxo-quinazoline-6-sulfonamide;
1-[2-(dimethylamino)ethyl]-3-methyl-N-(1-methylcyclopropyl)-2,4-dioxo-quinazoline-6-sulfonamide;
1-isobutyl-3-methyl-N-(1-methylcyclopropyl)-2,4-dioxo-quinazoline-6-sulfonamide;
3-ethyl-2-isobutoxy-N-(1-methylcyclopropyl)-4-oxo-quinazoline-6-sulfonamide;
2-isobutoxy-3-methyl-N-(1-methylcyclopropyl)-4-oxo-quinazoline-6-sulfonamide;
1-methyl-N-(1-methylcyclopropyl)-2,4-dioxo-3-(3-pyridylmethyl)quinazoline-6-sulfonamide;
3-(cyanomethyl)-1-methyl-N-(1-methylcyclopropyl)-2,4-dioxo-quinazoline-6-sulfonamide;
3-methyl-N-(1-methylcyclopropyl)-1-[(1-methylcyclopropyl)methyl]-2,4-dioxo-quinazoline-6-sulfonamide;
3-methyl-N-(1-methylcyclopropyl)-2-[(1-methylcyclopropyl)methoxy]-4-oxo-quinazoline-6-sulfonamide;
1-(cyclohexylmethyl)-3-methyl-N-(1-methylcyclopropyl)-2,4-dioxo-quinazoline-6-sulfonamide;
3-methyl-N-(1-methylcyclopropyl)-1-[(2-methylcyclopropyl)methyl]-2,4-dioxo-quinazoline-6-sulfonamide;
1-[(2,2-difluorocyclopropyl)methyl]-3-methyl-N-(1-methylcyclopropyl)-2,4-dioxo-quinazoline-6-sulfonamide;
3-methyl-N-(1-methylcyclopropyl)-2,4-dioxo-1-(tetrahydrofuran-3-ylmethyl)quinazoline-6-sulfonamide;
3-methyl-N-(1-methylcyclopropyl)-2,4-dioxo-1-(tetrahydropyran-2-ylmethyl)quinazoline-6-sulfonamide;
3-methyl-N-(1-methylcyclopropyl)-2,4-dioxo-1-prop-2-ynyl-quinazoline-6-sulfonamide;
1-benzyl-4-methyl-N-(1-methylcyclopropyl)-2,3-dioxo-quinoxaline-6-sulfonamide;
4-methyl-2-(methylamino)-N-(1-methylcyclopropyl)-3-oxo-quinoxaline-6-sulfonamide;
3-methyl-N-(1-methylcyclopropyl)-1-[(3-methyloxetan-3-yl)methyl]-2,4-dioxo-quinazoline-6-sulfonamide;
1-(2-cyclopropylethyl)-3-methyl-N-(1-methylcyclopropyl)-2,4-dioxo-quinazoline-6-sulfonamide;
2-(2-cyclopropylethoxy)-3-methyl-N-(1-methylcyclopropyl)-4-oxo-quinazoline-6-sulfonamide;
1-allyl-3-methyl-N-(1-methylcyclopropyl)-2,4-dioxo-quinazoline-6-sulfonamide;
1-(cyclopentylmethyl)-3-methyl-N-(1-methylcyclopropyl)-2,4-dioxo-quinazoline-6-sulfonamide;
1-methyl-N-(1-methylcyclopropyl)-2,4-dioxo-3-prop-2-ynyl-quinazoline-6-sulfonamide;
3-methyl-N-(1-methylcyclopropyl)-1-[(1-methylimidazol-2-yl)methyl]-2,4-dioxo-quinazoline-6-sulfonamide;
3-methyl-N-(1-methylcyclopropyl)-2,4-dioxo-1-(tetrahydrofuran-2-ylmethyl)quinazoline-6-sulfonamide;
3-[(2,2-difluorocyclopropyl)methyl]-1-methyl-N-(1-methylcyclopropyl)-2,4-dioxo-quinazoline-6-sulfonamide;
2,3-dimethyl-N-(1-methylcyclopropyl)-4-oxo-quinazoline-6-sulfonamide;
2-methyl-N-(1-methylcyclopropyl)-4-oxo-3H-quinazoline-6-sulfonamide;
1-methyl-N-(1-methylcyclopropyl)-2,4-dioxo-3-(4-pyridylmethyl)quinazoline-6-sulfonamide;
2-cyclopropyl-N-(1-methylcyclopropyl)-4-oxo-3H-quinazoline-6-sulfonamide;
2-isopropyl-N-(1-methylcyclopropyl)-4-oxo-3H-quinazoline-6-sulfonamide;
3-methyl-N-(1-methylcyclopropyl)-1-(o-tolylmethyl)-2,4-dioxo-quinazoline-6-sulfonamide;
3-methyl-N-(1-methylcyclopropyl)-1-(m-tolylmethyl)-2,4-dioxo-quinazoline-6-sulfonamide;
3-methyl-N-(1-methylcyclopropyl)-2,4-dioxo-1-(p-tolylmethyl)quinazoline-6-sulfonamide;
1-[(2-methoxyphenyl)methyl]-3-methyl-N-(1-methylcyclopropyl)-2,4-dioxo-quinazoline-6-sulfonamide;
1-[(3-methoxyphenyl)methyl]-3-methyl-N-(1-methylcyclopropyl)-2,4-dioxo-quinazoline-6-sulfonamide;
1-[(4-methoxyphenyl)methyl]-3-methyl-N-(1-methylcyclopropyl)-2,4-dioxo-quinazoline-6-sulfonamide;
1-[(2-chlorophenyl)methyl]-3-methyl-N-(1-methylcyclopropyl)-2,4-dioxo-quinazoline-6-sulfonamide;
1-[(3-chlorophenyl)methyl]-3-methyl-N-(1-methylcyclopropyl)-2,4-dioxo-quinazoline-6-sulfonamide;
1-[(4-chlorophenyl)methyl]-3-methyl-N-(1-methylcyclopropyl)-2,4-dioxo-quinazoline-6-sulfonamide;
1-[(2-fluorophenyl)methyl]-3-methyl-N-(1-methylcyclopropyl)-2,4-dioxo-quinazoline-6-sulfonamide;

1-[(3-fluorophenyl)methyl]-3-methyl-N-(1-methylcyclopropyl)-2,4-dioxo-quinazoline-6-sulfonamide;
1-[(4-fluorophenyl)methyl]-3-methyl-N-(1-methylcyclopropyl)-2,4-dioxo-quinazoline-6-sulfonamide;
1-[(2-cyanophenyl)methyl]-3-methyl-N-(1-methylcyclopropyl)-2,4-dioxo-quinazoline-6-sulfonamide;
1-[(3-cyanophenyl)methyl]-3-methyl-N-(1-methylcyclopropyl)-2,4-dioxo-quinazoline-6-sulfonamide;
1-[(4-cyanophenyl)methyl]-3-methyl-N-(1-methylcyclopropyl)-2,4-dioxo-quinazoline-6-sulfonamide;
3-methyl-N-(1-methylcyclopropyl)-2,4-dioxo-1-[[2-(trifluoromethyl)phenyl]methyl]quinazoline-6-sulfonamide;
3-methyl-N-(1-methylcyclopropyl)-2,4-dioxo-1-[[3-(trifluoromethyl)phenyl]methyl]quinazoline-6-sulfonamide;
3-methyl-N-(1-methylcyclopropyl)-2,4-dioxo-1-[[4-(trifluoromethyl)phenyl]methyl]quinazoline-6-sulfonamide;
1-[(2,6-dichlorophenyl)methyl]-3-methyl-N-(1-methylcyclopropyl)-2,4-dioxo-quinazoline-6-sulfonamide;
1-[(2,6-difluorophenyl)methyl]-3-methyl-N-(1-methylcyclopropyl)-2,4-dioxo-quinazoline-6-sulfonamide;
1-[(3,5-dichlorophenyl)methyl]-3-methyl-N-(1-methylcyclopropyl)-2,4-dioxo-quinazoline-6-sulfonamide;
1-[(3,5-dimethylphenyl)methyl]-3-methyl-N-(1-methylcyclopropyl)-2,4-dioxo-quinazoline-6-sulfonamide;
1-[(3,5-dimethoxyphenyl)methyl]-3-methyl-N-(1-methylcyclopropyl)-2,4-dioxo-quinazoline-6-sulfonamide;
1-[(3,5-difluorophenyl)methyl]-3-methyl-N-(1-methylcyclopropyl)-2,4-dioxo-quinazoline-6-sulfonamide;
2-cyclopropyl-3-methyl-N-(1-methylcyclopropyl)-4-oxo-quinazoline-6-sulfonamide;
2-isobutyl-3-methyl-N-(1-methylcyclopropyl)-4-oxo-quinazoline-6-sulfonamide;
3-methyl-N-(1-methylcyclopropyl)-2,4-dioxo-1-(2-pyridylmethyl)quinazoline-6-sulfonamide;
3-methyl-N-(1-methylcyclopropyl)-2,4-dioxo-1-(3-pyridylmethyl)quinazoline-6-sulfonamide;
3-methyl-N-(1-methylcyclopropyl)-2,4-dioxo-1-(4-pyridylmethyl)quinazoline-6-sulfonamide;
2-[1-methyl-6-[(1-methylcyclopropyl)sulfamoyl]-2,4-dioxo-quinazolin-3-yl]-N-phenyl-acetamide;
(2S)-1-[2-[1-methyl-6-[(1-methylcyclopropyl)sulfamoyl]-2,4-dioxo-quinazolin-3-yl]acetyl]pyrrolidine-2-carboxamide;
3-[2-(4-aminophenyl)-2-oxo-ethyl]-1-methyl-N-(1-methylcyclopropyl)-2,4-dioxo-quinazoline-6-sulfonamide;
3-[[1-methyl-6-[(1-methylcyclopropyl)sulfamoyl]-2,4-dioxo-quinazolin-3-yl]methyl]-1,2,4-oxadiazole-5-carboxamide;
4-[[1-methyl-6-[(1-methylcyclopropyl)sulfamoyl]-2,4-dioxo-quinazolin-3-yl]methyl]benzamide;
2-[1-methyl-6-[(1-methylcyclopropyl)sulfamoyl]-2,4-dioxo-quinazolin-3-yl]-N-(1-methylpyrazol-4-yl)acetamide;
3-[2-(4-hydroxyphenyl)-2-oxo-ethyl]-1-methyl-N-(1-methylcyclopropyl)-2,4-dioxo-quinazoline-6-sulfonamide;
2-[3-methyl-6-[(1-methylcyclopropyl)sulfamoyl]-2,4-dioxo-quinazolin-1-yl]-N-phenyl-acetamide;
3-[[3-methyl-6-[(1-methylcyclopropyl)sulfamoyl]-2,4-dioxo-quinazolin-1-yl]methyl]benzamide;
1-[[3-(difluoromethyl)phenyl]methyl]-3-methyl-N-(1-methylcyclopropyl)-2,4-dioxo-quinazoline-6-sulfonamide;
3-[[3-methyl-6-[(1-methylcyclopropyl)sulfamoyl]-2,4-dioxo-quinazolin-1-yl]methyl]-1,2,4-oxadiazole-5-carboxamide;
4-[[3-methyl-6-[(1-methylcyclopropyl)sulfamoyl]-2,4-dioxo-quinazolin-1-yl]methyl]benzamide;
3-methyl-N-(1-methylcyclopropyl)-4-oxo-2-phenyl-quinazoline-6-sulfonamide;
N-(1-methylcyclopropyl)-4-oxo-2-pyrrolidin-1-yl-3H-quinazoline-6-sulfonamide;
N-methyl-5-[[1-methyl-6-[(1-methylcyclopropyl)sulfamoyl]-2,4-dioxo-quinazolin-3-yl]methyl]-1,2,4-oxadiazole-3-carboxamide;
1-[(4-cyano-3-fluoro-phenyl)methyl]-3-methyl-N-(1-methylcyclopropyl)-2,4-dioxo-quinazoline-6-sulfonamide;
N-methyl-5-[[3-methyl-6-[(1-methylcyclopropyl)sulfamoyl]-2,4-dioxo-quinazolin-1-yl]methyl]-1,2,4-oxadiazole-3-carboxamide;
3-[2-(4-fluorophenyl)-2-oxo-ethyl]-1-methyl-N-(1-methylcyclopropyl)-2,4-dioxo-quinazoline-6-sulfonamide;
1-methyl-N-(1-methylcyclopropyl)-3-[(5-methylisoxazol-3-yl)methyl]-2,4-dioxo-quinazoline-6-sulfonamide;
3-methyl-N-(1-methylcyclopropyl)-1-[(4-methylsulfonylphenyl)methyl]-2,4-dioxo-quinazoline-6-sulfonamide;
3-methyl-N-(1-methylcyclopropyl)-1-[(5-methylisoxazol-3-yl)methyl]-2,4-dioxo-quinazoline-6-sulfonamide;
2-[3-methyl-6-[(1-methylcyclopropyl)sulfamoyl]-2,4-dioxo-quinazolin-1-yl]-N-(1-methylpyrazol-4-yl)acetamide;
1-[2-(4-hydroxyphenyl)-2-oxo-ethyl]-3-methyl-N-(1-methylcyclopropyl)-2,4-dioxo-quinazoline-6-sulfonamide;
1-methyl-N-(1-methylcyclopropyl)-2,4-dioxo-3-(pyrazin-2-ylmethyl)quinazoline-6-sulfonamide;
1-methyl-N-(1-methylcyclopropyl)-3-[(2-methylthiazol-5-yl)methyl]-2,4-dioxo-quinazoline-6-sulfonamide;
3-[2-[4-(diethylamino)phenyl]-2-oxo-ethyl]-1-methyl-N-(1-methylcyclopropyl)-2,4-dioxo-quinazoline-6-sulfonamide;
1-methyl-N-(1-methylcyclopropyl)-3-[(5-nitro-2-furyl)methyl]-2,4-dioxo-quinazoline-6-sulfonamide;
3-(1H-benzimidazol-2-ylmethyl)-1-methyl-N-(1-methylcyclopropyl)-2,4-dioxo-quinazoline-6-sulfonamide;
1-methyl-N-(1-methylcyclopropyl)-3-[(1-methylimidazol-2-yl)methyl]-2,4-dioxo-quinazoline-6-sulfonamide;
1-methyl-N-(1-methylcyclopropyl)-2,4-dioxo-3-[2-oxo-2-(4-pyrrolidin-1-ylphenyl)ethyl]quinazoline-6-sulfonamide;
3-[(3,5-dimethylisoxazol-4-yl)methyl]-1-methyl-N-(1-methylcyclopropyl)-2,4-dioxo-quinazoline-6-sulfonamide;
1-(1H-benzimidazol-2-ylmethyl)-3-methyl-N-(1-methylcyclopropyl)-2,4-dioxo-quinazoline-6-sulfonamide;
3-methyl-N-(1-methylcyclopropyl)-2,4-dioxo-1-[2-oxo-2-(4-pyrrolidin-1-ylphenyl)ethyl]quinazoline-6-sulfonamide;
N-[4-[[3-methyl-6-[(1-methylcyclopropyl)sulfamoyl]-2,4-dioxo-quinazolin-1-yl]methyl]phenyl]acetamide;
1-[(5-tert-butyl-1,2,4-oxadiazol-3-yl)methyl]-3-methyl-N-(1-methylcyclopropyl)-2,4-dioxo-quinazoline-6-sulfonamide;
3-methyl-N-(1-methylcyclopropyl)-1-[(5-nitro-2-furyl)methyl]-2,4-dioxo-quinazoline-6-sulfonamide;
1-[(3,5-dimethylisoxazol-4-yl)methyl]-3-methyl-N-(1-methylcyclopropyl)-2,4-dioxo-quinazoline-6-sulfonamide;
1-methyl-N-(1-methylcyclopropyl)-3-[(2-methylpyrazol-3-yl)methyl]-2,4-dioxo-quinazoline-6-sulfonamide;
3-[(2,5-dimethylpyrazol-3-yl)methyl]-1-methyl-N-(1-methylcyclopropyl)-2,4-dioxo-quinazoline-6-sulfonamide;
3-methyl-N-(1-methylcyclopropyl)-2,4-dioxo-1-(pyrazin-2-ylmethyl)quinazoline-6-sulfonamide;
3-methyl-N-(1-methylcyclopropyl)-1-[(2-methylpyrazol-3-yl)methyl]-2,4-dioxo-quinazoline-6-sulfonamide;

3-methyl-N-(1-methylcyclopropyl)-1-[(2-methylthiazol-5-yl)methyl]-2,4-dioxo-quinazoline-6-sulfonamide;
1-[(2,5-dimethylpyrazol-3-yl)methyl]-3-methyl-N-(1-methylcyclopropyl)-2,4-dioxo-quinazoline-6-sulfonamide;
1-[(4-fluorophenyl)methyl]-N-(1-methylcyclopropyl)-2,3-dioxo-4H-quinoxaline-6-sulfonamide;
1,3-bis[(3,5-dimethylisoxazol-4-yl)methyl]-N-(1-methylcyclopropyl)-2,4-dioxo-quinazoline-6-sulfonamide;
1-[(4-fluorophenyl)methyl]-4-methyl-N-(1-methylcyclopropyl)-2,3-dioxo-quinoxaline-6-sulfonamide;
N-(3-hydroxypropyl)-4-[[3-methyl-6-[(1-methylcyclopropyl)sulfamoyl]-2,4-dioxo-quinazolin-1-yl]methyl]benzamide;
3-methyl-N-(1-methylcyclopropyl)-2,4-dioxo-1-[(1S)-1-phenylethyl]quinazoline-6-sulfonamide;
1-[(2,4-dimethylthiazol-5-yl)methyl]-3-methyl-N-(1-methylcyclopropyl)-2,4-dioxo-quinazoline-6-sulfonamide;
3-methyl-N-(1-methylcyclopropyl)-1-[(2-methyl-4-phenyl-thiazol-5-yl)methyl]-2,4-dioxo-quinazoline-6-sulfonamide;
1-[(2-bromothiazol-5-yl)methyl]-3-methyl-N-(1-methylcyclopropyl)-2,4-dioxo-quinazoline-6-sulfonamide;
1-but-2-ynyl-3-methyl-N-(1-methylcyclopropyl)-2,4-dioxo-quinazoline-6-sulfonamide;
3-methyl-N-(1-methylcyclopropyl)-2,4-dioxo-1-pent-2-ynyl-quinazoline-6-sulfonamide;
3-methyl-N-(1-methylcyclopropyl)-2,4-dioxo-1-[[4-(piperazine-1-carbonyl)phenyl]methyl]quinazoline-6-sulfonamide;
3-methyl-N-(1-methylcyclopropyl)-1-[(1S)-1-methylprop-2-ynyl]-2,4-dioxo-quinazoline-6-sulfonamide;
3-methyl-N-(1-methylcyclopropyl)-1-[(1R)-1-methylprop-2-ynyl]-2,4-dioxo-quinazoline-6-sulfonamide;
3-[(2-bromothiazol-5-yl)methyl]-1-methyl-N-(1-methylcyclopropyl)-2,4-dioxo-quinazoline-6-sulfonamide;
3-[(2,4-dimethylthiazol-5-yl)methyl]-1-methyl-N-(1-methylcyclopropyl)-2,4-dioxo-quinazoline-6-sulfonamide;
3-methyl-N-(1-methylcyclopropyl)-2,4-dioxo-1-(thiazol-5-ylmethyl)quinazoline-6-sulfonamide;
3-[(2-chlorothiazol-5-yl)methyl]-1-methyl-N-(1-methylcyclopropyl)-2,4-dioxo-quinazoline-6-sulfonamide;
1-[(2-chlorothiazol-5-yl)methyl]-3-methyl-N-(1-methylcyclopropyl)-2,4-dioxo-quinazoline-6-sulfonamide;
3-methyl-N-(1-methylcyclopropyl)-2,4-dioxo-1-(thiazol-2-ylmethyl)quinazoline-6-sulfonamide;
1-methyl-N-(1-methylcyclopropyl)-2,4-dioxo-3-(thiazol-5-ylmethyl)quinazoline-6-sulfonamide;
3-methyl-N-(1-methylcyclopropyl)-2,4-dioxo-1-(thiazol-4-ylmethyl)quinazoline-6-sulfonamide;
1-[(5-tert-butyl-2-methyl-pyrazol-3-yl)methyl]-3-methyl-N-(1-methylcyclopropyl)-2,4-dioxo-quinazoline-6-sulfonamide;
1-methyl-N-(1-methylcyclopropyl)-3-[(4-methylthiazol-2-yl)methyl]-2,4-dioxo-quinazoline-6-sulfonamide;
3-methyl-N-(1-methylcyclopropyl)-1-[(1-methylpyrazol-3-yl)methyl]-2,4-dioxo-quinazoline-6-sulfonamide;
3-methyl-N-(1-methylcyclopropyl)-1-[(1-methylpyrazol-4-yl)methyl]-2,4-dioxo-quinazoline-6-sulfonamide;
1-methyl-N-(1-methylcyclopropyl)-2,4-dioxo-3-(thiadiazol-4-ylmethyl)quinazoline-6-sulfonamide;
1-methyl-N-(1-methylcyclopropyl)-3-[(3-methylimidazol-4-yl)methyl]-2,4-dioxo-quinazoline-6-sulfonamide;
1-methyl-N-(1-methylcyclopropyl)-3-[(1-methylpyrazol-4-yl)methyl]-2,4-dioxo-quinazoline-6-sulfonamide;
1-(cyclopropylmethyl)-N-(1-methylcyclopropyl)-3-[(2-methylthiazol-5-yl)methyl]-2,4-dioxo-quinazoline-6-sulfonamide;
2-(cyclopropylmethoxy)-N-(1-methylcyclopropyl)-3-[(2-methylthiazol-5-yl)methyl]-4-oxo-quinazoline-6-sulfonamide;
1-(cyclopropylmethyl)-3-[(3,5-dimethylisoxazol-4-yl)methyl]-N-(1-methylcyclopropyl)-2,4-dioxo-quinazoline-6-sulfonamide;
3-[(3,5-dimethylisoxazol-4-yl)methyl]-N-(1-methylcyclopropyl)-2,4-dioxo-1-prop-2-ynyl-quinazoline-6-sulfonamide;
1-methyl-N-(1-methylcyclopropyl)-3-[(5-methyl-1,3,4-oxadiazol-2-yl)methyl]-2,4-dioxo-quinazoline-6-sulfonamide;
N-(1-methylcyclopropyl)-3-[(2-methylthiazol-5-yl)methyl]-2,4-dioxo-1-prop-2-ynyl-quinazoline-6-sulfonamide;
1-[(2,4-dimethylthiazol-5-yl)methyl]-N-(1-methylcyclopropyl)-3-[(2-methylthiazol-5-yl)methyl]-2,4-dioxo-quinazoline-6-sulfonamide;
1-[(2,5-dimethylpyrazol-3-yl)methyl]-N-(1-methylcyclopropyl)-3-[(2-methylthiazol-5-yl)methyl]-2,4-dioxo-quinazoline-6-sulfonamide;
2-[(2,5-dimethylpyrazol-3-yl)methoxy]-N-(1-methylcyclopropyl)-3-[(2-methylthiazol-5-yl)methyl]-4-oxo-quinazoline-6-sulfonamide;
3-[(3,5-dimethylisoxazol-4-yl)methyl]-1-[(2,4-dimethylthiazol-5-yl)methyl]-N-(1-methylcyclopropyl)-2,4-dioxo-quinazoline-6-sulfonamide;
3-[(3,5-dimethylisoxazol-4-yl)methyl]-1-[(2,5-dimethylpyrazol-3-yl)methyl]-N-(1-methylcyclopropyl)-2,4-dioxo-quinazoline-6-sulfonamide;
3-[(3,5-dimethylisoxazol-4-yl)methyl]-2-[(2,5-dimethylpyrazol-3-yl)methoxy]-N-(1-methylcyclopropyl)-4-oxo-quinazoline-6-sulfonamide;
3-[(3,5-dimethylisoxazol-4-yl)methyl]-1-[(4-fluorophenyl)methyl]-N-(1-methylcyclopropyl)-2,4-dioxo-quinazoline-6-sulfonamide;
3-[(3,5-dimethylisoxazol-4-yl)methyl]-1-[(3-methoxyphenyl)methyl]-N-(1-methylcyclopropyl)-2,4-dioxo-quinazoline-6-sulfonamide;
1-[(2,4-dimethylthiazol-5-yl)methyl]-N-(1-methylcyclopropyl)-3-[(1-methylpyrazol-4-yl)methyl]-2,4-dioxo-quinazoline-6-sulfonamide;
1-[(4-fluorophenyl)methyl]-N-(1-methylcyclopropyl)-3-[(1-methylpyrazol-4-yl)methyl]-2,4-dioxo-quinazoline-6-sulfonamide;
1-[(3-methoxyphenyl)methyl]-N-(1-methylcyclopropyl)-3-[(1-methylpyrazol-4-yl)methyl]-2,4-dioxo-quinazoline-6-sulfonamide;
1-[(2,5-dimethylpyrazol-3-yl)methyl]-N-(1-methylcyclopropyl)-3-[(1-methylpyrazol-4-yl)methyl]-2,4-dioxo-quinazoline-6-sulfonamide;
1-(cyclopropylmethyl)-N-(1-methylcyclopropyl)-3-[(1-methylpyrazol-4-yl)methyl]-2,4-dioxo-quinazoline-6-sulfonamide;
1-(cyanomethyl)-3-methyl-N-(1-methylcyclopropyl)-2,4-dioxo-quinazoline-6-sulfonamide;
1-[(4-fluorophenyl)methyl]-N-(1-methylcyclopropyl)-3-[(2-methylthiazol-5-yl)methyl]-2,4-dioxo-quinazoline-6-sulfonamide;
1-[(3-methoxyphenyl)methyl]-N-(1-methylcyclopropyl)-3-[(2-methylthiazol-5-yl)methyl]-2,4-dioxo-quinazoline-6-sulfonamide;
N-(1-methylcyclopropyl)-3-[(1-methylpyrazol-4-yl)methyl]-2,4-dioxo-1-prop-2-ynyl-quinazoline-6-sulfonamide;
1-methyl-N-(1-methylcyclopropyl)-3-[[2-methyl-4-(trifluoromethyl)thiazol-5-yl]methyl]-2,4-dioxo-quinazoline-6-sulfonamide;

1-methyl-N-(1-methylcyclopropyl)-3-[(3-methylisoxazol-5-yl)methyl]-2,4-dioxo-quinazoline-6-sulfonamide;
3-[(1-ethylpyrazol-4-yl)methyl]-1-methyl-N-(1-methylcyclopropyl)-2,4-dioxo-quinazoline-6-sulfonamide;
1-methyl-N-(1-methylcyclopropyl)-3-(2-morpholino-2-oxo-ethyl)-2,4-dioxo-quinazoline-6-sulfonamide;
1-methyl-N-(1-methylcyclopropyl)-2,4-dioxo-3-(1H-pyrazol-4-ylmethyl)quinazoline-6-sulfonamide;
1-methyl-N-(1-methylcyclopropyl)-2,4-dioxo-3-[[(2S)-5-oxopyrrolidin-2-yl]methyl]quinazoline-6-sulfonamide;
1-methyl-N-(1-methylcyclopropyl)-2,4-dioxo-3-[[(2R)-5-oxopyrrolidin-2-yl]methyl]quinazoline-6-sulfonamide;
3-(cyanomethyl)-1-[(4-fluorophenyl)methyl]-N-(1-methylcyclopropyl)-2,4-dioxo-quinazoline-6-sulfonamide;
3-(cyanomethyl)-1-[(3-methoxyphenyl)methyl]-N-(1-methylcyclopropyl)-2,4-dioxo-quinazoline-6-sulfonamide;
1-methyl-N-(1-methylcyclopropyl)-3-[(4-methyloxazol-5-yl)methyl]-2,4-dioxo-quinazoline-6-sulfonamide;
3-[(2,4-dimethyloxazol-5-yl)methyl]-1-methyl-N-(1-methylcyclopropyl)-2,4-dioxo-quinazoline-6-sulfonamide;
1-methyl-N-(1-methylcyclopropyl)-3-[(3-methyl-1,2,4-oxadiazol-5-yl)methyl]-2,4-dioxo-quinazoline-6-sulfonamide;
1-methyl-N-(1-methylcyclopropyl)-3-[(4-methylthiadiazol-5-yl)methyl]-2,4-dioxo-quinazoline-6-sulfonamide;
3-(cyanomethyl)-1-[(2,5-dimethylpyrazol-3-yl)methyl]-N-(1-methylcyclopropyl)-2,4-dioxo-quinazoline-6-sulfonamide;
3-(cyanomethyl)-1-(cyclopropylmethyl)-N-(1-methylcyclopropyl)-2,4-dioxo-quinazoline-6-sulfonamide;
3-(cyanomethyl)-N-(1-methylcyclopropyl)-2,4-dioxo-1-prop-2-ynyl-quinazoline-6-sulfonamide
1-methyl-N-(1-methylcyclopropyl)-3-[(3-methyl-1H-pyrazol-5-yl)methyl]-2,4-dioxo-quinazoline-6-sulfonamide;
N-[[1-methyl-6-[(1-methylcyclopropyl)sulfamoyl]-2,4-dioxo-quinazolin-3-yl]methyl]acetamide
1-(cyclopropylmethyl)-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-2,4-dioxo-1-prop-2-ynyl-quinazoline-6-sulfonamide;
1-[(4-fluorophenyl)methyl]-N-(1-methylcyclopropyl)-3-[(3-methylisoxazol-5-yl)methyl]-2,4-dioxo-quinazoline-6-sulfonamide;
1-[(3-methoxyphenyl)methyl]-N-(1-methylcyclopropyl)-3-[(3-methylisoxazol-5-yl)methyl]-2,4-dioxo-quinazoline-6-sulfonamide;
N-cyclopropyl-1-[(2,4-dimethylthiazol-5-yl)methyl]-3-methyl-2,4-dioxo-quinazoline-6-sulfonamide;
N-tert-butyl-1-[(2,4-dimethylthiazol-5-yl)methyl]-3-methyl-2,4-dioxo-quinazoline-6-sulfonamide;
2-[4-[[1-methyl-6-[(1-methylcyclopropyl)sulfamoyl]-2,4-dioxo-quinazolin-3-yl]methyl]pyrazol-1-yl]acetamide;
N-(1-cyanocyclopropyl)-1-[(2,4-dimethylthiazol-5-yl)methyl]-3-methyl-2,4-dioxo-quinazoline-6-sulfonamide;
1-methyl-N-(1-methylcyclopropyl)-3-[(3-methylisoxazol-5-yl)methyl]-2,4-dioxo-pyrido[2,3-d]pyrimidine-6-sulfonamide;
1-[(2,4-dimethylthiazol-5-yl)methyl]-3-methyl-N-(2-methylcyclopropyl)-2,4-dioxo-quinazoline-6-sulfonamide;
1-[(2,5-dimethylpyrazol-3-yl)methyl]-N-(1-methylcyclopropyl)-3-[(3-methylisoxazol-5-yl)methyl]-2,4-dioxo-quinazoline-6-sulfonamide;
N-(1-methylcyclopropyl)-1,3-bis[(3-methylisoxazol-5-yl)methyl]-2,4-dioxo-quinazoline-6-sulfonamide;
4-chloro-N-(1-methylcyclopropyl)-2-[(3-methylisoxazol-5-yl)methyl]-1-oxo-isoquinoline-7-sulfonamide;
N-(1-methylcyclopropyl)-3-[(3-methylisoxazol-5-yl)methyl]-4-oxo-quinazoline-6-sulfonamide;
7-fluoro-3-methyl-N-(1-methylcyclopropyl)-2,4-dioxo-1H-quinazoline-6-sulfonamide;
3-[[1-[(4-methoxyphenyl)methyl]pyrazol-4-yl]methyl]-1-methyl-N-(1-methylcyclopropyl)-2,4-dioxo-quinazoline-6-sulfonamide;
1-[(2,5-dimethylpyrazol-3-yl)methyl]-7-fluoro-3-methyl-N-(1-methylcyclopropyl)-2,4-dioxo-quinazoline-6-sulfonamide;
tert-butyl N-[5-[[1-methyl-6-[(1-methylcyclopropyl)sulfamoyl]-2,4-dioxo-quinazolin-3-yl]methyl]thiazol-2-yl]carbamate;
3-[(1-benzylpyrazol-4-yl)methyl]-1-methyl-N-(1-methylcyclopropyl)-2,4-dioxo-quinazoline-6-sulfonamide;
1-methyl-N-(1-methylcyclopropyl)-2,4-dioxo-3-[(1-prop-2-ynylpyrazol-4-yl)methyl]quinazoline-6-sulfonamide;
3-[[1-(cyanomethyl)pyrazol-4-yl]methyl]-1-methyl-N-(1-methylcyclopropyl)-2,4-dioxo-quinazoline-6-sulfonamide;
3-[[1-(cyclopropylmethyl)pyrazol-4-yl]methyl]-1-methyl-N-(1-methylcyclopropyl)-2,4-dioxo-quinazoline-6-sulfonamide;
3-[[1-[2-(dimethylamino)ethyl]pyrazol-4-yl]methyl]-1-methyl-N-(1-methylcyclopropyl)-2,4-dioxo-quinazoline-6-sulfonamide;
N-(1-methylcyclopropyl)-3-[(2-methylthiazol-5-yl)methyl]-2,4-dioxo-1H-quinazoline-6-sulfonamide;
N-(1-methylcyclopropyl)-3-[(3-methylisoxazol-5-yl)methyl]-2,4-dioxo-1H-quinazoline-6-sulfonamide;
3-(cyanomethyl)-N-(1-methylcyclopropyl)-2,4-dioxo-1H-quinazoline-6-sulfonamide;
2-[6-[(1-methylcyclopropyl)sulfamoyl]-2,4-dioxo-1H-quinazolin-3-yl]acetamide;
7-fluoro-1,3-dimethyl-N-(1-methylcyclopropyl)-2,4-dioxo-quinazoline-6-sulfonamide;
8-fluoro-1,3-dimethyl-N-(1-methylcyclopropyl)-2,4-dioxo-quinazoline-6-sulfonamide;
3-(isoxazol-5-ylmethyl)-1-methyl-N-(1-methylcyclopropyl)-2,4-dioxo-quinazoline-6-sulfonamide;
1-chloro-3-methyl-N-(1-methylcyclopropyl)-4-oxo-phthalazine-6-sulfonamide;
N-(1-cyanocyclopropyl)-3-[(3-methylisoxazol-5-yl)methyl]-2,4-dioxo-1H-quinazoline-6-sulfonamide;
N-(1-cyanocyclopropyl)-1-methyl-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[[2-methyl-5-(trifluoromethyl)pyrazol-3-yl]methyl]-2,4-dioxo-quinazoline-6-sulfonamide;
N-(1-methylcyclopropyl)-3-[(2-methylthiazol-5-yl)methyl]-1-[[2-methyl-5-(trifluoromethyl)pyrazol-3-yl]methyl]-2,4-dioxo-quinazoline-6-sulfonamide;
3-[(2-aminothiazol-5-yl)methyl]-1-methyl-N-(1-methylcyclopropyl)-2,4-dioxo-quinazoline-6-sulfonamide;
3-[(3-aminoisoxazol-5-yl)methyl]-1-methyl-N-(1-methylcyclopropyl)-2,4-dioxo-quinazoline-6-sulfonamide;
3-methyl-1-(methylamino)-N-(1-methylcyclopropyl)-4-oxo-phthalazine-6-sulfonamide;
1-[2-(dimethylamino)ethyl]-N-(1-methylcyclopropyl)-3-[(1-methylpyrazol-4-yl)methyl]-2,4-dioxo-quinazoline-6-sulfonamide;
N-(1-methylcyclopropyl)-1-[(1-methyl-3-piperidyl)methyl]-3-[(1-methylpyrazol-4-yl)methyl]-2,4-dioxo-quinazoline-6-sulfonamide;

1-[3-(dimethylamino)propyl]-N-(1-methylcyclopropyl)-3-[(1-methylpyrazol-4-yl)methyl]-2,4-dioxo-quinazoline-6-sulfonamide;

N-(1-methylcyclopropyl)-1-[(1-methyl-2-piperidyl)methyl]-3-[(1-methylpyrazol-4-yl)methyl]-2,4-dioxo-quinazoline-6-sulfonamide;

1-(3-methoxypropyl)-N-(1-methylcyclopropyl)-3-[(1-methylpyrazol-4-yl)methyl]-2,4-dioxo-quinazoline-6-sulfonamide;

3-cyclopropyl-N-(1-methylcyclopropyl)-2,4-dioxo-1H-quinazoline-6-sulfonamide;

3-cyclopropyl-1-[(2,5-dimethylpyrazol-3-yl)methyl]-N-(1-methylcyclopropyl)-2,4-dioxo-quinazoline-6-sulfonamide;

N-(1-methylcyclopropyl)-2-[(3-methylisoxazol-5-yl)methyl]-1-oxo-isoquinoline-7-sulfonamide;

N-(1-methylcyclopropyl)-3-[(3-methylisoxazol-5-yl)methyl]-1-[(5-methyl-1,2,4-oxadiazol-3-yl)methyl]-2,4-dioxo-quinazoline-6-sulfonamide;

1-(methylamino)-N-(1-methylcyclopropyl)-3-[(3-methylisoxazol-5-yl)methyl]-4-oxo-phthalazine-6-sulfonamide;

1-methyl-N-(1-methylcyclopropyl)-2,4-dioxo-3-[[3-(trifluoromethyl)isoxazol-5-yl]methyl]quinazoline-6-sulfonamide;

1-[2-(dimethylamino)ethyl]-N-(1-methylcyclopropyl)-3-[(3-methylisoxazol-5-yl)methyl]-2,4-dioxo-quinazoline-6-sulfonamide;

1-[3-(dimethylamino)propyl]-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-(2-pyrrolidin-1-ylethyl)quinazoline-6-sulfonamide;

N-(1-methylcyclopropyl)-3-[(3-methylisoxazol-5-yl)methyl]-1-[(1-methylpyrrolidin-2-yl)methyl]-2,4-dioxo-quinazoline-6-sulfonamide;

1-[3-(methylamino)propyl]-N-(1-methylcyclopropyl)-3-[(3-methylisoxazol-5-yl)methyl]-2,4-dioxo-quinazoline-6-sulfonamide;

1-(3-methoxypropyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-1-[(3-methyl-1,2,4-oxadiazol-5-yl)methyl]-2,4-dioxo-quinazoline-6-sulfonamide;

1-[2-(dimethylamino)ethylamino]-N-(1-methylcyclopropyl)-3-[(3-methylisoxazol-5-yl)methyl]-4-oxo-phthalazine-6-sulfonamide;

tert-butyl N-[2-[6-[(1-methylcyclopropyl)sulfamoyl]-3-[(1-methylpyrazol-4-yl)methyl]-2,4-dioxo-quinazolin-1-yl]ethyl]carbamate;

4-(4-fluorophenyl)-2-methyl-N-(1-methylcyclopropyl)-1-oxo-isoquinoline-7-sulfonamide;

4-methyl-N-(1-methylcyclopropyl)-2-[(3-methylisoxazol-5-yl)methyl]-1-oxo-isoquinoline-7-sulfonamide;

N-(1-methylcyclopropyl)-3-[(1-methylpyrazol-4-yl)methyl]-2,4-dioxo-1-(tetrahydropyran-2-ylmethyl)quinazoline-6-sulfonamide;

N-(1-methylcyclopropyl)-3-[(1-methylpyrazol-4-yl)methyl]-2,4-dioxo-1-(tetrahydrofuran-2-ylmethyl)quinazoline-6-sulfonamide;

N-(1-methylcyclopropyl)-3-[(1-methylpyrazol-4-yl)methyl]-2,4-dioxo-1-(tetrahydrofuran-3-ylmethyl)quinazoline-6-sulfonamide;

N-cyclopropyl-1-methyl-3-[(3-methylisoxazol-5-yl)methyl]-2,4-dioxo-quinazoline-6-sulfonamide;

N-(1-ethylcyclopropyl)-1-methyl-3-[(3-methylisoxazol-5-yl)methyl]-2,4-dioxo-quinazoline-6-sulfonamide;

1-chloro-N-(1-methylcyclopropyl)-3-[(3-methylisoxazol-5-yl)methyl]-4-oxo-phthalazine-6-sulfonamide;

1-(2-aminoethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-2,4-dioxo-1-[3-(trifluoromethoxy)propyl]quinazoline-6-sulfonamide;

N,N-dimethyl-2-[6-[(1-methylcyclopropyl)sulfamoyl]-3-[(1-methylpyrazol-4-yl)methyl]-2,4-dioxo-quinazolin-1-yl]acetamide;

N-(1-methylcyclopropyl)-3-[(3-methylisoxazol-5-yl)methyl]-2,4-dioxo-1-(tetrahydropyran-2-ylmethyl)quinazoline-6-sulfonamide;

N-(1-methylcyclopropyl)-3-[(3-methylisoxazol-5-yl)methyl]-2,4-dioxo-1-(tetrahydrofuran-2-ylmethyl)quinazoline-6-sulfonamide;

N-(1-methylcyclopropyl)-3-[(3-methylisoxazol-5-yl)methyl]-2,4-dioxo-1-(tetrahydrofuran-3-ylmethyl)quinazoline-6-sulfonamide;

N-(1-methylcyclopropyl)-3-[(1-methylpyrazol-4-yl)methyl]-2,4-dioxo-1-(tetrahydropyran-4-ylmethyl)quinazoline-6-sulfonamide;

1-(2-methoxyethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-1-(2-morpholinoethyl)-2,4-dioxo-quinazoline-6-sulfonamide;

N-(1-methylcyclopropyl)-3-[(1-methylpyrazol-4-yl)methyl]-2,4-dioxo-1-(2-pyrrolidin-1-ylethyl)quinazoline-6-sulfonamide;

3-[6-[(1-methylcyclopropyl)sulfamoyl]-3-[(1-methylpyrazol-4-yl)methyl]-2,4-dioxo-quinazolin-1-yl]propanamide;

1-(2-methoxyethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-1-[(1-methyl-2-piperidyl)methyl]-2,4-dioxo-quinazoline-6-sulfonamide;

N-(1-methylcyclopropyl)-3-[(3-methylisoxazol-5-yl)methyl]-1-(2-morpholinoethyl)-2,4-dioxo-quinazoline-6-sulfonamide;

3-[6-[(1-methylcyclopropyl)sulfamoyl]-3-[(3-methylisoxazol-5-yl)methyl]-2,4-dioxo-quinazolin-1-yl]propanamide;

N-(1-methylcyclopropyl)-3-[(3-methylisoxazol-5-yl)methyl]-2,4-dioxo-1-[2-(1-piperidyl)ethyl]quinazoline-6-sulfonamide;

1-(cyclopentylmethyl)-N-(1-methylcyclopropyl)-3-[(1-methylpyrazol-4-yl)methyl]-2,4-dioxo-quinazoline-6-sulfonamide;

1-(cyclohexylmethyl)-N-(1-methylcyclopropyl)-3-[(1-methylpyrazol-4-yl)methyl]-2,4-dioxo-quinazoline-6-sulfonamide;

1-(cyclobutylmethyl)-N-(1-methylcyclopropyl)-3-[(1-methylpyrazol-4-yl)methyl]-2,4-dioxo-quinazoline-6-sulfonamide;

1-(dimethylamino)-N-(1-methylcyclopropyl)-3-[(3-methylisoxazol-5-yl)methyl]-4-oxo-phthalazine-6-sulfonamide;

1-[3-(dimethylamino)prop-1-ynyl]-N-(1-methylcyclopropyl)-3-[(3-methylisoxazol-5-yl)methyl]-4-oxo-phthalazine-6-sulfonamide;

1-methyl-N-(1-methylcyclopropyl)-3-[(3-methylisoxazol-5-yl)methyl]-4-oxo-phthalazine-6-sulfonamide;

3-[(3-aminoisoxazol-5-yl)methyl]-1-[(2,5-dimethylpyrazol-3-yl)methyl]-N-(1-methylcyclopropyl)-2,4-dioxo-quinazoline-6-sulfonamide;

4-[3-(dimethylamino)prop-1-ynyl]-N-(1-methylcyclopropyl)-2-[(3-methylisoxazol-5-yl)methyl]-1-oxo-isoquinoline-7-sulfonamide;

4-[3-(dimethylamino)propyl]-N-(1-methylcyclopropyl)-2-[(3-methylisoxazol-5-yl)methyl]-1-oxo-isoquinoline-7-sulfonamide;

1-(cyclobutylmethyl)-N-(1-methylcyclopropyl)-3-[(3-methylisoxazol-5-yl)methyl]-2,4-dioxo-quinazoline-6-sulfonamide;

1-(cyclopentylmethyl)-N-(1-methylcyclopropyl)-3-[(3-methylisoxazol-5-yl)methyl]-2,4-dioxo-quinazoline-6-sulfonamide;

1-(cyclohexylmethyl)-N-(1-methylcyclopropyl)-3-[(3-methylisoxazol-5-yl)methyl]-2,4-dioxo-quinazoline-6-sulfonamide;

1-ethyl-N-(1-methylcyclopropyl)-3-[(1-methylpyrazol-4-yl)methyl]-2,4-dioxo-quinazoline-6-sulfonamide;

1-isopropyl-N-(1-methylcyclopropyl)-3-[(1-methylpyrazol-4-yl)methyl]-2,4-dioxo-quinazoline-6-sulfonamide;

2-isopropoxy-N-(1-methylcyclopropyl)-3-[(1-methylpyrazol-4-yl)methyl]-4-oxo-quinazoline-6-sulfonamide;

N-(1-methylcyclopropyl)-1-[(3-methyloxetan-3-yl)methyl]-3-[(1-methylpyrazol-4-yl)methyl]-2,4-dioxo-quinazoline-6-sulfonamide;

1-isobutyl-N-(1-methylcyclopropyl)-3-[(1-methylpyrazol-4-yl)methyl]-2,4-dioxo-quinazoline-6-sulfonamide;

1-(2-cyclopropylethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-1-(oxetan-3-ylmethyl)-2,4-dioxo-quinazoline-6-sulfonamide;

1-benzyl-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl)methyl]-4-oxo-phthalazine-6-sulfonamide;

N-(1-methylcyclopropyl)-3-[(1-methylpyrazol-4-yl)methyl]-2,4-dioxo-1-[(5-oxopyrrolidin-2-yl)methyl]quinazoline-6-sulfonamide;

methyl 6-[(1-methylcyclopropyl)sulfamoyl]-3-[(3-methylisoxazol-5-yl)methyl]-4-oxo-phthalazine-1-carboxylate;

6-[(1-methylcyclopropyl)sulfamoyl]-3-[(3-methylisoxazol-5-yl)methyl]-4-oxo-phthalazine-1-carboxylic acid;

N-methyl-6-[(1-methylcyclopropyl)sulfamoyl]-3-[(3-methylisoxazol-5-yl)methyl]-4-oxo-phthalazine-1-carboxamide;

1-ethyl-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-1-(oxetan-3-ylmethyl)-2,4-dioxo-quinazoline-6-sulfonamide;

N-(1-methylcyclopropyl)-3-[(3-methylisoxazol-5-yl)methyl]-4-oxo-1-(tetrahydropyran-4-ylamino)phthalazine-6-sulfonamide;

4-bromo-N-(1-methylcyclopropyl)-2-[(3-methylisoxazol-5-yl)methyl]-1-oxo-isoquinoline-7-sulfonamide;

N-(1-methylcyclopropyl)-3-[(3-methylisoxazol-5-yl)methyl]-4-oxo-1-(tetrahydropyran-4-ylmethyl)phthalazine-6-sulfonamide;

1-cyclopentyl-N-(1-methylcyclopropyl)-3-[(3-methylisoxazol-5-yl)methyl]-4-oxo-phthalazine-6-sulfonamide;

1-isopropyl-N-(1-methylcyclopropyl)-3-[(3-methylisoxazol-5-yl)methyl]-4-oxo-phthalazine-6-sulfonamide;

4-(cyclopropanecarbonyl)-N-(1-methylcyclopropyl)-2-[(3-methylisoxazol-5-yl)methyl]-1-oxo-isoquinoline-7-sulfonamide;

1-methoxy-N-(1-methylcyclopropyl)-3-[(3-methylisoxazol-5-yl)methyl]-4-oxo-phthalazine-6-sulfonamide;

1-cyclopropyl-N-(1-methylcyclopropyl)-3-[(3-methylisoxazol-5-yl)methyl]-4-oxo-phthalazine-6-sulfonamide;

1-(cyclohexylmethyl)-N-(1-methylcyclopropyl)-3-[(3-methylisoxazol-5-yl)methyl]-4-oxo-phthalazine-6-sulfonamide;

1-[(3-methoxyphenyl)methyl]-N-(1-methylcyclopropyl)-3-[(3-methylisoxazol-5-yl)methyl]-4-oxo-phthalazine-6-sulfonamide;

1-ethoxy-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl)methyl]-1-(oxetan-3-yloxy)-4-oxo-phthalazine-6-sulfonamide;

1-(cyclopropylmethyl)-N-(1-methylcyclopropyl)-3-[(3-methylisoxazol-5-yl)methyl]-4-oxo-phthalazine-6-sulfonamide;

1-(cyclobutoxy)-N-(1-methylcyclopropyl)-3-[(3-methylisoxazol-5-yl)methyl]-4-oxo-phthalazine-6-sulfonamide;

1-(cyclobutylmethyl)-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl)methyl]-2,4-dioxo-1-(tetrahydropyran-4-ylmethyl)quinazoline-6-sulfonamide;

4-[(4-fluorophenyl)methyl]-N-(1-methylcyclopropyl)-2-[(3-methylisoxazol-5-yl)methyl]-1-oxo-isoquinoline-7-sulfonamide;

1-acetonyl-N-(1-methylcyclopropyl)-3-[(3-methylisoxazol-5-yl)methyl]-2,4-dioxo-quinazoline-6-sulfonamide;

1-(2,2-difluoroethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-(2,2,2-trifluoroethyl)quinazoline-6-sulfonamide;

N,N-dimethyl-6-[(1-methylcyclopropyl)sulfamoyl]-3-[(3-methylisoxazol-5-yl)methyl]-4-oxo-phthalazine-1-carboxamide;

6-[(1-methylcyclopropyl)sulfamoyl]-3-[(3-methylisoxazol-5-yl)methyl]-N-(oxetan-3-yl)-4-oxo-phthalazine-1-carboxamide;

N-(1-methylcyclopropyl)-1,3-bis[(1-methylpyrazol-4-yl)methyl]-2,4-dioxo-quinazoline-6-sulfonamide;

1-[(2,2-difluoro-1-methyl-cyclopropyl)methyl]-N-(1-methylcyclopropyl)-3-[(1-methylpyrazol-4-yl)methyl]-2,4-dioxo-quinazoline-6-sulfonamide;

N-(1-methylcyclopropyl)-3-[(3-methylisoxazol-5-yl)methyl]-1-[(1-methylpyrazol-4-yl)methyl]-2,4-dioxo-quinazoline-6-sulfonamide;

6-[(1-methylcyclopropyl)sulfamoyl]-3-[(3-methylisoxazol-5-yl)methyl]-4-oxo-N-(tetrahydropyran-4-ylmethyl)phthalazine-1-carboxamide;

ethyl 2-[6-[(1-methylcyclopropyl)sulfamoyl]-3-[(3-methylisoxazol-5-yl)methyl]-2,4-dioxo-quinazolin-1-yl]acetate;

6-[(1-methylcyclopropyl)sulfamoyl]-3-[(3-methylisoxazol-5-yl)methyl]-N-[(1-methyl-4-piperidyl)methyl]-4-oxo-phthalazine-1-carboxamide;

N-(1-methylcyclopropyl)-3-[(1-methylpyrazol-4-yl)methyl]-2,4-dioxo-1-[2-(2-oxopyrrolidin-1-yl)ethyl]quinazoline-6-sulfonamide;

ethyl 2-fluoro-2-[6-[(1-methylcyclopropyl)sulfamoyl]-3-[(3-methylisoxazol-5-yl)methyl]-2,4-dioxo-quinazolin-1-yl]acetate;
N-(1-cyanocyclopropyl)-3-[(1-methylpyrazol-4-yl)methyl]-2,4-dioxo-1H-quinazoline-6-sulfonamide;
1-(2-hydroxyethyl)-N-(1-methylcyclopropyl)-3-[(3-methylisoxazol-5-yl)methyl]-2,4-dioxo-quinazoline-6-sulfonamide;
1-(2-hydroxypropyl)-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-(oxetan-3-yl)-2,4-dioxo-quinazoline-6-sulfonamide;
1-[[3-(hydroxymethyl)oxetan-3-yl]methyl]-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[2-(4-methylpiperazin-1-yl)ethyl]-2,4-dioxo-quinazoline-6-sulfonamide;
N-(1-methylcyclopropyl)-3-[(3-methylisoxazol-5-yl)methyl]-1-[3-(4-methylpiperazin-1-yl)propyl]-2,4-dioxo-quinazoline-6-sulfonamide;
N-(1-methylcyclopropyl)-3-[(1-methylpyrazol-4-yl)methyl]-1-(oxetan-2-ylmethyl)-2,4-dioxo-quinazoline-6-sulfonamide;
N-(1-cyanocyclopropyl)-1-methyl-3-[(1-methylpyrazol-4-yl)methyl]-2,4-dioxo-quinazoline-6-sulfonamide;
N-(1-cyanocyclopropyl)-1-[(2,5-dimethylpyrazol-3-yl)methyl]-3-[(1-methylpyrazol-4-yl)methyl]-2,4-dioxo-quinazoline-6-sulfonamide;
N-(1-cyanocyclopropyl)-1-(cyclopropylmethyl)-3-[(1-methylpyrazol-4-yl)methyl]-2,4-dioxo-quinazoline-6-sulfonamide;
N-(1-cyanocyclopropyl)-1-ethyl-3-[(1-methylpyrazol-4-yl)methyl]-2,4-dioxo-quinazoline-6-sulfonamide;
1-[(3-fluorooxetan-3-yl)methyl]-N-(1-methylcyclopropyl)-3-[(1-methylpyrazol-4-yl)methyl]-2,4-dioxo-quinazoline-6-sulfonamide;
N-(1-methylcyclopropyl)-3-[(3-methylisoxazol-5-yl)methyl]-1-(oxetan-2-ylmethyl)-2,4-dioxo-quinazoline-6-sulfonamide;
1-[(3-fluorooxetan-3-yl)methyl]-N-(1-methylcyclopropyl)-3-[(3-methylisoxazol-5-yl)methyl]-2,4-dioxo-quinazoline-6-sulfonamide;
1-[(4,4-dimethyloxetan-2-yl)methyl]-N-(1-methylcyclopropyl)-3-[(1-methylpyrazol-4-yl)methyl]-2,4-dioxo-quinazoline-6-sulfonamide;
1-[(4,4-dimethyloxetan-2-yl)methyl]-N-(1-methylcyclopropyl)-3-[(3-methylisoxazol-5-yl)methyl]-2,4-dioxo-quinazoline-6-sulfonamide;
1-ethyl-N-(1-methylcyclopropyl)-3-[(3-methylisoxazol-5-yl)methyl]-4-oxo-phthalazine-6-sulfonamide;
N-(1-cyanocyclopropyl)-3-[(1-methylpyrazol-4-yl)methyl]-1-(oxetan-3-ylmethyl)-2,4-dioxo-quinazoline-6-sulfonamide;
N-(1-cyanocyclopropyl)-3-[(1-methylpyrazol-4-yl)methyl]-2,4-dioxo-1-prop-2-ynyl-quinazoline-6-sulfonamide;
N-(1-cyanocyclopropyl)-1-(cyanomethyl)-3-[(1-methylpyrazol-4-yl)methyl]-2,4-dioxo-quinazoline-6-sulfonamide;
N-(1-cyanocyclopropyl)-1-(2-methoxyethyl)-3-[(1-methylpyrazol-4-yl)methyl]-2,4-dioxo-quinazoline-6-sulfonamide;
N-(1-cyanocyclopropyl)-1-[(4-fluorophenyl)methyl]-3-[(1-methylpyrazol-4-yl)methyl]-2,4-dioxo-quinazoline-6-sulfonamide;
N-(1-cyanocyclopropyl)-1-[(3-methylisoxazol-5-yl)methyl]-3-[(1-methylpyrazol-4-yl)methyl]-2,4-dioxo-quinazoline-6-sulfonamide;
1-(3-hydroxy-3-methyl-butyl)-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[(1-methylpyrrolidin-3-yl)methyl]-2,4-dioxo-quinazoline-6-sulfonamide;
N-(1-methylcyclopropyl)-3-[(3-methylisoxazol-5-yl)methyl]-1-(2-methylsulfanylethyl)-2,4-dioxo-quinazoline-6-sulfonamide;
1-[(3,3-difluorocyclobutyl)methyl]-N-(1-methylcyclopropyl)-3-[(3-methylisoxazol-5-yl)methyl]-2,4-dioxo-quinazoline-6-sulfonamide;
1-[(2,2-difluorocyclopropyl)methyl]-N-(1-methylcyclopropyl)-3-[(3-methylisoxazol-5-yl)methyl]-2,4-dioxo-quinazoline-6-sulfonamide;
tert-butyl 3-[[6-[(1-methylcyclopropyl)sulfamoyl]-3-[(1-methylpyrazol-4-yl)methyl]-2,4-dioxo-quinazolin-1-yl]methyl]azetidine-1-carboxylate;
N-(1-methylcyclopropyl)-3-[(1-methylpyrazol-4-yl)methyl]-1-(2-methylsulfanylethyl)-2,4-dioxo-quinazoline-6-sulfonamide;
1-acetonyl-N-(1-methylcyclopropyl)-3-[(1-methylpyrazol-4-yl)methyl]-2,4-dioxo-quinazoline-6-sulfonamide;
1-(3-hydroxy-3-methyl-butyl)-N-(1-methylcyclopropyl)-3-[(1-methylpyrazol-4-yl)methyl]-2,4-dioxo-quinazoline-6-sulfonamide;
N-(1-methylcyclopropyl)-3-[(1-methylpyrazol-4-yl)methyl]-1-(2-methylsulfinylethyl)-2,4-dioxo-quinazoline-6-sulfonamide;
N-(1-methylcyclopropyl)-3-[(1-methylpyrazol-4-yl)methyl]-1-(2-methylsulfonylethyl)-2,4-dioxo-quinazoline-6-sulfonamide;
N-(1-methylcyclopropyl)-3-[(3-methylisoxazol-5-yl)methyl]-1-[(1-methyl-4-piperidyl)methyl]-2,4-dioxo-quinazoline-6-sulfonamide;
N-(1-methylcyclopropyl)-1-[(1-methyl-4-piperidyl)methyl]-3-[(1-methylpyrazol-4-yl)methyl]-2,4-dioxo-quinazoline-6-sulfonamide;
N-(1-methylcyclopropyl)-3-[(3-methylisoxazol-5-yl)methyl]-2,4-dioxo-1-(2-oxo-2-pyrrolidin-1-yl-ethyl)quinazoline-6-sulfonamide;
N-(1-cyanocyclopropyl)-1-[(2,4-dimethylthiazol-5-yl)methyl]-3-[(1-methylpyrazol-4-yl)methyl]-2,4-dioxo-quinazoline-6-sulfonamide;
N-(1-cyanocyclopropyl)-3-[(1-methylpyrazol-4-yl)methyl]-1-[(2-methylthiazol-5-yl)methyl]-2,4-dioxo-quinazoline-6-sulfonamide;
N-(1-cyanocyclopropyl)-1-[(3-methyloxetan-3-yl)methyl]-3-[(1-methylpyrazol-4-yl)methyl]-2,4-dioxo-quinazoline-6-sulfonamide;
N-(1-cyanocyclopropyl)-3-[(1-methylpyrazol-4-yl)methyl]-2,4-dioxo-1-(tetrahydrofuran-3-ylmethyl)quinazoline-6-sulfonamide;
N-(1-cyanocyclopropyl)-1,3-bis[(1-methylpyrazol-4-yl)methyl]-2,4-dioxo-quinazoline-6-sulfonamide;
N-(1-methylcyclopropyl)-1-[(3-methylisoxazol-5-yl)methyl]-3-[(1-methylpyrazol-4-yl)methyl]-2,4-dioxo-quinazoline-6-sulfonamide;
N-(1-methylcyclopropyl)-3-[(1-methylpyrazol-4-yl)methyl]-2,4-dioxo-1-(tetrahydrothiopyran-4-ylmethyl)quinazoline-6-sulfonamide;
N-(1-methylcyclopropyl)-3-[(3-methylisoxazol-5-yl)methyl]-2,4-dioxo-1-(tetrahydrothiopyran-4-ylmethyl)quinazoline-6-sulfonamide;

1-[(1,1-dioxothian-4-yl)methyl]-N-(1-methylcyclopropyl)-3-[(3-methylisoxazol-5-yl)methyl]-2,4-dioxo-quinazoline-6-sulfonamide;

1-[(1,1-dioxothian-4-yl)methyl]-N-(1-methylcyclopropyl)-3-[(1-methylpyrazol-4-yl)methyl]-2,4-dioxo-quinazoline-6-sulfonamide;

7-fluoro-N-(1-methylcyclopropyl)-3-[(1-methylpyrazol-4-yl)methyl]-2,4-dioxo-1H-quinazoline-6-sulfonamide;

7-fluoro-1-methyl-N-(1-methylcyclopropyl)-3-[(1-methylpyrazol-4-yl)methyl]-2,4-dioxo-quinazoline-6-sulfonamide;

N-(1-cyanocyclopropyl)-3-[(2-methylthiazol-5-yl)methyl]-2,4-dioxo-1H-quinazoline-6-sulfonamide;

N-(1-cyanocyclopropyl)-7-fluoro-3-[(1-methylpyrazol-4-yl)methyl]-2,4-dioxo-1H-quinazoline-6-sulfonamide;

1-(cyclopropylmethyl)-7-fluoro-N-(1-methylcyclopropyl)-3-[(1-methylpyrazol-4-yl)methyl]-2,4-dioxo-quinazoline-6-sulfonamide;

1-ethyl-7-fluoro-N-(1-methylcyclopropyl)-3-[(1-methylpyrazol-4-yl)methyl]-2,4-dioxo-quinazoline-6-sulfonamide;

7-fluoro-1-[(4-fluorophenyl)methyl]-N-(1-methylcyclopropyl)-3-[(1-methylpyrazol-4-yl)methyl]-2,4-dioxo-quinazoline-6-sulfonamide;

7-fluoro-N-(1-methylcyclopropyl)-1-[(3-methylisoxazol-5-yl)methyl]-3-[(1-methylpyrazol-4-yl)methyl]-2,4-dioxo-quinazoline-6-sulfonamide;

1-[(2,5-dimethylpyrazol-3-yl)methyl]-7-fluoro-N-(1-methylcyclopropyl)-3-[(1-methylpyrazol-4-yl)methyl]-2,4-dioxo-quinazoline-6-sulfonamide;

7-fluoro-N-(1-methylcyclopropyl)-1,3-bis[(1-methylpyrazol-4-yl)methyl]-2,4-dioxo-quinazoline-6-sulfonamide;

7-fluoro-N-(1-methylcyclopropyl)-3-[(1-methylpyrazol-4-yl)methyl]-1-(oxetan-3-ylmethyl)-2,4-dioxo-quinazoline-6-sulfonamide;

7-fluoro-N-(1-methylcyclopropyl)-3-[(1-methylpyrazol-4-yl)methyl]-2,4-dioxo-1-(tetrahydrofuran-3-ylmethyl)quinazoline-6-sulfonamide;

1-[(2,4-dimethylthiazol-5-yl)methyl]-7-fluoro-N-(1-methylcyclopropyl)-3-[(1-methylpyrazol-4-yl)methyl]-2,4-dioxo-quinazoline-6-sulfonamide;

7-fluoro-N-(1-methylcyclopropyl)-2-[(3-methyloxetan-3-yl)methoxy]-3-[(1-methylpyrazol-4-yl)methyl]-4-oxo-quinazoline-6-sulfonamide;

7-fluoro-N-(1-methylcyclopropyl)-1-[(3-methyloxetan-3-yl)methyl]-3-[(1-methylpyrazol-4-yl)methyl]-2,4-dioxo-quinazoline-6-sulfonamide;

N-(1-cyanocyclopropyl)-1-(cyclopropylmethyl)-3-[(2-methylthiazol-5-yl)methyl]-2,4-dioxo-quinazoline-6-sulfonamide;

N-(1-cyanocyclopropyl)-1-[(3-methylisoxazol-5-yl)methyl]-3-[(2-methylthiazol-5-yl)methyl]-2,4-dioxo-quinazoline-6-sulfonamide;

N-(1-cyanocyclopropyl)-1-[(2,4-dimethylthiazol-5-yl)methyl]-3-[(2-methylthiazol-5-yl)methyl]-2,4-dioxo-quinazoline-6-sulfonamide;

N-(1-cyanocyclopropyl)-1-[(4-fluorophenyl)methyl]-3-[(2-methylthiazol-5-yl)methyl]-2,4-dioxo-quinazoline-6-sulfonamide;

N-(1-cyanocyclopropyl)-3-[(2-methylthiazol-5-yl)methyl]-2,4-dioxo-1-prop-2-ynyl-quinazoline-6-sulfonamide;

N-(1-cyanocyclopropyl)-7-fluoro-1-[(3-methylisoxazol-5-yl)methyl]-3-[(1-methylpyrazol-4-yl)methyl]-2,4-dioxo-quinazoline-6-sulfonamide;

1-[(4,4-difluorocyclohexyl)methyl]-N-(1-methylcyclopropyl)-3-[(3-methylisoxazol-5-yl)methyl]-2,4-dioxo-quinazoline-6-sulfonamide;

N,N-dimethyl-3-[6-[(1-methylcyclopropyl)sulfamoyl]-3-[(3-methylisoxazol-5-yl)methyl]-2,4-dioxo-quinazolin-1-yl]propanamide;

1-(3-hydroxypropyl)-N-(1-methylcyclopropyl)-3-[(3-methylisoxazol-5-yl)methyl]-2,4-dioxo-quinazoline-6-sulfonamide;

N-[1-(fluoromethyl)cyclopropyl]-1-methyl-3-[(1-methylpyrazol-4-yl)methyl]-2,4-dioxo-quinazoline-6-sulfonamide;

tert-butyl 3-[[6-[(1-methylcyclopropyl)sulfamoyl]-3-[(3-methylisoxazol-5-yl)methyl]-2,4-dioxo-quinazolin-1-yl]methyl]azetidine-1-carboxylate;

1-(2-fluoroethyl)-N-(1-methylcyclopropyl)-3-[(1-methylpyrazol-4-yl)methyl]-2,4-dioxo-quinazoline-6-sulfonamide;

1-(2-fluoroethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-[(3-oxocyclobutyl)methyl]quinazoline-6-sulfonamide;

1-(2-methoxy-2-methyl-propyl)-N-(1-methylcyclopropyl)-3-[(3-methylisoxazol-5-yl)methyl]-2,4-dioxo-quinazoline-6-sulfonamide;

1-[2-(azetidin-1-yl)-2-oxo-ethyl]-N-(1-methylcyclopropyl)-3-[(3-methylisoxazol-5-yl)methyl]-2,4-dioxo-quinazoline-6-sulfonamide;

1-(azetidin-3-ylmethyl)-N-(1-methylcyclopropyl)-3-[(3-methylisoxazol-5-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1H-quinazoline-6-sulfonamide;

1-(cyclopropylmethyl)-N-[1-(fluoromethyl)cyclopropyl]-3-[(1-methylpyrazol-4-yl)methyl]-2,4-dioxo-quinazoline-6-sulfonamide;

1-methyl-N-(1-methylcyclopropyl)-3-[(5-methyl-3-pyridyl)methyl]-2,4-dioxo-quinazoline-6-sulfonamide;

N-[1-(fluoromethyl)cyclopropyl]-1-[(4-fluorophenyl)methyl]-3-[(1-methylpyrazol-4-yl)methyl]-2,4-dioxo-quinazoline-6-sulfonamide;

1-[(1-cyanocyclopropyl)methyl]-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-[(4-oxocyclohexyl)methyl]quinazoline-6-sulfonamide;

8-bromo-N-(1-methylcyclopropyl)-3-[(1-methylpyrazol-4-yl)methyl]-2,4-dioxo-1H-quinazoline-6-sulfonamide;

1-methyl-N-(1-methylcyclopropyl)-3-[(6-methyl-3-pyridyl)methyl]-2,4-dioxo-quinazoline-6-sulfonamide;

6-[(1-methylcyclopropyl)sulfamoyl]-3-[(1-methylpyrazol-4-yl)methyl]-2,4-dioxo-1H-quinazoline-8-carboxamide;

1-[(1-formylazetidin-3-yl)methyl]-N-(1-methylcyclopropyl)-3-[(3-methylisoxazol-5-yl)methyl]-2,4-dioxo-quinazoline-6-sulfonamide;

1-(cyclopropylmethyl)-3-methyl-N-(1-methylcyclopropyl)-2-oxo-quinoline-6-sulfonamide;

N-(1-ethynylcyclopropyl)-1-methyl-3-[(1-methylpyrazol-4-yl)methyl]-2,4-dioxo-quinazoline-6-sulfonamide;

N-[[6-[(1-methylcyclopropyl)sulfamoyl]-3-[(1-methylpyrazol-4-yl)methyl]-2,4-dioxo-1H-quinazolin-8-yl]methyl]acetamide;

8-[3-(dimethylamino)prop-1-ynyl]-N-(1-methylcyclopropyl)-3-[(1-methylpyrazol-4-yl)methyl]-2,4-dioxo-1H-quinazoline-6-sulfonamide;

N-(1-methylcyclopropyl)-3-[(1-methylpyrazol-4-yl)methyl]-2,4-dioxo-1H-quinazoline-6-sulfonamide;

N-(1-ethynylcyclopropyl)-3-[(1-methylpyrazol-4-yl)methyl]-2,4-dioxo-1H-quinazoline-6-sulfonamide;

1-(cyclopropylmethyl)-N-(1-ethynylcyclopropyl)-3-[(1-methylpyrazol-4-yl)methyl]-2,4-dioxo-quinazoline-6-sulfonamide;

1-methyl-N-(1-methylcyclopropyl)-3-[(2-methylpyrimidin-5-yl)methyl]-2,4-dioxo-quinazoline-6-sulfonamide;

1-methyl-N-(1-methylcyclopropyl)-2,4-dioxo-3-(pyrazolo[1,5-a]pyridin-3-ylmethyl)quinazoline-6-sulfonamide;

1-[(2,2-difluorocyclopropyl)methyl]-N-(1-methylcyclopropyl)-3-[(1-methylpyrazol-4-yl)methyl]-2,4-dioxo-quinazoline-6-sulfonamide;

1-[(3,3-difluorocyclobutyl)methyl]-N-(1-methylcyclopropyl)-3-[(1-methylpyrazol-4-yl)methyl]-2,4-dioxo-quinazoline-6-sulfonamide;

1-[(2,5-dimethylpyrazol-3-yl)methyl]-N-[1-(fluoromethyl)cyclopropyl]-3-[(1-methylpyrazol-4-yl)methyl]-2,4-dioxo-quinazoline-6-sulfonamide;

1-ethyl-N-[1-(fluoromethyl)cyclopropyl]-3-[(1-methylpyrazol-4-yl)methyl]-2,4-dioxo-quinazoline-6-sulfonamide;

1-(cyanomethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-prop-2-ynyl-quinazoline-6-sulfonamide;

N-[1-(fluoromethyl)cyclopropyl]-1-[(3-methylisoxazol-5-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(tetrahydropyran-4-ylmethyl)quinazoline-6-sulfonamide;

1-[(2,2-difluorocyclopropyl)methyl]-N-[1-(fluoromethyl)cyclopropyl]-3-[(1-methylpyrazol-4-yl)methyl]-2,4-dioxo-quinazoline-6-sulfonamide;

1-[(3,3-difluorocyclobutyl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-(oxetan-3-ylmethyl)-2,4-dioxo-quinazoline-6-sulfonamide;

1-methyl-N-(1-methylcyclopropyl)-2,4-dioxo-3-(pyridazin-4-ylmethyl)quinazoline-6-sulfonamide;

N-(1-methylcyclopropyl)-1,3-dioxo-benzo[de]isoquinoline-5-sulfonamide;

methyl 6-[(1-methylcyclopropyl)sulfamoyl]-3-[(1-methylpyrazol-4-yl)methyl]-2,4-dioxo-1H-quinazoline-8-carboxylate;

N,N-dimethyl-6-[(1-methylcyclopropyl)sulfamoyl]-3-[(1-methylpyrazol-4-yl)methyl]-2,4-dioxo-1H-quinazoline-8-carboxamide;

N-methyl-6-[(1-methylcyclopropyl)sulfamoyl]-3-[(1-methylpyrazol-4-yl)methyl]-2,4-dioxo-1H-quinazoline-8-carboxamide;

N-methoxy-N-methyl-6-[(1-methylcyclopropyl)sulfamoyl]-3-[(1-methylpyrazol-4-yl)methyl]-2,4-dioxo-1H-quinazoline-8-carboxamide;

1-(2-cyano-2-methyl-propyl)-N-(1-methylcyclopropyl)-3-[(3-methylisoxazol-5-yl)methyl]-2,4-dioxo-quinazoline-6-sulfonamide;

1-(2-fluoro-2-methyl-propyl)-N-(1-methylcyclopropyl)-3-[(3-methylisoxazol-5-yl)methyl]-2,4-dioxo-quinazoline-6-sulfonamide;

N-(1-methylcyclopropyl)-2-[(1-methylpyrazol-4-yl)methyl]-1,3-dioxo-benzo[de]isoquinoline-5-sulfonamide;

N-(1-cyanocyclopropyl)-1-ethyl-3-[(2-methylthiazol-5-yl)methyl]-2,4-dioxo-quinazoline-6-sulfonamide;

N-[1-(difluoromethyl)cyclopropyl]-3-[(1-methylpyrazol-4-yl)methyl]-2,4-dioxo-1H-quinazoline-6-sulfonamide;

N-(1-cyanocyclopropyl)-1-[(1-methylpyrazol-4-yl)methyl]-3-[(2-methylthiazol-5-yl)methyl]-2,4-dioxo-quinazoline-6-sulfonamide;

1-(cyclopropylmethyl)-N-[1-(difluoromethyl)cyclopropyl]-3-[(1-methylpyrazol-4-yl)methyl]-2,4-dioxo-quinazoline-6-sulfonamide;

N-[1-(difluoromethyl)cyclopropyl]-1-[(2,5-dimethylpyrazol-3-yl)methyl]-3-[(1-methylpyrazol-4-yl)methyl]-2,4-dioxo-quinazoline-6-sulfonamide;

N-[1-(difluoromethyl)cyclopropyl]-1-[(4-fluorophenyl)methyl]-3-[(1-methylpyrazol-4-yl)methyl]-2,4-dioxo-quinazoline-6-sulfonamide;

1-(cyclobutylmethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(2-methoxyethyl)-3-[(1-methylpyrazol-4-yl)methyl]-2,4-dioxo-quinazoline-6-sulfonamide;

1-[(2,4-dimethylthiazol-5-yl)methyl]-N-[1-(fluoromethyl)cyclopropyl]-3-[(1-methylpyrazol-4-yl)methyl]-2,4-dioxo-quinazoline-6-sulfonamide;

N-(1-methylcyclopropyl)-2-[(3-methylisoxazol-5-yl)methyl]-1,3-dioxo-benzo[de]isoquinoline-5-sulfonamide;

1-(2,2-dimethylpropyl)-N-(1-methylcyclopropyl)-3-[(3-methylisoxazol-5-yl)methyl]-2,4-dioxo-quinazoline-6-sulfonamide;

1-[(2S)-2-methylbutyl]-N-(1-methylcyclopropyl)-3-[(3-methylisoxazol-5-yl)methyl]-2,4-dioxo-quinazoline-6-sulfonamide;

1-[(1-methylcyclobutyl)methyl]-N-(1-methylcyclopropyl)-3-[(3-methylisoxazol-5-yl)methyl]-2,4-dioxo-quinazoline-6-sulfonamide;

ethyl 2-[1-methyl-6-[(1-methylcyclopropyl)sulfamoyl]-2,4-dioxo-quinazolin-3-yl]acetate 1-methyl-N-(1-methylcyclopropyl)-2,4-dioxo-3-(2-oxobutyl)quinazoline-6-sulfonamide;

1-(2-ethylbutyl)-N-(1-methylcyclopropyl)-3-[(3-methylisoxazol-5-yl)methyl]-2,4-dioxo-quinazoline-6-sulfonamide;

1-[(1-methoxycyclopentyl)methyl]-N-(1-methylcyclopropyl)-3-[(3-methylisoxazol-5-yl)methyl]-2,4-dioxo-quinazoline-6-sulfonamide;

1-isopentyl-N-(1-methylcyclopropyl)-3-[(3-methylisoxazol-5-yl)methyl]-2,4-dioxo-quinazoline-6-sulfonamide;

1-[(1-isopropylpyrazol-4-yl)methyl]-N-(1-methylcyclopropyl)-3-[(3-methylisoxazol-5-yl)methyl]-2,4-dioxo-quinazoline-6-sulfonamide;

1-isohexyl-N-(1-methylcyclopropyl)-3-[(3-methylisoxazol-5-yl)methyl]-2,4-dioxo-quinazoline-6-sulfonamide;

1-methyl-N-(1-methylcyclopropyl)-2,4-dioxo-3-(2-oxo-2-pyrrolidin-1-yl-ethyl)quinazoline-6-sulfonamide;

N,N-dimethyl-2-[1-methyl-6-[(1-methylcyclopropyl)sulfamoyl]-2,4-dioxo-quinazolin-3-yl]acetamide;

1-[(3,3-dimethylcyclobutyl)methyl]-N-(1-methylcyclopropyl)-3-[(3-methylisoxazol-5-yl)methyl]-2,4-dioxo-quinazoline-6-sulfonamide;

1-[(3,3-dimethylcyclobutyl)methyl]-N-(1-methylcyclopropyl)-3-[(2-methylthiazol-5-yl)methyl]-2,4-dioxo-quinazoline-6-sulfonamide;

N-(1-formylcyclopropyl)-3-[(1-methylpyrazol-4-yl)methyl]-2,4-dioxo-1H-quinazoline-6-sulfonamide;

N-tert-butyl-1-[(2,5-dimethylpyrazol-3-yl)methyl]-3-[(1-methylpyrazol-4-yl)methyl]-2,4-dioxo-quinazoline-6-sulfonamide;

1-methyl-N-(1-methylcyclopropyl)-3-(oxetan-3-ylmethyl)-2,4-dioxo-quinazoline-6-sulfonamide;

8-bromo-1-methyl-N-(1-methylcyclopropyl)-3-[(3-methylisoxazol-5-yl)methyl]-2,4-dioxo-quinazoline-6-sulfonamide;

1-methyl-N-(1-methylcyclopropyl)-3-[(3-methylisoxazol-5-yl)methyl]-8-(1-methylpyrazol-4-yl)-2,4-dioxo-quinazoline-6-sulfonamide;

1-chloro-N-(1-methylcyclopropyl)isoquinoline-7-sulfonamide;

1-[(2,5-dimethylpyrazol-3-yl)methyl]-3-[(1-methylpyrazol-4-yl)methyl]-2,4-dioxo-N-[1-(trifluoromethyl)cyclopropyl]quinazoline-6-sulfonamide;

N-(1-methylcyclopropyl)-3-[(1-methylpyrazol-4-yl)methyl]-2-oxo-1H-quinoline-6-sulfonamide 3-bromo-N-(1-methylcyclopropyl)-2-oxo-1H-quinoline-6-sulfonamide;

3-[(1-methylpyrazol-4-yl)methyl]-2,4-dioxo-N-[1-(trideuteriomethyl)cyclopropyl]-1H-quinazoline-6-sulfonamide;

1-methyl-3-[(1-methylpyrazol-4-yl)methyl]-2,4-dioxo-N-[1-(trideuteriomethyl)cyclopropyl]quinazoline-6-sulfonamide;

1-[(2,5-dimethylpyrazol-3-yl)methyl]-3-[(1-methylpyrazol-4-yl)methyl]-2,4-dioxo-N-[1-(trideuteriomethyl)cyclopropyl]quinazoline-6-sulfonamide;

1-methyl-N-(1-methylcyclopropyl)-3-[(1-methylpyrazol-4-yl)methyl]-2-oxo-quinoline-6-sulfonamide;

1-[(2,5-dimethylpyrazol-3-yl)methyl]-N-(1-methylcyclopropyl)-3-[(1-methylpyrazol-4-yl)methyl]-2-oxo-quinoline-6-sulfonamide;

1-methyl-N-(1-methylcyclopropyl)-3-[(3-methylisoxazol-5-yl)methyl]-8-(5-methyl-2-thienyl)-2,4-dioxo-quinazoline-6-sulfonamide;

N-[1-(fluoromethyl)cyclopropyl]-3-(isothiazol-4-ylmethyl)-1-methyl-2,4-dioxo-quinazoline-6-sulfonamide;

N-(1-methylcyclopropyl)-2,4-dioxo-3-[2-(2-pyridyl)ethyl]-1H-quinazoline-6-sulfonamide;

3-(2-cyanoethyl)-N-(1-methylcyclopropyl)-2,4-dioxo-1H-quinazoline-6-sulfonamide;

3-(2-cyanoethyl)-1-methyl-N-(1-methylcyclopropyl)-2,4-dioxo-quinazoline-6-sulfonamide;

1-methyl-N-(1-methylcyclopropyl)-2,4-dioxo-3-[2-(2-pyridyl)ethyl]quinazoline-6-sulfonamide;

1-methyl-N-(1-methylcyclopropyl)-3-[(4-methyl-1,2,4-triazol-3-yl)methyl]-2,4-dioxo-quinazoline-6-sulfonamide;

1-methyl-N-(1-methylcyclopropyl)-3-[(5-methyl-1,3,4-thiadiazol-2-yl)methyl]-2,4-dioxo-quinazoline-6-sulfonamide;

1-methyl-N-(1-methylcyclopropyl)-2,4-dioxo-3-[[5-(trifluoromethyl)-1,3,4-oxadiazol-2-yl]methyl]quinazoline-6-sulfonamide;

1-(cyanomethyl)-N-(1-methylcyclopropyl)-3-[(2-methylthiazol-5-yl)methyl]-2,4-dioxo-quinazoline-6-sulfonamide;

1-(cyanomethyl)-N-(1-methylcyclopropyl)-3-[(3-methylisoxazol-5-yl)methyl]-2,4-dioxo-quinazoline-6-sulfonamide;

3-(3-furylmethyl)-1-methyl-N-(1-methylcyclopropyl)-2,4-dioxo-quinazoline-6-sulfonamide;

3-(1H-imidazol-4-ylmethyl)-1-methyl-N-(1-methylcyclopropyl)-2,4-dioxo-quinazoline-6-sulfonamide;

1-methyl-N-(1-methylcyclopropyl)-3-[(5-methylisoxazol-4-yl)methyl]-2,4-dioxo-quinazoline-6-sulfonamide;

3-[(1-isopropylpyrazol-4-yl)methyl]-1-methyl-N-(1-methylcyclopropyl)-2,4-dioxo-quinazoline-6-sulfonamide;

1-methyl-N-(1-methylcyclopropyl)-3-[(1-methyltetrazol-5-yl)methyl]-2,4-dioxo-quinazoline-6-sulfonamide;

3-[(4-isopropylthiadiazol-5-yl)methyl]-1-methyl-N-(1-methylcyclopropyl)-2,4-dioxo-quinazoline-6-sulfonamide;

3-(isothiazol-5-ylmethyl)-1-methyl-N-(1-methylcyclopropyl)-2,4-dioxo-quinazoline-6-sulfonamide;

1-methyl-N-(1-methylcyclopropyl)-3-[(4-methyl-1,2,5-oxadiazol-3-yl)methyl]-2,4-dioxo-quinazoline-6-sulfonamide;

N-[1-(fluoromethyl)cyclopropyl]-1-methyl-2,4-dioxo-quinazoline-6-sulfonamide;

N-[1-(fluoromethyl)cyclopropyl]-3-(isoxazol-5-ylmethyl)-1-methyl-2,4-dioxo-quinazoline-6-sulfonamide;

N-[1-(fluoromethyl)cyclopropyl]-1-methyl-3-[(3-methylisoxazol-5-yl)methyl]-2,4-dioxo-quinazoline-6-sulfonamide;

N-[1-(fluoromethyl)cyclopropyl]-1-methyl-3-[(5-methyl-1,3,4-thiadiazol-2-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1H-quinazoline-6-sulfonamide;

1-(cyclopropylmethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1-[(4-fluorophenyl)methyl]-3-[(3-methylisoxazol-5-yl)methyl]-2,4-dioxo-quinazoline-6-sulfonamide;

1-[(2,5-dimethylpyrazol-3-yl)methyl]-N-[1-(fluoromethyl)cyclopropyl]-3-[(3-methylisoxazol-5-yl)methyl]-2,4-dioxo-quinazoline-6-sulfonamide;

1-ethyl-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1,3-bis[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-1-(oxetan-3-ylmethyl)-2,4-dioxo-quinazoline-6-sulfonamide;

1-(cyanomethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1-(tetrahydrofuran-3-ylmethyl)quinazoline-6-sulfonamide;

N-[1-(fluoromethyl)cyclopropyl]-1-(3-methoxypropyl)-3-[(3-methylisoxazol-5-yl)methyl]-2,4-dioxo-quinazoline-6-sulfonamide;

1-(2-fluoroethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1-(2-methoxyethyl)-3-[(3-methylisoxazol-5-yl)methyl]-2,4-dioxo-quinazoline-6-sulfonamide;

1-methyl-N-(1-methylcyclopropyl)-2,4-dioxo-3-[2-oxo-2-(4-pyridyl)ethyl]quinazoline-6-sulfonamide;

1-methyl-N-(1-methylcyclopropyl)-2,4-dioxo-3-[2-oxo-2-(2-thienyl)ethyl]quinazoline-6-sulfonamide;

1-methyl-N-(1-methylcyclopropyl)-2,4-dioxo-3-phenacyl-quinazoline-6-sulfonamide;

3-[2-(4-cyanophenyl)-2-oxo-ethyl]-1-methyl-N-(1-methylcyclopropyl)-2,4-dioxo-quinazoline-6-sulfonamide;

N-[1-(fluoromethyl)cyclopropyl]-3-[(3-methylisoxazol-5-yl)methyl]-2,4-dioxo-1-prop-2-ynyl-quinazoline-6-sulfonamide;

N-[1-(fluoromethyl)cyclopropyl]-1-methyl-3-[(2-methylthiazol-5-yl)methyl]-2,4-dioxo-quinazoline-6-sulfonamide;

N-[1-(fluoromethyl)cyclopropyl]-1-methyl-2,4-dioxo-3-(thiazol-5-ylmethyl)quinazoline-6-sulfonamide;

N-[1-(fluoromethyl)cyclopropyl]-3-[(3-methylisoxazol-5-yl)methyl]-2,4-dioxo-1-propyl-quinazoline-6-sulfonamide;

1-butyl-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(1-methylpyrazol-4-yl)methyl]-1-[(5-methyl-2-pyridyl)methyl]-2,4-dioxo-quinazoline-6-sulfonamide;

1-[(6-cyano-2-pyridyl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(5-methyl-3-pyridyl)methyl]-2,4-dioxo-quinazoline-6-sulfonamide;

N-[1-(fluoromethyl)cyclopropyl]-1-[(6-fluoro-2-pyridyl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(2-methyl-4-pyridyl)methyl]-2,4-dioxo-quinazoline-6-sulfonamide;

N-[1-(fluoromethyl)cyclopropyl]-1-[(3-fluoro-2-pyridyl)methyl]-3-[(1-methylpyrazol-4-yl)methyl]-2,4-dioxo-quinazoline-6-sulfonamide;

1-[(4-cyanophenyl)methyl]-N-[1-(fluoromethyl)cyclopropyl]-3-[(1-methylpyrazol-4-yl)methyl]-2,4-dioxo-quinazoline-6-sulfonamide;

1-(2-fluoroethyl)-N-[1-(fluoromethyl)cyclopropyl]-3-[(1-methylpyrazol-4-yl)methyl]-2,4-dioxo-quinazoline-6-sulfonamide;

1-[(3,5-dimethylisoxazol-4-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-[(5-methyl-1,2,4-oxadiazol-3-yl)methyl]-3-[(1-methylpyrazol-4-yl)methyl]-2,4-dioxo-quinazoline-6-sulfonamide;

1-[(2,5-dimethyl-1,2,4-triazol-3-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-[(2-methyloxazol-5-yl)methyl]-3-[(1-methylpyrazol-4-yl)methyl]-2,4-dioxo-quinazoline-6-sulfonamide;

N-[1-(fluoromethyl)cyclopropyl]-1-isobutyl-3-[(1-methylpyrazol-4-yl)methyl]-2,4-dioxo-quinazoline-6-sulfonamide;

N-[1-(fluoromethyl)cyclopropyl]-3-[(3-methylisoxazol-5-yl)methyl]-1-[(2-methylthiazol-4-yl)methyl]-2,4-dioxo-quinazoline-6-sulfonamide;

N-[1-(fluoromethyl)cyclopropyl]-3-[(3-methylisoxazol-5-yl)methyl]-1-[(4-methyl-1,2,4-triazol-3-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,3,4-thiadiazol-2-yl)methyl]-2,4-dioxo-quinazoline-6-sulfonamide;

N-[1-(fluoromethyl)cyclopropyl]-3-[(3-methylisoxazol-5-yl)methyl]-1-[(1-methyl-1,2,4-triazol-3-yl)methyl]-2,4-dioxo-quinazoline-6-sulfonamide;

1-[(2,5-dimethyl-1,2,4-triazol-3-yl)methyl]-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-1-[(1-methylpyrazol-4-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,3,4-oxadiazol-2-yl)methyl]-2,4-dioxo-quinazoline-6-sulfonamide;

N-[1-(fluoromethyl)cyclopropyl]-3-[(3-methylisoxazol-5-yl)methyl]-1-[(2-methyl-1,2,4-triazol-3-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,2,4-oxadiazol-3-yl)methyl]-2,4-dioxo-quinazoline-6-sulfonamide;

N-[1-(fluoromethyl)cyclopropyl]-3-[(3-methylisoxazol-5-yl)methyl]-1-(oxazol-4-ylmethyl)-2,4-dioxo-quinazoline-6-sulfonamide;

N-[1-(fluoromethyl)cyclopropyl]-3-[(1-methylpyrazol-4-yl)methyl]-2,4-dioxo-1-(2-pyrazol-1-ylethyl)quinazoline-6-sulfonamide;

N-[1-(fluoromethyl)cyclopropyl]-3-[(1-methylpyrazol-4-yl)methyl]-1-[(3-methyl-1H-pyrazol-5-yl)methyl]-2,4-dioxo-quinazoline-6-sulfonamide;

N-[1-(fluoromethyl)cyclopropyl]-3-[(1-methylpyrazol-4-yl)methyl]-1-[(2-methyl-1,2,4-triazol-3-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(thiazol-5-ylmethyl)quinazoline-6-sulfonamide;

N-[1-(fluoromethyl)cyclopropyl]-3-[(1-methylpyrazol-4-yl)methyl]-1-(oxazol-5-ylmethyl)-2,4-dioxo-quinazoline-6-sulfonamide;

N-[1-(fluoromethyl)cyclopropyl]-1-[(1-methylimidazol-2-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-[2-(2-pyridyl)ethyl]quinazoline-6-sulfonamide;

N-[1-(fluoromethyl)cyclopropyl]-1-[(5-methyl-1,3,4-oxadiazol-2-yl)methyl]-3-[(1-methylpyrazol-4-yl)methyl]-2,4-dioxo-quinazoline-6-sulfonamide;

N-[1-(fluoromethyl)cyclopropyl]-1-[(2-methyl-1H-imidazol-4-yl)methyl]-3-[(1-methylpyrazol-4-yl)methyl]-2,4-dioxo-quinazoline-6-sulfonamide;

N-[1-(fluoromethyl)cyclopropyl]-1-[(5-methylpyrazin-2-yl)methyl]-3-[(1-methylpyrazol-4-yl)methyl]-2,4-dioxo-quinazoline-6-sulfonamide;

N-[1-(fluoromethyl)cyclopropyl]-1-[[1-(hydroxymethyl)cyclopropyl]methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(4-methyl-2-pyridyl)methyl]-2,4-dioxo-quinazoline-6-sulfonamide;

N-[1-(fluoromethyl)cyclopropyl]-3-[(1-methylpyrazol-4-yl)methyl]-1-[(4-methylthiazol-5-yl)methyl]-2,4-dioxo-quinazoline-6-sulfonamide;

N-[1-(fluoromethyl)cyclopropyl]-3-[(1-methylpyrazol-4-yl)methyl]-1-[(6-methyl-3-pyridyl)methyl]-2,4-dioxo-quinazoline-6-sulfonamide;

1-(2-cyanoethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(1H-imidazol-4-ylmethyl)-3-[(1-methylpyrazol-4-yl)methyl]-2,4-dioxo-quinazoline-6-sulfonamide;

1-[(3-ethylimidazol-4-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(isothiazol-4-ylmethyl)-3-[(1-methylpyrazol-4-yl)methyl]-2,4-dioxo-quinazoline-6-sulfonamide;

N-[1-(fluoromethyl)cyclopropyl]-1-(isothiazol-5-ylmethyl)-3-[(1-methylpyrazol-4-yl)methyl]-2,4-dioxo-quinazoline-6-sulfonamide;

N-[1-(fluoromethyl)cyclopropyl]-1-[(5-methylisoxazol-4-yl)methyl]-3-[(1-methylpyrazol-4-yl)methyl]-2,4-dioxo-quinazoline-6-sulfonamide;
N-[1-(fluoromethyl)cyclopropyl]-1-[(2-methyloxazol-4-yl)methyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(thiazol-4-ylmethyl)quinazoline-6-sulfonamide;
N-[1-(fluoromethyl)cyclopropyl]-3-[(1-methylpyrazol-4-yl)methyl]-1-[(2-methylthiazol-4-yl)methyl]-2,4-dioxo-quinazoline-6-sulfonamide;
N-[1-(fluoromethyl)cyclopropyl]-3-[(1-methylpyrazol-4-yl)methyl]-1-[(5-methyl-1,3,4-thiadiazol-2-yl)methyl]-2,4-dioxo-quinazoline-6-sulfonamide;
N-[1-(fluoromethyl)cyclopropyl]-3-[(1-methylpyrazol-4-yl)methyl]-1-[(4-methyl-1,2,4-triazol-3-yl)methyl]-2,4-dioxo-quinazoline-6-sulfonamide;
N-[1-(fluoromethyl)cyclopropyl]-1-(isoxazol-5-ylmethyl)-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(1H-pyrazol-3-ylmethyl)quinazoline-6-sulfonamide;
N-[1-(fluoromethyl)cyclopropyl]-3-[(1-methylpyrazol-4-yl)methyl]-2,4-dioxo-1-(1H-1,2,4-triazol-3-ylmethyl)quinazoline-6-sulfonamide;
N-[1-(fluoromethyl)cyclopropyl]-1-[(3-methylimidazol-4-yl)methyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(1,3,4-thiadiazol-2-ylmethyl)quinazoline-6-sulfonamide;
N-[1-(fluoromethyl)cyclopropyl]-3-[(1-methylpyrazol-4-yl)methyl]-2,4-dioxo-1-(1H-pyrazol-4-ylmethyl)quinazoline-6-sulfonamide;
N-[1-(fluoromethyl)cyclopropyl]-1-[(3-methylisothiazol-5-yl)methyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-1-[(3-methyl-1H-1,2,4-triazol-5-yl)methyl]-2,4-dioxo-quinazoline-6-sulfonamide;
N-[1-(fluoromethyl)cyclopropyl]-3-[(1-methylpyrazol-4-yl)methyl]-1-[(1-methyltriazol-4-yl)methyl]-2,4-dioxo-quinazoline-6-sulfonamide;
N-[1-(fluoromethyl)cyclopropyl]-3-[(1-methylpyrazol-4-yl)methyl]-1-[(2-methylthiazol-5-yl)methyl]-2,4-dioxo-quinazoline-6-sulfonamide;
N-[1-(fluoromethyl)cyclopropyl]-1,3-bis[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-1-[(2-methyltriazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-propyl-quinazoline-6-sulfonamide;
N-[1-(fluoromethyl)cyclopropyl]-3-[(1-methylpyrazol-4-yl)methyl]-2,4-dioxo-1-(tetrahydrofuran-3-ylmethyl)quinazoline-6-sulfonamide;
1-(2,2-difluoroethyl)-N-(1-methylcyclopropyl)-3-[(1-methylpyrazol-4-yl)methyl]-2,4-dioxo-quinazoline-6-sulfonamide;
1-(2,2-difluoroethyl)-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-3-[(5-methyl-1,3,4-thiadiazol-2-yl)methyl]-2,4-dioxo-1H-quinazoline-6-sulfonamide;
1-ethyl-N-[1-(fluoromethyl)cyclopropyl]-3-[(5-methyl-1,3,4-thiadiazol-2-yl)methyl]-2,4-dioxo-quinazoline-6-sulfonamide;
1-[(2,5-dimethylpyrazol-3-yl)methyl]-N-[1-(fluoromethyl)cyclopropyl]-3-[(5-methyl-1,3,4-thiadiazol-2-yl)methyl]-2,4-dioxo-quinazoline-6-sulfonamide;
1-(difluoromethyl)-N-[1-(fluoromethyl)cyclopropyl]-3-[(3-methylisoxazol-5-yl)methyl]-2,4-dioxo-quinazoline-6-sulfonamide;
1-(difluoromethyl)-N-(1-methylcyclopropyl)-3-[(3-methylisoxazol-5-yl)methyl]-2,4-dioxo-quinazoline-6-sulfonamide;
1-(difluoromethyl)-N-(1-methylcyclopropyl)-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-1-(oxazol-4-ylmethyl)-2,4-dioxo-quinazoline-6-sulfonamide;
1-(cyclopentylmethyl)-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-1-(3-methylbut-2-enyl)-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(4-pyridylmethyl)quinazoline-6-sulfonamide;
1-[2-(diethylamino)ethyl]-N-[1-(fluoromethyl)cyclopropyl]-3-[(1-methylpyrazol-4-yl)methyl]-2,4-dioxo-quinazoline-6-sulfonamide;
1-(2-ethoxyethyl)-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-1-isopentyl-3-[(1-methylpyrazol-4-yl)methyl]-2,4-dioxo-quinazoline-6-sulfonamide;
1-ethyl-N-(1-methylcyclopropyl)-3-[(5-methyl-1,3,4-thiadiazol-2-yl)methyl]-2,4-dioxo-quinazoline-6-sulfonamide;
1-[(2,5-dimethylpyrazol-3-yl)methyl]-N-(1-methylcyclopropyl)-3-[(5-methyl-1,3,4-thiadiazol-2-yl)methyl]-2,4-dioxo-quinazoline-6-sulfonamide;
1-[(2,4-dimethylthiazol-5-yl)methyl]-N-[1-(fluoromethyl)cyclopropyl]-3-[(3-methylisoxazol-5-yl)methyl]-2,4-dioxo-quinazoline-6-sulfonamide;
1-butyl-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-1-[2-(2-methoxyethoxy)ethyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(tetrahydrofuran-2-ylmethyl)quinazoline-6-sulfonamide;
N-[1-(fluoromethyl)cyclopropyl]-3-[(1-methylpyrazol-4-yl)methyl]-2,4-dioxo-1-(2-oxobutyl)quinazoline-6-sulfonamide;
N-(1-methylcyclopropyl)-3-[(1-methylpyrazol-4-yl)methyl]-2,4-dioxo-1-(2,2,2-trifluoroethyl)quinazoline-6-sulfonamide;
N-[1-(fluoromethyl)cyclopropyl]-3-[(3-methylisoxazol-5-yl)methyl]-2,4-dioxo-1-(2,2,2-trifluoroethyl)quinazoline-6-sulfonamide;
N-[1-(fluoromethyl)cyclopropyl]-3-[(1-methylpyrazol-4-yl)methyl]-2,4-dioxo-1-(2,2,2-trifluoroethyl)quinazoline-6-sulfonamide;
N-[1-(fluoromethyl)cyclopropyl]-1-methyl-2,4-dioxo-3-(1,3,4-thiadiazol-2-ylmethyl)quinazoline-6-sulfonamide;

N-[1-(fluoromethyl)cyclopropyl]-1-methyl-3-[(3-methyl-isothiazol-5-yl)methyl]-2,4-dioxo-quinazoline-6-sulfonamide;

N-[1-(fluoromethyl)cyclopropyl]-1-methyl-3-[(2-methyltriazol-4-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1-(1,3,4-thiadiazol-2-ylmethyl)quinazoline-6-sulfonamide;

3-[(5-ethyl-1,3,4-thiadiazol-2-yl)methyl]-N-[1-(fluoromethyl)cyclopropyl]-1-methyl-2,4-dioxo-quinazoline-6-sulfonamide;

1-(2-fluoroethyl)-N-[1-(fluoromethyl)cyclopropyl]-3-[(5-methyl-1,3,4-thiadiazol-2-yl)methyl]-2,4-dioxo-quinazoline-6-sulfonamide;

N-[1-(fluoromethyl)cyclopropyl]-1-[(1-methylpyrazol-4-yl)methyl]-3-[(5-methyl-1,3,4-thiadiazol-2-yl)methyl]-2,4-dioxo-quinazoline-6-sulfonamide;

N-[1-(fluoromethyl)cyclopropyl]-1-[(5-methyl-1,2,4-oxadiazol-3-yl)methyl]-3-[(5-methyl-1,3,4-thiadiazol-2-yl)methyl]-2,4-dioxo-quinazoline-6-sulfonamide;

or a pharmaceutically acceptable salt or solvate thereof.

The various functional groups and substituents making up the compounds of the formula I are typically chosen such that the molecular weight of the compound of the formula I does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula I may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

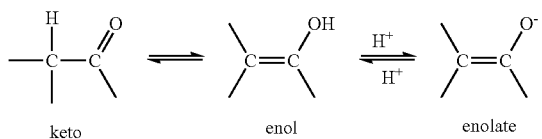

keto      enol      enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of $X_1$, $X_2$, $X_3$, $X_4$, $X_5$, $X_6$, $X_7$, W, $R_{1a}$, $R_{1b}$, $R_{1c}$, $R_{1d}$, and $R_{1e}$ and any substituent groups associated therewith. Suitable processes for their preparation are described further in the accompanying Examples.

Once a compound of formula I has been synthesised by any one of the processes defined herein, the processes may then further comprise the additional steps of:
(i) removing any protecting groups present;
(ii) converting the compound formula I into another compound of formula I;
(iii) forming a pharmaceutically acceptable salt, hydrate or solvate thereof; and/or
(iv) forming a prodrug thereof.

An example of (ii) above is when a compound of formula I is synthesised and then one or more of the groups of $X_1$, $X_2$, $X_3$, $X_4$, $X_5$, $X_6$, $X_7$, W, $R_{1a}$, $R_{1b}$, $R_{1c}$, $R_{1d}$, and $R_{1e}$, may be further reacted to change the nature of the group and provide an alternative compound of formula I. For example, the compound can be reacted to covert $R_1$ into a substituent group other than hydrogen.

The resultant compounds of formula I can be isolated and purified using techniques well known in the art.

In one aspect of the present invention, the compounds of formula I, or a pharmaceutically acceptable salt or solvate thereof, may be synthesised by a method comprising either:
a) reacting a compound of formula A:

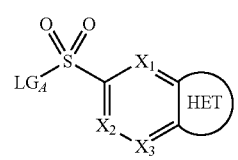

Formula A wherein $X_1$, $X_2$, $X_3$ and HET are as defined hereinabove, and $LG_A$ is a suitable leaving group;
with a compound of formula B:

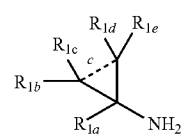

Formula B wherein $R_{1a}$, $R_{1b}$, $R_{1c}$, $R_{1d}$, $R_{1e}$ and c are as defined hereinabove;
b) reacting a compound of formula C:

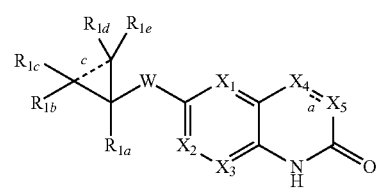

Formula C wherein $X_1$, $X_2$, $X_3$, $X_4$, $X_5$, W, $R_{1a}$, $R_{1b}$, $R_{1c}$, $R_{1d}$, $R_{1e}$, a and c are as defined hereinabove;
with a compound of formula D:

$$R_{8N}\text{-L} \qquad \text{Formula D}$$

wherein $R_{8N}$ is as defined hereinabove, and L is a suitable leaving group (e.g. halo, OMs, hydroxyl);
c) reacting a compound of formula E:

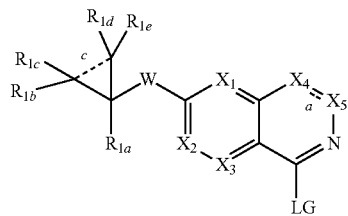

Formula E wherein $X_1$, $X_2$, $X_3$, $X_4$, $X_5$, W, $R_{1a}$, $R_{1b}$, $R_{1c}$, $R_{1d}$, $R_{1e}$, a and c are as defined hereinabove, and LG is a suitable leaving group (e.g. halo, OMs, OTs);
with a compound of formula F:

$$R_{8C}\text{-Q} \qquad \text{Formula F}$$

wherein $R_{8C}$ is as defined hereinabove, and Q is a suitable coupling group (e.g. amino, hydroxyl);
d) reacting a compound of formula G:

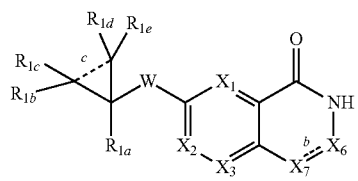

Formula G wherein $X_1$, $X_2$, $X_3$, $X_4$, $X_6$, $X_7$, W, $R_{1a}$, $R_{1b}$, $R_{1c}$, $R_{1d}$, $R_{1e}$, b and c are as herein;
with a compound of formula H:

$$R_{6N}\text{—Z} \qquad \text{Formula H}$$

wherein $R_{6N}$ is as defined hereinabove, and Z is a suitable leaving group (e.g. halo, OMs, hydroxyl);
e) reacting a compound of formula J:

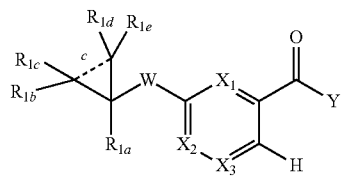

Formula J wherein $X_1$, $X_2$, $X_3$, W, $R_{1a}$, $R_{1b}$, $R_{1c}$, $R_{1d}$, $R_{1e}$ and c are defined herein, H is halo and Y is $NHR_{6N}$ or OH, and wherein $R_{6N}$ is as defined hereinabove;
with a compound of formula K:

$$R_{7c}\text{—P} \qquad \text{Formula K}$$

wherein $R_{7c}$ is as defined in claim 1, and P is either $H_2NC(NH)$— or $H_2NC(O)$—; and optionally thereafter, and if necessary:
i) removing any protecting groups present;
ii) converting the compound formula I into another compound of formula I; and/or
iii) forming a pharmaceutically acceptable salt or solvate thereof.

Biological Activity

The PARG enzyme and cell assays described in accompanying Example section may be used to measure the pharmacological effects of the compounds of the present invention.

Although the pharmacological properties of the compounds of formula I vary with structural change, as expected, the compounds of the invention were found to be active in these PARG assays.

In general, the compounds of the invention demonstrate an $IC_{50}$ of 1 μM or less in the PARG enzyme assay described herein, with preferred compounds of the invention demonstrating an $IC_{50}$ of 500 nM or less and the most preferred compounds of the invention demonstrating an $IC_{50}$ of 200 nM or less.

In the PARG cell assay described in the Example section, the compounds of formula I suitably possess an activity of less than 5 μM, with the preferred compounds demonstrating an activity of 1 μM or less.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of PARG.

The present invention therefore provides a method of inhibiting PARG enzyme activity in vitro or in vivo, said method comprising contacting a cell with an effective amount of a compound, or a pharmaceutically acceptable salt, hydrate or solvate thereof, as defined herein.

The present invention also provides a method of selectively inhibiting PARG enzyme activity over PARP1 or ARH3 enzyme activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which PARG activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of PARG enzyme activity.

The present invention provides a compound, or a pharmaceutically acceptable salt, hydrate or solvate thereof, as defined herein for use in the treatment of a disease or disorder in which PARG activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of PARG enzyme activity.

The present invention provides a use of a compound, or a pharmaceutically acceptable salt, hydrate or solvate thereof, as defined herein in the manufacture of a medicament for the selective inhibition of PARG enzyme activity over PARP1 or ARH3 enzyme activity.

The present invention provides a use of a compound, or a pharmaceutically acceptable salt, hydrate or solvate thereof, as defined herein in the manufacture of a medicament for the treatment of a disease or disorder in which PARG activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their inhibition of PARG enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Materials, Equipment, and General Experimental Details
General Experimental

Flash chromatography was performed using pre-packed silica gel cartridges (KP-Sil SNAP, Biotage, Hengoed UK or RediSep Rf, Isco). Thin layer chromatography was conducted with 5×10 cm plates coated with Merck Type 60 $F_{254}$ silica gel to a thickness of 0.25 mm. All reagents obtained from commercial sources were used without further purification. Anhydrous solvents were obtained from the Sigma-Aldrich Chemical Company Ltd. or Fisher Chemicals Ltd., and used without further drying. HPLC grade solvents were obtained from Fisher Chemicals Ltd. or Romil Ltd.

All compounds were >90% purity as determined by examination of both the LC-MS and $^1$H NMR spectra unless otherwise indicated. Where Cl or Br were present, expected isotopic distribution patterns were observed.

$^1$H NMR

Proton ($^1$H) NMR spectra were recorded on either a 300 MHz or 400 MHz Bruker spectrometer or ECX 300 MHz or ECX 400 MHz JEOL Spectrometer. Solutions were typically prepared in either deuterochloroform (CDCl$_3$) or deuterated dimethylsulfoxide (DMSO-d$_6$) with chemical shifts referenced to tetramethylsilane (TMS) or deuterated solvent as an internal standard. $^1$H NMR data are reported indicating the chemical shift (δ), the integration (e.g. 1H), the multiplicity (s, singlet; d, doublet; t, triplet; q, quartet; m, multiplet; br, broad; dd, doublet of doublets etc.) and the coupling constant (J) in Hz (app. implies apparent coupling on broadened signals). Deuterated solvents were obtained from the Sigma-Aldrich Chemical Company, Goss or Fluorochem.

Analytical LC-MS.

LC-MS analyses were performed using one of the following methods (denoted in Table 2):

LC-MS Method A

A Waters Acquity UPLC system fitted with BEH C18 1.7 µM columns (2.1×50 mm) and with UV diode array detection (210-400 nm). Positive and negative mass ion detection was performed using a Waters SQD detector. Analyses were performed with either buffered acidic or basic solvents and gradients as detailed below:

Low pH:

Solvent A—Water+10 mM ammonium formate+0.1% formic acid

Solvent B—Acetonitrile+5% water+0.1% formic acid

High pH:

Solvent A—Water+10 mM ammonium hydrogen carbonate+0.1% ammonia solution

Solvent B—Acetonitrile+0.1% ammonia solution

Gradient:

| Time | Flow rate (mL/min) | % Solvent A | % Solvent B |
|------|--------------------|-------------|-------------|
| 0    | 0.6                | 95          | 5           |
| 1.2  | 0.6                | 5           | 95          |
| 1.7  | 0.6                | 5           | 95          |
| 1.8  | 0.6                | 95          | 5           |

LC-MS Method B

A Waters Acquity ZQD (ESI) UPLC system fitted with XBridge C18 2.1×50 mm, 2.5 µm or equivalent and with UV diode array detection (215-350 nm)

Low pH:

Solvent A—MeCN

Solvent B—0.1% Formic Acid (pH 3)

High pH:

Solvent A—MeCN

Solvent B—10 mM NH$_4$HCO$_3$ (pH 10)

Gradient:

| Time | Flow rate (mL/min) | % Solvent A | % Solvent B |
|------|--------------------|-------------|-------------|
| 0    | 0.8                | 98          | 2           |
| 0.8  | 0.8                | 2           | 98          |
| 1.2  | 0.8                | 2           | 98          |
| 1.25 | 0.8                | 98          | 2           |

LC-MS Method C

Waters X Bridge C18: 50 mm×4.6 mm, 3.5 µm Column, UV diode array detection (214-350 nm)

High pH:

Solvent A—Water (0.01 mol/L NH$_4$HCO$_3$)

Solvent B—MeCN

Gradient:

| Time | Flow rate (mL/min) | % Solvent A | % Solvent B |
|---|---|---|---|
| 0 | 2 | 95 | 5 |
| 1.6 | 2 | 5 | 95 |
| 3 | 2 | 95 | 95 |

Preparative HPLC

Some compounds were purified by preparative HPLC using the following systems. A Waters FractionLynx MS autopurification system, with a Waters XBridge 5 μm C18, 100 mm×19 mm i.d. column, running at a flow rate of 20 mL/min with UV diode array detection (210-400 nm) and mass-directed collection using both positive and negative mass ion detection.

Purifications were performed using buffered acidic or basic solvent systems as appropriate. Compound retention times on the system were routinely assessed using a 30-50 μL test injection and a standard gradient, and then purified using an appropriately chosen focussed gradient as detailed below, based upon observed retention time.

Low pH:
Solvent A—Water+10 mM ammonium formate+0.1% formic acid
Solvent B—Acetonitrile+5% water+0.1% formic acid
High pH:
Solvent A—Water+10 mM ammonium formate+0.1% ammonia solution
Solvent B—Acetonitrile+5% water+0.1% ammonia solution
Standard Gradient:

| Time | Flow rate (mL/min) | % Solvent A | % Solvent B |
|---|---|---|---|
| 0 | 20 | 90 | 10 |
| 0.3 | 20 | 90 | 10 |
| 8.5 | 20 | 2 | 98 |
| 12 | 20 | 2 | 98 |
| 12.5 | 0 | 2 | 98 |

Focussed Gradients:

| | | % Solvent B Retention time on standard gradient (min.) | | | | |
|---|---|---|---|---|---|---|
| Time | Flow rate (mL/min) | 0-5.2 | 4.9-6.6 | 6.3-7.5 | 7.3-9.5 | 9.3-12 |
| 0 | 20 | 10 | 10 | 10 | 10 | 10 |
| 0.25 | 20 | 10 | 10 | 10 | 10 | 10 |
| 0.35 | 20 | 10 | 20 | 35 | 45 | 60 |
| 10 | 20 | 45 | 55 | 65 | 75 | 98 |
| 12 | 20 | 98 | 98 | 98 | 98 | 98 |
| 12.5 | 0 | 98 | 98 | 98 | 98 | 98 |

A Gilson-GX281 autopurification system, with a Waters XBridge 5 μm C18, 100 mm×30 mm i.d. or Waters XSelect 5 μm C18, 150 mm×19 mm i.d running at a flow rate of 20 mL/min with UV detection (214 nm, 254 nm). Purifications were performed using buffered basic solvent systems as appropriate. Compound retention times on the system were routinely assessed using Analytical LC-MS test as a standard gradient, then purified using an appropriately chosen focussed gradient as detailed below, based upon observed retention time.
Column: Waters X-Bridge C18: 100 mm*30 mm 5 um
Mobile Phase: A: Water (0.05% Ammonia) B$_2$: Methanol Focussed Gradients:

| Flow rate | Solvent B$_2$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 45 | 65 | 95 | 95 | 95 |
| 20 | 50 | 70 | 95 | 95 | 95 |
| 20 | 55 | 75 | 95 | 95 | 95 |

Column: Waters X-Select 5 μm C18, 150 mm×19 mm
Mobile Phase: A: Water (0.05% Ammonia) B$_2$: Methanol
Focussed Gradients:

| Flow rate | Solvent B$_2$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 45 | 65 | 95 | 95 | 95 |
| 20 | 50 | 70 | 95 | 95 | 95 |
| 20 | 55 | 75 | 95 | 95 | 95 |

Column: Waters X-Select 5 μm C18, 150 mm×19 mm
Mobile Phase: A: Water (10 mmol NH$_4$HCO$_3$) B$_1$: Acetonitrile
Focussed Gradients:

| Flow rate | Solvent B$_1$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 30 | 50 | 95 | 95 | 95 |
| 20 | 35 | 55 | 95 | 95 | 95 |
| 20 | 40 | 60 | 95 | 95 | 95 |

General Reaction Schemes

Scheme 1

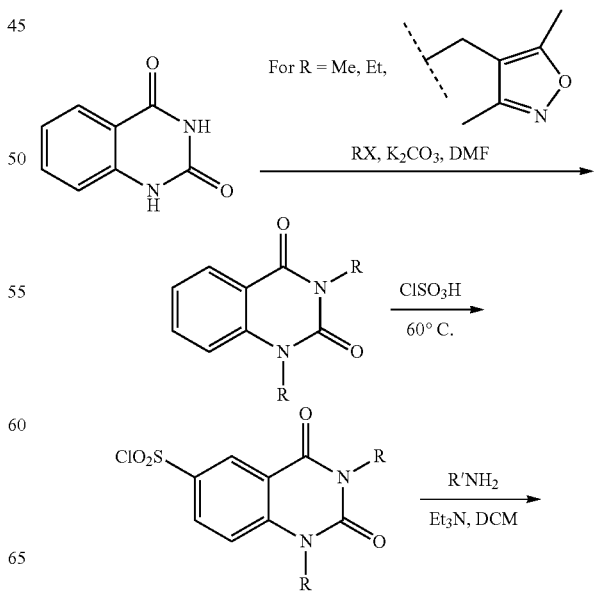

73
-continued
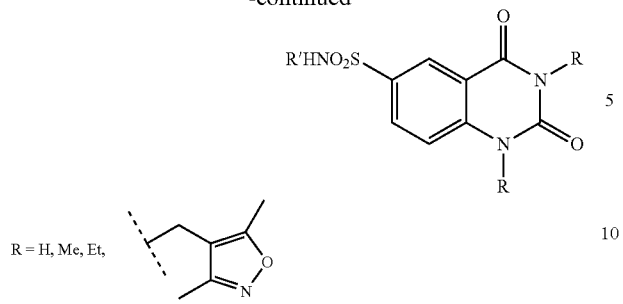
R = H, Me, Et,
74
-continued
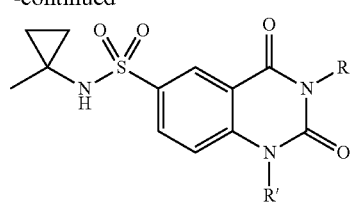
R = Me or Et
Scheme 2
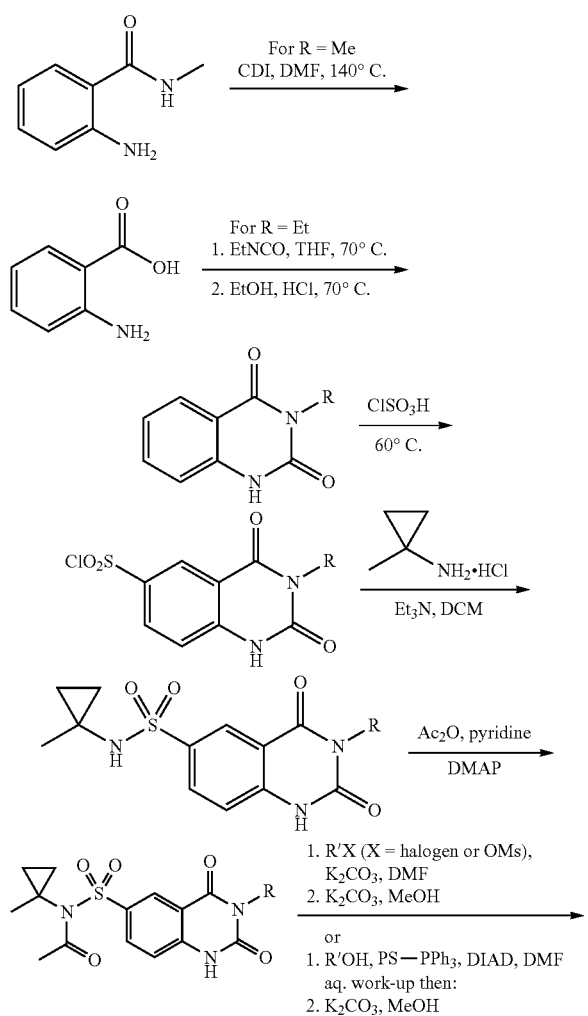
Scheme 3
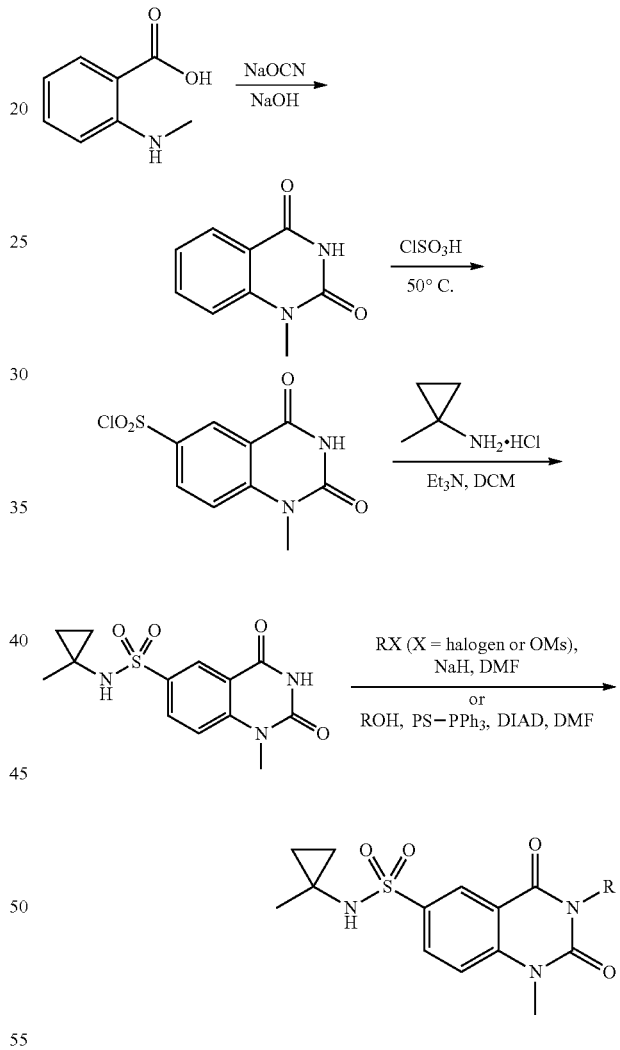

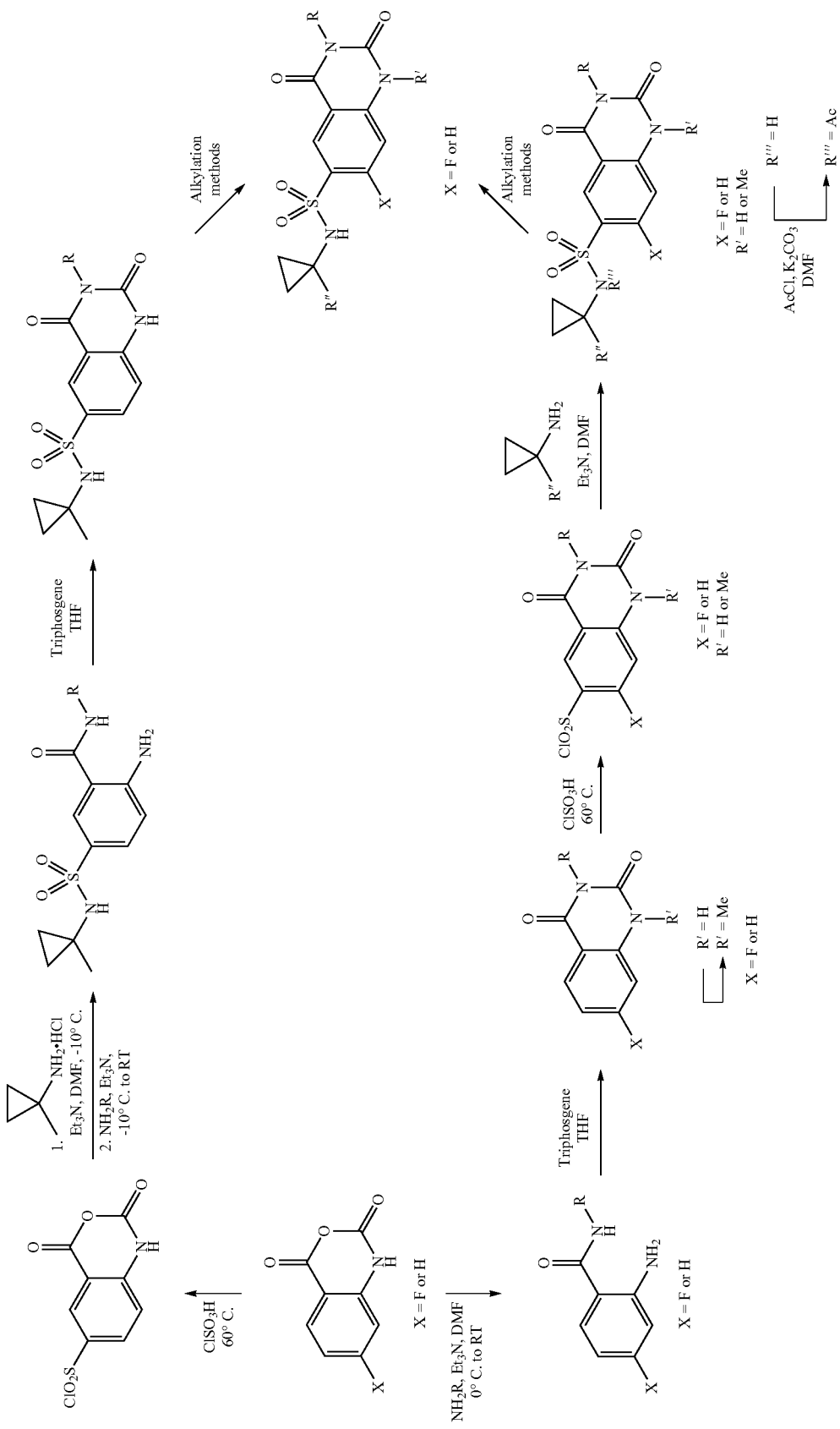

Scheme 5
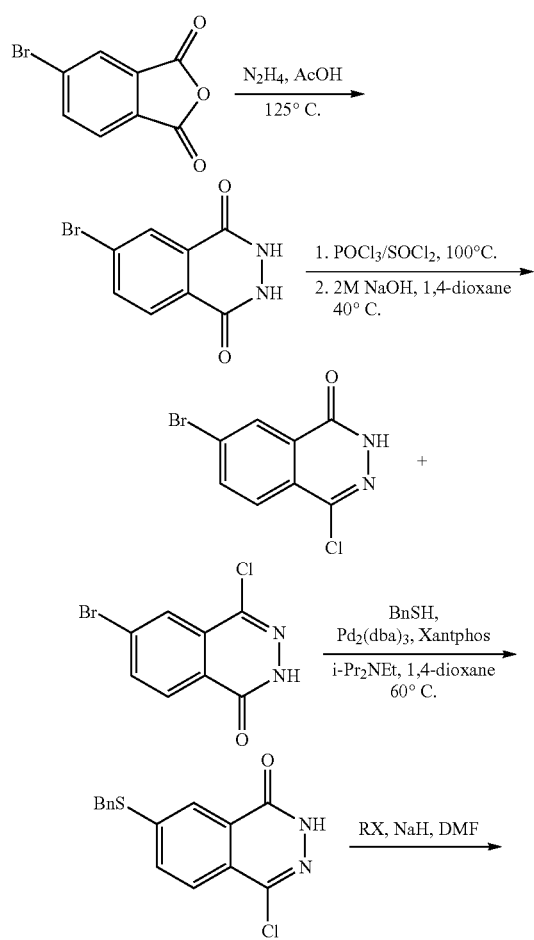
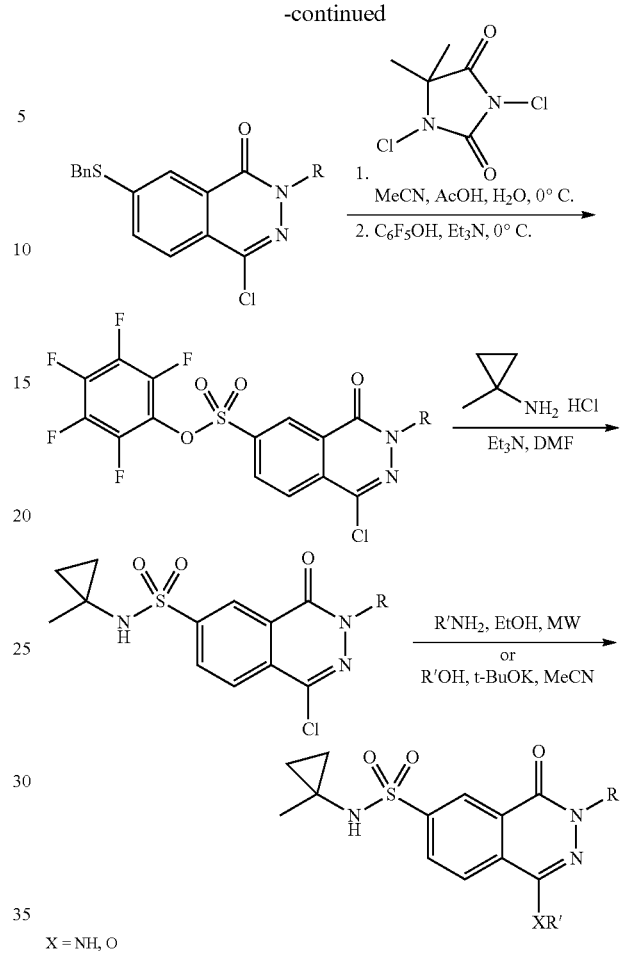
Scheme 6
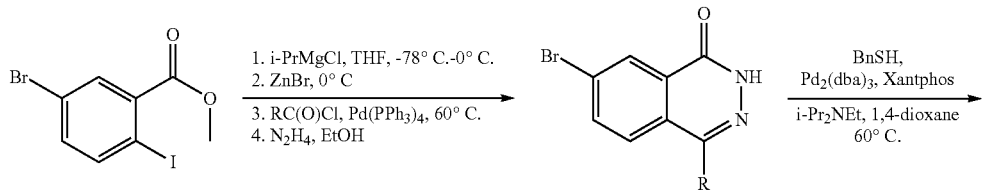
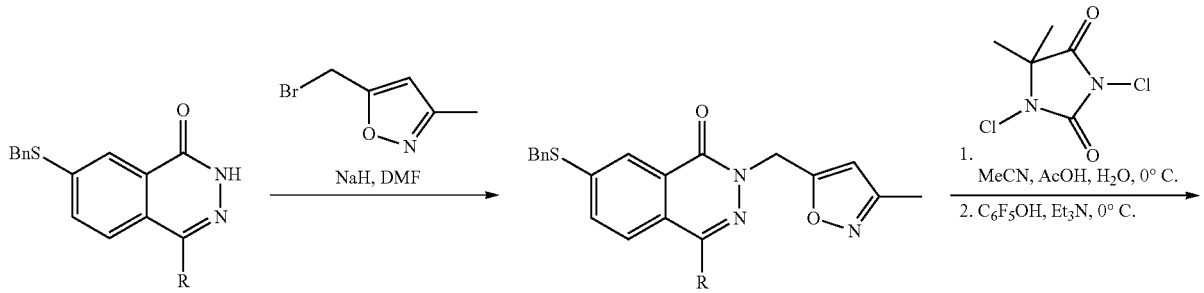

-continued
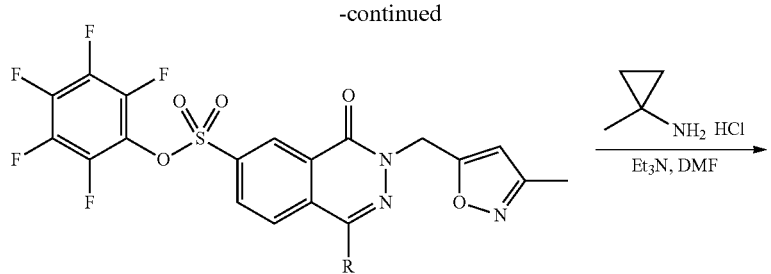
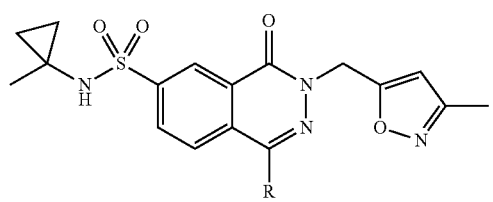
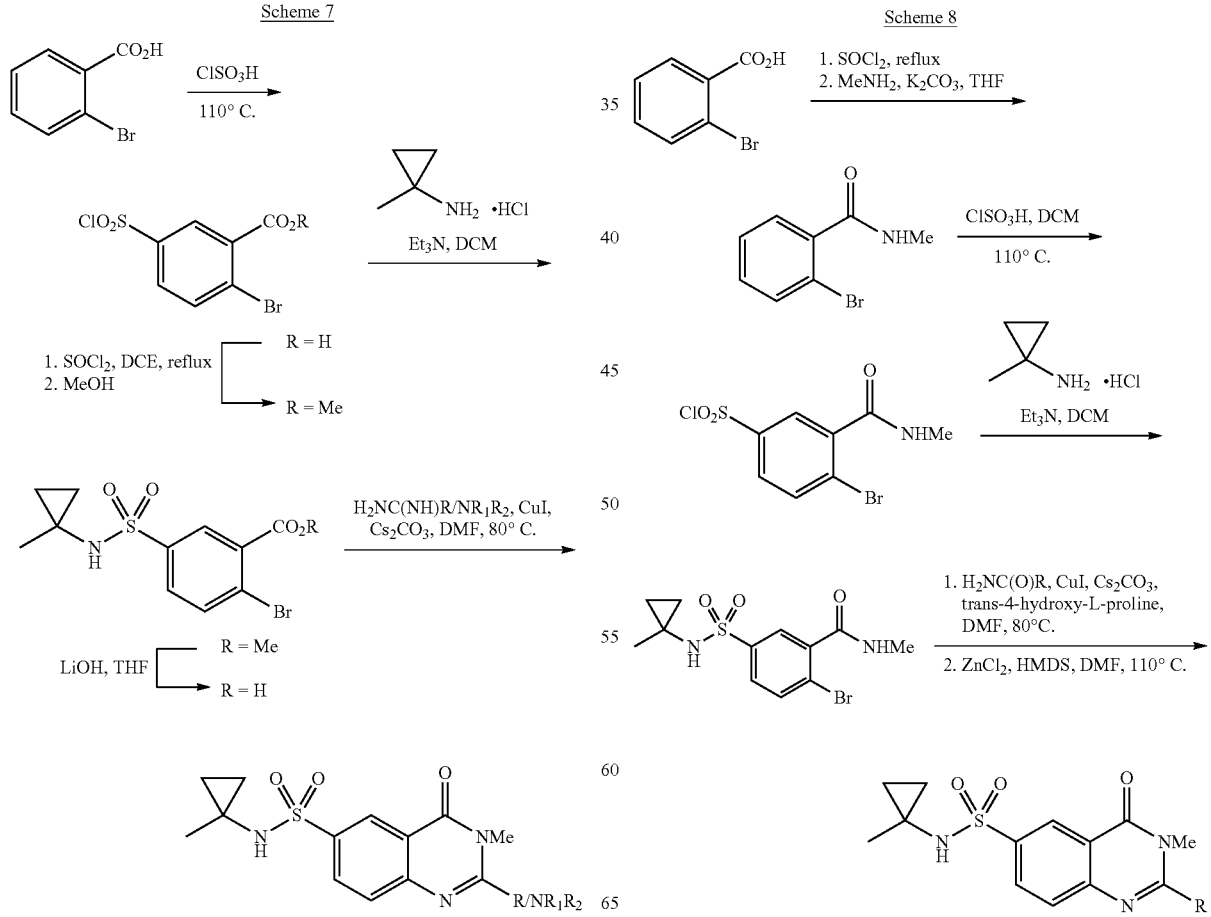

Scheme 9
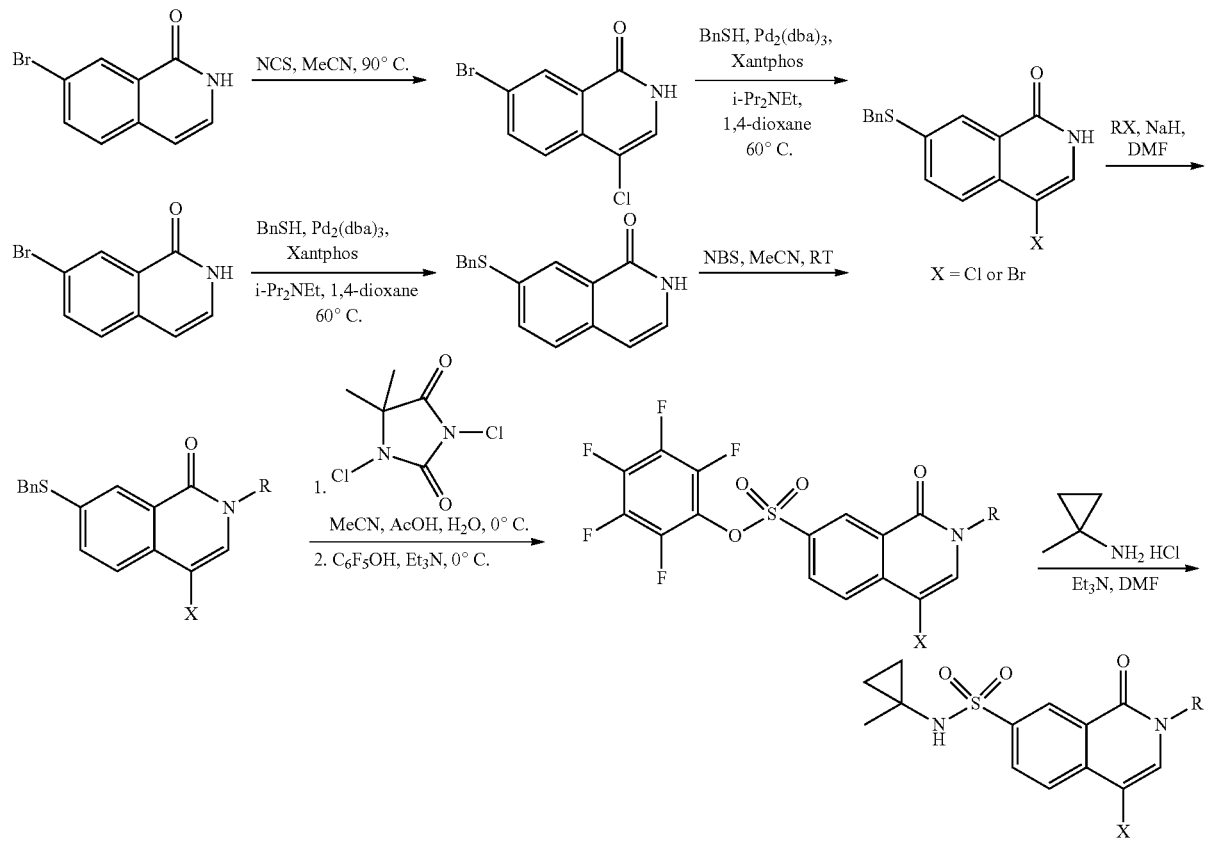
Scheme 10
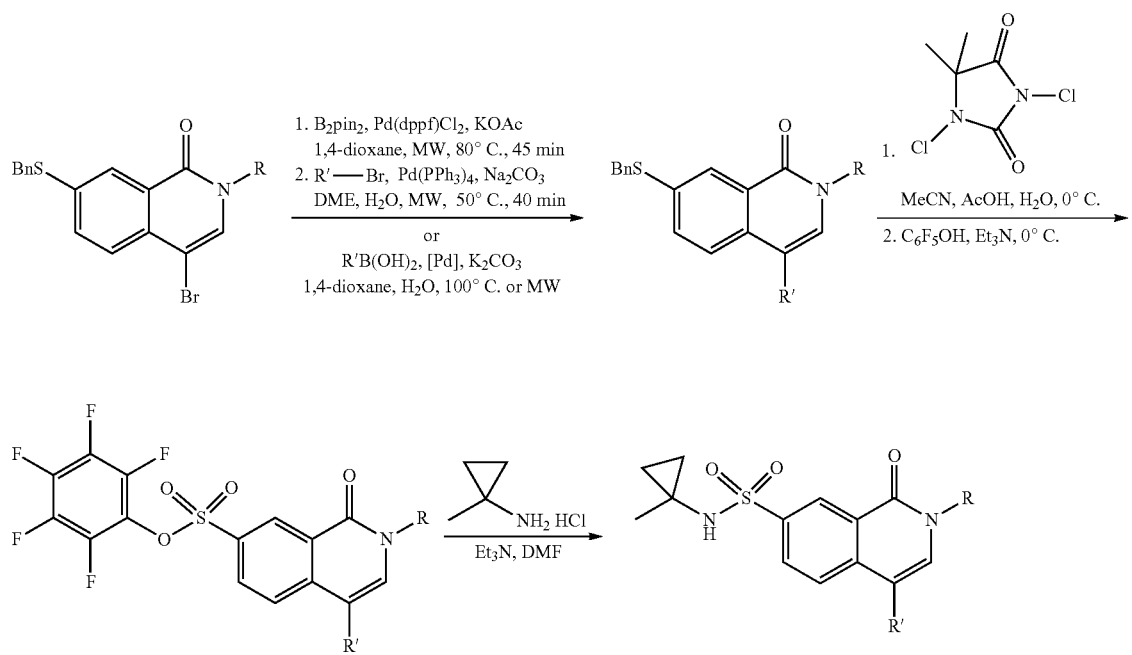

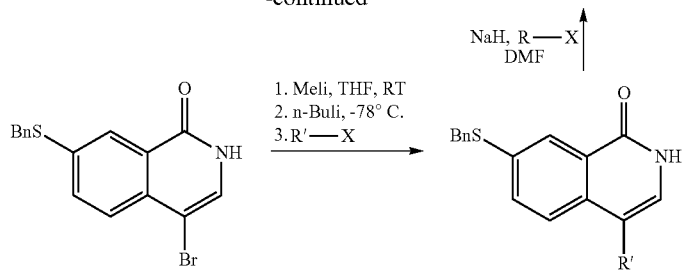
Scheme 11
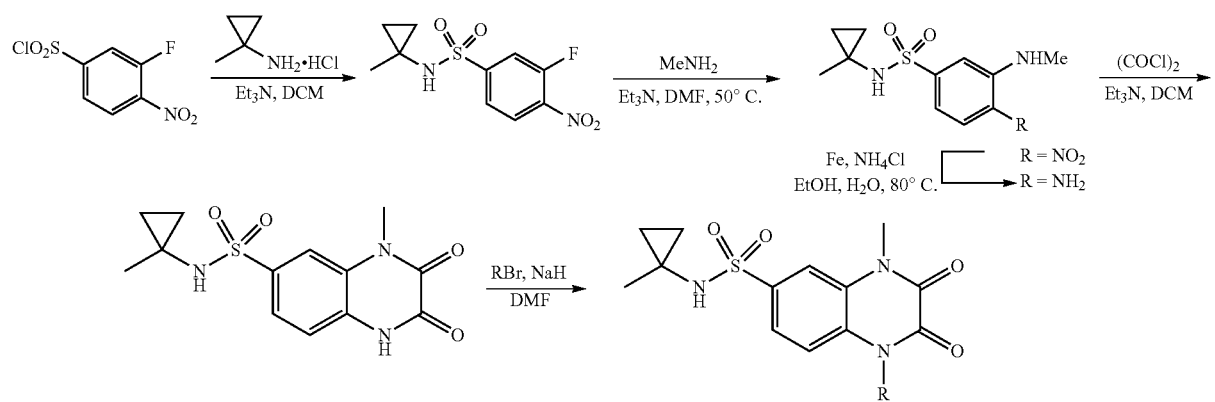
Scheme 12
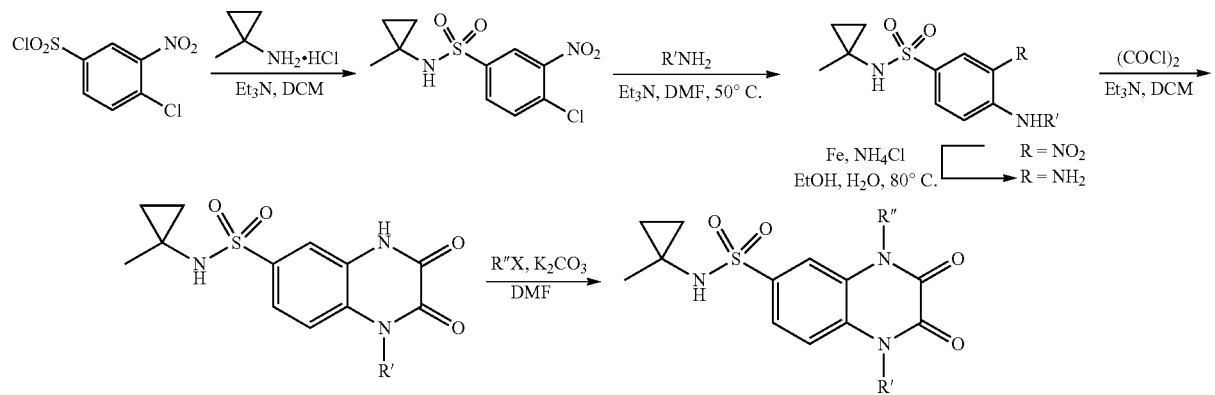
Scheme 13
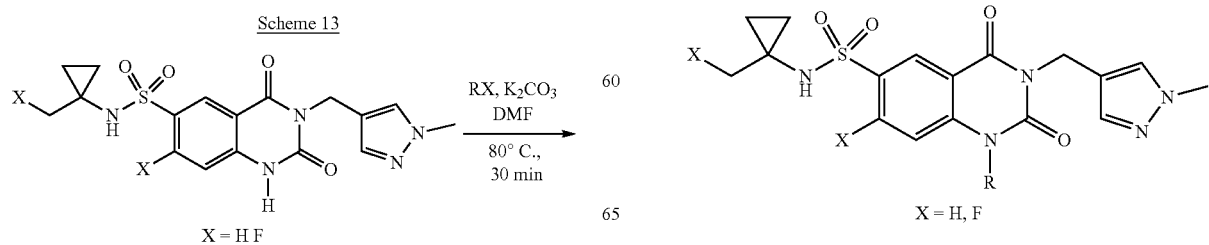
X = H, F Scheme 14
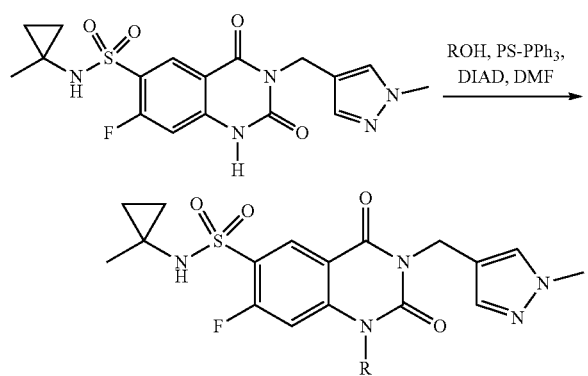
Scheme 15
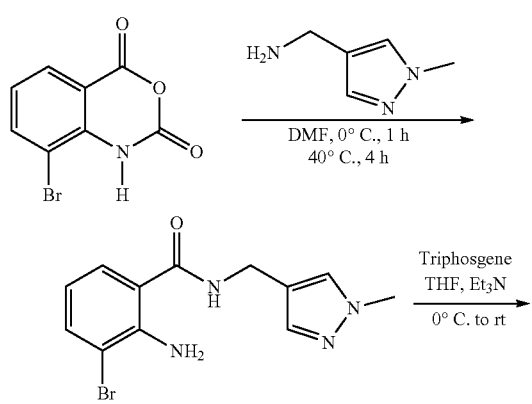
Scheme 16
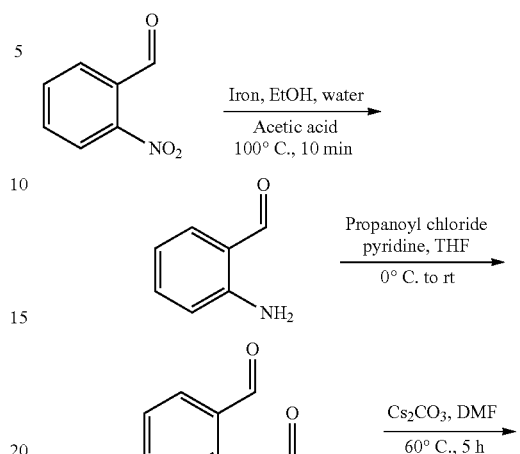
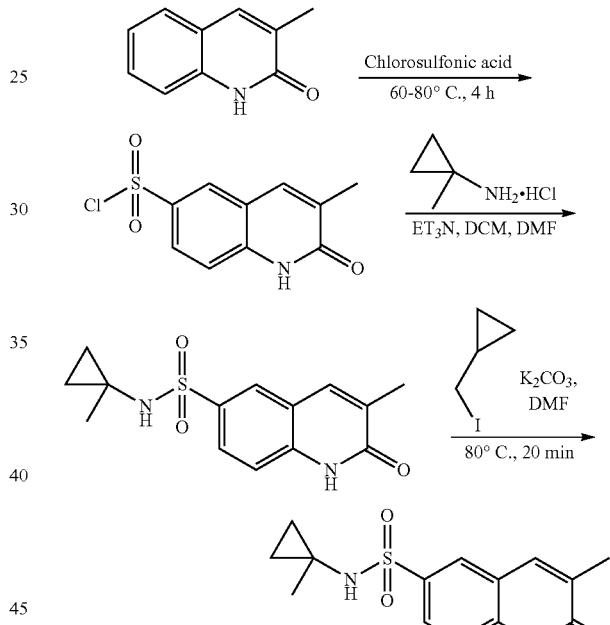
Scheme 17
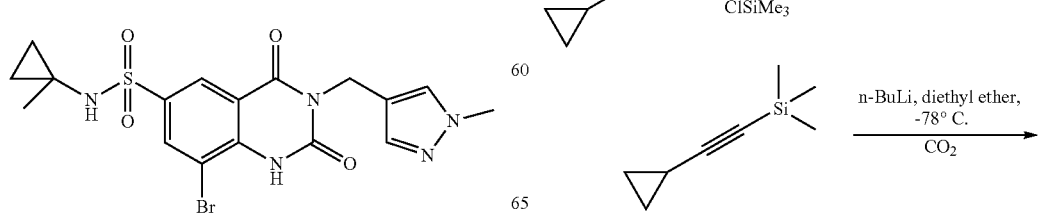

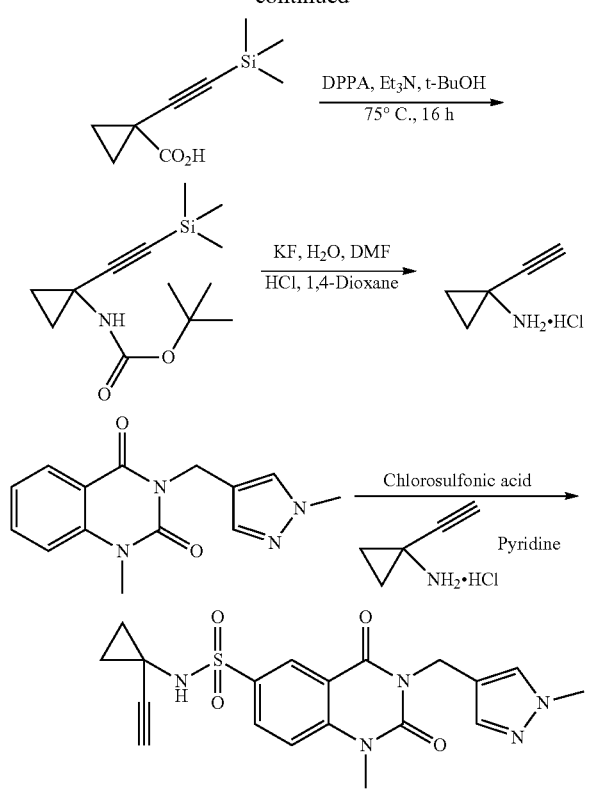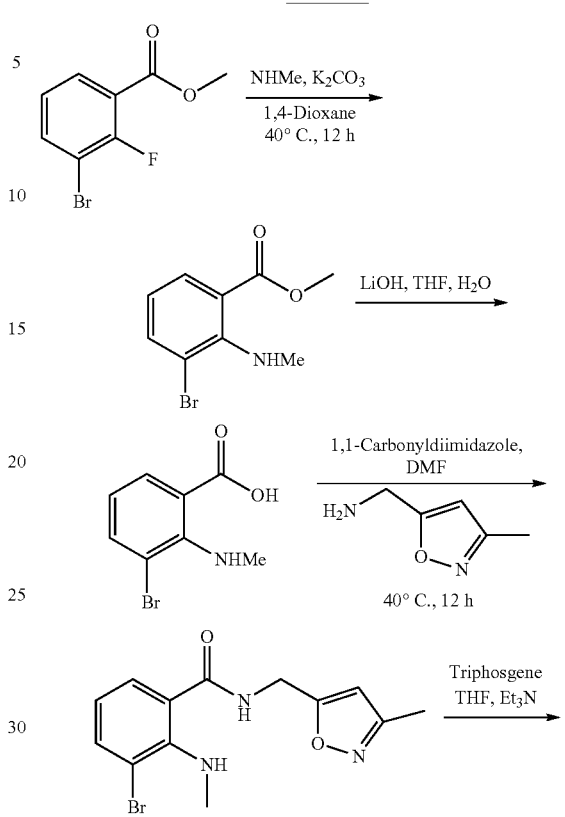
Scheme 18
Scheme 19
Scheme 20
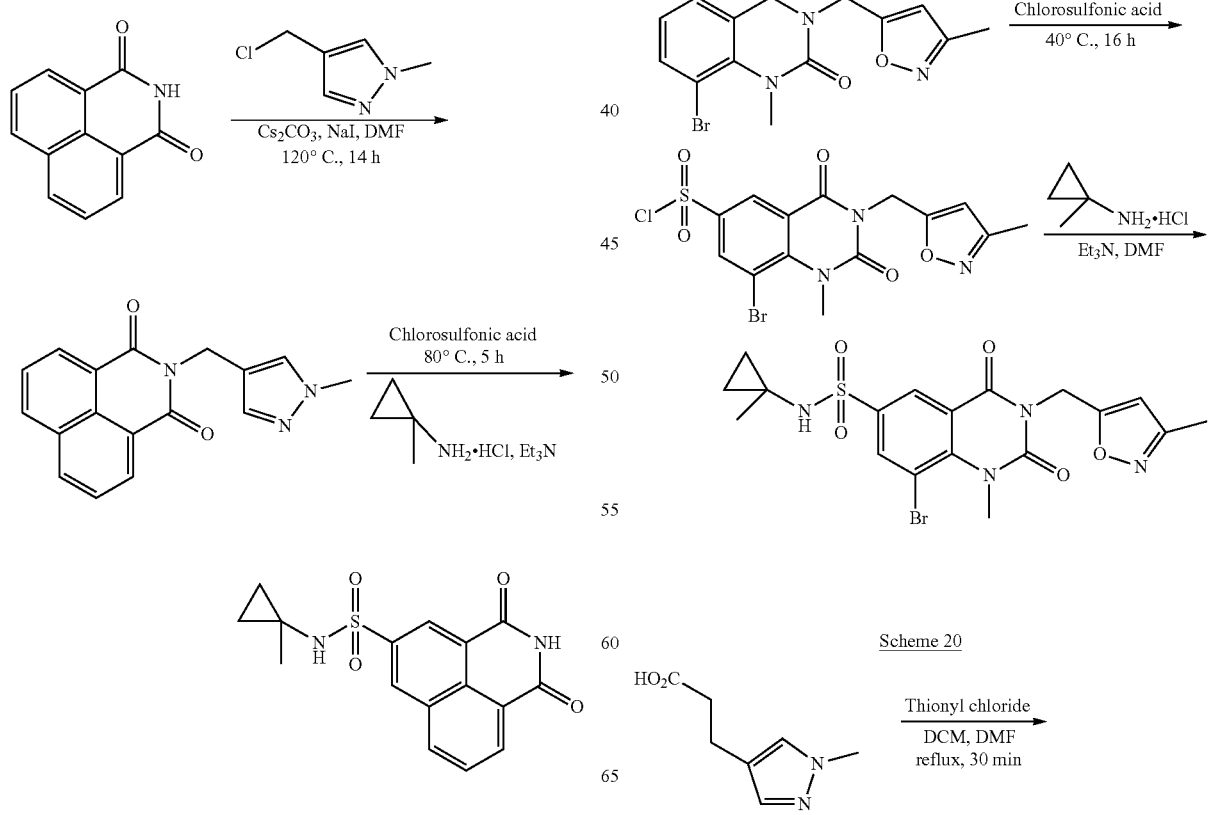

89
-continued
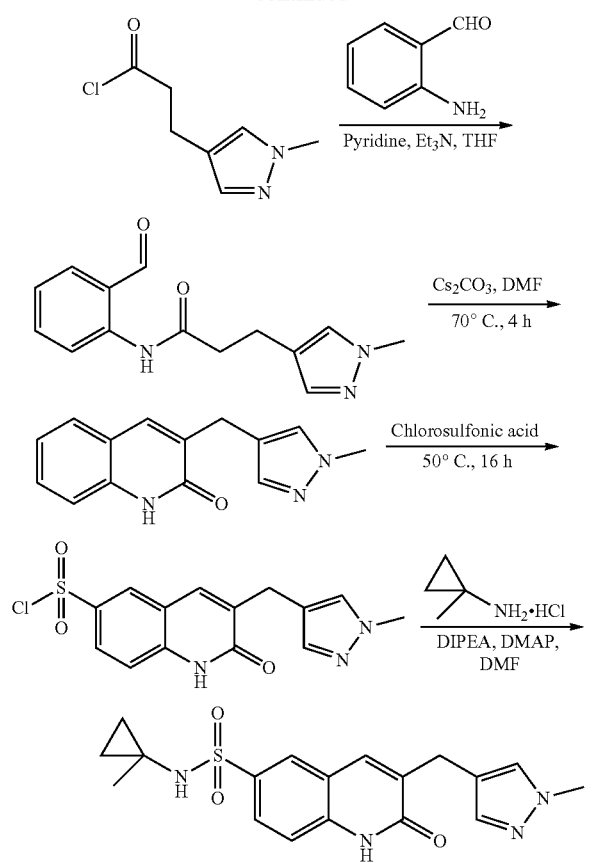
Scheme 21
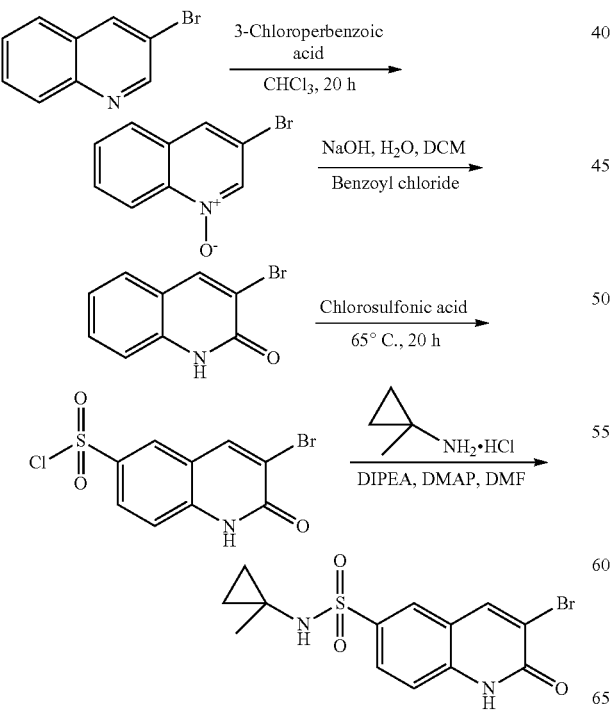
90
Scheme 22
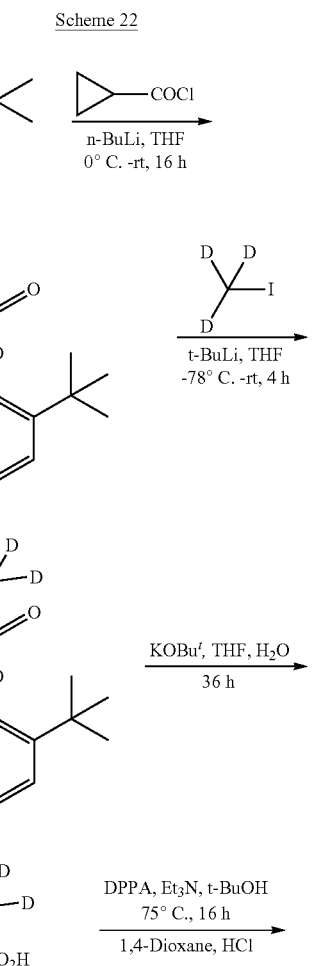
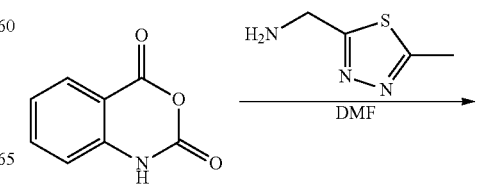
Scheme 23

-continued

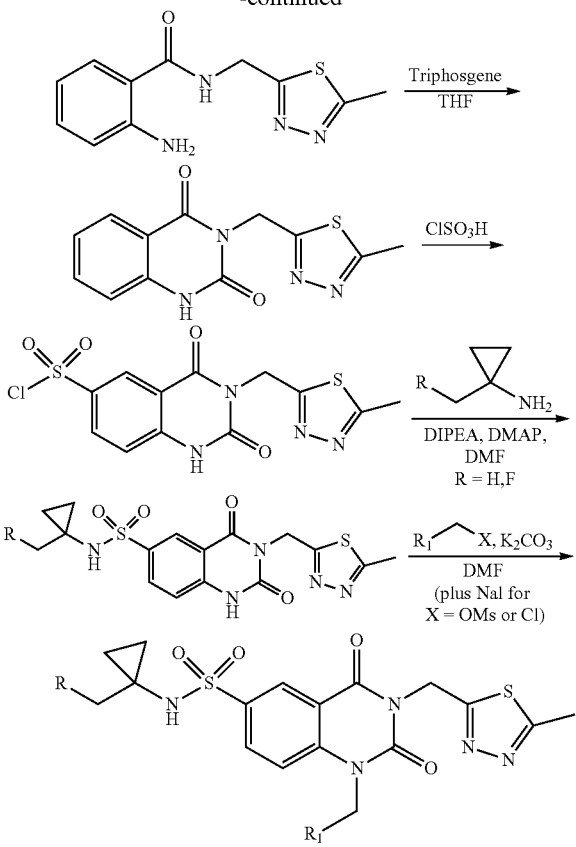

General Methods

1-Methylcyclopropanamine hydrochloride

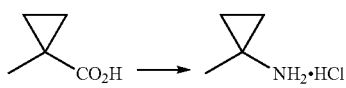

1-Methylcyclopropane carboxylic acid (73.3 g, 0.73 mol), diphenylphosphoryl azide (221.7 g, 0.81 mol) and triethylamine (148.1 g, 1.46 mol) were stirred in tert-butanol (330 mL) and heated at 75° C. overnight. The reaction mixture was cooled to room temperature, poured into a mixture of ethyl acetate (750 mL) and water (1500 mL) and stirred for 15 min. The resulting precipitate was removed by filtration and the phases separated. The aqueous layer was extracted with ethyl acetate (2×750 mL) and the combined organic extracts were washed with water (750 mL), dried (MgSO$_4$) and concentrated to give a pale brown solid (88 g). The solid was suspended in 1,4-dioxane (295 mL) and 4 M hydrochloric acid (366 mL) was added. The reaction mixture was stirred at room temperature for 2 h. Diethyl ether was added and the mixture chilled in a methanol/ice bath for 15 min. The precipitate was collected by filtration, washing with diethyl ether (2×220 mL) before drying the filter cake for 10 min to give 1-methylcyclopropanamine hydrochloride as a shiny white solid (40.5 g, 0.38 mol, 51%).

$^1$H NMR (CDCl$_3$): δ (1.32 (s, 3H), 0.75-0.68 (m, 2H), 0.60-0.51 (m, 2H)

General Procedures Relating to Scheme 1:

Intermediate S1-A1
1,3-Dimethylquinazoline-2,4(1H,3H)-dione

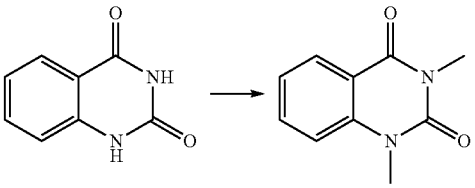

A suspension of benzoyleneurea (2.0 g, 12.33 mmol) in DMF (24 mL) was treated with potassium carbonate (8.5 g, 61.67 mmol) and was left to stir, under nitrogen, at room temperature for 30 min. The solution was then treated with iodomethane (2.3 mL, 37 mmol) and stirred at room temperature for 2 h. The suspension was filtered then water (40 mL) and EtOAc (40 mL) were added. The organic layer was extracted, washed with brine (2×20 mL), dried over MgSO$_4$ and concentrated to give 1,3-dimethylquinazoline-2,4-dione (0.96 g, 5.05 mmol, 41%).

$^1$H NMR (300 MHz, DMSO-d$_6$) δ=8.06 (dd, J=1.7, 7.8 Hz, 1H), 7.81-7.75 (m, 1H), 7.47 (d, J=8.5 Hz, 1H), 7.31 (app. t, J=7.5 Hz, 1H), 3.53 (s, 3H), 3.32 (s, 3H)

The following intermediates were prepared by a similar method:

Intermediate S1-A2
1,3-Diethylquinazoline-2,4(1H,3H)-dione

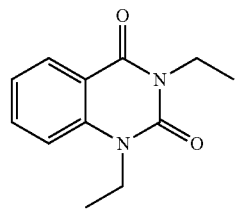 [SMILES: CCn1c(=O)c2ccccc2n(CC)c1=O]

Prepared from benzoyleneurea and iodoethane.

$^1$H NMR (300 MHz, DMSO-d$_6$) δ=8.07 (dd, J=1.6, 7.9 Hz, 1H), 7.78 (ddd, J=1.8, 7.3, 8.5 Hz, 1H), 7.51 (d, J=8.6 Hz, 1H), 7.30 (app. t, J=7.5 Hz, 1H), 4.15 (q, J=7.2 Hz, 2H), 3.99 (q, J=7.2 Hz, 2H), 1.22 (t, J=7.1 Hz, 3H), 1.16 (t, J=7.1 Hz, 3H)

Intermediate S1-A3 1,3-Bis[(3,5-dimethylisoxazol-4-yl)methyl]quinazoline-2,4-dione

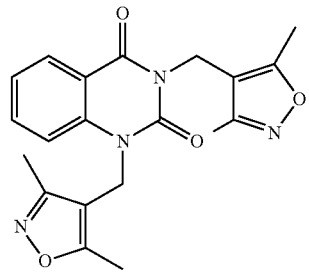 [SMILES: Cc1noc(C)c1Cn1c(=O)c2ccccc2n(Cc2c(C)noc2C)c1=O]

Prepared from benzoyleneurea and 4-(bromomethyl)-3,5-dimethyl-isoxazole.

$^1$H NMR (300 MHz, DMSO-d$_6$) δ=8.13 (dd, J=1.6, 7.9 Hz, 1H), 7.77 (ddd, J=1.6, 7.1, 8.6 Hz, 1H), 7.37 (d, J=8.6 Hz, 1H), 7.33 (t, J=7.7 Hz, 1H), 5.16 (s, 2H), 4.95 (s, 2H), 2.40 (s, 3H), 2.22 (s, 3H), 2.19 (s, 3H), 2.02 (s, 3H)

Intermediate S1-B1 1,3-Dimethyl-2,4-dioxo-1,2,3,4-tetrahydroquinazoline-6-sulfonyl chloride

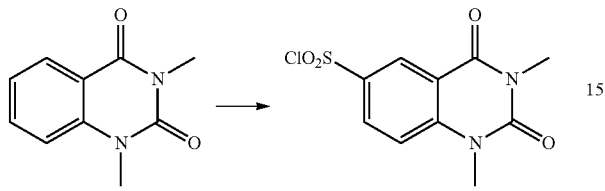

Chlorosulfonic acid (1.68 mL, 25.24 mmol) was added portionwise to stirring 1,3-dimethylquinazoline-2,4-dione (960 mg, 5.05 mmol) cooled to 5-10° C. The reaction mixture was heated at 60° C. for 4 h. The reaction mixture was cooled and poured into crushed ice where an off white precipitate formed. The precipitate was filtered, washed with water and dried in the vacuum oven to give 1,3-dimethyl-2,4-dioxo-1,2,3,4-tetrahydroquinazoline-6-sulfonyl chloride (0.98 g, 3.4 mmol, 67%).

$^1$H NMR (300 MHz, DMSO-d$_6$) δ=8.25 (d, J=2.1 Hz, 1H), 7.93 (dd, J=2.2, 8.7 Hz, 1H), 7.42 (d, J=8.8 Hz, 1H), 3.52 (s, 3H), 3.31 (s, 3H)

The following intermediates were prepared by a similar method:

Intermediate S1-B2
2,4-Dioxo-1,2,3,4-tetrahydroquinazoline-6-sulfonyl chloride

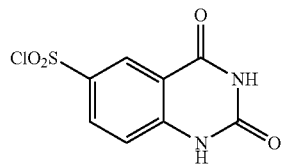 [SMILES: O=c1[nH]c(=O)c2cc(S(=O)(=O)Cl)ccc2[nH]1]

Prepared from benzoyleneurea and chlorosulfonic acid.

$^1$H NMR (300 MHz, DMSO-d$_6$) δ=11.31 (s, 1H), 11.22 (s, 1H), 8.10 (d, J=2.1 Hz, 1H), 7.82 (dd, J=2.0, 8.4 Hz, 1H), 7.11 (d, J=8.4 Hz, 1H)

Intermediate S1-B3 1,3-Diethyl-2,4-dioxo-1,2,3,4-tetrahydroquinazoline-6-sulfonyl chloride

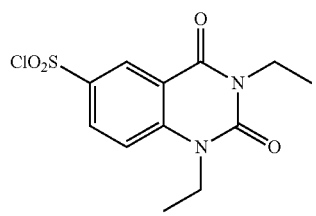 [SMILES: CCn1c(=O)c2cc(S(=O)(=O)Cl)ccc2n(CC)c1=O]

Prepared from 1,3-diethylquinazoline-2,4(1H,3H)-dione and chlorosulfonic acid.

$^1$H NMR (300 MHz, DMSO-d$_6$) δ=8.26 (d, J=2.5 Hz, 1H), 7.92 (dd, J=2.1, 8.7 Hz, 1H), 7.46 (d, J=8.9 Hz, 1H), 4.14 (q, J=6.8 Hz, 2H), 3.99 (q, J=7.0 Hz, 2H), 1.25-1.13 (m, 6H)

Intermediate S1-B4 1,3-Bis[(3,5-dimethylisoxazol-4-yl)methyl]-2,4-dioxo-quinazoline-6-sulfonyl chloride

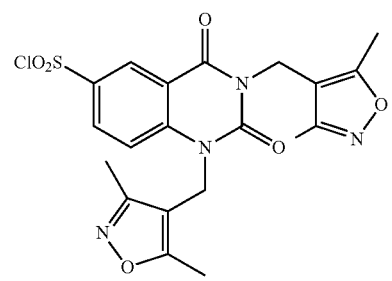 [SMILES: Cc1noc(C)c1Cn1c(=O)c2cc(S(=O)(=O)Cl)ccc2n(Cc2c(C)noc2C)c1=O]

Prepared from 1,3-bis[(3,5-dimethylisoxazol-4-yl)methyl]quinazoline-2,4-dione and chlorosulfonic acid in DCM.

$^1$H NMR (300 MHz, CDCl$_3$) δ=8.93 (d, J=2.4 Hz, 1H), 8.23 (dd, J=2.4, 9.0 Hz, 1H), 7.22 (d, J=9.0 Hz, 1H), 5.18 (s, 2H), 5.08 (s, 2H), 2.53 (s, 3H), 2.32 (s, 6H), 2.13 (s, 3H)

General Procedures Relating to Scheme 2:

Intermediate S2-A1
3-Methyl-1H-quinazoline-2,4-dione

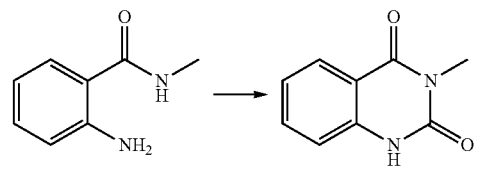

A solution of 2-amino-N-methylbenzamide (15 g, 0.10 mol) and 1,1-carbonyldiimidazole (21 g, 0.13 mol) in N,N-dimethylformamide (150 mL) was heated at 135-145° C. overnight. The reaction showed 30% starting material by LC so more 1,1-carbonyldiimidazole (14 g, 0.086 mol) was added and the reaction mixture was heated at ° C. overnight. The reaction showed complete conversion so was cooled and poured into ice/water (300 mL) and stirred for 10 min. The suspension was filtered and the product was washed with water. The solid was dried in the vacuum oven at 50° C. overnight to give 3-methylquinazoline-2,4(1H,3H)-dione (15.8 g, 0.090 mol, 90%).

$^1$H NMR (300 MHz, DMSO-d$_6$) δ=11.44 (br. s, 1H), 7.93 (dd, J=1.5, 7.8 Hz, 1H), 7.65 (app. t, J=7.7 Hz, 1H), 7.23-7.15 (m, 2H), 3.33 (s, 3H)

Intermediate S2-A2
3-Ethyl-1H-quinazoline-2,4-dione

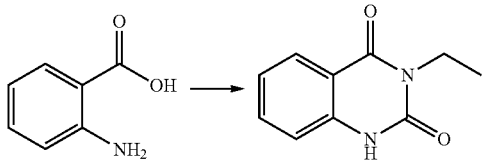

Ethyl isocyanate (1.27 mL, 16.04 mmol) was added to a solution of anthranilic acid (2.0 g, 14.58 mmol) in THF (20 mL), the reaction mixture was heated at 70° C. for 2.5 h. The reaction mixture was evaporated to dryness, then EtOH (20 mL) and conc. HCl (4 mL, 2 mL/g) were added and the mixture heated at 70° C. for 30 min. The reaction mixture was cooled in an ice bath, water (40 mL) was added and a white precipitate formed. The solid was filtered and dried in the vacuum oven to give 3-ethyl-1H-quinazoline-2,4-dione (2.22 g, 11.67 mmol, 80%).
$^1$H NMR (300 MHz, DMSO-d$_6$) δ=11.41 (s, 1H), 7.93 (dd, J=1.6, 7.9 Hz, 1H), 7.65 (app. t, J=7.6 Hz, 1H), 7.23-7.14 (m, 2H), 3.93 (q, J=7.0 Hz, 2H), 1.15 (t, J=7.1 Hz, 3H)

Intermediate S2-B1 3-Methyl-2,4-dioxo-1,2,3,4-tetrahydroquinazoline-6-sulfonyl chloride

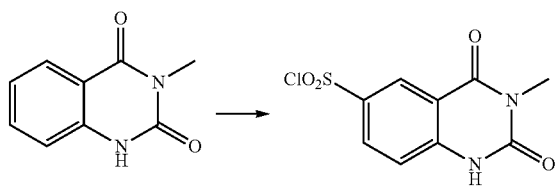 [SMILES: Cn1c(=O)[nH]c2ccccc2c1=O ; Cn1c(=O)[nH]c2ccc(S(=O)(=O)Cl)cc2c1=O]

3-Methylquinazoline-2,4(1H,3H)-dione (15 g, 0.085 mol) was added portionwise with cooling to chlorosulfonic acid (60 mL, 0.9 mol) maintaining the temperature <20° C. The reaction mixture was heated to 60° C. and stirred for 2 h then allowed to cool. The reaction mixture was added carefully to ice (500 mL) over 30 min. The resultant precipitate was stirred for 30 min, collected by filtration and washed with water. The solid was dried in the vacuum oven to give 3-methyl-2,4-dioxo-1,2,3,4-tetrahydroquinazoline-6-sulfonyl chloride (23 g, 0.084 mol, 99%).
$^1$H NMR (300 MHz, DMSO-d$_6$) δ=11.54 (s, 1H), 8.15 (d, J=2.1 Hz, 1H), 7.83 (dd, J=2.0, 8.4 Hz, 1H), 7.13 (d, J=8.5 Hz, 1H), 3.25 (s, 3H)
The following intermediate was prepared by a similar method:

Intermediate S2-B2 3-Ethyl-2,4-dioxo-1,2,3,4-tetrahydroquinazoline-6-sulfonyl chloride

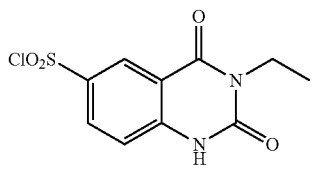 [SMILES: CCn1c(=O)[nH]c2ccc(S(=O)(=O)Cl)cc2c1=O]

Prepared from 3-ethyl-1H-quinazoline-2,4-dione and chlorosulfonic acid.
$^1$H NMR (300 MHz, DMSO-d$_6$) δ=11.50 (s, 1H), 8.15 (d, J=2.0 Hz, 1H), 7.83 (dd, J=2.0, 8.4 Hz, 1H), 7.12 (d, J=8.5 Hz, 1H), 3.93 (q, J=7.1 Hz, 2H), 1.15 (t, J=7.0 Hz, 3H)

Example 7 3-Methyl-N-(1-methylcyclopropyl)-2,4-dioxo-1,2,3,4-tetrahydroquinazoline-6-sulfonamide

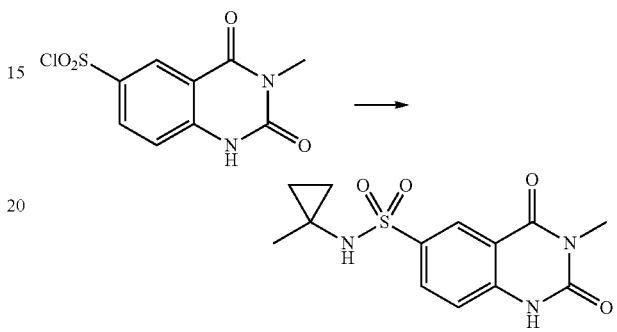

3-Methyl-2,4-dioxo-1,2,3,4-tetrahydroquinazoline-6-sulfonyl chloride (12 g, 43.7 mmol) and 1-methylcyclopropanamine hydrochloride (5.16 g, 48 mmol) were slurried in dichloromethane (120 mL) at 20° C. Triethylamine (13.4 mL, 96 mmol) was added over 15 min: this was exothermic and the temperature was allowed to rise to 34° C. As the reaction cooled, a precipitate formed. After stirring for 2 h the reaction was complete by HPLC. 1 M hydrochloric acid (100 mL) was added and stirred for 25 min. The product was filtered from the biphasic mixture and washed with water (100 mL). The solid was dried in the vacuum oven to give 3-methyl-N-(1-methylcyclopropyl)-2,4-dioxo-1,2,3,4-tetrahydroquinazoline-6-sulfonamide (12.03 g, 0.039 mol, 89%).
$^1$H NMR (300 MHz, DMSO-d$_6$) δ=11.83 (br. s, 1H), 8.32 (d, J=2.2 Hz, 1H), 8.13 (s, 1H), 7.99 (dd, J=2.2, 8.6 Hz, 1H), 7.32 (d, J=8.6 Hz, 1H), 1.06 (s, 3H), 0.62-0.55 (m, 2H), 0.42-0.35 (m, 2H)
The following intermediates were prepared by a similar method:

Example 6 3-Ethyl-N-(1-methylcyclopropyl)-2,4-dioxo-1,2,3,4-tetrahydroquinazoline-6-sulfonamide

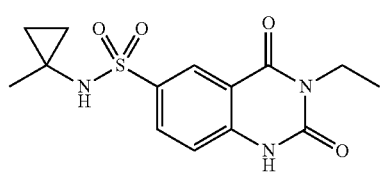 [SMILES: CCn1c(=O)[nH]c2ccc(S(=O)(=O)NC3(C)CC3)cc2c1=O]

Prepared from 3-ethyl-2,4-dioxo-1,2,3,4-tetrahydroquinazoline-6-sulfonyl chloride and 1-methylcyclopropanamine hydrochloride.
$^1$H NMR (300 MHz, DMSO-d$_6$) δ=14.48 (br. s, 2H), 11.54 (s, 1H), 8.15 (d, J=2.1 Hz, 1H), 7.83 (dd, J=2.0, 8.4 Hz, 1H), 7.13 (d, J=8.5 Hz, 2H), 3.25 (s, 3H)

Intermediate S2-C3 1-Methyl-N-(1-methylcyclopropyl)-2,4-dioxo-pyrido[2,3-d]pyrimidine-6-sulfonamide

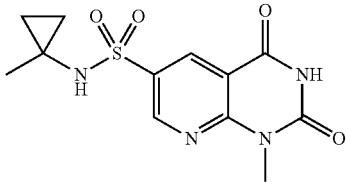 [SMILES: Cn1c(=O)[nH]c(=O)c2cc(S(=O)(=O)NC3(C)CC3)cnc21]

Prepared from 1-methyl-2,4-dioxo-1H,2H,3H,4H-pyrido[2,3-d]pyrimidine-6-sulfonyl chloride (Enamine) and 1-methylcyclopropanamine hydrochloride.

$^1$H NMR (300 MHz, DMSO-$d_6$) δ=12.00 (s, 1H), 8.98 (d, J=2.4 Hz, 1H), 8.54 (d, J=2.4 Hz, 1H), 8.35 (s, 1H), 3.50-3.42 (m, 3H), 1.12 (s, 3H), 0.71-0.54 (m, 2H), 0.52-0.37 (m, 2H)

Intermediate S2-D1 N-((3-Methyl-2,4-dioxo-1,2,3,4-tetrahydroquinazolin-6-yl)sulfonyl)-N-(1-methylcyclopropyl)acetamide

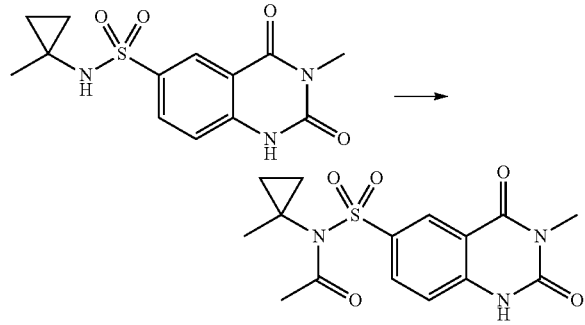

3-Methyl-N-(1-methylcyclopropyl)-2,4-dioxo-1,2,3,4-tetrahydroquinazoline-6-sulfonamide (11 g, 35.6 mmol) was slurried in pyridine (30 mL) and 4-dimethylaminopyridine (430 mg, 3.5 mmol) was added. Acetic anhydride (33.6 mL, 356 mmol) was added over 10 min and the resultant thick slurry was stirred overnight at ambient temperature. The reaction mixture was diluted with ethyl acetate (25 mL) and filtered. The solid was washed with ethyl acetate. The solid was transferred to a conical flask and slurried in water (40 mL) at 60° C. for 2 h. The slurry was cooled to 35° C. and filtered washing with water (20 mL). The solid was dried in the vacuum oven to give N-((3-methyl-2,4-dioxo-1,2,3,4-tetrahydroquinazolin-6-yl)sulfonyl)-N-(1-methylcyclopropyl)acetamide (10.4 g, 0.030 mol, 83%).

$^1$H NMR (300 MHz, DMSO-$d_6$) δ=11.91 (br. s, 1H), 8.39 (d, J=2.3 Hz, 1H), 8.09 (dd, J=2.3, 8.7 Hz, 1H), 7.33 (d, J=8.8 Hz, 1H), 3.26 (s, 3H), 2.23 (s, 3H), 1.54 (s, 3H), 1.25-1.16 (m, 2H), 1.10-0.97 (m, 2H)

The following intermediates were prepared by a similar method:

Intermediate S2-D2 N-((3-Ethyl-2,4-dioxo-1,2,3,4-tetrahydroquinazolin-6-yl)sulfonyl)-N-(1-methylcyclopropyl)acetamide

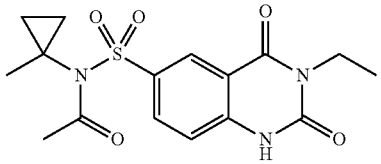 [SMILES: CCn1c(=O)[nH]c2ccc(S(=O)(=O)N(C(C)=O)C3(C)CC3)cc2c1=O]

Prepared from 3-ethyl-N-(1-methylcyclopropyl)-2,4-dioxo-1,2,3,4-tetrahydroquinazoline-6-sulfonamide and acetic anhydride.

$^1$H NMR (300 MHz, CDCl$_3$) δ=10.47 (s, 1H), 8.65 (d, J=2.3 Hz, 1H), 8.29 (dd, J=2.3, 8.7 Hz, 1H), 7.23 (d, J=8.8 Hz, 1H), 4.15 (q, J=7.1 Hz, 2H), 2.29 (s, 3H), 1.65 (s, 3H), 1.40-1.27 (m, 4H), 1.21-1.10 (m, 2H)

Intermediate S2-D3 N-(1-Cyanocyclopropyl)-N-[[3-[(3-methylisoxazol-5-yl)methyl]-2,4-dioxo-1H-quinazolin-6-yl]sulfonyl]acetamide

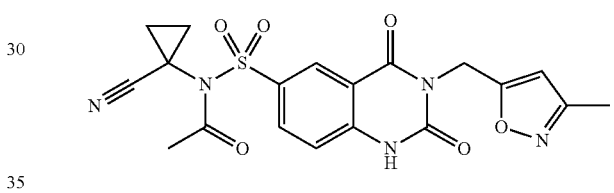

Prepared from N-(1-cyanocyclopropyl)-3-[(3-methylisoxazol-5-yl)methyl]-2,4-dioxo-1H-quinazoline-6-sulfonamide (Intermediate S4-C6) and acetic anhydride $^1$H NMR (300 MHz, DMSO-$d_6$) δ=12.17 (s, 1H), 8.47 (d, J=2.3 Hz, 1H), 8.18 (dd, J=2.3, 8.7 Hz, 1H), 7.41 (d, J=8.7 Hz, 1H), 6.33 (s, 1H), 5.16 (s, 2H), 2.31 (s, 3H), 2.18 (s, 3H), 2.12-2.03 (m, 1H), 2.01-1.92 (m, 2H), 1.82-1.71 (m, 1H)

General Procedures Relating to Scheme 3:

Intermediate S3-A 1-Methylquinazoline-2,4(1H,3H)-dione

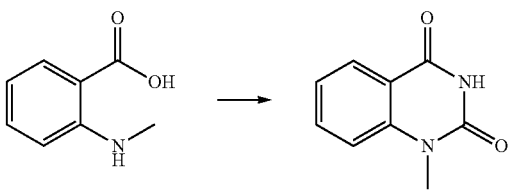

Sodium cyanate (30.15 g, 0.46 mol) was added to a slurry of N-methylanthranilic acid (50.0 g, 0.33 mol) in water (1.75 L) and acetic acid (3.3 mL). The reaction mixture was heated to 50° C. for 1 h. The solution was slowly basified by the addition of sodium hydroxide (exothermic). The resulting solution was heated to 80° C. and stirred overnight. The reaction mixture was cooled to 0° C. and the resultant precipitate collected by filtration. The solid was dissolved in boiling water (200 mL) and acidified with conc. sulfuric acid to pH 2. The slurry was cooled to room temperature and filtered. The solid was dried in a vacuum oven to give 1-methylquinazoline-2,4(1H,3H)-dione (53 g, 0.30 mol, 77%).

$^1$H NMR (300 MHz, DMSO-d$_6$) δ=11.54 (br. s., 1H), 8.00 (d, J=7.7 Hz, 1H), 7.77 (t, J=7.9 Hz, 1H), 7.43 (d, J=8.6 Hz, 1H), 7.28 (t, J=7.5 Hz, 1H), 3.33 (s, 3H)

Intermediate S3-B 1-Methyl-2,4-dioxo-1,2,3,4-tetra-hydroquinazoline-6-sulfonyl chloride

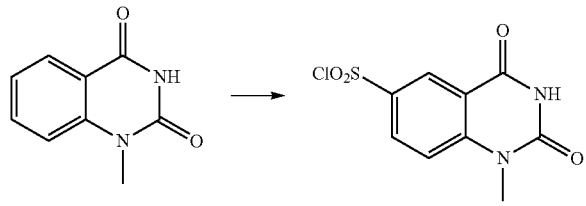 [SMILES: Cn1c(=O)[nH]c(=O)c2ccccc21 ; Cn1c(=O)[nH]c(=O)c2cc(S(=O)(=O)Cl)ccc21]

1-Methylquinazoline-2,4(1H,3H)-dione (25 g, 0.142 mol) was added portionwise to chlorosulfonic acid (125 mL, 1.88 mol) at 50° C. The reaction mixture was heated to 50° C. and stirred overnight then allowed to cool. The reaction mixture was added carefully to ice/water (1.5 L) maintaining the temperature <20° C. The resultant precipitate was collected by filtration and dried in an open atmosphere to give 1-methyl-2,4-dioxo-1,2,3,4-tetrahydroquinazoline-6-sulfonyl chloride as a white powder (44 g, 0.16 mol, 113%—contains water).

$^1$H NMR (300 MHz, DMSO-d$_6$) δ=11.57 (s, 1H), 8.19 (d, J=2.1 Hz, 1H), 7.91 (dd, J=2.2, 8.7 Hz, 1H), 7.38 (d, J=8.7 Hz, 1H)

Example 19 1-Methyl-N-(1-methylcyclopropyl)-2,4-dioxo-1,2,3,4-tetrahydroquinazoline-6-sulfonamide

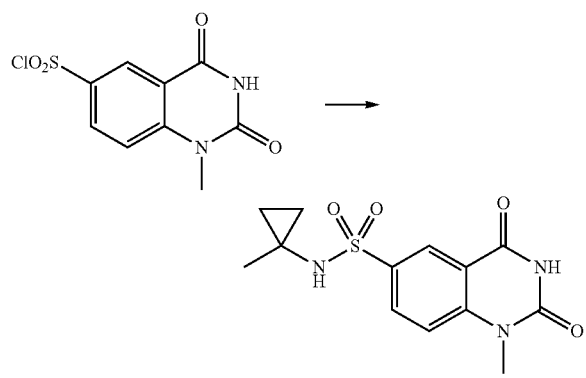

Triethylamine (8.1 g, 80.1 mmol) was added to a stirred solution of 1-methyl-2,4-dioxo-1,2,3,4-tetrahydroquinazoline-6-sulfonyl chloride (11.3 g, 36.4 mmol) in dichloromethane (250 mL). 1-Methylcyclopropanamine hydrochloride (4.3 g, 40.0 mmol) was added portionwise over 10 min and the reaction mixture was stirred at room temperature for 3 h. TLC showed the reaction to be complete. The reaction mixture was poured onto water (250 mL) and filtered to give the desired product 1-methyl-N-(1-methylcyclopropyl)-2,4-dioxo-1,2,3,4-tetrahydroquinazoline-6-sulfonamide (10.5 g, 0.034 mol, 93%).

$^1$H NMR (300 MHz, DMSO-d$_6$) δ=11.83 (br. s, 1H), 8.35 (d, J=2.4 Hz, 1H), 8.17 (s, 1H), 8.06 (dd, J=2.3, 8.8 Hz, 1H), 7.61 (d, J=8.9 Hz, 1H), 3.48 (s, 3H), 1.07 (s, 3H), 0.64-0.55 (m, 2H), 0.44-0.35 (m, 2H)

General Procedures Relating to Scheme 4:

Intermediate S4-A
2,4-Dioxo-1H-3,1-benzoxazine-6-sulfonyl chloride

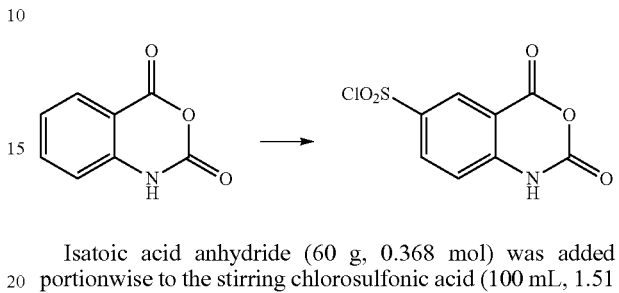

Isatoic acid anhydride (60 g, 0.368 mol) was added portionwise to the stirring chlorosulfonic acid (100 mL, 1.51 mol) at room temperature, the mixture was heated at 50° C. for 3 h. After cooling to room temperature, the reaction mixture was added dropwise into the ice/water. The precipitated solid was filtered and dried to give 2,4-dioxo-1H-3,1-benzoxazine-6-sulfonyl chloride (74 g, 0.283 mol, 77%).

$^1$H NMR (300 MHz, DMSO-d$_6$) δ=11.82 (s, 1H), 8.06 (d, J=2.0 Hz, 1H), 7.91 (dd, J=2.0, 8.5 Hz, 1H), 7.11 (d, J=8.5 Hz, 1H)

Intermediate S4-B1 2-Amino-5-[(1-methylcyclopropyl)sulfamoyl]-N-[(1-methylpyrazol-4-yl)methyl]benzamide

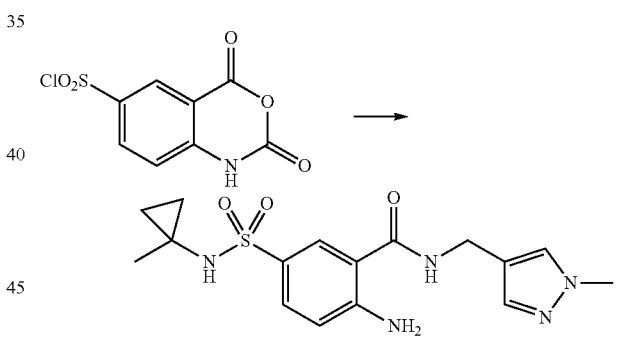

A suspension of compound 2,4-dioxo-1H-3,1-benzoxazine-6-sulfonyl chloride (10 g, 38.3 mmol) in DMF (100 mL) was treated with 1-methylcyclopropanamine hydrochloride (4.1 g, 38.3 mmol) and cooled to −10° C. in an ice/MeOH bath. Triethylamine (8.51 g, 87.5 mmol) was added to the mixture and the resulting solution was stirred at −10° C. for 1 h. (1-Methyl-1H-pyrazol-4-yl)methanamine (8.45 g, 57.5 mmol) in DMF (10 mL) was added to the mixture at 0° C., followed by triethylamine (11.6 g, 115 mmol) and the reaction mixture was stirred at room temperature for 3 h. Water (200 mL) was added to the reaction mixture, then extracted with EtOAc (2×100 mL). The combined organic phase was washed with brine (100 mL), dried over sodium sulfate, filtered and evaporated. The crude product was purified by automated column chromatography SiO$_2$ (Biotage, 120 g, eluent: 0-80% EtOAc in petroleum ether) to give 2-amino-5-[(1-methylcyclopropyl)sulfamoyl]-N-[(1-methylpyrazol-4-yl)methyl]benzamide (4.7 g, 12.9 mmol, 34%).

¹H NMR (300 MHz, DMSO-d₆) δ=8.83 (t, J=5.7 Hz, 1H), 7.87 (d, J=2.3 Hz, 1H), 7.58 (s, 1H), 7.55 (s, 1H), 7.46 (dd, J=2.2, 8.7 Hz, 1H), 7.35 (s, 1H), 7.09 (br. s, 2H), 6.79 (d, J=8.8 Hz, 1H), 4.22 (d, J=5.7 Hz, 2H), 3.78 (s, 3H), 1.04 (s, 3H), 0.65-0.51 (m, 2H), 0.36-0.29 (m, 2H)

The following intermediates were prepared by a similar method:

Intermediate S4-B2 2-Amino-5-[(1-methylcyclopropyl)sulfamoyl]-N-[(3-methylisoxazol-5-yl)methyl]benzamide

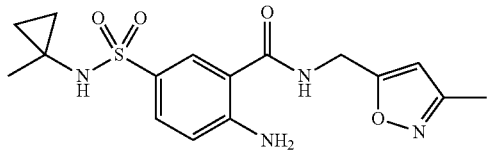

Prepared from 2,4-dioxo-1H-3,1-benzoxazine-6-sulfonyl chloride, 1-methylcyclopropanamine hydrochloride and (3-methylisoxazol-5-ylmethyl)amine.

¹H NMR (300 MHz, CDCl₃) δ=7.95 (d, J=2.1 Hz, 1H), 7.65 (dd, J=2.2, 9.1 Hz, 1H), 6.99 (br. s, 1H), 6.72 (d, J=8.6 Hz, 1H), 6.10 (s, 1H), 4.68 (d, J=5.7 Hz, 2H), 2.29 (s, 3H), 1.22 (s, 3H), 0.79-0.75 (m, 2H), 0.49-0.44 (m, 2H)

Intermediate S4-B3 2-Amino-N-[(3,5-dimethylisoxazol-4-yl)methyl]-5-[(1-ethylcyclopropyl)sulfamoyl]benzamide

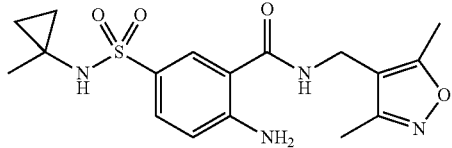 [SMILES: Cc1noc(C)c1CNC(=O)c1cc(S(=O)(=O)NC2(C)CC2)ccc1N]

Prepared from 2,4-dioxo-1H-3,1-benzoxazine-6-sulfonyl chloride, 1-methylcyclopropanamine hydrochloride and (3,5-dimethyl-1,2-oxazol-4-yl)methanamine.

¹H NMR (300 MHz, CDCl₃) δ=7.82 (d, J=2.2 Hz, 1H), 7.61 (dd, J=2.2, 8.8 Hz, 1H), 6.70 (d, J=8.8 Hz, 1H), 6.58 (br. s, 1H), 4.98 (br. s, 1H), 4.35 (d, J=5.4 Hz, 2H), 2.45 (s, 3H), 2.27 (s, 3H), 1.21 (s, 3H), 0.79-0.73 (m, 2H), 0.48-0.43 (m, 2H)

Intermediate S4-B4 2-Amino-5-[(1-methylcyclopropyl)sulfamoyl]-N-[(2-methylthiazol-5-yl)methyl]benzamide

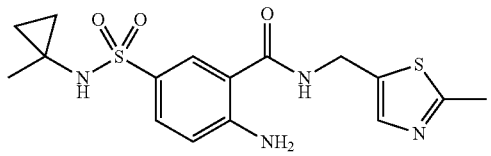

Prepared from 2,4-dioxo-1H-3,1-benzoxazine-6-sulfonyl chloride, 1-methylcyclopropanamine hydrochloride and (2-methyl-1,3-thiazol-5-yl)methanamine.

¹H NMR (300 MHz, CDCl₃) δ=7.90 (d, J=2.2 Hz, 1H), 7.62 (dd, J=2.2, 8.8 Hz, 1H), 7.53 (br. s, 1H), 7.12 (t, J=6.0 Hz, 1H), 6.70 (d, J=8.8 Hz, 1H), 6.24 (br. s, 2H), 5.11 (s, 1H), 4.71 (d, J=5.7 Hz, 2H), 3.08 (s, 1H), 2.68 (s, 3H), 1.18 (s, 3H), 0.80-0.72 (m, 2H), 0.47-0.42 (m, 2H)

Intermediate S4-B5 2-Amino-N-(cyanomethyl)-5-[(1-methylcyclopropyl)sulfamoyl]benzamide

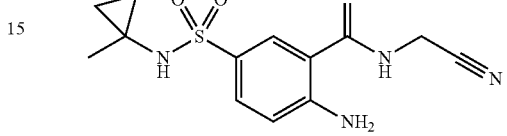

Prepared from 2,4-dioxo-1H-3,1-benzoxazine-6-sulfonyl chloride, 1-methylcyclopropanamine hydrochloride and aminoacetonitrile bisulfate.

¹H NMR (300 MHz, CDCl₃) δ=7.19 (s, 1H), 7.99 (d, J=2.2 Hz, 1H), 7.67 (dd, J=2.1, 8.8 Hz, 1H), 7.22-7.16 (m, 1H), 6.73 (d, J=8.8 Hz, 1H), 5.06 (br. s, 1H), 4.32 (d, J=5.7 Hz, 2H), 1.23 (s, 2H), 0.81-0.76 (m, 2H), 0.50-0.45 (m, 2H)

Intermediate S4-B6 2-Amino-5-[(1-cyanocyclopropyl)sulfamoyl]-N-[(3-methylisoxazol-5-yl)methyl]benzamide

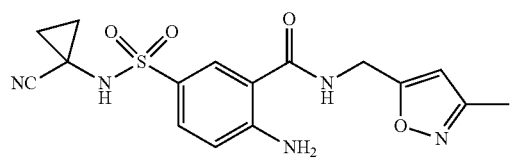 [SMILES: Cc1cc(CNC(=O)c2cc(S(=O)(=O)NC3(C#N)CC3)ccc2N)on1]

Prepared from 2,4-dioxo-1H-3,1-benzoxazine-6-sulfonyl chloride, 1-amino-1-cyclopropanecarbonitrile hydrochloride and (3-methylisoxazol-5-ylmethyl)amine.

¹H NMR (300 MHz, DMSO-d₆) δ=9.21 (t, J=5.7 Hz, 1H), 8.68 (s, 1H), 8.03 (d, J=2.3 Hz, 1H), 7.53 (dd, J=2.2, 8.9 Hz, 1H), 7.31 (s, 2H), 6.85 (d, J=8.9 Hz, 1H), 6.20 (s, 1H), 4.50 (d, J=5.5 Hz, 2H), 2.20 (s, 3H), 1.42-1.32 (m, 2H), 1.23-1.16 (m, 2H)

Intermediate S4-B7 2-Amino-N-cyclopropyl-5-[(1-methylcyclopropyl)sulfamoyl]benzamide

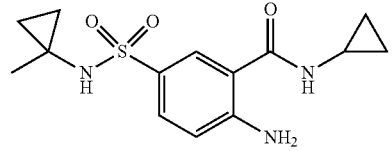 [SMILES: CC1(NS(=O)(=O)c2ccc(N)c(C(=O)NC3CC3)c2)CC1]

Prepared from 2,4-dioxo-1H-3,1-benzoxazine-6-sulfonyl chloride, 1-methylcyclopropanamine hydrochloride and cyclopropylamine.

¹H NMR (300 MHz, DMSO-d₆) δ=8.50 (d, J=4.0 Hz, 1H), 7.83 (d, J=2.3 Hz, 1H), 7.55 (s, 1H), 7.46 (dd, J=2.2, 8.7 Hz, 1H), 7.05 (br. s, 2H), 6.78 (d, J=8.8 Hz, 1H), 2.87-2.77 (m, 1H), 1.04 (s, 3H), 0.71-0.63 (m, 2H), 0.61-0.51 (m, 4H), 0.37-0.28 (m, 2H)

Intermediate S4-B8 2-Amino-4-fluoro-N-methyl-5-[(1-methylcyclopropyl)sulfamoyl]benzamide

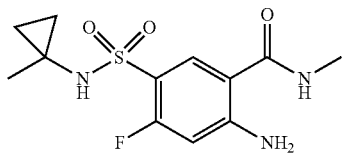

Prepared from 7-fluoro-2,4-dioxo-1H-3,1-benzoxazine-6-sulfonyl chloride, 1-amino-1-cyclopropanecarbonitrile hydrochloride and methylamine.

$^1$H NMR (300 MHz, DMSO-d$_6$) δ=8.53-8.46 (m, 1H), 7.91 (s, 1H), 7.35 (br. s, 2H), 6.55 (d, J=13.0 Hz, 1H), 2.72 (d, J=4.4 Hz, 3H), 1.10 (s, 3H), 0.67-0.60 (m, 2H), 0.39-0.32 (m, 2H)

Intermediate S4-C1 N-(1-Methylcyclopropyl)-3-[(1-methylpyrazol-4-yl)methyl]-2,4-dioxo-1H-quinazoline-6-sulfonamide

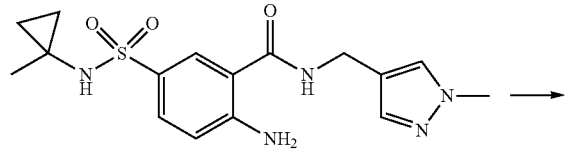

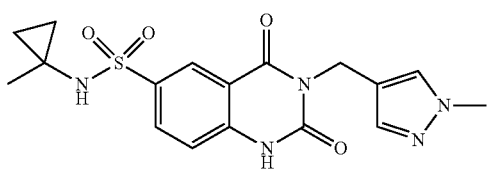

Triphosgene (1.9 g, 6.5 mmol) was added to a solution of compound 2-amino-5-[(1-methylcyclopropyl)sulfamoyl]-N-[(1-methylpyrazol-4-yl)methyl]benzamide (4.7 g, 12.9 mmol) in THF (50 mL) at 0° C. and the resulting mixture was warmed to room temperature over 1.5 h. The reaction mixture was quenched with 2 M NaOH (10 mL) and stirred overnight. EtOAc (50 mL) was added to the mixture which was then cooled and acidified with 2 M HCl (to pH 3). The organic phase was separated, dried and evaporated to afford N-(1-methylcyclopropyl)-3-[(1-methylpyrazol-4-yl)methyl]-2,4-dioxo-1H-quinazoline-6-sulfonamide (5.2 g, 10.6 mmol, 82%).

$^1$H NMR (400 MHz, CD$_3$OD): δ 8.51 (d, J=2.0 Hz, 1H), 8.03-8.05 (m, 1H), 7.68 (s, 1H), 7.54 (s, 1H), 7.29 (d, J=8.8 Hz, 1H), 5.05 (s, 2H), 3.84 (s, 3H), 1.16 (s, 3H), 0.7-0.71 (m, 2H), 0.43-0.46 (m, 2H)

The following intermediates were prepared by a similar method:

Example 221 N-(1-methylcyclopropyl)-3-[(3-isoxazol-5-yl)methyl]-2,4-dioxo-1H-quinazoline-6-sulfonamide

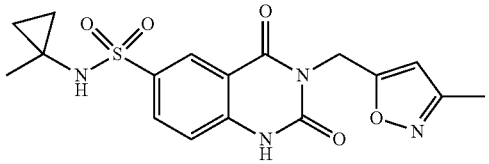

Prepared from 2-amino-5-[(1-methylcyclopropyl)sulfamoyl]-N-[(3-methylisoxazol-5-yl)methyl]benzamide and triphosgene.

$^1$H NMR (400 MHz, DMSO-d$_6$): δ 12.03 (s, 1H), 8.31 (d, J=8.3 Hz, 1H), 8.17 (s, 1H), 8.02-8.04 (m, 1H), 7.36 (d, J=8.8 Hz, 1H), 6.33 (s, 1H), 5.16 (s, 2H), 2.17 (s, 3H), 1.07 (s, 3H), 0.58 (m, 2H), 0.37-0.40 (m, 2H).

Intermediate S4-C3 3-[(3,5-Dimethylisoxazol-4-yl)methyl]-N-(1-methylcyclopropyl)-2,4-dioxo-1H-quinazoline-6-sulfonamide

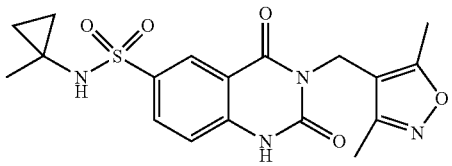 [SMILES: Cc1noc(C)c1Cn1c(=O)[nH]c2ccc(S(=O)(=O)NC3(C)CC3)cc2c1=O]

Prepared from 2-amino-N-[(3,5-dimethylisoxazol-4-yl)methyl]-5-[(1-methylcyclopropyl)sulfamoyl]benzamide and triphosgene.

$^1$H NMR (300 MHz, DMSO-d$_6$) δ=11.88 (s, 1H), 8.32 (d, J=2.2 Hz, 1H), 8.11 (s, 1H), 7.99 (dd, J=2.2, 8.6 Hz, 1H), 7.32 (d, J=8.6 Hz, 1H), 4.85 (s, 2H), 2.42 (s, 3H), 2.23 (s, 3H), 1.07 (s, 3H), 0.63-0.55 (m, 2H), 0.38 (d, J=2.3 Hz, 2H)

Example 220 N-(1-Methylcyclopropyl)-3-[(2-methylthiazol-5-yl)methyl]-2,4-dioxo-1H-quinazoline-6-sulfonamide

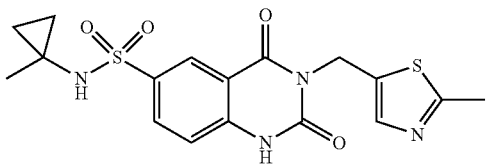

Prepared from 2-amino-5-[(1-methylcyclopropyl)sulfamoyl]-N-[(2-methylthiazol-5-yl)methyl]benzamide and triphosgene.

$^1$H NMR (300 MHz, DMSO-d$_6$) δ=11.98 (s, 1H), 8.32 (d, J=2.2 Hz, 1H), 8.14 (s, 1H), 8.01 (dd, J=2.2, 8.6 Hz, 1H), 7.61 (s, 1H), 7.33 (d, J=8.6 Hz, 1H), 5.19 (s, 2H), 1.06 (s, 3H), 0.65-0.51 (m, 2H), 0.45-0.31 (m, 2H)

Example 222 3-(Cyanomethyl)-N-(1-methylcyclopropyl)-2,4-dioxo-1H-quinazoline-6-sulfonamide

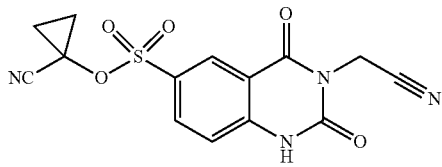 [SMILES: N#CCn1c(=O)[nH]c2ccc(S(=O)(=O)OC3(C#N)CC3)cc2c1=O]

Prepared from 2-amino-N-(cyanomethyl)-5-[(1-methylcyclopropyl)sulfamoyl]benzamide and triphosgene. The reaction mixture was cooled in an ice bath and then saturated aq. NaHCO₃ was added dropwise over 15 min, monitoring the pH. At pH 8 a precipitate formed. The aqueous phase was extracted with EtOAc (2×25 mL), the combined organic phase was passed through a hydrophobic frit and evaporated to dryness to yield the desired product.

$^1$H NMR (300 MHz, DMSO-$d_6$) δ=12.13 (s, 1H), 8.33 (d, J=2.2 Hz, 1H), 8.17 (s, 1H), 8.04 (dd, J=2.2, 8.6 Hz, 1H), 7.36 (d, J=8.7 Hz, 1H), 4.91 (s, 2H), 1.07 (s, 3H), 0.68-0.51 (m, 2H), 0.42-0.35 (m, 2H)

Example 228 N-(1-Cyanocyclopropyl)-3-[(3-methylisoxazol-5-yl)methyl]-2,4-dioxo-1H-quinazoline-6-sulfonamide

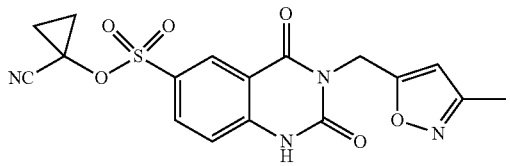 [SMILES: Cc1cc(Cn2c(=O)[nH]c3ccc(S(=O)(=O)OC4(C#N)CC4)cc3c2=O)on1]

Prepared from 2-amino-5-[(1-cyanocyclopropyl)sulfamoyl]-N-[(3-methylisoxazol-5-yl)methyl]benzamide and triphosgene.

$^1$H NMR (300 MHz, DMSO-$d_6$) δ=12.11 (s, 1H), 9.23 (s, 1H), 8.37 (d, J=2.3 Hz, 1H), 8.09 (dd, J=2.3, 8.7 Hz, 1H), 7.41 (d, J=8.7 Hz, 1H), 6.32 (s, 1H), 5.18 (s, 2H), 2.18 (s, 3H), 1.49-1.40 (m, 2H), 1.30-1.23 (m, 2H)

Example 240 3-Cyclopropyl-N-(1-methylcyclopropyl)-2,4-dioxo-1H-quinazoline-6-sulfonamide

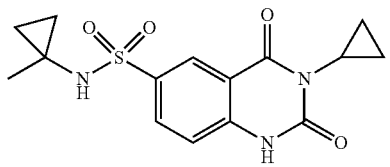 [SMILES: CC1(NS(=O)(=O)c2ccc3[nH]c(=O)n(C4CC4)c(=O)c3c2)CC1]

Prepared from 2-amino-N-cyclopropyl-5-[(1-methylcyclopropyl)sulfamoyl]benzamide and triphosgene.

$^1$H NMR (300 MHz, DMSO-$d_6$) δ=11.63 (br. s., 1H), 8.28 (d, J=2.1 Hz, 1H), 8.10 (s, 1H), 7.96 (dd, J=2.2, 8.6 Hz, 1H), 7.27 (d, J=8.6 Hz, 1H), 2.69-2.62 (m, 1H), 1.09-1.04 (m, 3H), 1.04-0.98 (m, 2H), 0.80-0.72 (m, 2H), 0.62-0.55 (m, 2H), 0.41-0.35 (m, 2H)

Example 211 7-Fluoro-3-methyl-N-(1-methylcyclopropyl)-2,4-dioxo-1H-quinazoline-6-sulfonamide

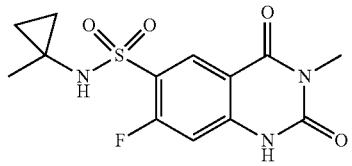 [SMILES: Cn1c(=O)[nH]c2cc(F)c(S(=O)(=O)NC3(C)CC3)cc2c1=O]

Prepared from 2-amino-4-fluoro-N-methyl-5-[(1-methylcyclopropyl)sulfamoyl]benzamide and triphosgene.

Example 223 2-[6-[(1-Methylcyclopropyl)sulfamoyl]-2,4-dioxo-1H-quinazolin-3-yl]acetamide

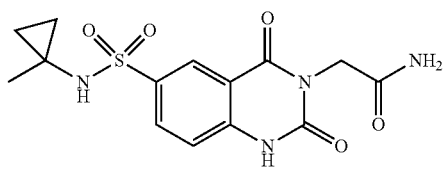 [SMILES: CC1(NS(=O)(=O)c2ccc3[nH]c(=O)n(CC(N)=O)c(=O)c3c2)CC1]

Prepared from 2-amino-N-(cyanomethyl)-5-[(1-methylcyclopropyl)sulfamoyl]benzamide and triphosgene. Hydrolysis of the nitrile occurred during work-up used as described for Intermediate S4-C1.

Intermediate S4-D1 2-Amino-4-fluoro-N-[(1-methylpyrazol-4-yl)methyl]benzamide

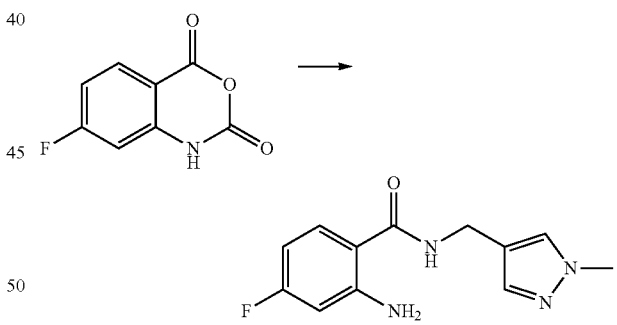

C-(1-Methyl-1H-pyrazol-4-yl)-methylamine (1.29 g, 11.59 mmol) was added to a solution of 7-fluoroisatoic anhydride (2.00 g, 11.04 mmol) in DMF (20 mL) at 0° C., and the resulting mixture was stirred at ambient temperature for 3 h, then heated at 40° C. for 1 h. The solvent was removed in vacuo and the crude product was suspended in ether (40 mL) with stirring for 30 min. The solid was then filtered and the filter cake washed with ether (2×20 mL) to yield 2-amino-4-fluoro-N-[(1-methylpyrazol-4-yl)methyl]benzamide (2.37 g, 9.56 mmol, 87%).

$^1$H NMR (300 MHz, DMSO-$d_6$) δ=8.55 (t, J=6.0 Hz, 1H), 7.57 (s, 1H), 7.54 (dd, J=6.6, 8.9 Hz, 1H), 7.33 (s, 1H), 6.76 (br. s, 2H), 6.44 (dd, J=2.6, 11.9 Hz, 1H), 6.29 (app. td, J=2.6, 8.6 Hz, 1H), 4.21 (d, J=5.7 Hz, 2H), 3.78 (s, 3H)

The following intermediates were prepared in a similar manner:

Intermediate S4-D2
2-Amino-4-fluoro-N-methyl-benzamide

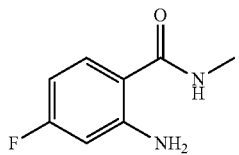

Prepared from 7-fluoroisatoic anhydride and methylamine (2 M in THF) in DCM, stirred at ambient temperature for 2 h.

$^1$H NMR (300 MHz, DMSO-d$_6$) δ=8.16 (br. s, 1H), 7.50 (dd, J=6.6, 8.8 Hz, 1H), 6.75 (br. s, 2H), 6.44 (dd, J=2.6, 11.9 Hz, 1H), 6.30 (app. td, J=2.6, 8.6 Hz, 1H), 2.71 (d, J=4.5 Hz, 3H)

Intermediate S4-D3 2-Amino-N-[(1-methylpyrazol-4-yl)methyl]benzamide

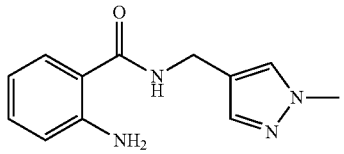 [SMILES: Cn1cc(CNC(=O)c2ccccc2N)cn1]

Prepared from isatoic acid anhydride and C-(1-methyl-1H-pyrazol-4-yl)-methylamine, heated at 50° C. for 3 h.

$^1$H NMR (300 MHz, DMSO-d$_6$) δ=8.54 (t, J=5.8 Hz, 1H), 7.57 (s, 1H), 7.46 (dd, J=1.6, 7.9 Hz, 1H), 7.33 (s, 1H), 7.12 (ddd, J=1.6, 7.0, 8.3 Hz, 1H), 6.68 (dd, J=1.3, 8.2 Hz, 1H), 6.48 (ddd, J=1.2, 6.9, 8.0 Hz, 1H), 6.41 (s, 2H), 4.22 (d, J=5.7 Hz, 2H), 3.78 (s, 3H)

Intermediate S4-D4 2-Amino-N-[(2-methylthiazol-5-yl)methyl]benzamide

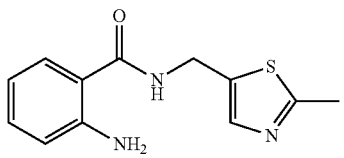 [SMILES: Cc1ncc(CNC(=O)c2ccccc2N)s1]

Prepared from isatoic acid anhydride and (2-methyl-1,3-thiazol-5-yl)methanamine, stirred at 50° C. for 3 h.

LCMS (high pH): RT 0.81 min, [M−H]$^−$ 246.1, 100% purity

Intermediate S4-D5 2-Amino-N-[(3-methylisoxazol-5-yl)methyl]benzamide

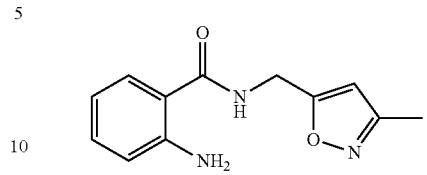

Prepared from isatoic acid anhydride and (3-methylisoxazol-5-ylmethyl)amine, stirred at ambient temperature overnight.

$^1$H NMR (300 MHz, DMSO-d$_6$) δ=8.84 (t, J=5.9 Hz, 1H), 7.53 (dd, J=1.6, 8.0 Hz, 1H), 7.16 (ddd, J=1.5, 7.0, 8.4 Hz, 1H), 6.70 (dd, J=1.2, 8.3 Hz, 1H), 6.52 (ddd, J=1.3, 7.0, 8.1 Hz, 1H), 6.46 (s, 2H), 6.18 (s, 1H), 4.48 (dd, J=0.9, 5.9 Hz, 2H), 2.22-2.18 (m, 3H)

Intermediate S4-E1
7-Fluoro-3-methyl-1H-quinazoline-2,4-dione

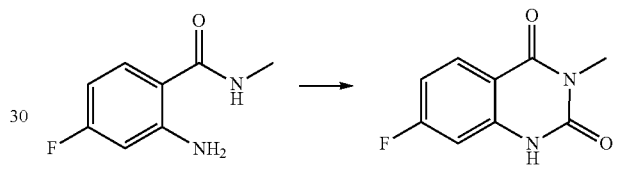

Triphosgene (564.67 mg, 1.9 mmol) was added to a solution of 2-amino-4-fluoro-N-methyl-benzamide (800. mg, 4.76 mmol) in 1,4-dioxane (10 mL) the resulting solution was stirred at ambient temperature for 2 h. The reaction was quenched by the addition of 1 N NaOH (10 mL) and allowed to stir overnight at ambient temperature. The volatiles were removed in vacuo and the resulting suspension diluted with water (20 mL) and filtered. The filter cake was washed with water (2×10 mL) and dried to give the desired product 7-fluoro-3-methyl-1H-quinazoline-2,4-dione (512.1 mg, 2.63 mmol, 55%).

$^1$H NMR (300 MHz, DMSO-d$_6$) δ=11.56 (br. s, 1H), 7.99 (dd, J=6.2, 8.9 Hz, 1H), 7.05 (app. td, J=2.5, 8.8 Hz, 1H), 6.90 (dd, J=2.4, 9.9 Hz, 1H), 3.24 (s, 3H), 1.23 (s, 1H)

The following intermediates were prepared in a similar manner:

Intermediate S4-E2 7-Fluoro-3-[(1-methylpyrazol-4-yl)methyl]-1H-quinazoline-2,4-dione

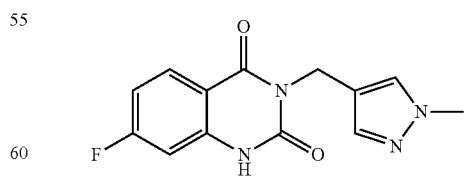

Prepared from 2-amino-4-fluoro-N-[(1-methylpyrazol-4-yl)methyl]benzamide and triphosgene in THF, after 1 h at ambient temperature triethylamine (1 eq) was added and the reaction mixture stirred for a further 1 h at ambient temperature.

¹H NMR (300 MHz, DMSO-d₆) δ=11.56 (br. s, 1H), 8.00 (dd, J=6.1, 8.9 Hz, 1H), 7.64 (s, 1H), 7.36 (s, 1H), 7.06 (app. td, J=2.4, 8.8 Hz, 1H), 6.90 (dd, J=2.4, 9.9 Hz, 1H), 4.87 (s, 2H), 3.33 (s, 3H)

Intermediate S4-E3 3-[(1-Methylpyrazol-4-yl)methyl]-1H-quinazoline-2,4-dione

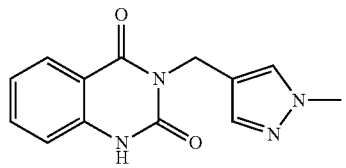 [SMILES: Cn1cc(Cn2c(=O)[nH]c3ccccc3c2=O)cn1]

Prepared from 2-amino-N-[(1-methylpyrazol-4-yl)methyl]benzamide and triphosgene in THF, stirred at ambient temperature overnight.

¹H NMR (300 MHz, DMSO-d₆) δ=11.43 (br. s, 1H), 7.94 (dd, J=1.6, 8.0 Hz, 1H), 7.68-7.62 (m, 2H), 7.36 (s, 1H), 7.23-7.15 (m, 2H), 4.89 (s, 2H), 3.75 (s, 3H)

Intermediate S4-E4 3-[(2-Methylthiazol-5-yl)methyl]-1H-quinazoline-2,4-dione

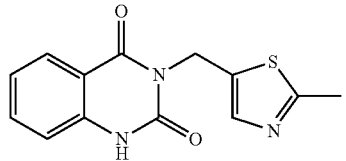 [SMILES: Cc1ncc(Cn2c(=O)[nH]c3ccccc3c2=O)s1]

Prepared from 2-amino-N-[(2-methylthiazol-5-yl)methyl]benzamide and triphosgene in THF, stirred at ambient temperature overnight.

LCMS (high pH): RT 0.83 min, [M+H]⁺ 274.1, 87% purity

Intermediate S4-E5 3-[(3-Methylisoxazol-5-yl)methyl]-1H-quinazoline-2,4-dione

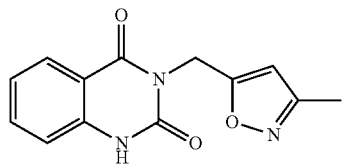 [SMILES: Cc1cc(Cn2c(=O)[nH]c3ccccc3c2=O)on1]

Prepared from 2-amino-N-[(3-methylisoxazol-5-yl)methyl]benzamide and triphosgene in THF, stirred at ambient temperature overnight.

¹H NMR (300 MHz, DMSO-d₆) δ=11.63 (br. s., 1H), 7.95 (ddd, J=0.8, 1.6, 7.9 Hz, 1H), 7.70 (ddd, J=1.5, 7.3, 8.2 Hz, 1H), 7.27-7.20 (m, 2H), 6.26 (s, 1H), 5.17 (s, 2H), 2.17 (s, 3H)

Intermediate S4-E6 7-Fluoro-1,3-dimethyl-quinazoline-2,4-dione

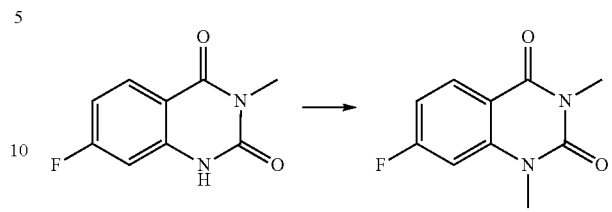

Sodium hydride (60% w/w) (113.31 mg, 2.83 mmol) was added to a solution of 7-fluoro-3-methyl-1H-quinazoline-2,4-dione (500. mg, 2.58 mmol) in DMF (10 mL), the reaction mixture was stirred at ambient temperature for 1 h. Iodomethane (0.18 mL, 2.83 mmol) was then added and the resulting mixture stirred at ambient temperature for 4 h. Following aqueous work-up the desired product was isolated 7-fluoro-1,3-dimethyl-quinazoline-2,4-dione (470 mg, 2.26 mmol, 88%).

¹H NMR (300 MHz, DMSO-d₆) δ=8.10 (dd, J=6.5, 8.8 Hz, 1H), 7.37 (dd, J=2.4, 11.2 Hz, 1H), 7.14 (app. td, J=2.4, 8.6 Hz, 1H), 3.49 (s, 3H), 3.29 (s, 3H)

The following intermediate was prepared in a similar manner:

Intermediate S4-E7 1-Methyl-3-[(3-methylisoxazol-5-yl)methyl]quinazoline-2,4-dione

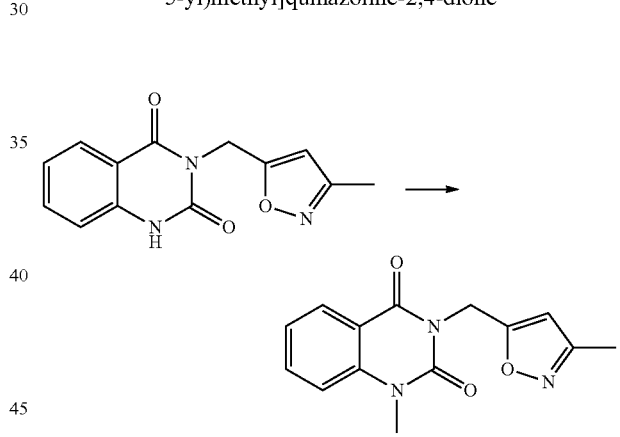

Prepared from 3-[(3-methylisoxazol-5-yl)methyl]-1H-quinazoline-2,4-dione, sodium hydride (60% w/w) and iodomethane.

¹H NMR (300 MHz, DMSO-d₆) δ=8.07 (dd, J=1.6, 7.8 Hz, 1H), 7.82 (ddd, J=1.6, 7.3, 8.5 Hz, 1H), 7.50 (d, J=8.3 Hz, 1H), 7.34 (ddd, J=0.8, 7.3, 7.9 Hz, 1H), 6.27 (s, 1H), 5.22 (s, 2H), 3.54 (s, 3H), 2.17 (s, 3H)

Intermediate S4-F1

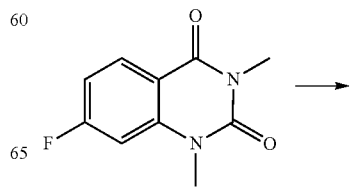

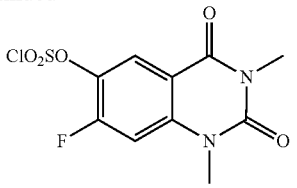

A solution of 7-fluoro-1,3-dimethyl-quinazoline-2,4-dione (400. mg, 1.92 mmol) in chlorosulfonic acid (3. mL, 1.92 mmol) was heated at 60° C. for 24 h. The reaction mixture was poured into ice (40 mL) and the resulting suspension was filtered. The filter-cake was washed with water (2×10 mL) to give the desired product 7-fluoro-1,3-dimethyl-2,4-dioxo-quinazoline-6-sulfonyl chloride (570 mg, 1.86 mmol, 97%).

$^1$H NMR (300 MHz, DMSO-d$_6$) δ=8.24 (d, J=7.9 Hz, 1H), 7.21 (d, J=11.7 Hz, 1H), 3.21 (s, 3H)

The following intermediate was prepared in a similar manner:

Intermediate S4-F2 7-Fluoro-3-[(1-methylpyrazol-4-yl)methyl]-2,4-dioxo-1H-quinazoline-6-sulfonyl chloride

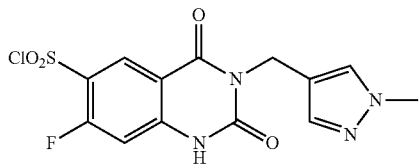 [SMILES: Cn1cc(Cn2c(=O)[nH]c3cc(F)c(S(=O)(=O)Cl)cc3c2=O)cn1]

Prepared from 7-fluoro-3-[(1-methylpyrazol-4-yl)methyl]-1H-quinazoline-2,4-dione and chlorosulfonic acid.

LCMS (high pH): RT 0.84 min, [M+H]$^+$ 373.0, 90% purity

Intermediate 1A 1-[(2,4-Dimethylthiazol-5-yl)methyl]-3-methyl-2,4-dioxo-quinazoline-6-sulfonyl chloride

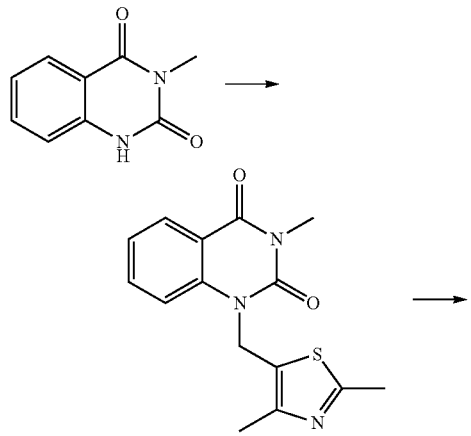

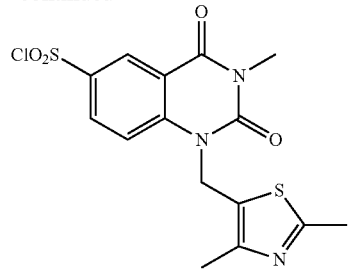

Step 1

To a stirred solution of 3-methyl-1H-quinazoline-2,4-dione (846.75 mg, 4.81 mmol) and potassium carbonate (1.4 g, 10.12 mmol) in DMF (10 mL) at 0° C. was added portionwise 5-(chloromethyl)-2,4-dimethyl-1,3-thiazole hydrochloride (1.0 g, 5.06 mmol). The reaction mixture was stirred at ambient temperature overnight. The reaction mixture was poured into ice/water (50 mL) and the resulting precipitate collected by vacuum filtration to afford 1-[(2,4-dimethylthiazol-5-yl)methyl]-3-methyl-quinazoline-2,4-dione (1.3 g, 4.17 mmol, 82%).

$^1$H NMR (300 MHz, DMSO-d$_6$) δ=8.09 (dd, J=1.5, 7.7 Hz, 1H), 7.80 (ddd, J=1.6, 7.2, 8.6 Hz, 1H), 7.46 (d, J=8.2 Hz, 1H), 7.32 (ddd, J=0.9, 7.2, 7.9 Hz, 1H), 5.43 (s, 2H), 3.34 (s, 3H), 2.48 (s, 3H), 2.47 (s, 3H)

Step 2

1-[(2,4-Dimethylthiazol-5-yl)methyl]-3-methyl-quinazoline-2,4-dione (1.2 g, 4.00 mmol) was added portionwise to chlorosulfonic acid (3.98 mL, 59.7 mmol), the reaction mixture was heated to 60° C. overnight. DCM (20 mL) was added to the reaction mixture, which was then added dropwise to a stirred 1:1 v/v mixture of ice/water and DCM. The organic layer was separated and the aqueous layer washed with DCM (2×30 mL). The organic layers were combined, washed with brine, passed through a hydrophobic frit then concentrated to dryness. The product was dried in the vacuum oven at 40° C. for 1 h and used without further purification, 1-[(2,4-dimethylthiazol-5-yl)methyl]-3-methyl-2,4-dioxo-quinazoline-6-sulfonyl chloride (1.5 g, 3.83 mmol, 96%).

$^1$H NMR (300 MHz, CDCl$_3$) δ=8.91 (d, J=2.4 Hz, 1H), 8.26 (dd, J=2.4, 8.9 Hz, 1H), 7.39 (d, J=9.0 Hz, 1H), 5.44 (s, 2H), 3.55 (s, 3H), 2.61 (s, 3H), 2.58 (s, 3H)

Method 1: Sulfonamide Formation

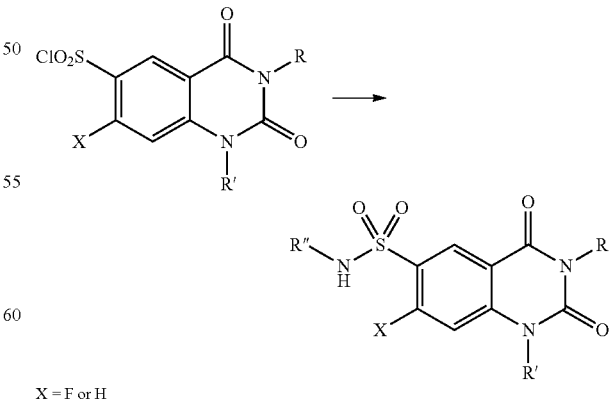

X = F or H

Quinazolinedione sulfonyl chloride derivative (1 eq), amine (2-3 eq) and triethylamine (2-3 eq) in DCM was stirred at ambient temperature and monitored by LCMS; reaction times vary from 1 h to overnight. The reaction mixture was diluted with 2 M HCl (5 mL) and DCM (5 mL) and stirred vigorously for 10 min, then filtered through a hydrophobic frit, the organic layer was concentrated to dryness. Alternatively, the reaction mixture was evaporated to dryness. The crude product was purified by automated column chromatography or prep. HPLC, high pH, to yield the desired product. For Examples 5 and 204, pyridine was used without addition of triethylamine.

The following intermediates were prepared using Method 1:

Example 384 7-Fluoro-N-(1-methylcyclopropyl)-3-[(1-methylpyrazol-4-yl)methyl]-2,4-dioxo-1H-quinazoline-6-sulfonamide

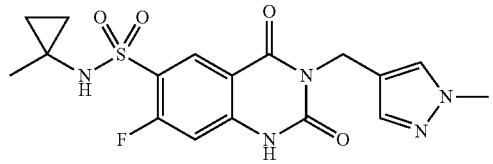

Prepared from 7-fluoro-3-[(1-methylpyrazol-4-yl)methyl]-2,4-dioxo-1H-quinazoline-6-sulfonyl chloride, 1-methylcyclopropanamine hydrochloride and diisopropylamine in place of triethylamine.

Intermediate S4-G2 N-(1-Cyanocyclopropyl)-7-fluoro-3-[(1-methylpyrazol-4-yl)methyl]-2,4-dioxo-1H-quinazoline-6-sulfonamide

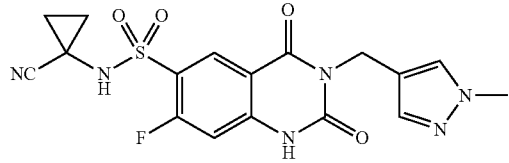 [SMILES: Cn1cc(Cn2c(=O)[nH]c3cc(F)c(S(=O)(=O)NC4(C#N)CC4)cc3c2=O)cn1]

Prepared from 7-fluoro-3-[(1-methylpyrazol-4-yl)methyl]-2,4-dioxo-1H-quinazoline-6-sulfonyl chloride, 1-amino-1-cyclopropanecarbonitrile hydrochloride and pyridine (5 mL) instead of DCM and triethylamine.

LCMS (high pH): RT 0.60 min, [M+H]$^+$ 419.1, >95% purity

Method 2: One-Pot Sulfonyl Chloride Formation/Sulfonamide Synthesis

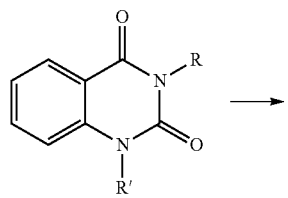

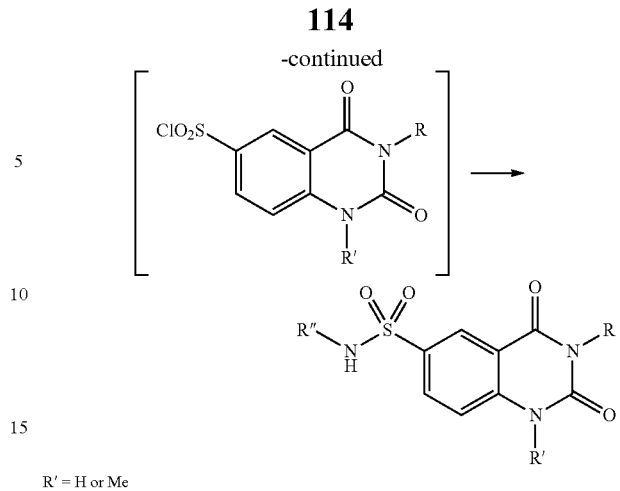

R' = H or Me

Step 1

Quinazolinedione intermediate (1 eq) in chlorosulfonic acid (20 eq) was heated at 60° C. for 3 h. The cooled reaction mixture was added to crushed ice (50 mL water) with stirring and once the addition was complete DCM (30 mL) was added and the mixture stirred for 5 min. The DCM layer was isolated by passing through a hydrophobic frit and the aqueous layer washed with DCM. The combined DCM extracts were concentrated under reduced pressure.

Step 2

The crude sulfonyl chloride was dissolved in DMF (5 mL) and the solution was added dropwise to a stirring solution of amine (1.5-3 eq), 4-dimethylaminopyridine (0.02 eq) and N,N-diisopropylethylamine (3 eq) in DMF (5 mL) and heated at 60° C. overnight. The reaction mixture was cooled and concentrated under reduced pressure. DCM (20 mL) and 1 M HCl (15 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography to yield the desired product. Used to prepare Examples 260 and 261.

The following intermediates were prepared using Method 2:

Example 336 N-(1-Cyanocyclopropyl)-3-[(1-methylpyrazol-4-yl)methyl]-2,4-dioxo-1H-quinazoline-6-sulfonamide

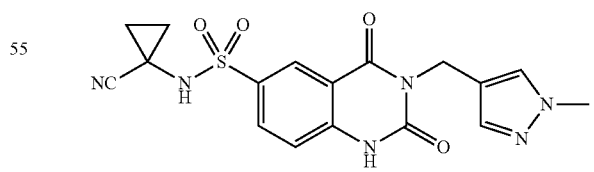

Prepared from 3-[(1-methylpyrazol-4-yl)methyl]-1H-quinazoline-2,4-dione and chlorosulfonic acid. Then, intermediate sulfonyl chloride, 1-amino-1-cyclopropanecarbonitrile hydrochloride and pyridine (5 mL) was used instead of 4-dimethylaminopyridine, N,N-diisopropylethylamine and DMF.

Intermediate S4-G4 N-(1-Cyanocyclopropyl)-3-[(2-methylthiazol-5-yl)methyl]-2,4-dioxo-1H-quinazoline-6-sulfonamide

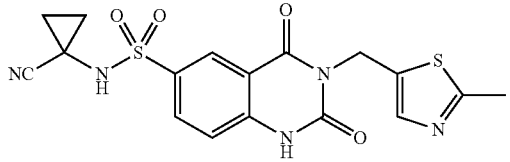 [SMILES: Cc1ncc(Cn2c(=O)[nH]c3ccc(S(=O)(=O)NC4(C#N)CC4)cc3c2=O)s1]

Prepared from 3-[(2-methylthiazol-5-yl)methyl]-1H-quinazoline-2,4-dione and chlorosulfonic acid. Then, intermediate sulfonyl chloride, 1-amino-1-cyclopropanecarbonitrile hydrochloride and pyridine (5 mL) was used instead of 4-dimethylaminopyridine, N,N-diisopropylethylamine and DMF.

LCMS (high pH): RT 0.68 min, [M+H]$^+$ 418.1, >95% purity

Intermediate S4-H1 N-(1-Cyanocyclopropyl)-N-[[3-[(1-methylpyrazol-4-yl)methyl]-2,4-dioxo-1H-quinazolin-6-yl]sulfonyl]acetamide

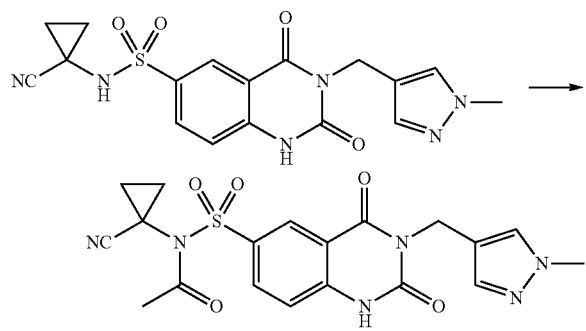

Acetyl chloride (0.36 mL, 4.99 mmol) was added to a mixture of N-(1-cyanocyclopropyl)-3-[(1-methylpyrazol-4-yl)methyl]-2,4-dioxo-1H-quinazoline-6-sulfonamide (1. g, 2.5 mmol) and potassium carbonate (1.73 g, 12.49 mmol) in DMF (20 mL), the reaction mixture was stirred at ambient temperature for 2 h. EtOAc (100 mL) and saturated aq. NaHCO$_3$ (100 mL) were added and the mixture stirred for 5 min. The organic layer was separated and the aqueous layer washed with EtOAc. The combined organic extracts were passed through a hydrophobic frit and concentrated under reduced pressure giving the crude product in a minimum volume of DMF. Water was added causing a precipitate to form. The precipitate was filtered, washed with water and allowed to dry to yield N-(1-cyanocyclopropyl)-N-[[3-[(1-methylpyrazol-4-yl)methyl]-2,4-dioxo-1H-quinazolin-6-yl]sulfonyl]acetamide (0.720 g, 1.59 mmol, 64%).

$^1$H NMR (300 MHz, DMSO-d$_6$) δ=11.99 (br. s, 1H), 11.99 (br. s, 1H), 8.13 (dd, J=2.5, 8.8 Hz, 1H), 7.67 (s, 1H), 7.43-7.32 (m, 2H), 4.89 (s, 2H), 3.76 (s, 3H), 2.30 (s, 3H), 2.14-2.02 (m, 1H), 1.98-1.85 (m, 2H), 1.83-1.68 (m, 1H)

The following intermediates were prepared in a similar manner:

Intermediate S4-H2 N-(1-Cyanocyclopropyl)-N-[[3-[(2-methylthiazol-5-yl)methyl]-2,4-dioxo-1H-quinazolin-6-yl]sulfonyl]acetamide

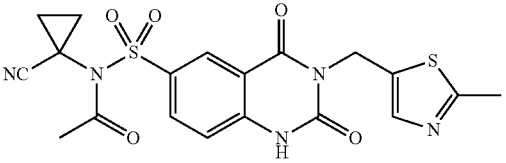 [SMILES: CC(=O)N(C1(C#N)CC1)S(=O)(=O)c1ccc2[nH]c(=O)n(Cc3cnc(C)s3)c(=O)c2c1]

Prepared from N-(1-cyanocyclopropyl)-3-[(2-methylthiazol-5-yl)methyl]-2,4-dioxo-1H-quinazoline-6-sulfonamide, acetyl chloride and potassium carbonate.

$^1$H NMR (300 MHz, DMSO-d$_6$) δ=12.12 (br. s., 1H), 8.46 (d, J=2.3 Hz, 1H), 8.15 (dd, J=2.4, 8.7 Hz, 1H), 7.61 (s, 1H), 7.37 (d, J=8.9 Hz, 1H), 5.19 (s, 2H), 2.57 (s, 3H), 2.30 (s, 3H), 2.14-2.03 (m, 1H), 2.01-1.88 (m, 2H), 1.82-1.69 (m, 1H)

Intermediate S4-H3 N-(1-Cyanocyclopropyl)-N-[[7-fluoro-3-[(1-methylpyrazol-4-yl)methyl]-2,4-dioxo-1H-quinazolin-6-yl]sulfonyl]acetamide

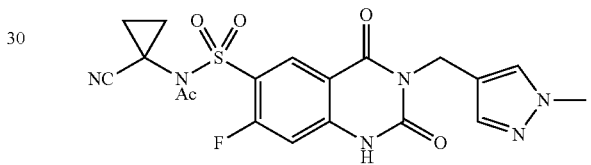

Prepared from N-(1-cyanocyclopropyl)-7-fluoro-3-[(1-methylpyrazol-4-yl)methyl]-2,4-dioxo-1H-quinazoline-6-sulfonamide, acetyl chloride and potassium carbonate.

$^1$H NMR (300 MHz, DMSO-d$_6$) δ=12.09 (br. s, 1H), 8.42 (d, J=7.8 Hz, 1H), 7.67 (s, 1H), 7.38 (s, 1H), 7.09 (d, J=11.2 Hz, 1H), 4.88 (s, 2H), 3.76 (s, 3H), 2.36 (s, 3H), 2.11-1.82 (m, 4H)

Method 3: Pyrazole Alkylation

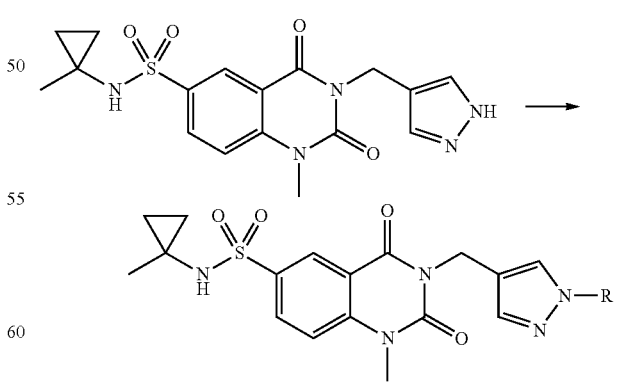

A solution of 1-methyl-N-(1-methylcyclopropyl)-2,4-dioxo-3-(1H-pyrazol-4-ylmethyl)quinazoline-6-sulfonamide (Example 183) (1 eq) and sodium hydride (60% w/w) (2.2 eq) in DMF was stirred at ambient temperature for 0.5 h.

Alkyl bromide (1 eq) was added to the reaction mixture, and the reaction mixture stirred at ambient temperature for 1-2 h. Water (1 mL) was carefully added to the reaction mixture followed by 2 M HCl (1 mL). DCM (10 mL) was added and the mixture was stirred vigorously for 10 min and then passed through a hydrophobic frit. The aqueous layer was washed with DCM (5 mL) and the combined organic phase concentrated to dryness in vacuo. The crude product was purified by prep. HPLC, high pH, to yield the desired product.

Alkylation of Quinazolinediones

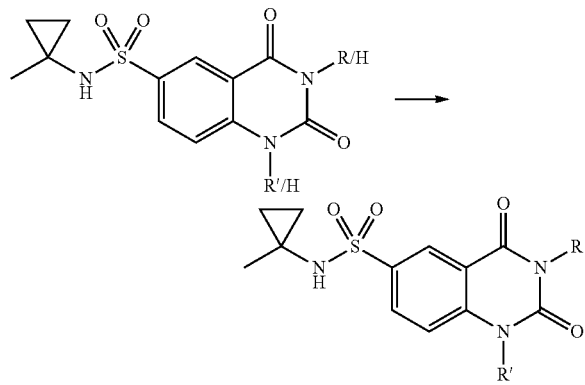

Method A1

Quinazolinedione intermediate (Intermediates S2-D1-S2-D3, S4-C1, S4-C4, S4-C7 and S4-H1) (1 eq), potassium carbonate (1.2 eq), alkyl halide or mesylate (1.2-1.5 eq) (if mesylate was used, NaI (0.2 eq.) added) in DMF was stirred at ambient temperature for 16 h (less if LCMS indicated reaction complete).

Examples 344-347, 355-359, 378 and 379 were prepared using potassium carbonate (4 eq.).

When using N-acyl sulfonamide intermediate; once alkylation was complete potassium carbonate (1 eq) and MeOH were added and the reaction mixture stirred at ambient temperature for 3 h. Alternatively, 500 µL of conc. ammonia was added and the reaction mixture left to stir for 2 h. DCM (10 mL) and saturated aq. NH₄Cl solution (10 mL) was added and the mixture stirred for 5 min. The DCM layer was isolated by passing through a hydrophobic frit and the aqueous layer washed with DCM.

Method A2

Quinazolinedione intermediate (Intermediates S2-D1, S2-D2, S3-C, S4-C1-S4-C5 and S4-H1) (1 eq), diisopropyl azodicarboxylate (2 eq), alkyl alcohol (2 eq), PS-PPh₃ (2 eq) and DMF were stirred at RT or 50° C. for 16 h (less if LCMS indicated reaction complete).

For Examples 341 and 342 the reaction was heated at 100° C.

When using N-acyl sulfonamide intermediate; once alkylation was complete the reaction mixture was filtered through a frit and then potassium carbonate (1 eq) and MeOH were added to the filtrate, the mixture was stirred at ambient temperature for 3 h. Alternatively, 500 µL of conc. ammonia was added and the reaction mixture left to stir for 2 h. DCM (10 mL) and saturated aq. NH₄Cl solution (10 mL) was added and the mixture stirred for 5 min. The DCM layer was isolated by passing through a hydrophobic frit and the aqueous layer washed with DCM.

Method A3

1-Methyl-N-(1-methylcyclopropyl)-2,4-dioxo-1,2,3,4-tetrahydroquinazoline-6-sulfonamide (Intermediate S3-C) (1 eq), sodium hydride (60% w/w) (1.1 eq), alkyl halide or mesylate (1.1 eq), (if mesylate was used, NaI (0.2 eq. added) in DMF was stirred at ambient temperature for 16 h (less if LCMS indicated reaction complete).

Method A4

Methane sulfonyl chloride (1.5 eq) and triethylamine (1.5 eq) were added to a solution of alcohol (1.5 eq) in THF, the reaction mixture was stirred for 2 h. Caesium carbonate (1.5 eq) and quinazolinedione intermediate (Intermediate S2-D1) (1 eq) were added sequentially to the mesylate THF solution, DMF was added to aid solubilisation and then potassium iodide (0.14 eq). The reaction mixture was stirred at ambient temperature for 64 h. DCM and saturated aq. NaHCO₃ were added, the organic phase was separated and evaporated to dryness in the Genevac. The resulting crude product was purified by prep. HPLC, high pH. The resulting N-acyl product was solubilised in DCM, potassium carbonate (10 mg) was added as the mixture stirred for 2 h. Water was added, the organic phase was separated using a hydrophobic frit and evaporated to dryness in the Genevac to give the desired product.

Method A5

Quinazolinedione intermediate (Intermediates S3-C, S4-C1-S4-C5 and S4-C8) (1 eq), caesium carbonate (1.1 eq), alkyl halide or mesylate (1.1 eq) in DMF was stirred at ambient temperature for 1-16 h (until LCMS indicated reaction complete).

Method A6

Quinazolinedione intermediate (Intermediates S4-C1 and S4-C2) (1 eq), caesium carbonate (3 eq), alkyl mesylate (1.1 eq), potassium iodide (1.2 eq) in DMF was heated by microwave irradiation at 100° C. for 1 h.

Method A7

Quinazolinedione intermediate (Intermediate S4-C2) (1 eq), caesium carbonate (3 eq), alkyl halide or mesylate (1.1 eq), potassium iodide (1.2 eq) in DMF was heated by microwave irradiation at 70° C. for 1 h.

Method A8

Quinazolinedione intermediate (Intermediates S3-C, S4-C1 and S4-C2) (1 eq), potassium carbonate (3 eq), alkyl halide or mesylate (1 eq), potassium iodide (1 eq) in DMF was stirred at ambient temperature for 48 h.

Method A9

Quinazolinedione intermediate (Intermediates S3-C, S4-C1 and S4-C2) (1 eq), potassium carbonate (2.2 eq), alkyl halide or mesylate (1.2 eq), potassium iodide (1 eq) in DMF was heated by microwave irradiation at 80° C. for 15 min.

Method A10

Quinazolinedione intermediate (Intermediates S4-C1 and S4-C2) (1 eq), potassium carbonate (1.2 eq), alkyl halide, mesylate or tosylate (1.2 eq), in DMF was heated by microwave irradiation at 80° C. for 10-20 min. The reaction mixture was monitored by LCMS and if <10% product conversion, further heated by microwave irradiation at 100° C. for 1-2 h. In certain cases, as indicated, sodium iodide (1.2 eq) was added to the reaction mixture.

For Example 324 further alkyl halide (1.2 eq) was added and the reaction mixture heated by microwave irradiation at 120° C. for 1 h.

For Examples 337 and 338 potassium carbonate (2 eq) and alkyl bromide (2 eq) were used. These reactions were further heated by microwave irradiation at 100° C. for 2 h.

Method A11

Quinazolinedione intermediate (Intermediate S4-C1), tert-BuOK (3 eq), alkyl halide (1.2 eq) and potassium iodide (1.2 eq) in DMF were heated at 100° C. for 24 h.

Method A12

Quinazolinedione intermediate (Intermediate S4-C2) (1 eq), potassium carbonate (1.2 eq), alkyl halide, mesylate or tosylate (1.2 eq) and sodium iodide (1.2 eq.) in DMF was heated by microwave irradiation at 120° C. for 30 min.

Examples 332 and 339 were further heated by microwave irradiation at 130° C. for 1-2 h.

Method A13

Quinazolinedione intermediate (Intermediates S4-C1, S4-C2) (1 eq), potassium carbonate (1.2 eq), alkyl halide, mesylate or tosylate (1.2 eq), in DMF was heated by microwave irradiation at 100° C. for 30 min.

Examples 321, 361 and 340 were further heated by microwave irradiation at ° C. or 120° C. respectively for 30 min and then 1 h.

Example 368, further alkyl bromide (0.6 eq) and sodium iodide (0.1 eq) were added and the reaction mixture further heated by microwave irradiation at 100° C. for 30 min, then 120° C. for 5 h.

Method A14

Quinazolinedione intermediate (Intermediates S4-C1, S4-C2) (1 eq), potassium carbonate (1.2 eq), alkyl halide, mesylate or tosylate (1.2 eq) and sodium iodide (1.2 eq.), in DMF was heated by microwave irradiation at 130° C. for 1 h and then a further 1 h.

Examples 343 and 348 were only heated for 1 h.

Example 330 potassium carbonate (3 eq) and alkyl chloride (3 eq) used.

Examples 371 and 372 potassium carbonate (3 eq) used and the reaction mixtures further heated by microwave irradiation at 135° C. for 5 h.

Work-up for Methods A1-A14; the mixture was concentrated in vacuo and either purified directly or underwent the following work-up, water and ethyl acetate were added and the layers separated. The organic layer was washed with water and concentrated under reduced pressure. Purification by mass directed prep. HPLC or automated column chromatography gave the desired products.

Amine Deprotection

Example 232 3-[(2-Aminothiazol-5-yl)methyl]-1-methyl-N-(1-methylcyclopropyl)-2,4-dioxo-quinazoline-6-sulfonamide

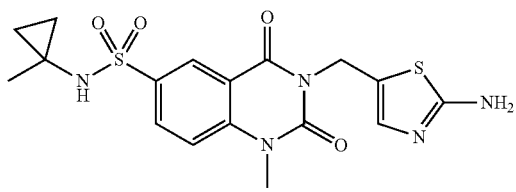 [SMILES: Cn1c(=O)n(Cc2cnc(N)s2)c(=O)c2cc(S(=O)(=O)NC3(C)CC3)ccc21]

Step 1

3-[[2-(2,5-Dimethylpyrrol-1-yl)thiazol-5-yl]methyl]-1-methyl-N-(1-methylcyclopropyl)-2,4-dioxo-quinazoline-6-sulfonamide prepared using Method A2, from Intermediate S3-C and [2-(2,5-dimethylpyrrol-1-yl)thiazol-5-yl]methanol.

Step 2

3-[[2-(2,5-Dimethylpyrrol-1-yl)thiazol-5-yl]methyl]-1-methyl-N-(1-methylcyclopropyl)-2,4-dioxo-quinazoline-6-sulfonamide (100. mg, 0.16 mmol), hydroxylamine hydrochloride (171.08 mg, 2.46 mmol) and 2 M NaOH (0.82 mL, 1.64 mmol). The reaction mixture was concentrated and the residue taken up in DCM, saturated aq. NaHCO$_3$ and water were added, stirred for 5 min and then passed through a hydrophobic frit and washed with DCM. The combined organics were concentrated and the residue purified by prep. HPLC to give 3-[(2-aminothiazol-5-yl)methyl]-1-methyl-N-(1-methylcyclopropyl)-2,4-dioxo-quinazoline-6-sulfonamide (8 mg, 0.019 mmol, 12%).

Example 233 3-[(3-Aminoisoxazol-5-yl)methyl]-1-methyl-N-(1-methylcyclopropyl)-2,4-dioxo-quinazoline-6-sulfonamide

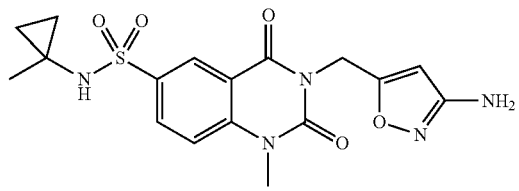 [SMILES: Cn1c(=O)n(Cc2cc(N)no2)c(=O)c2cc(S(=O)(=O)NC3(C)CC3)ccc21]

Step 1 tert-Butyl N-[5-[[1-methyl-6-[(1-methylcyclopropyl)sulfamoyl]-2,4-dioxo-quinazolin-3-yl]methyl]isoxazol-3-yl]carbamate prepared using Method A3, from Intermediate S3-C and tert-butyl N-[5-(bromomethyl)isoxazol-3-yl]carbamate.

Step 2

A solution of tert-butyl N-[5-[[1-methyl-6-[(1-methylcyclopropyl)sulfamoyl]-2,4-dioxo-quinazolin-3-yl]methyl]isoxazol-3-yl]carbamate (130.74 mg, 0.26 mmol) in 1,4-dioxane (2 mL) was treated with 4N HCl in 1,4-dioxane (0.5 mL, 2 mmol) and stirred at ambient temperature for 2 h, followed by heating at 45° C. for 27 h. The reaction mixture was concentrated in vacuo and purified by prep. HPLC to yield 3-[(3-aminoisoxazol-5-yl)methyl]-1-methyl-N-(1-methylcyclopropyl)-2,4-dioxo-quinazoline-6-sulfonamide (24 mg, 0.059 mmol, 23%).

Example 263 1-(2-Aminoethyl)-N-(1-methylcyclopropyl)-3-[(1-methylpyrazol-4-yl)methyl]-2,4-dioxo-quinazoline-6-sulfonamide hydrochloride

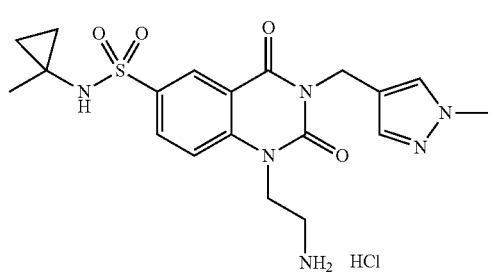

Step 1 tert-Butyl N-[2-[6-[(1-methylcyclopropyl)sulfamoyl]-3-[(1-methylpyrazol-4-yl)methyl]-2,4-dioxo-quinazolin-1-yl]ethyl]carbamate was prepared using Method A9, from Intermediate S4-C1 and N-Boc-bromoethylamine.

Step 2 tert-Butyl N-[2-[6-[(1-methylcyclopropyl)sulfamoyl]-3-[(1-methylpyrazol-4-yl)methyl]-2,4-dioxo-quinazolin-1-yl]ethyl]carbamate (38.5 mg, 0.070 mmol) in 4M HCl in dioxane (2. mL, 8 mmol) was stirred at ambient temperature for 2.5 h. The reaction mixture was evaporated to dryness in vacuo and dried in the vacuum oven to yield 1-(2-aminoethyl)-N-(1-methylcyclopropyl)-3-[(1-methylpyrazol-4-yl)methyl]-2,4-dioxo-quinazoline-6-sulfonamide hydrochloride (26 mg, 0.060 mmol, 83%).

Example 285 3-[(3-aminoisoxazol-5-yl)methyl]-1-[(2,5-dimethylpyrazol-3-yl)methyl]-N-(1-methylcyclopropyl)-2,4-dioxo-quinazoline-6-sulfonamide

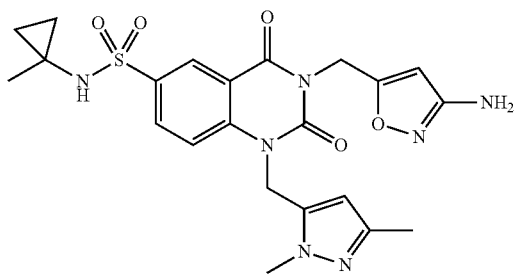 [SMILES: Cc1cc(Cn2c(=O)n(Cc3cc(N)no3)c(=O)c3cc(S(=O)(=O)NC4(C)CC4)ccc32)n(C)n1]

Step 1 tert-Butyl N-[5-[[[2-amino-5-[(1-methylcyclopropyl)sulfamoyl]benzoyl]amino]methyl]isoxazol-3-yl]carbamate was prepared using the route in Scheme 4 for Intermediates S4-B, from 2,4-dioxo-1H-3,1-benzoxazine-6-sulfonyl chloride, 1-amino-1-cyclopropanecarbonitrile hydrochloride and tert-butyl N-[5-(aminomethyl)isoxazol-3-yl]carbamate, and then used directly in Step 2, without purification.

Step 2 tert-butyl N-[5-[[6-[(1-methylcyclopropyl)sulfamoyl]-2,4-dioxo-1H-quinazolin-3-yl]methyl]isoxazol-3-yl]carbamate was prepared using the route in Scheme 4 for Intermediates S4-C, from tert-butyl N-[5-[[[2-amino-5-[(1-methylcyclopropyl)sulfamoyl]benzoyl]amino]methyl]isoxazol-3-yl]carbamate and triphosgene, and then used directly in Step 3, without purification.

Step 3 tert-Butyl N-[5-[[1-[(2,5-dimethylpyrazol-3-yl)methyl]-6-[(1-methylcyclopropyl)sulfamoyl]-2,4-dioxo-quinazolin-3-yl]methyl]isoxazol-3-yl]carbamate was prepared using Method A10, from tert-butyl N-[5-[[6-[(1-methylcyclopropyl)sulfamoyl]-2,4-dioxo-1H-quinazolin-3-yl]methyl]isoxazol-3-yl]carbamate and 5-(chloromethyl)-1,3-dimethylpyrazole.

Step 4

A solution of tert-butyl N-[5-[[1-[(2,5-dimethylpyrazol-3-yl)methyl]-6-[(1-methylcyclopropyl)sulfamoyl]-2,4-dioxo-quinazolin-3-yl]methyl]isoxazol-3-yl]carbamate (20. mg, 0.030 mmol) and 4M HCl in dioxane (0.05 mL, 0.20 mmol) in 1,4-dioxane (1 mL) was stirred at ambient temperature for 2 h, then heated at 50° C. for 5 h followed by heating at 35° C. for 16 h for 2 days. The reaction mixture was evaporated to dryness and purified by prep. HPLC to give 3-[(3-aminoisoxazol-5-yl)methyl]-1-[(2,5-dimethylpyrazol-3-yl)methyl]-N-(1-methylcyclopropyl)-2,4-dioxoquinazoline-6-sulfonamide (4 mg, 0.008 mmol, 30%).

Amide Formation

Intermediate 1B Methyl 4-[[6-[acetyl-(1-methylcyclopropyl)sulfamoyl]-3-methyl-2,4-dioxo-quinazolin-1-yl]methyl]benzoate

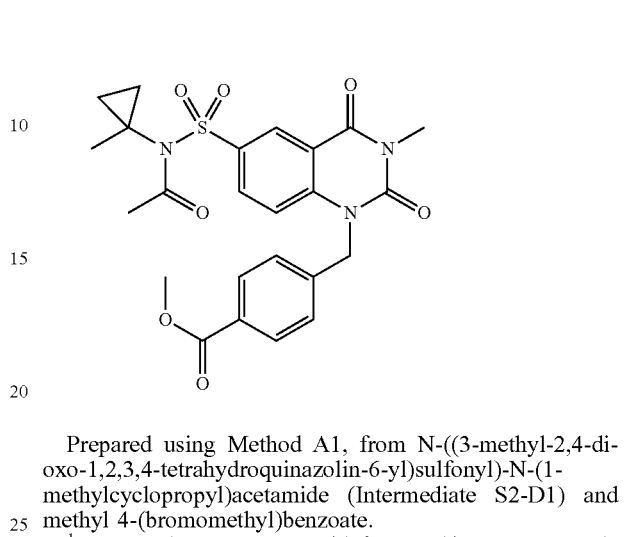

Prepared using Method A1, from N-((3-methyl-2,4-dioxo-1,2,3,4-tetrahydroquinazolin-6-yl)sulfonyl)-N-(1-methylcyclopropyl)acetamide (Intermediate S2-D1) and methyl 4-(bromomethyl)benzoate.

$^1$H NMR (300 MHz, CDCl$_3$) δ=8.75 (d, J=2.4 Hz, 1H), 8.20 (dd, J=2.4, 8.9 Hz, 1H), 8.03 (d, J=8.6 Hz, 2H), 7.32 (d, J=8.3 Hz, 2H), 7.14 (d, J=8.9 Hz, 1H), 5.45 (br. s, 2H), 3.92 (s, 3H), 3.57 (s, 3H), 2.25 (s, 3H), 1.58-1.37 (m, 1H), 1.29-1.11 (m, 1H), 1.08-0.85 (m, 2H)

Example 131 N-(3-Hydroxypropyl)-4-[[3-methyl-6-[(1-methylcyclopropyl)sulfamoyl]-2,4-dioxo-quinazolin-1-yl]methyl]benzamide

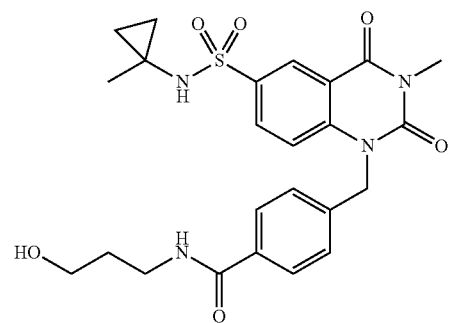 [SMILES: Cn1c(=O)c2cc(S(=O)(=O)NC3(C)CC3)ccc2n(Cc2ccc(C(=O)NCCCO)cc2)c1=O]

A suspension of methyl 4-[[6-[acetyl-(1-methylcyclopropyl)sulfamoyl]-3-methyl-2,4-dioxo-quinazolin-1-yl]methyl]benzoate (Intermediate 1B) (75. mg, 0.15 mmol) and 3-amino-1-propanol (0.5 mL, 6.54 mmol) was heated at 120° C. by microwave irradiation for 30 min. LCMS indicated formation of the carboxylic acid and desired product, the reaction mixture was heated for a further 30 min at 120° C. by microwave irradiation to observe if carboxylic acid would react. LCMS indicated decrease in desired product, little change in carboxylic acid. EtOAc (10 mL) and water (10 mL) were added to the reaction mixture, the organic phase was separated, passed through a hydrophobic frit and evaporated to dryness. The crude product was purified by prep. HPLC, high pH, to yield N-(3-hydroxypropyl)-4-[[3-methyl-6-[(1-methylcyclopropyl)sulfamoyl]-2,4-dioxo-quinazolin-1-yl]methyl]benzamide (9.5 mg, 0.0190 mmol, 13%).

Example 138 3-Methyl-N-(1-methylcyclopropyl)-2,4-dioxo-1-[[4-(piperazine-1-carbonyl)phenyl]methyl]quinazoline-6-sulfonamide

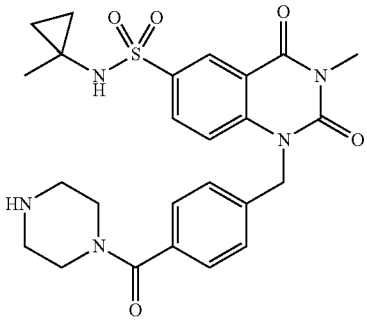 [SMILES: Cn1c(=O)c2cc(S(=O)(=O)NC3(C)CC3)ccc2n(Cc2ccc(C(=O)N3CCNCC3)cc2)c1=O]

Step 1

Methyl 4-[[6-[acetyl-(1-methylcyclopropyl)sulfamoyl]-3-methyl-2,4-dioxo-quinazolin-1-yl]methyl]benzoate (Intermediate 1B) (160. mg, 0.32 mmol) and lithium hydroxide (15.3 mg, 0.64 mmol) in THF (5 mL) and water (2 mL) were heated at reflux for 4.5 h. The reaction mixture was removed from heating, cooled and treated with 2 M HCl until acidic and a white precipitate formed. The white solid was filtered and dried in the vacuum oven to give 4-[[3-methyl-6-[(1-methylcyclopropyl)sulfamoyl]-2,4-dioxo-quinazolin-1-yl]methyl]benzoic acid (115 mg, 0.26 mmol, 81%), which was used without further purification.

Step 2

A solution of 4-[[3-methyl-6-[(1-methylcyclopropyl)sulfamoyl]-2,4-dioxo-quinazolin-1-yl]methyl]benzoic acid (55.0 mg, 0.12 mmol) and 1,1'-carbonyldiimidazole (20.1 mg, 0.12 mmol) in DMF (2 mL) were stirred at ambient temperature for 1 h. Piperazine (12.8 mg, 0.15 mmol) was added and the reaction mixture was heated at 60° C. overnight. Water (10 mL) and EtOAc (10 mL) were added to the reaction mixture, the organic phase was separated, passed through a hydrophobic frit and evaporated to dryness. The crude product was purified by prep. HPLC, high pH, to yield 3-methyl-N-(1-methylcyclopropyl)-2,4-dioxo-1-[[4-(piperazine-1-carbonyl)phenyl]methyl]quinazoline-6-sulfonamide (20 mg, 0.039 mmol, 32%).

Example 373 N-(1-methylcyclopropyl)-3-[(3-methylisoxazol-5-yl)methyl]-2,4-dioxo-1-(2-oxo-2-pyrrolidin-1-yl-ethyl)quinazoline-6-sulfonamide

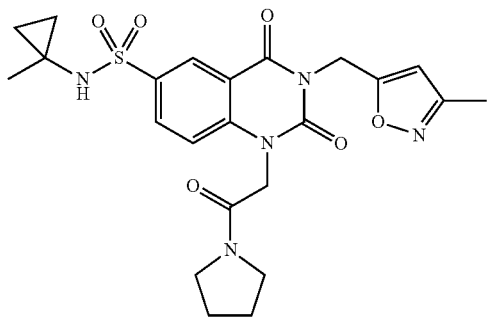

A mixture of ethyl 2-[6-[(1-methylcyclopropyl)sulfamoyl]-3-[(3-methylisoxazol-5-yl)methyl]-2,4-dioxo-quinazolin-1-yl]acetate (30. mg, 0.060 mmol) and pyrrolidine (0.05 mL, 0.63 mmol) in DMF (1 mL) were heated by microwave irradiation at 150° C. for 1 h and then 150° C. for 2 h. The reaction mixture was diluted with water (10 mL), acidified to pH 4 and extracted with EtOAc (2×20 mL), the combined organic phase was washed with brine (10 mL), passed through a hydrophobic frit and evaporated to dryness. The crude product was purified by prep. HPLC, low pH, to yield N-(1-methylcyclopropyl)-3-[(3-methylisoxazol-5-yl)methyl]-2,4-dioxo-1-(2-oxo-2-pyrrolidin-1-yl-ethyl)quinazoline-6-sulfonamide (1 mg, 0.002 mmol, 3%).

Thiol Oxidation

Example 370 N-(1-Methylcyclopropyl)-3-[(1-methylpyrazol-4-yl)methyl]-1-(2-methylsulfonylethyl)-2,4-dioxo-quinazoline-6-sulfonamide

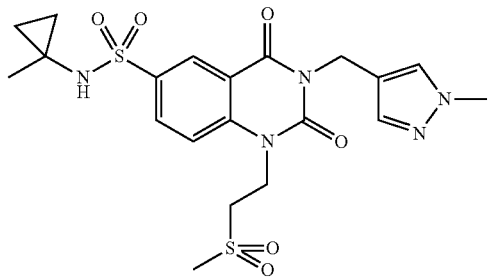

Example 369 N-(1-Methylcyclopropyl)-3-[(1-methylpyrazol-4-yl)methyl]-1-(2-methylsulfinylethyl)-2,4-dioxo-quinazoline-6-sulfonamide

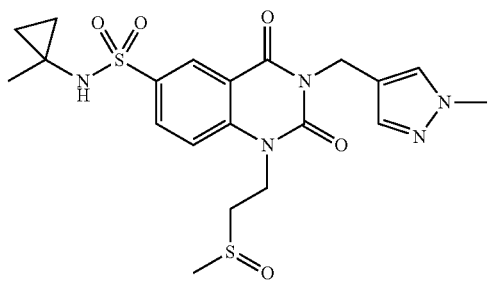

A solution of N-(1-methylcyclopropyl)-3-[(1-methylpyrazol-4-yl)methyl]-1-(2-methylsulfanylethyl)-2,4-dioxo-quinazoline-6-sulfonamide (76. mg, 0.12 mmol) in acetic acid (2 mL) was treated with hydrogen peroxide (0.1 mL, 3.26 mmol) and stirred at ambient temperature for 4.5 h, then 45° C. for 30 min. LCMS indicated 1:1 sulfoxide and sulfone present. Saturated aq. sodium sulphite (5 mL) was added to the reaction mixture, followed by extraction with EtOAc (2×10 mL), the combined organics were washed with water (20 mL), passed through a hydrophobic frit and concentrated to dryness. The crude product was purified by prep. HPLC, high pH, to yield N-(1-methylcyclopropyl)-3-[(1-methylpyrazol-4-yl)methyl]-1-(2-methylsulfinylethyl)-2,4-dioxo-quinazoline-6-sulfonamide (7 mg, 0.015 mmol, 12%) and N-(1-methylcyclopropyl)-3-[(1-methylpyrazol-4-yl)

methyl]-1-(2-methylsulfonylethyl)-2,4-dioxo-quinazoline-6-sulfonamide (23 mg, 0.046 mmol, 37%).

Example 382 1-[(1,1-Dioxothian-4-yl)methyl]-N-(1-methylcyclopropyl)-3-[(3-methylisoxazol-5-yl)methyl]-2,4-dioxo-quinazoline-6-sulfonamide

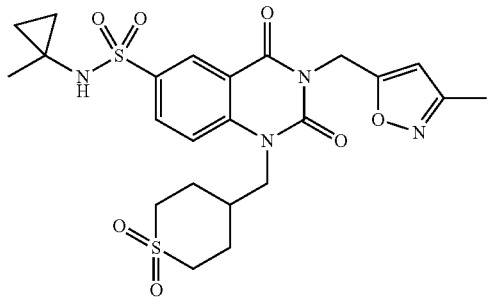

Hydrogen peroxide (30% w/w) (0.93 mL, 30.23 mmol) was added to a solution of N-(1-methylcyclopropyl)-3-[(3-methylisoxazol-5-yl)methyl]-2,4-dioxo-1-(tetrahydrothiopyran-4-ylmethyl)quinazoline-6-sulfonamide (45. mg, 0.090 mmol) in 1,4-dioxane (2 mL) at ambient temperature. The reaction mixture was stirred at ambient temperature overnight. LCMS indicated 100% conversion to sulphoxide but no conversion to the sulfone. 3-Chloroperbenzoic acid (15.39 mg, 0.090 mmol) was added and the reaction mixture stirred at ambient temperature for 2 h. The reaction mixture was diluted with water (20 mL) and extracted with EtOAc (2×20 mL) the combined organic phase was washed with aq. sodium metabisulphite (10 mL), passed through a hydrophobic frit and evaporated to dryness. The crude product was purified by prep. HPLC, high pH, to yield 1-[(1,1-dioxothian-4-yl)methyl]-N-(1-methylcyclopropyl)-3-[(3-methylisoxazol-5-yl)methyl]-2,4-dioxo-quinazoline-6-sulfonamide (23.0 mg, 0.043 mmol, 48%).

The following example was prepared in a similar manner:

Example 383 1-[(1,1-Dioxothian-4-yl)methyl]-N-(1-methylcyclopropyl)-3-[(1-methylpyrazol-4-yl)methyl]-2,4-dioxo-quinazoline-6-sulfonamide

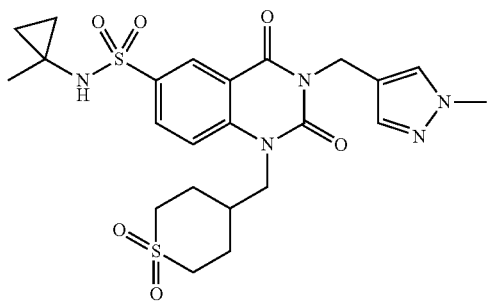

Prepared from N-(1-methylcyclopropyl)-3-[(3-methylisoxazol-5-yl)methyl]-2,4-dioxo-1-(tetrahydrothiopyran-4-ylmethyl)quinazoline-6-sulfonamide, hydrogen peroxide (30% w/w) and 3-chloroperbenzoic acid.

General Procedures Relating to Scheme 5

Intermediate S5-A
6-Bromo-2,3-dihydrophthalazine-1,4-dione

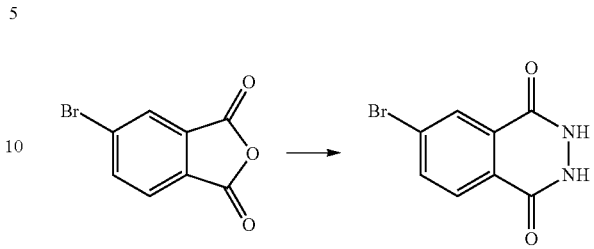

A stirred solution of 4-bromophthalic anhydride (50. g, 0.22 mol) in acetic acid (150 mL) was heated at 125° C. for 1 h. The mixture was then cooled to ambient temperature and hydrazine hydrate (11.25 mL, 0.23 mol) was added dropwise over 5 min, resulting in the formation of a thick white solid, further acetic acid (50 mL) was added and the mixture was heated at 125° C. for 30 min. The mixture was cooled and diluted with acetic acid (200 mL) before being filtered. The filter cake was washed with acetic acid (3×100 mL) and dried under vacuum. The cake was then dissolved in 5% (w/w) NaOH solution (250 mL), the suspension was acidified with acetic acid (30 mL) to give a thick white precipitate. The mixture was filtered and the filter cake washed sequentially with water (2×200 mL) and methanol (2×200 mL), and then dried under vacuum at 40° C. to give a white solid, 6-bromo-2,3-dihydrophthalazine-1,4-dione (55 g, 0.23 mol, quant.).

$^1$H NMR (300 MHz, DMSO-$d_6$) δ=8.16 (dd, J=0.7, 2.0 Hz, 1H), 7.98 (dd, J=0.7, 8.4 Hz, 1H), 7.93 (d, J=8.4 Hz, 1H), 1.84 (s, 2H)

Intermediate S5-B
7-Bromo-4-chlorophthalazin-1(2H)-one

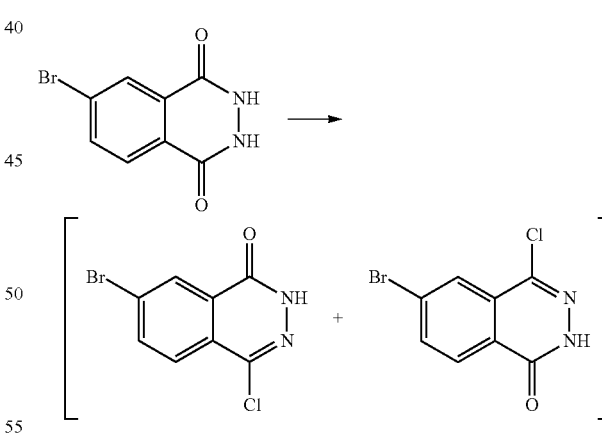

6-Bromo-2,3-dihydrophthalazine-1,4-dione (25. g, 0.10 mol) was added to a mixture of phosphorus oxychloride (100. mL, 1.06 mol) and thionyl chloride (100. mL, 1.37 mol) under nitrogen, cooled to 0° C. Once the initial exotherm had subsided the reaction mixture was allowed to warm to ambient temperature and then heated at 100° C. for 4 h. The reaction mixture was then cooled to ambient temperature and then concentrated in vacuo. The residue was dissolved in iPrOAc (350 mL) and washed with saturated sodium bicarbonate solution (added until effervescence stopped), a precipitate formed, the two layers were filtered to isolate the first crop of the intermediate. The organic layer was collected and distilled to dryness to give the second crop of the intermediate. The solids were combined and partitioned between 1,4-dioxane (200 mL) and 2 N NaOH (100 mL). The resulting mixture was heated at 40° C. overnight and then cooled to ambient temperature and left to stand. The solid precipitate was filtered (first crop of product) and the resulting solution partitioned between EtOAc (250 mL) and water (200 mL). Further precipitate formed which was filtered and combined with the first crop of the product, the organic phase was separated and evaporated to dryness to give the second crop of the product. Product isolated is a mixture of two regioisomers, 7-bromo-4-chloro-2H-phthalazin-1-one and 6-bromo-4-chloro-2H-phthalazin-1-one, total yield isolated (17.6 g, 68.0 mmol, 66%).

$^1$H NMR (300 MHz, DMSO-d$_6$) δ=13.02 (s, 1H), 12.98 (s, 1H), 8.36 (d, J=2.1 Hz, 1H), 8.22 (dd, J=2.1, 8.6 Hz, 1H), 8.17-8.11 (m, 3H), 7.93 (d, J=8.7 Hz, 1H). 1:1 mixture of the two regioisomers.

Intermediate S5-C1
7-(Benzylsulfanyl)-4-chlorophthalazin-1(2H)-one

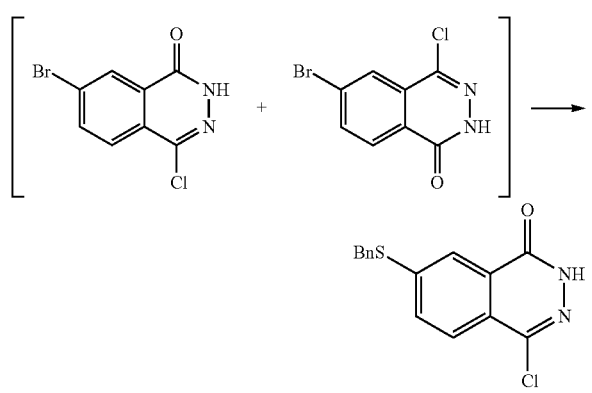

Reaction conducted in two flasks containing the reagents detailed below, then combined for work-up.

A stirred solution of 7-bromo-4-chloro-2H-phthalazin-1-one and 6-bromo-4-chloro-2H-phthalazin-1-one (8.82 g, 33.99 mmol) (1:1 mixture of isomers), tris(dibenzylideneacetone)dipalladium(0) (1.56 g, 1.7 mmol) and Xantphos (1.97 g, 3.4 mmol) in 1,4-dioxane (200 mL) was degassed with nitrogen. N,N-Diisopropylethylamine (12.1 mL, 68.0 mmol) and benzyl mercaptan (7.98 mL, 68.0 mmol) were then added sequentially to the flask, and the resulting mixture was heated at 60° C. for 18 h.

The two flasks were combined and distilled to dryness, the residue was suspended in DCM (200 mL). The mixture was agitated for 30 min and filtered to give the desired product as a ~1:1 mixture of regioisomers 7-benzylsulfanyl-4-chloro-2H-phthalazin-1-one and 6-benzylsulfanyl-4-chloro-2H-phthalazin-1-one. The mixture of isomers was recrystallised with acetic acid (200 mL), with a hot filtration to remove inorganic impurities. The resulting crystalline solid was filtered, washed with AcOH and minimal amount of ether, yielding a white solid which was dried in the vacuum oven at 40° C., 7-benzylsulfanyl-4-chloro-2H-phthalazin-1-one (5.35 g, 17.7 mmol, 26%).

$^1$H NMR (300 MHz, DMSO-d$_6$) δ=12.86 (s, 1H), 8.07 (d, J=2.1 Hz, 1H), 7.95 (dd, J=2.1, 8.6 Hz, 1H), 7.87 (d, J=8.6 Hz, 1H), 7.49-7.44 (m, 2H), 7.37-7.24 (m, 3H), 4.49 (s, 2H)

The following compound was prepared by a similar method:

Intermediate S5-C2 7-Benzylsulfanyl-4-chloro-2-methyl-phthalazin-1-one

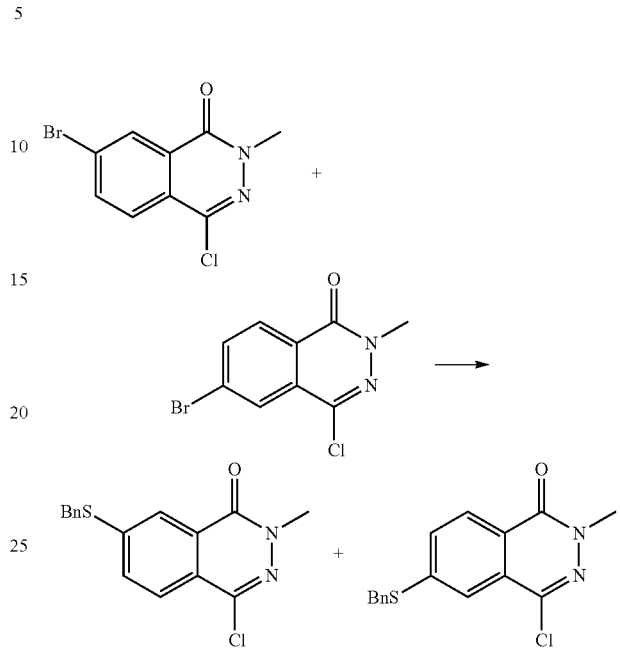

Prepared from a 1:1 regioisomeric mixture of 7-bromo-4-chloro-2-methyl-phthalazin-1-one and 6-bromo-4-chloro-2-methyl-phthalazin-1-one, benzyl mercaptan, tris(dibenzylideneacetone)dipalladium(0), Xantphos and N,N-diisopropylethylamine.

LCMS (high pH): RT 1.34 min, [M]+ 317.2, 93% purity

Intermediate S5-D1 7-Benzylsulfanyl-4-chloro-2-[(3-methylisoxazol-5-yl)methyl]phthalazin-1-one

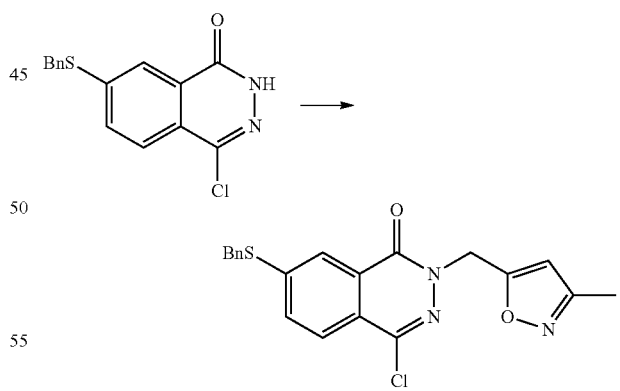

7-Benzylsulfanyl-4-chloro-2H-phthalazin-1-one (500. mg, 1.65 mmol) in DMF (15 mL) was cooled in an ice bath, treated with sodium hydride (60% w/w) (69.35 mg, 1.73 mmol), and the resulting mixture was stirred at ambient temperature for 1 h. 5-(Bromomethyl)-3-methyl-1,2-oxazole (0.22 mL, 1.73 mmol) was added to the reaction, and the resulting mixture was stirred at ambient temperature for 1 h. The reaction mixture was diluted with water (50 mL) and extracted with DCM (2×50 mL). The organic layer was passed through a hydrophobic frit and concentrated to dryness, the crude product was purified by automated column chromatography, eluent 0-40% EtOAc in iso-hexane to yield the desired product 7-benzylsulfanyl-4-chloro-2-[(3-methylisoxazol-5-yl)methyl]phthalazin-1-one (554 mg, 1.37 mmol, 83%).

$^1$H NMR (300 MHz, CDCl$_3$) δ=8.26 (d, J=2.0 Hz, 1H), 7.84 (d, J=8.6 Hz, 1H), 7.69 (dd, J=2.0, 8.6 Hz, 1H), 7.44-7.28 (m, 5H), 6.14 (s, 1H), 5.43 (s, 2H), 4.33 (s, 2H), 2.28 (s, 3H)

The following compound was prepared by a similar method:

Intermediate S5-D2
7-Bromo-4-chloro-2-methyl-phthalazin-1-one

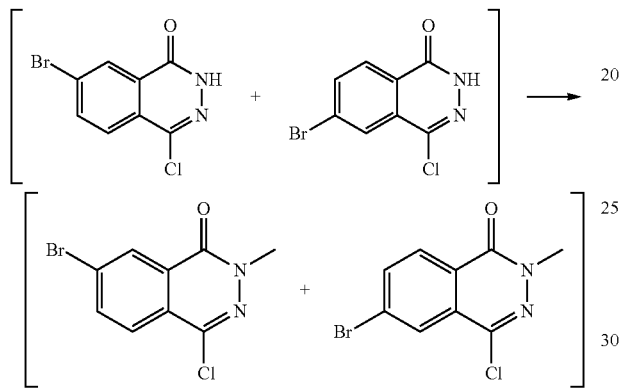

Prepared from a mixture of 7-bromo-4-chloro-2H-phthalazin-1-one and 6-bromo-4-chloro-2H-phthalazin-1-one and iodomethane.

$^1$H NMR (300 MHz, DMSO-d$_6$) δ=8.38 (d, J=2.0 Hz, 1H), 8.23-8.17 (m, 2H), 8.16-8.12 (m, 2H), 7.94 (d, J=8.6 Hz, 1H), 3.70 (s, 3H), 3.69 (s, 3H). 1:1 mixture of the two regioisomers.

Intermediate S5-E1 (2,3,4,5,6-Pentafluorophenyl) 1-chloro-3-[(3-methylisoxazol-5-yl)methyl]-4-oxo-phthalazine-6-sulfonate

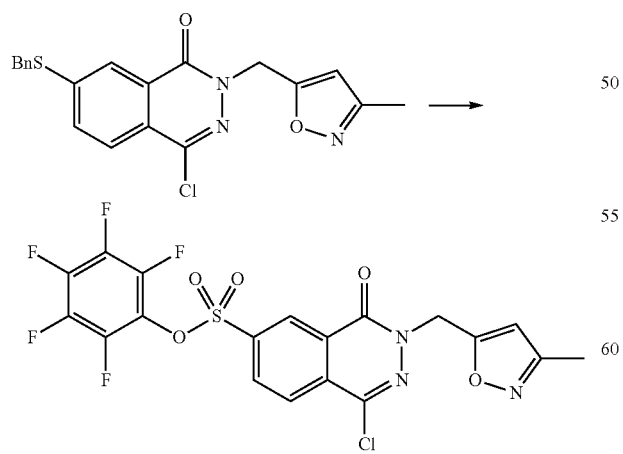

To a solution of 7-benzylsulfanyl-4-chloro-2-[(3-methylisoxazol-5-yl)methyl]phthalazin-1-one (1.80 g, 4.52 mmol) in a mixture of MeCN (50 mL), acetic acid (5 mL) and water (3 mL) at 0° C. was added 1,3-dichloro-5,5-dimethylhydantoin (1.78 g, 9.05 mmol), and the resulting mixture was stirred at 0° C. for 1 h. Pentafluorophenol (0.95 mL, 9.05 mmol) was added and the resulting mixture was stirred at 0° C. for 15 min, triethylamine (1.77 mL, 12.7 mmol) was added and the resulting mixture was stirred at 0° C. for 30 min. The reaction mixture was evaporated to dryness and the crude product purified by automated column chromatography (SiO$_2$, RediSep, 12 g) 0-80% EtOAc in iso-hexane to yield (2,3,4,5,6-pentafluorophenyl) 1-chloro-3-[(3-methyl-isoxazol-5-yl)methyl]-4-oxo-phthalazine-6-sulfonate (1.90 g, 3.64 mmol, 80%).

$^1$H NMR (300 MHz, CDCl$_3$) δ=9.04 (d, J=2.4 Hz, 1H), 8.45 (dd, J=2.0, 8.6 Hz, 1H), 8.27 (d, J=8.6 Hz, 1H), 6.22 (s, 1H), 5.48 (s, 2H), 2.30 (s, 3H) The following compound was prepared by a similar method:

Intermediate S5-E2 (2,3,4,5,6-Pentafluorophenyl) 1-chloro-3-methyl-4-oxo-phthalazine-6-sulfonate

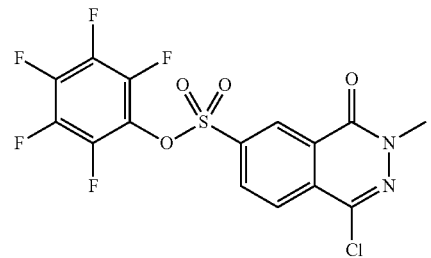 [SMILES: Cn1nc(Cl)c2ccc(S(=O)(=O)Oc3c(F)c(F)c(F)c(F)c3F)cc2c1=O]

Prepared from a 1:1 mixture of regioisomers, 7-benzylsulfanyl-4-chloro-2-methyl-phthalazin-1-one and 6-benzylsulfanyl-4-chloro-2-methyl-phthalazin-1-one, 1,3-dichloro-5,5-dimethylhydantoin, pentafluorophenol and triethylamine. Purification by automated column chromatography allowed for separation of the desired isomer for the product.

$^1$H NMR (300 MHz, CDCl$_3$) δ=9.04 (d, J=1.9 Hz, 1H), 8.42 (dd, J=2.0, 8.6 Hz, 1H), 8.25 (d, J=8.6 Hz, 1H), 3.89 (s, 3H)

Example 262 1-Chloro-N-(1-methylcyclopropyl)-3-[(3-methylisoxazol-5-yl)methyl]-4-oxo-phthalazine-6-sulfonamide

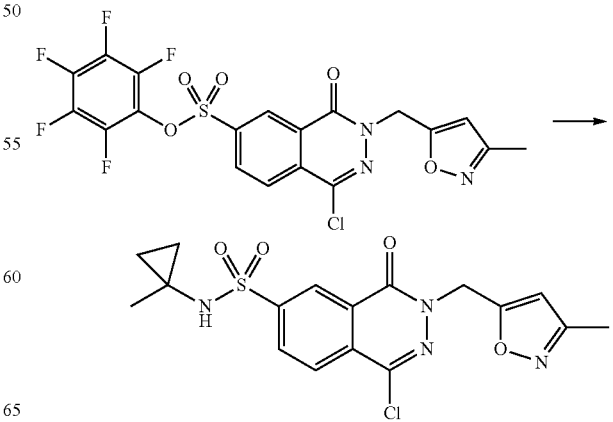

To a stirred solution of (2,3,4,5,6-pentafluorophenyl) 1-chloro-3-[(3-methylisoxazol-5-yl)methyl]-4-oxo-phthalazine-6-sulfonate (900. mg, 1.72 mmol) and 1-methylcyclopropanamine hydrochloride (204.09 mg, 1.9 mmol) in DMF (20 mL) at ambient temperature, under nitrogen, was added triethylamine (0.53 mL, 3.79 mmol) the reaction mixture was heated at 40° C. for 2 h. The reaction mixture was evaporated to dryness and partitioned between DCM (10 mL) and water (10 mL). The organic phase was collected and evaporated to dryness, the crude product was purified by automated column chromatography (SiO$_2$, RediSep, 12 g) eluent 0-70% EtOAc in iso-hexane to afford 1-chloro-N-(1-methylcyclopropyl)-3-[(3-methylisoxazol-5-yl)methyl]-4-oxo-phthalazine-6-sulfonamide (400.0 mg, 0.98 mmol, 57%).

$^1$H NMR (300 MHz, DMSO-d$_6$) δ=8.65 (d, J=8.0 Hz, 1H), 8.57 (s, 1H), 8.37 (dd, J=2.1, 8.6 Hz, 1H), 8.26 (d, J=8.5 Hz, 1H), 6.43 (s, 1H), 5.45 (s, 2H), 2.20 (s, 3H), 1.08 (s, 3H), 0.64-0.57 (m, 2H), 0.47-0.39 (m, 2H)

The following compound was prepared by a similar method:

Example 227 1-Chloro-3-methyl-N-(1-methylcyclopropyl)-4-oxo-phthalazine-6-sulfonamide

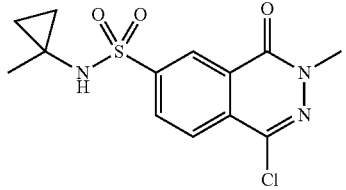

Prepared from (2,3,4,5,6-Pentafluorophenyl) 1-chloro-3-methyl-4-oxo-phthalazine-6-sulfonate, 1-methylcyclopropanamine hydrochloride and triethylamine.

$^1$H NMR (300 MHz, CDCl$_3$) δ=8.95 (d, J=1.9 Hz, 1H), 8.35 (dd, J=2.0, 8.5 Hz, 1H), 8.13 (d, J=8.5 Hz, 1H), 5.21 (s, 1H), 3.87 (s, 3H), 1.25 (s, 3H), 0.81-0.74 (m, 2H), 0.59-0.51 (m, 2H)

N-Substituted Phthalazinones

Method 4: Amine Substitution

A mixture of 1-chloro-N-(1-methylcyclopropyl)-3-[(3-methylisoxazol-5-yl)methyl]-4-oxo-phthalazine-6-sulfonamide (Intermediate S5-F1) (1 eq) and amine (20 eq) in ethanol (1 mL) was heated by microwave irradiation at 180° C. for 30 min. LCMS analysis incomplete reaction. The reaction mixture was further heated by microwave irradiation at 180° C. for 1 h, twice.

The reaction mixture was evaporated to dryness and the crude product purified by prep. HPLC, high pH, to give the desired product.

Example 234 3-Methyl-1-(methylamino)-N-(1-methylcyclopropyl)-4-oxo-phthalazine-6-sulfonamide

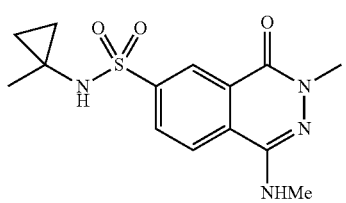

A mixture of 1-chloro-3-methyl-N-(1-methylcyclopropyl)-4-oxo-phthalazine-6-sulfonamide (80. mg, 0.2400 mmol) and methylamine (2 M in THF) (1. mL, 24.34 mmol) was heated by microwave irradiation at 180° C. for 1 h. The reaction mixture was partitioned between EtOAc (4 mL) and water (4 mL). The EtOAc layer was collected and washed with water (4 mL) before being distilled to dryness. The crude product was purified by prep. HPLC, low pH, to give the desired product 3-methyl-1-(methylamino)-N-(1-methylcyclopropyl)-4-oxo-phthalazine-6-sulfonamide (20 mg, 0.062 mmol, 25%).

The following compound was prepared by a similar method:

Example 244 1-(methylamino)-N-(1-methylcyclopropyl)-3-[(3-methylisoxazol-5-yl)methyl]-4-oxo-phthalazine-6-sulfonamide

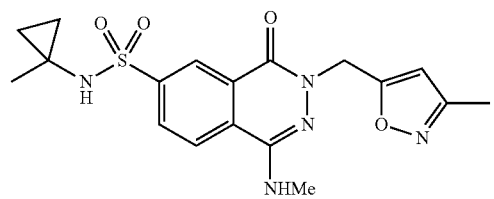

Prepared from 1-chloro-N-(1-methylcyclopropyl)-3-[(3-methylisoxazol-5-yl)methyl]-4-oxo-phthalazine-6-sulfonamide and methylamine (2 M in THF).

Example 299 N-(1-Methylcyclopropyl)-3-[(3-methylisoxazol-5-yl)methyl]-4-oxo-phthalazine-6-sulfonamide

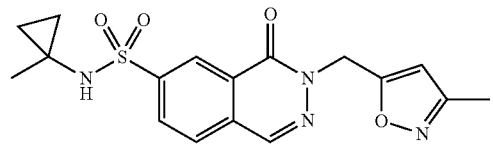

Prepared as a by-product under Method 4 conditions from 1-chloro-N-(1-methylcyclopropyl)-3-[(3-methylisoxazol-5-yl)methyl]-4-oxo-phthalazine-6-sulfonamide and cyclopropylamine, after heating by microwave irradiation at 180° C. for 30 min.

O-Substituted Phthalazinones

Method 5: Alcohol Substitution

1-Chloro-N-(1-methylcyclopropyl)-3-[(3-methylisoxazol-5-yl)methyl]-4-oxo-phthalazine-6-sulfonamide (Intermediate S5-F1) (1 eq) was added to a suspension of alcohol (3 eq) and potassium tert-butoxide (4 eq) in MeCN (1 mL). The reaction mixture was heated at reflux in a sealed Wheaton vial for 30 min, then stirred at ambient temperature overnight. Water (20 mL) and EtOAc (20 mL) were added to the reaction mixture, the aqueous phase was acidified to pH 2 with 2 M HCl. The organic phase was separated, further extraction with EtOAc (20 mL), the organic phases were combined, passed through a hydrophobic frit and evaporated to dryness. The crude product was purified by automated column chromatography, eluent EtOAc in iso-Hexane.

Example 312 1-Methoxy-N-(1-methylcyclopropyl)-3-[(3-methylisoxazol-5-yl)methyl]-4-oxo-phthalazine-6-sulfonamide

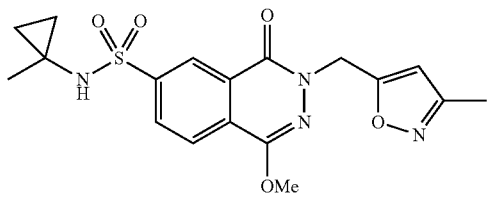

Sodium methoxide (0.5 N in methanol) (22.65 uL, 0.12 mmol) was added dropwise to a suspension of 1-chloro-N-(1-methylcyclopropyl)-3-[(3-methylisoxazol-5-yl)methyl]-4-oxo-phthalazine-6-sulfonamide (50. mg, 0.12 mmol) in MeCN (1 mL) at ambient temperature. The reaction mixture was stirred at ambient temperature for 4.5 h then further sodium methoxide (0.5 N in methanol) (45.2 uL, 0.24 mmol) was added and the reaction mixture was heated in a sealed Wheaton vial at reflux for 24 h. Water (20 mL) and EtOAc (20 mL) were added to the reaction mixture, the aqueous phase was acidified to pH 2 with 2 M HCl, then the organic phase was separated. The aqueous phase was further extracted with EtOAc (20 mL), and the combined organic phases were passed through a hydrophobic frit and evaporated to dryness. The crude product was purified by automated column chromatography SiO₂ (RediSep, 4 g) wet loaded in DCM, eluent 0-50% EtOAc in iso-Hexane, to yield 1-methoxy-N-(1-methylcyclopropyl)-3-[(3-methylisoxazol-5-yl)methyl]-4-oxo-phthalazine-6-sulfonamide (25.2 mg, 0.062 mmol, 51%).

Example 316 1-Ethoxy-N-(1-methylcyclopropyl)-3-[(3-methylisoxazol-5-yl)methyl]-4-oxo-phthalazine-6-sulfonamide

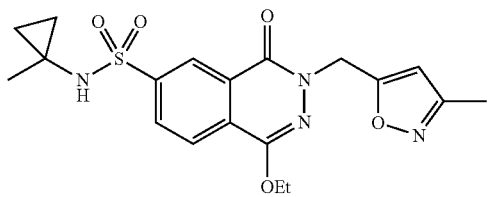

A suspension of 1-chloro-N-(1-methylcyclopropyl)-3-[(3-methylisoxazol-5-yl)methyl]-4-oxo-phthalazine-6-sulfonamide (40. mg, 0.10 mmol), cyclohexylamine (0.22 mL, 1.96 mmol) and caesium fluoride (14.86 mg, 0.10 mmol) in ethanol (1 mL) was heated at reflux in a sealed Wheaton vial for 7 days (LCMS indicated the ethoxy product was forming no the amine substituted product). Water (10 mL) and EtOAc (20 mL) were added to the reaction mixture, the aqueous phase was acidified with 2 M HCl to pH 2 and the reaction mixture was extracted EtOAc (20 mL). The organic phase was separated, passed through a hydrophobic frit and evaporated to dryness. The crude product was purified by prep. HPLC, high pH, to yield 1-ethoxy-N-(1-methylcyclopropyl)-3-[(3-methylisoxazol-5-yl)methyl]-4-oxo-phthalazine-6-sulfonamide (13.1 mg, 0.031 mmol, 32%).

C-Substituted Phthalazinones

Example 283 1-[3-(dimethylamino)prop-1-ynyl]-N-(1-methylcyclopropyl)-3-[(3-methylisoxazol-5-yl)methyl]-4-oxo-phthalazine-6-sulfonamide

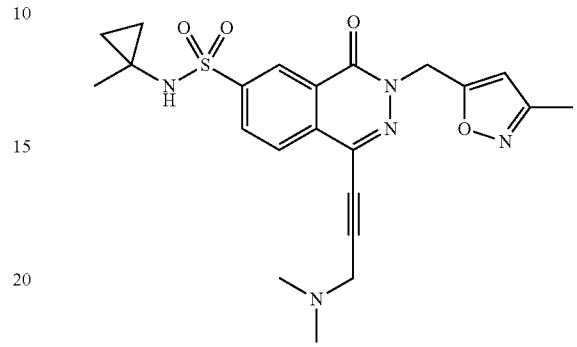

A mixture of 1-chloro-N-(1-methylcyclopropyl)-3-[(3-methylisoxazol-5-yl)methyl]-4-oxo-phthalazine-6-sulfonamide (Intermediate S5-F1) (50. mg, 0.12 mmol), 3-dimethylamino-1-propyne (19.75 uL, 0.18 mmol), iso-propylamine (15.76 uL, 0.18 mmol), tetra-N-butylammonium iodide (45.17 mg, 0.12 mmol), tetrakis(triphenylphosphine)palladium(0) (8.49 mg, 0.01 mmol), and copper (I) iodide (2.79 mg, 0.01 mmol) in THF (1 mL) was placed in a reactor vial. The tube was sealed, and the mixture was heated in the absence of light for 16 h. The solvent and volatiles had escaped from the flask to leave a residue. THF (2 mL) was added to dissolve the residue. The flask was recharged with diisopropylamine (25.71 uL, 0.18 mmol), tetrakis(triphenylphosphine)palladium(0) (8.49 mg, 0.01 mmol), copper (I) iodide (2.79 mg, 0.01 mmol) and 3-dimethylamino-1-propyne (19.75 uL, 0.18 mmol). The flask was sealed and heated at 80° C. overnight. The mixture was distilled to dryness and the residue was partitioned between DCM (10 mL) and water (10 mL). The DCM layer was collected and distilled to dryness to give a residue, which was purified by prep. HPLC, high pH, to give the desired product with triphenylphosphine oxide and tetra-N-butylammonium iodide present. The material was purified by automated column chromatography, SiO₂ (RediSep, 4 g) eluent 0-10% MeOH in DCM to afford the desired product 1-[3-(dimethylamino)prop-1-ynyl]-N-(1-methylcyclopropyl)-3-[(3-methylisoxazol-5-yl)methyl]-4-oxo-phthalazine-6-sulfonamide (20 mg, 0.044 mmol, 36%).

Example 284 1-methyl-N-(1-methylcyclopropyl)-3-[(3-methylisoxazol-5-yl)methyl]-4-oxo-phthalazine-6-sulfonamide

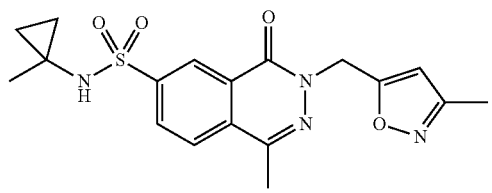

Nitrogen was bubbled through a stirred solution of 1-chloro-N-(1-methylcyclopropyl)-3-[(3-methylisoxazol-5-yl)methyl]-4-oxo-phthalazine-6-sulfonamide (Intermediate S5-F1) (40. mg, 0.10 mmol) and iron(III) acetylacetonate (1.3 mg, 0.04 mmol) in THF (2 mL) at 0° C. for 5 min. Methyl magnesium bromide (104.82 uL, 0.15 mmol) was added to the solution in a drop-wise manner and the resulting mixture was agitated at 0° C. for 30 min. The reaction mixture was quenched with water (2 mL), acidified with 2 N HCl (2 mL) and extracted with EtOAc (2×10 mL). The combined organics were distilled to dryness to give the crude product as a residue, which was purified by prep. HPLC, high pH, to give the desired product 1-methyl-N-(1-methylcyclopropyl)-3-[(3-methylisoxazol-5-yl)methyl]-4-oxo-phthalazine-6-sulfonamide (10.1 mg, 0.026 mmol, 26%).

General Procedures Relating to Scheme 6

Method 6: General Procedure for the Synthesis of 7-bromo-4-substituted-phthalazin-1(2H)-ones

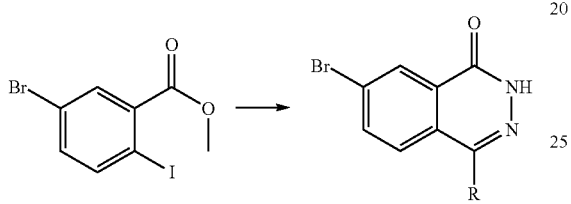

A 2.0 M solution of isopropylmagnesium chloride in THF (1.65 mmol) was added to a magnetically stirred solution of methyl 5-bromo-2-iodobenzoate (1.50 mmol) in THF (10 mL) at −78° C., and the resulting mixture was stirred at 0° C. for 30 min. Zinc bromide (1.65 mmol dried under vacuum with a heat gun) was added to the orange solution, resulting in a thick yellow precipitate, which was agitated for 15 min at 0° C. Acyl chloride (1.80 mmol) and tetrakis(triphenylphosphine)palladium(0) (0.070 mmol) were then added to the reaction, and the resulting mixture was heated at 60° C. for 2 h. The mixture was cooled to ambient and quenched by the addition of saturated NH$_4$Cl (10 mL). The resulting solution was extracted with diethyl ether (2×20 mL) and the combined extracts were dried over MgSO$_4$. The solvent was removed in vacuo to give the crude acylated product as a residue, which was dissolved in ethanol (10 mL). Hydrazine (1.50 mmol) was added to the ethanolic solution, and the resulting mixture was agitated at ambient for 2 h. The solvent was removed in vacuo to give the crude phthalazinone product as a residue, which was purified by column chromatography over silica gel eluting with a gradient of 0 to 80% EtOAc in hexane to give the desired product.

The following intermediates were prepared by a similar method:

Intermediate S6-A1 7-Bromo-4-ethylphthalazin-1(2H)-one

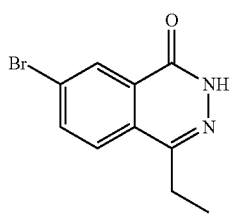

This compound was prepared according to the general procedure described above for the synthesis of 7-bromo-4-substituted-phthalazin-1(2H)-ones using propionyl chloride as the acyl chloride component. The desired product was isolated as a white solid in 52% yield.

$^1$H NMR (300 MHz, CDCl$_3$) δ=10.11 (br. s., 1H), 8.63 (d, J=2.0 Hz, 1H), 7.96 (dd, J=2.1, 8.6 Hz, 1H), 7.72 (d, J=8.6 Hz, 1H), 2.98 (q, J=7.4 Hz, 2H), 1.37 (t, J=7.4 Hz, 4H)

Intermediate S6-A2 7-Bromo-4-isopropylphthalazin-1(2H)-one

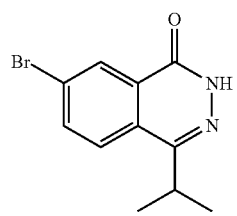

This compound was prepared according to the general procedure described above for the synthesis of 7-bromo-4-substituted-phthalazin-1(2H)-ones using isopropyl chloride as the acyl chloride component. The desired product was isolated as a white solid in 40% yield.

$^1$H NMR (300 MHz, DMSO-d$_6$) δ=12.66 (s, 1H), 8.36 (d, J=2.0 Hz, 1H), 8.12 (dd, J=2.2, 8.7 Hz, 1H), 8.02 (d, J=8.7 Hz, 1H), 3.54 (quin, J=6.8 Hz, 1H), 1.26 (d, J=6.8 Hz, 6H)

Intermediate S6-A3 7-Bromo-4-cyclopropylphthalazin-1 (2H)-one

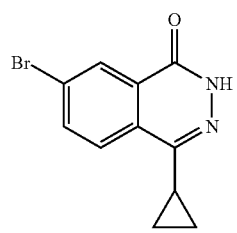 [SMILES: O=c1[nH]nc(C2CC2)c2ccc(Br)cc12]

This compound was prepared according to the general procedure described above for the synthesis of 7-bromo-4-substituted-phthalazin-1 (2H)-ones using cyclopropanecarbonyl chloride as the acyl chloride component. The desired product was isolated as a white solid in 46% yield.

$^1$H NMR (300 MHz, DMSO-d$_6$) δ=12.55 (s, 1H), 8.33 (d, J=1.7 Hz, 1H), 8.20 (d, J=8.5 Hz, 1H), 8.17 (dd, J=2.1, 8.7 Hz, 1H), 2.47-2.36 (m, 1H), 1.02-0.84 (m, 4H)

Intermediate S6-A4
7-Bromo-4-cyclopentylphthalazin-(2H)-one

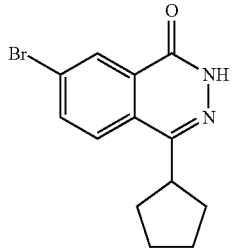 [SMILES: O=c1[nH]nc(C2CCCC2)c2ccc(Br)cc12]

This compound was prepared according to the general procedure described above for the synthesis of 7-bromo-4-substituted-phthalazin-1 (2H)-ones using cyclopentanecarbonyl chloride as the acyl chloride component. The desired product was isolated as a white solid in 39% yield.

$^1$H NMR (300 MHz, DMSO-$d_6$) δ=12.61 (s, 1H), 8.34 (d, J=2.1 Hz, 1H), 8.10 (dd, J=2.2, 8.7 Hz, 1H), 8.03 (d, J=8.7 Hz, 1H), 3.63 (quin, J=7.7 Hz, 1H), 2.10-1.94 (m, 2H), 1.89-1.60 (m, 6H)

Intermediate S6-A5
7-Bromo-4-(cyclopropylmethyl)phthalazin-1 (2H)-one

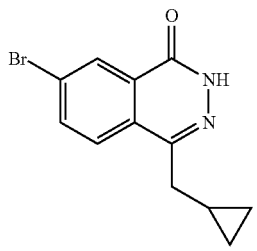 [SMILES: O=c1[nH]nc(CC2CC2)c2ccc(Br)cc12]

This compound was prepared according to the general procedure described above for the synthesis of 7-bromo-4-substituted-phthalazin-1 (2H)-ones using 2-cyclopropylacetyl chloride as the acyl chloride component. The desired product was isolated as a white solid in 46% yield.

$^1$H NMR (300 MHz, DMSO-$d_6$) δ=12.64 (s, 1H), 8.35 (d, J=2.2 Hz, 1H), 8.11 (t, J=4.9 Hz, 1H), 7.98 (d, J=8.7 Hz, 1H), 2.83 (d, J=6.8 Hz, 2H), 1.14-1.03 (m, 1H), 0.54-0.43 (m, 2H), 0.27-0.20 (m, 2H)

Intermediate S6-A6
7-Bromo-4-(cyclobutylmethyl)phthalazin-1(2H)-one

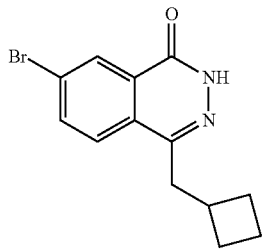 [SMILES: O=c1[nH]nc(CC2CCC2)c2ccc(Br)cc12]

This compound was prepared according to the general procedure described above for the synthesis of 7-bromo-4-substituted-phthalazin-1(2H)-ones using 2-cyclobutylacetyl chloride as the acyl chloride component. The desired product was isolated as a white solid in 47% yield.

$^1$H NMR (300 MHz, DMSO-$d_6$) δ=12.62 (s, 1H), 8.33 (d, J=2.0 Hz, 1H), 8.10 (dd, J=2.2, 8.6 Hz, 1H), 7.95 (d, J=8.7 Hz, 1H), 3.01 (d, J=7.4 Hz, 2H), 2.81-2.65 (m, 1H), 2.11-1.95 (m, 2H), 1.89-1.65 (m, 4H)

Intermediate S6-A7
7-Bromo-4-(cyclohexylmethyl)phthalazin-1(2H)-one

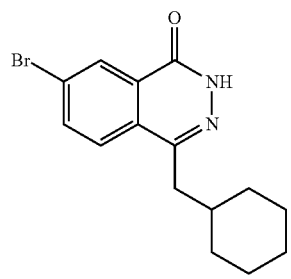 [SMILES: O=c1[nH]nc(CC2CCCCC2)c2ccc(Br)cc12]

This compound was prepared according to the general procedure described above for the synthesis of 7-bromo-4-substituted-phthalazin-1 (2H)-ones using cyclohexanecarbonyl chloride as the acyl chloride component. The desired product was isolated as a white solid in 48% yield.

$^1$H NMR (300 MHz, CDCl$_3$) δ=9.93 (br. s., 1H), 8.63 (d, J=2.1 Hz, 1H), 7.96 (dd, J=2.1, 8.6 Hz, 1H), 7.70 (d, J=8.6 Hz, 1H), 2.79 (d, J=6.7 Hz, 2H), 1.75 (d, J=12.2 Hz, 5H), 1.29-1.01 (m, 6H)

Intermediate S6-A8 7-Bromo-4-((tetrahydro-2H-pyran-4-yl)methyl)phthalazin-1 (2H)-one

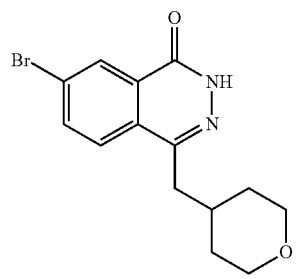 [SMILES: O=c1[nH]nc(CC2CCOCC2)c2ccc(Br)cc12]

This compound was prepared according to the general procedure described above for the synthesis of 7-bromo-4-substituted-phthalazin-1 (2H)-ones using 2-(tetrahydro-2H-pyran-4-yl)acetyl chloride as the acyl chloride component. The desired product was isolated as a white solid in 41% yield.

$^1$H NMR (300 MHz, DMSO-$d_6$) δ=12.78-12.53 (m, 1H), 8.35 (d, J=2.2 Hz, 1H), 8.10 (dd, J=2.2, 8.6 Hz, 1H), 8.00 (d, J=8.5 Hz, 1H), 3.88-3.72 (m, 2H), 3.30-3.17 (m, 2H), 2.84 (d, J=7.2 Hz, 2H), 2.05-1.88 (m, 1H), 1.58 (m, 2H), 1.39-1.19 (m, 2H)

Intermediate S6-A9 4-Benzyl-7-bromophthalazin-1(2H)-one

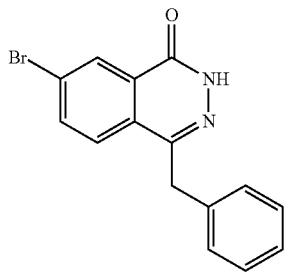 [SMILES: O=c1[nH]nc(Cc2ccccc2)c2ccc(Br)cc12]

This compound was prepared according to the general procedure described above for the synthesis of 7-bromo-4-substituted-phthalazin-1 (2H)-ones using 2-phenylacetyl chloride as the acyl chloride component. The desired product was isolated as a white solid in 48% yield.

$^1$H NMR (300 MHz, DMSO-$d_6$) δ=12.76 (s, 1H), 8.34 (d, J=2.1 Hz, 1H), 8.05 (dd, J=2.2, 8.7 Hz, 1H), 7.88 (d, J=8.7 Hz, 1H), 7.33-7.14 (m, 5H), 4.29 (s, 2H)

Intermediate S6-A10 7-Bromo-4-(3-methoxybenzyl)phthalazin-1(2H)-one

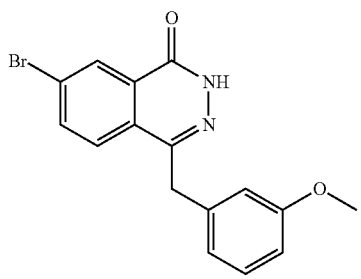 [SMILES: COc1cccc(Cc2n[nH]c(=O)c3cc(Br)ccc23)c1]

This compound was prepared according to the general procedure described above for the synthesis of 7-bromo-4-substituted-phthalazin-1(2H)-ones using 2-(3-methoxyphenyl)acetyl chloride as the acyl chloride component. The desired product was isolated as a white solid in 45% yield.

$^1$H NMR (300 MHz, CDCl$_3$) δ=10.01 (br. s., 1H), 8.60 (d, J=2.1 Hz, 1H), 7.84 (dd, J=2.1, 8.6 Hz, 1H), 7.63 (d, J=8.7 Hz, 1H), 7.27-7.20 (m, 1H), 6.89-6.76 (m, 3H), 4.26 (s, 2H), 3.79 (s, 3H)

Intermediate S6-A11 Methyl 6-bromo-4-oxo-3,4-dihydrophthalazine-1-carboxylate

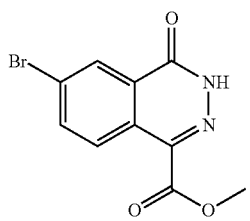 [SMILES: COC(=O)c1n[nH]c(=O)c2cc(Br)ccc12]

This compound was prepared according to the general procedure described above for the synthesis of 7-bromo-4-substituted-phthalazin-1 (2H)-ones using methyl 2-chloro-2-oxoacetate as the acyl chloride component. The desired product was isolated as a white solid in 50% yield.

$^1$H NMR (300 MHz, DMSO-$d_6$) δ=13.36 (s, 1H), 8.51 (d, J=8.9 Hz, 1H), 8.38 (d, J=2.0 Hz, 1H), 8.19 (dd, J=2.2, 8.8 Hz, 1H), 3.92 (s, 3H)

Method 7: General Procedure for the Synthesis of 7-(benzylthio)-4-substituted-phthalazin-S(2H)-ones

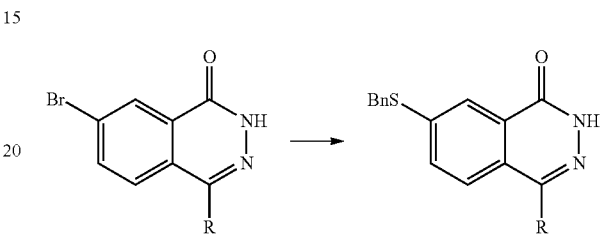

To a magnetically stirred solution of 7-bromo-4-substituted-phthalazin-1(2H)-one (0.65 mmol) and tris(dibenzylideneacetone)dipalladium(0) (0.030 mmol) in 1,4-dioxane (10 mL) at 20° C. under nitrogen was added Xantphos (0.060 mmol), and the resulting mixture was stirred at ambient for 5 min. N,N-Diisopropylethylamine (0.68 mmol) was then added to the reaction followed by benzyl mercaptan (81.58 uL, 0.6800 mmol), and the resulting mixture was heated at 60° C. for 1 h. The mixture was cooled to ambient and distilled to dryness to give a residue, which was solid loaded onto silica and purified by automated column chromatography over silica gel eluting with a gradient of 0 to 100% EtOAc in hexane to afford the desired product.

Intermediate S6-B1
7-(Benzylthio)-4-ethylphthalazin-1 (2H)-one

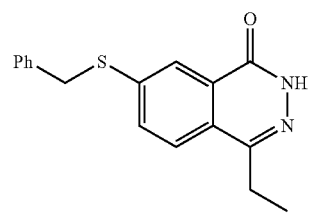 [SMILES: CCc1n[nH]c(=O)c2cc(SCc3ccccc3)ccc12]

This compound was prepared according to the general procedure described above for the synthesis of 7-(benzylthio)-4-substituted-phthalazin-1 (2H)-ones using 7-bromo-4-ethylphthalazin-1 (2H)-one. The desired product was isolated as a yellow solid in 95% yield.

$^1$H NMR (300 MHz, DMSO-$d_6$) δ=8.08 (d, J=1.7 Hz, 1H), 7.87 (d, J=8.3 Hz, 1H), 7.85 (dd, J=2.0, 8.6 Hz, 1H), 7.48-7.41 (m, 2H), 7.37-7.22 (m, 3H), 4.45 (s, 2H), 2.91 (q, J=7.4 Hz, 2H), 1.23 (d, J=7.4 Hz, 4H)

Intermediate S6-B2
7-(Benzylthio)-4-isopropylphthalazin-1 (2H)-one

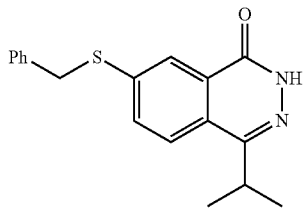 [SMILES: CC(C)c1n[nH]c(=O)c2cc(SCc3ccccc3)ccc12]

This compound was prepared according to the general procedure described above for the synthesis of 7-(benzylthio)-4-substituted-phthalazin-1 (2H)-ones using 7-bromo-4-isopropylphthalazin-1(2H)-one. The desired product was isolated as a yellow solid in 79% yield.

$^1$H NMR (300 MHz, DMSO-$d_6$) δ=12.48 (s, 1H), 8.09 (d, J=2.1 Hz, 1H), 7.95 (d, J=8.7 Hz, 1H), 7.83 (dd, J=2.2, 8.6 Hz, 1H), 7.52-7.41 (m, 2H), 7.37-7.25 (m, 3H), 4.45 (s, 2H), 3.58-3.44 (m, 1H), 1.24 (d, J=6.8 Hz, 6H).

Intermediate S6-B3
7-(Benzylthio)-4-cyclopropylphthalazin-1 (2H)-one

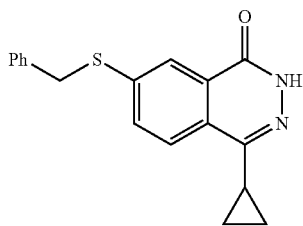 [SMILES: O=c1[nH]nc(C2CC2)c2ccc(SCc3ccccc3)cc12]

This compound was prepared according to the general procedure described above for the synthesis of 7-(benzylthio)-4-substituted-phthalazin-1 (2H)-ones using 7-bromo-4-cyclopropylphthalazin-1 (2H)-one. The desired product was isolated as an orange solid in 92% yield.

$^1$H NMR (300 MHz, DMSO-$d_6$) δ=12.37 (s, 1H), 8.14 (d, J=8.6 Hz, 1H), 8.07 (d, J=1.9 Hz, 1H), 7.88 (dd, J=2.2, 8.6 Hz, 1H), 7.48-7.42 (m, 2H), 7.37-7.23 (m, 3H), 4.46 (s, 2H), 2.44-2.33 (m, 1H), 0.96-0.83 (m, 4H).

Intermediate S6-B4
7-(Benzylthio)-4-cyclopentylphthalazin-1 (2H)-one

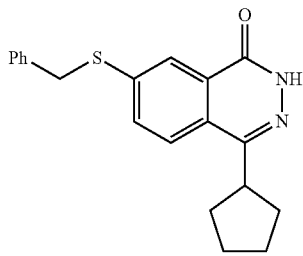 [SMILES: O=c1[nH]nc(C2CCCC2)c2ccc(SCc3ccccc3)cc12]

This compound was prepared according to the general procedure described above for the synthesis of 7-(benzylthio)-4-substituted-phthalazin-1 (2H)-ones using 7-bromo-4-cyclopentylphthalazin-1 (2H)-one. The desired product was isolated as a brown solid in 88% yield.

$^1$H NMR (300 MHz, DMSO-$d_6$) δ=12.44 (s, 1H), 8.08 (d, J=2.1 Hz, 1H), 7.95 (d, J=8.7 Hz, 1H), 7.82 (dd, J=2.1, 8.6 Hz, 1H), 7.47-7.42 (m, 2H), 7.36-7.23 (m, 3H), 4.45 (s, 2H), 3.59 (t, J=7.7 Hz, 1H), 2.08-1.90 (m, 2H), 1.86-1.60 (m, 6H).

Intermediate S6-B5 7-(Benzylthio)-4-(cyclopropylmethyl)phthalazin-1(2H)-one

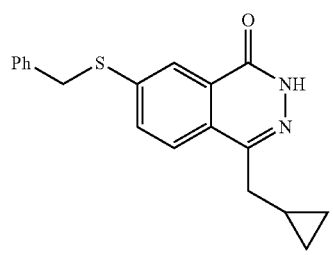 [SMILES: O=c1[nH]nc(CC2CC2)c2ccc(SCc3ccccc3)cc12]

This compound was prepared according to the general procedure described above for the synthesis of 7-(benzylthio)-4-substituted-phthalazin-1 (2H)-ones using 7-bromo-4-(cyclopropylmethyl)phthalazin-1(2H)-one. The desired product was isolated as a yellow solid in 87% yield.

$^1$H NMR (300 MHz, DMSO-$d_6$) δ=12.46 (s, 1H), 8.08 (d, J=2.1 Hz, 1H), 7.93-7.87 (m, 1H), 7.87-7.81 (m, 1H), 7.51-7.39 (m, 2H), 7.38-7.22 (m, 3H), 4.45 (s, 2H), 2.80 (d, J=6.9 Hz, 2H), 1.13-1.03 (m, 1H), 0.51-0.43 (m, 2H), 0.25-0.19 (m, 2H)

Intermediate S6-B6 7-(Benzylthio)-4-(cyclobutyllmethyl)phthalazin-1 (2H)-one

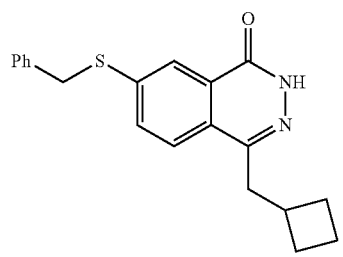 [SMILES: O=c1[nH]nc(CC2CCC2)c2ccc(SCc3ccccc3)cc12]

This compound was prepared according to the general procedure described above for the synthesis of 7-(benzylthio)-4-substituted-phthalazin-1 (2H)-ones using 7-bromo-4-(cyclobutylmethyl)phthalazin-1(2H)-one. The desired product was isolated as a white solid in 95% yield.

$^1$H NMR (300 MHz, DMSO-$d_6$) δ=12.44 (s, 1H), 8.06 (d, J=2.0 Hz, 1H), 7.88 (d, J=8.6 Hz, 1H), 7.82 (dd, J=2.1, 8.5 Hz, 1H), 7.47-7.42 (m, 2H), 7.37-7.24 (m, 3H), 4.45 (s, 2H), 2.97 (d, J=7.4 Hz, 2H), 2.10-1.95 (m, 2H), 1.89-1.68 (m, 5H)

Intermediate S6-B7 7-(Benzylthio)-4-(cyclohexylmethyl)phthalazin-1 (2H)-one

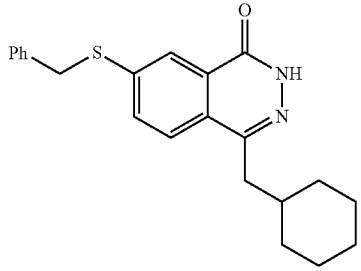 [SMILES: O=c1[nH]nc(CC2CCCCC2)c2ccc(SCc3ccccc3)cc12]

This compound was prepared according to the general procedure described above for the synthesis of 7-(benzylthio)-4-substituted-phthalazin-1 (2H)-ones using 7-bromo-4-(cyclohexylmethyl)phthalazin-1 (2H)-one. The desired product was isolated as a white solid in 95% yield.

$^1$H NMR (300 MHz, CDCl$_3$) δ=9.78 (br. s., 1H), 8.35-8.31 (m, 1H), 7.68-7.63 (m, 2H), 7.45-7.40 (m, 1H), 7.37-7.28 (m, 3H), 4.33 (s, 2H), 2.75 (d, J=6.6 Hz, 2H), 1.81-1.66 (m, 6H), 1.26-1.02 (m, 5H)

Intermediate S6-B8 7-(Benzylthio)-4-((tetrahydro-2H-pyran-4-yl)methyl)phthalazin-1(2H)-one

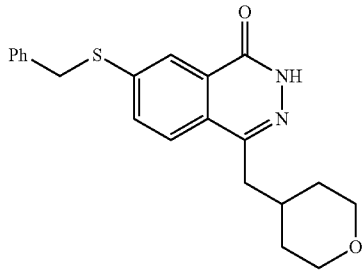 [SMILES: O=c1[nH]nc(CC2CCOCC2)c2ccc(SCc3ccccc3)cc12]

This compound was prepared according to the general procedure described above for the synthesis of 7-(benzylthio)-4-substituted-phthalazin-1 (2H)-ones using 7-bromo-4-((tetrahydro-2H-pyran-4-yl)methyl)phthalazin-1(2H)-one. The desired product was isolated as a yellow solid in 79% yield.

$^1$H NMR (300 MHz, DMSO-d$_6$) δ=12.49 (s, 1H), 8.08 (d, J=2.1 Hz, 1H), 7.93 (d, J=8.7 Hz, 1H), 7.82 (dd, J=2.1, 8.5 Hz, 1H), 7.46 (d, J=7.5 Hz, 2H), 7.37-7.23 (m, 3H), 4.46 (s, 2H), 3.81 (dd, J=2.7, 11.8 Hz, 2H), 3.28-3.16 (m, 2H), 2.80 (d, J=7.1 Hz, 2H), 2.02-1.87 (m, 1H), 1.57 (d, J=12.2 Hz, 2H), 1.33-1.21 (m, 2H).

Intermediate S6-B9 4-Benzyl-7-(benzylthio)phthalazin-1(2H)-one

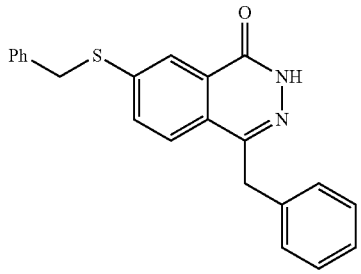 [SMILES: O=c1[nH]nc(Cc2ccccc2)c2ccc(SCc3ccccc3)cc12]

This compound was prepared according to the general procedure described above for the synthesis of 7-(benzylthio)-4-substituted-phthalazin-1 (2H)-ones using 4-benzyl-7-bromophthalazin-1(2H)-one. The desired product was isolated as a white solid in 95% yield.

$^1$H NMR (300 MHz, DMSO-d$_6$) δ=8.06 (d, J=1.8 Hz, 1H), 7.82 (d, J=8.6 Hz, 1H), 7.76 (dd, J=2.0, 8.6 Hz, 1H), 7.47-7.39 (m, 2H), 7.36-7.15 (m, 8H), 4.43 (s, 2H), 4.25 (s, 2H)

Intermediate S6-B10 7-(Benzylthio)-4-(3-methoxybenzyl)phthalazin-1(2H)-one

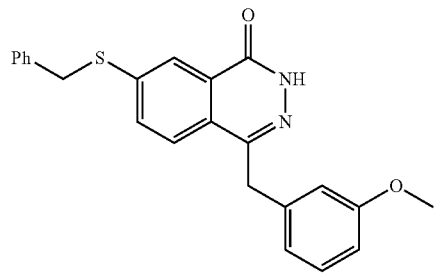 [SMILES: COc1cccc(Cc2n[nH]c(=O)c3cc(SCc4ccccc4)ccc23)c1]

This compound was prepared according to the general procedure described above for the synthesis of 7-(benzylthio)-4-substituted-phthalazin-1 (2H)-ones using 7-bromo-4-(3-methoxybenzyl)phthalazin-1 (2H)-one. The desired product was isolated as a white solid in 89% yield.

$^1$H NMR (300 MHz, CDCl$_3$) δ=9.89 (s, 1H), 8.30 (d, J=1.9 Hz, 1H), 7.61 (d, J=8.6 Hz, 1H), 7.55 (dd, J=2.1, 8.6 Hz, 1H), 7.45-7.19 (m, 11H), 6.89-6.75 (m, 3H), 4.30 (s, 2H), 4.23 (s, 2H), 3.78 (s, 3H)

Intermediate S6-B11 Methyl 6-(benzylthio)-4-oxo-3,4-dihydrophthalazine-1-carboxylate

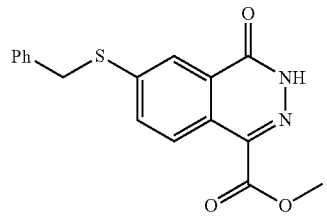 [SMILES: COC(=O)c1n[nH]c(=O)c2cc(SCc3ccccc3)ccc12]

This compound was prepared according to the general procedure described above for the synthesis of 7-(benzylthio)-4-substituted-phthalazin-1 (2H)-ones using methyl 6-bromo-4-oxo-3,4-dihydrophthalazine-1-carboxylate. The desired product was isolated as a white solid in 95% yield.

$^1$H NMR (300 MHz, DMSO-d$_6$) δ=13.17 (br. s., 1H), 8.08 (d, J=2.1 Hz, 1H), 7.91 (dd, J=2.2, 8.8 Hz, 1H), 7.49-7.42 (m, 2H), 7.37-7.22 (m, 3H), 4.47 (s, 2H), 3.90 (s, 3H)

Method 8: General Procedure for the Synthesis of 7-(Benzylthio)-4-substituted-2-((3-methylisoxazol-5-yl)methyl)phthalazin-1(2H)-ones

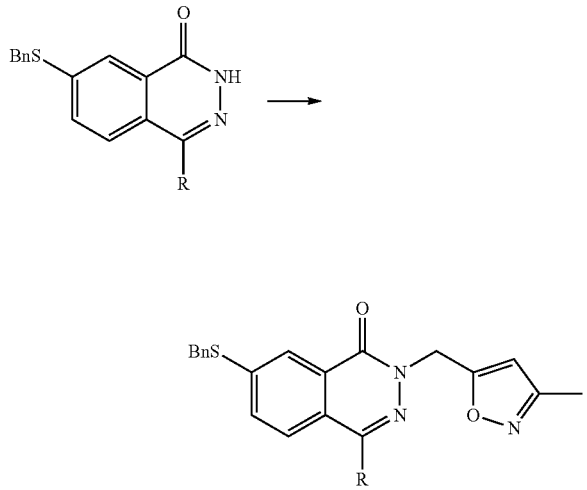

To a magnetically stirred solution of 7-(benzylthio)-4-substituted-phthalazin-1(2H)-one (0.40 mmol) in DMF (8 mL) at 20° C. under nitrogen was added sodium hydride (0.44 mmol, 60% w/w), and the resulting mixture was agitated at ambient temperature for 1 h. 5-(Bromomethyl)-3-methyl-1,2-oxazole (0.44 mmol) was then added to the reaction, and the resulting mixture was agitated for 1 h at ambient temperature. Methanol (100 uL) was added to quench the reaction and the solvent was removed in vacuo to give the crude product as a residue. The residue was adsorbed onto silica and purified by automated column chromatography over silica gel eluting with a gradient of 0 to 100% EtOAc in hexane to give the desired product.

Intermediate S6-C1 7-(Benzylthio)-4-ethyl-2-((3-methylisoxazol-5-yl)methyl)phthalazin-1(2H)-one

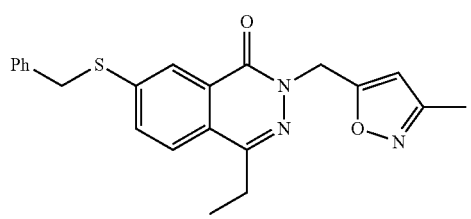 [SMILES: CCc1nn(Cc2cc(C)no2)c(=O)c2cc(SCc3ccccc3)ccc12]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-ethyl-phthalazin-1(2H)-one. The desired product was isolated as an off-white solid in 90% yield.

$^1$H NMR (300 MHz, DMSO-$d_6$) δ=8.11 (d, J=1.7 Hz, 1H), 7.93 (d, J=8.6 Hz, 1H), 7.87 (dd, J=2.0, 8.6 Hz, 1H), 7.49-7.42 (m, 2H), 7.37-7.22 (m, 3H), 6.25 (s, 1H), 5.76 (s, 1H), 5.38 (s, 2H), 4.47 (s, 2H), 2.18 (s, 3H)

Intermediate S6-C2 7-(Benzylthio)-4-isopropyl-2-((3-methylisoxazol-5-yl)methyl)phthalazin-1(2H)-one

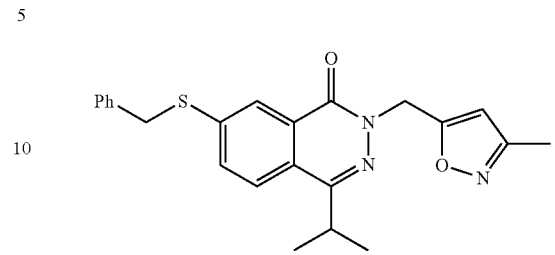

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-isopropyl-phthalazin-1(2H)-one. The desired product was isolated as a pale yellow oil in 34% yield.

$^1$H NMR (300 MHz, DMSO-$d_6$) δ=8.12 (d, J=2.1 Hz, 1H), 7.99 (d, J=8.8 Hz, 1H), 7.87 (dd, J=2.1, 8.6 Hz, 1H), 7.49-7.42 (m, 2H), 7.37-7.25 (m, 3H), 6.24 (s, 1H), 5.38 (s, 2H), 4.46 (s, 2H), 3.59-3.48 (m, 1H), 2.18 (s, 3H), 1.24 (d, J=6.8 Hz, 6H).

Intermediate S6-C3 7-(Benzylthio)-4-cyclopropyl-2-((3-methylisoxazol-5-yl)methyl)phthalazin-1(2H)-one

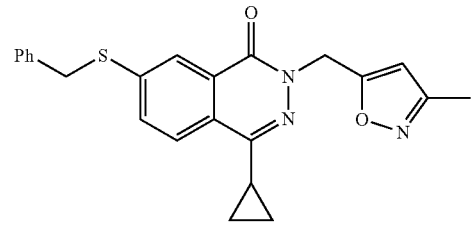 [SMILES: Cc1cc(Cn2nc(C3CC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-cyclopropyl-phthalazin-1(2H)-one. The desired product was isolated as a thick amber oil in 75% yield.

$^1$H NMR (300 MHz, DMSO-$d_6$) δ=8.17 (d, J=8.6 Hz, 1H), 8.09 (d, J=2.1 Hz, 1H), 7.91 (dd, J=2.1, 8.6 Hz, 1H), 7.55-7.40 (m, 2H), 7.40-7.22 (m, 3H), 6.22 (s, 1H), 5.33 (s, 2H), 4.47 (s, 2H), 2.46-2.37 (m, 1H), 2.18 (s, 3H), 1.01-0.91 (m, 2H), 0.90-0.82 (m, 2H).

Intermediate S6-C4 7-(Benzylthio)-4-cyclopentyl-2-((3-methylisoxazol-5-yl)methyl)phthalazin-1(2H)-one

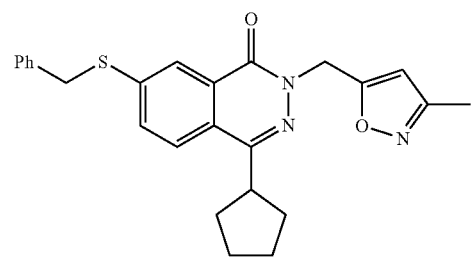 [SMILES: Cc1cc(Cn2nc(C3CCCC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-cyclopentyl-phthalazin-1 (2H)-one. The desired product was isolated as an orange oil in 90% yield.

¹H NMR (300 MHz, DMSO-d₆) δ=8.10 (d, J=2.1 Hz, 1H), 7.99 (d, J=8.7 Hz, 1H), 7.85 (dd, J=2.2, 8.6 Hz, 1H), 7.46 (d, J=7.6 Hz, 2H), 7.37-7.23 (m, 3H), 6.24 (s, 1H), 5.37 (s, 2H), 4.46 (s, 2H), 3.71-3.55 (m, 1H), 2.18 (s, 3H), 1.98 (q, J=5.9 Hz, 2H), 1.86-1.57 (m, 6H).

Intermediate S6-C5 7-(Benzylthio)-4-(cyclopropylmethyl)-2-((3-methylisoxazol-5-yl)methyl)phthalazin-1(2H)-one

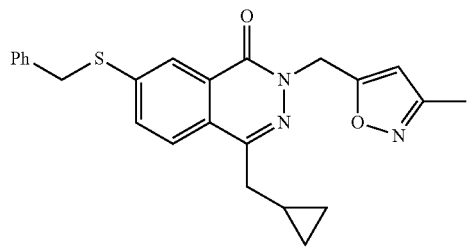 [SMILES: Cc1cc(Cn2nc(CC3CC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1 (2H)-ones using 7-(benzylthio)-4-(cyclopropylmethyl)phthalazin-1 (2H)-one. The desired product was isolated as an off-white solid in 90% yield.

¹H NMR (300 MHz, CDCl₃) δ=8.09 (d, J=2.0 Hz, 1H), 7.47 (d, J=8.5 Hz, 1H), 7.40 (dd, J=2.0, 8.6 Hz, 1H), 7.21-7.14 (m, 2H), 7.14-7.04 (m, 3H), 5.85 (s, 1H), 5.21 (s, 2H), 4.08 (s, 2H), 2.57 (d, J=6.8 Hz, 2H), 1.58 (s, 3H), 0.95-0.85 (m, 1H), 0.35-0.25 (m, 2H), 0.08--0.01 (m, 2H)

Intermediate S6-C6 7-(Benzylthio)-4-(cyclobutylmethyl)-2-((3-methylisoxazol-5-yl)methyl)phthalazin-1(2H)-one

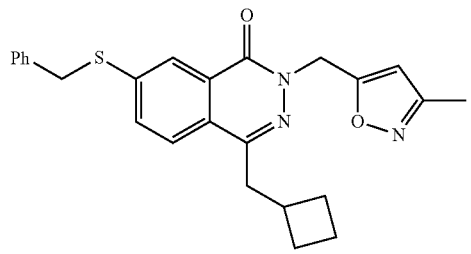 [SMILES: Cc1cc(Cn2nc(CC3CCC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-(cyclobutylmethyl)phthalazin-1 (2H)-one. The desired product was isolated as an off-white solid in 90% yield.

¹H NMR (300 MHz, CDCl₃) δ=8.32 (m, 1H), 7.69-7.59 (m, 2H), 7.46-7.24 (m, 5H), 6.08 (s, 1H), 5.44 (s, 2H), 4.32 (s, 2H), 2.99 (d, J=7.4 Hz, 2H), 2.84-2.71 (m, 1H), 2.27 (s, 3H), 2.15-2.02 (m, 2H), 1.97-1.73 (m, 4H)

Intermediate S6-C7 7-(Benzylthio)-4-(cyclohexylmethyl)-2-((3-methylisoxazol-5-yl)methyl)phthalazin-1(2H)-one

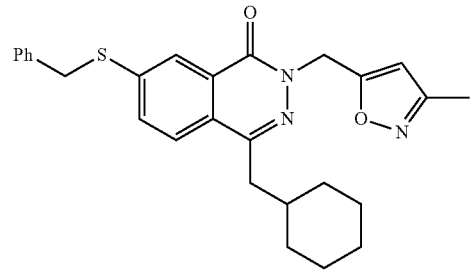 [SMILES: Cc1cc(Cn2nc(CC3CCCCC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-(cyclohexylmethyl)phthalazin-1(2H)-one. The desired product was isolated as an off-white solid in 88% yield.

¹H NMR (300 MHz, DMSO-d₆) δ=8.10 (dd, J=2.0, 9.4 Hz, 1H), 7.92 (d, J=8.7 Hz, 1H), 7.88-7.82 (m, 1H), 7.50-7.41 (m, 2H), 7.39-7.22 (m, 3H), 5.76 (s, 1H), 5.38 (s, 2H), 4.51-4.43 (m, 2H), 2.81-2.70 (m, 2H), 2.17 (s, 3H), 1.64 (d, J=11.3 Hz, 7H), 1.22-0.88 (m, 6H)

Intermediate S6-C8 7-(Benzylthio)-2-((3-methylisoxazol-5-yl)methyl)-4-((tetrahydro-2H-pyran-4-yl)methyl)phthalazin-1 (2H)-one

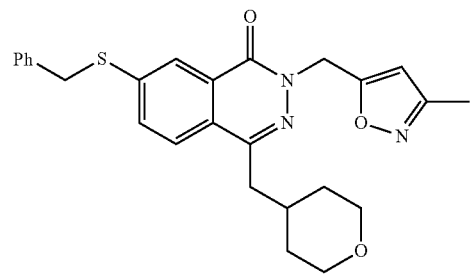 [SMILES: Cc1cc(Cn2nc(CC3CCOCC3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1 (2H)-ones using 7-(benzylthio)-4-((tetrahydro-2H-pyran-4-yl)methyl)phthalazin-1(2H)-one. The desired product was isolated as a yellow oil in 84% yield.

¹H NMR (300 MHz, DMSO-d₆) δ=8.11 (d, J=2.0 Hz, 1H), 7.96 (d, J=8.6 Hz, 1H), 7.87 (d, J=8.3 Hz, 1H), 7.49-7.43 (m, 2H), 7.37-7.23 (m, 3H), 6.25 (s, 1H), 5.38 (s, 2H), 4.47 (s, 2H), 3.79 (dd, J=2.7, 11.5 Hz, 2H), 3.27-3.15 (m, 2H), 2.82 (d, J=7.1 Hz, 2H), 2.17 (s, 3H), 1.96-1.83 (m, 1H), 1.62-1.47 (m, 2H), 1.34-1.20 (m, 2H).

Intermediate S6-C9 4-Benzyl-7-(benzylthio)-2-((3-methylisoxazol-5-yl)methyl)phthalazin-1(2H)-one

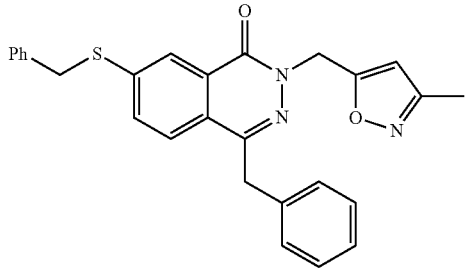 [SMILES: Cc1cc(Cn2nc(Cc3ccccc3)c3ccc(SCc4ccccc4)cc3c2=O)on1]

This compound was prepared according to the general procedure described above for the synthesis of 7-(benzylthio)-4-substituted-2-((3-methylisoxazol-5-yl)methyl)phthalazin-1(2H)-ones using 4-benzyl-7-(benzylthio)phthalazin-1(2H)-one. The desired product was isolated as an off-white solid in 86% yield.

$^1$H NMR (300 MHz, DMSO-$d_6$) δ=8.08 (d, J=1.9 Hz, 1H), 7.84 (d, J=8.4 Hz, 1H), 7.78 (dd, J=2.1, 8.5 Hz, 1H), 7.46-7.39 (m, 2H), 7.35-7.18 (m, 8H), 6.28 (s, 1H), 5.44 (s, 2H), 4.44 (s, 2H), 4.27 (s, 2H), 2.20 (s, 3H)

Intermediate S6-C10 7-(Benzylthio)-4-(3-methoxybenzyl)-2-((3-methylisoxazol-5-yl)methyl)phthalazin-1(2H)-one

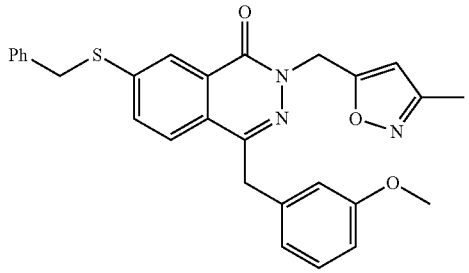 [SMILES: COc1cccc(Cc2nn(Cc3cc(C)no3)c(=O)c3cc(SCc4ccccc4)ccc23)c1]

This compound was prepared according to the general procedure described above for the synthesis of 7-(benzylthio)-4-substituted-2-((3-methylisoxazol-5-yl)methyl)phthalazin-1(2H)-ones using 7-(benzylthio)-4-(3-methoxybenzyl)phthalazin-1 (2H)-one. The desired product was isolated as an off-white solid in 74% yield.

$^1$H NMR (300 MHz, DMSO-$d_6$) δ=8.08 (d, J=1.9 Hz, 1H), 7.86 (d, J=8.4 Hz, 1H), 7.80 (dd, J=2.0, 8.6 Hz, 1H), 7.48-7.39 (m, 2H), 7.36-7.13 (m, 4H), 6.89-6.82 (m, 2H), 6.78-6.71 (m, 1H), 6.28 (s, 1H), 5.44 (s, 2H), 4.43 (s, 2H), 4.23 (s, 2H), 3.68 (s, 3H), 2.20 (s, 3H)

Intermediate S6-C11 Methyl 6-(benzylthio)-3-((3-methylisoxazol-5-yl)methyl)-4-oxo-3,4-dihydrophthalazine-1-carboxylate

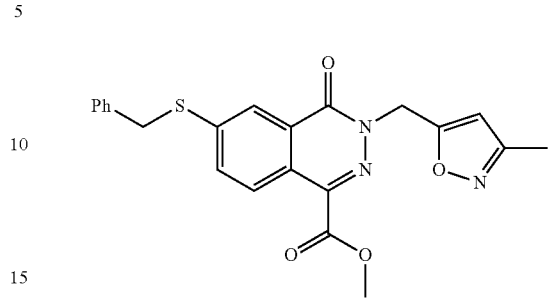

This compound was prepared according to the general procedure described above for the synthesis of 7-(benzylthio)-4-substituted-2-((3-methylisoxazol-5-yl)methyl) phthalazin-1 (2H)-ones using methyl 6-(benzylthio)-4-oxo-3,4-dihydrophthalazine-1-carboxylate. The desired product was isolated as an off-white solid in 81% yield.

$^1$H NMR (300 MHz, CDCl$_3$) δ=8.50 (d, J=8.8 Hz, 1H), 8.29 (d, J=2.1 Hz, 1H), 7.69 (dd, J=2.1, 8.8 Hz, 1H), 7.47-7.39 (m, 2H), 7.39-7.29 (m, 3H), 6.14 (s, 1H), 5.54 (s, 2H), 4.33 (s, 2H), 4.02 (s, 3H), 2.28 (s, 3H)

Method 9: General Procedure for the Synthesis of perfluorophenyl 1-substituted-3-((3-methylisoxazol-5-yl)methyl)-4-oxo-3,4-dihydrophthalazine-6-sulfonates

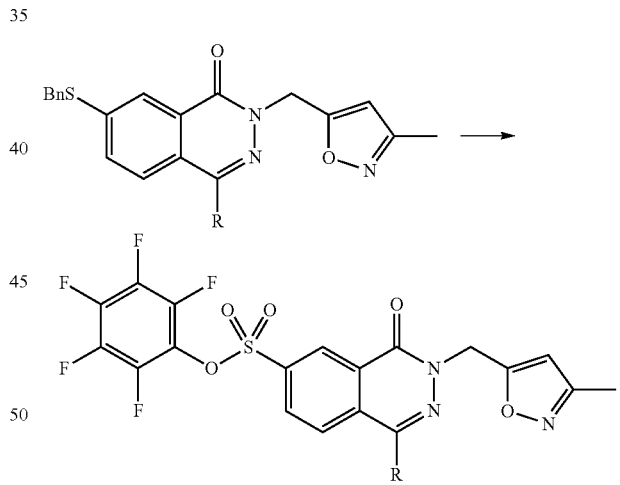

To a magnetically stirred solution of 7-(benzylthio)-4-substituted-2-((3-methylisoxazol-5-yl)methyl)phthalazin-1 (2H)-ones (1.0 mmol) in a mixture of MeCN (10 mL), water (0.6 mL) and acetic acid (1.0 mL) at 0° C. was added 1,3-dichloro-5,5-dimethylhydantoin (2.0 mmol), and the resulting mixture was stirred at 0° C. for 2 h. Pentafluorophenol (2.0 mmol) was then added to the reaction followed by triethylamine (2.8 mmol), and the resulting mixture was stirred at ambient temperature for 2 h. The solvent was removed in vacuo to give the crude product as a residue, which was suspended in EtOAc (10 mL) and filtered. The filtrate was collected and distilled to dryness to give a residue, which was purified by automated column chromatography over silica gel eluting with a gradient of 0 to 80% (v/v) EtOAc in hexane to give the desired product as a solid.

Intermediate S6-D1 Perfluorophenyl 1-ethyl-3-((3-methylisoxazol-5-yl)methyl)-4-oxo-3,4-dihydrophthalazine-6-sulfonate

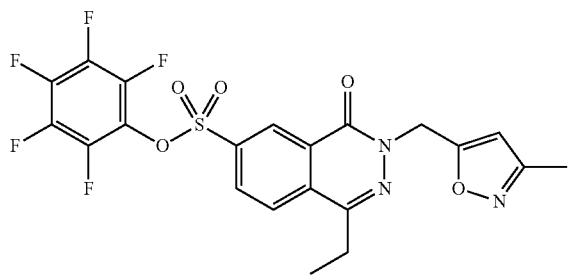 [SMILES: CCc1nn(Cc2cc(C)no2)c(=O)c2cc(S(=O)(=O)Oc3c(F)c(F)c(F)c(F)c3F)ccc12]

This compound was prepared according to the general procedure described above for the synthesis of perfluorophenyl 1-substituted-3-((3-methylisoxazol-5-yl)methyl)-4-oxo-3,4-dihydrophthalazine-6-sulfonates using 7-(benzylthio)-4-ethyl-2-((3-methylisoxazol-5-yl)methyl)phthalazin-1(2H)-one. The desired product was isolated as an off-white solid in 61% yield.

$^1$H NMR (300 MHz, DMSO-$d_6$) δ=8.74 (d, J=1.9 Hz, 1H), 8.54 (dd, J=2.1, 8.6 Hz, 1H), 8.38 (d, J=8.7 Hz, 1H), 6.35 (s, 1H), 5.75 (s, 3H), 5.45 (s, 2H), 3.06 (q, J=7.3 Hz, 2H), 2.19 (s, 3H), 1.34 (s, 2H), 1.26 (t, J=7.4 Hz, 4H)

Intermediate S6-D2 Perfluorophenyl 1-(cyclopropylmethyl)-3-((3-methylisoxazol-5-yl)methyl)-4-oxo-3,4-dihydrophthalazine-6-sulfonate

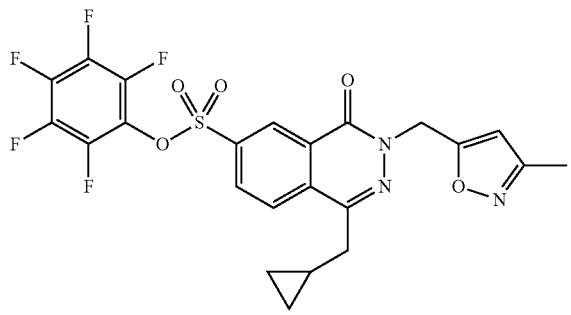 [SMILES: Cc1cc(Cn2nc(CC3CC3)c3ccc(S(=O)(=O)Oc4c(F)c(F)c(F)c(F)c4F)cc3c2=O)on1]

This compound was prepared according to the general procedure described above for the synthesis of 7-(benzylthio)-4-substituted-2-(isoxazol-3-ylmethyl)phthalazin-1(2H)-ones using 7-benzylsulfanyl-4-(cyclopropylmethyl)-2-[(3-methylisoxazol-5-yl)methyl]phthalazin-1-one. The desired product was isolated as an off-white solid in 92% yield.

$^1$H NMR (300 MHz, CDCl$_3$) δ=9.09-9.04 (m, 1H), 8.37 (dd, J=2.1, 8.6 Hz, 1H), 8.10 (d, J=8.7 Hz, 1H), 6.17 (s, 1H), 5.49 (s, 2H), 2.96-2.88 (m, 2H), 2.29 (s, 3H), 0.99-0.77 (m, 1H), 0.67-0.56 (m, 2H), 0.32 (d, J=5.8 Hz, 2H)

Intermediate S6-D3 Perfluorophenyl 1-(cyclobutylmethyl)-3-((3-methylisoxazol-5-yl)methyl)-4-oxo-3,4-dihydrophthalazine-6-sulfonate

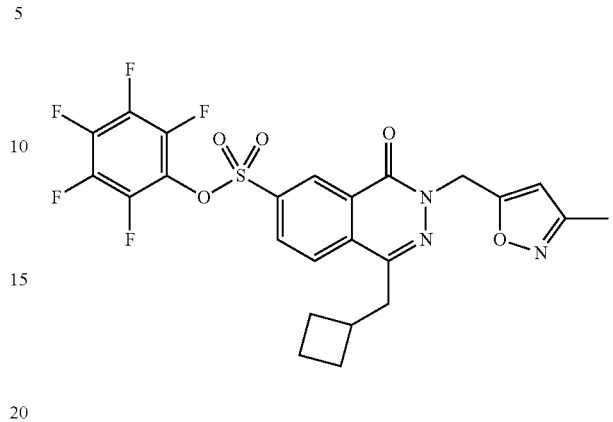

This compound was prepared according to the general procedure described above for the synthesis of 7-(benzylthio)-4-substituted-2-(isoxazol-3-ylmethyl)phthalazin-1(2H)-ones using 7-(benzylthio)-4-(cyclobutylmethyl)-2-((3-methylisoxazol-5-yl)methyl)phthalazin-1(2H)-one. The desired product was isolated as an off-white solid in 78% yield.

$^1$H NMR (300 MHz, DMSO-$d_6$) δ=8.74 (d, J=2.0 Hz, 1H), 8.53 (dd, J=2.2, 8.6 Hz, 1H), 8.38 (d, J=8.7 Hz, 1H), 6.33 (s, 1H), 5.45 (s, 2H), 3.13 (d, J=7.3 Hz, 2H), 2.81-2.66 (m, 1H), 2.19 (s, 3H), 1.99 (s, 3H), 1.80 (d, J=5.1 Hz, 5H)

Intermediate S6-D4 Perfluorophenyl 1-(cyclohexylmethyl)-3-((3-methylisoxazol-5-yl)methyl)-4-oxo-3,4-dihydrophthalazine-6-sulfonate

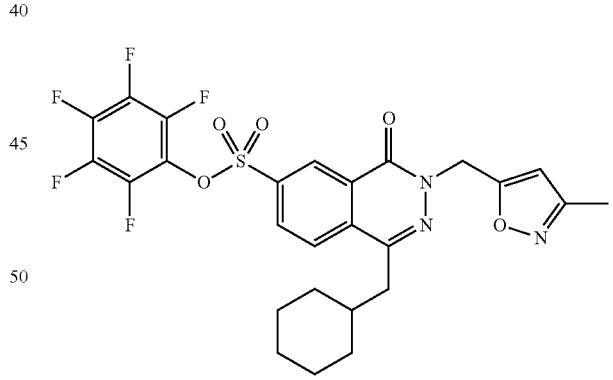

This compound was prepared according to the general procedure described above for the synthesis of 7-(benzylthio)-4-substituted-2-(isoxazol-3-ylmethyl)phthalazin-1(2H)-ones using 7-benzylsulfanyl-4-(cyclohexylmethyl)-2-[(3-methylisoxazol-5-yl)methyl]phthalazin-1-one. The desired product was isolated as an off-white solid in 78% yield.

$^1$H NMR (300 MHz, DMSO-$d_6$) δ=8.76 (d, J=2.1 Hz, 1H), 8.55-8.48 (dd, J=2.1, 8.6 Hz, 1H), 8.43-8.37 (m, 1H), 6.34 (s, 1H), 5.46 (s, 2H), 2.89 (d, J=6.5 Hz, 2H), 2.19 (s, 3H), 1.83-1.53 (m, 5H), 1.30-0.93 (m, 6H)

Intermediate S6-D5 Perfluorophenyl 1-benzyl-3-((3-methylisoxazol-5-yl)methyl)-4-oxo-3,4-dihydrophthalazine-6-sulfonate

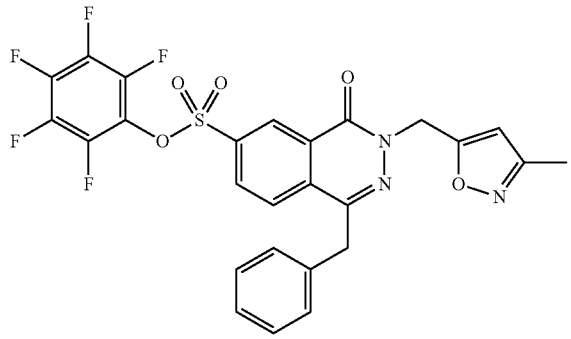 [SMILES: Cc1cc(Cn2nc(Cc3ccccc3)c3ccc(S(=O)(=O)Oc4c(F)c(F)c(F)c(F)c4F)cc3c2=O)on1]

This compound was prepared according to the general procedure described above for the synthesis of 7-(benzylthio)-4-substituted-2-(isoxazol-3-ylmethyl)phthalazin-1 (2H)-ones using 4-benzyl-7-benzylsulfanyl-2-[(3-methylisoxazol-5-yl)methyl]phthalazin-1-one. The desired product was isolated as an off-white solid in 78% yield.

$^1$H NMR (300 MHz, DMSO-d$_6$) δ=8.74 (d, J=1.9 Hz, 1H), 8.48 (dd, J=2.1, 8.6 Hz, 1H), 8.29 (s, 1H), 7.36-7.18 (m, 5H), 6.36 (s, 1H), 5.50 (s, 2H), 4.42 (s, 2H), 2.21 (s, 3H), 1.35 (s, 3H)

Intermediate S6-D6 Perfluorophenyl 1-(3-methoxybenzyl)-3-((3-methylisoxazol-5-yl)methyl)-4-oxo-3,4-dihydrophthalazine-6-sulfonate

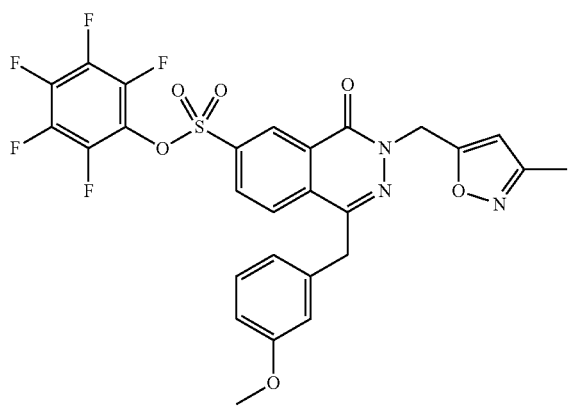 [SMILES: COc1cccc(Cc2nn(Cc3cc(C)no3)c(=O)c3cc(S(=O)(=O)Oc4c(F)c(F)c(F)c(F)c4F)ccc23)c1]

This compound was prepared according to the general procedure described above for the synthesis of 7-(benzylthio)-4-substituted-2-(isoxazol-3-ylmethyl)phthalazin-1 (2H)-ones using 7-benzylsulfanyl-4-[(3-methoxyphenyl) methyl]-2-[(3-methylisoxazol-5-yl)methyl]phthalazin-1-one. The desired product was isolated as an off-white solid in 78% yield.

$^1$H NMR (300 MHz, CDCl$_3$) δ=9.04 (d, J=2.0 Hz, 1H), 8.24 (dd, J=2.1, 8.6 Hz, 1H), 7.96 (d, J=8.6 Hz, 1H), 6.88-6.76 (m, 3H), 6.19 (s, 1H), 5.53 (s, 2H), 4.33 (s, 2H), 3.82-3.75 (m, 3H), 2.30-2.26 (m, 3H)

Intermediate S6-D7 Methyl 3-((3-methylisoxazol-5-yl)methyl)-4-oxo-6-((perfluorophenoxy)sulfonyl)-3,4-dihydrophthalazine-1-carboxylate

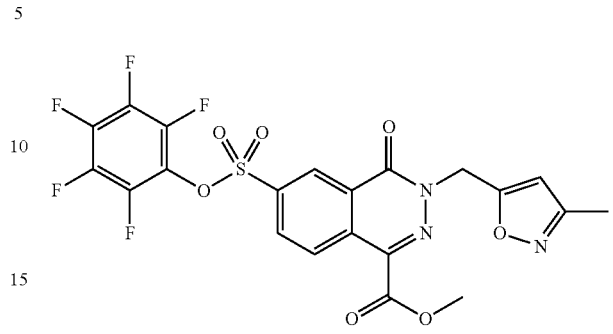

This compound was prepared according to the general procedure described above for the synthesis of 7-(benzylthio)-4-substituted-2-(isoxazol-3-ylmethyl)phthalazin-1 (2H)-ones using methyl 6-(benzylthio)-3-((3-methylisoxazol-5-yl)methyl)-4-oxo-3,4-dihydrophthalazine-1-carboxylate. The desired product was isolated as an off-white solid in 90% yield.

$^1$H NMR (300 MHz, CDCl$_3$) δ=9.13-8.97 (m, 2H), 8.40 (dd, J=2.4, 6.7 Hz, 1H), 6.22 (s, 1H), 5.58 (s, 2H), 4.09-4.03 (m, 3H), 2.33-2.26 (m, 3H)

Method 10: General Procedure for the Synthesis of 1-substituted-N-(1-methylcyclopropyl)-3-((3-methylisoxazol-5-yl)meth yl)-4-oxo-3,4-dihydrophthalazine-6-sulfonamides

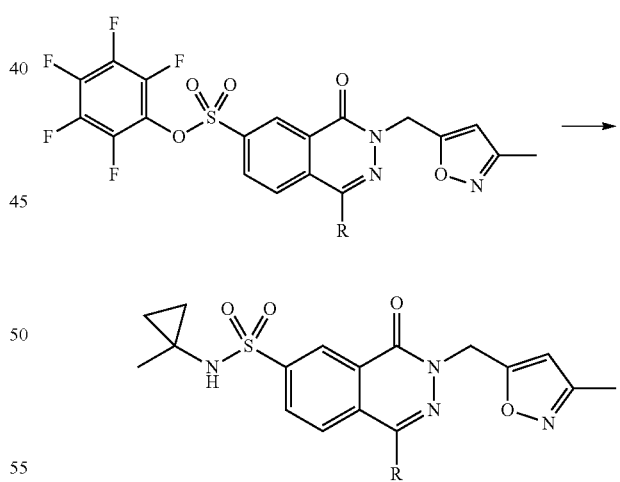

To a magnetically stirred solution of perfluorophenyl 1-substituted-3-(isoxazol-3-ylmethyl)-4-oxo-3,4-dihydrophthalazine-6-sulfonate (1.0 mmol) in DMF (8.0 mL) at 20° C. was added 1-methylcyclopropanamine hydrochloride (1.2 mmol) followed by triethylamine (2.4 mmol), and the resulting mixture was stirred at 60° C. for 2 h. The solvent was removed in vacuo to give the crude product as a residue, which was purified by automated column chromatography over silica gel eluting with a gradient of 0 to 80% (v/v) EtOAc in hexane to give the desired product as a solid.

Example 302 6-(N-(1-Methylcyclopropyl)sulfamoyl)-3-((3-methylisoxazol-5-yl)methyl)-4-oxo-3,4-dihydrophthalazine-1-carboxylic acid

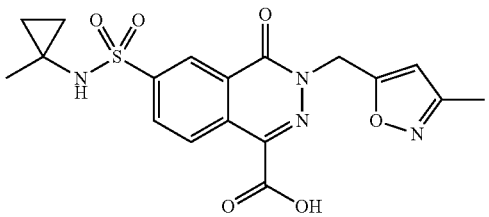

Lithium hydroxide (5 mmol) was added to solution of methyl 6-(N-(1-methylcyclopropyl)sulfamoyl)-3-((5-methylisoxazol-3-yl)methyl)-4-oxo-3,4-dihydrophthalazine-1-carboxylate (1.0 mmol) in 1:1 (v/v) mixture of THF and water (10 mL), and the resulting mixture was agitated at ambient for 1 h. The solvent was removed in vacuo and the residue was partitioned between DCM (10 mL) and 1 N HCl (10 mL). The organic phase was collected and distilled to dryness to give the desired product as a white solid in 98% yield.

Method 11: Amide Formation

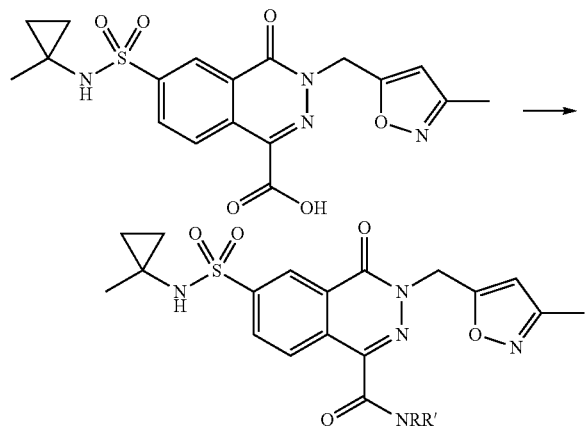

To a magnetically stirred solution of 6-[(1-methylcyclopropyl)sulfamoyl]-3-[(3-methylisoxazol-5-yl)methyl]-4-oxo-phthalazine-1-carboxylic acid (0.060 mmol) and HATU (0.060 mmol) in DMF (4 mL) at 20° C. under nitrogen was added desired amine (0.12 mmol), and the resulting mixture was agitated at ambient temperature for 2 h. Reaction distilled to dryness to give a residue, which was adsorbed onto silica and purified by automated column chromatography over silica gel eluting with a gradient of 0 to 100% EtOAc in hexane to afford the desired product.

Method 12: General Procedure for the Synthesis of 1-substituted-N-(1-methylcyclopropyl)-3-((3-methylisoxazol-5-yl)methyl)-4-oxo-3,4-dihydrophthalazine-6-sulfonamides The following examples were prepared by telescoping the intermediate through to the final product:

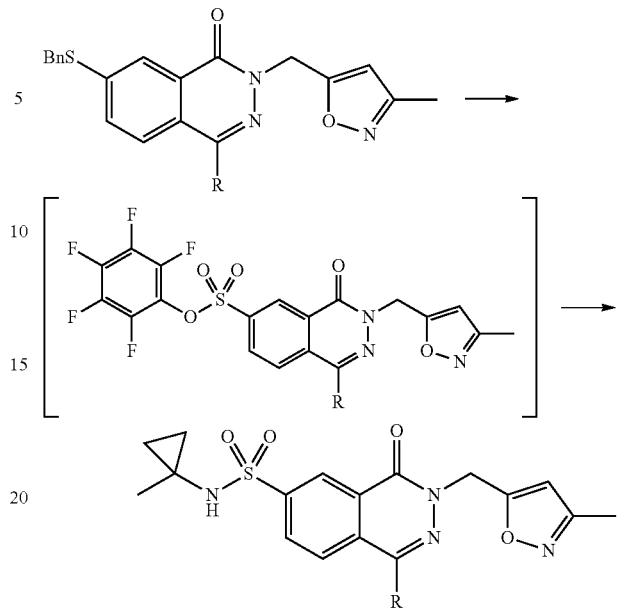

A solution of 7-(benzylthio)-4-substituted-2-((3-methylisoxazol-5-yl)methyl)phthalazin-1(2H)-ones (0.36 mmol) in a mixture of acetonitrile (3 mL), water (0.1 mL) and acetic acid (0.2 mL) at 0° C. was treated with 1,3-dichloro-5,5-dimethylhydantoin (0.72 mmol), and the resulting mixture was stirred at 0° C. for 2 h. Pentafluorophenol (0.72 mmol) was then added to the reaction followed by triethylamine (1.07 mmol), and the resulting mixture was stirred at ambient temperature for 2 h. The solvent was removed in vacuo to give the crude product as a residue, which was suspended in EtOAc (10 mL) and filtered. The filtrate was collected and distilled to dryness to give the crude sulfonate ester.

This was taken up in acetonitrile (2 mL) and treated with 1-methylcyclopropanamine hydrochloride (0.54 mmol) and diisopropylethylamine (1.44 mmol) and stirred at 60° C. for 2 h. The cooled reaction mixture was then diluted with EtOAc (10 mL) and water (5 mL) and layers separated. The aqueous layer was re-extracted with EtOAc and the combined organics were passed through a hydrophobic frit and concentrated. Purification by prep. HPLC, high pH, afforded the desired product.

General Procedures Relating to Scheme 7:

Intermediate S7-A
2-Bromo-5-chlorosulfonyl-benzoic acid

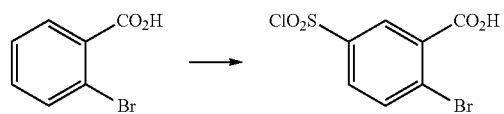 [SMILES: O=C(O)c1ccccc1Br ; O=C(O)c1cc(S(=O)(=O)Cl)ccc1Br]

Following the procedure from WO2011072174. 2-Bromobenzoic acid (2. g, 9.95 mmol) was added portionwise to stirred chlorosulfonic acid (6.62 mL, 99.5 mmol) at 0° C., under nitrogen. The reaction mixture was heated at 110° C. for 6 h. The reaction mixture was cooled and then added dropwise to stirring ice, a white precipitate formed which was filtered and dried in the vacuum oven to yield 2-bromo-5-chlorosulfonyl-benzoic acid (2.5 g, 8.35 mmol, 84%).

$^1$H NMR (300 MHz, DMSO-d$_6$) δ=7.92 (d, J=2.2 Hz, 1H), 7.68 (d, J=8.1 Hz, 1H), 7.59 (dd, J=2.1, 8.2 Hz, 1H)

Intermediate S7-B Methyl 2-bromo-5-chlorosulfonyl-benzoate

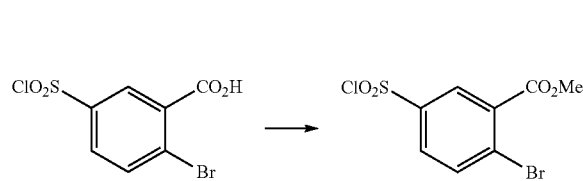 [SMILES: O=C(O)c1cc(S(=O)(=O)Cl)ccc1Br ; COC(=O)c1cc(S(=O)(=O)Cl)ccc1Br]

Following the procedure in WO2009005998. Thionyl Chloride (2.44 mL, 33.4 mmol) was added to a stirring suspension of 2-bromo-5-chlorosulfonyl-benzoic acid (1. g, 3.34 mmol) in DCE (5 mL), the reaction mixture was heated at reflux for 1 h. The reaction mixture was cooled to room temperature and then concentrated in vacuo, toluene (10 mL) was added to the resulting brown liquid and then removed in vacuo to give crude 2-bromo-5-chlorosulfonyl-benzoyl chloride as a brown liquid. The crude 2-bromo-5-chlorosulfonyl-benzoyl chloride was cooled in an ice bath, cold methanol (8 mL) was added and the reaction mixture stirred for 10 min in the ice bath, then stirred at room temperature for 15 min. The reaction mixture was added to ice-cold water (8 mL) and the resulting white precipitate was filtered, washed with cold water (10 mL) and dried in the vacuum oven to yield methyl 2-bromo-5-chlorosulfonyl-benzoate (854 mg, 2.72 mmol, 82%).

$^1$H NMR (300 MHz, DMSO-d$_6$) δ=7.96 (d, J=1.8 Hz, 1H), 7.73 (d, J=8.3 Hz, 1H), 7.64 (dd, J=2.2, 8.3 Hz, 1H), 3.87 (s, 3H)

Intermediate S7-C Methyl 2-bromo-5-[(1-methylcyclopropyl)sulfamoyl]benzoate

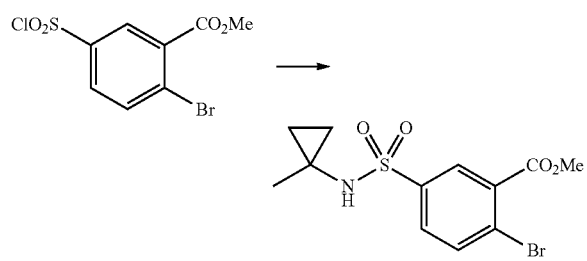

1-Methylcyclopropanamine hydrochloride (281.1 mg, 2.61 mmol) and triethylamine (726.6 uL, 5.23 mmol) were added sequentially to a stirring solution of methyl 2-bromo-5-chlorosulfonyl-benzoate (745. mg, 2.38 mmol) in DCM (15 mL) at ambient temperature. The reaction mixture was stirred for 1 h then 2 M HCl (10 mL) was added and the reaction mixture stirred vigorously for 15 min. The organic phase was separated using a hydrophobic frit and evaporated to dryness. The crude product was purified by automated column chromatography SiO$_2$ (RediSep, 24 g) eluent 30% EtOAc in iso-hexane to yield methyl 2-bromo-5-[(1-methylcyclopropyl)sulfamoyl]benzoate (630.2 mg, 1.81 mmol, 76%).

$^1$H NMR (300 MHz, CDCl$_3$) δ=8.32-8.30 (m, 1H), 7.86-7.79 (m, 2H), 4.99 (s, 1H), 3.99 (s, 3H), 1.25 (s, 3H), 0.82-0.75 (m, 2H), 0.57-0.50 (m, 2H)

Intermediate S7-D 2-Bromo-5-[(1-methylcyclopropyl)sulfamoyl]benzoic acid

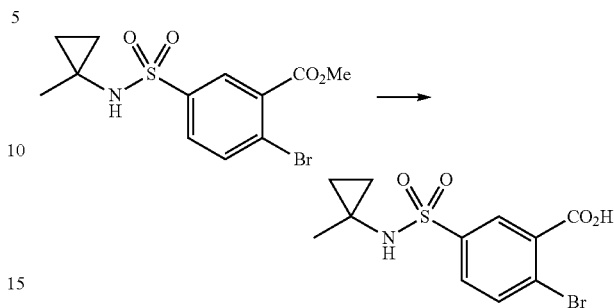

Methyl 2-bromo-5-[(1-methylcyclopropyl)sulfamoyl]benzoate (95. mg, 0.27 mmol) and lithium hydroxide (13.1 mg, 0.55 mmol) in THF (2 mL) were stirred at ambient temperature overnight. Water (10 mL) was added and the aqueous phase was washed with DCM (10 mL), the organic phase was separated and the resulting aqueous phase was cooled in an ice bath and acidified with 2 M HCl (to pH 1). The resulting precipitate was filtered and dried in the vacuum oven to yield 2-bromo-5-[(1-methylcyclopropyl)sulfamoyl]benzoic acid (68.5 mg, 0.21 mmol, 75%).

$^1$H NMR (300 MHz, DMSO-d$_6$) δ=13.91 (s, 1H), 8.30 (s, 1H), 8.12 (d, J=2.4 Hz, 1H), 7.98 (d, J=8.4 Hz, 1H), 7.80 (dd, J=2.4, 8.4 Hz, 1H), 1.07 (s, 3H), 0.67-0.57 (m, 2H), 0.49-0.38 (m, 2H)

Method 13: Synthesis of 4-oxo-3H-quinazoline-6-sulfonamides

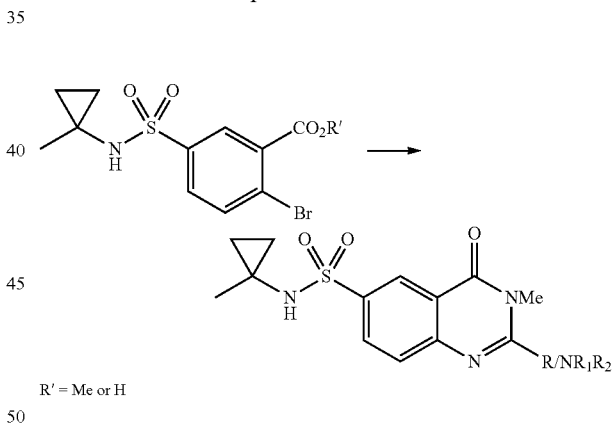

R' = Me or H

Following the procedure in Angew. Chem. Int. Ed. 2009, 48, 348-351. A solution of methyl 2-bromo-5-[(1-methylcyclopropyl)sulfamoyl]benzoate (for Example 52 and 55) or 2-bromo-5-[(1-methylcyclopropyl)sulfamoyl]benzoic acid (for Example 54 and 98) (1 eq) and carboxamidine (2 eq) in DMF was stirred at ambient temperature for 10 min. Caesium carbonate (2 eq) was added and after a further 15 min copper (I) iodide (0.2 eq) was added to the reaction mixture. The mixture was stirred under nitrogen and heated at 80° C. for 16 h (for Example 98 the reaction mixture was heated at 110° C. for 16 h). The reaction mixture was cooled and filtered through Celite, which was washed with MeOH, the organic phase was evaporated to dryness. Alternatively, saturated aq. NH$_4$Cl (10 mL) was added to the reaction mixture which was then extracted with EtOAc (2×20 mL), the organic phase was separated, passed through a hydrophobic frit and evaporated to dryness. The crude product was purified by prep. HPLC, high pH, to yield the desired product.

General Procedures Relating to Scheme 8:

Intermediate S8-A 2-Bromo-N-methyl-benzamide

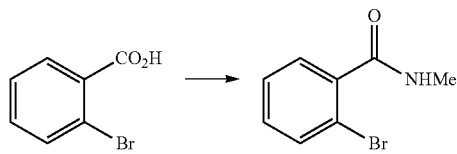 [SMILES: O=C(O)c1ccccc1Br ; CNC(=O)c1ccccc1Br]

Following the procedure in Chem. Commun. 2011, 47, 2074-12076. 2-Bromobenzoic acid (1. g, 4.97 mmol) and thionyl chloride (5. mL, 68.6 mmol) were stirred at reflux for 2 h. The solvent was removed in vacuo to give the crude acyl chloride. Potassium carbonate (1.72 g, 12.4 mmol) and THF (3 mL) were added to the crude acyl chloride, the reaction mixture was cooled in an ice bath and methylamine (2 M in THF) (3.73 mL, 7.46 mmol) was added slowly to the reaction mixture which was stirred at ambient temperature overnight. The reaction mixture was quenched slowly with 2 M HCl (10 mL) whilst cooled in an ice bath, and extracted with EtOAc (3×30 mL). The organic phase was washed with saturated aq. $NaHCO_3$ and brine and then dried over sodium sulfate. The organic phase was evaporated to dryness to yield the product 2-bromo-N-methyl-benzamide (941.8 mg, 4.40 mmol, 88%).

$^1$H NMR (300 MHz, $CDCl_3$) δ=7.58 (dd, J=1.2, 8.0 Hz, 1H), 7.53 (dd, J=1.9, 7.5 Hz, 1H), 7.35 (dt, J=1.3, 7.5 Hz, 1H), 7.27 (dt, J=1.8, 7.6 Hz, 1H), 6.03 (br. s, 1H), 3.02 (d, J=4.9 Hz, 3H)

Intermediate S8-B
4-Bromo-3-(methylcarbamoyl)benzenesulfonyl chloride

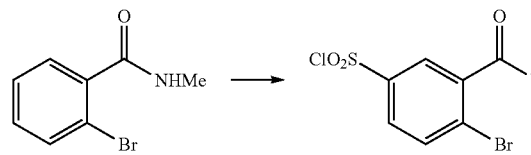

Chlorosulfonic acid (1.45 mL, 21.7 mmol) was added dropwise to a stirred solution of 2-bromo-N-methyl-benzamide (465. mg, 2.17 mmol) in DCM (1 mL) at 0° C., under nitrogen. The reaction mixture was heated at 110° C. for 7 h. The reaction mixture was cooled and then added dropwise to stirring ice, a beige precipitate formed which was filtered and dried in the vacuum oven to yield 4-bromo-3-(methylcarbamoyl)benzenesulfonyl chloride (528.6 mg, 1.69 mmol, 78%).

$^1$H NMR (300 MHz, DMSO-$d_6$) δ=8.46-8.36 (m, 1H), 7.59 (d, J=8.6 Hz, 1H), 7.54-7.49 (m, 2H), 2.74 (d, J=4.6 Hz, 3H)

Intermediate S8-C 2-Bromo-N-methyl-5-[(1-methylcyclopropyl)sulfamoyl]benzamide

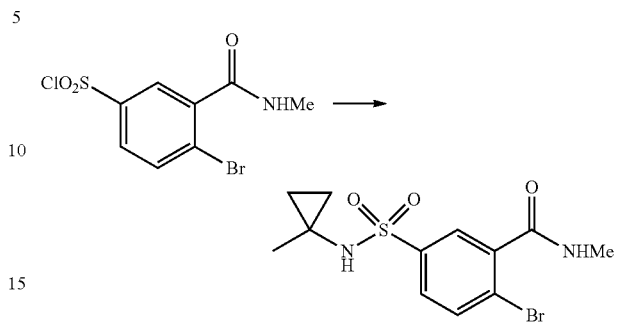

1-Methylcyclopropanamine hydrochloride (386.2 mg, 3.59 mmol) and triethylamine (997.9 uL, 7.18 mmol) were added sequentially to a stirring solution of 4-bromo-3-(methylcarbamoyl)benzenesulfonyl chloride (1.02 g, 3.26 mmol) in DCM (20 mL) at ambient temperature. The reaction mixture was stirred for 1 h then 2M HCl (10 mL) was added and the mixture stirred for 10 min. The mixture was passed through a hydrophobic frit and the resulting organic phase collected. The acidic aqueous phase was neutralised to pH 7 with saturated aq. $NaHCO_3$, extracted with EtOAc (25 mL), the organic phase separated and passed through a hydrophobic frit. The combined organic phase was evaporated to dryness. The resulting crude product was purified by automated column chromatography $SiO_2$ (Biotage, 24 g) eluent 0-75% EtOAc in iso-Hexane, to yield 2-bromo-N-methyl-5-[(1-methylcyclopropyl)sulfamoyl]benzamide (510 mg, 1.47 mmol, 45%).

$^1$H NMR (300 MHz, $CDCl_3$) δ=8.00 (dd, J=0.8, 2.0 Hz, 1H), 7.78-7.75 (m, 2H), 6.06 (br. s, 1H), 5.06 (br. s., 1H), 3.05 (d, J=4.9 Hz, 3H), 1.26 (s, 3H), 0.81-0.76 (m, 2H), 0.56-0.49 (m, 2H)

Method 14: Synthesis of 4-oxo-3H-quinazoline-6-sulfonamides

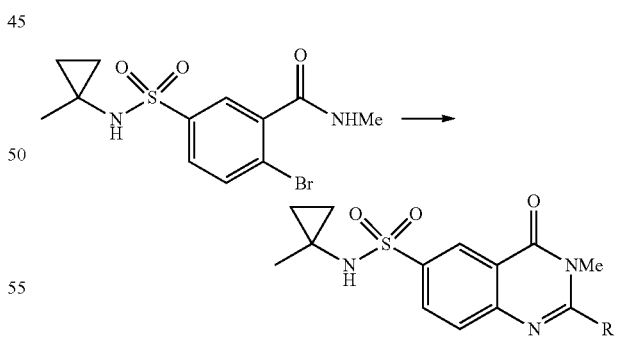

A suspension of 2-bromo-N-methyl-5-[(1-methylcyclopropyl)sulfamoyl]benzamide (1 eq), amide (2 eq), trans-4-hydroxy-L-proline (0.07 eq), copper (I) iodide (0.07 eq) and caesium carbonate (2 eq) in DMF was heated at 80° C. for 2 h. The reaction mixture was removed from heating, saturated aq. $NH_4Cl$ was added, the aqueous phase was extracted with EtOAc (2×10 mL), the combined organic phase was dried over sodium sulfate, filtered and evaporated to dryness to give the crude uncyclised intermediate.

The crude intermediate was dissolved in DMF, then zinc chloride (0.5 eq) and hexamethyldisilazane (3 eq) were added and the reaction mixture heated at 110° C. for 16 h. The reaction mixture was cooled, saturated aq. NH₄Cl was added and the reaction mixture extracted with EtOAc (2×20 mL), the combined organic phase was dried over sodium sulfate, filtered and evaporated to dryness. The crude product was purified by prep. HPLC, high pH, to yield the desired product.

General Procedures Relating to Scheme 9:

Intermediate S9-A
7-Bromo-4-chloro-2H-isoquinolin-1-one

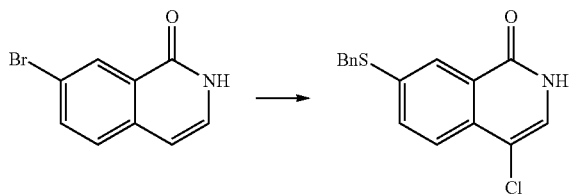

Following the procedure in WO2009060209. A suspension of 7-bromo-1-hydroxyisoquinoline (2.73 g, 12.2 mmol) and N-chlorosuccinimide (1.95 g, 14.6 mmol) in MeCN (50 mL) was heated at 90° C. for 2 h. The reaction mixture was cooled to room temperature and the resulting precipitate was collected and washed with MeOH, to yield 7-bromo-4-chloro-2H-isoquinolin-1-one (2.24 g, 8.67 mmol, 71%).

¹H NMR (300 MHz, DMSO-d₆) δ=11.77 (br. s., 1H), 8.31 (d, J=2.2 Hz, 1H), 8.02 (dd, J=2.2, 8.7 Hz, 1H), 7.75 (d, J=8.7 Hz, 1H), 7.54 (s, 1H)

Intermediate S9-B
7-Benzylsulfanyl-2H-isoquinolin-1-one

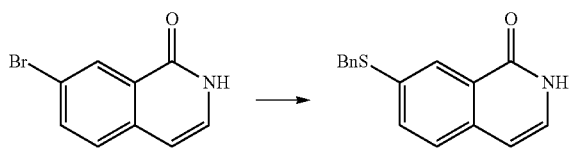

A solution of 7-bromo-1-hydroxyisoquinoline (2.0 g, 8.93 mmol), tris(dibenzylideneacetone)dipalladium(0) (408.7 mg, 0.45 mmol) and Xantphos (516.51 mg, 0.89 mmol) in 1,4-dioxane (250 mL) was degassed with nitrogen. N,N-Diisopropylethylamine (1.67 mL, 9.37 mmol) and benzyl mercaptan (1.1 mL, 9.37 mmol) were then added sequentially to the flask, and the resulting mixture was heated at 80° C. for 5 h. The reaction mixture was evaporated to dryness and the residue suspended in DCM (80 mL), the resulting mixture was stirred for 15 min. The mixture was filtered to give a solid, which was air-dried to give the desired product 7-benzylsulfanyl-2H-isoquinolin-1-one (1.4 g, 5.24 mmol, 59%).

¹H NMR (300 MHz, DMSO-d₆) δ=11.28 (br. s, 1H), 8.05 (d, J=2.1 Hz, 1H), 7.65 (dd, J=2.0, 8.3 Hz, 1H), 7.58 (d, J=8.3 Hz, 1H), 7.39-7.20 (m, 5H), 7.13 (dd, J=5.8, 7.1 Hz, 1H), 6.51 (d, J=6.8 Hz, 1H), 4.33 (s, 2H)

Intermediate S9-C1
7-Benzylsulfanyl-4-chloro-2H-isoquinolin-1-one

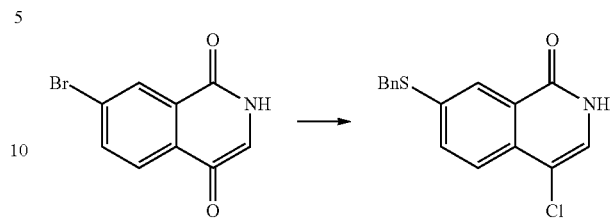

A solution of 7-bromo-4-chloro-2H-isoquinolin-1-one (1.94 g, 7.5 mmol), tris(dibenzylideneacetone)dipalladium (0) (171.81 mg, 0.19 mmol) and Xantphos (217.12 mg, 0.38 mmol) in 1,4-dioxane (50 mL) was degassed with nitrogen for 10 min, N,N-diisopropylethylamine (2.48 mL, 15.01 mmol) and benzyl mercaptan (0.99 mL, 8.26 mmol) were sequentially added to the mixture. The reaction mixture was heated by microwave irradiation at 80° C. for 20 min. The reaction mixture was diluted with EtOAc (100 mL), and the organic phase was washed with water (100 mL). The organic phase was filtered and the solid washed with water and ether then dried in the vacuum oven to yield the desired product. The aqueous phase was further extracted with EtOAc (2×50 mL) and the combined organic phase washed with water (100 mL). The organic phase was separated and evaporated to dryness. The crude product was recrystallised with EtOAc (50 mL), the precipitate which formed was filtered, washed with water and ether, dried in the vacuum oven and combined with the first crop to yield 7-benzylsulfanyl-4-chloro-2H-isoquinolin-1-one (2.38 g, 7.89 mmol, 105%) contains inorganic impurities, used without further purification.

¹H NMR (300 MHz, DMSO-d₆) δ=11.61 (br. s., 1H), 8.09 (d, J=2.1 Hz, 1H), 7.82 (dd, J=2.1, 8.5 Hz, 1H), 7.72 (d, J=8.6 Hz, 1H), 7.44 (s, 1H), 7.42-7.37 (m, 2H), 7.34-7.21 (m, 3H), 4.38 (s, 2H)

Intermediate S9-C2
7-Benzylsulfanyl-4-bromo-2H-isoquinolin-1-one

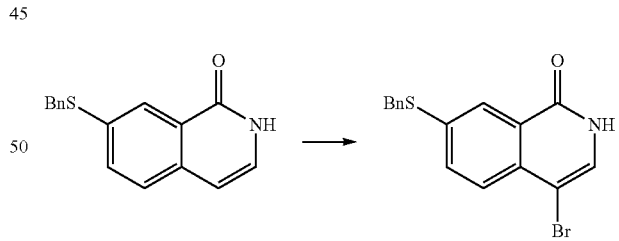

N-Bromosuccinimide (1.76 g, 9.87 mmol) was added to a stirred suspension of 7-benzylsulfanyl-2H-isoquinolin-1-one (2.4 g, 8.98 mmol) in MeCN (100 mL) under nitrogen, and the resulting mixture was stirred at ambient temperature for 2 h. The reaction mixture was filtered and the filter-cake washed with MeCN (2×20 mL) to give the desired product 7-benzylsulfanyl-4-bromo-2H-isoquinolin-1-one (2.3 mg, 6.64 mmol, 74%).

¹H NMR (300 MHz, DMSO-d₆) δ=11.63 (d, J=5.9 Hz, 1H), 8.08 (d, J=1.8 Hz, 1H), 7.81 (dd, J=2.1, 8.5 Hz, 1H), 7.67 (d, J=8.5 Hz, 1H), 7.51 (d, J=6.0 Hz, 1H), 7.42-7.35 (m, 2H), 7.35-7.20 (m, 3H), 4.38 (s, 2H)

Intermediate S9-D1 7-Benzylsulfanyl-4-bromo-2-[(3-methylisoxazol-5-yl)methyl]isoquinolin-1-one

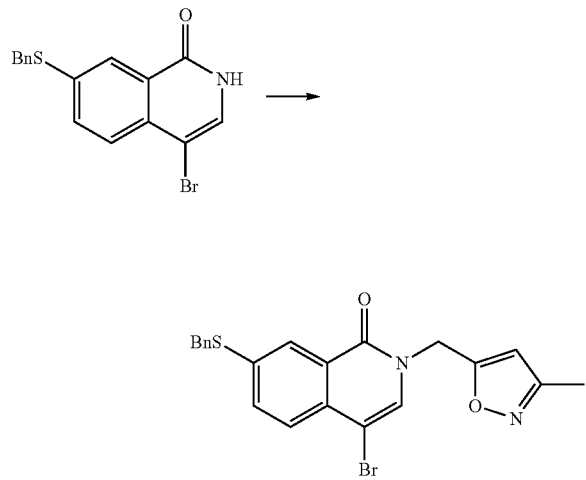

Sodium hydride (60% w/w) (0.46 g, 11.4 mmol) was added portionwise to a solution of 7-benzylsulfanyl-4-bromo-2H-isoquinolin-1-one (2.82 g, 8.14 mmol) in DMF (40 mL) at 0° C. After 1 h 5-(bromomethyl)-3-methyl-1,2-oxazole (1.72 g, 9.77 mmol) was added and the mixture stirred at ambient temperature overnight. EtOAc (150 mL) and saturate aq. NaHCO$_3$ (150 mL) were added and the mixture stirred for 5 min. The EtOAc layer was separated and the aqueous layer washed with EtOAc (100 mL). The combined organic extracts were passed through a hydrophobic frit, concentrated under reduced pressure and purified by automated column chromatography, eluent 0-100% EtOAc in iso-hexane, yielding 7-benzylsulfanyl-4-bromo-2-[(3-methylisoxazol-5-yl)methyl]isoquinolin-1-one (1.78 g, 4.03 mmol, 49%).

LCMS (high pH): RT 1.40 min, [M+H]+ 441.0, 94% purity

The following intermediates were prepared by a similar method:

Intermediate S9-D2 7-Benzylsulfanyl-4-chloro-2-[(3-methylisoxazol-5-yl)methyl]isoquinolin-1-one

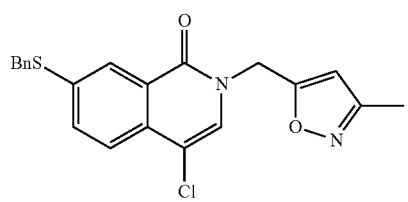

Prepared from 7-benzylsulfanyl-4-chloro-2H-isoquinolin-1-one and 5-(bromomethyl)-3-methyl-1,2-oxazole.

$^1$H NMR (300 MHz, DMSO-d$_6$) δ=8.12 (d, J=1.6 Hz, 1H), 7.96 (s, 1H), 7.86 (d, J=8.7 Hz, 1H), 7.75 (d, J=8.5 Hz, 1H), 7.44-7.38 (m, 2H), 7.38-7.19 (m, 3H), 6.29 (s, 1H), 5.29 (s, 2H), 4.39 (s, 2H), 2.18 (s, 3H)

Intermediate S9-D3 7-Benzylsulfanyl-4-bromo-2-methyl-isoquinolin-1-one

Prepared from 7-benzylsulfanyl-4-bromo-2H-isoquinolin-1-one and iodomethane.

$^1$H NMR (300 MHz, DMSO-d$_6$) δ=8.11 (d, J=2.2 Hz, 1H), 7.92 (s, 1H), 7.81 (dd, J=2.1, 8.6 Hz, 1H), 7.66 (d, J=9.0 Hz, 1H), 7.42-7.37 (m, 2H), 7.34-7.21 (m, 3H), 4.38 (s, 2H), 3.50 (s, 3H)

Intermediate S9-E1 (2,3,4,5,6-Pentafluorophenyl) 4-chloro-2-[(3-methylisoxazol-5-yl)methyl]-1-oxo-isoquinoline-7-sulfonate

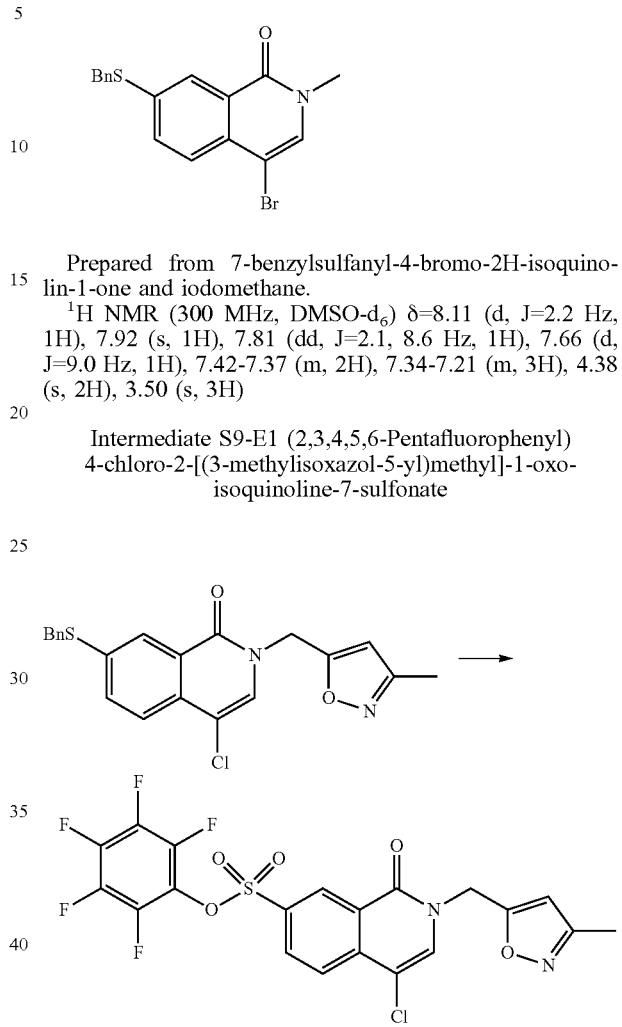

A suspension of 7-benzylsulfanyl-4-chloro-2-[(3-methylisoxazol-5-yl)methyl]isoquinolin-1-one (150. mg, 0.38 mmol), acetic acid (2.4 mL), water (1.6 mL) and MeCN (20 mL) was cooled to 0° C. After 5 minutes of stirring, 1,3-dichloro-5,5-dimethylhydantoin (148.92 mg, 0.76 mmol) was added portionwise and the stirring continued at 0-5° C. for 40 min. Pentafluorophenol (139.13 mg, 0.76 mmol) in MeCN (2 mL) and triethylamine (147.09 uL, 1.06 mmol) were added sequentially to the reaction mixture. The mixture was stirred at 0° C. for 20 min before removing from the cooling bath and stirring at ambient temperature overnight. Water (20 mL) and EtOAc (20 mL) were added, the organic phase was separated and washed with water (10 mL), the organic phase was passed through a hydrophobic frit and evaporated to dryness. The crude product was purified by automated column chromatography SiO$_2$ (Biotage, 10 g) eluent 0-50% EtOAc in iso-Hexane, yielding (2,3,4,5,6-pentafluorophenyl) 4-chloro-2-[(3-methylisoxazol-5-yl)methyl]-1-oxo-isoquinoline-7-sulfonate (110.8 mg, 0.21 mmol, 56%).

$^1$H NMR (300 MHz, CDCl$_3$) δ=9.03 (d, J=2.0 Hz, 1H), 8.29 (dd, J=2.0, 8.7 Hz, 1H), 8.11 (d, J=8.6 Hz, 1H), 7.62 (s, 1H), 6.25 (s, 1H), 5.27 (s, 2H), 2.30 (s, 3H)

The following intermediate was prepared by a similar method:

Intermediate S9-E2 (2,3,4,5,6-Pentafluorophenyl) 4-bromo-2-[(1-methylpyrazol-4-yl)methyl]-1-oxo-isoquinoline-7-sulfonate

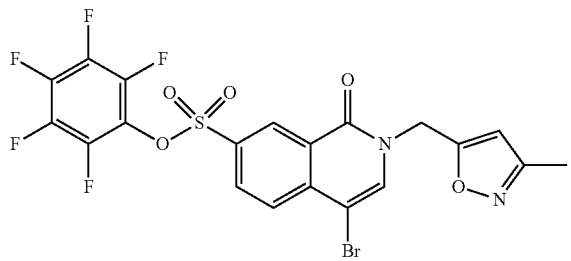 [SMILES: Cc1cc(Cn2cc(Br)c3ccc(S(=O)(=O)Oc4c(F)c(F)c(F)c(F)c4F)cc3c2=O)on1]

Prepared from 7-benzylsulfanyl-4-bromo-2-[(3-methylisoxazol-5-yl)methyl]isoquinolin-1-one, 1,3-dichloro-5,5-dimethylhydantoin, pentafluorophenol and triethylamine.

LCMS (high pH): RT 1.31 min, [M+H]+ 522.0, 100% purity

Example 209 4-Chloro-N-(1-methylcyclopropyl)-2-[(3-methylisoxazol-5-yl)methyl]-1-oxo-isoquinoline-7-sulfonamide

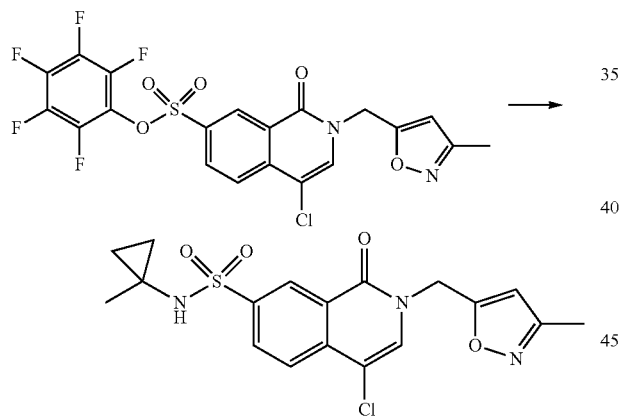

1-Methylcyclopropanamine hydrochloride (193.65 mg, 1.8 mmol) and triethylamine (417.01 uL, 3 mmol) were added to a solution of (2,3,4,5,6-pentafluorophenyl) 4-chloro-2-[(3-methylisoxazol-5-yl)methyl]-1-oxo-isoquinoline-7-sulfonate (625. mg, 1.2 mmol) in DMF (10 mL) at ambient temperature, the reaction mixture was heated at 60° C. for 1.5 h. The reaction mixture was cooled then water (50 mL) and EtOAc (50 mL) were added, the organic phase was separated and the aqueous phase further extracted with EtOAc (50 mL). The combined organic phase was washed with water (50 mL), separated, passed through a hydrophobic frit and evaporated to dryness. The crude product was triturated with a minimal volume of EtOAc, to yield 4-chloro-N-(1-methylcyclopropyl)-2-[(3-methylisoxazol-5-yl)methyl]-1-oxo-isoquinoline-7-sulfonamide (442 mg, 1.08 mmol, 90%).

$^1$H NMR (300 MHz, DMSO-$d_6$) δ=8.67 (d, J=2.4 Hz, 1H), 8.35 (s, 1H), 8.23 (dd, J=2.0, 8.6 Hz, 1H), 8.21 (s, 1H), 8.06 (d, J=8.5 Hz, 1H), 6.36 (s, 1H), 5.34 (s, 2H), 2.19 (s, 3H), 1.06 (s, 3H), 0.67-0.51 (m, 2H), 0.44-0.36 (m, 2H)

The following intermediate was prepared by a similar method:

Example 307 4-Bromo-N-(1-methylcyclopropyl)-2-[(3-methylisoxazol-5-yl)methyl]-1-oxo-isoquinoline-7-sulfonamide

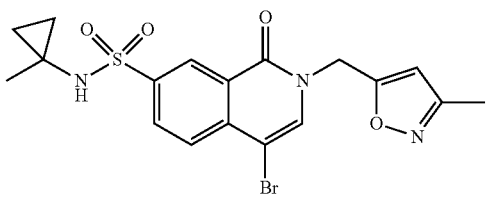

Prepared from (2,3,4,5,6-pentafluorophenyl) 4-bromo-2-[(1-methylpyrazol-4-yl)methyl]-1-oxo-isoquinoline-7-sulfonate, 1-methylcyclopropanamine hydrochloride and triethylamine.

$^1$H NMR (300 MHz, DMSO-$d_6$) δ=8.66 (d, J=2.1 Hz, 1H), 8.34 (s, 1H), 8.28 (s, 1H), 8.22 (dd, J=2.0, 8.5 Hz, 1H), 8.00 (d, J=9.0 Hz, 1H), 6.36 (s, 1H), 5.34 (s, 2H), 2.19 (s, 3H), 1.06 (s, 3H), 0.66-0.51 (m, 2H), 0.47-0.33 (m, 2H)

1-Oxo-isoquinoline-7-sulfonamide Examples

Example 242 N-(1-Methylcyclopropyl)-2-[(3-methylisoxazol-5-yl)methyl]-1-oxo-isoquinoline-7-sulfonamide

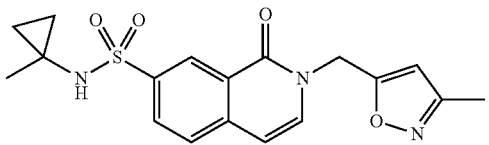

To a solution of 4-bromo-N-(1-methylcyclopropyl)-2-[(3-methylisoxazol-5-yl)methyl]-1-oxo-isoquinoline-7-sulfonamide (Intermediate S9-F2) (90. mg, 0.20 mmol) and lithium chloride (8.44 mg, 0.20 mmol) in THF (10 mL) at −20° C., under nitrogen, was added methylmagnesium chloride (66.33 uL, 0.20 mmol), the resulting mixture was stirred at −20° C. for 45 min. Isopropylmagnesium chloride lithium chloride complex solution (33.43 uL, 0.22 mmol) was then added, and the resulting mixture was stirred at −20° C. for 45 min. Allyl bromide (17.22 uL, 0.20 mmol) was added, and the mixture was allowed to warm to ambient temperature. LCMS indicated debromination had occurred in favour of the desired reaction. The reaction was quenched by the addition of saturated aq. NH$_4$Cl (10 mL) and extracted with ether (20 mL). The ether layer was collected and distilled to dryness. The crude product was purified by prep. HPLC, low pH, to yield N-(1-methylcyclopropyl)-2-[(3-methylisoxazol-5-yl)methyl]-1-oxo-isoquinoline-7-sulfonamide (10 mg, 0.0268 mmol, 13%).

Example 286 4-[3-(Dimethylamino)prop-1-ynyl]-N-(1-methylcyclopropyl)-2-[(3-methylisoxazol-5-yl)methyl]-1-oxo-isoquinoline-7-sulfonamide

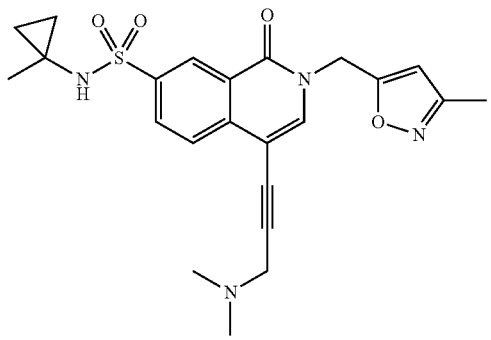

A mixture of 4-bromo-N-(1-methylcyclopropyl)-2-[(3-methylisoxazol-5-yl)methyl]-1-oxo-isoquinoline-7-sulfonamide (Intermediate S9-F2) (100. mg, 0.22 mmol), 3-dimethylamino-1-propyne (35.71 uL, 0.33 mmol), tetra-N-butylammonium iodide (81.66 mg, 0.22 mmol), tetrakis(triphenylphosphine)palladium(0) (15.36 mg, 0.010 mmol), copper (I) iodide (5.05 mg, 0.03 mmol), and diisopropylamine (46.48 uL, 0.33 mmol) in THF (2 mL) was heated in a sealed tube, in the absence of light, for 48 h. The mixture was evaporated to dryness and the residue partitioned between DCM (10 mL) and water (10 mL). The DCM layer was collected and distilled to dryness to give a residue, which was purified by automated column chromatography SiO$_2$ (RediSep, 4 g) eluent 0 to 10% MeOH in DCM to yield 4-[3-(dimethylamino)prop-1-ynyl]-N-(1-methylcyclopropyl)-2-[(3-methylisoxazol-5-yl)methyl]-1-oxo-isoquinoline-7-sulfonamide (40 mg, 0.088 mmol, 40%).

Example 287 4-[3-(dimethylamino)propyl]-N-(1-methylcyclopropyl)-2-[(3-methylisoxazol-5-yl)methyl]-1-oxo-isoquinoline-7-sulfonamide

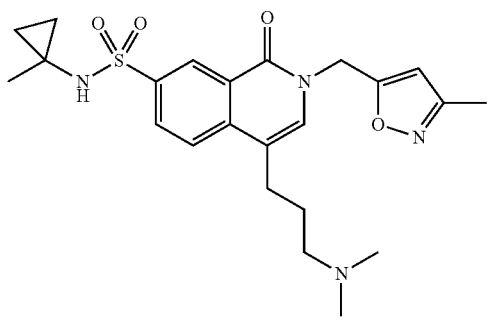

4-[3-(Dimethylamino)prop-1-ynyl]-N-(1-methylcyclopropyl)-2-[(3-methylisoxazol-5-yl)methyl]-1-oxo-isoquinoline-7-sulfonamide (30. mg, 0.070 mmol) was dissolved in EtOH (2 mL) with agitation at ambient temperature, and the solution was vacuum purged with nitrogen 3 times. Palladium on activated carbon (20.75 mg, 0.070 mmol) was then added to the reaction mixture, and the resulting suspension was vacuum purged with nitrogen 3 times. The reaction mixture was then vacuum purged with hydrogen 3 times and stirred under a positive pressure of hydrogen for 2 h. The mixture was vacuum purged with nitrogen and filtered through a pad of celite. The cake was washed with EtOH (2×4 mL) and the combined filtrates distilled to dryness under vacuum to give the crude product as a residue, which was purified by automated column chromatography, SiO$_2$ (RediSep, 4 g) eluent 0-10% MeOH in DCM to afford the desired product 4-[3-(dimethylamino)propyl]-N-(1-methylcyclopropyl)-2-[(3-methylisoxazol-5-yl)methyl]-1-oxo-isoquinoline-7-sulfonamide (10 mg, 0.0218 mmol, 33%).

General Procedures Relating to Scheme 10:

Intermediate S10-A 7-Benzylsulfanyl-4-(cyclopropanecarbonyl)-2H-isoquinolin-1-one

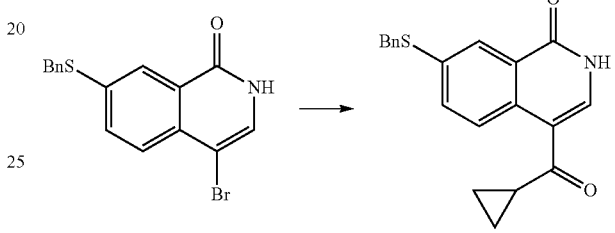

Methyllithium (1.6 M in diethyl ether) (1.29 mL, 2.07 mmol) was added to a suspension of 7-benzylsulfanyl-4-bromo-2H-isoquinolin-1-one (Intermediate S9-C2) (650. mg, 1.88 mmol) in THF (10 mL). After 10 min the reaction mixture was cooled to −78° C. and n-butyllithium (1.6 M in hexanes) (1.41 mL, 2.25 mmol) added dropwise. After 10 min cyclopropanecarbonyl chloride (0.19 mL, 2.07 mmol) was added and the reaction mixture stirred at −78° C. for 10 min, then warmed to ambient temperature. Following 1 h at ambient temperature DCM (30 mL) and saturated aq. NaHCO$_3$ (20 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography, SiO$_2$, eluent 0-100% EtOAc in iso-hexane, to yield 7-benzylsulfanyl-4-(cyclopropanecarbonyl)-2H-isoquinolin-1-one (320 mg, 0.954 mmol, 51%).

LCMS (high pH): RT 1.22 min, [M+H]$^+$ 336.2, 82% purity

Intermediate S10-B1 7-Benzylsulfanyl-4-(cyclopropanecarbonyl)-2-[(3-methylisoxazol-5-yl)methyl]isoquinolin-1-one

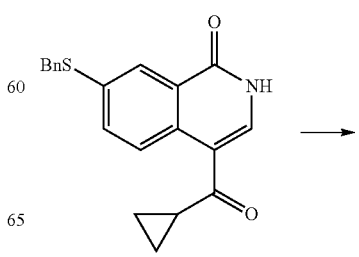

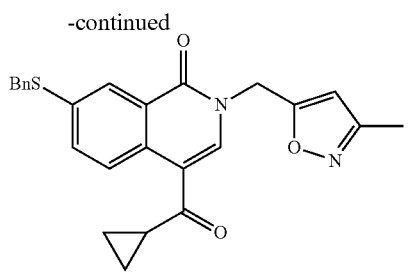

Sodium hydride (60% w/w) (34.1 mg, 0.85 mmol) was added to a stirring solution of 7-benzylsulfanyl-4-(cyclopropanecarbonyl)-2H-isoquinolin-1-one (220. mg, 0.66 mmol) in DMF (8 mL). After 15 min 5-(bromomethyl)-3-methyl-1,2-oxazole (0.15 mL, 0.85 mmol) was added and the reaction mixture stirred at ambient temperature for 1 h. DCM (25 mL) and saturated aq. NaHCO₃ (25 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography, SiO$_2$, eluent 0-100% EtOAc in iso-Hexane to yield 7-benzylsulfanyl-4-(cyclopropanecarbonyl)-2-[(3-methylisoxazol-5-yl)methyl]isoquinolin-1-one (263 mg, 0.61 mmol, 93%). Used directly in the synthesis of Intermediate S10-C1.

Intermediate S10-B2 7-Benzylsulfanyl-4-[(4-fluorophenyl)methyl]-2-[(3-methylisoxazol-5-yl)methyl]isoquinolin-1-one

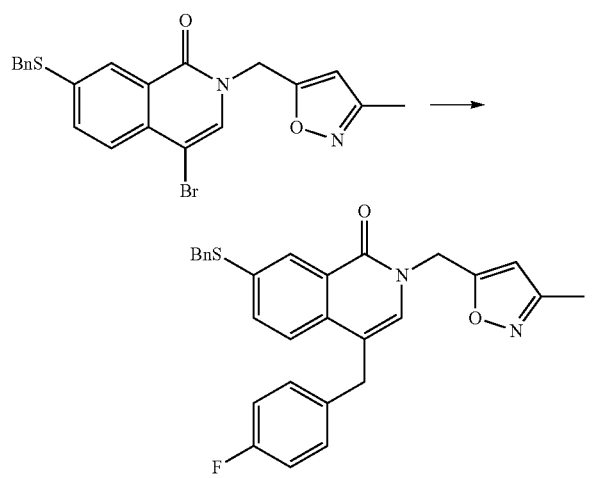

Step 1

A solution of 7-benzylsulfanyl-4-bromo-2-[(3-methylisoxazol-5-yl)methyl]isoquinolin-1-one (Intermediate S9-D1) (2. g, 4.53 mmol), bis(pinacolato)diboron (3.45 g, 13.59 mmol) and potassium acetate (1.33 g, 13.59 mmol) in 1,4-dioxane (40 mL) was degassed with nitrogen. 1,1'-Bis(diphenylphosphino)ferrocene-palladium(II)dichloride dichloromethane adduct (370.07 mg, 0.45 mmol) was added and the reaction mixture heated by microwave irradiation at 80° C. for 45 min. DCM (80 mL) and saturated aq. NaHCO₃ (80 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography, SiO$_2$, eluent 0-100% EtOAc in iso-hexane to yield 7-benzylsulfanyl-2-[(3-methylisoxazol-5-yl)methyl]-4-(4,4,5,5-tetramethyl-1,3,2-dioxaborolan-2-yl)isoquinolin-1-one (1.1 g, 2.25 mmol, 50%).

LCMS (high pH): RT 1.52 min, [M−H]⁻ 489.3, 80% purity

Step 2

A solution of 7-benzylsulfanyl-2-[(3-methylisoxazol-5-yl)methyl]-4-(4,4,5,5-tetramethyl-1,3,2-dioxaborolan-2-yl)isoquinolin-1-one (100. mg, 0.20 mmol) and sodium carbonate (54.25 mg, 0.51 mmol) in DME (1 mL) and water (0.5 mL) was degassed with nitrogen. Tetrakis(triphenylphosphine)palladium(0) (11.85 mg, 0.010 mmol) was added followed by 4-fluorobenzyl bromide (0.04 mL, 0.31 mmol) and the reaction mixture heated by microwave irradiation at 50° C. for 40 min. DCM (8 mL) and saturated aq. NaHCO₃ (8 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography 0-100% EtOAc in iso-hexane to yield 7-benzylsulfanyl-4-[(4-fluorophenyl)methyl]-2-[(3-methylisoxazol-5-yl)methyl]isoquinolin-1-one (78 mg, 0.17 mmol, 81%) as a yellow oil with several impurities that can be removed in subsequent steps.

LCMS (high pH): RT 1.42 min, [M+H]⁺ 471.2, 87% purity

Intermediate S10-B3 7-Benzylsulfanyl-4-(4-fluorophenyl)-2-methyl-isoquinolin-1-one

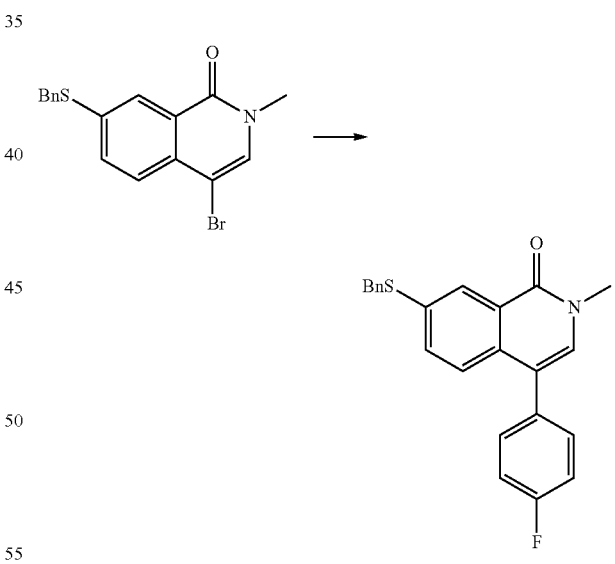

7-Benzylsulfanyl-4-bromo-2-methyl-isoquinolin-1-one (Intermediate S9-D3) (100. mg, 0.2800 mmol), potassium carbonate (28.09 mg, 0.28 mmol) and 1,1'-bis(diphenylphosphino)ferrocene-palladium(II)dichloride dichloromethane adduct (16.33 mg, 0.020 mmol) were suspended in a mixture of 1,4-dioxane (4 mL) and water (0.40 mL), and the resulting mixture was vacuum purged with nitrogen. 4-Fluorobenzene boronic acid (38.84 mg, 0.28 mmol) was added, and the resulting mixture was heated by microwave irradiation at 140° C. for 30 min. The reaction was partitioned between DCM (10 mL) and water (10 mL) and the organic phase collected. The mixture was evaporated to dryness and the crude product purified by automated column chromatography, SiO$_2$ (RediSep 12 g) eluent 0-80% EtOAc in iso-hexane to yield 7-benzylsulfanyl-4-(4-fluorophenyl)-2-methyl-isoquinolin-1-one (100 mg, 0.27 mmol, 96%).

$^1$H NMR (300 MHz, DMSO-d$_6$) δ=8.19 (d, J=1.9 Hz, 1H), 7.66 (dd, J=2.2, 8.6 Hz, 1H), 7.51-7.43 (m, 3H), 7.42-7.20 (m, 8H), 4.35 (s, 2H), 3.33 (s, 3H)

Intermediate S10-B4 7-Benzylsulfanyl-4-methyl-2-[(3-methylisoxazol-5-yl)methyl]isoquinolin-1-one

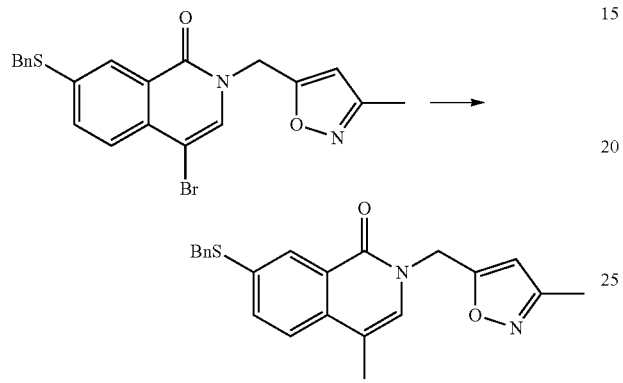

A stirred solution of 7-benzylsulfanyl-4-bromo-2-[(3-methylisoxazol-5-yl)methyl]isoquinolin-1-one (Intermediate S9-D1) (300. mg, 0.68 mmol), potassium carbonate (206.35 mg, 2.04 mmol) and trimethylboroxine (95.02 uL, 0.68 mmol) in 1,4-dioxane (8 mL) and water (0.80 mL) was vacuum purged three times with nitrogen. Tetrakis(triphenylphosphine)palladium(0) (78.55 mg, 0.070 mmol) was added and the resulting mixture was heated at 100° C. for 48 h. The reaction mixture was cooled and evaporated dryness to give a residue, the crude product was purified by automated column chromatography, SiO$_2$ (Biotage 12 g) eluent 0-80% EtOAc in iso-hexane, to yield 7-benzylsulfanyl-4-methyl-2-[(3-methylisoxazol-5-yl)methyl]isoquinolin-1-one (160 mg, 0.43 mmol, 63%).

LCMS (High pH): RT 1.29 min, [M+H]$^+$ 377.3, 88% purity

Intermediate S10-C1 (2,3,4,5,6-Pentafluorophenyl) 4-(cyclopropanecarbonyl)-2-[(3-methylisoxazol-5-yl)methyl]-1-oxo-isoquinoline-7-sulfonate

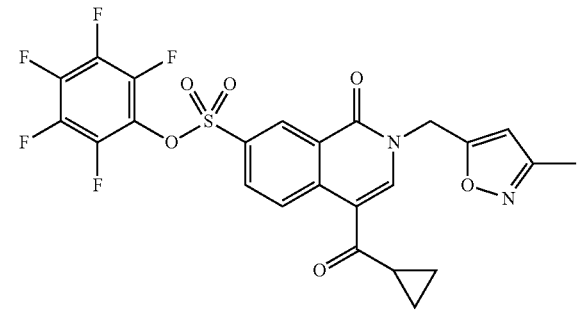 [SMILES: Cc1cc(Cn2cc(C(=O)C3CC3)c3ccc(S(=O)(=O)Oc4c(F)c(F)c(F)c(F)c4F)cc3c2=O)on1]

Prepared using the procedure detailed for Intermediate S9-E1, from 7-benzylsulfanyl-4-(cyclopropanecarbonyl)-2-[(3-methylisoxazol-5-yl)methyl]isoquinolin-1-one (Intermediate S10-B1), 1,3-dichloro-5,5-dimethylhydantoin, pentafluorophenol and triethylamine.

LCMS (high pH): RT 1.36 min [M+H]$^+$ 553.1, 70% purity

Intermediate S10-C2 (2,3,4,5,6-Pentafluorophenyl) 4-[(4-fluorophenyl)methyl]-2-[(3-methylisoxazol-5-yl)methyl]-1-oxo-isoquinoline-7-sulfonate

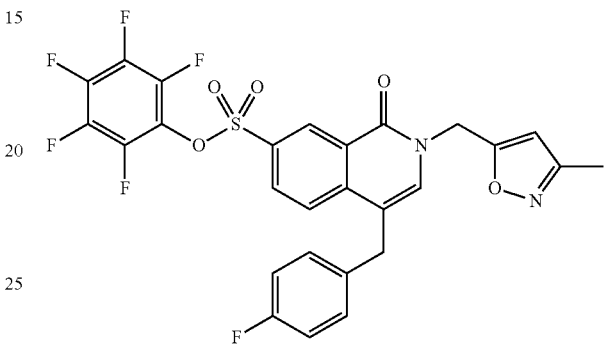

Prepared using the procedure detailed for Intermediate S9-E1, from 7-benzylsulfanyl-4-[(4-fluorophenyl)methyl]-2-[(3-methylisoxazol-5-yl)methyl]isoquinolin-1-one (Intermediate S10-B2), 1,3-dichloro-5,5-dimethylhydantoin, pentafluorophenol and triethylamine.

LCMS (high pH): RT 1.36 min [M+H]$^+$ 595.2, 70% purity

Intermediate S10-C3 (2,3,4,5,6-Pentafluorophenyl) 4-(4-fluorophenyl)-2-methyl-1-oxo-isoquinoline-7-sulfonate

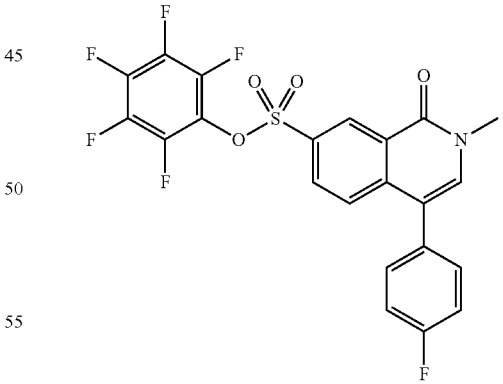

Prepared using the procedure detailed for Intermediate S9-E1, from 7-benzylsulfanyl-4-(4-fluorophenyl)-2-methyl-isoquinolin-1-one (Intermediate S10-B2), 1,3-dichloro-5,5-dimethylhydantoin, pentafluorophenol and triethylamine.

$^1$H NMR (300 MHz, DMSO-d$_6$) δ=8.80 (d, J=1.9 Hz, 1H), 8.23 (dd, J=2.3, 8.8 Hz, 1H), 7.90 (s, 1H), 7.77 (d, J=8.8 Hz, 1H), 7.58-7.50 (m, 2H), 7.44-7.35 (m, 2H), 3.62 (s, 3H)

Intermediate S10-C4 (2,3,4,5,6-Pentafluorophenyl) 4-methyl-2-[(3-methylisoxazol-5-yl)methyl]-1-oxo-isoquinoline-7-sulfonate

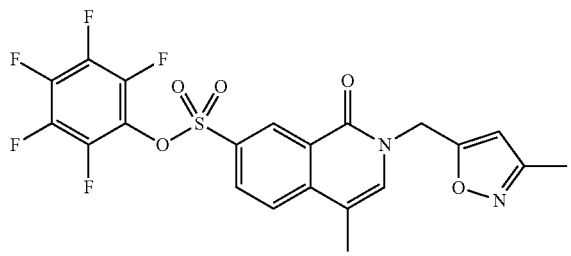 [SMILES: Cc1cc(Cn2cc(C)c3ccc(S(=O)(=O)Oc4c(F)c(F)c(F)c(F)c4F)cc3c2=O)on1]

Prepared using the procedure detailed for Intermediate S9-E1, from 7-benzylsulfanyl-4-methyl-2-[(3-methylisoxazol-5-yl)methyl]isoquinolin-1-one (Intermediate S10-B4), 1,3-dichloro-5,5-dimethylhydantoin, pentafluorophenol and triethylamine.

LCMS (high pH): RT 1.29 min, [M+H]$^+$ 501.3, 70% purity. Material progressed into next step (Example 256)

Example 311 4-(Cyclopropanecarbonyl)-N-(1-methylcyclopropyl)-2-[(3-methylisoxazol-5-yl)methyl]-1-oxo-isoquinoline-7-sulfonamide

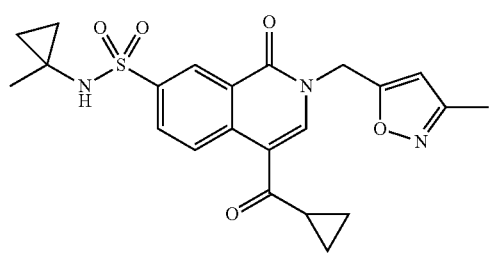

Prepared using the procedure detailed for Example 209, from (2,3,4,5,6-pentafluorophenyl) 4-(cyclopropanecarbonyl)-2-[(3-methylisoxazol-5-yl)methyl]-1-oxo-isoquinoline-7-sulfonate, 1-methylcyclopropanamine hydrochloride and triethylamine.

Example 322 4-[(4-Fluorophenyl)methyl]-N-(1-methylcyclopropyl)-2-[(3-methylisoxazol-5-yl)methyl]-1-oxo-isoquinoline-7-sulfonamide

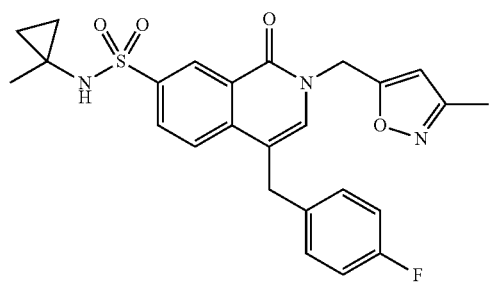

Prepared using the procedure detailed for Example 209, from (2,3,4,5,6-pentafluorophenyl) 4-[(4-fluorophenyl)methyl]-2-[(3-methylisoxazol-5-yl)methyl]-1-oxo-isoquinoline-7-sulfonate, 1-methylcyclopropanamine hydrochloride and triethylamine.

Example 255 4-(4-Fluorophenyl)-2-methyl-N-(1-methylcyclopropyl)-1-oxo-isoquinoline-7-sulfonamide

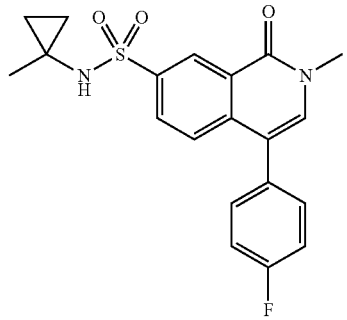

Prepared using the procedure detailed for Example 209, from (2,3,4,5,6-pentafluorophenyl) 4-(4-fluorophenyl)-2-methyl-1-oxo-isoquinoline-7-sulfonate, 1-methylcyclopropanamine hydrochloride and triethylamine.

Example 256 4-Methyl-N-(1-methylcyclopropyl)-2-[(3-methylisoxazol-5-yl)methyl]-1-oxo-isoquinoline-7-sulfonamide

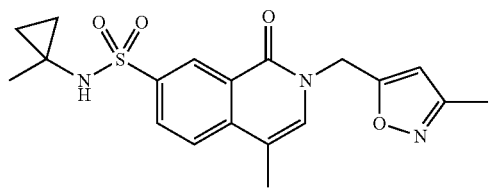

Prepared using the procedure detailed for Example 209, from (2,3,4,5,6-pentafluorophenyl) 4-methyl-2-[(3-methylisoxazol-5-yl)methyl]-1-oxo-isoquinoline-7-sulfonate, 1-methylcyclopropanamine hydrochloride and triethylamine.

General Procedures Relating to Scheme 11 and Scheme 12

Intermediate S11-A 3-Fluoro-N-(1-methylcyclopropyl)-4-nitro-benzenesulfonamide

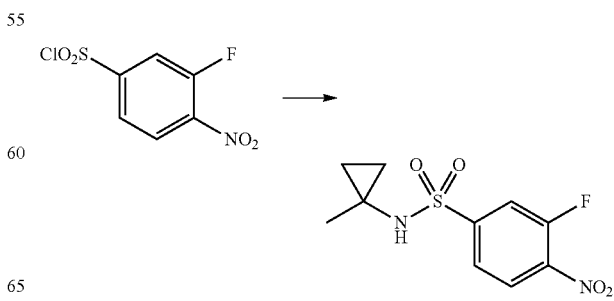

Triethylamine (1.18 mL, 8.47 mmol) was added to a stirring solution of 3-fluoro-4-nitrobenzenesulfonyl chloride (2.03 g, 8.47 mmol) and 1-methylcyclopropanamine hydrochloride (911.43 mg, 8.47 mmol) in DCM (40 mL) at 0° C. After 5 min pyridine (0.68 mL, 8.47 mmol) was added dropwise and the reaction mixture allowed to warm to ambient temperature, and stir overnight. Water (50 mL) was added, the organic layer was separated, and the aqueous layer extracted with DCM (2×10 mL). The organics were combined, passed through a hydrophobic frit and evaporated to dryness. The crude product was purified by automated column chromatography, SiO$_2$, eluent 0-50% EtOAc in iso-hexane, to yield 3-fluoro-N-(1-methylcyclopropyl)-4-nitro-benzenesulfonamide (1.44 g, 5.26 mmol, 62%).

$^1$H NMR (300 MHz, CDCl$_3$) δ=8.19 (t, J=7.7 Hz, 1H), 7.88-7.79 (m, 2H), 5.10 (s, 1H), 1.30 (s, 3H), 0.83-0.72 (m, 2H), 0.69-0.49 (m, 2H)

The following intermediate was prepared in a similar manner:

Intermediate S12-A 4-Chloro-N-(1-methylcyclopropyl)-3-nitro-benzenesulfonamide

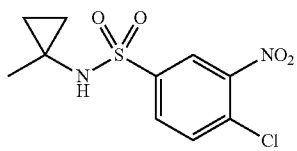 [SMILES: CC1(NS(=O)(=O)c2ccc(Cl)c([N+](=O)[O-])c2)CC1]

Prepared from 4-chloro-3-nitro-benzenesulfonyl chloride, 1-methylcyclopropanamine hydrochloride and triethylamine.

$^1$H NMR (300 MHz, CDCl$_3$) δ=8.38 (d, J=3.6 Hz, 1H), 8.02 (dd, J=2.2, 8.4 Hz, 1H), 7.73 (t, J=6.1 Hz, 1H), 5.09 (s, 1H), 1.30 (s, 3H), 0.83-0.72 (m, 2H), 0.66-0.50 (m, 2H)

Intermediate S11-B 3-(Methylamino)-N-(1-methylcyclopropyl)-4-nitro-benzenesulfonamide

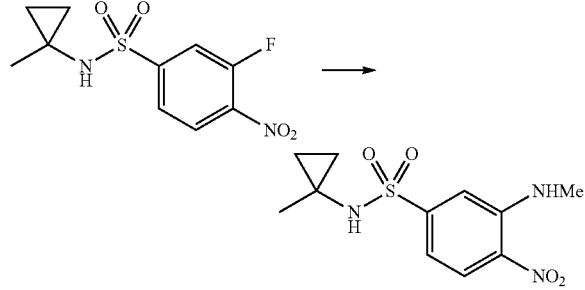

Methylamine solution (2 M in THF) (8.26 mL, 16.53 mmol) was added dropwise to a stirring solution 3-fluoro-N-(1-methylcyclopropyl)-4-nitro-benzenesulfonamide (1.51 g, 5.51 mmol) and triethylamine (1.15 mL, 8.26 mmol) in DMF (15 mL). The reaction mixture was heated at 50° C. for 2 h. Water (15 mL) and EtOAc (20 mL) was added and the organic layer separated. The aqueous layer was extracted with DCM (2×15 mL). The combined organics were passed through a hydrophobic frit and concentrated under vacuum. The crude product was purified by automated column chromatography, SiO$_2$, eluent 0-50% EtOAc in iso-hexane to yield 3-(methylamino)-N-(1-methylcyclopropyl)-4-nitro-benzenesulfonamide (1.378 g, 4.83 mmol, 88%).

$^1$H NMR (300 MHz, CDCl$_3$) δ=8.30 (d, J=8.9 Hz, 1H), 8.14 (br. s, 1H), 7.43 (d, J=2.0 Hz, 1H), 7.05 (dd, J=1.9, 8.9 Hz, 1H), 5.00 (s, 1H), 3.11 (d, J=4.2 Hz, 3H), 1.29 (s, 3H), 0.92-0.77 (m, 2H), 0.60-0.52 (m, 2H)

The following intermediate was prepared in a similar manner:

Intermediate S12-B 4-[(4-Fluorophenyl)methylamino]-N-(1-methylcyclopropyl)-3-nitro-benzenesulfonamide

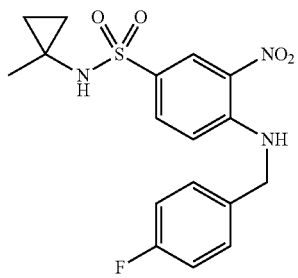 [SMILES: CC1(NS(=O)(=O)c2ccc(NCc3ccc(F)cc3)c([N+](=O)[O-])c2)CC1]

Prepared from 4-chloro-N-(1-methylcyclopropyl)-3-nitro-benzenesulfonamide, 4-fluorobenzylamine and triethylamine.

$^1$H NMR (300 MHz, CDCl$_3$) δ=8.75 (d, J=2.3 Hz, 1H), 8.68 (t, J=5.6 Hz, 1H), 7.82 (dd, J=2.3, 9.0 Hz, 1H), 7.36-7.29 (m, 2H), 7.15-7.04 (m, 2H), 6.90 (d, J=9.1 Hz, 1H), 4.58 (d, J=5.8 Hz, 2H), 1.27 (s, 3H), 0.88-0.70 (m, 2H), 0.60-0.42 (m, 2H)

Intermediate S11-C 4-Amino-3-(methylamino)-N-(1-methylcyclopropyl)benzenesulfonamide

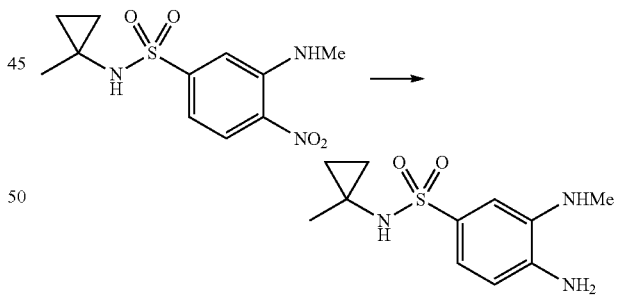

To a stirred suspension of 3-(methylamino)-N-(1-methylcyclopropyl)-4-nitro-benzenesulfonamide (4.97 g, 17.42 mmol) in EtOH (75 mL) was added iron (4.86 g, 87.1 mmol), ammonium chloride (4.66 g, 87.1 mmol) and water (75 mL). The mixture was stirred at 80° C. for 2 h and then filtered through celite, washing with hot EtOH. The filtrate was concentrated under vacuum to a slurry and water (80 mL) and DCM (80 mL) added. The organic layer was separated and the aqueous layer extracted with DCM (2×30 mL). The combined organics were passed through a hydrophobic frit and concentrated to dryness. The crude product was purified by automated column chromatography, SiO$_2$, eluent 0-10% MeOH in DCM to yield 4-amino-3-(methylamino)-N-(1-methylcyclopropyl)benzenesulfonamide (3.83 g, 15.0 mmol, 86%).

$^1$H NMR (300 MHz, CDCl$_3$) δ=7.25 (dd, J=2.1, 8.1 Hz, 1H), 7.13 (d, J=2.1 Hz, 1H), 6.72 (d, J=8.1 Hz, 1H), 5.01 (s, 1H), 3.73 (br. s., 2H), 2.89 (s, 3H), 1.18 (s, 3H), 0.89-0.71 (m, 2H), 0.51-0.34 (m, 2H)

The following intermediate was prepared in a similar manner:

Intermediate S12-C 3-Amino-4-[(4-fluorophenyl)methylamino]-N-(1-methylcyclopropyl)benzenesulfonamide

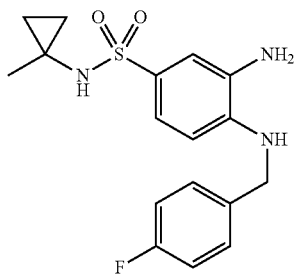

Prepared from 4-[(4-fluorophenyl)methylamino]-N-(1-methylcyclopropyl)-3-nitro-benzenesulfonamide, iron and ammonium chloride.

$^1$H NMR (300 MHz, CDCl$_3$) δ=7.42-7.30 (m, 4H), 7.09-6.98 (m, 2H), 6.60 (d, J=8.3 Hz, 1H), 5.08 (br. s., 1H), 4.36 (s, 2H), 1.17 (s, 3H), 0.81-0.72 (m, 2H), 0.46-0.37 (m, 2H)

Example 21 4-Methyl-N-(1-methylcyclopropyl)-2,3-dioxo-1H-quinoxaline-6-sulfonamide

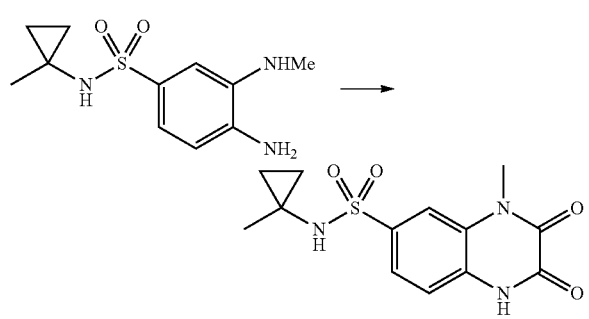

Oxalyl chloride (0.05 mL, 0.56 mmol) was added to a stirring solution of 4-amino-3-(methylamino)-N-(1-methylcyclopropyl)benzenesulfonamide (120. mg, 0.47 mmol) and triethylamine (0.33 mL, 2.35 mmol) in DCM (2 mL) under nitrogen. The reaction mixture was stirred at ambient temperature for 1 h. Water (5 mL) and DCM (5 mL) were added and the mixture stirred for 5 min. The DCM layer was isolated by passing through a hydrophobic frit and washing the aqueous layer with DCM (2×2 mL). The combined DCM extracts were evaporated to dryness and the crude product purified by automated column chromatography, SiO$_2$, eluent 0-10% MeOH in DCM, to yield 4-methyl-N-(1-methylcyclopropyl)-2,3-dioxo-1H-quinoxaline-6-sulfonamide (29 mg, 0.0937 mmol, 20%).

$^1$H NMR (300 MHz, DMSO-d$_6$) δ=12.31 (br. s., 1H), 8.05 (s, 1H), 7.64 (d, J=1.8 Hz, 1H), 7.59 (dd, J=1.9, 8.3 Hz, 1H), 7.29 (d, J=8.3 Hz, 1H), 3.53 (s, 3H), 1.06 (s, 3H), 0.65-0.59 (m, 2H), 0.42-0.35 (m, 2H)

The following intermediate was prepared in a similar manner:

Example 128 1-[(4-Fluorophenyl)methyl]-N-(1-methylcyclopropyl)-2,3-dioxo-4H-quinoxaline-6-sulfonamide

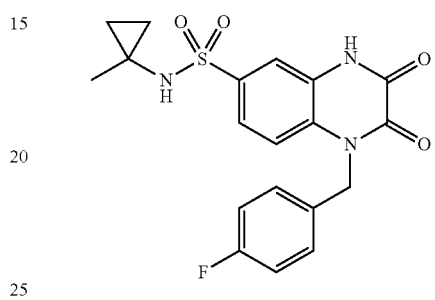

Prepared from 3-amino-4-[(4-fluorophenyl)methylamino]-N-(1-methylcyclopropyl)benzenesulfonamide, oxalyl chloride and triethylamine.

LCMS (high pH): RT 0.89 min, [M−H]− 402.5, >95% purity

Example 22 1-(Cyclopropylmethyl)-4-methyl-N-(1-methylcyclopropyl)-2,3-dioxo-quinoxaline-6-sulfonamide

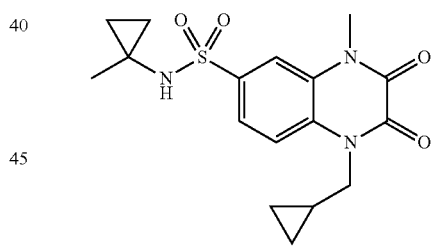

Sodium hydride (60% w/w) (3.27 mg, 0.0800 mmol) was added to a stirring solution of 4-methyl-N-(1-methylcyclopropyl)-2,3-dioxo-1H-quinoxaline-6-sulfonamide (23. mg, 0.070 mmol) in DMF (1 mL). After 5 min 1-(bromomethyl)cyclopropane (0.01 mL, 0.080 mmol) was added and the reaction mixture stirred under nitrogen overnight. DCM (5 mL) and saturated aq. NaHCO$_3$ (5 mL) were added and the DCM layer separated by passing through a hydrophobic frit, washing the aqueous layer with DCM (2×2 mL). The combined DCM extracts were concentrated to dryness and the crude product purified by automated column chromatography 0-100% EtOAc in iso-hexane to yield 1-(cyclopropylmethyl)-4-methyl-N-(1-methylcyclopropyl)-2,3-dioxo-quinoxaline-6-sulfonamide (17.6 mg, 0.048 mmol, 65%).

The following examples were prepared in a similar manner:

Example 40 1-Benzyl-4-methyl-N-(1-methylcyclopropyl)-2,3-dioxo-quinoxaline-6-sulfonamide

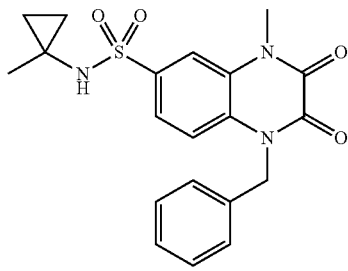 [SMILES: Cn1c(=O)c(=O)n(Cc2ccccc2)c2ccc(S(=O)(=O)NC3(C)CC3)cc21]

Prepared from 4-methyl-N-(1-methylcyclopropyl)-2,3-dioxo-1H-quinoxaline-6-sulfonamide (Intermediate S11-D), benzyl bromide and sodium hydride (60% w/w).

Example 130 1-[(4-Fluorophenyl)methyl]-4-methyl-N-(1-methylcyclopropyl)-2,3-dioxo-quinoxaline-6-sulfonamide

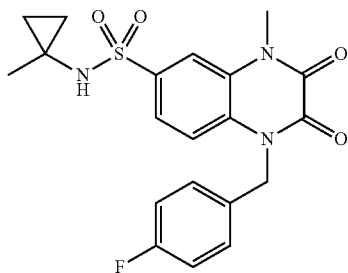 [SMILES: Cn1c(=O)c(=O)n(Cc2ccc(F)cc2)c2ccc(S(=O)(=O)NC3(C)CC3)cc21]

Prepared from 1-[(4-fluorophenyl)methyl]-N-(1-methylcyclopropyl)-2,3-dioxo-4H-quinoxaline-6-sulfonamide (Intermediate S12-D), iodomethane and potassium carbonate.

Example 41 4-Methyl-2-(methylamino)-N-(1-methylcyclopropyl)-3-oxo-quinoxaline-6-sulfonamide

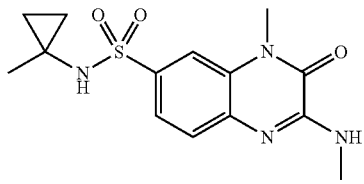

Step 1
A solution of 4-methyl-N-(1-methylcyclopropyl)-2,3-dioxo-1H-quinoxaline-6-sulfonamide (Intermediate S11-D) (300. mg, 0.9700 mmol) in phosphorus oxychloride (3. mL, 32.19 mmol) and heated at reflux for 4 h. The reaction mixture was cooled and excess phosphorus oxychloride removed under reduced pressure. The residue was taken up in anhydrous DMF (10 mL) and used as a stock solution without further purification.
Step 2
Methylamine solution (2 M in THF) (0.11 mL, 3.05 mmol) was added to a solution of 2-chloro-4-methyl-N-(1-methylcyclopropyl)-3-oxo-quinoxaline-6-sulfonamide (100. mg, 0.31 mmol) in anhydrous DMF (2 mL). The reaction mixture was stirred under nitrogen at ambient temperature overnight. The reaction mixture was evaporated to dryness and the residue purified by prep. HPLC, low pH, to yield 4-methyl-2-(methylamino)-N-(1-methylcyclopropyl)-3-oxo-quinoxaline-6-sulfonamide (26 mg, 0.081 mmol, 26%).
General Procedures Relating to Scheme 13:

S13-A1 7-Fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides A mixture of 7-fluoro-N-(1-methylcyclopropyl)-3-[(1-methylpyrazol-4-yl)methyl]-2,4-dioxo-1H-quinazoline-6-sulfonamide (0.20 mmol), alkylating agent (0.20 mmol) and potassium carbonate (0.40 mmol) in DMF (2 mL) was heated with agitation under microwave irradiation at 80° C. for 30 min. The solvent was removed in vacuo to give the crude product as a residue, which was purified by prep HPLC (high pH) affording the desired product.
The following intermediates were prepared by a similar method:

S13-A2 N-(1-(Fluoromethyl)cyclopropyl)-1-substituted-3-((1-methyl-1H-pyrazol-4-yl)methyl)-2,4-dioxo-1,2,3,4-tetrahydroquinazoline-6-sulfonamides General Procedures Relating to Scheme 14:

S14-A1 Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides To a magnetically stirred solution of 7-fluoro-N-(1-methylcyclopropyl)-3-[(1-methylpyrazol-4-yl)methyl]-2,4-dioxo-1H-quinazoline-6-sulfonamide (0.20 mmol) and alcohol (0.40 mmol) in DMF (4 mL) at 20° C. under nitrogen was added polymer-supported triphenylphosphine (0.60 mmol), and the resulting mixture was agitated at ambient for 15 min. Diisopropyl azodicarboxylate (0.40 mmol) was added and the resulting mixture was agitated for 12 h. The mixture was then filtered and the solvent removed in vacuo to give a residue which was purified by prep HPLC (high pH) affording the desired product.
General Procedures Relating to Scheme 23:

2-Amino-N-[(5-methyl-1,3,4-thiadiazol-2-yl)methyl]benzamide (5-Methyl-1,3,4-thiadiazol-2-yl)methanamine (2.4 g, 17.28 mmol) was added to a magnetically stirred solution of isatoic acid anhydride (2.7 g, 16.55 mmol) in DMF (20 mL) at 0° C. After the addition, the resulting mixture was heated to 60° C. for 5 h and then stirred at RT for 16 h. The solvent was removed in vacuo to give a light brown solid, which was preabsorbed onto silica and columned, eluting with 0-5% MeOH/DCM to give the desired product with 89% purity (3.0 g, 10.753 mmol, 65%) as a light brown solid.
$^1$H NMR (300 MHz, DMSO-d$_6$) δ=9.12 (t, J=5.8 Hz, 1H), 7.51 (dd, J=1.4, 8.0 Hz, 1H), 7.16 (ddd, J=1.5, 7.0, 8.3 Hz, 1H), 6.71 (dd, J=1.1, 8.2 Hz, 1H), 6.59-6.43 (m, 3H), 4.72 (d, J=5.9 Hz, 2H), 2.67 (s, 3H).

3-[(5-methyl-1,3,4-thiadiazol-2-yl)methyl]-1H-quinazoline-2,4-dione

A solution of 2-amino-N-[(5-methyl-1,3,4-thiadiazol-2-yl)methyl]benzamide (3.0 g, 10.75 mmol) in THF (100 mL)

was cooled to 0° C. and treated with triphosgene (1.6 g, 5.38 mmol), causing precipitate formation. The mixture was stirred in the cool bath for 15 min and then stirred at RT for 18 h. The mixture was quenched with sat. aq. $K_2CO_3$ (50 mL) and stirred at RT for 24 h. The resulting precipitate was collected by filtration, washed with water and oven-dried to give the desired product (1.7 g, 6.1976 mmol, 58%) as an off-white solid.

$^1$H NMR (300 MHz, DMSO-$d_6$) δ=11.80 (br s, 1H), 7.96 (d, J=7.8 Hz, 1H), 7.69 (dt, J=1.5, 7.7 Hz, 1H), 7.28-7.16 (m, 2H), 5.44 (s, 2H), 2.67 (s, 3H).

3-[(5-Methyl-1,3,4-thiadiazol-2-yl)methyl]-2,4-dioxo-1H-quinazoline-6-sulfonyl chloride A solution of 3-[(5-methyl-1,3,4-thiadiazol-2-yl)methyl]-1H-quinazoline-2,4-dione (1.7 g, 6.2 mmol) in chlorosulfonic acid (5 mL, 6.2 mmol) was heated to 50° C. LCMS after 2 h, shows no remaining SM, the mixture was stood at RT for 3 d and then added dropwise to crushed ice (20 mL) at −10° C. and stirred for 20 min. The precipitated solid was collected by filtration, washed with water and oven dried to give a sticky solid. This was azeotroped with PhMe (×3) to give the desired product (1.6 g, 4.2917 mmol, 69%) as a pale yellow solid.

$^1$H NMR (300 MHz, DMSO-$d_6$) δ=11.76 (s, 1H), 8.16 (d, J=2.0 Hz, 1H), 7.88 (dd, J=2.0, 8.4 Hz, 1H), 7.17 (d, J=8.5 Hz, 1H), 5.44 (s, 2H), 2.67 (s, 3H).

Example 385 7-Fluoro-1-methyl-N-(1-methylcyclopropyl)-3-[(1-methylpyrazol-4-yl)methyl]-2,4-dioxo-quinazoline-6-sulfonamide

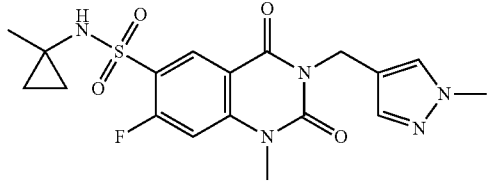

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using iodomethane to give the desired product (20 mg, 0.047 mmol, 24%) as a white powder.

Example 386 N-(1-Cyanocyclopropyl)-3-[(2-methylthiazol-5-yl)methyl]-2,4-dioxo-1H-quinazoline-6-sulfonamide

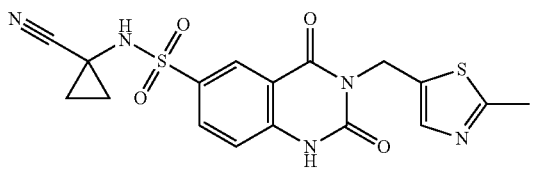 [SMILES: Cc1ncc(Cn2c(=O)[nH]c3ccc(S(=O)(=O)NC4(C#N)CC4)cc3c2=O)s1]

3-[(2-Methylthiazol-5-yl)methyl]-1H-quinazoline-2,4-dione (1.25 g, 4.57 mmol) in chlorosulfonic acid (4.0 mL, 4.57 mmol) was heated to 60° C. under stirring for 3 h. The mixture was allowed to cool and added in drops to crushed ice (300 mL). 5% MeOH/DCM (300 mL) was added and the mixture stirred for 5 min. The DCM layer was separated and the aqueous layer extracted with 5% MeOH/DCM (100 mL). The combined extracts were passed through a hydrophobic frit and concentrated under reduced pressure. The crude product was added to 1-amino-1-cyclopropanecarbonitrile hydrochloride (1.08 g, 9.15 mmol) in pyridine (5 mL) under stirring. After 1 h the reaction mixture was added to EtOAc (300 mL) and saturated aqueous ammonium chloride (300 mL) and stirred for 5 min. The EtOAc layer was separated and the aqueous layer extracted with EtOAc (100 mL). The combined extracts were passed through a hydrophobic frit and concentrated under reduced pressure. The solid residue was sonicated in water, filtered and dried to yield the desired product (358 mg, 0.858 mmol, 18.7%) as a white solid.

Example 387 N-(1-Cyanocyclopropyl)-7-fluoro-3-[(1-methylpyrazol-4-yl)methyl]-2,4-dioxo-1H-quinazoline-6-sulfonamide

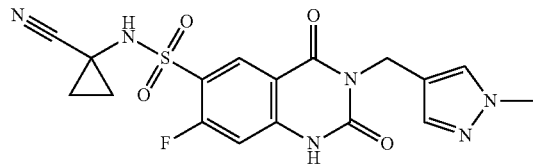 [SMILES: Cn1cc(Cn2c(=O)[nH]c3cc(F)c(S(=O)(=O)NC4(C#N)CC4)cc3c2=O)cn1]

7-Fluoro-3-[(1-methylpyrazol-4-yl)methyl]-2,4-dioxo-1H-quinazoline-6-sulfonyl chloride (0.44 g, 1.18 mmol) was added to 1-amino-1-cyclopropanecarbonitrile hydrochloride (0.28 g, 2.36 mmol) and pyridine (5 mL) added under stirring. The mixture was added to EtOAc (300 mL) and saturated aqueous sodium bicarbonate solution (300 mL) and the mixture stirred for 5 min. The EtOAc layer was separated and the aqueous layer extracted with EtOAc (100 mL). The combined extracts were passed through a hydrophobic frit and concentrated under reduced pressure and purified by column chromatography (DCM->10% MeOH/DCM) to yield the desired product (150 mg, 0.359 mmol, 30.4%) as a white solid.

Example 388 N-(1-Cyanocyclopropyl)-7-fluoro-3-[(1-methylpyrazol-4-yl)methyl]-2,4-dioxo-1H-quinazoline-6-sulfonamide

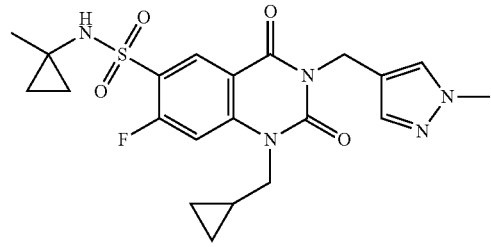

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using iodomethylcyclopropane to give the desired product (20 mg, 0.043 mmol, 22%) as a white powder.

Example 389 1-Ethyl-7-fluoro-N-(1-methylcyclopropyl)-3-[(1-methylpyrazol-4-yl)methyl]-2,4-dioxoquinazoline-6-sulfonamide

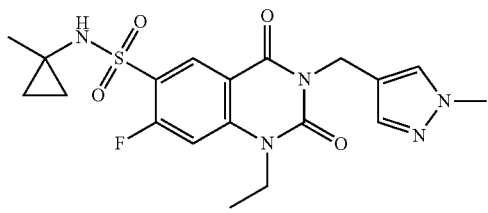

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using iodoethane to give the desired product (20 mg, 0.046 mmol, 23%) as a white powder.

Example 390 7-Fluoro-1-[(4-fluorophenyl)methyl]-N-(1-methylcyclopropyl)-3-[(1-methylpyrazol-4-yl)methyl]-2,4-dioxo-quinazoline-6-sulfonamide

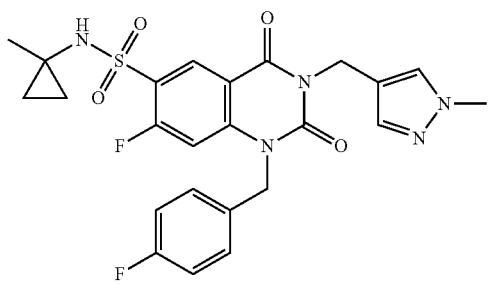

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using 4-fluorobenzyl bromide to give the desired product (25 mg, 0.048 mmol, 25%) as a white powder.

Example 391 7-Fluoro-N-(1-methylcyclopropyl)-1-[(3-methylisoxazol-5-yl)methyl]-3-[(1-methylpyrazol-4-yl)methyl]-2,4-dioxo-quinazoline-6-sulfonamide

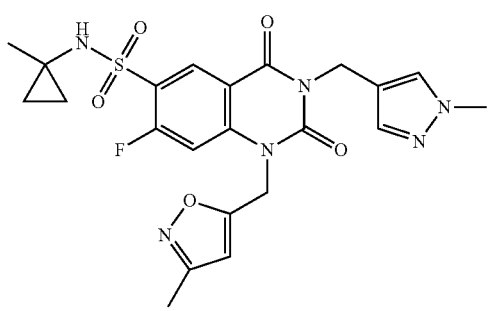

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using 5-(bromomethyl)-3-methyl-1,2-oxazole to give the desired product (20 mg, 0.040 mmol, 20%) as a white powder.

Example 392 1-[(2,5-Dimethylpyrazol-3-yl)methyl]-7-fluoro-N-(1-methylcyclopropyl)-3-[(1-methylpyrazol-4-yl)methyl]-2,4-dioxo-quinazoline-6-sulfonamide

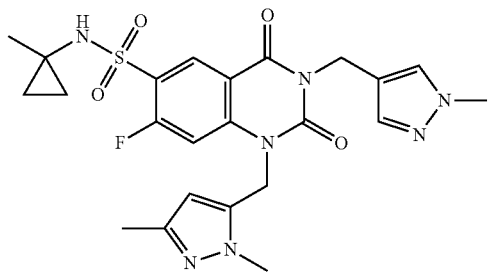

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using 5-(chloromethyl)-1,3-dimethyl-1H-pyrazole to give the desired product (25 mg, 0.048 mmol, 25%) as a white powder.

Example 393 7-Fluoro-N-(1-methylcyclopropyl)-1,3-bis[(1-methylpyrazol-4-yl)methyl]-2,4-dioxo-quinazoline-6-sulfonamide

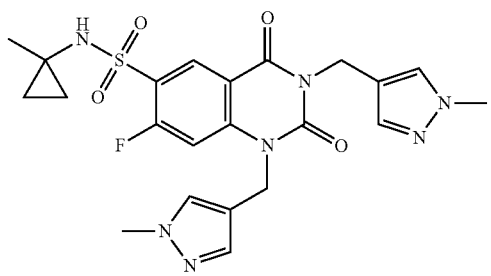

This compound was prepared according to the general procedure for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 13) using 4-(chloromethyl)-1-methyl-1H-pyrazole hydrochloride to give the desired product (24 mg, 0.048 mmol, 24%) as a white powder.

Example 394 7-Fluoro-N-(1-methylcyclopropyl)-3-[(1-methylpyrazol-4-yl)methyl]-1-(oxetan-3-ylmethyl)-2,4-dioxo-quinazoline-6-sulfonamide

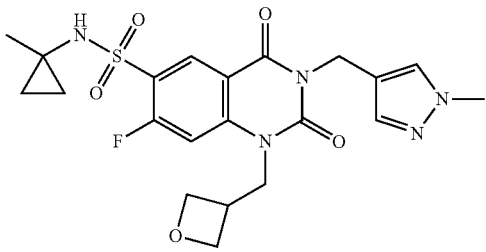

This compound was prepared according to the Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 14) using oxetan-3-ylmethanol to give the desired product (20 mg, 0.042 mmol, 21%) as a white powder.

Example 395 7-Fluoro-N-(1-methylcyclopropyl)-3-[(1-methylpyrazol-4-yl)methyl]-2,4-dioxo-1-(tetrahydrofuran-3-ylmethyl)quinazoline-6-sulfonamide

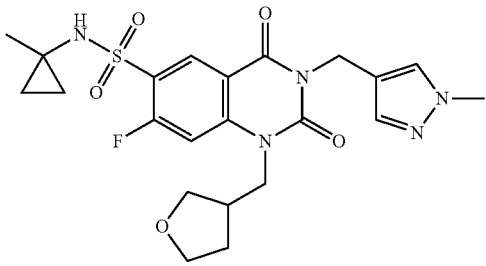

This compound was prepared according to the Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 14) using 3-tetrahydrofuran methanol to give the desired product (20 mg, 0.041 mmol, 21%) as a white powder.

Example 396 1-[(2,4-Dimethylthiazol-5-yl)methyl]-7-fluoro-N-(1-methylcyclopropyl)-3-[(1-methylpyrazol-4-yl)methyl]-2,4-dioxo-quinazoline-6-sulfonamide

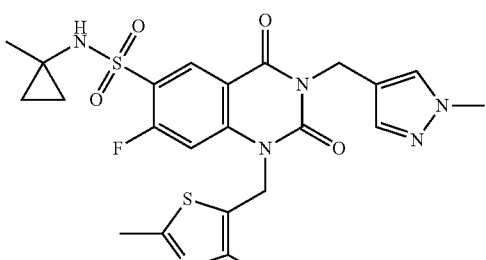

This compound was prepared according to the Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 14) using (2,4-dimethyl-1,3-thiazol-5-yl)methanol to give the desired product (20 mg, 0.038 mmol, 19%) as a white powder.

Example 397 7-Fluoro-3-((1-methyl-1H-pyrazol-4-yl)methyl)-N-(1-methylcyclopropyl)-2-((3-methyl-oxetan-3-yl)methoxy)-4-oxo-3,4-dihydroquinazoline-6-sulfonamide

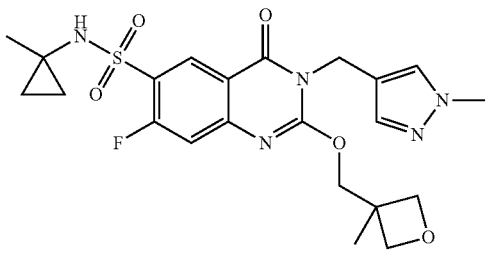

This compound was prepared according to the Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 14) using 3-methyl-3-oxetanemethanol to give the desired product (20 mg, 0.031 mmol, 16%) as a white powder.

Example 398 7-Fluoro-3-((1-methyl-1H-pyrazol-4-yl)methyl)-N-(1-methylcyclopropyl)-1-((3-methyl-oxetan-3-yl)methyl)-2,4-dioxo-1,2,3,4-tetrahydro-quinazoline-6-sulfonamide

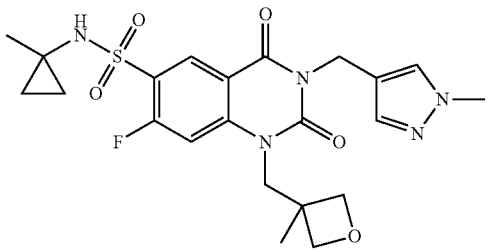

This compound was prepared according to the Mitsunobu strategy for the synthesis of 7-fluoro-1-substituted-3-((1-methyl-1H-pyrazol-4-yl)methyl)-N-(1-methylcyclopropyl)-2,4-dioxo-1,2,3,4-tetrahydroquinazoline-6-sulfonamides (Scheme 14) using 3-methyl-3-oxetanemethanol to give the desired product (20 mg, 0.031 mmol, 16%) as a white powder.

Example 399 N-(1-Cyanocyclopropyl)-1-(cyclopropylmethyl)-3-[(2-methylthiazol-5-yl)methyl]-2,4-dioxo-quinazoline-6-sulfonamide

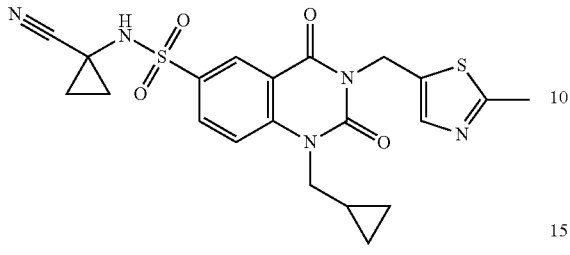

Iodomethylcyclopropane (0.03 mL, 0.20 mmol) was added to a stirring mixture of N-(1-cyanocyclopropyl)-N-[[3-[(2-methylthiazol-5-yl)methyl]-2,4-dioxo-H-quinazolin-6-yl]sulfonyl]acetamide (76 mg, 0.170 mmol) and potassium carbonate (92 mg, 0.66 mmol) in DMF (3 mL) and left to stir at room temperature for 16 h. Concentrated ammonia (100 µL) was added and the mixture heated to 40° C. for 10 min. The mixture was allowed to cool and DCM (8 mL) and saturated aqueous ammonium chloride solution (8 mL) was added and the mixture stirred for 5 min. The DCM layer was isolated by passing through a hydrophobic frit and the aqueous layer washed with DCM (10 mL). The combined DCM extracts were concentrated under reduced pressure and purified by prep HPLC (low pH) yielding the desired product (8 mg, 0.017 mmol, 10%) as a white powder.

Example 400 N-(1-Cyanocyclopropyl)-1-[(3-methylisoxazol-5-yl)methyl]-3-[(2-methylthiazol-5-yl)methyl]-2,4-dioxo-quinazoline-6-sulfonamide

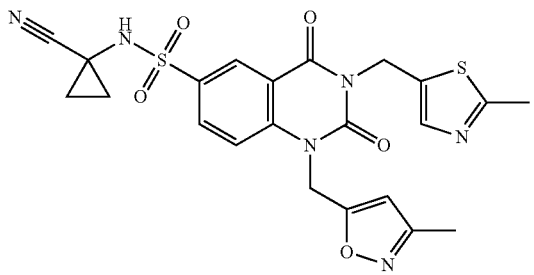 [SMILES: Cc1cc(Cn2c(=O)n(Cc3cnc(C)s3)c(=O)c3cc(S(=O)(=O)NC4(C#N)CC4)ccc32)on1]

This compound was prepared from 5-(bromomethyl)-3-methyl-1,2-oxazole (0.02 mL, 0.20 mmol) and N-(1-cyanocyclopropyl)-N-[[3-[(2-methylthiazol-5-yl)methyl]-2,4-dioxo-1H-quinazolin-6-yl]sulfonyl]acetamide (76 mg, 0.170 mmol) according to the method described in Example 399. This gave the desired product (10 mg, 0.020 mmol, 12%) as a white powder.

Example 401 N-(1-Cyanocyclopropyl)-1-[(2,4-dimethylthiazol-5-yl)methyl]-3-[(2-methylthiazol-5-yl)methyl]-2,4-dioxo-quinazoline-6-sulfonamide

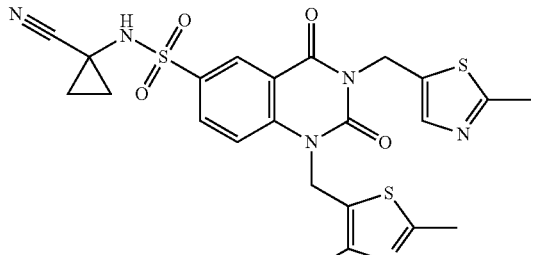

Diisopropyl azodicarboxylate (0.07 mL, 0.330 mmol) was added to a stirring mixture of N-(1-cyanocyclopropyl)-N-[[3-[(2-methylthiazol-5-yl)methyl]-2,4-dioxo-H-quinazolin-6-yl]sulfonyl]acetamide (76 mg, 0.170 mmol), (2,4-dimethyl-1,3-thiazol-5-yl)methanol (0.04 mL, 0.33 mmol) and triphenylphosphine, polymer bound 1.6 mmol/g (310 mg, 0.500 mmol) in DMF (5 mL). After stirring at room temperature for 3 h, concentrated ammonia (500 µL) was added and the mixture left to stir for 2 h. DCM (10 mL) and saturated aqueous ammonium chloride solution (10 mL) was added and the mixture stirred for 5 min. The DCM layer was isolated by passing through a hydrophobic frit and the aqueous layer extracted with DCM. The combined DCM extracts were concentrated under reduced pressure and purified by prep HPLC (low pH) yielding the desired product (15 mg, 0.028 mmol, 17%) as a white powder.

Example 402 N-(1-Cyanocyclopropyl)-1-[(4-fluorophenyl)methyl]-3-[(2-methylthiazol-5-yl)methyl]-2,4-dioxo-quinazoline-6-sulfonamide

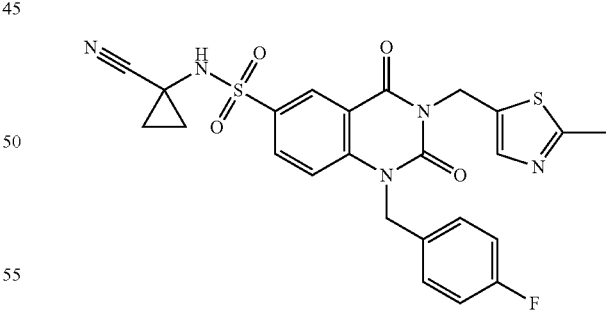

This compound was prepared from 4-fluorobenzyl bromide (0.02 mL, 0.20 mmol) and N-(1-cyanocyclopropyl)-N-[[3-[(2-methylthiazol-5-yl)methyl]-2,4-dioxo-1H-quinazolin-6-yl]sulfonyl]acetamide (76 mg, 0.170 mmol) according to the method described in Example 399. This gave the desired product (10 mg, 0.019 mmol, 12%) as a white powder.

Example 403 N-(1-Cyanocyclopropyl)-3-[(2-methylthiazol-5-yl)methyl]-2,4-dioxo-1-prop-2-ynyl-quinazoline-6-sulfonamide

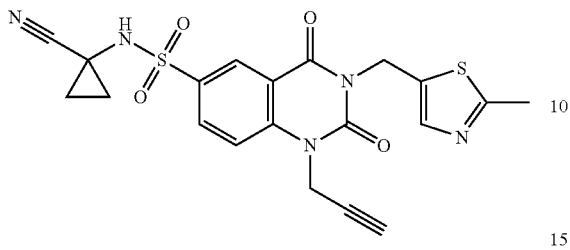

This compound was prepared from 3-bromopropyne (0.03 mL, 0.270 mmol) and N-(1-cyanocyclopropyl)-N-[[3-[(2-methylthiazol-5-yl)methyl]-2,4-dioxo-1H-quinazolin-6-yl]sulfonyl]acetamide (104 mg, 0.230 mmol) according to the method described in Example 399. This gave the desired product (18 mg, 0.04 mmol, 17%) as a white powder.

Example 404 N-(1-Cyanocyclopropyl)-7-fluoro-1-[(3-methylisoxazol-5-yl)methyl]-3-[(1-methylpyrazol-4-yl)methyl]-2,4-dioxo-quinazoline-6-sulfonamide

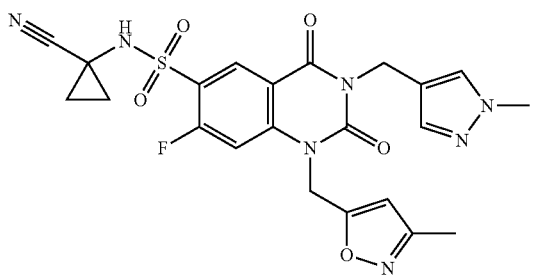 [SMILES: Cc1cc(Cn2c(=O)n(Cc3cnn(C)c3)c(=O)c3cc(S(=O)(=O)NC4(C#N)CC4)c(F)cc32)on1]

This compound was prepared from 5-(bromomethyl)-3-methyl-1,2-oxazole (0.02 mL, 0.170 mmol) and N-(1-cyanocyclopropyl)-N-[[7-fluoro-3-[(1-methylpyrazol-4-yl)methyl]-2,4-dioxo-1H-quinazolin-6-yl]sulfonyl]acetamide (65 mg, 0.140 mmol) according to the method described in Example 399. This gave the desired product (6 mg, 0.012 mmol, 8.3%) as a white powder.

Example 405 1-[(4,4-Difluorocyclohexyl)methyl]-N-(1-methylcyclopropyl)-3-[(3-methylisoxazol-5-yl)methyl]-2,4-dioxo-quinazoline-6-sulfonamide

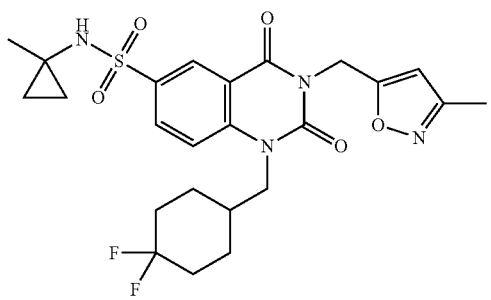

Prepared using Method A2, from N-(1-methylcyclopropyl)-3-((3-methylisoxazol-5-yl)methyl)-2,4-dioxo-1,2,3,4-tetrahydroquinazoline-6-sulfonamide and (4,4-difluorocyclohexyl)methanol. This gave the desired product (48 mg, 0.092 mmol, 8.3%) as a white powder.

Example 406 N, N-Dimethyl-3-[6-[(1-methylcyclopropyl)sulfamoyl]-3-[(3-methylisoxazol-5-yl)methyl]-2,4-dioxo-quinazolin-1-yl]propanamide

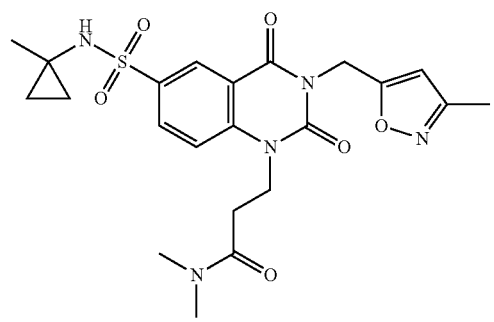

Prepared using Method A2, from N-(1-methylcyclopropyl)-3-((3-methylisoxazol-5-yl)methyl)-2,4-dioxo-1,2,3,4-tetrahydroquinazoline-6-sulfonamide and 3-hydroxy-N,N-dimethylpropanamide. This gave the desired product (12 mg, 0.025 mmol, 12%) as a white powder.

Example 407 1-(3-Hydroxypropyl)-N-(1-methylcyclopropyl)-3-[(3-methylisoxazol-5-yl)methyl]-2,4-dioxo-quinazoline-6-sulfonamide

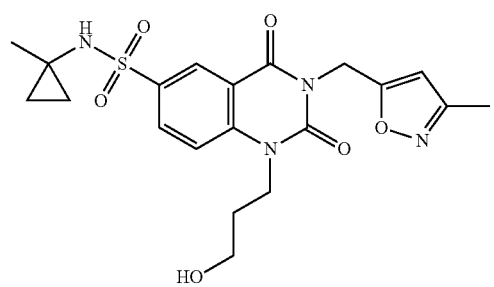

Prepared using Method A1, from N-(1-methylcyclopropyl)-3-((3-methylisoxazol-5-yl)methyl)-2,4-dioxo-1,2,3,4-tetrahydroquinazoline-6-sulfonamide and 3-bromopropan-1-ol. This gave the desired product (6 mg, 0.013 mmol, 6.5%) as a white powder.

Example 408 N-[1-(Fluoromethyl)cyclopropyl]-1-methyl-3-[(1-methylpyrazol-4-yl)methyl]-2,4-dioxo-quinazoline-6-sulfonamide

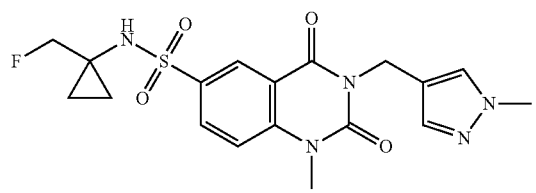 [SMILES: Cn1cc(Cn2c(=O)c3cc(S(=O)(=O)NC4(CF)CC4)ccc3n(C)c2=O)cn1]

This compound was prepared according to the general procedure for the synthesis of N-(1-(fluoromethyl)cyclopropyl)-1-substituted-3-((1-methyl-1H-pyrazol-4-yl)methyl)-2,4-dioxo-1,2,3,4-tetrahydroquinazoline-6-sulfonamides (Scheme 13) using iodomethane to give the desired product (20 mg, 0.047 mmol, 35%) as a white powder.

Example 409 tert-Butyl 3-[[6-[(1-methylcyclopropyl)sulfamoyl]-3-[(3-methylisoxazol-5-yl)methyl]-2,4-dioxo-quinazolin-1-yl]methyl]azetidine-1-carboxylate

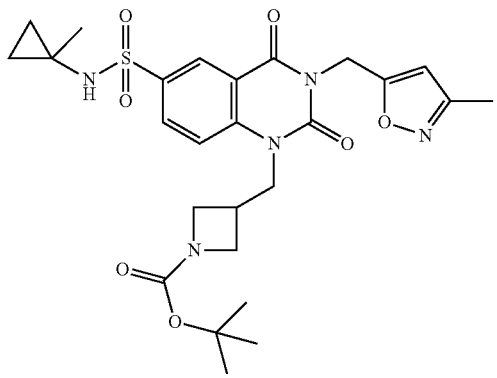 [SMILES: Cc1cc(Cn2c(=O)c3cc(S(=O)(=O)NC4(C)CC4)ccc3n(CC3CN(C(=O)OC(C)(C)C)C3)c2=O)on1]

Prepared using Method A14, from N-(1-methylcyclopropyl)-3-((3-methylisoxazol-5-yl)methyl)-2,4-dioxo-1,2,3,4-tetrahydroquinazoline-6-sulfonamide (300 mg, 0.770 mmol), and 1-boc-3-(bromomethyl)azetidine (231 mg, 0.920 mmol), with heating for only 1 h. This gave the desired product (190 mg, 0.34 mmol, 44.2%) as an off-white powder.

Example 410 1-(2-Fluoroethyl)-N-(1-methylcyclopropyl)-3-[(1-methylpyrazol-4-yl)methyl]-2,4-dioxo-quinazoline-6-sulfonamide

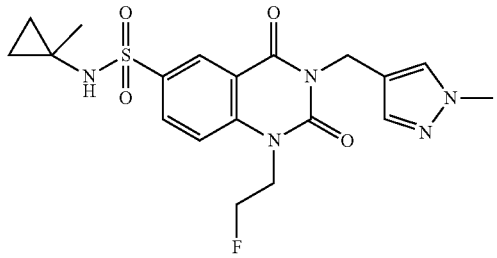 [SMILES: Cn1cc(Cn2c(=O)c3cc(S(=O)(=O)NC4(C)CC4)ccc3n(CCF)c2=O)cn1]

Prepared using Method A14, from 3-((1-methyl-1H-pyrazol-4-yl)methyl)-N-(1-methylcyclopropyl)-2,4-dioxo-1,2,3,4-tetrahydroquinazoline-6-sulfonamide (80 mg, 0.20 mmol), and 1-bromo-2-fluoroethane (0.02 mL, 0.25 mmol), with heating for only 1 h. This gave the desired product (15 mg, 0.034 mmol, 17%) as a white powder.

Example 411 1-(2-Fluoroethyl)-N-(1-methylcyclopropyl)-3-[(3-methylisoxazol-5-yl)methyl]-2,4-dioxo-quinazoline-6-sulfonamide

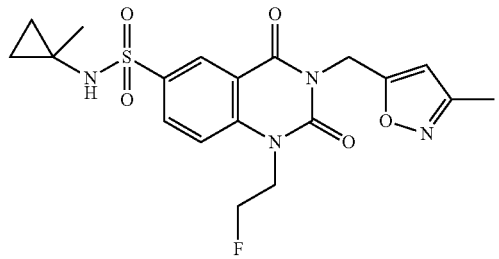 [SMILES: Cc1cc(Cn2c(=O)c3cc(S(=O)(=O)NC4(C)CC4)ccc3n(CCF)c2=O)on1]

Prepared using Method A14, from N-(1-methylcyclopropyl)-3-((3-methylisoxazol-5-yl)methyl)-2,4-dioxo-1,2,3,4-tetrahydroquinazoline-6-sulfonamide (80 mg, 0.20 mmol), and 1-bromo-2-fluoroethane (0.02 mL, 0.25 mmol), with heating for only 1 h. This gave the desired product (22 mg, 0.05 mmol, 25%) as a white powder.

Example 412 N-(1-Methylcyclopropyl)-3-[(3-methylisoxazol-5-yl)methyl]-2,4-dioxo-1-[(3-oxocyclobutyl)methyl]quinazoline-6-sulfonamide

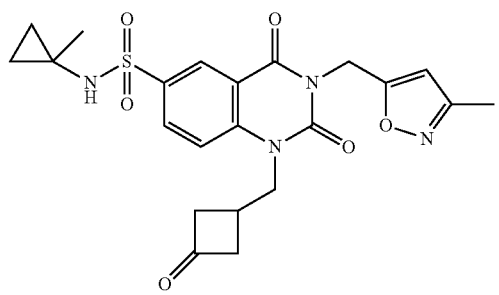 [SMILES: Cc1cc(Cn2c(=O)c3cc(S(=O)(=O)NC4(C)CC4)ccc3n(CC3CC(=O)C3)c2=O)on1]

Prepared using Method A14, from N-(1-methylcyclopropyl)-3-((3-methylisoxazol-5-yl)methyl)-2,4-dioxo-1,2,3,4-tetrahydroquinazoline-6-sulfonamide (80 mg, 0.20 mmol), and 1-3-(bromomethyl)cyclobutanone (0.02 mL, 0.25 mmol), with heating by microwave irradiation to 130° C. for 1 h. More potassium carbonate (34 mg, 0.25 mmol) and 3-(bromomethyl)cyclobutanone (0.02 mL, 0.25 mmol) were added and the mixture was then heated by microwave irradiation to 135° C. for 2 h. Work-up gave the desired product (7 mg, 0.015 mmol, 7%) as a tan powder.

Example 413 1-(2-Methoxy-2-methyl-propyl)-N-(1-methylcyclopropyl)-3-[(3-methylisoxazol-5-yl)methyl]-2,4-dioxo-quinazoline-6-sulfonamide

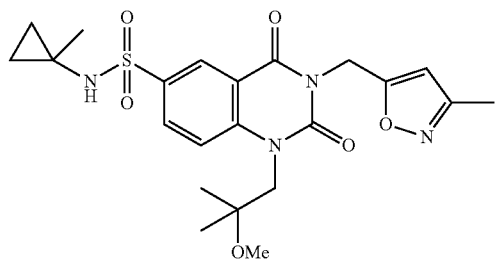 [SMILES: COC(C)(C)Cn1c(=O)n(Cc2cc(C)no2)c(=O)c2cc(S(=O)(=O)NC3(C)CC3)ccc21]

N-(1-Methylcyclopropyl)-3-((3-methylisoxazol-5-yl) methyl)-2,4-dioxo-1,2,3,4-tetrahydroquinazoline-6-sulfonamide (80 mg, 0.20 mmol), potassium carbonate (68 mg, 0.25 mmol) and 1-bromo-2-methoxy-2-methyl-propane (0.04 mL, 0.50 mmol) in DMF (2 mL) were heated by microwave irradiation to 150° C. for 2 h. The reaction mixture was diluted with water (10 mL) and extracted with EtOAc (2×20 mL). The organic phase was combined, washed with brine (10 mL), passed through a hydrophobic frit and evaporated to dryness. The crude product mixture was purified by prep HPLC (high pH) to give the desired product (4 mg, 0.008 mmol, 4%) as a white powder.

Example 414 1-[2-(Azetidin-1-yl)-2-oxo-ethyl]-N-(1-methylcyclopropyl)-3-[(3-methylisoxazol-5-yl) methyl]-2,4-dioxo-quinazoline-6-sulfonamide

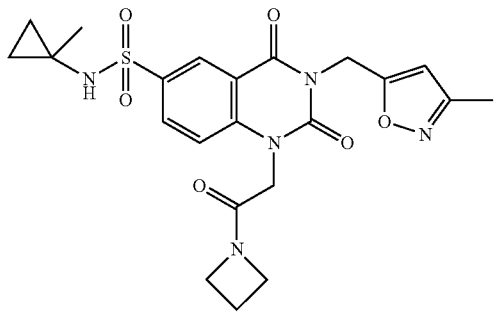 [SMILES: Cc1cc(Cn2c(=O)c3cc(S(=O)(=O)NC4(C)CC4)ccc3n(CC(=O)N3CCC3)c2=O)on1]

Prepared using Method A14, from N-(1-methylcyclopropyl)-3-((3-methylisoxazol-5-yl)methyl)-2,4-dioxo-1,2,3,4-tetrahydroquinazoline-6-sulfonamide (80 mg, 0.20 mmol), and 1-(chloroacetyl)azetidine (0.02 mL, 0.250 mmol), with heating for only 1 h. This gave the desired product (24 mg, 0.049 mmol, 24%) as a white powder.

Example 415 1-(Azetidin-3-ylmethyl)-N-(1-methylcyclopropyl)-3-[(3-methylisoxazol-5-yl)methyl]-2,4-dioxo-quinazoline-6-sulfonamide

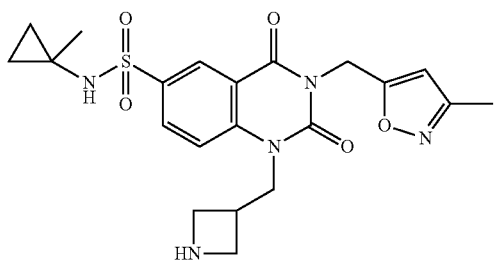 [SMILES: Cc1cc(Cn2c(=O)c3cc(S(=O)(=O)NC4(C)CC4)ccc3n(CC3CNC3)c2=O)on1]

tert-Butyl 3-[[6-[(1-methylcyclopropyl)sulfamoyl]-3-[(3-methylisoxazol-5-yl)methyl]-2,4-dioxo-quinazolin-1-yl] methyl]azetidine-1-carboxylate (160 mg, 0.29 mmol), trifluoroacetic acid (1.0 mL, 13.5 mmol) and DCM (10 mL) were stirred at ambient temperature. After 2 h the reaction mixture was concentrated to dryness under reduced pressure. The crude product mixture was purified by prep HPLC (high pH) to give the desired product (50 mg, 0.109 mmol, 38%) as a white powder.

Example 416 N-[1-(Fluoromethyl)cyclopropyl]-3-[(1-methylpyrazol-4-yl)methyl]-2,4-dioxo-1H-quinazoline-6-sulfonamide

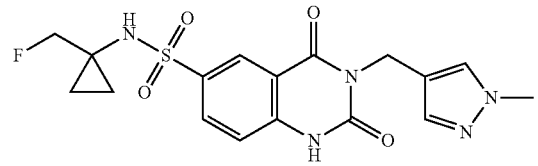 [SMILES: Cn1cc(Cn2c(=O)[nH]c3ccc(S(=O)(=O)NC4(CF)CC4)cc3c2=O)cn1]

3-[(1-Methylpyrazol-4-yl)methyl]-2,4-dioxo-H-quinazoline-6-sulfonyl chloride (200 mg, 0.56 mmol) was added to a stirred solution of 1-(fluoromethyl)cyclopropan-1-amine hydrochloride (34 mg, 0.27 mmol), N,N-diisopropylethylamine (301 uL, 1.69 mmol) and 4-dimethylaminopyridine (69 mg, 0.56 mmol) in DMF (8 mL), and the resulting mixture was agitated at 60° C. for 30 min. The mixture cooled to ambient and distilled to dryness to give the crude as a residue, which was purified by automated column chromatography (SiO$_2$; RediSep—12 g; 0 to 10% MeOH in DCM) to afford to give the desired product (150 mg, 0.368 mmol, 65%) as a white solid.

Example 417 1-(Cyclopropylmethyl)-N-[1-(fluoromethyl)cyclopropyl]-3-[(1-methylpyrazol-4-yl) methyl]-2,4-dioxo-quinazoline-6-sulfonamide

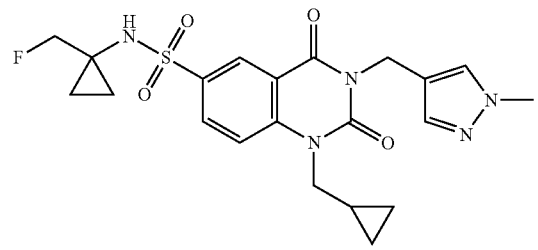 [SMILES: Cn1cc(Cn2c(=O)c3cc(S(=O)(=O)NC4(CF)CC4)ccc3n(CC3CC3)c2=O)cn1]

This compound was prepared according to the general procedure for the synthesis of N-(1-(fluoromethyl)cyclopropyl)-1-substituted-3-((1-methyl-1H-pyrazol-4-yl)methyl)-2, 4-dioxo-1,2,3,4-tetrahydroquinazoline-6-sulfonamides using iodomethylcyclopropane to give the desired product (20 mg, 0.043 mmol, 22%) as a white powder.

Example 418 1-Methyl-N-(1-methylcyclopropyl)-3-[(5-methyl-3-pyridyl)methyl]-2,4-dioxo-quinazoline-6-sulfonamide

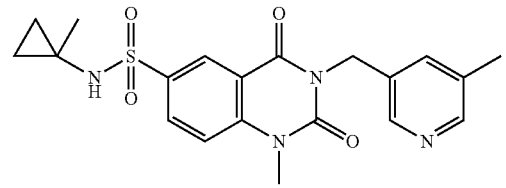 [SMILES: Cc1cncc(Cn2c(=O)c3cc(S(=O)(=O)NC4(C)CC4)ccc3n(C)c2=O)c1]

3-(Bromomethyl)-5-methylpyridine hydrobromide (1:1) (45 mg, 0.17 mmol) was added to a solution of 1-methyl- N-(1-methylcyclopropyl)-2,4-dioxo-1,2,3,4-tetrahydroquinazoline-6-sulfonamide (50 mg, 0.160 mmol) and potassium carbonate (47 mg, 0.34 mmol) in DMF (1 mL). The reaction mixture was stirred at ambient temperature overnight. LCMS confirmed conversion to the desired product. The reaction mixture was carefully poured into dilute aqueous sodium bicarbonate (50 mL) and extracted with EtOAc (2×20 mL). The organic liquors were combined, washed with brine (10 mL), passed through a hydrophobic frit and evaporated to dryness. The crude product mixture was purified by prep HPLC (high pH) to give the desired product (16 mg, 0.039 mmol, 24%) as a white powder.

Example 419 N-[1-(Fluoromethyl)cyclopropyl]-1-[(4-fluorophenyl)methyl]-3-[(1-methylpyrazol-4-yl)methyl]-2,4-dioxo-quinazoline-6-sulfonamide

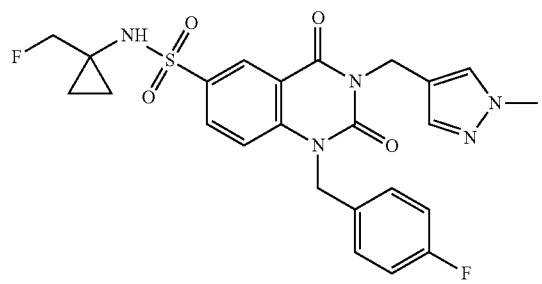 [SMILES: Cn1cc(Cn2c(=O)c3cc(S(=O)(=O)NC4(CF)CC4)ccc3n(Cc3ccc(F)cc3)c2=O)cn1]

This compound was prepared according to the general procedure for the synthesis of N-(1-(fluoromethyl)cyclopropyl)-1-substituted-3-((1-methyl-1H-pyrazol-4-yl)methyl)-2,4-dioxo-1,2,3,4-tetrahydroquinazoline-6-sulfonamides using 4-fluorobenzyl bromide to give the desired product (20 mg, 0.039 mmol, 23%) as a white powder.

Example 420 1-[(1-Cyanocyclopropyl)methyl]-N-(1-methylcyclopropyl)-3-[(3-methylisoxazol-5-yl)methyl]-2,4-dioxo-quinazoline-6-sulfonamide

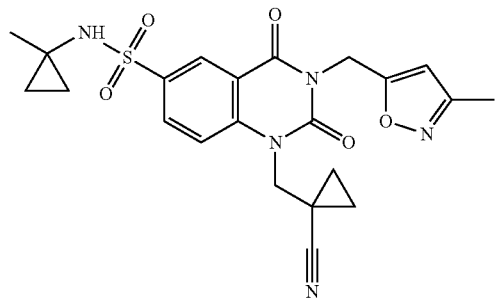

Prepared using Method A10 (tosylate), from N-(1-methylcyclopropyl)-3-((3-methylisoxazol-5-yl)methyl)-2,4-dioxo-1,2,3,4-tetrahydroquinazoline-6-sulfonamide and (1-cyanocyclopropyl)methyl 4-methylbenzenesulfonate. This gave the desired product (12 mg, 0.026 mmol, 13%) as a white powder.

Example 421 N-(1-Methylcyclopropyl)-3-[(3-methylisoxazol-5-yl)methyl]-2,4-dioxo-1-[(4-oxocyclohexyl)methyl]quinazoline-6-sulfonamide

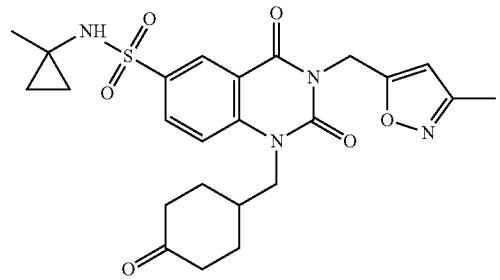

Prepared using Method A10 (tosylate), from N-(1-methylcyclopropyl)-3-((3-methylisoxazol-5-yl)methyl)-2,4-dioxo-1,2,3,4-tetrahydroquinazoline-6-sulfonamide and (4-oxocyclohexyl)methyl 4-methylbenzenesulfonate. This gave the desired product (8 mg, 0.016 mmol, 8%) as a white powder.

Example 422 8-Bromo-N-(1-methylcyclopropyl)-3-[(1-methylpyrazol-4-yl)methyl]-2,4-dioxo-1H-quinazoline-6-sulfonamide

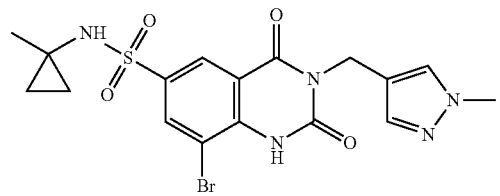

Intermediate S15-A 2-Amino-3-bromo-N-[(1-methylpyrazol-4-yl)methyl]benzamide

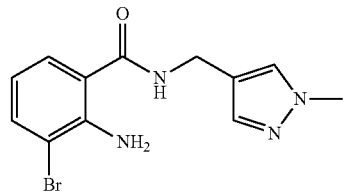 [SMILES: Cn1cc(CNC(=O)c2cccc(Br)c2N)cn1]

C-(1-Methyl-1H-pyrazol-4-yl)-methylamine (506 mg, 4.56 mmol) was added to a magnetically stirred solution of 8-bromoisatoic anhydride (1050 mg, 4.34 mmol) in DMF (20 mL) at 0° C., and the resulting mixture was heated at 40° C. for 4 h. The solvent was removed in vacuo to give a light brown solid, which was suspended in ether (40 mL) with stirring for 30 min. The solid was then filtered and the filter cake washed with ether (2×20 mL) to give the desired product (1300 mg, 97%) as an off-white solid.

$^1$H NMR (300 MHz, DMSO-$d_6$) δ=8.77 (s, 1H), 7.59 (s, 1H), 7.52 (d, J=7.8 Hz, 2H), 7.34 (s, 1H), 6.58-6.44 (m, 3H), 4.24 (d, J=5.7 Hz, 2H), 3.78 (s, 3H)

Intermediate S15-B 8-Bromo-3-((1-methyl-1H-pyrazol-4-yl)methyl)quinazoline-2,4(1H,3H)-dione

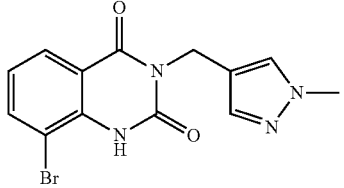 [SMILES: Cn1cc(Cn2c(=O)[nH]c3c(Br)cccc3c2=O)cn1]

To a magnetically stirred solution of 2-amino-3-bromo-N-[(1-methylpyrazol-4-yl)methyl]benzamide (1300 mg, 4.2 mmol) in THF (100 mL) at 0° C. was added triphosgene (624 mg, 2.1 mmol), and the resulting mixture was agitated at ambient for 1 h. Triethylamine (0.59 mL, 4.2 mmol) was added, and the resulting suspension was stirred for 12 h. The reaction was quenched by the addition of saturated potassium carbonate (150 mL), and the resulting suspension was stirred for 12 h. The mixture was partitioned between EtOAc (200 mL) and water (100 mL) and the organic phase was collected. The aqueous was extracted with EtOAc (100 mL) and the combined organics were washed with brine (100 mL) and dried ($Na_2SO_4$). The solvent was removed to give the crude, which was suspended in ether and stirred for 30 minutes. The mixture was then filtered to give the desired product (970 mg, 69%) as a white solid.

$^1$H NMR (300 MHz, DMSO-$d_6$) δ=10.61 (br. s., 1H), 7.97 (ddd, J=1.4, 7.9, 9.2 Hz, 2H), 7.65 (s, 1H), 7.37 (s, 1H), 7.16 (t, J=7.9 Hz, 1H), 4.90 (s, 2H), 3.76 (s, 3H)

Intermediate S15-C 8-Bromo-3-((1-methyl-1H-pyrazol-4-yl)methyl)-2,4-dioxo-1,2,3,4-tetrahydroquinazoline-6-sulfonyl chloride

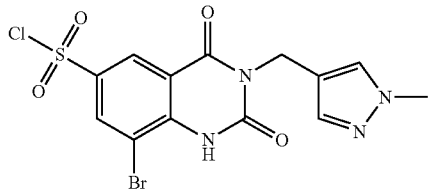 [SMILES: Cn1cc(Cn2c(=O)[nH]c3c(Br)cc(S(=O)(=O)Cl)cc3c2=O)cn1]

8-Bromo-3-[(1-methylpyrazol-4-yl)methyl]-1H-quinazoline-2,4-dione (970 mg, 2.89 mmol) added to stirred chlorosulfonic acid (10 mL, 2.89 mmol) at 20° C., and the resulting mixture was heated at 60° C. for 12 h. The mixture was cooled to ambient and poured carefully into ice (100 mL). The milky suspension was then extracted with 5% MeOH in DCM (4×50 mL) and the combined extracts were dried ($Na_2SO_4$) and evaporated to dryness to give the desired product (1170 mg, 93%) as a white solid.

$^1$H NMR (300 MHz, CHLOROFORM-d) δ=8.79 (d, J=2.2 Hz, 1H), 8.41 (d, J=2.1 Hz, 1H), 8.33 (s, 1H), 7.65 (s, 1H), 7.57 (s, 1H), 5.09 (s, 2H), 3.90 (s, 3H)

S15-D 8-Bromo-N-(1-methylcyclopropyl)-3-[(1-methylpyrazol-4-yl)methyl]-2,4-dioxo-1H-quinazoline-6-sulfonamide

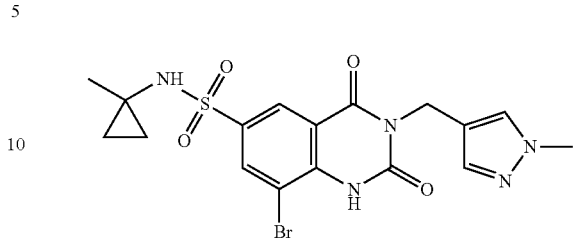

8-Bromo-3-[(1-methylpyrazol-4-yl)methyl]-2,4-dioxo-1H-quinazoline-6-sulfonyl chloride (1.0 g, 2.31 mmol) was added to a stirred solution of 1-methylcyclopropanamine hydrochloride (372 mg, 3.46 mmol), N,N-diisopropylethylamine (1.23 mL, 6.92 mmol) and 4-dimethylaminopyridine (282 mg, 2.31 mmol) in DMF (8 mL), and the resulting mixture was agitated at 60° C. for 60 min. LCMS revealed TM (rt=0.79 mins, 94%), as well as several minor impurities. The mixture was cooled to ambient temperature and evaporated to dryness to give a residue which was purified by automated column chromatography ($SiO_2$; RediSep—24 g; 0 to 10% MeOH in DCM) to afford the desired product (850 mg, 1.82 mmol, 78.7%) as a white solid.

Example 423 1-Methyl-N-(1-methylcyclopropyl)-3-[(6-methyl-3-pyridyl)methyl]-2,4-dioxo-quinazoline-6-sulfonamide

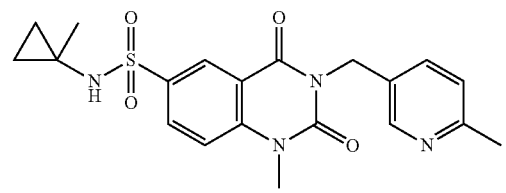 [SMILES: Cc1ccc(Cn2c(=O)c3cc(S(=O)(=O)NC4(C)CC4)ccc3n(C)c2=O)cn1]

This compound was prepared according to Example 418 using 5-(bromomethyl)-2-methylpyridine hydrobromide (1:1) (45 mg, 0.170 mmol) and 1-methyl-N-(1-methylcyclopropyl)-2,4-dioxo-1,2,3,4-tetrahydroquinazoline-6-sulfonamide (50 mg, 0.16 mmol). This afforded the desired product (5 mg, 0.012 mmol, 7.5%) as a white powder.

Example 424 6-[(1-Methylcyclopropyl)sulfamoyl]-3-[(1-methylpyrazol-4-yl)methyl]-2,4-dioxo-1H-quinazoline-8-carboxamide

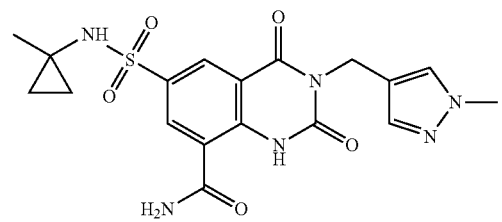

A mixture of 8-bromo-N-(1-methylcyclopropyl)-3-[(1-methylpyrazol-4-yl)methyl]-2,4-dioxo-1H-quinazoline-6-sulfonamide (80 mg, 0.17 mmol) and tetrakis(triphenylphosphine)palladium(0) (19.77 mg, 0.02 mmol) in DMF (2 mL) was vacuum purged with nitrogen three times. Zinc cyanide (24 mg, 0.20 mmol) was added to the reaction, and the resulting mixture was heated with agitation at 80° C. for 16 h. The mixture was cooled to ambient temperature and filtered through celite. The filtrate were distilled to dryness to give a residue, which was purified by automated column chromatography (SiO$_2$; RediSep—4 g; 0 to 10% MeOH in DCM) to afford 8-cyano-3-((1-methyl-1H-pyrazol-4-yl)methyl)-N-(1-methylcyclopropyl)-2,4-dioxo-1,2,3,4-tetrahydroquinazoline-6-sulfonamide (50 mg, 71%) as a white solid.

$^1$H NMR (300 MHz, DMSO-d$_6$) δ=8.50 (d, J=2.2 Hz, 1H), 8.35 (d, J=2.2 Hz, 1H), 8.29 (s, 1H), 7.67 (s, 1H), 7.39 (s, 1H), 4.90 (s, 2H), 3.78-3.75 (m, 3H), 1.09 (s, 3H), 0.65-0.55 (m, 2H), 0.49-0.36 (m, 2H).

To a magnetically stirred solution of 8-cyano-N-(1-methylcyclopropyl)-3-[(1-methylpyrazol-4-yl)methyl]-2,4-dioxo-1H-quinazoline-6-sulfonamide (20 mg, 0.05 mmol) and potassium carbonate (0.67 mg, 0.05 mmol) in water (2 mL) at 20° C. under nitrogen was added hydrogen peroxide (1.64 mg, 0.05 mmol), and the resulting mixture was agitated at ambient temperature for 16 h. The mixture was concentrated and a white solid precipitated, which was collected by filtration. The solid was washed with water (2×2 mL) and dried under vacuum at 40° C. to give the desired product 6-[(1-methylcyclopropyl)sulfamoyl]-3-[(1-methylpyrazol-4-yl)methyl]-2,4-dioxo-H-quinazoline-8-carboxamide (10 mg, 0.023 mmol, 48%) as a white solid.

Example 425 1-[(1-Formylazetidin-3-yl)methyl]-N-(1-methylcyclopropyl)-3-[(3-methylisoxazol-5-yl)methyl]-2,4-dioxo-quinazoline-6-sulfonamide

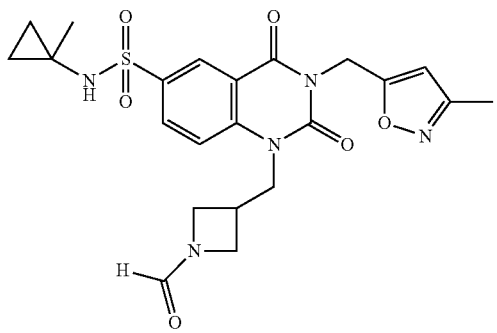 [SMILES: Cc1cc(Cn2c(=O)c3cc(S(=O)(=O)NC4(C)CC4)ccc3n(CC3CN(C=O)C3)c2=O)on1]

1-(Azetidin-3-ylmethyl)-N-(1-methylcyclopropyl)-3-[(3-methylisoxazol-5-yl)methyl]-2,4-dioxo-quinazoline-6-sulfonamide (40 mg, 0.090 mmol), potassium carbonate (14 mg, 0.10 mmol) and iodomethane (0.01 mL, 0.090 mmol) in DMF (2 mL) were heated by microwave irradiation to 100° C. for 20 min. LCMS showed good conversion to product. The reaction mixture was diluted with water (10 mL) and extracted with EtOAc (2×20 mL). The organic phase was combined, washed with brine (10 mL), passed through a hydrophobic frit and evaporated to dryness. The crude product mixture was purified by prep HPLC (high pH) to give the desired product (3 mg, 0.006 mmol, 7%) as a white powder.

Example 426 1-(Cyclopropylmethyl)-3-methyl-N-(1-methylcyclopropyl)-2-oxo-quinoline-6-sulfonamide

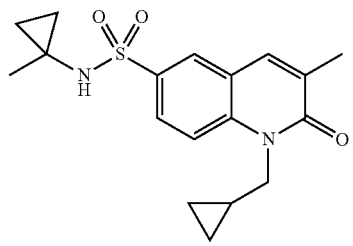 [SMILES: Cc1cc2cc(S(=O)(=O)NC3(C)CC3)ccc2n(CC2CC2)c1=O]

Intermediate S16-B
N-(2-formylphenyl)propanamide

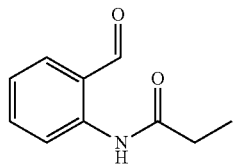

Following the procedure from Heterocycles, 65, (9) p. 2095-2105, a solution of 2-nitrobenzaldehyde (2.0 g, 13.2 mmol) in ethanol (32 mL), acetic acid (32 mL) and water (16 mL) was treated with iron (5.2 g, 92.7 mmol), heated to 100° C. for 10 min then stirred at room temperature for 10 min. The cooled reaction mixture was filtered through celite, and re-filtered through a filter paper into a separating funnel. The mixture was diluted with water and EtOAc and separated. The aqueous layer was re-extracted with EtOAc and the combined organic layers were washed with saturated aqueous NaHCO$_3$ (3×75 mL-until pH 8), dried (hydrophobic frit) and concentrated to give the crude aniline Intermediate S16-A as a yellow oil (1.25 g) which was used without further purification.

The yellow oil was taken up in THF (80 mL) and treated with pyridine (1.6 mL, 19.85 mmol) and then slowly with propanoyl chloride (1.7 mL, 19.9 mmol), a cloudy precipitate formed halfway through the addition. After stirring at room temperature for 30 min, the reaction mixture was quenched with 1M HCl (40 mL) and then the THF was removed under vacuum. The aqueous residue was extracted with EtOAc (2×60 mL) and the organic layer was washed with water, dried (hydrophobic frit) and concentrated to give a yellow oil, 2.0 g. Purification by flash column chromatography, eluting with isohexane—1:1 isohexane:EtOAc afforded Intermediate S16-B N-(2-formylphenyl)propanamide (717 mg, 4.0 mmol, 31%) as a pale yellow oil.

$^1$H NMR (300 MHz, CHLOROFORM-d) δ=11.17 (br. s., 1H), 9.94 (s, 1H), 8.78 (d, J=8.5 Hz, 1H), 7.69 (dd, J=1.6, 7.7 Hz, 1H), 7.66-7.59 (m, 1H), 7.24 (dt, J=0.9, 7.5 Hz, 1H), 2.52 (q, J=7.6 Hz, 2H), 1.30 (t, J=7.6 Hz, 3H)

LCMS (high pH) found 176.1 [M−H] T=0.96 min, 92% purity by UV.

Intermediate S16-C 3-Methyl-1H-quinolin-2-one

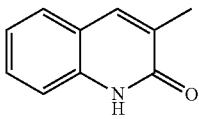

Following the procedure described in Heterocycles, 65, (9), 2005, p. 2095-2105, a mixture of N-(2-formylphenyl)propanamide (200 mg, 1.13 mmol) and cesium carbonate (1.84 g, 5.64 mmol) in DMF (5 mL) was heated to 60° C. for 5 h. The reaction mixture was then cooled, diluted with DCM (20 mL) and washed with saturated aqueous NH$_4$Cl and water, and the organic layer dried (hydrophobic frit) and concentrated. Purification by flash column chromatography, eluting with isohexane—80% EtOAc/isohexane afforded 3-methyl-1H-quinolin-2-one (84 mg, 0.53 mmol, 47%) as an off-white solid.

$^1$H NMR (300 MHz, CHLOROFORM-d) δ=11.24 (br. s., 1H), 7.70-7.65 (m, 1H), 7.52 (d, J=7.8 Hz, 1H), 7.50-7.44 (m, 1H), 7.39-7.33 (m, 1H), 7.25-7.18 (m, 1H), 2.32 (d, J=1.1 Hz, 3H)

LCMS (high pH) found 160.1 [M+H]+ T=0.81 min, 100% purity by UV.

Intermediate S16-D
3-Methyl-2-oxo-1H-quinoline-6-sulfonyl chloride

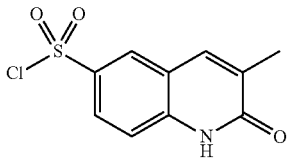 [SMILES: Cc1cc2cc(S(=O)(=O)Cl)ccc2[nH]c1=O]

A solution of 3-methyl-1H-quinolin-2-one (92 mg, 0.58 mmol) in chlorosulfonic acid (1.0 mL, 0.5800 mmol) was heated to 60° C. for 2 h in a sealed Reacti-Vial behind a blast shield, then the temperature was increased to 80° C. for 2 h. The reaction mixture was allowed to stand overnight then carefully pipetted into stirring ice/water and the precipitate collected by filtration and oven-dried to give 3-methyl-2-oxo-1H-quinoline-6-sulfonyl chloride (115 mg, 0.45 mmol, 77%) as a white powder. The material was used in the next step without purification.

$^1$H NMR (300 MHz, DMSO-d$_6$) δ=11.80 (br. s., 1H), 7.85-7.78 (m, 2H), 7.63 (dd, J=1.8, 8.4 Hz, 1H), 7.21 (d, J=8.5 Hz, 1H), 2.08 (d, J=1.0 Hz, 3H)

Intermediate S16-E 3-Methyl-N-(1-methylcyclopropyl)-2-oxo-1H-quinoline-6-sulfonamide

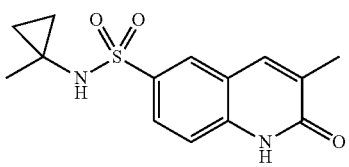 [SMILES: Cc1cc2cc(S(=O)(=O)NC3(C)CC3)ccc2[nH]c1=O]

A suspension of 3-methyl-2-oxo-1H-quinoline-6-sulfonyl chloride (40 mg, 0.12 mmol) and 1-methylcyclopropanamine hydrochloride (20 mg, 0.19 mmol) in DCM (1 mL) was treated with triethylamine (0.05 mL, 0.37 mmol) and stirred at RT. After 1 h, 1 mL DMF was added to fully dissolve the reagents, after 3 h a further portion of triethylamine (0.05 mL, 0.37 mmol) was added and the mixture was stirred for 18 h and then diluted with water (2 mL) and DCM (10 mL). The aqueous layer was re-extracted with DCM, and the combined organic extracts were washed with water, dried (hydrophobic frit) and concentrated. Purification by flash column chromatography, eluting with EtOAc—5% MeOH/EtOAc afforded 3-methyl-N-(1-methylcyclopropyl)-2-oxo-1H-quinoline-6-sulfonamide (20 mg, 0.068 mmol, 55%) as a white solid.

$^1$H NMR (300 MHz, DMSO-d$_6$) δ=12.10 (br. s., 1H), 8.05 (d, J=2.1 Hz, 1H), 8.00 (br. s., 1H), 7.96-7.92 (m, 1H), 7.78 (dd, J=2.0, 8.6 Hz, 1H), 7.41 (d, J=8.7 Hz, 1H), 2.11 (d, J=1.0 Hz, 3H), 1.04 (s, 3H), 0.64-0.53 (m, 2H), 0.40-0.30 (m, 2H)

LCMS: high pH—found 293.1 [M+H]+ T=0.86 min, 100% purity by UV; low pH—found 293.1 [M+H]+ T=0.85 min, 100% purity by UV.

S16-F1-(Cyclopropylmethyl)-3-methy-N-(1-methylcyclopropyl)-2-oxo-quinoline-6-sulfonamide

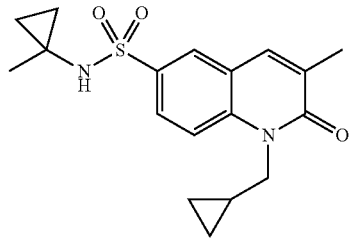 [SMILES: Cc1cc2cc(S(=O)(=O)NC3(C)CC3)ccc2n(CC2CC2)c1=O]

A solution of 3-methyl-N-(1-methylcyclopropyl)-2-oxo-1H-quinoline-6-sulfonamide (17 mg, 0.06 mmol) and iodomethylcyclopropane (16 mg, 0.09 mmol) in DMF (1 mL) was treated with potassium carbonate (16 mg, 0.12 mmol) and stirred at 80° C. under microwave irradiation for 20 min. The reaction mixture was diluted with water (2 mL) and DCM (5 mL) and stirred vigorously for 10 min and then passed through a hydrophobic frit. The aqueous layer was re-extracted with DCM, and organic layer dried (hydrophobic frit), concentrated and purified by prep. HPLC (high pH) to afford the desired product 1-(cyclopropylmethyl)-3-methyl-N-(1-methylcyclopropyl)-2-oxo-quinoline-6-sulfonamide (4 mg, 0.012 mmol, 20%) as a white powder.

Example 427 N-(1-Ethynylcyclopropyl)-1-methyl-3-[(1-methylpyrazol-4-yl)methyl]-2,4-dioxo-quinazoline-6-sulfonamide

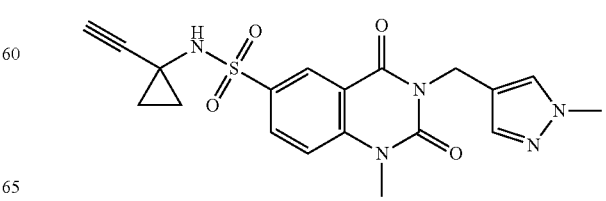

Intermediate S17-A
(Cyclopropylethynyl)trimethylsilane

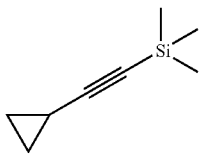

A magnetically stirred solution of ethynylcyclopropane (8.8 mL, 104 mmol) in anhydrous ether (50 mL) was cooled to −78° C. and treated with methyllithium (65. mL, 104 mmol) over a period of 10 min. After stirring for 2 h TMS-chloride (13.2 mL, 104 mmol) was added over a 5 min period, stirred for a further 2 h and then allowed to warm to ambient temperature. After stirring for an additional 1 h the mixture was poured into ice-cold water (100 mL) and extracted with EtOAc (3×100 mL). The combined organic extracts were passed through a hydrophobic frit and concentrated to dryness yielding crude 2-cyclopropylethynyl (trimethyl)silane (13.5 g, 92.6 mmol, 89.0%) which was used without further purification.

$^1$H NMR (300 MHz, CHLOROFORM-d) δ=1.08 (s, 1H), 0.68-0.55 (m, 4H), 0.04-−0.04 (m, 9H)

Intermediate S17-B
1-(2-Trimethylsilylethynyl)cyclopropanecarboxylic acid

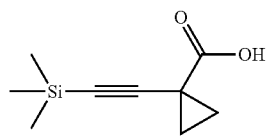

To a solution of 2-cyclopropylethynyl(trimethyl)silane (7.14 g, 51.6 mmol) in ether (70 mL) was added a 1.6 M n-butyllithium solution in hexanes (30.7 mL, 49.1 mmol). After 6 h the mixture was cooled to −78° C. and CO$_2$ was bubbled through under vigorous stirring for 2 h. The mixture was allowed to warm to room ambient temperature and poured onto a stirring mixture of ice-water (300 mL) and ether (300 mL). The ether layer was separated and the aqueous extracted with ether (3×100 mL). The aqueous layer was then acidified with 1 mole equivalent of conc. HCl then extracted with ether (3×100 mL). The combined ether extracts were dried with magnesium sulfate and passed through a hydrophobic frit and concentrated under reduced pressure to yield crude 1-(2-trimethylsilylethynyl)cyclopropanecarboxylic acid (4.6 g, 25.2 mmol, 48.9%) as a white solid.

$^1$H NMR (300 MHz, CHLOROFORM-d) δ=11.71-9.06 (m, 1H), 1.62 (q, J=3.9 Hz, 2H), 1.45-1.36 (m, 2H), 0.26-0.02 (m, 7H), 0.39-−0.18 (m, 1H)

Intermediate S17-C tert-Butyl N-[1-(2-trimethylsilylethynyl)cyclopropyl]carbamate

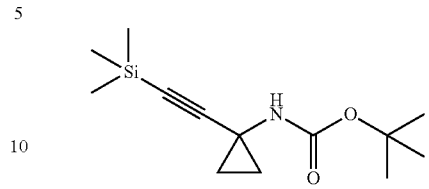

A solution of 1-(2-trimethylsilylethynyl)cyclopropanecarboxylic acid (3.0 g, 16.5 mmol), diphenyl phosphoryl azide (3.37 mL, 15.63 mmol) and triethylamine (4.58 mL, 32.9 mmol) in tert-butanol (10 mL) was heated at 75° C. After 16 h the reaction mixture was cooled to ambient and poured into a bi-phasic mixture of water (200 mL) and EtOAc (100 mL). The bi-phasic mixture was allowed to stir for 15 min and the organic layer was then separated and the aqueous layer extracted with EtOAc (2×100 mL). The combined extracts were then washed with water (100 mL) and then dried with magnesium sulfate before being distilled to dryness to give to give the desired product, tert-butyl N-[1-(2-trimethylsilylethynyl)cyclopropyl]carbamate (3.1 g, 12.2 mmol, 74.3%) as a white solid that was used without further purification.

$^1$H NMR (300 MHz, CHLOROFORM-d) δ=5.15-4.83 (m, 1H), 1.47 (s, 9H), 1.17 (br s, 4H), 0.13 (s, 9H)

Intermediate S17-D 1-Ethynylcyclopropanamine hydrochloride

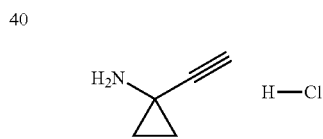

A mixture of tert-butyl N-[1-(2-trimethylsilylethynyl)cyclopropyl]carbamate (1.31 g, 5.17 mmol) and potassium fluoride (901. mg, 15.51 mmol) in DMF (75 mL) and water (75 mL) was stirred for 16 h. EtOAc (200 mL) and saturated aqueous sodium bicarbonate (200 mL) were added and the mixture stirred for 5 mins. The EtOAc layer was separated and the aqueous layer extracted with EtOAc (100 mL). The combined EtOAc layers were passed through a hydrophobic frit and concentrated to dryness. The crude mixture was purified by column chromatography (hex->50:50 EtOAc:Hex) to give an oil. This was taken up in 4M HCl in dioxane (50 mL) and stirred for 16 h. The resultant white precipitate was filtered, washed with ether and dried yielding 1-ethynylcyclopropanamine hydrochloride (830 mg, 7.06 mmol, 136%) as a white solid.

$^1$H NMR (300 MHz, DMSO-d$_6$) δ=9.13-8.79 (m, 1H), 8.96 (br s, 2H), 3.60 (s, 1H), 1.38-1.28 (m, 2H), 1.16 (d, J=2.6 Hz, 2H)

S17-E N-(1-Ethynylcyclopropyl)-1-methyl-3-[(1-methylpyrazol-4-yl)methyl]-2,4-dioxo-quinazoline-6-sulfonamide

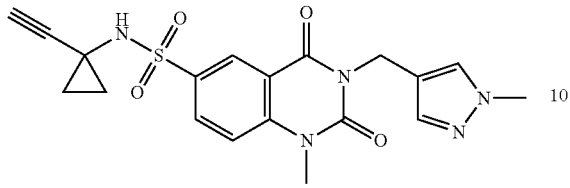

1-Methyl-3-[(1-methylpyrazol-4-yl)methyl]quinazoline-2,4-dione (120 mg, 0.440 mmol) in chlorosulfonic acid (1.0 mL, 0.440 mmol) was stirred at room temperature for 16 h. The mixture was added in drops to stirring EtOAc (20 mL) and ice (20 mL). After addition was complete the mixture was stirred for 5 min and the EtOAc layer was separated and the aqueous extracted with EtOAc (20 mL). The combined extracts were passed through a hydrophobic frit and concentrated under reduced pressure. The resultant white solid was added to a stirring solution of 1-ethynylcyclopropan-amine hydrochloride (52 mg, 0.44 mmol) in pyridine (3 mL) and left to stir for 16 h. EtOAc (10 mL) and 1 M HCL (aq) (10 mL) was added and the mixture stirred for 5 min. The EtOAc layer was separated and the aqueous phase extracted with EtOAc. The combined EtOAc layers were passed through a hydrophobic frit, concentrated under reduced pressure and purified by prep HPLC (high pH) yielding N-(1-ethynylcyclopropyl)-1-methyl-3-[(1-methylpyrazol-4-yl)methyl]-2,4-dioxo-quinazoline-6-sulfonamide (20 mg, 0.05 mmol, 11%) as a white powder.

Example 428 N-[[6-[(1-Methylcyclopropyl)sulfa-moyl]-3-[(1-methylpyrazol-4-yl)methyl]-2,4-dioxo-1H-quinazolin-8-yl]methyl]acetamide

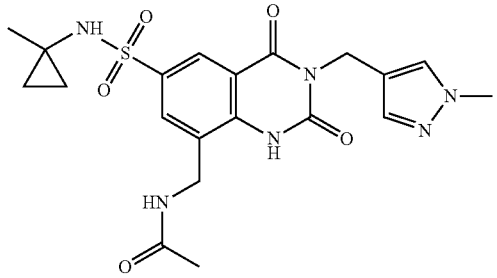

A suspension of 8-cyano-N-(1-methylcyclopropyl)-3-[(1-methylpyrazol-4-yl)methyl]-2,4-dioxo-1H-quinazoline-6-sulfonamide (80 mg, 0.19 mmol), acetic anhydride (36.5 µL, 0.39 mmol) and nickel(II) chloride hexahydrate (46 mg, 0.19 mmol) in methanol (4 mL) was cooled to 0° C. and treated with sodium borohydride (51 mg, 1.35 mmol). The resulting mixture was stirred overnight at ambient temperature. The solvent was removed in vacuo to give a residue, which was partitioned between EtOAc (10 mL) and saturated NaHCO₃ (10 mL). The EtOAc layer was collected and evaporated to dryness to give a residue, which was purified by prep HPLC (high pH) to give the desired product (10 mg, 0.022 mmol, 11%) as a white powder.

Example 429 8-[3-(Dimethylamino)prop-1-ynyl]-N-(1-methylcyclopropyl)-3-[(1-methylpyrazol-4-yl)methyl]-2,4-dioxo-1H-quinazoline-6-sulfonamide

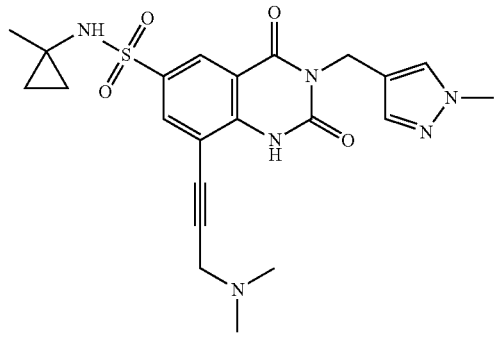

A mixture of 8-bromo-N-(1-methylcyclopropyl)-3-[(1-methylpyrazol-4-yl)methyl]-2,4-dioxo-1H-quinazoline-6-sulfonamide (50 mg, 0.11 mmol), tetrakis(triphenylphosphine)palladium(0) (12.3 mg, 0.01 mmol), triethylamine (60 uL, 0.43 mmol) and 3-dimethylamino-1-propyne (23 µL, 0.21 mmol) in THF (2 mL) was degassed with nitrogen for 5 min. Copper iodide (2.03 mg, 0.010 mmol) was added to the reaction, and the resulting mixture was heated at 80° C. overnight. The mixture was cooled to ambient temperature and filtered through celite. The solvent was then removed under vacuum to give a residue, which was purified by prep HPLC (high pH) to give the desired product (20 mg, 0.043 mmol, 40%) as a white powder.

Example 430 N-(1-Methylcyclopropyl)-3-[(1-methylpyrazol-4-yl)methyl]-2,4-dioxo-1H-quinazoline-6-sulfonamide

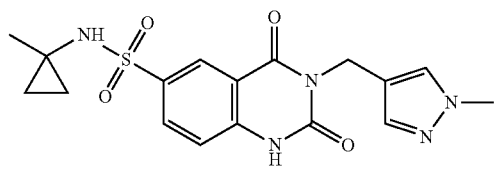

Prepared using Method Intermediate S4-C1. This gave the desired product (2 mg) as a white powder.

Example 431 N-(1-Ethynylcyclopropyl)-3-[(1-methylpyrazol-4-yl)methyl]-2,4-dioxo-1H-quinazoline-6-sulfonamide

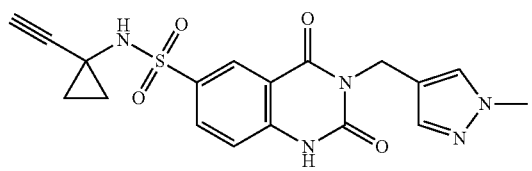 [SMILES: C#CC1(NS(=O)(=O)c2ccc3[nH]c(=O)n(Cc4cnn(C)c4)c(=O)c3c2)CC1]

Prepared from 3-[(1-methylpyrazol-4-yl)methyl]-1H-quinazoline-2,4-dione (90 mg, 0.350 mmol) in a similar manner to N-(1-ethynylcyclopropyl)-1-methyl-3-[(1-methylpyrazol-4-yl)methyl]-2,4-dioxo-quinazoline-6-sulfonamide (Scheme 17). This afforded the desired product (42 mg, 0.105 mmol, 30%) as a white powder.

Example 432 1-(Cyclopropylmethyl)-N-(1-ethynyl-cyclopropyl)-3-[(1-methylpyrazol-4-yl)methyl]-2,4-dioxo-quinazoline-6-sulfonamide

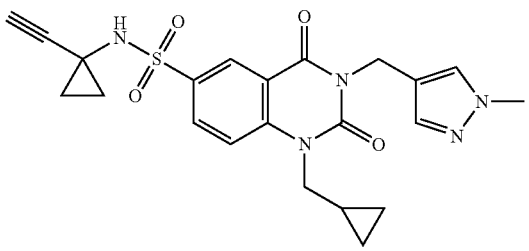 [SMILES: C#CC1(NS(=O)(=O)c2ccc3c(c2)c(=O)n(Cc2cnn(C)c2)c(=O)n3CC2CC2)CC1]

A mixture of N-(1-ethynylcyclopropyl)-3-[(1-methyl-pyrazol-4-yl)methyl]-2,4-dioxo-1H-quinazoline-6-sulfonamide (42 mg, 0.110 mmol), iodomethylcyclopropane (9.2 µL, 0.120 mmol) and potassium carbonate (29 mg, 0.210 mmol) in DMF (2 mL) was heated with agitation in the microwave at 80° C. for 45 min. The solvent was removed in vacuo to leave a residue which was purified by prep HPLC (high pH) to give the desired product (10 mg, 0.022 mmol, 21%) as a white powder.

Example 433 1-Methyl-N-(1-methylcyclopropyl)-3-[(2-methylpyrimidin-5-yl)methyl]-2,4-dioxo-quinazoline-6-sulfonamide

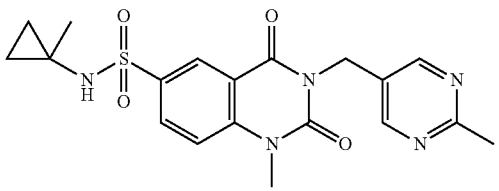 [SMILES: Cc1ncc(Cn2c(=O)c3cc(S(=O)(=O)NC4(C)CC4)ccc3n(C)c2=O)cn1]

To a solution of (2-methyl-5-pyrimidinyl)methanol (26 mg, 0.21 mmol) in THF (2.5 mL) was added triethylamine (21 mg, 0.21 mmol) and methanesulfonyl chloride (0.08 mL, 1 mmol), and the mixture stirred at room temp for 2 h. After 2 h a solution of 1-methyl-N-(1-methylcyclopropyl)-2,4-dioxo-1,2,3,4-tetrahydroquinazoline-6-sulfonamide (65 mg, 0.21 mmol) and sodium hydride, 60% dispersion in mineral oil (13 mg, 0.53 mmol) in DMF was added by syringe and the mixture stirred at ambient temperature overnight. LCMS confirmed conversion to the desired product. The reaction mixture was diluted with water (25 mL) and extracted with EtOAc (2×25 mL). The organic phase was combined, washed with brine (10 mL), passed through a hydrophobic frit and evaporated to dryness. The crude product mixture was purified by prep HPLC (high pH) to give the desired product (23 mg, 0.055 mmol, 26.4%) as a colourless gum.

Example 434 1-Methyl-N-(1-methylcyclopropyl)-2,4-dioxo-3-(pyrazolo[1,5-a]pyridin-3-ylmethyl)quinazoline-6-sulfonamide

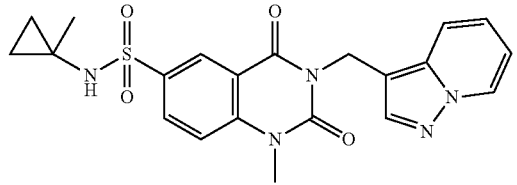 [SMILES: Cn1c(=O)n(Cc2cnn3ccccc23)c(=O)c2cc(S(=O)(=O)NC3(C)CC3)ccc21]

This compound was prepared according to Example 433 using pyrazolo[1,5-a]pyridin-3-ylmethanol (31 mg, 0.21 mmol). This afforded the desired product (3 mg, 0.007 mmol, 3.2%) as a yellow powder.

Example 435 1-[(2,2-Difluorocyclopropyl)methyl]-N-(1-methylcyclopropyl)-3-[(1-methylpyrazol-4-yl)methyl]-2,4-dioxo-quinazoline-6-sulfonamide

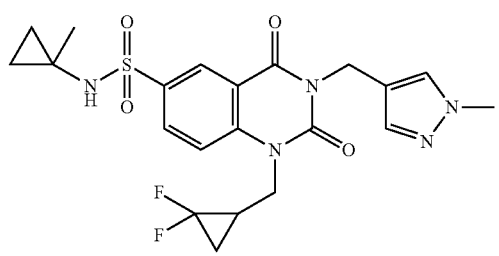 [SMILES: Cn1cc(Cn2c(=O)c3cc(S(=O)(=O)NC4(C)CC4)ccc3n(CC3CC3(F)F)c2=O)cn1]

Prepared using Method A12 (100° C.), from 3-((1-methyl-1H-pyrazol-4-yl)methyl)-N-(1-methylcyclopropyl)-2,4-dioxo-1,2,3,4-tetrahydroquinazoline-6-sulfonamide and 1-(bromomethyl)-2,2-difluorocyclopropane. This gave the desired product (28 mg, 0.058 mmol, 28%) as a white powder.

Example 436 1-[(3,3-Difluorocyclobutyl)methyl]-N-(1-methylcyclopropyl)-3-[(1-methylpyrazol-4-yl)methyl]-2,4-dioxo-quinazoline-6-sulfonamide

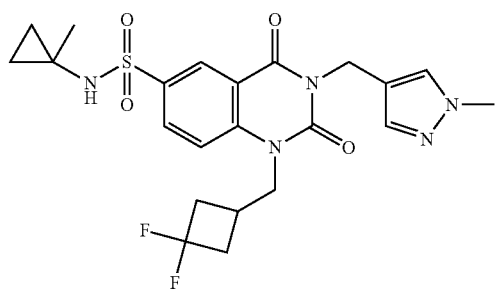 [SMILES: Cn1cc(Cn2c(=O)c3cc(S(=O)(=O)NC4(C)CC4)ccc3n(CC3CC(F)(F)C3)c2=O)cn1]

Prepared using Method A12 (100° C.), from 3-((1-methyl-1H-pyrazol-4-yl)methyl)-N-(1-methylcyclopropyl)-2,4-dioxo-1,2,3,4-tetrahydroquinazoline-6-sulfonamide and 3-(bromomethyl)-1,1-difluorocyclobutane. This gave the desired product (20 mg, 0.041 mmol, 20%) as a white powder.

Example 437 1-[(2,5-Dimethylpyrazol-3-yl)methyl]-N-[1-(fluoromethyl)cyclopropyl]-3-[(1-methylpyrazol-4-yl)methyl]-2,4-dioxo-quinazoline-6-sulfonamide

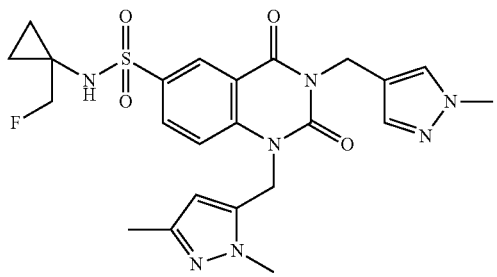 [SMILES: Cc1cc(Cn2c(=O)n(Cc3cnn(C)c3)c(=O)c3cc(S(=O)(=O)NC4(CF)CC4)ccc32)n(C)n1]

Prepared using Method A10, from N-[1-(fluoromethyl)cyclopropyl]-3-[(1-methylpyrazol-4-yl)methyl]-2,4-dioxo-H-quinazoline-6-sulfonamide and 5-(chloromethyl)-1,3-dimethyl-1H-pyrazole. This gave the desired product (16 mg, 0.031 mmol, 21%) as a white powder.

Example 438 1-Ethyl-N-[1-(fluoromethyl)cyclopropyl]-3-[(1-methylpyrazol-4-yl)methyl]-2,4-dioxo-quinazoline-6-sulfonamide

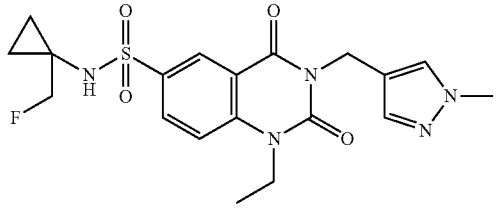 [SMILES: CCn1c(=O)n(Cc2cnn(C)c2)c(=O)c2cc(S(=O)(=O)NC3(CF)CC3)ccc21]

Prepared using Method A10, from N-[1-(fluoromethyl)cyclopropyl]-3-[(1-methylpyrazol-4-yl)methyl]-2,4-dioxo-1H-quinazoline-6-sulfonamide and iodoethane. This gave the desired product (14 mg, 0.032 mmol, 22%) as a white powder.

Example 439 1-(Cyanomethyl)-N-[1-(fluoromethyl)cyclopropyl]-3-[(1-methylpyrazol-4-yl)methyl]-2,4-dioxo-quinazoline-6-sulfonamide

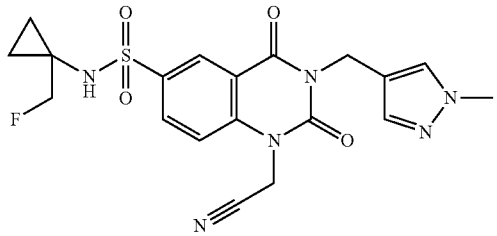 [SMILES: Cn1cc(Cn2c(=O)c3cc(S(=O)(=O)NC4(CF)CC4)ccc3n(CC#N)c2=O)cn1]

Prepared using Method A10, from N-[1-(fluoromethyl)cyclopropyl]-3-[(1-methylpyrazol-4-yl)methyl]-2,4-dioxo-H-quinazoline-6-sulfonamide and bromoacetonitrile. This gave the desired product (5 mg, 0.011 mmol, 8%) as a white powder.

Example 440 N-[1-(Fluoromethyl)cyclopropyl]-3-[(1-methylpyrazol-4-yl)methyl]-2,4-dioxo-1-prop-2-ynyl-quinazoline-6-sulfonamide

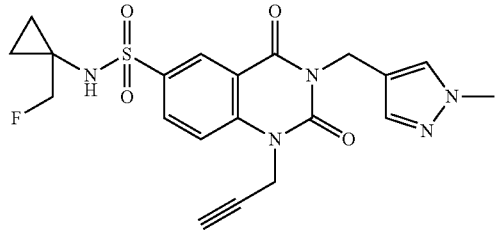 [SMILES: C#CCn1c(=O)n(Cc2cnn(C)c2)c(=O)c2cc(S(=O)(=O)NC3(CF)CC3)ccc21]

Prepared using Method A10, from N-[1-(fluoromethyl)cyclopropyl]-3-[(1-methylpyrazol-4-yl)methyl]-2,4-dioxo-H-quinazoline-6-sulfonamide and 3-bromopropyne. This gave the desired product (8 mg, 0.018 mmol, 12%) as a white powder.

Example 441 N-[1-(Fluoromethyl)cyclopropyl]-1-[(3-methylisoxazol-5-yl)methyl]-3-[(1-methylpyrazol-4-yl)methyl]-2,4-dioxo-quinazoline-6-sulfonamide

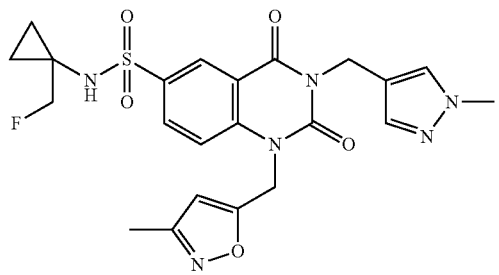 [SMILES: Cc1cc(Cn2c(=O)n(Cc3cnn(C)c3)c(=O)c3cc(S(=O)(=O)NC4(CF)CC4)ccc32)on1]

Prepared using Method A10, from N-[1-(fluoromethyl)cyclopropyl]-3-[(1-methylpyrazol-4-yl)methyl]-2,4-dioxo-1H-quinazoline-6-sulfonamide and 5-(bromomethyl)-3-methyl-1,2-oxazole. This gave the desired product (10 mg, 0.02 mmol, 14%) as a white powder.

Example 442 N-[1-(Fluoromethyl)cyclopropyl]-3-[(1-methylpyrazol-4-yl)methyl]-2,4-dioxo-1-(tetrahydropyran-4-ylmethyl)quinazoline-6-sulfonamide

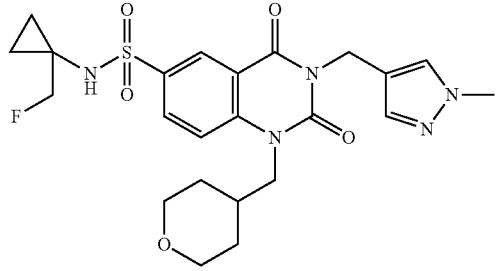 [SMILES: Cn1cc(Cn2c(=O)c3cc(S(=O)(=O)NC4(CF)CC4)ccc3n(CC3CCOCC3)c2=O)cn1]

Prepared using Method A10, from N-[1-(fluoromethyl)cyclopropyl]-3-[(1-methylpyrazol-4-yl)methyl]-2,4-dioxo-1H-quinazoline-6-sulfonamide and 4-(bromomethyl)tetrahydropyran. This gave the desired product (8 mg, 0.016 mmol, 11%) as a white powder.

Example 443 1-[(2,2-Difluorocyclopropyl)methyl]-N-[1-(fluoromethyl)cyclopropyl]-3-[(1-methylpyrazol-4-yl)methyl]-2,4-dioxo-quinazoline-6-sulfonamide

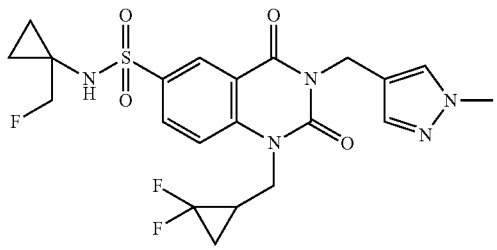 [SMILES: Cn1cc(Cn2c(=O)c3cc(S(=O)(=O)NC4(CF)CC4)ccc3n(CC3CC3(F)F)c2=O)cn1]

Prepared using Method A10, from N-[1-(fluoromethyl)cyclopropyl]-3-[(1-methylpyrazol-4-yl)methyl]-2,4-dioxo-H-quinazoline-6-sulfonamide and 1-(bromomethyl)-2,2-difluorocyclopropane. This gave the desired product (14 mg, 0.028 mmol, 19%) as a white powder.

Example 444 1-[(3,3-Difluorocyclobutyl)methyl]-N-[1-(fluoromethyl)cyclopropyl]-3-[(1-methylpyrazol-4-yl)methyl]-2,4-dioxo-quinazoline-6-sulfonamide

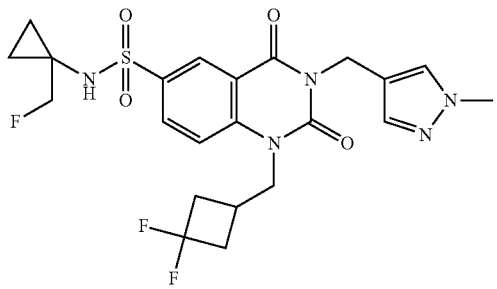 [SMILES: Cn1cc(Cn2c(=O)c3cc(S(=O)(=O)NC4(CF)CC4)ccc3n(CC3CC(F)(F)C3)c2=O)cn1]

Prepared using Method A10, from N-[1-(fluoromethyl)cyclopropyl]-3-[(1-methylpyrazol-4-yl)methyl]-2,4-dioxo-H-quinazoline-6-sulfonamide and 3-(bromomethyl)-1,1-difluorocyclobutane. This gave the desired product (8 mg, 0.016 mmol, 11%) as a white powder.

Example 445 N-[1-(Fluoromethyl)cyclopropyl]-3-[(1-methylpyrazol-4-yl)methyl]-1-(oxetan-3-ylmethyl)-2,4-dioxo-quinazoline-6-sulfonamide

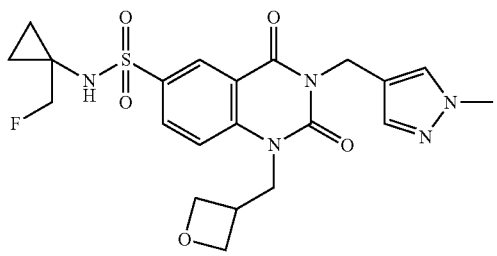

Prepared using Method A10 (tosylate), from N-[1-(fluoromethyl)cyclopropyl]-3-[(1-methylpyrazol-4-yl)methyl]-2,4-dioxo-1H-quinazoline-6-sulfonamide and oxetan-3-ylmethyl 4-methylbenzenesulfonate. This gave the desired product (12 mg, 0.025 mmol, 17%) as a white powder.

Example 446 1-Methyl-N-(1-methylcyclopropyl)-2,4-dioxo-3-(pyridazin-4-ylmethyl)quinazoline-6-sulfonamide

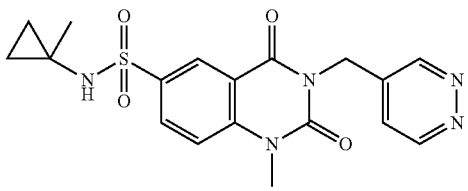 [SMILES: Cn1c(=O)n(Cc2ccnnc2)c(=O)c2cc(S(=O)(=O)NC3(C)CC3)ccc21]

This compound was prepared according to Example 433 using pyridazin-4-ylmethanol (23 mg, 0.21 mmol). This afforded the desired product (8 mg, 0.02 mmol, 9.5%) as a pink powder.

Example 447 N-(1-Methylcyclopropyl)-1,3-dioxo-benzo[de]isoquinoline-5-sulfonamide

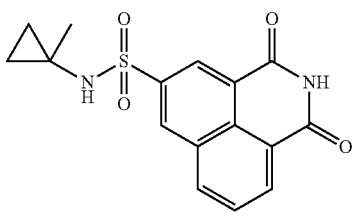 [SMILES: CC1(NS(=O)(=O)c2cc3c4c(cccc4c2)C(=O)NC3=O)CC1]

Chlorosulfonic acid (2.0 mL) was added to 1,8-naphthalimide (200 mg, 0.690 mmol) and the resulting solution stirred at 80° C. for 5 h under nitrogen. The reaction mixture was left to stand overnight and then added in drops to a stirred slurry of ice/water (approx 30 mL). After the addition was complete EtOAc (40 mL) was added and the mixture stirred for 5 min. The EtOAc layer was isolated by passing through a hydrophobic frit and the aqueous phase washed with EtOAc (2×40 mL). The EtOAc extracts were combined and dried over anhydrous MgSO4. The solution was filtered and a mixture of 1-methylcyclopropanamine hydrochloride (148 mg, 1.37 mmol) and triethylamine (348 mg, 3.43 mmol) in EtOAc/DCM (10 mL) was added dropwise with stirring. After 1 h at ambient temperature water (30 mL) was added and the mixture stirred for 5 min. The organic layer was separated and the aqueous layer washed with EtOAc (2×40 mL). The combined EtOAc extracts were concentrated under reduced pressure and the crude residue flash chromatographed over silica and then subsequently purified by prep HPLC (high pH) to give the desired product (38 mg, 0.115 mmol, 17%) as a white powder.

Example 448 Methyl 6-[(1-methylcyclopropyl)sulfamoyl]-3-[(1-methylpyrazol-4-yl)methyl]-2,4-dioxo-1H-quinazoline-8-carboxylate

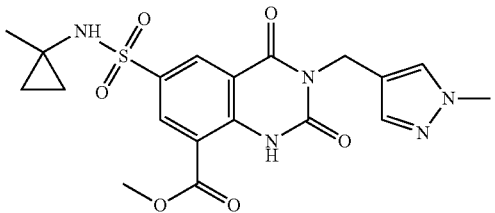

Methyl 6-chlorosulfonyl-3-[(1-methylpyrazol-4-yl)methyl]-2,4-dioxo-1H-quinazoline-8-carboxylate (550 mg, 1.33 mmol) was added to a stirred solution of 1-methylcyclopropanamine hydrochloride (143 mg, 1.33 mmol) and N,N-diisopropylethylamine (0.52 mL, 2.93 mmol) in DMF (10 mL), and the resulting mixture was agitated at ambient temperature for 12 h. The solvent was removed in vacuo and the resulting residue was purified by automated column chromatography (SiO$_2$; RediSep—4 g; 0 to 80% EtOAc in hexane) to afford the desired product (350 mg, 0.782 mmol, 59%) as a white foam.

Example 449 N,N-Dimethyl-6-[(1-methylcyclopropyl)sulfamoyl]-3-[(1-methylpyrazol-4-yl)methyl]-2,4-dioxo-1H-quinazoline-8-carboxamide

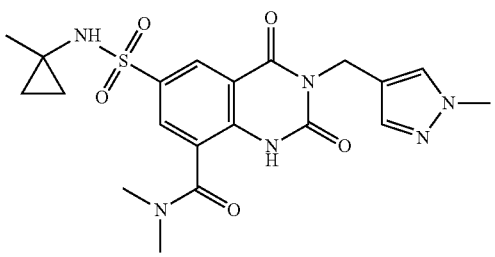

3-((1-Methyl-1H-pyrazol-4-yl)methyl)-6-(N-(1-methylcyclopropyl)sulfamoyl)-2,4-dioxo-1,2,3,4-tetrahydroquinazoline-8-carboxylic acid

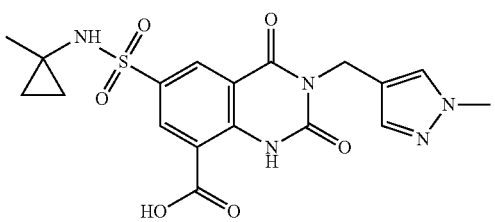

To a magnetically stirred suspension of methyl 6-[(1-methylcyclopropyl)sulfamoyl]-3-[(1-methylpyrazol-4-yl)methyl]-2,4-dioxo-1H-quinazoline-8-carboxylate (250 mg, 0.56 mmol) and in a 1:1 (v/v) mixture of THF (2 mL) and water (2 mL) was added lithium hydroxide (66.9 mg, 2.79 mmol), and the resulting mixture was agitated for 1 h at ambient temperature. The solvent was removed in vacuo to give a gum, which was partitioned between EtOAc (10 mL) and water (10 mL). The aqueous phase was collected and acidified (pH 1.0) with 1 N HCl to give a cloudy suspension. EtOAc (30 mL) and water (10 mL) was added and the resulting mixture was agitated for 5 min. The organic phase was collected and dried, and evaporated in vacuo to give 3-((1-methyl-1H-pyrazol-4-yl)methyl)-6-(N-(1-methylcyclopropyl)sulfamoyl)-2,4-dioxo-1,2,3,4-tetrahydroquinazoline-8-carboxylic acid as a white solid (220 mg, 91%).

$^1$H NMR (300 MHz, DMSO-d$_6$) δ=11.37 (br. s., 1H), 8.57 (d, J=2.2 Hz, 1H), 8.51 (d, J=2.2 Hz, 1H), 8.31 (s, 1H), 7.69 (s, 1H), 7.40 (s, 1H), 4.92 (s, 2H), 3.76 (s, 3H), 1.08 (s, 3H), 0.59 (s, 2H), 0.44-0.38 (m, 2H)

N,N-Dimethyl-6-[(1-methylcyclopropyl)sulfamoyl]-3-[(1-methylpyrazol-4-yl)methyl]-2,4-dioxo-1H-quinazoline-8-carboxamide

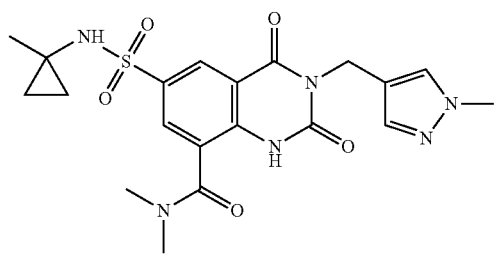

HATU (48 mg, 0.13 mmol) was added to a stirred solution of 6-[(1-methylcyclopropyl) sulfamoyl]-3-[(1-methylpyrazol-4-yl)methyl]-2,4-dioxo-H-quinazoline-8-carboxylic acid (50 mg, 0.12 mmol) in DMF (2 mL), and the resulting mixture was agitated for 30 min. Dimethylamine solution (63 µL, 0.13 mmol) was then added to the reaction, and the resulting mixture was agitated for 16 h. The solvent was removed in vacuo to give a residue which was purified by prep HPLC (low pH) to give the desired product (20 mg, 0.043 mmol, 38%) as a white powder.

Example 450 N-Methyl-6-[(1-methylcyclopropyl)sulfamoyl]-3-[(1-methylpyrazol-4-yl)methyl]-2,4-dioxo-1H-quinazoline-8-carboxamide

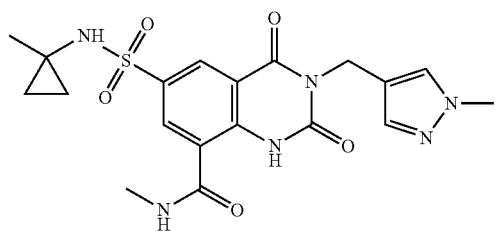

HATU (48 mg, 0.13 mmol) was added to a stirred solution of 6-[(1-methylcyclopropyl) sulfamoyl]-3-[(1-methylpyrazol-4-yl)methyl]-2,4-dioxo-H-quinazoline-8-carboxylic acid (50 mg, 0.12 mmol) in DMF (2 mL), and the resulting mixture was agitated for 30 min. Methylamine solution (63 µL, 0.13 mmol) was then added to the reaction, and the resulting mixture was agitated for 16 h. The solvent was removed in vacuo to give a residue which was purified by Example 451 N-Methoxy-N-methyl-6-[(1-methylcyclopropyl)sulfamoyl]-3-[(1-methylpyrazol-4-yl)methyl]-2,4-dioxo-1H-quinazoline-8-carboxamide

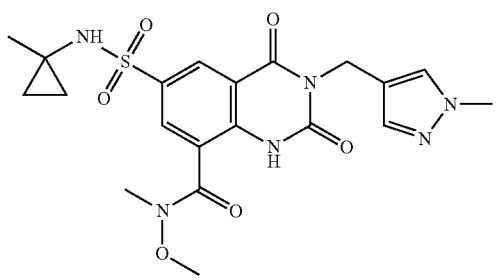

HATU (96.5 mg, 0.250 mmol) was added to a stirred solution of 6-[(1-methylcyclopropyl)sulfamoyl]-3-[(1-methylpyrazol-4-yl)methyl]-2,4-dioxo-1H-quinazoline-8-carboxylic acid (100 mg, 0.2300 mmol) in DMF (4 mL), and the resulting mixture was agitated for 30 min. N,O-Dimethylhydroxylamine hydrochloride (127 µL, 0.25 mmol) and triethylamine (0.07 mL, 0.5100 mmol) were then added to the reaction, and the resulting mixture was agitated for 12 h. The solvent was removed in vacuo to give a residue which was purified by automated column chromatography ($SiO_2$; SNAP—10 g; 0 to 10% MeOH in DCM) to afford the desired (100 mg, 0.21 mmol, 91%) as a white solid.

Example 452 1-(2-Cyano-2-methyl-propyl)-N-(1-methylcyclopropyl)-3-[(3-methylisoxazol-5-yl)methyl]-2,4-dioxo-quinazoline-6-sulfonamide

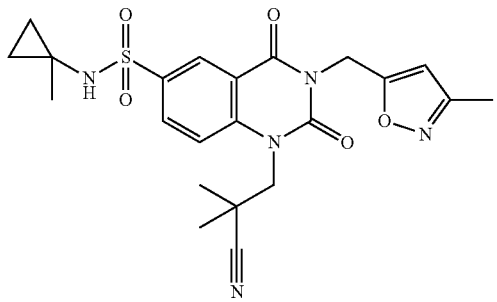 [SMILES: Cc1cc(Cn2c(=O)c3cc(S(=O)(=O)NC4(C)CC4)ccc3n(CC(C)(C)C#N)c2=O)on1]

Prepared using Method A12 (6 h at 120° C.), from N-(1-methylcyclopropyl)-3-((3-methylisoxazol-5-yl)methyl)-2,4-dioxo-1,2,3,4-tetrahydroquinazoline-6-sulfonamide and (2-cyano-2-methyl-propyl)-4-methylbenzenesulfonate. This gave the desired product (11 mg, 0.023 mmol, 11%) as a white powder.

Example 453 1-(2-Fluoro-2-methyl-propyl)-N-(1-methylcyclopropyl)-3-[(3-methylisoxazol-5-yl)methyl]-2,4-dioxo-quinazoline-6-sulfonamide

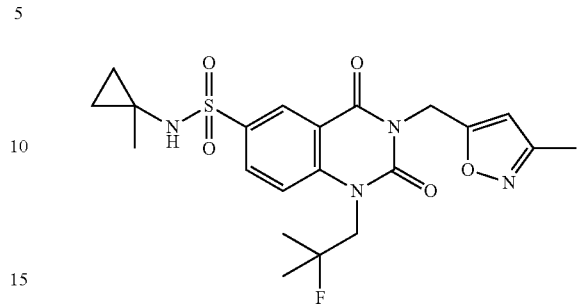

Prepared using Method A12 (6 h at 120° C.), from N-(1-methylcyclopropyl)-3-((3-methylisoxazol-5-yl)methyl)-2,4-dioxo-1,2,3,4-tetrahydroquinazoline-6-sulfonamide and 1-bromo-2-fluoro-2-methyl-propane. This gave the desired product (3 mg, 0.006 mmol, 3%) as a white powder.

Example 454 N-(1-Methylcyclopropyl)-2-[(1-methylpyrazol-4-yl)methyl]-1,3-dioxo-benzo[de]isoquinoline-5-sulfonamide

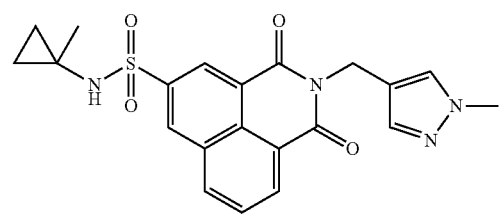 [SMILES: Cn1cc(CN2C(=O)c3cccc4cc(S(=O)(=O)NC5(C)CC5)cc(c34)C2=O)cn1]

S18

To a solution of 1,8-naphthalimide (395 mg, 2.0 mmol) in DMF (10 mL) was added sodium iodide (60 mg, 0.40 mmol), cesium carbonate (1371 mg, 4.21 mmol) and 4-(chloromethyl)-1-methyl-1H-pyrazole hydrochloride (0.24 mL, 2.2 mmol). The resulting mixture was heated in a microwave at 120° C. for 14 h. The reaction mixture was diluted with water (100 mL) and extracted with EtOAc (2×100 mL). The combined extracts were washed with brine and the solution was passed through a hydrophobic frit and concentrated under reduced pressure to leave a residue of crude 2-[(1-methylpyrazol-4-yl)methyl]benzo[de]isoquinoline-1,3-dione (~200 mg) which was used without characterisation or purification.

Chlorosulfonic acid (2.0 mL) was added to 2-[(1-methylpyrazol-4-yl)methyl]benzo[de]isoquinoline-1,3-dione (200 mg, 0.69 mmol) and the resulting solution stirred at 80° C. for 5 h under nitrogen. The reaction mixture was left to stand overnight and then added in drops to a stirred slurry of ice/water (approx 30 mL). After the addition was complete EtOAc (40 mL) was added and the mixture stirred for 5 min. The EtOAc layer was isolated by passing through a hydrophobic frit and the aqueous phase washed with EtOAc (2×40 mL). The EtOAc extracts were combined and dried over anhydrous MgSO4. The solution was filtered and a mixture of 1-methylcyclopropanamine hydrochloride (148 mg, 1.37 mmol) and triethylamine (348 mg, 3.43 mmol) in EtOAc/ prep HPLC (low pH) to give the desired product (20 mg, 0.045 mmol, 39%) as a white powder.

DCM (10 mL) was added in drops with stirring. After 1 h at ambient temperature water (30 mL) was added and the mixture stirred for 5 min. The organic layer was separated and the aqueous layer washed with EtOAc (2×40 mL). The combined EtOAc extracts were concentrated under reduced pressure and the crude residue flash chromatographed over silica and then subsequently purified by prep HPLC (high pH) to give the desired product (11 mg, 0.026 mmol, 3.8%) as a white powder.

Example 455 N-(1-Cyanocyclopropyl)-1-ethyl-3-[(2-methylthiazol-5-yl)methyl]-2,4-dioxo-quinazoline-6-sulfonamide

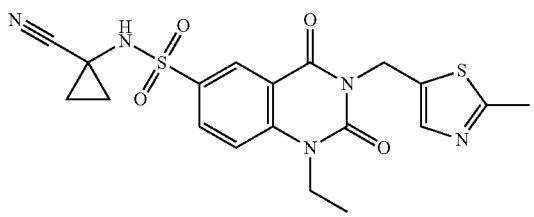 [SMILES: CCn1c(=O)n(Cc2cnc(C)s2)c(=O)c2cc(S(=O)(=O)NC3(C#N)CC3)ccc21]

Iodoethane (0.02 mL, 0.2600 mmol) was added to a stirring mixture of N-(1-cyanocyclopropyl)-N-[[3-[(2-methylthiazol-5-yl)methyl]-2,4-dioxo-1H-quinazolin-6-yl]sulfonyl]acetamide (100 mg, 0.220 mmol) and potassium carbonate (120 mg, 0.870 mmol) in DMF (3 mL) and left to stir at room temperature for 16 h. Concentrated ammonia (100 μL) was added and the mixture heated to 40° C. for 10 min. The mixture was allowed to cool and DCM (8 mL) and saturated aqueous ammonium chloride solution (8 mL) was added and the mixture stirred for 5 min. The DCM layer was isolated by passing through a hydrophobic frit and the aqueous layer washed with DCM (8 mL). The combined DCM extracts were concentrated under reduced pressure and purified by prep HPLC (low pH) yielding N-(1-cyanocyclopropyl)-1-ethyl-3-[(2-methylthiazol-5-yl)methyl]-2,4-dioxo-quinazoline-6-sulfonamide (12 mg, 0.027 mmol, 12%) as a white solid.

Example 456 N-[1-(Difluoromethyl)cyclopropyl]-3-[(1-methylpyrazol-4-yl)methyl]-2,4-dioxo-1H-quinazoline-6-sulfonamide

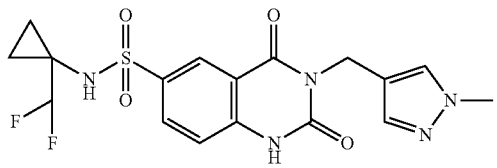 [SMILES: Cn1cc(Cn2c(=O)[nH]c3ccc(S(=O)(=O)NC4(C(F)F)CC4)cc3c2=O)cn1]

Prepared using Method A1 (sulfonamide formation), from 3-[(1-methylpyrazol-4-yl)methyl]-2,4-dioxo-1H-quinazoline-6-sulfonyl chloride and 1-(difluoromethyl)cyclopropan-1-amine hydrochloride. This gave the desired product (187 mg, 0.440 mmol, 47.3%) as a white powder.

Example 457 N-(1-Cyanocyclopropyl)-1-[(1-methylpyrazol-4-yl)methyl]-3-[(2-methylthiazol-5-yl)methyl]-2,4-dioxo-quinazoline-6-sulfonamide

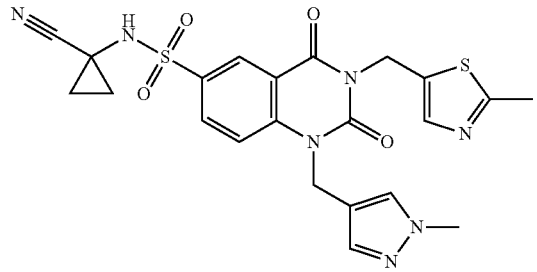 [SMILES: Cc1ncc(Cn2c(=O)c3cc(S(=O)(=O)NC4(C#N)CC4)ccc3n(Cc3cnn(C)c3)c2=O)s1]

This compound was prepared according to Example 455 using N-(1-cyanocyclopropyl)-N-[[3-[(2-methylthiazol-5-yl)methyl]-2,4-dioxo-H-quinazolin-6-yl]sulfonyl]acetamide (100 mg, 0.2200 mmol) and 4-(chloromethyl)-1-methyl-1H-pyrazole hydrochloride (0.02 mL, 0.2600 mmol). This afforded the desired product (5 mg, 0.010 mmol, 4.5%) as a white solid.

Example 458 1-(Cyclopropylmethyl)-N-[1-(difluoromethyl)cyclopropyl]-3-[(1-methylpyrazol-4-yl)methyl]-2,4-dioxo-quinazoline-6-sulfonamide

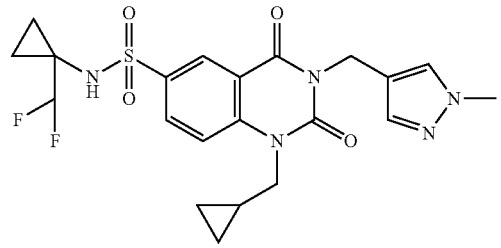 [SMILES: Cn1cc(Cn2c(=O)c3cc(S(=O)(=O)NC4(C(F)F)CC4)ccc3n(CC3CC3)c2=O)cn1]

Prepared using Method A10 from N-[1-(difluoromethyl)cyclopropyl]-3-[(1-methylpyrazol-4-yl)methyl]-2,4-dioxo-1H-quinazoline-6-sulfonamide and iodomethylcyclopropane. This gave the desired product (11 mg, 0.023 mmol, 22%) as a white powder.

Example 459 N-[1-(Difluoromethyl)cyclopropyl]-1-[(2,5-dimethylpyrazol-3-yl)methyl]-3-[(1-methylpyrazol-4-yl)methyl]-2,4-dioxo-quinazoline-6-sulfonamide

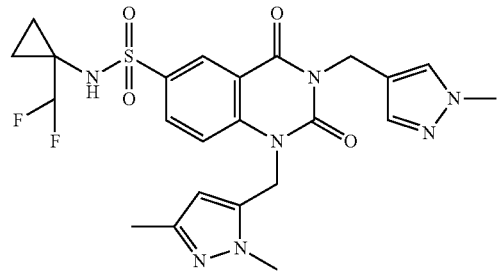 [SMILES: Cc1cc(Cn2c(=O)n(Cc3cnn(C)c3)c(=O)c3cc(S(=O)(=O)NC4(C(F)F)CC4)ccc32)n(C)n1]

Prepared using Method A10 from N-[1-(difluoromethyl)cyclopropyl]-3-[(1-methylpyrazol-4-yl)methyl]-2,4-dioxo-H-quinazoline-6-sulfonamide and 5-(chloromethyl)-1,3-dimethyl-1H-pyrazole. This gave the desired product (12 mg, 0.022 mmol, 21%) as a white powder.

Example 460 N-[1-(Difluoromethyl)cyclopropyl]-1-[(4-fluorophenyl)methyl]-3-[(1-methylpyrazol-4-yl)methyl]-2,4-dioxo-quinazoline-6-sulfonamide

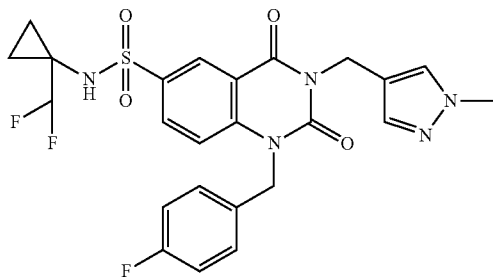 [SMILES: Cn1cc(Cn2c(=O)c3cc(S(=O)(=O)NC4(C(F)F)CC4)ccc3n(Cc3ccc(F)cc3)c2=O)cn1]

Prepared using Method A10 from N-[1-(difluoromethyl)cyclopropyl]-3-[(1-methylpyrazol-4-yl)methyl]-2,4-dioxo-1H-quinazoline-6-sulfonamide and 4-fluorobenzyl bromide. This gave the desired product (10 mg, 0.019 mmol, 18%) as a white powder.

Example 461 1-(Cyclobutylmethyl)-N-[1-(fluoromethyl)cyclopropyl]-3-[(1-methylpyrazol-4-yl)methyl]-2,4-dioxo-quinazoline-6-sulfonamide

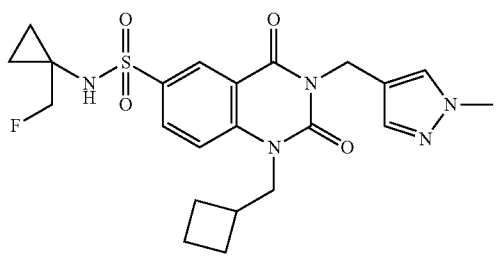 [SMILES: Cn1cc(Cn2c(=O)c3cc(S(=O)(=O)NC4(CF)CC4)ccc3n(CC3CCC3)c2=O)cn1]

Prepared using Method A10 from N-[1-(fluoromethyl)cyclopropyl]-3-[(1-methylpyrazol-4-yl)methyl]-2,4-dioxo-1H-quinazoline-6-sulfonamide and (bromomethyl)cyclobutane. This gave the desired product (10 mg, 0.021 mmol, 18%) as a white powder.

Example 462 N-[1-(Fluoromethyl)cyclopropyl]-1-(2-methoxyethyl)-3-[(1-methylpyrazol-4-yl)methyl]-2,4-dioxo-quinazoline-6-sulfonamide

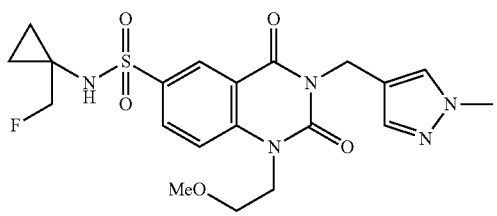 [SMILES: COCCn1c(=O)n(Cc2cnn(C)c2)c(=O)c2cc(S(=O)(=O)NC3(CF)CC3)ccc21]

Prepared using Method A10 from N-[1-(fluoromethyl)cyclopropyl]-3-[(1-methylpyrazol-4-yl)methyl]-2,4-dioxo-1H-quinazoline-6-sulfonamide and 2-bromoethyl methylether. This gave the desired product (7 mg, 0.015 mmol, 13%) as a white powder.

Example 463 1-[(2,4-Dimethylthiazol-5-yl)methyl]-N-[1-(fluoromethyl)cyclopropyl]-3-[(1-methylpyrazol-4-yl)methyl]-2,4-dioxo-quinazoline-6-sulfonamide

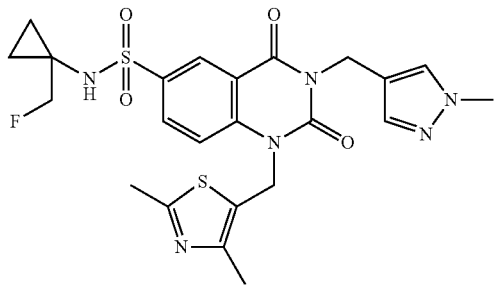 [SMILES: Cc1nc(C)c(Cn2c(=O)n(Cc3cnn(C)c3)c(=O)c3cc(S(=O)(=O)NC4(CF)CC4)ccc32)s1]

Prepared using Method A2 from N-[1-(fluoromethyl)cyclopropyl]-3-[(1-methylpyrazol-4-yl)methyl]-2,4-dioxo-1H-quinazoline-6-sulfonamide and (2,4-dimethyl-1,3-thiazol-5-yl)methanol. This gave the desired product (8 mg, 0.015 mmol, 13%) as a white powder.

Example 464 N-(1-Methylcyclopropyl)-2-[(3-methylisoxazol-5-yl)methyl]-1,3-dioxo-benzo[de]isoquinoline-5-sulfonamide

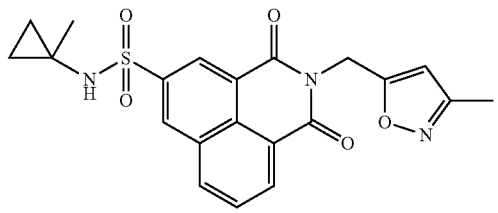 [SMILES: Cc1cc(CN2C(=O)c3cccc4cc(S(=O)(=O)NC5(C)CC5)cc(c34)C2=O)on1]

To a solution of 1,8-naphthalimide (395 mg, 2 mmol) in DMF (10 mL) was added sodium iodide (60 mg, 0.40 mmol), cesium carbonate (718 mg, 2.2 mmol) and 5-(bromomethyl)-3-methyl-1,2-oxazole (0.24 mL, 2.2 mmol). The resulting mixture was heated in a microwave at 70° C. for 50 min. The reaction mixture was diluted with water (100 mL) and extracted with EtOAc (2×100 mL). The combined extracts were washed with brine and the solution was passed through a hydrophobic frit and concentrated under reduced pressure. The residue (604 mg) was triturated from diethyl ether to give 2-[(3-methylisoxazol-5-yl)methyl]benzo[de]isoquinoline-1,3-dione (516 mg, 88.1% yield).

1H NMR (300 MHz, DMSO-d6) δ=8.53 (dt, J=1.1, 7.4 Hz, 4H), 7.92 (d, J=7.3 Hz, 1H), 7.89 (d, J=7.3 Hz, 1H), 6.32 (s, 1H), 5.33 (s, 2H), 2.16 (s, 3H)

Chlorosulfonic acid (4.0 mL) was added to 2-[(3-methylisoxazol-5-yl)methyl]benzo[de]isoquinoline-1,3-dione (466 mg, 1.59 mmol) and the resulting solution stirred at 80° C. for 3 h under nitrogen. The reaction mixture was added dropwise to a stirred slurry of ice/water (approx 30 mL).

After the addition was complete EtOAc (40 mL) was added and the mixture stirred for 5 min. The EtOAc layer was isolated by passing through a hydrophobic frit and the aqueous phase washed with EtOAc (2×40 mL). The EtOAc extracts were combined and dried over anhydrous MgSO4. The solution was filtered and a mixture of 1-methylcyclopropanamine hydrochloride (343 mg, 3.19 mmol) and triethylamine (1.11 mL, 7.97 mmol) in EtOAc/DCM (10 mL) was added in drops with stirring. After 1 h at ambient temperature water (30 mL) was added and the mixture stirred for 5 min. The organic layer was separated and the aqueous layer washed with EtOAc (2×40 mL). The combined EtOAc extracts were concentrated under reduced pressure and the residue was triturated with MeOH/diethyl ether to give the desired product (254 mg, 0.697 mmol, 37.5%) as an off-white powder.

Example 465 1-(2,2-Dimethylpropyl)-N-(1-methylcyclopropyl)-3-[(3-methylisoxazol-5-yl)methyl]-2,4-dioxo-quinazoline-6-sulfonamide

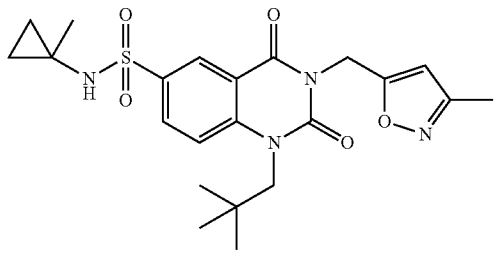 [SMILES: Cc1cc(Cn2c(=O)c3cc(S(=O)(=O)NC4(C)CC4)ccc3n(CC(C)(C)C)c2=O)on1]

N-(1-Methylcyclopropyl)-3-((3-methylisoxazol-5-yl)methyl)-2,4-dioxo-1,2,3,4-tetrahydroquinazoline-6-sulfonamide (100 mg, 0.260 mmol), cesium carbonate (100 mg, 0.3100 mmol), sodium iodide (8 mg, 0.05 mmol) and 1-bromo-2,2-dimethylpropane (426 mg, 2.8 mmol) in DMF (2 mL) was heated by microwave irradiation to 130° C. for 1.5 h. The reaction mixture was diluted with water (10 mL) and extracted with EtOAc (2×20 mL). The organic phase was combined, washed with brine (10 mL), passed through a hydrophobic frit and evaporated to dryness. The crude product mixture was purified by prep HPLC (high pH) to give the desired product (14 mg, 0.03 mmol, 12%) as an off-white powder.

Example 466 1-[(2S)-2-Methylbutyl]-N-(1-methylcyclopropyl)-3-[(3-methylisoxazol-5-yl)methyl]-2,4-dioxo-quinazoline-6-sulfonamide

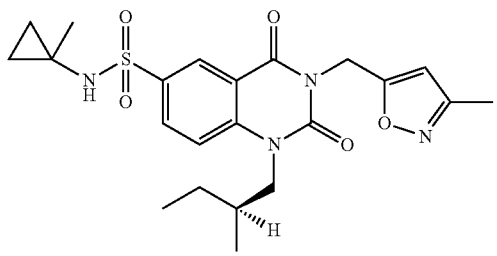 [SMILES: CC[C@H](C)Cn1c(=O)n(Cc2cc(C)no2)c(=O)c2cc(S(=O)(=O)NC3(C)CC3)ccc21]

This compound was prepared according to Example 465 using N-(1-methylcyclopropyl)-3-((3-methylisoxazol-5-yl) methyl)-2,4-dioxo-1,2,3,4-tetrahydroquinazoline-6-sulfonamide (100 mg, 0.260 mmol) and (S)-1-bromo-2-methylbutane (43 mg, 0.28 mmol). The reaction mixture was heated by microwave irradiation to 100° C. for 1 h. This afforded the desired product (25 mg, 0.054 mmol, 21%) as a white powder.

Example 467 1-[(1-Methylcyclobutyl)methyl]-N-(1-methylcyclopropyl)-3-[(3-methylisoxazol-5-yl)methyl]-2,4-dioxo-quinazoline-6-sulfonamide

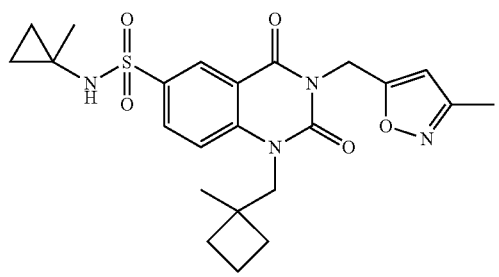 [SMILES: Cc1cc(Cn2c(=O)c3cc(S(=O)(=O)NC4(C)CC4)ccc3n(CC3(C)CCC3)c2=O)on1]

This compound was prepared according to Example 465 using N-(1-methylcyclopropyl)-3-((3-methylisoxazol-5-yl) methyl)-2,4-dioxo-1,2,3,4-tetrahydroquinazoline-6-sulfonamide (100 mg, 0.260 mmol) and 1-(bromomethyl)-1-methylcyclobutane (251 mg, 1.54 mmol). The reaction mixture was heated by microwave irradiation to 130° C. for 1 h. This afforded the desired product (24 mg, 0.051 mmol, 20%) as a white powder.

Example 468 Ethyl 2-[1-methyl-6-[(1-methylcyclopropyl)sulfamoyl]-2,4-dioxo-quinazolin-3-yl]acetate

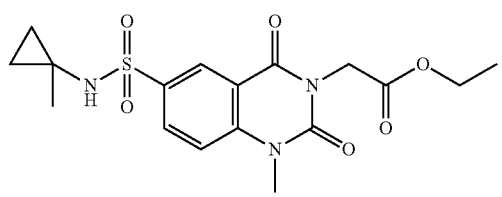 [SMILES: CCOC(=O)Cn1c(=O)c2cc(S(=O)(=O)NC3(C)CC3)ccc2n(C)c1=O]

Prepared using Method A3 from 1-methyl-N-(1-methylcyclopropyl)-2,4-dioxo-quinazoline-6-sulfonamide and ethyl bromoacetate. This gave the desired product (23 mg, 0.058 mmol, 30%) as a white powder.

Example 469 1-Methyl-N-(1-methylcyclopropyl)-2,4-dioxo-3-(2-oxobutyl)quinazoline-6-sulfonamide

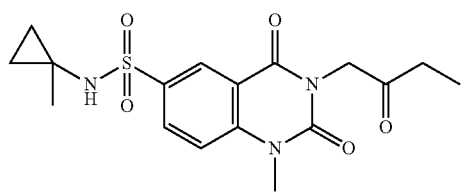 [SMILES: CCC(=O)Cn1c(=O)c2cc(S(=O)(=O)NC3(C)CC3)ccc2n(C)c1=O]

Prepared using Method A3 from 1-methyl-N-(1-methylcyclopropyl)-2,4-dioxo-quinazoline-6-sulfonamide and 1-bromobutan-2-one. This gave the desired product (20 mg, 0.053 mmol, 27%) as a white powder.

Example 470 1-(2-Ethylbutyl)-N-(1-methylcyclopropyl)-3-[(3-methylisoxazol-5-yl)methyl]-2,4-dioxo-quinazoline-6-sulfonamide

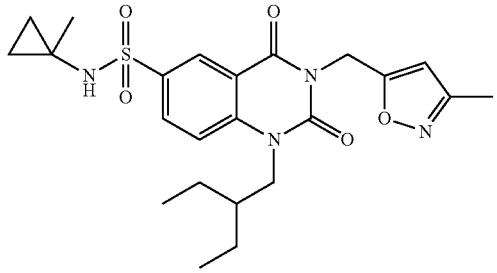 [SMILES: CCC(CC)Cn1c(=O)n(Cc2cc(C)no2)c(=O)c2cc(S(=O)(=O)NC3(C)CC3)ccc21]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 1-bromo-2-ethylbutane (46 mg, 0.28 mmol). The reaction mixture was heated by microwave irradiation to 100° C. for 1 h. This afforded the desired product (37 mg, 0.078 mmol, 30%) as a white powder.

Example 471 1-[(1-Methoxycyclopentyl)methyl]-N-(1-methylcyclopropyl)-3-[(3-methylisoxazol-5-yl)methyl]-2,4-dioxo-quinazoline-6-sulfonamide

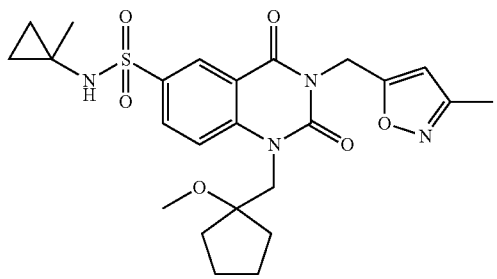 [SMILES: COC1(Cn2c(=O)n(Cc3cc(C)no3)c(=O)c3cc(S(=O)(=O)NC4(C)CC4)ccc32)CCCC1]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 1-(bromomethyl)-1-methoxycyclopentane (247 mg, 1.28 mmol). The reaction mixture was heated by microwave irradiation to 130° C. for 1 h. This afforded the desired product (17 mg, 0.034 mmol, 13%) as a colourless gum.

Example 472 1-Isopentyl-N-(1-methylcyclopropyl)-3-[(3-methylisoxazol-5-yl)methyl]-2,4-dioxo-quinazoline-6-sulfonamide

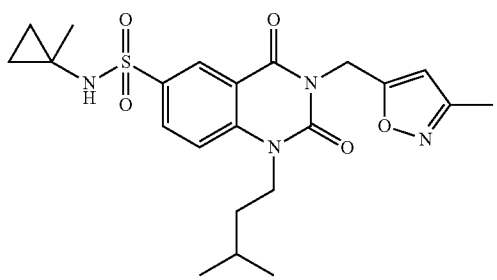 [SMILES: Cc1cc(Cn2c(=O)c3cc(S(=O)(=O)NC4(C)CC4)ccc3n(CCC(C)C)c2=O)on1]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 1-bromo-3-methylbutane (43 mg, 0.28 mmol). The reaction mixture was heated by microwave irradiation to 100° C. for 1 h. This afforded the desired product (22 mg, 0.048 mmol, 19%) as an off-white powder.

Example 473 1-[(1-Isopropylpyrazol-4-yl)methyl]-N-(1-methylcyclopropyl)-3-[(3-methylisoxazol-5-yl)methyl]-2,4-dioxo-quinazoline-6-sulfonamide

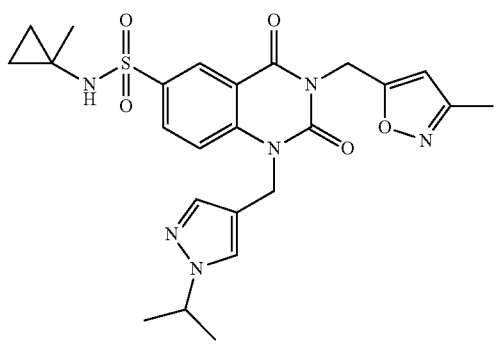 [SMILES: Cc1cc(Cn2c(=O)c3cc(S(=O)(=O)NC4(C)CC4)ccc3n(Cc3cnn(C(C)C)c3)c2=O)on1]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 4-(bromomethyl)-1-isopropyl-pyrazole (57 mg, 0.28 mmol). The reaction mixture was heated by microwave irradiation to 100° C. for 1 h. This afforded the desired product (62 mg, 0.121 mmol, 47%) as a white powder.

Example 474 1-Isohexyl-N-(1-methylcyclopropyl)-3-[(3-methylisoxazol-5-yl)methyl]-2,4-dioxo-quinazoline-6-sulfonamide

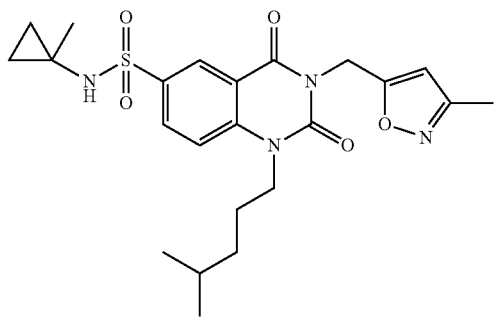 [SMILES: Cc1cc(Cn2c(=O)c3cc(S(=O)(=O)NC4(C)CC4)ccc3n(CCCC(C)C)c2=O)on1]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 1-bromo-4-methylpentane (0.04 mL, 0.2800 mmol). The reaction mixture was heated by microwave irradiation to 100° C. for 1 h. This afforded the desired product (13 mg, 0.027 mmol, 11%) as a white powder.

Example 475 1-Methyl-N-(1-methylcyclopropyl)-2,4-dioxo-3-(2-oxo-2-pyrrolidin-1-yl-ethyl)quinazoline-6-sulfonamide

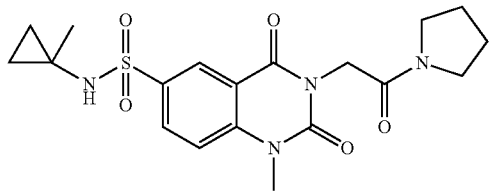 [SMILES: Cn1c(=O)n(CC(=O)N2CCCC2)c(=O)c2cc(S(=O)(=O)NC3(C)CC3)ccc21]

Prepared using Method A3, from 1-methyl-N-(1-methylcyclopropyl)-2,4-dioxo-quinazoline-6-sulfonamide and 2-bromo-1-pyrrolidin-1-yl-ethanone. This gave the desired product (21 mg, 0.05 mmol, 26%) as a white powder.

Example 476 N,N-Dimethyl-2-[1-methyl-6-[(1-methylcyclopropyl)sulfamoyl]-2,4-dioxo-quinazolin-3-yl]acetamide

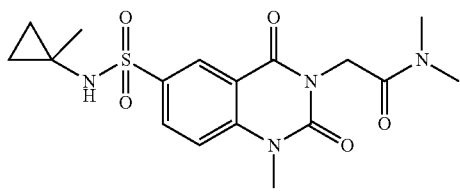 [SMILES: CN(C)C(=O)Cn1c(=O)c2cc(S(=O)(=O)NC3(C)CC3)ccc2n(C)c1=O]

Prepared using Method A3, from 1-methyl-N-(1-methylcyclopropyl)-2,4-dioxo-quinazoline-6-sulfonamide and 2-chloro-N,N-dimethylacetamide. This gave the desired product (39 mg, 0.099 mmol, 51%) as a white powder.

Example 477 1-[(3,3-Dimethylcyclobutyl)methyl]-N-(1-methylcyclopropyl)-3-[(3-methylisoxazol-5-yl)methyl]-2,4-dioxo-quinazoline-6-sulfonamide

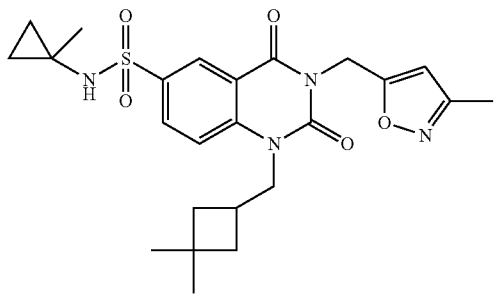 [SMILES: Cc1cc(Cn2c(=O)c3cc(S(=O)(=O)NC4(C)CC4)ccc3n(CC3CC(C)(C)C3)c2=O)on1]

This compound was prepared according to Example 465 using N-(1-methylcyclopropyl)-3-((3-methylisoxazol-5-yl)methyl)-2,4-dioxo-1,2,3,4-tetrahydroquinazoline-6-sulfonamide (100 mg, 0.260 mmol) and 3-(bromomethyl)-1,1-dimethylcyclobutane (50 mg, 0.280 mmol). The reaction mixture was heated by microwave irradiation to 120° C. for 1 h. This afforded the desired product (5 mg, 0.01 mmol, 4%) as a white powder.

Example 478 1-[(3,3-dimethylcyclobutyl)methyl]-N-(1-methylcyclopropyl)-3-[(2-methylthiazol-5-yl)methyl]-2,4-dioxo-quinazoline-6-sulfonamide

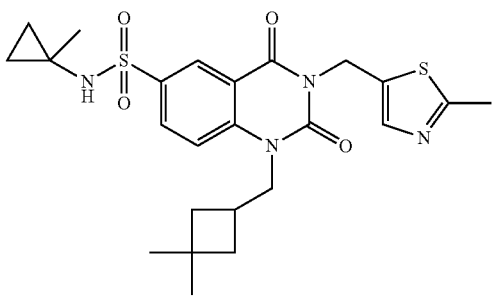 [SMILES: Cc1ncc(Cn2c(=O)c3cc(S(=O)(=O)NC4(C)CC4)ccc3n(CC3CC(C)(C)C3)c2=O)s1]

This compound was prepared according to Example 465 using N-(1-methylcyclopropyl)-3-[(2-methylthiazol-5-yl)methyl]-2,4-dioxo-1H-quinazoline-6-sulfonamide (104 mg, 0.260 mmol) and 3-(bromomethyl)-1,1-dimethyl-cyclobutane (50 mg, 0.280 mmol). The reaction mixture was heated by microwave irradiation to 120° C. for 1 h. This afforded the desired product (3 mg, 0.006 mmol, 2%) as an off-white powder.

Example 479 N-(1-Formylcyclopropyl)-3-[(1-methylpyrazol-4-yl)methyl]-2,4-dioxo-1H-quinazoline-6-sulfonamide

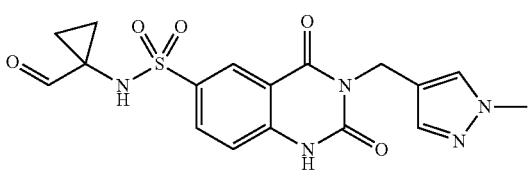 [SMILES: Cn1cc(Cn2c(=O)[nH]c3ccc(S(=O)(=O)NC4(C=O)CC4)cc3c2=O)cn1]

A suspension of N-[1-(hydroxymethyl)cyclopropyl]-3-[(1-methylpyrazol-4-yl)methyl]-2,4-dioxo-1H-quinazoline-6-sulfonamide (53 mg, 0.13 mmol) in DCM (2 mL) was treated with Dess-Martin periodinane, 15 wt. % solution in DCM (0.41 mL, 0.14 mmol) and stirred at room temperature. After 20 min, DMF (0.5 mL) was added to fully dissolve the reagents. After a further 1 h, the reaction mixture was quenched with saturated aqueous $Na_2S_2O_3$ (2 mL) and saturated aqueous $NaHCO_3$ (2 mL), diluted with DCM (5 mL) and stirred vigorously until the mixture became clear (20 min). The mixture was passed through a hydrophobic frit and the aqueous layer was re-extracted with DCM (5 mL). The combined organic extracts were dried, concentrated and purified by flash column chromatography, eluting with DCM—10% MeOH/DCM to afford N-(1-formylcyclopropyl)-3-[(1-methylpyrazol-4-yl)methyl]-2,4-dioxo-1H-quinazoline-6-sulfonamide (46 mg, 0.11 mmol, 87%) as a white powder.

Example 480 N-tert-Butyl-1-[(2,5-dimethylpyrazol-3-yl)ethyl]-3-[(1-methylpyrazol-4-yl)methyl]-2,4-dioxo-quinazoline-6-sulfonamide

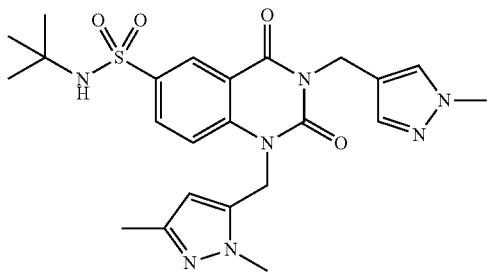 [SMILES: Cc1cc(Cn2c(=O)n(Cc3cnn(C)c3)c(=O)c3cc(S(=O)(=O)NC(C)(C)C)ccc32)n(C)n1]

Prepared using Method A10, from N-tert-butyl-3-[(1-methylpyrazol-4-yl)methyl]-2,4-dioxo-1H-quinazoline-6-sulfonamide and 5-(chloromethyl)-1,3-dimethyl-1H-pyrazole. This gave the desired product (17 mg, 0.034 mmol, 38%) as a white powder.

Example 481 1-Methyl-N-(1-methylcyclopropyl)-3-(oxetan-3-ylmethyl)-2,4-dioxo-quinazoline-6-sulfonamide

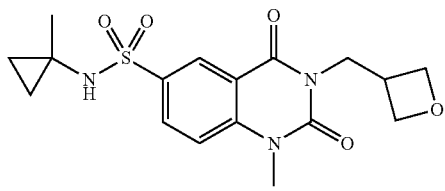 [SMILES: Cn1c(=O)n(CC2COC2)c(=O)c2cc(S(=O)(=O)NC3(C)CC3)ccc21]

Prepared using Method A3 (tosylate), from 1-methyl-N-(1-methylcyclopropyl)-2,4-dioxo-quinazoline-6-sulfonamide and oxetan-3-ylmethyl 4-methylbenzenesulfonate. This gave the desired product (31 mg, 0.082 mmol, 42%) as a white powder.

Example 482 8-Bromo-1-methyl-N-(1-methylcyclopropyl)-3-[(3-methylisoxazol-5-yl)methyl]-2,4-dioxo-quinazoline-6-sulfonamide

Intermediate S19-A Methyl 3-bromo-2-(methylamino)benzoate

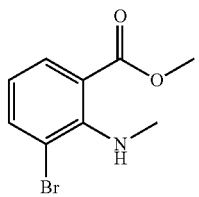

To a magnetically stirred solution of methyl 3-bromo-2-fluorobenzoate (5.20 g, 22.31 mmol) and potassium carbonate (6.17 g, 44.63 mmol) in 1,4-dioxane (20 mL) at 20° C. under nitrogen was added methylamine solution (22.31 mL, 44.63 mmol) and the resulting mixture was heated at 40° C. for 12 h. The solvent was removed in vacuo and the resulting residue was partitioned between DCM (100 mL) and water (100 mL). The DCM layer was collected and washed with brine (50 mL) before being dried (Na$_2$SO$_4$) and distilled to dryness to give the methyl 3-bromo-2-(methylamino)benzoate (5.40 g, 99%) as a yellow oil.

$^1$H NMR (300 MHz, DMSO-d$_6$) δ ppm 2.84 (d, J=5.37 Hz, 3H) 3.83 (s, 3H) 6.32 (d, J=5.27 Hz, 1H) 6.68 (t, J=7.82 Hz, 1H) 7.63 (ddd, J=15.40, 7.86, 1.60 Hz, 2H).

Intermediate S19-B 3-Bromo-2-(methylamino)benzoic acid

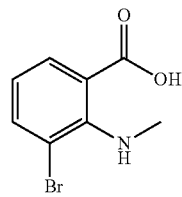

To a magnetically stirred solution of methyl 3-bromo-2-(methylamino)benzoate (1.0 g, 4.1 mmol) in THF (10 mL) and water (10 mL) at 20° C. was added lithium hydroxide (490 mg, 20.48 mmol), and the resulting mixture was agitated at ambient for 1 h. The mixture was partitioned between DCM (50 mL) and water (40 mL), and the water phase was collected and acidified to pH 1-2 with 2 N HCl. The solution was then extracted with DCM (3×50 mL) and the combined organics were distilled to dryness to give 3-bromo-2-(methylamino)benzoic acid (700 mg, 74%) as a colourless oil.

$^1$H NMR (300 MHz, DMSO-d$_6$) δ ppm 2.91 (s, 3H) 5.76 (s, 1H) 6.71 (t, J=7.82 Hz, 1H) 7.66 (dd, J=7.82, 1.60 Hz, 1H) 7.73 (dd, J=7.77, 1.55 Hz, 1H)

Intermediate S19-C 3-Bromo-N-((1-methyl-1H-pyrazol-4-yl)methyl)-2-(methylamino)benzamide

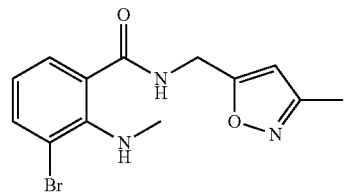 [SMILES: CNc1c(Br)cccc1C(=O)NCc1cc(C)no1]

To a magnetically stirred solution of 3-bromo-2-(methylamino)benzoic acid (750 mg, 3.26 mmol) in DMF (10 mL) was added 1,1'-carbonyldiimidazole (581 mg, 3.59 mmol), and the resulting mixture was agitated at ambient for 30 min. (3-Methylisoxazol-5-ylmethyl)amine (365 mg, 3.26 mmol) was added, and the resulting mixture was agitated at 40° C. for 12 h. Solvent removed in vacuo and the residue was partitioned between DCM (20 mL) and water (20 mL). The organic layer was collected and dried (MgSO$_4$) and evaporated to dryness to give a residue, which was purified by automated column chromatography (SiO2; RediSep—24 g; 0 to 40%—EtOAc in hexane) to afford 3-bromo-N-((1-methyl-1H-pyrazol-4-yl)methyl)-2-(methylamino)benzamide (570 mg, 54%) as a white solid.

$^1$H NMR (300 MHz, DMSO-d$_6$) δ ppm 2.21 (s, 3H) 2.73 (d, J=5.37 Hz, 3H) 3.32 (s, 2H) 5.52 (q, J=5.53 Hz, 1H) 6.24 (s, 1H) 6.64 (t, J=7.72 Hz, 1H) 7.26 (dd, J=7.68, 1.46 Hz, 1H) 7.53 (dd, J=7.82, 1.51 Hz, 1H) 9.07 (t, J=5.79 Hz, 1H)

Intermediate S19-D 8-Bromo-1-methyl-3-((3-methylisoxazol-5-yl)methyl)quinazoline-2,4(1H,3H)-dione

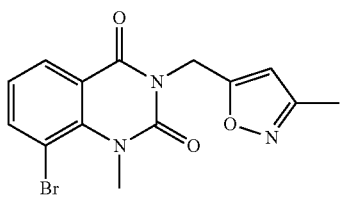 [SMILES: Cc1cc(Cn2c(=O)c3cccc(Br)c3n(C)c2=O)on1]

To a magnetically stirred solution of 3-bromo-2-(methylamino)-N-[(3-methylisoxazol-5-yl)methyl]benzamide (500 mg, 1.54 mmol) in THF (50 mL) at 20° C. under nitrogen was added triphosgene (229 mg, 0.77 mmol), and the resulting mixture was agitated at ambient for 1 h. Triethylamine (0.21 mL, 1.54 mmol) was added to the reaction, and resulting mixture was stirred for 12 h. The reaction was quenched by the addition of saturated aqueous NaHCO$_3$ (50 mL), and the resulting mixture was agitated for 30 min (pH 8.0). The mixture was partitioned between EtOAc (100 mL) and water (50 mL). The EtOAc layer was collected and dried (Na$_2$SO$_4$), and the solvent was removed in vacuo to give the 8-bromo-1-methyl-3-((3-methylisoxazol-5-yl)methyl)quinazoline-2,4(1H,3H)-dione (540 mg, %) as a white solid.

$^1$H NMR (300 MHz, DMSO-d$_6$) δ ppm 2.17 (s, 3H) 3.70 (s, 3H) 5.17 (s, 2H) 6.32 (s, 1H) 7.26 (t, J=7.82 Hz, 1H) 8.07 (q, J=1.57 Hz, 1H) 8.09 (q, J=1.60 Hz, 1H)

Intermediate S19-E 8-Bromo-1-methyl-3-((3-methylisoxazol-5-yl)methyl)-2,4-dioxo-1,2,3,4-tetrahydroquinazoline-6-sulfonyl chloride

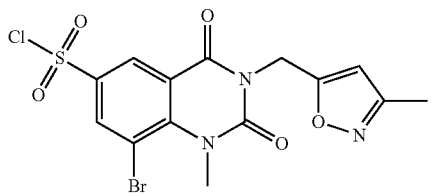 [SMILES: Cc1cc(Cn2c(=O)c3cc(S(=O)(=O)Cl)cc(Br)c3n(C)c2=O)on1]

8-Bromo-1-methyl-3-[(3-methylisoxazol-5-yl)methyl]quinazoline-2,4-dione (550 mg, 1.57 mmol) was treated with chlorosulfonic acid (183 mg, 1.57 mmol) at 20° C., and the resulting brown solution was heated at 40° C. for 16 h. The reaction was then poured into ice and the resulting precipitate was extracted with EtOAc (2×20 mL). The combined extracts were dried and evaporated to dryness to give the 8-bromo-1-methyl-3-((3-methylisoxazol-5-yl)methyl)-2,4-dioxo-1,2,3,4-tetrahydroquinazoline-6-sulfonyl chloride (690 mg, 98%) as a buff solid.

$^1$H NMR (300 MHz, DMSO-d$_6$) δ ppm 2.17 (s, 3H) 3.70 (s, 3H) 5.17 (s, 2H) 6.32 (s, 1H) 8.09 (d, J=1.98 Hz, 1H) 8.22 (d, J=1.98 Hz, 1H)

S19-F 8-Bromo-1-methyl-N-(1-methylcyclopropyl)-3-[(3-methylisoxazol-5-yl)methyl]-2,4-dioxo-quinazoline-6-sulfonamide

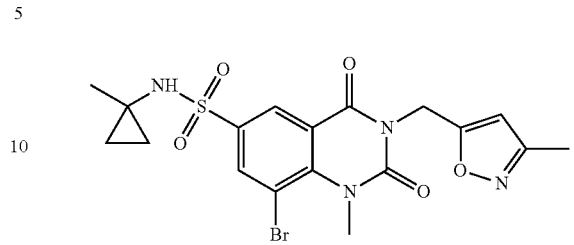

To a magnetically stirred solution of 8-bromo-1-methyl-3-[(3-methylisoxazol-5-yl)methyl]-2,4-dioxo-quinazoline-6-sulfonyl chloride (700 mg, 1.56 mmol) and 1-methylcyclopropanamine hydrochloride (185 mg, 1.72 mmol) in DMF (20 mL) at 20° C. under nitrogen was added triethylamine (0.73 mL, 3.43 mmol), and the resulting mixture was stirred at 20° C. for 2 h. The solvent was removed in vacuo and the resulting residue was purified by automated column chromatography (SiO$_2$; RediSep—24 g; 0 to 5% MeOH in DCM) to afford the desired product (560 mg, 1.16 mmol, 74%) as a white foam.

Example 483 1-Methyl-N-(1-methylcyclopropyl)-3-[(3-methylisoxazol-5-yl)methyl]-8-(1-methylpyrazol-4-yl)-2,4-dioxo-quinazoline-6-sulfonamide

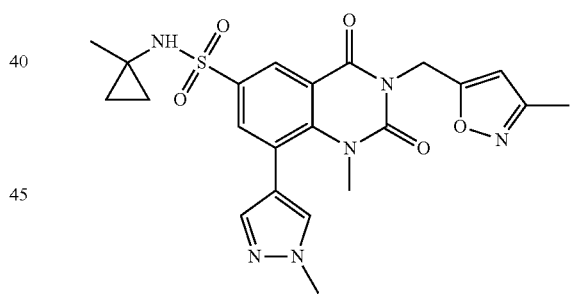

8-Bromo-1-methyl-N-(1-methylcyclopropyl)-3-[(3-methylisoxazol-5-yl)methyl]-2,4-dioxo-quinazoline-6-sulfonamide (80 mg, 0.17 mmol), (1-methyl-1H-pyrazol-4-yl)boronic acid (43.77 mg, 0.35 mmol), caesium carbonate (173 mg, 0.53 mmol) and 1,1'-bis(diphenylphosphino)ferrocenepalladium(II)dichloride dichloromethane adduct (20.3 mg, 0.02 mmol) were placed in a 7 mL microwave vial followed by THF (2.5 mL) and water (0.5 mL), and the resulting mixture was degassed with nitrogen for 5 min. The vial was then sealed and heated under microwave irradiation at 80° C. for 20 min. The mixture was filtered through celite and evaporated to dryness to give a residue, which was purified by prep HPLC (high pH) to give the desired product (20 mg, 0.041 mmol, 25%) as a white powder.

Example 484 1-Chloro-N-(1-methylcyclopropyl)isoquinoline-7-sulfonamide

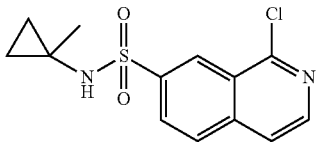 [SMILES: CC1(NS(=O)(=O)c2ccc3ccnc(Cl)c3c2)CC1]

To a solution of N,N-diisopropylethylamine (0.14 mL, 0.81 mmol) in THF (5 mL) cooled in an ice bath, was added a mixture of 1-methylcyclopropanamine hydrochloride (0.05 mL, 0.40 mmol) and 1-chloroisoquinoline-7-sulfonyl chloride (100 mg, 0.38 mmol) in DCM (3 mL) and the mixture stirred overnight at room temperature. The mixture was diluted with water (30 mL) and extracted with DCM (2×30 mL). The organic phase was dried with anhydrous sodium sulfate and evaporated to dryness. The crude product mixture was purified by prep HPLC (high pH) to give the desired product (48 mg, 0.16 mmol, 42%) as a white powder.

Example 485 1-[(2,5-Dimethylpyrazol-3-yl)methyl]-3-[(1-methylpyrazol-4-yl)methyl]-2,4-dioxo-N-[1-(trifluoromethyl)cyclopropyl]quinazoline-6-sulfonamide

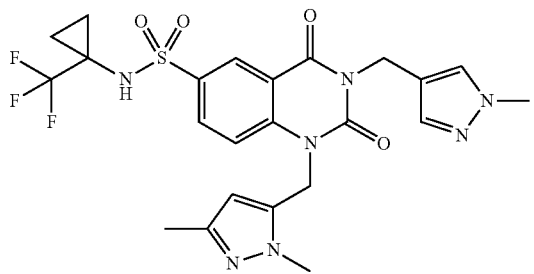 [SMILES: Cc1cc(Cn2c(=O)n(Cc3cnn(C)c3)c(=O)c3cc(S(=O)(=O)NC4(C(F)(F)F)CC4)ccc32)n(C)n1]

Prepared using Method A1, from N-[[3-[(1-methylpyrazol-4-yl)methyl]-2,4-dioxo-1H-quinazolin-6-yl]sulfonyl]-N-[1-(trifluoromethyl)cyclopropyl]acetamide and 5-(chloromethyl)-1,3-dimethyl-1H-pyrazole. The reaction mixture was stirred at room temperature for 2 h and the crude product chromatographed over silica, eluting with EtOAc—5% MeOH/EtOAc, and triturated from diethyl ether to give the desired product (15 mg, 0.027 mmol, 49%) as a white powder.

Example 486 N-(1-Methylcyclopropyl)-3-[(1-methylpyrazol-4-yl)methyl]-2-oxo-1H-quinoline-6-sulfonamide

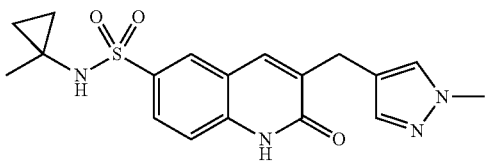

Intermediate S20-A 3-(1-Methylpyrazol-4-yl)propanoyl chloride

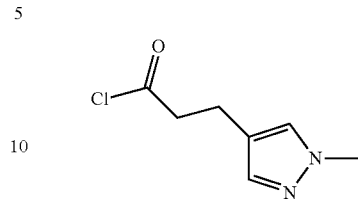

Following the procedure from WO2010/66829 A1, a suspension of 3-(1-methylpyrazol-4-yl)propanoic acid (0.5 g, 3.2 mmol) in DCM (5 mL) was treated with 5 drops of DMF (0.0500 mL) and thionyl chloride (0.24 mL, 3.2 mmol). The resultant solution was heated to reflux for 30 min and then cooled to RT and concentrated. The oily residue 3-(1-methylpyrazol-4-yl)propanoyl chloride (560 mg, 3.26 mmol, 100%) was used without purification.

$^1$H NMR (300 MHz, CHLOROFORM-d) δ=7.87 (s, 1H), 7.67 (s, 1H), 4.30 (s, 3H), 3.30-3.20 (m, 2H), 2.98-2.91 (m, 2H)

Intermediate S20-B N-(2-Formylphenyl)-3-(1-methylpyrazol-4-yl)propanamide

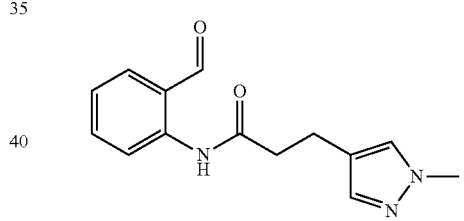

Crude 2-aminobenzaldehyde (7 mmol), (a yellow oil prepared as described in Scheme 16) was taken up in THF (40 mL) and added to 3-(1-methylpyrazol-4-yl)propanoyl chloride (1.5 g, 8.9 mmol), and then pyridine (0.9 mL, 11.2 mmol) was added. Triethylamine (1.6 mL, 11.2 mmol) was added to try to dissolve the thick sticky oil around the bottom of the flask. The mixture was stirred at room temperature for 90 min and then diluted with water (20 mL) and extracted with EtOAc (2×50 mL). The combined organic extracts were washed with water, passed through a hydrophobic frit and concentrated. Purification by flash column chromatography, eluting with 1:1 isohexane:EtOAc—EtOAc afforded N-(2-formylphenyl)-3-(1-methylpyrazol-4-yl)propanamide (640 mg, 2.5 mmol, 33%) as a pale yellow oil.

$^1$H NMR (300 MHz, CHLOROFORM-d) δ=11.15 (br. s., 1H), 9.92 (s, 1H), 8.76 (d, J=8.5 Hz, 1H), 7.68 (dd, J=1.6, 7.6 Hz, 1H), 7.66-7.59 (m, 1H), 7.39 (s, 1H), 7.27-7.21 (m, 2H), 3.86 (s, 3H), 2.99-2.88 (m, 2H), 2.77-2.67 (m, 2H)

LCMS (high pH) found 256.1 [M−H]− T=0.89 min, 62% purity by UV. 18% impurity at 1.35 min (mass=566).

Intermediate S20-C 3-[(1-Methylpyrazol-4-yl)methyl]-1H-quinolin-2-one

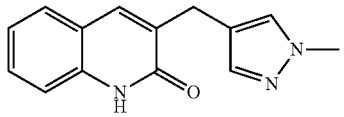 [SMILES: Cn1cc(Cc2cc3ccccc3[nH]c2=O)cn1]

Following the procedure in Heterocycles, 2005, 65, 9, 2095-2105, a solution of N-(2-formylphenyl)-3-(1-methylpyrazol-4-yl)propanamide (640 mg, 2.5 mmol) in DMF (15 mL) was treated with cesium carbonate (4.1 g, 12.4 mmol) and heated to 70° C. for 4 h. The reaction mixture was then diluted with DCM (50 mL) and saturated aqueous NH$_4$Cl (25 mL). The aqueous layer was re-extracted with DCM and the combined organic extracts were washed with saturated aqueous NH$_4$Cl, dried (hydrophobic frit) and concentrated. The crude material was purified by flash column chromatography, eluting with EtOAc—10% MeOH/EtOAc to afford 3-[(1-methylpyrazol-4-yl)methyl]-1H-quinolin-2-one (274 mg, 1.15 mmol, 45%) as a pale yellow solid.

$^1$H NMR (300 MHz, DMSO-d$_6$) δ=11.78 (s, 1H), 7.61 (s, 1H), 7.57 (d, J=7.8 Hz, 1H), 7.52 (s, 1H), 7.42 (dd, J=1.3, 7.1 Hz, 1H), 7.32-7.26 (m, 2H), 7.17-7.09 (m, 1H), 3.78 (s, 3H), 3.62 (s, 2H)

LCMS: high pH—found 238.0 [M−H]− T=0.83 min, 100% purity by UV; low pH—found 240.1 [M+H]+ T=0.79 min, 100% purity by UV.

Intermediate S20-D 3-[(1-Methylpyrazol-4-yl)methyl]-2-oxo-1H-quinoline-6-sulfonyl chloride

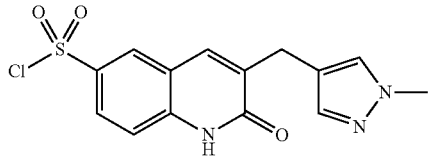 [SMILES: Cn1cc(Cc2cc3cc(S(=O)(=O)Cl)ccc3[nH]c2=O)cn1]

3-[(1-Methylpyrazol-4-yl)methyl]-1H-quinolin-2-one (400 mg, 1.67 mmol) was added to stirring chlorosulfonic acid (4 mL, 1.67 mmol), and the resulting mixture was stirred at 50° C. for 16 h. The reaction was then cooled to room temperature and added to ice (10 g, which was cooled in an acetone/ice bath at −10° C.) in drops with stirring. The resulting precipitate was stirred at 0° C. for 15 min and then filtered. The filter cake was washed with cold water (2×4 mL) and dried under vacuum at 40° C. for 16 h to afford 3-[(1-methylpyrazol-4-yl)methyl]-2-oxo-1H-quinoline-6-sulfonyl chloride (400 mg, 1.18 mmol, 71%) as a brown solid.

$^1$H NMR (300 MHz, DMSO-d$_6$) δ ppm 3.63 (s, 2H) 3.80 (s, 3H) 7.22 (d, J=8.48 Hz, 1H) 7.41 (s, 1H) 7.59 (s, 1H) 7.65 (dd, J=8.48, 1.88 Hz, 1H) 7.80 (d, J=1.79 Hz, 1H) 7.74 (s, 1H) 11.85 (br. s., 1H)

S20-E N-(1-Methylcyclopropyl)-3-[(1-methylpyrazol-4-yl)methyl]-2-oxo-1H-quinoline-6-sulfonamide

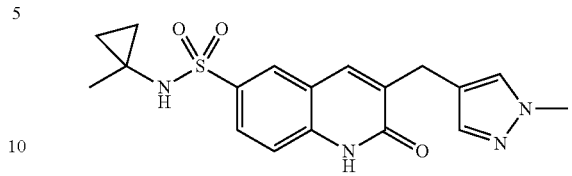

A solution of 3-[(1-methylpyrazol-4-yl)methyl]-2-oxo-1H-quinoline-6-sulfonyl chloride (43 mg, 0.13 mmol), 1-methylcyclopropanamine hydrochloride (21 mg, 0.19 mmol), N,N-diisopropylethylamine (0.07 mL, 0.38 mmol) and 4-dimethylaminopyridine (16 mg, 0.13 mmol) in DMF (1 mL) was stirred at RT for 10 min. The reaction mixture was concentrated to dryness and purified by automated column chromatography, eluting with DCM—10% MeOH/DCM, to afford the desired product N-(1-methylcyclopropyl)-3-[(1-methylpyrazol-4-yl)methyl]-2-oxo-1H-quinoline-6-sulfonamide (30 mg, 0.081 mmol, 63%) as a white powder.

Example 487 3-Bromo-N-(1-methylcyclopropyl)-2-oxo-1H-quinoline-6-sulfonamide

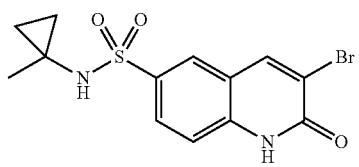 [SMILES: CC1(NS(=O)(=O)c2ccc3[nH]c(=O)c(Br)cc3c2)CC1]

Intermediate S21-A 3-Bromo-1-oxido-quinolin-1-ium

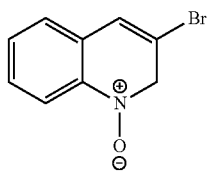 [SMILES: [O-][NH+]1CC(Br)=Cc2ccccc21]

Following the procedure described in Synth. Comm. 30, (3), 427-432, a solution of 3-bromoquinoline (0.65 mL, 4.8 mmol) in chloroform (8 mL) was treated in portions at room temperature with 3-chloroperbenzoic acid (1.2 g, 5.3 mmol) and the mixture was stirred under nitrogen behind a blast shield for 20 h. The reaction mixture was diluted with saturated aqueous NaHCO$_3$ (6 mL) and 1M NaOH (2 mL). The layers were separated and the aqueous phase was re-extracted with CHCl$_3$ (15 mL) and combined organics washed with 5% wt. aqueous sodium sulphite (10 mL), saturated aqueous NaHCO$_3$ (10 mL), water (10 mL) and brine (10 mL), passed through a hydrophobic frit and concentrated to give 3-bromo-1-oxido-quinolin-1-ium (1.1 g, 4.7 mmol, 98%) as an off-white solid.

$^1$H NMR (300 MHz, CHLOROFORM-d) δ=8.74-8.58 (m, 2H), 7.91 (s, 1H), 7.85-7.65 (m, 3H)

LCMS (high pH) found 224/226 [M+H]+, T=0.80 min, 98% purity by UV.

Intermediate S21-B 3-Bromo-1H-quinolin-2-one

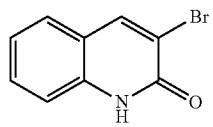 [SMILES: O=c1[nH]c2ccccc2cc1Br]

A mixture of 3-bromo-1-oxido-quinolin-1-ium (1.1 g, 4.7 mmol) and sodium hydroxide (431 mg, 10.8 mmol) in water (14 mL) and DCM (7 mL) was stirred vigorously and treated slowly at room temperature with benzoyl chloride (0.65 mL, 5.6 mmol). The mixture was stirred vigorously at room temperature for 2 h. The reaction mixture was then filtered and the solid was washed well with water and DCM and oven-dried to give 3-bromo-1H-quinolin-2-one (637 mg, 2.8 mmol, 61%) as a white solid.

$^1$H NMR (300 MHz, DMSO-d$_6$) δ=12.27 (br. s., 1H), 8.51 (s, 1H), 7.68 (d, J=7.8 Hz, 1H), 7.55 (t, J=7.8 Hz, 1H), 7.33 (d, J=8.2 Hz, 1H), 7.22 (t, J=7.6 Hz, 1H)

LCMS (high pH) found 223.9/225.9 [M+H]+, T=0.87 min, 100% purity by UV.

Intermediate S21-C
3-Bromo-2-oxo-1H-quinoline-6-sulfonyl chloride

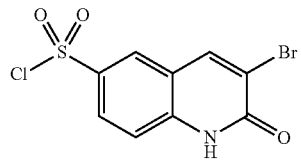 [SMILES: O=c1[nH]c2ccc(S(=O)(=O)Cl)cc2cc1Br]

A solution of 3-bromo-1H-quinolin-2-one (637 mg, 2.84 mmol) in chlorosulfonic acid (2 mL, 30 mmol) was stirred at room temperature for 1 h and then heated to 65° C. (sealed tube) for 20 h. The reaction mixture was cooled and carefully pipetted into stirring water (5 mL) and the resulting precipitate was collected by filtration, washed with water (2×5 mL) and oven-dried to give a white powder (333 mg) used without further purification.

LCMS (high pH) shows a mixture of 47% SM (0.86 min) and 49% product (0.98 min). For product peak, found 321.9, 323.9 [M+H]+.

S21-D 3-Bromo-N-(1-methylcyclopropyl)-2-oxo-1H-quinoline-6-sulfonamide

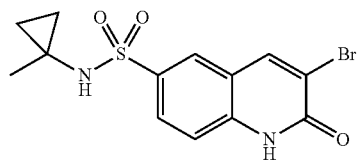 [SMILES: CC1(NS(=O)(=O)c2ccc3[nH]c(=O)c(Br)cc3c2)CC1]

A solution of 3-bromo-2-oxo-1H-quinoline-6-sulfonyl chloride (150 mg, 0.23 mmol), 1-methylcyclopropanamine hydrochloride (38 mg, 0.35 mmol), N,N-diisopropylethylamine (0.12 mL, 0.7 mmol) and 4-dimethylaminopyridine (28 mg, 0.23 mmol) in DMF (2 mL) was stirred at room temperature for 20 min. The reaction mixture was then concentrated to dryness to give an oily residue, which was purified by automated column chromatography (DCM—10% MeOH/DCM—weak chromophore) to afford 3-bromo-N-(1-methylcyclopropyl)-2-oxo-1H-quinoline-6-sulfonamide (46 mg, 0.13 mmol, 55%) as a white powder.

Example 488 3-[(1-Methylpyrazol-4-yl)methyl]-2,4-dioxo-N-[1-(trideuteriomethyl)cyclopropyl]-1H-quinazoline-6-sulfonamide

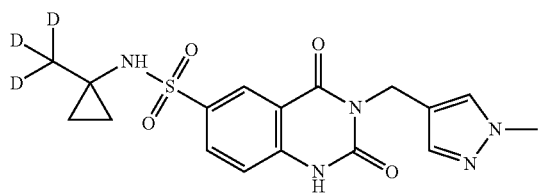 [SMILES: [2H]C([2H])([2H])C1(NS(=O)(=O)c2ccc3[nH]c(=O)n(Cc4cnn(C)c4)c(=O)c3c2)CC1]

Intermediate S22-A
2,6-Di-tert-butyl-4-methylphenyl cyclopropanecarboxylate

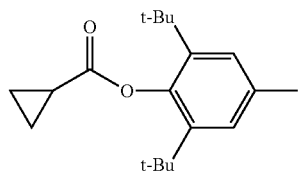 [SMILES: Cc1cc(C(C)(C)C)c(OC(=O)C2CC2)c(C(C)(C)C)c1]

A 2.0 M solution n-butyllithium (36.3 mL, 90.8 mmol) in hexanes was added to a magnetically stirred solution of 2,6-di-tert-butyl-4-methylphenol (20 g, 90.8 mmol) in THF (100 mL) at 0° C. under nitrogen, and the resulting mixture was agitated at this temperature for 15 mins. Cyclopropanecarbonyl chloride (8.65 mL, 95.3 mmol) was then added to the reaction over 5 mins, and the resulting cloudy suspension was stirred overnight at ambient temperature. The mixture was poured into a saturated aqueous solution of NH$_4$Cl (100 mL), and the resulting mixture was stirred for 5 mins. The organic phase was collected, and the aqueous was extracted with diethyl ether (2×100 mL). The organics liquors were combined and washed sequentially with saturated aqueous NaHCO$_3$ (100 mL) and brine (100 mL) and dried (Na$_2$SO$_4$). The solvent was removed in vacuo to give the crude product as an oil (23.4 g). The oil was taken into methanol (50 mL), and the resulting solution was stirred for 30 mins. A white precipitate formed, which was collected by filtration. The filter cake was washed with methanol (3×15 mL) and dried under vacuum for 2 h at 40° C. to give the desired product (24 g, 94%) as a white solid.

$^1$H NMR (300 MHz, DMSO-d$_6$) δ=7.08 (s, 2H), 2.27 (s, 3H), 2.08-1.93 (m, 1H), 1.28 (s, 18H), 1.15-1.03 (m, 2H), 0.99-0.89 (m, 2H)

Intermediate S22-B 2,6-Di-tert-butyl-4-methylphenyl 1-(methyl-d₃)cyclopropane-1-carboxylate

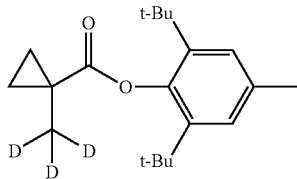 [SMILES: [2H]C([2H])([2H])C1(C(=O)Oc2c(C(C)(C)C)cc(C)cc2C(C)(C)C)CC1]

To a magnetically stirred solution of (2,6-di-tert-butyl-4-methyl-phenyl) cyclopropanecarboxylate (7.8 g, 27.0 mmol) in THF (50 mL) at −78° C. under nitrogen was added a 1.6 M solution of tert-butyllithium in hexanes (21.3 mL, 29.8 mmol) over 10 minutes, and the resulting mixture was agitated at −78° C. for 30 min. A solution of iodomethane-d₃ (2.02 mL, 32.45 mmol) in THF (5 mL) was then added to the reaction, and the resulting mixture was allowed to warm to ambient temperature with stirring over a period of 4 h. The mixture was diluted with diethyl ether (60 mL) and washed sequentially with saturated aqueous NH₄Cl (50 mL) and brine (50 mL) before being dried (Na₂SO₄). The solvent was then removed under vacuum to give the crude product which was purified by automated column chromatography (SiO₂; RediSep—100 g; 0 to 40%—EtOAc in hexane) to afford the desired product (6.8 g, 82%) as a white solid.

¹H NMR (300 MHz, DMSO-d₆) δ=7.08 (s, 2H), 2.27 (s, 3H), 1.28 (s, 18H), 1.20-1.15 (m, 2H), 0.98-0.92 (m, 2H)

Intermediate S22-C
1-(Methyl-d₃)cyclopropane-1-carboxylic acid

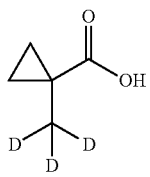

To a magnetically stirred solution of (2,6-ditert-butyl-4-methyl-phenyl) 1-(trideuteriomethyl)cyclopropanecarboxylate (6.4 g, 20.9 mmol) and potassium tert-butoxide (14.1 g, 126 mmol) in THF (150 mL) at 20° C. under nitrogen was added water (0.75 mL, 41.9 mmol), and the resulting mixture was agitated at reflux for 36 h. The mixture was cooled to ambient and extracted with 2 N KOH (2×20 mL). The combined extracts were cooled on ice and acidified with 6 N HCl to pH 1. The mixture was extracted with ether (2×40 mL), and the combined extracts were dried over Na₂SO₄. The solvent was removed in vacuo to give the desired product (2.0 g, 93%) as a yellow oil.

¹H NMR (300 MHz, DMSO-d₆) δ=12.01 (br. s., 1H), 1.03 (q, J=3.4 Hz, 2H), 0.65 (q, J=3.6 Hz, 2H)

Intermediate S22-D
1-(Methyl-d₃)cyclopropan-1-amine hydrochloride

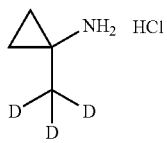

A solution of 1-(trideuteriomethyl)cyclopropanecarboxylic acid (2.0 g, 19.39 mmol), diphenyl phosphoryl azide (3.76 mL, 17.45 mmol) and triethylamine (5.39 mL, 38.79 mmol) in tert-butanol (10 mL) was heated at 75° C. overnight. The reaction mixture was cooled and poured into a bi-phasic mixture of water (40 mL) and EtOAc (30 mL). The bi-phasic mixture was allowed to stir for 15 minutes, during which time a solid participate formed that was removed by filtration. The aqueous layer was collected and extracted with EtOAc (2×30 mL). The combined extracts were then washed with water (20 mL) and then dried with magnesium sulfate before being distilled to dryness to give an off-white solid (1.6 g). The solid material was suspended in 1,4-dioxane (10 mL) and treated with a 4 N solution of hydrogen chloride in dioxane (10 mL). The reaction mixture was then stirred at room temperature for 2 h, during which time a precipitate formed. Ether (100 mL) was added to the mixture in portions manner over a 5 min period and the resulting mixture was agitated for a further 15 min. The mixture was then filtered and the filter cake washed with ether (2×30 mL) and air dried for 5 min to give the desired product (0.5 g, 23%) as a white solid.

¹H NMR (300 MHz, DMSO-d₆) δ=8.38 (br. s., 3H), 0.93-0.86 (m, 2H), 0.63-0.56 (m, 2H)

S22-E 3-[(1-Methylpyrazol-4-yl)methyl]-2,4-dioxo-N-[1-(trideuteriomethyl)cyclopropyl]-1H-quinazoline-6-sulfonamide

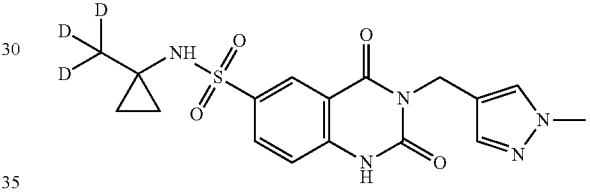

To a magnetically stirred solution of 1-(trideuteriomethyl)cyclopropanamine hydrochloride (200 mg, 1.81 mmol) and N,N-diisopropylethylamine (1.08 mL, 6.51 mmol) in DMF (5 mL) at 20° C. under nitrogen was added 3-[(1-methyl-pyrazol-4-yl)methyl]-2,4-dioxo-1H-quinazoline-6-sulfonyl chloride (770 mg, 2.17 mmol), and the resulting mixture was agitated at ambient temperature for 30 min. The solvent was removed under vacuum to give a residue, which was partitioned between DCM (50 mL) and water (50 mL). The organic phase was collected and dried over MgSO₄ before being distilled to dryness to give the crude product, which was purified by automated column chromatography (SiO₂; RediSep—24 g; 0 to 10% MeOH in DCM) to afford the desired product (430 mg, 1.096 mmol, 60.6%) as a white solid.

Example 489 1-Methyl-3-[(1-methylpyrazol-4-yl)methyl]-2,4-dioxo-N-[1-(trideuteriomethyl)cyclopropyl]quinazoline-6-sulfonamide

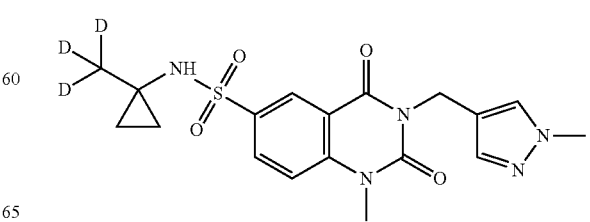

1-Methyl-3-[(1-methylpyrazol-4-yl)methyl]-2,4-dioxo-quinazoline-6-sulfonyl chloride (240 mg, 0.65 mmol) was added to a stirred solution of 1-(trideuteriomethyl)cyclopropanamine hydrochloride (60 mg, 0.54 mmol) and N-ethyl-N-isopropyl-propan-2-amine (0.43 mL, 2.44 mmol) in DMF (4 mL), and the resulting mixture was stirred overnight. The solvent was removed in vacuo and the residue purified by prep HPLC (high pH) to give the desired product (50 mg, 0.12 mmol, 23%) as a white powder.

Example 490 1-[(2,5-Dimethylpyrazol-3-yl)methyl]-3-[(1-methylpyrazol-4-yl)methyl]-2,4-dioxo-N-[1-(trideuteriomethyl)cyclopropyl]quinazoline-6-sulfonamide

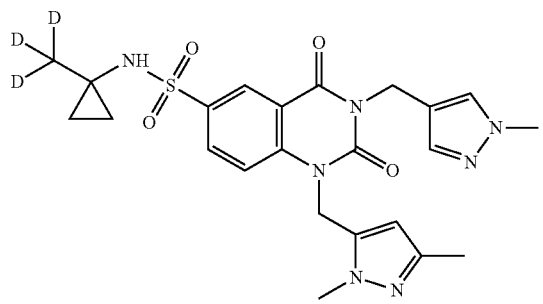 [SMILES: [2H]C([2H])([2H])C1(NS(=O)(=O)c2ccc3c(c2)c(=O)n(Cc2cnn(C)c2)c(=O)n3Cc2cc(C)nn2C)CC1]

A mixture of 3-[(1-methylpyrazol-4-yl)methyl]-2,4-dioxo-N-[1-(trideuteriomethyl)cyclopropyl]-1H-quinazoline-6-sulfonamide (100 mg, 0.25 mmol), 5-(chloromethyl)-1,3-dimethyl-1H-pyrazole (37 mg, 0.25 mmol), potassium carbonate (70 mg, 0.51 mmol) and potassium iodide (42 mg, 0.25 mmol) in DMF (2 mL) was heated with agitation in the microwave at 80° C. for 30 minutes. The solvent was removed in vacuo and the residue purified by prep HPLC (high pH) to give the desired product (68 mg, 0.136 mmol, 53%) as a white powder.

Example 491 1-Methyl-N-(1-methylcyclopropyl)-3-[(1-methylpyrazol-4-yl)methyl]-2-oxo-quinoline-6-sulfonamide

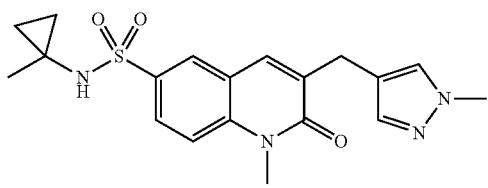

A solution of N-(1-methylcyclopropyl)-3-[(1-methylpyrazol-4-yl)methyl]-2-oxo-1H-quinoline-6-sulfonamide (30 mg, 0.08 mmol) and iodomethane (0.01 mL, 0.1 mmol) in DMF (2 mL) was treated with potassium carbonate (13 mg, 0.1 mmol) and heated to 80° C. for 20 min under microwave irradiation. The reaction mixture was diluted with water (2 mL) and DCM (5 mL) and stirred vigorously for 10 min. The aqueous layer was re-extracted with DCM and the combined organic extracts were passed through a hydrophobic frit, concentrated and purified by prep HPLC (high pH) to afford 1-methyl-N-(1-methylcyclopropyl)-3-[(1-methylpyrazol-4-yl)methyl]-2-oxo-quinoline-6-sulfonamide (8 mg, 0.021 mmol, 26%) as a white powder.

Example 492 1-[(2,5-Dimethylpyrazol-3-yl)methyl]-N-(1-methylcyclopropyl)-3-[(1-methylpyrazol-4-yl)methyl]-2-oxo-quinoline-6-sulfonamide

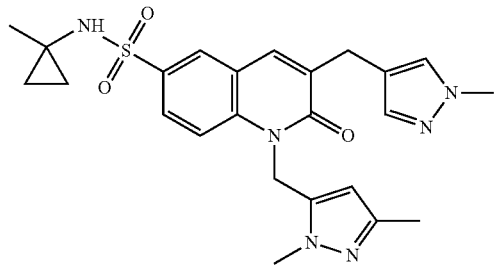

A mixture of N-(1-methylcyclopropyl)-3-[(1-methylpyrazol-4-yl)methyl]-2-oxo-1H-quinoline-6-sulfonamide (60 mg, 0.16 mmol), 5-(chloromethyl)-1,3-dimethyl-1H-pyrazole (23 mg, 0.16 mmol), potassium carbonate (45 mg, 0.32 mmol) and potassium iodide (27 mg, 0.16 mmol) in DMF (2 mL) was heated with agitation in the microwave at 80° C. for 30 minutes. The solvent was removed in vacuo and the residue purified by prep HPLC (high pH) affording the desired product (20 mg, 0.042 mmol, 26%) as a white powder.

Example 493 1-Methyl-N-(1-methylcyclopropyl)-3-[(3-methylisoxazol-5-yl)methyl]-8-(5-methyl-2-thienyl)-2,4-dioxo-quinazoline-6-sulfonamide

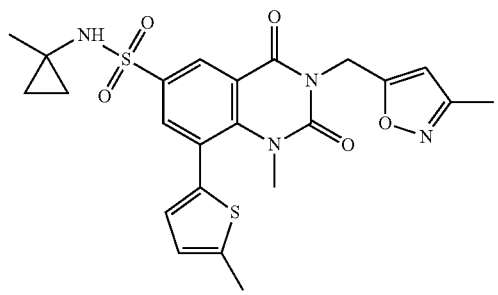

8-Bromo-1-methyl-N-(1-methylcyclopropyl)-3-[(3-methylisoxazol-5-yl)methyl]-2,4-dioxo-quinazoline-6-sulfonamide (80 mg, 0.17 mmol), (1-methyl-1H-pyrazol-4-yl)boronic acid (44 mg, 0.35 mmol), caesium carbonate (173 mg, 0.53 mmol) and 1,1'-bis(diphenylphosphino)ferrocene-palladium(II)dichloride dichloromethane adduct (20 mg, 0.02 mmol) were placed in a 7 mL microwave vial followed by THF (2.5 mL) and water (0.5 mL), and the resulting mixture was degassed with nitrogen for 5 min. The vial was then sealed and heated under microwave irradiation at 80° C. for 20 min. The mixture was filtered through celite and evaporated to dryness to give a residue, which was purified by prep HPLC (high pH) affording the desired product (20 mg, 0.04 mmol, 32%) as a white powder.

Example 494 N-[1-(Fluoromethyl)cyclopropyl]-3-(isothiazol-4-ylmethyl)-1-methyl-2,4-dioxo-quinazoline-6-sulfonamide

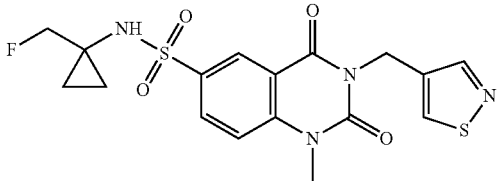 [SMILES: Cn1c(=O)n(Cc2cnsc2)c(=O)c2cc(S(=O)(=O)NC3(CF)CC3)ccc21]

A mixture of N-[1-(fluoromethyl)cyclopropyl]-1-methyl-2,4-dioxo-quinazoline-6-sulfonamide (74 mg, 0.23 mmol), isothiazol-4-ylmethyl methanesulfonate (43.7 mg, 0.23 mmol), potassium carbonate (62.5 mg, 0.45 mmol) and potassium iodide (37.53 mg, 0.23 mmol) in DMF (4 mL) was heated with agitation in the microwave at 80° C. for 45 min. The mixture was partitioned between DCM (10 mL) and water (10 mL) and the organic phase was collected and distilled to dryness to give a residue. The residue was purified by prep. HPLC (high pH) to give the desired product N-[1-(fluoromethyl)cyclopropyl]-3-(isothiazol-4-ylmethyl)-1-methyl-2,4-dioxo-quinazoline-6-sulfonamide as a white solid (20 mg, 0.0471 mmol, 21%).

Example 495 N-(1-Methylcyclopropyl)-2,4-dioxo-3-[2-(2-pyridyl)ethyl]-1H-quinazoline-6-sulfonamide

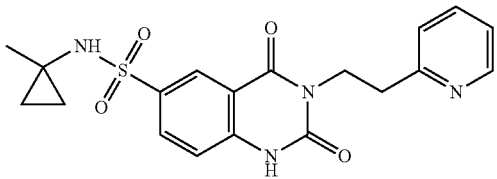 [SMILES: CC1(NS(=O)(=O)c2ccc3[nH]c(=O)n(CCc4ccccn4)c(=O)c3c2)CC1]

A suspension of 2,4-dioxo-1H-3,1-benzoxazine-6-sulfonyl chloride (261 mg, 1 mmol) in DMF (2 mL) was treated with 1-methylcyclopropanamine hydrochloride (0.11 g, 1 mmol) and cooled to −10° C. in an ice/MeOH bath. The solution was treated over 5 min with triethylamine (0.31 mL, 2.2 mmol). 2-(2-Pyridyl)ethylamine (0.16 mL, 1.3 mmol) in DMF (2 mL) was added to the reaction mixture at 0° C. More triethylamine (0.31 mL, 2.2 mmol) was added and the reaction mixture stirred at ambient temperature overnight. The reaction mixture was diluted with water (40 mL) and extracted with EtOAc (3×30 mL). The combined extracts were washed with water, passed through a hydrophobic frit and evaporated to dryness. Flash chromatographic purification over silica (CH2Cl2/ether/MeOH/Et3N eluent) of the residue afforded 2-amino-5-[(1-methylcyclopropyl)sulfamoyl]-N-[2-(2-pyridyl)ethyl]benzamide (257 mg, 0.686 mmol, 69%).

$^1$H NMR (300 MHz, CHLOROFORM-d) 3 ppm 8.73-8.69 (m, 1H), 8.14-8.08 (m, 2H), 7.86-7.78 (m, 1H), 7.68-7.62 (m, 1H), 7.39-7.32 (m, 1H), 7.33 (d, J=8.2 Hz, 1H), 6.68 (d, J=8.7 Hz, 1H), 6.14 (br s, 2H), 5.32 (br s, 1H), 3.89-3.81 (m, 2H), 3.28-3.22 (m, 2H), 1.23, (s, 3H), 0.86-0.78 (m, 2H), 0.48-0.42 (m, 2H)

Triphosgene (99 mg, 0.33 mmol) was added to a solution of 2-amino-5-[(1-methylcyclopropyl)sulfamoyl]-N-[2-(2-pyridyl)ethyl]benzamide (250 mg, 0.668 mmol) in THF (10 mL) at 0° C. The reaction mixture was stirred 0° C. for 15 min and then stirred at ambient temperature overnight. 2M Aqueous sodium hydroxide (2 mL, 2M) was added and the reaction mixture was stirred at ambient temperature for 30 min. The mixture was cooled and acidified to pH 2 with 2M HCl. The product was extracted with EtOAc. The combined extracts were washed with water, evaporated and purified by prep hplc to give the desired product (160 mg, 0.40 mmol, 60%) as a white powder.

Example 496 3-(2-Cyanoethyl)-N-(1-methylcyclopropyl)-2,4-dioxo-1H-quinazoline-6-sulfonamide

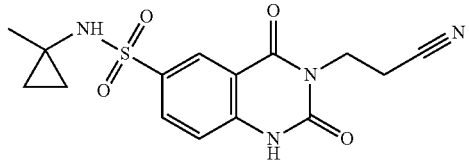 [SMILES: CC1(NS(=O)(=O)c2ccc3[nH]c(=O)n(CCC#N)c(=O)c3c2)CC1]

A suspension of 2,4-dioxo-1H-3,1-benzoxazine-6-sulfonyl chloride (261 mg, 1 mmol) in DMF (2 mL) was treated with 1-methylcyclopropanamine hydrochloride (0.11 g, 1 mmol) and cooled to −10° C. in an ice/MeOH bath. The solution was treated over 5 min with triethylamine (0.31 mL, 2.2 mmol). 3-Aminopropionitrile (0.1 mL, 1.3 mmol) in DMF (2 mL) was added to the reaction mixture at 0° C. More triethylamine (0.31 mL, 2.2 mmol) was added and the reaction mixture stirred at ambient temperature overnight. The reaction mixture was diluted with water (40 mL) and extracted with EtOAc (3×30 mL). The combined extracts were washed with water, passed through a hydrophobic frit and evaporated to dryness. Flash chromatographic purification over silica (CH2Cl2/ether/MeOH/Et3N eluent) of the residue afforded 2-amino-N-(2-cyanoethyl)-5-[(1-methylcyclopropyl)sulfamoyl]benzamide (87 mg, 0.27 mmol, 27%).

$^1$H NMR (300 MHz, CHLOROFORM-d) δ ppm 7.86-7.84 (m, 1H), 7.80-7.76 (m, 2H), 7.61-7.56 (m, 1H), 6.66 (d, J=8.7 Hz, 1H), 3.68-3.58 (m, 2H), 2.72-2.66 (m, 2H), 1.19, 1.16, (s, 3H), 0.75-0.68 (m, 2H), 0.46-0.38 (m, 2H)

Triphosgene (40 mg, 0.13 mmol) was added to a solution of 2-amino-N-(2-cyanoethyl)-5-[(1-methylcyclopropyl)sulfamoyl]benzamide (87 mg, 0.27 mmol) in THF (10 mL) at 0° C. The reaction mixture was stirred 0° C. for 15 min and then stirred at ambient temperature overnight. 2M Aqueous sodium hydroxide (2 mL, 2M) was added and the reaction mixture was stirred at ambient temperature for 30 min. The mixture was cooled and acidified to pH 2 with 2M HCl. The product was extracted with EtOAc. The combined extracts were washed with water, evaporated and purified by prep hplc to give the desired product (67 mg, 0.192 mmol, 71%) as a white powder.

Example 497 3-(2-Cyanoethyl)-1-methyl-N-(1-methylcyclopropyl)-2,4-dioxo-quinazoline-6-sulfonamide

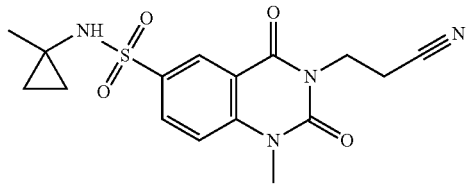 [SMILES: Cn1c(=O)n(CCC#N)c(=O)c2cc(S(=O)(=O)NC3(C)CC3)ccc21]

Prepared using Method A10 using 3-(2-cyanoethyl)-N-(1-methylcyclopropyl)-2,4-dioxo-1H-quinazoline-6-sulfonamide (50 mg, 0.144 mmol), potassium carbonate (24 mg, 0.172 mmol) and iodomethane (20 μL, 0.34 mmol). The reaction mixture was heated to 80° C. in a microwave for 1 h. This afforded the desired product (25 mg, 0.069 mmol, 48%) as a white powder.

Example 498 1-Methyl-N-(1-methylcyclopropyl)-2,4-dioxo-3-[2-(2-pyridyl)ethyl]quinazoline-6-sulfonamide

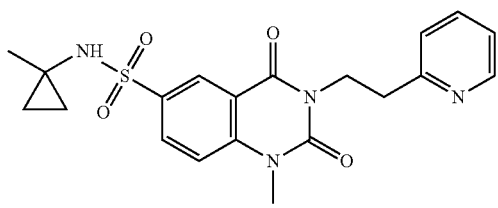 [SMILES: Cn1c(=O)n(CCc2ccccn2)c(=O)c2cc(S(=O)(=O)NC3(C)CC3)ccc21]

Prepared using Method A10 using N-(1-methylcyclopropyl)-2,4-dioxo-3-[2-(2-pyridyl)ethyl]-1H-quinazoline-6-sulfonamide (145 mg, 0.362 mmol), potassium carbonate (60 mg, 0.435 mmol) and iodomethane (27 μL, 0.435 mmol). The reaction mixture was heated to 80° C. in a microwave for 30 min. This afforded the desired product (52 mg, 0.126 mmol, 35%) as a white powder.

Example 499 1-Methyl-N-(1-methylcyclopropyl)-3-[(4-methyl-1,2,4-triazol-3-yl)methyl]-2,4-dioxo-quinazoline-6-sulfonamide

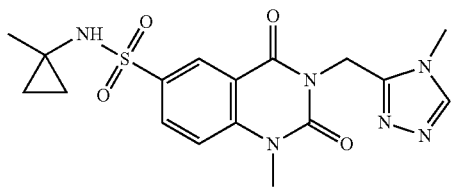 [SMILES: Cn1cnnc1Cn1c(=O)c2cc(S(=O)(=O)NC3(C)CC3)ccc2n(C)c1=O]

Prepared using Method A3 (with 2 eq. NaH), from 1-methyl-N-(1-methylcyclopropyl)-2,4-dioxo-quinazoline-6-sulfonamide, 3-(chloromethyl)-4-methyl-4H-1,2,4-triazole hydrochloride and 1 eq. NaI. This gave the desired product (5 mg, 0.0124 mmol, 6%) as a white powder.

Example 500 1-Methyl-N-(1-methylcyclopropyl)-3-[(5-methyl-1,3,4-thiadiazol-2-yl)methyl]-2,4-dioxo-quinazoline-6-sulfonamide

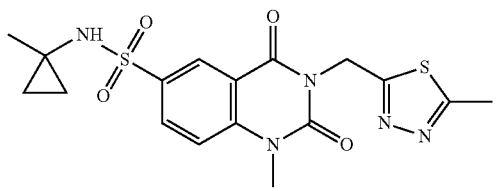

Prepared using Method A3, from 1-methyl-N-(1-methylcyclopropyl)-2,4-dioxo-quinazoline-6-sulfonamide, 2-(chloromethyl)-5-methyl-1,3,4-thiadiazole and 1 eq. NaI. This gave the desired product (28 mg, 0.0664 mmol, 34%) as a white powder.

Example 501 1-Methyl-N-(1-methylcyclopropyl)-2,4-dioxo-3-[[5-(trifluoromethyl)-1,3,4-oxadiazol-2-yl]methyl]quinazoline-6-sulfonamide

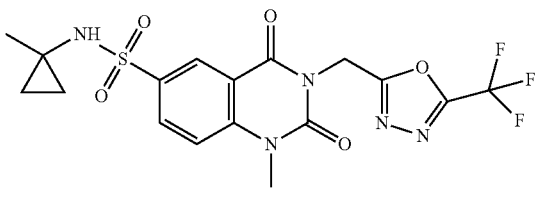 [SMILES: Cn1c(=O)n(Cc2nnc(C(F)(F)F)o2)c(=O)c2cc(S(=O)(=O)NC3(C)CC3)ccc21]

Prepared using Method A3, from 1-methyl-N-(1-methylcyclopropyl)-2,4-dioxo-quinazoline-6-sulfonamide, 2-(chloromethyl)-5-(trifluoromethyl)-1,3,4-oxadiazole and 1 eq. NaI. This gave the desired product (12 mg, 0.0261 mmol, 13%) as a white powder.

Example 502 1-(Cyanomethyl)-N-(1-methylcyclopropyl)-3-[(2-methylthiazol-5-yl)methyl]-2,4-dioxo-quinazoline-6-sulfonamide

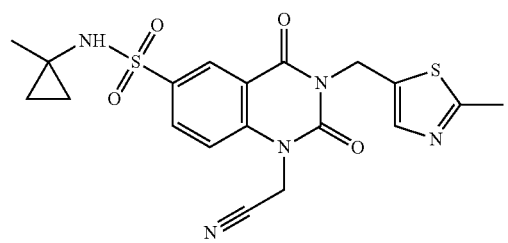

Prepared using Method A10 using N-(1-methylcyclopropyl)-3-[(2-methylthiazol-5-yl)methyl]-2,4-dioxo-1H-quinazoline-6-sulfonamide (60 mg, 0.148 mmol), potassium carbonate (25 mg, 0.177 mmol) and bromoacetonitrile (11 μL, 0.155 mmol). The reaction mixture was heated to 100° C. in a microwave for 30 min. This afforded the desired product (17 mg, 0.038 mmol, 26%) as a white powder.

Example 503 1-(Cyanomethyl)-N-(1-methylcyclopropyl)-3-[(3-methylisoxazol-5-yl)methyl]-2,4-dioxo-quinazoline-6-sulfonamide

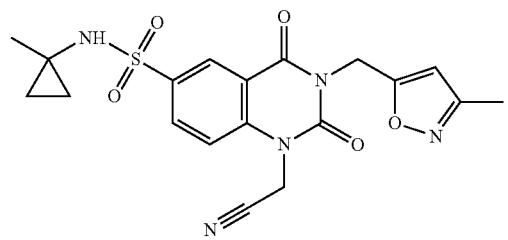

Prepared using Method A10 using N-(1-methylcyclopropyl)-3-((3-methylisoxazol-5-yl)methyl)-2,4-dioxo-1,2,3,4-tetrahydroquinazoline-6-sulfonamide (58 mg, 0.148 mmol), potassium carbonate (25 mg, 0.177 mmol) and bromoacetonitrile (11 µL, 0.155 mmol). The reaction mixture was heated to 100° C. in a microwave for 30 min. This afforded the desired product (16 mg, 0.037 mmol, 25%) as an off-white powder.

Example 504 3-(Furylmethyl)-1-methyl-N-(1-methylcyclopropyl)-2,4-dioxo-quinazoline-6-sulfonamide

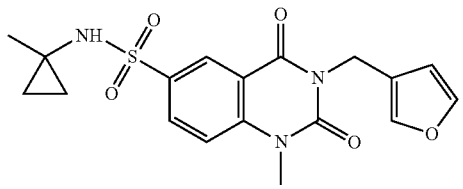 [SMILES: Cn1c(=O)n(Cc2ccoc2)c(=O)c2cc(S(=O)(=O)NC3(C)CC3)ccc21]

Prepared using Method A2, from 1-methyl-N-(1-methylcyclopropyl)-2,4-dioxo-quinazoline-6-sulfonamide and furan-3-methanol. This gave the desired product (10 mg, 0.0257 mmol, 10%) as a white powder.

Example 505 3-(1H-Imidazol-4-ylmethyl)-1-methyl-N-(1-methylcyclopropyl)-2,4-dioxo-quinazoline-6-sulfonamide

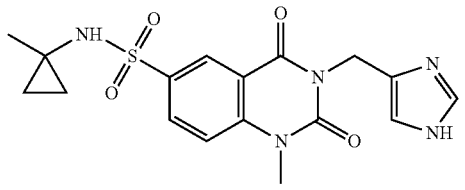 [SMILES: Cn1c(=O)n(Cc2c[nH]cn2)c(=O)c2cc(S(=O)(=O)NC3(C)CC3)ccc21]

Prepared using Method A2, from 1-methyl-N-(1-methylcyclopropyl)-2,4-dioxo-quinazoline-6-sulfonamide and 4-imidazolemethanol. This gave the desired product (4 mg, 0.0103 mmol, 5%) as a white powder.

Example 506 1-Methyl-N-(1-methylcyclopropyl)-3-[(5-methylisoxazol-4-yl)methyl]-2,4-dioxo-quinazoline-6-sulfonamide

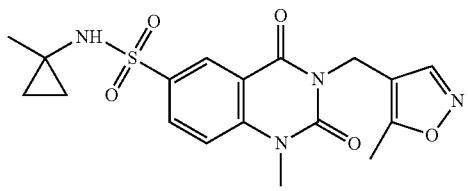 [SMILES: Cc1oncc1Cn1c(=O)c2cc(S(=O)(=O)NC3(C)CC3)ccc2n(C)c1=O]

Prepared using Method A2, from 1-methyl-N-(1-methylcyclopropyl)-2,4-dioxo-quinazoline-6-sulfonamide and (5-methyl-1,2-oxazol-4-yl)methanol. This gave the desired product (18 mg, 0.0445 mmol, 23%) as a white powder.

Example 507 3-[(1-Isopropylpyrazol-4-yl)methyl]-1-methyl-N-(1-methylcyclopropyl)-2,4-dioxo-quinazoline-6-sulfonamide

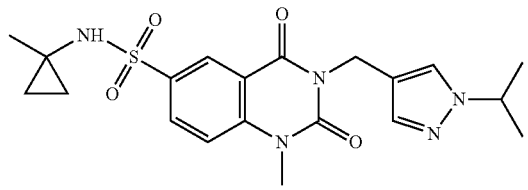 [SMILES: CC(C)n1cc(Cn2c(=O)c3cc(S(=O)(=O)NC4(C)CC4)ccc3n(C)c2=O)cn1]

Prepared using Method A2 using 1-methyl-N-(1-methylcyclopropyl)-2,4-dioxo-quinazoline-6-sulfonamide (160 mg, 0.517 mmol) and (1-isopropyl-1H-pyrazol-4-yl)methanol (127 µL, 1.034 mmol). This afforded the desired product (15 mg, 0.035 mmol, 6.7%) as a colourless gum.

Example 508 1-Methyl-N-(1-methylcyclopropyl)-3-[(1-methyltetrazol-5-yl)methyl]-2,4-dioxo-quinazoline-6-sulfonamide

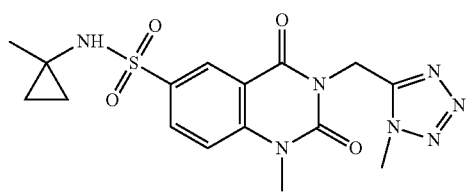 [SMILES: Cn1nnnc1Cn1c(=O)c2cc(S(=O)(=O)NC3(C)CC3)ccc2n(C)c1=O]

Prepared using Method A3 using 1-methyl-N-(1-methylcyclopropyl)-2,4-dioxo-quinazoline-6-sulfonamide (100 mg, 0.323 mmol) and 5-(chloromethyl)-1-methyl-1H,1,2,3,4-tetrazole (43 mg, 0.323 mmol). This afforded the desired product (39 mg, 0.096 mmol, 30%) as a white powder.

Example 509 3-[(4-Isopropylthiadiazol-5-yl)methyl]-1-methyl-N-(1-methylcyclopropyl)-2,4-dioxo-quinazoline-6-sulfonamide

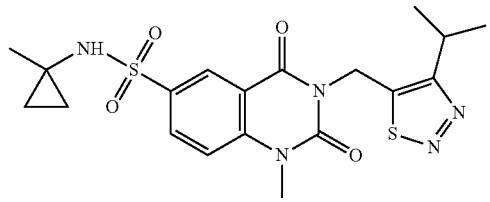 [SMILES: CC(C)c1nnsc1Cn1c(=O)c2cc(S(=O)(=O)NC3(C)CC3)ccc2n(C)c1=O]

Prepared using Method A3 using 1-methyl-N-(1-methylcyclopropyl)-2,4-dioxo-quinazoline-6-sulfonamide (100 mg, 0.323 mmol) and 5-(chloromethyl)-4-isopropyl-1,2,3-thiadiazole (57 mg, 0.323 mmol). This afforded the desired product (26 mg, 0.058 mmol, 18%) as an off-white powder.

Example 510 3-(Isothiazol-5-ylmethyl)-1-methyl-N-(1-methylcyclopropyl)-2,4-dioxo-quinazoline-6-sulfonamide

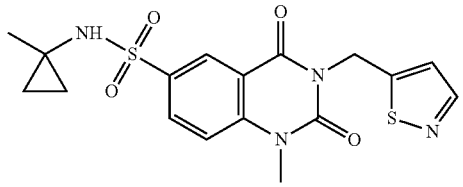 [SMILES: Cn1c(=O)n(Cc2ccns2)c(=O)c2cc(S(=O)(=O)NC3(C)CC3)ccc21]

Prepared using Method A2 using 1-methyl-N-(1-methylcyclopropyl)-2,4-dioxo-quinazoline-6-sulfonamide (160 mg, 0.517 mmol) and isothiazol-5-ylmethanol (119 mg, 1.034 mmol). This afforded the desired product (9 mg, 0.022 mmol, 4.3%) as a white powder.

Example 511 1-Methyl-N-(1-methylcyclopropyl)-3-[(4-methyl-1,2,5-oxadiazol-3-yl)methyl]-2,4-dioxo-quinazoline-6-sulfonamide

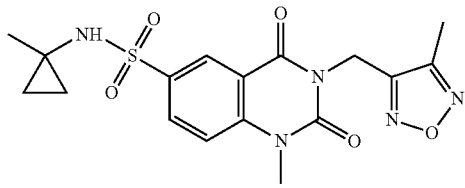 [SMILES: Cc1nonc1Cn1c(=O)c2cc(S(=O)(=O)NC3(C)CC3)ccc2n(C)c1=O]

Prepared using Method A2 using 1-methyl-N-(1-methylcyclopropyl)-2,4-dioxo-quinazoline-6-sulfonamide (135 mg, 0.436 mmol) and (4-methyl-1,2,5-oxadiazol-3-yl)methanol (100 mg, 0.873 mmol). This afforded the desired product (21 mg, 0.052 mmol, 12%) as a white powder.

Example 512 N-[1-(Fluoromethyl)cyclopropyl]-1-methyl-2,4-dioxo-quinazoline-6-sulfonamide

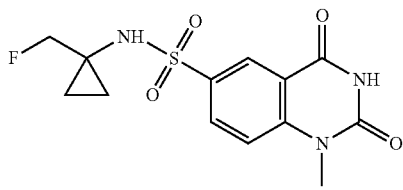 [SMILES: Cn1c(=O)[nH]c(=O)c2cc(S(=O)(=O)NC3(CF)CC3)ccc21]

To a stirred solution of N,N-diisopropylethylamine (3.9 mL, 22.4 mmol) in THF (50 mL) and DCM (30 mL) at 0° C. was added a mixture of 1-(fluoromethyl)cyclopropan-1-amine hydrochloride (1.07 g, 8.51 mmol) and then 1-methyl-2,4-dioxo-quinazoline-6-sulfonyl chloride (2.46 g, 8.96 mmol) and the mixture stirred overnight at ambient temperature. The solvent was evaporated and the resulting white solid triturated from MeOH, filtered off and dried under vacuum to give the desired product (1.43 g, 4.37 mmol, 49%) as a white powder.

Example 513 N-[1-(Fluoromethyl)cyclopropyl]-3-(isoxazol-5-ylmethyl)-1-methyl-2,4-dioxo-quinazoline-6-sulfonamide

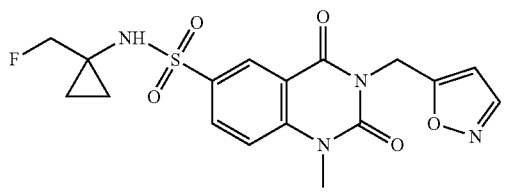 [SMILES: Cn1c(=O)n(Cc2ccno2)c(=O)c2cc(S(=O)(=O)NC3(CF)CC3)ccc21]

Prepared using Method A3 using N-[1-(fluoromethyl)cyclopropyl]-1-methyl-2,4-dioxo-quinazoline-6-sulfonamide (200 mg, 0.611 mmol) and 5-(bromomethyl)-1,2-oxazole (99 mg, 0.611 mmol). This afforded the desired product (77 mg, 0.189 mmol, 31%) as a white powder.

Example 514 N-[1-(Fluoromethyl)cyclopropyl]-1-methyl-3-[(3-methylisoxazol-5-yl)methyl]-2,4-dioxo-quinazoline-6-sulfonamide

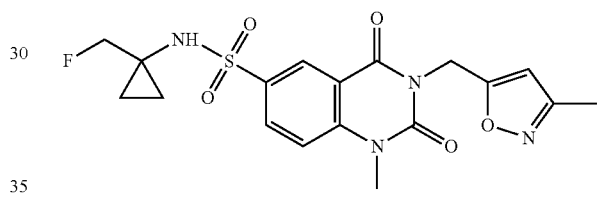

Prepared using Method A3 using N-[1-(fluoromethyl)cyclopropyl]-1-methyl-2,4-dioxo-quinazoline-6-sulfonamide (100 mg, 0.323 mmol) and 5-(bromomethyl)-3-methyl-1,2-oxazole (57 mg, 0.323 mmol). This afforded the desired product (64 mg, 0.152 mmol, 47%) as a white powder.

Example 515 N-[1-(Fluoromethyl)cyclopropyl]-1-methyl-3-[(5-methyl-1,3,4-thiadiazol-2-yl)methyl]-2,4-dioxo-quinazoline-6-sulfonamide

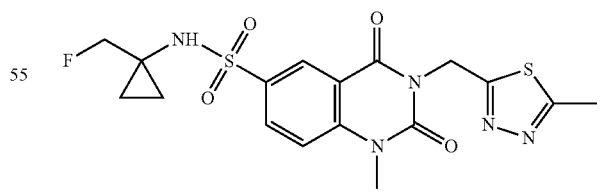

Prepared using Method A3 using N-[1-(fluoromethyl)cyclopropyl]-1-methyl-2,4-dioxo-quinazoline-6-sulfonamide (120 mg, 0.367 mmol) and 2-(chloromethyl)-5-methyl-1,3,4-thiadiazole (54 mg, 0.367 mmol). This afforded the desired product (15 mg, 0.034 mmol, 9.3%) as a white powder.

Example 516 N-[1-(Fluoromethyl)cyclopropyl]-3-[(3-methylisoxazol-5-yl)methyl]-2,4-dioxo-1H-quinazoline-6-sulfonamide

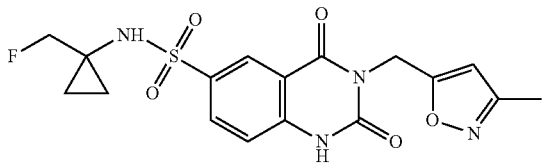 [SMILES: Cc1cc(Cn2c(=O)[nH]c3ccc(S(=O)(=O)NC4(CF)CC4)cc3c2=O)on1]

A suspension of 1,4-dihydro-2,4-dioxo-2H-3,1-benzoxazine-6-sulfonyl chloride (14 g, 53.5 mmol), prepared by chlorosulfonylation of isatoic anhydride chlorosulfonic acid at 60° C., in DMF (200 mL) was treated with 1-fluoromethylcyclopropanamine hydrochloride (8.0 g, 64 mmol) and cooled to −10° C. in an ice/MeOH bath. The solution was treated slowly with triethylamine (16.3 mL, 96.7 mmol) and the resulting solution was stirred at −10° C. for 1 h. (3-Methylisoxazol-5-ylmethyl)amine (8.97 g, 80.0 mmol) in DMF (40 mL) was added to the reaction mixture at 0° C., followed by triethylamine (14.8 mL, 107 mmol), and the reaction mixture was stirred at ambient temperature for 3 h. Water (450 mL) was added to the reaction mixture, which was then extracted with EtOAc (2×900 mL), the organic phase was washed with brine (450 mL), dried over sodium sulfate, filtered and evaporated to dryness. The crude product was chromatographed over silica and dried to give 2-amino-5-[(1-fluoromethylcyclopropyl)sulfamoyl]-N-[(3-methylisoxazol-5-yl)methyl]benzamide (6.0 g, 16.4 mmol, 31%) as a white solid.

Triphosgene (2.31 g, 7.73 mmol) was added to a solution of 2-amino-5-[(1-fluoromethylcyclopropyl)sulfamoyl]-N-[(3-methylisoxazol-5-yl)methyl]benzamide (6.0 g, 16.4 mmol) in THF (120 mL) cooled in an ice bath. A white precipitate formed, then triethylamine (2.35 mL, 17 mmol) was added. The reaction mixture was removed from cooling and stirred at ambient temperature for 1.5 h. The reaction mixture was quenched with 2 M NaOH (120 mL) and stirred overnight. Next morning, EtOAc (240 mL) was added to the reaction mixture, which was then cooled and acidified with 2 M HCl (to pH 3). The organic phase was separated and evaporated to dryness to give the desired product (5.1 g, 12.5 mmol, 76%) as a white powder.

Example 517 1-(Cyclopropylmethyl)-N-[1-(fluoromethyl)cyclopropyl]-3-[(3-methylisoxazol-5-yl)methyl]-2,4-dioxo-quinazoline-6-sulfonamide

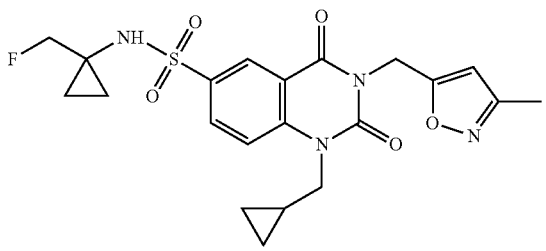 [SMILES: Cc1cc(Cn2c(=O)c3cc(S(=O)(=O)NC4(CF)CC4)ccc3n(CC3CC3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide and iodomethylcyclopropane. This gave the desired product (22 mg, 0.0476 mmol, 32%) as a white powder.

Example 518 N-[1-(Fluoromethyl)cyclopropyl]-1-[(4-fluorophenyl)methyl]-3-[(3-methylisoxazol-5-yl)methyl]-2,4-dioxo-quinazoline-6-sulfonamide

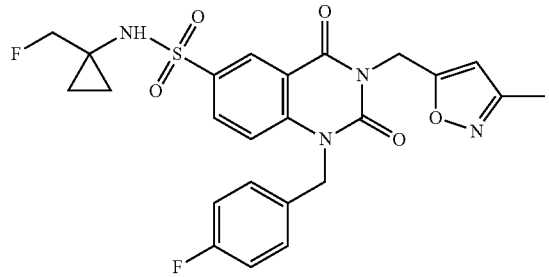 [SMILES: Cc1cc(Cn2c(=O)c3cc(S(=O)(=O)NC4(CF)CC4)ccc3n(Cc3ccc(F)cc3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide and 4-fluorobenzyl bromide. This gave the desired product (24 mg, 0.0465 mmol, 32%) as a white powder.

Example 519 1-[(2,5-Dimethylpyrazol-3-yl)methyl]-N-[1-(fluoromethyl)cyclopropyl]-3-[(3-methylisoxazol-5-yl)methyl]-2,4-dioxo-quinazoline-6-sulfonamide

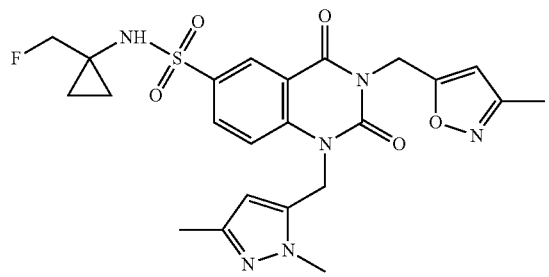 [SMILES: Cc1cc(Cn2c(=O)c3cc(S(=O)(=O)NC4(CF)CC4)ccc3n(Cc3cc(C)nn3C)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 5-(chloromethyl)-1,3-dimethyl-1H-pyrazole and 0.2 eq. NaI. This gave the desired product (30 mg, 0.0581 mmol, 40%) as a white powder.

Example 520 1-Ethyl-N-[1-(fluoromethyl)cyclopropyl]-3-[(3-methylisoxazol-5-yl)methyl]-2,4-dioxo-quinazoline-6-sulfonamide

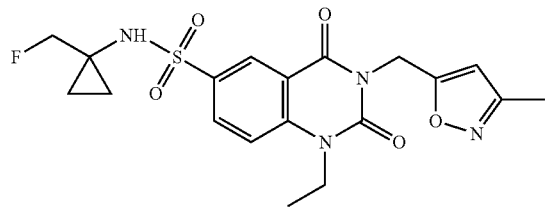 [SMILES: CCn1c(=O)n(Cc2cc(C)no2)c(=O)c2cc(S(=O)(=O)NC3(CF)CC3)ccc21]

Prepared using Method A10, from N-[1-(fluoromethyl)cyclopropyl]-3-[(3-methylisoxazol-5-yl)methyl]-2,4-dioxo-1H-quinazoline-6-sulfonamide and iodoethane. This gave the desired product (20 mg, 0.0458 mmol, 31%) as a white powder.

Example 521 N-[1-(Fluoromethyl)cyclopropyl]-1,3-bis[(3-methylisoxazol-5-yl)methyl]-2,4-dioxo-quinazoline-6-sulfonamide

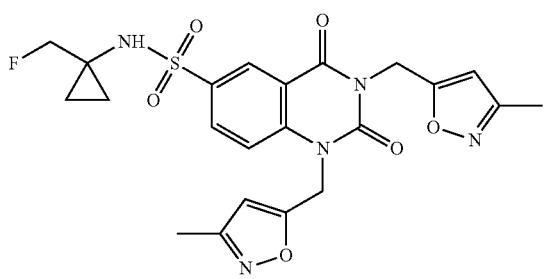 [SMILES: Cc1cc(Cn2c(=O)c3cc(S(=O)(=O)NC4(CF)CC4)ccc3n(Cc3cc(C)no3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide and 5-(bromomethyl)-3-methyl-1,2-oxazole. This gave the desired product (20 mg, 0.0397 mmol, 27%) as a white powder.

Example 522 N-[1-(Fluoromethyl)cyclopropyl]-3-[(3-methylisoxazol-5-yl)methyl]-1-(oxetan-3-ylmethyl)-2,4-dioxo-quinazoline-6-sulfonamide

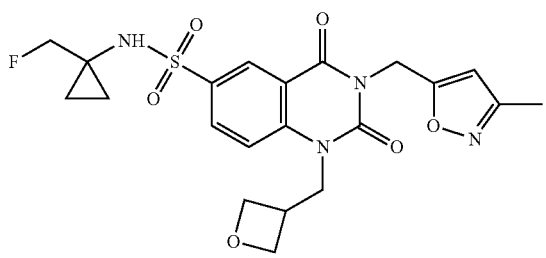 [SMILES: Cc1cc(Cn2c(=O)c3cc(S(=O)(=O)NC4(CF)CC4)ccc3n(CC3COC3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, oxetan-3-ylmethyl 4-methylbenzenesulfonate and 0.2 eq. NaI. This gave the desired product (22 mg, 0.0460 mmol, 31%) as a white powder.

Example 523 1-(Cyanomethyl)-N-[1-(fluoromethyl)cyclopropyl]-3-[(3-methylisoxazol-5-yl)methyl]-2,4-dioxo-quinazoline-6-sulfonamide

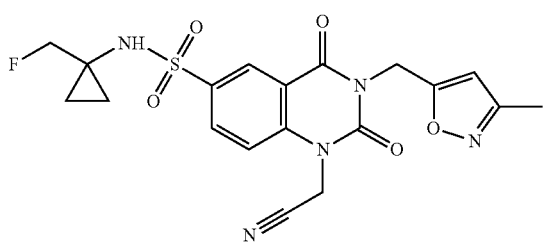 [SMILES: Cc1cc(Cn2c(=O)c3cc(S(=O)(=O)NC4(CF)CC4)ccc3n(CC#N)c2=O)on1]

This compound was prepared according to Example 465 using N-[1-(fluoromethyl)cyclopropyl]-3-[(3-methylisoxazol-5-yl)methyl]-2,4-dioxo-1H-quinazoline-6-sulfonamide (100 mg, 0.245 mmol) and bromoacetonitrile (19 μL, 0.269 mmol). The reaction mixture was heated by microwave irradiation to 120° C. for 1 h. This afforded the desired product (17 mg, 0.038 mmol, 16%) as a beige powder.

Example 524 N-[1-(Fluoromethyl)cyclopropyl]-3-[(3-methylisoxazol-5-yl)methyl]-2,4-dioxo-1-(tetrahydrofuran-3-ylmethyl)quinazoline-6-sulfonamide

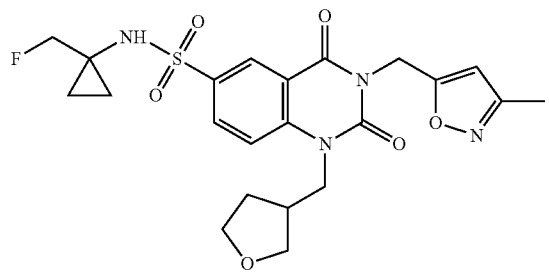 [SMILES: Cc1cc(Cn2c(=O)c3cc(S(=O)(=O)NC4(CF)CC4)ccc3n(CC3CCOC3)c2=O)on1]

This compound was prepared according to Example 465 using N-[1-(fluoromethyl)cyclopropyl]-3-[(3-methylisoxazol-5-yl)methyl]-2,4-dioxo-1H-quinazoline-6-sulfonamide (100 mg, 0.245 mmol) and 3-(bromomethyl)tetrahydrofuran (60 μL, 0.538 mmol). The reaction mixture was heated by microwave irradiation to 120° C. for 2 h. This afforded the desired product (21 mg, 0.042 mmol, 25%) as a beige powder.

Example 525 N-[1-(Fluoromethyl)cyclopropyl]-1-(3-methoxypropyl)-3-[(3-methylisoxazol-5-yl)methyl]-2,4-dioxo-quinazoline-6-sulfonamide

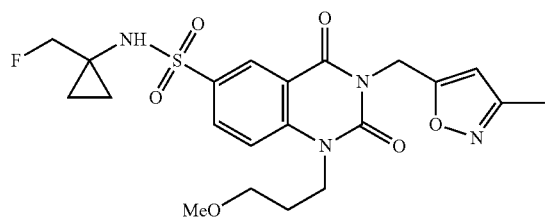 [SMILES: COCCCn1c(=O)n(Cc2cc(C)no2)c(=O)c2cc(S(=O)(=O)NC3(CF)CC3)ccc21]

This compound was prepared according to Example 465 using N-[1-(fluoromethyl)cyclopropyl]-3-[(3-methylisoxazol-5-yl)methyl]-2,4-dioxo-1H-quinazoline-6-sulfonamide (105 mg, 0.256 mmol) and 1-bromo-3-methoxypropane (62 μL, 0.564 mmol). The reaction mixture was heated by microwave irradiation to 120° C. for 2 h. This afforded the desired product (34 mg, 0.071 mmol, 28%) as a white powder.

Example 526 1-(2-Fluoroethyl)-N-[1-(fluoromethyl)cyclopropyl]-3-[(3-methylisoxazol-5-yl)methyl]-2,4-dioxo-quinazoline-6-sulfonamide

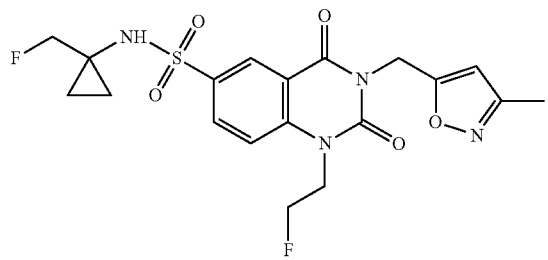 [SMILES: Cc1cc(Cn2c(=O)c3cc(S(=O)(=O)NC4(CF)CC4)ccc3n(CCF)c2=O)on1]

Prepared using Method A2, using N-[1-(fluoromethyl)cyclopropyl]-3-[(3-methylisoxazol-5-yl)methyl]-2,4-dioxo-1H-quinazoline-6-sulfonamide (306 mg, 0.749 mmol) and 1-bromo-2-fluoroethane (61 μL, 0.824 mmol). After stirring overnight at ambient temperature more 1-bromo-2-fluoroethane (61 μL, 0.824 mmol) was added and the reaction mixture was heated by microwave irradiation to 80° C. This afforded the desired product (16 mg, 0.035 mmol, 4.7%) as a white powder.

Example 527 N-[1-(Fluoromethyl)cyclopropyl]-1-(2-methoxyethyl)-3-[(3-methylisoxazol-5-yl)methyl]-2,4-dioxo-quinazoline-6-sulfonamide

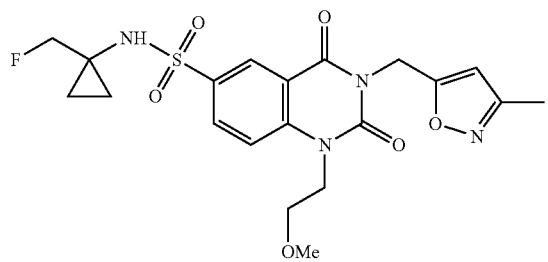 [SMILES: COCCn1c(=O)n(Cc2cc(C)no2)c(=O)c2cc(S(=O)(=O)NC3(CF)CC3)ccc21]

This compound was prepared according to Example 465 using N-[1-(fluoromethyl)cyclopropyl]-3-[(3-methylisoxazol-5-yl)methyl]-2,4-dioxo-1H-quinazoline-6-sulfonamide (100 mg, 0.245 mmol) and 2-bromoethyl methylether (22 μL, 0.269 mmol). The reaction mixture was heated by microwave irradiation to 120° C. for 1 h. This afforded the desired product (5 mg, 0.01 mmol, 4.4%) as an off-white powder.

Example 528 1-Methyl-N-(1-methylcyclopropyl)-2,4-dioxo-3-[2-oxo-2-(4-pyridyl)ethyl]quinazoline-6-sulfonamide

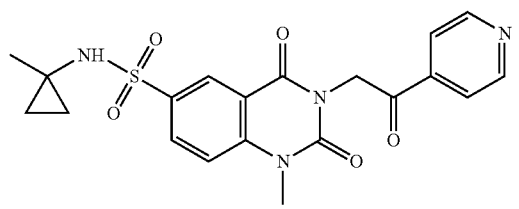 [SMILES: Cn1c(=O)n(CC(=O)c2ccncc2)c(=O)c2cc(S(=O)(=O)NC3(C)CC3)ccc21]

Prepared using Method A3 (with 2 eq. NaH), from 1-methyl-N-(1-methylcyclopropyl)-2,4-dioxo-quinazoline-6-sulfonamide and 4-(bromoacetyl)pyridine hydrobromide. This gave the desired product (5 mg, 0.0117 mmol, 6%) as a white powder.

Example 529 1-Methyl-N-(1-methylcyclopropyl)-2,4-dioxo-3-[2-oxo-2-(2-thienyl)ethyl]quinazoline-6-sulfonamide

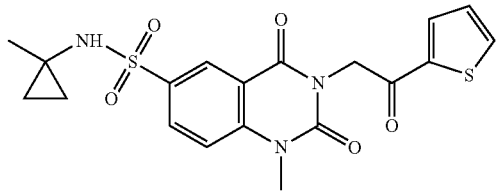 [SMILES: Cn1c(=O)n(CC(=O)c2cccs2)c(=O)c2cc(S(=O)(=O)NC3(C)CC3)ccc21]

Prepared using Method A3, from 1-methyl-N-(1-methylcyclopropyl)-2,4-dioxo-quinazoline-6-sulfonamide and 2-bromo-1-(2-thienyl)ethanone. This gave the desired product (34 mg, 0.0784 mmol, 40%) as a white powder.

Example 530 1-Methyl-N-(1-methylcyclopropyl)-2,4-dioxo-3-phenacyl-quinazoline-6-sulfonamide

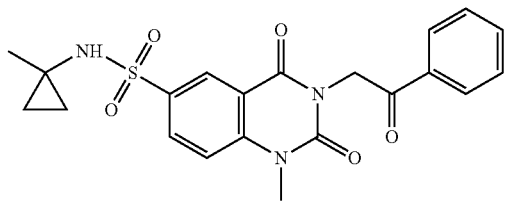 [SMILES: Cn1c(=O)n(CC(=O)c2ccccc2)c(=O)c2cc(S(=O)(=O)NC3(C)CC3)ccc21]

Prepared using Method A3, from 1-methyl-N-(1-methylcyclopropyl)-2,4-dioxo-quinazoline-6-sulfonamide and 2-bromoacetophenone. This gave the desired product (31 mg, 0.0725 mmol, 37%) as a white powder.

Example 531 3-[2-(4-Cyanophenyl)-2-oxo-ethyl]-1-methyl-N-(1-methylcyclopropyl)-2,4-dioxo-quinazoline-6-sulfonamide

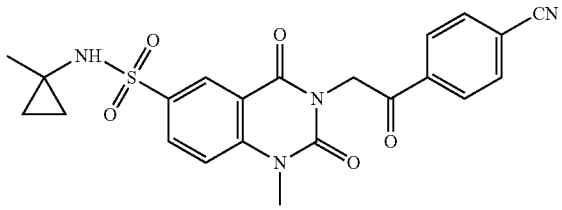 [SMILES: Cn1c(=O)n(CC(=O)c2ccc(C#N)cc2)c(=O)c2cc(S(=O)(=O)NC3(C)CC3)ccc21]

Prepared using Method A3, from 1-methyl-N-(1-methylcyclopropyl)-2,4-dioxo-quinazoline-6-sulfonamide and 4-(bromoacetyl)benzonitrile. This gave the desired product (29 mg, 0.0641 mmol, 33%) as a white powder.

Example 532 N-[1-(Fluoromethyl)cyclopropyl]-3-[(3-methylisoxazol-5-yl)methyl]-2,4-dioxo-1-prop-2-ynyl-quinazoline-6-sulfonamide

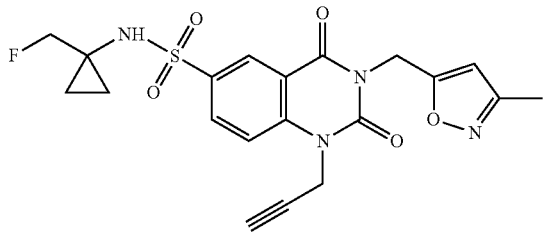 [SMILES: C#CCn1c(=O)n(Cc2cc(C)no2)c(=O)c2cc(S(=O)(=O)NC3(CF)CC3)ccc21]

This compound was prepared according to Example 465 using N-[1-(fluoromethyl)cyclopropyl]-3-[(3-methylisoxazol-5-yl)methyl]-2,4-dioxo-1H-quinazoline-6-sulfonamide (100 mg, 0.245 mmol) and 3-bromopropyne (19 µL, 0.269 mmol). The reaction mixture was heated by microwave irradiation to 120° C. for 1 h. This afforded the desired product (6 mg, 0.054 mmol, 5.5%) as a white powder.

Example 533 N-[1-(Fluoromethyl)cyclopropyl]-1-methyl-3-[(2-methylthiazol-5-yl)methyl]-2,4-dioxo-quinazoline-6-sulfonamide

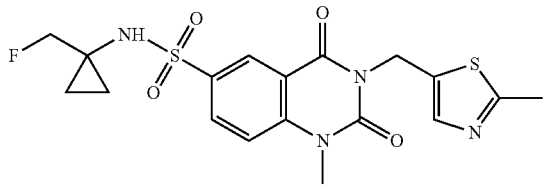 [SMILES: Cc1ncc(Cn2c(=O)c3cc(S(=O)(=O)NC4(CF)CC4)ccc3n(C)c2=O)s1]

Prepared using Method A2, from N-[1-(fluoromethyl)cyclopropyl]-1-methyl-2,4-dioxo-quinazoline-6-sulfonamide and (2-methyl-1,3-thiazol-5-yl)methanol. This gave the desired product (19 mg, 0.043 mmol, 8.4%) as a white powder.

Example 534 N-[1-(Fluoromethyl)cyclopropyl]-1-methyl-2,4-dioxo-3-(thiazol-5-ylmethyl)quinazoline-6-sulfonamide

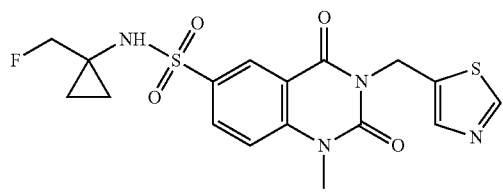 [SMILES: Cn1c(=O)n(Cc2cncs2)c(=O)c2cc(S(=O)(=O)NC3(CF)CC3)ccc21]

Prepared using Method A2, from N-[1-(fluoromethyl)cyclopropyl]-1-methyl-2,4-dioxo-quinazoline-6-sulfonamide and 5-(hydroxymethyl)-1,3-thiazole. This gave the desired product (8 mg, 0.019 mmol, 3.6%) as a white powder.

Example 535 N-[1-(Fluoromethyl)cyclopropyl]-3-[(3-methylisoxazol-5-yl)methyl]-2,4-dioxo-1-propyl-quinazoline-6-sulfonamide

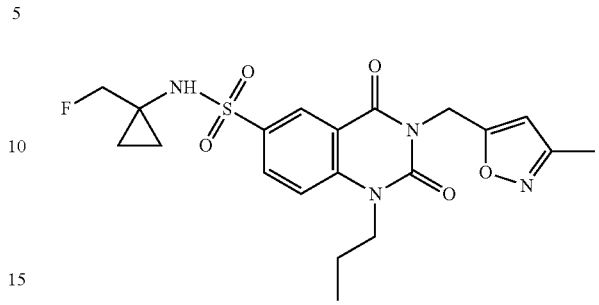

Prepared using Method A10 using N-[1-(fluoromethyl)cyclopropyl]-3-[(3-methylisoxazol-5-yl)methyl]-2,4-dioxo-1H-quinazoline-6-sulfonamide (200 mg, 0.49 mmol), potassium carbonate (136 mg, 0.979 mmol) and 1-bromopropane (53 µL, 0.59 mmol). This afforded the desired product (13 mg, 0.029 mmol, 5.9%) as an off-white powder.

Example 536 1-Butyl-N-[1-(fluoromethyl)cyclopropyl]-3-[(3-methylisoxazol-5-yl)methyl]-2,4-dioxo-quinazoline-6-sulfonamide

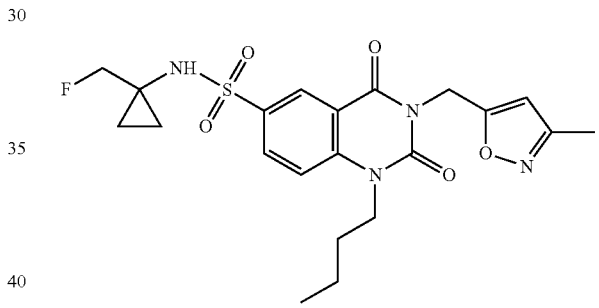

Prepared using Method A10 using N-[1-(fluoromethyl)cyclopropyl]-3-[(3-methylisoxazol-5-yl)methyl]-2,4-dioxo-1H-quinazoline-6-sulfonamide (200 mg, 0.49 mmol), potassium carbonate (136 mg, 0.979 mmol) and 1-bromobutane (63 µL, 0.59 mmol). This afforded the desired product (66 mg, 0.142 mmol, 29%) as a white powder.

General Experimental for Examples 537-549, 560-598, 607-613 and 617-620

Flash chromatography was performed using pre-packed silica gel cartridges (YMC 4 g, 40 to 60 µm silica particle) max operating pressure 200 psi/14 bar. Thin layer chromatography was conducted with 5×10 cm plates coated with Merck Type 60 $F_{254}$ silica gel to a thickness of 0.25 mm. All reagents obtained from commercial sources were used without further purification. Anhydrous solvents were obtained from the Sigma-Aldrich Chemical Company Ltd., and used without further drying. HPLC grade solvents were obtained from Merck Chemicals Ltd.

All compounds were >95% purity as determined by examination of both the LC-MS and $^1$H NMR spectra unless otherwise indicated. Where Cl or Br were present, expected isotopic distribution patterns were observed.

$^1$H NMR

Proton ($^1$H) and carbon ($^{13}$C) NMR spectra were recorded on a 400 MHz Varian spectrometer. Solutions were typically prepared in either deuteromethanol (CD₃OD) or deuterated dimethylsulfoxide (d⁶-DMSO) with chemical shifts referenced to tetramethylsilane (TMS) or deuterated solvent as an internal standard. ¹H NMR data are reported indicating the chemical shift (δ), the integration (e.g. 1H), the multiplicity (s, singlet; d, doublet; t, triplet; q, quartet; m, multiplet; br, broad; dd, doublet of doublets etc.) and the coupling constant (J) in Hz (app implies apparent coupling on broadened signals). Deuterated solvents were obtained from the Sigma-Aldrich Chemical Company.

Analytical LC-MS (Method D).

LC-MS analyses were performed on a Shimadzu LCMS system fitted with YMC triat C18 or YMC ODS C18, 3.0 μM columns (4.6×50 mm) and with UV diode array detection (210-400 nm). Positive and negative mass ion detection was performed using a Shimadzu SQD detector. Analyses were performed with either buffered acidic or basic solvents or gradients as detailed below:

Low pH:

Solvent A—Water+5 mM ammonium formate+0.1% formic acid

Solvent B—5% Solvent A in Acetonitrile+0.1% formic acid

High pH:

Solvent A—Water+5 mM ammonium formate+0.1% ammonia solution

Solvent B—Acetonitrile+5% Solvent A+0.1% ammonia solution

Gradient:

| Time | Flow rate (mL/min) | % Solvent A | % Solvent B |
|------|--------------------|-------------|-------------|
| 0    | 1.20 mL/min        | 80          | 20          |
| 2.5  | 1.20 mL/min        | 05          | 95          |
| 3.0  | 1.20 mL/min        | 05          | 95          |
| 4.0  | 1.20 mL/min        | 80          | 20          |
| 4.5  | 1.20 mL/min        | 80          | 20          |

Preparative HPLC

Some compounds were purified by preparative HPLC with a YMC-ODS 10 μm C18, 500 mm×30 mm i.e. column, running at a flow rate of 40 mL/min with UV diode array detection (210-400 nm) and mass-directed collection using both positive and negative mass ion detection.

Purifications were performed using buffered acidic or basic solvent systems as appropriate. Compound retention times on the system were routinely assessed using a 30-50 μL test injection and a standard gradient, then purified using an appropriately chosen focussed gradient as detailed below, based upon observed retention time.

Low pH:

Solvent A—Water+10 mM ammonium bicarbonate+0.1% formic acid

Solvent B—Acetonitrile+5% water+0.1% formic acid

Standard Gradient:

| Time | Flow rate (mL/min) | % Solvent A | % Solvent B |
|------|--------------------|-------------|-------------|
| 0.01 | 40 mL/min          | 95          | 5           |
| 2    | 40 mL/min          | 95          | 5           |
| 30   | 40 mL/min          | 70          | 30          |
| 40   | 40 mL/min          | 60          | 40          |

Example 537 N-[1-(Fluoromethyl)cyclopropyl]-3-[(1-methylpyrazol-4-yl)methyl]-1-[(5-methyl-2-pyridyl)methyl]-2,4-dioxo-quinazoline-6-sulfonamide

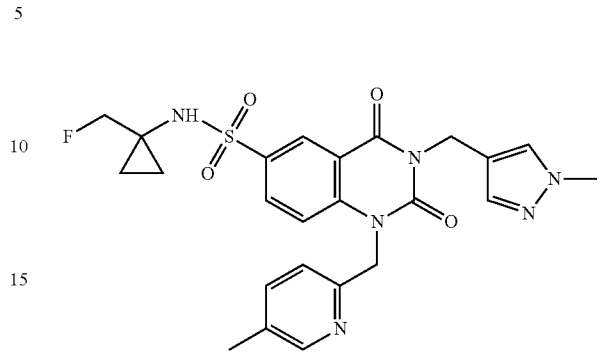

The mesylate of (5-methylpyridin-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (58 mg, 0.286 mmol) and potassium carbonate (43 mg, 0.312 mmol) in DMF was conventionally heated to 70° C. for 4 h. Usual work-up afforded the desired product (14 mg, 0.027 mmol, 11%) as a white powder.

Example 538 1-[(6-Cyano-2-pyridyl)methyl]-N-[1-(fluoromethyl)cyclopropyl]-3-[(1-methylpyrazol-4-yl)methyl]-2,4-dioxo-quinazoline-6-sulfonamide

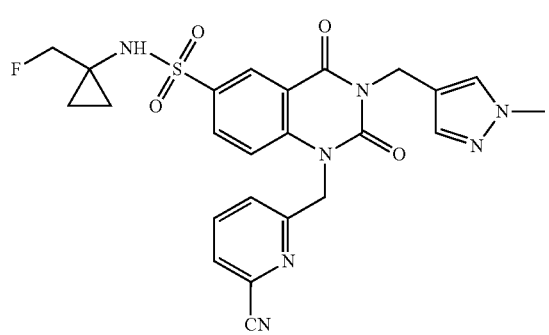 [SMILES: Cn1cc(Cn2c(=O)c3cc(S(=O)(=O)NC4(CF)CC4)ccc3n(Cc3cccc(C#N)n3)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 6-(chloromethyl)picolinonitrile (65 mg, 0.429 mmol) and potassium carbonate (65 mg, 0.468 mmol) in DMF was conventionally heated to 70° C. for 4 h. Usual work-up afforded the desired product (15 mg, 0.029 mmol, 7.3%) as a white powder.

Example 539 N-[1-(Fluoromethyl)cyclopropyl]-3-[(1-methylpyrazol-4-yl)methyl]-1-[(5-methyl-3-pyridyl)methyl]-2,4-dioxo-quinazoline-6-sulfonamide

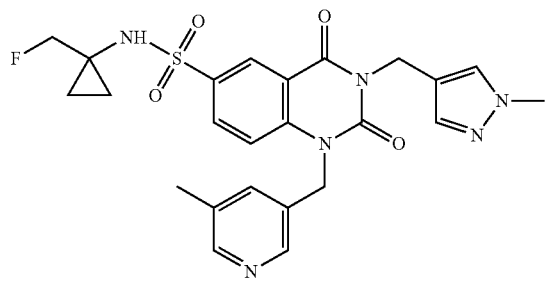 [SMILES: Cc1cncc(Cn2c(=O)n(Cc3cnn(C)c3)c(=O)c3cc(S(=O)(=O)NC4(CF)CC4)ccc32)c1]

The mesylate of (5-methylpyridin-3-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (58 mg, 0.286 mmol) and potassium carbonate (43 mg, 0.312 mmol) in DMF was conventionally heated to 70° C. for 4 h. Usual work-up afforded the desired product (11 mg, 0.021 mmol, 8.3%) as a white powder.

Example 540 N-[1-(Fluoromethyl)cyclopropyl]-1-[(6-fluoro-2-pyridyl)methyl]-3-[(1-methylpyrazol-4-yl)methyl]-2,4-dioxo-quinazoline-6-sulfonamide

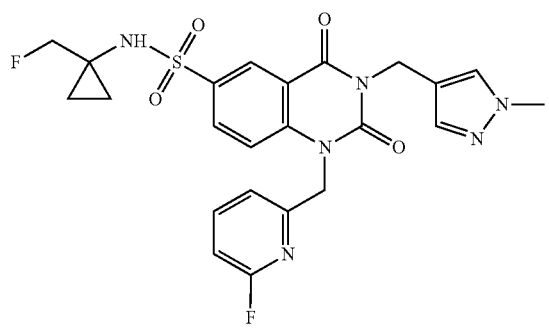 [SMILES: Cn1cc(Cn2c(=O)c3cc(S(=O)(=O)NC4(CF)CC4)ccc3n(Cc3cccc(F)n3)c2=O)cn1]

The mesylate of (6-fluoropyridin-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (26 mg, 0.050 mmol, 19%) as a white powder.

Example 541 N-[1-(Fluoromethyl)cyclopropyl]-3-[(1-methylpyrazol-4-yl)methyl]-1-[(2-methyl-4-pyridyl)methyl]-2,4-dioxo-quinazoline-6-sulfonamide

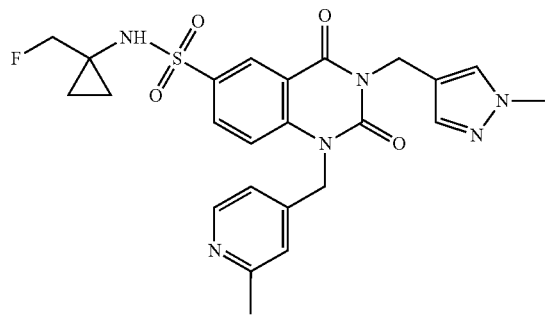 [SMILES: Cc1cc(Cn2c(=O)n(Cc3cnn(C)c3)c(=O)c3cc(S(=O)(=O)NC4(CF)CC4)ccc32)ccn1]

The mesylate of (2-methylpyridin-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (58 mg, 0.286 mmol) and potassium carbonate (43 mg, 0.312 mmol) in DMF was conventionally heated to 70° C. for 4 h. Usual work-up afforded the desired product (46 mg, 0.090 mmol, 35%) as a white powder.

Example 542 N-[1-(Fluoromethyl)cyclopropyl]-1-[(3-fluoro-2-pyridyl)methyl]-3-[(1-methylpyrazol-4-yl)methyl]-2,4-dioxo-quinazoline-6-sulfonamide

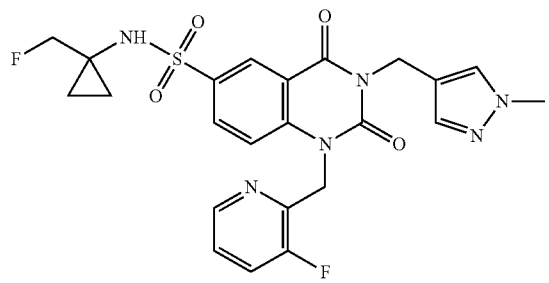 [SMILES: Cn1cc(Cn2c(=O)c3cc(S(=O)(=O)NC4(CF)CC4)ccc3n(Cc3ncccc3F)c2=O)cn1]

The mesylate of (3-fluoropyridin-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (15 mg, 0.030 mmol, 11%) as a white powder.

Example 543 1-[(4-Cyanophenyl)methyl]-N-[1-(fluoromethyl)cyclopropyl]-3-[(1-methylpyrazol-4-yl)methyl]-2,4-dioxo-quinazoline-6-sulfonamide

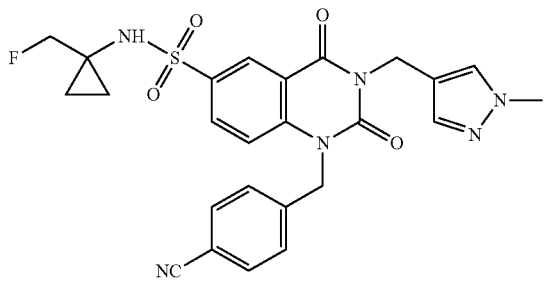 [SMILES: Cn1cc(Cn2c(=O)c3cc(S(=O)(=O)NC4(CF)CC4)ccc3n(Cc3ccc(C#N)cc3)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 4-(bromomethyl)benzonitrile (84 mg, 0.429 mmol) and potassium carbonate (65 mg, 0.468 mmol) in DMF was conventionally heated to 70° C. for 4 h. Usual work-up afforded the desired product (60 mg, 0.115 mmol, 29%) as a white powder.

Example 544 1-(2-Fluoroethyl)-N-[1-(fluoromethyl)cyclopropyl]-3-[(1-methylpyrazol-4-yl)methyl]-2,4-dioxo-quinazoline-6-sulfonamide

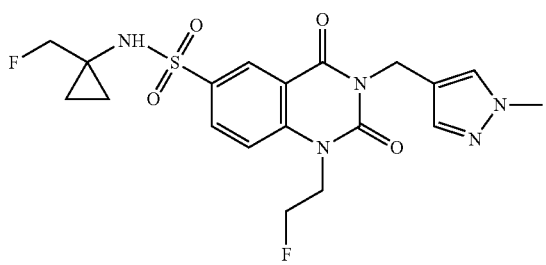 [SMILES: Cn1cc(Cn2c(=O)c3cc(S(=O)(=O)NC4(CF)CC4)ccc3n(CCF)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-fluoro-2-iodoethane (75 mg, 0.429 mmol) and potassium carbonate (65 mg, 0.468 mmol) in DMF was conventionally heated to 70° C. for 4 h. Usual work-up afforded the desired product (14 mg, 0.031 mmol, 7.9%) as a white powder.

Example 545 1-[(3,5-Dimethylisoxazol-4-yl)methyl]-N-[1-(fluoromethyl)cyclopropyl]-3-[(1-methylpyrazol-4-yl)methyl]-2,4-dioxo-quinazoline-6-sulfonamide

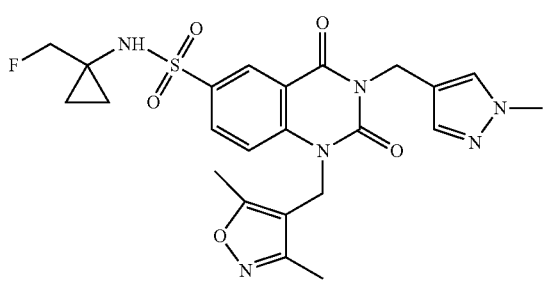 [SMILES: Cc1noc(C)c1Cn1c(=O)n(Cc2cnn(C)c2)c(=O)c2cc(S(=O)(=O)NC3(CF)CC3)ccc21]

The mesylate of (3,5-dimethylisoxazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (25 mg, 0.048 mmol, 19%) as a white powder.

Example 546 N-[1-(Fluoromethyl)cyclopropyl]-1-[(5-methyl-1,2,4-oxadiazol-3-yl)methyl]-3-[(1-methylpyrazol-4-yl)methyl]-2,4-dioxo-quinazoline-6-sulfonamide

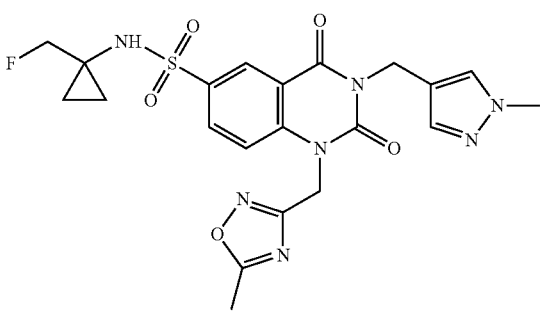 [SMILES: Cc1nc(Cn2c(=O)n(Cc3cnn(C)c3)c(=O)c3cc(S(=O)(=O)NC4(CF)CC4)ccc32)no1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 3-(bromomethyl)-5-methyl-1,2,4-oxadiazole (76 mg, 0.429 mmol) and potassium carbonate (65 mg, 0.468 mmol) in DMF was conventionally heated to 70° C. for 4 h. Usual work-up afforded the desired product (21 mg, 0.042 mmol, 11%) as a white powder.

Example 547 1-[(2,5-Dimethyl-1,2,4-triazol-3-yl)methyl]-N-[1-(fluoromethyl)cyclopropyl]-3-[(1-methylpyrazol-4-yl)methyl]-2,4-dioxo-quinazoline-6-sulfonamide

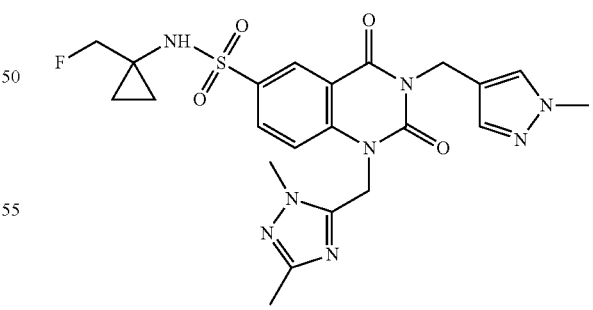

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 5-(chloromethyl)-1,3-dimethyl-1H-1,2,4-triazole (62 mg, 0.429 mmol) and potassium carbonate (65 mg, 0.468 mmol) in DMF was conventionally heated to 70° C. for 4 h. Usual work-up afforded the desired product (10 mg, 0.019 mmol, 5.0%) as a white powder.

Example 548 N-[1-(Fluoromethyl)cyclopropyl]-1-[(2-methyloxazol-5-yl)methyl]-3-[(1-methylpyrazol-4-yl)methyl]-2,4-dioxo-quinazoline-6-sulfonamide

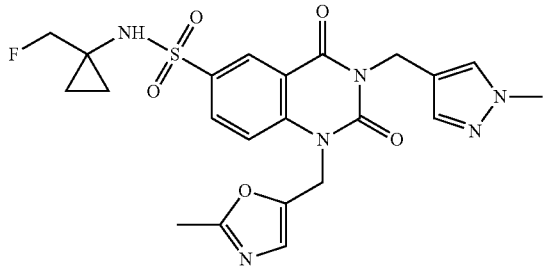 [SMILES: Cc1ncc(Cn2c(=O)n(Cc3cnn(C)c3)c(=O)c3cc(S(=O)(=O)NC4(CF)CC4)ccc32)o1]

The mesylate of (2-methyloxazol-5-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (51 mg, 0.286 mmol) and potassium carbonate (43 mg, 0.312 mmol) in DMF was conventionally heated to 70° C. for 4 h. Usual work-up afforded the desired product (25 mg, 0.050 mmol, 19%) as a white powder.

Example 549 N-[1-(Fluoromethyl)cyclopropyl]-1-isobutyl-3-[(1-methylpyrazol-4-yl)methyl]-2,4-dioxo-quinazoline-6-sulfonamide

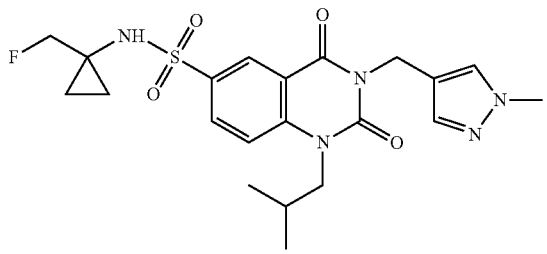 [SMILES: CC(C)Cn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromo-2-methylpropane (59 mg, 0.429 mmol) and potassium carbonate (65 mg, 0.468 mmol) in DMF was conventionally heated to 70° C. for 4 h. Usual work-up afforded the desired product (37 mg, 0.080 mmol, 20%) as a white powder.

Example 550 N-[1-(Fluoromethyl)cyclopropyl]-3-[(3-methylisoxazol-5-yl)methyl]-1-[(2-methylthiazol-4-yl)methyl]-2,4-dioxo-quinazoline-6-sulfonamide

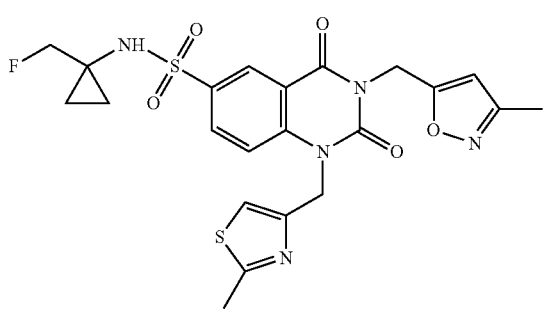 [SMILES: Cc1cc(Cn2c(=O)c3cc(S(=O)(=O)NC4(CF)CC4)ccc3n(Cc3csc(C)n3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 4-(chloromethyl)-2-methyl-1,3-thiazole and 0.2 eq. NaI. This gave the desired product (28 mg, 0.0539 mmol, 37%) as a white powder.

Example 551 N-[1-(Fluoromethyl)cyclopropyl]-3-[(3-methylisoxazol-5-yl)methyl]-1-[(4-methyl-1,2,4-triazol-3-yl)methyl]-2,4-dioxo-quinazoline-6-sulfonamide

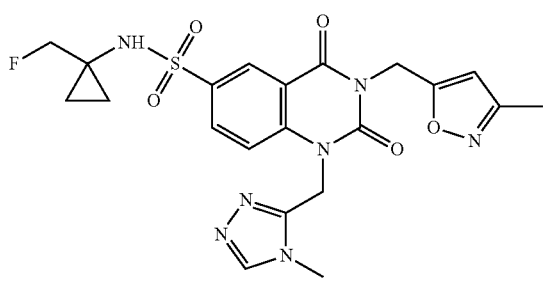 [SMILES: Cc1cc(Cn2c(=O)c3cc(S(=O)(=O)NC4(CF)CC4)ccc3n(Cc3nncn3C)c2=O)on1]

Prepared using Method A10 (with 2.2 eq. $K_2CO_3$), from N-[1-(fluoromethyl)cyclopropyl]-3-[(3-methylisoxazol-5-yl)methyl]-2,4-dioxo-1H-quinazoline-6-sulfonamide, 3-(chloromethyl)-4-methyl-4H-1,2,4-triazole hydrochloride and 0.2 eq. NaI. This gave the desired product (17 mg, 0.0338 mmol, 23%) as a white powder.

Example 552 N-[1-(Fluoromethyl)cyclopropyl]-3-[(3-methylisoxazol-5-yl)methyl]-1-[(5-methyl-1,3,4-thiadiazol-2-yl)methyl]-2,4-dioxo-quinazoline-6-sulfonamide

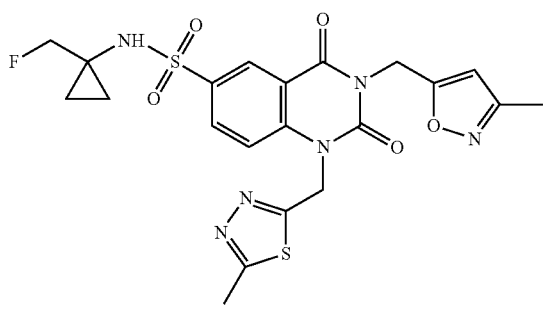 [SMILES: Cc1cc(Cn2c(=O)c3cc(S(=O)(=O)NC4(CF)CC4)ccc3n(Cc3nnc(C)s3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 2-(chloromethyl)-5-methyl-1,3,4-thiadiazole and 0.2 eq. NaI. This gave the desired product (12 mg, 0.0231 mmol, 16%) as a white powder.

Example 553 N-[1-(Fluoromethyl)cyclopropyl]-3-[(3-methylisoxazol-5-yl)methyl]-1-[(1-methyl-1,2,4-triazol-3-yl)methyl]-2,4-dioxo-quinazoline-6-sulfonamide

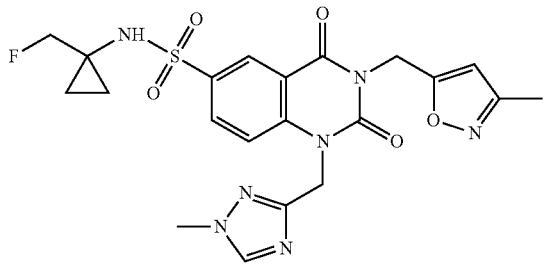 [SMILES: Cc1cc(Cn2c(=O)c3cc(S(=O)(=O)NC4(CF)CC4)ccc3n(Cc3ncn(C)n3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 3-(chloromethyl)-1-methyl-1H-1,2,4-triazole and 0.2 eq. NaI. This gave the desired product (30 mg, 0.0596 mmol, 41%) as a white powder.

Example 554 1-[(2,5-Dimethyl-1,2,4-triazol-3-yl)methyl]-N-[1-(fluoromethyl)cyclopropyl]-3-[(3-methylisoxazol-5-yl)methyl]-2,4-dioxo-quinazoline-6-sulfonamide

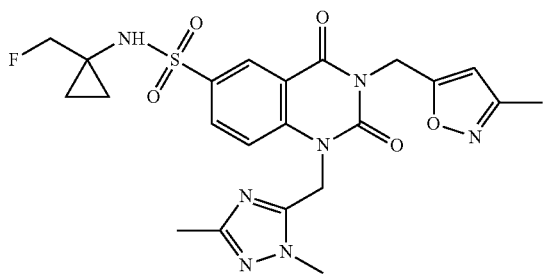 [SMILES: Cc1cc(Cn2c(=O)c3cc(S(=O)(=O)NC4(CF)CC4)ccc3n(Cc3nc(C)nn3C)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 5-(chloromethyl)-1,3-dimethyl-1H-1,2,4-triazole and 0.2 eq. NaI. This gave the desired product (29 mg, 0.0560 mmol, 38%) as a white powder.

Example 555 N-[1-(Fluoromethyl)cyclopropyl]-3-[(3-methylisoxazol-5-yl)methyl]-1-[(1-methylpyrazol-4-yl)methyl]-2,4-dioxo-quinazoline-6-sulfonamide

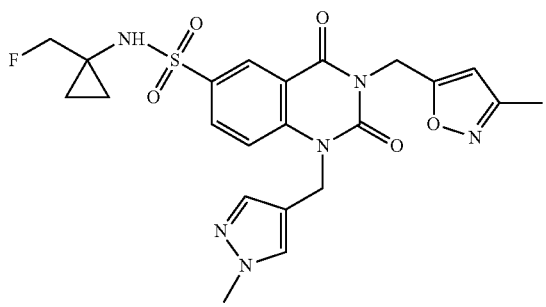 [SMILES: Cc1cc(Cn2c(=O)c3cc(S(=O)(=O)NC4(CF)CC4)ccc3n(Cc3cnn(C)c3)c2=O)on1]

Prepared using Method A10 (with 2.2 eq. K$_2$CO$_3$), from N-[1-(fluoromethyl)cyclopropyl]-3-[(3-methylisoxazol-5-yl)methyl]-2,4-dioxo-1H-quinazoline-6-sulfonamide, 4-(chloromethyl)-1-methyl-1H-pyrazole hydrochloride and 0.2 eq. NaI. This gave the desired product (28 mg, 0.0557 mmol, 38%) as a white powder.

Example 556 N-[1-(Fluoromethyl)cyclopropyl]-3-[(3-methylisoxazol-5-yl)methyl]-1-[(5-methyl-1,3,4-oxadiazol-2-yl)methyl]-2,4-dioxo-quinazoline-6-sulfonamide

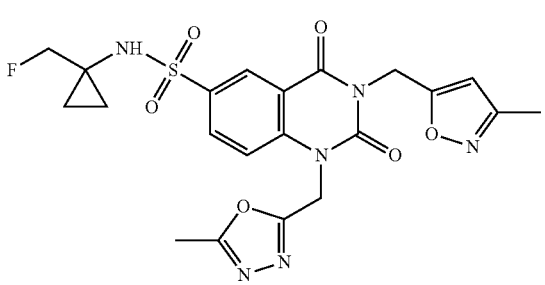 [SMILES: Cc1cc(Cn2c(=O)c3cc(S(=O)(=O)NC4(CF)CC4)ccc3n(Cc3nnc(C)o3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 2-(chloromethyl)-5-methyl-1,3,4-oxadiazole and 0.2 eq. NaI. This gave the desired product (8 mg, 0.0159 mmol, 11%) as a white powder.

Example 557 N-[1-(Fluoromethyl)cyclopropyl]-3-[(3-methylisoxazol-5-yl)methyl]-1-[(2-methyl-1,2,4-triazol-3-yl)methyl]-2,4-dioxo-quinazoline-6-sulfonamide

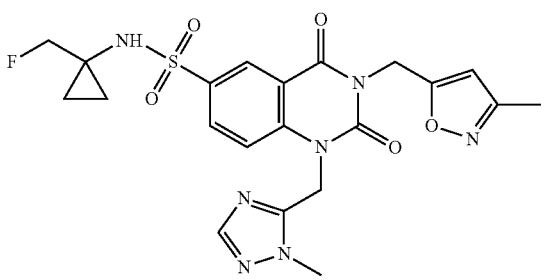 [SMILES: Cc1cc(Cn2c(=O)c3cc(S(=O)(=O)NC4(CF)CC4)ccc3n(Cc3ncnn3C)c2=O)on1]

Prepared using Method A10 (with 2.2 eq. K$_2$CO$_3$), from N-[1-(fluoromethyl)cyclopropyl]-3-[(3-methylisoxazol-5-yl)methyl]-2,4-dioxo-1H-quinazoline-6-sulfonamide, 5-(chloromethyl)-1-methyl-1H-1,2,4-triazole hydrochloride and 0.2 eq. NaI. This gave the desired product (28 mg, 0.0556 mmol, 38%) as a white powder.

Example 558 N-[1-(Fluoromethyl)cyclopropyl]-3-[(3-methylisoxazol-5-yl)methyl]-1-[(5-methyl-1,2,4-oxadiazol-3-yl)methyl]-2,4-dioxo-quinazoline-6-sulfonamide

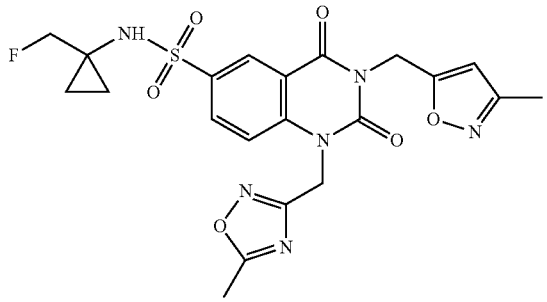 [SMILES: Cc1cc(Cn2c(=O)c3cc(S(=O)(=O)NC4(CF)CC4)ccc3n(Cc3noc(C)n3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, (5-methyl-1,2,4-oxadiazol-3-yl)methyl methanesulfonate and 0.2 eq. NaI. This gave the desired product (30 mg, 0.0595 mmol, 17%) as a white powder.

Example 559 N-[1-(Fluoromethyl)cyclopropyl]-3-[(3-methylisoxazol-5-yl)methyl]-1-(oxazol-4-ylmethyl)-2,4-dioxo-quinazoline-6-sulfonamide

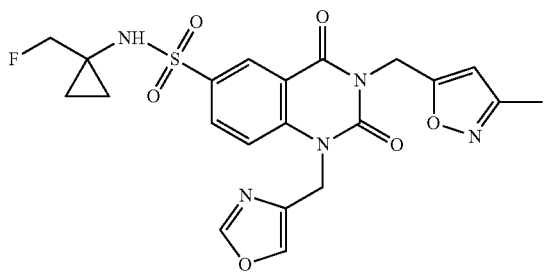 [SMILES: Cc1cc(Cn2c(=O)c3cc(S(=O)(=O)NC4(CF)CC4)ccc3n(Cc3cocn3)c2=O)on1]

Prepared using Method A2, from N-[1-(fluoromethyl)cyclopropyl]-3-[(3-methylisoxazol-5-yl)methyl]-2,4-dioxo-1H-quinazoline-6-sulfonamide and 1,3-oxazol-4-ylmethanol. Bis(4-chlorobenzyl)azodicarboxylate was used in place of DIAD, and the crude product was triturated with DCM to remove the hydrazine by-product. This gave the desired product (8 mg, 0.0163 mmol, 7%) as a white powder.

Example 560 N-[1-(Fluoromethyl)cyclopropyl]-3-[(1-methylpyrazol-4-yl)methyl]-2,4-dioxo-1-(2-pyrazol-1-ylethyl)quinazoline-6-sulfonamide

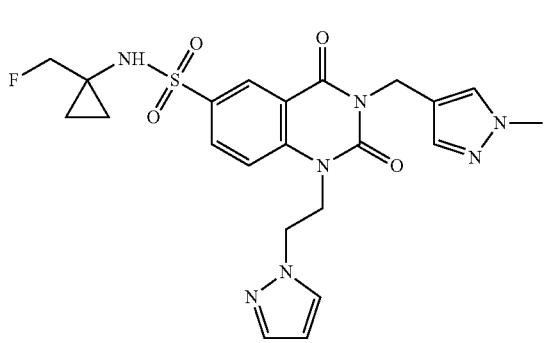 [SMILES: Cn1cc(Cn2c(=O)c3cc(S(=O)(=O)NC4(CF)CC4)ccc3n(CCn3cccn3)c2=O)cn1]

1-(2-Chloroethyl)-1H-pyrazole was prepared by reacting pyrazole with 1-bromo-2-chloroethane. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), 1-(2-chloroethyl)-1H-pyrazole (37 mg, 0.286 mmol) and potassium carbonate (43 mg, 0.312 mmol) in DMF was conventionally heated to 70° C. for 4 h. Usual work-up afforded the desired product (7 mg, 0.014 mmol, 5.4%) as a white powder.

Example 561 N-[1-(Fluoromethyl)cyclopropyl]-3-[(1-methylpyrazol-4-yl)methyl]-1-[(3-methyl-1H-pyrazol-5-yl)methyl]-2,4-dioxo-quinazoline-6-sulfonamide

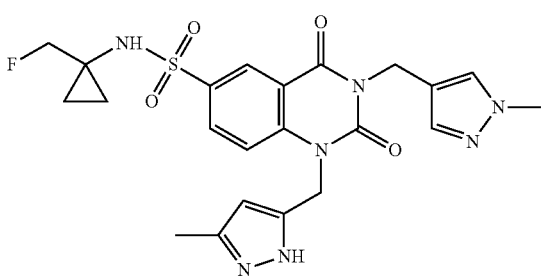 [SMILES: Cc1cc(Cn2c(=O)n(Cc3cnn(C)c3)c(=O)c3cc(S(=O)(=O)NC4(CF)CC4)ccc32)[nH]n1]

(3-Methyl-1H-pyrazol-5-yl)methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (83 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (6 mg, 0.012 mmol, 4.6%) as a white powder.

Example 562 N-[1-(Fluoromethyl)cyclopropyl]-3-[(1-methylpyrazol-4-yl)methyl]-1-[(2-methyl-1,2,4-triazol-3-yl)methyl]-2,4-dioxo-quinazoline-6-sulfonamide

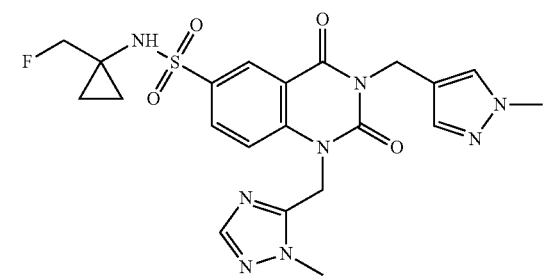

The mesylate of (1-methyl-1H-1,2,4-triazol-5-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (30 mg, 0.060 mmol, 23%) as a white powder.

Example 563 N-[1-(Fluoromethyl)cyclopropyl]-3-[(1-methylpyrazol-4-yl)methyl]-2,4-dioxo-1-(thiazol-5-ylmethyl)quinazoline-6-sulfonamide

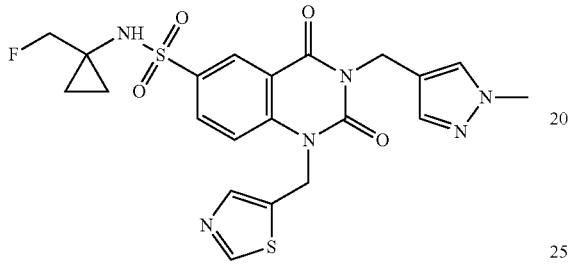

The mesylate of thiazol-5-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (15 mg, 0.030 mmol, 11%) as a white powder.

Example 564 N-[1-(Fluoromethyl)cyclopropyl]-3-[(1-methylpyrazol-4-yl)methyl]-1-(oxazol-5-ylmethyl)-2,4-dioxo-quinazoline-6-sulfonamide

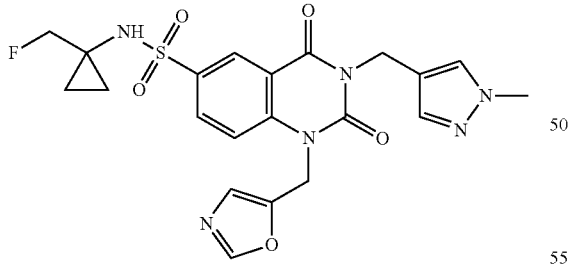

The mesylate of oxazol-5-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (51 mg, 0.286 mmol) and potassium carbonate (43 mg, 0.312 mmol) in DMF was conventionally heated to 70° C. for 4 h. Usual work-up afforded the desired product (20 mg, 0.041 mmol, 16%) as a white powder.

Example 565 N-[1-(Fluoromethyl)cyclopropyl]-1-[(1-methylimidazol-2-yl)methyl]-3-[(1-methylpyrazol-4-yl)methyl]-2,4-dioxo-quinazoline-6-sulfonamide

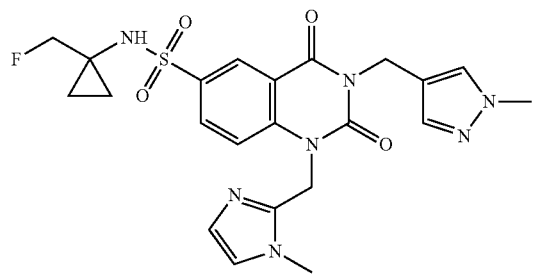

(1-Methyl-1H-imidazol-2-yl)methanol was converted to the corresponding alkyl chloride by reaction with thionyl chloride in DCM. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the alkyl chloride (37 mg, 0.286 mmol) and potassium carbonate (43 mg, 0.312 mmol) in DMF was conventionally heated to 70° C. for 4 h. Usual work-up afforded the desired product (66 mg, 0.132 mmol, 51%) as a white powder.

Example 566 N-[1-(Fluoromethyl)cyclopropyl]-3-[(1-methylpyrazol-4-yl)methyl]-2,4-dioxo-1-[2-(2-pyridyl)ethyl]quinazoline-6-sulfonamide

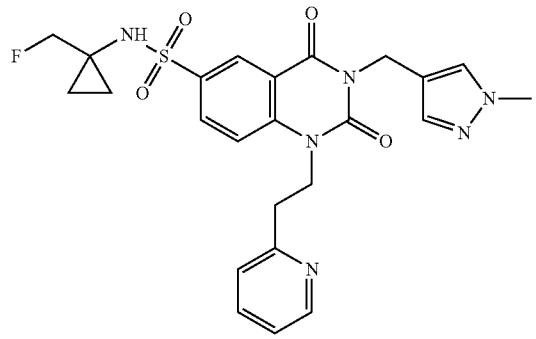 [SMILES: Cn1cc(Cn2c(=O)c3cc(S(=O)(=O)NC4(CF)CC4)ccc3n(CCc3ccccn3)c2=O)cn1]

The mesylate of 2-(2-pyridyl)ethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (57 mg, 0.286 mmol) and potassium carbonate (43 mg, 0.312 mmol) in DMF was conventionally heated to 70° C. for 4 h. Usual work-up afforded the desired product (11 mg, 0.021 mmol, 8.2%) as a white powder.

Example 567 N-[1-(Fluoromethyl)cyclopropyl]-1-[(5-methyl-1,3,4-oxadiazol-2-yl)methyl]-3-[(1-methylpyrazol-4-yl)methyl]-2,4-dioxo-quinazoline-6-sulfonamide

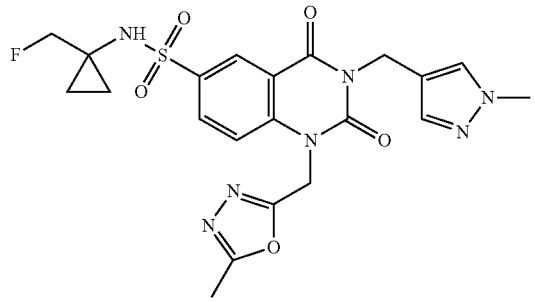 [SMILES: Cc1nnc(Cn2c(=O)n(Cc3cnn(C)c3)c(=O)c3cc(S(=O)(=O)NC4(CF)CC4)ccc32)o1]

The mesylate of (5-methyl-1,3,4-oxadiazol-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (28 mg, 0.056 mmol, 21%) as a powder.

Example 568 N-[1-(Fluoromethyl)cyclopropyl]-1-[(2-methyl-1H-imidazol-4-yl)methyl]-3-[(1-methylpyrazol-4-yl)methyl]-2,4-dioxo-quinazoline-6-sulfonamide

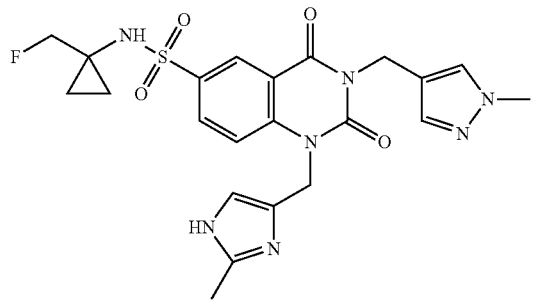 [SMILES: Cc1nc(Cn2c(=O)n(Cc3cnn(C)c3)c(=O)c3cc(S(=O)(=O)NC4(CF)CC4)ccc32)c[nH]1]

2-Methyl-1H-imidazole-5-methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (83 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (11 mg, 0.022 mmol, 8.4%) as a white powder.

Example 569 N-[1-(Fluoromethyl)cyclopropyl]-1-[(5-methylpyrazin-2-yl)methyl]-3-[(1-methylpyrazol-4-yl)methyl]-2,4-dioxo-quinazoline-6-sulfonamide

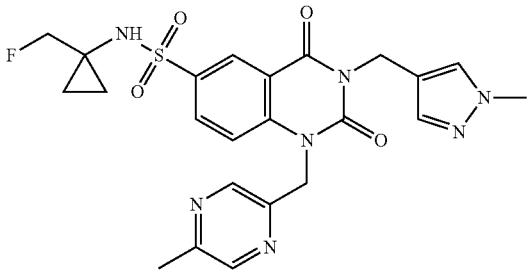 [SMILES: Cc1cnc(Cn2c(=O)n(Cc3cnn(C)c3)c(=O)c3cc(S(=O)(=O)NC4(CF)CC4)ccc32)cn1]

The mesylate of (5-methylpyrazin-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (54 mg, 0.286 mmol) and potassium carbonate (43 mg, 0.312 mmol) in DMF was conventionally heated to 70° C. for 4 h. Usual work-up afforded the desired product (35 mg, 0.068 mmol, 26%) as a white powder.

Example 570 N-[1-(Fluoromethyl)cyclopropyl]-1-[[1-(hydroxymethyl)cyclopropyl]methyl]-3-[(1-methylpyrazol-4-yl)methyl]-2,4-dioxo-quinazoline-6-sulfonamide

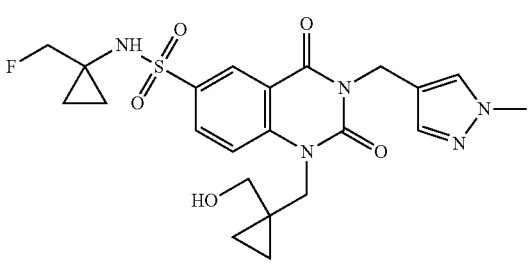 [SMILES: Cn1cc(Cn2c(=O)c3cc(S(=O)(=O)NC4(CF)CC4)ccc3n(CC3(CO)CC3)c2=O)cn1]

Cyclopropane-1,1-diyldimethanol was mono-protected as a TBDMS ether using TBDMS chloride and triethylamine in DCM. The free alcohol was then converted to the mesylate using methanesulfonyl chloride and triethylamine in DCM. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (84 mg, 0.286 mmol) and potassium carbonate (43 mg, 0.312 mmol) in DMF was conventionally heated to 70° C. for 4 h. After deprotection of the TBDMS group, usual work-up afforded the desired product (13 mg, 0.026 mmol, 10%) as a white powder.

Example 571 N-[1-(Fluoromethyl)cyclopropyl]-3-[(1-methylpyrazol-4-yl)methyl]-1-[(4-methyl-2-pyridyl)methyl]-2,4-dioxo-quinazoline-6-sulfonamide

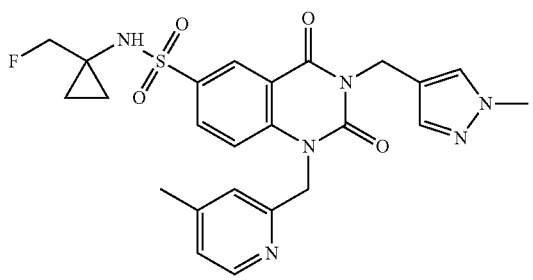 [SMILES: Cc1ccnc(Cn2c(=O)n(Cc3cnn(C)c3)c(=O)c3cc(S(=O)(=O)NC4(CF)CC4)ccc32)c1]

The mesylate of (4-methylpyridin-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (57 mg, 0.286 mmol) and potassium carbonate (43 mg, 0.312 mmol) in DMF was conventionally heated to 70° C. for 4 h. Usual work-up afforded the desired product (14 mg, 0.027 mmol, 11%) as a white powder.

Example 572 N-[1-(Fluoromethyl)cyclopropyl]-3-[(1-methylpyrazol-4-yl)methyl]-1-[(4-methylthiazol-5-yl)methyl]-2,4-dioxo-quinazoline-6-sulfonamide

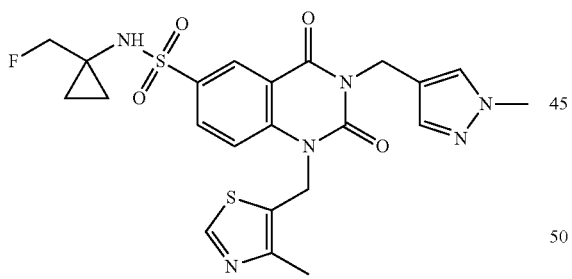

The mesylate of (4-methylthiazol-5-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (56 mg, 0.286 mmol) and potassium carbonate (43 mg, 0.312 mmol) in DMF was conventionally heated to 70° C. for 4 h. Usual work-up afforded the desired product (15 mg, 0.029 mmol, 11%) as a white powder.

Example 573 N-[1-(Fluoromethyl)cyclopropyl]-3-[(1-methylpyrazol-4-yl)methyl]-1-[(6-methyl-3-pyridyl)methyl]-2,4-dioxo-quinazoline-6-sulfonamide

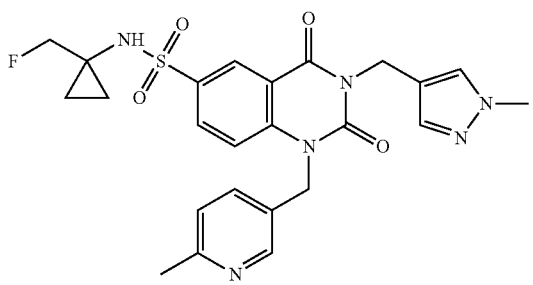 [SMILES: Cc1ccc(Cn2c(=O)n(Cc3cnn(C)c3)c(=O)c3cc(S(=O)(=O)NC4(CF)CC4)ccc32)cn1]

The mesylate of (6-methylpyridin-3-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (57 mg, 0.286 mmol) and potassium carbonate (43 mg, 0.312 mmol) in DMF was conventionally heated to 70° C. for 4 h. Usual work-up afforded the desired product (11 mg, 0.021 mmol, 8.2%) as a white powder.

Example 574 1-(2-Cyanoethyl)-N-[1-(fluoromethyl)cyclopropyl]-3-[(1-methylpyrazol-4-yl)methyl]-2,4-dioxo-quinazoline-6-sulfonamide

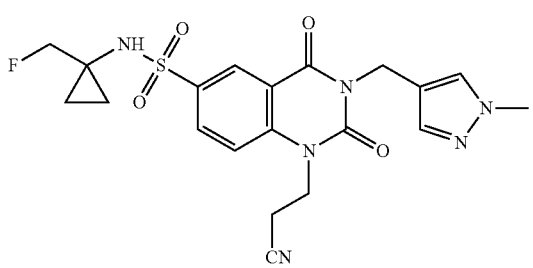 [SMILES: Cn1cc(Cn2c(=O)c3cc(S(=O)(=O)NC4(CF)CC4)ccc3n(CCC#N)c2=O)cn1]

3-Hydroxypropanenitrile was converted to the corresponding mesylate by reaction with methanesulfonyl chloride and triethylamine in DCM. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the m (26 mg, 0.286 mmol) and potassium carbonate (43 mg, 0.312 mmol) in DMF was conventionally heated to 70° C. for 4 h. Usual work-up afforded the desired product (10 mg, 0.022 mmol, 8.4%) as a white powder.

Example 575 N-[1-(Fluoromethyl)cyclopropyl]-1-(1H-imidazol-4-ylmethyl)-3-[(1-methylpyrazol-4-yl)methyl]-2,4-dioxo-quinazoline-6-sulfonamide

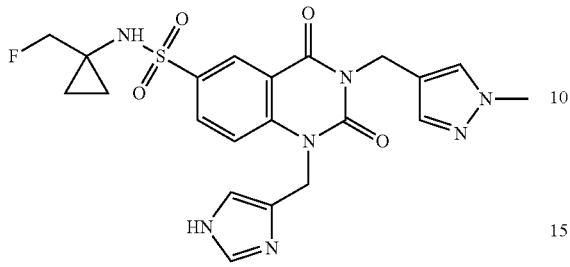

1H-Imidazole-5-methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (79 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (31 mg, 0.064 mmol, 24%) as an off-white powder.

Example 576 1-[(3-Ethylimidazol-4-yl)methyl]-N-[1-(fluoromethyl)cyclopropyl]-3-[(1-methylpyrazol-4-yl)methyl]-2,4-dioxo-quinazoline-6-sulfonamide

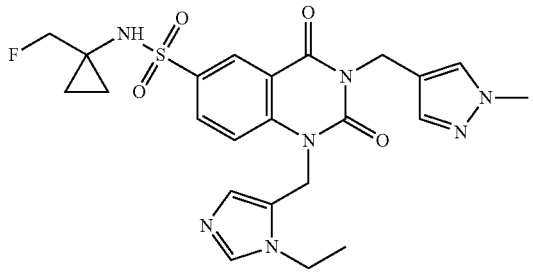 [SMILES: CCn1cncc1Cn1c(=O)n(Cc2cnn(C)c2)c(=O)c2cc(S(=O)(=O)NC3(CF)CC3)ccc21]

(1-Ethyl-1H-imidazol-5-yl)methanol was converted to the corresponding alkyl chloride by reaction with thionyl chloride in DCM. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the alkyl chloride (41 mg, 0.286 mmol) and potassium carbonate (43 mg, 0.312 mmol) in DMF was conventionally heated to 70° C. for 4 h. Usual work-up afforded the desired product (12 mg, 0.023 mmol, 9%) as a white powder.

Example 577 N-[1-(Fluoromethyl)cyclopropyl]-1-(isothiazol-4-ylmethyl)-3-[(1-methylpyrazol-4-yl)methyl]-2,4-dioxo-quinazoline-6-sulfonamide

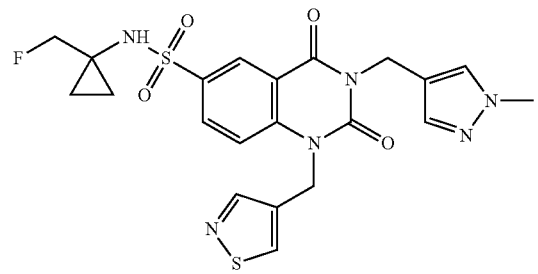 [SMILES: Cn1cc(Cn2c(=O)c3cc(S(=O)(=O)NC4(CF)CC4)ccc3n(Cc3cnsc3)c2=O)cn1]

The mesylate of isothiazol-4-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (33 mg, 0.065 mmol, 25%) as a white powder.

Example 578 N-[1-(Fluoromethyl)cyclopropyl]-1-(isothiazol-5-ylmethyl)-3-[(1-methylpyrazol-4-yl)methyl]-2,4-dioxo-quinazoline-6-sulfonamide

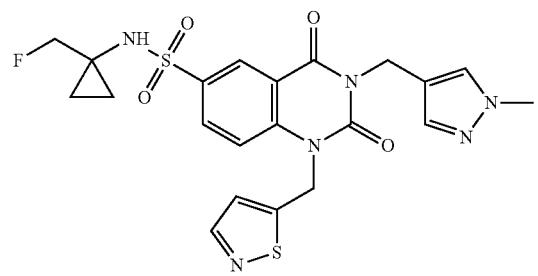

The mesylate of isothiazol-5-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (52 mg, 0.286 mmol) and potassium carbonate (43 mg, 0.312 mmol) in DMF was conventionally heated to 70° C. for 4 h. Usual work-up afforded the desired product (21 mg, 0.042 mmol, 16%) as a white powder.

Example 579 N-[1-(Fluoromethyl)cyclopropyl]-1-[(5-methylisoxazol-4-yl)methyl]-3-[(1-methylpyrazol-4-yl)methyl]-2,4-dioxo-quinazoline-6-sulfonamide

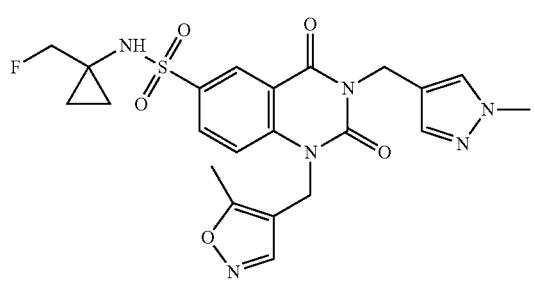 [SMILES: Cc1oncc1Cn1c(=O)n(Cc2cnn(C)c2)c(=O)c2cc(S(=O)(=O)NC3(CF)CC3)ccc21]

The mesylate of (5-methylisoxazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (17 mg, 0.034 mmol, 13%) as a white powder.

Example 580 N-[1-(Fluoromethyl)cyclopropyl]-1-[(2-methyloxazol-4-yl)methyl]-3-[(1-methylpyrazol-4-yl)methyl]-2,4-dioxo-quinazoline-6-sulfonamide

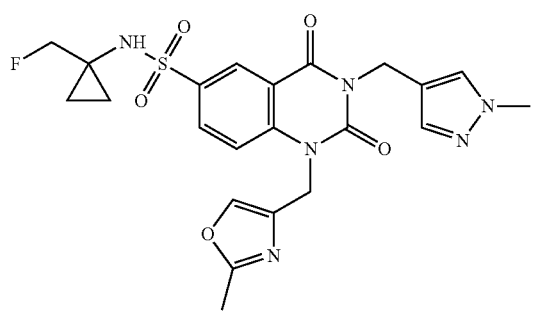 [SMILES: Cc1nc(Cn2c(=O)n(Cc3cnn(C)c3)c(=O)c3cc(S(=O)(=O)NC4(CF)CC4)ccc32)co1]

The mesylate of (2-methyloxazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (54 mg, 0.286 mmol) and potassium carbonate (43 mg, 0.312 mmol) in DMF was conventionally heated to 70° C. for 4 h. Usual work-up afforded the desired product (16 mg, 0.032 mmol, 12%) as a white powder.

Example 581 N-[1-(Fluoromethyl)cyclopropyl]-3-[(1-methylpyrazol-4-yl)methyl]-2,4-dioxo-1-(thiazol-4-ylmethyl)quinazoline-6-sulfonamide

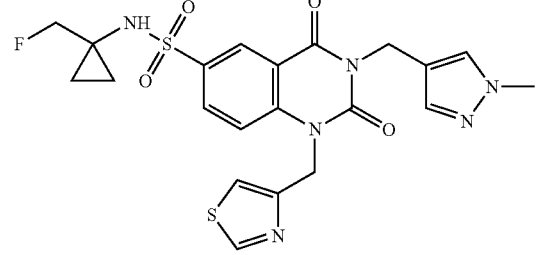

The mesylate of thiazol-4-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (52 mg, 0.286 mmol) and potassium carbonate (43 mg, 0.312 mmol) in DMF was conventionally heated to 70° C. for 4 h. Usual work-up afforded the desired product (11 mg, 0.022 mmol, 8.4%) as a white powder.

Example 582 N-[1-(Fluoromethyl)cyclopropyl]-3-[(1-methylpyrazol-4-yl)methyl]-1-[(2-methylthiazol-4-yl)methyl]-2,4-dioxo-quinazoline-6-sulfonamide

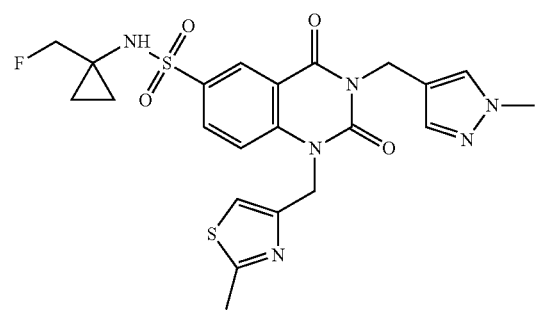 [SMILES: Cc1nc(Cn2c(=O)n(Cc3cnn(C)c3)c(=O)c3cc(S(=O)(=O)NC4(CF)CC4)ccc32)cs1]

The mesylate of (2-methylthiazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (59 mg, 0.286 mmol) and potassium carbonate (43 mg, 0.312 mmol) in DMF was conventionally heated to 70° C. for 4 h. Usual work-up afforded the desired product (13 mg, 0.025 mmol, 10%) as a white powder.

Example 583 N-[1-(Fluoromethyl)cyclopropyl]-3-[(1-methylpyrazol-4-yl)methyl]-1-[(5-methyl-1,3,4-thiadiazol-2-yl)methyl]-2,4-dioxo-quinazoline-6-sulfonamide

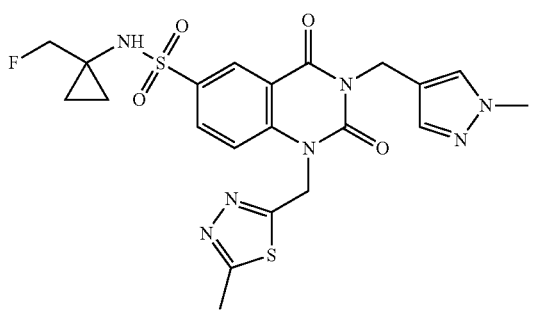 [SMILES: Cc1nnc(Cn2c(=O)n(Cc3cnn(C)c3)c(=O)c3cc(S(=O)(=O)NC4(CF)CC4)ccc32)s1]

The mesylate of (5-methyl-1,3,4-thiadiazol-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (60 mg, 0.286 mmol) and potassium carbonate (43 mg, 0.312 mmol) in DMF was conventionally heated to 70° C. for 4 h. Usual work-up afforded the desired product (19 mg, 0.037 mmol, 14%) as a white powder.

Example 584 N-[1-(Fluoromethyl)cyclopropyl]-3-[(1-methylpyrazol-4-yl)methyl]-1-[(4-methyl-1,2,4-triazol-3-yl)methyl]-2,4-dioxo-quinazoline-6-sulfonamide

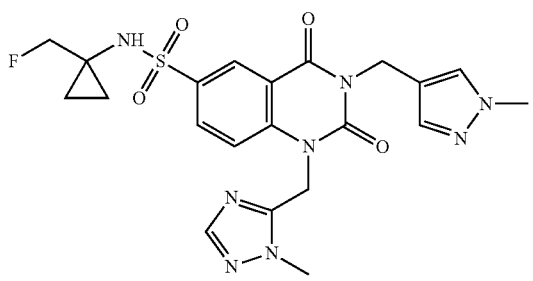 [SMILES: Cn1cc(Cn2c(=O)c3cc(S(=O)(=O)NC4(CF)CC4)ccc3n(Cc3ncnn3C)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 3-(chloromethyl)-4-methyl-4H-1,2,4-triazole (66 mg, 0.429 mmol) and potassium carbonate (65 mg, 0.468 mmol) in DMF was conventionally heated to 70° C. for 4 h. Usual work-up afforded the desired product (19 mg, 0.038 mmol, 9.7%) as a white powder.

Example 585 N-[1-(Fluoromethyl)cyclopropyl]-1-(isoxazol-5-ylmethyl)-3-[(1-methylpyrazol-4-yl)methyl]-2,4-dioxo-quinazoline-6-sulfonamide

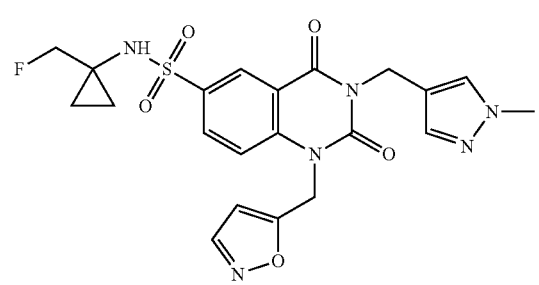 [SMILES: Cn1cc(Cn2c(=O)c3cc(S(=O)(=O)NC4(CF)CC4)ccc3n(Cc3ccno3)c2=O)cn1]

The mesylate of isoxazol-5-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (51 mg, 0.286 mmol) and potassium carbonate (43 mg, 0.312 mmol) in DMF was conventionally heated to 70° C. for 4 h. Usual work-up afforded the desired product (13 mg, 0.027 mmol, 10%) as a white powder.

Example 586 N-[1-(Fluoromethyl)cyclopropyl]-3-[(1-methylpyrazol-4-yl)methyl]-2,4-dioxo-1-(1H-pyrazol-3-ylmethyl)quinazoline-6-sulfonamide

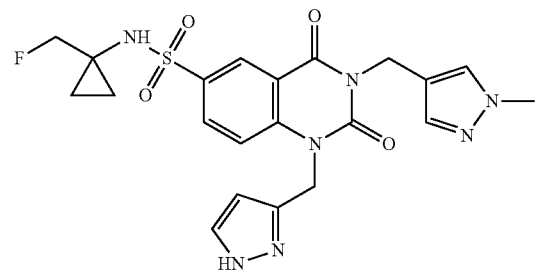 [SMILES: Cn1cc(Cn2c(=O)c3cc(S(=O)(=O)NC4(CF)CC4)ccc3n(Cc3cc[nH]n3)c2=O)cn1]

(1H-Pyrazol-3-yl)methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (79 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (6 mg, 0.012 mmol, 4.7%) as a white powder.

Example 587 N-[1-(Fluoromethyl)cyclopropyl]-3-[(1-methylpyrazol-4-yl)methyl]-2,4-dioxo-1-(1H-1,2,4-triazol-3-ylmethyl)quinazoline-6-sulfonamide

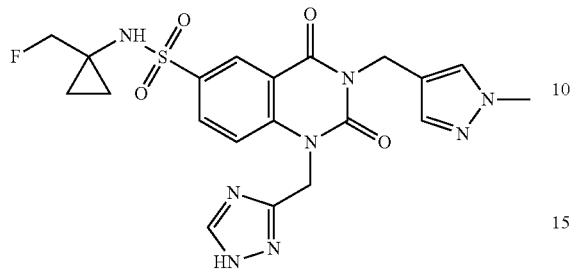

1H-1,2,4-Triazole-5-methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (79 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (8 mg, 0.016 mmol, 6.3%) as a white powder.

Example 588 N-[1-(Fluoromethyl)cyclopropyl]-1-[(3-methylimidazol-4-yl)methyl]-3-[(1-methylpyrazol-4-yl)methyl]-2,4-dioxo-quinazoline-6-sulfonamide

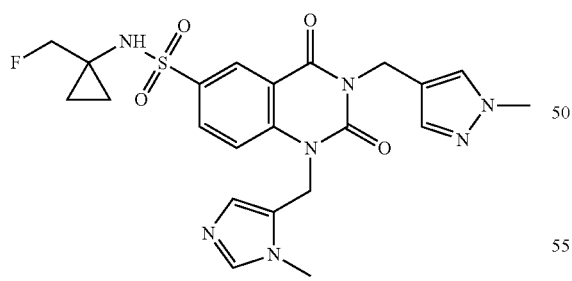

(1-Methyl-1H-imidazol-5-yl)methanol was converted to the corresponding alkyl chloride by reaction with thionyl chloride in DCM. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the alkyl chloride (37 mg, 0.286 mmol) and potassium carbonate (43 mg, 0.312 mmol) in DMF was conventionally heated to 70° C. for 4 h. Usual work-up afforded the desired product (37 mg, 0.074 mmol, 28%) as an off-white powder.

Example 589 N-[1-(Fluoromethyl)cyclopropyl]-3-[(1-methylpyrazol-4-yl)methyl]-2,4-dioxo-1-(1,3,4-thiadiazol-2-ylmethyl)quinazoline-6-sulfonamide

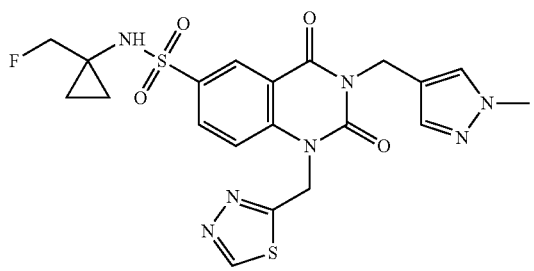 [SMILES: Cn1cc(Cn2c(=O)c3cc(S(=O)(=O)NC4(CF)CC4)ccc3n(Cc3nncs3)c2=O)cn1]

The mesylate of (1,3,4-thiadiazol-2-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (56 mg, 0.286 mmol) and potassium carbonate (43 mg, 0.312 mmol) in DMF was conventionally heated to 70° C. for 4 h. Usual work-up afforded the desired product (24 mg, 0.047 mmol, 18%) as a white powder.

Example 590 N-[1-(Fluoromethyl)cyclopropyl]-3-[(1-methylpyrazol-4-yl)methyl]-2,4-dioxo-1-(1H-pyrazol-4-ylmethyl)quinazoline-6-sulfonamide

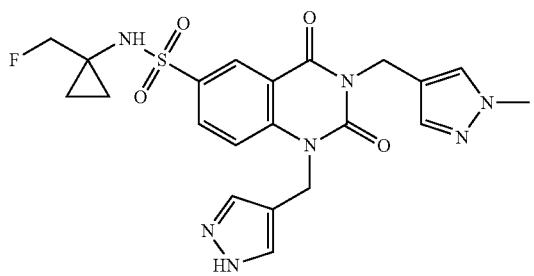 [SMILES: Cn1cc(Cn2c(=O)c3cc(S(=O)(=O)NC4(CF)CC4)ccc3n(Cc3cn[nH]c3)c2=O)cn1]

(1H-Pyrazol-4-yl)methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (79 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (14 mg, 0.029 mmol, 11%) as a white powder.

Example 591 N-[1-(Fluoromethyl)cyclopropyl]-1-[(3-methylisothiazol-5-yl)methyl]-3-[(1-methylpyrazol-4-yl)methyl]-2,4-dioxo-quinazoline-6-sulfonamide

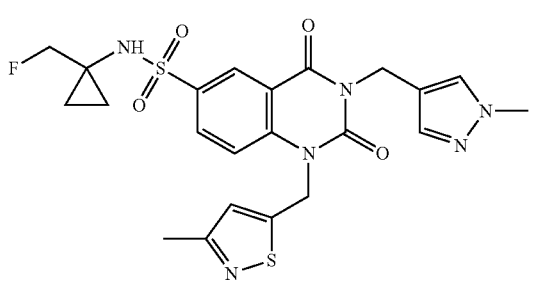 [SMILES: Cc1cc(Cn2c(=O)n(Cc3cnn(C)c3)c(=O)c3cc(S(=O)(=O)NC4(CF)CC4)ccc32)sn1]

The mesylate of (3-methylisothiazol-5-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (59 mg, 0.286 mmol) and potassium carbonate (43 mg, 0.312 mmol) in DMF was conventionally heated to 70° C. for 4 h. Usual work-up afforded the desired product (7 mg, 0.013 mmol, 5.2%) as a powder.

Example 592 N-[1-(Fluoromethyl)cyclopropyl]-3-[(1-methylpyrazol-4-yl)methyl]-1-[(3-methyl-1H-1,2,4-triazol-5-yl)methyl]-2,4-dioxo-quinazoline-6-sulfonamide

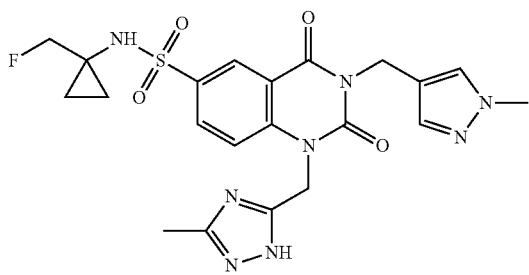 [SMILES: Cc1n[nH]c(Cn2c(=O)n(Cc3cnn(C)c3)c(=O)c3cc(S(=O)(=O)NC4(CF)CC4)ccc32)n1]

(3-Methyl-1H-1,2,4-triazol-5-yl)methanol was Boc-protected by reaction with Boc-anhydride (1.2 eq) and triethylamine (2.5 eq) in DCM at 0° C., with warming to ambient temperature. The alcohol of this Boc-protected amine was then converted to the mesylate by reaction with methanesulfonyl chloride (1.5 eq) and triethylamine (2.5 eq) in DCM at 0° C., with warming to ambient temperature for 2 h. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the mesylate (83 mg, 0.286 mmol) and potassium carbonate (54 mg, 0.39 mmol) in DMF was conventionally heated to 70° C. for 4 h. After Boc-deprotection with HCl in dioxane, usual work-up afforded the desired product (12 mg, 0.030 mmol, 11%) as a white powder.

Example 593 N-[1-(Fluoromethyl)cyclopropyl]-3-[(1-methylpyrazol-4-yl)methyl]-1-[(1-methyltriazol-4-yl)methyl]-2,4-dioxo-quinazoline-6-sulfonamide

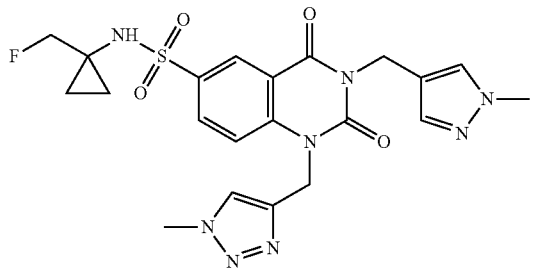 [SMILES: Cn1cc(Cn2c(=O)c3cc(S(=O)(=O)NC4(CF)CC4)ccc3n(Cc3cn(C)nn3)c2=O)cn1]

The mesylate of (1-methyl-1H-1,2,3-triazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (29 mg, 0.058 mmol, 22%) as a white powder.

Example 594 N-[1-(Fluoromethyl)cyclopropyl]-3-[(1-methylpyrazol-4-yl)methyl]-1-[(2-methylthiazol-5-yl)methyl]-2,4-dioxo-quinazoline-6-sulfonamide

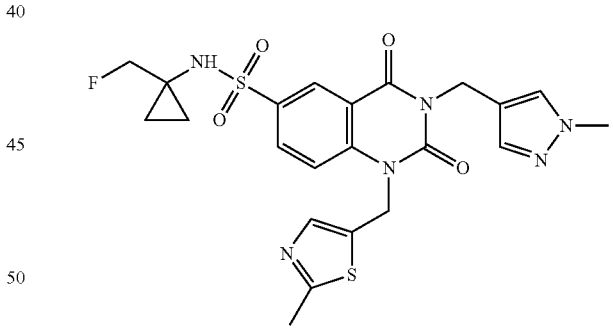

The mesylate of (2-methylthiazol-5-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (56 mg, 0.286 mmol) and potassium carbonate (43 mg, 0.312 mmol) in DMF was conventionally heated to 70° C. for 4 h. Usual work-up afforded the desired product (12 mg, 0.023 mmol, 8.9%) as a white powder.

Example 595 N-[1-(Fluoromethyl)cyclopropyl]-1,3-bis[(1-methylpyrazol-4-yl)methyl]-2,4-dioxo-quinazoline-6-sulfonamide

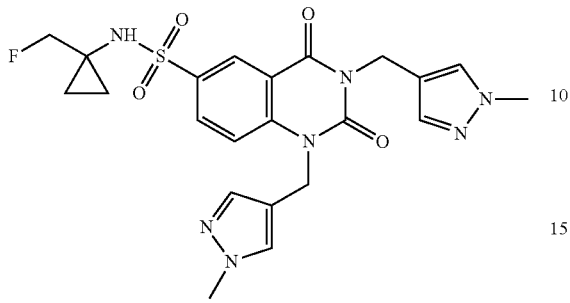

The mesylate of (1-methyl-1H-pyrazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (54 mg, 0.286 mmol) and potassium carbonate (43 mg, 0.312 mmol) in DMF was conventionally heated to 70° C. for 4 h. Usual work-up afforded the desired product (12 mg, 0.024 mmol, 9.2%) as a white powder.

Example 596 N-[1-(Fluoromethyl)cyclopropyl]-3-[(1-methylpyrazol-4-yl)methyl]-1-[(2-methyltriazol-4-yl)methyl]-2,4-dioxo-quinazoline-6-sulfonamide

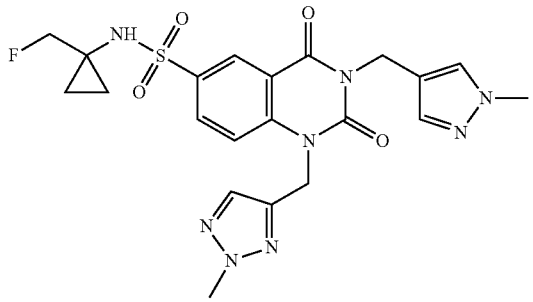 [SMILES: Cn1cc(Cn2c(=O)c3cc(S(=O)(=O)NC4(CF)CC4)ccc3n(Cc3cnn(C)n3)c2=O)cn1]

The mesylate of (2-methyl-2H-1,2,3-triazol-4-yl)methanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (55 mg, 0.286 mmol) and potassium carbonate (43 mg, 0.312 mmol) in DMF was conventionally heated to 70° C. for 4 h. Usual work-up afforded the desired product (22 mg, 0.044 mmol, 17%) as a white powder.

Example 597 N-[1-(Fluoromethyl)cyclopropyl]-3-[(1-methylpyrazol-4-yl)methyl]-2,4-dioxo-1-propyl-quinazoline-6-sulfonamide

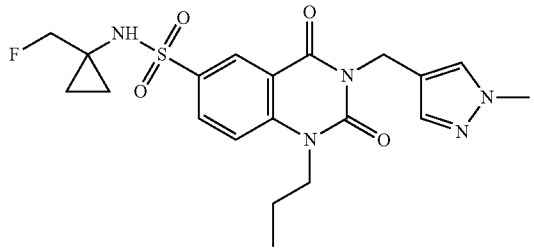 [SMILES: CCCn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromopropane (52 mg, 0.429 mmol) and potassium carbonate (65 mg, 0.468 mmol) in DMF was conventionally heated to 70° C. for 4 h. Usual work-up afforded the desired product (6 mg, 0.013 mmol, 3.4%) as a white powder.

Example 598 N-[1-(Fluoromethyl)cyclopropyl]-3-[(1-methylpyrazol-4-yl)methyl]-2,4-dioxo-1-(tetrahydrofuran-3-ylmethyl)quinazoline-6-sulfonamide

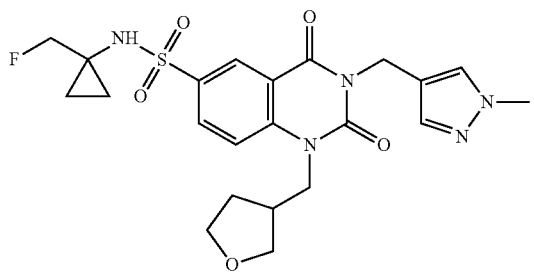 [SMILES: Cn1cc(Cn2c(=O)c3cc(S(=O)(=O)NC4(CF)CC4)ccc3n(CC3CCOC3)c2=O)cn1]

The tosylate of (tetrahydrofuran-3-yl)methanol was prepared by reaction with tosyl chloride and triethylamine in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude tosylate (73 mg, 0.286 mmol) and potassium carbonate (43 mg, 0.312 mmol) in DMF was conventionally heated to 70° C. for 4 h. Usual work-up afforded the desired product (17 mg, 0.035 mmol, 13%) as a white powder.

Example 599 1-(2,2-Difluoroethyl)-N-(1-methylcyclopropyl)-3-[(1-methylpyrazol-4-yl)methyl]-2,4-dioxo-quinazoline-6-sulfonamide

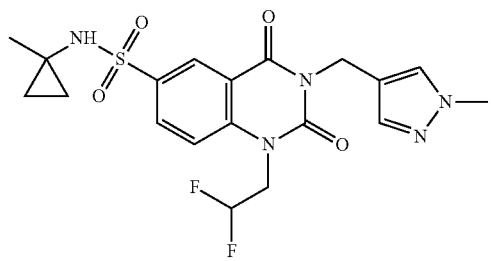

A stirred solution of 3-[(1-methylpyrazol-4-yl)methyl]-1H-quinazoline-2,4-dione (800 mg, 3.12 mmol) in DMF (10 mL) was treated with 2-iodo-1,1-difluoroethane (330 μL, 3.75 mmol) and potassium carbonate (863 mg, 6.24 mmol) and the mixture stirred at room temp over the weekend. More 2-iodo-1,1-difluoroethane (1.5 mmol) was added and the mixture heated in the microwave at 80° C. for 2 h. The reaction mixture was diluted with water (100 mL) and extracted with EtOAc (2×200 mL), the organic phase was combined, washed with brine (10 mL), passed through a hydrophobic frit and evaporated to dryness to give 1-(2,2-difluoroethyl)-3-[(1-methylpyrazol-4-yl)methyl]quinazoline-2,4-dione (602 mg, 1.88 mmol, 60%) used in the next step without further purification.

$^1$H NMR (300 MHz, DMSO-d$_6$) δ=8.09 (dd, J=7.9, 1.6 Hz, 1H), 7.81-7.74 (m, 1H), 7.66 (s, 1H), 7.60 (d, J=8.5 Hz, 1H), 7.38 (m, 1H), 7.33 (d, J=7.6 Hz, 1H), 6.35 (tt, J=55, 3.9 Hz, 1H), 4.96 (s, 2H), 4.70-4.57 (m, 2H), 3.76 (s, 3H).

Chlorosulfonic acid (6 mL) was added to 1-(2,2-difluoroethyl)-3-[(1-methylpyrazol-4-yl)methyl]quinazoline-2,4-dione (600 mg, 1.87 mmol) at 5° C. The mixture was heated at 50° C. for 4 h and then left to cool. The reaction mixture was added dropwise to stirring ice/water and quickly extracted with DCM and 5% MeOH/DCM. The combined extracts were evaporated to dryness to yield 1-(2,2-difluoroethyl)-3-[(1-methylpyrazol-4-yl)methyl]-2,4-dioxo-quinazoline-6-sulfonyl chloride (765 mg, 1.83 mmol, 97%) which was used in the next step without purification.

To a solution of N,N-diisopropylethylamine (0.49 mL, 2.79 mmol) in THF (10 mL) and DCM (6 mL) cooled in an ice bath, was added a mixture of methylcyclopropanamine hydrochloride (0.2 g, 1.87 mmol) and then portionwise 1-(2,2-difluoroethyl)-3-[(1-methylpyrazol-4-yl)methyl]-2,4-dioxo-quinazoline-6-sulfonyl chloride (0.39 g, 0.93 mmol). After stirring overnight, the solvent was evaporated and the residue purified by prep hplc to give the desired product (58 mg, 0.128 mmol, 14%) as a white powder.

Example 600 1-(2,2-Difluoroethyl)-N-[1-(fluoromethyl)cyclopropyl]-3-[(1-methylpyrazol-4-yl)methyl]-2,4-dioxo-quinazoline-6-sulfonamide

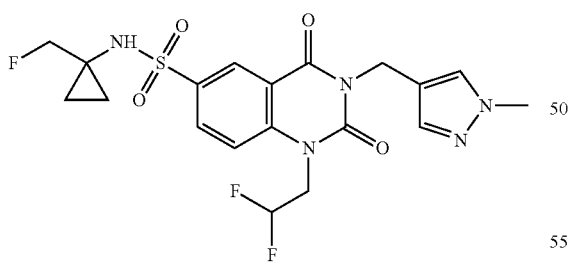

To a solution of N,N-diisopropylethylamine (0.49 mL, 2.79 mmol) in THF (10 mL) and DCM (6 mL) cooled in an ice bath, was added a mixture of 1-(fluoromethyl)cyclopropan-1-amine hydrochloride (0.23 g, 1.86 mmol) and then portionwise 1-(2,2-difluoroethyl)-3-[(1-methylpyrazol-4-yl)methyl]-2,4-dioxo-quinazoline-6-sulfonyl chloride (0.39 g, 0.93 mmol), prepared as described in Example 599. After stirring overnight, the solvent was evaporated and the residue purified by prep hplc to give the desired product (50 mg, 0.12 mmol, 13%) as an off-white powder.

Example 601 N-[1-(Fluoromethyl)cyclopropyl]-3-[(5-methyl-1,3,4-thiadiazol-2-yl)methyl]-2,4-dioxo-1H-quinazoline-6-sulfonamide

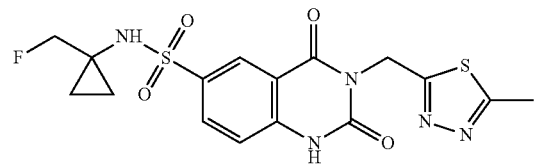 [SMILES: Cc1nnc(Cn2c(=O)[nH]c3ccc(S(=O)(=O)NC4(CF)CC4)cc3c2=O)s1]

Prepared using General method 1, from 3-[(5-methyl-1,3,4-thiadiazol-2-yl)methyl]-2,4-dioxo-1H-quinazoline-6-sulfonyl chloride and 1-(fluoromethyl)cyclopropan-1-amine hydrochloride. This gave the desired product (222 mg, 0.5218 mmol, 48%) as a white powder.

Example 602 1-Ethyl-N-[1-(fluoromethyl)cyclopropyl]-3-[(5-methyl-1,3,4-thiadiazol-2-yl)methyl]-2,4-dioxo-quinazoline-6-sulfonamide

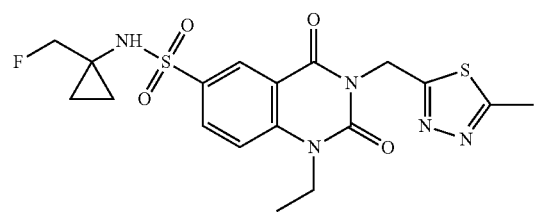 [SMILES: CCn1c(=O)n(Cc2nnc(C)s2)c(=O)c2cc(S(=O)(=O)NC3(CF)CC3)ccc21]

Prepared using Method A10, from N-[1-(fluoromethyl)cyclopropyl]-3-[(5-methyl-1,3,4-thiadiazol-2-yl)methyl]-2,4-dioxo-1H-quinazoline-6-sulfonamide and iodoethane. This gave the desired product (12 mg, 0.0265 mmol, 19%) as a white powder.

Example 603 1-[(2,5-Dimethylpyrazol-3-yl)methyl]-N-[1-(fluoromethyl)cyclopropyl]-3-[(5-methyl-1,3,4-thiadiazol-2-yl)methyl]-2,4-dioxo-quinazoline-6-sulfonamide

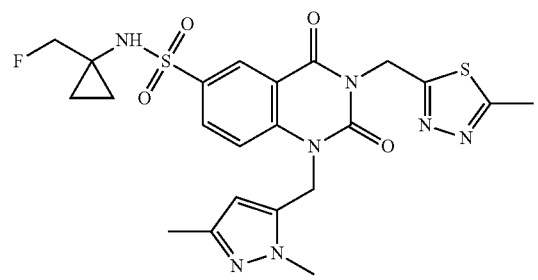 [SMILES: Cc1cc(Cn2c(=O)n(Cc3nnc(C)s3)c(=O)c3cc(S(=O)(=O)NC4(CF)CC4)ccc32)n(C)n1]

Prepared using Method A10, from N-[1-(fluoromethyl)cyclopropyl]-3-[(5-methyl-1,3,4-thiadiazol-2-yl)methyl]-2,4-dioxo-1H-quinazoline-6-sulfonamide, 5-(chloromethyl)-1,3-dimethyl-1H-pyrazole and 0.2 eq. NaI. This gave the desired product (17 mg, 0.0319 mmol, 23%) as a white powder.

Example 604 1-(Difluoromethyl)-N-[1-(fluoromethyl)cyclopropyl]-3-[(3-methylisoxazol-5-yl)methyl]-2,4-dioxo-quinazoline-6-sulfonamide

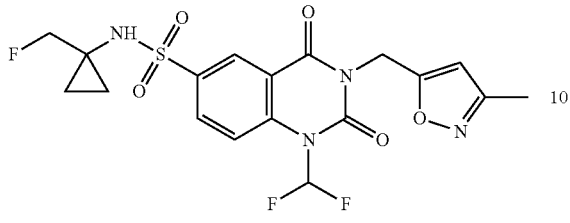

Prepared using Method A10 using N-[1-(fluoromethyl)cyclopropyl]-3-[(3-methylisoxazol-5-yl)methyl]-2,4-dioxo-1H-quinazoline-6-sulfonamide (100 mg, 0.245 mmol), potassium carbonate (102 mg, 0.74 mmol) and difluoro(iodo)methane (218 mg, 1.2 mmol). The reaction mixture was heated to 120° C. in a microwave for 2 h. This afforded the desired product (4 mg, 0.009 mmol, 3.6%) as an off-white powder.

Example 605 1-(Difluoromethyl)-N-(1-methylcyclopropyl)-3-[(3-methylisoxazol-5-yl)methyl]-2,4-dioxo-quinazoline-6-sulfonamide

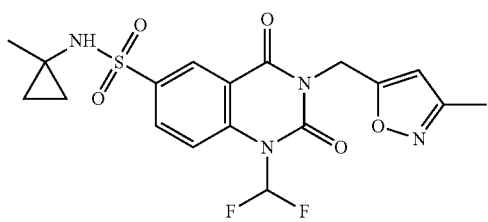

Prepared using Method A10 using N-(1-methylcyclopropyl)-3-((3-methylisoxazol-5-yl)methyl)-2,4-dioxo-1,2,3,4-tetrahydroquinazoline-6-sulfonamide (96 mg, 0.245 mmol), potassium carbonate (102 mg, 0.74 mmol) and difluoro(iodo)methane (109 mg, 0.61 mmol). The reaction mixture was heated to 120° C. in a microwave for 2 h. This afforded the desired product (12 mg, 0.027 mmol, 11%) as a white powder.

Example 606 1-(Difluoromethyl)-N-(1-methylcyclopropyl)-3-[(1-methylpyrazol-4-yl)methyl]-2,4-dioxo-quinazoline-6-sulfonamide

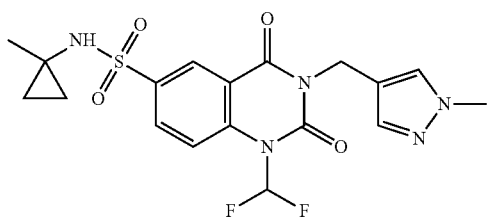

Prepared using Method A10 using N-(1-methylcyclopropyl)-N-[[3-[(1-methylpyrazol-4-yl)methyl]-2,4-dioxo-1H-quinazolin-6-yl]sulfonyl]acetamide (106 mg, 0.245 mmol), potassium carbonate (102 mg, 0.74 mmol) and difluoro(iodo)methane (109 mg, 0.61 mmol). The reaction mixture was heated to 120° C. in a microwave for 1 h. This afforded the desired product (55 mg, 0.125 mmol, 51%) as a white powder.

Example 607 N-[1-(Fluoromethyl)cyclopropyl]-3-[(1-methylpyrazol-4-yl)methyl]-1-(oxazol-4-ylmethyl)-2,4-dioxo-quinazoline-6-sulfonamide

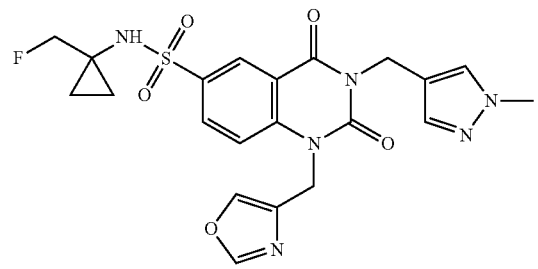 [SMILES: Cn1cc(Cn2c(=O)c3cc(S(=O)(=O)NC4(CF)CC4)ccc3n(Cc3cocn3)c2=O)cn1]

The mesylate of oxazol-4-ylmethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (51 mg, 0.286 mmol) and potassium carbonate (43 mg, 0.312 mmol) in DMF was conventionally heated to 70° C. for 4 h. Usual work-up afforded the desired product (31 mg, 0.063 mmol, 24%) as a white powder.

Example 608 1-(Cyclopentylmethyl)-N-[1-(fluoromethyl)cyclopropyl]-3-[(1-methylpyrazol-4-yl)methyl]-2,4-dioxo-quinazoline-6-sulfonamide

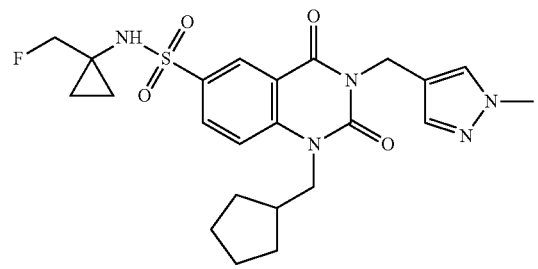 [SMILES: Cn1cc(Cn2c(=O)c3cc(S(=O)(=O)NC4(CF)CC4)ccc3n(CC3CCCC3)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), (bromomethyl)cyclopentane (70 mg, 0.429 mmol) and potassium carbonate (65 mg, 0.468 mmol) in DMF was conventionally heated to 70° C. for 4 h. Usual work-up afforded the desired product (26 mg, 0.053 mmol, 14%) as a white powder.

Example 609 N-[1-(Fluoromethyl)cyclopropyl]-1-(3-methylbut-2-enyl)-3-[(1-methylpyrazol-4-yl)methyl]-2,4-dioxo-quinazoline-6-sulfonamide

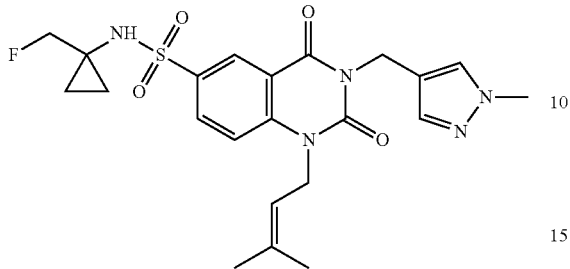

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromo-3-methyl-2-butene (64 mg, 0.429 mmol) and potassium carbonate (65 mg, 0.468 mmol) in DMF was conventionally heated to 70° C. for 4 h. Usual work-up afforded the desired product (52 mg, 0.109 mmol, 28%) as a white powder.

Example 610 N-[1-(Fluoromethyl)cyclopropyl]-3-[(1-methylpyrazol-4-yl)methyl]-2,4-dioxo-1-(4-pyridylmethyl)quinazoline-6-sulfonamide

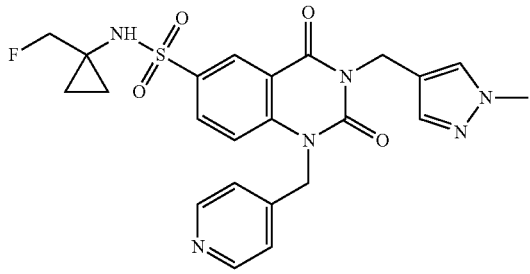 [SMILES: Cn1cc(Cn2c(=O)c3cc(S(=O)(=O)NC4(CF)CC4)ccc3n(Cc3ccncc3)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 4-(bromomethyl)pyridine (74 mg, 0.429 mmol) and potassium carbonate (65 mg, 0.468 mmol) in DMF was conventionally heated to 70° C. for 4 h. Usual work-up afforded the desired product (37 mg, 0.074 mmol, 19%) as a white powder.

Example 611 1-[2-(Diethylamino)ethyl]-N-[1-(fluoromethyl)cyclopropyl]-3-[(1-methylpyrazol-4-yl)methyl]-2,4-dioxo-quinazoline-6-sulfonamide

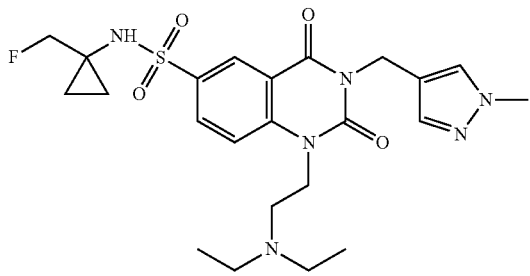 [SMILES: CCN(CC)CCn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 2-chloro-N,N-diethylethylamine hydrochloride (74 mg, 0.429 mmol) and potassium carbonate (130 mg, 0.936 mmol) in DMF was conventionally heated to 70° C. for 4 h. Usual work-up afforded the desired product (40 mg, 0.079 mmol, 20%) as a white powder.

Example 612 1-(2-Ethoxyethyl)-N-[1-(fluoromethycyclopropyl]-3-[(1-methylpyrazol-4-yl)methyl]-2,4-dioxo-quinazoline-6-sulfonamide

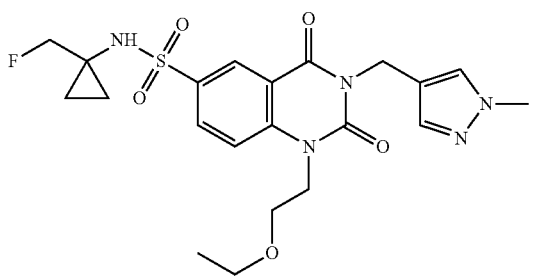 [SMILES: CCOCCn1c(=O)n(Cc2cnn(C)c2)c(=O)c2cc(S(=O)(=O)NC3(CF)CC3)ccc21]

The mesylate of 2-ethoxyethanol (100 mg) was prepared by reaction with methanesulfonyl chloride (1.1 eq) and triethylamine (2 eq) in DCM at 0° C., with warming to ambient temperature. N-[1-(Fluoromethyl)cyclopropyl]-3-[(1-methylpyrazol-4-yl)methyl]-2,4-dioxo-1H-quinazoline-6-sulfonamide (100 mg, 0.260 mmol), the crude mesylate (58 mg, 0.286 mmol) and potassium carbonate (43 mg, 0.312 mmol) in DMF was conventionally heated to 70° C. for 4 h. Usual work-up afforded the desired product (31 mg, 0.066 mmol, 25%) as a white powder.

Example 613 N-[1-(Fluoromethyl)cyclopropyl]-1-isopentyl-3-[(1-methylpyrazol-4-yl)methyl]-2,4-dioxo-quinazoline-6-sulfonamide

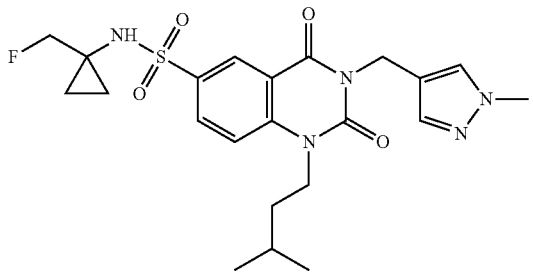 [SMILES: CC(C)CCn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromo-3-methylbutane (65 mg, 0.429 mmol) and potassium carbonate (65 mg, 0.468 mmol) in DMF was conventionally heated to 70° C. for 4 h. Usual work-up afforded the desired product (17 mg, 0.035 mmol, 9.1%) as a white powder.

Example 614 1-Ethyl-N-(1-methylcyclopropyl)-3-[(5-methyl-1,3,4-thiadiazol-2-yl)methyl]-2,4-dioxo-quinazoline-6-sulfonamide

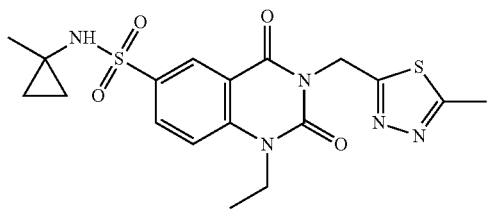

Prepared using Method A10, from N-(1-methylcyclopropyl)-3-[(5-methyl-1,3,4-thiadiazol-2-yl)methyl]-2,4-dioxo-1H-quinazoline-6-sulfonamide and iodoethane. This gave the desired product (6 mg, 0.0138 mmol, 20%) as a white powder.

Example 615 1-[(2,5-Dimethylpyrazol-3-yl)methyl]-N-(1-methylcyclopropyl)-3-[(5-methyl-1,3,4-thiadiazol-2-yl)methyl]-2,4-dioxo-quinazoline-6-sulfonamide

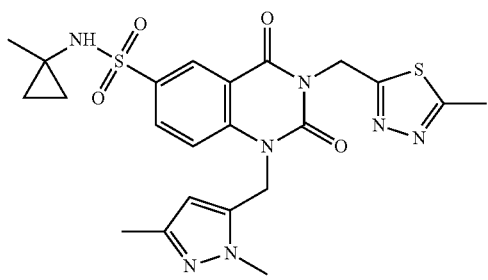

Prepared using Method A10, from N-(1-methylcyclopropyl)-3-[(5-methyl-1,3,4-thiadiazol-2-yl)methyl]-2,4-dioxo-1H-quinazoline-6-sulfonamide, 5-(chloromethyl)-1,3-dimethyl-1H-pyrazole and 0.2 eq. NaI. This gave the desired product (28 mg, 0.0543 mmol, 44%) as a white powder.

Example 616 1-[(2,4-Dimethylthiazol-5-yl)methyl]-N-[1-(fluoromethyl)cyclopropyl]-3-[(3-methylisoxazol-5-yl)methyl]-2,4-dioxo-quinazoline-6-sulfonamide

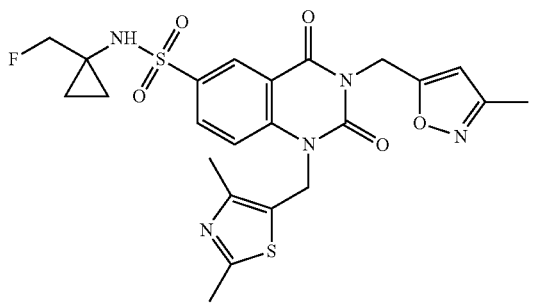 [SMILES: Cc1cc(Cn2c(=O)c3cc(S(=O)(=O)NC4(CF)CC4)ccc3n(Cc3sc(C)nc3C)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, (2,4-dimethylthiazol-5-yl)methyl methanesulfonate and 0.2 eq. NaI. This gave the desired product (50 mg, 0.0937 mmol, 38%) as a white powder.

Example 617 1-Butyl-N-[1-(fluoromethyl)cyclopropyl]-3-[(1-methylpyrazol-4-yl)methyl]-2,4-dioxo-quinazoline-6-sulfonamide

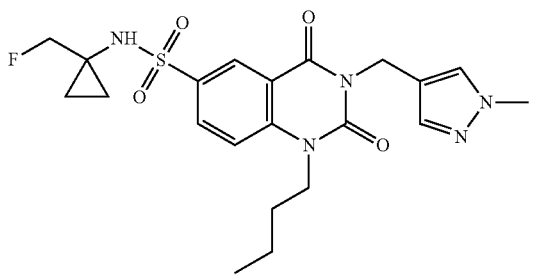 [SMILES: CCCCn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromobutane (59 mg, 0.429 mmol) and potassium carbonate (65 mg, 0.468 mmol) in DMF was conventionally heated to 70° C. for 4 h. Usual work-up afforded the desired product (8 mg, 0.017 mmol, 4.4%) as a white powder.

Example 618 N-[1-(Fluoromethyl)cyclopropyl]-1-[2-(2-methoxyethoxy)ethyl]-3-[(1-methylpyrazol-4-yl)methyl]-2,4-dioxo-quinazoline-6-sulfonamide

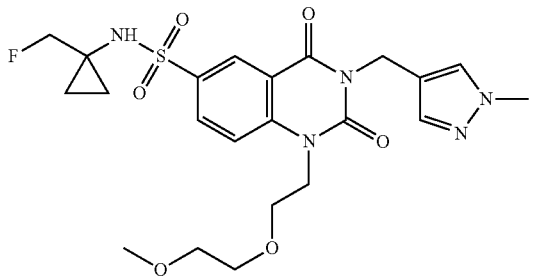 [SMILES: COCCOCCn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromo-2-(2-methoxyethoxy)ethane (79 mg, 0.429 mmol) and potassium carbonate (65 mg, 0.468 mmol) in DMF was conventionally heated to 70° C. for 4 h. Usual work-up afforded the desired product (13 mg, 0.026 mmol, 6.5%) as a white powder.

Example 619 N-[1-(Fluoromethyl)cyclopropyl]-3-[(1-methylpyrazol-4-yl)methyl]-2,4-dioxo-1-(tetrahydrofuran-2-ylmethyl)quinazoline-6-sulfonamide

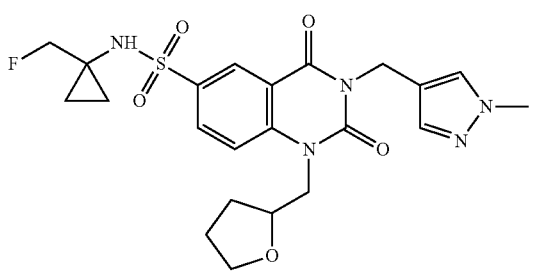 [SMILES: Cn1cc(Cn2c(=O)c3cc(S(=O)(=O)NC4(CF)CC4)ccc3n(CC3CCCO3)c2=O)cn1]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 2-(bromomethyl)tetrahydrofuran (71 mg, 0.429 mmol) and potassium carbonate (65 mg, 0.468 mmol) in DMF was conventionally heated to 70° C. for 4 h. Usual work-up afforded the desired product (6 mg, 0.012 mmol, 3.1%) as a white powder.

Example 620 N-[1-(Fluoromethyl)cyclopropyl]-3-[(1-methylpyrazol-4-yl)methyl]-2,4-dioxo-1-(2-oxobutyl)quinazoline-6-sulfonamide

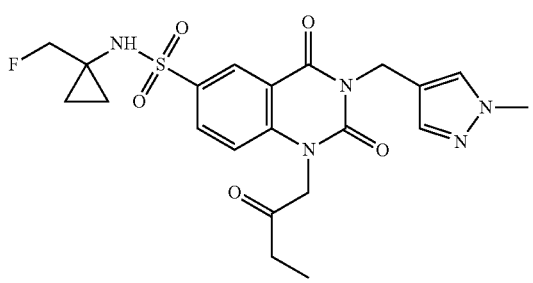 [SMILES: CCC(=O)Cn1c(=O)n(Cc2cnn(C)c2)c(=O)c2cc(S(=O)(=O)NC3(CF)CC3)ccc21]

N-[1-(Fluoromethyl)cyclopropyl]-3-[(1-methylpyrazol-4-yl)methyl]-2,4-dioxo-1H-quinazoline-6-sulfonamide (150 mg, 0.390 mmol), 1-bromo-2-butanone, (65 mg, 0.429 mmol) and potassium carbonate (65 mg, 0.468 mmol) in DMF was conventionally heated to 70° C. for 4 h. Usual work-up afforded the desired product (38 mg, 0.080 mmol, 20%) as a white powder.

Example 621 N-(1-Methylcyclopropyl)-3-[(1-methylpyrazol-4-yl)methyl]-2,4-dioxo-1-(2,2,2-trifluoroethyl)quinazoline-6-sulfonamide

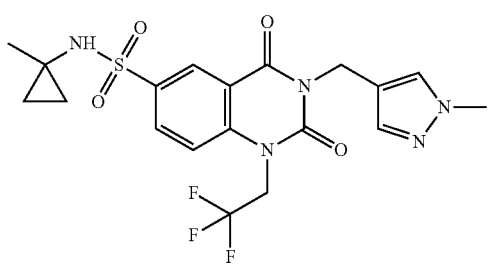

Prepared using Method A10 using N-[1-(fluoromethyl)cyclopropyl]-3-[(1-methylpyrazol-4-yl)methyl]-2,4-dioxo-1H-quinazoline-6-sulfonamide (200 mg, 0.46 mmol), potassium carbonate (160 mg, 1.16 mmol) and 1,1,1-trifluoro-2-iodoethane (0.11 mL, 1.1 mmol). The reaction mixture was conventionally heated to 120° C. for 18 h. This afforded the desired product (20 mg, 0.04 mmol, 9%) as a white powder.

Example 622 N-[1-(Fluoromethyl)cyclopropyl]-3-[(3-methylisoxazol-5-yl)methyl]-2,4-dioxo-1-(2,2,2-trifluoroethyl)quinazoline-6-sulfonamide

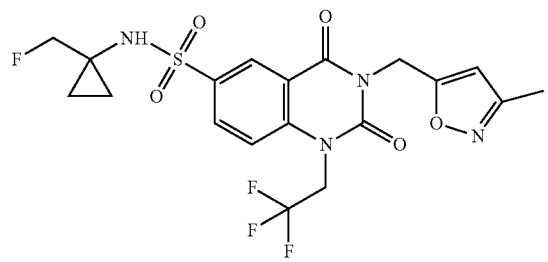 [SMILES: Cc1cc(Cn2c(=O)c3cc(S(=O)(=O)NC4(CF)CC4)ccc3n(CC(F)(F)F)c2=O)on1]

Prepared using Method A10 using N-[1-(fluoromethyl)cyclopropyl]-3-[(3-methylisoxazol-5-yl)methyl]-2,4-dioxo-1H-quinazoline-6-sulfonamide (100 mg, 0.260 mmol), potassium carbonate (85 mg, 0.61 mmol) and 1,1,1-trifluoro-2-iodoethane (0.06 mL, 0.59 mmol). The reaction mixture was conventionally heated to 120° C. for 18 h. This afforded the desired product (5 mg, 0.01 mmol, 4.2%) as a beige powder.

Example 623 N-[1-(Fluoromethyl)cyclopropyl]-3-[(1-methylpyrazol-4-yl)methyl]-2,4-dioxo-1-(2,2,2-trifluoroethyl)quinazoline-6-sulfonamide

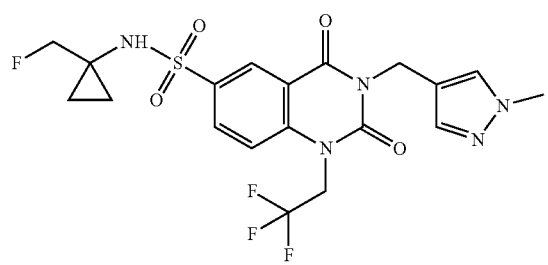 [SMILES: Cn1cc(Cn2c(=O)c3cc(S(=O)(=O)NC4(CF)CC4)ccc3n(CC(F)(F)F)c2=O)cn1]

Prepared using Method A10 using N-[1-(fluoromethyl)cyclopropyl]-3-[(1-methylpyrazol-4-yl)methyl]-2,4-dioxo-1H-quinazoline-6-sulfonamide (100 mg, 0.260 mmol), potassium carbonate (85 mg, 0.61 mmol) and 1,1,1-trifluoro-2-iodoethane (0.06 mL, 0.59 mmol). The reaction mixture was conventionally heated to 120° C. for 18 h. This afforded the desired product (2 mg, 0.004 mmol, 1.7%) as a beige powder.

Example 624 N-[1-(Fluoromethyl)cyclopropyl]-1-methyl-2,4-dioxo-3-(1,3,4-thiadiazol-2-ylmethyl)quinazoline-6-sulfonamide

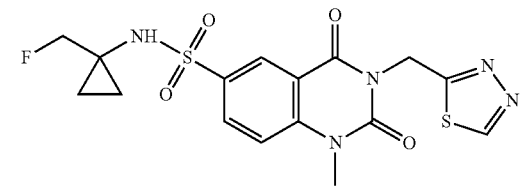 [SMILES: Cn1c(=O)n(Cc2nncs2)c(=O)c2cc(S(=O)(=O)NC3(CF)CC3)ccc21]

Prepared like Example 494 with N-[1-(fluoromethyl)cyclopropyl]-1-methyl-2,4-dioxo-quinazoline-6-sulfonamide (80 mg, 0.24 mmol), 1,3,4-thiadiazol-2-ylmethyl methanesulfonate (47.5 mg, 0.24 mmol), potassium carbonate (67.6 mg, 0.49 mmol) and potassium iodide (40.6 mg, 0.24 mmol) in DMF (4 mL) to give the desired product N-[1-(fluoromethyl)cyclopropyl]-1-methyl-2,4-dioxo-3-(1,3,4-thiadiazol-2-ylmethyl)quinazoline-6-sulfonamide as a white solid (30 mg, 0.071 mmol, 29%).

Example 625 N-[1-(Fluoromethyl)cyclopropyl]-1-methyl-3-[(3-methylisothiazol-5-yl)methyl]-2,4-dioxo-quinazoline-6-sulfonamide

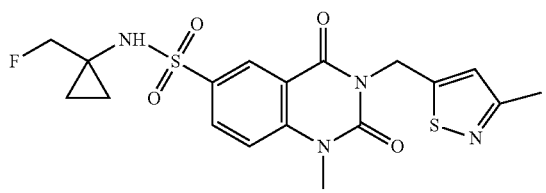 [SMILES: Cc1cc(Cn2c(=O)c3cc(S(=O)(=O)NC4(CF)CC4)ccc3n(C)c2=O)sn1]

Prepared like Example 494 with N-[1-(fluoromethyl)cyclopropyl]-1-methyl-2,4-dioxo-quinazoline-6-sulfonamide (70 mg, 0.21 mmol), (3-methylisothiazol-5-yl)methyl methanesulfonate (44.3 mg, 0.21 mmol), potassium carbonate (59.1 mg, 0.43 mmol) and potassium iodide (35.5 mg, 0.21 mmol) in DMF (4 mL) to give the desired product N-[1-(fluoromethyl)cyclopropyl]-1-methyl-N,3-bis[(3-methylisothiazol-5-yl)methyl]-2,4-dioxo-quinazoline-6-sulfonamide as a white solid (31 mg, 0.070 mmol, 28%).

Example 626 N-[1-(Fluoromethyl)cyclopropyl]-1-methyl-3-[(2-methyltriazol-4-yl)methyl]-2,4-dioxo-quinazoline-6-sulfonamide

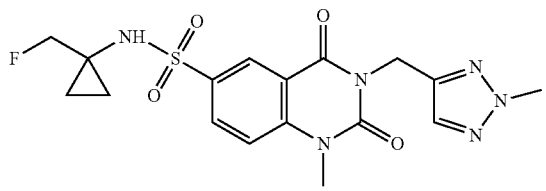 [SMILES: Cn1ncc(Cn2c(=O)c3cc(S(=O)(=O)NC4(CF)CC4)ccc3n(C)c2=O)n1]

Prepared like Example 494 with N-[1-(fluoromethyl)cyclopropyl]-1-methyl-2,4-dioxo-quinazoline-6-sulfonamide (70 mg, 0.21 mmol), (2-methyltriazol-4-yl)methyl methanesulfonate (40.9 mg, 0.21 mmol), potassium carbonate (59.1 mg, 0.43 mmol) and potassium iodide (35.5 mg, 0.21 mmol) in DMF (4 mL) to give the desired product N-[1-(fluoromethyl)cyclopropyl]-1-methyl-3-[(2-methyltriazol-4-yl)methyl]-2,4-dioxo-quinazoline-6-sulfonamide as a white solid (20 mg, 0.047 mmol, 22%).

Example 627 N-[1-(Fluoromethyl)cyclopropyl]-3-[(3-methylisoxazol-5-yl)methyl]-2,4-dioxo-1-(1,3,4-thiadiazol-2-ylmethyl)quinazoline-6-sulfonamide

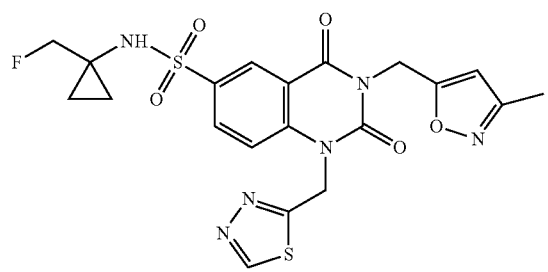 [SMILES: Cc1cc(Cn2c(=O)c3cc(S(=O)(=O)NC4(CF)CC4)ccc3n(Cc3nncs3)c2=O)on1]

Prepared using Method A10, from N-[1-(fluoromethyl)cyclopropyl]-3-[(3-methylisoxazol-5-yl)methyl]-2,4-dioxo-1H-quinazoline-6-sulfonamide, 1,3,4-thiadiazol-2-ylmethyl methanesulfonate and 0.2 eq. NaI. This gave the desired product (12 mg, 0.0237 mmol, 16%) as a white powder.

Example 628 3-[(5-Ethyl-1,3,4-thiadiazol-2-yl)methyl]-N-[1-(fluoromethyl)cyclopropyl]-1-methyl-2,4-dioxo-quinazoline-6-sulfonamide

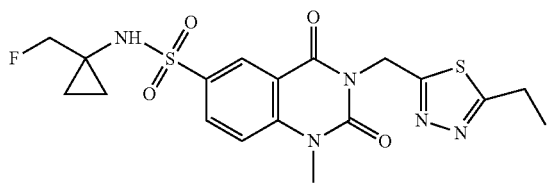 [SMILES: CCc1nnc(Cn2c(=O)c3cc(S(=O)(=O)NC4(CF)CC4)ccc3n(C)c2=O)s1]

Prepared like Example 494 with N-[1-(fluoromethyl)cyclopropyl]-1-methyl-2,4-dioxo-quinazoline-6-sulfonamide (70 mg, 0.21 mmol), 2-(chloromethyl)-5-ethyl-1,3,4-thiadiazole (34.8 mg, 0.21 mmol), potassium carbonate (59.1 mg, 0.43 mmol) and potassium iodide (35.5 mg, 0.21 mmol) in DMF (4 mL) to give the desired product 3-[(5-ethyl-1,3,4-thiadiazol-2-yl)methyl]-N-[1-(fluoromethyl)cyclopropyl]-1-methyl-2,4-dioxo-quinazoline-6-sulfonamide as a tan solid (10 mg, 0.022 mmol, 10%).

Example 629 1-(2-Fluoroethyl)-N-[1-(fluoromethyl)cyclopropyl]-3-[(5-methyl-1,3,4-thiadiazol-2-yl)methyl]-2,4-dioxo-quinazoline-6-sulfonamide

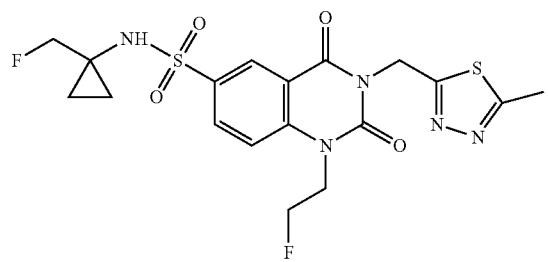 [SMILES: Cc1nnc(Cn2c(=O)c3cc(S(=O)(=O)NC4(CF)CC4)ccc3n(CCF)c2=O)s1]

Prepared using Method A10, from N-[1-(fluoromethyl)cyclopropyl]-3-[(5-methyl-1,3,4-thiadiazol-2-yl)methyl]-2, 4-dioxo-1H-quinazoline-6-sulfonamide and 1-fluoro-2-iodoethane. This gave the desired product (5 mg, 0.0106 mmol, 11%) as a white powder.

Example 630 N-[1-(Fluoromethyl)cyclopropyl]-1-[(1-methylpyrazol-4-yl)methyl]-3-[(5-methyl-1,3,4-thiadiazol-2-yl)methyl]-2,4-dioxo-quinazoline-6-sulfonamide

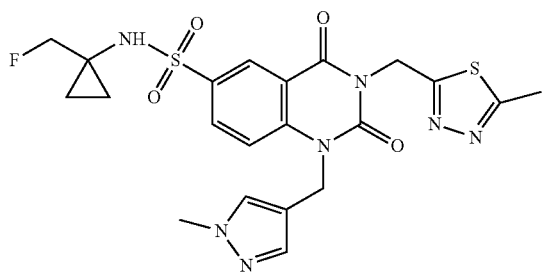 [SMILES: Cc1nnc(Cn2c(=O)c3cc(S(=O)(=O)NC4(CF)CC4)ccc3n(Cc3cnn(C)c3)c2=O)s1]

Prepared using Method A10 (using 2.2 eq. K$_2$CO$_3$), from N-[1-(fluoromethyl)cyclopropyl]-3-[(5-methyl-1,3,4-thiadiazol-2-yl)methyl]-2,4-dioxo-1H-quinazoline-6-sulfonamide, 4-(chloromethyl)-1-methyl-1H-pyrazole hydrochloride and 0.2 eq. NaI. This gave the desired product (7 mg, 0.0135 mmol, 14%) as a white powder.

Example 631 N-[1-(Fluoromethyl)cyclopropyl]-1-[(5-methyl-1,2,4-oxadiazol-3-yl)methyl]-3-[(5-methyl-1,3,4-thiadiazol-2-yl)methyl]-2,4-dioxo-quinazoline-6-sulfonamide

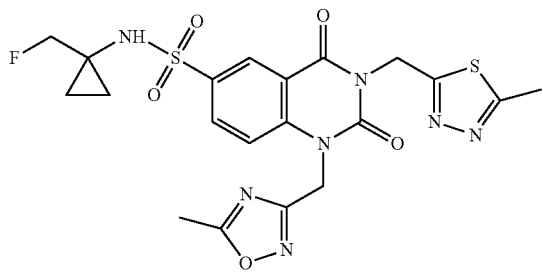 [SMILES: Cc1nc(Cn2c(=O)n(Cc3nnc(C)s3)c(=O)c3cc(S(=O)(=O)NC4(CF)CC4)ccc32)no1]

Prepared using Method A10, from N-[1-(fluoromethyl)cyclopropyl]-3-[(5-methyl-1,3,4-thiadiazol-2-yl)methyl]-2,4-dioxo-1H-quinazoline-6-sulfonamide and 3-(bromomethyl)-5-methyl-1,2,4-oxadiazole. This gave the desired product (8 mg, 0.0153 mmol, 20%) as a white powder.

PARG Assays (Biological Activity)
PARG Assay

PARG In vitro assays were conducted in a total volume of 15 ul in a standard 384 well format. 5 ul of Human Full Length PARG (Produced internally by Astra Zeneca), used at a final reaction concentration of 80 pM, was added to 5 ul of Ribosylated PARP substrate (also produced internally by Astra Zeneca) at final reaction concentration of 4.5 nM in assay buffer (50 mM Tris pH7.4, 0.1 mg/ml BSA, 3 mM EDTA, 0.4 mM EGTA, 1 mM DTT, 0.01% Tween 20, 50 mM KCl). The reaction was incubated at room temperature for 10 minutes and then 5 ul detection reagent was added. Detection Reagent consists of 42 nM MAb Anti-6HIS XL665 (CisBio: 61HISXLB) and 2.25 nM Streptavidin Europium Cryptate (CisBio: 610SAKLB), both at 3× working stock concentrations (final concentrations of 14 nM and 0.75 nM respectively), in a detection buffer of 50 mM Tris pH7.4, BSA at 0.1 mg/ml and KF at 100 mM. Following incubation at room temperature for 60 minutes in the dark, TR-FRET signal was measured at Ex 340 and Em 665 and Em 620. A ratio was calculated as Em665/EM620×104 for each well and used to calculate percent inhibition for test compounds.

PARG Cell Assays

This method is based on the detection of endogenous levels of poly (ADP) ribose chains present in the nucleus of HeLa cell line using indirect immunofluorescence. MMS stimulation increases PAR chains for up to 25 mins. After that point, PARG is active and breaks down the PAR chains, until by one hour after stimulation no PAR chains are detectable. Inhibition of PARG maintains PAR chains.

Briefly, following compound treatment and treatment with the DNA damaging agent methylmethanesulfonate (MMS), the cell monolayer is fixed, then permeabilised and incubated with a mouse monoclonal antibody raised against multimers of poly(ADP) ribose. After an overnight incubation, excess antibody is removed by washing and an Alexafluor 488-linked secondary antibody which recognises the mouse monoclonal is added together with a nuclear stain (Hoechst 33342). Images of the cells are then captured and analysed on a High Content Screening platform and the total intensity of the nuclear fluorescent signal at 488 nM is quantified. An increase in fluorescence indicates that more PAR chains are present and therefore the magnitude of PARG inhibition.

HeLa cells, seeded in 384-well plates, at 4000/well in 30 μL RPMI 1640 media, supplemented with 10% FBS and 2 mM Glutamax, were incubated overnight at 37° C., 5% CO2.

The following day, cells were dosed in quadruplicate with compound (10 point dose response) and incubated for 1 h at 37° C., 5% CO2.

At the end of the 1 h dosing period, MMS was added to duplicates at a final concentration of 50 μg/mL, for a further hour.

Media was tipped off and the cells fixed with 50 μL ice-cold 95% MetOH/PBS for 15 mins at −20° C. Following a PBS wash, 50 μL PBS/0.1% Triton was added to the cells for 20 mins. Following another PBS wash, anti-PAR antibody (Calbiochem AM80) was diluted 1:4000 in a buffer (PBS+0.5% FBS+0.05% Tween20) and added to the cells and incubated overnight at 4° C.

The following day, cells were washed three times with PBS and then incubated for 1 hr with secondary antibody (Alexa Fluor® 488 goat anti mouse IgG (H+L)) diluted 1:1000 and Hoechst diluted 1:5000 in buffer (5% FBS in PBS+0.05% Tween20).

Cells were washed three times with PBS and the plate sealed with a light-proof seal.

Images of the cells were captured on a ThermoFisher CellInsight and the mean total intensity of spots fluorescent at 485 nm in the nucleus was reported.

TABLE 1

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 1 | 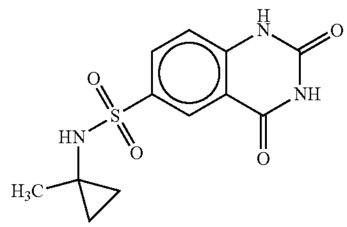 | 1 | 9.170 | |
| Example 2 | 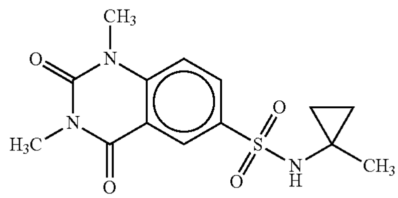 | 1 | 4.740 | |
| Example 3 | 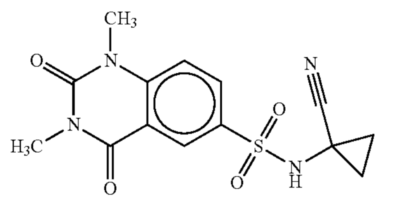 | 1 | 4.960 | |
| Example 4 | 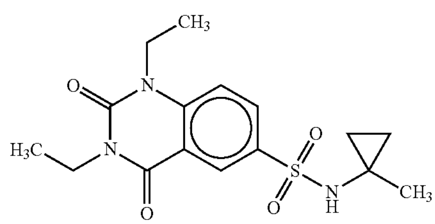 | 1 | 1.470 | |
| Example 5 | 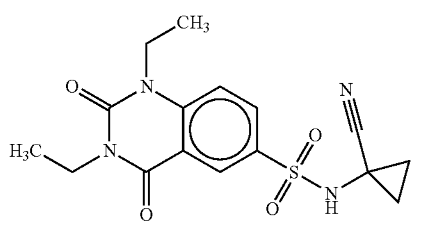 | 1 | 1.820 | |
| Example 6 | 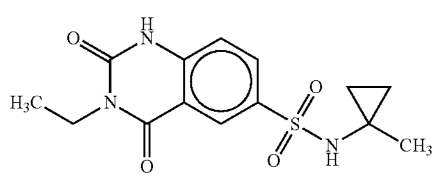 | Intermediate S2-C2 | 9.070 | |
| Example 7 | 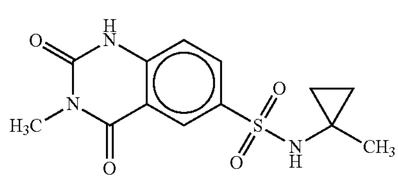 | Intermediate S2-C1 | 4.630 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 8 | 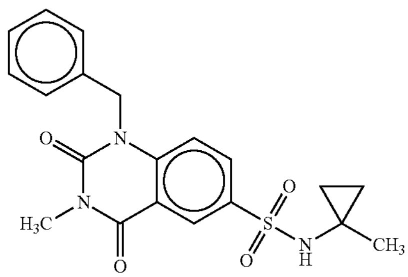 | A1 | 1.330 | |
| Example 9 | 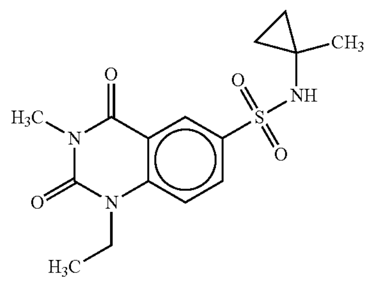 | A1 | 4.110 | |
| Example 10 | 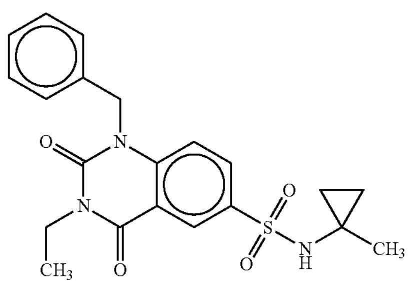 | A2 | 2.420 | |
| Example 11 | 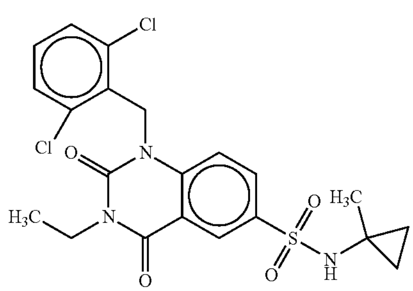 | A1 | 6.930 | |
| Example 12 | 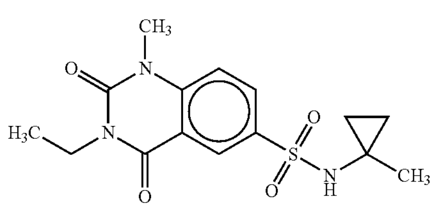 | A1 | 3.970 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 13 | 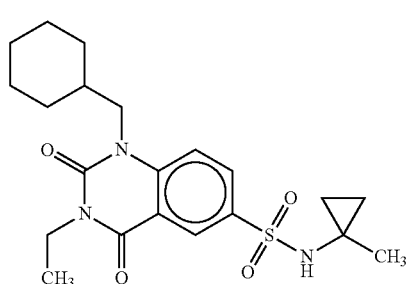 | A1 | 3.100 | |
| Example 14 | 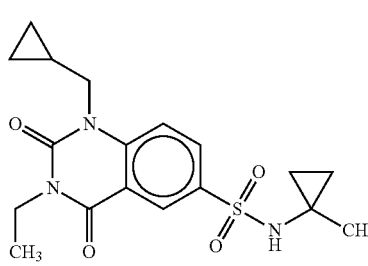 | A1 | 0.592 | |
| Example 15 | 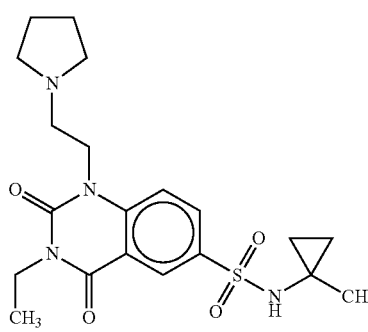 | A1 | 5.520 | |
| Example 16 | 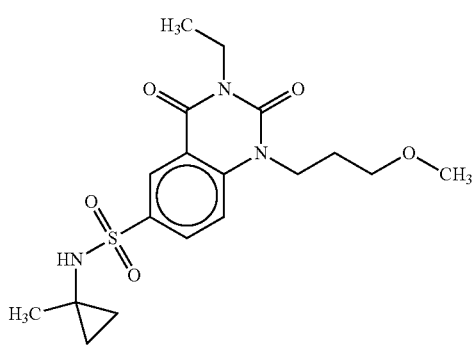 | A1 | 1.970 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 17 | 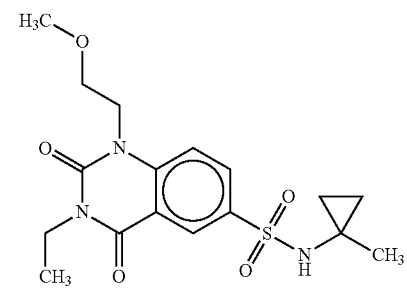 | A1 | 1.570 | |
| Example 18 | 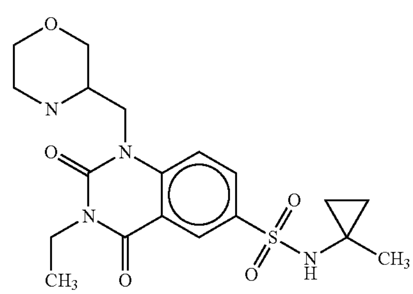 | A1 | 2.230 | |
| Example 19 | 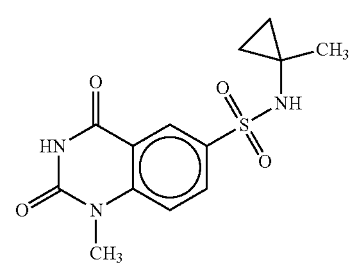 | Intermediate S3-C | 5.070 | |
| Example 20 | 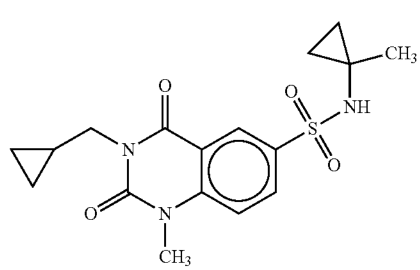 | A3 | 4.650 | |
| Example 21 | 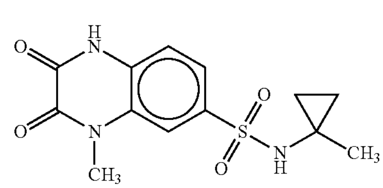 | Intermediate S11-D | 6.926 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 22 | 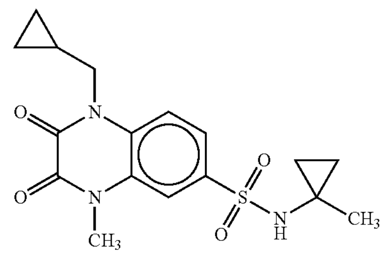 | Scheme 11 | 1.016 | |
| Example 23 | 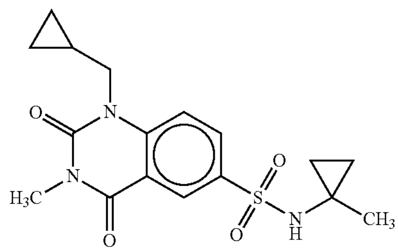 | A1 | 0.355 | 0.519 |
| Example 24 | 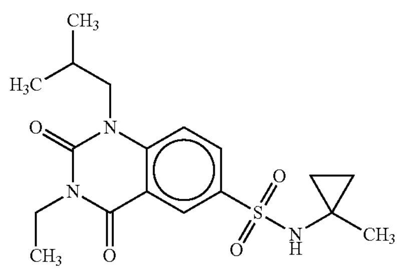 | A2 | 1.830 | |
| Example 25 | 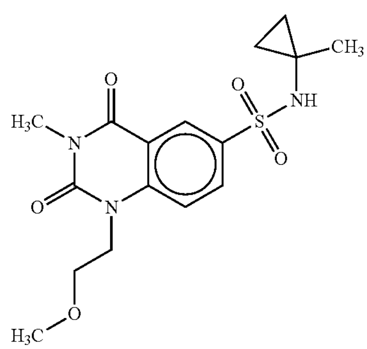 | A1 | 1.100 | |
| Example 26 | 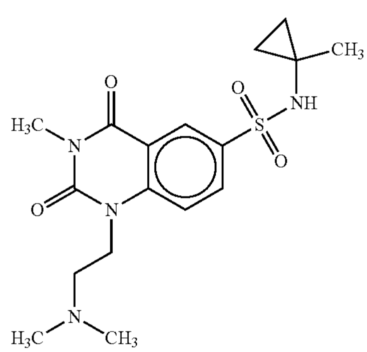 | A1 | 1.990 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 27 | 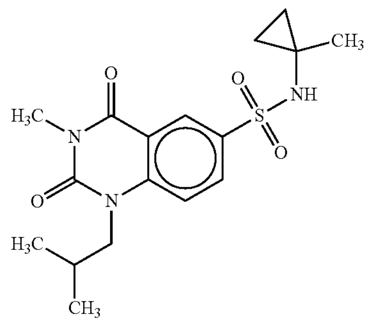 | A1 | 1.470 | |
| Example 28 | 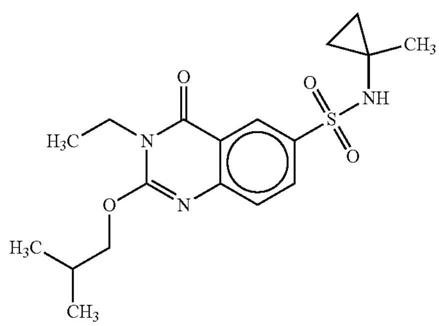 | A2 | 7.813 | |
| Example 29 | 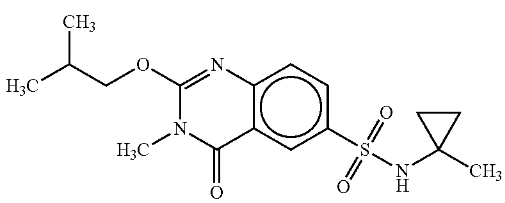 | A2 | 3.506 | |
| Example 30 | 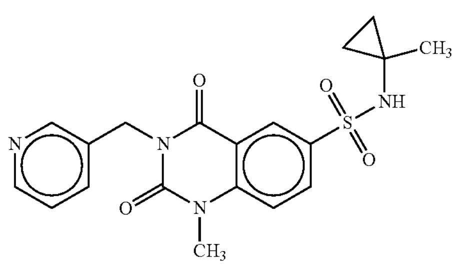 | A3 | 2.550 | |
| Example 31 | 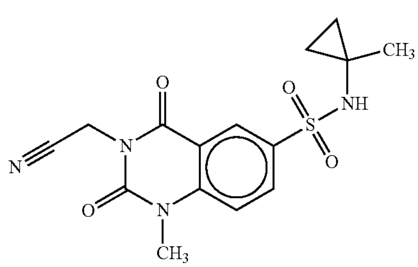 | A3 | 1.140 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 32 | 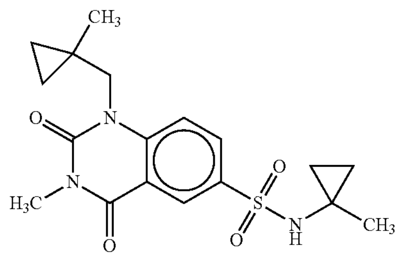 | A2 | 0.307 | 0.796 |
| Example 33 | 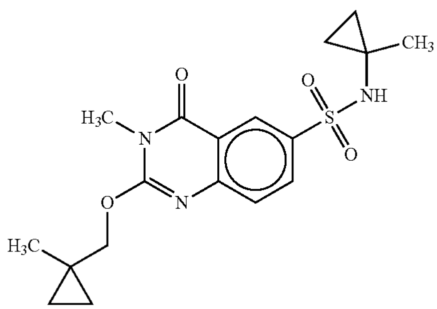 | A2 | 4.448 | |
| Example 34 | 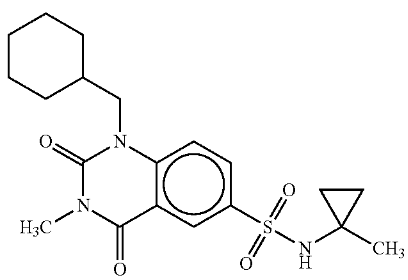 | A1 | 0.563 | |
| Example 35 | 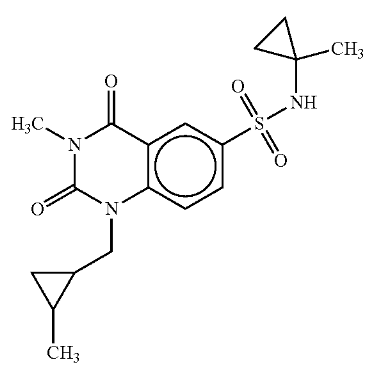 | A2 | 0.246 | 0.409 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 36 | 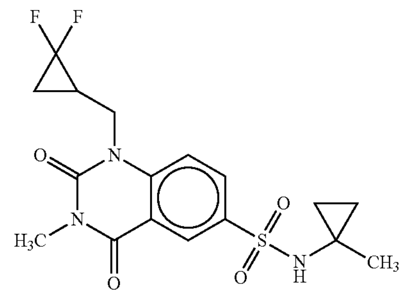 | A2 | 0.373 | 0.591 |
| Example 37 | 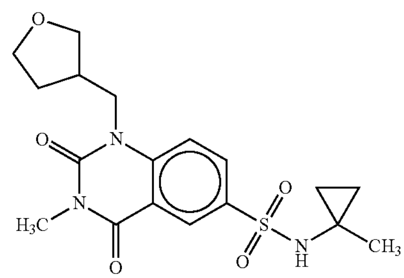 | A2 | 1.480 | |
| Example 38 | 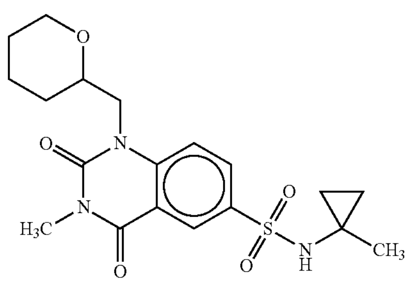 | A2 | 1.550 | |
| Example 39 | 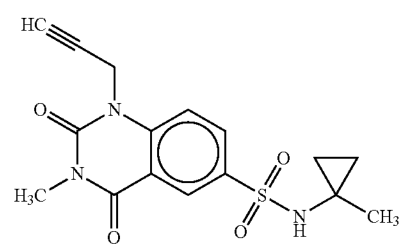 | A2 | 0.706 | |
| Example 40 | 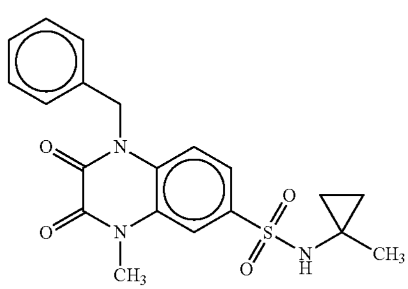 | Scheme 11 | 2.790 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 41 | 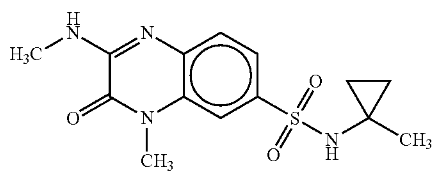 | 3-oxo-quinoxaline-6-sulfonamide | 5.550 | |
| Example 42 | 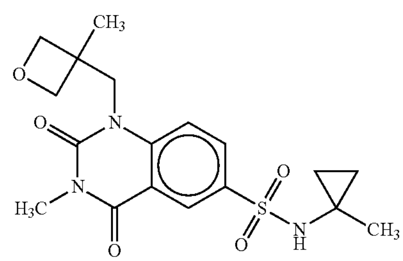 | A2 | 2.450 | |
| Example 43 | 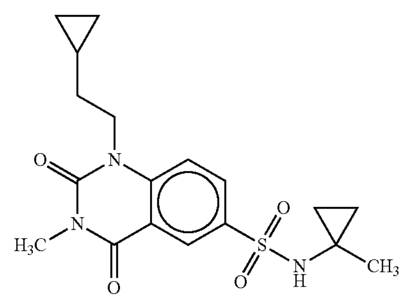 | A2 | 1.170 | |
| Example 44 | 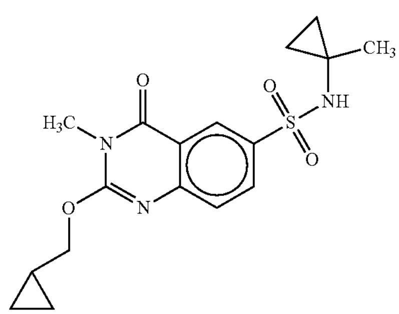 | A2 | 9.423 | |
| Example 45 | 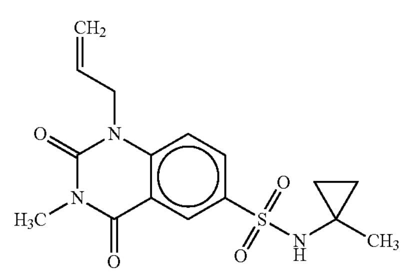 | A2 | 2.390 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---------|-----------|--------|--------------------------------|------------------------------|
| Example 46 | 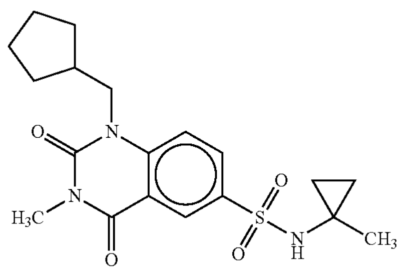 | A2 | 1.280 | |
| Example 47 | 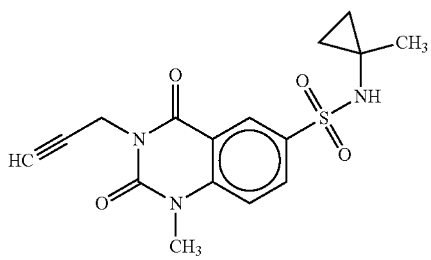 | A2 | 2.970 | |
| Example 48 | 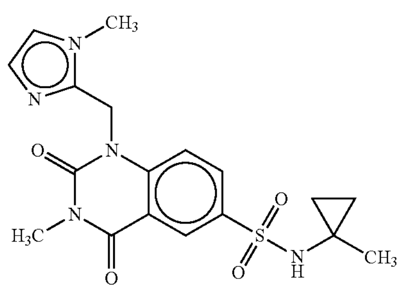 | A2 | 0.750 | |
| Example 49 | 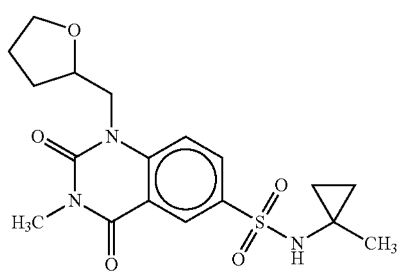 | A2 | 2.420 | |
| Example 50 | 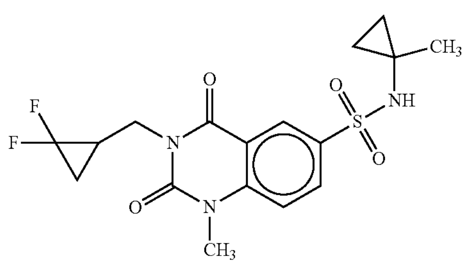 | A2 | 3.410 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 51 | 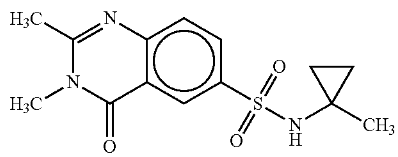 | 14 | 4.163 | |
| Example 52 | 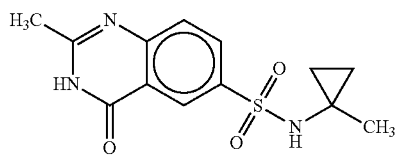 | 13 | 6.959 | |
| Example 53 | 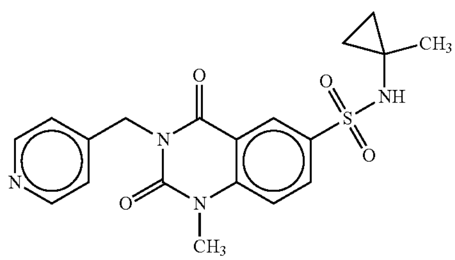 | A3 | 7.980 | |
| Example 54 | 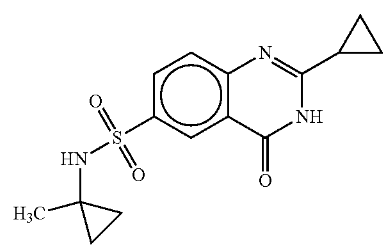 | 13 | 2.418 | |
| Example 55 | 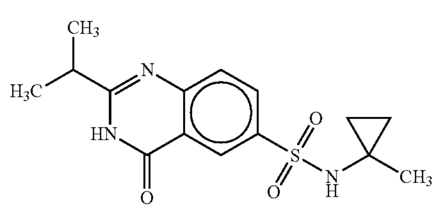 | 13 | 2.009 | |
| Example 56 | 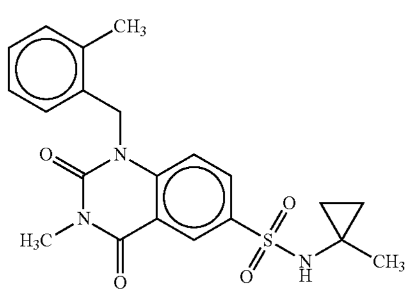 | A1 | 3.340 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 57 | 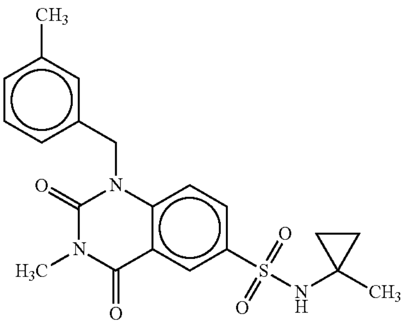 | A1 | 1.110 | |
| Example 58 | 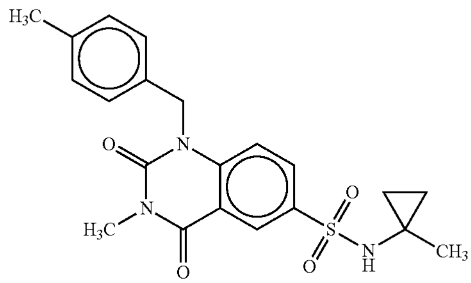 | A1 | 1.570 | |
| Example 59 | 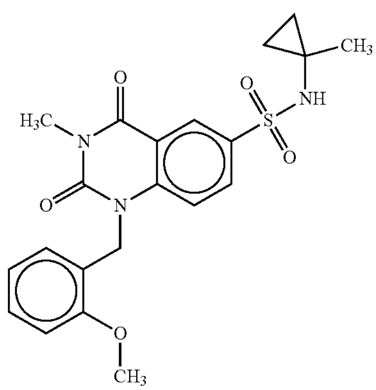 | A1 | 3.240 | |
| Example 60 | 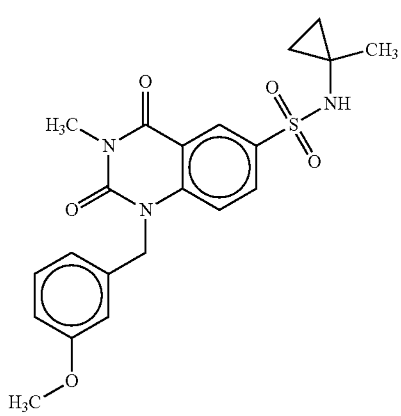 | A1 | 0.860 | |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 61 | 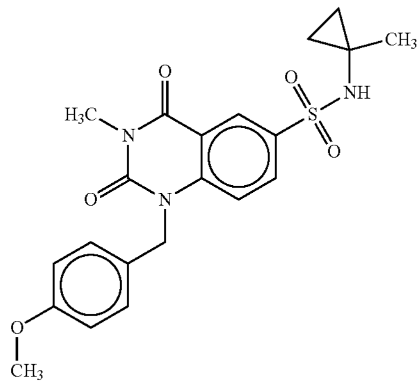 | A1 | 0.454 | 0.199 |
| Example 62 | 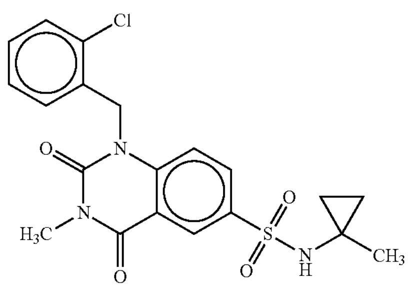 | A1 | 1.270 | |
| Example 63 | 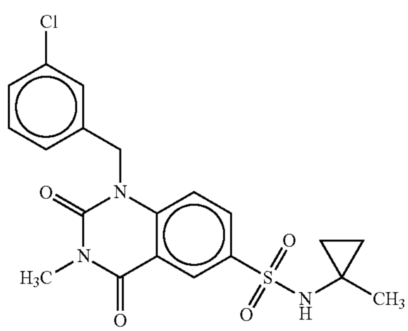 | A1 | 1.010 | |
| Example 64 | 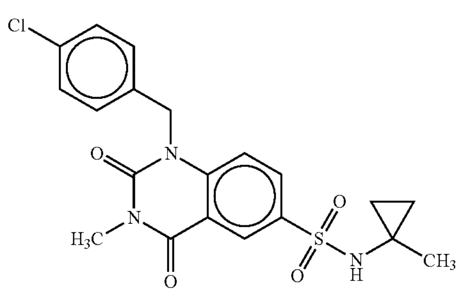 | A1 | 0.607 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 65 | 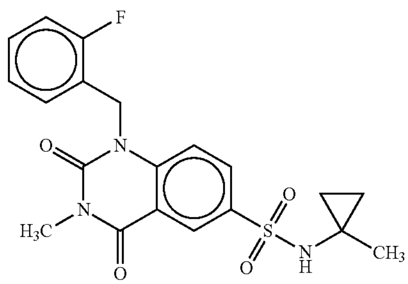 | A1 | 1.450 | |
| Example 66 | 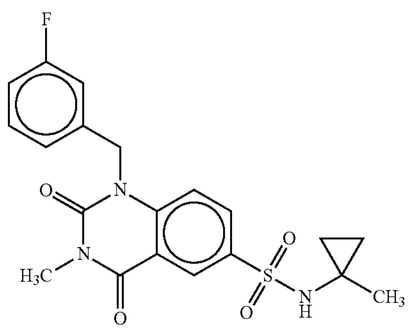 | A1 | 1.550 | |
| Example 67 | 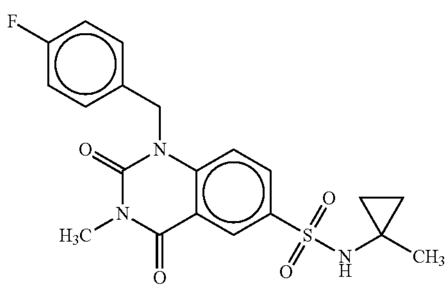 | A1 | 0.533 | |
| Example 68 | 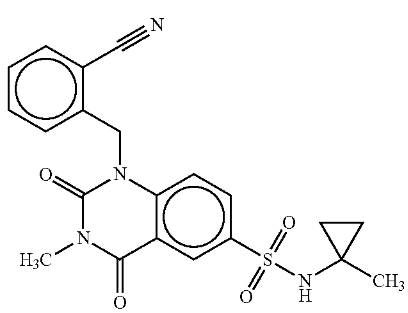 | A1 | 0.324 | 0.306 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 69 | 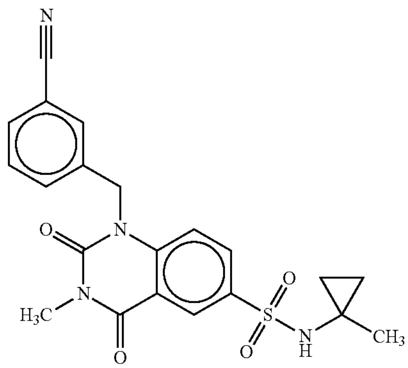 | A1 | 1.140 | |
| Example 70 | 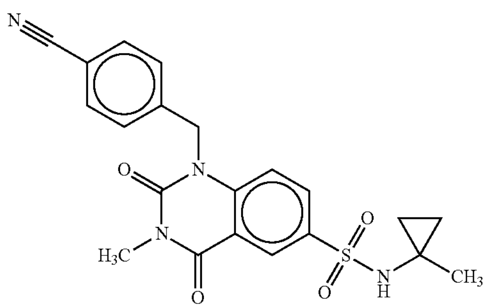 | A1 | 0.779 | |
| Example 71 | 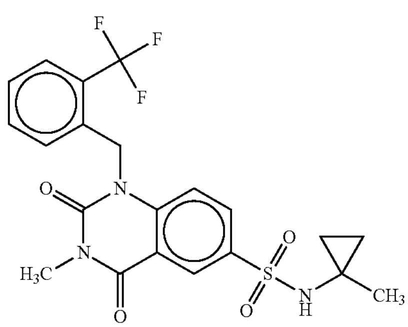 | A1 | 2.390 | |
| Example 72 | 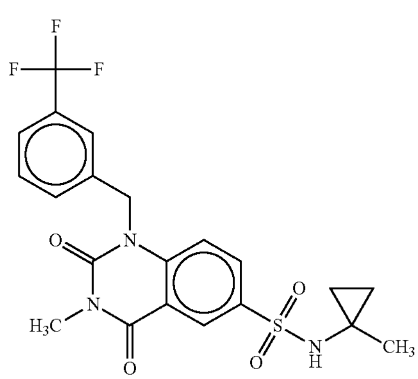 | A1 | 3.410 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 73 | 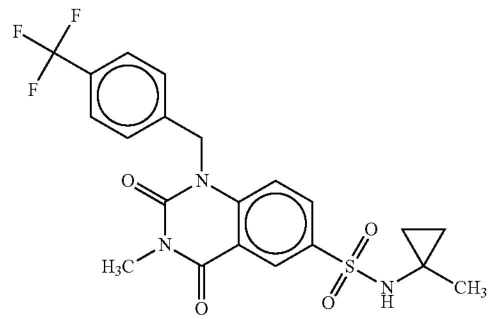 | A1 | 5.400 | |
| Example 74 | 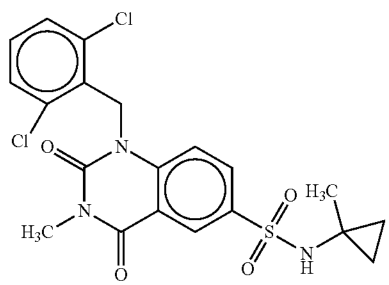 | A1 | 2.100 | |
| Eample 75 | 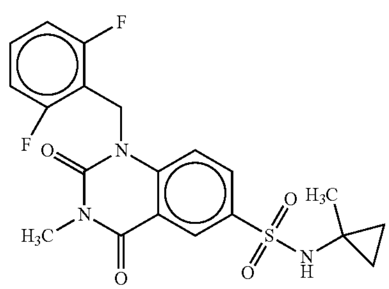 | A1 | 0.714 | |
| Example 76 | 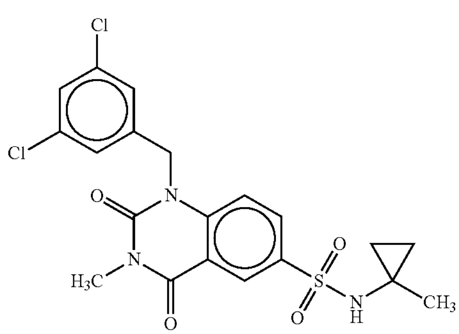 | A1 | 4.230 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 77 | 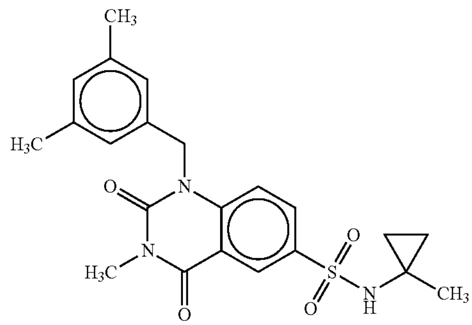 | A1 | 1.680 | |
| Example 78 | 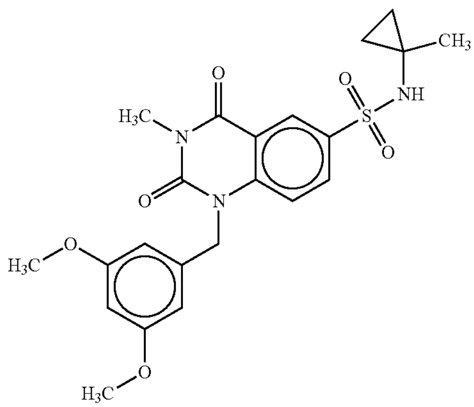 | A1 | 0.621 | |
| Example 79 | 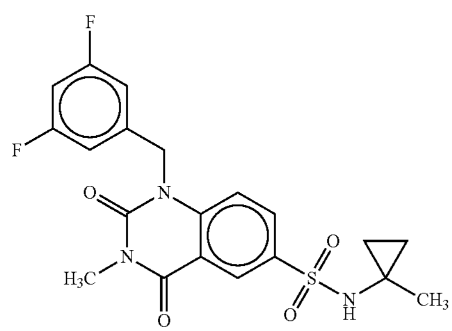 | A1 | 2.190 | |
| Example 80 | 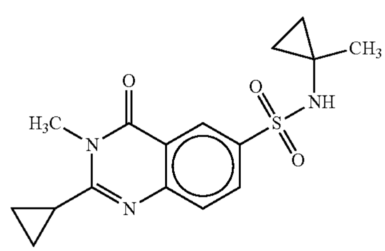 | 14 | 2.175 | |
| Example 81 | 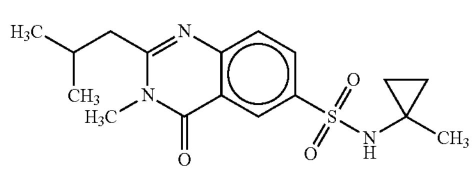 | 14 | 1.841 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 82 | 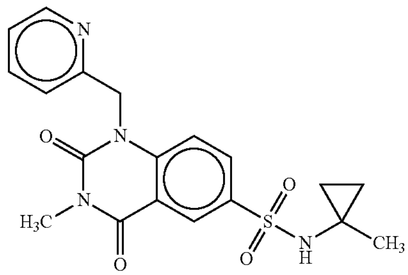 | A1 | 5.770 | |
| Example 83 | 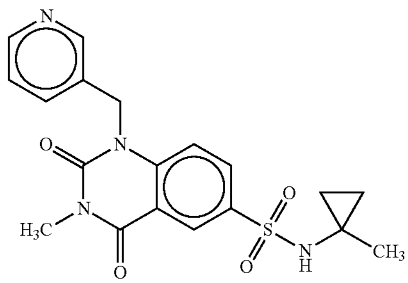 | A1 | 1.330 | |
| Example 84 | 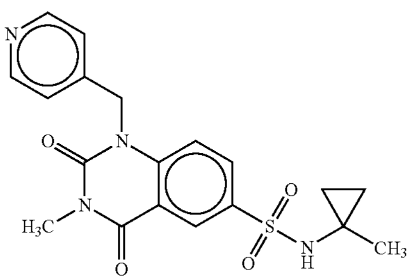 | A1 | 2.370 | |
| Example 85 | 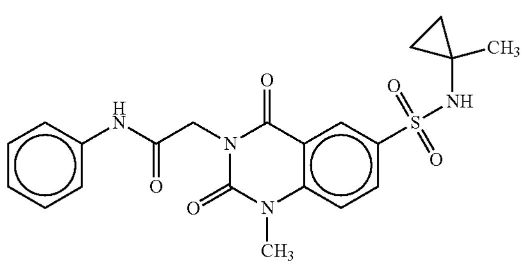 | A3 | 2.250 | |
| Example 86 | 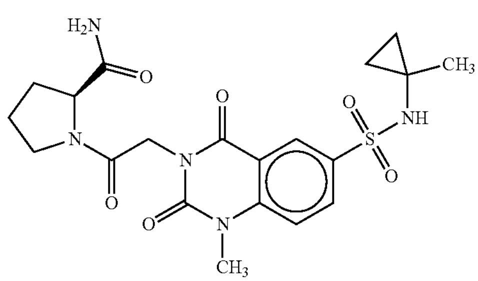 | A3 | 5.470 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 87 | 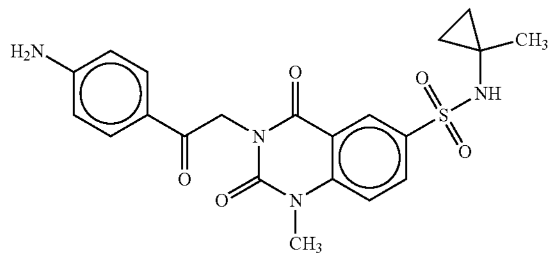 | A3 | 1.160 | |
| Example 88 | 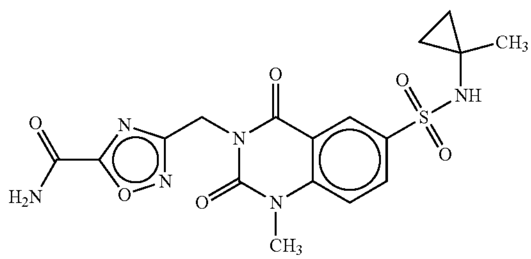 | A3 | 5.470 | |
| Example 89 | 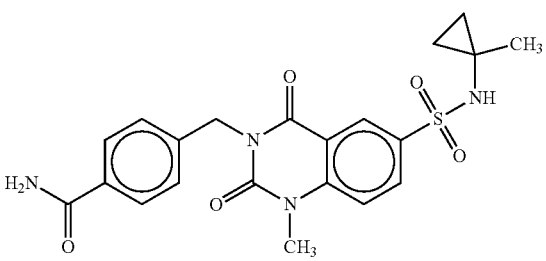 | A3 | 5.890 | |
| Example 90 | 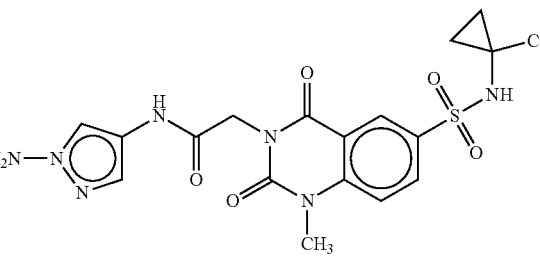 | A3 | 4.230 | |
| Example 91 | 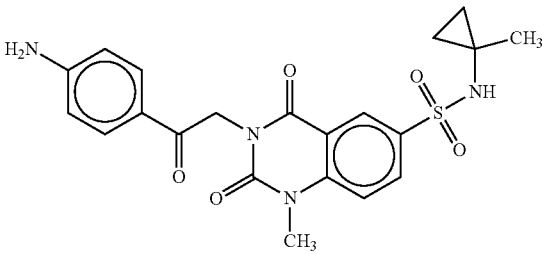 | A3 | 1.610 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---------|-----------|--------|--------------------------------|------------------------------|
| Example 92 | 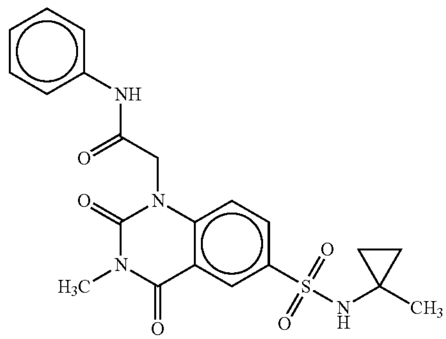 | A1 | 4.130 | |
| Example 93 | 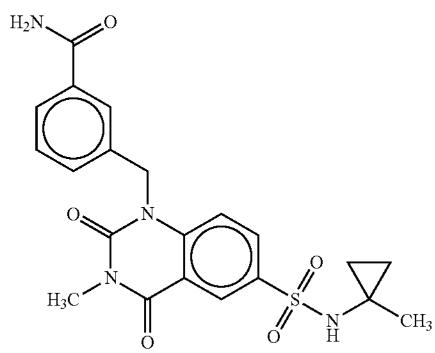 | A1 | 1.350 | |
| Example 94 | 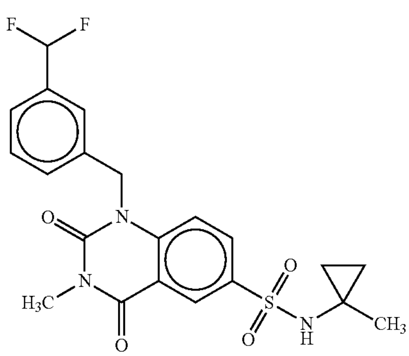 | A1 | 2.250 | |
| Example 95 | 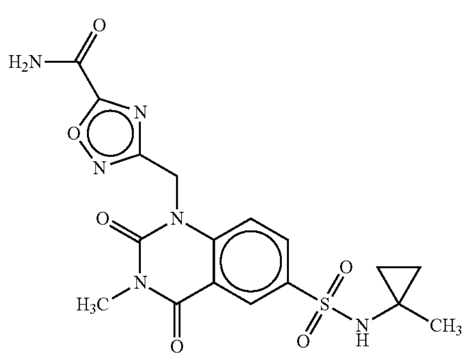 | A1 | 0.758 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 96 | 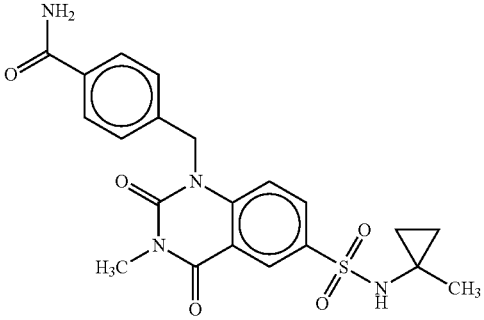 | A1 | 0.469 | 3.770 |
| Example 97 | 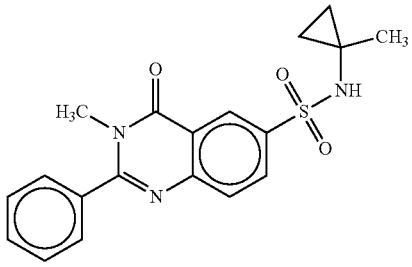 | 14 | 2.186 | |
| Example 98 | 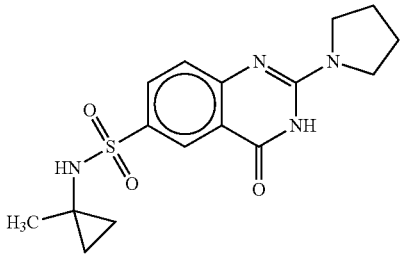 | 13 | 9.437 | |
| Example 99 | 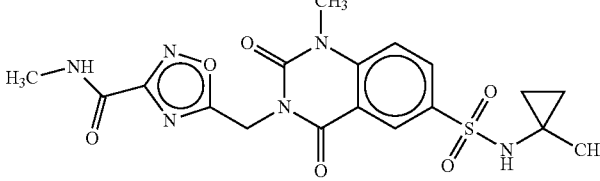 | A3 | 4.580 | |
| Example 100 | 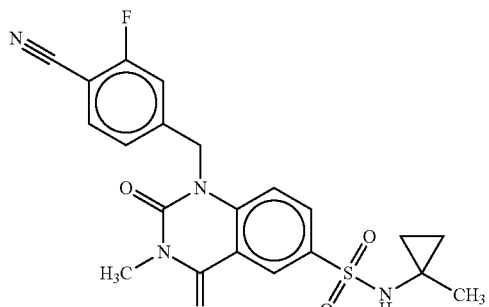 | A1 | 1.280 | |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 101 | 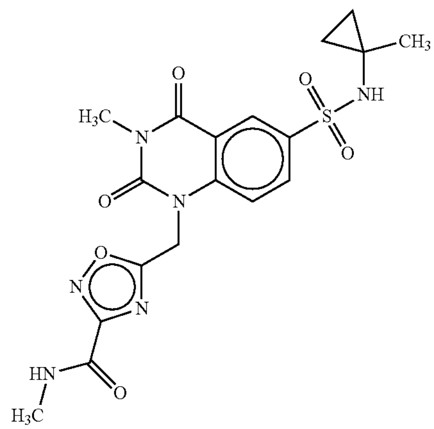 | A1 | 0.857 | |
| Example 102 | 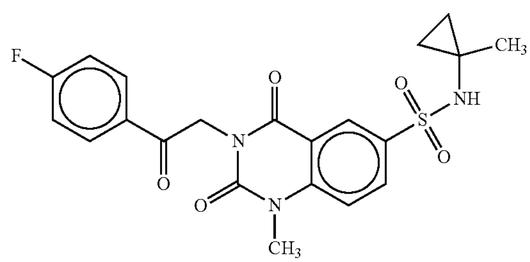 | A3 | 3.000 | |
| Example 103 | 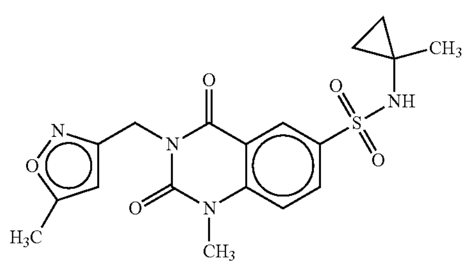 | A3 | 5.190 | |
| Example 104 | 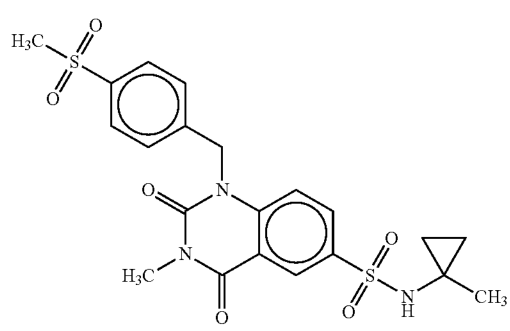 | A1 | 0.896 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 105 | 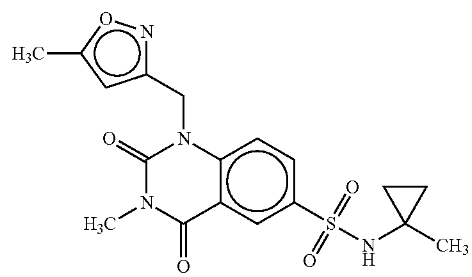 | A1 | 1.430 | |
| Example 106 | 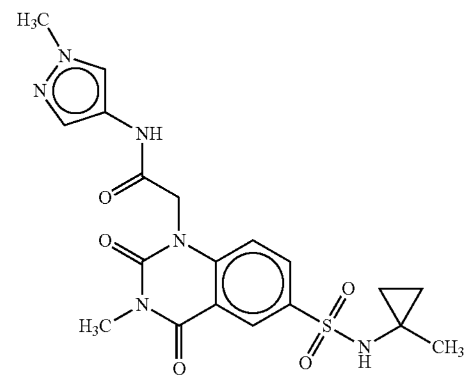 | A1 | 3.880 | |
| Example 107 | 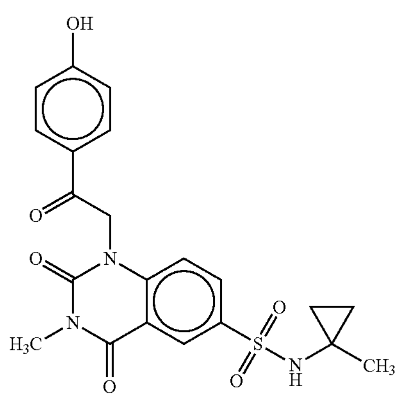 | A1 | 8.940 | |
| Example 108 | 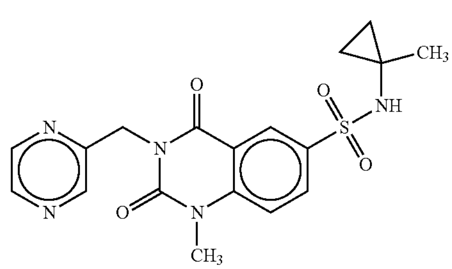 | A3 | 7.800 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 109 | 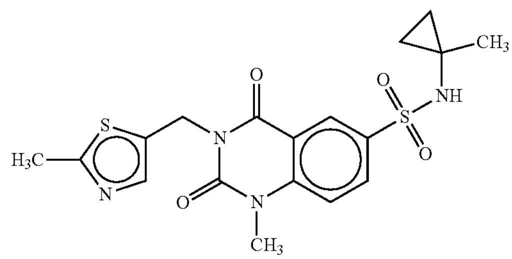 | A3 | 0.483 | 0.288 |
| Example 110 | 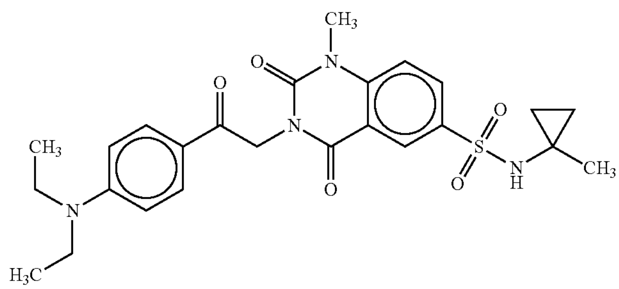 | A3 | 6.700 | |
| Example 111 | 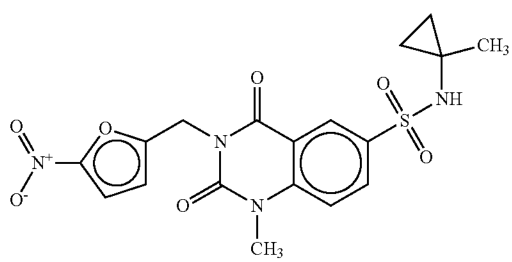 | A3 | 7.740 | |
| Example 112 | 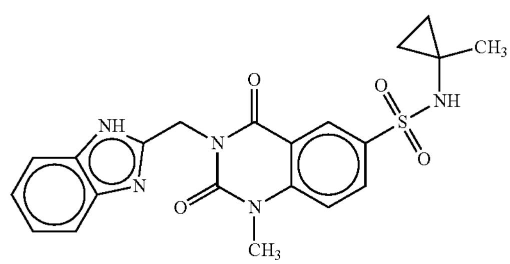 | A3 | 5.710 | |
| Example 113 | 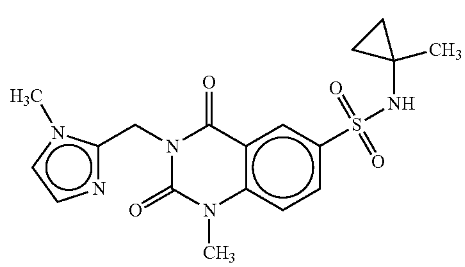 | A3 | 7.350 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 114 | 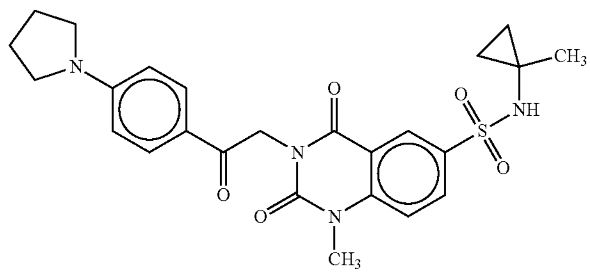 | A3 | 1.510 | |
| Example 115 | 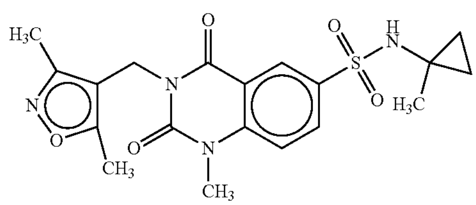 | A3 | 0.616 | 0.386 |
| Example 116 | 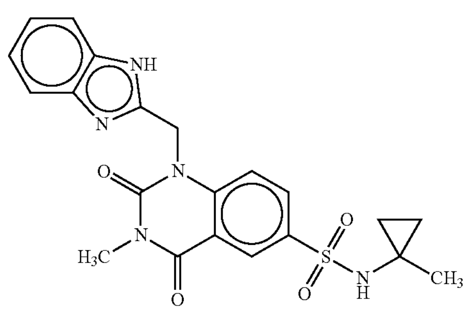 | A1 | 1.050 | |
| Example 117 | 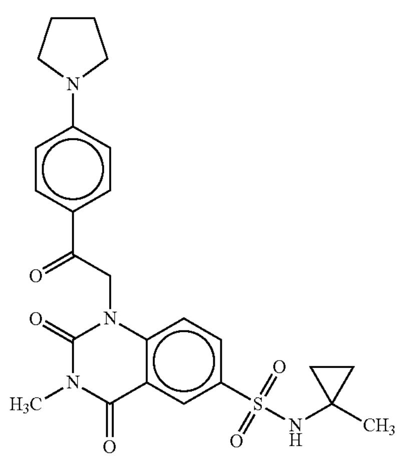 | A1 | 4.810 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 118 | 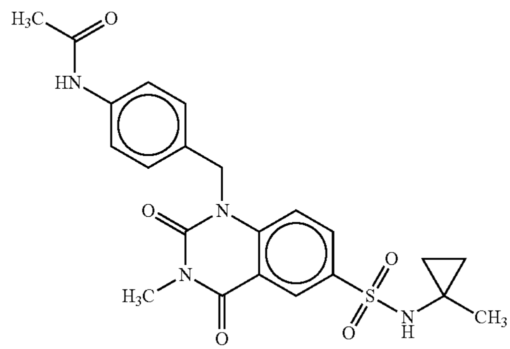 | A1 | 0.586 | |
| Example 119 | 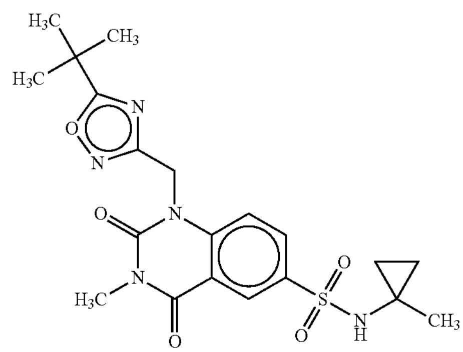 | A1 | 1.420 | |
| Example 120 | 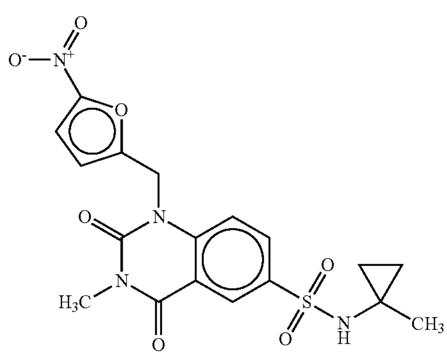 | A1 | 4.110 | |
| Example 121 | 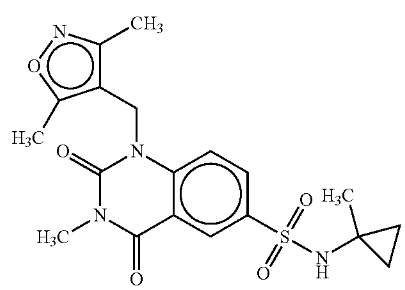 | A1 | 2.540 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 122 | 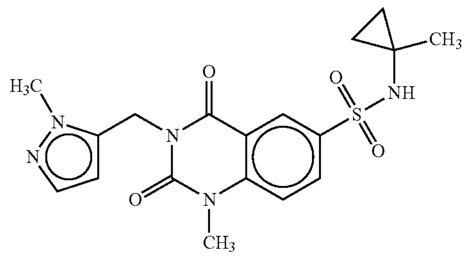 | A3 | 4.130 | |
| Example 123 | 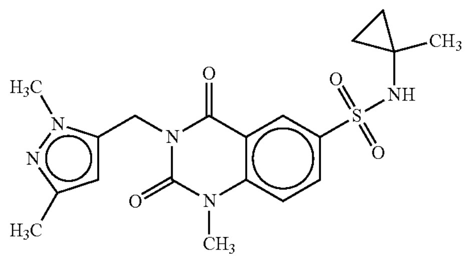 | A3 | 2.420 | |
| Example 124 | 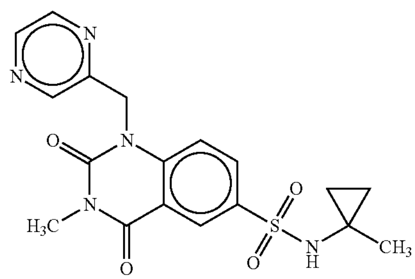 | A1 | 2.240 | |
| Example 125 | 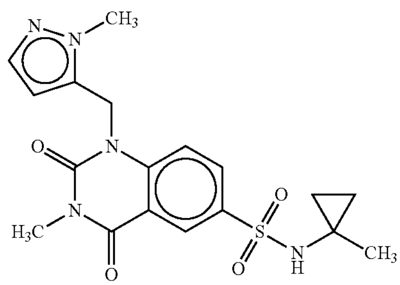 | A1 | 1.230 | |
| Example 126 | 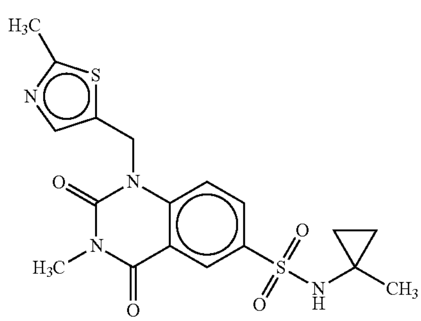 | A1 | 0.240 | 0.214 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 127 | 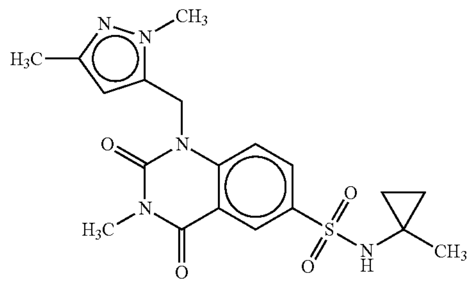 | A1 | 0.384 | 0.413 |
| Example 128 | 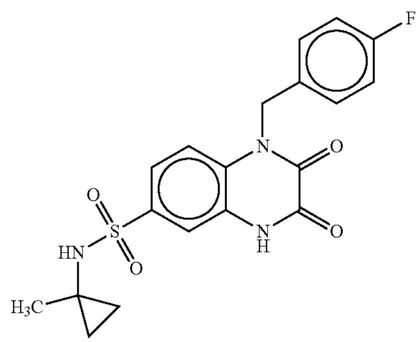 | Intermediate S12-D | 5.104 | |
| Eaxmple 129 | 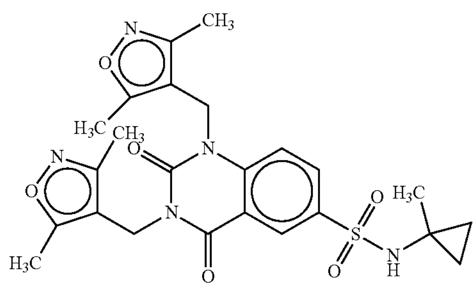 | 1 | 1.040 | |
| Example 130 | 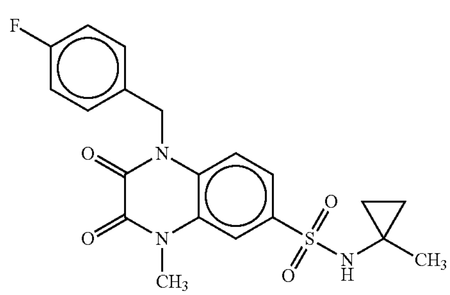 | Scheme 12 | 3.363 | |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 131 | 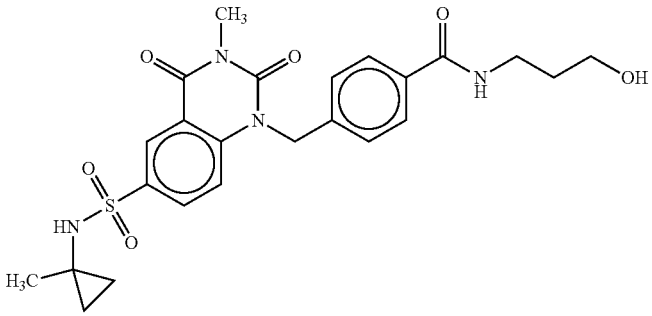 | Quinazolinedione; amide formation | 0.873 | |
| Exampel 132 | 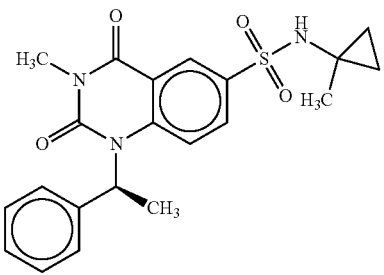 | A2 | 5.300 | |
| Example 133 | 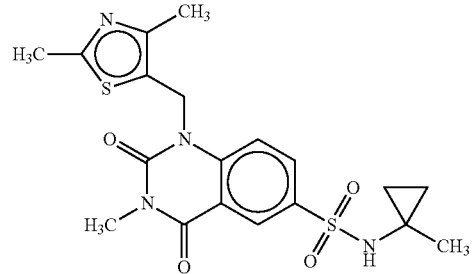 | A2 | 0.184 | 0.124 |
| Example 134 | 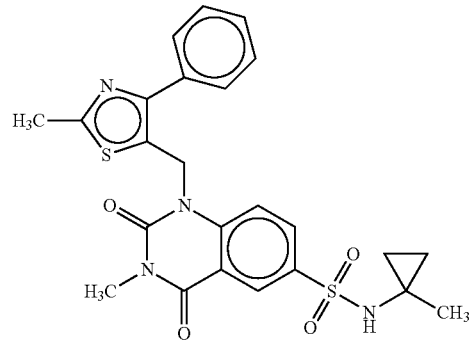 | A4 | 0.760 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 135 | 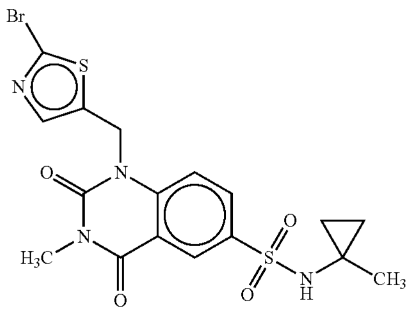 | A2 | 0.521 | |
| Example 136 | 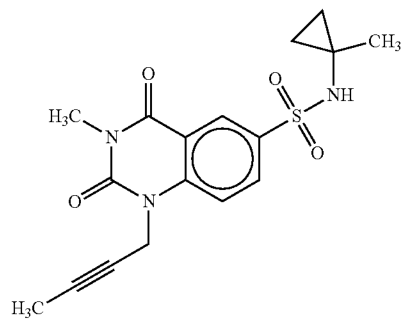 | A1 | 1.110 | |
| Example 137 | 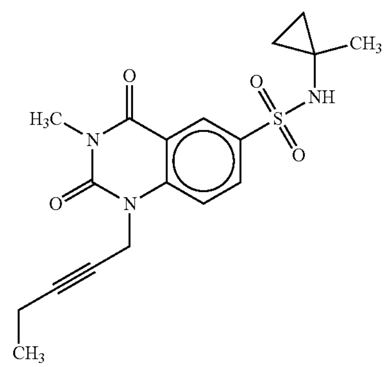 | A1 | 0.477 | 0.608 |
| Example 138 | 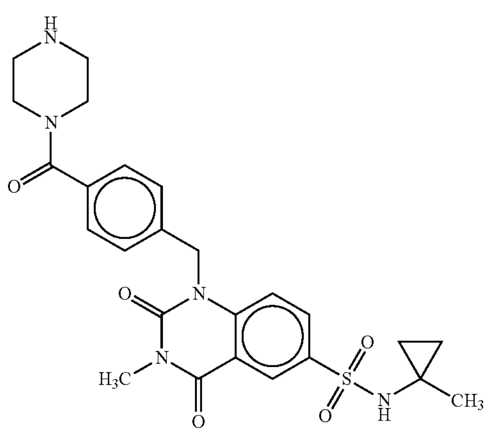 | Quinazolinedione; amide formation | 2.450 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 139 | 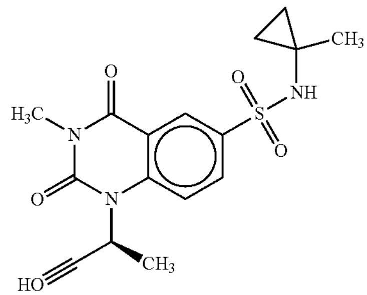 | A2 | 3.680 | |
| Example 140 | 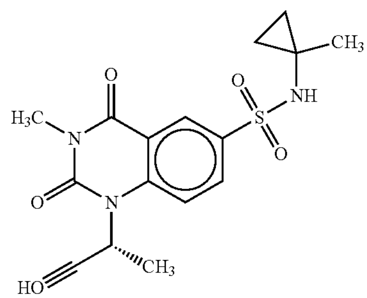 | A2 | 2.790 | |
| Example 141 | 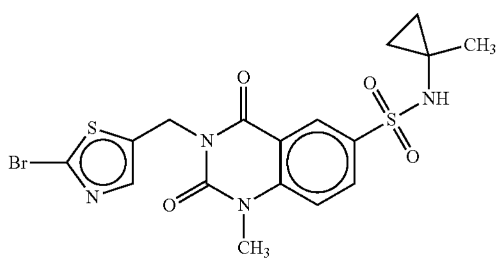 | A2 | 2.820 | |
| Example 142 | 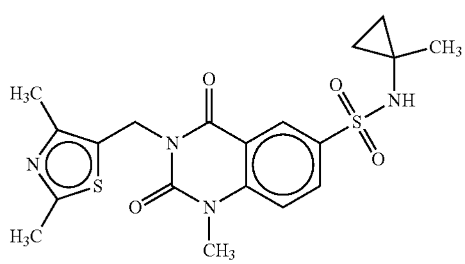 | A2 | 0.907 | |
| Example 143 | 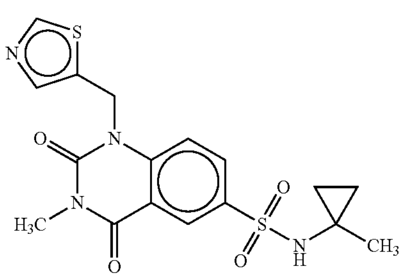 | A2 | 0.342 | 0.538 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 144 | 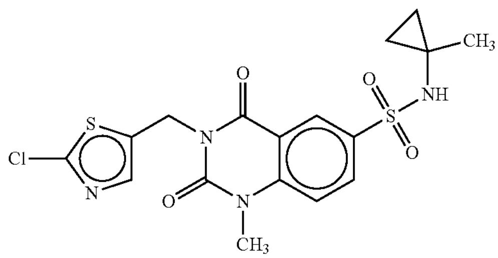 | A2 | 1.600 | |
| Example 145 | 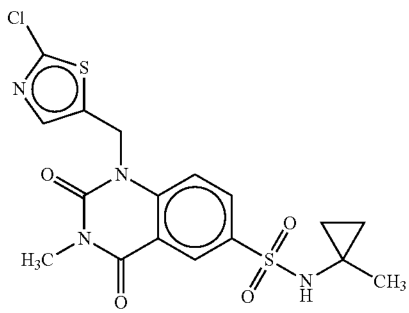 | A2 | 0.151 | 0.342 |
| Example 146 | 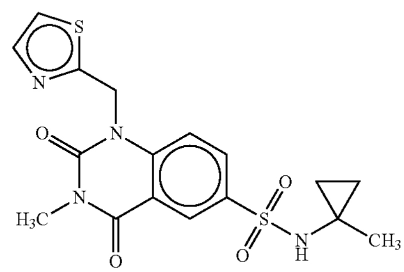 | A2 | 0.671 | |
| Example 147 | 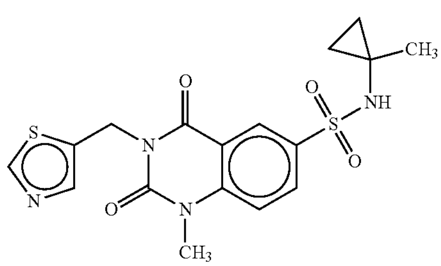 | A2 | 1.210 | |
| Example 148 | 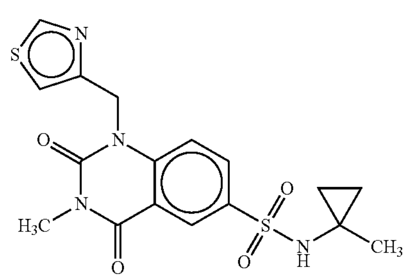 | A2 | 0.855 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---------|-----------|--------|-------------------------------|-----------------------------|
| Example 149 | 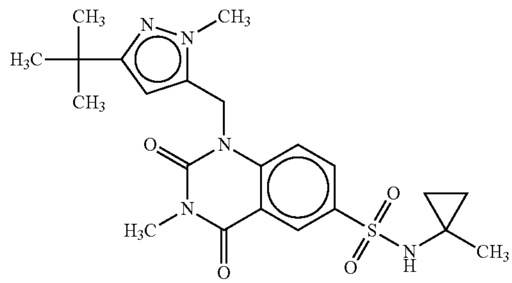 | A2 | 0.293 | 0.518 |
| Example 150 | 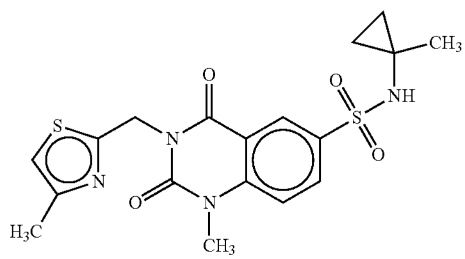 | A2 | 4.780 | |
| Example 151 | 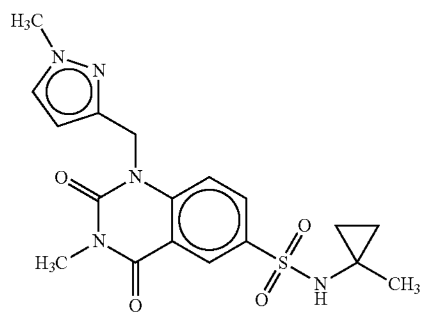 | A2 | 1.070 | |
| Example 152 | 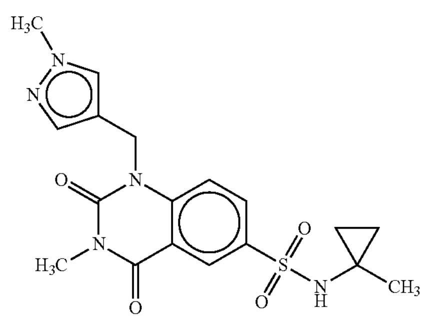 | A2 | 0.463 | 0.520 |
| Example 153 | 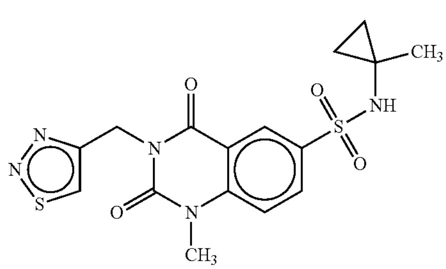 | A2 | 2.690 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 154 | 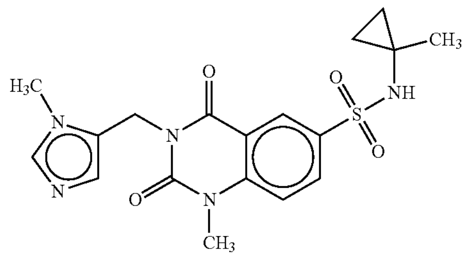 | A2 | 3.310 | |
| Example 155 | 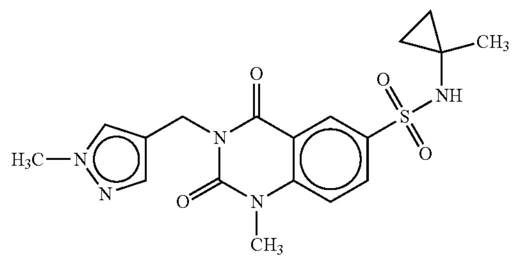 | A1 or A2 | 0.341 | 0.334 |
| Example 156 | 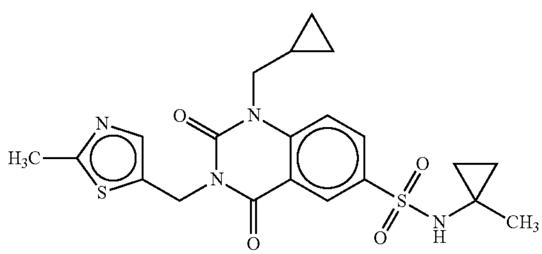 | A2 | 0.019 | 0.028 |
| Example 157 | 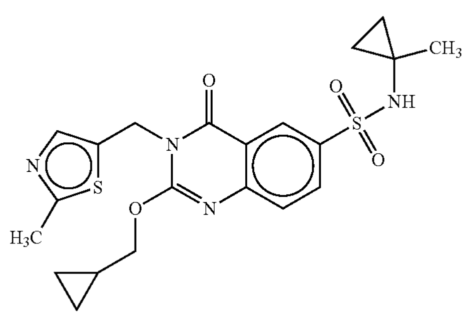 | A2 | 0.302 | 0.138 |
| Example 158 | 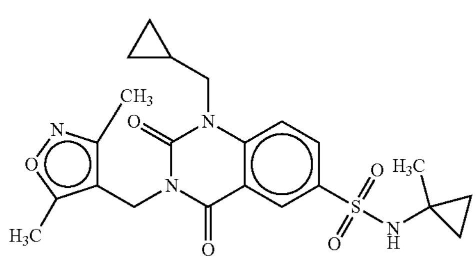 | A2 | 0.092 | 0.088 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 159 | 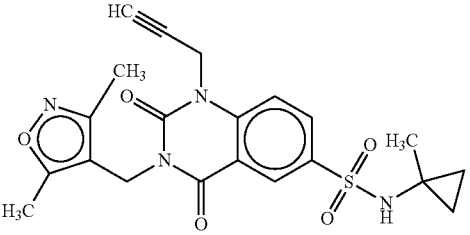 | A2 | 0.109 | 0.153 |
| Example 160 | 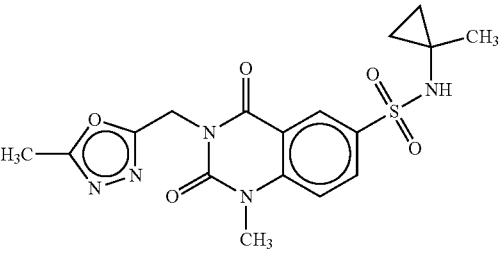 | A2 | 1.880 | |
| Example 161 | 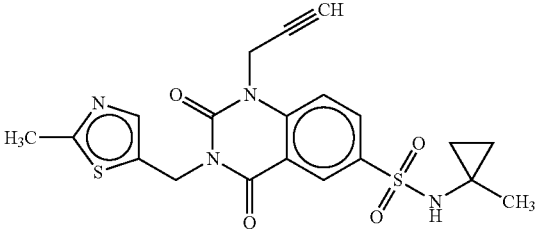 | A2 | 0.045 | 0.082 |
| Example 162 | 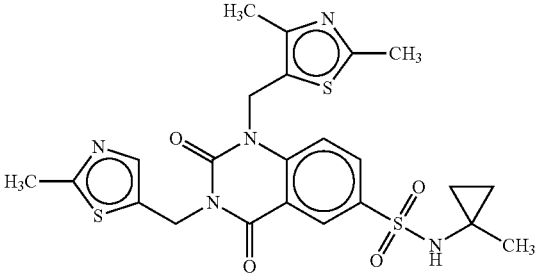 | A2 | 0.004 | 0.009 |
| Example 163 | 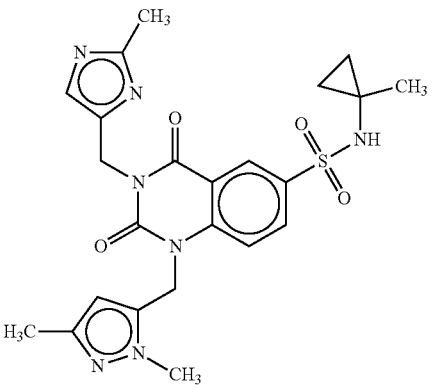 | A1 or A2 | 0.012 | 0.041 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 164 | 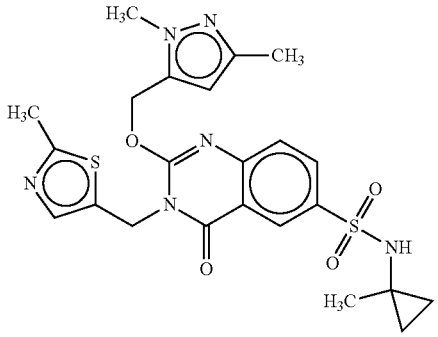 | A2 | 0.343 | 0.782 |
| Example 165 | 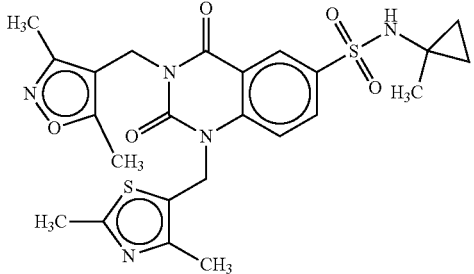 | A2 | 0.033 | 0.063 |
| Example 166 | 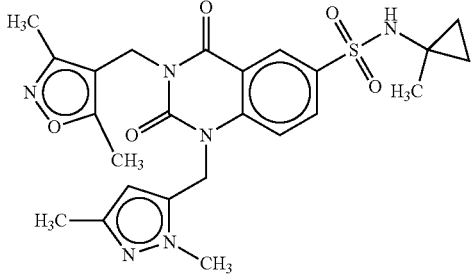 | A2 | 0.131 | 0.229 |
| Example 167 | 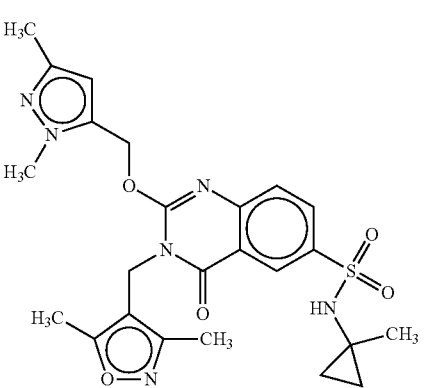 | A2 | 0.700 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 168 | 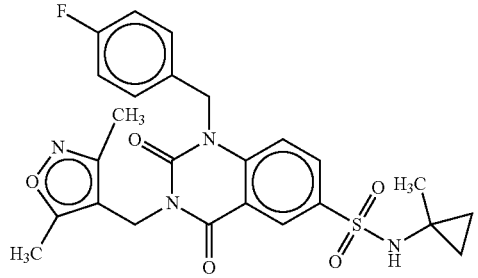 | A5 | 0.160 | 0.146 |
| Example 169 | 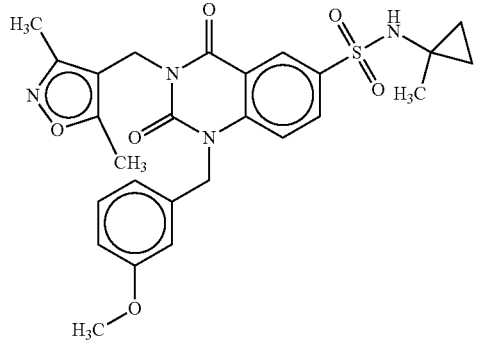 | A5 | 0.294 | 0.288 |
| Example 170 | 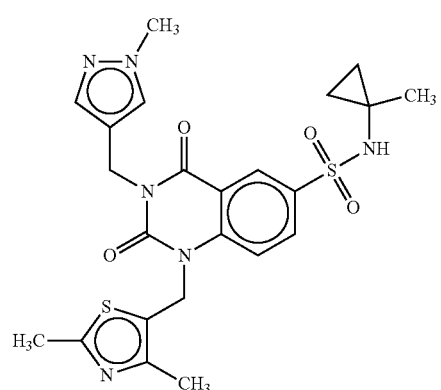 | A2 | 0.006 | 0.020 |
| Example 171 | 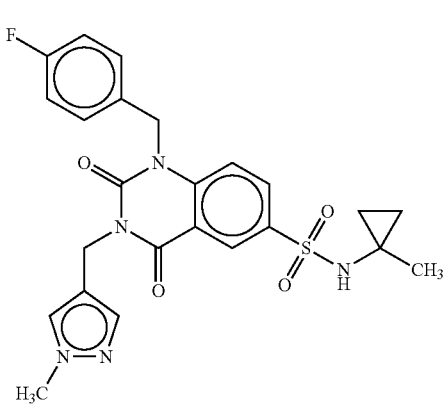 | A5 | 0.049 | 0.103 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 172 | 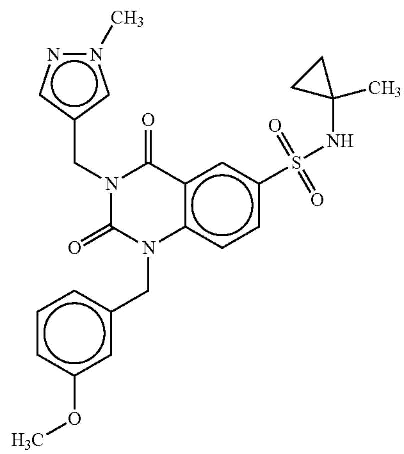 | A5 | 0.100 | 0.193 |
| Example 173 | 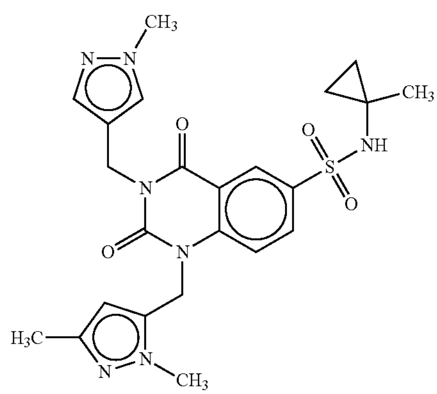 | A2 or A5 | 0.018 | 0.088 |
| Example 174 | 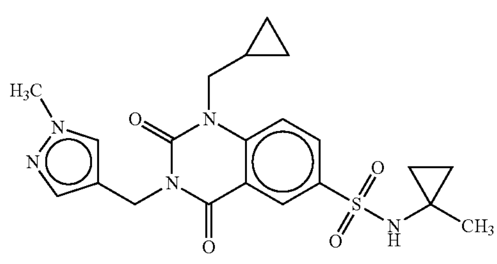 | A2 | 0.029 | 0.056 |
| Example 175 | 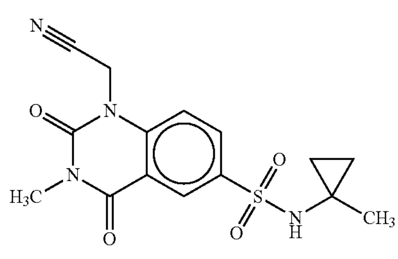 | A5 | 4.410 | |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 176 | 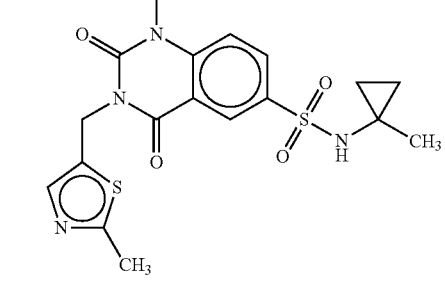 | A5 | 0.089 | 0.085 |
| Example 177 | 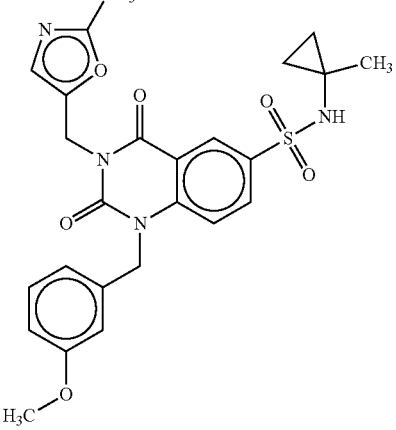 | A5 | 0.132 | 0.177 |
| Example 178 | 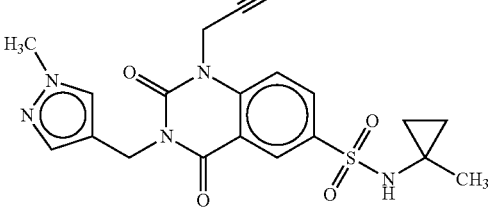 | A2 | 0.052 | 0.126 |
| Example 179 | 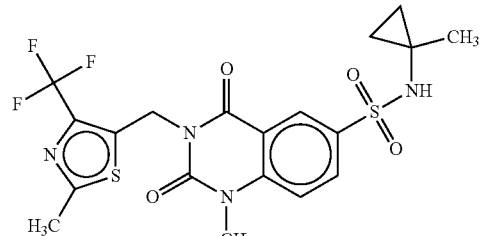 | A9 | 0.725 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 180 | 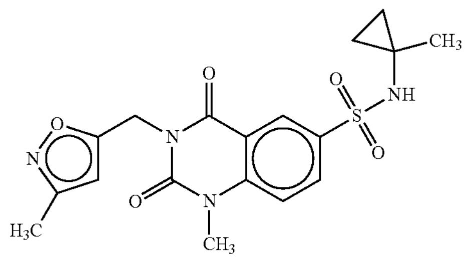 | A3 or A9 | 0.426 | 0.460 |
| Example 181 | 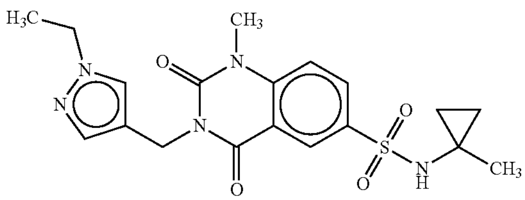 | A2 | 0.447 | 0.680 |
| Example 182 | 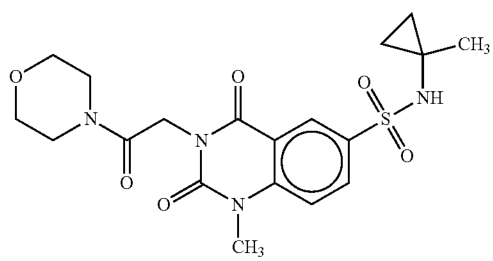 | A8 | 4.410 | |
| Example 183 | 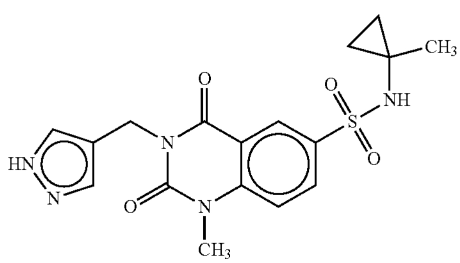 | A2 | 0.379 | 0.931 |
| Example 184 | 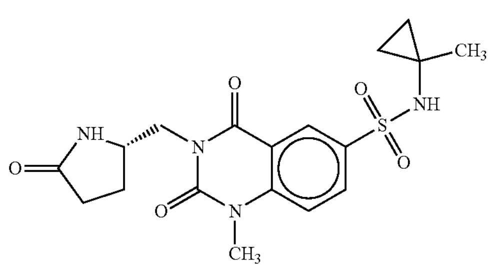 | A9 | 8.160 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 185 | 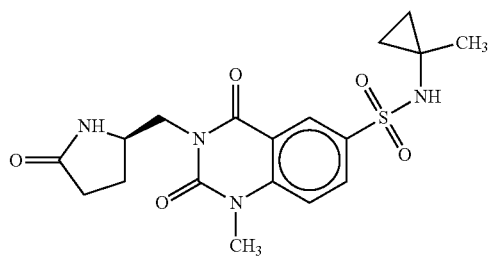 | A9 | 6.330 | |
| Example 186 | 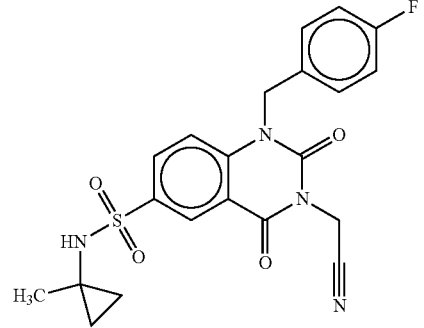 | A5 | 0.441 | 0.307 |
| Example 187 | 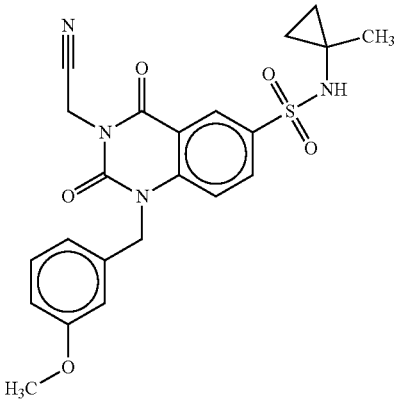 | A5 | 0.467 | 0.343 |
| Example 188 | 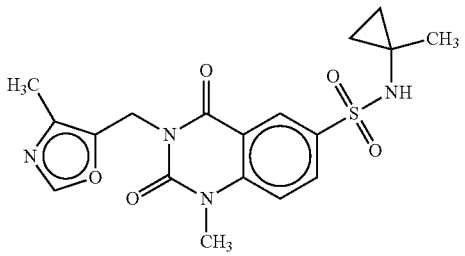 | A2 | 1.840 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 189 | 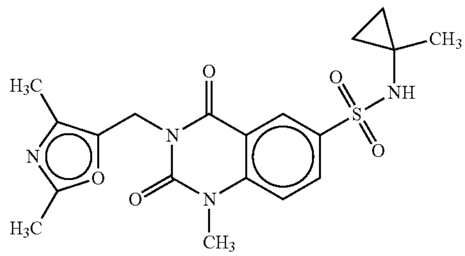 | A2 | 1.330 | |
| Example 190 | 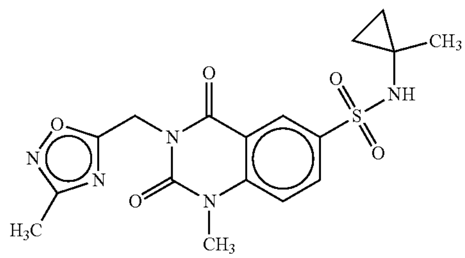 | A2 | 3.180 | |
| Example 191 | 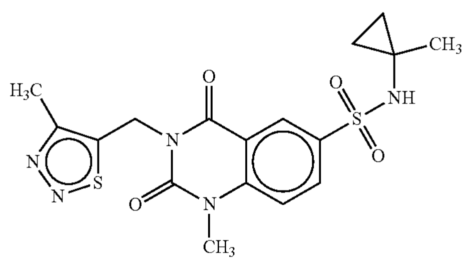 | A2 | 0.877 | |
| Example 192 | 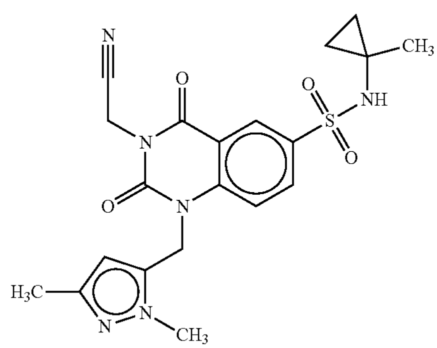 | A2 | 0.274 | 1.100 |
| Example 193 | 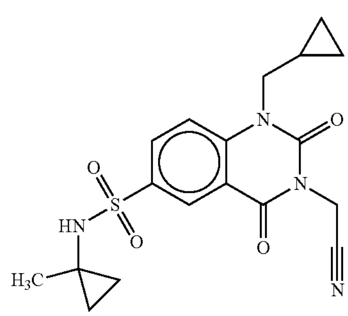 | A5 | 0.277 | 0.556 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 194 | 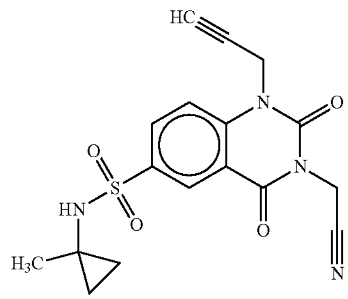 | A5 | 0.245 | 0.273 |
| Example 195 | 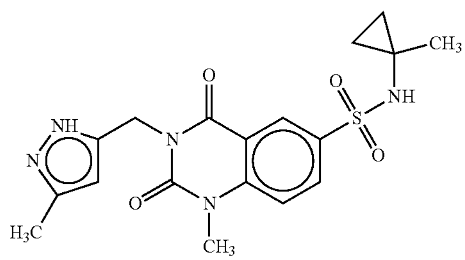 | A2 | 3.220 | |
| Example 196 | 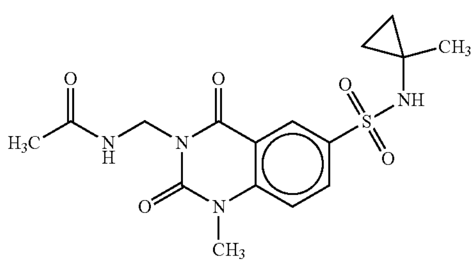 | A2 | 4.530 | |
| Example 197 | 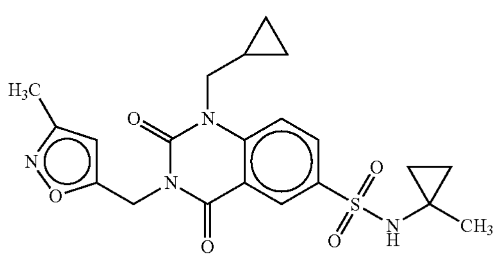 | A5 | 0.055 | 0.049 |
| Example 198 | 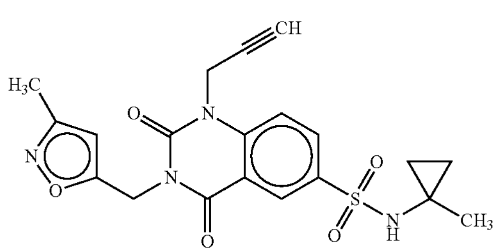 | A5 | 0.105 | 0.076 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 199 | 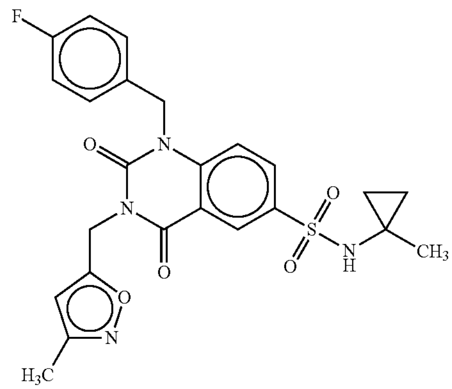 | A5 | 0.092 | 0.099 |
| Example 200 | 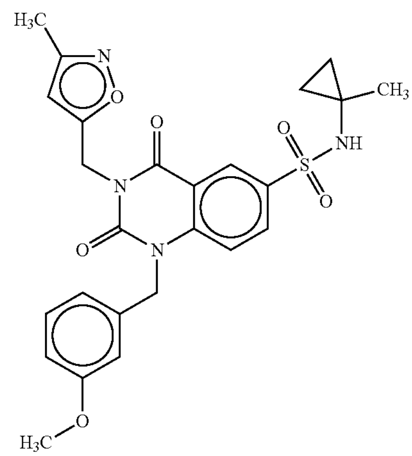 | A5 | 0.250 | 0.223 |
| Example 201 | 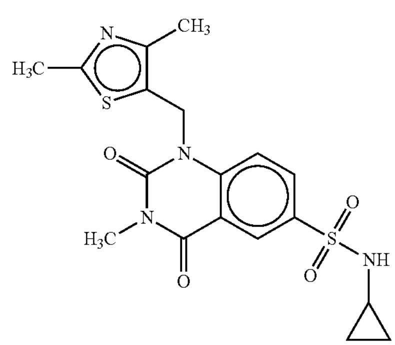 | 1 | 0.190 | 0.224 |
| Example 202 | 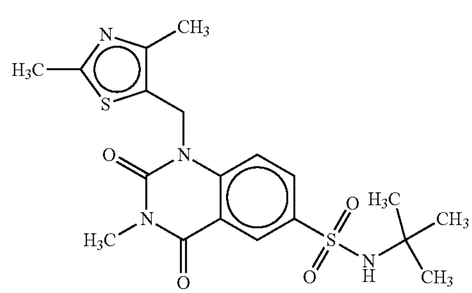 | 1 | 1.390 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 203 | 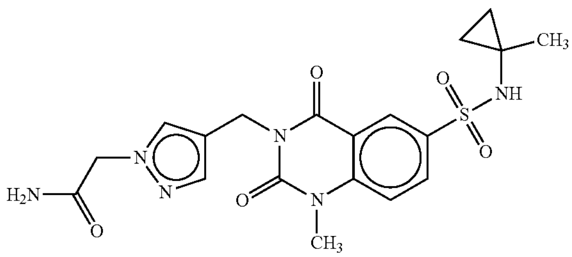 | 3 | 0.635 | |
| Example 204 | 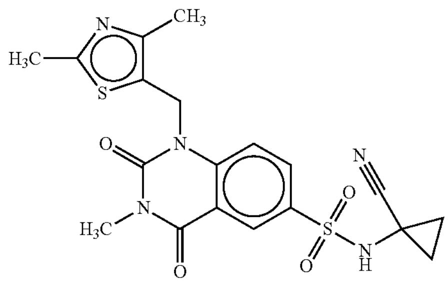 | 1 | 0.118 | 0.646 |
| Example 205 | 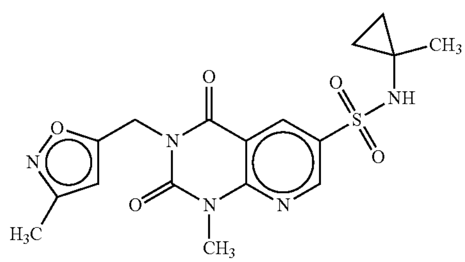 | A2 | 2.598 | |
| Example 206 | 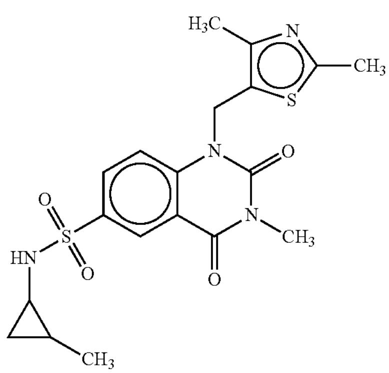 | 1 | 0.813 | |
| Example 207 | 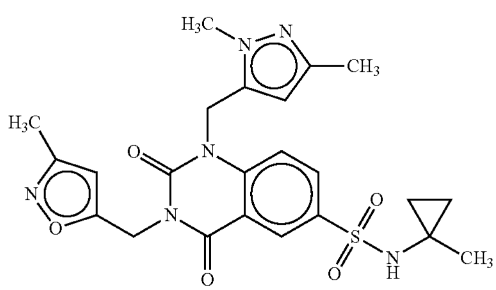 | A5 | 0.038 | 0.116 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 208 | 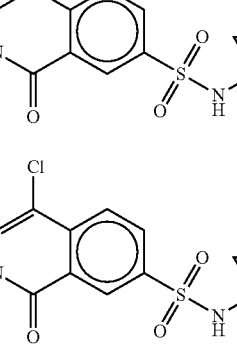 | A1 | 0.036 | 0.069 |
| Example 209 | 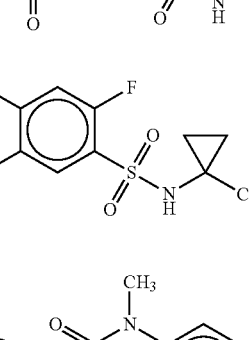 | Intermediate S9-F1 | 1.637 | |
| Example 210 | 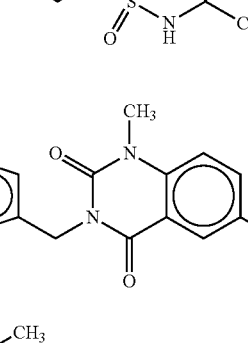 | A3 | 1.228 | |
| Example 211 | 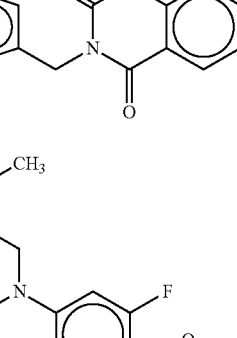 | Intermediate S4-C8 | 1.560 | |
| Example 212 | 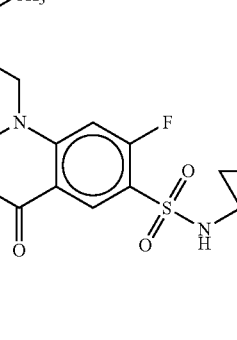 | A3 | 1.370 | |
| Example 213 | 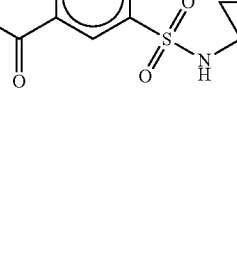 | A5 | 0.473 | 0.787 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 214 | 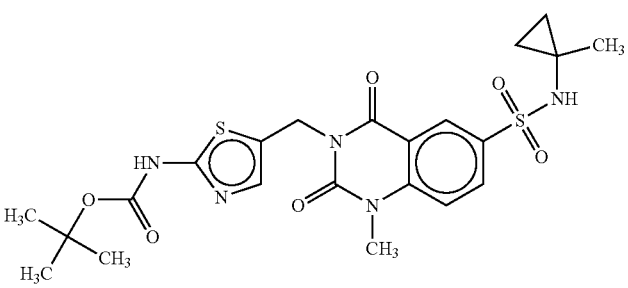 | A3 | 0.411 | 3.470 |
| Example 215 | 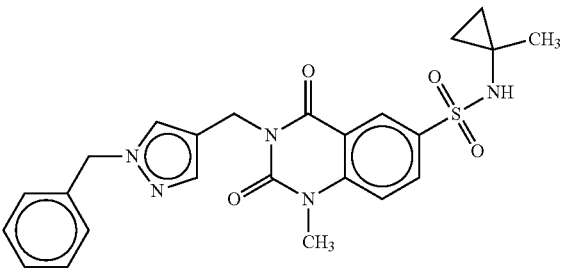 | A3 | 0.592 | |
| Example 216 | 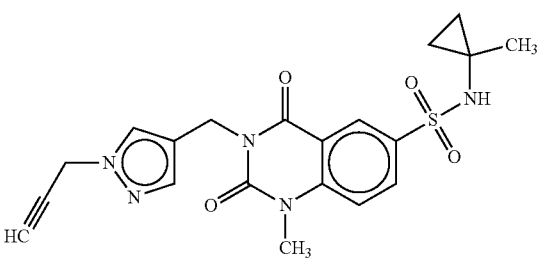 | 3 | 0.560 | |
| Example 217 | 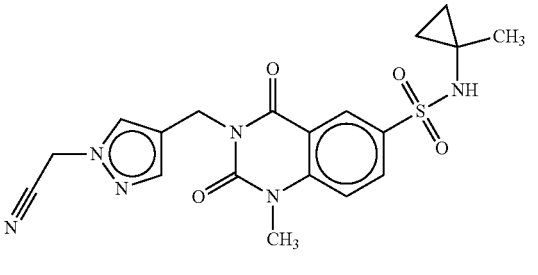 | 3 | 0.365 | 0.529 |
| Example 218 | 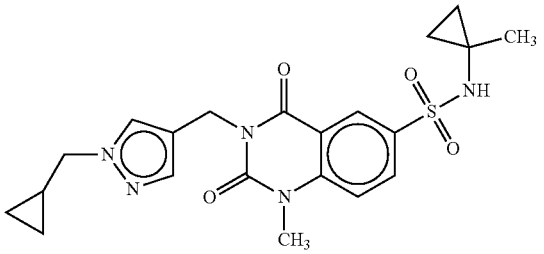 | 3 | 0.681 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 219 | 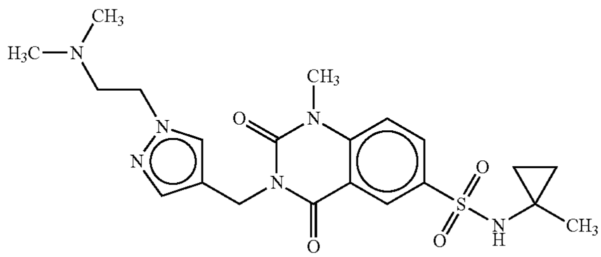 | 3 | 2.480 | |
| Example 220 | 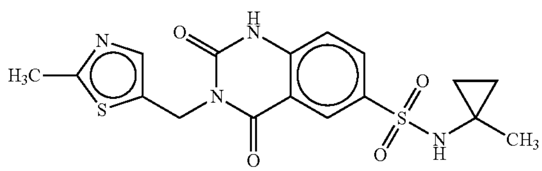 | Intermediate S4-C4 | 0.273 | 0.481 |
| Example 221 | 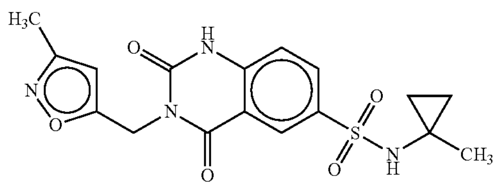 | Intermediate S4-C2 | 0.649 | |
| Example 222 | 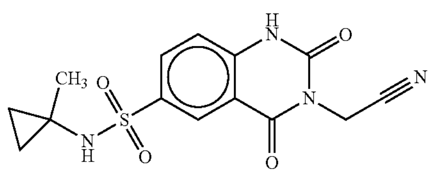 | Intermediate S4-C5 | 2.200 | |
| Example 223 | 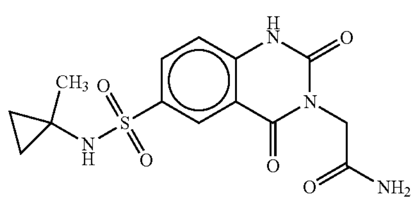 | Scheme 4 | 7.470 | |
| Example 224 | 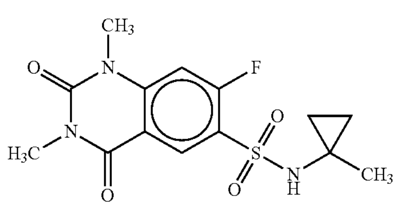 | 1 | 1.440 | |
| Example 225 | 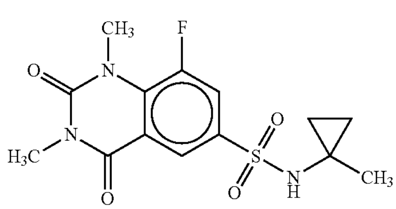 | 1 | 7.490 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 226 | 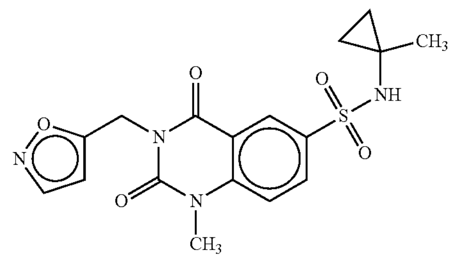 | A3 | 1.180 | |
| Example 227 | 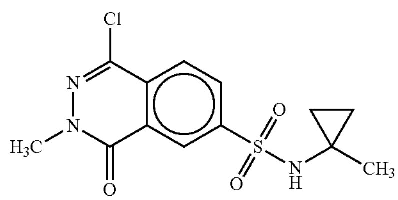 | Intermediate S5-F2 | 5.143 | |
| Example 228 | 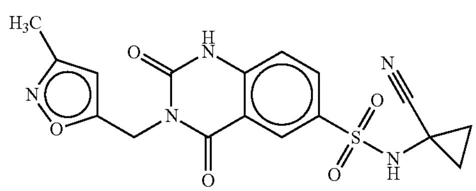 | Intermediate S4-C6 | 0.356 | 15.200 |
| Example 229 | 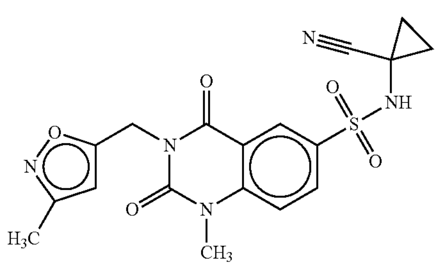 | A1 | 0.446 | 1.470 |
| Example 230 | 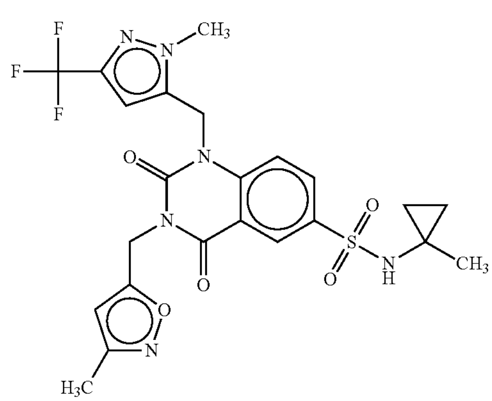 | A2 | 0.127 | 0.213 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 231 | 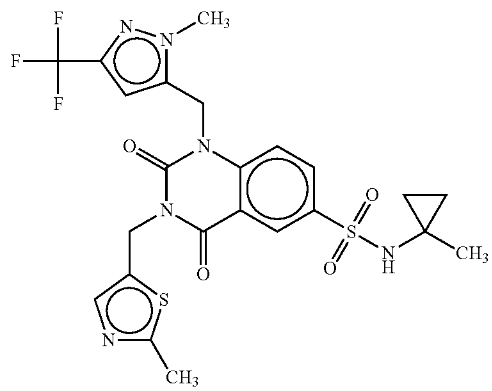 | A2 | 0.055 | 0.047 |
| Example 232 | 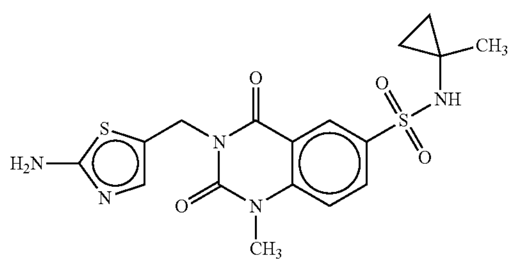 | Quinazolinedione; amine deprotection | 0.479 | 1.560 |
| Example 233 | 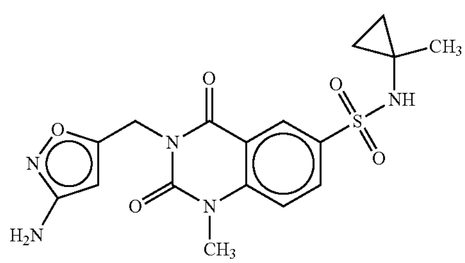 | Quinazolinedione; amine deprotection | 0.643 | 2.410 |
| Example 234 | 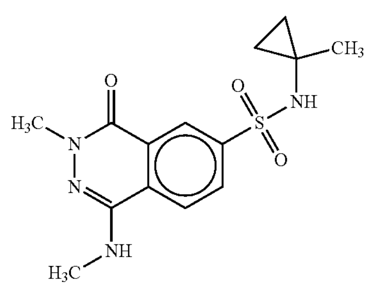 | N-substituted phthalazinone examples | 1.983 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 235 | 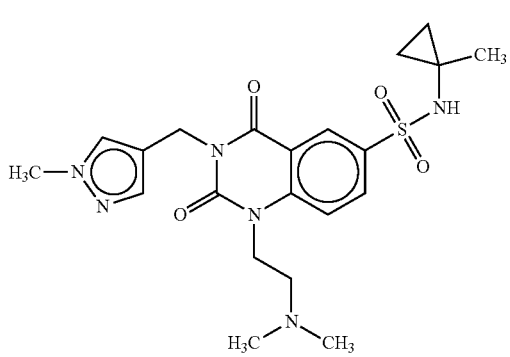 | A6 | 0.224 | 0.314 |
| Example 236 | 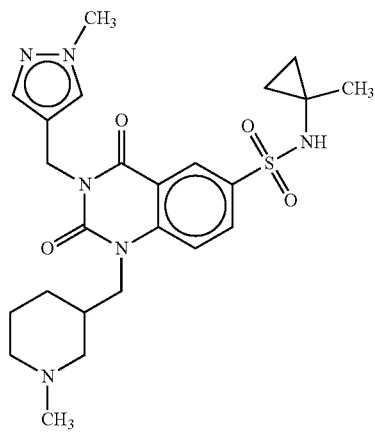 | A6 | 6.740 | |
| Example 237 | 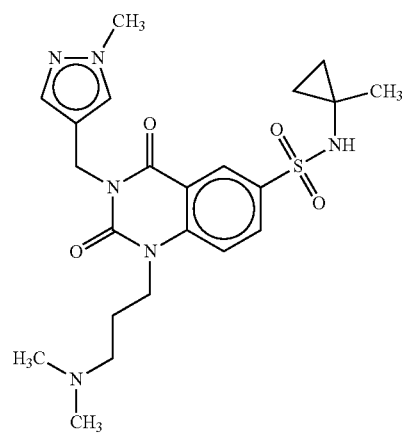 | A6 or A9 | 0.232 | 0.285 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 238 | 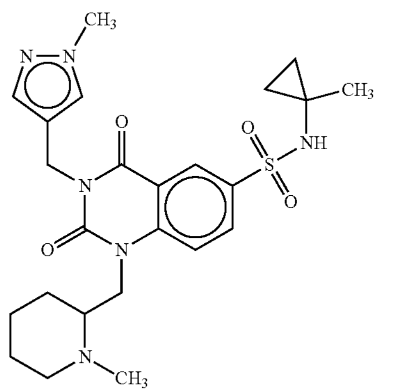 | A6 | 0.158 | 0.220 |
| Example 239 | 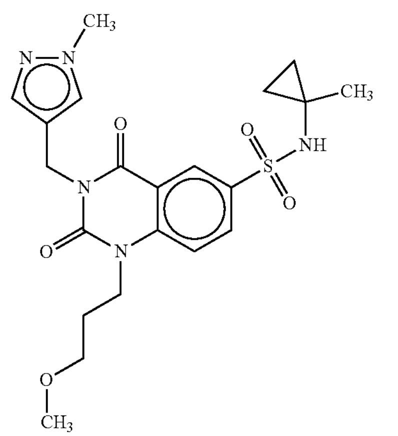 | A11 | 0.209 | 0.127 |
| Example 240 | 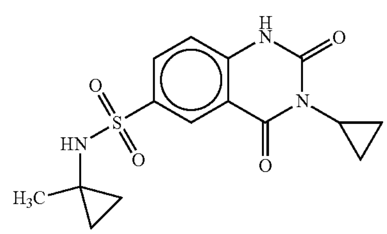 | Intermediate S4-C7 | 4.120 | |
| Example 241 | 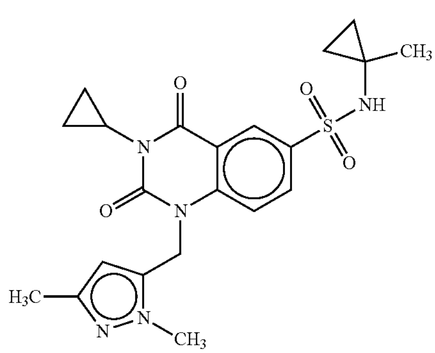 | A1 | 0.642 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 242 | 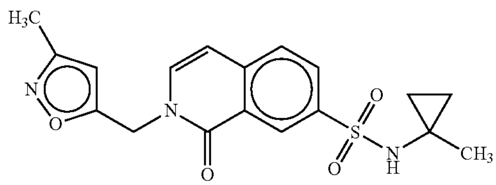 | 1-Oxo-isoquinoline-7-sulfonamide examples | 7.348 | |
| Example 243 | 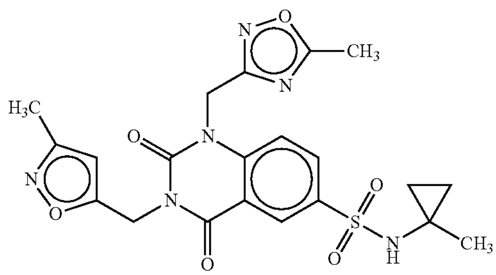 | A2 | 0.312 | 0.221 |
| Example 244 | 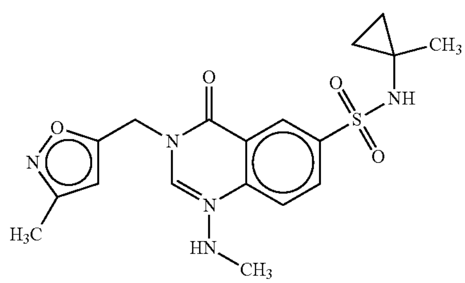 | N-substituted phthalazinone examples | 0.666 | |
| Example 245 | 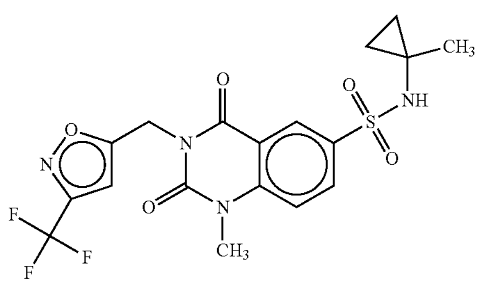 | A2 | 1.830 | |
| Example 246 | 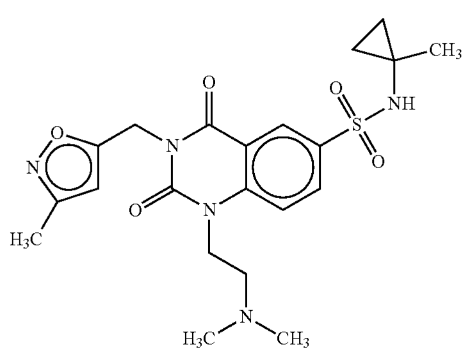 | A6 | 0.469 | 0.431 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 247 | 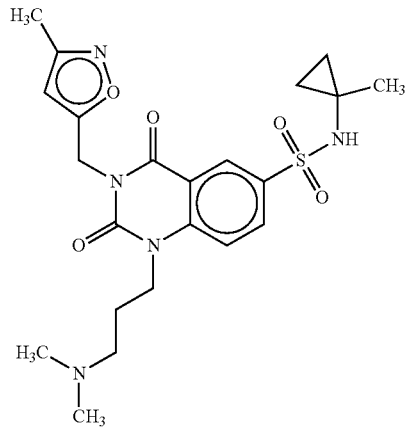 | A6 | 0.404 | 0.310 |
| Example 248 | 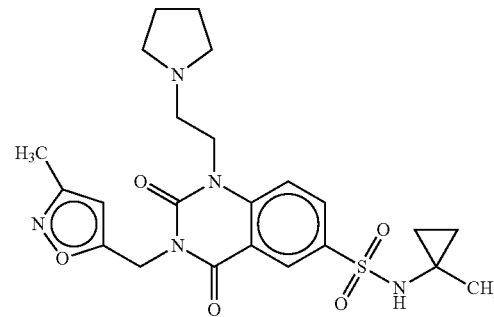 | A6 | 0.521 | |
| Example 249 | 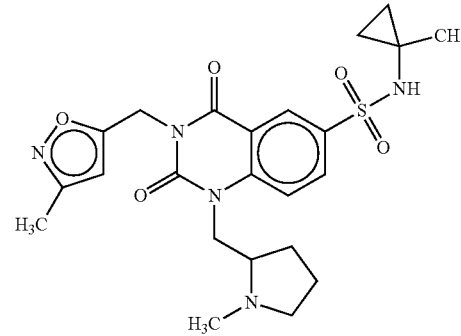 | A6 | 0.402 | 0.315 |

… TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 250 | 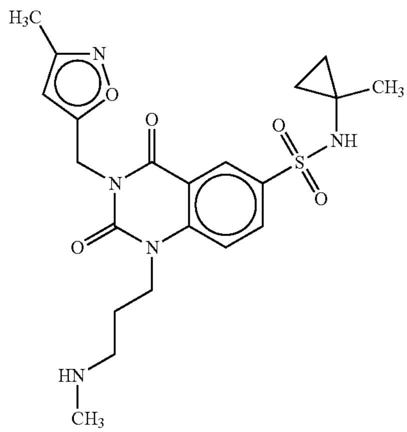 | A7 | 0.323 | 0.328 |
| Example 251 | 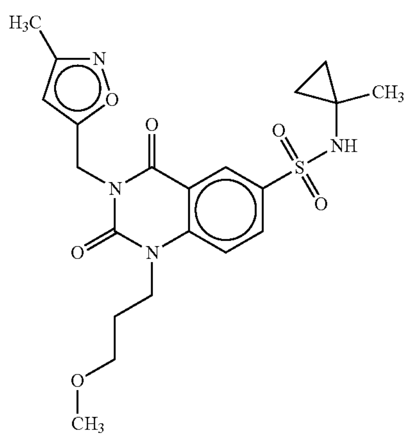 | A7 | 0.392 | 0.178 |
| Example 252 | 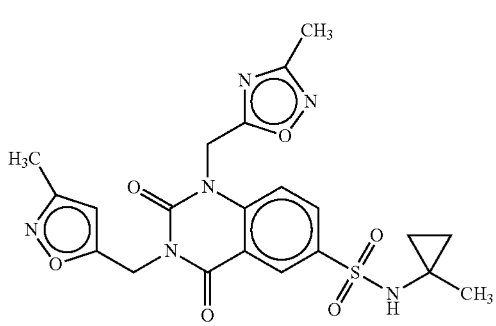 | A2 | 0.391 | 0.297 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 253 | 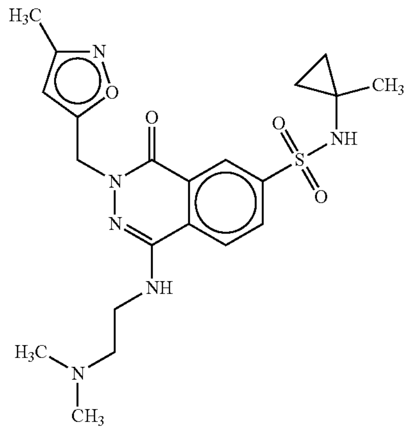 | 4 | 0.376 | 2.021 |
| Example 254 | 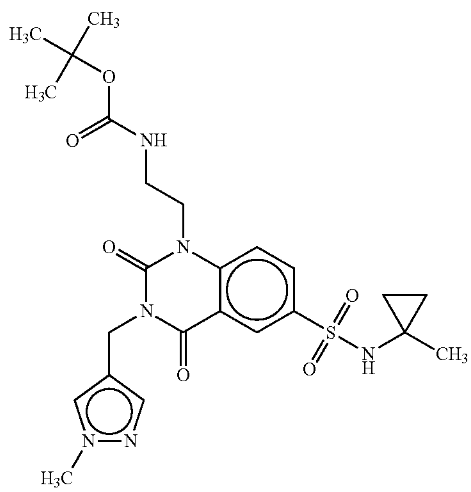 | A9 | 0.998 | |
| Example 255 | 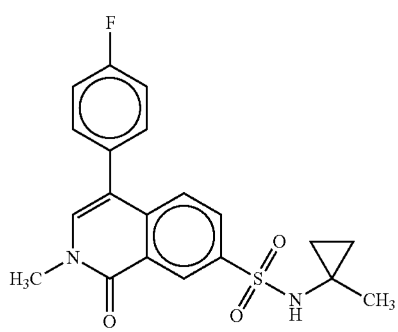 | Scheme 10 | 8.525 | |
| Example 256 | 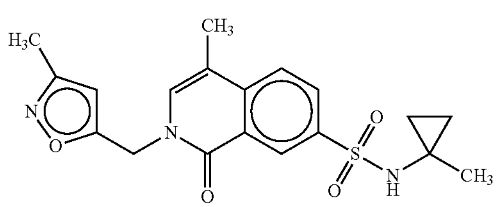 | Scheme 10 | 1.281 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 257 | 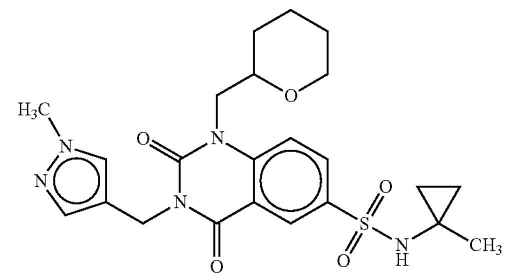 | A9 | 0.103 | 0.098 |
| Example 258 | 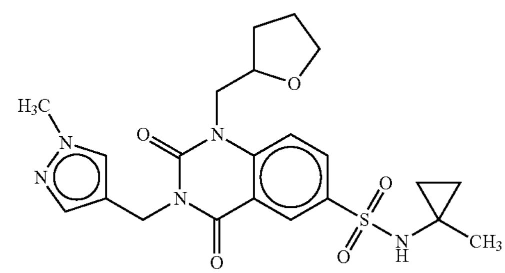 | A9 | 0.169 | 0.131 |
| Example 259 | 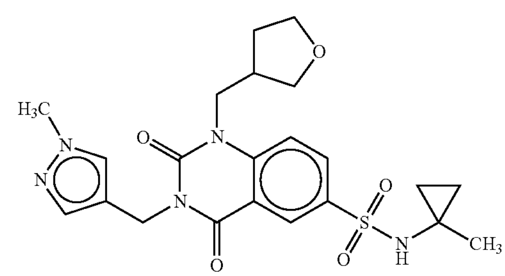 | A10 | 0.108 | 0.108 |
| Example 260 | 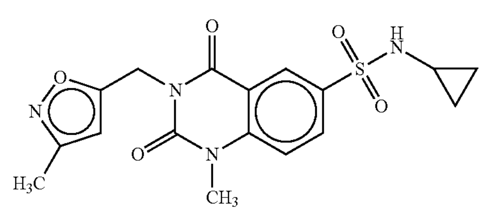 | 2 | 3.790 | |
| Example 261 | 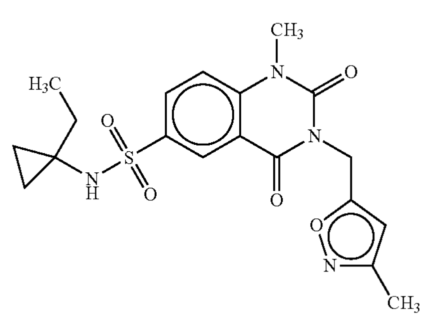 | 2 | 3.040 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 262 | 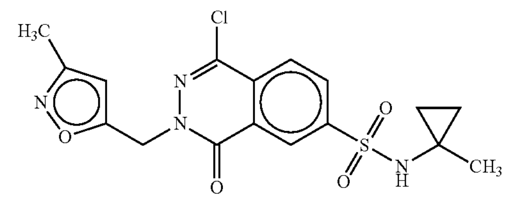 | Intermediate S5-F1 | 1.109 | |
| Example 263 | 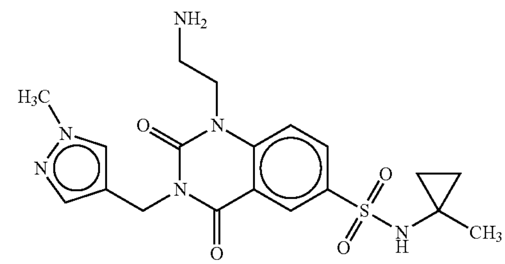 | Quinazolinedione; amine deprotection | 0.350 | 14.700 |
| Example 264 | 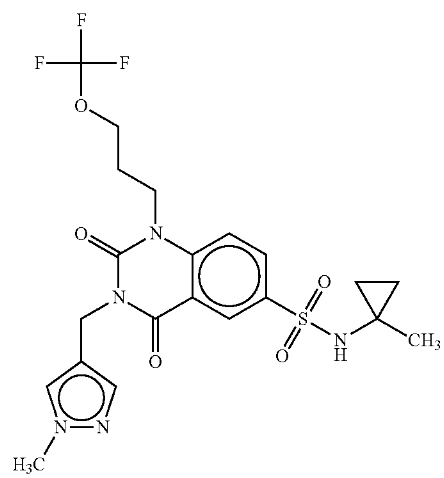 | A10 | 0.256 | 0.187 |
| Example 265 | 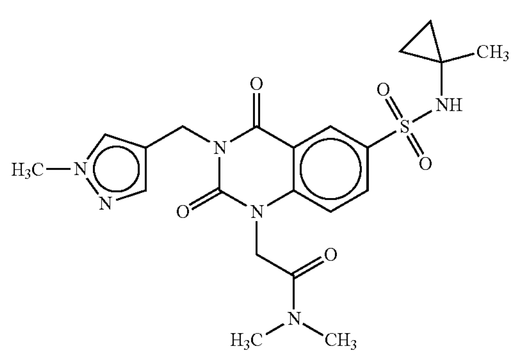 | A10 | 0.418 | 6.480 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 266 | 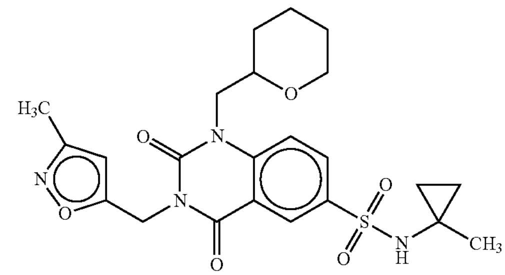 | A10 | 0.296 | 0.214 |
| Example 267 | 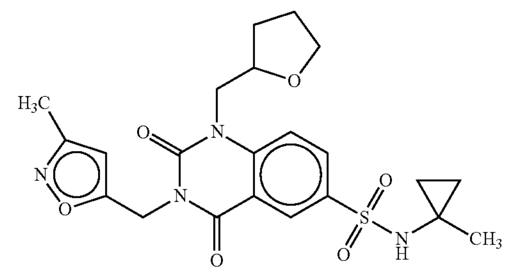 | A10 | 0.234 | 0.248 |
| Example 268 | 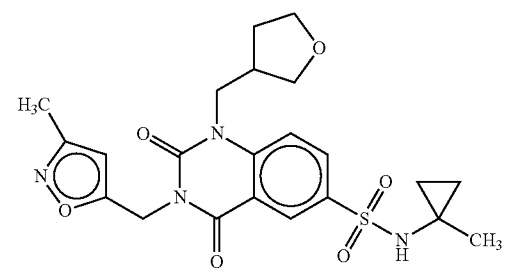 | A10 | 0.111 | 0.217 |
| Example 269 | 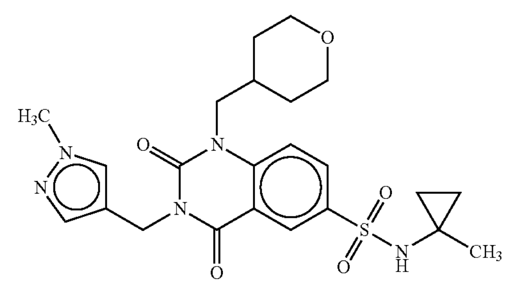 | A10 | 0.057 | 0.098 |
| Example 270 | 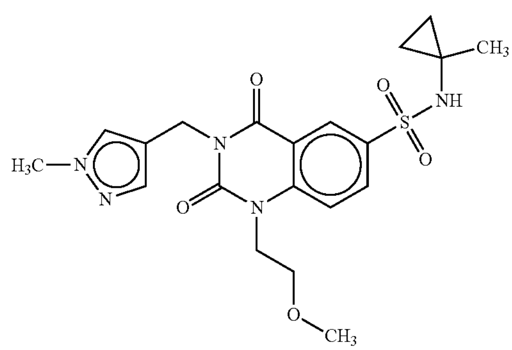 | A8 | 0.128 | 0.102 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 271 | 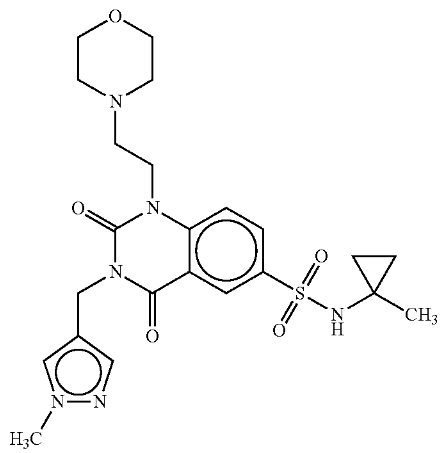 | A8 | 0.097 | 0.161 |
| Example 272 | 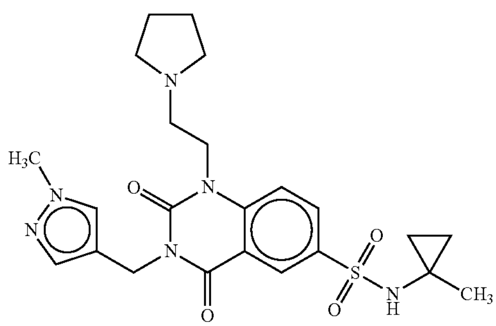 | A8 | 0.317 | 0.467 |
| Example 273 | 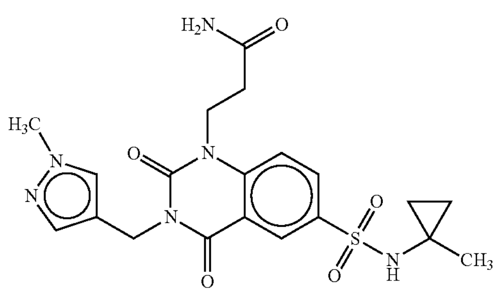 | A8 | 0.291 | 14.500 |
| Example 274 | 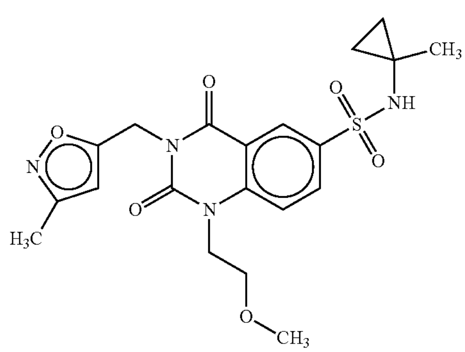 | A8 | 0.237 | 0.166 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 275 | 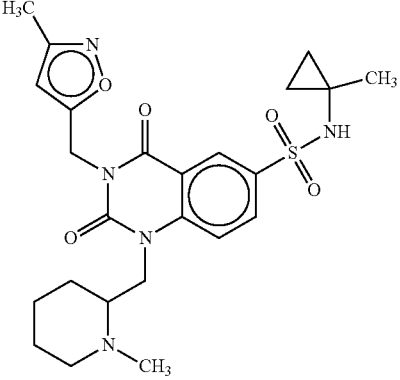 | A8 | 0.333 | 0.304 |
| Example 276 | 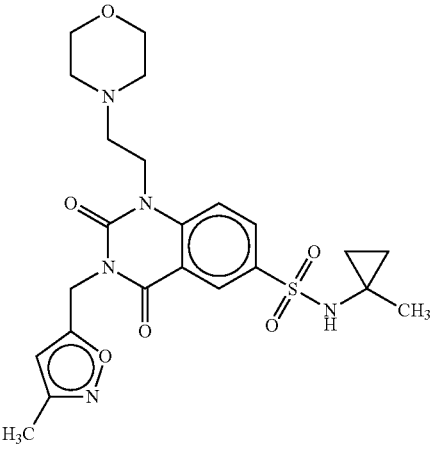 | A8 | 0.255 | 0.536 |
| Example 277 | 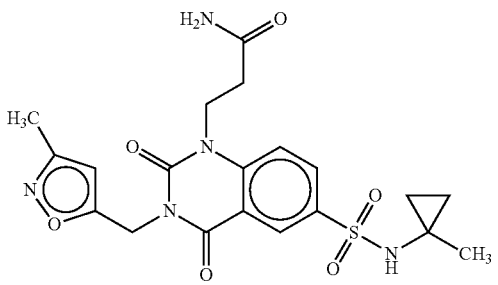 | A6 | 0.432 | 5.760 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 278 | 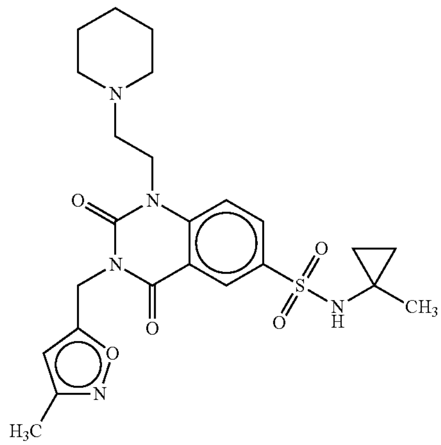 | A9 | 0.526 | |
| Example 279 | 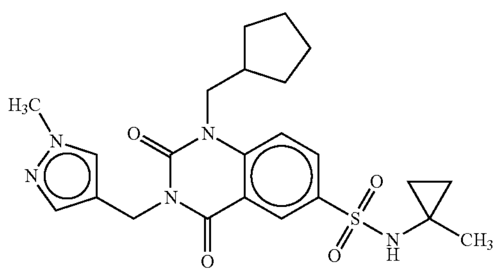 | A10 | 0.168 | 0.051 |
| Example 280 | 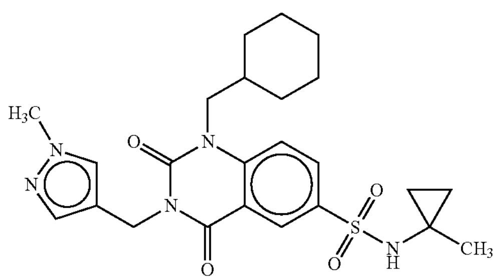 | A10 | 0.177 | 0.103 |
| Example 281 | 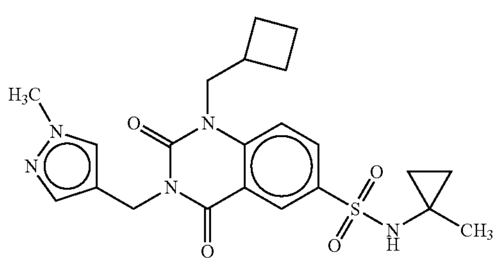 | A10 | 0.076 | 0.044 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 282 | 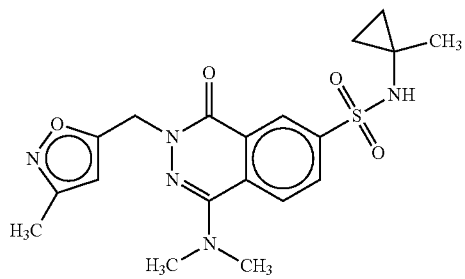 | 4 | 0.638 | |
| Example 283 | 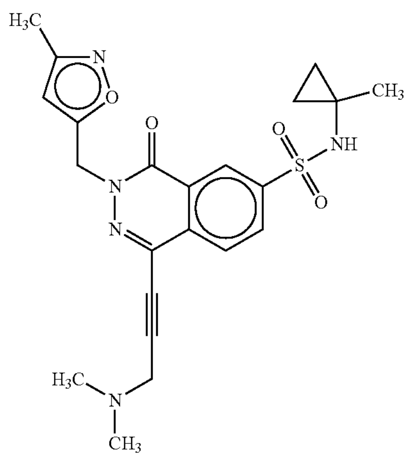 | C-substituted phthalazinone examples | 0.512 | |
| Example 284 | 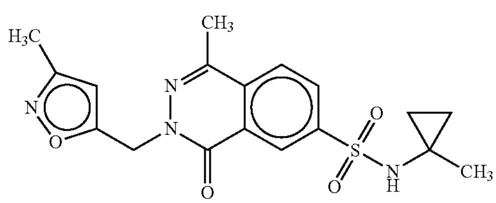 | C-substituted phthalazinone examples | 1.178 | |
| Example 285 | 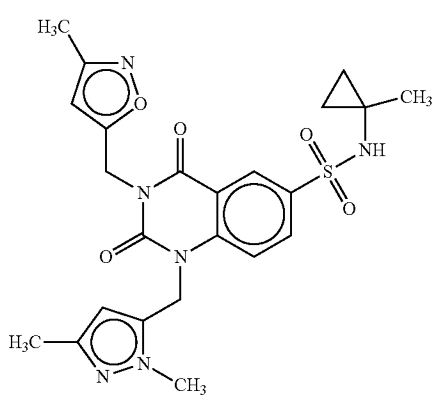 | Quinazolinedione; amine deprotection | 0.134 | 4.830 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 286 | 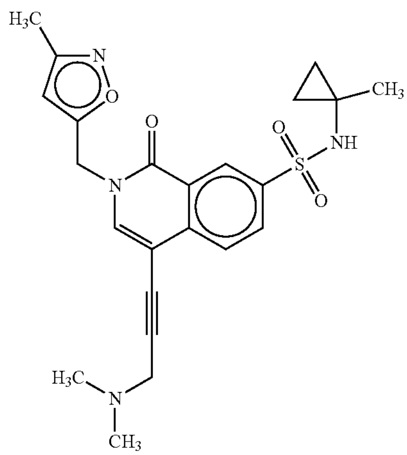 | 1-Oxo-isoquinoline-7-sulfonamide examples | 0.842 | |
| Example 287 | 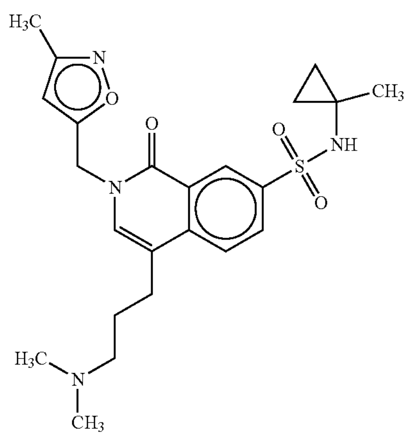 | 1-Oxo-isoquinoline-7-sulfonamide examples | 1.073 | |
| Example 288 | 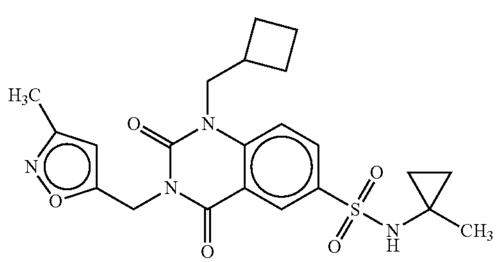 | A10 | 0.175 | 0.079 |
| Example 289 | 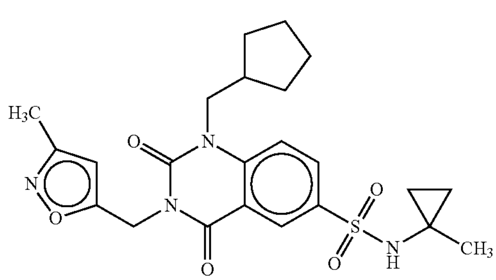 | A10 | 0.280 | 0.129 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 290 | 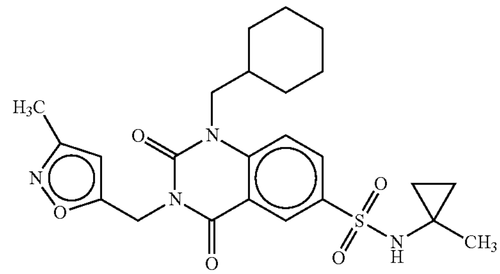 | A10 | 0.497 | 0.260 |
| Example 291 | 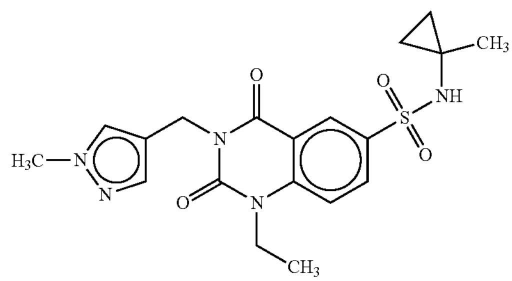 | A10 | 0.134 | 0.078 |
| Example 292 | 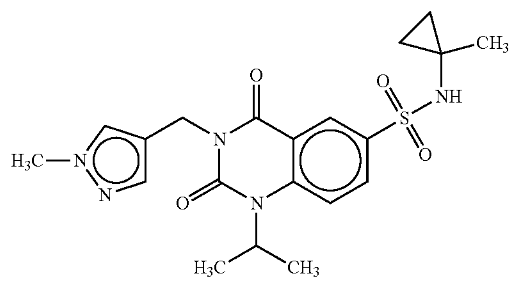 | A10 | 0.341 | 0.221 |
| Example 293 | 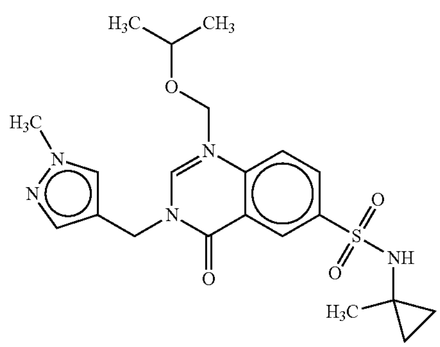 | A10 | 0.237 | 0.132 |
| Example 294 | 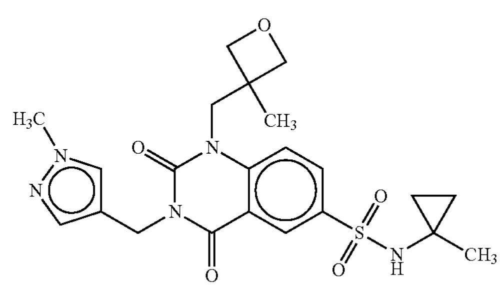 | A10 | 0.047 | 0.226 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 295 | 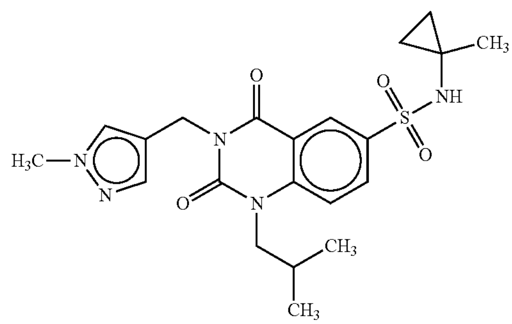 | A10 + NaI | 0.070 | 0.085 |
| Example 296 | 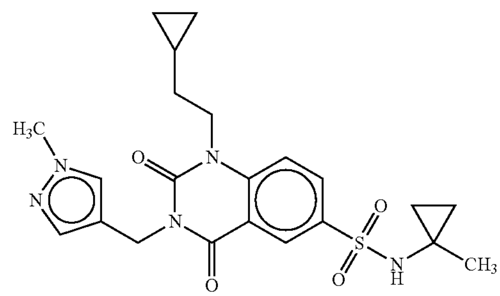 | A10 + NaI | 0.073 | 0.070 |
| Example 297 | 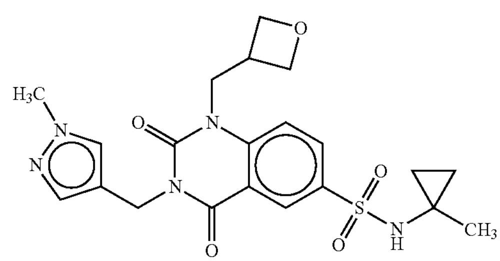 | A10 + NaI | 0.069 | 0.272 |
| Example 298 | 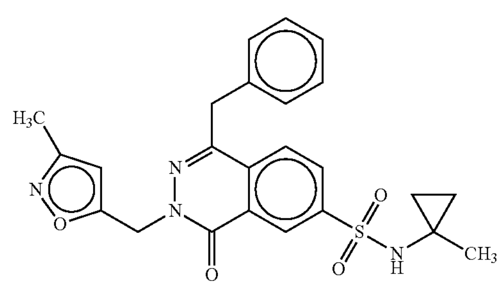 | 10 | | 0.648 |
| Example 299 | 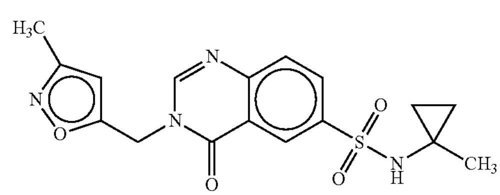 | 4 | | 1.271 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 300 | 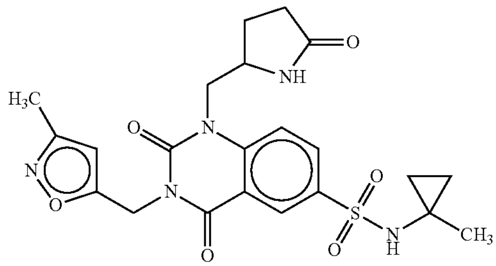 | A10 | 0.127 | 5.540 |
| Example 301 | 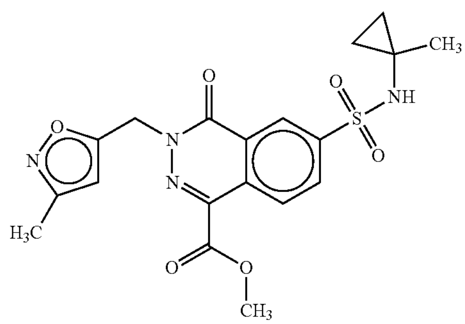 | 10 | 0.836 | |
| Example 302 | 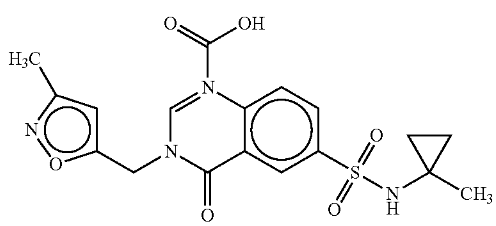 | C-substituted phthalazinone examples | 6.719 | |
| Example 303 | 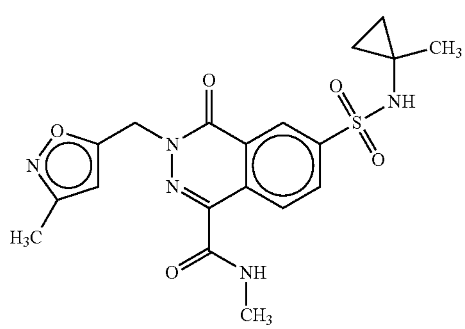 | 11 | 0.800 | |
| Example 304 | 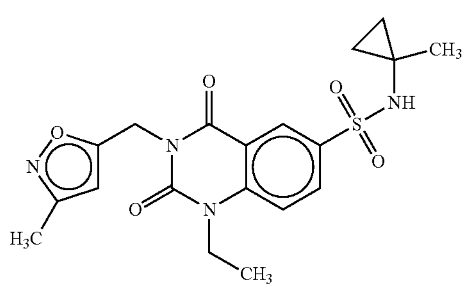 | A10 | 0.329 | 0.113 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 305 | 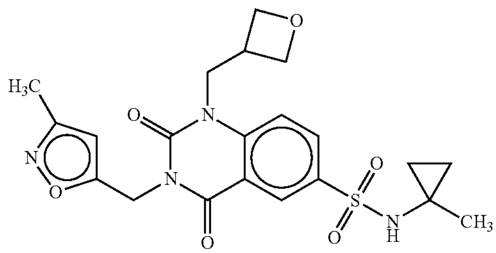 | A10 + NaI | 0.340 | 0.323 |
| Example 306 | 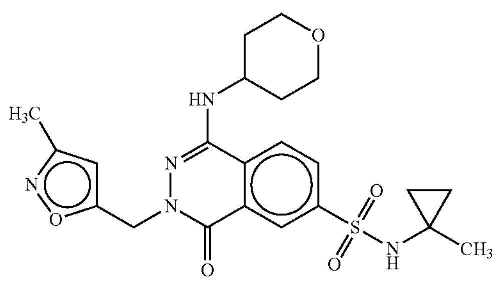 | 4 | 0.367 | 0.471 |
| Example 307 | 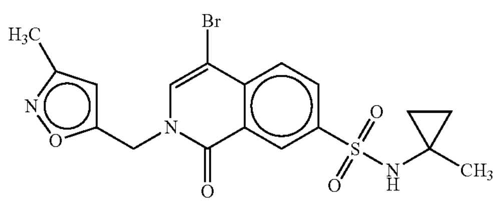 | Intermediate S9-F2 | 2.682 | |
| Example 308 | 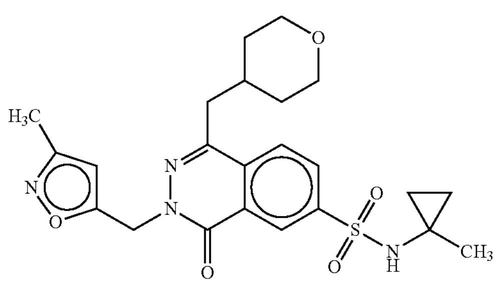 | 12 | 0.274 | 0.201 |
| Example 309 | 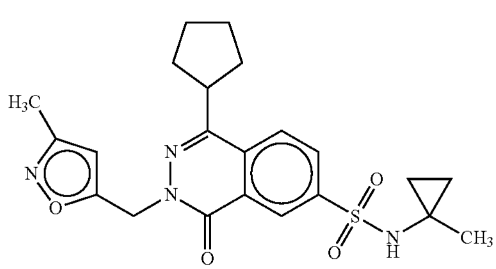 | 12 | 2.523 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 310 | 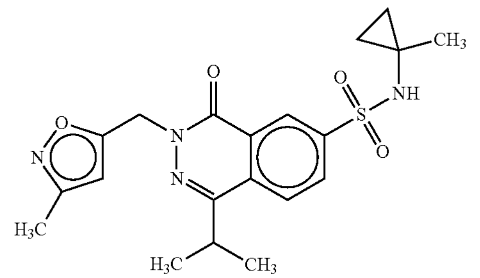 | 12 | 0.307 | 0.455 |
| Example 311 | 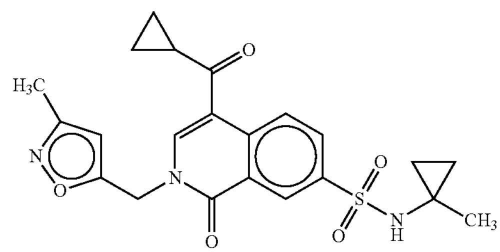 | Scheme 10 | 0.549 | |
| Example 312 | 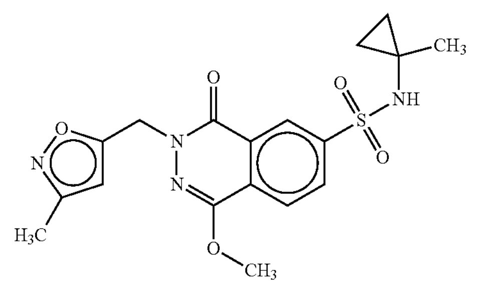 | O-substituted phthalazinone examples | 1.228 | |
| Example 313 | 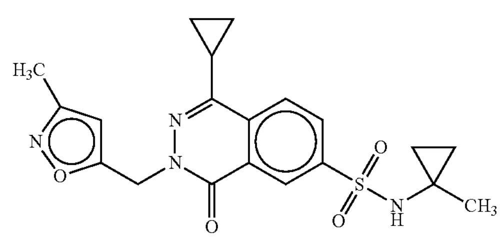 | 12 | 0.349 | 0.420 |
| Example 314 | 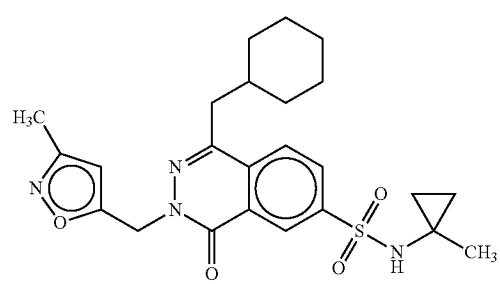 | 10 | 1.371 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 315 | 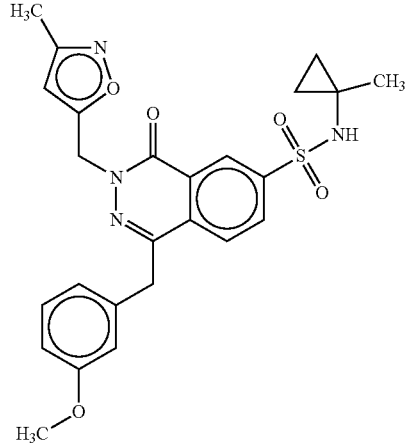 | 10 | 0.871 | |
| Example 316 | 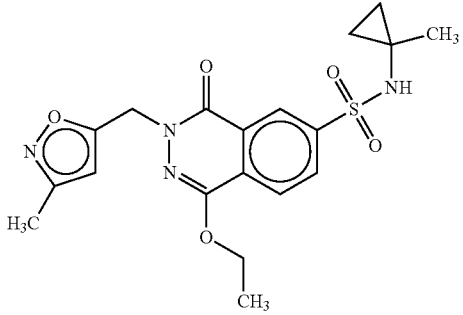 | O-substituted phthalazinone examples | 0.737 | |
| Example 317 | 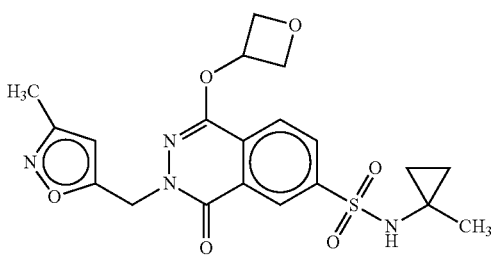 | 5 | 0.487 | 0.912 |
| Example 318 | 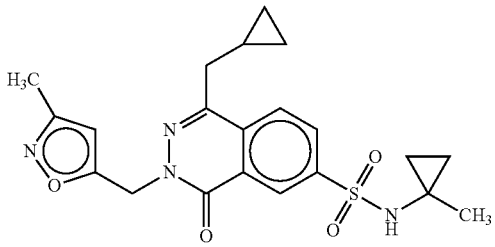 | 10 | 0.352 | 0.319 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 319 | 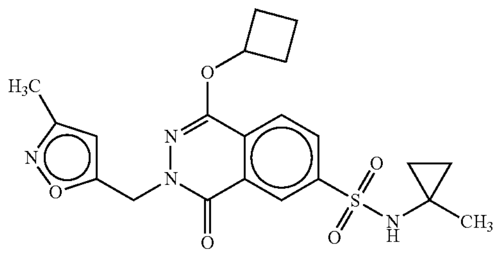 | 5 | 0.859 | |
| Example 320 | 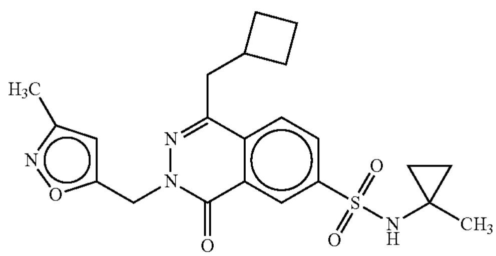 | 10 | 0.674 | |
| Example 321 | 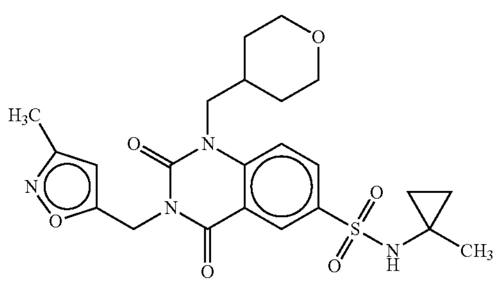 | A13 | 0.138 | 0.195 |
| Example 322 | 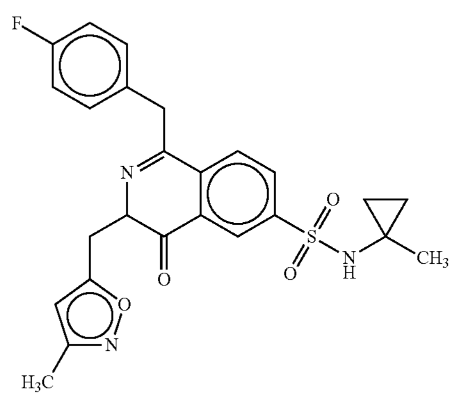 | Scheme 10 | 2.100 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 323 | 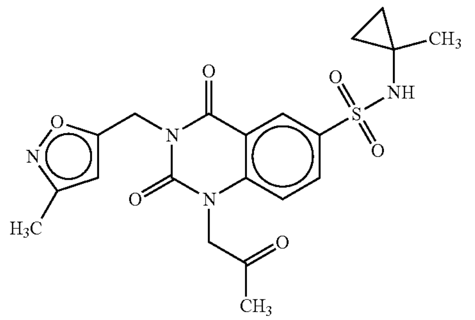 | A10 + NaI | 0.417 | 0.736 |
| Example 324 | 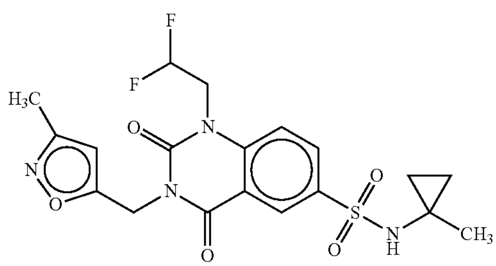 | A10 + NaI | 0.331 | 0.272 |
| Example 325 | 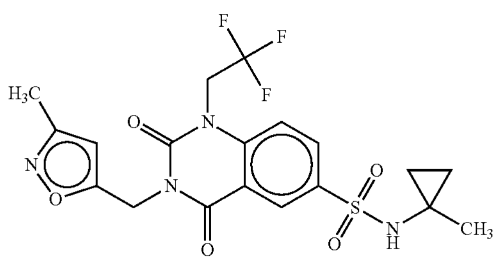 | A10 + NaI | 0.431 | 0.320 |
| Example 326 | 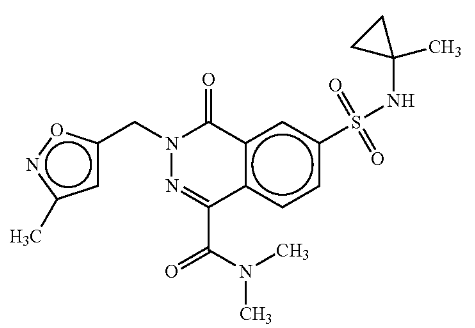 | 11 | 8.633 | |
| Example 327 | 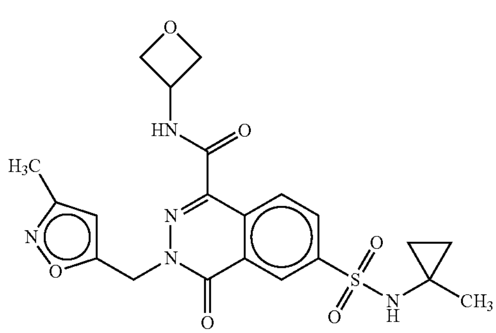 | 11 | 2.010 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 328 | 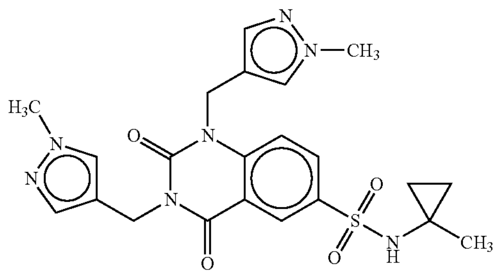 | A12 | 0.048 | 0.116 |
| Example 329 | 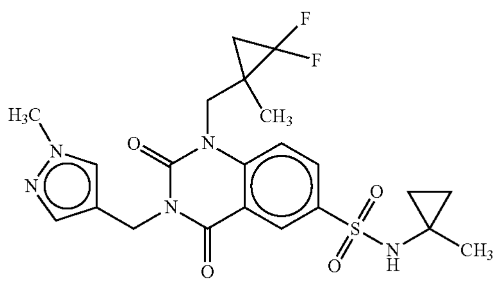 | A10 + NaI | 0.114 | 0.129 |
| Example 330 | 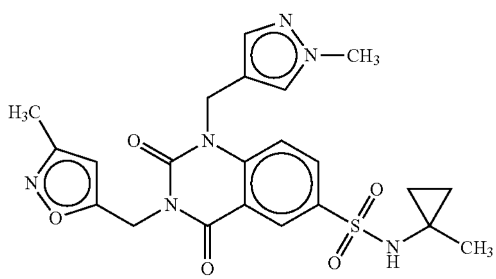 | A14 | 0.096 | 0.164 |
| Example 331 | 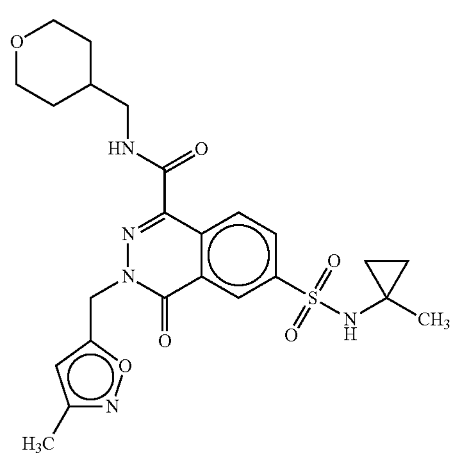 | 11 | 0.795 | |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 332 | 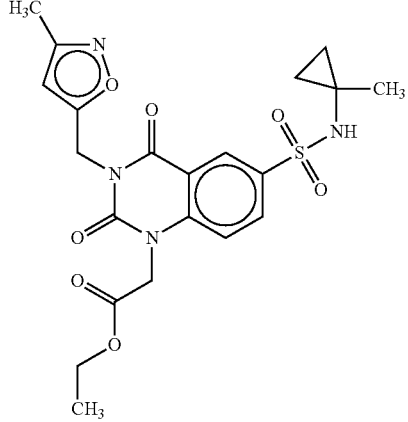 | A12 | 0.356 | 0.462 |
| Example 333 | 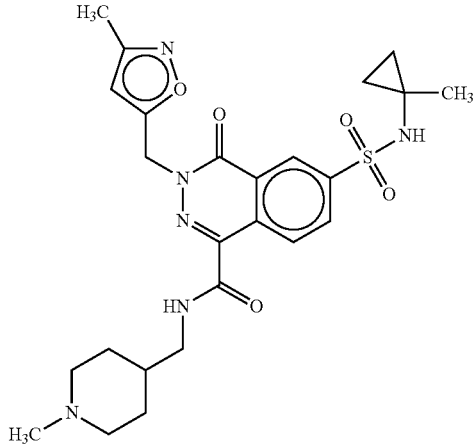 | 11 | 0.781 | |
| Example 334 | 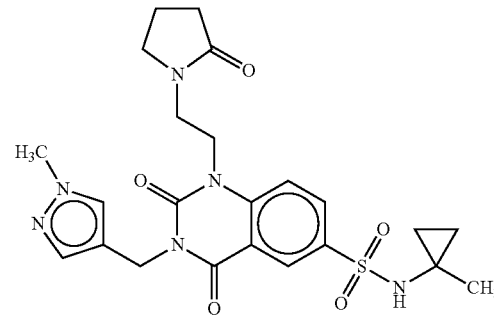 | A10 + NaI | 4.225 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 335 | 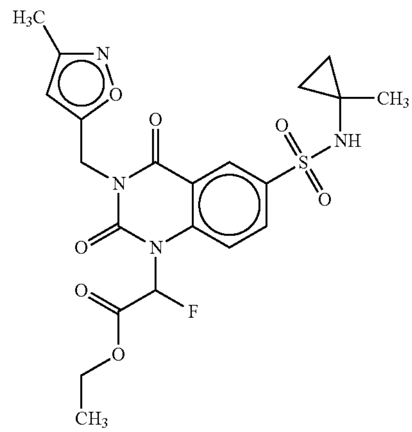 | A12 | 1.053 | |
| Example 336 | 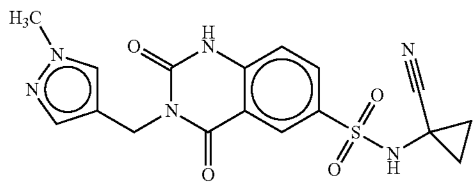 | 2 | 0.401 | 17.920 |
| Example 337 | 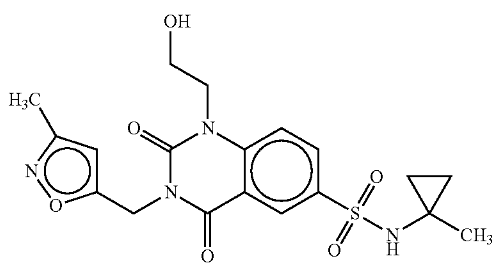 | A10 | 0.417 | 0.772 |
| Example 338 | 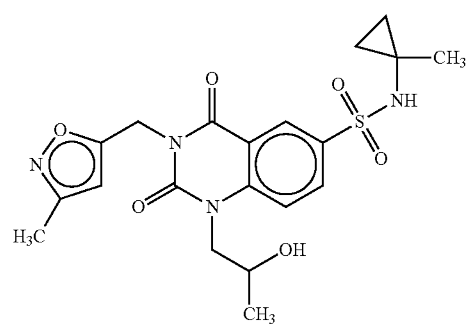 | A10 + NaI | 0.523 | |
| Example 339 | 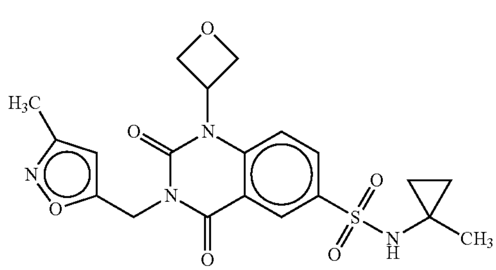 | A12 | 0.479 | 0.487 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 340 | 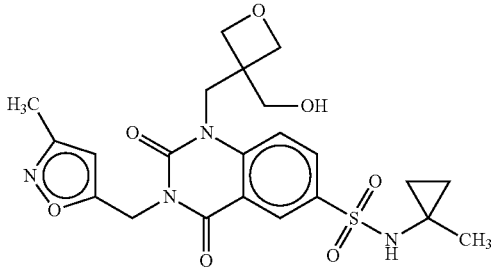 | A13 | 0.389 | 3.475 |
| Example 341 | 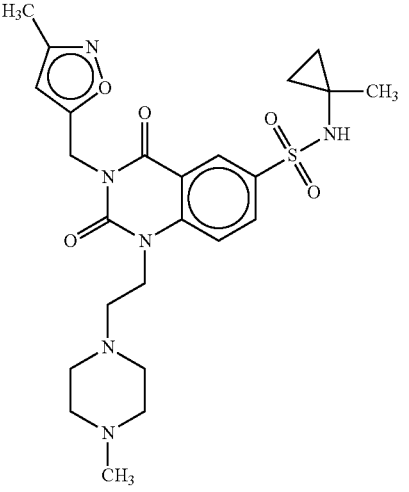 | A2 | 0.511 | |
| Example 342 | 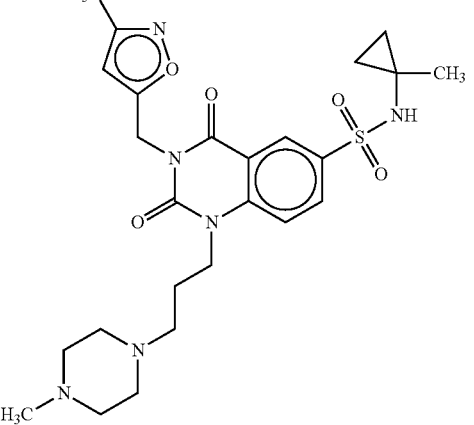 | A2 | 0.307 | 0.853 |
| Example 343 | 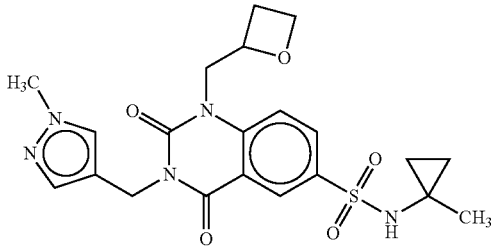 | A14 | 0.195 | 0.351 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 344 | 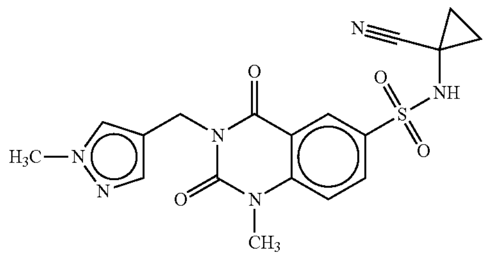 | A1 | 0.491 | 2.108 |
| Example 345 | 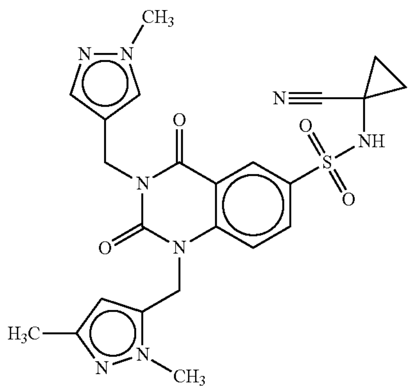 | A1 | 0.061 | 2.880 |
| Example 346 | 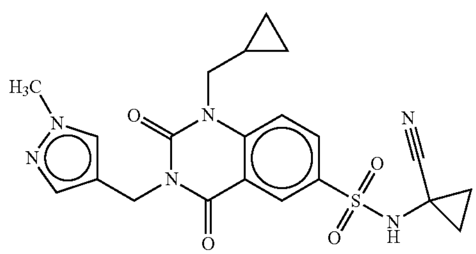 | A1 | 0.047 | 0.390 |
| Example 347 | 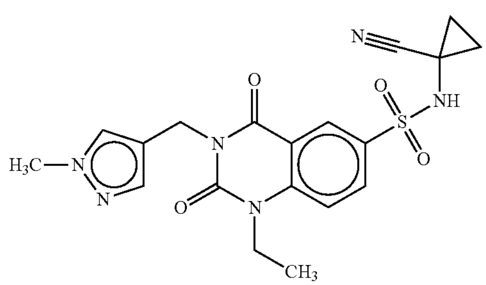 | A1 | 0.210 | 0.916 |
| Example 348 | 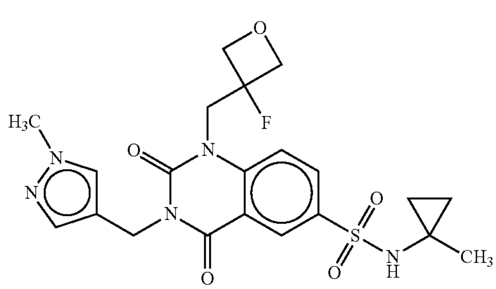 | A14 | 0.101 | 0.328 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 349 | 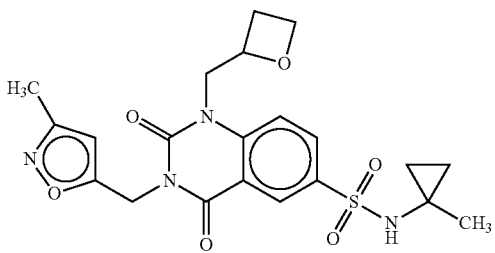 | A14 | 0.252 | 0.632 |
| Example 350 | 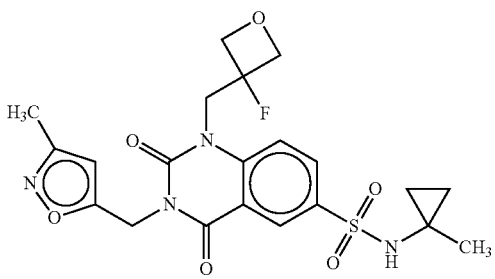 | A14 | 0.320 | 0.341 |
| Example 351 | 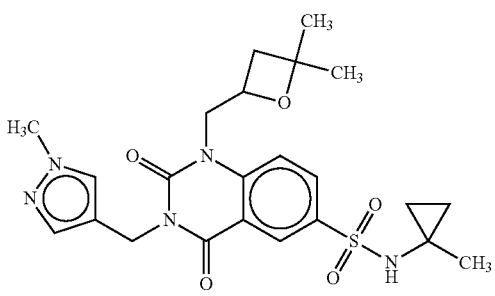 | A14 | 0.229 | 0.358 |
| Example 352 | 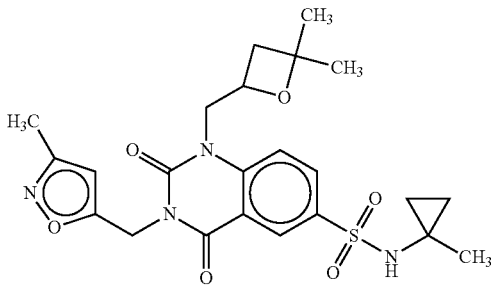 | A14 | 0.385 | 0.608 |
| Example 353 | 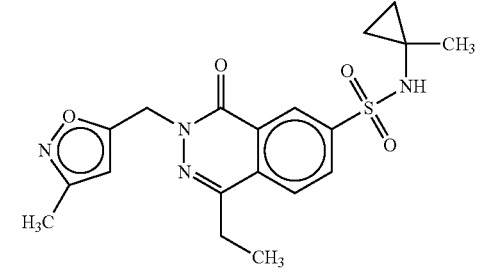 | 10 | 0.408 | 0.574 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 354 | 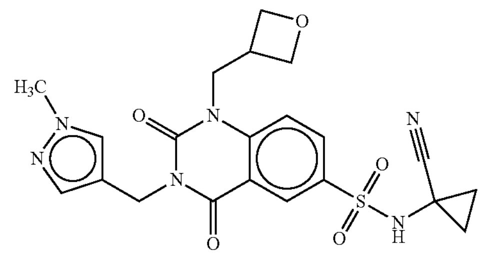 | A2 | 0.164 | 17.960 |
| Example 355 | 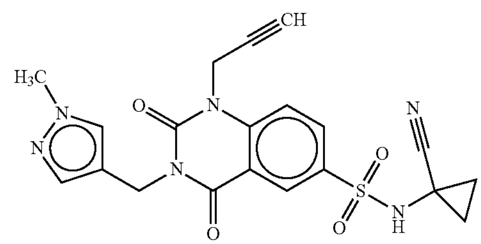 | A1 | 0.122 | 0.953 |
| Example 356 | 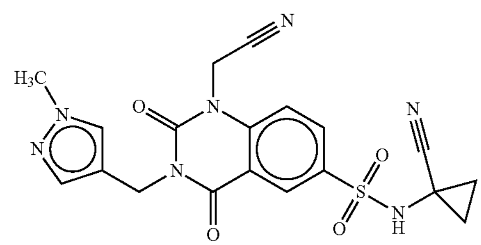 | A1 | 0.396 | 16.600 |
| Example 357 | 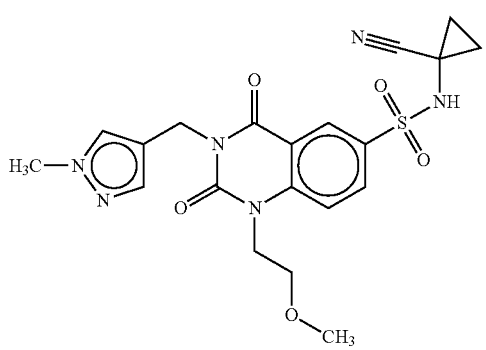 | A1 | 0.153 | 1.603 |
| Example 358 | 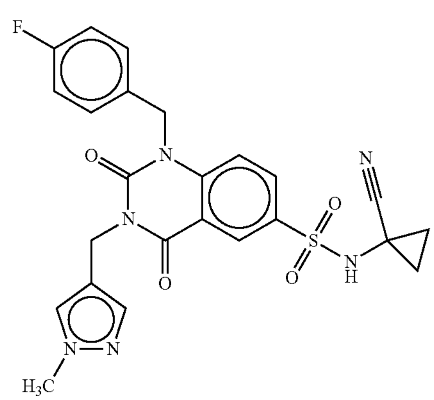 | A1 | 0.059 | 0.346 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 359 | 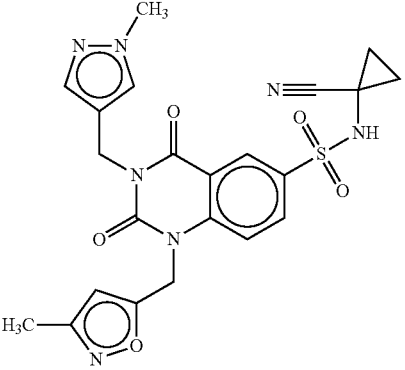 | A1 | 0.043 | 1.097 |
| Example 360 | 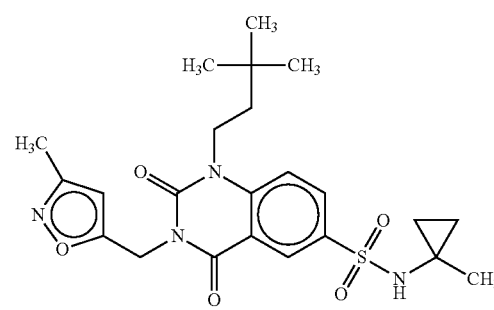 | A13 | 0.245 | 0.597 |
| Example 361 | 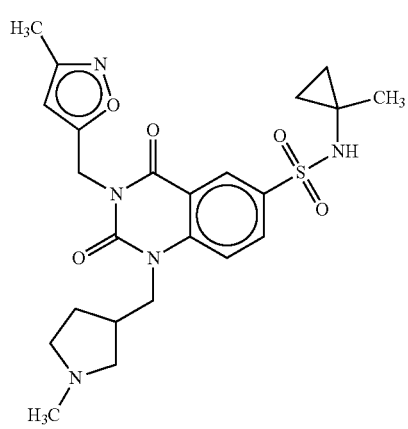 | A13 | 0.332 | 1.409 |
| Example 362 | 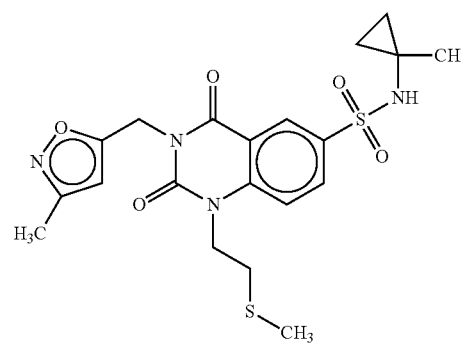 | A13 | 0.331 | 0.126 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 363 | 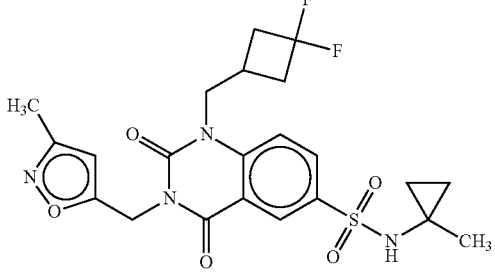 | A13 | 0.353 | 0.382 |
| Example 364 | 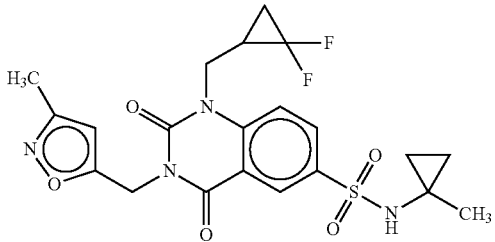 | A13 | 0.408 | 0.106 |
| Example 365 | 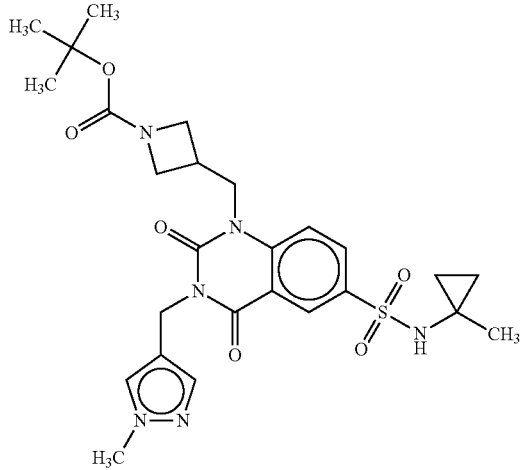 | A13 | 0.380 | 0.218 |
| Example 366 | 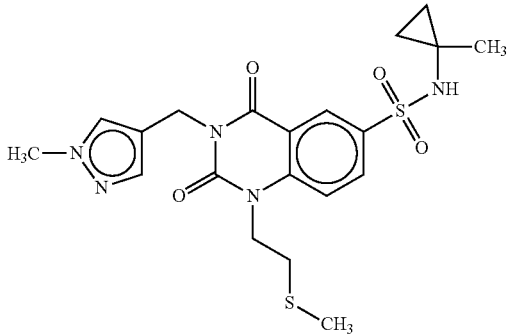 | A10 | 0.160 | 0.030 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 367 | 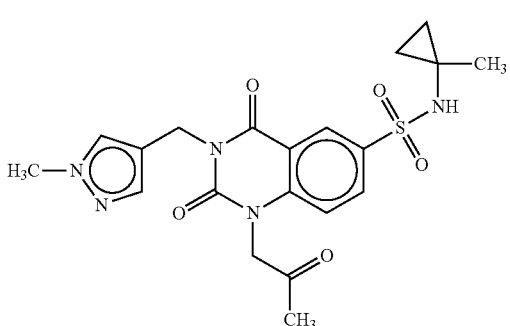 | A10 + NaI | 0.353 | 0.340 |
| Example 368 | 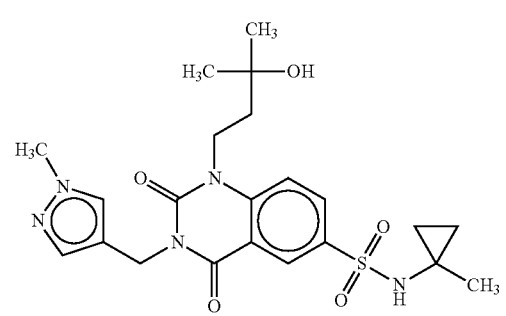 | A13 | 0.108 | 0.217 |
| Example 369 | 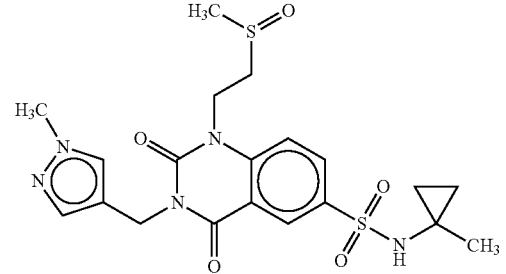 | Quinazolinedione; thiol oxidation | 0.124 | 7.146 |
| Example 370 | 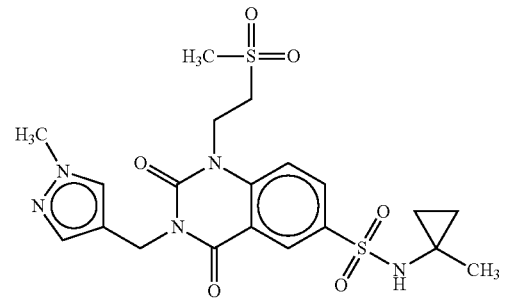 | Quinazolinedione; thiol oxidation | 0.303 | 6.071 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 371 | 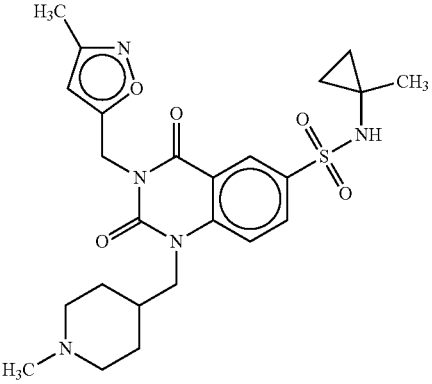 | A14 | 0.258 | 1.113 |
| Example 372 | 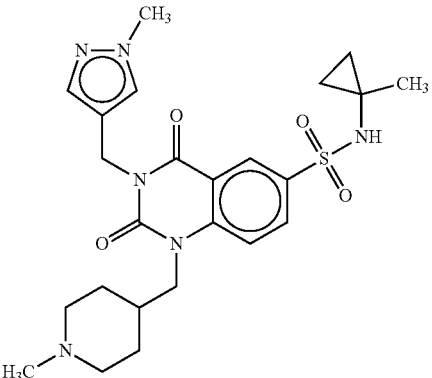 | A14 | 0.146 | 2.140 |
| Example 373 | 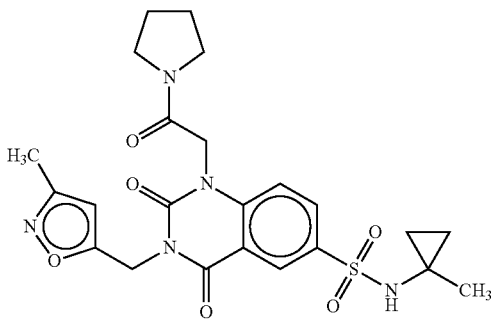 | Quinazolinedione; amide formation | 1.007 | |
| Example 374 | 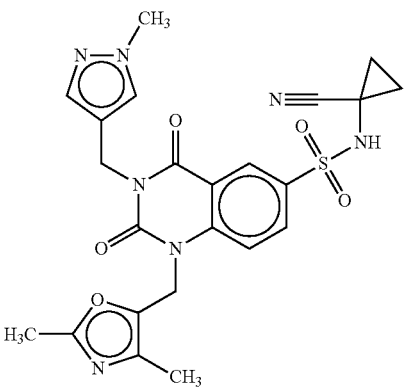 | A2 | 0.011 | 0.236 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 375 | 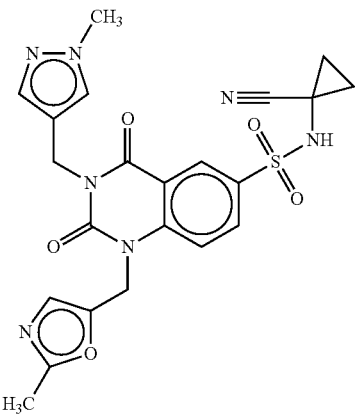 | A2 | 0.020 | 0.385 |
| Example 376 | 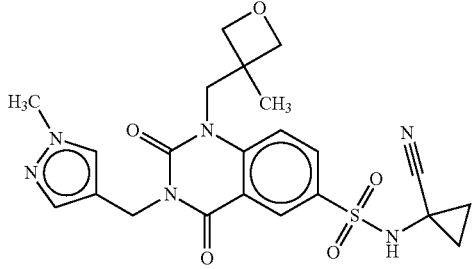 | A2 | 0.124 | 14.330 |
| Example 377 | 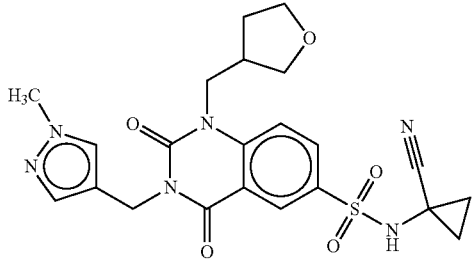 | A2 | 0.096 | 3.993 |
| Example 378 | 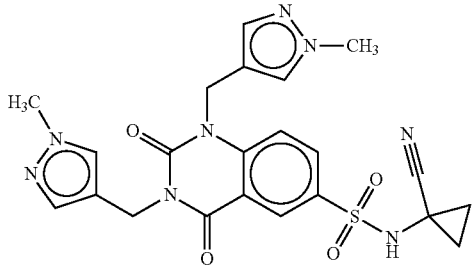 | A1 | 0.044 | 1.964 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 379 | 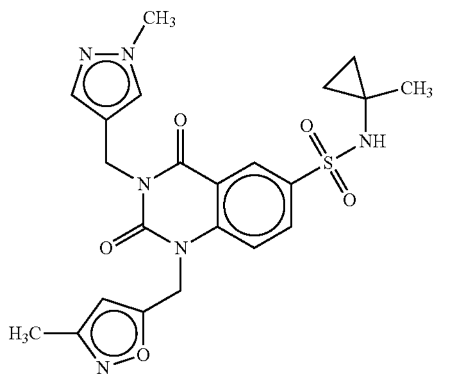 | A1 | 0.035 | 0.077 |
| Example 380 | 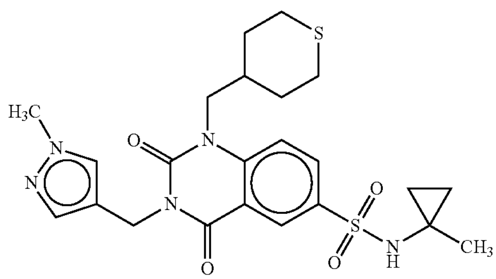 | A2 | 0.059 | 0.090 |
| Example 381 | 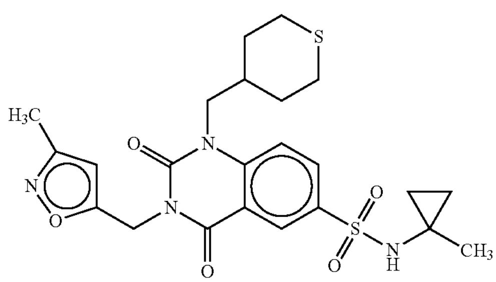 | A2 | 0.126 | 0.208 |
| Example 382 | 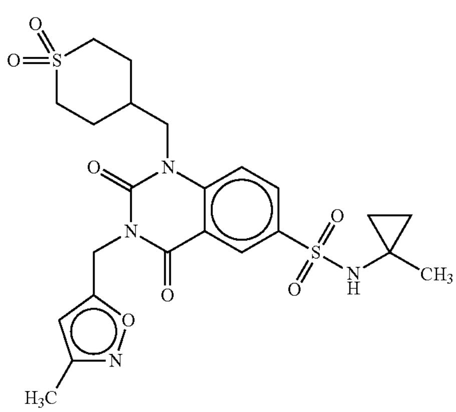 | Quinazolinedione; thiol oxidation | 0.197 | 3.853 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 383 | 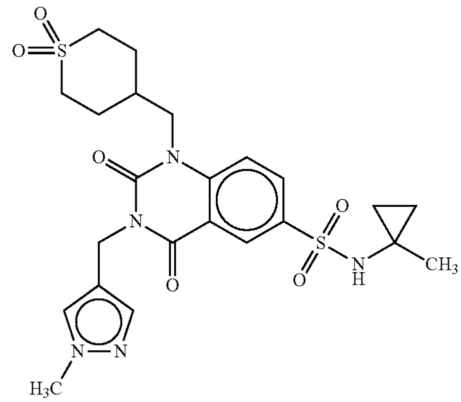 | Quinazolinedione; thiol oxidation | 0.084 | 4.632 |
| Example 384 | 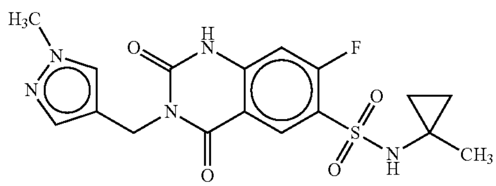 | 1 | 0.374 | 0.974 |
| Example 385 | 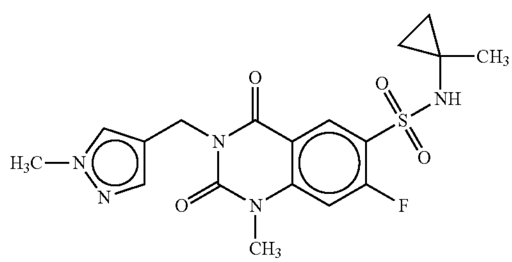 | Scheme 13 | 0.341 | 0.184 |
| Example 386 | 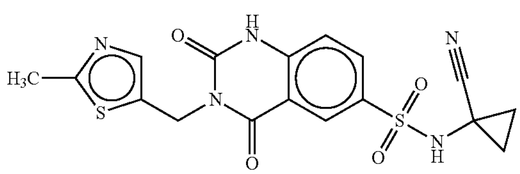 | Quinazolinedione sulfonamide formation | 0.369 | 8.385 |
| Example 387 | 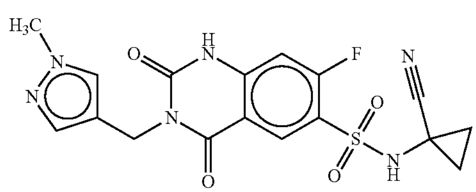 | Quinazolinedione sulfonamide formation | 0.452 | 1.523 |
| Example 388 | 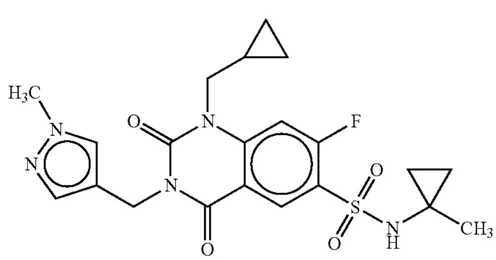 | Scheme 13 | 0.025 | 0.031 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 389 | 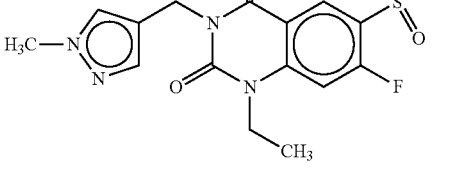 | Scheme 13 | 0.060 | 0.079 |
| Example 390 | 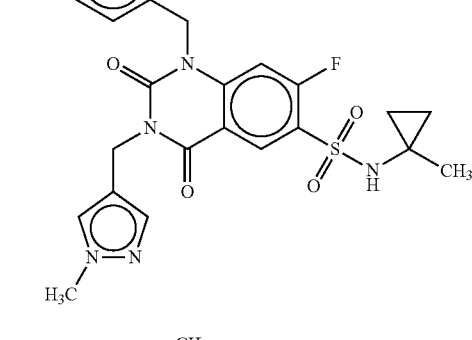 | Scheme 13 | 0.102 | 0.070 |
| Example 391 | 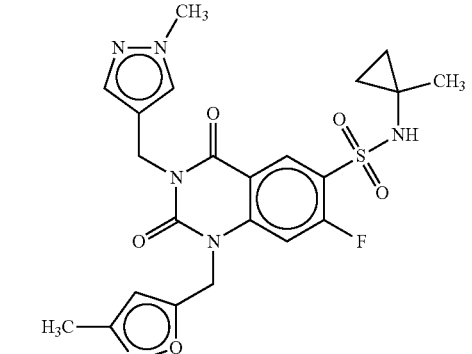 | Scheme 13 | 0.024 | 0.067 |
| Example 392 | 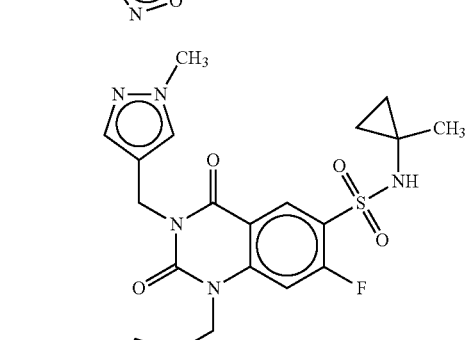 | Scheme 13 | 0.047 | 0.113 |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 393 | 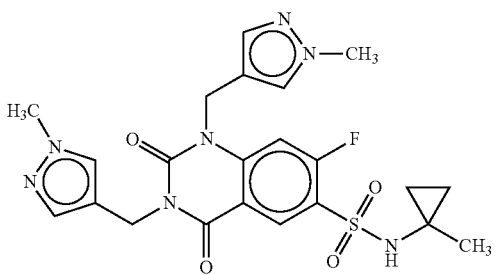 | Scheme 13 | 0.028 | 0.084 |
| Example 394 | 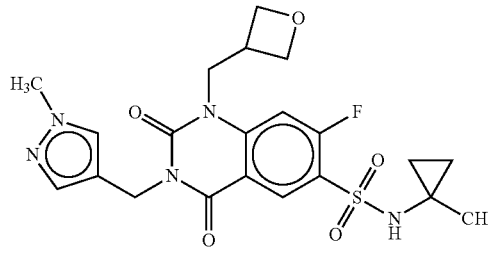 | Scheme 14 | 0.066 | 0.326 |
| Example 395 | 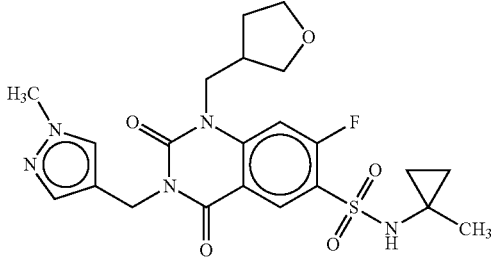 | Scheme 14 | 0.060 | 0.156 |
| Example 396 | 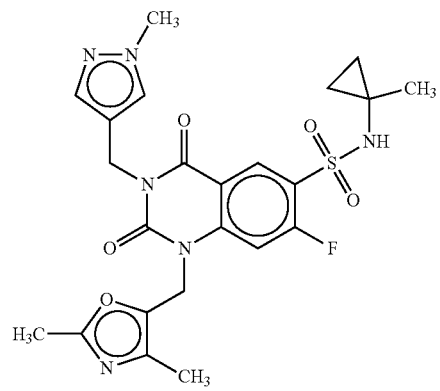 | Scheme 14 | 0.011 | 0.017 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 397 | 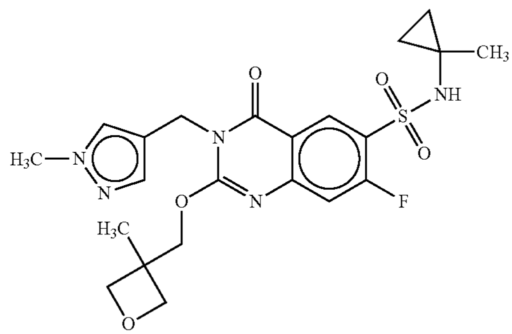 | Scheme 14 | 0.282 | 0.256 |
| Example 398 | 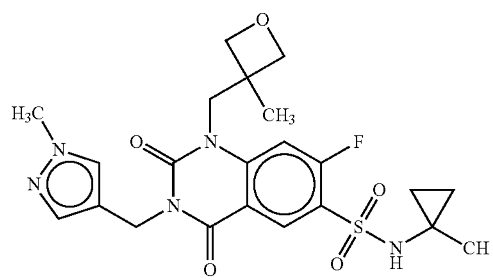 | Scheme 14 | 0.044 | 0.257 |
| Example 399 | 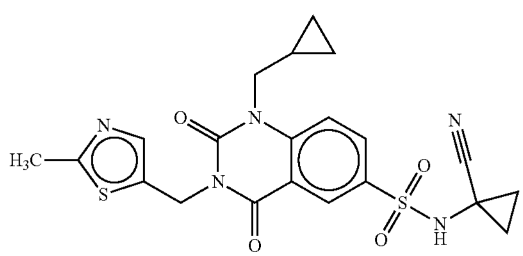 | Quinazolinedione N1-alkylation | 0.031 | 0.087 |
| Example 400 | 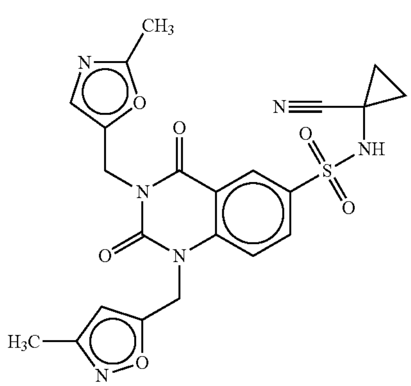 | Quinazolinedione N1-alkylation | 0.027 | 0.320 |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 401 | 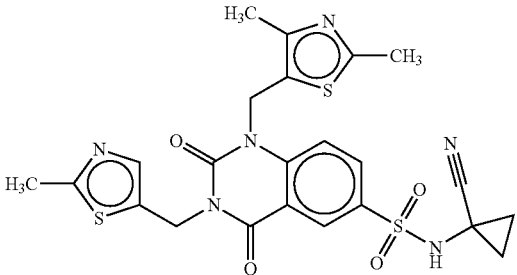 | Quinazolinedione N1-alkylation | 0.008 | 0.101 |
| Example 402 | 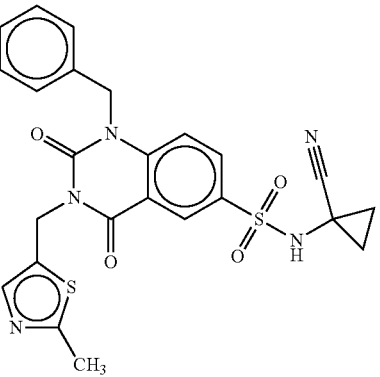 | Quinazolinedione N1-alkylation | 0.066 | 0.167 |
| Example 403 | 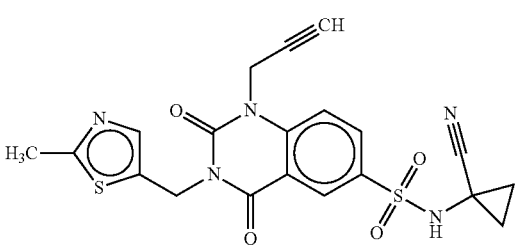 | Quinazolinedione N1-alkylation | 0.084 | 0.265 |
| Example 404 | 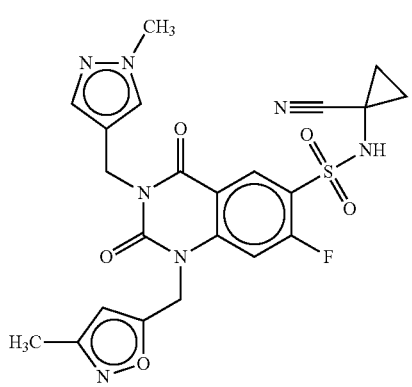 | Quinazolinedione N1-alkylation | 0.071 | 3.859 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 405 | 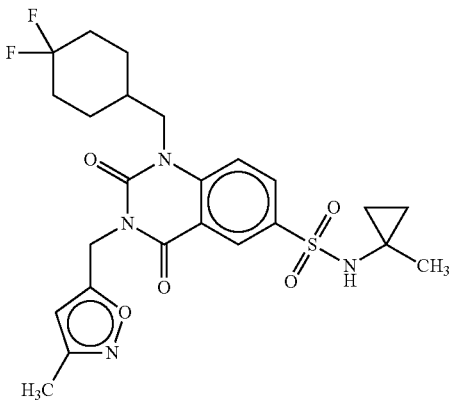 | A2 | 0.248 | 0.144 |
| Example 406 | 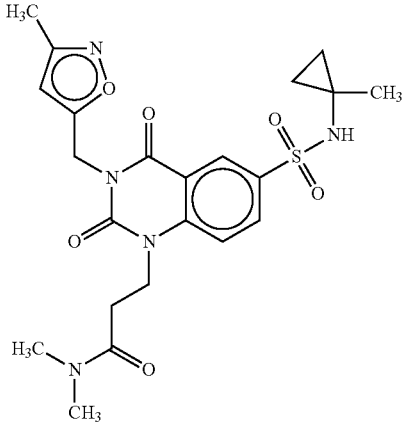 | A2 | 0.456 | 0.800 |
| Example 407 | 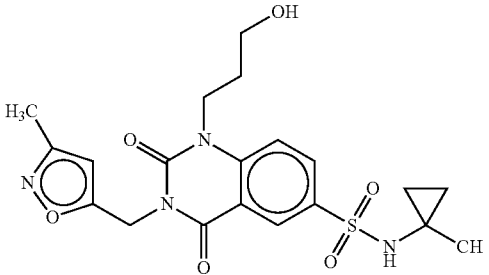 | A1 | 0.394 | 0.625 |
| Example 408 | 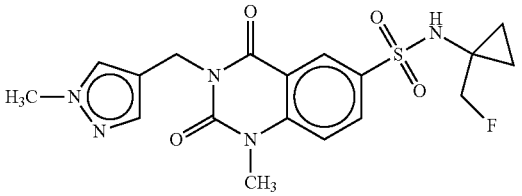 | Scheme 13 | 0.648 | 0.287 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 409 | 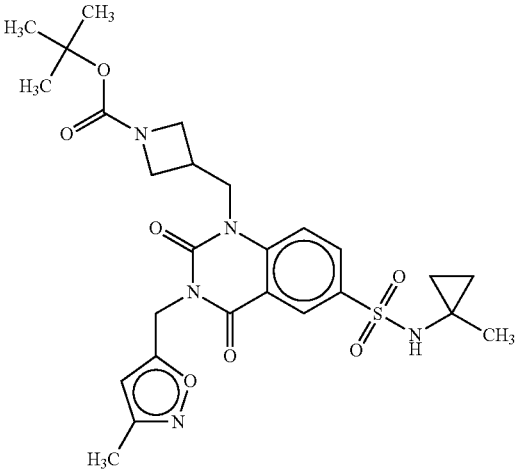 | A14 | 0.391 | 0.350 |
| Example 410 | 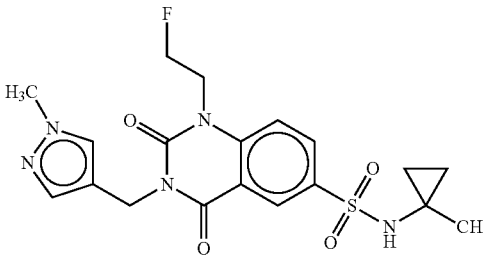 | A14 | 0.263 | 0.126 |
| Example 411 | 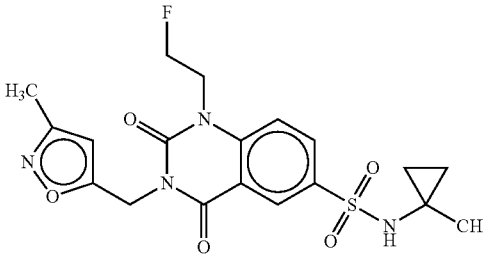 | A14 | 0.409 | 0.104 |
| Example 412 | 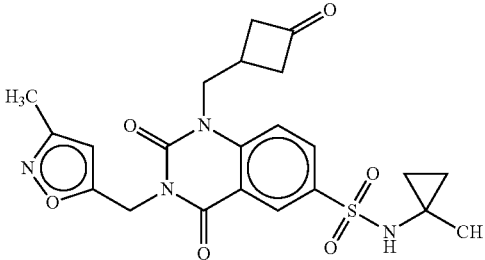 | A14 | 0.440 | 0.289 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 413 | 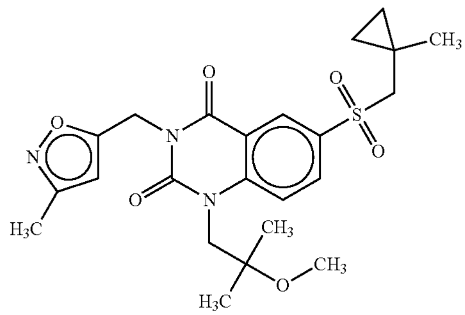 | Quinazolinedione N1-alkylation | 0.469 | 0.305 |
| Example 414 | 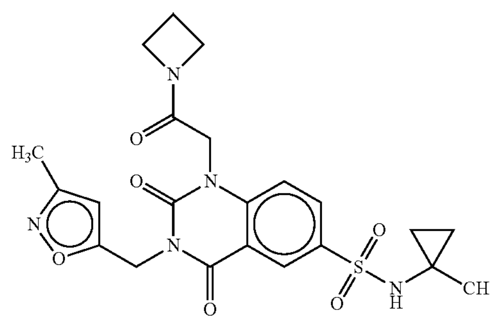 | A14 | 2.082 | 9.221 |
| Example 415 | 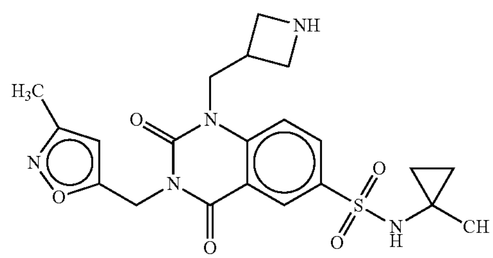 | BOC deprotection with TFA | 0.609 | 1.438 |
| Example 416 | 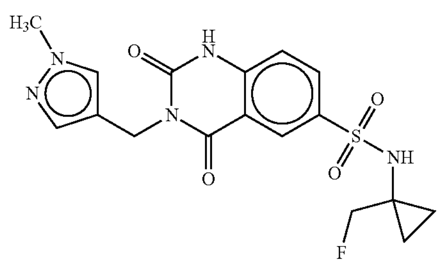 | Quinazolinedione sulfonamide formation | 0.430 | 1.320 |
| Example 417 | 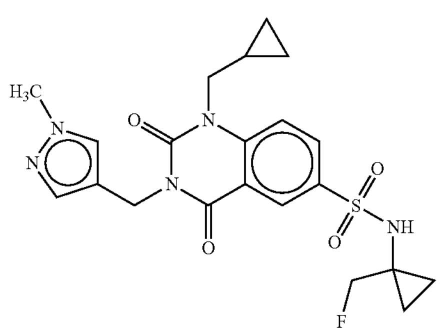 | Scheme 13 | 0.040 | 0.042 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 418 | 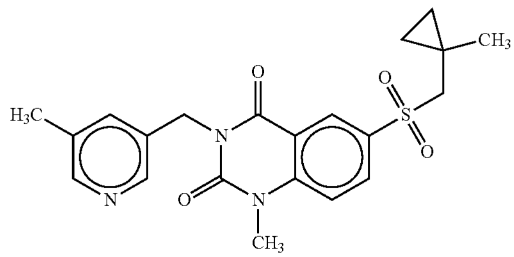 | Quinazolinedione N3-alkylation | 2.273 | 2.112 |
| Example 419 | 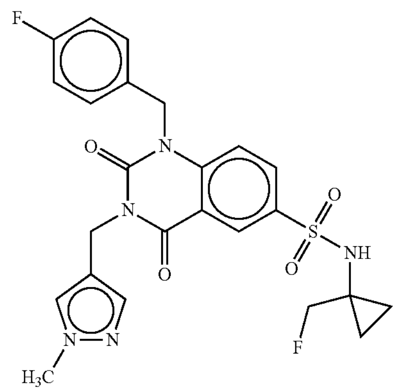 | Scheme 13 | 0.106 | 0.118 |
| Example 420 | 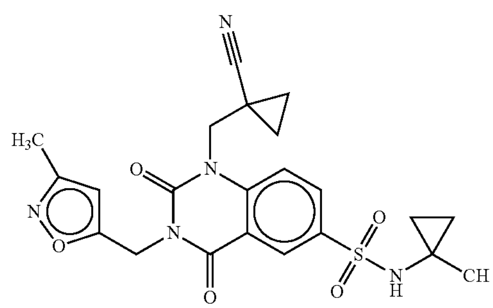 | A10 (tosylate) | 0.140 | 0.163 |
| Example 421 | 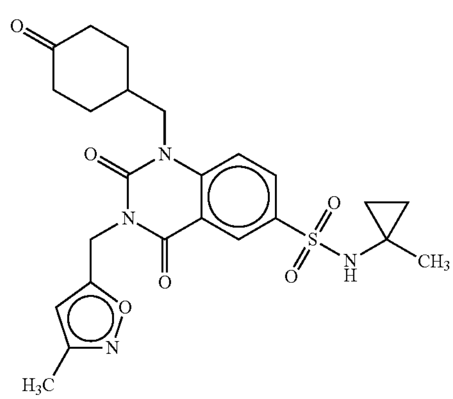 | A10 (tosylate) | 0.193 | 0.589 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 422 | 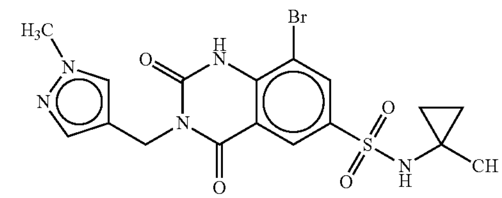 | Scheme 15 | 0.512 | 0.611 |
| Example 423 | 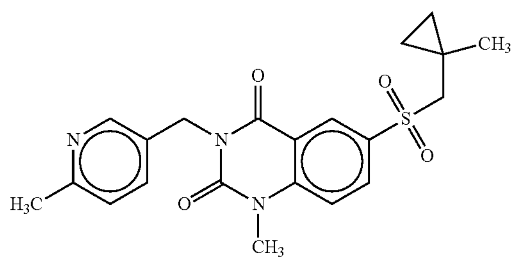 | Quinazolinedione N3-alkylation | 1.596 | 1.354 |
| Example 424 | 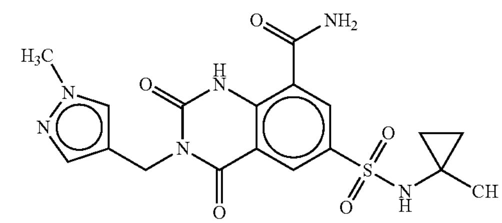 | Quinazolinedione 8-Br substitution with CN and hydrolysis | 0.223 | 12.960 |
| Example 425 | 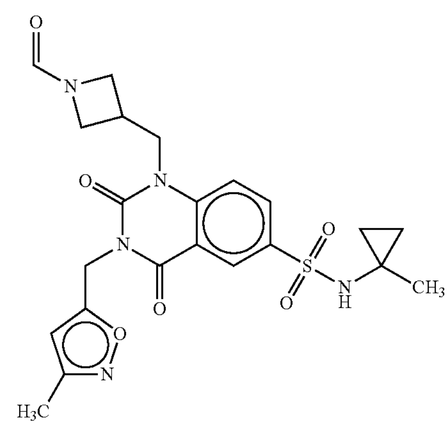 | Formylation in DMF | 0.214 | 7.814 |
| Example 426 | 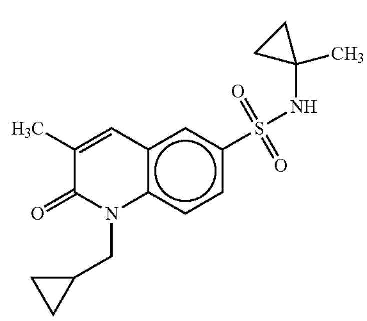 | Scheme 16 | 2.035 | 1.405 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 427 | 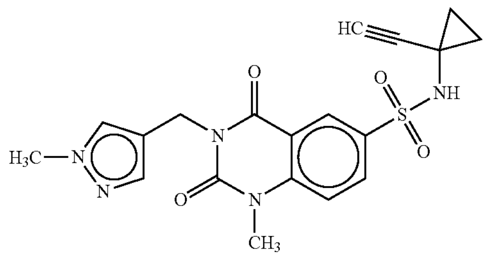 | Scheme 17 | 5.398 | 1.265 |
| Example 428 | 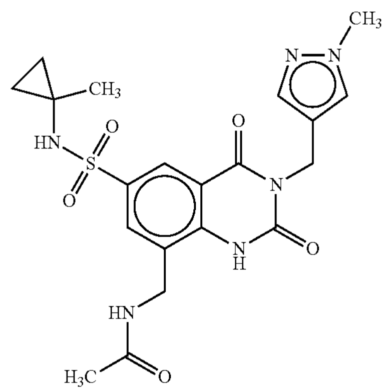 | Quinazolinedione 8-CN reduction and acrylation | 0.494 | 26.990 |
| Example 429 | 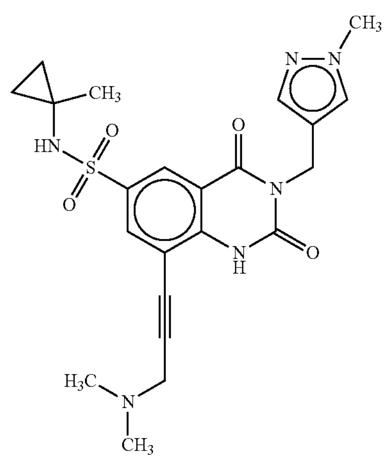 | Pd-catalysed alkyne-aryl coupling | 1.770 | 1.520 |
| Example 430 | 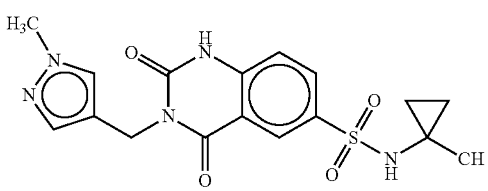 | Intermediate S4-C1 | 0.730 | 1.079 |
| Example 431 | 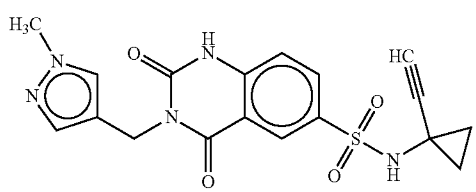 | Scheme 17 | 3.720 | 3.033 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 432 | 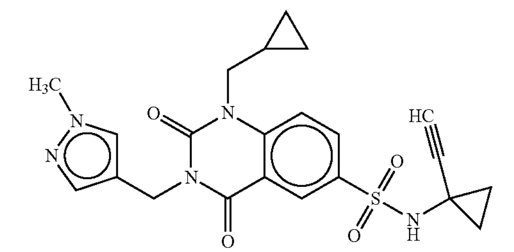 | Quinazolinedione N1-alkylation | 0.486 | 0.261 |
| Example 433 | 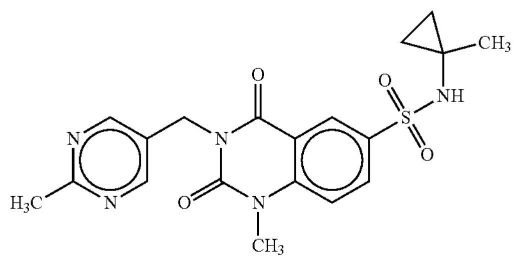 | Quinazolinedione N3-alkylation | 3.344 | 1.131 |
| Example 434 | 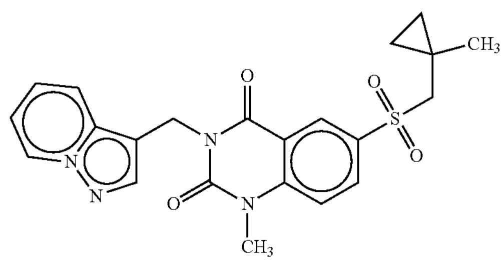 | Quinazolinedione N3-alkylation | 5.914 | 0.609 |
| Example 435 | 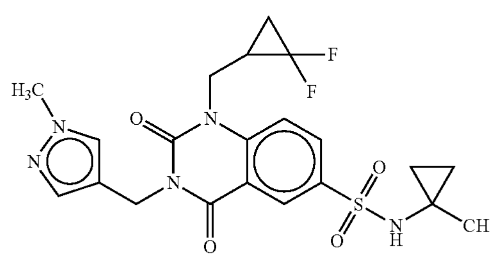 | A12 (100° C.) | 0.104 | 0.046 |
| Example 436 | 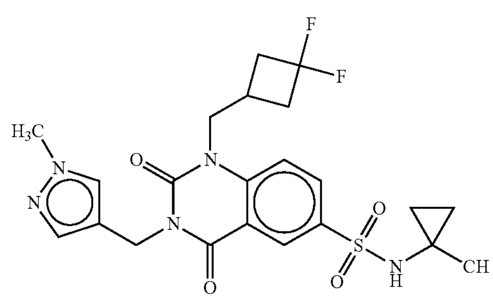 | A12 (100° C.) | 0.118 | 0.070 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 437 | 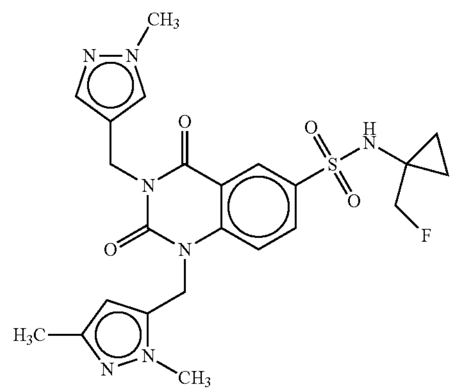 | A10 | 0.023 | 0.165 |
| Example 438 | 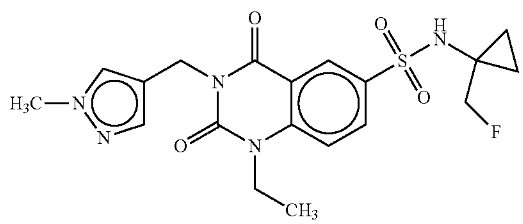 | A10 | 0.106 | 0.084 |
| Example 439 | 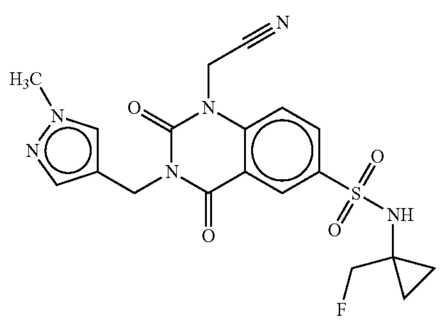 | A10 | 0.310 | 0.420 |
| Example 440 | 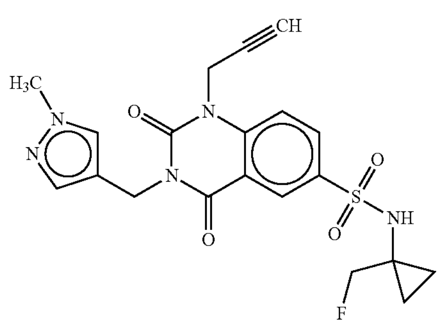 | A10 | 0.068 | 0.050 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 441 | 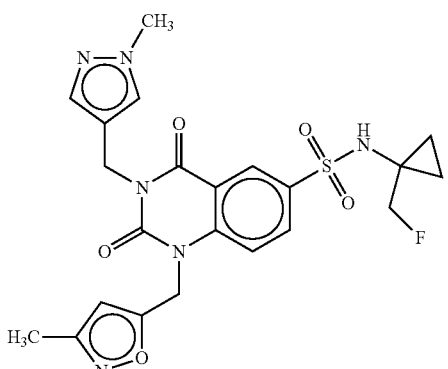 | A10 | 0.024 | 0.074 |
| Example 442 | 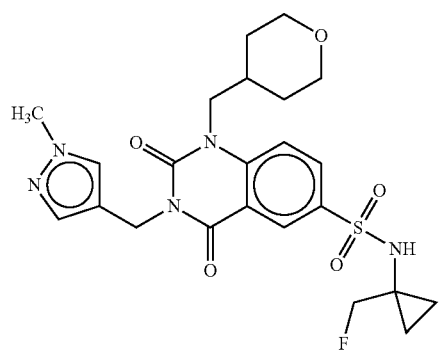 | A10 | 0.043 | 0.134 |
| Example 443 | 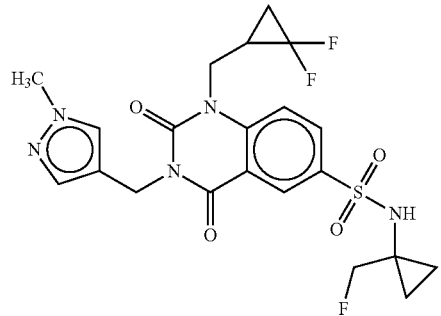 | A10 | 0.058 | 0.067 |
| Example 444 | 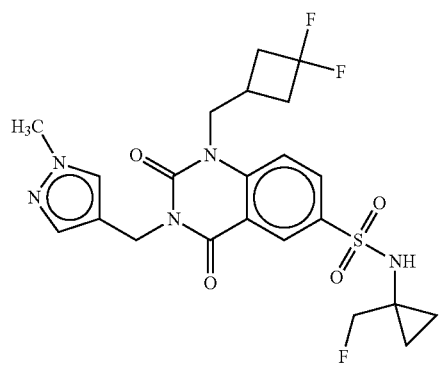 | A10 | 0.063 | 0.090 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 445 | 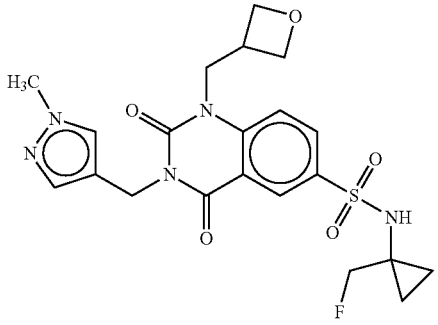 | A10 (tosylate) | 0.102 | 0.417 |
| Eaxmple 446 | 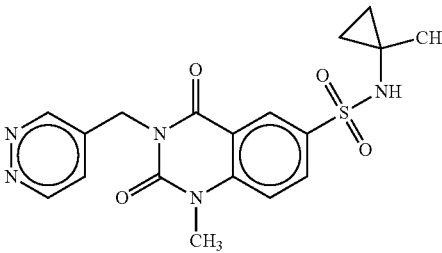 | Quinazolinedione N3-alkylation | 13.370 | 18.900 |
| Example 447 | 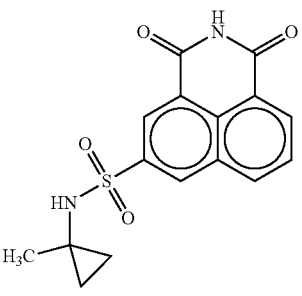 | Naphthalimide chlorosulfonylation, and sulfonamide formation | 3.470 | |
| Example 448 | 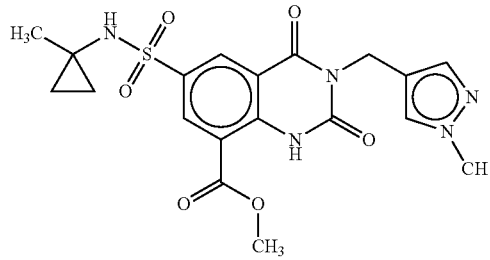 | Quinazolinedione sulfonamide formation | 0.424 | 0.329 |
| Example 449 | 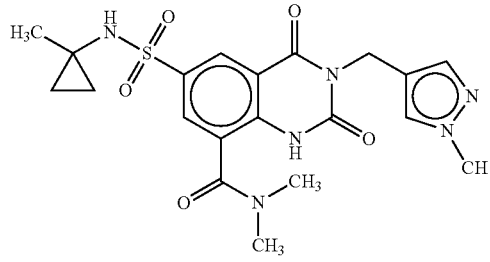 | Ester hydrolysis and HATU amide coupling | 5.775 | 13.170 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 450 | 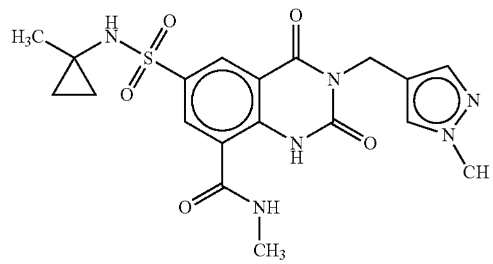 | HATU amide coupling | 0.213 | 2.523 |
| Example 451 | 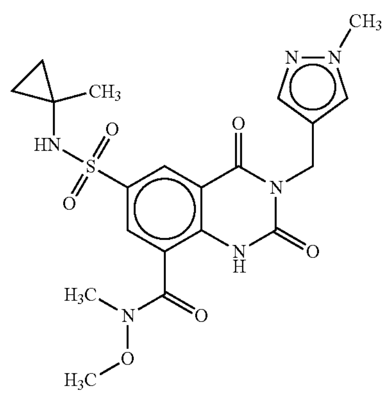 | HATU amide coupling | 3.849 | 4.495 |
| Example 452 | 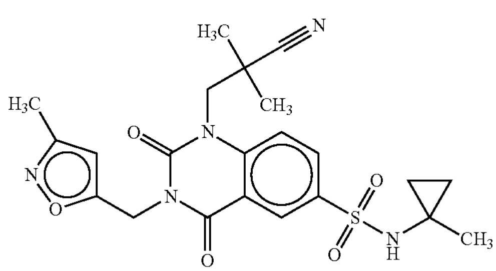 | A12 (6 h at 120° C.) | 0.202 | 0.280 |
| Example 453 | 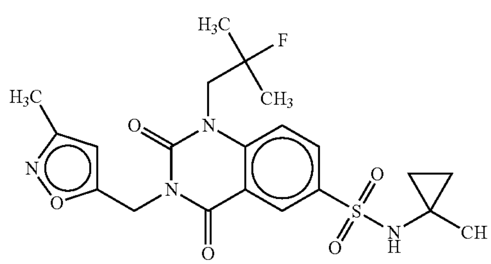 | A12 (6 h at 120° C.) | 0.348 | |
| Example 454 | 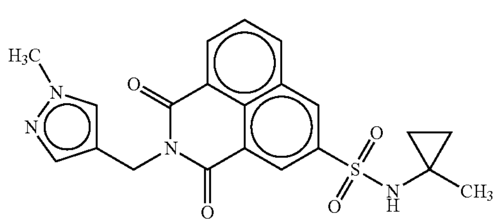 | Scheme 18 | 0.728 | 2.072 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 455 | 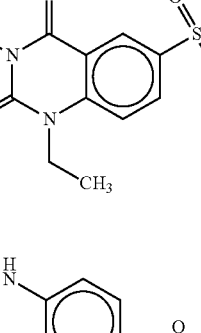 | A1 (40° C. deacylation) | 0.177 | 0.283 |
| Example 456 | 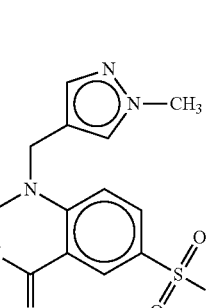 | A1 | 4.112 | 5.595 |
| Example 457 | 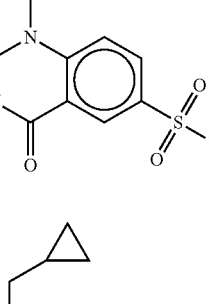 | A1 (40° C. deacylation) | 0.042 | 0.494 |
| Example 458 | 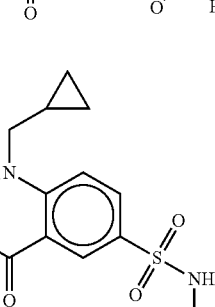 | A10 | 1.067 | 0.555 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 459 | 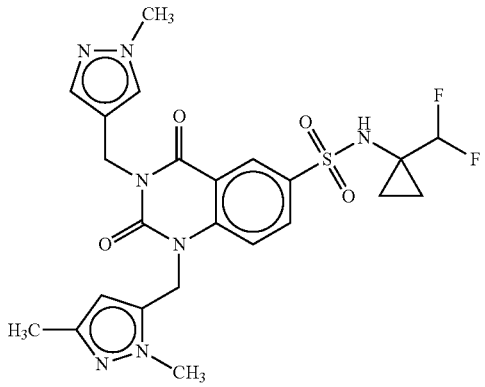 | A10 | 0.325 | 1.246 |
| Example 460 | 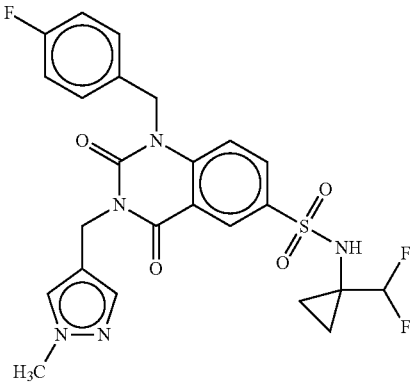 | A10 | 0.333 | 0.487 |
| Example 461 | 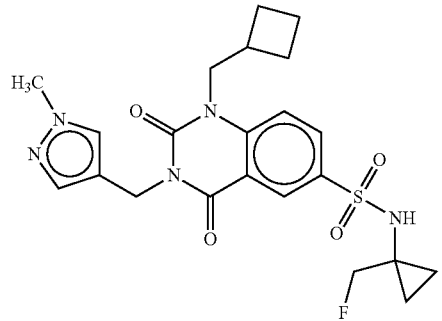 | A10 | 0.039 | 0.030 |
| Example 462 | 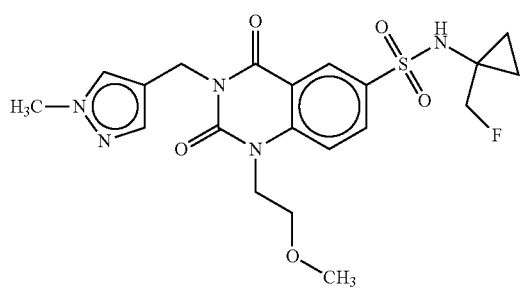 | A10 | 0.244 | 0.322 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 463 | 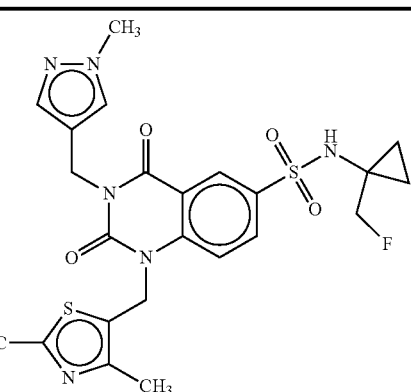 | A2 | 0.006 | 0.009 |
| Example 464 | 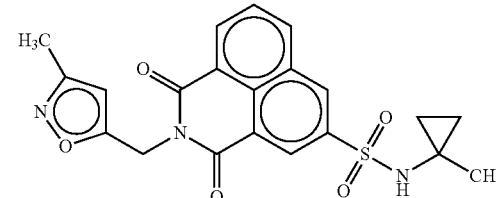 | Naphthalimide N-alkylation, then chlorosulfonylation, and sulfonamide formation | 1.045 | 1.084 |
| Example 465 | 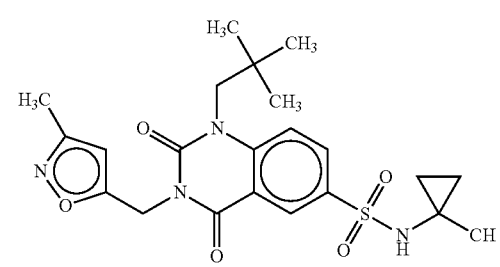 | Quinazolinedione N1-alkylation | 0.283 | 0.188 |
| Example 466 | 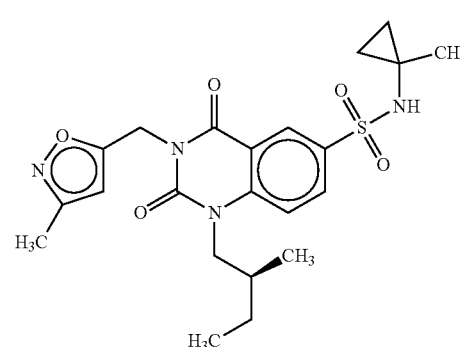 | Quinazolinedione N1-alkylation | 0.274 | 0.232 |
| Example 467 | 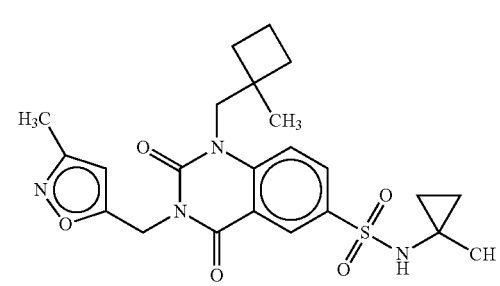 | Quinazolinedione N1-alkylation | 0.361 | 0.214 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 468 | 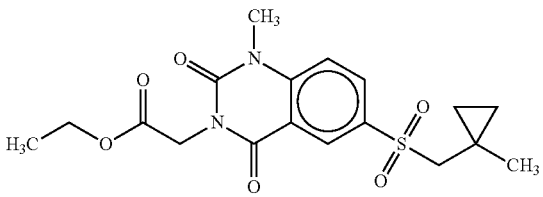 | A3 | 3.982 | 1.117 |
| Example 469 | 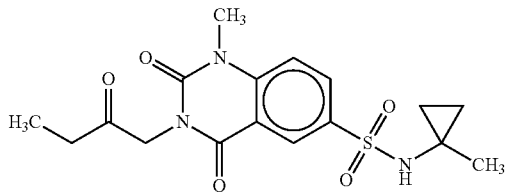 | A3 | 1.203 | 0.663 |
| Example 470 | 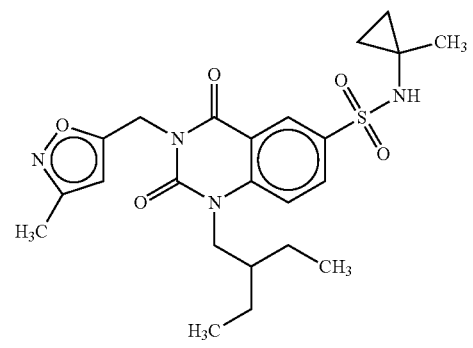 | Quinazolinedione N1-alkylation | 0.546 | 0.266 |
| Example 471 | 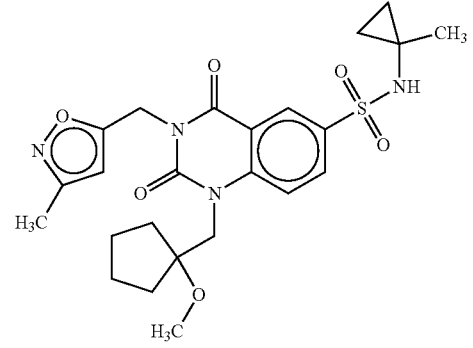 | Quinazolinedione N1-alkylation | 0.550 | 0.241 |
| Example 472 | 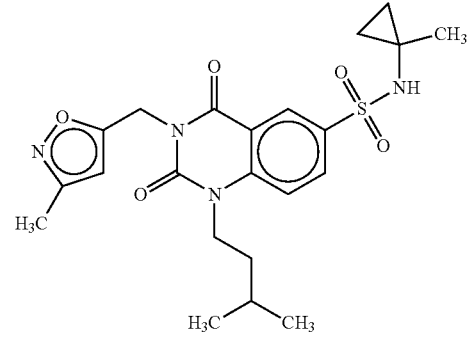 | Quinazolinedione N1-alkylation | 0.273 | 0.198 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 473 | 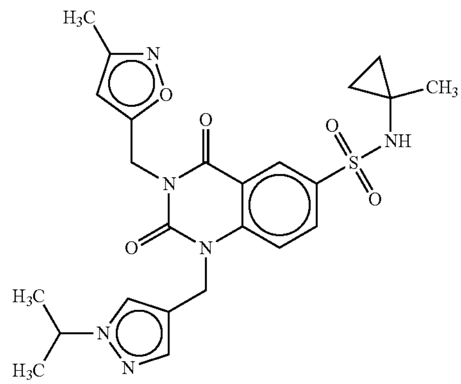 | Quinaozlinedione N1-alkylation | 0.196 | 0.144 |
| Example 474 | 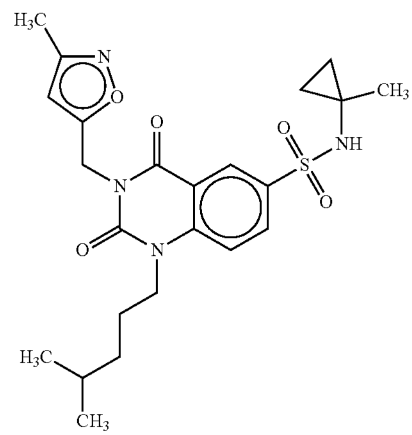 | Quinazolinedione N1-alkylation | 0.331 | 0.548 |
| Example 475 | 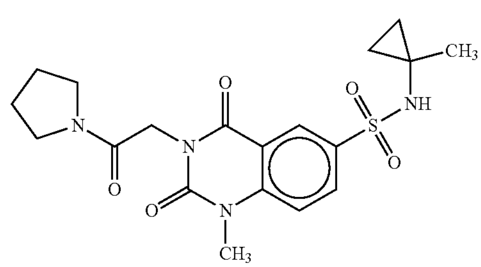 | A3 | 6.122 | 1.173 |
| Example 476 | 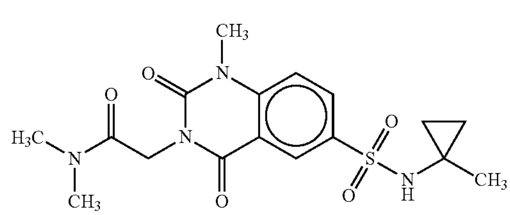 | A3 | 3.711 | 1.337 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 477 | 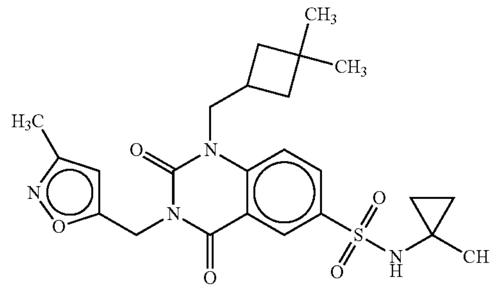 | Quinazolinedione N1-alkylation | 0.208 | 0.403 |
| Example 478 | 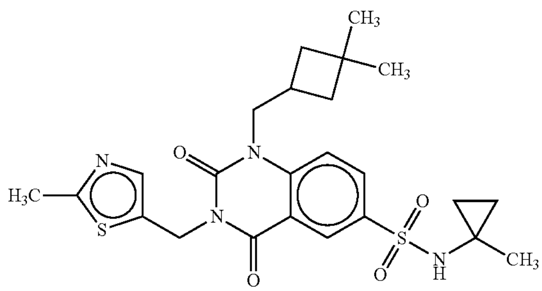 | Quinazolinedione N1-alkylation | 0.109 | 0.121 |
| Example 479 | 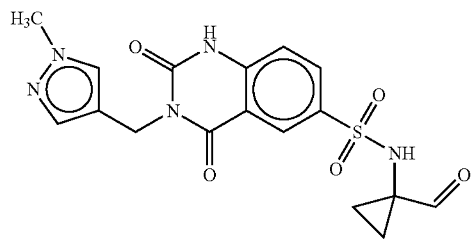 | Dess-Martin oxidation | 10.210 | 3.651 |
| Example 480 | 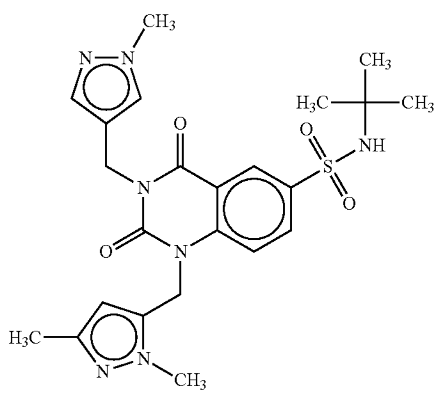 | A10 | 0.784 | 1.527 |
| Example 481 | 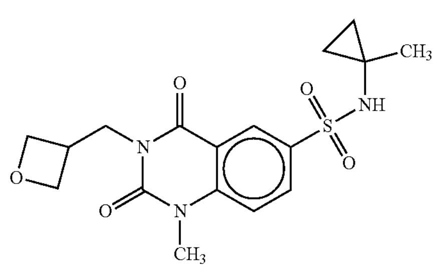 | A3 (tosylate) | 6.997 | 2.837 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 482 | 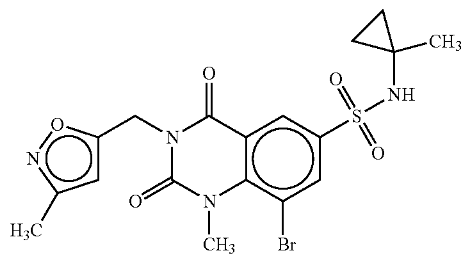 | Scheme 19 | 0.830 | 0.274 |
| Example 483 | 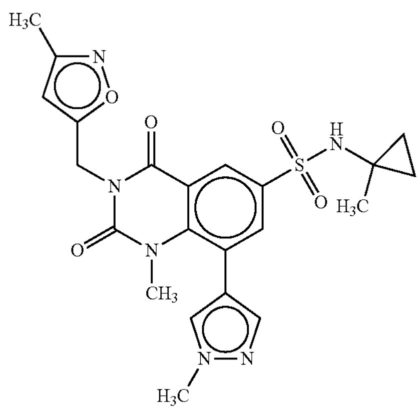 | Pd-catalysed aryl coupling | 1.691 | 0.845 |
| Example 484 | 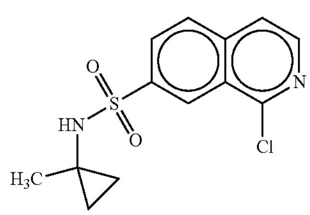 | Isoquinoline sulfonamide formation | 4.122 | 1.610 |
| Example 485 | 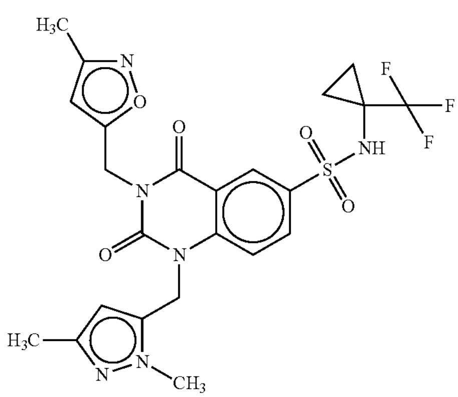 | A1 | 7.103 | 4.067 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 486 | 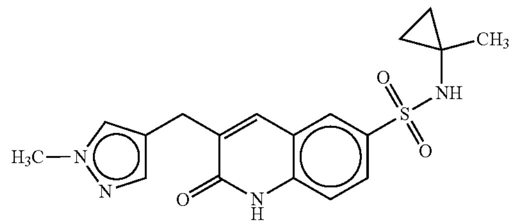 | Scheme 20 | 1.623 | 2.285 |
| Example 487 | 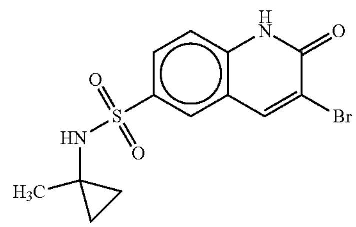 | Scheme 21 | 8.970 | >30 |
| Example 488 | 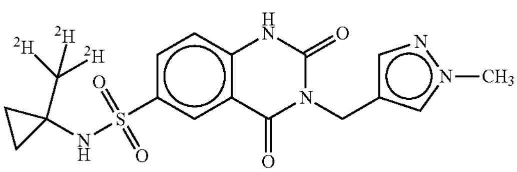 | Scheme 22 | 0.250 | 0.720 |
| Example 489 | 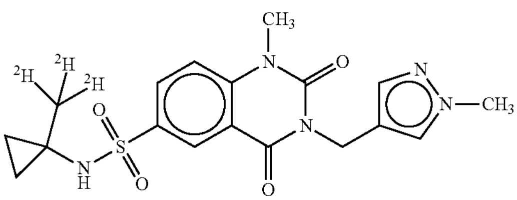 | Quinazolinedione sulfonamide formation | 0.317 | 0.334 |
| Example 490 | 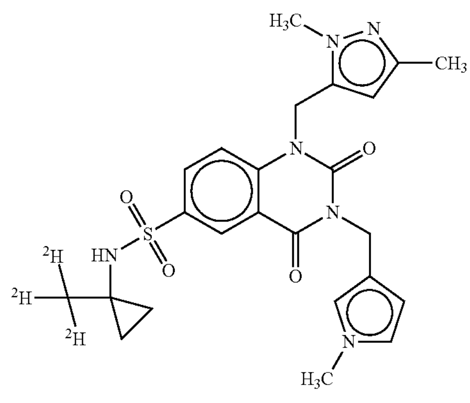 | Quinazolinedione N1-alkylation | 0.029 | 0.070 |
| Example 491 | 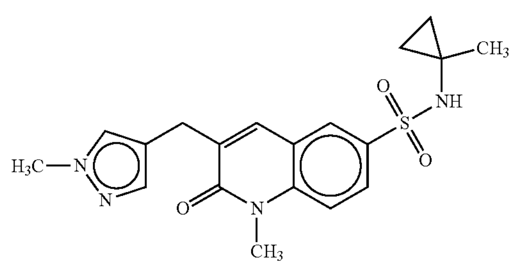 | Quinoline N-akylation | 3.440 | 1.787 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 492 | 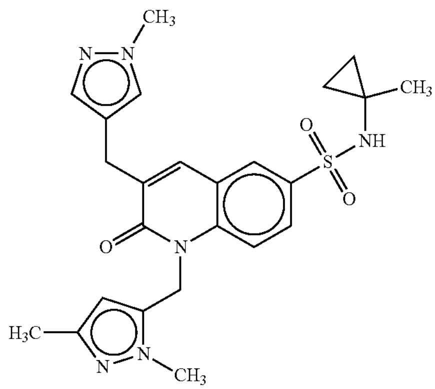 | Quinolinone N-alkylation | 0.489 | 0.741 |
| Example 493 | 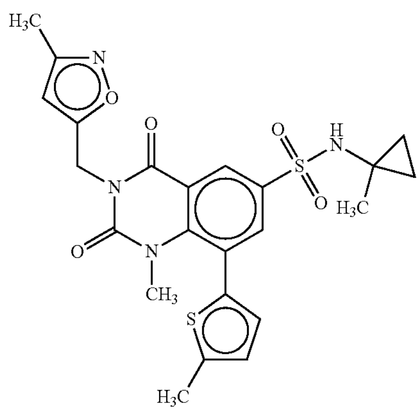 | Pd-catalysed aryl coupling | 0.453 | 0.524 |
| Example 494 | 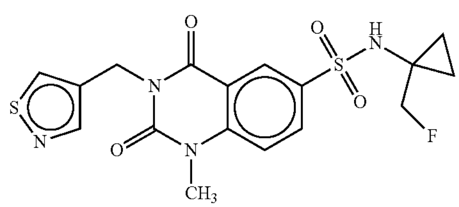 | Quinazolinedione N3-alkylation | 1.262 | 1.105 |
| Example 495 | 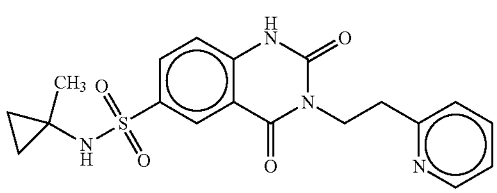 | Triphosgene cyclisation | 7.066 | |
| Example 496 | 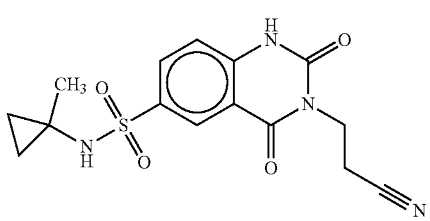 | Triphosgene cyclisation | 2.669 | 5.491 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 497 | 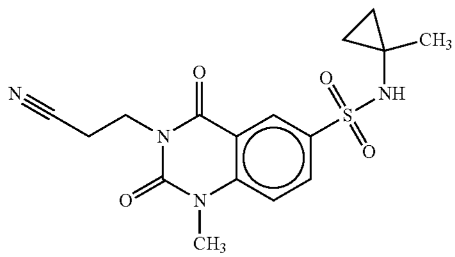 | A10 | 2.710 | 2.247 |
| Example 498 | 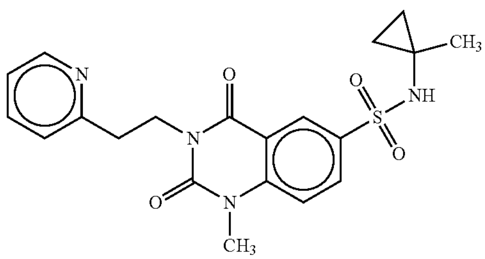 | A10 | 3.919 | |
| Example 499 | 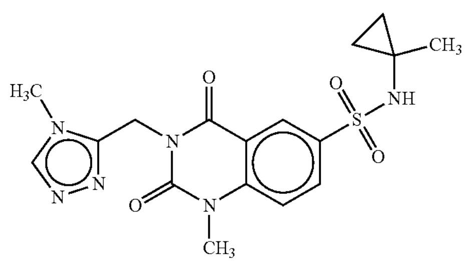 | A3 | 2.458 | |
| Example 500 | 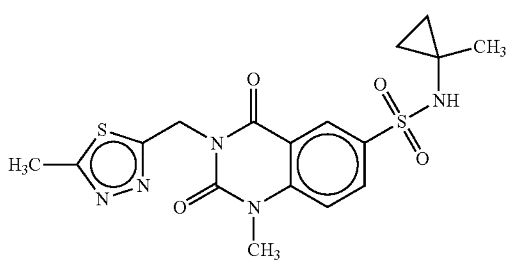 | A3 | 0.472 | 0.350 |
| Example 501 | 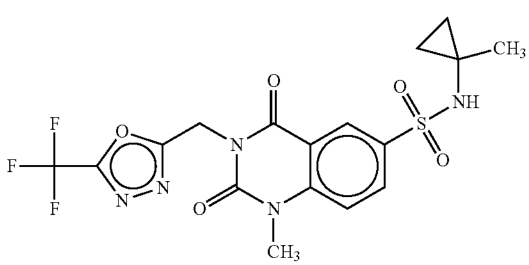 | A3 | 1.610 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 502 | 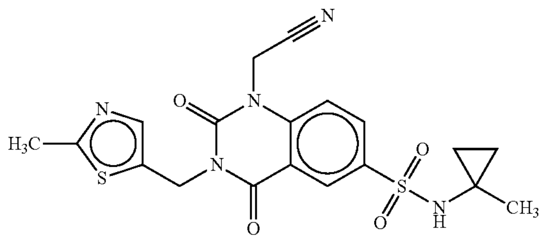 | A10 | 0.284 | 0.171 |
| Eaxmple 503 | 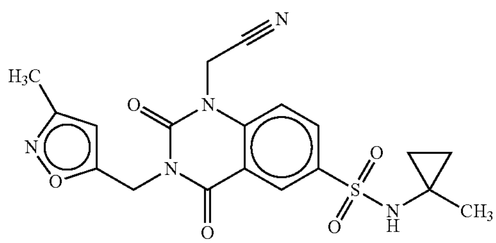 | A10 | 0.604 | 0.350 |
| Example 504 | 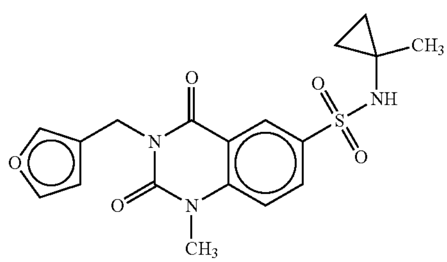 | A2 | 5.103 | |
| Example 505 | 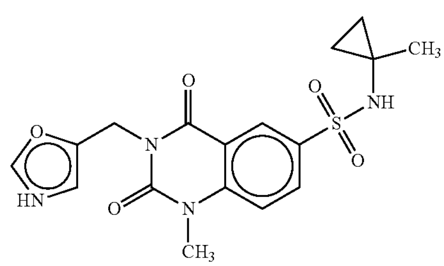 | A2 | 3.787 | |
| Example 506 | 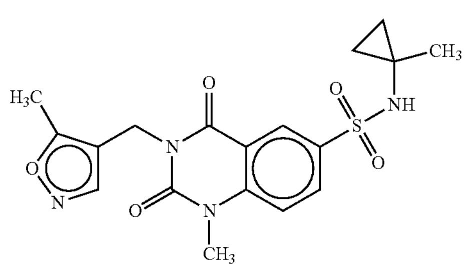 | A2 | 0.770 | 0.539 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 507 | 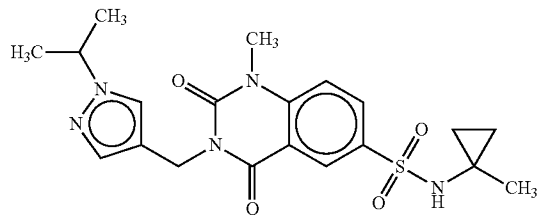 | A2 | 4.133 | |
| Example 508 | 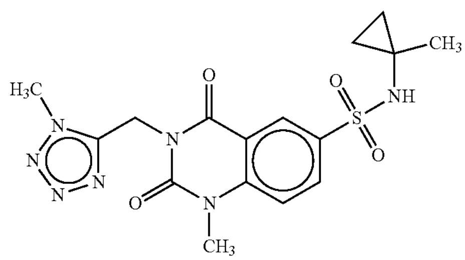 | A3 | 2.767 | |
| Example 509 | 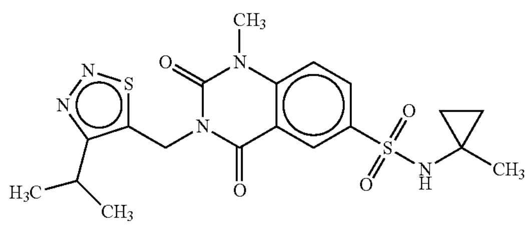 | A3 | 7.220 | |
| Example 510 | 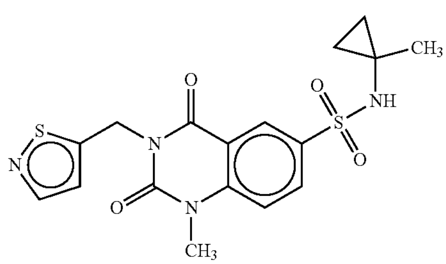 | A2 | 2.291 | |
| Example 511 | 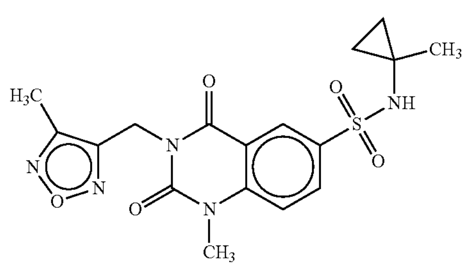 | A3 | 2.060 | |
| Example 512 | 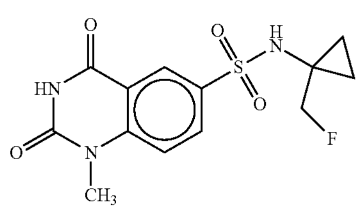 | Quinazolinedione sulfonamide formation | 2.951 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 513 | 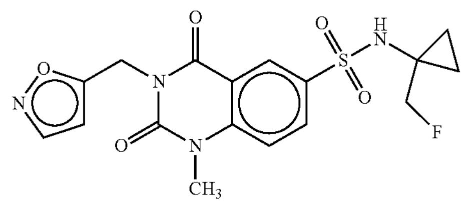 | A3 | 0.948 | 0.534 |
| Example 514 | 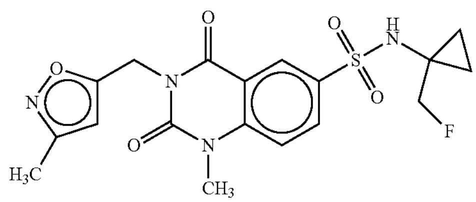 | A3 | 0.384 | 0.178 |
| Example 515 | 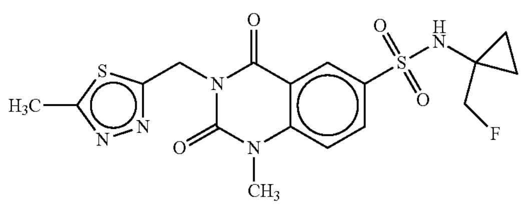 | A3 | 0.579 | 0.698 |
| Example 516 | 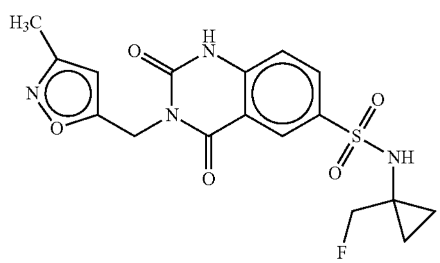 | Triphosgene cyclisation | 0.443 | 0.807 |
| Example 517 | 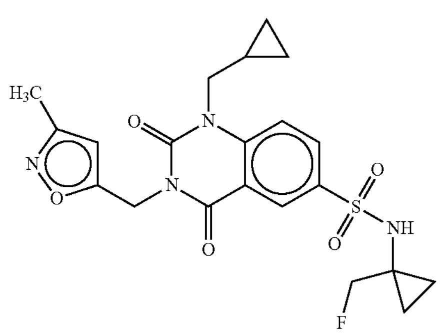 | A10 | 0.056 | 0.041 |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 518 | 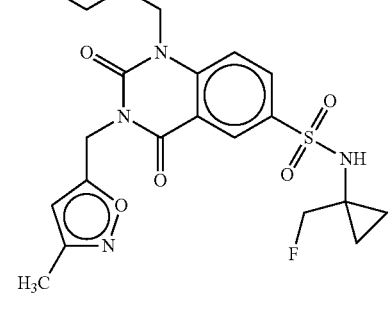 | A10 | 0.117 | 0.095 |
| Example 519 | 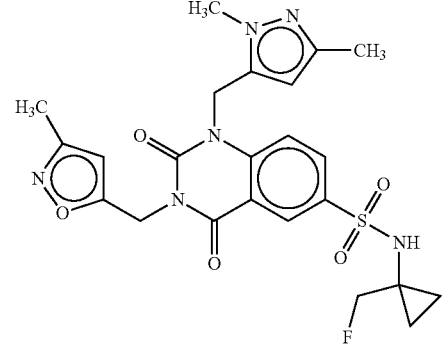 | A10 | 0.050 | 0.312 |
| Example 520 | 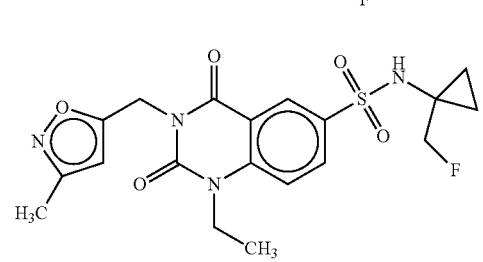 | A10 | 0.162 | 0.092 |
| Example 521 | 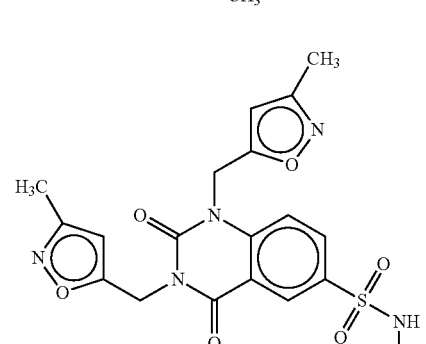 | A10 | 0.054 | 0.092 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 522 | 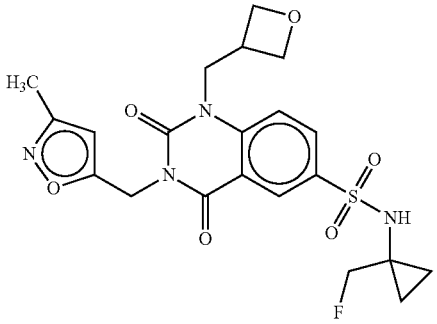 | A10 | 0.112 | 0.923 |
| Example 523 | 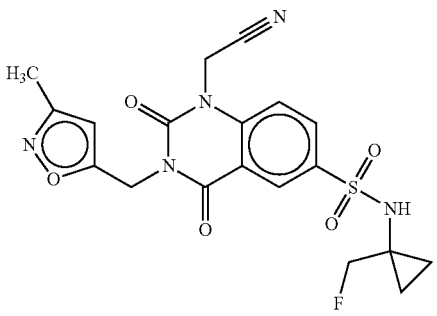 | Quinazolinedione N1-alkylation | 0.411 | 0.571 |
| Example 524 | 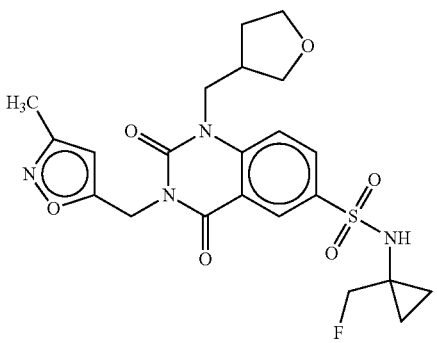 | Quinazolinedione N1-alkylation | 0.125 | 0.310 |
| Example 525 | 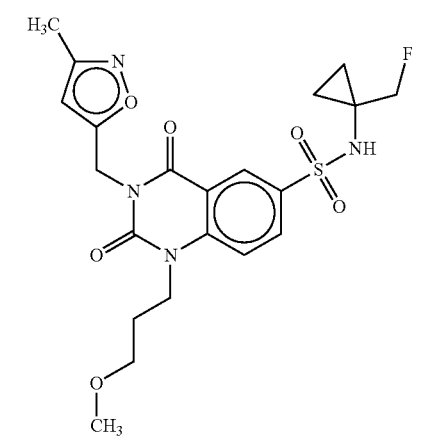 | Quinazolinedione N1-alkylation | 0.169 | 0.315 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 526 | 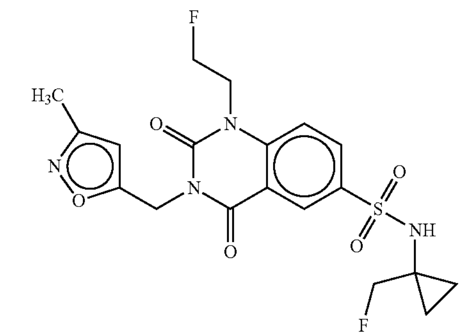 | A2 | 0.202 | 0.133 |
| Example 527 | 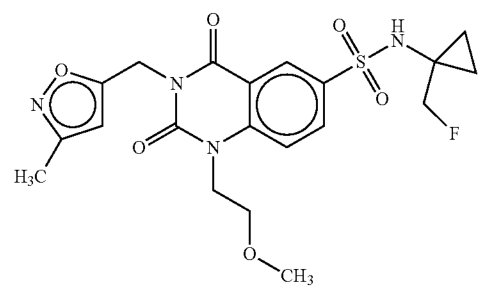 | Quinazolinedione N1-alkylation | 0.208 | |
| Example 528 | 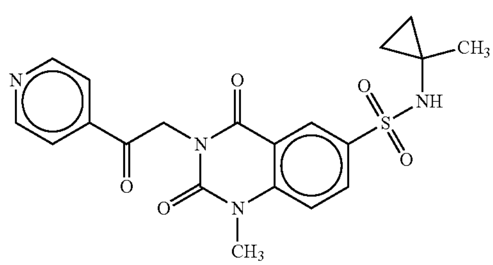 | A3 | 1.743 | |
| Example 529 | 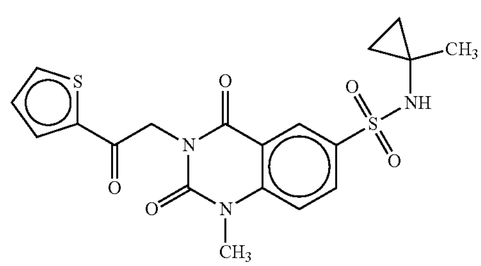 | A3 | 1.050 | |
| Example 530 | 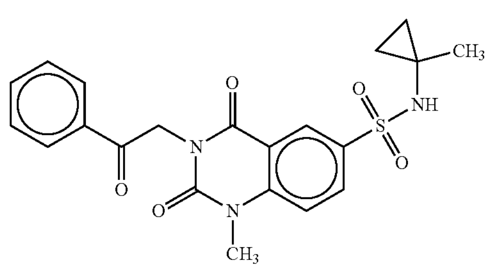 | A3 | 1.614 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 531 | 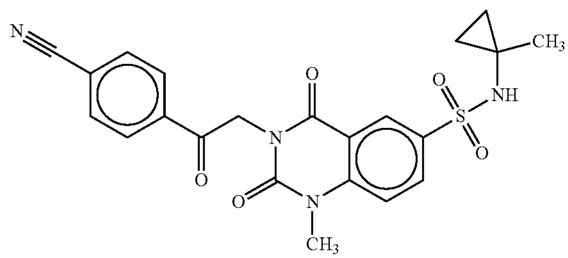 | A3 | 3.270 | |
| Example 532 | 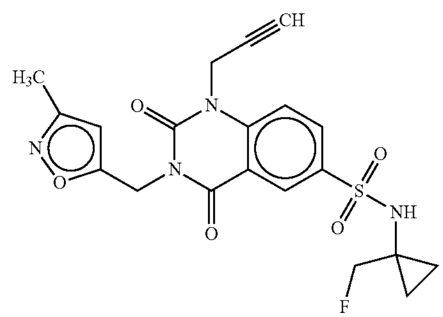 | Quinazolinedione N1-alkylation | 0.120 | 0.087 |
| Example 533 | 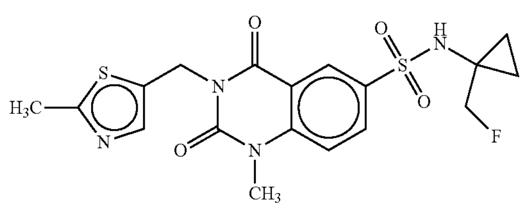 | A2 | 0.287 | 0.282 |
| Example 534 | 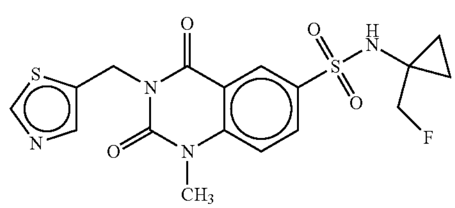 | A2 | 0.578 | |
| Example 535 | 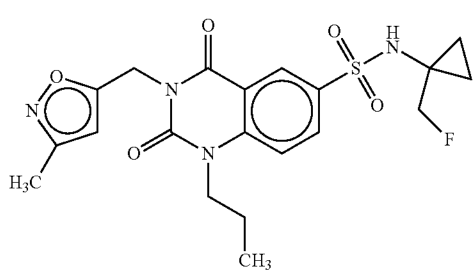 | A10 | 0.191 | 0.147 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 536 | 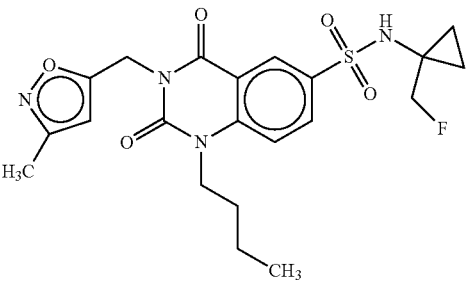 | A10 | 0.261 | 0.376 |
| Example 537 | 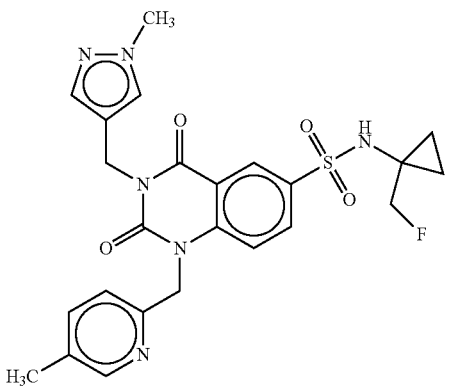 | Quinazolinedione N1-alkylation | 0.189 | 0.181 |
| Example 538 | 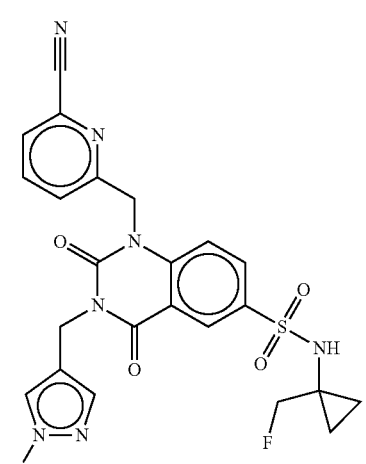 | Quinazolinedione N1-alkylation | 0.162 | 0.393 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 539 | 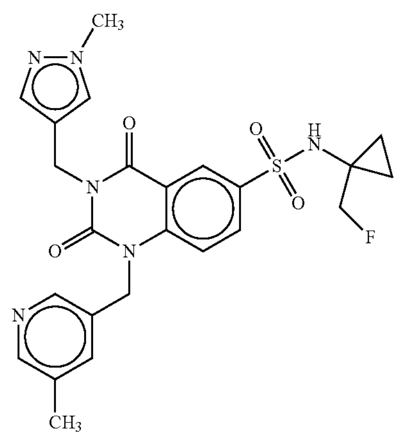 | Quinazolinedione N1-alkylation | 0.073 | 0.187 |
| Example 540 | 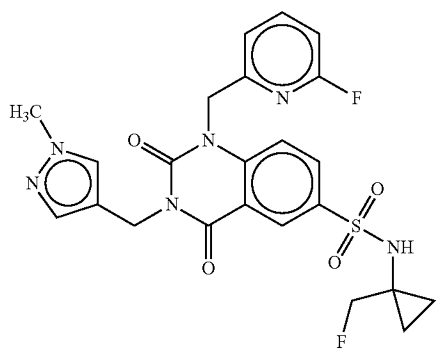 | Quinazolinedione N1-alkylation | 0.160 | 0.096 |
| Example 541 | 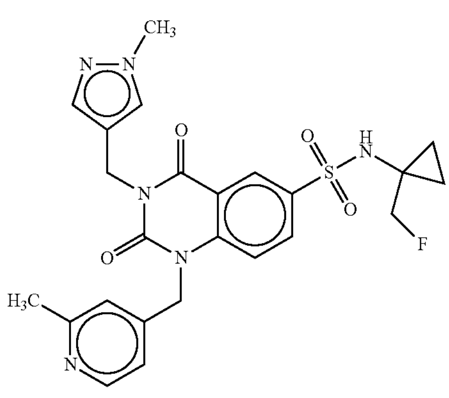 | Quinazolinedione N1-alkylation | 0.113 | 0.227 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 542 | 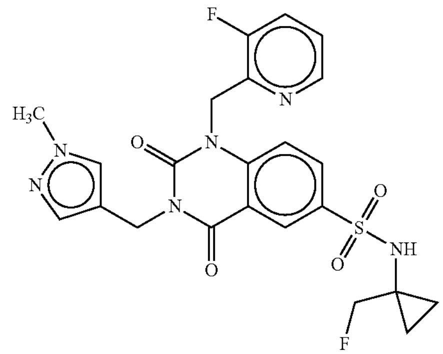 | Quinazolinedione N1-alkylation | 0.349 | 0.330 |
| Example 543 | 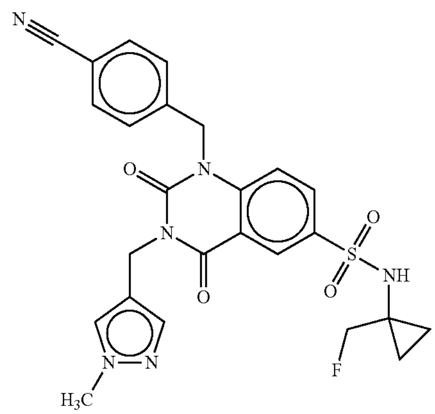 | Quinazolinedione N1-alkylation | 0.058 | 0.070 |
| Example 544 | 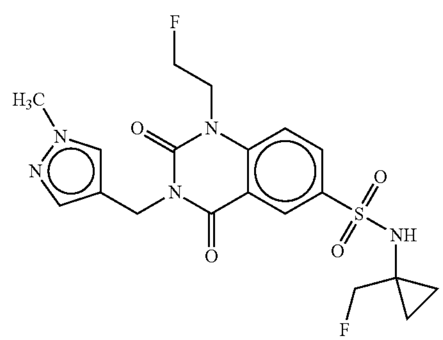 | Quinazolinedione N1-alkylation | 0.151 | 0.086 |
| Example 545 | 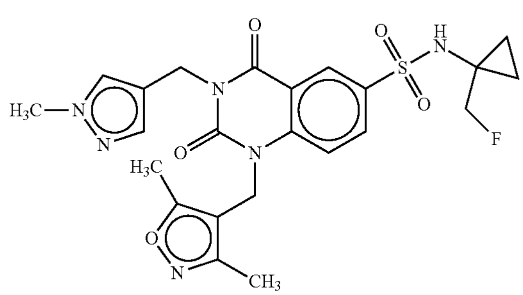 | Quinazolinedione N1-alkylation | 0.145 | 0.168 |

TABLE 1-continued

Method of synthesis and PARG activity (Biochem and Cell Activity)

| Example | Structure | Method | PARG Biochem IC50 Geomean (µM) | PARG Cell IC50 Geomean (µM) |
|---|---|---|---|---|
| Example 546 | 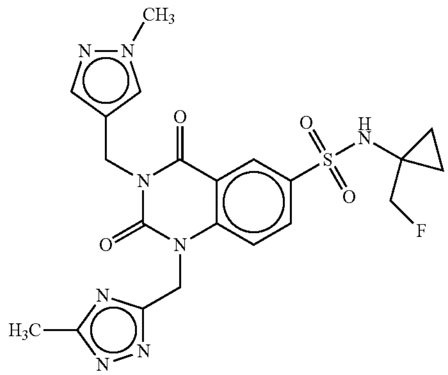 | Quinazolinedione N1-alkylation | 0.152 | 0.182 |
| Example 547 | 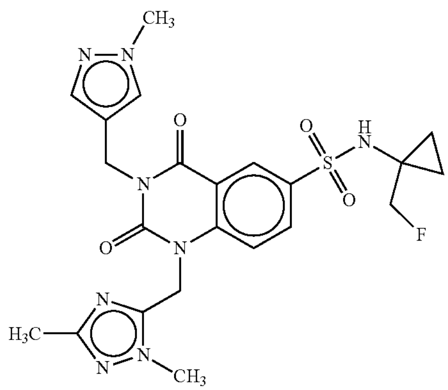 | Quinazolinedione N1-alkylation | 0.188 | 0.751 |
| Example 548 | 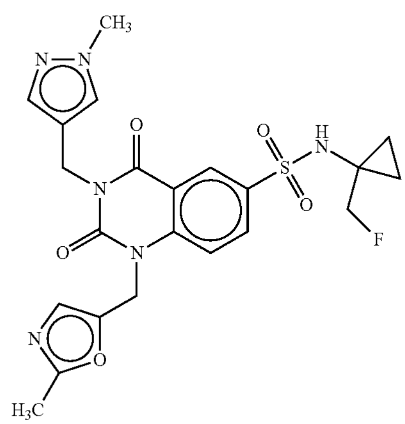 | Quinazolinedione N1-alkylation | 0.034 | 0.063 |
| Example 549 | 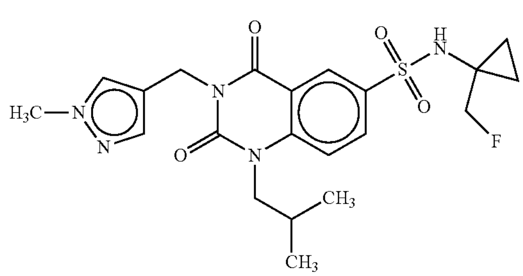 | Quinazolinedione N1-alkylation | 0.140 | 0.091 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 550 | 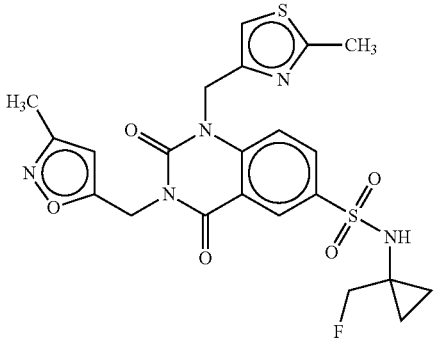 | A10 | 0.191 | 0.134 |
| Example 551 | 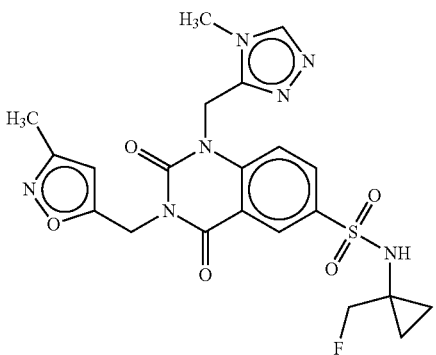 | A10 | 0.404 | 20.450 |
| Example 552 | 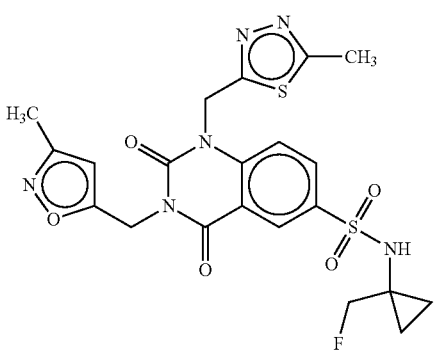 | A10 | 0.175 | 0.157 |
| Example 553 | 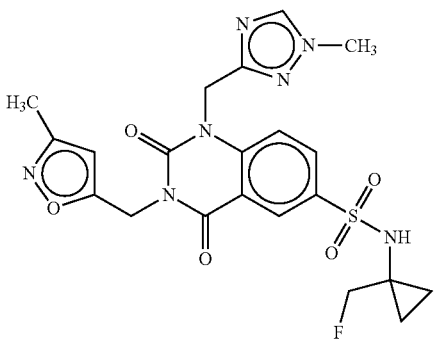 | A10 | 0.451 | 1.512 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 554 | 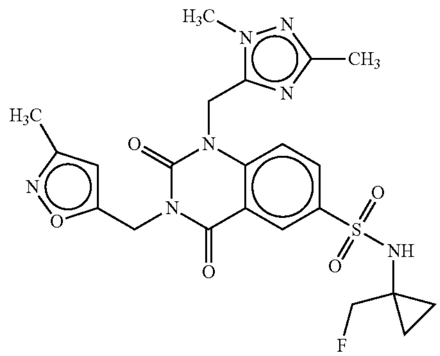 | A10 | 0.499 | 0.604 |
| Example 555 | 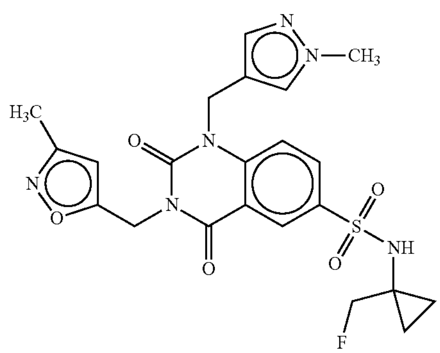 | A10 | 0.049 | 0.086 |
| Example 556 | 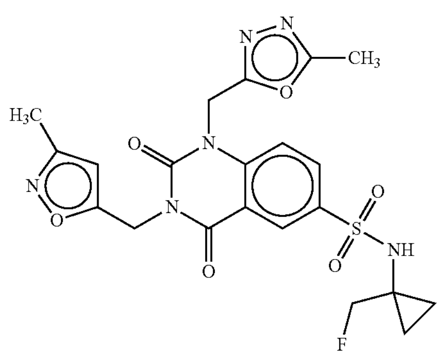 | A10 | 0.348 | 1.026 |
| Example 557 | 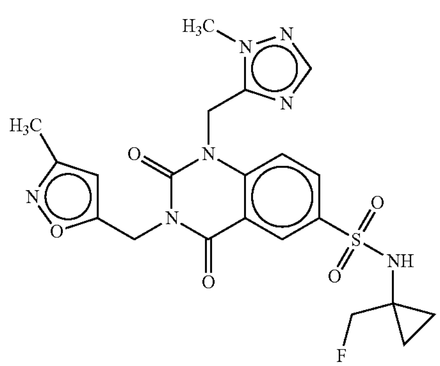 | A10 | 0.368 | 0.857 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 558 | 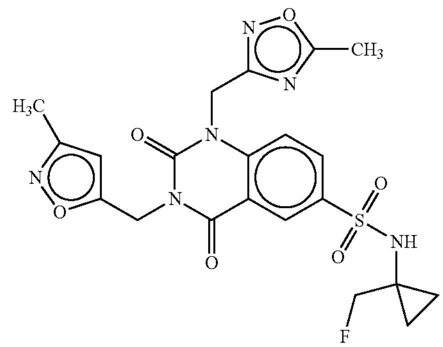 | A10 | 0.207 | 0.177 |
| Example 559 | 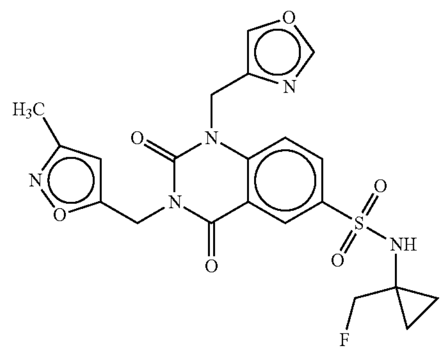 | A2 | 0.085 | 0.060 |
| Example 560 | 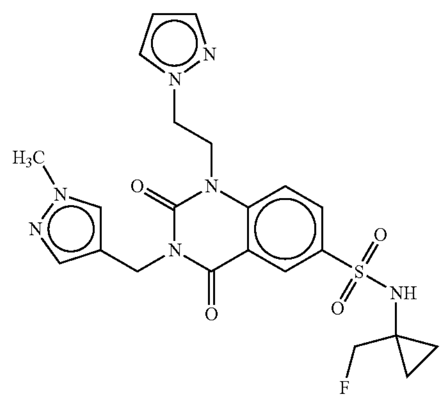 | Quinazolinedione N1-alkylation | 0.530 | 0.810 |
| Example 561 | 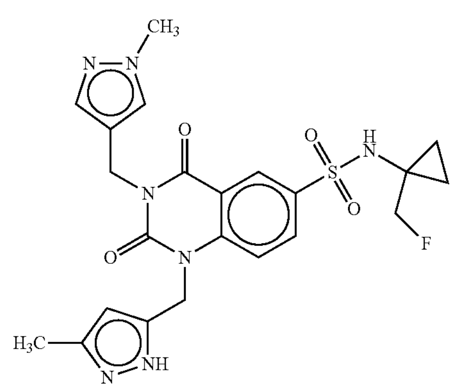 | Quinazolinedione N1-alkylation | 0.095 | 0.570 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 562 | 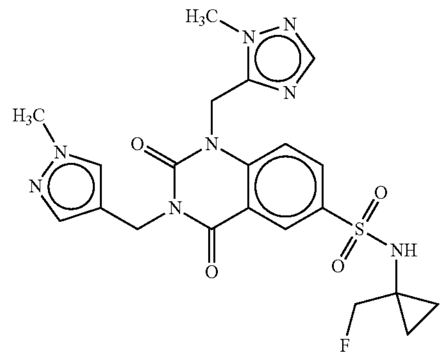 | Quinazolinedione N1-alkylation | 0.192 | 0.598 |
| Example 563 | 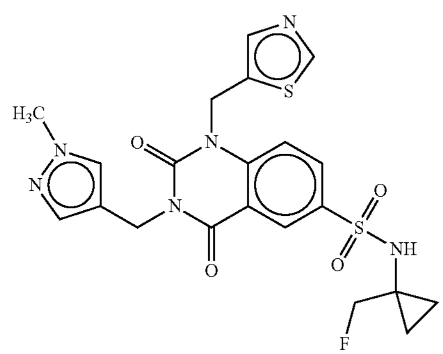 | Quinazolinedione N1-alkylation | 0.008 | 0.066 |
| Example 564 | 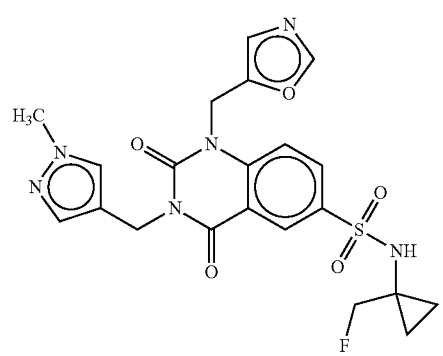 | Quinazolinedione N1-alkylation | 0.038 | 0.127 |
| Example 565 | 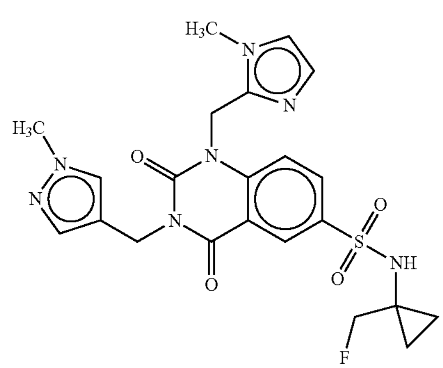 | Quinazolinedione N1-alkylation | 0.156 | 0.558 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 566 | 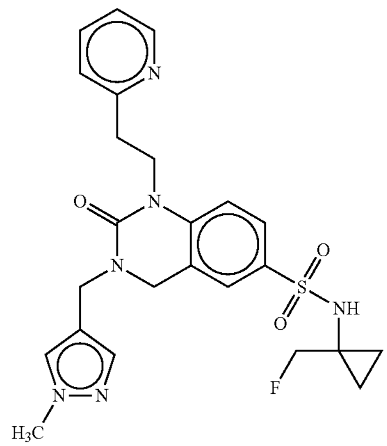 | Quinazolinedione N1-alkylation | 0.687 | 0.562 |
| Example 567 | 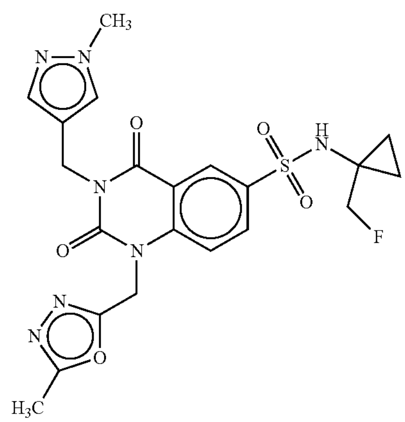 | Quinazolinedione N1-alkylation | 0.225 | 0.855 |
| Example 568 | 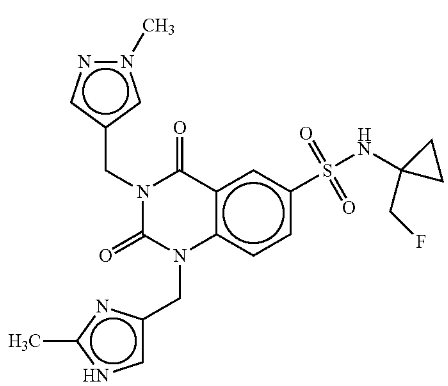 | Quinazolinedione N1-alkylation | 0.100 | 5.292 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 569 | 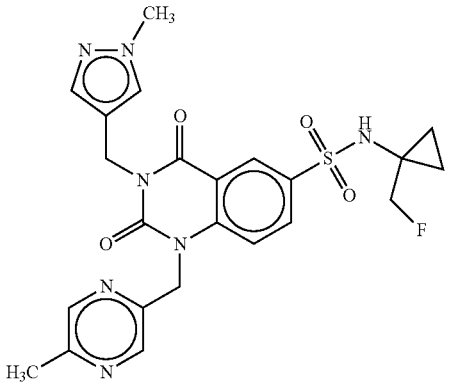 | Quinazolinedione N1-alkylation | 0.130 | 0.128 |
| Example 570 | 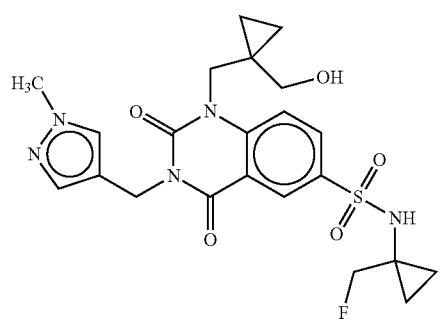 | Quinazolinedione N1-alkylation | 0.126 | 0.238 |
| Example 571 | 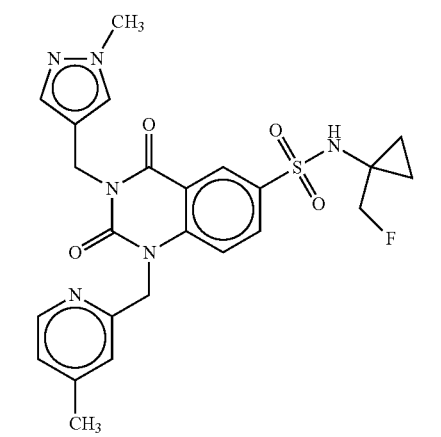 | Quinazolinedione N1-alkylation | 0.330 | 0.373 |
| Example 572 | 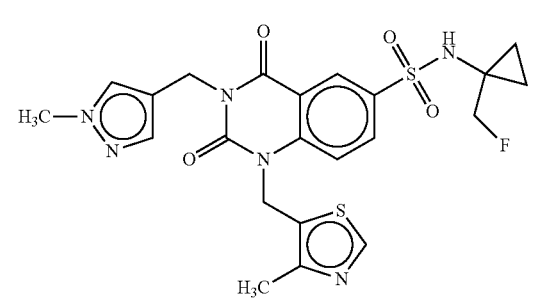 | Quinazolinedione N1-alkylation | 0.007 | |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 573 | 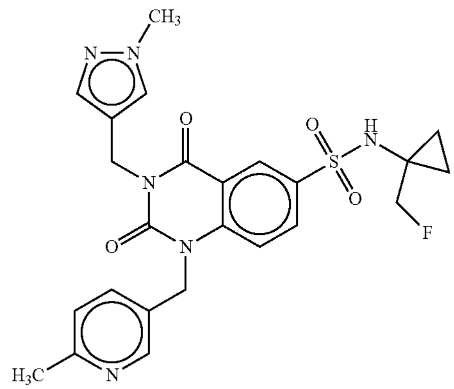 | Quinazolinedione N1-alkylation | 0.071 | 0.167 |
| Example 574 | 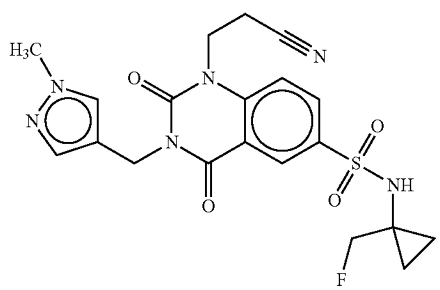 | Quinazolinedione N1-alkylation | 0.170 | 0.530 |
| Example 575 | 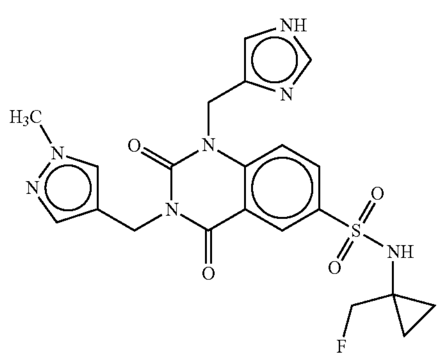 | Quinazolinedione N1-alkylation | 0.088 | 1.571 |
| Example 576 | 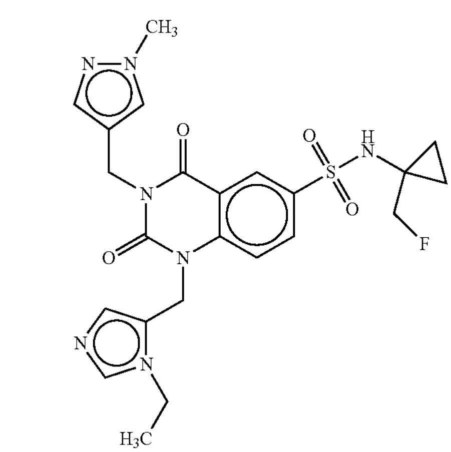 | Quinazolinedione N1-alkylation | 0.042 | 2.164 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 577 | 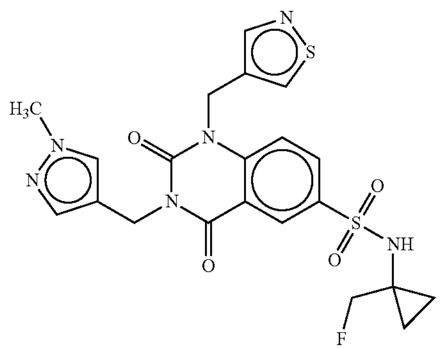 | Quinazolinedione N1-alkylation | 0.024 | 0.036 |
| Example 578 | 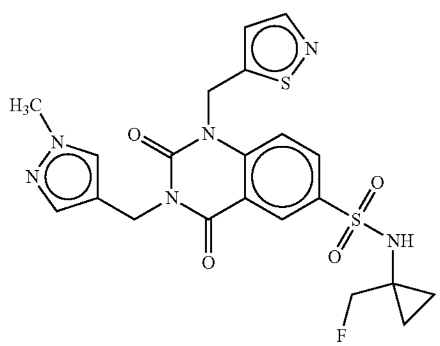 | Quinazolinedione N1-alkylation | 0.010 | |
| Example 579 | 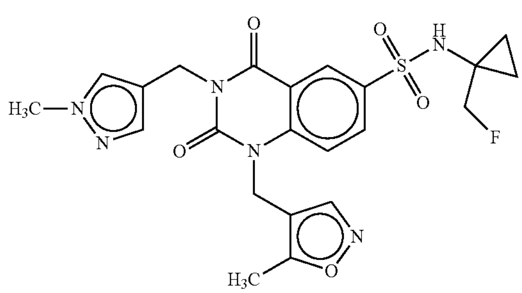 | Quinazolinedione N1-alkylation | 0.009 | |
| Example 580 | 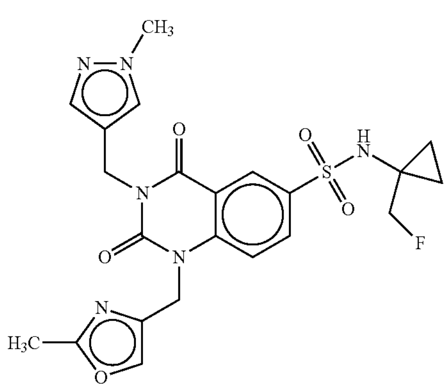 | Quinazolinedione N1-alkylation | 0.069 | 0.046 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
|---|---|---|---|---|
| Example 581 | 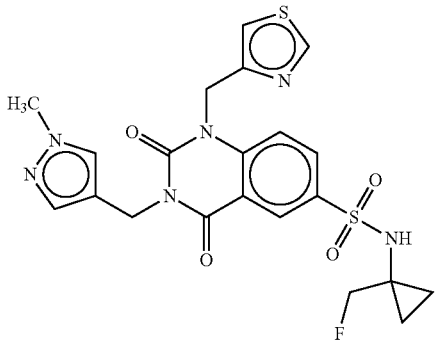 | Quinazolinedione N1-alkylation | 0.057 | 0.055 |
| Example 582 | 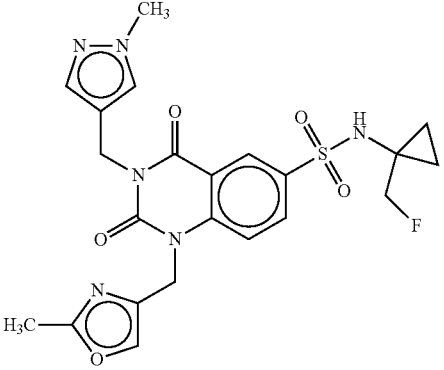 | Quinazolinedione N1-alkylation | 0.160 | 0.073 |
| Example 583 | 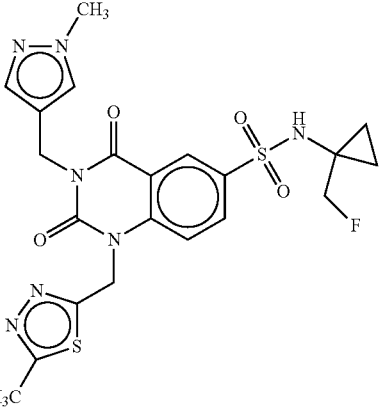 | Quinaozlinedione N1-alkylation | 0.093 | 0.153 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
| --- | --- | --- | --- | --- |
| Example 584 | 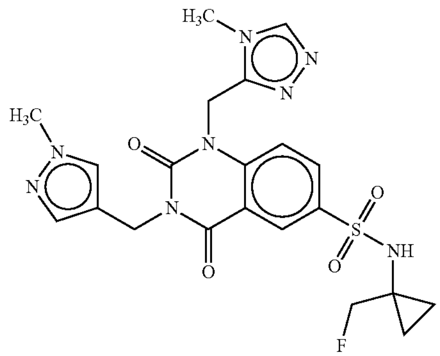 | Quinazolinedione N1-alkylation | 0.171 | 25.820 |
| Example 585 | 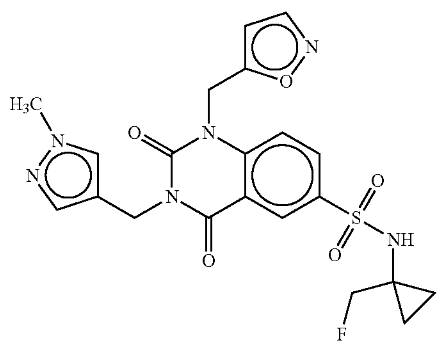 | Quinazolinedione N1-alkylation | 0.038 | 0.052 |
| Example 586 | 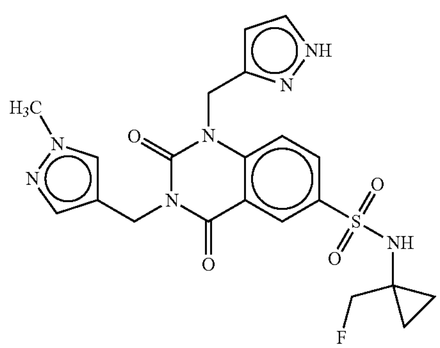 | Quinazolinedione N1-alkylation | 0.082 | 0.530 |
| Example 587 | 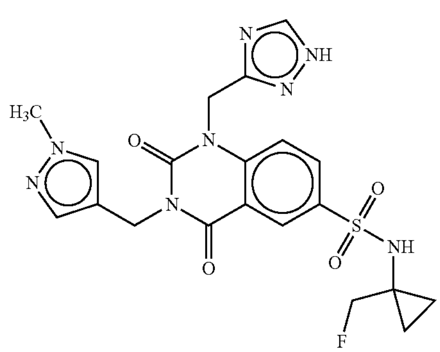 | Quinazolinedione N1-alkylation | 0.207 | 7.977 |

TABLE 1-continued
Method of synthesis and PARG activity (Biochem and Cell Activity)
| Example | Structure | Method | PARG Biochem IC50 Geomean (μM) | PARG Cell IC50 Geomean (μM) |
| --- | --- | --- | --- | --- |
| Example 588 | 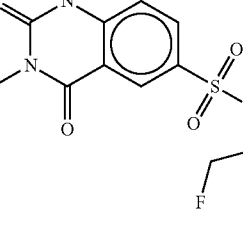 | Quinazolinedione N1-alkylation | 0.019 | 1.500 |
| Example 589 | 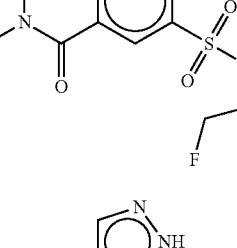 | Quinazolinedione N1-alkylation | 0.055 | 0.187 |
| Example 590 | 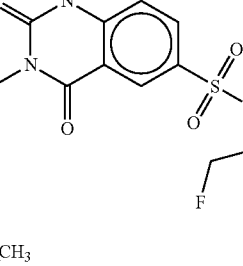 | Quinazolinedione N1-alkylation | 0.030 | 0.773 |
| Example 591 | 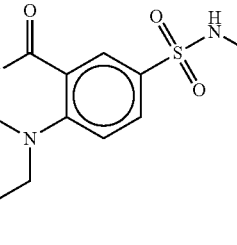 | Quinazolinedione N1-alkylation | 0.030 | 0.032 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 592 | 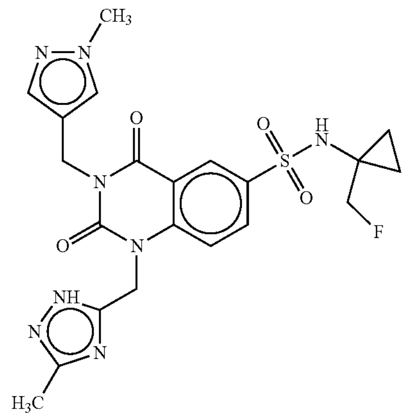 | Quinaozlinedione N1-alkylation | 0.300 | 11.390 |
| Example 593 | 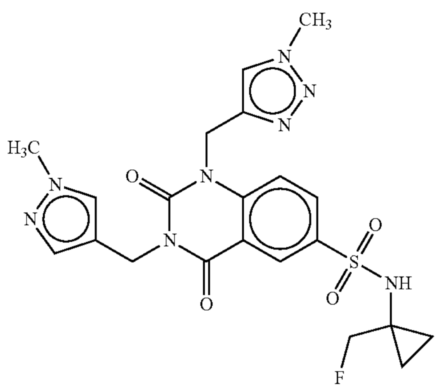 | Quinazolinedione N1-alkylation | 0.112 | 0.523 |
| Example 594 | 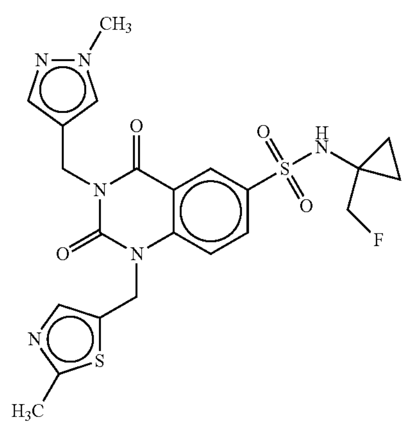 | Quinazolinedione N1-alkylation | 0.025 | 0.022 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 595 | 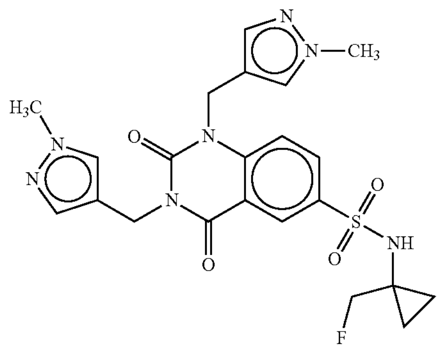 | Quinazolinedione N1-alkylation | 0.048 | 0.134 |
| Example 596 | 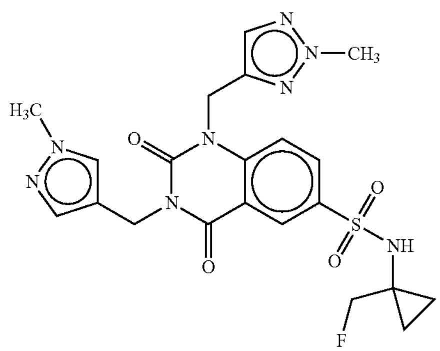 | Quinazolinedione N1-alkylation | 0.085 | 0.096 |
| Example 597 | 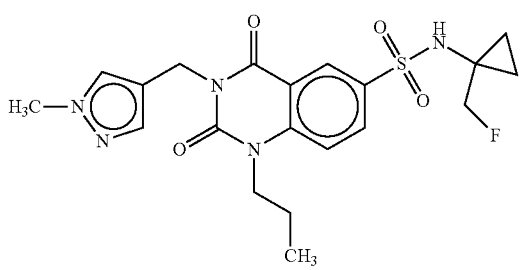 | Quinazolinedione N1-alkylation | 0.100 | 0.086 |
| Example 598 | 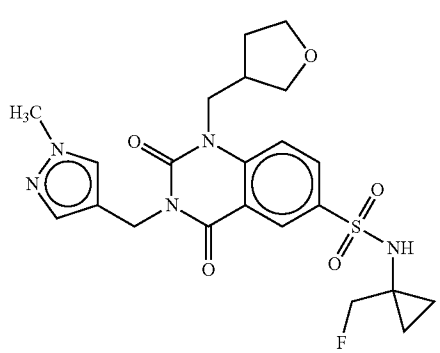 | Quinazolinedione N1-alkylation | 0.082 | 0.240 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 599 | 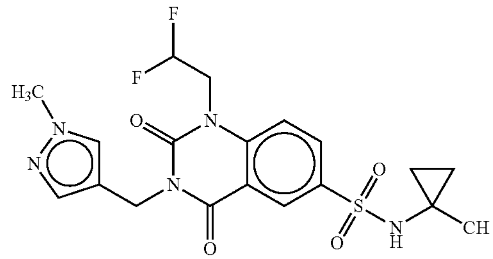 | Quinazolinedione sulfonamide formation | 0.263 | 0.093 |
| Example 600 | 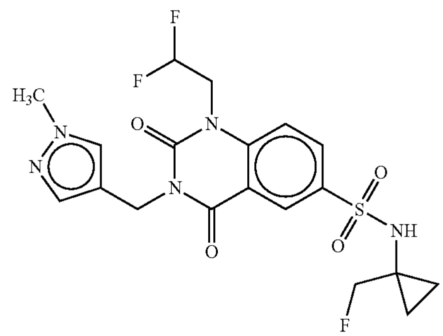 | Quinazolinedione sulfonamide formation | 0.127 | 0.109 |
| Example 601 | 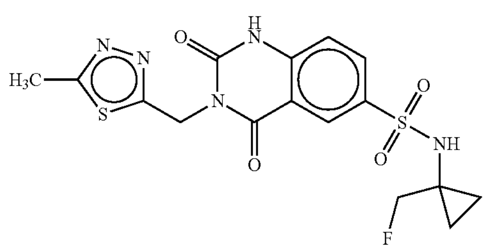 | 1 | 0.710 | 13.480 |
| Example 602 | 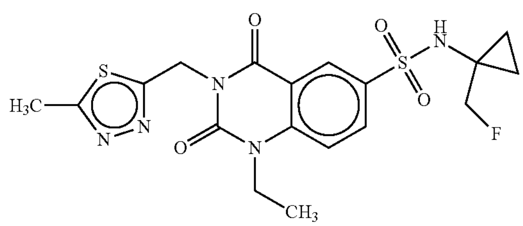 | A10 | 0.131 | 0.135 |
| Example 603 | 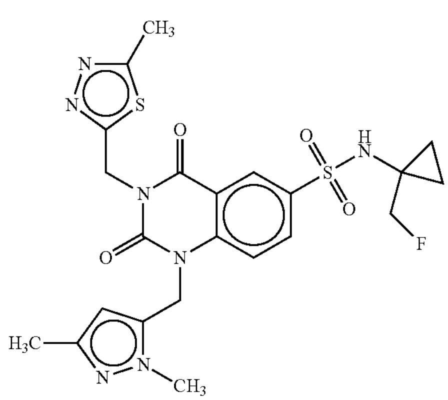 | A10 | 0.029 | 0.496 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 604 | 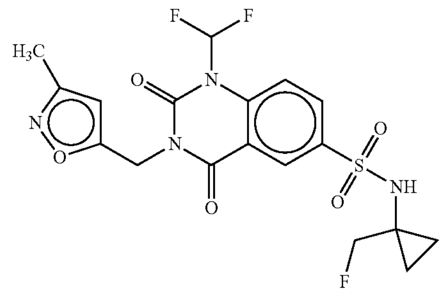 | A10 | 0.788 | 0.295 |
| Example 605 | 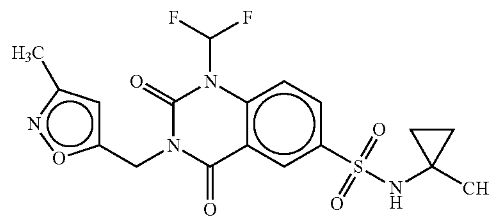 | A10 | 1.369 | 0.588 |
| Exampel 606 | 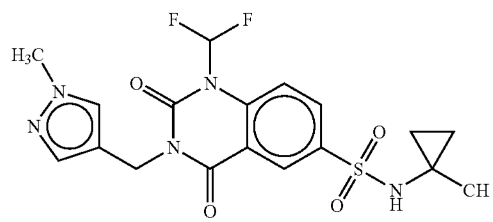 | A10 | 1.465 | 0.248 |
| Example 607 | 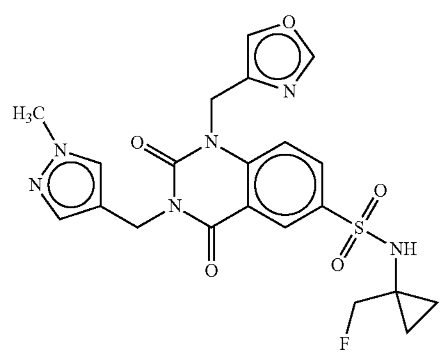 | Quinazolinedione N1-alkylation | 0.063 | 0.076 |
| Example 608 | 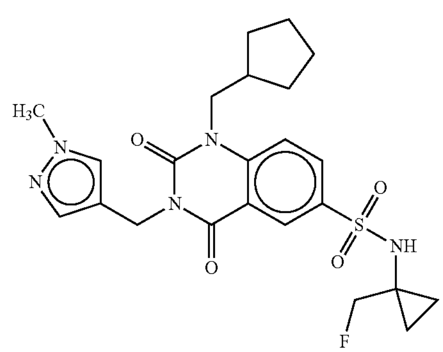 | Quinazolinedione N1-alkylation | 0.064 | 0.050 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 609 | 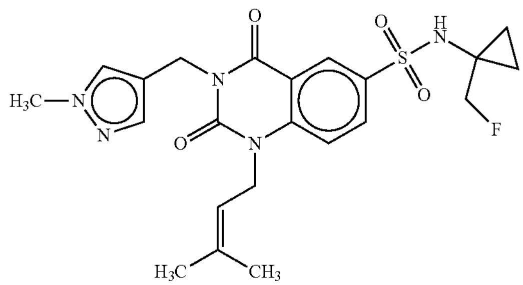 | Quinazolinedione N1-alkylation | 0.051 | 0.056 |
| Example 610 | 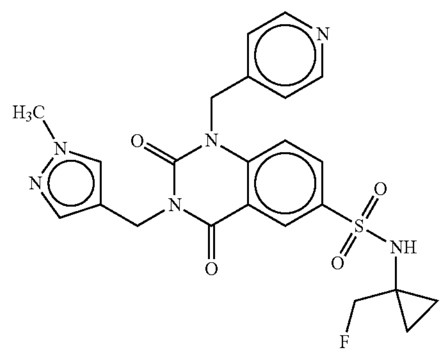 | Quinazolinedione N1-alkylation | 0.111 | 0.669 |
| Example 611 | 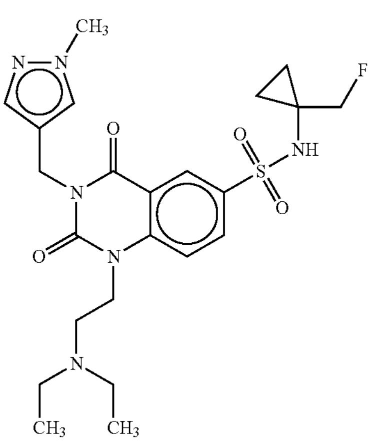 | Quinazolinedione N1-alkylation | 0.113 | 0.249 |

TABLE 1-continued
Method of synthesis and PARG activity (Biochem and Cell Activity)
| Example | Structure | Method | PARG Biochem IC50 Geomean (µM) | PARG Cell IC50 Geomean (µM) |
|---|---|---|---|---|
| Example 612 | 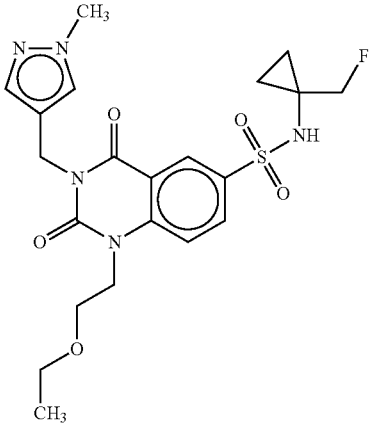 | Quinazolinedione N1-alkylation | 0.194 | 0.178 |
| Example 613 | 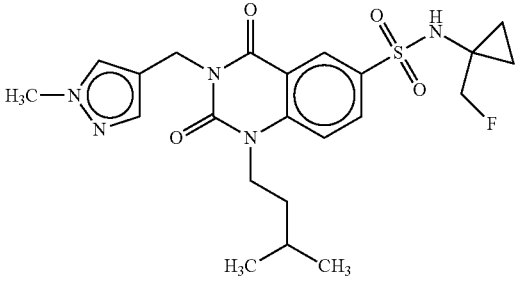 | Quinazolinedione N1-alkylation | 0.042 | 0.056 |
| Example 614 | 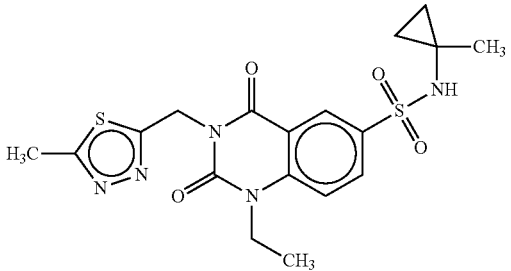 | A10 | 0.239 | 0.122 |
| Example 615 | 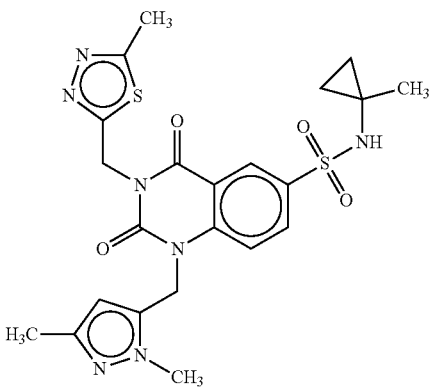 | A10 | 0.064 | 0.274 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 616 | 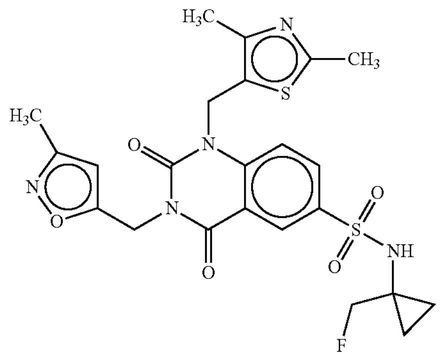 | A10 | 0.017 | 0.025 |
| Example 617 | 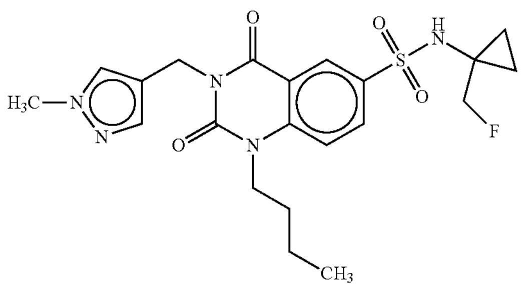 | Quinazolinedione N1-alkylation | 0.039 | 0.037 |
| Example 618 | 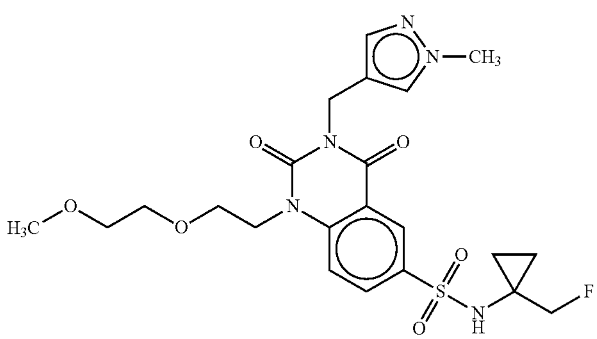 | Quinazolinedione N1-alkylation | 0.247 | 0.325 |
| Example 619 | 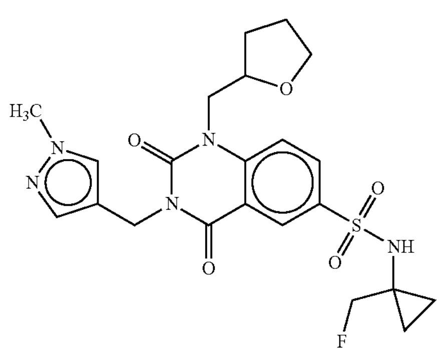 | Quinazolinedione N1-alkylation | 0.190 | 0.233 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 620 | 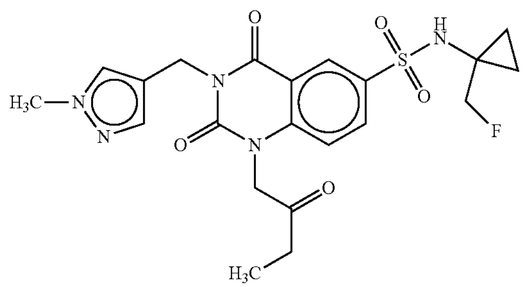 | Quinazolinedione N1-alkylation | 0.144 | 0.238 |
| Example 621 | 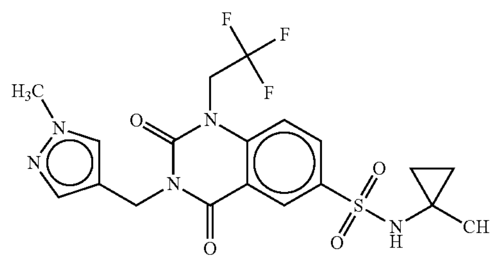 | A10 | 0.257 | 0.135 |
| Example 622 | 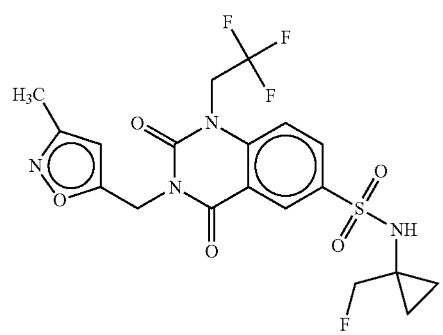 | A10 | 0.355 | 0.228 |
| Example 623 | 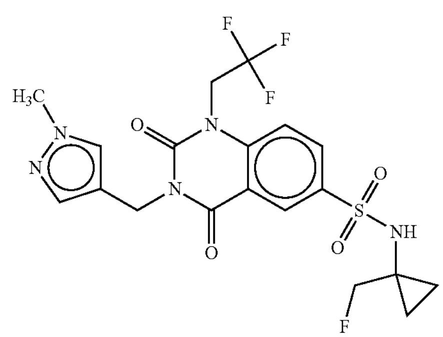 | A10 | 2.667 | 10.020 |
| Exampel 624 | 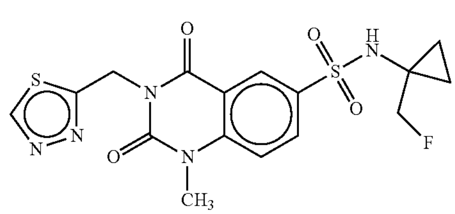 | Quinazolinedione N3-alkylation | 1.035 | 4.347 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 625 | 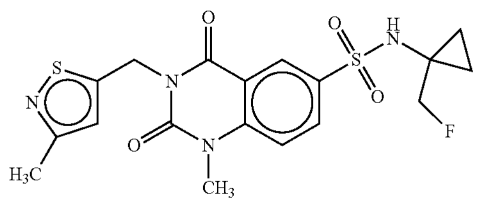 | Quinazolinedione N3-alkylation | 0.597 | 0.730 |
| Example 626 | 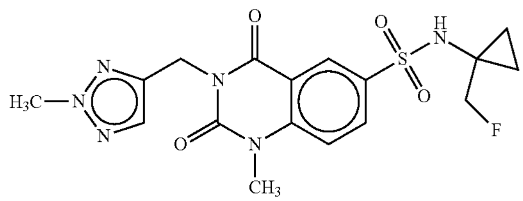 | Quinazolinedione N3-alkylation | 3.157 | 1.810 |
| Example 627 | 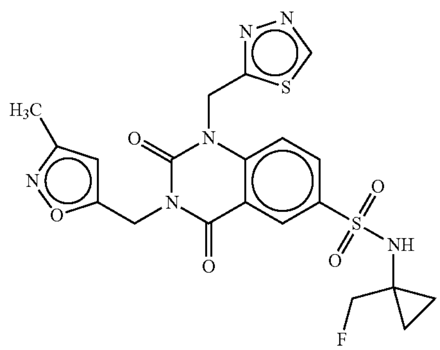 | A10 | 0.159 | 0.351 |
| Example 628 | 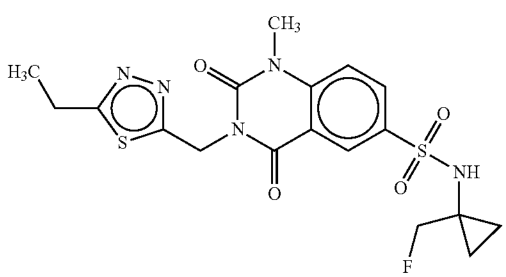 | Quinazolinedione N3-alkylation | 2.692 | 0.736 |
| Example 629 | 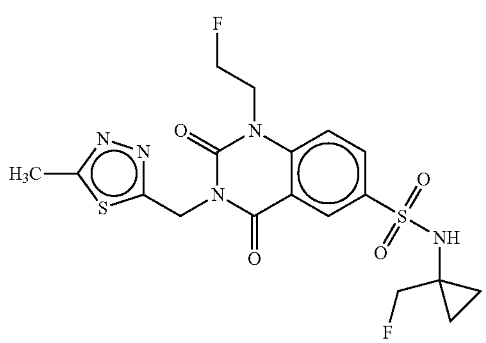 | A10 | 0.082 | 0.226 |

TABLE 1-continued

Method of synthesis and PARG activity (Biochem and Cell Activity)

| Example | Structure | Method | PARG Biochem IC50 Geomean (μM) | PARG Cell IC50 Geomean (μM) |
|---|---|---|---|---|
| Example 630 | 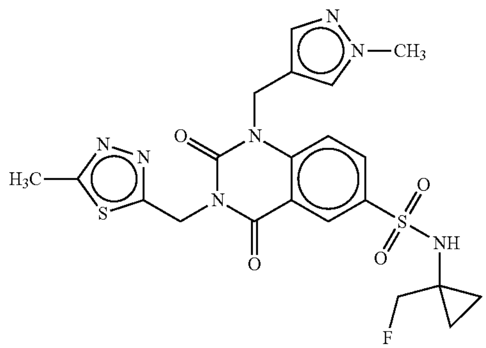 | A10 | 0.016 | 0.542 |
| Example 631 | 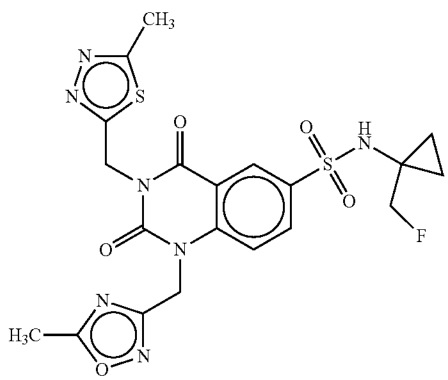 | A10 | 0.121 | 0.706 |

TABLE 2

LC-MS data

| | High pH | | | | | Low pH | | | | |
|---|---|---|---|---|---|---|---|---|---|---|
| Ex. | LC-MS Method | LC-MS Purity | Adduct | Observed MW | RT (min) | LC-MS Method | LC-MS Purity | Adduct | Observed MW | RT (min) |
| 1 | A | >95 | [M + H]+ | 296.5 | 0.67 | A | 90-95 | [M + H]+ | 296.5 | 0.69 |
| 2 | A | 90-95 | [M + H]+ | 324.5 | 0.91 | A | 85-90 | [M + H]+ | 324.5 | 0.89 |
| 3 | A | >95 | [M + H]+ | 335.5 | 0.65 | A | >95 | [M + H]+ | 335.5 | 0.80 |
| 4 | A | >95 | [M + H]+ | 351.6 | 1.06 | A | >95 | [M + H]+ | 351.6 | 1.06 |
| 5 | A | >95 | [M + H]+ | 363.6 | 0.81 | A | >95 | [M − H]− | 361.6 | 0.95 |
| 6 | A | >95 | [M − H]− | 322.6 | 0.87 | A | >95 | [M − H]− | 322.6 | 0.87 |
| 7 | A | >95 | [M − H]− | 308.6 | 0.80 | A | 90-95 | not obs | | 0.80 |
| 8 | A | >95 | [M − H]− | 398.6 | 1.12 | A | >95 | [M − H]− | 398.6 | 1.13 |
| 9 | A | 90-95 | [M + H]+ | 338.6 | 0.97 | A | 90-95 | [M − H]− | 336.6 | 0.95 |
| 10 | A | >95 | [M − H]− | 412.6 | 1.20 | A | >95 | [M − H]− | 412.6 | 1.20 |
| 11 | A | >95 | [M − H]− | 480.6 | 1.30 | A | >95 | [M − H]− | 480.6 | 1.30 |
| 12 | A | >95 | [M − H]− | 336.6 | 1.00 | A | >95 | [M − H]− | 336.6 | 0.98 |
| 13 | A | >95 | [M + H]+ | 420.6 | 1.35 | A | >95 | [M − H]− | 418.6 | 1.35 |
| 14 | A | >95 | [M − H]− | 376.6 | 1.16 | A | >95 | [M − H]− | 376.6 | 1.16 |
| 15 | A | >95 | [M − H]− | 419.6 | 1.08 | A | >95 | [M − H]− | 419.6 | 0.76 |
| 16 | A | >95 | [M − H]− | 394.6 | 1.07 | A | >95 | [M − H]− | 394.6 | 1.07 |
| 17 | A | >95 | [M + H]+ | 382.6 | 1.03 | A | >95 | [M − H]− | 380.6 | 1.03 |
| 18 | A | >95 | [M − H]− | 435.6 | 0.98 | A | 90-95 | [M − H]− | 435.6 | 0.77 |
| 19 | A | >95 | [M + H]+ | 310.5 | 0.76 | A | >95 | [M + H]+ | 310.5 | 0.78 |
| 20 | A | >95 | [M + H]+ | 364.5 | 1.11 | A | 90-95 | [M + H]+ | 364.5 | 1.11 |
| 21 | A | >95 | [M + H]+ | 310.4 | 0.67 | A | >95 | [M + H]+ | 310.5 | 0.72 |
| 22 | A | >95 | [M + H]+ | 364.5 | 0.94 | A | >95 | [M + H]+ | 364.5 | 0.94 |
| 23 | A | 90-95 | [M − H]− | 362.6 | 1.09 | A | >95 | [M − H]− | 362.5 | 1.09 |
| 24 | A | >95 | [M − H]− | 378.6 | 1.20 | A | >95 | [M − H]− | 378.5 | 1.21 |
| 25 | A | >95 | [M − H]− | 366.6 | 0.96 | A | >95 | [M − H]− | 366.5 | 0.96 |

TABLE 2-continued

| | LC-MS data | | | | | | | | | |
|---|---|---|---|---|---|---|---|---|---|---|
| | | High pH | | | | | Low pH | | | |
| Ex. | LC-MS Method | LC-MS Purity | Adduct | Observed MW | RT (min) | LC-MS Method | LC-MS Purity | Adduct | Observed MW | RT (min) |
| 26 | A | >95 | [M − H]− | 379.6 | 0.92 | A | >95 | [M − H]− | 379.6 | 0.67 |
| 27 | A | >95 | [M − H]− | 364.6 | 1.13 | A | >95 | [M − H]− | 364.6 | 1.13 |
| 28 | A | >95 | [M − H]− | 378.5 | 1.34 | A | >95 | [M − H]− | 378.5 | 1.35 |
| 29 | A | >95 | [M − H]− | 364.6 | 1.28 | A | >95 | [M − H]− | 364.6 | 1.28 |
| 30 | A | >95 | [M + H]+ | 401.5 | 0.93 | A | >95 | [M + H]+ | 401.5 | 0.86 |
| 31 | A | >95 | [M + H]+ | 349.5 | 0.93 | A | >95 | [M + H]+ | 349.5 | 0.93 |
| 32 | A | >95 | [M − H]− | 376.6 | 1.14 | A | >95 | [M − H]− | 376.6 | 1.15 |
| 33 | A | 90-95 | [M − H]− | 376.7 | 1.28 | A | 85-90 | not obs | | 1.29 |
| 34 | A | >95 | [M − H]− | 404.6 | 1.28 | A | >95 | [M − H]− | 404.6 | 1.29 |
| 35 | A | >95 | [M − H]− | 376.6 | 1.16 | A | >95 | [M + H]+ | 378.5 | 1.16 |
| 36 | A | >95 | [M − H]− | 398.6 | 1.08 | A | >95 | [M − H]− | 398.6 | 1.08 |
| 37 | A | >95 | [M + H]+ | 394.4 | 0.94 | A | >95 | [M + H]+ | 394.6 | 0.94 |
| 38 | A | >95 | [M + H]+ | 408.6 | 1.11 | A | >95 | [M + H]+ | 408.6 | 1.12 |
| 39 | A | >95 | [M − H]− | 346.5 | 0.98 | A | >95 | [M + H]+ | 346.6 | 0.98 |
| 40 | A | >95 | [M + H]+ | 400.5 | 1.01 | A | >95 | [M + H]+ | 400.5 | 1.01 |
| 41 | A | >95 | [M + H]+ | 323.5 | 0.92 | A | >95 | [M + H]+ | 323.6 | 0.91 |
| 42 | A | >95 | [M + H]+ | 394.5 | 0.94 | A | >95 | [M + H]+ | 394.5 | 0.94 |
| 43 | A | >95 | [M − H]− | 378.5 | 1.14 | A | >95 | [M − H]− | 376.5 | 1.15 |
| 44 | A | 85-90 | [M − H]− | 376.5 | 1.28 | A | <85 | [M + H]+ | 378.5 | 1.29 |
| 45 | A | >95 | [M − H]− | 348.5 | 1.01 | A | >95 | [M − H]− | 348.5 | 1.01 |
| 46 | A | 90-95 | [M − H]− | 390.6 | 1.23 | A | 90-95 | [M − H]− | 390.5 | 1.23 |
| 47 | A | >95 | [M + H]+ | 348.5 | 0.97 | A | >95 | [M + H]+ | 346.6 | 0.97 |
| 48 | A | >95 | [M + H]+ | 402.5 | 0.88 | A | 85-90 | [M + H]+ | 404.4 | 0.71 |
| 49 | A | >95 | [M + H]+ | 394.5 | 1.01 | A | >95 | [M + H]+ | 394.5 | 1.01 |
| 50 | A | >95 | [M + H]+ | 400.5 | 1.10 | A | >95 | [M + H]+ | 400.4 | 1.10 |
| 51 | A | >95 | [M + H]+ | 308.5 | 0.85 | A | >95 | [M + H]+ | 308.5 | 0.84 |
| 52 | A | >95 | [M + H]+ | 294.5 | 0.75 | A | >95 | [M − H]− | 292.5 | 0.75 |
| 53 | B | 90-95 | [M + H]+ | 401.0 | 0.63 | B | >95 | [M + H]+ | 401.0 | 0.70 |
| 54 | A | >95 | [M + H]+ | 320.5 | 0.89 | A | >95 | [M − H]− | 318.5 | 0.91 |
| 55 | A | >95 | [M − H]− | 320.5 | 0.96 | A | >95 | [M − H]− | 320.5 | 0.93 |
| 56 | B | >95 | [M + H]+ | 414.0 | 0.81 | B | >95 | [M − H]− | 412.0 | 0.81 |
| 57 | B | >95 | [M − H]− | 412.0 | 0.82 | B | >95 | [M + H]+ | 414.0 | 0.81 |
| 58 | B | >95 | [M − H]− | 412.0 | 0.82 | B | >95 | [M + H]+ | 414.1 | 0.82 |
| 59 | B | >95 | [M − H]− | 428.0 | 0.80 | B | >95 | [M + H]+ | 430.0 | 0.80 |
| 60 | B | >95 | [M − H]− | 428.0 | 0.78 | B | >95 | [M − H]− | 428.0 | 0.78 |
| 61 | B | >95 | [M − H]− | 428.0 | 0.77 | B | >95 | [M + H]+ | 430.1 | 0.77 |
| 62 | B | >95 | [M + H]+ | 434.0 | 0.83 | B | >95 | [M − H]− | 431.9 | 0.83 |
| 63 | B | >95 | [M − H]− | 431.9 | 0.82 | B | >95 | [M − H]− | 431.9 | 0.82 |
| 64 | B | >95 | [M − H]− | 432.0 | 0.82 | B | >95 | [M − H]− | 432.0 | 0.83 |
| 65 | B | >95 | [M + H]+ | 418.1 | 0.79 | B | >95 | [M − H]− | 416.0 | 0.79 |
| 66 | B | >95 | [M − H]− | 416.0 | 0.79 | B | >95 | [M − H]− | 416.0 | 0.78 |
| 67 | B | >95 | [M − H]− | 416.0 | 0.78 | B | >95 | [M − H]− | 416.0 | 0.78 |
| 68 | B | >95 | [M − H]− | 423.0 | 0.75 | B | >95 | [M + H]+ | 425.0 | 0.75 |
| 69 | B | >95 | [M − H]− | 423.0 | 0.74 | B | >95 | [M + H]+ | 425.0 | 0.74 |
| 70 | B | >95 | [M − H]− | 423.0 | 0.74 | B | >95 | [M − H]− | 423.0 | 0.74 |
| 71 | B | >95 | [M − H]− | 466.0 | 0.84 | B | >95 | [M + H]+ | 468.0 | 0.84 |
| 72 | B | >95 | [M − H]− | 466.0 | 0.83 | B | >95 | [M − H]− | 466.0 | 0.83 |
| 73 | B | >95 | [M − H]− | 466.0 | 0.83 | B | >95 | [M − H]− | 466.0 | 0.84 |
| 74 | B | >95 | [M + H]+ | 468.0 | 0.84 | B | >95 | [M − H]− | 465.9 | 0.84 |
| 75 | B | >95 | [M − H]− | 434.0 | 0.78 | B | >95 | [M + H]+ | 436.0 | 0.78 |
| 76 | B | >95 | [M − H]− | 465.9 | 0.87 | B | >95 | [M − H]− | 465.9 | 0.87 |
| 77 | B | >95 | [M − H]− | 426.0 | 0.85 | B | >95 | [M + H]+ | 428.1 | 0.85 |
| 78 | B | >95 | [M + H]+ | 458.0 | 0.78 | B | >95 | [M + H]+ | 460.0 | 0.78 |
| 79 | B | >95 | [M − H]− | 434.0 | 0.80 | B | >95 | [M − H]− | 434.0 | 0.80 |
| 80 | A | >95 | [M + H]+ | 334.5 | 1.04 | A | >95 | [M + H]+ | 334.5 | 1.04 |
| 81 | A | >95 | [M + H]+ | 350.6 | 1.12 | A | >95 | [M + H]+ | 350.6 | 1.12 |
| 82 | B | >95 | [M + H]+ | 401.0 | 0.67 | B | >95 | [M + H]+ | 401.0 | 0.67 |
| 83 | B | >95 | [M + H]+ | 401.1 | 0.63 | B | >95 | [M + H]+ | 401.0 | 0.67 |
| 84 | B | >95 | [M + H]+ | 401.0 | 0.63 | B | >95 | [M + H]+ | 401.0 | 0.66 |
| 85 | B | >95 | [M + H]+ | 443.0 | 0.71 | B | >95 | [M + H]+ | 443.0 | 0.71 |
| 86 | B | >95 | [M + H]+ | 464.0 | 0.54 | B | >95 | [M + H]+ | 464.0 | 0.54 |
| 87 | B | >95 | [M + H]+ | 443.0 | 0.67 | B | >95 | [M + H]+ | 443.0 | 0.67 |
| 88 | B | 85-90 | [M − H]− | 433.0 | 0.59 | B | 85-90 | [M + H]+ | 887.0 | 0.59 |
| 89 | B | >95 | [M + H]+ | 443.0 | 0.62 | B | >95 | [M + H]+ | 443.1 | 0.62 |
| 90 | B | >95 | [M + H]+ | 447.1 | 0.58 | B | >95 | [M + H]+ | 447.0 | 0.58 |
| 91 | B | >95 | [M + H]+ | 444.0 | 0.54 | B | 90-95 | [M + H]+ | 444.0 | 0.67 |
| 92 | B | >95 | [M + H]+ | 443.1 | 0.71 | B | >95 | [M + H]+ | 443.0 | 0.71 |
| 93 | B | >95 | [M − H]− | 441.0 | 0.62 | B | >95 | [M + H]+ | 460.1 | 0.62 |
| 94 | B | >95 | [M − H]− | 448.0 | 0.78 | B | >95 | [M − H]− | 448.0 | 0.79 |
| 95 | B | >95 | [M + H]+ | 452.0 | 0.59 | B | >95 | [M + H]+ | 435.0 | 0.59 |
| 96 | B | >95 | [M + H]+ | 460.1 | 0.61 | B | >95 | [M + H]+ | 460.1 | 0.61 |
| 97 | A | >95 | [M + H]+ | 370.5 | 1.08 | A | >95 | [M + H]+ | 370.5 | 1.08 |
| 98 | A | 90-95 | [M + H]+ | 349.5 | 0.83 | A | 90-95 | [M + H]+ | 349.5 | 0.82 |

TABLE 2-continued

LC-MS data

| | High pH | | | | | Low pH | | | | |
|---|---|---|---|---|---|---|---|---|---|---|
| Ex. | LC-MS Method | LC-MS Purity | Adduct | Observed MW | RT (min) | LC-MS Method | LC-MS Purity | Adduct | Observed MW | RT (min) |
| 99 | B | >95 | [M + H]+ | 466.0 | 0.61 | B | >95 | [M + H]+ | 466.0 | 0.61 |
| 100 | B | >95 | [M − H]− | 441.0 | 0.75 | B | 90-95 | [M + H]+ | 443.0 | 0.75 |
| 101 | B | 85-90 | [M − H]− | 447.0 | 0.61 | B | 85-90 | [M + H]+ | 466.0 | 0.61 |
| 102 | B | >95 | [M − H]− | 444.0 | 0.77 | B | >95 | [M − H]− | 444.0 | 0.54 |
| 103 | B | >95 | [M + H]+ | 405.0 | 0.70 | B | >95 | [M + H]+ | 405.0 | 0.70 |
| 104 | B | >95 | [M − H]− | 476.0 | 0.68 | B | >95 | [M − H]− | 4476.0 | 0.68 |
| 105 | B | >95 | [M + H]+ | 405.0 | 0.70 | B | >95 | [M − H]− | 403.0 | 0.70 |
| 106 | B | 85-90 | [M + H]+ | 447.0 | 0.58 | B | 85-90 | [M + H]+ | 447.0 | 0.58 |
| 107 | B | >95 | [M + H]+ | 444.0 | 0.53 | B | 90-95 | [M + H]+ | 444.0 | 0.68 |
| 108 | B | >95 | [M − H]− | 402.0 | 0.61 | B | >95 | [M − H]− | 402.0 | 0.61 |
| 109 | B | >95 | [M + H]+ | 421.0 | 0.67 | B | >95 | [M − H]− | 421.0 | 0.67 |
| 110 | B | >95 | [M + H]+ | 499.0 | 0.84 | B | >95 | [M − H]− | 499.0 | 0.85 |
| 111 | B | >95 | [M + H]+ | 886.0 | 0.73 | B | >95 | [M + H]+ | 886.0 | 0.73 |
| 112 | B | 85-90 | [M + H]+ | 440.0 | 0.65 | B | 85-90 | [M + H]+ | 440.0 | 0.81 |
| 113 | B | >95 | [M + H]+ | 404.0 | 0.59 | B | 90-95 | [M + H]+ | 404.0 | 0.70 |
| 114 | B | >95 | [M + H]+ | 497.0 | 0.84 | B | >95 | [M + H]+ | 497.0 | 0.84 |
| 115 | A | >95 | [M + H]+ | 419.6 | 1.03 | A | >95 | [M + H]+ | 419.6 | 1.07 |
| 116 | B | >95 | [M + H]+ | 440.0 | 0.66 | B | >95 | [M + H]+ | 440.0 | 0.74 |
| 117 | B | >95 | [M + H]+ | 497.0 | 0.83 | B | >95 | [M + H]+ | 497.0 | 0.83 |
| 118 | B | >95 | [M + H]+ | 474.0 | 0.65 | B | >95 | [M + H]+ | 474.0 | 0.65 |
| 119 | B | >95 | [M − H]− | 446.0 | 0.78 | B | >95 | [M + H]+ | 448.0 | 0.78 |
| 120 | B | 85-90 | [M − H]− | 432.9 | 0.72 | B | 85-90 | [M − H]− | 432.9 | 0.73 |
| 121 | B | >95 | [M − H]− | 417.0 | 0.70 | B | >95 | [M + H]+ | 419.0 | 0.70 |
| 122 | A | >95 | [M − H]− | 402.6 | 0.93 | A | >95 | [M − H]− | 402.6 | 0.93 |
| 123 | B | >95 | [M + H]+ | 418.1 | 0.65 | B | >95 | [M + H]+ | 418.1 | 0.66 |
| 124 | B | >95 | [M − H]− | 400.0 | 0.62 | B | >95 | [M − H]− | 400.0 | 0.62 |
| 125 | B | >95 | [M + H]+ | 404.0 | 0.63 | B | 85-90 | [M + H]+ | 404.0 | 0.63 |
| 126 | A | >95 | [M + H]+ | 421.5 | 0.96 | A | >95 | [M + H]+ | 421.5 | 0.96 |
| 127 | B | >95 | [M + H]+ | 418.1 | 0.65 | B | >95 | [M + H]+ | 418.6 | 0.93 |
| 128 | A | >95 | [M − H]− | 402.5 | 0.89 | A | >95 | [M − H]− | 402.5 | 0.98 |
| 129 | A | >95 | [M + H]+ | 514.5 | 1.10 | A | >95 | [M + H]+ | 514.6 | 1.12 |
| 130 | A | >95 | [M + H]+ | 418.5 | 1.03 | A | >95 | [M + H]+ | 418.5 | 1.03 |
| 131 | A | >95 | [M − H]− | 499.6 | 0.88 | A | >95 | [M − H]− | 499.6 | 0.88 |
| 132 | A | >95 | [M − H]− | 412.5 | 1.18 | A | >95 | [M − H]− | 412.5 | 1.19 |
| 133 | A | >95 | [M + H]+ | 435.5 | 1.00 | A | >95 | [M − H]− | 435.5 | 1.00 |
| 134 | A | >95 | [M + H]+ | 497.5 | 1.16 | A | >95 | [M − H]− | 495.5 | 1.17 |
| 135 | A | 90-95 | [M − H]− | 483.4 | 1.11 | A | >95 | [M − H]− | 483.4 | 1.11 |
| 136 | A | 90-95 | [M − H]− | 360.5 | 1.05 | A | 90-95 | [M + H]+ | 362.5 | 1.05 |
| 137 | A | >95 | [M − H]− | 374.5 | 1.11 | A | >95 | [M − H]− | 374.5 | 1.12 |
| 138 | A | >95 | [M + H]+ | 512.6 | 0.85 | A | <85 | [M − H]− | 512.6 | 0.76 |
| 139 | A | >95 | [M + H]+ | 362.6 | 1.03 | A | >95 | [M + H]+ | 362.5 | 1.04 |
| 140 | A | >95 | [M + H]+ | 362.6 | 1.04 | A | >95 | [M + H]+ | 362.5 | 1.04 |
| 141 | A | >95 | [M + H]+ | 487.5 | 1.10 | A | >95 | [M + H]+ | 487.4 | 1.12 |
| 142 | A | >95 | [M + H]+ | 435.5 | 1.00 | A | >95 | [M + H]+ | 435.5 | 1.00 |
| 143 | A | >95 | [M + H]+ | 407.5 | 0.92 | A | >95 | [M − H]− | 405.5 | 0.90 |
| 144 | A | >95 | [M + H]+ | 441.5 | 1.09 | A | >95 | [M + H]+ | 441.4 | 1.11 |
| 145 | A | >95 | [M + H]+ | 441.5 | 1.08 | A | >95 | [M + H]+ | 441.5 | 1.09 |
| 146 | A | >95 | [M + H]+ | 407.5 | 0.96 | A | >95 | [M + H]+ | 407.5 | 0.97 |
| 147 | A | 85-90 | [M + H]+ | 407.5 | 0.93 | A | 90-95 | [M + H]+ | 407.5 | 0.94 |
| 148 | A | >95 | [M + H]+ | 407.5 | 0.94 | A | >95 | [M + H]+ | 407.5 | 0.96 |
| 149 | A | >95 | [M + H]+ | 460.6 | 1.08 | A | >95 | [M + H]+ | 460.6 | 1.10 |
| 150 | A | >95 | [M + H]+ | 421.5 | 1.00 | A | >95 | [M + H]+ | 421.5 | 1.01 |
| 151 | A | >95 | [M − H]− | 402.6 | 0.93 | A | >95 | [M − H]− | 402.6 | 0.94 |
| 152 | A | >95 | [M + H]+ | 404.5 | 0.90 | A | >95 | [M + H]+ | 404.6 | 0.90 |
| 153 | A | >95 | [M − H]− | 406.5 | 0.89 | A | >95 | [M − H]− | 406.5 | 0.96 |
| 154 | A | >95 | [M + H]+ | 404.6 | 0.86 | A | >95 | [M + H]+ | 404.6 | 0.69 |
| 155 | A | >95 | [M + H]+ | 404.4 | 0.92 | A | >95 | [M + H]+ | 404.3 | 0.92 |
| 156 | A | >95 | [M + H]+ | 461.4 | 1.12 | A | >95 | [M + H]+ | 461.9 | 1.15 |
| 157 | A | >95 | [M − H]− | 459.7 | 1.21 | A | >95 | [M + H]+ | 461.6 | 1.24 |
| 158 | A | >95 | [M + H]+ | 459.6 | 1.18 | A | >95 | [M + H]+ | 459.6 | 1.22 |
| 159 | A | >95 | [M + H]+ | 443.6 | 1.09 | A | >95 | [M + H]+ | 443.6 | 1.12 |
| 160 | A | >95 | [M + H]+ | 404.6 | 0.86 | A | >95 | [M + H]+ | 404.6 | 0.80 |
| 161 | A | >95 | [M + H]+ | 445.6 | 1.03 | A | >95 | [M + H]+ | 445.6 | 1.06 |
| 162 | A | >95 | [M + H]+ | 532.7 | 1.03 | A | >95 | [M + H]+ | 532.7 | 1.06 |
| 163 | A | >95 | [M + H]+ | 515.7 | 0.98 | A | >95 | [M + H]+ | 515.7 | 1.01 |
| 164 | A | >95 | [M + H]+ | 515.7 | 1.04 | A | >95 | [M + H]+ | 515.7 | 1.08 |
| 165 | A | >95 | [M + H]+ | 530.7 | 1.08 | A | >95 | [M + H]+ | 530.7 | 1.12 |
| 166 | A | >95 | [M + H]+ | 513.7 | 1.03 | A | >95 | [M + H]+ | 513.7 | 1.06 |
| 167 | A | 90-95 | [M + H]+ | 513.7 | 1.08 | A | 90-95 | [M + H]+ | 513.7 | 1.11 |
| 168 | A | >95 | [M + H]+ | 513.7 | 1.21 | A | >95 | [M + H]+ | 513.7 | 1.22 |
| 169 | A | >95 | [M + H]+ | 525.7 | 1.20 | A | >95 | [M + H]+ | 525.8 | 1.22 |
| 170 | A | 90-95 | [M + H]+ | 515.7 | 0.98 | A | 90-95 | [M + H]+ | 515.7 | 0.99 |
| 171 | A | >95 | [M + H]+ | 498.7 | 1.11 | A | >95 | [M + H]+ | 498.7 | 1.12 |

TABLE 2-continued

| | LC-MS data | | | | | | | | | |
|---|---|---|---|---|---|---|---|---|---|---|
| | High pH | | | | | Low pH | | | | |
| Ex. | LC-MS Method | LC-MS Purity | Adduct | Observed MW | RT (min) | LC-MS Method | LC-MS Purity | Adduct | Observed MW | RT (min) |
| 172 | A | >95 | [M + H]+ | 510.7 | 1.09 | A | >95 | [M + H]+ | 510.7 | 1.11 |
| 173 | A | >95 | [M + H]+ | 498.7 | 0.93 | A | >95 | [M + H]+ | 498.7 | 0.94 |
| 174 | A | >95 | [M + H]+ | 444.7 | 1.05 | A | >95 | [M + H]+ | 444.6 | 1.06 |
| 175 | A | >95 | [M + H]+ | 349.6 | 0.94 | A | >95 | [2M − H]− | 695.8 | 0.93 |
| 176 | A | >95 | [M + H]+ | 515.7 | 1.16 | A | >95 | [M + H]+ | 515.7 | 1.17 |
| 177 | A | >95 | [M + H]+ | 527.7 | 1.15 | A | >95 | [M + H]+ | 527.7 | 1.16 |
| 178 | A | >95 | [M + H]+ | 428.6 | 0.97 | A | >95 | [M + H]+ | 428.6 | 0.97 |
| 179 | A | >95 | [M + H]+ | 489.6 | 1.13 | A | >95 | [M + H]+ | 489.6 | 1.15 |
| 180 | A | >95 | [M + H]+ | 405.6 | 0.98 | A | >95 | [M + H]+ | 405.6 | 0.99 |
| 181 | A | >95 | [M + H]+ | 418.4 | 0.96 | A | >95 | [M + H]+ | 418.4 | 0.97 |
| 182 | A | >95 | [M + H]+ | 437.4 | 0.84 | A | >95 | [M + H]+ | 437.4 | 0.84 |
| 183 | A | >95 | [M + H]+ | 390.4 | 0.86 | A | >95 | [M + H]+ | 390.4 | 0.86 |
| 184 | A | >95 | [M − H]− | 405.3 | 0.82 | A | >95 | [M − H]− | 405.4 | 0.83 |
| 185 | A | >95 | [M − H]− | 405.4 | 0.82 | A | >95 | [M − H]− | 405.3 | 0.82 |
| 186 | A | >95 | [M + H]+ | 443.4 | 1.12 | A | >95 | [M + H]+ | 443.4 | 1.14 |
| 187 | A | >95 | [M + H]+ | 455.4 | 1.12 | A | >95 | [M − H]− | 453.4 | 1.13 |
| 188 | A | >95 | [M − H]− | 403.4 | 0.93 | A | >95 | [M + H]+ | 405.3 | 0.93 |
| 189 | A | >95 | [M + H]+ | 419.3 | 0.95 | A | >95 | [M + H]+ | 419.4 | 0.93 |
| 190 | A | >95 | [M − H]− | 404.4 | 0.96 | A | >95 | [M − H]− | 406.3 | 0.96 |
| 191 | A | >95 | [M + H]+ | 422.3 | 1.01 | A | >95 | [M + H]+ | 422.3 | 1.01 |
| 192 | A | >95 | [M + H]+ | 443.4 | 0.95 | A | >95 | [M + H]+ | 443.4 | 0.96 |
| 193 | A | >95 | [M + H]+ | 389.3 | 1.07 | A | >95 | [M + H]+ | 389.4 | 1.08 |
| 194 | A | >95 | [M + H]+ | 373.3 | 0.99 | A | >95 | [M + H]+ | 373.3 | 0.99 |
| 195 | A | >95 | [M − H]− | 402.2 | 0.92 | A | 90-95 | [M − H]− | 402.2 | 0.90 |
| 196 | A | >95 | [M − H]− | 379.4 | 0.80 | A | >95 | [M − H]− | 379.4 | 0.79 |
| 197 | A | >95 | [M + H]+ | 445.4 | 1.12 | A | >95 | [M + H]+ | 445.4 | 1.14 |
| 198 | A | >95 | [M + H]+ | 429.4 | 1.04 | A | >95 | [M + H]+ | 429.4 | 1.05 |
| 199 | A | >95 | [M + H]+ | 499.4 | 1.16 | A | >95 | [M + H]+ | 499.5 | 1.18 |
| 200 | A | >95 | [M + H]+ | 511.5 | 1.16 | A | >95 | [M + H]+ | 511.4 | 1.17 |
| 201 | A | >95 | [M + H]+ | 421.3 | 0.95 | A | >95 | [M + H]+ | 421.3 | 0.96 |
| 202 | A | >95 | [M + H]+ | 437.4 | 1.03 | A | >95 | [M + H]+ | 437.4 | 1.04 |
| 203 | A | >95 | [M + H]+ | 447.4 | 0.81 | A | 90-95 | [M + H]+ | 447.4 | 0.81 |
| 204 | A | >95 | [M + H]+ | 466.4 | 0.76 | A | >95 | [M + H]+ | 446.3 | 0.94 |
| 205 | A | >95 | [M + H]+ | 406.4 | 1.03 | A | >95 | [M + H]+ | 406.4 | 1.04 |
| 206 | A | >95 | [M − H]− | 433.4 | 1.01 | A | >95 | [M − H]− | 433.4 | 1.02 |
| 207 | A | >95 | [M + H]+ | 499.4 | 0.99 | A | >95 | [M + H]+ | 499.4 | 1.00 |
| 208 | A | >95 | [M + H]+ | 486.4 | 1.04 | A | >95 | [M + H]+ | 486.4 | 1.05 |
| 209 | A | >95 | [M + H]+ | 408.3 | 1.09 | A | >95 | [M + H]+ | 408.3 | 1.10 |
| 210 | A | >95 | [M + H]+ | 375.3 | 0.92 | A | 90-95 | [M + H]+ | 375.3 | 0.92 |
| 211 | A | 80-85 | [M + H]+ | 328.8 | 0.78 | A | <85 | [M + H]+ | 328.3 | 0.86 |
| 212 | A | >95 | [M + H]+ | 510.4 | 1.08 | A | >95 | [M + H]+ | 510.4 | 1.11 |
| 213 | A | >95 | [M + H]+ | 436.3 | 0.96 | A | >95 | [M + H]+ | 436.3 | 0.98 |
| 214 | A | >95 | [M + H]+ | 522.4 | 1.11 | A | >95 | [M − H]− | 522.4 | 1.14 |
| 215 | A | >95 | [M + H]+ | 480.4 | 1.09 | A | >95 | [M − H]− | 480.4 | 1.11 |
| 216 | A | >95 | [M + H]+ | 428.3 | 0.97 | A | >95 | [M − H]− | 428.3 | 0.98 |
| 217 | A | >95 | [M + H]+ | 429.3 | 0.93 | A | >95 | [M + H]+ | 429.3 | 0.94 |
| 218 | A | >95 | [M + H]+ | 444.4 | 1.03 | A | >95 | [M + H]+ | 444.4 | 1.04 |
| 219 | A | >95 | [M + H]+ | 461.4 | 0.92 | A | >95 | [M + H]+ | 461.4 | 0.75 |
| 220 | A | >95 | [M + H]+ | 407.3 | 0.86 | A | 85-90 | [M + H]+ | 407.3 | 0.90 |
| 221 | A | >95 | [M + H]+ | 391.3 | 0.86 | A | >95 | [M + H]+ | 391.3 | 0.91 |
| 222 | A | >95 | [M + NH4]+ | 352.3 | 0.73 | A | 90-95 | [M + NH4]+ | 352.3 | 0.85 |
| 223 | A | >95 | [M + H]+ | 353.6 | 0.65 | A | >95 | [M + H]+ | 353.6 | 0.69 |
| 224 | A | >95 | [M + H]+ | 342.3 | 0.94 | A | >95 | [M + H]+ | 342.3 | 0.95 |
| 225 | A | >95 | [M + H]+ | 342.3 | 0.99 | A | >95 | [M + H]+ | 342.2 | 1.00 |
| 226 | A | >95 | [M + H]+ | 391.2 | 0.95 | A | >95 | [M + H]+ | 391.3 | 0.96 |
| 227 | A | >95 | [M + H]+ | 328.3 | 1.05 | A | >95 | [M + H]+ | 328.1 | 1.07 |
| 228 | A | >95 | [M + H]+ | 402.2 | 0.65 | A | >95 | [M + H]+ | 402.2 | 0.85 |
| 229 | A | >95 | [M + H]+ | 416.2 | 0.74 | A | >95 | [M + H]+ | 416.3 | 0.93 |
| 230 | A | >95 | [M + H]+ | 553.3 | 1.13 | A | >95 | [M + H]+ | 553.4 | 1.14 |
| 231 | A | >95 | [M + H]+ | 569.3 | 1.11 | A | >95 | [M + H]+ | 569.3 | 1.13 |
| 232 | A | 90-95 | [M + H]+ | 422.2 | 0.89 | A | 85-90 | [M + H]+ | 422.2 | 0.77 |
| 233 | A | >95 | [M + H]+ | 406.2 | 0.87 | A | >95 | [M + H]+ | 406.3 | 0.85 |
| 234 | A | 85-90 | [M + H]+ | 323.2 | 0.90 | A | 85-90 | [M + H]+ | 323.3 | 0.90 |
| 235 | C | >95 | [M + H]+ | 461.4 | 0.92 | A | >95 | [M + H]+ | 461.4 | 0.70 |
| 236 | C | >95 | [M + H]+ | 501.4 | 0.91 | A | >95 | [M + H]+ | 501.5 | 0.71 |
| 237 | C | >95 | [M + H]+ | 475.4 | 0.90 | A | >95 | [M + H]+ | 475.4 | 0.72 |
| 238 | C | >95 | [M + H]+ | 501.4 | 0.98 | A | >95 | [M + H]+ | 501.4 | 0.74 |
| 239 | C | >95 | [M + H]+ | 462.3 | 1.62 | A | >95 | [M + H]+ | 462.3 | 0.98 |
| 240 | A | 90-95 | [M + H]+ | 336.3 | 0.85 | A | 90-95 | [M + H]+ | 336.3 | 0.86 |
| 241 | A | >95 | [M + H]+ | 444.4 | 0.95 | A | >95 | [M + H]+ | 444.4 | 0.96 |
| 242 | A | >95 | [M + H]+ | 374.3 | 0.96 | A | 90-95 | [M + H]+ | 374.3 | 0.96 |
| 243 | A | 90-95 | [M + H]+ | 487.3 | 1.00 | A | >95 | [M + H]+ | 487.3 | 1.02 |
| 244 | A | >95 | [M + H]+ | 404.3 | 0.98 | A | >95 | [M + H]+ | 404.3 | 0.99 |

TABLE 2-continued

| | | | LC-MS data | | | | | | |
|---|---|---|---|---|---|---|---|---|---|
| | | High pH | | | | Low pH | | | |
| Ex. | LC-MS Method | LC-MS Purity | Adduct | Observed MW | RT (min) | LC-MS Method | LC-MS Purity | Adduct | Observed MW | RT (min) |
| 245 | A | >95 | [M − H]− | 457.3 | 1.15 | A | >95 | [M − H]− | 457.3 | 1.16 |
| 246 | C | 90-95 | [M + H]+ | 462.4 | 1.62 | A | 90-95 | [M + H]+ | 462.4 | 0.75 |
| 247 | C | >95 | [M + H]+ | 476.3 | 1.59 | A | 90-95 | [M + H]+ | 476.4 | 0.77 |
| 248 | C | 90-95 | [M + H]+ | 488.4 | 1.70 | A | 90-95 | [M + H]+ | 488.4 | 0.78 |
| 249 | C | >95 | [M + H]+ | 488.3 | 1.69 | A | 90-95 | [M + H]+ | 488.4 | 0.77 |
| 250 | C | >95 | [M + H]+ | 462.3 | 1.87 | A | >95 | [M + H]+ | 462.3 | 1.19 |
| 251 | C | >95 | [M + H]+ | 463.2 | 1.71 | A | >95 | [M + H]+ | 463.3 | 1.05 |
| 252 | A | >95 | [M + H]+ | 487.3 | 1.02 | A | >95 | [M + H]+ | 487.3 | 1.03 |
| 253 | A | >95 | [M + H]+ | 461.4 | 0.97 | A | >95 | [M + H]+ | 461.3 | 0.74 |
| 254 | A | >95 | [M − H]− | 531.5 | 1.03 | A | >95 | [M − H]− | 531.5 | 1.04 |
| 255 | A | >95 | [M + H]+ | 387.3 | 1.15 | A | 85-90 | [M + H]+ | 387.3 | 1.14 |
| 256 | A | >95 | [M + H]+ | 388.3 | 1.03 | A | >95 | [M + H]+ | 388.3 | 1.03 |
| 257 | A | >95 | [M + H]+ | 488.4 | 1.07 | A | >95 | [M + H]+ | 488.4 | 1.09 |
| 258 | A | >95 | [M + H]+ | 474.4 | 0.99 | A | >95 | [M + H]+ | 474.4 | 1.00 |
| 259 | A | >95 | [M + H]+ | 474.4 | 0.93 | A | >95 | [M + H]+ | 474.4 | 0.94 |
| 260 | A | >95 | [M + H]+ | 391.3 | 0.94 | A | >95 | [M + H]+ | 391.3 | 0.94 |
| 261 | A | >95 | [M + H]+ | 419.3 | 1.04 | A | >95 | [M + H]+ | 419.3 | 1.05 |
| 262 | A | 90-95 | [M + H]+ | 409.2 | 1.10 | A | >95 | [M + H]+ | 409.2 | 1.11 |
| 263 | A | >95 | [M + H]+ | 433.3 | 0.79 | A | >95 | [M + H]+ | 433.3 | 0.69 |
| 264 | A | >95 | [M + H]+ | 516.4 | 1.10 | A | >95 | [M + H]+ | 516.4 | 1.12 |
| 265 | A | >95 | [M + H]+ | 475.4 | 0.86 | A | >95 | [M + H]+ | 475.4 | 0.86 |
| 266 | A | >95 | [M + H]+ | 489.4 | 1.14 | A | >95 | [M + H]+ | 489.4 | 1.15 |
| 267 | A | >95 | [M + H]+ | 475.4 | 1.05 | A | >95 | [M + H]+ | 475.4 | 1.07 |
| 268 | A | >95 | [M + H]+ | 475.4 | 0.99 | A | >95 | [M + H]+ | 475.4 | 1.00 |
| 269 | A | >95 | [M + H]+ | 488.4 | 0.95 | A | >95 | [M + H]+ | 488.4 | 0.97 |
| 270 | C | 90-95 | [M + H]+ | 448.3 | 1.68 | A | 90-95 | [M + H]+ | 448.2 | 0.95 |
| 271 | C | >95 | [M + H]+ | 503.2 | 1.52 | A | >95 | [M + H]+ | 503.2 | 0.73 |
| 272 | C | >95 | [M + H]+ | 487.3 | 1.82 | A | >95 | [M + H]+ | 487.2 | 0.72 |
| 273 | C | >95 | [M + H]+ | 461.2 | 1.41 | A | >95 | [M + H]+ | 461.2 | 0.80 |
| 274 | C | 85-90 | [M + H]+ | 449.3 | 1.67 | A | <85 | [M + H]+ | 449.1 | 1.02 |
| 275 | C | >95 | [M + H]+ | 502.3 | 1.70 | A | >95 | [M + H]+ | 502.2 | 0.79 |
| 276 | C | >95 | [M + H]+ | 504.3 | 1.60 | A | >95 | [M + H]+ | 504.2 | 0.79 |
| 277 | C | 90-95 | [M + H]+ | 462.2 | 1.48 | A | 85-90 | [M + H]+ | 462.1 | 0.86 |
| 278 | C | >95 | [M + H]+ | 502.2 | 1.80 | A | >95 | [M + H]+ | 502.2 | 0.80 |
| 279 | A | >95 | [M + H]+ | 472.5 | 1.16 | A | >95 | [M + H]+ | 472.5 | 1.18 |
| 280 | A | >95 | [M + H]+ | 486.5 | 1.21 | A | >95 | [M + H]+ | 486.5 | 1.23 |
| 281 | A | >95 | [M + H]+ | 458.4 | 1.11 | A | 90-95 | [M + H]+ | 458.4 | 1.12 |
| 282 | A | 85-90 | [M + H]+ | 418.1 | 1.10 | A | 85-90 | [M + H]+ | 418.1 | 1.11 |
| 283 | A | 90-95 | [M + H]+ | 456.2 | 1.04 | A | 85-90 | [M + H]+ | 456.2 | 0.81 |
| 284 | A | >95 | [M + H]+ | 389.1 | 1.03 | A | 90-95 | [M + H]+ | 389.1 | 1.03 |
| 285 | A | >95 | [M + H]+ | 500.2 | 0.88 | A | >95 | [M + H]+ | 500.2 | 0.88 |
| 286 | A | >95 | [M + H]+ | 455.2 | 1.03 | A | >95 | [M + H]+ | 455.2 | 0.79 |
| 287 | A | >95 | [M + H]+ | 459.2 | 1.01 | A | >95 | [M + H]+ | 459.2 | 0.76 |
| 288 | A | >95 | [M + H]+ | 459.2 | 1.20 | A | >95 | [M + H]+ | 459.2 | 1.20 |
| 289 | A | >95 | [M + H]+ | 473.2 | 1.25 | A | >95 | [M + H]+ | 473.2 | 1.26 |
| 290 | A | >95 | [M + H]+ | 487.2 | 1.29 | A | >95 | [M + H]+ | 487.2 | 1.31 |
| 291 | A | >95 | [M + H]+ | 418.2 | 0.96 | A | >95 | [M − H]− | 418.2 | 0.97 |
| 292 | A | >95 | [M + H]+ | 432.2 | 1.02 | A | >95 | [M + H]+ | 432.2 | 1.03 |
| 293 | A | >95 | [M + H]+ | 432.2 | 1.13 | A | >95 | [M + H]+ | 432.2 | 1.14 |
| 294 | A | >95 | [M + H]+ | 474.2 | 0.93 | A | >95 | [M + H]+ | 474.2 | 0.94 |
| 295 | A | >95 | [M + H]+ | 446.2 | 1.09 | A | >95 | [M − H]− | 446.2 | 1.11 |
| 296 | A | >95 | [M + H]+ | 458.2 | 1.10 | A | >95 | [M + H]+ | 458.2 | 1.11 |
| 297 | A | >95 | [M + H]+ | 460.2 | 0.88 | A | >95 | [M + H]+ | 460.2 | 0.89 |
| 298 | A | >95 | [M + H]+ | 465.2 | 1.21 | A | 90-95 | [M + H]+ | 465.2 | 1.22 |
| 299 | A | 90-95 | [M + H]+ | 375.1 | 0.98 | A | >95 | [M + H]+ | 375.1 | 0.98 |
| 300 | A | 85-90 | [M + H]+ | 487.3 | 0.83 | A | >95 | [M + H]+ | 487.3 | 0.83 |
| 301 | A | >95 | [M + H]+ | 433.2 | 1.05 | A | 90-95 | [M + H]+ | 433.2 | 1.06 |
| 302 | A | >95 | [M + H]+ | 419.2 | 0.67 | A | >95 | [M + H]+ | 419.2 | 0.80 |
| 303 | A | >95 | [M + H]+ | 432.2 | 0.96 | A | >95 | [M + H]+ | 432.2 | 0.96 |
| 304 | A | >95 | [M + H]+ | 419.2 | 1.05 | A | >95 | [M + H]+ | 419.1 | 1.05 |
| 305 | A | >95 | [M + H]+ | 461.2 | 0.96 | A | >95 | [M + H]+ | 461.2 | 0.96 |
| 306 | A | >95 | [M + H]+ | 474.2 | 1.01 | A | >95 | [M + H]+ | 474.2 | 1.01 |
| 307 | A | >95 | [M + H]+ | 454.1 | 1.11 | A | >95 | [M + H]+ | 454.1 | 1.12 |
| 308 | A | >95 | [M + H]+ | 473.3 | 1.07 | A | >95 | [M + H]+ | 473.3 | 1.08 |
| 309 | A | 85-90 | [M + H]+ | 443.2 | 1.27 | A | <85 | [M + H]+ | 443.2 | 1.29 |
| 310 | A | >95 | [M + H]+ | 417.2 | 1.19 | A | >95 | [M + H]+ | 417.2 | 1.20 |
| 311 | A | >95 | [M + H]+ | 442.2 | 1.11 | A | >95 | [M + H]+ | 442.2 | 1.12 |
| 312 | A | 90-95 | [M + H]+ | 405.2 | 1.09 | A | >95 | [M + H]+ | 405.2 | 1.09 |
| 313 | A | >95 | [M + H]+ | 415.2 | 1.14 | A | >95 | [M + H]+ | 415.2 | 1.14 |
| 314 | A | 85-90 | [M + H]+ | 471.3 | 1.36 | A | 85-90 | [M + H]+ | 471.2 | 1.38 |
| 315 | A | 90-95 | [M + H]+ | 495.3 | 1.28 | A | 85-90 | [M + H]+ | 495.2 | 1.30 |
| 316 | A | >95 | [M + H]+ | 419.2 | 1.17 | A | >95 | [M + H]+ | 419.2 | 1.17 |
| 317 | A | <85 | [M + H]+ | 447.2 | 1.02 | A | <85 | [M + H]+ | 447.2 | 1.01 |

TABLE 2-continued

| | | LC-MS data | | | | | | | |
|---|---|---|---|---|---|---|---|---|---|
| | | High pH | | | | Low pH | | | |
| Ex. | LC-MS Method | LC-MS Purity | Adduct | Observed MW | RT (min) | LC-MS Method | LC-MS Purity | Adduct | Observed MW | RT (min) |
|---|---|---|---|---|---|---|---|---|---|---|
| 318 | A | >95 | [M + H]+ | 429.2 | 1.19 | A | >95 | [M + H]+ | 429.2 | 1.19 |
| 319 | A | 85-90 | [M + H]+ | 445.2 | 1.26 | A | 85-90 | [M + H]+ | 445.2 | 1.27 |
| 320 | A | 90-95 | [M + H]+ | 443.2 | 1.28 | A | 90-95 | [M + H]+ | 443.2 | 1.28 |
| 321 | A | >95 | [M + H]+ | 489.2 | 1.04 | A | >95 | [M + H]+ | 489.2 | 1.04 |
| 322 | A | >95 | [M + H]+ | 482.2 | 1.20 | A | >95 | [M + H]+ | 482.2 | 1.21 |
| 323 | A | >95 | [M + H]+ | 447.2 | 0.99 | A | >95 | [M + H]+ | 447.2 | 0.96 |
| 324 | A | >95 | [M + H]+ | 455.2 | 1.06 | A | >95 | [M + H]+ | 455.2 | 1.06 |
| 325 | A | >95 | [M + H]+ | 473.2 | 1.11 | A | >95 | [M + H]+ | 473.2 | 1.11 |
| 326 | A | 85-90 | [M + H]+ | 446.2 | 0.96 | A | 85-90 | [M + H]+ | 446.2 | 0.95 |
| 327 | A | 85-90 | [M + H]+ | 475.2 | 0.96 | A | 85-90 | [M + H]+ | 475.2 | 0.95 |
| 328 | A | 90-95 | [M + H]+ | 484.3 | 0.92 | A | 90-95 | [M + H]+ | 484.3 | 0.91 |
| 329 | A | >95 | [M + H]+ | 494.2 | 1.10 | A | >95 | [M + H]+ | 494.2 | 1.11 |
| 330 | A | >95 | [M + H]+ | 485.2 | 0.99 | A | 90-95 | [M + H]+ | 485.2 | 0.98 |
| 331 | A | >95 | [M + H]+ | 516.3 | 1.04 | A | >95 | [M + H]+ | 516.3 | 1.03 |
| 332 | A | >95 | [M + H]+ | 477.2 | 1.09 | A | >95 | [M + H]+ | 477.2 | 1.08 |
| 333 | A | >95 | [M + H]+ | 529.3 | 1.04 | A | >95 | [M + H]+ | 529.3 | 0.80 |
| 334 | A | 90-95 | [M + H]+ | 501.3 | 0.87 | A | 90-95 | [M + H]+ | 501.3 | 0.86 |
| 335 | A | >95 | [M + H]+ | 495.2 | 1.10 | A | >95 | [M + H]+ | 495.2 | 1.11 |
| 336 | A | >95 | [M + H]+ | 401.1 | 0.65 | A | >95 | [M + H]+ | 401.1 | 0.78 |
| 337 | A | 90-95 | [M + H]+ | 435.2 | 0.90 | A | >95 | [M + H]+ | 435.2 | 0.90 |
| 338 | A | >95 | [M + H]+ | 449.2 | 0.95 | A | >95 | [M + H]+ | 449.2 | 0.94 |
| 339 | A | 90-95 | [M + H]+ | 447.2 | 1.02 | A | 90-95 | [M + H]+ | 447.2 | 1.02 |
| 340 | A | >95 | [M + H]+ | 491.2 | 0.91 | A | >95 | [M + H]+ | 491.3 | 0.90 |
| 341 | A | 85-90 | [M + H]+ | 517.3 | 0.95 | A | >95 | [M + H]+ | 517.3 | 0.80 |
| 342 | A | >95 | [M + H]+ | 531.3 | 0.96 | A | >95 | [M + H]+ | 531.3 | 0.78 |
| 343 | A | >95 | [M + H]+ | 460.2 | 0.93 | A | >95 | [M + H]+ | 460.2 | 0.93 |
| 344 | A | >95 | [M + H]+ | 415.2 | 0.72 | A | >95 | [M + H]+ | 415.1 | 0.85 |
| 345 | A | >95 | [M + H]+ | 509.3 | 0.74 | A | >95 | [M + H]+ | 509.3 | 0.88 |
| 346 | A | >95 | [M + H]+ | 455.2 | 0.84 | A | >95 | [M + H]+ | 455.2 | 1.00 |
| 347 | A | 90-95 | [M + H]+ | 429.2 | 0.75 | A | >95 | [M + H]+ | 429.2 | 0.90 |
| 348 | A | 85-90 | [M + H]+ | 478.3 | 0.94 | A | 85-90 | [M + H]+ | 478.3 | 0.94 |
| 349 | A | >95 | [M + H]+ | 461.2 | 1.00 | A | >95 | [M + H]+ | 461.3 | 1.00 |
| 350 | A | >95 | [M + H]+ | 479.2 | 1.01 | A | >95 | [M + H]+ | 479.2 | 1.01 |
| 351 | A | >95 | [M + H]+ | 488.3 | 1.02 | A | >95 | [M + H]+ | 488.3 | 1.02 |
| 352 | A | 90-95 | [M − H]− | 487.2 | 1.09 | A | 90-95 | [M − H]− | 487.3 | 1.09 |
| 353 | A | >95 | [M + H]+ | 403.2 | 1.11 | A | >95 | [M + H]+ | 403.2 | 1.12 |
| 354 | A | >95 | [M + H]+ | 471.3 | 0.68 | A | >95 | [M + H]+ | 471.2 | 0.84 |
| 355 | A | >95 | [M + H]+ | 439.2 | 0.74 | A | >95 | [M + H]+ | 439.2 | 0.91 |
| 356 | A | >95 | [M + H]+ | 440.2 | 0.68 | A | >95 | [M + H]+ | 440.2 | 0.86 |
| 357 | A | >95 | [M + H]+ | 459.2 | 0.74 | A | 90-95 | [M + H]+ | 459.2 | 0.89 |
| 358 | A | >95 | [M + H]+ | 509.3 | 0.93 | A | >95 | [M + H]+ | 509.3 | 1.06 |
| 359 | A | >95 | [M + H]+ | 496.2 | 0.76 | A | >95 | [M + H]+ | 496.2 | 0.92 |
| 360 | A | >95 | [M + H]+ | 477.3 | 1.01 | A | >95 | [M + H]+ | 477.3 | 1.01 |
| 361 | A | >95 | [M + H]+ | 488.3 | 1.03 | A | >95 | [M + H]+ | 488.3 | 0.77 |
| 362 | A | >95 | [M + H]+ | 465.2 | 1.10 | A | >95 | [M + H]+ | 465.2 | 1.11 |
| 363 | A | >95 | [M + H]+ | 495.2 | 1.15 | A | >95 | [M + H]+ | 495.3 | 1.16 |
| 364 | A | >95 | [M + H]+ | 481.2 | 1.12 | A | >95 | [M + H]+ | 481.2 | 1.13 |
| 365 | A | 90-95 | [M − H]− | 557.4 | 1.11 | A | 85-90 | [M − H]− | 557.3 | 1.12 |
| 366 | A | >95 | [M + H]+ | 464.2 | 1.05 | A | >95 | [M − H]− | 464.2 | 1.04 |
| 367 | A | >95 | [M + H]+ | 446.2 | 0.91 | A | >95 | [M + H]+ | 446.2 | 0.90 |
| 368 | A | >95 | [M + H]+ | 476.3 | 0.95 | A | >95 | [M + H]+ | 476.3 | 0.93 |
| 369 | A | >95 | [M + H]+ | 480.2 | 0.79 | A | 85-90 | [M + H]+ | 480.2 | 0.80 |
| 370 | A | >95 | [M + H]+ | 496.2 | 0.86 | A | >95 | [M + H]+ | 496.2 | 0.87 |
| 371 | A | >95 | [M + H]+ | 502.3 | 1.08 | A | >95 | [M + H]+ | 502.3 | 0.80 |
| 372 | A | >95 | [M + H]+ | 501.3 | 0.99 | A | >95 | [M + H]+ | 501.3 | 0.74 |
| 373 | A | >95 | [M + H]+ | 502.3 | 0.98 | A | >95 | [M + H]+ | 502.3 | 0.99 |
| 374 | A | 90-95 | [M + H]+ | 526.3 | 0.80 | A | >95 | [M + H]+ | 526.3 | 0.93 |
| 375 | A | >95 | [M + H]+ | 512.2 | 0.78 | A | >95 | [M + H]+ | 512.2 | 0.91 |
| 376 | A | 90-95 | [M + H]+ | 485.3 | 0.74 | A | 90-95 | [M + H]+ | 485.3 | 0.84 |
| 377 | A | >95 | [M + H]+ | 485.3 | 0.74 | A | >95 | [M + H]+ | 485.3 | 0.88 |
| 378 | A | >95 | [M + H]+ | 495.3 | 0.73 | A | >95 | [M + H]+ | 495.3 | 0.85 |
| 379 | A | >95 | [M + H]+ | 485.3 | 0.98 | A | >95 | [M + H]+ | 485.3 | 0.98 |
| 380 | A | >95 | [M + H]+ | 504.3 | 1.11 | A | >95 | [M + H]+ | 504.3 | 1.13 |
| 381 | A | >95 | [M + H]+ | 505.2 | 1.18 | A | >95 | [M + H]+ | 505.2 | 1.20 |
| 382 | A | >95 | [M + H]+ | 537.2 | 0.97 | A | >95 | [M + H]+ | 537.2 | 0.98 |
| 383 | A | >95 | [M + H]+ | 536.3 | 0.90 | A | >95 | [M + H]+ | 536.3 | 0.92 |
| 384 | A | >95 | [M + H]+ | 408.2 | 0.79 | A | >95 | [M + H]+ | 408.1 | 0.87 |
| 385 | A | >95 | [M + H]+ | 422.2 | 0.93 | A | >95 | [M + H]+ | 422.2 | 0.94 |
| 386 | A | >95 | [M + H]+ | 418.1 | 0.68 | A | >95 | [M + H]+ | 418.1 | 0.82 |
| 387 | A | >95 | [M + H]+ | 419.1 | 0.60 | A | >95 | [M + H]+ | 419.2 | 0.81 |
| 388 | A | >95 | [M + H]+ | 462.3 | 1.07 | A | >95 | [M + H]+ | 462.3 | 1.08 |
| 389 | A | >95 | [M + H]+ | 436.2 | 0.98 | A | >95 | [M + H]+ | 436.2 | 0.97 |
| 390 | A | >95 | [M + H]+ | 516.3 | 1.12 | A | >95 | [M + H]+ | 516.3 | 1.14 |

TABLE 2-continued

LC-MS data

| | | High pH | | | | | Low pH | | | |
|---|---|---|---|---|---|---|---|---|---|---|
| Ex. | LC-MS Method | LC-MS Purity | Adduct | Observed MW | RT (min) | LC-MS Method | LC-MS Purity | Adduct | Observed MW | RT (min) |
| 391 | A | >95 | [M + H]+ | 503.3 | 0.99 | A | >95 | [M + H]+ | 503.3 | 1.00 |
| 392 | A | >95 | [M + H]+ | 516.3 | 0.94 | A | >95 | [M + H]+ | 516.3 | 0.96 |
| 392 | A | >95 | [M + H]+ | 502.3 | 0.91 | A | >95 | [M + H]+ | 502.3 | 0.93 |
| 394 | A | >95 | [M + H]+ | 478.2 | 0.91 | A | >95 | [M + H]+ | 478.3 | 0.92 |
| 395 | A | >95 | [M + H]+ | 492.3 | 0.95 | A | >95 | [M + H]+ | 492.3 | 0.97 |
| 396 | A | >95 | [M + H]+ | 533.2 | 0.99 | A | >95 | [M + H]+ | 533.2 | 1.02 |
| 397 | A | 90-95 | [M + H]+ | 492.2 | 0.95 | A | >95 | [M + H]+ | 492.2 | 0.95 |
| 398 | A | 90-95 | [M + H]+ | 492.2 | 1.02 | A | >95 | [M + H]+ | 492.2 | 1.02 |
| 399 | A | >95 | [M + H]+ | 472.2 | 0.94 | A | >95 | [M + H]+ | 472.2 | 1.04 |
| 400 | A | >95 | [M + H]+ | 513.2 | 0.98 | A | >95 | [M + H]+ | 513.2 | 0.98 |
| 401 | A | >95 | [M + H]+ | 543.2 | 0.98 | A | >95 | [M + H]+ | 543.2 | 0.99 |
| 402 | A | >95 | [M + H]+ | 526.2 | 1.02 | A | >95 | [M + H]+ | 526.2 | 1.12 |
| 403 | A | >95 | [M + H]+ | 456.1 | 0.80 | A | >95 | [M + H]+ | 456.1 | 0.97 |
| 404 | A | >95 | [M + H]+ | 514.2 | 0.72 | A | >95 | [M + H]+ | 514.2 | 0.94 |
| 405 | A | >95 | [M + H]+ | 523.3 | 1.19 | A | >95 | [M + H]+ | 523.3 | 1.21 |
| 406 | A | >95 | [M + H]+ | 490.3 | 0.94 | A | >95 | [M + H]+ | 490.3 | 0.94 |
| 407 | A | >95 | [M + H]+ | 449.2 | 0.91 | A | >95 | [M + H]+ | 449.2 | 0.91 |
| 408 | A | >95 | [M + H]+ | 422.2 | 0.87 | A | >95 | [M + H]+ | 422.1 | 0.88 |
| 409 | A | >95 | [M − H]+ | 558.3 | 1.16 | A | >95 | [M − H]+ | 558.3 | 1.18 |
| 410 | A | >95 | [M + H]+ | 436.2 | 0.93 | A | >95 | [M + H]+ | 436.2 | 0.94 |
| 411 | A | >95 | [M + H]+ | 437.2 | 1.01 | A | >95 | [M + H]+ | 437.2 | 1.02 |
| 412 | A | >95 | [M + H]+ | 473.3 | 1.00 | A | >95 | [M + H]+ | 473.3 | 1.01 |
| 413 | A | 90-95 | [M + H]+ | 477.3 | 1.14 | A | >95 | [M + H]+ | 477.3 | 1.15 |
| 414 | A | >95 | [M + H]+ | 488.3 | 0.93 | A | >95 | [M + H]+ | 488.3 | 0.93 |
| 415 | A | >95 | [M + H]+ | 460.2 | 0.83 | A | >95 | [M + H]+ | 460.2 | 0.76 |
| 416 | A | >95 | [M + H]+ | 408.1 | 0.77 | A | >95 | [M + H]+ | 408.1 | 0.80 |
| 417 | A | >95 | [M + H]+ | 462.2 | 1.00 | A | >95 | [M + H]+ | 462.2 | 1.00 |
| 418 | A | >95 | [M + H]+ | 415.1 | 0.98 | A | >95 | [M + H]+ | 415.2 | 0.87 |
| 419 | A | >95 | [M + H]+ | 516.2 | 1.09 | A | >95 | [M + H]+ | 516.2 | 1.09 |
| 420 | A | >95 | [M + H]+ | 470.2 | 1.04 | A | >95 | [M + H]+ | 470.2 | 1.04 |
| 421 | A | >95 | [M + H]+ | 501.2 | 1.03 | A | >95 | [M + H]+ | 501.2 | 1.03 |
| 422 | A | >95 | [M]+ | 468.1 | 0.76 | A | >95 | [M]+ | 468.1 | 0.93 |
| 423 | A | >95 | [M + H]+ | 415.2 | 0.97 | A | >95 | [M + H]+ | 415.2 | 0.80 |
| 424 | A | >95 | [M + H]+ | 433.1 | 0.68 | A | >95 | [M + H]+ | 433.2 | 0.82 |
| 425 | A | >95 | [M + H]+ | 488.2 | 0.89 | A | >95 | [M + H]+ | 488.3 | 0.89 |
| 426 | A | >95 | [M + H]+ | 347.2 | 1.16 | A | >95 | [M + H]+ | 347.2 | 1.12 |
| 427 | A | >95 | [M + H]+ | 414.2 | 0.90 | A | >95 | [M + H]+ | 414.2 | 0.90 |
| 428 | A | >95 | [M + H]+ | 461.2 | 0.79 | A | >95 | [M + H]+ | 461.2 | 0.83 |
| 429 | A | 85-90 | [M + H]+ | 471.3 | 1.01 | A | 85-90 | [M + H]+ | 471.3 | 0.74 |
| 430 | A | >95 | [M + H]+ | 390.1 | 0.83 | A | >95 | [M + H]+ | 390.1 | 0.84 |
| 431 | A | >95 | [M + H]+ | 400.1 | 0.81 | A | >95 | [M + H]+ | 400.1 | 0.83 |
| 432 | A | >95 | [M + H]+ | 454.2 | 1.03 | A | >95 | [M + H]+ | 454.2 | 1.02 |
| 433 | A | >95 | [M + H]+ | 416.1 | 0.89 | A | >95 | [M + H]+ | 416.1 | 0.89 |
| 434 | A | >95 | [M + H]+ | 440.2 | 1.06 | A | 90-95 | [M + H]+ | 440.2 | 1.05 |
| 435 | A | >95 | [M + H]+ | 480.2 | 1.06 | A | >95 | [M + H]+ | 480.2 | 1.06 |
| 436 | A | >95 | [M + H]+ | 494.2 | 1.08 | A | >95 | [M + H]+ | 494.2 | 1.09 |
| 437 | A | >95 | [M + H]+ | 516.2 | 0.90 | A | >95 | [M + H]+ | 516.2 | 0.91 |
| 438 | A | >95 | [M + H]+ | 436.3 | 0.92 | A | >95 | [M + H]+ | 436.3 | 0.92 |
| 439 | A | >95 | [M + H]+ | 447.1 | 0.89 | A | >95 | [M + H]+ | 447.1 | 0.88 |
| 440 | A | >95 | [M + H]+ | 446.2 | 0.95 | A | >95 | [M + H]+ | 446.2 | 0.93 |
| 441 | A | >95 | [M + H]+ | 503.2 | 0.96 | A | >95 | [M + H]+ | 503.2 | 0.94 |
| 442 | A | >95 | [M + H]+ | 506.3 | 0.94 | A | >95 | [M + H]+ | 506.3 | 0.93 |
| 443 | A | >95 | [M + H]+ | 498.2 | 1.03 | A | >95 | [M + H]+ | 498.2 | 1.02 |
| 444 | A | >95 | [M + H]+ | 512.3 | 1.06 | A | >95 | [M + H]+ | 512.3 | 1.05 |
| 445 | A | >95 | [M + H]+ | 478.2 | 0.87 | A | >95 | [M + H]+ | 478.2 | 0.85 |
| 446 | A | >95 | [M + H]+ | 402.1 | 0.86 | A | >95 | [M + H]+ | 402.1 | 0.83 |
| 447 | A | >95 | [M + H]+ | 331.2 | 0.93 | A | >95 | [M + H]+ | 331.0 | 0.92 |
| 448 | A | >95 | [M + H]+ | 448.1 | 1.00 | A | >95 | [M + H]+ | 448.1 | 0.98 |
| 449 | A | >95 | [M + H]+ | 461.2 | 0.70 | A | >95 | [M + H]+ | 461.2 | 0.82 |
| 450 | A | >95 | [M + H]+ | 447.2 | 0.70 | A | >95 | [M + H]+ | 447.2 | 0.89 |
| 451 | A | 90-95 | [M + H]+ | 477.2 | 0.75 | A | 90-95 | [M + H]+ | 477.2 | 0.87 |
| 452 | A | >95 | [M + H]+ | 472.2 | 1.07 | A | >95 | [M + H]+ | 472.2 | 1.06 |
| 453 | A | >95 | [M + H]+ | 465.2 | 1.13 | A | >95 | [M + H]+ | 465.2 | 1.12 |
| 454 | A | >95 | [M + H]+ | 425.1 | 1.06 | A | 90-95 | [M + H]+ | 425.1 | 1.04 |
| 455 | A | >95 | [M + H]+ | 446.1 | 0.85 | A | >95 | [M + H]+ | 446.1 | 0.94 |
| 456 | A | >95 | [M + H]+ | 426.1 | 0.83 | A | >95 | [M + H]+ | 426.1 | 0.84 |
| 457 | A | >95 | [M + H]+ | 512.1 | 0.78 | A | >95 | [M + H]+ | 512.1 | 0.91 |
| 458 | A | >95 | [M + H]+ | 480.2 | 1.05 | A | >95 | [M + H]+ | 480.2 | 1.05 |
| 459 | A | 85-90 | [M + H]+ | 534.2 | 0.93 | A | 90-95 | [M + H]+ | 534.2 | 0.93 |
| 460 | A | >95 | [M + H]+ | 534.2 | 1.10 | A | >95 | [M + H]+ | 534.2 | 1.11 |
| 461 | A | >95 | [M + H]+ | 476.2 | 1.08 | A | >95 | [M + H]+ | 476.2 | 1.08 |
| 462 | A | >95 | [M + H]+ | 466.1 | 0.91 | A | >95 | [M + H]+ | 466.2 | 0.90 |
| 463 | A | >95 | [M + H]+ | 533.2 | 0.94 | A | >95 | [M + H]+ | 533.1 | 0.94 |

TABLE 2-continued

| | | | High pH | | | | | Low pH | | |
|---|---|---|---|---|---|---|---|---|---|---|
| | | | | | LC-MS data | | | | | |
| Ex. | LC-MS Method | LC-MS Purity | Adduct | Observed MW | RT (min) | LC-MS Method | LC-MS Purity | Adduct | Observed MW | RT (min) |
| 464 | A | >95 | [M + H]+ | 426.1 | 1.11 | A | >95 | [M + H]+ | 426.1 | 1.11 |
| 465 | A | >95 | [M + H]+ | 461.2 | 1.21 | A | >95 | [M + H]+ | 461.2 | 1.20 |
| 466 | A | >95 | [M + H]+ | 461.2 | 1.22 | A | >95 | [M + H]+ | 461.2 | 1.20 |
| 467 | A | >95 | [M + H]+ | 473.2 | 1.23 | A | >95 | [M + H]+ | 473.2 | 1.23 |
| 468 | A | >95 | [M + H]+ | 396.1 | 1.03 | A | >95 | [M + H]+ | 396.1 | 1.02 |
| 469 | A | >95 | [M + H]+ | 380.1 | 0.99 | A | >95 | [M + H]+ | 380.1 | 0.97 |
| 470 | A | >95 | [M + H]+ | 475.2 | 1.28 | A | >95 | [M + H]+ | 475.2 | 1.27 |
| 471 | A | 90-95 | [M + H]+ | 503.2 | 1.20 | A | >95 | [M + H]+ | 503.2 | 1.20 |
| 472 | A | >95 | [M + H]+ | 461.2 | 1.23 | A | >95 | [M + H]+ | 461.2 | 1.23 |
| 473 | A | >95 | [M + H]+ | 513.2 | 1.06 | A | >95 | [M + H]+ | 513.2 | 1.06 |
| 474 | A | >95 | [M + H]+ | 475.2 | 1.28 | A | >95 | [M + H]+ | 475.2 | 1.29 |
| 475 | A | >95 | [M + H]+ | 421.2 | 0.92 | A | >95 | [M + H]+ | 421.2 | 0.90 |
| 476 | A | >95 | [M + H]+ | 395.1 | 0.86 | A | >95 | [M + H]+ | 395.1 | 0.84 |
| 477 | A | >95 | [M + H]+ | 487.2 | 1.31 | A | >95 | [M + H]+ | 487.2 | 1.31 |
| 478 | A | >95 | [M + H]+ | 503.2 | 1.33 | A | >95 | [M + H]+ | 503.2 | 1.32 |
| 479 | A | >95 | [M + H]+ | 404.1 | 0.70 | A | >95 | [M + H]+ | 404.1 | 0.73 |
| 480 | A | >95 | [M + H]+ | 500.2 | 0.95 | A | >95 | [M + H]+ | 500.2 | 0.95 |
| 481 | A | >95 | [M + H]+ | 380.1 | 0.89 | A | >95 | [M + H]+ | 380.1 | 0.88 |
| 482 | A | >95 | [M + H]+ | 483.0 | 1.12 | A | >95 | [M + H]+ | 483.0 | 1.11 |
| 483 | A | >95 | [M + H]+ | 485.2 | 0.98 | A | >95 | [M + H]+ | 485.2 | 0.97 |
| 484 | A | >95 | [M + H]+ | 297.0 | 1.08 | A | >95 | [M + H]+ | 297.1 | 1.06 |
| 485 | A | >95 | [M + H]+ | 552.2 | 0.97 | A | >95 | [M + H]+ | 552.2 | 0.96 |
| 486 | A | >95 | [M + H]+ | 373.1 | 0.84 | A | >95 | [M + H]+ | 373.1 | 0.83 |
| 487 | A | >95 | [M − H]+ | 355.0 | 0.89 | A | >95 | [M + H]+ | 357.2 | 0.88 |
| 488 | A | >95 | [M + H]+ | 393.1 | 0.82 | A | >95 | [M + H]+ | 393.2 | 0.82 |
| 489 | A | >95 | [M + H]+ | 407.3 | 0.91 | A | >95 | [M + H]+ | 407.2 | 0.90 |
| 490 | A | >95 | [M + H]+ | 500.1 | 0.92 | A | >95 | [M + H]+ | 500.2 | 0.92 |
| 491 | A | >95 | [M + H]+ | 387.1 | 0.91 | A | >95 | [M + H]+ | 387.1 | 0.91 |
| 492 | A | >95 | [M + H]+ | 481.6 | 0.93 | A | >95 | [M + H]+ | 481.0 | 0.93 |
| 493 | A | >95 | [M + H]+ | 501.2 | 1.24 | A | >95 | [M + H]+ | 501.2 | 1.24 |
| 494 | A | >95 | [M + H]+ | 425.1 | 0.95 | A | >95 | [M + H]+ | 425.1 | 0.96 |
| 495 | A | >95 | [M + H]+ | 401.1 | 0.88 | A | >95 | [M + H]+ | 401.3 | 0.73 |
| 496 | A | >95 | [M − H]− | 347.1 | 0.81 | A | >95 | [M + H]+ | 349.0 | 0.80 |
| 497 | A | 90-95 | [M + H]+ | 363.2 | 0.92 | A | 90-95 | [M + H]+ | 363.1 | 0.90 |
| 498 | A | >95 | [M + H]+ | 415.2 | 0.98 | A | >95 | [M + H]+ | 415.2 | 0.83 |
| 499 | A | >95 | [M + H]+ | 405.2 | 0.77 | A | >95 | [M + H]+ | 405.1 | 0.74 |
| 500 | A | >95 | [M + H]+ | 422.1 | 0.90 | A | >95 | [M + H]+ | 422.1 | 0.88 |
| 501 | A | >95 | [M + H]+ | 460.1 | 1.08 | A | >95 | [M + H]+ | 460.1 | 1.07 |
| 502 | A | >95 | [M + H]+ | 446.1 | 0.98 | A | >95 | [M + H]+ | 446.1 | 0.98 |
| 503 | A | >95 | [M + H]+ | 430.1 | 1.00 | A | >95 | [M + H]+ | 430.1 | 0.99 |
| 504 | A | >95 | [M + H]+ | 390.1 | 1.08 | A | >95 | [M + H]+ | 390.1 | 1.07 |
| 505 | A | 85-90 | [M + H]+ | 390.1 | 0.80 | A | 85-90 | [M + H]+ | 390.1 | 0.67 |
| 506 | A | >95 | [M + H]+ | 405.1 | 1.02 | A | 90-95 | [M + H]+ | 405.1 | 1.02 |
| 507 | A | >95 | [M + H]+ | 432.2 | 1.02 | A | 90-95 | [M + H]+ | 432.2 | 1.02 |
| 508 | A | >95 | [M + H]+ | 406.1 | 0.86 | A | >95 | [M + H]+ | 406.1 | 0.85 |
| 509 | A | >95 | [M + H]+ | 450.1 | 1.15 | A | >95 | [M + H]+ | 450.1 | 1.15 |
| 510 | A | >95 | [M + H]+ | 407.1 | 1.00 | A | >95 | [M + H]+ | 407.1 | 1.00 |
| 511 | A | >95 | [M + H]+ | 406.1 | 1.01 | A | >95 | [M + H]+ | 406.1 | 1.03 |
| 512 | A | >95 | [M + H]+ | 328.1 | 0.71 | A | >95 | [M + H]+ | 328.0 | 0.73 |
| 513 | A | >95 | [M − H]− | 407.1 | 0.91 | A | >95 | [M − H]− | 407.1 | 0.90 |
| 514 | A | 90-95 | [M + H]+ | 423.1 | 0.95 | A | >95 | [M + H]+ | 423.1 | 0.94 |
| 515 | A | >95 | [M + H]+ | 440.1 | 0.86 | A | >95 | [M + H]+ | 440.1 | 0.83 |
| 516 | A | >95 | [M + H]+ | 409.1 | 0.80 | A | 90-95 | [M + H]+ | 409.1 | 0.86 |
| 517 | A | >95 | [M + H]+ | 463.2 | 1.08 | A | >95 | [M + H]+ | 463.2 | 1.09 |
| 518 | A | >95 | [M + H]+ | 517.2 | 1.14 | A | >95 | [M + H]+ | 517.2 | 1.15 |
| 519 | A | 90-95 | [M + H]+ | 517.3 | 0.96 | A | 85-90 | [M + H]+ | 517.3 | 0.96 |
| 520 | A | >95 | [M + H]+ | 437.2 | 1.02 | A | >95 | [M + H]+ | 437.2 | 1.00 |
| 521 | A | >95 | [M + H]+ | 504.2 | 1.01 | A | >95 | [M + H]+ | 504.2 | 1.01 |
| 522 | A | >95 | [M + H]+ | 479.2 | 0.92 | A | >95 | [M + H]+ | 479.2 | 0.92 |
| 523 | A | >95 | [M + H]+ | 448.1 | 0.96 | A | >95 | [M + H]+ | 448.2 | 0.96 |
| 524 | A | >95 | [M + H]+ | 493.2 | 0.97 | A | >95 | [M + H]+ | 493.3 | 0.97 |
| 525 | A | >95 | [M + H]+ | 481.2 | 1.01 | A | >95 | [M + H]+ | 481.2 | 1.01 |
| 526 | A | >95 | [M − H]− | 453.2 | 0.99 | A | >95 | [M − H]− | 453.2 | 0.97 |
| 527 | A | 90-95 | [M + H]+ | 467.2 | 0.98 | A | 85-90 | [M + H]+ | 467.2 | 0.99 |
| 528 | A | >95 | [M + H]+ | 429.2 | 0.93 | A | >95 | [M + H]+ | 429.2 | 0.93 |
| 529 | A | >95 | [M + H]+ | 434.1 | 1.06 | A | >95 | [M + H]+ | 434.1 | 1.06 |
| 530 | A | >95 | [M + H]+ | 428.2 | 1.10 | A | >95 | [M + H]+ | 428.2 | 1.11 |
| 531 | A | >95 | [M + H]+ | 453.2 | 1.07 | A | >95 | [M + H]+ | 453.1 | 1.08 |
| 532 | A | >95 | [M + H]+ | 447.2 | 1.00 | A | >95 | [M − H]− | 445.2 | 1.00 |
| 533 | A | >95 | [M + H]+ | 439.1 | 0.94 | A | >95 | [M + H]+ | 439.2 | 0.94 |
| 534 | A | >95 | [M + H]+ | 425.1 | 0.89 | A | >95 | [M + H]+ | 425.1 | 0.89 |
| 535 | A | >95 | [M + H]+ | 451.2 | 1.06 | A | >95 | [M + H]+ | 451.2 | 1.06 |
| 536 | A | >95 | [M + H]+ | 465.3 | 1.13 | A | >95 | [M + H]+ | 465.2 | 1.13 |

TABLE 2-continued

| | | | LC-MS data | | | | | | |
|---|---|---|---|---|---|---|---|---|---|
| | | High pH | | | | Low pH | | | |
| Ex. | LC-MS Method | LC-MS Purity | Adduct | Observed MW | RT (min) | LC-MS Method | LC-MS Purity | Adduct | Observed MW | RT (min) |
| 537 | A | >95 | [M + H]+ | 513.3 | 0.97 | D | >95 | [M]+ | 512.85 | 2.6 |
| 538 | A | 90-95 | [M + H]+ | 524.3 | 0.95 | D | >95 | [M + H]+ | 524.18 | 2.54 |
| 539 | A | >95 | [M + H]+ | 513.3 | 0.91 | D | >95 | [M + H]+ | 513.13 | 2.01 |
| 540 | A | >95 | [M + H]+ | 517.2 | 0.98 | D | >95 | [M + H]+ | 517.12 | 2.58 |
| 541 | A | 90-95 | [M + H]+ | 513.2 | 0.88 | D | >95 | [M + H]+ | 513.13 | 1.74 |
| 542 | A | >95 | [M + H]+ | 517.3 | 0.95 | D | >95 | [M + H]+ | 517.12 | 2.53 |
| 543 | A | 90-95 | [M + H]+ | 523.1 | 1.00 | D | >95 | [M + H]+ | 523.18 | 2.65 |
| 544 | A | >95 | [M + H]+ | 454.2 | 0.89 | D | >95 | [M + H]+ | 454.16 | 2.42 |
| 545 | A | >95 | [M + H]+ | 517.3 | 0.94 | D | >95 | [M + H]+ | 517.19 | 2.51 |
| 546 | A | >95 | [M + H]+ | 504.3 | 0.89 | D | >95 | [M + H]+ | 504.14 | 2.41 |
| 547 | A | >95 | [M + H]+ | 517.2 | 0.82 | D | >95 | [M + H]+ | 517.19 | 2.21 |
| 548 | A | >95 | [M + H]+ | 503.3 | 0.86 | D | >95 | [M + H]+ | 503.14 | 2.4 |
| 549 | A | 90-95 | [M + H]+ | 464.3 | 1.04 | D | >95 | [M + H]+ | 464.21 | 2.72 |
| 550 | A | >95 | [M + H]+ | 520.2 | 1.03 | A | >95 | [M + H]+ | 520.2 | 1.03 |
| 551 | A | >95 | [M − H]− | 502.3 | 0.82 | A | >95 | [M + H]+ | 504.2 | 0.81 |
| 552 | A | 90-95 | [M + H]+ | 521.2 | 0.94 | A | 85-90 | [M + H]+ | 521.2 | 0.94 |
| 553 | A | >95 | [M − H]− | 502.3 | 0.87 | A | >95 | [M + H]+ | 504.2 | 0.86 |
| 554 | A | >95 | [M + H]+ | 518.0 | 0.89 | A | >95 | [M + H]+ | 518.2 | 0.89 |
| 555 | A | >95 | [M + H]+ | 503.3 | 0.95 | A | 90-95 | [M + H]+ | 503.3 | 0.93 |
| 556 | A | 85-90 | [M + H]+ | 505.2 | 0.90 | A | 85-90 | [M + H]+ | 505.2 | 0.90 |
| 557 | A | >95 | [M + H]+ | 504.2 | 0.88 | A | >95 | [M + H]+ | 504.3 | 0.88 |
| 558 | A | >95 | [M + H]+ | 505.2 | 0.99 | A | >95 | [M + H]+ | 505.2 | 0.97 |
| 559 | A | >95 | [M + H]+ | 490.2 | 0.97 | A | >95 | [M + H]+ | 490.2 | 0.95 |
| 560 | A | >95 | [M + H]+ | 502.2 | 0.87 | D | >95 | [M + H]+ | 502.20 | 2.39 |
| 561 | A | >95 | [M + H]+ | 502.2 | 0.87 | D | >95 | [M + H]+ | 502.30 | 2.37 |
| 562 | A | >95 | [M + H]+ | 503.3 | 0.81 | D | >95 | [M + H]+ | 503.25 | 2.23 |
| 563 | A | >95 | [M + H]+ | 505.2 | 0.87 | D | >95 | [M + H]+ | 505.17 | 2.35 |
| 564 | A | >95 | [M + H]+ | 489.3 | 0.84 | D | >95 | [M]+ | 488.80 | 2.47 |
| 565 | A | 90-95 | [M + H]+ | 502.3 | 0.84 | D | >95 | [M + H]+ | 502.30 | 1.68 |
| 566 | A | >95 | [M + H]+ | 513.3 | 0.91 | D | >95 | [M + H]+ | 513.19 | 1.97 |
| 567 | A | <85 | [M + H]+ | 504.3 | 0.83 | D | >95 | [M + H]+ | 504.25 | 2.27 |
| 568 | A | >95 | [M + H]+ | 502.3 | 0.79 | D | >95 | [M + H]+ | 502.35 | 1.67 |
| 569 | A | 85-90 | [M + H]+ | 514.3 | 0.89 | D | >95 | [M + H]+ | 514.45 | 2.40 |
| 570 | A | >95 | [M + H]+ | 492.2 | 0.87 | D | >95 | [M + H]+ | 492.30 | 2.37 |
| 571 | A | 90-95 | [M + H]+ | 513.3 | 0.96 | D | >95 | [M + H]+ | 513.23 | 2.30 |
| 572 | A | 90-95 | [M + H]+ | 519.2 | 0.90 | D | >95 | [M + H]+ | 519.12 | 2.48 |
| 573 | A | >95 | [M + H]+ | 513.3 | 0.91 | D | >95 | [M + H]+ | 513.35 | 1.82 |
| 574 | A | >95 | [M + H]+ | 461.3 | 0.86 | D | >95 | [M + H]+ | 461.15 | 2.36 |
| 575 | A | >95 | [M + H]+ | 488.3 | 0.78 | D | >95 | [M + H]+ | 488.15 | 1.68 |
| 576 | A | 90-95 | [M + H]+ | 516.3 | 0.85 | D | >95 | [M + H]+ | 516.15 | 1.71 |
| 577 | A | 90-95 | [M + H]+ | 505.2 | 0.92 | D | >95 | [M + H]+ | 505.17 | 2.47 |
| 578 | A | 90-95 | [M + H]+ | 505.2 | 0.92 | D | >95 | [M + H]+ | 505.30 | 2.48 |
| 579 | A | 90-95 | [M + H]+ | 503.2 | 0.93 | D | >95 | [M + H]+ | 503.14 | 2.5 |
| 580 | A | >95 | [M + H]+ | 503.3 | 0.90 | D | >95 | [M + H]+ | 503.15 | 2.41 |
| 581 | A | >95 | [M + H]+ | 505.2 | 0.90 | D | >95 | [M + H]+ | 505.25 | 2.48 |
| 582 | A | 90-95 | [M + H]+ | 519.3 | 0.95 | D | >95 | [M + H]+ | 519.30 | 2.54 |
| 583 | A | 90-95 | [M + H]+ | 520.3 | 0.87 | D | >95 | [M + H]+ | 520.30 | 2.37 |
| 584 | A | 90-95 | [M + H]+ | 503.3 | 0.76 | D | >95 | [M]+ | 502.85 | 2.24 |
| 585 | A | >95 | [M + H]+ | 489.2 | 0.89 | D | >95 | [M + H]+ | 489.13 | 2.41 |
| 586 | A | >95 | [M + H]+ | 488.3 | 0.84 | D | >95 | [M + H]+ | 488.15 | 2.27 |
| 587 | A | >95 | [M + H]+ | 489.3 | 0.74 | D | >95 | [M + H]+ | 489.15 | 2.12 |
| 588 | A | 90-95 | [M + H]+ | 502.3 | 0.81 | D | >95 | [M + H]+ | 502.15 | 1.67 |
| 589 | A | 90-95 | [M + H]+ | 506.2 | 0.84 | D | >95 | [M + H]+ | 505.75 | 2.44 |
| 590 | A | >95 | [M + H]+ | 488.2 | 0.81 | D | >95 | [M + H]+ | 488.30 | 2.25 |
| 591 | A | 90-95 | [M + H]+ | 519.2 | 0.95 | D | >95 | [M + H]+ | 519.30 | 2.55 |
| 592 | A | >95 | [M + H]+ | 503.2 | 0.76 | D | >95 | [M + H]+ | 503.35 | 2.12 |
| 593 | A | 85-90 | [M + H]+ | 503.3 | 0.82 | D | >95 | [M + H]+ | 503.35 | 2.28 |
| 594 | A | 90-95 | [M + H]+ | 519.3 | 0.91 | D | 90-95 | [M + H]+ | 519.25 | 2.55 |
| 595 | A | 90-95 | [M + H]+ | 502.3 | 0.86 | D | >95 | [M + H]+ | 502.15 | 2.39 |
| 596 | A | >95 | [M + H]+ | 503.3 | 0.89 | D | >95 | [M + H]+ | 503.21 | 2.39 |
| 597 | A | >95 | [M + H]+ | 450.3 | 0.98 | D | >95 | [M + H]+ | 450.16 | 2.67 |
| 598 | A | >95 | [M + H]+ | 492.2 | 0.89 | D | >95 | [M + H]+ | 492.10 | 2.38 |
| 599 | A | >95 | [M + H]+ | 454.2 | 1.00 | A | >95 | [M + H]+ | 454.2 | 0.97 |
| 600 | A | 90-95 | [M + H]+ | 472.2 | 0.96 | A | >95 | [M + H]+ | 472.2 | 0.94 |
| 601 | A | >95 | [M + H]+ | 426.2 | 0.75 | A | 90-95 | [M + H]+ | 426.1 | 0.78 |
| 602 | A | >95 | [M + H]+ | 454.4 | 0.92 | A | >95 | [M + H]+ | 454.2 | 0.90 |
| 603 | A | >95 | [M + H]+ | 534.2 | 0.90 | A | >95 | [M + H]+ | 534.2 | 0.88 |
| 604 | A | >95 | [M + H]+ | 459.2 | 1.06 | A | >95 | [M + H]+ | 459.2 | 1.06 |
| 605 | A | >95 | [M + H]+ | 441.2 | 1.10 | A | >95 | [M + H]+ | 441.2 | 1.10 |
| 606 | A | >95 | [M + H]+ | 440.2 | 1.03 | A | >95 | [M + H]+ | 440.2 | 1.03 |
| 607 | A | 90-95 | [M + H]+ | 489.3 | 0.87 | D | >95 | [M + H]+ | 489.3 | 2.38 |
| 608 | A | >95 | [M + H]+ | 490.3 | 1.13 | D | >95 | [M + H]+ | 490.3 | 2.93 |
| 609 | A | >95 | [M + H]+ | 476.3 | 1.08 | D | >95 | [M + H]+ | 476.35 | 2.81 |

TABLE 2-continued

| | | | LC-MS data | | | | | | |
|---|---|---|---|---|---|---|---|---|---|
| | High pH | | | | | Low pH | | | |
| Ex. | LC-MS Method | LC-MS Purity | Adduct | Observed MW | RT (min) | LC-MS Method | LC-MS Purity | Adduct | Observed MW | RT (min) |
| 610 | A | 90-95 | [M + H]+ | 499.3 | 0.85 | D | >95 | [M + H]+ | 499.3 | 1.87 |
| 611 | A | >95 | [M + H]+ | 507.3 | 1.01 | D | >95 | [M + H]+ | 507.35 | 1.69 |
| 612 | A | 90-95 | [M + H]+ | 480.3 | 0.96 | D | >95 | [M + H]+ | 480.3 | 2.57 |
| 613 | A | >95 | [M + H]+ | 478.3 | 1.12 | D | >95 | [M + H]+ | 477.85 | 2.96 |
| 614 | A | >95 | [M + H]+ | 436.2 | 0.96 | A | >95 | [M + H]+ | 436.2 | 0.95 |
| 615 | A | >95 | [M + H]+ | 516.2 | 0.94 | A | 90-95 | [M + H]+ | 516.2 | 0.92 |
| 616 | A | >95 | [M + H]+ | 534.2 | 1.01 | A | >95 | [M + H]+ | 534.2 | 1.02 |
| 617 | A | >95 | [M + H]+ | 464.3 | 0.90 | D | >95 | [M]+ | 463.9 | 2.84 |
| 618 | A | >95 | [M + H]+ | 510.3 | 0.90 | D | >95 | [M + H]+ | 510.35 | 2.42 |
| 619 | A | >95 | [M + H]+ | 492.3 | 0.94 | D | >95 | [M + H]+ | 492.35 | 2.54 |
| 620 | A | >95 | [M + H]+ | 478.3 | 0.92 | D | >95 | [M + H]+ | 478.3 | 2.51 |
| 621 | A | >95 | [M + H]+ | 472.2 | 1.03 | A | >95 | [M + H]+ | 472.2 | 1.03 |
| 622 | A | >95 | [M + H]+ | 491.2 | 1.07 | A | 85-90 | [M + H]+ | 491.2 | 1.07 |
| 623 | A | >95 | [M + H]+ | 490.2 | 0.98 | A | >95 | [M + H]+ | 490.2 | 0.99 |
| 624 | A | >95 | [M + H]+ | 426.2 | 0.81 | A | >95 | [M + H]+ | 426.2 | 0.82 |
| 625 | A | >95 | [M + H]+ | 439.0 | 0.99 | A | >95 | [M + H]+ | 439.0 | 1.00 |
| 626 | A | >95 | [M + H]+ | 423.2 | 0.88 | A | >95 | [M + H]+ | 423.2 | 0.88 |
| 627 | A | >95 | [M + H]+ | 507.2 | 0.91 | A | >95 | [M + H]+ | 507.2 | 0.91 |
| 628 | A | >95 | [M + H]+ | 454.2 | 0.92 | A | >95 | [M + H]+ | 454.2 | 0.93 |
| 629 | A | >95 | [M + H]+ | 472.2 | 0.88 | A | >95 | [M + H]+ | 472.1 | 0.89 |
| 630 | A | 90-95 | [M + H]+ | 520.2 | 0.85 | A | 90-95 | [M + H]+ | 520.2 | 0.86 |
| 631 | A | 90-95 | [M + H]+ | 522.2 | 0.88 | A | >95 | [M + H]+ | 522.2 | 0.89 |

TABLE 3

$^1$H NMR data

| Example | NMR Purity | $^1$H NMR |
|---|---|---|
| 23 | >95 | $^1$H NMR (300 MHz, CDCl$_3$) δ = 8.75 (d, J = 2.3 Hz, 1H), 8.15 (dd, J = 2.3, 8.9 Hz, 1H), 7.44 (d, J = 8.9 Hz, 1H), 5.02 (s, 1H), 4.12 (d, J = 6.9 Hz, 2H), 3.51 (s, 3H), 1.26 (s, 3H), 0.83-0.75 (m, 2H), 0.64-0.49 (m, 6H) |
| 32 | >95 | $^1$H NMR (300 MHz, CDCl$_3$) δ = 8.49 (d, J = 2.4 Hz, 1H), 7.90 (d, J = 8.9 Hz, 1H), 7.19 (d, J = 8.9 Hz, 1H), 7.05-7.03 (m, 2H), 4.77 (s, 1H), 4.00 (s, 2H), 3.30-3.25 (m, 3H), 1.34 (s, 1H), 1.06-0.99 (m, 5H), 0.91-0.85 (m, 4H), 0.58-0.52 (m, 2H), 0.37-0.16 (m, 7H), 0.07 (s, 1H) |
| 35 | >95 | $^1$H NMR (300 MHz, CDCl$_3$) δ = 8.74 (d, J = 2.3 Hz, 1H), 8.15 (d, J = 8.9 Hz, 1H), 7.43 (d, J = 8.8 Hz, 1H), 4.99 (s, 1H), 4.11 (d, J = 6.7 Hz, 2H), 3.51 (s, 3H), 1.57 (s, 1H), 1.29-1.24 (m, 4H), 1.12-0.87 (m, 5H), 0.85-0.65 (m, 3H), 0.59-0.45 (m, 2H), 0.40-0.32 (m, 2H) |
| 36 | >95 | $^1$H NMR (300 MHz, CDCl$_3$) δ = 8.76 (d, J = 2.3 Hz, 1H), 8.17 (d, J = 8.9 Hz, 1H), 7.37 (d, J = 8.9 Hz, 1H), 5.02 (s, 1H), 4.55 (dd, J = 7.3, 14.5 Hz, 1H), 4.15 (dd, J = 6.3, 15.4 Hz, 1H), 3.52 (s, 3H), 2.13-1.80 (m, 1H), 1.67-1.42 (m, 3H), 1.26 (s, 3H), 0.85-0.71 (m, 2H), 0.60-0.45 (m, 2H) |
| 61 | >95 | $^1$H NMR (400 MHz, CDCl$_3$) δ = 8.72 (d, J = 2.7 Hz, 1H), 8.02 (dd, J = 2.5, 8.9 Hz, 1H), 7.28 (d, J = 8.9 Hz, 1H), 7.21 (d, J = 8.7 Hz, 2H), 6.88 (d, J = 9.2 Hz, 2H), 5.35 (s, 2H), 4.92 (s, 1H), 3.79 (s, 3H), 3.57 (s, 3H), 1.24 (s, 3H), 0.78-0.73 (m, 2H), 0.52-0.48 (m, 2H) |
| 68 | >95 | $^1$H NMR (400 MHz, CDCl$_3$) δ = 8.77 (d, J = 2.3 Hz, 1H), 8.04 (dd, J = 2.3, 8.7 Hz, 1H), 7.78 (d, J = 7.8 Hz, 1H), 7.55 (t, J = 7.3 Hz, 1H), 7.45 (t, J = 7.3 Hz, 1H), 7.15 (d, J = 7.8 Hz, 1H), 7.07 (d, J = 9.2 Hz, 1H), 5.65 (s, 2H), 4.93 (s, 1H), 3.59 (s, 3H), 1.25 (s, 3H), 0.79-0.73 (m, 2H), 0.54-0.48 (m, 2H) |
| 96 | 85-90 | $^1$H NMR (400 MHz, DMSO-d$_6$) δ = 8.41 (d, J = 2.3 Hz, 1H), 8.14 (s, 1H), 7.94-7.87 (m, 3H), 7.78 (d, J = 8.2 Hz, 2H), 7.38-7.34 (m, 3H), 5.41 (s, 2H), 3.34 (s, 4H), 1.02 (s, 3H), 0.56-0.51 (m, 2H), 0.36-0.30 (m, 2H) |
| 109 | >95 | $^1$H NMR (300 MHz, CDCl$_3$) δ = 8.73 (d, J = 2.3 Hz, 1H), 8.16 (dd, J = 2.4, 8.9 Hz, 1H), 7.75 (s, J = 4.5 Hz, 1H), 7.30 (d, J = 8.9 Hz, 1H), 5.38 (s, 2H), 4.99 (s, 1H), 3.66 (s, 3H), 2.65 (s, 3H), 1.25 (s, 3H), 0.80-0.74 (m, 2H), 0.55-0.49 (m, 2H) |
| 115 | >95 | $^1$H NMR (300 MHz, DMSO-d$_6$) δ = 8.43 (d, J = 2.3 Hz, 1H), 8.07 (dd, J = 2.4, 8.9 Hz, 1H), 7.64 (d, J = 8.9 Hz, 1H), 4.91 (s, 2H), 3.54 (s, 3H), 2.42 (s, 3H), 2.21 (s, 3H), 1.07 (s, 3H), 0.62-0.56 (m, 2H), 0.41-0.35 (m, 2H) |
| 126 | >95 | $^1$H NMR (300 MHz, CDCl$_3$) δ = 8.73 (d, J = 2.4 Hz, 1H), 8.15 (dd, J = 2.3, 8.8 Hz, 1H), 7.68 (s, 1H), 7.44 (d, J = 8.9 Hz, 1H), 5.48 (s, 2H), 5.02 (s, 1H), 3.54 (s, 3H), 2.67 (s, 3H), 1.25 (s, 3H), 0.80-0.73 (m, 2H), 0.55-0.48 (m, 2H) |
| 127 | >95 | $^1$H NMR (300 MHz, DMSO-d$_6$) δ = 8.44 (d, J = 2.3 Hz, 1H), 8.21 (s, 1H), 8.02 (dd, J = 2.4, 8.9 Hz, 1H), 7.55 (d, J = 8.9 Hz, 1H), 5.77 (s, 1H), 5.38 (s, 2H), 3.83 (s, 3H), 3.35 (s, 3H), 1.99 (s, 3H), 1.07 (s, 3H), 0.62-0.56 (m, 2H), 0.42-0.36 (m, 2H) |
| 133 | >95 | $^1$H NMR (300 MHz, DMSO-d$_6$) δ = 8.43 (d, J = 2.3 Hz, 1H), 8.21 (s, 1H), 8.10 (t, J = 10.3 Hz, 1H), 7.70-7.64 (m, 1H), 5.45 (s, 2H), 3.34 (s, 3H), 3.17 (d, J = 5.2 Hz, 1H), 2.47 (s, 3H), 1.07 (s, 3H), 0.63-0.55 (m, 2H), 0.43-0.35 (m, 2H) |

TABLE 3-continued

¹H NMR data

| Example | NMR Purity | ¹H NMR |
|---|---|---|
| 137 | >95 | ¹H NMR (300 MHz, DMSO-$d_6$) δ = 8.43 (d, J = 2.3 Hz, 1H), 8.21 (s, 1H), 8.13 (dd, J = 2.3, 8.8 Hz, 1H), 7.69 (d, J = 8.9 Hz, 1H), 4.96 (s, 2H), 2.28-2.04 (m, 2H), 1.07 (s, 3H), 1.01 (t, J = 7.5 Hz, 3H), 0.67-0.52 (m, 2H), 0.47-0.32 (m, 2H) |
| 143 | >95 | ¹H NMR (300 MHz, CDCl$_3$) δ = 8.80 (d, J = 0.8 Hz, 1H), 8.75 (d, J = 2.3 Hz, 1H), 8.16 (dd, J = 2.4, 8.9 Hz, 1H), 7.99 (s, J = 4.8 Hz, 1H), 7.43 (d, J = 8.8 Hz, 1H), 5.57 (s, 2H), 4.93 (s, 1H), 3.55 (s, 3H), 2.18 (s, 1H), 1.55 (s, 3H), 1.26 (s, 4H), 0.77 (s, 2H), 0.52 (d, J = 1.7 Hz, 2H) |
| 145 | >95 | ¹H NMR (300 MHz, CDCl$_3$) δ = 8.74 (d, J = 2.9 Hz, 1H), 8.17 (d, J = 8.9 Hz, 1H), 7.65 (s, J = 4.4 Hz, 1H), 7.40 (d, J = 8.9 Hz, 1H), 7.29-7.26 (m, 4H), 5.44 (s, 2H), 4.99 (s, 1H), 3.55 (s, 3H), 1.25 (s, 3H), 0.80-0.73 (m, 2H), 0.56-0.49 (m, 2H) |
| 149 | >95 | ¹H NMR (300 MHz, CDCl$_3$) δ = 8.75 (d, J = 2.2 Hz, 1H), 8.12 (d, J = 8.9 Hz, 1H), 7.32 (t, J = 9.3 Hz, 1H), 5.79 (s, 1H), 5.36 (s, 2H), 5.04 (s, 1H), 3.95 (s, 3H), 3.54 (s, 3H), 1.24 (s, 3H), 0.83-0.75 (m, 2H), 0.59-0.44 (m, 2H) |
| 152 | >95 | ¹H NMR (300 MHz, CDCl$_3$) δ = 8.72 (d, J = 2.4 Hz, 1H), 8.13 (d, J = 8.9 Hz, 1H), 7.55-7.43 (m, 3H), 5.22 (s, 2H), 5.01 (s, 1H), 3.88 (s, 3H), 3.54 (s, 3H), 1.30-1.21 (m, 4H), 0.80-0.74 (m, 2H), 0.55-0.47 (m, 2H) |
| 155 | >95 | ¹H NMR (300 MHz, DMSO-$d_6$) δ = 8.42 (d, J = 2.3 Hz, 1H), 8.19 (br. s., 1H), 8.07 (dd, J = 2.3, 8.8 Hz, 1H), 7.67 (d, J = 5.4 Hz, 1H), 7.64 (d, J = 8.9 Hz, 1H), 7.39 (s, 1H), 4.95 (s, 2H), 3.76 (s, 3H), 3.55 (s, 3H), 1.07 (s, 3H), 0.65-0.52 (m, 2H), 0.45-0.33 (m, 2H) |
| 156 | >95 | ¹H NMR (300 MHz, DMSO-$d_6$) δ = 8.43 (d, J = 2.3 Hz, 1H), 8.08 (dd, J = 2.3, 8.9 Hz, 1H), 7.81 (d, J = 8.9 Hz, 1H), 7.62 (s, 1H), 5.25 (s, 2H), 4.09 (d, J = 6.9 Hz, 2H), 2.57 (s, 3H), 1.22 (br. s., 1H), 1.07 (s, 3H), 0.62-0.56 (m, 2H), 0.53-0.43 (m, 4H), 0.43-0.37 (m, 2H) |
| 157 | >95 | ¹H NMR (300 MHz, DMSO-$d_6$) δ = 8.40 (d, J = 2.2 Hz, 1H), 8.13 (br. s, 1H), 7.99 (dd, J = 2.3, 8.6 Hz, 1H), 7.65 (s, 1H), 7.57 (d, J = 8.6 Hz, 1H), 5.30 (s, 2H), 4.33 (d, J = 7.3 Hz, 2H), 1.00 (s, 3H), 0.65-0.51 (m, 5H), 0.44-0.38 (m, 2H), 0.34 (d, J = 2.0 Hz, 2H) |
| 158 | >95 | ¹H NMR (300 MHz, DMSO-$d_6$) δ = 8.43 (d, J = 2.4 Hz, 1H), 8.19 (s, 1H), 8.07 (dd, J = 2.2, 8.9 Hz, 1H), 7.80 (d, J = 8.9 Hz, 1H), 4.92 (s, 2H), 4.08 (d, J = 6.9 Hz, 2H), 2.42 (s, 3H), 2.22 (s, 3H), 1.27-1.16 (m, 1H), 1.08 (s, 3H), 0.59 (s, 2H), 0.51-0.43 (m, 4H), 0.43-0.37 (m, 2H) |
| 159 | >95 | ¹H NMR (300 MHz, DMSO-$d_6$) δ = 8.45 (d, J = 2.1 Hz, 1H), 8.22 (s, 1H), 8.13 (dd, J = 2.3, 8.8 Hz, 1H), 7.70 (d, J = 8.8 Hz, 1H), 4.98 (s, 2H), 4.91 (s, 2H), 3.40 (s, 1H), 2.42 (s, 3H), 2.21 (s, 3H), 1.08 (s, 3H), 0.65-0.54 (m, 2H), 0.44-0.36 (m, 2H) |
| 161 | >95 | ¹H NMR (300 MHz, DMSO-$d_6$) δ = 8.44 (d, J = 2.2 Hz, 1H), 8.15 (dd, J = 2.3, 8.9 Hz, 1H), 7.71 (d, J = 8.9 Hz, 1H), 7.64 (s, 1H), 5.25 (s, 2H), 5.00 (d, J = 2.4 Hz, 2H), 3.44-3.39 (m, 1H), 2.57 (s, 3H), 1.08 (s, 3H), 0.65-0.54 (m, 2H), 0.48-0.32 (m, 2H) |
| 162 | >95 | ¹H NMR (300 MHz, DMSO-$d_6$) δ = 8.44 (d, J = 2.3 Hz, 1H), 8.22 (br. s., 1H), 8.12 (dd, J = 2.3, 8.8 Hz, 1H), 7.70-7.63 (m, 2H), 5.46 (s, 2H), 5.27 (s, 2H), 2.58 (s, 3H), 2.47 (s, 3H), 1.07 (s, 4H), 0.58 (s, 2H), 0.40 (d, J = 1.9 Hz, 2H) |
| 163 | >95 | ¹H NMR (300 MHz, DMSO-$d_6$) δ = 8.44 (d, J = 2.3 Hz, 1H), 8.21 (br. s., 1H), 8.03 (dd, J = 2.3, 8.9 Hz, 1H), 7.64 (s, 1H), 7.57 (d, J = 8.9 Hz, 1H), 5.75 (s, 1H), 5.38 (s, 2H), 5.27 (s, 2H), 3.82 (s, 3H), 3.33 (s, 12H), 2.58 (s, 3H), 1.99 (s, 3H), 1.07 (s, 3H), 0.58 (s, 2H), 0.39 (d, J = 2.0 Hz, 2H) |
| 164 | 85-90 | ¹H NMR (300 MHz, DMSO-$d_6$) δ = 8.41 (d, J = 2.2 Hz, 1H), 8.16 (br. s, 1H), 8.03 (dd, J = 2.3, 8.7 Hz, 1H), 7.66 (d, J = 8.6 Hz, 1H), 7.48 (s, 1H), 6.22 (s, 1H), 5.55 (s, 2H), 5.24 (s, 2H), 3.78 (s, 3H), 2.63 (s, 3H), 2.10 (s, 3H), 1.01 (s, 3H), 0.59-0.50 (m, 2H), 0.38-0.30 (m, 2H) |
| 165 | >95 | ¹H NMR (300 MHz, DMSO-$d_6$) δ = 8.44 (d, J = 2.3 Hz, 1H), 8.11 (dd, J = 2.3, 8.8 Hz, 1H), 7.65 (d, J = 8.9 Hz, 1H), 5.45 (s, 2H), 4.93 (s, 2H), 2.44 (d, J = 10.7 Hz, 6H), 2.22 (s, 3H), 1.07 (s, 3H), 0.59 (s, 2H), 0.43-0.37 (m, 2H) |
| 166 | >95 | ¹H NMR (300 MHz, DMSO-$d_6$) δ = 8.45 (d, J = 2.2 Hz, 1H), 8.19 (s, 1H), 8.02 (dd, J = 2.3, 8.9 Hz, 1H), 7.54 (d, J = 8.9 Hz, 1H), 5.75 (s, 1H), 5.36 (s, 2H), 4.93 (s, 2H), 3.81 (s, 3H), 3.37-3.31 (m, 20H), 2.42 (s, 3H), 2.21 (s, 3H), 1.99 (s, 3H), 1.08 (s, 4H), 0.59 (br. s., 2H), 0.39 (s, 2H) |
| 168 | >95 | ¹H NMR (300 MHz, DMSO-$d_6$) δ = 8.52-8.35 (m, 1H), 8.18 (s, 1H), 8.01-7.90 (m, 1H), 7.52-7.31 (m, 3H), 7.18 (t, J = 8.3 Hz, 2H), 5.37 (s, 2H), 4.95 (s, 2H), 2.44 (s, 3H), 2.23 (s, 3H), 1.06 (s, 3H), 0.57 (s, 2H), 0.38 (d, J = 2.1 Hz, 2H) |
| 169 | >95 | ¹H NMR (300 MHz, DMSO-$d_6$) δ = 8.45 (d, J = 2.3 Hz, 1H), 8.17 (s, 1H), 8.02-7.91 (m, 1H), 7.45 (d, J = 8.9 Hz, 1H), 7.24 (t, J = 7.9 Hz, 1H), 6.96-6.76 (m, 3H), 5.36 (s, 2H), 4.96 (s, 2H), 3.70 (s, 3H), 2.44 (s, 3H), 2.23 (s, 3H), 1.06 (s, 3H), 0.57 (s, 2H), 0.37 (d, J = 2.0 Hz, 2H) |
| 170 | 90-95 | ¹H NMR (300 MHz, CDCl$_3$) δ = 8.71 (d, J = 2.3 Hz, 1H), 8.10 (dd, J = 2.3, 8.8 Hz, 1H), 7.63 (s, 1H), 7.56 (s, 1H), 7.26 (d, J = 8.9 Hz, 3H), 5.39 (s, 2H), 5.15-5.06 (m, 3H), 3.86 (s, 3H), 2.63-2.53 (m, 6H), 1.25 (s, 3H), 0.78-0.71 (m, 2H), 0.54-0.46 (m, 2H) |
| 171 | >95 | ¹H NMR (300 MHz, DMSO-$d_6$) δ = 8.44 (d, J = 2.2 Hz, 1H), 8.18 (s, 1H), 7.96 (dd, J = 2.3, 8.9 Hz, 1H), 7.70 (s, 1H), 7.50-7.34 (m, 4H), 7.20-7.13 (m, 2H), 5.38 (s, 2H), 5.00 (s, 2H), 3.77 (s, 3H), 1.05 (s, 3H), 0.64-0.49 (m, 2H), 0.42-0.32 (m, 2H) |
| 172 | >95 | ¹H NMR (300 MHz, DMSO-$d_6$) δ = 8.44 (d, J = 2.3 Hz, 1H), 7.97 (dd, J = 2.3, 8.9 Hz, 1H), 7.71 (s, 1H), 7.47 (d, J = 8.9 Hz, 1H), 7.42-7.40 (m, 1H), 7.24 (t, J = 7.9 Hz, 1H), 6.90-6.81 (m, 3H), 5.37 (s, 2H), 5.01 (s, 2H), 3.77 (s, 3H), 3.70 (s, 3H), 3.17 (s, 1H), 1.05 (s, 3H), 0.63-0.50 (m, 2H), 0.41-0.33 (m, 2H) |
| 173 | >95 | ¹H NMR (300 MHz, DMSO-$d_6$) δ = 8.44 (d, J = 2.3 Hz, 1H), 8.20 (s, 1H), 8.02 (d, J = 8.9 Hz, 1H), 7.68 (s, 1H), 7.56 (d, J = 8.9 Hz, 1H), 7.39 (s, 1H), 5.73 (s, 1H), 5.37 (s, 2H), 4.97 (s, 2H), 3.82 (s, 3H), 3.76 (s, 3H), 1.99 (s, 3H), 1.17 (d, J = 6.2 Hz, 3H), 1.07 (s, 3H), 0.59 (s, 2H), 0.39 (d, J = 2.1 Hz, 2H) |

TABLE 3-continued

<sup>1</sup>H NMR data

| Example | NMR Purity | <sup>1</sup>H NMR |
|---|---|---|
| 174 | >95 | $^1$H NMR (300 MHz, DMSO-$d_6$) δ = 8.44 (d, J = 2.4 Hz, 1H), 8.05 (s, 1H), 7.80 (d, J = 8.9 Hz, 1H), 7.68 (s, 1H), 7.39 (s, 1H), 4.96 (s, 2H), 4.08 (d, J = 6.9 Hz, 2H), 3.76 (s, 3H), 2.54 (s, 2H), 1.28-1.14 (m, 4H), 1.08 (s, 3H), 0.59 (s, 2H), 0.53-0.43 (m, 4H), 0.40 (d, J = 2.1 Hz, 2H) |
| 176 | >95 | $^1$H NMR (300 MHz, DMSO-$d_6$) δ = 8.44 (d, J = 2.3 Hz, 1H), 8.20 (s, 1H), 7.98 (dd, J = 2.3, 8.9 Hz, 1H), 7.65 (s, 1H), 7.49 (d, J = 8.9 Hz, 1H), 7.39 (dd, J = 5.5, 8.5 Hz, 2H), 7.17 (t, J = 8.3 Hz, 2H), 5.38 (s, 2H), 5.30 (s, 2H), 2.59 (s, 3H), 1.06 (s, 3H), 0.61-0.52 (m, 2H), 0.42-0.33 (m, 2H) |
| 177 | >95 | $^1$H NMR (300 MHz, DMSO-$d_6$) δ = 8.44 (d, J = 2.3 Hz, 1H), 7.98 (dd, J = 2.3, 8.9 Hz, 1H), 7.66 (s, 1H), 7.48 (d, J = 8.9 Hz, 1H), 7.24 (t, J = 7.9 Hz, 1H), 6.91-6.82 (m, 3H), 5.37 (s, 2H), 5.30 (s, 2H), 3.71 (s, 3H), 2.59-2.54 (m, 3H), 1.05 (s, 3H), 0.61-0.51 (m, 2H), 0.42-0.33 (m, 2H) |
| 178 | >95 | $^1$H NMR (300 MHz, DMSO-$d_6$) δ = 8.44 (d, J = 2.3 Hz, 1H), 8.24 (br. s, 1H), 8.14 (dd, J = 2.3, 8.8 Hz, 1H), 7.71 (s, 1H), 7.69 (s, J = 7.9 Hz, 1H), 7.40 (s, 1H), 4.99 (d, J = 2.2 Hz, 2H), 4.95 (s, 2H), 3.76 (s, 3H), 3.40 (s, 1H), 1.08 (s, 3H), 0.65-0.55 (m, 2H), 0.45-0.35 (m, 2H) |
| 180 | >95 | $^1$H NMR (300 MHz, CDCl$_3$) δ = 8.73 (d, J = 2.3 Hz, 1H), 8.19 (dd, J = 2.3, 8.8 Hz, 1H), 7.33 (d, J = 8.9 Hz, 1H), 6.16 (s, 1H), 5.39 (s, 2H), 4.95 (s, 1H), 3.67 (s, 3H), 2.27 (s, 3H), 1.26 (s, 3H), 0.80-0.75 (m, 2H), 0.55-0.50 (m, 2H) |
| 181 | >95 | $^1$H NMR (300 MHz, CDCl$_3$) δ = 8.73 (d, J = 2.3 Hz, 1H), 8.15 (dd, J = 2.3, 8.9 Hz, 1H), 7.65 (s, 1H), 7.60 (s, 1H), 7.29 (d, J = 8.9 Hz, 2H), 5.13 (s, 2H), 5.06 (s, 1H), 4.13 (q, J = 7.3 Hz, 2H), 3.65 (s, 3H), 1.51-1.43 (m, 3H), 1.25 (s, 3H), 0.82-0.74 (m, 2H), 0.55-0.49 (m, 2H) |
| 183 | >95 | $^1$H NMR (300 MHz, CDCl$_3$) δ = 8.72 (d, J = 2.4 Hz, 1H), 8.15 (dd, J = 2.4, 8.9 Hz, 1H), 7.78 (s, 2H), 7.29 (d, J = 8.9 Hz, 1H), 5.18 (s, 2H), 4.97 (s, 1H), 3.65 (s, 3H), 2.18 (s, 1H), 1.24 (s, 3H), 0.80-0.74 (m, 2H), 0.54-0.48 (m, 2H) |
| 186 | >95 | $^1$H NMR (300 MHz, DMSO-$d_6$) δ = 8.44 (d, J = 2.2 Hz, 1H), 8.22 (s, 1H), 8.01 (dd, J = 2.4, 8.9 Hz, 1H), 7.55-7.38 (m, 3H), 7.23-7.12 (m, 2H), 5.40 (s, 2H), 5.01 (s, 2H), 1.07 (s, 3H), 0.64-0.52 (m, 2H), 0.43-0.34 (m, 2H) |
| 187 | >95 | $^1$H NMR (300 MHz, DMSO-$d_6$) δ = 8.44 (d, J = 2.3 Hz, 1H), 8.22 (s, 1H), 8.01 (dd, J = 2.3, 8.9 Hz, 1H), 7.48 (d, J = 8.9 Hz, 1H), 7.30-7.20 (m, 1H), 6.99-6.81 (m, 3H), 5.38 (s, 2H), 5.01 (s, 2H), 3.72 (s, 3H), 1.07 (s, 4H), 0.63-0.52 (m, 2H), 0.43-0.33 (m, 2H) |
| 192 | >95 | $^1$H NMR (300 MHz, DMSO-$d_6$) δ = 8.44 (d, J = 2.3 Hz, 1H), 8.23 (s, 1H), 8.06 (dd, J = 2.3, 8.8 Hz, 1H), 7.60 (d, J = 8.9 Hz, 1H), 6.36 (s, 1H), 5.80 (s, 1H), 5.38 (s, 2H), 5.23 (s, 2H), 3.81 (s, 3H), 2.18 (s, 3H), 2.00 (s, 3H), 1.08 (s, 3H), 0.64-0.55 (m, 2H), 0.43-0.35 (m, 2H) |
| 193 | >95 | $^1$H NMR (300 MHz, DMSO-$d_6$) δ = 8.44 (d, J = 2.3 Hz, 1H), 8.25 (s, 1H), 8.11 (dd, J = 2.3, 8.9 Hz, 1H), 7.85 (d, J = 9.0 Hz, 1H), 4.97 (s, 2H), 4.10 (d, J = 6.9 Hz, 2H), 2.09 (s, 1H), 1.09 (s, 3H), 0.92-0.78 (m, 1H), 0.65-0.56 (m, 2H), 0.56-0.44 (m, 4H), 0.44-0.36 (m, 2H) |
| 194 | >95 | $^1$H NMR (300 MHz, CDCl$_3$) δ = 8.75 (d, J = 2.3 Hz, 1H), 8.25 (dd, J = 2.3, 8.9 Hz, 1H), 7.55 (d, J = 8.9 Hz, 1H), 5.03-4.95 (m, 5H), 2.41 (t, J = 2.4 Hz, 1H), 1.28 (s, 3H), 0.83-0.72 (m, 2H), 0.59-0.50 (m, 2H) |
| 197 | >95 | $^1$H NMR (300 MHz, DMSO-$d_6$) δ = 8.44 (d, J = 2.3 Hz, 1H), 8.24 (s, 1H), 8.11 (dd, J = 2.3, 8.9 Hz, 1H), 7.84 (d, J = 8.9 Hz, 1H), 6.32 (s, 1H), 5.23 (s, 2H), 4.09 (d, J = 6.9 Hz, 2H), 2.18 (s, 3H), 1.30-1.18 (m, 1H), 1.09 (s, 3H), 0.65-0.56 (m, 2H), 0.54-0.35 (m, 6H) |
| 198 | >95 | $^1$H NMR (300 MHz, DMSO-$d_6$) δ = 8.44 (d, J = 2.2 Hz, 1H), 8.17 (dd, J = 2.3, 8.8 Hz, 1H), 7.74 (d, J = 8.9 Hz, 1H), 6.35 (s, 1H), 5.22 (s, 2H), 5.01 (d, J = 2.3 Hz, 2H), 3.46-3.40 (m, 1H), 2.18 (s, 3H), 1.09 (s, 3H), 0.64-0.55 (m, 2H), 0.46-0.36 (m, 2H) |
| 199 | >95 | $^1$H NMR (300 MHz, DMSO-$d_6$) δ = 8.44 (d, J = 2.3 Hz, 1H), 8.22 (br. s., 1H), 8.01 (dd, J = 2.3, 8.9 Hz, 1H), 7.57-7.36 (m, 3H), 7.18 (t, J = 8.9 Hz, 2H), 6.38 (s, 1H), 5.39 (s, 2H), 5.33-5.20 (m, 2H), 2.19 (s, 3H), 1.07 (s, 3H), 0.61-0.52 (m, 2H), 0.43-0.33 (m, 2H) |
| 200 | >95 | $^1$H NMR (300 MHz, DMSO-$d_6$) δ = 8.44 (d, J = 2.3 Hz, 1H), 8.21 (br. s., 1H), 8.01 (dd, J = 2.4, 8.9 Hz, 1H), 7.50 (d, J = 8.9 Hz, 1H), 7.25 (t, J = 7.9 Hz, 1H), 6.96-6.77 (m, 3H), 6.38 (s, 1H), 5.38 (s, 2H), 5.27 (s, 2H), 3.77-3.67 (m, 3H), 2.19 (s, 3H), 1.07 (s, 3H), 0.62-0.53 (m, 2H), 0.43-0.33 (m, 2H) |
| 201 | >95 | $^1$H NMR (300 MHz, DMSO-$d_6$) δ = 8.45 (d, J = 2.3 Hz, 1H), 8.18-8.03 (m, 2H), 7.68 (d, J = 8.9 Hz, 1H), 5.46 (s, 2H), 3.35 (s, 3H), 2.49 (s, 3H), 2.48 (s, 3H), 2.17-2.03 (m, 1H), 0.54-0.43 (m, 2H), 0.42-0.31 (m, 2H) |
| 204 | >95 | $^1$H NMR (300 MHz, DMSO-$d_6$) δ = 9.28 (br. s., 1H), 8.49 (d, J = 2.3 Hz, 1H), 8.17 (dd, J = 2.4, 8.9 Hz, 1H), 7.73 (d, J = 8.9 Hz, 1H), 5.47 (s, 2H), 3.33 (s, 3H), 2.48 (s, 3H), 2.47 (s, 3H), 1.48-1.40 (m, 2H), 1.30-1.24 (m, 2H) |
| 207 | >95 | $^1$H NMR (300 MHz, DMSO-$d_6$) δ = 8.44 (d, J = 2.3 Hz, 1H), 8.23 (s, 1H), 8.06 (dd, J = 2.3, 8.8 Hz, 1H), 7.60 (d, J = 8.9 Hz, 1H), 6.36 (s, 1H), 5.80 (s, 1H), 5.38 (s, 2H), 5.23 (s, 2H), 3.81 (s, 3H), 2.18 (s, 3H), 2.00 (s, 3H), 1.08 (s, 3H), 0.64-0.55 (m, 2H), 0.44-0.36 (m, 2H) |
| 208 | >95 | $^1$H NMR (300 MHz, CDCl$_3$) δ = 8.72 (d, J = 2.3 Hz, 1H), 8.16 (dd, J = 2.3, 8.9 Hz, 1H), 7.50 (d, J = 8.9 Hz, 1H), 6.17 (d, J = 1.0 Hz, 2H), 5.40 (d, J = 11.4 Hz, 4H), 5.02 (s, 1H), 2.28 (d, J = 1.5 Hz, 6H), 1.26 (s, 3H), 0.81-0.73 (m, 2H), 0.57-0.49 (m, 2H) |
| 213 | >95 | $^1$H NMR (300 MHz, DMSO-$d_6$) δ = 8.55 (s, 1H), 8.42 (d, J = 8.0 Hz, 1H), 7.54 (d, J = 12.2 Hz, 1H), 5.78 (s, 1H), 5.34 (s, 2H), 3.33 (s, 6H), 2.02-1.99 (m, 3H), 1.15-1.12 (m, 3H), 0.67-0.60 (m, 2H), 0.47-0.40 (m, 2H) |
| 214 | >95 | $^1$H NMR (300 MHz, DMSO-$d_6$) δ = 11.35 (br. s., 1H), 8.43 (d, J = 2.3 Hz, 1H), 8.19 (s, 1H), 8.07 (d, J = 2.4 Hz, 1H), 7.66 (d, J = 8.9 Hz, 1H), 7.36 (s, 1H), 5.19 (s, 2H), 3.57 (s, 3H), 1.45 (s, 9H), 1.07 (s, 3H), 0.64-0.54 (m, 3H), 0.43-0.34 (m, 2H) |

TABLE 3-continued $^1$H NMR data

| Example | NMR Purity | $^1$H NMR |
|---|---|---|
| 217 | >95 | $^1$H NMR (300 MHz, DMSO-$d_6$) δ = 8.42 (d, J = 2.3 Hz, 1H), 8.08 (dd, J = 2.3, 8.9 Hz, 1H), 7.87 (s, 1H), 7.65 (d, J = 8.9 Hz, 1H), 7.57 (s, 1H), 5.42 (s, 2H), 4.98 (s, 2H), 3.55 (s, 3H), 1.07 (s, 3H), 0.63-0.54 (m, 2H), 0.43-0.33 (m, 2H) |
| 220 | 90-95 | $^1$H NMR (300 MHz, DMSO-$d_6$) δ = 11.98 (s, 1H), 8.32 (d, J = 2.2 Hz, 1H), 8.14 (s, 1H), 8.01 (dd, J = 2.2, 8.6 Hz, 1H), 7.61 (s, 1H), 7.33 (d, J = 8.6 Hz, 1H), 5.19 (s, 2H), 2.59-2.55 (m, 3H), 1.06 (s, 3H), 0.62-0.55 (m, 2H), 0.41-0.34 (m, 2H) |
| 228 | >95 | $^1$H NMR (300 MHz, DMSO-$d_6$) δ = 12.11 (s, 1H), 9.23 (s, 1H), 8.37 (d, J = 2.2 Hz, 1H), 8.09 (dd, J = 2.2, 8.7 Hz, 1H), 7.41 (d, J = 8.7 Hz, 1H), 6.32 (s, 1H), 5.18 (s, 2H), 2.18 (s, 3H), 1.48-1.40 (m, 2H), 1.29-1.22 (m, 2H) |
| 229 | >95 | $^1$H NMR (300 MHz, DMSO-$d_6$) δ = 9.29 (s, 1H), 8.47 (d, J = 2.3 Hz, 1H), 8.17 (dd, J = 2.4, 8.9 Hz, 1H), 7.75 (d, J = 8.9 Hz, 1H), 6.33 (s, 1H), 5.23 (s, 2H), 3.58 (s, 3H), 2.18 (s, 3H), 1.49-1.41 (m, 2H), 1.31-1.21 (m, 2H) |
| 230 | >95 | $^1$H NMR (300 MHz, DMSO-$d_6$) δ = 8.45 (d, J = 2.3 Hz, 1H), 8.24 (s, 1H), 8.04 (dd, J = 2.3, 8.8 Hz, 1H), 7.60 (d, J = 9.0 Hz, 1H), 6.66 (s, 1H), 6.39 (s, 1H), 5.49 (s, 2H), 5.23 (s, 2H), 4.01 (s, 3H), 2.18 (s, 3H), 1.07 (s, 3H), 0.63-0.56 (m, 2H), 0.42-0.35 (m, 2H) |
| 231 | >95 | $^1$H NMR (300 MHz, CDCl$_3$) δ = 8.74 (d, J = 2.2 Hz, 1H), 8.12 (dd, J = 2.3, 8.9 Hz, 1H), 7.77-7.70 (m, 1H), 7.28 (d, J = 8.9 Hz, 1H), 6.28 (s, 1H), 5.39 (d, J = 6.0 Hz, 4H), 5.17 (s, 1H), 4.08 (s, 3H), 2.70-2.60 (m, 3H), 1.25 (s, 3H), 0.81-0.71 (m, 2H), 0.56-0.47 (m, 2H) |
| 232 | 90-95 | $^1$H NMR (300 MHz, DMSO-$d_6$) δ = 8.42 (d, J = 2.4 Hz, 1H), 8.19 (br. s., 1H), 8.08 (dd, J = 2.3, 8.8 Hz, 1H), 7.65 (d, J = 8.9 Hz, 1H), 6.96-6.82 (m, 3H), 5.06 (s, 2H), 3.56 (s, 3H), 1.07 (s, 3H), 0.64-0.53 (m, 2H), 0.45-0.32 (m, 2H) |
| 233 | >95 | $^1$H NMR (300 MHz, DMSO-$d_6$) δ = 8.42 (d, J = 2.3 Hz, 1H), 8.11 (dd, J = 2.4, 8.9 Hz, 1H), 7.69 (d, J = 8.9 Hz, 1H), 5.79 (s, 1H), 5.53 (s, 2H), 5.09 (s, 2H), 3.57 (s, 3H), 1.08 (s, 3H), 0.64-0.55 (m, 2H), 0.43-0.35 (m, 2H) |
| 235 | 90-95 | $^1$H NMR (400 MHz, CDCl$_3$) δ = 8.71 (d, J = 2.1 Hz, 1H), 8.15-8.08 (m, 1H), 7.61 (s, 1H), 7.56-7.51 (m, 1H), 7.36-7.30 (m, 1H), 5.10 (s, 3H), 4.30-4.21 (m, 2H), 3.85 (s, 3H), 2.64-2.54 (m, 2H), 2.35 (s, 6H), 1.24 (s, 3H), 0.80-0.73 (m, 2H), 0.54-0.47 (m, 2H) |
| 237 | >95 | $^1$H NMR (300 MHz, DMSO-$d_6$) δ = 8.41 (d, J = 2.2 Hz, 1H), 8.04 (dd, J = 2.2, 8.9 Hz, 1H), 7.74-7.65 (m, 2H), 7.39 (s, 1H), 4.95 (s, 2H), 4.14 (t, J = 7.3 Hz, 2H), 3.76 (s, 3H), 2.29 (t, J = 6.6 Hz, 2H), 2.16-2.06 (m, 6H), 1.83-1.68 (m, 2H), 1.06 (s, 3H), 0.55 (s, 2H), 0.39-0.30 (m, 2H) |
| 238 | >95 | $^1$H NMR (300 MHz, DMSO-$d_6$) δ = 8.41 (d, J = 2.3 Hz, 1H), 8.18 (br. s., 1H), 8.07 (dd, J = 2.3, 8.9 Hz, 1H), 7.70-7.60 (m, 2H), 7.38 (s, 1H), 4.96 (s, 2H), 4.40-4.15 (m, 2H), 3.76 (s, 3H), 2.87-2.73 (m, 1H), 2.37 (s, 3H), 2.15-2.04 (m, 1H), 1.67-1.16 (m, 7H), 1.08 (s, 3H), 0.61-0.54 (m, 2H), 0.41-0.32 (m, 2H) |
| 239 | >95 | $^1$H NMR (400 MHz, DMSO-$d_6$) δ = 8.42 (d, J = 2.0 Hz, 1H), 8.06 (dd, J = 1.9, 8.9 Hz, 1H), 7.71-7.59 (m, 2H), 7.71-7.59 (m, 2H), 7.39 (s, 1H), 6.07 (br. s., 1H), 4.95 (s, 2H), 4.18 (t, J = 7.0 Hz, 2H), 3.75 (s, 3H), 3.42-3.40 (m, 2H), 3.19 (s, 3H), 1.93-1.79 (m, 2H), 1.07 (s, 3H), 0.66-0.51 (m, 2H), 0.43-0.29 (m, 2H) |
| 243 | >95 | $^1$H NMR (300 MHz, CDCl$_3$) δ = 8.74-8.70 (m, 1H), 8.15-8.07 (m, 1H), 7.35 (d, J = 8.9 Hz, 1H), 6.23-6.08 (m, 1H), 5.53-5.44 (m, 2H), 5.44-5.33 (m, 2H), 5.02-4.90 (m, 1H), 2.58 (s, 3H), 2.27 (s, 3H), 1.26 (s, 3H), 0.80-0.71 (m, 2H), 0.58-0.46 (m, 2H) |
| 246 | >95 | $^1$H NMR (400 MHz, CDCl$_3$) δ = 8.71 (d, J = 2.3 Hz, 1H), 8.15 (dd, J = 2.3, 8.8 Hz, 1H), 7.38 (d, J = 8.9 Hz, 1H), 6.14 (s, 1H), 5.37 (s, 2H), 4.28 (t, J = 7.3 Hz, 2H), 2.61 (t, J = 7.2 Hz, 2H), 2.34 (s, 6H), 2.27 (s, 4H), 1.26 (s, 3H), 0.80-0.75 (m, 2H), 0.55-0.48 (m, 2H) |
| 247 | >95 | $^1$H NMR (400 MHz, CDCl$_3$) δ = 8.70 (d, J = 2.1 Hz, 1H), 8.18-8.12 (m, 1H), 7.53 (d, J = 8.9 Hz, 1H), 6.15 (s, 1H), 5.38-5.33 (m, 2H), 4.23 (t, J = 7.5 Hz, 2H), 2.38 (t, J = 6.6 Hz, 2H), 2.29-2.23 (m, 10H), 1.96-1.82 (m, 2H), 1.24 (s, 3H), 0.80-0.72 (m, 2H), 0.52-0.46 (m, 2H) |
| 249 | >95 | $^1$H NMR (400 MHz, CDCl$_3$) δ = 8.71 (d, J = 2.3 Hz, 1H), 8.14 (dd, J = 2.3, 8.9 Hz, 1H), 7.55 (d, J = 8.9 Hz, 1H), 6.14 (s, 1H), 5.38 (s, 2H), 4.96 (s, 1H), 4.31 (dd, J = 7.2, 14.4 Hz, 1H), 4.09 (dd, J = 5.6, 14.4 Hz, 1H), 3.10 (t, J = 7.1 Hz, 1H), 2.78 (t, J = 6.3 Hz, 1H), 2.38 (s, 3H), 2.34-2.23 (m, 4H), 1.95-1.79 (m, 2H), 1.78-1.69 (m, 2H), 1.26 (s, 3H), 0.80-0.74 (m, 2H), 0.55-0.48 (m, 2H) |
| 250 | >95 | $^1$H NMR (400 MHz, CDCl$_3$) δ = 8.72 (d, J = 2.1 Hz, 1H), 8.15 (dd, J = 2.2, 8.8 Hz, 1H), 7.41-7.28 (m, 1H), 6.15 (s, 1H), 5.36 (s, 2H), 4.22-4.08 (m, 2H), 3.40 (br. s., 2H), 2.92 (s, 3H), 2.27 (s, 3H), 2.04-1.89 (m, 2H), 1.58 (s, 2H), 1.25 (s, 3H), 0.82-0.70 (m, 2H), 0.57-0.44 (m, 2H) |
| 251 | >95 | $^1$H NMR (400 MHz, CDCl$_3$) δ = 8.71 (d, J = 2.3 Hz, 1H), 8.16 (dd, J = 2.4, 8.9 Hz, 1H), 7.48 (d, J = 8.9 Hz, 1H), 6.15 (s, 1H), 5.36 (s, 2H), 5.00 (br. s., 1H), 4.33-4.20 (m, 2H), 3.47 (t, J = 5.5 Hz, 2H), 3.39-3.31 (m, 3H), 2.32-2.20 (m, 3H), 2.01 (dd, J = 6.0, 8.2 Hz, 2H), 1.25 (s, 3H), 0.80-0.73 (m, 2H), 0.54-0.47 (m, 2H) |
| 252 | >95 | $^1$H NMR (300 MHz, CDCl$_3$) δ = 8.74 (d, J = 2.3 Hz, 1H), 8.14 (dd, J = 2.2, 8.9 Hz, 1H), 7.22 (d, J = 8.8 Hz, 1H), 6.17 (s, 1H), 5.58 (s, 2H), 5.39 (s, 2H), 4.95 (s, 1H), 2.38 (s, 3H), 2.28 (s, 3H), 1.26 (s, 3H), 0.80-0.72 (m, 2H), 0.57-0.48 (m, 2H) |
| 253 | >95 | $^1$H NMR (300 MHz, DMSO-$d_6$) δ = 8.64 (d, J = 2.1 Hz, 1H), 8.42 (br. s., 1H), 8.33 (d, J = 8.6 Hz, 1H), 8.26 (dd, J = 2.0, 8.6 Hz, 1H), 6.98 (t, J = 5.4 Hz, 1H), 6.31 (s, 1H), 5.28 (s, 2H), 3.35-3.42 (m, 1H), 2.46 (t, J = 7.1 Hz, 2H), 2.19 (s, 3H), 2.16 (s, 6H), 1.09 (t, J = 7.0 Hz, 1H), 1.05 (s, 3H), 0.62-0.56 (m, 2H), 0.48-0.37 (m, 2H) |
| 257 | >95 | $^1$H NMR (300 MHz, DMSO-$d_6$) δ = 8.43 (s, 1H), 8.41 (d, J = 2.3 Hz, 1H), 8.03 (dd, J = 2.3, 9.0 Hz, 1H), 7.74 (d, J = 9.0 Hz, 1H), 7.67 (s, 1H), 7.39 (s, 1H), 4.95 (s, 2H), 4.25-4.07 (m, 2H), 3.79 (br. s., 1H), 3.76 (s, 3H), 3.29-3.14 (m, 2H), 1.84-1.63 (m, 2H), 1.44 (d, J = 3.5 Hz, 4H), 1.07 (s, 3H), 0.66-0.52 (m, 2H), 0.42-0.36 (m, 2H) |

TABLE 3-continued

<sup>1</sup>H NMR data

| Example | NMR Purity | <sup>1</sup>H NMR |
|---|---|---|
| 258 | >95 | <sup>1</sup>H NMR (300 MHz, DMSO-d$_6$) δ = 8.41 (d, J = 2.4 Hz, 1H), 8.34 (s, 1H), 8.03 (dd, J = 2.4, 8.9 Hz, 1H), 7.77 (d, J = 9.0 Hz, 1H), 7.67 (s, 1H), 7.39 (s, 1H), 4.96 (s, 2H), 4.29-4.12 (m, 3H), 3.76 (s, 3H), 3.80-3.72 (m, 1H), 3.65-3.53 (m, 1H), 2.04-1.76 (m, 3H), 1.74-1.65 (m, 1H), 1.07 (s, 3H), 0.69-0.52 (m, 2H), 0.43-0.36 (m, 2H) |
| 259 | >95 | <sup>1</sup>H NMR (300 MHz, DMSO-d$_6$) δ = 8.43 (d, J = 2.4 Hz, 1H), 8.21 (br. s., 1H), 8.04 (dd, J = 2.3, 8.9 Hz, 1H), 7.74 (d, J = 8.9 Hz, 1H), 7.67 (s, 1H), 7.39 (s, 1H), 4.96 (s, 2H), 4.22-4.15 (m, 2H), 3.89-3.78 (m, 1H), 3.76 (s, 3H), 3.71-3.58 (m, 2H), 3.52 (dd, J = 5.5, 8.6 Hz, 1H), 2.74-2.59 (m, 1H), 1.96 (dd, J = 5.6, 12.3 Hz, 1H), 1.75-1.61 (m, 1H), 1.08 (s, 3H), 0.64-0.55 (m, 2H), 0.43-0.36 (m, 2H) |
| 263 | >95 | <sup>1</sup>H NMR (300 MHz, DMSO-d$_6$) δ = 8.45 (d, J = 2.3 Hz, 1H), 8.24 (s, 1H), 8.08-8.02 (m, 3H), 7.81 (d, J = 9.0 Hz, 1H), 7.69 (s, 1H), 7.42 (s, 1H), 4.96 (s, 2H), 4.42 (t, J = 6.2 Hz, 2H), 3.77 (s, 3H), 3.11 (d, J = 5.2 Hz, 2H), 1.08 (s, 3H), 0.61-0.56 (m, 2H), 0.43-0.38 (m, 2H) |
| 264 | >95 | <sup>1</sup>H NMR (300 MHz, DMSO-d$_6$) δ = 8.43 (d, J = 2.4 Hz, 1H), 8.40 (s, 1H), 8.05 (dd, J = 2.3, 8.9 Hz, 1H), 7.71 (d, J = 8.9 Hz, 1H), 7.67 (s, 1H), 7.39 (s, 1H), 4.95 (s, 2H), 4.29-4.16 (m, 4H), 3.75 (s, 3H), 2.09-1.99 (m, 2H), 1.07 (s, 3H), 0.59 (s, 2H), 0.39 (d, J = 2.0 Hz, 2H) |
| 265 | >95 | <sup>1</sup>H NMR (300 MHz, DMSO-d$_6$) δ = 8.44 (d, J = 2.2 Hz, 1H), 8.36 (s, 1H), 8.01 (dd, J = 2.3, 8.9 Hz, 1H), 7.67 (s, 1H), 7.49 (d, J = 8.9 Hz, 1H), 7.38 (s, 1H), 5.08 (s, 2H), 4.95 (s, 2H), 3.76 (s, 3H), 3.13 (s, 3H), 2.85 (s, 3H), 1.07 (s, 3H), 0.62-0.52 (m, 2H), 0.47-0.35 (m, 2H) |
| 266 | >95 | <sup>1</sup>H NMR (300 MHz, DMSO-d$_6$) δ = 8.41 (d, J = 2.3 Hz, 1H), 8.22 (br. s., 1H), 8.07 (dd, J = 2.4, 8.9 Hz, 1H), 7.79 (d, J = 8.9 Hz, 1H), 6.31 (s, 1H), 5.22 (s, 2H), 4.25-4.09 (m, 2H), 3.83-3.57 (m, 2H), 3.29-3.19 (m, 1H), 2.18 (s, 3H), 1.82-1.60 (m, 3H), 1.48-1.38 (m, 3H), 1.09 (s, 3H), 0.65-0.57 (m, 2H), 0.43-0.38 (m, 2H) |
| 267 | >95 | <sup>1</sup>H NMR (300 MHz, DMSO-d$_6$) δ = 8.42 (d, J = 2.3 Hz, 1H), 8.38 (s, 1H), 8.07 (dd, J = 2.4, 8.9 Hz, 1H), 7.82 (d, J = 9.0 Hz, 1H), 6.31 (s, 1H), 5.23 (s, 2H), 4.27-4.12 (m, 3H), 3.83-3.51 (m, 3H), 2.18 (s, 3H), 2.04-1.60 (m, 4H), 1.09 (s, 3H), 0.67-0.54 (m, 2H), 0.46-0.34 (m, 2H) |
| 268 | >95 | <sup>1</sup>H NMR (300 MHz, DMSO-d$_6$) δ = 8.43 (d, J = 2.3 Hz, 1H), 8.23 (br. s., 1H), 8.09 (dd, J = 2.3, 8.9 Hz, 1H), 7.79 (d, J = 8.9 Hz, 1H), 6.33 (s, 1H), 5.22 (s, 2H), 4.19 (d, J = 6.4 Hz, 2H), 3.87-3.76 (m, 1H), 3.71-3.48 (m, 3H), 2.72-2.60 (m, 1H), 2.18 (s, 3H), 2.08-1.92 (m, J = 5.5, 12.6 Hz, 1H), 1.76-1.62 (m, J = 6.5, 13.6 Hz, 1H), 1.10 (s, 3H), 0.68-0.54 (m, 2H), 0.43-0.38 (m, 2H) |
| 269 | >95 | <sup>1</sup>H NMR (300 MHz, DMSO-d$_6$) δ = 8.42 (d, J = 2.4 Hz, 1H), 8.21 (s, 1H), 8.03 (dd, J = 2.3, 8.9 Hz, 1H), 7.73 (d, J = 8.9 Hz, 1H), 7.67 (s, 1H), 7.38 (s, 1H), 4.95 (s, 2H), 4.06 (d, J = 7.3 Hz, 2H), 3.86-3.78 (m, 2H), 3.75 (s, 3H), 3.26-3.16 (m, 2H), 2.31-2.22 (m, 1H), 1.56 (d, J = 12.6 Hz, 2H), 1.35 (dt, J = 8.0, 12.1 Hz, 2H), 1.08 (s, 3H), 0.65-0.56 (m, 2H), 0.43-0.35 (m, 2H) |
| 270 | 90-95 | <sup>1</sup>H NMR (400 MHz, CDCl$_3$) δ = 8.69 (d, J = 2.3 Hz, 1H), 8.08 (dd, J = 2.3, 8.9 Hz, 1H), 7.62 (s, 1H), 7.55 (s, 1H), 7.52 (d, J = 8.9 Hz, 1H), 5.11 (s, 2H), 5.02 (s, 1H), 4.34 (t, J = 5.4 Hz, 2H), 3.85 (s, 3H), 3.73 (t, J = 5.3 Hz, 2H), 3.33 (s, 3H), 1.25 (s, 3H), 0.81-0.73 (m, 2H), 0.54-0.47 (m, 2H) |
| 271 | >95 | <sup>1</sup>H NMR (400 MHz, CDCl$_3$) δ = 8.72 (d, J = 2.3 Hz, 1H), 8.12 (dd, J = 2.3, 8.9 Hz, 1H), 7.61 (s, 1H), 7.55 (s, 1H), 7.33 (d, J = 8.9 Hz, 1H), 5.10 (s, 2H), 5.09 (s, 1H), 4.29 (t, J = 7.0 Hz, 2H), 3.85 (s, 3H), 3.73-3.64 (m, 4H), 2.66 (t, J = 7.1 Hz, 2H), 2.61-2.52 (m, 4H), 1.25 (s, 3H), 0.81-0.73 (m, 2H), 0.54-0.48 (m, 2H) |
| 272 | >95 | <sup>1</sup>H NMR (400 MHz, CDCl$_3$) δ = 8.71 (d, J = 2.3 Hz, 1H), 8.11 (dd, J = 2.3, 8.8 Hz, 1H), 7.62 (s, 1H), 7.55 (s, 1H), 7.36 (d, J = 8.9 Hz, 1H), 5.10 (s, 2H), 4.97 (s, 1H), 4.34-4.25 (m, 2H), 3.85 (s, 3H), 2.82-2.74 (m, 2H), 2.69-2.60 (m, 4H), 1.87-1.76 (m, 4H), 1.25 (s, 3H), 0.83-0.71 (m, 2H), 0.58-0.45 (m, 2H) |
| 273 | >95 | <sup>1</sup>H NMR (400 MHz, CDCl$_3$) δ = 8.71 (d, J = 2.1 Hz, 1H), 8.12 (dd, J = 2.3, 8.9 Hz, 1H), 7.60 (s, 1H), 7.55 (s, 1H), 7.52 (d, J = 8.9 Hz, 1H), 5.75 (br. s., 1H), 5.52 (br. s., 1H), 5.20 (s, 1H), 5.09 (s, 2H), 4.53-4.44 (m, 2H), 3.85 (s, 3H), 2.74-2.66 (m, 2H), 1.24 (s, 3H), 0.83-0.70 (m, 2H), 0.57-0.45 (m, 2H) |
| 274 | 90-95 | <sup>1</sup>H NMR (400 MHz, CDCl$_3$) δ = 8.70 (d, J = 2.3 Hz, 1H), 8.12 (dd, J = 2.3, 9.0 Hz, 1H), 7.57 (d, J = 9.0 Hz, 1H), 6.16 (s, 1H), 5.38 (s, 2H), 5.00 (s, 1H), 4.36 (t, J = 5.3 Hz, 2H), 3.76-3.73 (m, 2H), 3.33 (s, 3H), 2.28 (s, 3H), 1.26 (s, 3H), 0.81-0.77 (m, 2H), 0.54-0.51 (m, 2H) |
| 275 | >95 | <sup>1</sup>H NMR (400 MHz, CDCl$_3$) δ = 8.71 (d, J = 2.3 Hz, 1H), 8.15 (dd, J = 2.3, 8.9 Hz, 1H), 7.43 (d, J = 9.0 Hz, 1H), 6.13 (s, 1H), 5.37 (s, 2H), 5.00 (br. s., 1H), 4.41-4.26 (m, 2H), 2.95-2.87 (m, 1H), 2.53-2.50 (m, 1H), 2.49 (s, 3H), 2.27 (s, 3H), 2.25-2.21 (m, 1H), 1.83-1.63 (m, 2H), 1.57-1.54 (m, 1H), 1.51-1.42 (m, 1H), 1.42-1.31 (m, 1H), 1.27 (s, 3H), 1.22-1.14 (m, 1H), 0.84-0.73 (m, 2H), 0.58-0.48 (m, 2H) |
| 276 | >95 | <sup>1</sup>H NMR (400 MHz, CDCl$_3$) δ = 8.71 (d, J = 2.3 Hz, 1H), 8.16 (dd, J = 2.3, 8.8 Hz, 1H), 7.38 (d, J = 8.9 Hz, 1H), 6.15 (s, 1H), 5.36 (s, 2H), 5.23 (s, 1H), 4.31 (t, J = 6.8 Hz, 2H), 3.72-3.62 (m, 4H), 2.68 (t, J = 6.9 Hz, 2H), 2.60-2.50 (m, 4H), 2.27 (s, 3H), 1.25 (s, 3H), 0.83-0.71 (m, 2H), 0.57-0.46 (m, 2H) |
| 277 | >95 | <sup>1</sup>H NMR (400 MHz, CDCl$_3$) δ = 8.70 (d, J = 2.3 Hz, 1H), 8.15 (dd, J = 2.3, 8.8 Hz, 1H), 7.58 (d, J = 8.9 Hz, 1H), 6.16 (s, 1H), 5.76 (br. s., 1H), 5.50 (br. s., 1H), 5.35 (s, 2H), 5.19 (s, 1H), 4.55-4.45 (m, 2H), 2.76-2.68 (m, 2H), 2.27 (s, 3H), 1.24 (s, 3H), 0.85-0.69 (m, 2H), 0.57-0.46 (m, 2H) |
| 279 | >95 | <sup>1</sup>H NMR (300 MHz, DMSO-d$_6$) δ = 8.42 (d, J = 2.3 Hz, 1H), 8.20 (br. s., 1H), 8.04 (dd, J = 2.3, 8.9 Hz, 1H), 7.72 (d, J = 9.0 Hz, 1H), 7.67 (s, 1H), 7.38 (s, 1H), 4.96 (s, 2H), 4.13 (d, J = 7.5 Hz, 2H), 3.76 (s, 3H), 2.39-2.24 (m, 1H), 1.66 (br. s., 2H), 1.55-1.43 (m, 2H), |

TABLE 3-continued

<sup>1</sup>H NMR data

| Example | NMR Purity | <sup>1</sup>H NMR |
|---|---|---|
| | | 1.34 (d, J = 7.2 Hz, 2H), 1.24 (s, 1H), 1.16 (s, 1H), 1.08 (s, 3H), 0.70-0.52 (m, 2H), 0.42-0.36 (m, 2H) |
| 280 | >95 | $^1$H NMR (300 MHz, DMSO-$d_6$) δ = 8.42 (d, J = 2.4 Hz, 1H), 8.20 (s, 1H), 8.03 (dd, J = 2.3, 8.9 Hz, 1H), 7.70-7.65 (m, 2H), 7.38 (s, 1H), 4.95 (s, 2H), 4.01 (d, J = 7.1 Hz, 2H), 3.75 (s, 3H), 1.66 (br. s., 6H), 1.23-1.01 (m, 8H), 0.64-0.55 (m, 2H), 0.42-0.35 (m, 2H) |
| 281 | >95 | $^1$H NMR (300 MHz, DMSO-$d_6$) δ = 8.41 (d, J = 2.3 Hz, 1H), 8.20 (s, 1H), 8.03 (dd, J = 2.3, 8.9 Hz, 1H), 7.71-7.66 (m, 2H), 7.38 (s, 1H), 4.95 (s, 2H), 4.22 (d, J = 7.0 Hz, 2H), 3.76 (s, 3H), 2.06-1.90 (m, 2H), 1.90-1.76 (m, 5H), 1.07 (s, 3H), 0.64-0.56 (m, 2H), 0.41-0.36 (m, 2H) |
| 285 | >95 | $^1$H NMR (300 MHz, DMSO-$d_6$) δ = 8.45 (d, J = 2.3 Hz, 1H), 8.23 (br. s., 1H), 8.06 (dd, J = 2.4, 8.9 Hz, 1H), 7.60 (d, J = 8.9 Hz, 1H), 5.82 (s, 1H), 5.78 (s, 1H), 5.55 (s, 2H), 5.39 (s, 2H), 5.10 (s, 2H), 3.82 (s, 3H), 2.00 (s, 3H), 1.08 (s, 3H), 0.62-0.58 (m, 2H), 0.43-0.38 (m, 2H) |
| 288 | >95 | $^1$H NMR (300 MHz, DMSO-$d_6$) δ = 8.42 (d, J = 2.3 Hz, 1H), 8.23 (s, 1H), 8.07 (dd, J = 2.3, 8.9 Hz, 1H), 7.73 (d, J = 8.9 Hz, 1H), 6.31 (s, 1H), 5.22 (s, 2H), 4.23 (d, J = 7.1 Hz, 2H), 2.80-2.54 (m, 1H), 2.17 (s, 3H), 2.03-1.91 (m, 2H), 1.89-1.72 (m, 4H), 1.09 (s, 3H), 0.69-0.52 (m, 2H), 0.46-0.35 (m, 2H) |
| 289 | >95 | $^1$H NMR (300 MHz, DMSO-$d_6$) δ = 8.43 (d, J = 2.3 Hz, 1H), 8.24 (s, 1H), 8.08 (dd, J = 2.3, 8.9 Hz, 1H), 7.77 (d, J = 8.9 Hz, 1H), 6.31 (s, 1H), 5.23 (s, 2H), 4.14 (d, J = 7.6 Hz, 2H), 2.38-2.24 (m, 1H), 2.17 (s, 3H), 1.66 (br. s., 4H), 1.48 (d, J = 4.1 Hz, 2H), 1.32 (d, J = 6.0 Hz, 2H), 1.09 (s, 3H), 0.64-0.57 (m, 2H), 0.44-0.38 (m, 2H) |
| 290 | >95 | $^1$H NMR (300 MHz, DMSO-$d_6$) δ = 8.42 (d, J = 2.3 Hz, 1H), 8.37 (s, 1H), 8.07 (dd, J = 2.3, 8.9 Hz, 1H), 7.72 (d, J = 9.0 Hz, 1H), 6.31 (s, 1H), 5.22 (s, 2H), 4.02 (d, J = 7.1 Hz, 2H), 2.17 (s, 3H), 1.72-1.57 (m, 5H), 1.20-1.00 (m, 9H), 0.64-0.54 (m, 2H), 0.43-0.38 (m, 2H) |
| 291 | >95 | $^1$H NMR (300 MHz, DMSO-$d_6$) δ = 8.43 (d, J = 2.3 Hz, 1H), 8.20 (s, 1H), 8.06 (dd, J = 2.3, 8.9 Hz, 1H), 7.70 (d, J = 9.0 Hz, 1H), 7.67 (s, J = 6.5, 6.5 Hz, 1H), 7.39 (s, 1H), 4.95 (s, 2H), 4.17 (q, J = 6.9 Hz, 2H), 3.76 (s, 3H), 1.23 (t, J = 7.0 Hz, 3H), 1.07 (s, 3H), 0.59 (s, 2H), 0.39 (d, J = 2.0 Hz, 2H) |
| 292 | >95 | $^1$H NMR (300 MHz, DMSO-$d_6$) δ = 8.43 (d, J = 2.4 Hz, 1H), 8.03 (dd, J = 2.4, 9.0 Hz, 1H), 7.84 (d, J = 9.1 Hz, 1H), 7.67 (s, 1H), 7.39 (d, J = 0.7 Hz, 1H), 5.14-4.97 (m, 1H), 4.93 (s, 2H), 3.76 (s, 3H), 2.54 (s, 1H), 1.53 (d, J = 6.8 Hz, 6H), 1.08 (s, 3H), 0.63-0.57 (m, 2H), 0.42-0.37 (m, 2H) |
| 293 | >95 | $^1$H NMR (300 MHz, DMSO-$d_6$) δ = 8.43 (d, J = 2.4 Hz, 1H), 8.18 (br. s, 1H), 8.03 (dd, J = 2.4, 9.0 Hz, 1H), 7.84 (d, J = 9.1 Hz, 1H), 7.67 (s, 1H), 7.39 (d, J = 0.7 Hz, 1H), 5.07 (br. s, 1H), 4.93 (s, 2H), 3.76 (s, 3H), 1.54 (s, 3H), 1.52 (s, 3H), 1.08 (s, 3H), 0.63-0.57 (m, 2H), 0.42-0.37 (m, 2H) |
| 294 | >95 | $^1$H NMR (300 MHz, DMSO-$d_6$) δ = 8.44 (d, J = 2.4 Hz, 1H), 8.38 (s, 1H), 8.01 (dd, J = 2.3, 8.9 Hz, 1H), 7.73-7.66 (m, 2H), 7.39 (s, 1H), 4.96 (s, 2H), 4.54 (d, J = 6.0 Hz, 2H), 4.24 (s, 2H), 4.08 (d, J = 6.2 Hz, 2H), 3.76 (s, 3H), 1.37 (s, 3H), 1.06 (s, 3H), 0.66-0.51 (m, 2H), 0.45-0.32 (m, 2H) |
| 295 | >95 | $^1$H NMR (300 MHz, DMSO-$d_6$) δ = 8.43 (d, J = 2.3 Hz, 1H), 8.20-8.09 (m, 1H), 8.03 (dd, J = 2.3, 8.9 Hz, 1H), 7.73-7.65 (m, 2H), 7.38 (s, 1H), 4.96 (s, 2H), 4.00 (d, J = 7.5 Hz, 2H), 3.75 (s, 3H), 2.16-2.01 (m, 1H), 1.07 (s, 3H), 0.92 (d, J = 6.7 Hz, 6H), 0.68-0.51 (m, 2H), 0.47-0.31 (m, 2H) |
| 296 | >95 | $^1$H NMR (300 MHz, DMSO-$d_6$) δ = 8.40 (d, J = 2.3 Hz, 1H), 8.16 (s, 1H), 8.02 (dd, J = 2.4, 8.8 Hz, 1H), 7.68 (d, J = 9.0 Hz, 1H), 7.65 (s, 1H), 7.36 (s, 1H), 4.93 (s, 2H), 4.20 (t, J = 7.5 Hz, 2H), 3.73 (s, 3H), 1.52 (d, J = 6.9 Hz, 3H), 1.04 (s, 3H), 0.60-0.53 (m, 2H), 0.38-0.29 (m, 4H), −0.01 (d, J = 4.9 Hz, 2H) |
| 297 | >95 | $^1$H NMR (300 MHz, DMSO-$d_6$) δ = 8.41 (d, J = 2.3 Hz, 1H), 8.37 (s, 1H), 8.02 (d, J = 8.9 Hz, 1H), 7.73-7.66 (m, 2H), 7.39 (s, 1H), 4.95 (s, 2H), 4.61 (dd, J = 6.2, 7.8 Hz, 2H), 4.52-4.44 (m, 4H), 3.76 (s, 3H), 3.44-3.39 (m, 1H), 1.07 (s, 3H), 0.59 (s, 2H), 0.42-0.37 (m, 2H) |
| 300 | 85-90 | $^1$H NMR (300 MHz, DMSO-$d_6$) δ = 8.42 (d, J = 2.3 Hz, 1H), 8.20 (s, 1H), 8.00 (dd, J = 2.3, 8.9 Hz, 1H), 7.73 (d, J = 9.0 Hz, 1H), 7.67 (s, 1H), 7.64 (s, 1H), 7.40 (d, J = 5.3 Hz, 1H), 4.96 (s, 2H), 4.29 (dd, J = 9.3, 14.3 Hz, 1H), 4.17-4.05 (m, 1H), 3.98 (br. s., 1H), 3.76 (s, 3H), 2.19-2.01 (m, 2H), 1.93-1.68 (m, 2H), 1.09 (s, 3H), 0.66-0.52 (m, 2H), 0.42-0.36 (m, 2H) |
| 304 | >95 | $^1$H NMR (300 MHz, DMSO-$d_6$) δ = 8.43 (d, J = 2.3 Hz, 1H), 8.23 (br. s., 1H), 8.10 (dd, J = 2.2, 8.9 Hz, 1H), 7.75 (d, J = 8.9 Hz, 1H), 6.33 (s, 1H), 5.22 (s, 2H), 4.18 (s, 2H), 2.18 (s, 3H), 1.24 (t, J = 7.0 Hz, 3H), 1.09 (s, 3H), 0.60 (s, 2H), 0.41 (d, J = 2.0 Hz, 2H) |
| 305 | >95 | $^1$H NMR (300 MHz, DMSO-$d_6$) δ = 8.42 (d, J = 2.3 Hz, 1H), 8.36 (s, 1H), 8.06 (dd, J = 2.4, 8.9 Hz, 1H), 7.76 (d, J = 9.0 Hz, 1H), 6.33 (s, 1H), 5.21 (s, 2H), 4.61 (dd, J = 6.1, 7.8 Hz, 2H), 4.53-4.42 (m, 4H), 3.45-3.39 (m, 1H), 2.18 (s, 3H), 1.09 (s, 3H), 0.60 (s, 2H), 0.43-0.38 (m, 2H) |
| 306 | 85-90 | $^1$H NMR (300 MHz, DMSO-$d_6$) δ = 8.64 (d, J = 2.1 Hz, 1H), 8.45-8.39 (m, 2H), 8.26 (dd, J = 1.9, 8.5 Hz, 1H), 6.78 (d, J = 6.8 Hz, 1H), 6.32 (s, 1H), 5.28 (s, 2H), 3.93-3.84 (m, 2H), 3.84-3.70 (m, 1H), 3.43-3.36 (m, 2H), 2.19 (s, 3H), 1.97-1.87 (m, 2H), 1.60-1.44 (m, 2H), 1.05 (s, 3H), 0.62-0.57 (m, 2H), 0.44-0.39 (m, 2H) |
| 308 | >95 | $^1$H NMR (300 MHz, DMSO-$d_6$) δ = 8.66 (d, J = 1.6 Hz, 1H), 8.46 (br. s, 1H), 8.30 (d, J = 8.5 Hz, 1H), 8.26 (dd, J = 1.9, 8.6 Hz, 1H), 6.33 (s, 1H), 5.43 (s, 2H), 3.85-3.76 (m, 2H), 3.30-3.18 (m, 2H), 2.90 (d, J = 6.8 Hz, 2H), 2.19 (s, 3H), 2.06-1.92 (m, 1H), 1.64-1.54 (m, 2H), 1.36-1.22 (m, 2H), 1.08 (s, 3H), 0.63-0.56 (m, 2H), 0.45-0.39 (m, 2H) |
| 310 | >95 | $^1$H NMR (300 MHz, DMSO-$d_6$) δ = 8.68 (d, J = 1.8 Hz, 1H), 8.45 (br. s., 1H), 8.34 (d, J = 9.1 Hz, 1H), 8.27 (dd, J = 2.3, 9.4 Hz, 1H), 6.32 (s, 1H), 5.44 (s, 2H), 3.62 (spt, J = 6.8 Hz, |

TABLE 3-continued

¹H NMR data

| Example | NMR Purity | ¹H NMR |
|---|---|---|
| | | 1H), 2.19 (s, 3H), 1.28 (d, J = 6.7 Hz, 6H), 1.07 (s, 3H), 0.63-0.56 (m, 2H), 0.45-0.39 (m, 2H) |
| 313 | >95 | ¹H NMR (300 MHz, DMSO-d₆) δ = 8.55 (d, J = 1.6 Hz, 1H), 8.41 (d, J = 8.7 Hz, 1H), 8.21 (dd, J = 2.0, 8.5 Hz, 1H), 6.20 (s, 1H), 5.28 (s, 2H), 2.09 (s, 3H), 0.97 (s, 3H), 0.94-0.88 (m, 2H), 0.85-0.80 (m, 2H), 0.53-0.47 (m, 2H), 0.35-0.29 (m, 2H) |
| 317 | 90-95 | ¹H NMR (300 MHz, CDCl₃) δ = 8.90 (dd, J = 0.7, 1.9 Hz, 1H), 8.33 (dd, J = 1.9, 8.4 Hz, 1H), 8.16 (dd, J = 0.7, 8.3 Hz, 1H), 6.15 (s, 1H), 5.64-5.55 (m, 1H), 5.32 (s, 2H), 5.22 (s, 1H), 5.04-4.96 (m, 2H), 4.83-4.76 (m, 2H), 2.29 (s, 3H), 1.25 (s, 3H), 0.81-0.74 (m, 2H), 0.57-0.51 (m, 2H) |
| 318 | >95 | ¹H NMR (300 MHz, CDCl₃) δ = 8.96 (d, J = 2.0 Hz, 1H), 8.29 (dd, J = 2.1, 8.5 Hz, 1H), 7.98 (d, J = 8.4 Hz, 1H), 6.15 (s, 1H), 5.48 (s, 2H), 5.03 (s, 1H), 2.89 (d, J = 6.9 Hz, 2H), 2.28 (s, 3H), 1.26 (s, 3H), 1.24-1.19 (m, 1H), 0.81-0.75 (m, 2H), 0.62-0.51 (m, 4H), 0.34-0.27 (m, 2H) |
| 321 | >95 | ¹H NMR (300 MHz, DMSO-d₆) δ = 8.42 (d, J = 2.4 Hz, 1H), 8.24 (br. s, 1H), 8.07 (dd, J = 2.3, 8.9 Hz, 1H), 7.78 (d, J = 8.9 Hz, 1H), 6.32 (s, 1H), 5.22 (s, 2H), 4.07 (d, J = 7.2 Hz, 2H), 3.89-3.77 (m, 2H), 3.30-3.17 (m, 2H), 2.37-2.26 (m, 2H), 2.17 (s, 3H), 1.60 (s, 2H), 1.42-1.26 (m, 2H), 1.10 (s, 3H), 0.67-0.54 (m, 2H), 0.45-0.37 (m, 2H) |
| 323 | >95 | ¹H NMR (300 MHz, DMSO-d₆) δ = 8.44 (d, J = 2.2 Hz, 1H), 8.24 (s, 1H), 8.03 (dd, J = 2.3, 8.9 Hz, 1H), 7.54 (d, J = 8.9 Hz, 1H), 6.29 (s, 1H), 5.20 (d, J = 13.7 Hz, 4H), 2.32 (s, 3H), 2.18 (s, 3H), 1.08 (s, 3H), 0.60 (m, 2H), 0.41 (m, 2H) |
| 324 | >95 | ¹H NMR (300 MHz, DMSO-d₆) δ = 8.44 (d, J = 2.3 Hz, 1H), 8.26 (s, 1H), 8.10 (dd, J = 2.3, 8.9 Hz, 1H), 7.85 (d, J = 8.9 Hz, 1H), 6.35 (s, 2H), 5.23 (s, 2H), 4.78-4.58 (m, 2H), 2.18 (s, 3H), 0.60 (m, 2H), 0.46-0.36 (m, 2H) |
| 325 | >95 | ¹H NMR (300 MHz, DMSO-d₆) δ = 8.45 (d, J = 2.4 Hz, 1H), 8.27 (s, 1H), 8.13 (dd, J = 2.3, 8.9 Hz, 1H), 7.89 (d, J = 8.9 Hz, 1H), 6.35 (s, 1H), 5.23 (s, 2H), 5.14 (q, J = 8.9 Hz, 2H), 2.21-2.14 (m, 3H), 1.12-1.06 (m, 3H), 0.66-0.54 (m, 2H), 0.46-0.36 (m, 2H) |
| 328 | 90-95 | ¹H NMR (300 MHz, DMSO-d₆) δ = 8.40 (d, J = 2.3 Hz, 1H), 8.04 (dd, J = 2.4, 8.9 Hz, 1H), 7.78-7.64 (m, 3H), 7.46 (s, 1H), 7.40 (s, 1H), 5.16 (s, 2H), 4.96 (s, 2H), 3.77 (s, 3H), 3.73 (s, 3H), 1.04 (s, 3H), 0.55 (m, 2H), 0.37 (m, 2H) |
| 329 | >95 | ¹H NMR (300 MHz, DMSO-d₆) δ = 8.44 (d, J = 2.3 Hz, 1H), 8.40 (br. s., 1H), 8.06 (dd, J = 2.3, 8.9 Hz, 1H), 7.79 (d, J = 8.9 Hz, 1H), 7.68 (s, 1H), 7.39 (s, 1H), 4.97 (s, 2H), 4.46-4.28 (m, 2H), 3.76 (s, 3H), 1.78-1.64 (m, 1H), 1.43-1.31 (m, 1H), 1.09-1.06 (m, 6H), 0.62-0.56 (m, 2H), 0.42-0.36 (m, 2H) |
| 330 | 90-95 | ¹H NMR (300 MHz, DMSO-d₆) δ = 8.45-8.36 (m, 3H), 8.07 (dd, J = 2.3, 8.9 Hz, 1H), 7.80 (d, J = 8.9 Hz, 1H), 7.73 (s, 1H), 7.48 (d, J = 0.7 Hz, 1H), 6.35 (s, 1H), 5.24 (s, 2H), 5.20 (s, 2H), 3.76 (s, 3H), 2.18 (s, 3H), 1.08 (s, 3H), 0.59 (m, 2H), 0.40 (m, 2H) |
| 332 | >95 | ¹H NMR (300 MHz, DMSO-d₆) δ = 8.45 (d, J = 2.3 Hz, 1H), 8.26 (s, 1H), 8.09 (dd, J = 2.3, 8.9 Hz, 1H), 7.68 (d, J = 8.9 Hz, 1H), 6.30 (s, 1H), 5.24 (s, 2H), 5.03 (s, 2H), 4.18 (q, J = 7.1 Hz, 2H), 2.18 (s, 3H), 1.21 (t, J = 7.1 Hz, 3H), 1.08 (s, 3H), 0.65-0.55 (m, 2H), 0.45-0.37 (m, 2H) |
| 336 | >95 | ¹H NMR (300 MHz, DMSO-d₆) δ = 11.92 (br. s., 1H), 9.21 (br. s., 1H), 8.37 (d, J = 2.2 Hz, 1H), 8.05 (dd, J = 2.2, 8.6 Hz, 1H), 7.66 (s, 1H), 7.45-7.25 (m, 2H), 4.90 (s, 2H), 3.76 (s, 3H), 1.59-1.35 (m, 2H), 1.34-1.11 (m, 2H) |
| 337 | >95 | ¹H NMR (300 MHz, DMSO-d₆) δ = 8.42 (d, J = 2.3 Hz, 1H), 8.38 (s, 1H), 8.07 (dd, J = 2.3, 8.9 Hz, 1H), 7.81 (d, J = 9.0 Hz, 1H), 6.32 (s, 1H), 5.23 (s, 2H), 4.24 (t, J = 5.7 Hz, 2H), 3.69 (t, J = 5.8 Hz, 2H), 2.18 (s, 3H), 1.09 (s, 3H), 0.63-0.57 (m, 2H), 0.43-0.37 (m, 2H) |
| 339 | 90-95 | ¹H NMR (300 MHz, DMSO-d₆) δ = 8.45 (d, J = 2.0 Hz, 1H), 8.21 (s, 1H), 8.07 (dd, J = 2.3, 8.7 Hz, 1H), 7.61 (d, J = 8.6 Hz, 1H), 6.44 (s, 1H), 5.76 (quin, J = 5.5 Hz, 1H), 5.38 (s, 2H), 4.92 (dd, J = 4.9, 8.5 Hz, 2H), 4.67 (dd, J = 4.9, 8.5 Hz, 2H), 2.20 (s, 3H), 1.06 (s, 3H), 0.62-0.57 (m, 2H), 0.43-0.36 (m, 2H) |
| 340 | 90-95 | ¹H NMR (300 MHz, DMSO-d₆) δ = 8.44 (d, J = 2.3 Hz, 1H), 8.29-8.17 (m, 1H), 8.04 (dd, J = 2.4, 9.0 Hz, 1H), 7.64 (d, J = 9.0 Hz, 1H), 6.34 (s, 1H), 5.24 (s, 2H), 4.43 (d, J = 6.3 Hz, 2H), 4.28 (s, 2H), 4.14 (d, J = 6.2 Hz, 2H), 3.79 (d, J = 5.2 Hz, 2H), 2.18 (s, 3H), 2.08 (s, 1H), 1.08 (s, 3H), 0.65-0.54 (m, 2H), 0.44-0.35 (m, 2H) |
| 342 | >95 | ¹H NMR (300 MHz, DMSO) δ = 8.43 (d, J = 2.4 Hz, 1H), 8.33 (s, 1H), 8.08 (dd, J = 2.4, 8.9 Hz, 1H), 7.81 (d, J = 9.0 Hz, 1H), 6.33 (s, 1H), 5.22 (s, 2H), 4.27-4.13 (m, 2H), 2.35 (m, 7H), 2.18 (s, 3H), 2.10 (s, 3H), 1.87-1.71 (m, 3H), 1.09 (s, 3H), 0.65-0.55 (m, 2H), 0.44-0.35 (m, 2H) |
| 343 | >95 | ¹H NMR (300 MHz, DMSO-d₆) δ = 8.41 (d, J = 2.3 Hz, 1H), 8.19 (s, 1H), 8.01 (dd, J = 2.4, 8.9 Hz, 1H), 7.86 (d, J = 9.0 Hz, 1H), 7.67 (s, 1H), 7.39 (d, J = 0.7 Hz, 1H), 5.03-4.95 (m, 1H), 4.96 (s, 2H), 4.60-4.31 (m, 4H), 3.76 (s, 3H), 2.77-2.62 (m, 1H), 1.07 (s, 3H), 0.65-0.53 (m, 2H), 0.43-0.34 (m, 2H) |
| 344 | >95 | ¹H NMR (300 MHz, CDCl₃) δ = 8.78 (d, J = 2.4 Hz, 1H), 8.21 (dd, J = 2.3, 8.9 Hz, 1H), 7.58 (d, J = 17.2 Hz, 2H), 7.36 (d, J = 8.9 Hz, 1H), 7.27 (s, 3H), 6.06-5.79 (m, 1H), 5.11 (s, 2H), 3.85 (s, 3H), 3.65 (s, 3H), 1.79-1.71 (m, 1H), 1.67-1.57 (m, 2H), 1.48-1.39 (m, 2H), 1.52-1.36 (m, 2H) |
| 345 | >95 | ¹H NMR (300 MHz, CDCl₃) δ = 8.88-8.62 (m, 1H), 8.15 (dd, J = 2.4, 8.9 Hz, 1H), 7.64-7.56 (m, 1H), 7.54 (s, 1H), 7.35 (d, J = 8.9 Hz, 1H), 6.08 (br. s., 1H), 5.73 (s, 1H), 5.34 (s, 2H), 5.11 (s, 2H), 5.18-5.01 (m, 2H), 3.91 (s, 3H), 3.86 (s, 3H), 2.14 (s, 3H), 1.64 (d, J = 3.3 Hz, 2H), 1.49-1.42 (m, 2H) |
| 346 | >95 | ¹H NMR (300 MHz, CDCl₃) δ = 8.80 (d, J = 2.1 Hz, 1H), 8.21 (dd, J = 2.1, 8.9 Hz, 1H), 7.72-7.42 (m, 3H), 6.32-5.82 (m, 1H), 5.11 (s, 2H), 4.11 (d, J = 6.9 Hz, 2H), 3.86 (s, 3H), 1.67-1.57 (m, 2H), 1.52-1.37 (m, 2H), 1.26-1.18 (m, 1H), 1.32-1.12 (m, 2H), 0.56 (d, J = 4.9 Hz, 4H) |

TABLE 3-continued

| Example | NMR Purity | ¹H NMR |
|---|---|---|
| 347 | >95 | ¹H NMR (300 MHz, CDCl₃) δ = 8.78 (d, J = 2.3 Hz, 1H), 8.20 (dd, J = 2.3, 8.9 Hz, 1H), 7.61 (s, 1H), 7.56 (s, 1H), 7.37 (d, J = 8.9 Hz, 1H), 6.45-5.84 (m, 1H), 5.18-5.01 (m, 2H), 4.23 (q, J = 7.1 Hz, 2H), 3.86 (s, 3H), 1.67-1.54 (m, 5H) |
| 348 | 85-90 | ¹H NMR (300 MHz, DMSO-d₆) δ = 8.41 (d, J = 2.3 Hz, 1H), 8.20 (s, 1H), 8.02 (dd, J = 2.3, 9.0 Hz, 1H), 7.78 (dd, J = 2.3, 9.0 Hz, 1H), 7.68 (s, 1H), 7.40 (s, 1H), 4.96 (s, 2H), 4.90-4.54 (m, 7H), 3.76 (s, 3H), 1.06 (s, 3H), 0.65-0.53 (m, 2H), 0.44-0.34 (m, 2H) |
| 349 | >95 | ¹H NMR (300 MHz, DMSO-d₆) δ = 8.41 (d, J = 2.3 Hz, 1H), 8.22 (s, 1H), 8.05 (dd, J = 2.3, 8.9 Hz, 1H), 7.91 (d, J = 9.0 Hz, 1H), 6.33 (s, 1H), 5.22 (s, 2H), 5.04 (d, J = 7.2 Hz, 1H), 4.60-4.33 (m, 4H), 2.76-2.63 (m, 1H), 2.18 (s, 3H), 1.09 (s, 3H), 0.65-0.56 (m, 2H), 0.44-0.36 (m, 2H) |
| 350 | >95 | ¹H NMR (300 MHz, DMSO-d₆) δ = 8.41 (d, J = 2.3 Hz, 1H), 8.23 (s, 1H), 8.06 (dd, J = 2.3, 9.0 Hz, 1H), 7.83 (dd, J = 2.3, 9.0 Hz, 1H), 6.36 (s, 1H), 5.22 (s, 2H), 4.90-4.73 (m, 4H), 4.71-4.55 (m, 2H), 2.18 (s, 3H), 1.08 (s, 3H), 0.66-0.55 (m, 2H), 0.44-0.36 (m, 2H) |
| 351 | >95 | ¹H NMR (300 MHz, DMSO-d₆) δ = 8.39 (d, J = 2.3 Hz, 1H), 8.01 (dd, J = 2.3, 8.9 Hz, 1H), 7.77 (d, J = 9.0 Hz, 1H), 7.65 (s, 1H), 7.38 (s, 1H), 4.96 (s, 2H), 4.89-4.78 (m, 1H), 4.51-4.27 (m, 2H), 3.74 (s, 3H), 2.40 (dd, J = 7.7, 11.2 Hz, 1H), 2.27-2.18 (dd, J = 7.7, 11.2 Hz, 1H), 1.31 (s, 3H), 1.14 (s, 3H), 1.04 (s, 3H), 0.63-0.52 (m, 2H), 0.43-0.34 (m, 2H) |
| 352 | 90-95 | ¹H NMR (300 MHz, DMSO-d₆) δ = 8.41 (d, J = 2.3 Hz, 1H), 8.21 (s, 1H), 8.06 (dd, J = 2.4, 8.9 Hz, 1H), 7.85 (d, J = 9.1 Hz, 1H), 6.32 (s, 1H), 5.24 (s, 2H), 4.91-4.80 (m, 1H), 4.51-4.31 (m, 2H), 2.46-2.35 (m, 1H), 2.34-2.24 (m, 1H), 2.18 (s, 3H), 1.34 (s, 3H), 1.20 (s, 3H), 1.08 (s, 3H), 0.65-0.55 (m, 2H), 0.44-0.35 (m, 2H) |
| 353 | >95 | ¹H NMR (300 MHz, DMSO-d₆) δ = 8.66 (t, J = 1.2 Hz, 1H), 8.47 (s, 1H), 8.27 (d, J = 1.2 Hz, 2H), 6.33 (s, 1H), 5.44 (s, 2H), 3.02 (d, J = 7.4 Hz, 2H), 2.19 (s, 3H), 1.26 (t, J = 7.3 Hz, 4H), 1.07 (s, 3H), 0.65-0.55 (m, 2H), 0.46-0.37 (m, 2H) |
| 354 | >95 | ¹H NMR (300 MHz, CDCl₃) δ = 8.76 (d, J = 2.3 Hz, 1H), 8.18 (dd, J = 2.3, 8.9 Hz, 1H), 7.58 (d, J = 10.1 Hz, 2H), 7.36 (d, J = 8.9 Hz, 1H), 6.47-6.02 (m, 1H), 5.09 (s, 2H), 4.88-4.75 (m, 2H), 4.64 (t, J = 6.3 Hz, 2H), 4.55 (d, J = 7.2 Hz, 2H), 3.87 (s, 3H), 3.57-3.39 (m, 1H), 1.67-1.57 (m, 2H), 1.49-1.39 (m, 2H) |
| 355 | >95 | ¹H NMR (300 MHz, CDCl₃) δ = 8.80 (d, J = 2.3 Hz, 1H), 8.24 (dd, J = 2.3, 8.9 Hz, 1H), 8.03 (s, 1H), 7.63 (s, 1H), 7.58-7.49 (m, 2H), 5.80 (br. s., 1H), 5.11 (s, 2H), 4.97 (d, J = 2.4 Hz, 2H), 3.87 (s, 3H), 3.54-3.46 (m, 2H), 2.36 (s, 1H), 1.67-1.56 (m, 3H), 1.52-1.40 (m, 2H) |
| 356 | >95 | ¹H NMR (300 MHz, CDCl₃) δ = 8.78 (d, J = 2.0 Hz, 1H), 8.27 (dd, J = 2.1, 8.8 Hz, 1H), 7.57 (d, J = 9.6 Hz, 2H), 7.40 (d, J = 8.8 Hz, 1H), 6.19 (br. s., 1H), 5.12 (d, J = 9.0 Hz, 4H), 3.87 (s, 3H), 1.66-1.58 (m, 2H), 1.50-1.41 (m, 2H) |
| 357 | >95 | ¹H NMR (300 MHz, CDCl₃) δ = 8.77 (s, 1H), 8.16 (d, J = 7.6 Hz, 1H), 7.70-7.51 (m, 3H), 5.81 (s, 1H), 5.11 (s, 2H), 4.44-4.28 (m, 2H), 3.87 (s, 3H), 3.78-3.70 (m, 2H), 3.81-3.61 (m, 3H), 3.33 (s, 3H), 1.50-1.42 (m, 2H), 1.50-1.39 (m, 3H), 1.34-1.15 (m, 2H) |
| 358 | >95 | ¹H NMR (300 MHz, CDCl₃) δ = 8.76 (d, J = 1.8 Hz, 1H), 8.08 (dd, J = 1.8, 8.9 Hz, 1H), 7.62 (s, 1H), 7.57 (s, 1H), 7.25-7.17 (m, 2H), 7.25-7.13 (m, 3H), 7.08-6.96 (m, 2H), 6.33-6.01 (m, 1H), 5.37 (s, 2H), 5.14 (s, 2H), 3.86 (s, 3H), 1.58 (br. s., 2H), 1.47-1.34 (m, 2H) |
| 359 | >95 | ¹H NMR (300 MHz, CDCl₃) δ = 8.78 (d, J = 2.2 Hz, 1H), 8.22-8.12 (m, 1H), 7.58 (d, J = 15.2 Hz, 2H), 7.48 (d, J = 8.9 Hz, 1H), 6.09 (s, 2H), 5.42 (s, 2H), 5.10 (s, 2H), 3.86 (s, 3H), 2.26 (s, 3H), 1.65-1.56 (m, 2H), 1.48-1.39 (m, 2H) |
| 360 | >95 | ¹H NMR (300 MHz, DMSO-d₆) δ = 8.43 (d, J = 2.3 Hz, 1H), 8.36 (s, 1H), 8.12 (dd, J = 2.3, 8.9 Hz, 1H), 7.64 (d, J = 8.9 Hz, 1H), 6.33 (s, 1H), 5.21 (s, 2H), 4.60 (br. s., 1H), 4.30-4.12 (m, 2H), 2.18 (s, 3H), 1.79-1.66 (m, 2H), 1.21 (s, 6H), 1.09 (s, 3H), 0.66-0.55 (m, 2H), 0.48-0.33 (m, 2H) |
| 361 | >95 | ¹H NMR (300 MHz, DMSO-d₆) δ = 8.43 (d, J = 2.3 Hz, 1H), 8.25 (br. s., 1H), 8.09 (dd, J = 2.4, 8.9 Hz, 1H), 7.77 (d, J = 8.9 Hz, 1H), 6.32 (s, 1H), 5.22 (s, 2H), 4.25-4.11 (m, 2H), 2.72-2.53 (m, 4H), 2.47-2.38 (m, 1H), 2.30 (s, 3H), 2.17 (s, 3H), 2.01-1.86 (m, 1H), 1.59 (d, J = 5.7 Hz, 1H), 1.09 (s, 3H), 0.63-0.57 (m, 2H), 0.44-0.37 (m, 2H) |
| 362 | >95 | ¹H NMR (300 MHz, DMSO-d₆) δ = 8.43 (d, J = 2.3 Hz, 1H), 8.24 (br. s., 1H), 8.09 (dd, J = 2.3, 8.9 Hz, 1H), 7.75 (d, J = 8.9 Hz, 1H), 6.32 (s, 1H), 5.23 (s, 2H), 4.40-4.28 (m, 2H), 2.83-2.73 (m, 2H), 2.18 (s, 3H), 2.17 (s, 3H), 1.09 (s, 3H), 0.65-0.56 (m, 2H), 0.46-0.35 (m, 2H) |
| 363 | >95 | ¹H NMR (300 MHz, DMSO-d₆) δ = 8.42 (d, J = 2.3 Hz, 1H), 8.25 (s, 1H), 8.08 (dd, J = 2.4, 8.9 Hz, 1H), 7.79 (d, J = 8.9 Hz, 1H), 6.33 (s, 1H), 5.22 (s, 2H), 4.35 (d, J = 5.1 Hz, 2H), 2.73-2.53 (m, 4H), 2.47 (br. s., 1H), 2.18 (s, 3H), 1.10 (s, 3H), 0.69-0.52 (m, 2H), 0.48-0.34 (m, 2H) |
| 364 | >95 | ¹H NMR (300 MHz, DMSO-d₆) δ = 8.44 (d, J = 2.3 Hz, 1H), 8.26 (s, 1H), 8.11 (dd, J = 2.3, 8.9 Hz, 1H), 7.82 (d, J = 8.9 Hz, 1H), 6.34 (s, 1H), 5.23 (s, 2H), 4.35 (d, J = 6.9 Hz, 2H), 2.34-2.19 (m, 1H), 2.18 (s, 3H), 1.73-1.58 (m, 1H), 1.57-1.41 (m, 1H), 1.10 (s, 3H), 0.64-0.59 (m, 2H), 0.44-0.39 (m, 2H) |
| 365 | 90-95 | ¹H NMR (300 MHz, DMSO-d₆) δ = 8.42 (d, J = 2.3 Hz, 1H), 8.21 (s, 1H), 8.02 (d, J = 8.9 Hz, 1H), 7.73 (d, J = 8.9 Hz, 1H), 7.67 (s, 1H), 7.39 (s, 1H), 4.95 (s, 2H), 4.40 (d, J = 7.3 Hz, 2H), 3.87 (s, 2H), 3.80-3.70 (m, 5H), 3.00-2.85 (m, 1H), 1.38 (s, 9H), 1.08 (s, 3H), 0.59 (s, 2H), 0.39 (d, J = 1.8 Hz, 2H) |
| 366 | >95 | ¹H NMR (300 MHz, CDCl₃) δ = 8.74 (d, J = 2.3 Hz, 1H), 8.14 (dd, J = 2.3, 8.8 Hz, 1H), 7.63 (s, 1H), 7.56 (s, 1H), 7.32-7.26 (m, 1H), 5.12 (s, 2H), 4.97 (s, 1H), 4.40-4.32 (m, 2H), 3.87 (s, 3H), 2.86-2.76 (m, 2H), 2.27 (s, 3H), 1.27 (s, 3H), 0.81-0.75 (m, 2H), 0.56-0.50 (m, 2H) |

TABLE 3-continued

¹H NMR data

| Example | NMR Purity | ¹H NMR |
|---|---|---|
| 367 | 90-95 | ¹H NMR (300 MHz, DMSO-d$_6$) δ = 8.44 (d, J = 2.3 Hz, 1H), 7.99 (dd, J = 2.3, 8.9 Hz, 1H), 7.66 (s, 1H), 7.49 (d, J = 8.9 Hz, 1H), 7.37 (s, 1H), 5.16 (s, 2H), 4.95 (s, 2H), 3.76 (s, 3H), 2.34-2.28 (m, 3H), 1.06 (s, 3H), 0.62-0.54 (m, 2H), 0.43-0.35 (m, 2H) |
| 368 | >95 | ¹H NMR (300 MHz, CDCl$_3$) δ = 8.73 (d, J = 2.3 Hz, 1H), 8.13 (dd, J = 2.3, 8.9 Hz, 1H), 7.64 (s, 1H), 7.57 (s, 1H), 7.46 (d, J = 8.9 Hz, 1H), 7.29 (br. s., 1H), 5.11 (s, 2H), 4.96 (s, 1H), 4.38-4.29 (m, 2H), 3.87 (s, 3H), 1.94-1.83 (m, 2H), 1.38 (s, 6H), 1.26 (s, 3H), 0.81-0.71 (m, 2H), 0.56-0.48 (m, 2H) |
| 369 | 90-95 | ¹H NMR (300 MHz, CDCl$_3$) δ = 8.75 (d, J = 2.4 Hz, 1H), 8.16 (d, J = 9.2 Hz, 1H), 7.64-7.55 (m, 3H), 5.11 (s, 2H), 5.05 (s, 1H), 4.80-4.49 (m, 2H), 3.87 (s, 3H), 3.07 (s, 2H), 2.72 (s, 3H), 1.26 (s, 3H), 0.81-0.73 (m, 2H), 0.55-0.48 (m, 2H) |
| 370 | >95 | ¹H NMR (300 MHz, CDCl$_3$) δ = 8.74 (d, J = 2.3 Hz, 1H), 8.17 (dd, J = 2.3, 8.8 Hz, 1H), 7.61 (s, 1H), 7.56 (s, 1H), 7.44 (d, J = 8.9 Hz, 1H), 5.10 (s, 2H), 5.05 (s, 1H), 4.70-4.60 (m, 2H), 3.87 (s, 3H), 3.53-3.41 (m, 2H), 3.09 (s, 3H), 1.26 (s, 3H), 0.80-0.70 (m, 2H), 0.56-0.50 (m, 2H) |
| 371 | 90-95 | ¹H NMR (300 MHz, DMSO-d$_6$) δ = 8.42 (d, J = 2.3 Hz, 1H), 8.31 (br. s., 1H), 8.13-8.03 (m, 1H), 7.69 (d, J = 8.9 Hz, 1H), 6.31 (s, 1H), 5.21 (s, 2H), 4.10 (d, J = 9.0 Hz, 2H), 3.11-2.91 (m, 2H), 2.60 (s, 3H), 2.41-2.30 (m, 2H), 2.16 (s, 3H), 2.08 (d, J = 7.4 Hz, 1H), 1.89-1.63 (m, 4H), 1.07 (s, 3H), 0.70-0.52 (m, 2H), 0.48-0.34 (m, 2H) |
| 372 | >95 | ¹H NMR (300 MHz, DMSO-d$_6$) δ = 8.43 (d, J = 2.2 Hz, 1H), 8.30 (br. s., 1H), 8.06 (dd, J = 2.3, 8.8 Hz, 1H), 7.77-7.63 (m, 2H), 7.43-7.35 (m, 1H), 4.95 (s, 2H), 4.18-3.98 (m, 2H), 3.76 (s, 3H), 2.97-2.83 (m, 1H), 2.79-2.64 (m, 2H), 2.42 (s, 3H), 2.15-1.91 (m, 2H), 1.77-1.62 (m, 2H), 1.58-1.34 (m, 2H), 1.08 (s, 3H), 0.62-0.55 (m, 2H), 0.42-0.34 (m, 2H) |
| 374 | >95 | ¹H NMR (300 MHz, CDCl$_3$) δ = 8.79 (d, J = 2.2 Hz, 1H), 8.18 (dd, J = 2.2, 8.9 Hz, 1H), 7.63 (s, 1H), 7.55 (s, 1H), 7.35 (d, J = 9.0 Hz, 1H), 5.77 (s, 1H), 5.40 (s, 2H), 5.12 (s, 2H), 3.87 (s, 3H), 2.57 (d, J = 7.8 Hz, 6H), 2.53-2.52 (m, 1H), 1.66-1.61 (m, 3H), 1.64 (br. s., 2H), 1.61-1.60 (m, 1H), 1.60 (br. s., 1H), 1.49-1.44 (m, 2H) |
| 375 | >95 | ¹H NMR (300 MHz, CDCl$_3$) δ = 8.76 (d, J = 2.0 Hz, 1H), 8.17 (d, J = 8.7 Hz, 1H), 7.73 (s, 1H), 7.63 (s, 1H), 7.59-7.46 (m, 2H), 6.49 (s, 1H), 5.47 (s, 2H), 5.12 (s, 2H), 3.86 (s, 3H), 2.68 (s, 3H), 1.60 (d, J = 2.8 Hz, 2H), 1.44 (br. s., 2H) |
| 376 | >95 | ¹H NMR (300 MHz, CDCl$_3$) δ = 8.78 (br. s., 1H), 8.17 (d, J = 7.3 Hz, 1H), 7.60 (d, J = 14.3 Hz, 2H), 7.25-7.18 (m, 1H), 5.95 (br. s., 1H), 5.11 (br. s., 2H), 4.67 (d, J = 6.1 Hz, 2H), 4.31-4.22 (m, 4H), 4.26 (br. s., 5H), 3.95-3.84 (m, 3H), 3.89 (s, 4H), 1.61 (br. s., 2H), 1.48 (br. s., 5H), 0.00-0.00 (m, 1H) |
| 377 | >95 | ¹H NMR (300 MHz, CDCl$_3$) δ = 8.76 (br. s., 1H), 8.19 (br. s., 1H), 7.67-7.53 (m, 2H), 7.49-7.38 (m, 1H), 6.16 (br. s., 1H), 5.10 (br. s., 2H), 4.30-4.26 (m, 1H), 4.03 (br. s., 3H), 3.87 (br. s., 2H), 4.26-3.71 (m, 9H), 2.90-2.70 (m, 1H), 2.08 (br. s., 1H), 1.89-1.74 (m, 2H), 1.61 (br. s., 2H), 1.44 (br. s., 2H) |
| 378 | >95 | ¹H NMR (300 MHz, CDCl$_3$) δ = 8.78 (d, J = 2.1 Hz, 1H), 8.16 (dd, J = 2.1, 8.9 Hz, 1H), 8.04 (s, 1H), 7.63 (s, 1H), 7.57-7.52 (m, 2H), 7.35 (s, 1H), 6.01 (s, 1H), 5.22 (s, 2H), 5.11 (s, 2H), 3.86 (s, 3H), 3.83 (s, 3H), 1.62 (d, J = 2.6 Hz, 1H), 1.45 (d, J = 3.0 Hz, 2H) |
| 379 | >95 | ¹H NMR (300 MHz, CDCl$_3$) δ = 8.72 (d, J = 2.2 Hz, 1H), 8.12 (dd, J = 2.2, 8.8 Hz, 1H), 7.62 (s, 1H), 7.55 (s, 1H), 7.43 (d, J = 8.9 Hz, 1H), 6.13 (s, 1H), 5.40 (s, 2H), 5.11 (s, 2H), 5.02 (s, 1H), 3.86 (s, 3H), 2.28 (s, 3H), 1.25 (s, 4H), 0.85-0.68 (m, 2H), 0.57-0.46 (m, 2H) |
| 380 | 90-95 | ¹H NMR (300 MHz, DMSO-d$_6$) δ = 8.43 (d, J = 2.3 Hz, 1H), 8.21 (s, 1H), 8.06 (dd, J = 2.2, 8.8 Hz, 1H), 7.69-7.64 (m, 2H), 7.39 (s, 1H), 4.95 (s, 2H), 4.18 (d, J = 3.8 Hz, 2H), 3.76 (s, 3H), 3.02-2.92 (m, 1H), 2.88-2.70 (m, 2H), 2.24-2.10 (m, 2H), 1.75 (br. s., 2H), 1.64-1.53 (m, 1H), 1.08 (s, 3H), 0.65-0.54 (m, 2H), 0.44-0.34 (m, 2H) |
| 381 | 90-95 | ¹H NMR (300 MHz, DMSO-d$_6$) δ = 8.43 (d, J = 2.3 Hz, 1H), 8.28-8.21 (m, 1H), 8.10 (dd, J = 2.3, 8.9 Hz, 1H), 7.71 (d, J = 9.0 Hz, 1H), 6.33 (s, 1H), 5.22 (s, 2H), 4.17 (d, J = 5.5 Hz, 2H), 2.96 (dd, J = 6.3, 10.2 Hz, 1H), 2.87-2.69 (m, 2H), 2.18 (s, 5H), 1.97 (m, 1H), 1.77 (m, 3H), 1.60 (d, J = 7.3 Hz, 2H), 1.09 (s, 3H), 0.64-0.57 (m, 2H), 0.44-0.38 (m, 2H) |
| 382 | >95 | ¹H NMR (300 MHz, DMSO-d$_6$) δ = 8.43 (d, J = 2.3 Hz, 1H), 8.25 (s, 1H), 8.12-8.03 (m, 1H), 7.73 (d, J = 8.8 Hz, 1H), 6.34 (s, 1H), 5.22 (s, 2H), 4.25-4.07 (m, 2H), 3.12-2.75 (m, 4H), 2.18 (s, 3H), 1.90-1.68 (m, 5H), 1.10 (s, 3H), 0.67-0.56 (m, 2H), 0.41 (s, 2H) |
| 383 | >95 | ¹H NMR (300 MHz, DMSO-d$_6$) δ = 8.43 (d, J = 2.4 Hz, 1H), 8.22 (br. s., 1H), 8.09-8.00 (m, 1H), 7.71-7.65 (m, 2H), 7.42-7.36 (m, 1H), 4.95 (s, 2H), 4.25-4.01 (m, 2H), 3.76 (s, 3H), 3.28-2.92 (m, 4H), 2.36-2.24 (m, 1H), 1.89-1.66 (m, 4H), 1.08 (s, 3H), 0.62-0.57 (m, 2H), 0.44-0.36 (m, 2H) |
| 384 | >95 | ¹H NMR (300 MHz, DMSO-d$_6$) δ = 12.02-11.88 (m, 1H), 8.46 (s, 1H), 8.31 (d, J = 7.8 Hz, 1H), 7.66 (s, 1H), 7.38 (d, J = 0.7 Hz, 1H), 7.04 (d, J = 10.6 Hz, 1H), 4.88 (s, 2H), 3.76 (s, 3H), 1.12 (s, 3H), 0.66-0.58 (m, 2H), 0.47-0.37 (m, 2H) |
| 385 | >95 | ¹H NMR (300 MHz, DMSO-d6) Shift = 8.54-8.48 (m, 1H), 8.39 (d, J = 8.0 Hz, 1H), 7.68 (s, 1H), 7.59 (d, J = 12.2 Hz, 1H), 7.39 (s, 1H), 4.93 (s, 2H), 3.76 (s, 3H), 3.51 (s, 3H), 1.13 (s, 3H), 0.63 (s, 2H), 0.46-0.39 (m, 2H) |
| 386 | >95 | ¹H NMR (300 MHz, DMSO-d6) Shift = 12.35-11.62 (m, 1H), 12.57-11.46 (m, 1H), 9.22 (br s, 1H), 8.37 (d, J = 2.2 Hz, 1H), 8.06 (dd, J = 2.2, 8.7 Hz, 1H), 7.61 (s, 1H), 7.37 (d, J = 8.7 Hz, 1H), 5.20 (s, 2H), 2.57 (s, 3H), 1.52-1.34 (m, 2H), 1.34-1.14 (m, 2H) |
| 387 | >95 | ¹H NMR (300 MHz, DMSO-d6) Shift = 12.54-11.46 (m, 1H), 9.97-9.19 (m, 1H), 8.35 (d, J = 7.6 Hz, 1H), 7.67 (s, 1H), 7.38 (s, 1H), 7.09 (d, J = 10.7 Hz, 1H), 4.89 (s, 2H), 3.76 (s, 3H), 1.49-1.43 (m, 1H), 1.53-1.37 (m, 1H), 1.32-1.25 (m, 1H), 1.37-1.10 (m, 2H) |
| 388 | >95 | ¹H NMR (300 MHz, DMSO-d6) Shift = 8.57-8.47 (m, 1H), 8.41 (d, J = 8.1 Hz, 1H), 7.73 (d, J = 12.4 Hz, 1H), 7.68 (s, 1H), 7.38 (s, 1H), 4.94 (s, 2H), 4.05 (d, J = 7.1 Hz, 2H), 3.76 (s, 3H), 1.13 (s, 3H), 0.66-0.59 (m, 2H), 0.52-0.38 (m, 6H) |

TABLE 3-continued

¹H NMR data

| Example | NMR Purity | ¹H NMR |
|---|---|---|
| 389 | >95 | ¹H NMR (300 MHz, DMSO-d6) Shift = 8.55-8.48 (m, 1H), 8.44-8.38 (m, 1H), 7.67 (s, 2H), 7.39 (s, 1H), 4.93 (s, 2H), 4.19-4.07 (m, 2H), 3.76 (s, 3H), 1.20 (t, J = 7.1 Hz, 3H), 1.13 (s, 3H), 0.68-0.59 (m, 2H), 0.46-0.39 (m, 2H) |
| 390 | >95 | ¹H NMR (300 MHz, DMSO-d6) Shift = 8.52 (s, 1H), 8.42 (d, J = 8.0 Hz, 1H), 7.70 (s, 1H), 7.47-7.35 (m, 4H), 7.17 (t, J = 8.9 Hz, 2H), 5.35 (s, 2H), 4.98 (s, 2H), 3.77 (s, 3H), 1.11 (s, 3H), 0.65-0.57 (m, 2H), 0.46-0.38 (m, 2H) |
| 391 | >95 | ¹H NMR (300 MHz, DMSO-d6) Shift = 8.55 (s, 1H), 8.42 (d, J = 8.0 Hz, 1H), 7.68 (t, J = 6.1 Hz, 2H), 7.39 (s, 1H), 6.40 (s, 1H), 5.46 (s, 2H), 4.94 (s, 2H), 3.76 (s, 3H), 2.18 (s, 3H), 1.13 (s, 3H), 0.68-0.59 (m, 2H), 0.47-0.40 (m, 2H) |
| 392 | >95 | ¹H NMR (300 MHz, DMSO-d6) Shift = 8.42 (d, J = 8.0 Hz, 1H), 7.68 (s, 1H), 7.55 (d, J = 12.2 Hz, 1H), 7.38 (s, 1H), 5.33 (s, 2H), 4.95 (s, 2H), 3.78 (d, J = 9.3 Hz, 6H), 2.00 (s, 3H), 1.13 (s, 3H), 0.68-0.60 (m, 2H), 0.47-0.39 (m, 2H) |
| 393 | >95 | ¹H NMR (300 MHz, DMSO-d6) Shift = 8.52 (s, 1H), 8.39 (d, J = 8.1 Hz, 1H), 7.78-7.64 (m, 3H), 7.47 (s, 1H), 7.40 (s, 1H), 5.15 (s, 2H), 4.95 (s, 2H), 3.76 (d, J = 1.8 Hz, 6H), 1.11 (s, 3H), 0.66-0.58 (m, 2H), 0.45-0.38 (m, 2H) |
| 394 | >95 | ¹H NMR (300 MHz, DMSO-d6) Shift = 8.38 (d, J = 8.1 Hz, 1H), 7.70 (d, J = 12.5 Hz, 1H), 7.67 (s, 1H), 7.38 (s, 1H), 4.93 (s, 2H), 4.59 (dd, J = 6.2, 7.8 Hz, 2H), 4.44 (t, J = 6.1 Hz, 4H), 3.76 (s, 3H), 1.13 (s, 3H), 0.73-0.56 (m, 2H), 0.50-0.36 (m, 2H) |
| 395 | >95 | ¹H NMR (300 MHz, DMSO-d6) Shift = 8.53 (s, 1H), 8.40 (d, J = 8.1 Hz, 1H), 7.73-7.64 (m, 2H), 7.38 (s, 1H), 4.94 (s, 2H), 4.14 (br. s, 2H), 3.83 (d, J = 5.7 Hz, 1H), 3.76 (s, 3H), 3.72-3.57 (m, 3H), 3.49 (dd, J = 5.4, 8.6 Hz, 1H), 2.00-1.89 (m, 1H), 1.68 (s, 1H), 0.68-0.55 (m, 2H), 0.47-0.39 (m, 2H) |
| 396 | >95 | ¹H NMR (300 MHz, DMSO-d6) Shift = 8.56 (s, 1H), 8.41 (d, J = 7.9 Hz, 1H), 7.70-7.61 (m, 2H), 7.38 (s, 1H), 5.43 (s, 2H), 4.93 (s, 2H), 3.76 (s, 3H), 2.45 (s, 3H), 1.13-1.10 (m, 3H), 0.62 (s, 2H), 0.43 (d, J = 1.9 Hz, 2H) |
| 397 | >95 | ¹H NMR (300 MHz, DMSO-d6) Shift = 8.52 (s, 1H), 8.41 (d, J = 8.2 Hz, 1H), 7.77 (d, J = 12.2 Hz, 1H), 7.68 (s, 1H), 7.38 (s, 1H), 4.94 (s, 2H), 4.55 (d, J = 6.1 Hz, 2H), 4.20 (s, 2H), 4.08 (d, J = 6.2 Hz, 2H), 3.76 (s, 3H), 1.35 (s, 3H), 1.12 (s, 3H), 0.63 (s, 2H), 0.46-0.38 (m, 2H) |
| 398 | >95 | ¹H NMR (300 MHz, DMSO-d6) Shift = 8.51 (s, 1H), 8.46 (d, J = 8.1 Hz, 1H), 7.69 (s, 1H), 7.48 (d, J = 11.3 Hz, 1H), 7.40 (s, 1H), 5.04 (s, 2H), 4.59-4.51 (m, 4H), 4.36 (d, J = 5.9 Hz, 2H), 3.76 (s, 3H), 1.36 (s, 3H), 1.11 (s, 3H), 0.67-0.59 (m, 2H), 0.46-0.38 (m, 2H) |
| 399 | >95 | ¹H NMR (300 MHz, DMSO-d6) Shift = 9.29 (br s, 1H), 8.49 (br s, 1H), 8.13 (br d, J = 7.8 Hz, 1H), 7.87 (br d, J = 8.9 Hz, 1H), 7.63 (br s, 1H), 5.26 (br s, 2H), 4.11 (br s, 2H), 2.57 (br s, 3H), 1.44 (br s, 2H), 1.28 (br s, 3H), 0.47 (br s, 4H) |
| 400 | >95 | ¹H NMR (300 MHz, DMSO-d6) Shift = 8.47 (br s, 1H), 8.43-8.34 (m, 1H), 8.15-8.03 (m, 1H), 7.80-7.59 (m, 1H), 7.81-7.55 (m, 1H), 6.34 (s, 1H), 5.52 (br s, 2H), 5.27 (br s, 2H), 2.58 (s, 3H), 2.16 (s, 3H), 1.39-1.29 (m, 1H), 1.35 (br s, 1H), 1.23-1.12 (m, 2H) |
| 401 | >95 | ¹H NMR (300 MHz, DMSO-d6) Shift = 8.53-8.43 (m, 1H), 8.23-8.11 (m, 1H), 7.75-7.59 (m, 2H), 5.48 (br s, 2H), 5.27 (br s, 2H), 2.58 (br s, 3H), 2.55 (br s, 3H), 2.48-2.47 (m, 3H), 1.49-1.34 (m, 2H), 1.23 (br s, 2H) |
| 402 | >95 | ¹H NMR (300 MHz, DMSO-d6) Shift = 9.39-8.89 (m, 1H), 8.49 (br s, 1H), 8.03 (br s, 1H), 7.71-7.48 (m, 2H), 7.37 (br s, 2H), 7.16 (br t, J = 8.4 Hz, 2H), 5.52-5.22 (m, 4H), 2.58 (s, 3H), 1.41 (br s, 2H), 1.30-1.16 (m, 2H) |
| 403 | >95 | ¹H NMR (300 MHz, DMSO-d6) Shift = 8.47 (s, 1H), 8.36 (br s, 1H), 8.18 (br d, J = 8.9 Hz, 1H), 7.73 (br d, J = 9.1 Hz, 1H), 7.64 (s, 1H), 5.26 (s, 2H), 5.00 (br s, 2H), 3.43-3.41 (m, 1H), 2.57 (s, 3H), 1.36 (br s, 2H), 1.20 (br s, 2H) |
| 404 | >95 | ¹H NMR (300 MHz, DMSO-d6) Shift = 8.46-8.40 (m, 2H), 7.68 (s, 1H), 7.55 (br d, J = 12.1 Hz, 1H), 7.39 (s, 1H), 6.33 (s, 1H), 5.47 (s, 2H), 4.95 (s, 2H), 3.76 (s, 3H), 2.40-2.40 (m, 1H), 2.16 (s, 3H), 1.14 (br s, 2H), 0.99 (br s, 2H) |
| 405 | >95 | ¹H NMR (300 MHz, DMSO-d6) Shift = 8.43 (d, J = 2.4 Hz, 1H), 8.25 (s, 1H), 8.07 (dd, J = 2.3, 8.9 Hz, 1H), 7.77 (d, J = 8.9 Hz, 1H), 6.33 (s, 1H), 5.22 (s, 2H), 4.09 (d, J = 7.3 Hz, 2H), 2.18 (s, 3H), 2.03-1.89 (m, 3H), 1.83-1.74 (m, 3H), 1.74-1.62 (m, 1H), 1.42-1.28 (m, 2H), 1.10 (s, 3H), 0.72-0.53 (m, 2H), 0.44-0.38 (m, 2H) |
| 406 | >95 | ¹H NMR (300 MHz, DMSO-d6) Shift = 8.42 (d, J = 4.7 Hz, 1H), 8.24 (br. s., 1H), 8.09 (dd, J = 2.3, 8.8 Hz, 1H), 7.75 (d, J = 9.0 Hz, 1H), 6.34 (s, 1H), 5.22 (s, 2H), 4.41-4.27 (m, 2H), 2.98-2.90 (m, 3H), 2.82 (s, 3H), 2.78-2.67 (m, 2H), 2.18 (s, 3H), 1.10 (s, 3H), 0.63-0.53 (m, 2H), 0.44-0.37 (m, 2H) |
| 407 | >95 | ¹H NMR (300 MHz, DMSO-d6) Shift = 8.43 (d, J = 2.4 Hz, 1H), 8.38 (s, 1H), 8.09 (s, 1H), 7.74 (d, J = 9.1 Hz, 1H), 6.33 (s, 1H), 5.22 (s, 2H), 4.72-4.60 (m, 1H), 4.19 (t, J = 7.1 Hz, 2H), 3.59-3.48 (m, 2H), 2.18 (s, 3H), 1.88-1.73 (m, 2H), 1.09 (s, 3H), 0.65-0.55 (m, 2H), 0.45-0.36 (m, 2H) |
| 408 | >95 | ¹H NMR (300 MHz, DMSO-d6) Shift = 8.41 (d, J = 2.3 Hz, 1H), 8.06 (dd, J = 2.4, 8.9 Hz, 1H), 7.67 (s, 1H), 7.64 (d, J = 8.9 Hz, 1H), 7.39 (s, 1H), 4.95 (s, 2H), 4.30-4.07 (m, 2H), 3.76 (s, 3H), 3.55 (s, 3H), 0.76-0.62 (m, 4H) |
| 409 | >95 | ¹H NMR (300 MHz, DMSO-d6) Shift = 8.42 (d, J = 2.2 Hz, 1H), 8.24 (br s, 1H), 8.07 (dd, J = 2.2, 8.7 Hz, 1H), 7.78 (d, J = 8.7 Hz, 1H), 6.33 (s, 1H), 5.22 (s, 2H), 4.42 (d, J = 7.3 Hz, 2H), 3.91-3.83 (m, 2H), 3.77-3.65 (m, 2H), 3.01-2.89 (m, 2H), 2.18 (s, 3H), 1.37 (s, 9H), 1.10 (s, 3H), 0.63-0.57 (m, 2H), 0.43-0.38 (m, 2H) |
| 410 | >95 | ¹H NMR (300 MHz, DMSO-d6) Shift = 8.43 (d, J = 2.2 Hz, 1H), 8.20 (br s, 1H), 8.04 (dd, J = 2.2, 8.7 Hz, 1H), 7.76 (d, J = 8.7 Hz, 1H), 7.68 (s, 1H), 7.40 (s, 1H), 4.96 (s, 2H), 4.82 (t, J = 4.8 Hz, 1H), 4.67 (t, J = 4.8 Hz, 1H), 4.55 (t, J = 4.8 Hz, 1H), 4.47 (t, J = 4.8 Hz, 1H), 3.76 (s, 3H), 1.07 (s, 3H), 0.62-0.56 (m, 2H), 0.42-0.36 (m, 2H) |

TABLE 3-continued

| | | ¹H NMR data |
|---|---|---|
| Example | NMR Purity | ¹H NMR |
| 411 | >95 | ¹H NMR (300 MHz, DMSO-d6) Shift = 8.43 (d, J = 2.2 Hz, 1H), 8.24 (br s, 1H), 8.08 (dd, J = 2.2, 8.8 Hz, 1H), 7.80 (d, J = 8.8 Hz, 1H), 6.34 (s, 1H), 5.22 (s, 2H), 4.83 (t, J = 4.8 Hz, 1H), 4.68 (t, J = 4.8 Hz, 1H), 4.56 (t, J = 4.8 Hz, 1H), 4.48 (t, J = 4.8 Hz, 1H), 2.18 (s, 3H), 1.09 (s, 3H), 0.63-0.57 (m, 2H), 0.44-0.38 (m, 2H) |
| 412 | 90-95 | ¹H NMR (300 MHz, DMSO-d6) Shift = 8.44 (d, J = 2.4 Hz, 1H), 8.25 (br s, 1H), 8.10 (dd, J = 2.4, 8.8 Hz, 1H), 7.89 (d, J = 8.8 Hz, 1H), 6.33 (s, 1H), 5.22 (s, 2H), 4.45 (d, J = 7.4 Hz, 1H), 3.17-2.84 (m, 5H), 2.17 (s, 3H), 1.09 (s, 3H), 0.64-0.58 (m, 2H), 0.44-0.38 (m, 2H) |
| 413 | 90-95 | ¹H NMR (300 MHz, DMSO-d6) Shift = 8.39 (d, J = 2.3 Hz, 1H), 8.20 (br s, 1H), 8.03 (dd, J = 2.3, 8.8 Hz, 1H), 7.93 (d, J = 8.8 Hz, 1H), 6.31 (s, 1H), 5.23 (s, 2H), 3.05 (s, 3H), 2.17 (s, 3H), 1.18 (s, 6H), 1.08 (s, 3H), 0.64-0.57 (m, 2H), 0.43-0.36 (m, 2H) |
| 414 | 90-95 | ¹H NMR (300 MHz, DMSO-d6) Shift = 8.43 (d, J = 2.2 Hz, 1H), 8.25 (br s, 1H), 8.07 (dd, J = 2.2, 8.8 Hz, 1H), 7.56 (d, J = 8.8 Hz, 1H), 6.29 (s, 1H), 5.23 (s, 2H), 4.84 (s, 2H), 4.38-4.30 (m, 2H), 3.98-3.90 (m, 2H), 2.37-2.24 (m, 1H), 2.18 (s, 3H), 1.09 (s, 3H), 0.63-0.57 (m, 2H), 0.44-0.38 (m, 2H) |
| 415 | >95 | ¹H NMR (300 MHz, DMSO-d6) Shift = 8.43 (d, J = 2.4 Hz, 1H), 8.40 (br s, 1H), 8.07 (dd, J = 2.4, 8.9 Hz, 1H), 7.79 (d, J = 8.8 Hz, 1H), 6.34 (s, 1H), 5.21 (s, 2H), 4.41 (d, J = 6.6 Hz, 1H), 3.81-3.66 (m, 4H), 3.21-3.07 (m, 1H), 2.18 (s, 3H), 1.09 (s, 3H), 0.63-0.57 (m, 2H), 0.43-0.37 (m, 2H) |
| 416 | >95 | ¹H NMR (300 MHz, DMSO-d6) Shift = 11.86 (br. s., 1H), 8.53 (s, 1H), 8.31 (d, J = 2.1 Hz, 1H), 7.99 (dd, J = 2.2, 8.7 Hz, 1H), 7.67 (s, 1H), 7.39 (d, J = 0.7 Hz, 1H), 7.32 (d, J = 8.6 Hz, 1H), 4.90 (s, 2H), 4.27 (s, 1H), 4.11 (s, 1H), 3.77 (s, 4H), 0.76-0.62 (m, 4H) |
| 417 | >95 | ¹H NMR (300 MHz, DMSO-d6) Shift = 8.68-8.51 (m, 1H), 8.43 (s, 1H), 8.06 (d, J = 9.0 Hz, 1H), 7.79 (d, J = 8.9 Hz, 1H), 7.67 (s, 1H), 7.39 (s, 1H), 4.96 (s, 2H), 4.27 (s, 1H), 4.17-4.03 (m, 3H), 3.76 (s, 3H), 3.45-3.35 (m, 1H), 0.71 (d, J = 8.6 Hz, 4H), 0.55-0.43 (m, 4H) |
| 418 | >95 | ¹H NMR (300 MHz, DMSO-d6) Shift = 8.44-8.40 (m, 2H), 8.30 (br s, 1H), 8.21 (s, 1H), 8.09 (dd, J = 2.3, 8.8 Hz, 1H), 7.67 (d, J = 8.8 Hz, 1H), 7.58 (br s, 1H), 5.13 (s, 2H), 3.56 (s, 3H), 2.26 (s, 3H), 1.08 (s, 3H), 0.63-0.57 (m, 2H), 0.43-0.37 (m, 2H) |
| 419 | >95 | ¹H NMR (300 MHz, DMSO-d6) Shift = 8.43 (d, J = 2.26 Hz, 1H), 7.96 (dd, J = 8.85, 2.26 Hz, 1H), 7.70 (s, 1H), 7.48 (d, J = 8.85 Hz, 1H), 7.33-7.43 (m, 3H), 7.17 (t, J = 8.90 Hz, 2H), 5.38 (s, 2H), 5.00 (s, 2H), 4.25 (s, 1H), 4.09 (s, 1H), 3.77 (s, 3H), 0.58-0.77 (m, 4H) |
| 420 | >95 | ¹H NMR (300 MHz, CHLOROFORM-d) Shift = 8.73 (d, J = 2.3 Hz, 1H), 8.20 (dd, J = 2.3, 8.9 Hz, 1H), 7.68 (d, J = 8.9 Hz, 1H), 6.17 (s, 1H), 5.37 (s, 2H), 4.37 (s, 2H), 2.27 (s, 3H), 1.41 (s, 4H), 0.86-0.69 (m, 2H), 0.61-0.42 (m, 2H) |
| 421 | >95 | ¹H NMR (300 MHz, CHLOROFORM-d) Shift = 8.75 (d, J = 2.3 Hz, 1H), 8.19 (dd, J = 2.3, 8.9 Hz, 1H), 7.33 (d, J = 8.9 Hz, 1H), 6.18 (s, 1H), 5.40 (s, 2H), 4.19 (d, J = 7.3 Hz, 2H), 2.53-2.32 (m, 5H), 2.29 (s, 3H), 2.15-2.01 (m, 2H), 1.77-1.63 (m, 2H), 1.29 (s, 3H), 0.87-0.72 (m, 2H), 0.58-0.52 (m, 2H) |
| 422 | >95 | ¹H NMR (300 MHz, DMSO-d6) Shift = 11.11 (s, 1H), 8.31 (d, J = 2.1 Hz, 1H), 8.24 (s, 1H), 8.18 (d, J = 2.1 Hz, 1H), 7.67 (s, 1H), 7.39 (s, 1H), 4.91 (s, 2H), 3.76 (s, 3H), 1.08 (s, 3H), 0.66-0.56 (m, 2H), 0.46-0.38 (m, 2H) |
| 423 | >95 | ¹H NMR (300 MHz, DMSO-d6) Shift = 8.48 (br d, J = 2.0 Hz, 1H), 8.42 (d, J = 2.2 Hz, 1H), 8.20 (br s, 1H), 8.09 (dd, J = 2.3, 8.8 Hz, 1H), 7.69-7.63 (m, 2H), 7.19 (d, J = 8.0 Hz, 1H), 5.12 (s, 2H), 3.55 (s, 3H), 2.42 (s, 3H), 1.08 (s, 3H), 0.63-0.57 (m, 2H), 0.42-0.36 (m, 2H) |
| 424 | >95 | ¹H NMR (300 MHz, DMSO-d6) Shift = 12.14 (s, 1H), 8.84 (br. s, 1H), 8.57 (d, J = 2.1 Hz, 1H), 8.49 (s, 1H), 8.19 (s, 1H), 8.12 (br. s, 1H), 7.67 (s, 1H), 7.39 (s, 1H), 4.90 (s, 2H), 3.76 (s, 3H), 1.09 (s, 3H), 0.66-0.54 (m, 2H), 0.46-0.34 (m, 2H) |
| 425 | >95 | ¹H NMR (300 MHz, DMSO-d6) Shift = 8.42 (d, J = 2.3 Hz, 1H), 8.24 (br s, 1H), 8.07 (dd, J = 2.3, 8.9 Hz, 1H), 7.92 (s, 1H), 7.81 (d, J = 8.9 Hz, 1H), 6.34 (s, 1H), 5.22 (s, 2H), 4.45 (d, J = 7.5 Hz, 2H), 4.17 (t, J = 8.5 Hz, 1H), 4.03-3.87 (m, 2H), 3.79-3.71 (m, 2H), 3.12-3.05 (m, 1H), 2.18 (s, 3H), 1.10 (s, 3H), 0.64-0.58 (m, 2H), 0.44-0.38 (m, 2H) |
| 426 | >95 | ¹H NMR (300 MHz, DMSO-d6) Shift = 8.13-8.05 (m, 2H), 8.02-7.96 (m, 1H), 7.90-7.81 (m, 2H), 4.25 (d, J = 6.9 Hz, 2H), 2.15 (d, J = 1.0 Hz, 3H), 1.28-1.21 (m, 1H), 1.06 (s, 3H), 0.66-0.55 (m, 2H), 0.51-0.43 (m, 4H), 0.41-0.34 (m, 2H) |
| 427 | >95 | ¹H NMR (300 MHz, DMSO-d6) Shift = 8.85-8.58 (m, 1H), 8.47 (s, 1H), 8.10 (br d, J = 8.1 Hz, 1H), 7.76-7.58 (m, 2H), 7.39 (s, 1H), 4.96 (br s, 2H), 3.76 (s, 3H), 3.55 (s, 3H), 2.72-2.66 (m, 1H), 1.19-1.12 (m, 2H), 1.04-0.94 (m, 2H) |
| 428 | >95 | ¹H NMR (300 MHz, DMSO-d6) Shift = 8.71 (t, J = 6.08 Hz, 1H), 8.28 (d, J = 2.17 Hz, 1H), 8.17 (s, 1H), 7.87 (d, J = 2.07 Hz, 1H), 7.67 (s, 1H), 7.39 (s, 1H), 5.76 (s, 1H), 4.91 (s, 2H), 4.41 (d, J = 6.03 Hz, 2H), 3.76 (s, 3H), 1.92 (s, 3H), 1.07 (s, 3H), 0.52-0.64 (m, 2H), 0.33-0.44 (m, 2H) |
| 429 | 85-90 | ¹H NMR (300 MHz, CHLOROFORM-d) Shift = 8.56 (s, 1H), 8.43 (br s, 1H), 7.62 (d, J = 15.26 Hz, 2H), 7.14-7.21 (m, 1H), 5.16 (s, 2H), 4.46 (s, 2H), 3.87 (s, 3H), 2.69 (s, 6H), 1.24 (s, 3H), 0.71-0.82 (m, 2H), 0.46-0.57 (m, 2H) |
| 430 | >95 | ¹H NMR (300 MHz, DMSO-d6) Shift = 11.80 (br. s., 1H), 8.32 (d, J = 2.1 Hz, 1H), 8.13 (s, 1H), 7.99 (dd, J = 2.2, 8.6 Hz, 1H), 7.66 (s, 1H), 7.38 (s, 1H), 7.32 (d, J = 8.7 Hz, 1H), 4.90 (s, 2H), 3.76 (s, 3H), 1.06 (s, 3H), 0.62-0.54 (m, 2H), 0.41-0.34 (m, 2H) |
| 431 | >95 | ¹H NMR (300 MHz, DMSO-d6) Shift = 8.37 (br s, 1H), 8.01 (br d, J = 8.4 Hz, 1H), 7.67 (s, 1H), 7.43-7.25 (m, 2H), 4.90 (br s, 2H), 3.76 (br s, 3H), 2.72 (br s, 1H), 1.14 (br s, 2H), 0.99 (br s, 2H) |
| 432 | >95 | ¹H NMR (300 MHz, CHLOROFORM-d) Shift = 8.88-8.75 (m, 1H), 8.26-8.14 (m, 1H), 7.65-7.53 (m, 3H), 7.46-7.39 (m, 1H), 5.23 (s, 1H), 5.13 (s, 2H), 4.11 (br d, J = 6.5 Hz, 2H), 3.87 (s, 3H), 1.82-1.73 (m, 1H), 1.49-1.41 (m, 2H), 1.22-1.10 (m, 4H), 0.66-0.54 (m, 4H) |

TABLE 3-continued

<sup>1</sup>H NMR data

| Example | NMR Purity | <sup>1</sup>H NMR |
|---|---|---|
| 433 | >95 | <sup>1</sup>H NMR (300 MHz, DMSO-d6) Shift = 8.71 (br s, 2H), 8.41 (d, J = 2.3 Hz, 1H), 8.21 (br s, 1H), 8.09 (dd, J = 2.3, 8.8 Hz, 1H), 7.66 (d, J = 8.8 Hz, 1H), 5.12 (s, 2H), 3.55 (s, 3H), 2.58 (s, 3H), 1.08 (s, 3H), 0.63-0.56 (m, 2H), 0.42-0.36 (m, 2H) |
| 434 | 90-95 | <sup>1</sup>H NMR (300 MHz, CHLOROFORM-d) Shift = 8.74 (d, J = 2.2 Hz, 1H), 8.44 (br d, J = 5.2 Hz, 1H), 8.22 (br s, 1H), 8.14 (dd, J = 2.2, 8.8 Hz, 1H), 8.07 (d, J = 9.3 Hz, 1H), 7.74-7.44 (m, 2H), 7.24-7.16 (m, 1H), 6.81-6.74 (m, 1H), 5.44 (s, 2H), 3.65 (s, 3H), 1.24 (s, 3H), 0.80-0.74 (m, 2H), 0.54-0.47 (m, 2H) |
| 435 | >95 | <sup>1</sup>H NMR (300 MHz, DMSO-d6) Shift = 8.44 (d, J = 2.3 Hz, 1H), 8.23 (s, 1H), 8.06 (dd, J = 2.3, 8.8 Hz, 1H), 7.78 (d, J = 8.9 Hz, 1H), 7.68 (s, 1H), 7.39 (s, 1H), 4.96 (s, 2H), 4.34 (d, J = 7.4 Hz, 2H), 3.76 (s, 3H), 1.68-1.59 (m, 1H), 1.56-1.43 (m, 1H), 1.08 (s, 3H), 1.05-0.94 (m, 1H), 0.63-0.56 (m, 2H), 0.42-0.37 (m, 2H) |
| 436 | >95 | <sup>1</sup>H NMR (300 MHz, DMSO-d6) Shift = 8.42 (d, J = 2.2 Hz, 1H), 8.22 (s, J = 3.6, 3.6 Hz, 1H), 8.03 (t, J = 5.2 Hz, 1H), 7.74 (d, J = 9.1 Hz, 1H), 7.67 (s, 1H), 7.39 (s, 1H), 4.95 (s, 2H), 4.37-4.31 (m, 2H), 3.76 (s, 3H), 2.78-2.70 (m, 1H), 2.61 (d, J = 9.3 Hz, 4H), 1.08 (s, 3H), 0.62-0.56 (m, 2H), 0.42-0.36 (m, 2H) |
| 437 | >95 | <sup>1</sup>H NMR (300 MHz, DMSO-d6) Shift = 8.43 (d, J = 2.2 Hz, 1H), 8.31 (br. s., 1H), 8.02 (dd, J = 2.3, 8.9 Hz, 1H), 7.68 (s, 1H), 7.56 (d, J = 9.0 Hz, 1H), 7.39 (s, 1H), 5.74 (s, 1H), 5.37 (s, 2H), 4.97 (s, 2H), 4.19 (d, J = 47.4 Hz, 2H), 3.82 (s, 3H), 3.76 (s, 3H), 1.99 (s, 3H), 0.76-0.63 (m, 4H) |
| 438 | >95 | <sup>1</sup>H NMR (300 MHz, DMSO-d6) Shift = 8.59 (s, 1H), 8.41 (d, J = 2.3 Hz, 1H), 8.05 (dd, J = 2.3, 8.9 Hz, 1H), 7.73-7.64 (m, 2H), 7.39 (s, 1H), 4.95 (s, 2H), 4.19 (d, J = 49.5 Hz, 2H), 4.17 (q, J = 6.9 Hz, 2H), 3.76 (s, 3H), 1.22 (t, J = 6.9 Hz, 3H), 0.79-0.60 (m, 4H) |
| 439 | >95 | <sup>1</sup>H NMR (300 MHz, DMSO-d6) Shift = 8.44 (d, J = 2.3 Hz, 1H), 8.15 (dd, J = 2.2, 8.8 Hz, 1H), 7.78 (d, J = 8.9 Hz, 1H), 7.69 (s, 1H), 7.40 (s, 1H), 5.33 (s, 2H), 4.95 (s, 2H), 4.19 (d, J = 48.0 Hz, 2H), 3.76 (s, 3H), 0.78-0.64 (m, 4H) |
| 440 | >95 | <sup>1</sup>H NMR (300 MHz, DMSO-d6) Shift = 8.62 (s, 1H), 8.43 (d, J = 2.2 Hz, 1H), 8.13 (dd, J = 2.3, 8.9 Hz, 1H), 7.68 (s, 1H), 7.69 (d, J = 7.3 Hz, 1H), 7.40 (s, 1H), 4.99 (d, J = 2.2 Hz, 2H), 4.95 (s, 2H), 4.20 (d, J = 47.8 Hz, 2H), 3.76 (s, 3H), 3.41 (t, J = 2.3 Hz, 1H), 0.78-0.63 (m, 4H) |
| 441 | >95 | <sup>1</sup>H NMR (300 MHz, DMSO-d6) Shift = 8.43 (d, J = 2.3 Hz, 1H), 8.33 (br. s., 1H), 8.05 (dd, J = 2.3, 8.9 Hz, 1H), 7.71-7.64 (m, 2H), 7.40 (s, 1H), 6.38 (s, 1H), 5.49 (s, 2H), 4.97 (s, 2H), 4.19 (d, J = 47.8 Hz, 2H), 3.76 (s, 3H), 2.17 (s, 3H), 0.80-0.61 (m, 4H) |
| 442 | >95 | <sup>1</sup>H NMR (300 MHz, DMSO-d6) Shift = 8.58 (br. s., 1H), 8.41 (d, J = 2.3 Hz, 1H), 8.02 (dd, J = 2.2, 8.9 Hz, 1H), 7.73 (d, J = 9.0 Hz, 1H), 7.67 (s, 1H), 7.38 (s, 1H), 4.95 (s, 2H), 4.20 (d, J = 48.7 Hz, 2H), 4.06 (d, J = 7.3 Hz, 2H), 3.86-3.79 (m, 2H), 3.75 (s, 3H), 3.27-3.16 (m, 2H), 2.31-2.23 (m, 1H), 1.63-1.51 (m, 2H), 1.41-1.27 (m, 2H), 0.76-0.65 (m, 4H) |
| 443 | >95 | <sup>1</sup>H NMR (300 MHz, DMSO-d6) Shift = 8.59 (br. s., 1H), 8.43 (d, J = 2.3 Hz, 1H), 8.06 (dd, J = 2.3, 8.9 Hz, 1H), 7.78 (d, J = 8.9 Hz, 1H), 7.68 (s, 1H), 7.39 (s, 1H), 4.96 (s, 2H), 4.33 (d, J = 7.2 Hz, 2H), 4.20 (d, J = 49.8 Hz, 2H), 3.76 (s, 3H), 2.30-2.15 (m, 1H), 1.75-1.58 (m, 1H), 1.58-1.39 (m, 1H), 0.79-0.63 (m, 4H) |
| 444 | >95 | <sup>1</sup>H NMR (300 MHz, DMSO-d6) Shift = 8.59 (br. s., 1H), 8.41 (d, J = 2.3 Hz, 1H), 8.03 (dd, J = 2.3, 8.9 Hz, 1H), 7.74 (d, J = 8.9 Hz, 1H), 7.67 (s, 1H), 7.39 (s, 1H), 4.95 (s, 2H), 4.33 (d, J = 4.5 Hz, 2H), 4.19 (d, J = 49.3 Hz, 2H), 3.76 (s, 3H), 2.73 (s, 1H), 2.68-2.56 (m, 4H), 0.70 (d, J = 9.6 Hz, 4H) |
| 445 | >95 | <sup>1</sup>H NMR (300 MHz, DMSO-d6) Shift = 8.40 (d, J = 2.3 Hz, 1H), 8.35 (s, 1H), 8.01 (dd, J = 2.4, 8.9 Hz, 1H), 7.70 (d, J = 9.0 Hz, 1H), 7.67 (s, 1H), 7.38 (s, 1H), 4.95 (s, 2H), 4.60 (dd, J = 6.1, 7.8 Hz, 2H), 4.54-4.43 (m, 4H), 4.19 (d, J = 49.1 Hz, 2H), 3.76 (s, 3H), 3.40-3.36 (m, 1H), 0.76-0.64 (m, 4H) |
| 446 | 85-90 | <sup>1</sup>H NMR (300 MHz, DMSO-d6) Shift = 9.29-9.26 (m, 1H), 9.14 (dd, J = 1.1, 5.3 Hz, 1H), 8.89 (br s, 1H), 8.41 (d, J = 2.2 Hz, 1H), 8.11 (dd, J = 2.3, 8.9 Hz, 1H), 7.70 (d, J = 8.9 Hz, 1H), 7.66-7.62 (m, 1H), 5.19 (s, 2H), 3.56 (s, 3H), 1.09 (s, 3H), 0.64-0.57 (m, 2H), 0.43-0.37 (m, 2H) |
| 447 | >95 | <sup>1</sup>H NMR (300 MHz, DMSO-d6) Shift = 8.94 (d, J = 1.8 Hz, 1H), 8.73-8.68 (m, 3H), 8.56 (dd, J = 1.1, 7.3 Hz, 1H), 8.47 (br s, 1H), 8.02-7.96 (m, 1H), 1.08 (s, 3H), 0.65-0.58 (m, 2H), 0.44-0.38 (m, 2H) |
| 448 | >95 | <sup>1</sup>H NMR (300 MHz, DMSO-d6) Shift = 10.83 (s, 1H), 8.52-8.58 (m, 2H), 8.35 (s, 1H), 7.69 (s, 1H), 7.40 (s, 1H), 4.92 (s, 2H), 0.33-0.47 (m, 2 H) 3.98 (s, 3H), 3.76 (s, 3H), 1.08 (s, 3H), 0.51-0.67 (m, 2H) |
| 449 | >95 | <sup>1</sup>H NMR (300 MHz, DMSO-d6) Shift = 8.33 (s, 2H), 8.25 (d, J = 2.3 Hz, 1H), 7.66-7.59 (m, 2H), 7.37 (s, 1H), 4.88 (s, 2H), 3.75 (s, 3H), 2.99 (s, 3H), 2.78 (s, 3H), 1.05 (s, 3H), 0.64-0.55 (m, 2H), 0.36 (d, J = 2.0 Hz, 2H) |
| 450 | >95 | <sup>1</sup>H NMR (300 MHz, DMSO-d6) Shift = 8.50 (d, J = 2.1 Hz, 1H), 8.45 (s, 1H), 8.17 (br. s., 1H), 7.66 (s, 1H), 7.38 (s, 1H), 4.90 (s, 2H), 3.76 (s, 3H), 2.83 (d, J = 4.5 Hz, 3H), 1.08 (s, 3H), 0.63-0.56 (m, 2H), 0.42-0.34 (m, 2H) |
| 451 | 90-95 | <sup>1</sup>H NMR (300 MHz, DMSO-d6) Shift = 11.44 (s, 1H), 8.40 (d, J = 2.1 Hz, 1H), 8.21 (s, 1H), 7.96 (d, J = 2.2 Hz, 1H), 7.68 (s, 1H), 7.40 (s, 1H), 4.91 (s, 2H), 3.76 (s, 3H), 3.45 (s, 3H), 3.30 (s, 3H), 1.06 (s, 3H), 0.63-0.55 (m, 2H), 0.43-0.36 (m, 2H) |
| 452 | >95 | <sup>1</sup>H NMR (300 MHz, DMSO-d6) Shift = 8.43 (d, J = 2.1 Hz, 1H), 8.32 (br. s, 1H), 8.13-8.02 (m, 2H), 6.35 (s, 1H), 5.23 (s, 2H), 4.46 (s, 2H), 2.17 (s, 3H), 1.44 (s, 6H), 1.07 (s, 3H), 0.65-0.55 (m, 2H), 0.42-0.36 (m, 2H) |
| 453 | >95 | <sup>1</sup>H NMR (300 MHz, DMSO-d6) Shift = 8.44-8.40 (m, 1H), 8.23 (s, 1H), 8.06 (dd, J = 2.3, 9.0 Hz, 1H), 7.87-7.75 (m, 1H), 6.33 (s, 1H), 5.24 (s, 2H), 4.44 (d, J = 20.3 Hz, 2H), 2.17 (s, 3H), 1.44 (s, 3H), 1.37 (s, 3H), 1.09 (s, 3H), 0.64-0.58 (m, 2H), 0.44-0.38 (m, 2H) |

TABLE 3-continued

¹H NMR data

| Example | NMR Purity | ¹H NMR |
|---|---|---|
| 454 | 90-95 | ¹H NMR (300 MHz, DMSO-d6) Shift = 8.96 (d, J = 1.8 Hz, 1H), 8.77-8.68 (m, 2H), 8.63 (dd, J = 1.1, 7.4 Hz, 1H), 8.50 (br s, 1H), 8.05-7.97 (m, 1H), 7.70 (s, 1H), 7.42 (s, 1H), 5.07 (s, 2H), 3.75 (s, 3H), 1.08 (s, 3H), 0.64-0.57 (m, 2H), 0.44-0.37 (m, 2H) |
| 455 | >95 | ¹H NMR (300 MHz, DMSO-d6) Shift = 8.46 (d, J = 2.2 Hz, 1H), 8.41-8.35 (m, 1H), 8.16-8.07 (m, 1H), 7.80-7.72 (m, 1H), 7.63 (s, 1H), 5.26 (s, 2H), 4.26-4.10 (m, 2H), 2.60-2.55 (m, 3H), 1.42-1.32 (m, 2H), 1.27-1.16 (m, 5H) |
| 456 | >95 | ¹H NMR (300 MHz, DMSO-d6) Shift = 11.87 (s, 1H), 8.86 (s, 1H), 8.30 (d, J = 2.1 Hz, 1H), 7.98 (dd, J = 2.2, 8.7 Hz, 1H), 7.66 (s, 1H), 7.38 (s, 1H), 7.31 (d, J = 8.6 Hz, 1H), 5.78 (t, J = 57.6 Hz, 1H), 4.89 (s, 2H), 3.76 (s, 3H), 0.94-0.89 (m, 2H), 0.80-0.75 (m, 2H) |
| 457 | >95 | ¹H NMR (300 MHz, DMSO-d6) Shift = 8.49-8.42 (m, 1H), 8.41-8.32 (m, 1H), 8.16-8.03 (m, 1H), 7.92-7.78 (m, 1H), 7.74-7.59 (m, 2H), 7.52-7.40 (m, 1H), 5.28 (s, 4H), 3.74 (s, 3H), 2.57 (s, 3H), 1.48-1.30 (m, 2H), 1.28-1.12 (m, 5H) |
| 458 | >95 | ¹H NMR (300 MHz, DMSO-d6) Shift = 8.42 (d, J = 2.4 Hz, 1H), 8.05 (dd, J = 2.3, 8.9 Hz, 1H), 7.78 (d, J = 9.0 Hz, 1H), 7.69-7.64 (m, 1H), 7.39-7.34 (m, 1H), 5.77 (t, J = 57.1 Hz, 1H), 4.95 (s, 2H), 4.08 (d, J = 7.0 Hz, 2H), 3.75 (s, 3H), 1.27-1.14 (m, 1H), 0.96-0.78 (m, 4H), 0.51-0.44 (m, 4H) |
| 459 | 90-95 | ¹H NMR (300 MHz, DMSO-d6) Shift = 8.43 (d, J = 2.3 Hz, 1H), 8.02 (dd, J = 2.3, 8.9 Hz, 1H), 7.68 (s, 1H), 7.55 (d, J = 8.9 Hz, 1H), 7.39 (s, 1H), 5.96 (t, J = 57.3 Hz, 1H), 5.37 (s, 2H), 4.97 (s, 2H), 3.82 (s, 3H), 3.76 (s, 3H), 3.55 (s, 1H), 2.00 (s, 3H), 0.96-0.90 (m, 2H), 0.83-0.77 (m, 2H) |
| 460 | >95 | ¹H NMR (300 MHz, DMSO-d6) Shift = 8.93 (br. s., 1H), 8.42 (d, J = 2.3 Hz, 1H), 7.96 (dd, J = 2.4, 8.9 Hz, 1H), 7.70 (s, 1H), 7.48 (d, J = 8.9 Hz, 1H), 7.44-7.34 (m, 3H), 7.22-7.11 (m, 2H), 5.76 (t, J = 56.5 Hz, 1H), 5.38 (s, 2H), 5.00 (s, 2H), 3.78-3.75 (m, 3H), 0.96-0.87 (m, 2H), 0.81-0.73 (m, 2H) |
| 461 | >95 | ¹H NMR (300 MHz, DMSO-d6) Shift = 8.58 (br. s., 1H), 8.40 (d, J = 2.4 Hz, 1H), 8.02 (dd, J = 2.3, 8.9 Hz, 1H), 7.71-7.64 (m, 2H), 7.40-7.35 (m, 1H), 4.95 (s, 2H), 4.22 (d, J = 7.1 Hz, 2H), 4.19 (d, J = 48.6 Hz, 2H), 3.76 (s, 3H), 2.77-2.61 (m, 1H), 2.02-1.90 (m, 2H), 1.89-1.74 (m, 4H), 0.78-0.65 (m, 4H) |
| 462 | >95 | ¹H NMR (300 MHz, DMSO-d6) Shift = 8.40 (d, J = 2.3 Hz, 1H), 8.38 (br. s., 1H), 8.03 (dd, J = 2.3, 8.9 Hz, 1H), 7.74 (d, J = 9.0 Hz, 1H), 7.67 (s, 1H), 7.39 (s, 1H), 4.95 (s, 2H), 4.33 (t, J = 5.7 Hz, 2H), 4.19 (d, J = 48.9 Hz, 2H), 3.76 (s, 3H), 3.62 (t, J = 5.6 Hz, 2H), 3.24 (s, 3H), 0.77-0.64 (m, 4H) |
| 463 | >95 | ¹H NMR (300 MHz, CHLOROFORM-d) Shift = 8.73 (s, J = 4.5 Hz, 1H), 8.12 (dd, J = 2.3, 8.9 Hz, 1H), 7.65 (s, J = 4.4 Hz, 1H), 7.57 (s, 1H), 7.24-7.19 (m, 1H), 5.39 (s, 2H), 5.13 (s, 2H), 4.18 (d, J = 47.9 Hz, 2H), 3.87 (s, 3H), 2.72 (s, 3H), 2.65 (s, 3H), 1.04-0.93 (m, 2H), 0.84-0.76 (m, 2H) |
| 464 | >95 | ¹H NMR (300 MHz, DMSO-d6) Shift = 9.00 (d, J = 1.8 Hz, 1H), 8.80-8.74 (m, 2H), 8.65 (dd, J = 1.1, 7.4 Hz, 1H), 8.53 (br s, 1H), 8.08-8.00 (m, 1H), 6.38 (s, 1H), 5.33 (s, 2H), 2.17 (s, 3H), 1.10 (s, 3H), 0.64-0.58 (m, 2H), 0.45-0.39 (m, 2H) |
| 465 | >95 | ¹H NMR (300 MHz, DMSO-d6) Shift = 8.42 (d, J = 2.2 Hz, 1H), 8.21 (br s, 1H), 8.03 (dd, J = 2.2, 8.8 Hz, 1H), 7.93 (d, J = 8.9 Hz, 1H), 6.32 (s, 1H), 5.23 (s, 2H), 4.11 (s, 2H), 2.18 (s, 3H), 1.07 (s, 3H), 0.94 (s, 9H), 0.63-0.56 (m, 2H), 0.42-0.36 (m, 2H) |
| 466 | >95 | ¹H NMR (300 MHz, DMSO-d6) Shift = 8.43 (d, J = 2.3 Hz, 1H), 8.24 (br s, 1H), 8.08 (dd, J = 2.3, 8.9 Hz, 1H), 7.71 (d, J = 9.0 Hz, 1H), 6.31 (s, 1H), 5.23 (s, 2H), 4.04 (d, J = 7.2 Hz, 2H), 2.17 (s, 3H), 1.97-1.83 (m, 1H), 1.53-1.38 (m, 1H), 1.26-1.13 (m, 1H), 1.09 (s, 3H), 0.92-0.85 (m, 6H), 0.64-0.57 (m, 2H), 0.43-0.37 (m, 2H) |
| 467 | >95 | ¹H NMR (300 MHz, DMSO-d6) Shift = 8.43 (d, J = 2.3 Hz, 1H), 8.22 (br s, 1H), 8.05 (dd, J = 2.3, 8.9 Hz, 1H), 7.69 (d, J = 9.0 Hz, 1H), 6.32 (s, 1H), 5.24 (s, 2H), 4.10 (s, 2H), 2.17 (s, 3H), 2.06-1.80 (m, 3H), 1.65-1.45 (m, 3H), 1.22 (s, 3H), 1.08 (s, 3H), 0.63-0.56 (m, 2H), 0.42-0.36 (m, 2H) |
| 468 | >95 | ¹H NMR (300 MHz, DMSO-d6) Shift = 8.42 (d, J = 2.3 Hz, 1H), 8.24 (s, 1H), 8.14 (dd, J = 2.4, 8.9 Hz, 1H), 7.72 (d, J = 8.8 Hz, 1H), 4.72 (s, 2H), 4.16 (q, J = 7.1 Hz, 2H), 3.59 (s, 3H), 1.22 (t, J = 7.1 Hz, 3H), 1.08 (s, 3H), 0.64-0.57 (m, 2H), 0.40 (d, J = 2.1 Hz, 2H) |
| 469 | >95 | ¹H NMR (300 MHz, DMSO-d6) Shift = 8.40 (d, J = 2.3 Hz, 1H), 8.23 (s, 1H), 8.13 (dd, J = 2.3, 8.9 Hz, 1H), 7.71 (d, J = 8.9 Hz, 1H), 4.86 (s, 2H), 3.57 (s, 3H), 2.62 (q, J = 7.3 Hz, 2H), 1.08 (s, 3H), 0.99 (t, J = 7.3 Hz, 3H), 0.60 (s, 2H), 0.43-0.37 (m, 2H) |
| 470 | >95 | ¹H NMR (300 MHz, DMSO-d6) Shift = 8.43 (d, J = 2.3 Hz, 1H), 8.24 (br s, 1H), 8.10 (dd, J = 2.3, 8.9 Hz, 1H), 7.66 (d, J = 9.0 Hz, 1H), 6.30 (s, 1H), 5.23 (s, 2H), 4.08 (d, J = 7.3 Hz, 2H), 2.18 (s, 3H), 1.86-1.72 (m, 1H), 1.42-1.28 (m, 4H), 1.09 (s, 3H), 0.86 (t, J = 7.4 Hz, 6H), 0.64-0.57 (m, 2H), 0.43-0.37 (m, 2H) |
| 471 | 90-95 | ¹H NMR (300 MHz, DMSO-d6) Shift = 8.41 (d, J = 2.3 Hz, 1H), 8.21 (br s, 1H), 8.06 (dd, J = 2.3, 8.9 Hz, 1H), 7.88 (d, J = 9.0 Hz, 1H), 6.31 (s, 1H), 5.23 (s, 2H), 4.39 (s, 2H), 3.10 (s, 3H), 2.17 (s, 3H), 1.88-1.43 (m, 8H), 1.08 (s, 3H), 0.64-0.56 (m, 2H), 0.43-0.36 (m, 2H) |
| 472 | >95 | ¹H NMR (300 MHz, DMSO-d6) Shift = 8.43 (d, J = 2.3 Hz, 1H), 8.40 (br s, 1H), 8.11 (dd, J = 2.3, 8.9 Hz, 1H), 7.67 (d, J = 9.0 Hz, 1H), 6.33 (s, 1H), 5.22 (s, 2H), 4.19-4.08 (m, 2H), 2.18 (s, 3H), 1.80-1.64 (m, 2H), 1.59-1.46 (m, 2H), 1.09 (s, 3H), 0.97 (d, J = 6.6 Hz, 6H), 0.64-0.57 (m, 2H), 0.43-0.37 (m, 2H) |
| 473 | >95 | ¹H NMR (300 MHz, DMSO-d6) Shift = 8.42 (d, J = 2.3 Hz, 1H), 8.22 (br s, 1H), 8.07 (dd, J = 2.3, 8.9 Hz, 1H), 7.83-7.78 (m, 2H), 7.48 (s, 1H), 6.35 (s, 1H), 5.25 (s, 2H), 5.20 (s, 2H), 4.49-4.34 (m, 1H), 2.18 (s, 3H), 1.34 (d, J = 6.7 Hz, 6H), 1.07 (s, 3H), 0.62-0.56 (m, 2H), 0.42-0.36 (m, 2H) |

TABLE 3-continued

<sup>1</sup>H NMR data

| Example | NMR Purity | <sup>1</sup>H NMR |
|---|---|---|
| 474 | >95 | <sup>1</sup>H NMR (300 MHz, DMSO-d6) Shift = 8.43 (d, J = 2.3 Hz, 1H), 8.23 (br s, 1H), 8.09 (dd, J = 2.3, 8.7 Hz, 1H), 7.73 (d, J = 9.0 Hz, 1H), 6.32 (s, 1H), 5.22 (s, 2H), 4.16-4.06 (s, 2H), 2.17 (s, 3H), 1.70-1.49 (m, 4H), 1.31-1.19 (m, 2H), 1.09 (s, 3H), 0.86 (d, J = 6.6 Hz, 6H), 0.86-0.81 (m, 1H), 0.64-0.58 (m, 2H), 0.43-0.38 (m, 2H) |
| 475 | >95 | <sup>1</sup>H NMR (300 MHz, DMSO-d6) Shift = 8.41 (d, J = 2.3 Hz, 1H), 8.23 (br. s, 1H), 8.13 (dd, J = 2.4, 8.9 Hz, 1H), 7.71 (d, J = 8.9 Hz, 1H), 4.73 (s, 2H), 3.58 (s, 3H), 3.57-3.52 (m, 2H), 3.31-3.26 (m, 2H), 2.00-1.90 (m, 2H), 1.86-1.76 (m, 2H), 1.08 (s, 3H), 0.64-0.57 (m, 2H), 0.44-0.37 (m, 2H) |
| 476 | >95 | <sup>1</sup>H NMR (300 MHz, DMSO-d6) Shift = 8.40 (d, J = 2.3 Hz, 1H), 8.38 (s, 1H), 8.13 (dd, J = 2.4, 8.9 Hz, 1H), 7.71 (d, J = 8.9 Hz, 1H), 4.81 (s, 2H), 3.58 (s, 3H), 3.10 (s, 3H), 2.85 (s, 3H), 1.08 (s, 3H), 0.63-0.57 (m, 2H), 0.44-0.37 (m, 2H) |
| 477 | >95 | <sup>1</sup>H NMR (300 MHz, MeOD) Shift = 8.60 (d, J = 2.3 Hz, 1H), 8.16 (dd, J = 2.3, 8.9 Hz, 1H), 7.63 (d, J = 8.9 Hz, 1H), 6.24 (s, 1H), 5.36 (s, 2H), 4.31 (d, J = 7.2 Hz, 2H), 2.84-2.66 (m, 1H), 2.25 (s, 3H), 1.91-1.71 (m, 4H), 1.18 (s, 3H), 1.13 (s, 3H), 1.11 (s, 3H), 0.76-0.70 (m, 2H), 0.49-0.43 (m, 2H) |
| 478 | 90-95 | <sup>1</sup>H NMR (300 MHz, MeOD) Shift = 8.60 (d, J = 2.2 Hz, 1H), 8.14 (dd, J = 2.3, 8.9 Hz, 1H), 7.70 (s, 1H), 7.60 (d, J = 9.0 Hz, 1H), 5.38 (s, 2H), 4.31 (d, J = 7.2 Hz, 2H), 2.80-2.66 (m, 1H), 2.65 (s, 3H), 1.90-1.71 (m, 4H), 1.17 (s, 3H), 1.13 (s, 3H), 1.11 (s, 3H), 0.75-0.69 (m, 2H), 0.48-0.43 (m, 2H) |
| 479 | >95 | <sup>1</sup>H NMR (300 MHz, DMSO-d6) Shift = 11.89 (s, 1H), 9.08 (s, 1H), 8.88 (s, 1H), 8.28 (d, J = 2.2 Hz, 1H), 7.97 (dd, J = 2.2, 8.7 Hz, 1H), 7.66 (s, 1H), 7.38 (s, 1H), 7.31 (d, J = 8.6 Hz, 1H), 4.90 (s, 2H), 3.76 (s, 3H), 1.36-1.25 (m, 2H), 1.16-1.06 (m, 2H) |
| 480 | >95 | <sup>1</sup>H NMR (300 MHz, DMSO-d6) Shift = 8.47 (d, J = 2.3 Hz, 1H), 8.36 (s, 1H), 8.07 (dd, J = 2.3, 8.9 Hz, 1H), 7.68 (s, 1H), 7.54 (d, J = 8.9 Hz, 1H), 7.39 (s, 1H), 5.73 (s, 1H), 5.37 (s, 2H), 4.97 (s, 2H), 3.82 (s, 3H), 3.76 (s, 3H), 1.99 (s, 3H), 1.10 (s, 9H) |
| 481 | >95 | <sup>1</sup>H NMR (300 MHz, CHLOROFORM-d) Shift = 8.72 (d, J = 2.3 Hz, 1H), 8.18 (d, J = 8.9 Hz, 1H), 7.36-7.30 (m, 1H), 4.96 (s, 1H), 4.82-4.74 (m, 2H), 4.71-4.64 (m, 2H), 4.44 (d, J = 6.7 Hz, 2H), 3.66 (s, 3H), 3.55-3.38 (m, 1H), 1.27 (s, 3H), 0.81-0.75 (m, 2H), 0.56-0.49 (m, 2H) |
| 482 | >95 | <sup>1</sup>H NMR (300 MHz, DMSO-d6) Shift = 8.38 (d, J = 2.3 Hz, 1H), 8.36 (s, 1H), 8.28 (d, J = 2.3 Hz, 1H), 6.37 (s, 1H), 5.17 (s, 2H), 3.73 (s, 3H), 2.18 (s, 3H), 1.12 (s, 3H), 0.64-0.58 (m, 2H), 0.48-0.41 (m, 2H) |
| 483 | >95 | <sup>1</sup>H NMR (300 MHz, DMSO-d6) Shift = 8.37 (d, J = 2.4 Hz, 1H), 8.23 (s, 1H), 8.01 (s, 1H), 7.91 (d, J = 2.4 Hz, 1H), 7.66 (s, 1H), 6.36 (s, 1H), 5.22 (s, 2H), 3.92 (s, 3H), 3.04 (s, 3H), 2.19 (s, 3H), 1.11 (s, 3H), 0.66-0.58 (m, 2H), 0.47-0.38 (m, 2H) |
| 484 | >95 | <sup>1</sup>H NMR (300 MHz, DMSO-d6) Shift = 8.71-8.68 (m, 1H), 8.50 (d, J = 5.6 Hz, 1H), 8.46 (br s, 1H), 8.33 (d, J = 8.7 Hz, 1H), 8.17 (dd, J = 1.8, 8.7 Hz, 1H), 8.05 (dd, J = 0.7, 5.7 Hz, 1H), 1.07 (s, 3H), 0.64-0.58 (m, 2H), 0.45-0.39 (m, 2H) |
| 485 | >95 | <sup>1</sup>H NMR (300 MHz, DMSO-d6) Shift = 9.32 (s, 1H), 8.43 (d, J = 2.4 Hz, 1H), 8.02 (dd, J = 2.3, 8.9 Hz, 1H), 7.68 (s, 1H), 7.56 (d, J = 8.9 Hz, 1H), 7.39 (s, 1H), 5.73 (s, 1H), 5.37 (s, 2H), 4.97 (s, 2H), 3.82 (s, 3H), 3.76 (s, 3H), 1.99 (s, 3H), 1.25-1.16 (m, 2H), 1.11-1.00 (m, 2H) |
| 486 | >95 | <sup>1</sup>H NMR (300 MHz, DMSO-d6) Shift = 12.14 (s, 1H), 8.05 (d, J = 2.0 Hz, 1H), 7.97 (s, 1H), 7.82 (s, 1H), 7.78 (dd, J = 2.1, 8.7 Hz, 1H), 7.53 (s, 1H), 7.41 (d, J = 8.7 Hz, 1H), 7.31 (s, 1H), 3.78 (s, 3H), 3.63 (s, 2H), 1.03 (s, 3H), 0.57 (s, 2H), 0.40-0.30 (m, 2H) |
| 487 | >95 | <sup>1</sup>H NMR (300 MHz, DMSO-d6) Shift = 12.61 (br. s., 1H), 8.72 (s, 1H), 8.18 (d, J = 2.1 Hz, 1H), 8.08 (s, 1H), 7.88 (dd, J = 2.1, 8.8 Hz, 1H), 7.46 (d, J = 8.8 Hz, 1H), 1.06 (s, 3H), 0.58 (s, 2H), 0.42-0.33 (m, 2H) |
| 488 | >95 | <sup>1</sup>H NMR (300 MHz, DMSO-d6) Shift = 11.87 (s, 1H), 8.32 (d, J = 2.3 Hz, 1H), 8.11 (s, 1H), 8.03-7.94 (m, 1H), 7.66 (s, 1H), 7.38 (s, 1H), 7.32 (d, J = 8.6 Hz, 1H), 4.90 (s, 2H), 3.76 (s, 3H), 0.62-0.52 (m, 2H), 0.40-0.33 (m, 2H) |
| 489 | >95 | <sup>1</sup>H NMR (300 MHz, DMSO-d6) Shift = 8.42 (d, J = 2.3 Hz, 1H), 8.38 (s, 1H), 8.10-8.04 (m, 1H), 7.70-7.61 (m, 2H), 7.39 (s, 1H), 4.95 (s, 2H), 3.76 (s, 3H), 3.55 (s, 3H), 0.62-0.54 (m, 2H), 0.41-0.34 (m, 2H) |
| 490 | >95 | <sup>1</sup>H NMR (300 MHz, DMSO-d6) Shift = 8.44 (d, J = 2.3 Hz, 1H), 8.02 (dd, J = 2.3, 8.9 Hz, 1H), 7.68 (s, 1H), 7.56 (d, J = 8.9 Hz, 1H), 7.39 (s, 1H), 5.73 (s, 1H), 5.37 (s, 2H), 4.97 (s, 2H), 3.79 (d, J = 16.4 Hz, 6H), 1.99 (s, 3H), 0.58 (d, J = 2.0 Hz, 2H), 0.43-0.34 (m, 2H). |
| 491 | >95 | <sup>1</sup>H NMR (300 MHz, DMSO-d6) Shift = 8.10 (d, J = 2.1 Hz, 1H), 8.05 (s, 1H), 7.89 (dd, J = 2.2, 8.9 Hz, 1H), 7.85 (s, 1H), 7.70 (d, J = 9.0 Hz, 1H), 7.54 (s, 1H), 7.31 (s, 1H), 3.78 (s, 3H), 3.69 (s, 3H), 3.68 (br. s, 2H), 1.04 (s, 3H), 0.62-0.55 (m, 2H), 0.39-0.32 (m, 2H) |
| 492 | >95 | <sup>1</sup>H NMR (300 MHz, DMSO-d6) Shift = 8.38 (s, 1H), 8.14 (d, J = 2.1 Hz, 1H), 7.92 (s, 1H), 7.84 (dd, J = 2.2, 8.9 Hz, 1H), 7.64 (d, J = 9.0 Hz, 1H), 7.55 (s, 1H), 7.32 (s, 1H), 5.54 (s, 2H), 5.40 (s, 1H), 3.85 (s, 3H), 3.79 (s, 3H), 3.70 (s, 2H), 1.97 (s, 3H), 1.05 (s, 3H), 0.61-0.54 (m, 2H), 0.39-0.32 (m, 2H) |
| 493 | >95 | <sup>1</sup>H NMR (300 MHz, DMSO-d6) Shift = 8.42 (d, J = 2.4 Hz, 1H), 7.96 (d, J = 2.3 Hz, 1H), 7.04 (d, J = 3.5 Hz, 1H), 6.89 (dd, J = 1.1, 3.4 Hz, 1H), 6.37 (s, 1H), 5.76 (s, 2H), 5.21 (s, 2H), 3.07 (s, 3H), 2.19 (s, 3H), 1.11 (s, 3H), 0.66-0.59 (m, 2H), 0.45-0.40 (m, 2H) |
| 494 | >95 | <sup>1</sup>H NMR (300 MHz, DMSO-d6) Shift = 8.95 (s, 1H), 8.58 (s, 1H), 8.41 (d, J = 2.3 Hz, 1H), 8.08 (dd, J = 2.2, 8.9 Hz, 1H), 7.66 (d, J = 8.9 Hz, 1H), 5.21 (s, 2H), 4.34-4.06 (m, 2H), 3.56 (s, 3H), 0.70 (d, J = 12.3 Hz, 4H). |
| 495 | >95 | <sup>1</sup>H NMR (300 MHz, DMSO-d6) Shift = 11.83 (s, 1H), 8.48-8.43 (m, 1H), 8.30-8.27 (m, 1H), 8.13 (s, 1H), 8.03-7.97 (m, 1H), 7.74-7.67 (m, 1H), 7.35-7.26 (m, 2H), 7.25-7.19 (m, 1H), 4.30-4.20 (m, 2H), 3.10-3.00 (m, 2H), 1.07 (s, 3H), 0.62-0.55 (m, 2H), 0.42-0.34 (m, 2H) |

TABLE 3-continued

| Example | NMR Purity | ¹H NMR |
|---|---|---|
| 496 | >95 | ¹H NMR (300 MHz, DMSO-d6) Shift = 11.95 (s, 1H), 8.32 (d, J = 2.1 Hz, 1H), 8.15 (s, 1H), 8.05-8.00 (m, 1H), 7.35 (d, J = 8.6 Hz, 1H), 4.16 (t, J = 6.7 Hz, 2H), 2.89 (t, J = 6.7 Hz, 2H), 1.07 (s, 3H), 0.62-0.53 (m, 2H), 0.42-0.36 (m, 2H) |
| 497 | 90-95 | ¹H NMR (300 MHz, DMSO-d6) Shift = 8.42 (d, J = 2.2 Hz, 1H), 8.22 (s, 1H), 8.13-8.08 (m, 1H), 7.68 (d, J = 8.6 Hz, 1H), 4.22 (t, J = 6.7 Hz, 2H), 3.57 (s, 3H), 2.90 (t, J = 6.7 Hz, 2H), 1.08 (s, 3H), 0.63-0.57 (m, 2H), 0.43-0.37 (m, 2H) |
| 498 | >95 | ¹H NMR (300 MHz, DMSO-d6) Shift = 8.47-8.43 (m, 1H), 8.38 (d, J = 2.2 Hz, 1H), 8.20 (s, 1H), 8.1-8.05 (m, 1H), 7.74-7.63 (m, 2H), 7.32-7.27 (m, 1H), 7.25-7.19 (m, 1H), 4.34-4.26 (m, 2H), 3.56 (s, 3H), 3.09-3.01 (m, 2H), 1.08 (s, 3H), 0.63-0.57 (m, 2H), 0.42-0.37 (m, 2H) |
| 499 | >95 | ¹H NMR (300 MHz, DMSO-d6) Shift = 8.43 (d, J = 2.3 Hz, 1H), 8.40 (s, 1H), 8.23 (s, 1H), 8.13 (dd, J = 2.4, 8.9 Hz, 1H), 7.72 (d, J = 8.9 Hz, 1H), 5.27 (s, 2H), 3.75 (s, 3H), 3.58 (s, 3H), 1.08 (s, 3H), 0.65-0.57 (m, 2H), 0.44-0.37 (m, 2H) |
| 500 | >95 | ¹H NMR (300 MHz, DMSO-d6) Shift = 8.43 (d, J = 2.3 Hz, 1H), 8.23 (s, 1H), 8.12 (dd, J = 2.2, 8.9 Hz, 1H), 7.70 (d, J = 8.9 Hz, 1H), 5.50 (s, 2H), 3.58 (s, 3H), 2.68 (s, 3H), 1.08 (s, 3H), 0.64-0.56 (m, 2H), 0.44-0.37 (m, 2H) |
| 501 | >95 | ¹H NMR (300 MHz, CHLOROFORM-d) Shift = 8.61 (d, J = 2.2 Hz, 1H), 8.13 (dd, J = 2.2, 8.9 Hz, 1H), 7.31 (d, J = 8.9 Hz, 1H), 5.51 (s, 2H), 5.15 (s, 1H), 3.62 (s, 3H), 1.21-1.12 (m, 3H), 0.76-0.60 (m, 2H), 0.52-0.33 (m, 2H) |
| 502 | >95 | ¹H NMR (300 MHz, DMSO-d6) Shift = 8.45 (d, J = 2.3 Hz, 1H), 8.27 (s, 1H), 8.19-8.14 (m, 1H), 7.79 (d, J = 8.9 Hz, 1H), 7.64 (s, 1H), 5.34 (s, 2H), 5.24 (s, 2H), 2.58 (s, 3H), 1.08 (s, 3H), 0.63-0.57 (m, 2H), 0.43-0.38 (m, 2H) |
| 503 | >95 | ¹H NMR (300 MHz, DMSO-d6) Shift = 8.45 (d, J = 2.2 Hz, 1H), 8.29 (s, 1H), 8.22-8.16 (m, 1H), 7.82 (d, J = 8.9 Hz, 1H), 6.38 (s, 1H), 5.36 (s, 2H), 5.21 (s, 2H), 2.18 (s, 3H), 1.10 (s, 3H), 0.64-0.58 (m, 2H), 0.45-0.39 (m, 2H) |
| 504 | >95 | ¹H NMR (300 MHz, CHLOROFORM-d) Shift = 8.72 (d, J = 2.3 Hz, 1H), 8.15 (dd, J = 2.3, 8.8 Hz, 1H), 7.60 (d, J = 0.7 Hz, 1H), 7.34 (t, J = 1.6 Hz, 1H), 7.30 (d, J = 8.9 Hz, 1H), 6.55 (s, 1H), 5.12 (s, 1H), 5.11 (s, 2H), 3.65 (s, 3H), 1.24 (s, 3H), 0.81-0.73 (m, 2H), 0.54-0.46 (m, 2H) |
| 505 | 85-90 | ¹H NMR (300 MHz, DMSO-d6) Shift = 8.42 (d, J = 2.3 Hz, 1H), 8.26 (s, 1H), 8.09 (dd, J = 2.3, 8.9 Hz, 1H), 7.66 (d, J = 8.9 Hz, 1H), 7.48 (d, J = 0.9 Hz, 1H), 6.95 (s, 1H), 5.07 (s, 2H), 3.56 (s, 3H), 1.07 (s, 3H), 0.62-0.55 (m, 2H), 0.42-0.36 (m, 2H) |
| 506 | 85-90 | ¹H NMR (300 MHz, DMSO-d6) Shift = 8.43 (d, J = 2.3 Hz, 1H), 8.38 (s, 1H), 8.08 (dd, J = 2.3, 8.9 Hz, 1H), 7.65 (d, J = 8.9 Hz, 1H), 4.93 (s, 2H), 3.55 (s, 3H), 2.51 (s, 3H), 1.07 (s, 3H), 0.64-0.55 (m, 2H), 0.43-0.35 (m, 2H) |
| 507 | 90-95 | ¹H NMR (300 MHz, CHLOROFORM-d) Shift = 8.72 (d, J = 2.2 Hz, 1H), 8.17-8.12 (m, 1H), 7.63 (d, J = 11.4 Hz, 1H), 7.32-7.27 (m, 2H), 5.24 (s, 1H), 5.12 (s, 2H), 4.54-4.38 (m, 1H), 3.65 (s, 3H), 1.48 (d, J = 6.7 Hz, 6H), 1.24 (s, 3H), 0.81-0.74 (m, 2H), 0.54-0.48 (m, 2H) |
| 508 | >95 | ¹H NMR (300 MHz, DMSO-d6) Shift = 8.43 (d, J = 2.2 Hz, 1H), 8.23 (s, 1H), 8.16-8.11 (m, 1H), 7.72 (d, J = 8.9 Hz, 1H), 5.46 (s, 2H), 4.17 (s, 2H), 3.58 (s, 3H), 1.08 (s, 3H), 0.64-0.58 (m, 2H), 0.43-0.38 (m, 2H) |
| 509 | >95 | ¹H NMR (300 MHz, DMSO-d6) Shift = 8.43 (d, J = 2.2 Hz, 1H), 8.22 (s, 1H), 8.12-8.07 (m, 1H), 7.67 (d, J = 8.9 Hz, 1H), 5.41 (s, 2H), 3.76-3.64 (m, 1H), 3.56 (s, 3H), 1.41 (d, J = 6.8 Hz, 6H), 1.07 (s, 3H), 0.62-0.56 (m, 2H), 0.42-0.36 (m, 2H) |
| 510 | >95 | ¹H NMR (300 MHz, DMSO-d6) Shift = 8.46-8.42 (m, 2H), 8.21 (s, 1H), 8.13-8.07 (m, 1H), 7.68 (d, J = 8.9 Hz, 1H), 7.43 (d, J = 1.7 Hz, 1H), 5.41 (s, 2H), 3.57 (s, 3H), 1.08 (s, 3H), 0.63-0.57 (m, 2H), 0.42-0.37 (m, 2H) |
| 511 | 85-90 | ¹H NMR (300 MHz, DMSO-d6) Shift = 8.43 (d, J = 2.2 Hz, 1H), 8.22 (s, 1H), 8.15-8.09 (m, 1H), 7.70 (d, J = 8.9 Hz, 1H), 5.31 (s, 2H), 3.57 (s, 3H), 2.46 (s, 3H), 1.08 (s, 3H), 0.64-0.57 (m, 2H), 0.43-0.38 (m, 2H) |
| 512 | >95 | ¹H NMR (300 MHz, DMSO-d6) Shift = 11.82 (br s, 1H), 8.56 (br s, 1H), 8.34 (d, J = 2.2 Hz, 1H), 8.08-8.02 (m, 1H), 7.61 (d, J = 8.9 Hz, 1H), 4.28 (s, 1H), 4.12 (s, 1H), 3.47 (s, 3H), 0.77-0.63 (m, 4H) |
| 513 | >95 | ¹H NMR (300 MHz, DMSO-d6) Shift = 8.61 (br s, 1H), 8.50 (d, J = 1.8 Hz, 1H), 8.41 (d, J = 2.3 Hz, 1H), 8.14-8.08 (m, 1H), 7.69 (d, J = 8.9 Hz, 1H), 6.50-6.47 (m, 1H), 5.29 (s, 2H), 4.28 (s, 1H), 4.12 (s, 1H), 3.57 (s, 3H), 0.77-0.64 (m, 4H) |
| 514 | >95 | ¹H NMR (300 MHz, DMSO-d6) Shift = 8.61 (br s, 1H), 8.41 (d, J = 2.2 Hz, 1H), 8.14-8.08 (m, 1H), 7.69 (d, J = 8.9 Hz, 1H), 6.33 (s, 1H), 5.22 (s, 2H), 4.28 (s, 1H), 4.12 (s, 1H), 3.57 (s, 3H), 2.18 (s, 3H), 0.78-0.64 (m, 4H) |
| 515 | >95 | ¹H NMR (300 MHz, DMSO-d6) Shift = 8.60 (br s, 1H), 8.42 (d, J = 2.3 Hz, 1H), 8.14-8.08 (m, 1H), 7.69 (d, J = 8.9 Hz, 1H), 5.50 (s, 2H), 4.28 (s, 1H), 4.12 (s, 1H), 3.58 (s, 3H), 2.52 (s, 3H), 0.77-0.64 (m, 4H) |
| 516 | >95 | ¹H NMR (300 MHz, DMSO-d6) Shift = 12.02 (br s, 1H), 8.55 (br s, 1H), 8.31 (d, J = 2.1 Hz, 1H), 8.05-8.00 (m, 1H), 7.69 (d, J = 8.9 Hz, 1H), 6.32 (s, 1H), 5.16 (s, 2H), 4.28 (s, 1H), 4.11 (s, 1H), 2.18 (s, 3H), 0.77-0.64 (m, 4H) |
| 517 | >95 | ¹H NMR (300 MHz, DMSO-d6) Shift = 8.61 (s, 1H), 8.43 (d, J = 2.4 Hz, 1H), 8.10 (dd, J = 2.3, 8.9 Hz, 1H), 7.83 (d, J = 8.9 Hz, 1H), 6.31 (s, 1H), 5.23 (s, 2H), 4.21 (d, J = 48.9 Hz, 2H), 4.09 (d, J = 7.1 Hz, 2H), 2.18 (s, 3H), 1.30-1.20 (m, 1H), 0.76-0.65 (m, 4H), 0.53-0.43 (m, 4H) |
| 518 | >95 | ¹H NMR (300 MHz, DMSO-d6) Shift = 8.59 (s, 1H), 8.43 (d, J = 2.3 Hz, 1H), 8.00 (dd, J = 2.4, 8.9 Hz, 1H), 7.51 (d, J = 8.9 Hz, 1H), 7.42 (dd, J = 5.4, 8.7 Hz, 2H), 7.22-7.14 (m, 2H), 6.38 (s, 1H), 5.39 (s, 2H), 5.26 (s, 2H), 4.19 (d, J = 48.7 Hz, 2H), 2.19 (s, 3H), 0.77-0.63 (m, 4H) |

TABLE 3-continued

<sup>1</sup>H NMR data

| Example | NMR Purity | <sup>1</sup>H NMR |
|---|---|---|
| 519 | 90-95 | <sup>1</sup>H NMR (300 MHz, DMSO-d6) Shift = 8.61 (s, 1H), 8.44 (d, J = 2.3 Hz, 1H), 8.06 (dd, J = 2.3, 8.9 Hz, 1H), 7.60 (d, J = 8.9 Hz, 1H), 6.36 (s, 1H), 5.81 (s, 1H), 5.39 (s, 2H), 5.24 (s, 2H), 4.20 (d, J = 49.2 Hz, 2H), 3.81 (s, 3H), 2.18 (s, 3H), 2.01 (s, 3H), 0.79-0.66 (m, 4H) |
| 520 | >95 | <sup>1</sup>H NMR (300 MHz, DMSO-d6) Shift = 8.60 (s, 1H), 8.42 (d, J = 2.3 Hz, 1H), 8.09 (dd, J = 2.3, 8.9 Hz, 1H), 7.75 (d, J = 8.9 Hz, 1H), 6.33 (s, 1H), 5.22 (s, 2H), 4.21 (d, J = 48.0 Hz, 2H), 4.19 (q, J = 7.0 Hz, 2H), 2.18 (s, 3H), 1.24 (t, J = 7.1 Hz, 3H), 0.76-0.68 (m, 4H) |
| 521 | >95 | <sup>1</sup>H NMR (300 MHz, CHLOROFORM-d) Shift = 8.75 (d, J = 2.2 Hz, 1H), 8.17 (dd, J = 2.3, 8.9 Hz, 1H), 7.52 (d, J = 8.9 Hz, 1H), 6.18 (s, 1H), 5.43 (s, 2H), 5.39 (s, 2H), 4.21 (d, J = 47.6 Hz, 2H), 2.30 (s, 3H), 2.29 (s, 3H), 1.04-0.95 (m, 2H), 0.87-0.77 (m, 2H) |
| 522 | >95 | <sup>1</sup>H NMR (300 MHz, CHLOROFORM-d) Shift = 8.75 (d, J = 2.3 Hz, 1H), 8.16 (dd, J = 2.4, 8.9 Hz, 1H), 7.31 (d, J = 9.0 Hz, 1H), 6.18 (s, 1H), 5.47 (s, 1H), 5.38 (s, 2H), 4.84 (dd, J = 6.4, 7.7 Hz, 2H), 4.64 (t, J = 6.2 Hz, 2H), 4.56 (d, J = 7.2 Hz, 2H), 4.20 (d, J = 46.4 Hz, 2H), 3.50 (td, J = 6.8, 13.6 Hz, 1H), 2.29 (s, 3H), 1.05-0.98 (m, 2H), 0.86-0.79 (m, 2H) |
| 523 | >95 | <sup>1</sup>H NMR (300 MHz, DMSO-d6) Shift = 8.67 (br s, 1H), 8.44 (d, J = 2.2 Hz, 1H), 8.22-8.16 (m, 1H), 7.82 (d, J = 8.9 Hz, 1H), 6.38 (s, 1H), 5.36 (s, 2H), 5.12 (s, 2H), 4.29 (s, 1H), 4.13 (s, 1H), 2.18 (s, 3H), 0.78-0.66 (m, 4H) |
| 524 | >95 | <sup>1</sup>H NMR (300 MHz, DMSO-d6) Shift = 8.61 (br s, 1H), 8.42 (d, J = 2.2 Hz, 1H), 8.11-8.05 (m, 1H), 7.78 (d, J = 8.9 Hz, 1H), 6.33 (s, 1H), 5.22 (s, 2H), 4.29 (s, 1H), 4.19 (d, J = 5.8 Hz, 2H), 4.13 (s, 1H), 3.87-3.48 (m, 4H), 2.75-2.40 (m, 1H), 2.17 (s, 3H), 2.04-1.91 (m, 1H), 1.76-1.64 (m, 1H), 0.78-0.65 (m, 4H) |
| 525 | >95 | <sup>1</sup>H NMR (300 MHz, DMSO-d6) Shift = 8.60 (br s, 1H), 8.42 (d, J = 2.2 Hz, 1H), 8.12-8.06 (m, 1H), 7.71 (d, J = 8.9 Hz, 1H), 6.33 (s, 1H), 5.22 (s, 2H), 4.29 (s, 1H), 4.24-4.25 (m, 2H), 4.12 (s, 1H), 3.42 (d, J = 6.1 Hz, 2H), 3.21 (s, 3H), 2.18 (s, 3H), 1.94-1.83 (m, 2H), 0.78-0.65 (m, 4H) |
| 526 | >95 | <sup>1</sup>H NMR (300 MHz, DMSO-d6) Shift = 8.42 (d, J = 2.3 Hz, 1H), 8.10-8.05 (m, 1H), 7.80 (d, J = 8.9 Hz, 1H), 6.34 (s, 1H), 5.22 (s, 2H), 4.86-4.80 (m, 1H), 4.70-4.65 (m, 1H), 4.69-4.53 (m, 1H), 4.51-4.45 (m, 1H), 4.29 (s, 1H), 4.12 (s, 1H), 2.18 (s, 3H), 0.77-0.65 (m, 4H) |
| 527 | >95 | <sup>1</sup>H NMR (300 MHz, DMSO-d6) Shift = 8.60 (br s, 1H), 8.40 (d, J = 2.3 Hz, 1H), 8.10-8.05 (m, 1H), 7.79 (d, J = 9.0 Hz, 1H), 6.32 (s, 1H), 5.22 (s, 2H), 4.34 (t, J = 5.7 Hz, 2H), 4.29 (s, 1H), 4.12 (s, 1H), 3.63 (t, J = 5.7 Hz, 2H), 3.25 (s, 3H), 2.18 (s, 3H), 0.77-0.64 (m, 4H) |
| 528 | >95 | <sup>1</sup>H NMR (300 MHz, DMSO-d6) Shift = 8.90 (dd, J = 1.6, 4.7 Hz, 2H), 8.42 (d, J = 2.3 Hz, 1H), 8.24 (s, 1H), 8.16 (dd, J = 2.3, 8.9 Hz, 1H), 7.98 (dd, J = 1.8, 4.7 Hz, 2H), 7.75 (d, J = 8.9 Hz, 1H), 5.56 (s, 2H), 3.60 (s, 3H), 1.09 (s, 3H), 0.66-0.56 (m, 2H), 0.44-0.39 (m, 2H) |
| 529 | >95 | <sup>1</sup>H NMR (300 MHz, DMSO-d6) Shift = 8.42 (d, J = 2.3 Hz, 1H), 8.29 (dd, J = 1.1, 3.8 Hz, 1H), 8.24 (s, 1H), 8.18-8.15 (m, 1H), 8.14 (s, 1H), 7.74 (d, J = 8.9 Hz, 1H), 7.36 (dd, J = 3.8, 4.9 Hz, 1H), 5.46 (s, 2H), 3.60 (s, 3H), 1.09 (s, 3H), 0.64-0.57 (m, 2H), 0.44-0.38 (m, 2H) |
| 530 | >95 | <sup>1</sup>H NMR (300 MHz, DMSO-d6) Shift = 8.43 (d, J = 2.3 Hz, 1H), 8.24 (s, 1H), 8.18-8.09 (m, 3H), 7.78-7.72 (m, 2H), 7.65-7.58 (m, 2H), 5.53 (s, 2H), 3.60 (s, 3H), 1.09 (s, 3H), 0.65-0.59 (m, 2H), 0.44-0.38 (m, 2H) |
| 531 | >95 | <sup>1</sup>H NMR (300 MHz, DMSO-d6) Shift = 8.42 (d, J = 2.3 Hz, 1H), 8.30-8.21 (m, 3H), 8.16 (dd, J = 2.3, 8.9 Hz, 1H), 8.10 (d, J = 8.5 Hz, 2H), 7.75 (d, J = 8.9 Hz, 1H), 5.57 (s, 2H), 3.60 (s, 3H), 1.09 (s, 3H), 0.64-0.58 (m, 2H), 0.44-0.39 (m, 2H) |
| 532 | <85 | <sup>1</sup>H NMR (300 MHz, DMSO-d6) Shift = 8.64 (br s, 1H), 8.43 (d, J = 2.3 Hz, 1H), 8.20-8.14 (m, 1H), 7.74 (d, J = 8.9 Hz, 1H), 6.34 (s, 1H), 5.22 (s, 2H), 5.03-5.00 (m, 2H), 4.29 (s, 1H), 4.13 (s, 1H), 3.45-3.42 (m, 2H), 2.18 (s, 3H), 0.78-0.65 (m, 4H) |
| 533 | >95 | <sup>1</sup>H NMR (300 MHz, DMSO-d6) Shift = 8.59 (br s, 1H), 8.41 (d, J = 2.3 Hz, 1H), 8.11-8.05 (m, 1H), 7.68-7.62 (m, 2H), 5.25 (s, 2H), 4.27 (s, 1H), 4.11 (s, 1H), 3.56 (s, 3H), 2.57 (s, 3H), 0.77-0.64 (m, 4H) |
| 534 | 90-95 | <sup>1</sup>H NMR (300 MHz, DMSO-d6) Shift = 9.00 (s, 1H), 8.59 (br s, 1H), 8.41 (d, J = 2.3 Hz, 1H), 8.11-8.05 (m, 1H), 7.93 (s, 1H), 7.65 (d, J = 8.9 Hz, 1H), 5.34 (s, 2H), 4.28 (s, 1H), 4.11 (s, 1H), 3.56 (s, 3H), 0.76-0.63 (m, 4H) |
| 535 | >95 | <sup>1</sup>H NMR (300 MHz, DMSO-d6) Shift = 8.52 (br s, 1H), 8.41 (d, J = 2.3 Hz, 1H), 8.11-8.05 (m, 1H), 7.75 (d, J = 8.9 Hz, 1H), 6.32 (s, 1H), 5.22 (s, 2H), 4.29 (s, 1H), 4.14-4.04 (m, 2H), 4.12 (s, 1H), 2.18 (s, 3H), 1.73-1.59 (m, 2H), 0.96 (t, J = 7.5 Hz, 3H), 0.76-0.65 (m, 4H) |
| 536 | >95 | <sup>1</sup>H NMR (300 MHz, DMSO-d6) Shift = 8.35 (d, J = 2.2 Hz, 1H), 8.13-8.08 (m, 1H), 7.71 (d, J = 8.9 Hz, 1H), 6.32 (s, 1H), 5.21 (s, 2H), 4.46 (s, 1H), 4.30 (s, 1H), 4.17-4.08 (m, 2H), 3.27-3.19 (m, 2H), 2.18 (s, 3H), 1.68-1.16 (m, 2H), 1.02-0.90 (m, 4H), 0.85 (t, J = 7.5 Hz, 3H) |
| 537 | >95 | <sup>1</sup>H NMR (400 MHz, DMSO-d6) δ 8.55 (s, 1H), 8.43 (d, J = 2.3 Hz, 1H), 8.32-8.27 (m, 1H), 7.95 (dd, J = 8.9, 2.3 Hz, 1H), 7.68 (s, 1H), 7.63-7.56 (m, 1H), 7.47 (d, J = 8.9 Hz, 1H), 7.39 (s, 1H), 7.31 (d, J = 8.0 Hz, 1H), 5.44 (s, 2H), 4.99 (s, 2H), 4.24 (s, 1H), 4.12 (s, 1H), 3.77 (s, 3H), 2.25 (s, 3H), 0.76-0.62 (m, 4H). |
| 538 | >95 | <sup>1</sup>H NMR (400 MHz, DMSO-d6) δ 8.57 (s, 1H), 8.44 (d, J = 2.3 Hz, 1H), 8.05 (t, J = 7.9 Hz, 1H), 7.96 (d, J = 8.0 Hz, 2H), 7.77 (d, J = 8.0 Hz, 1H), 7.66 (s, 1H), 7.49 (d, J = 9.0 Hz, 1H), 7.38 (s, 1H), 5.54 (s, 2H), 4.98 (s, 2H), 4.24 (s, 1H), 4.12 (s, 1H), 3.76 (s, 3H), 0.75-0.61 (m, 4H). |
| 539 | >95 | <sup>1</sup>H NMR (400 MHz, DMSO-d6) δ 8.56 (s, 1H), 8.42 (dd, J = 9.9, 2.2 Hz, 2H), 8.35-8.29 (m, 1H), 7.97 (dd, J = 8.9, 2.4 Hz, 1H), 7.70 (s, 1H), 7.51 (d, J = 9.0 Hz, 2H), 7.41 (s, 1H), 5.39 (s, 2H), 5.00 (s, 2H), 4.23 (s, 1H), 4.11 (s, 1H), 3.76 (s, 3H), 2.24 (s, 3H), 0.75-0.61 (m, 4H). |

TABLE 3-continued

<sup>1</sup>H NMR data

| Example | NMR Purity | <sup>1</sup>H NMR |
|---|---|---|
| 540 | >95 | <sup>1</sup>H NMR (400 MHz, DMSO-d6) δ 8.56 (s, 1H), 8.44 (d, J = 2.2 Hz, 1H), 7.97 (dd, J = 8.4, 3.1 Hz, 2H), 7.67 (s, 1H), 7.49 (d, J = 8.9 Hz, 1H), 7.41-7.33 (m, 2H), 7.12-7.05 (m, 1H), 5.45 (s, 2H), 4.98 (s, 2H), 4.24 (s, 1H), 4.12 (s, 1H), 3.76 (s, 3H), 0.70-0.65 (m, 4H). |
| 541 | >95 | <sup>1</sup>H NMR (400 MHz, DMSO-d6) δ 8.57 (s, 1H), 8.44 (d, J = 2.2 Hz, 1H), 8.36 (d, J = 5.2 Hz, 1H), 7.95 (dd, J = 8.9, 2.3 Hz, 1H), 7.69 (s, 1H), 7.43-7.33 (m, 2H), 7.17 (s, 1H), 7.14-7.07 (m, 1H), 5.37 (s, 2H), 5.00 (s, 2H), 4.24 (s, 1H), 4.12 (s, 1H), 3.77 (s, 3H), 2.40 (s, 3H), 0.75-0.61 (m, 4H). |
| 542 | >95 | <sup>1</sup>H NMR (400 MHz, DMSO-d6) δ 8.57 (s, 1H), 8.44 (d, J = 2.4 Hz, 1H), 8.21 (d, J = 4.5 Hz, 1H), 7.95 (d, J = 8.7 Hz, 1H), 7.79 (t, J = 9.2 Hz, 1H), 7.65 (s, 1H), 7.57 (d, J = 9.1 Hz, 1H), 7.45-7.33 (m, 2H), 5.59 (s, 2H), 4.96 (s, 2H), 4.24 (s, 1H), 4.12 (s, 1H), 3.75 (d, J = 2.8 Hz, 3H), 0.72-0.65 (m, 4H). |
| 543 | >95 | <sup>1</sup>H NMR (400 MHz, DMSO-d6) δ 8.57 (s, 1H), 8.44 (d, J = 2.3 Hz, 1H), 7.94 (dd, J = 8.9, 2.3 Hz, 1H), 7.81 (d, J = 8.0 Hz, 2H), 7.69 (s, 1H), 7.52 (d, J = 8.0 Hz, 2H), 7.40 (t, J = 4.5 Hz, 2H), 5.48 (s, 2H), 4.99 (s, 2H), 4.24 (s, 1H), 4.11 (s, 1H), 3.77 (s, 3H), 0.75-0.61 (m, 4H). |
| 544 | >95 | <sup>1</sup>H NMR (400 MHz, DMSO-d6) δ 8.58 (s, 1H), 8.41 (d, J = 2.3 Hz, 1H), 8.03 (dd, J = 9.0, 2.3 Hz, 1H), 7.74 (d, J = 9.0 Hz, 1H), 7.67 (s, 1H), 7.39 (s, 1H), 4.95 (s, 2H), 4.80 (t, J = 4.9 Hz, 1H), 4.68 (t, J = 4.9 Hz, 1H), 4.50 (dt, J = 25.3, 5.0 Hz, 2H), 4.25 (s, 1H), 4.13 (s, 1H), 3.76 (s, 3H), 0.77-0.63 (m, 4H). |
| 545 | >95 | <sup>1</sup>H NMR (400 MHz, DMSO-d6) δ 8.57 (s, 1H), 8.42 (s, 1H), 8.05 (d, J = 8.6 Hz, 1H), 7.67 (s, 1H), 7.52 (d, J = 9.1 Hz, 1H), 7.37 (s, 1H), 5.18 (s, 2H), 4.97 (s, 2H), 4.22 (s, 1H), 4.10 (s, 1H), 3.75 (s, 3H), 2.24 (s, 3H), 2.03 (s, 3H), 0.71-0.66 (m, 4H). |
| 546 | >95 | <sup>1</sup>H NMR (400 MHz, DMSO-d6) δ 8.60 (s, 1H), 8.43 (s, 1H), 8.03 (d, J = 8.8 Hz, 1H), 7.65 (d, J = 11.0 Hz, 2H), 7.38 (s, 1H), 5.51 (s, 2H), 4.96 (s, 2H), 4.24 (s, 1H), 4.12 (s, 1H), 3.75 (s, 3H), 2.55 (s, 3H), 0.77-0.63 (m, 4H). |
| 547 | >95 | <sup>1</sup>H NMR (400 MHz, DMSO-d6) δ 8.58 (s, 1H), 8.42 (s, 1H), 8.03 (d, J = 8.7 Hz, 1H), 7.74-7.63 (m, 2H), 7.37 (s, 1H), 5.47 (s, 2H), 4.95 (s, 2H), 4.25 (s, 1H), 4.12 (s, 1H), 3.88 (s, 3H), 3.75 (s, 3H), 2.07 (s, 3H), 0.70 (d, J = 15.5 Hz, 4H). |
| 548 | >95 | <sup>1</sup>H NMR (400 MHz, DMSO-d6) δ 8.60 (s, 1H), 8.41 (d, J = 2.3 Hz, 1H), 8.05 (dd, J = 9.0, 2.3 Hz, 1H), 7.79 (d, J = 8.9 Hz, 1H), 7.68 (s, 1H), 7.40 (s, 1H), 7.10 (s, 1H), 5.40 (s, 2H), 4.96 (s, 2H), 4.24 (s, 1H), 4.12 (s, 1H), 3.76 (s, 3H), 2.33 (s, 3H), 0.77-0.63 (m, 4H). |
| 549 | >95 | <sup>1</sup>H NMR (400 MHz, DMSO-d6) δ 8.58 (s, 1H), 8.41 (d, J = 2.3 Hz, 1H), 8.02 (dd, J = 8.9, 2.4 Hz, 1H), 7.72-7.63 (m, 2H), 7.37 (s, 1H), 4.95 (s, 2H), 4.25 (s, 1H), 4.13 (s, 1H), 4.00 (d, J = 7.5 Hz, 2H), 3.75 (s, 3H), 2.08 (dp, J = 14.4, 7.5 Hz, 1H), 0.92 (d, J = 6.6 Hz, 6H), 0.70-0.65 (m, 4H). |
| 550 | >95 | <sup>1</sup>H NMR (300 MHz, DMSO-d6) Shift = 8.60 (br s, 1H), 8.42 (d, J = 2.2 Hz, 1H), 8.04 (dd, J = 2.3, 8.9 Hz, 1H), 7.65 (d, J = 9.0 Hz, 1H), 7.40 (s, 1H), 6.35 (s, 1H), 5.41 (s, 2H), 5.25 (s, 2H), 4.20 (d, J = 48.6 Hz, 2H), 2.62 (s, 3H), 2.18 (s, 3H), 0.76-0.64 (m, 4H) |
| 551 | >95 | <sup>1</sup>H NMR (300 MHz, DMSO-d6) Shift = 8.63 (br s, 1H), 8.47 (s, 1H), 8.44 (d, J = 2.3 Hz, 1H), 8.08 (dd, J = 2.2, 8.9 Hz, 1H), 7.89 (d, J = 8.9 Hz, 1H), 6.34 (s, 1H), 5.56 (s, 2H), 5.25 (s, 2H), 4.21 (d, J = 49.2 Hz, 2H), 3.75 (s, 3H), 2.18 (s, 3H), 0.77-0.66 (m, 4H) |
| 552 | 90-95 | <sup>1</sup>H NMR (300 MHz, DMSO-d6) Shift = 8.63 (s, 1H), 8.43 (d, J = 2.3 Hz, 1H), 8.11 (dd, J = 2.4, 8.9 Hz, 1H), 7.84 (d, J = 8.9 Hz, 1H), 6.35 (s, 1H), 5.76 (s, 2H), 5.24 (s, 2H), 4.20 (d, J = 49.8 Hz, 2H), 2.70 (s, 3H), 2.18 (s, 3H), 0.77-0.65 (m, 4H) |
| 553 | >95 | <sup>1</sup>H NMR (300 MHz, DMSO-d6) Shift = 8.61 (s, 1H), 8.43 (d, J = 2.3 Hz, 1H), 8.40 (s, 1H), 8.05 (dd, J = 2.3, 8.9 Hz, 1H), 7.67 (d, J = 9.0 Hz, 1H), 6.32 (s, 1H), 5.42 (s, 2H), 5.25 (s, 2H), 4.20 (d, J = 49.4 Hz, 2H), 3.79 (s, 3H), 2.18 (s, 3H), 0.79-0.64 (m, 4H) |
| 554 | >95 | <sup>1</sup>H NMR (300 MHz, DMSO-d6) Shift = 8.42 (d, J = 2.3 Hz, 1H), 8.33 (s, 1H), 8.08 (dd, J = 2.3, 8.9 Hz, 1H), 7.79 (d, J = 8.9 Hz, 1H), 6.32 (s, 1H), 5.49 (s, 2H), 5.22 (s, 2H), 4.20 (d, J = 47.0 Hz, 2H), 3.87 (s, 3H), 2.17 (s, 3H), 2.09 (s, 3H), 0.77-0.66 (m, 4H) |
| 555 | >95 | <sup>1</sup>H NMR (300 MHz, DMSO-d6) Shift = 8.56 (br s, 1H), 8.41 (d, J = 2.3 Hz, 1H), 8.06 (dd, J = 2.3, 8.9 Hz, 1H), 7.80 (d, J = 9.0 Hz, 1H), 7.73 (s, 1H), 7.48 (s, 1H), 6.35 (s, 1H), 5.24 (s, 2H), 5.19 (s, 2H), 4.19 (d, J = 51.0 Hz, 2H), 3.76 (s, 3H), 2.18 (s, 3H), 0.77-0.65 (m, 4H) |
| 556 | >95 | <sup>1</sup>H NMR (300 MHz, DMSO-d6) Shift = 8.44 (d, J = 2.3 Hz, 1H), 8.35 (br s, 1H), 8.11 (dd, J = 2.2, 8.9 Hz, 1H), 7.80 (d, J = 9.0 Hz, 1H), 6.34 (s, 1H), 5.63 (s, 2H), 5.24 (s, 2H), 4.21 (d, J = 48.7 Hz, 2H), 2.48 (s, 3H), 2.18 (s, 3H), 0.79-0.66 (m, 4H) |
| 557 | 90-95 | <sup>1</sup>H NMR (300 MHz, DMSO-d6) Shift = 8.44 (d, J = 2.3 Hz, 1H), 8.36 (s, 1H), 8.07 (dd, J = 2.3, 8.9 Hz, 1H), 7.86-7.74 (m, 2H), 6.33 (s, 1H), 5.58 (s, 2H), 5.24 (s, 2H), 4.21 (d, J = 47.8 Hz, 2H), 3.97 (s, 3H), 2.18 (s, 3H), 0.78-0.64 (m, 4H) |
| 558 | >95 | <sup>1</sup>H NMR (300 MHz, DMSO-d6) Shift = 8.64 (s, 1H), 8.44 (d, J = 2.3 Hz, 1H), 8.08 (dd, J = 2.3, 8.9 Hz, 1H), 7.72 (d, J = 9.0 Hz, 1H), 6.32 (s, 1H), 5.54 (s, 2H), 5.24 (s, 2H), 4.20 (d, J = 48.7 Hz, 2H), 2.57 (s, 3H), 2.18 (s, 3H), 0.79-0.66 (m, 4H) |
| 559 | >95 | <sup>1</sup>H NMR (300 MHz, DMSO-d6) Shift = 8.61 (s, 1H), 8.42 (d, J = 2.4 Hz, 1H), 8.36 (d, J = 0.9 Hz, 1H), 8.12 (d, J = 0.8 Hz, 1H), 8.06 (dd, J = 2.4, 8.9 Hz, 1H), 7.75 (d, J = 8.9 Hz, 1H), 6.34 (s, 1H), 5.30 (s, 2H), 5.24 (s, 2H), 4.20 (d, J = 48.4 Hz, 2H), 2.18 (s, 3H), 0.78-0.64 (m, 4H) |
| 560 | >95 | <sup>1</sup>H NMR (400 MHz, DMSO-d6) δ 8.53 (s, 1H), 8.36 (br. s, 1H), 7.86 (d, J = 6.89 Hz, 1H), 7.68 (br. s, 1H), 7.63 (s, 1H), 7.37 (s, 1H), 7.30 (br. s, 1H), 7.24 (d, J = 8.86 Hz, 1H), 6.09 (br. s, 1H), 4.93 (s, 2H), 4.45-4.51 (m, 4H), 4.24 (br. s, 1H), 4.12 (s, 1H), 3.77 (s, 3H), 0.71 (br. s, 2H) 0.64 (br. s, 2H). |
| 561 | >95 | <sup>1</sup>H NMR (400 MHz, DMSO-d6) δ 12.35 (br. s, 1H), 8.54 (br. s, 1H), 8.40 (br. s, 1H), 8.01 (d, J = 8.31 Hz, 1H), 7.65-7.72 (m, 2H), 7.40 (s, 1H), 5.92 (br. s, 1H), 5.25 (br. s, 2H), 4.98 (s, 2H), 4.24 (s, 1H), 4.12 (s, 1H), 3.76 (s, 3H), 2.15 (s, 3H), 0.69 (d, J = 14.67 Hz, 4H). |

TABLE 3-continued

| | NMR | |
|---|---|---|
| Example | Purity | ¹H NMR |
| 562 | >95 | ¹H NMR (400 MHz, DMSO-d6) δ 8.60 (s, 1H), 8.43 (d, J = 1.96 Hz, 1H), 8.02 (dd, J = 2.45, 8.80 Hz, 1H), 7.76 (s, 1H), 7.72 (d, J = 9.29 Hz, 1H), 7.67 (s, 1H), 7.37 (s, 1H), 5.56 (s, 2H), 4.96 (s, 2H), 4.25 (s, 1H), 4.13 (s, 1H), 3.97 (s, 3H), 3.75 (s, 3H), 0.64-0.75 (m, 4H). |
| 563 | >95 | ¹H NMR (400 MHz, DMSO-d6) δ 9.03 (s, 1H), 8.60 (s, 1H), 8.41 (d, J = 2.45 Hz, 1H), 8.11 (s, 1H), 8.05 (dd, J = 1.96, 8.80 Hz, 1H), 7.87 (d, J = 8.80 Hz, 1H), 7.69 (s, 1H), 7.41 (s, 1H), 5.58 (s, 2H), 4.98 (s, 2H), 4.23 (s, 1H), 4.11 (s, 1H), 3.76 (s, 3H), 0.64-0.75 (m, 4H). |
| 564 | >95 | ¹H NMR (400 MHz, DMSO-d6) δ 8.60 (s, 1H), 8.41 (d, J = 1.96 Hz, 1H), 8.32 (s, 1H), 8.05 (dd, J = 2.20, 9.05 Hz, 1H), 7.80 (d, J = 8.80 Hz, 1H), 7.68 (s, 1H), 7.39 (s, 1H), 7.27 (s, 1H), 5.47 (s, 2H), 4.96 (s, 2H), 4.24 (s, 1H), 4.12 (s, 1H), 3.76 (s, 3H), 0.65-0.75 (m, 4H). |
| 565 | >95 | ¹H NMR (400 MHz, DMSO-d6) δ 8.57 (s, 1H), 8.42 (d, J = 1.96 Hz, 1H), 8.00 (dd, J = 2.20, 9.05 Hz, 1H), 7.83 (d, J = 9.29 Hz, 1H), 7.67 (s, 1H), 7.38 (s, 1H), 7.11 (s, 1H), 6.71 (s, 1H), 5.42 (s, 2H), 4.97 (s, 2H), 4.25 (s, 1H), 4.13 (s, 1H), 3.75 (br. s, 3H), 3.74 (br. s, 3H), 0.65-0.74 (m, 4H). |
| 566 | >95 | ¹H NMR (400 MHz, DMSO-d6) δ 8.58 (s, 1H), 8.43 (d, J = 4.40 Hz, 1H), 8.41 (s, 1H), 8.01 (d, J = 8.80 Hz, 1H), 7.64-7.71 (m, 2H), 7.62 (s, 1H), 7.35 (s, 1H), 7.32 (d, J = 7.83 Hz, 1H), 7.18-7.24 (m, 1H), 4.92 (s, 2H), 4.49 (t, J = 7.09 Hz, 2H), 4.25 (s, 1H), 4.13 (s, 1H), 3.76 (s, 3H), 3.10 (t, J = 7.34 Hz, 2H), 0.64-0.75 (m, 4H). |
| 567 | >95 | ¹H NMR (400 MHz, DMSO-d6) δ 8.62 (s, 1H), 8.44 (d, J = 1.96 Hz, 1H), 8.06 (dd, J = 1.96, 8.80 Hz, 1H), 7.74 (d, J = 8.80 Hz, 1H), 7.68 (s, 1H), 7.38 (s, 1H), 5.61 (s, 2H), 4.96 (s, 2H), 4.25 (s, 1H), 4.13 (s, 1H), 3.76 (s, 3H), 2.48 (br. s, 3H), 0.65-0.76 (m, 4H). |
| 568 | >95 | ¹H NMR (400 MHz, DMSO-d6) δ 11.61 (br. s, 1H), 8.54 (br. s, 1H), 8.39 (d, J = 1.47 Hz, 1H), 7.99-8.04 (m, 1H), 7.81 (d, J = 9.29 Hz, 1H), 7.68 (s, 1H), 7.40 (s, 1H), 6.90 (s, 1H), 5.15 (br. s, 2H), 4.93-5.01 (m, 2H), 4.25 (s, 1H), 4.13 (s, 1H), 3.76 (s, 3H), 2.18 (s, 3H), 0.63-0.76 (m, 4H). |
| 569 | >95 | ¹H NMR (400 MHz, DMSO-d6) δ 8.64 (s, 1H), 8.55 (s, 1H), 8.43 (d, J = 1.96 Hz, 1H), 8.40 (s, 1H), 7.96 (dd, J = 1.96, 8.80 Hz, 1H), 7.67 (s, 1 H), 7.57 (d, J = 8.80 Hz, 1H), 7.38 (s, 1H), 5.52 (s, 2H), 4.97 (s, 2H), 4.24 (s, 1H), 4.12 (s, 1H), 3.76 (s, 3H), 2.45 (s, 3H), 0.64-0.74 (m, 4H). |
| 570 | >95 | ¹H NMR (400 MHz, DMSO-d6) δ 8.55 (br. s, 1H), 8.40 (br. s, 1H), 8.04 (dd, J = 8.80, 17.12 Hz, 1H), 7.86 (d, J = 8.80 Hz, 1H), 7.61-7.68 (m, 2H), 7.38 (d, J = 3.42 Hz, 1H), 4.95 (d, J = 3.42 Hz, 2H), 4.82 (t, J = 5.14 Hz, 1H), 4.31 (s, 1 H), 4.25 (s, 1H), 4.13 (s, 1H), 3.75 (s, 3H), 3.55 (s, 1H), 3.27 (d, J = 5.38 Hz, 2H), 0.70 (d, J = 12.23 Hz, 4H), 0.49-0.53 (m, 1H), 0.36-0.41 (m, 1H). |
| 571 | >95 | ¹H NMR (400 MHz, DMSO-d6) δ 8.55 (s, 1H), 8.43 (d, J = 1.47 Hz, 1H), 8.30 (d, J = 4.89 Hz, 1H), 7.95 (dd, J = 1.96, 8.80 Hz, 1H), 7.68 (s, 1H), 7.46 (d, J = 8.80 Hz, 1H), 7.39 (s, 1H), 7.25 (s, 1H), 7.11 (d, J = 4.89 Hz, 1H), 5.43 (s, 2H), 4.99 (s, 2H), 4.24 (s, 1H), 4.12 (s, 1H), 3.76 (s, 3H), 2.28 (s, 3H), 0.64-0.75 (m, 4H). |
| 572 | >95 | ¹H NMR (400 MHz, DMSO-d6) δ 8.88 (s, 1H), 8.60 (s, 1H), 8.43 (d, J = 2.45 Hz, 1H), 8.09 (dd, J = 2.20, 9.05 Hz, 1H), 7.68 (s, 1H), 7.64 (d, J = 8.80 Hz, 1H), 7.39 (s, 1H), 5.52 (s, 2H), 4.97 (s, 2H), 4.24 (s, 1H), 4.12 (s, 1H), 3.76 (s, 3H), 2.55 (s, 3H), 0.64-0.75 (m, 4H). |
| 573 | >95 | ¹H NMR (400 MHz, DMSO-d6) δ 8.56 (s, 1H), 8.48 (s, 1H), 8.42 (d, J = 1.96 Hz, 1H), 7.96 (dd, J = 2.20, 9.05 Hz, 1H), 7.69 (s, 1H), 7.60 (dd, J = 1.96, 7.83 Hz, 1H), 7.54 (d, J = 8.80 Hz, 1H), 7.40 (s, 1H), 7.20 (d, J = 8.31 Hz, 1H), 5.38 (s, 2H), 4.99 (s, 2H), 4.23 (s, 1H), 4.11 (s, 1H), 3.76 (s, 3H), 2.42 (s, 3H), 0.63-0.74 (m, 4H). |
| 574 | >95 | ¹H NMR (400 MHz, DMSO-d6) δ 8.59 (br. s, 1H), 8.42 (d, J = 1.96 Hz, 1H), 8.04 (dd, J = 2.20, 9.05 Hz, 1H), 7.83 (d, J = 8.80 Hz, 1H), 7.67 (s, 1H), 7.40 (s, 1H), 4.96 (s, 2H), 4.44 (t, J = 6.60 Hz, 2H), 4.25 (s, 1H), 4.13 (s, 1H), 3.75 (s, 3H), 2.95 (t, J = 6.60 Hz, 2H), 0.65-0.76 (m, 4H). |
| 575 | >95 | ¹H NMR (400 MHz, DMSO-d6) δ 12.00 (br. s, 1H), 8.55 (s, 1H), 8.40 (d, J = 1.47 Hz, 1H), 8.01 (dd, J = 1.96, 8.80 Hz, 1H), 7.83 (d, J = 8.80 Hz, 1H), 7.68 (s, 1H), 7.55 (s, 1H), 7.39 (s, 1H), 7.08 (s, 1H), 5.23 (s, 2H), 4.97 (s, 2H), 4.25 (s, 1H), 4.12 (s, 1H), 3.76 (s, 3H), 0.64-0.76 (m, 4H). |
| 576 | >95 | ¹H NMR (400 MHz, DMSO-d6) δ 8.58 (s, 1H), 8.43 (d, J = 2.19 Hz, 1H), 8.02 (dd, J = 2.37, 8.94 Hz, 1H), 7.63-7.69 (m, 3H), 7.39 (s, 1H), 6.73 (s, 1H), 5.39 (s, 2H), 4.97 (s, 2H), 4.25 (s, 1H), 4.12 (s, 1H), 4.05 (q, J = 7.30 Hz, 2H), 3.76 (s, 3H), 1.27 (t, J = 7.12 Hz, 3H), 0.66-0.73 (m, 4H). |
| 577 | >95 | ¹H NMR (400 MHz, DMSO-d6) δ 8.99 (s, 1H), 8.62 (s, 1H), 8.56 (s, 1H), 8.42 (d, J = 1.96 Hz, 1H), 7.99 (dd, J = 1.96, 8.80 Hz, 1H), 7.67-7.71 (m, 2H), 7.41 (s, 1H), 5.45 (s, 2H), 4.99 (s, 2H), 4.24 (s, 1H), 4.12 (s, 1H), 3.76 (s, 3H), 0.64-0.74 (m, 4H). |
| 578 | >95 | ¹H NMR (400 MHz, DMSO-d6) δ 8.60 (s, 1H), 8.47 (d, J = 1.96 Hz, 1H), 8.42 (d, J = 2.45 Hz, 1H), 8.03 (dd, J = 2.20, 8.56 Hz, 1H), 7.79 (d, J = 8.80 Hz, 1H), 7.70 (s, 1H), 7.54 (s, 1H), 7.41 (s, 1H), 5.67 (s, 2H), 4.99 (s, 2H), 4.23 (s, 1H), 4.11 (s, 1H), 3.76 (s, 3H), 0.65-0.73 (m, 4H). |
| 579 | >95 | ¹H NMR (400 MHz, DMSO-d6) δ 8.58 (s, 1H), 8.40-8.47 (m, 2H), 8.05 (dd, J = 1.96, 8.80 Hz, 1H), 7.65-7.71 (m, 2H), 7.40 (s, 1H), 5.19 (s, 2H), 4.97 (s, 2H), 4.24 (s, 1H), 4.12 (s, 1H), 3.76 (s, 3H), 2.48 (s, 3H), 0.65-0.75 (m, 4H). |
| 580 | >95 | ¹H NMR (400 MHz, DMSO-d6) δ 8.57 (s, 1H), 8.41 (d, J = 2.56 Hz, 1H), 8.02 (dd, J = 2.19, 8.76 Hz, 1H), 7.94 (s, 1H), 7.67-7.72 (m, 2H), 7.39 (s, 1H), 5.21 (s, 2H), 4.96 (s, 2H), 4.25 (s, 1H), 4.13 (s, 1H), 3.76 (s, 3H), 2.34 (s, 3H), 0.56-0.78 (m, 4H). |
| 581 | >95 | ¹H NMR (400 MHz, DMSO-d6) δ 9.07 (d, J = 1.47 Hz, 1H), 8.56 (s, 1H), 8.42 (d, J = 1.96 Hz, 1H), 7.99 (dd, J = 1.96, 8.80 Hz, 1H), 7.68 (s, 1H), 7.65 (d, J = 7.34 Hz, 2H), 7.40 (s, 1H), 5.50 (s, 2H), 4.98 (s, 2H), 4.25 (s, 1H), 4.12 (s, 1H), 3.76 (s, 3H), 0.65-0.73 (m, 4H). |
| 582 | >95 | ¹H NMR (400 MHz, DMSO-d6) δ 8.56 (s, 1H), 8.42 (d, J = 1.96 Hz, 1H), 7.99 (dd, J = 1.96, 8.80 Hz, 1H), 7.68 (s, 1H), 7.61 (d, J = 9.29 Hz, 1H), 7.38 (d, J = 11.25 Hz, 2H), 5.39 (s, 2H), 4.98 (s, 2H), 4.25 (s, 1H), 4.12 (s, 1H), 3.76 (s, 3H), 2.61 (s, 3H), 0.63-0.75 (m, 4H). |

TABLE 3-continued

<sup>1</sup>H NMR data

| Example | NMR Purity | <sup>1</sup>H NMR |
|---|---|---|
| 583 | >95 | <sup>1</sup>H NMR (400 MHz, DMSO-d6) δ 8.60 (s, 1H), 8.43 (d, J = 2.45 Hz, 1H), 8.06 (dd, J = 2.45, 8.80 Hz, 1H), 7.77 (d, J = 9.29 Hz, 1H), 7.68 (s, 1H), 7.39 (s, 1H), 5.74 (s, 2H), 4.97 (s, 2H), 4.24 (s, 1H), 4.12 (s, 1H), 3.76 (s, 3H), 2.68 (s, 3H), 0.66-0.73 (m, 4H). |
| 584 | >95 | <sup>1</sup>H NMR (400 MHz, DMSO-d6) δ 8.60 (s, 1H), 8.46 (s, 1H), 8.43 (d, J = 1.96 Hz, 1H), 8.02 (dd, J = 1.96, 8.80 Hz, 1H), 7.79 (d, J = 8.80 Hz, 1H), 7.67 (s, 1H), 7.38 (s, 1H), 5.53 (s, 2H), 4.97 (s, 2H), 4.25 (s, 1H), 4.13 (s, 1H), 3.75 (s, 6H), 0.65-0.74 (m, 4H). |
| 585 | >95 | <sup>1</sup>H NMR (400 MHz, DMSO-d6) δ 8.60 (s, 1H), 8.53 (d, J = 1.47 Hz, 1H), 8.43 (d, J = 2.45 Hz, 1H), 8.04 (dd, J = 2.45, 8.80 Hz, 1H), 7.67-7.70 (m, 1H), 7.67 (s, 1H), 7.39 (s, 1H), 6.54 (s, 1H), 5.56 (s, 2H), 4.97 (s, 2H), 4.25 (s, 1H), 4.13 (s, 1H), 3.76 (s, 3H), 0.66-0.73 (m, 4H). |
| 586 | >95 | <sup>1</sup>H NMR (400 MHz, DMSO-d6) δ 12.70 (br. s, 1H), 8.54 (s, 1H), 8.41 (br. s, 1H), 8.01 (d, J = 8.80 Hz, 1H), 7.64-7.72 (m, 3H), 7.40 (s, 1H), 6.20 (s, 1H), 5.33 (br. s, 1H), 4.98 (s, 2H), 4.24 (s, 1H), 4.12 (s, 1H), 3.76 (s, 3H), 0.63-0.75 (m, 4H). |
| 587 | >95 | <sup>1</sup>H NMR (400 MHz, DMSO-d6) δ 8.43 (d, J = 1.43 Hz, 1H), 8.32 (br. s., 1H), 7.97-8.02 (m, 1H), 7.68 (s, 1H), 7.57 (d, J = 9.06 Hz, 1H), 7.39 (s, 1H), 5.45 (s, 2H), 4.97 (s, 2H), 4.25 (s, 1H), 4.12 (s, 1H), 3.76 (s, 3H), 0.65-0.74 (m, 4H). |
| 588 | >95 | <sup>1</sup>H NMR (400 MHz, DMSO-d6) δ 9.07 (s, 1H), 8.62 (s, 1H), 8.44 (d, J = 1.96 Hz, 1H), 7.98 (dd, J = 2.45, 8.80 Hz, 1H), 7.68 (s, 1H), 7.58-7.63 (m, 2H), 7.40 (s, 1H), 5.48 (s, 2H), 4.98 (s, 2H), 4.25 (s, 1H), 4.13 (s, 1H), 3.95 (s, 3H), 3.76 (s, 3H), 0.66-0.76 (m, 4H). |
| 589 | >95 | <sup>1</sup>H NMR (400 MHz, DMSO-d6) δ 9.60 (s, 1H), 8.61 (s, 1H), 8.43 (d, J = 1.96 Hz, 1H), 8.06 (dd, J = 2.45, 8.80 Hz, 1H), 7.78 (d, J = 8.80 Hz, 1H), 7.68 (s, 1H), 7.39 (s, 1H), 5.83 (s, 2H), 4.98 (s, 2H), 4.24 (s, 1H), 4.12 (s, 1H), 3.76 (s, 3H), 0.62-0.74 (m, 4H). |
| 590 | >95 | <sup>1</sup>H NMR (400 MHz, DMSO-d6) δ 12.78 (br. s, 1H), 8.57 (br. s, 1H), 8.40 (d, J = 1.96 Hz, 1H), 8.02 (dd, J = 2.45, 8.80 Hz, 1H), 7.75-7.81 (m, 2H), 7.69 (s, 1H), 7.53 (br. s, 1H), 7.41 (s, 1H), 5.21 (s, 2H), 4.98 (s, 2H), 4.23 (s, 1H), 4.11 (s, 1H), 3.76 (s, 3H), 0.63-0.73 (m, 4H). |
| 591 | >95 | <sup>1</sup>H NMR (400 MHz, DMSO-d6) δ 8.60 (s, 1H), 8.42 (d, J = 2.45 Hz, 1H), 8.04 (dd, J = 2.20, 9.05 Hz, 1H), 7.75 (d, J = 9.29 Hz, 1H), 7.69 (s, 1H), 7.41 (s, 1H), 7.28 (s, 1H), 5.60 (s, 2H), 4.98 (s, 2H), 4.24 (s, 1H), 4.12 (s, 1H), 3.76 (s, 3H), 2.35 (s, 3H), 0.65-0.73 (m, 4H). |
| 592 | >95 | <sup>1</sup>H NMR (400 MHz, DMSO-d6) δ 13.49 (br. s, 1H), 8.57 (br. s, 1H), 8.42 (d, J = 1.96 Hz, 1H), 8.00 (dd, J = 1.96, 8.80 Hz, 1H), 7.68 (s, 1H), 7.56 (d, J = 8.31 Hz, 1H), 7.39 (s, 1H), 5.36 (br. s, 2H), 4.97 (s, 2H), 4.25 (s, 1H), 4.13 (s, 1H), 3.76 (s, 3H), 2.27 (br. s, 3H), 0.64-0.75 (m, 4H). |
| 593 | >95 | <sup>1</sup>H NMR (400 MHz, DMSO-d6) δ 8.58 (br. s, 1H), 8.41 (d, J = 1.96 Hz, 1H), 8.05 (s, 1H), 8.03 (d, J = 2.45 Hz, 1H), 7.77 (d, J = 8.80 Hz, 1H), 7.68 (s, 1H), 7.40 (s, 1H), 5.39 (s, 2H), 4.97 (s, 2H), 4.25 (s, 1H), 4.12 (s, 1H), 3.98 (s, 3H), 3.76 (s, 3H), 0.65-0.73 (m, 4H). |
| 594 | >95 | <sup>1</sup>H NMR (400 MHz, DMSO-d6) δ 8.60 (s, 1H), 8.41 (d, J = 1.96 Hz, 1H), 8.05 (dd, J = 1.96, 8.80 Hz, 1H), 7.86 (d, J = 9.29 Hz, 1H), 7.82 (s, 1H), 7.69 (s, 1H), 7.40 (s, 1H), 5.49 (s, 2H), 4.97 (s, 2H), 4.23 (s, 1H), 4.11 (s, 1H), 3.76 (s, 3H), 2.57 (s, 3H), 0.65-0.74 (m, 4H). |
| 595 | >95 | <sup>1</sup>H NMR (400 MHz, DMSO-d6) δ 8.58 (s, 1H), 8.40 (d, J = 1.96 Hz, 1H), 8.02 (dd, J = 2.45, 8.80 Hz, 1H), 7.77 (d, J = 8.80 Hz, 1H), 7.71 (d, J = 13.69 Hz, 2H), 7.48 (s, 1H), 7.40 (s, 1H), 5.17 (s, 2H), 4.97 (s, 2H), 4.24 (s, 1H), 4.12 (s, 1H), 3.76 (s, 3H), 3.75 (s, 3H), 0.66-0.74 (m, 4H). |
| 596 | >95 | <sup>1</sup>H NMR (400 MHz, DMSO-d6) δ 8.58 (s, 1H), 8.41 (d, J = 1.96 Hz, 1H), 8.03 (dd, J = 1.96, 8.80 Hz, 1H), 7.73 (s, 1H), 7.65-7.69 (m, 2H), 7.39 (s, 1H), 5.41 (s, 2H), 4.97 (s, 2H), 4.24 (s, 1H), 4.12 (s, 1H), 4.07 (s, 3H), 3.76 (s, 3H), 0.65-0.73 (m, 4H). |
| 597 | >95 | <sup>1</sup>H NMR (400 MHz, DMSO-d6) δ 8.58 (br. s, 1H), 8.41 (br. s, 1H), 8.03 (d, J = 8.31 Hz, 1H), 7.65-7.73 (m, 2H), 7.38 (s, 1H), 4.95 (br. s, 2H), 4.25 (br. s, 1H), 4.13 (br. s, 1H), 4.04-4.10 (m, 2H), 3.75 (s, 3H), 1.64 (d, J = 6.85 Hz, 2H), 0.95 (t, J = 6.60 Hz, 3H), 0.65-0.73 (m, 4H). |
| 598 | >95 | <sup>1</sup>H NMR (400 MHz, DMSO-d6) δ 8.59 (s, 1H), 8.41 (d, J = 2.45 Hz, 1H), 8.03 (dd, J = 1.96, 8.80 Hz, 1H), 7.73 (d, J = 8.80 Hz, 1H), 7.66 (s, 1H), 7.38 (s, 1H), 4.95 (s, 2H), 4.26 (s, 1H), 4.15-4.20 (m, 2H), 4.13 (s, 1H), 3.80-3.87 (m, 1H), 3.75 (s, 3H), 3.60-3.70 (m, 2H), 3.52 (dd, J = 5.62, 8.56 Hz, 1H), 2.62-2.69 (m, 1H), 1.92-2.00 (m, 1H), 1.69 (dt, J = 6.85, 13.21 Hz, 1H), 0.65-0.73 (m, 4H). |
| 599 | >95 | <sup>1</sup>H NMR (300 MHz, DMSO-d6) Shift = 8.44 (d, J = 2.3 Hz, 1H), 8.22 (br s, 1H), 8.09-8.03 (m, 1H), 7.80 (d, J = 8.9 Hz, 1H), 7.68 (s, 1H), 7.40 (s, 1H), 6.36 (tt, J = 55, 3.7 Hz, 1H), 4.96 (s, 2H), 4.73-4.58 (m, 2H), 3.76 (s, 3H), 1.07 (s, 3H), 0.63-0.56 (m, 2H), 0.43-0.36 (m, 2H) |
| 600 | 90-95 | <sup>1</sup>H NMR (300 MHz, DMSO-d6) Shift = 8.60 (br s, 1H), 8.42 (d, J = 2.3 Hz, 1H), 8.08-8.03 (m, 1H), 7.80 (d, J = 8.9 Hz, 1H), 7.68 (s, 1H), 7.40 (s, 1H), 6.36 (tt, J = 55, 3.7 Hz, 1H), 4.96 (s, 2H), 4.73-4.58 (m, 2H), 4.27 (s, 1H), 4.11 (s, 1H), 3.76 (s, 3H), 0.76-0.63 (m, 4H) |
| 601 | >95 | <sup>1</sup>H NMR (300 MHz, DMSO-d6) Shift = 12.07 (br s, 1H), 8.55 (s, 1H), 8.32 (d, J = 2.2 Hz, 1H), 8.03 (dd, J = 2.2, 8.6 Hz, 1H), 7.36 (d, J = 8.6 Hz, 1H), 5.44 (s, 2H), 4.19 (d, J = 48.7 Hz, 2H), 2.68 (s, 3H), 0.75-0.64 (m, 4H) |
| 602 | >95 | <sup>1</sup>H NMR (300 MHz, DMSO-d6) Shift = 8.61 (br s, 1H), 8.43 (d, J = 2.4 Hz, 1H), 8.10 (dd, J = 2.3, 8.9 Hz, 1H), 7.76 (d, J = 8.9 Hz, 1H), 5.50 (s, 2H), 4.20 (d, J = 48.0 Hz, 2H), 4.20 (q, J = 7.0 Hz, 2H), 2.68 (s, 3H), 1.24 (t, J = 7.0 Hz, 3H), 0.78-0.66 (m, 4H) |
| 603 | >95 | <sup>1</sup>H NMR (300 MHz, DMSO-d6) Shift = 8.63 (s, 1H), 8.44 (d, J = 2.3 Hz, 1H), 8.06 (dd, J = 2.3, 8.9 Hz, 1H), 7.60 (d, J = 8.9 Hz, 1H), 5.79 (s, 1H), 5.52 (s, 2H), 5.40 (s, 2H), 4.20 (d, J = 50.1 Hz, 2H), 3.82 (s, 3H), 2.68 (s, 3H), 2.00 (s, 3H), 0.77-0.66 (m, 4H) |
| 604 | 90-95 | <sup>1</sup>H NMR (300 MHz, DMSO-d6) Shift = 8.65 (br s, 1H), 8.46 (d, J = 2.3 Hz, 1H), 8.21-8.15 (m, 1H), 8.17 (t, J = 57 Hz, 1H), 7.89-7.83 (m, 1H), 6.44 (s, 1H), 5.18 (s, 2H), 4.29 (s, 1H), 4.13 (s, 1H), 2.18 (s, 3H), 0.78-0.66 (m, 4H) |

TABLE 3-continued

<sup>1</sup>H NMR data

| Example | NMR Purity | <sup>1</sup>H NMR |
|---|---|---|
| 605 | >95 | <sup>1</sup>H NMR (300 MHz, DMSO-d6) Shift = 8.47 (d, J = 2.3 Hz, 1H), 8.34 (br s, 1H), 8.21-8.15 (m, 1H), 8.18 (t, J = 57 Hz, 1H), 7.90-7.84 (m, 1H), 6.44 (s, 1H), 5.18 (s, 2H), 2.18 (s, 3H), 1.10 (s, 3H), 0.64-0.58 (m, 2H), 0.45-0.39 (m, 2H) |
| 606 | >95 | <sup>1</sup>H NMR (300 MHz, DMSO-d6) Shift = 8.47 (d, J = 2.3 Hz, 1H), 8.31 (br s, 1H), 8.18-8.12 (m, 1H), 8.16 (t, J = 57 Hz, 1H), 7.86-7.79 (m, 1H), 7.70 (s, 1H), 7.41 (s, 1H), 4.93 (s, 2H), 3.76 (s, 3H), 1.09 (s, 3H), 0.63-0.57 (m, 2H), 0.44-0.38 (m, 2H) |
| 607 | >95 | <sup>1</sup>H NMR (400 MHz, DMSO-d6) δ 8.56 (s, 1H), 8.41 (d, J = 2.5 Hz, 1H), 8.33 (s, 1H), 8.11 (s, 1H), 8.01 (dd, J = 9.3, 2.4 Hz, 1H), 7.69 (d, J = 9.8 Hz, 2H), 7.39 (s, 1H), 5.28 (s, 2H), 4.97 (s, 2H), 4.25 (s, 1H), 4.13 (s, 1H), 3.76 (s, 3H), 0.67 (dd, J = 15.4, 4.3 Hz, 4H). |
| 608 | >95 | <sup>1</sup>H NMR (400 MHz, DMSO-d6) δ 8.58 (s, 1H), 8.37 (d, J = 2.2 Hz, 1H), 7.99 (dd, J = 9.1, 2.2 Hz, 1H), 7.64 (d, J = 6.2 Hz, 2H), 7.36 (s, 1H), 4.94 (s, 2H), 4.24 (s, 1H), 4.15-4.07 (m, 3H), 3.74 (s, 3H), 2.28 (q, J = 7.4 Hz, 1H), 1.65-1.59 (m, 4H), 1.57-1.40 (m, 2H), 1.38-1.24 (m, 2H), 0.61 (d, J = 9.5 Hz, 4H). |
| 609 | >95 | <sup>1</sup>H NMR (400 MHz, DMSO-d6) δ 8.56 (s, 1H), 8.39 (d, J = 2.5 Hz, 1H), 8.07-8.00 (m, 1H), 7.65 (s, 1H), 7.44 (d, J = 8.9 Hz, 1H), 7.37 (s, 1H), 5.13 (d, J = 6.2 Hz, 1H), 4.93 (s, 2H), 4.73 (d, J = 6.1 Hz, 2H), 4.24 (s, 1H), 4.12 (s, 1H), 3.74 (s, 3H), 1.81 (s, 3H), 1.68 (s, 3H), 0.65 (d, J = 12.2 Hz, 4H). |
| 610 | >95 | <sup>1</sup>H NMR (400 MHz, DMSO-d6) δ 8.55 (s, 1H), 8.49 (d, J = 5.1 Hz, 2H), 8.41 (d, J = 2.5 Hz, 1H), 7.92 (dd, J = 8.9, 2.3 Hz, 1H), 7.67 (s, 1H), 7.41-7.27 (m, 4H), 5.40 (s, 2H), 4.98 (s, 2H), 4.23 (s, 1H), 4.10 (s, 1H), 3.75 (s, 3H), 0.62 (dd, J = 14.8, 4.1 Hz, 4H). |
| 611 | >95 | <sup>1</sup>H NMR (400 MHz, DMSO-d6) δ 8.57 (s, 1H), 8.38 (d, J = 2.2 Hz, 1H), 8.03 (d, J = 8.5 Hz, 1H), 7.65 (d, J = 9.5 Hz, 2H), 7.36 (s, 1H), 4.94 (s, 2H), 4.20 (dd, J = 12.7, 6.0 Hz, 3H), 4.10 (s, 1H), 3.74 (s, 3H), 2.60 (t, J = 6.6 Hz, 2H), 2.43 (t, J = 7.1 Hz, 4H), 0.78 (t, J = 7.1 Hz, 6H), 0.66 (dd, J = 16.4, 4.4 Hz, 4H). |
| 612 | >95 | <sup>1</sup>H NMR (400 MHz, DMSO-d6) δ 8.54 (s, 1H), 8.39 (d, J = 2.3 Hz, 1H), 8.01 (dd, J = 9.2, 2.2 Hz, 1H), 7.69 (d, J = 26.8 Hz, 2H), 7.38 (s, 1H), 4.95 (s, 2H), 4.32 (t, J = 5.7 Hz, 2H), 4.25 (s, 1H), 4.12 (s, 1H), 3.75 (s, 3H), 3.65 (t, J = 5.7 Hz, 2H), 3.45-3.40 (m, 2H), 1.00 (t, J = 7.0 Hz, 3H), 0.65 (d, J = 12.6 Hz, 4H). |
| 613 | >95 | <sup>1</sup>H NMR (400 MHz, DMSO-d6) δ 8.58 (s, 1H), 8.41 (d, J = 2.4 Hz, 1H), 8.06 (d, J = 8.6 Hz, 1H), 7.69-7.57 (m, 2H), 7.38 (s, 1H), 4.94 (s, 2H), 4.25 (s, 1H), 4.12 (d, J = 11.6 Hz, 3H), 3.75 (s, 3H), 1.77-1.69 (m, 1H), 1.55-1.49 (m, 2H), 0.96 (d, J = 6.6 Hz, 6H), 0.77-0.63 (m, 4H). |
| 614 | >95 | <sup>1</sup>H NMR (300 MHz, DMSO-d6) Shift = 8.44 (d, J = 2.3 Hz, 1H), 8.19 (br s, 1H), 8.11 (dd, J = 2.3, 8.9 Hz, 1H), 7.76 (d, J = 8.9 Hz, 1H), 5.50 (s, 2H), 4.20 (q, J = 7.1 Hz, 2H), 2.68 (s, 3H), 1.24 (t, J = 7.0 Hz, 3H), 1.08 (s, 3H), 0.63-0.56 (m, 2H), 0.43-0.37 (m, 2H) |
| 615 | >95 | <sup>1</sup>H NMR (300 MHz, DMSO-d6) Shift = 8.45 (d, J = 2.3 Hz, 1H), 8.25 (s, 1H), 8.07 (dd, J = 2.4, 8.9 Hz, 1H), 7.61 (d, J = 8.9 Hz, 1H), 5.79 (s, 1H), 5.52 (s, 2H), 5.40 (s, 2H), 3.82 (s, 3H), 2.68 (s, 3H), 2.00 (s, 3H), 1.08 (s, 3H), 0.63-0.56 (m, 2H), 0.42-0.37 (m, 2H) |
| 616 | >95 | <sup>1</sup>H NMR (300 MHz, DMSO-d6) Shift = 8.64 (s, 1H), 8.43 (d, J = 2.3 Hz, 1H), 8.14 (dd, J = 2.4, 8.9 Hz, 1H), 7.70 (d, J = 8.9 Hz, 1H), 6.33 (s, 1H), 5.46 (s, 2H), 5.24 (s, 2H), 4.20 (d, J = 51.1 Hz, 2H), 2.49 (s, 3H), 2.46 (s, 3H), 2.19 (s, 3H), 0.80-0.66 (m, 4H) |
| 617 | >95 | <sup>1</sup>H NMR (400 MHz, DMSO-d6) δ 8.58 (s, 1H), 8.41 (d, J = 2.4 Hz, 1H), 8.04 (dd, J = 8.9, 2.3 Hz, 1H), 7.66 (t, J = 4.5 Hz, 2H), 7.38 (s, 1H), 4.94 (s, 2H), 4.25 (s, 1H), 4.15-4.06 (m, 3H), 3.75 (s, 3H), 1.66-1.46 (m, 4H), 1.42-1.35 (m, 3H), 0.76-0.62 (m, 4H). |
| 618 | >95 | <sup>1</sup>H NMR (400 MHz, DMSO-d6) δ 8.56 (s, 1H), 8.40 (t, J = 2.0 Hz, 1H), 8.02 (dd, J = 8.9, 2.5 Hz, 1H), 7.75 (d, J = 9.2 Hz, 1H), 7.66 (s, 1H), 7.38 (d, J = 4.3 Hz, 1H), 4.95 (s, 2H), 4.32 (q, J = 6.9, 6.4 Hz, 2H), 4.25 (s, 1H), 4.13 (s, 1H), 3.78-3.66 (m, 3H), 3.62 (d, J = 7.0 Hz, 2H), 3.51 (dd, J = 5.5, 3.7 Hz, 2H), 3.36 (t, J = 5.1 Hz, 2H), 3.11 (d, J = 1.7 Hz, 3H), 0.76-0.62 (m, 4H). |
| 619 | >95 | <sup>1</sup>H NMR (400 MHz, DMSO-d6) δ 8.57 (s, 1H), 8.40 (d, J = 2.4 Hz, 1H), 8.05-7.96 (m, 1H), 7.76 (d, J = 8.9 Hz, 1H), 7.66 (d, J = 5.4 Hz, 1H), 7.38 (d, J = 5.0 Hz, 1H), 4.95 (s, 2H),, 4.29-4.10 (m, 4H), 4.03 (dd, J = 10.5, 4.2 Hz, 1H), 3.75 (s, 3H), 3.63-3.59 (m, 2H), 2.07-1.88 (m, 2H), 1.85-1.78 (m, 2H), 0.70 (dd, J = 15.5, 4.2 Hz, 4H). |
| 620 | >95 | <sup>1</sup>H NMR (400 MHz, DMSO-d6) δ 8.59 (s, 1H), 8.42 (q, J = 2.7, 1.9 Hz, 1H), 8.02-7.94 (m, 1H), 7.65 (s, 1H), 7.46 (d, J = 9.0 Hz, 1H), 7.36 (s, 1H), 5.14 (s, 2H), 4.94 (s, 2H), 4.24 (s, 1H), 4.12 (s, 1H), 3.76 (s, 3H), 2.75-2.69 (m, 2H), 1.00 (t, J = 7.2 Hz, 3H), 0.77-0.63 (m, 4H). |
| 621 | >95 | <sup>1</sup>H NMR (300 MHz, DMSO-d6) Shift = 8.45 (d, J = 2.2 Hz, 1H), 8.24 (br s, 1H), 8.12-8.06 (m, 1H), 7.88-7.82 (m, 1H), 7.68 (s, 1H), 7.39 (s, 1H), 5.93 (q, J = 18 Hz, 2H), 4.98 (s, 2H), 3.76 (s, 3H), 1.07 (s, 3H), 0.62-0.56 (m, 2H), 0.43-0.37 (m, 2H) |
| 622 | 85-90 | <sup>1</sup>H NMR (300 MHz, DMSO-d6) Shift = 8.65 (br s, 1H), 8.44 (d, J = 2.3 Hz, 1H), 8.15-8.10 (m, 1H), 7.89 (d, J = 8.9 Hz, 1H), 6.35 (s, 1H), 5.23 (s, 2H), 5.14 (q, J = 18 Hz, 2H), 4.28 (s, 1H), 4.11 (s, 1H), 2.18 (s, 3H), 0.77-0.62 (m, 4H) |
| 623 | 90-95 | <sup>1</sup>H NMR (300 MHz, DMSO-d6) Shift = 8.37 (d, J = 2.3 Hz, 1H), 8.13 (br s, 1H), 8.13-8.17 (m, 1H), 7.85 (d, J = 8.9 Hz, 1H), 7.69 (s, 1H), 7.40 (s, 1H), 5.16 (q, J = 18 Hz, 2H), 5.02-4.95 (m, 2H), 4.41 (s, 1H), 4.27 (s, 1H), 3.76 (s, 3H), 1.01-0.91 (m, 4H) |
| 624 | >95 | <sup>1</sup>H NMR (300 MHz, DMSO-d6) Shift = 9.56 (s, 1H), 8.42 (d, J = 2.3 Hz, 1H), 8.40 (s, 1H), 8.12 (dd, J = 2.3, 8.9 Hz, 1H), 7.70 (d, J = 9.0 Hz, 1H), 5.59 (s, 2H), 4.31-4.09 (m, 2H), 0.71 (d, J = 9.8 Hz, 4H) |
| 625 | >95 | <sup>1</sup>H NMR (300 MHz, DMSO-d6) Shift = 8.41 (d, J = 2.3 Hz, 1H), 8.09 (dd, J = 2.3, 8.9 Hz, 1H), 7.67 (d, J = 8.9 Hz, 1H), 7.19 (s, 1H), 5.34 (s, 2H), 4.34-4.05 (m, 2H), 3.57 (s, 3H), 2.36 (s, 3H), 0.71 (d, J = 10.9 Hz, 4H). |
| 626 | >95 | <sup>1</sup>H NMR (300 MHz, DMSO-d6) Shift = 8.60 (s, 1H), 8.41 (d, J = 2.3 Hz, 1H), 8.09 (dd, J = 2.3, 8.9 Hz, 1H), 7.71-7.63 (m, 2H), 5.18 (s, 2H), 4.31-4.09 (m, 2H), 4.07 (s, 3H), 3.56 (s, 3H), 0.71 (d, J = 10.7 Hz, 4H). |

TABLE 3-continued

¹H NMR data

| Example | NMR Purity | ¹H NMR |
|---|---|---|
| 627 | >95 | ¹H NMR (300 MHz, DMSO-d6) Shift = 9.61 (s, 1H), 8.44 (d, J = 2.2 Hz, 1H), 8.33 (br s, 1H), 8.11 (dd, J = 2.3, 8.9 Hz, 1H), 7.84 (d, J = 9.0 Hz, 1H), 6.35 (s, 1H), 5.85 (s, 2H), 5.25 (s, 2H), 4.20 (d, J = 47.1 Hz, 2H), 2.18 (s, 3H), 0.77-0.64 (m, 4H). |
| 628 | >95 | ¹H NMR (300 MHz, DMSO-d6) Shift = 8.42 (d, J = 2.4 Hz, 1H), 8.11 (dd, J = 2.2, 8.8 Hz, 1H), 7.70 (d, J = 8.9 Hz, 1H), 5.51 (s, 2H), 4.32-4.08 (m, 2H), 3.05 (q, J = 7.5 Hz, 2H), 1.28 (t, J = 7.5 Hz, 3H), 0.71 (d, J = 10.2 Hz, 4H). |
| 629 | >95 | ¹H NMR (300 MHz, DMSO-d6) Shift = 8.43 (d, J = 2.3 Hz, 1H), 8.08 (dd, J = 2.3, 8.9 Hz, 1H), 7.81 (d, J = 9.0 Hz, 1H), 5.50 (s, 2H), 4.87-4.79 (m, 1H), 4.71-4.64 (m, 1H), 4.61-4.54 (m, 1H), 4.53-4.45 (m, 1H), 4.20 (d, J = 49.1 Hz, 2H), 2.68 (s, 3H), 0.75-0.68 (m, 4H) |
| 630 | 90-95 | ¹H NMR (300 MHz, DMSO-d6) Shift = 8.41 (d, J = 2.3 Hz, 1H), 8.07 (dd, J = 2.3, 8.9 Hz, 1H), 7.82 (d, J = 8.9 Hz, 1H), 7.73 (s, 1H), 7.48 (s, 1H), 5.52 (s, 2H), 5.21 (s, 2H), 4.19 (d, J = 49.1 Hz, 2H), 3.76 (s, 3H), 3.17 (s, 1H), 2.68 (s, 3H), 0.78-0.63 (m, 4H) |
| 631 | 90-95 | ¹H NMR (300 MHz, DMSO-d6) Shift = 8.63 (br s, 1H), 8.45 (d, J = 2.3 Hz, 1H), 8.09 (dd, J = 2.3, 8.9 Hz, 1H), 7.73 (d, J = 8.9 Hz, 1H), 5.55 (s, 2H), 5.52 (s, 2H), 4.20 (d, J = 47.7 Hz, 2H), 2.68 (s, 3H), 2.58-2.56 (m, 3H), 0.79-0.67 (m, 4H) |

ARH3 and PARP1 Assays (Selectivity Data)

ARH3 Assay

ARH3 In vitro selectivity assays were conducted in a total volume of 15 ul in a standard 384 well format. 5 ul of Human Full Length ARH3 (Enzo Life Sciences: ALX-201-292), used at a final reaction concentration of 17.5 nM, was added to 5 ul of Ribosylated PARP substrate (also produced internally by Astra Zeneca) at final reaction concentration of 4.5 nM in assay buffer (50 mM Tris pH7.4, 0.1 mg/ml BSA, 3 mM EDTA, 0.4 mM EGTA, 1 mM DTT, 0.01% Tween 20, 50 mM KCl). The reaction was incubated at room temperature for 30 minutes and then 5 ul detection reagent was added. Detection Reagent consists of 42 nM MAb Anti-6HIS XL665 (CisBio: 61HISXLB) and 2.25 nM Streptavidin Europium Cryptate (CisBio: 610SAKLB), both at 3× working stock concentrations (final concentrations of 14 nM and 0.75 nM respectively), in a detection buffer of 50 mM Tris pH7.4, BSA at 0.1 mg/ml and KF at 100 mM. Following incubation at room temperature for 60 minutes in the dark, TR-FRET signal was measured at Ex 340 and Em 665 and Em 620. A ratio was calculated as Em665/EM620×104 for each well and used to calculate percent inhibition for test compounds.

PARP1 Assay

PARP1 In vitro selectivity assays were conducted as a 10 ul reaction volume in a NUNC Maxisorp 384-well assay plate pre-coated in-house with Histones. 5 ul of Human High specific Activity PARP1 (Trevigen: 4668-100-01) was used at a final reaction concentration of 0.02 units/ml in 1×PARP Buffer (Trevigen: 4671-096-02) with 5 ul of 1×PARP cocktail, which is a mixture of 10×PARP Cocktail (Trevigen: 4671-096-03), 10× Activate DNA (Trevigen: 4671-096-06) and 20×PARP Buffer (as above). The reaction was incubated at room temperature for 60 minutes to allow histones on the coated plate to become PARylated. The wells were then washed with PBS/0.1% Triton X100. PARP1 activity was then detected by measuring the extent of PARylation. Firstly, 10 ul of Streptavidin-HRP (Trevigen: 4800-30-06), diluted 1 in 250 in 1×PARG Assay Buffer (Trevigen: 4680-096-02), was added to each well and incubated at room temperature for 60 minutes. Secondly, following another wash with PBS/0.1% Triton X100, Peroxy Glow Reagents A and B (Trevigen: 4675-096-01 and 4675-096-02) were mixed in equal quantities immediately before use and 100 ul was added to each well. Luminescence signal was then measured immediately.

TABLE 4

ARH3 and PARP1 activity data (Selectivity Data)

| Example | ARH3 Biochem IC50 (µM) | PARP1 Biochem IC50 (µM) |
|---|---|---|
| Example 133 | >100 | >150 |
| Example 156 | >100 | >150 |
| Example 158 | >100 | >150 |
| Example 161 | >100 | >150 |
| Example 162 | >100 | >150 |
| Example 163 | >100 | >150 |
| Example 165 | >100 | >150 |
| Example 22 | >150 | >150 |
| Example 41 | >150 | >150 |
| Example 80 | >150 | >150 |
| Example 98 | >150 | >150 |
| Example 293 | >150 | >150 |
| Example 298 | >150 | >150 |
| Example 308 | >150 | >150 |
| Example 311 | >150 | >150 |
| Example 173 | >150 | >150 |
| Example 463 | >150 | >150 |
| Example 484 | >150 | >150 |
| Example 572 | >150 | |
| Example 578 | >150 | |
| Example 579 | >150 | |
| Example 602 | >150 | >150 |
| Example 614 | >150 | |
| Example 616 | >150 | |
| Example 617 | >150 | |
| Example 180 | >150 | >150 |
| Example 625 | >150 | |
| Example 629 | >150 | |
| Example 630 | >150 | |
| Example 631 | >150 | |

REFERENCES

[1] Ame, J. C., E. Fouquerel, L. R. Gauthier, D. Biard, F. D. Boussin, F. Dantzer, G. de Murcia and V. Schreiber (2009). "Radiation-induced mitotic catastrophe in PARG-deficient cells." J Cell Sci 122(Pt 12): 1990-2002.

[2] Barber, L. J., S. Sandhu, L. Chen, J. Campbell, I. Kozarewa, K. Fenwick, I. Assiotis, D. N. Rodrigues, J. S. Reis Filho, V. Moreno, J. Mateo, L. R. Molife, J. De Bono, S. Kaye, C. J. Lord and A. Ashworth (2013). "Secondary mutations in BRCA2 associated with clinical resistance to a PARP inhibitor." J Pathol 229(3): 422-429.

[3] Blenn, C., P. Wyrsch and F. R. Althaus (2011). "The ups and downs of tannins as inhibitors of poly(ADP-ribose) glycohydrolase." Molecules 16(2): 1854-1877.

[4] Caiafa, P., T. Guastafierro and M. Zampieri (2009). "Epigenetics: poly(ADP-ribosyl)ation of PARP-1 regulates genomic methylation patterns." FASEB J 23(3): 672-678.

[5] Curtin, N. J. and C. Szabo (2013). "Therapeutic applications of PARP inhibitors: anticancer therapy and beyond." Mol Aspects Med 34(6): 1217-1256.

[6] Dahl, M., V. Maturi, P. Lonn, P. Papoutsoglou, A. Zieba, M. Vanlandewijck, L. P. van der Heide, Y. Watanabe, O. Soderberg, M. O. Hottiger, C. H. Heldin and A. Moustakas (2014). "Fine-tuning of Smad protein function by poly(ADP-ribose) polymerases and poly(ADP-ribose) glycohydrolase during transforming growth factor beta signaling." PLoS One 9(8): e103651.

[7] Drost, R. and J. Jonkers (2014). "Opportunities and hurdles in the treatment of BRCA1-related breast cancer." Oncogene 33(29): 3753-3763.

[8] Erdelyi, K., P. Bai, I. Kovacs, E. Szabo, G. Mocsar, A. Kakuk, C. Szabo, P. Gergely and L. Virag (2009). "Dual role of poly(ADP-ribose) glycohydrolase in the regulation of cell death in oxidatively stressed A549 cells." FASEB J 23(10): 3553-3563.

[9] Fathers, C., R. M. Drayton, S. Solovieva and H. E. Bryant (2012). "Inhibition of poly(ADP-ribose) glycohydrolase (PARG) specifically kills BRCA2-deficient tumor cells." Cell Cycle 11(5): 990-997.

[10] Fisher, A. E., H. Hochegger, S. Takeda and K. W. Caldecott (2007). "Poly(ADP-ribose) polymerase 1 accelerates single-strand break repair in concert with poly(ADP-ribose) glycohydrolase." Mol Cell Biol 27(15): 5597-5605.

[11] Frizzell, K. M., M. J. Gamble, J. G. Berrocal, T. Zhang, R. Krishnakumar, Y. Cen, A. A. Sauve and W. L. Kraus (2009). "Global analysis of transcriptional regulation by poly(ADP-ribose) polymerase-1 and poly(ADP-ribose) glycohydrolase in MCF-7 human breast cancer cells." J Biol Chem 284(49): 33926-33938.

[12] Fujihara, H., H. Ogino, D. Maeda, H. Shirai, T. Nozaki, N. Kamada, K. Jishage, S. Tanuma, T. Takato, T. Ochiya, T. Sugimura and M. Masutani (2009). "Poly(ADP-ribose) Glycohydrolase deficiency sensitizes mouse ES cells to DNA damaging agents." Curr Cancer Drug Targets 9(8): 953-962.

[13] Guastafierro, T., A. Catizone, R. Calabrese, M. Zampieri, O. Martella, M. G. Bacalini, A. Reale, M. Di Girolamo, M. Miccheli, D. Farrar, E. Klenova, F. Ciccarone and P. Caiafa (2013). "ADP-ribose polymer depletion leads to nuclear Ctcf re-localization and chromatin rearrangement(1)." Biochem J 449(3): 623-630.

[14] Ji, Y. and A. V. Tulin (2009). "Poly(ADP-ribosyl)ation of heterogeneous nuclear ribonucleoproteins modulates splicing." Nucleic Acids Res 37(11): 3501-3513.

[15] Le May, N., I. Iltis, J. C. Ame, A. Zhovmer, D. Biard, J. M. Egly, V. Schreiber and F. Coin (2012). "Poly(ADP-ribose) glycohydrolase regulates retinoic acid receptor-mediated gene expression." Mol Cell 48(5): 785-798.

[16] Mashimo, M., J. Kato and J. Moss (2014). "Structure and function of the ARH family of ADP-ribosyl-acceptor hydrolases." DNA Repair (Amst).

[17] Mortusewicz, O., E. Fouquerel, J. C. Ame, H. Leonhardt and V. Schreiber (2011). "PARG is recruited to DNA damage sites through poly(ADP-ribose)- and PCNA-dependent mechanisms." Nucleic Acids Res 39(12): 5045-5056.

[18] Nakadate, Y., Y. Kodera, Y. Kitamura, T. Tachibana, T. Tamura and F. Koizumi (2013). "Silencing of poly(ADP-ribose) glycohydrolase sensitizes lung cancer cells to radiation through the abrogation of DNA damage checkpoint." Biochem Biophys Res Commun 441(4): 793-798.

[19] Shirai, H., H. Fujimori, A. Gunji, D. Maeda, T. Hirai, A. R. Poetsch, H. Harada, T. Yoshida, K. Sasai, R. Okayasu and M. Masutani (2013). "Parg deficiency confers radio-sensitization through enhanced cell death in mouse ES cells exposed to various forms of ionizing radiation." Biochem Biophys Res Commun 435(1): 100-106.

[20] Shirai, H., A. R. Poetsch, A. Gunji, D. Maeda, H. Fujimori, H. Fujihara, T. Yoshida, H. Ogino and M. Masutani (2013). "PARG dysfunction enhances DNA double strand break formation in S-phase after alkylation DNA damage and augments different cell death pathways." Cell Death Dis 4: e656.

[21] Sun, Y., T. Zhang, B. Wang, H. Li and P. Li (2012). "Tannic acid, an inhibitor of poly(ADP-ribose) glycohydrolase, sensitizes ovarian carcinoma cells to cisplatin." Anticancer Drugs 23(9): 979-990.

[22] Zhou, Y., X. Feng and D. W. Koh (2010). "Enhanced DNA accessibility and increased DNA damage induced by the absence of poly(ADP-ribose) hydrolysis." Biochemistry 49(34): 7360-7366.

[23] Zhou, Y., X. Feng and D. W. Koh (2011). "Synergistic cytotoxicity of N-methyl-N'-nitro-N-nitrosoguanidine and absence of poly(ADP-ribose) glycohydrolase involves chromatin decondensation." Int J Oncol 39(1): 121-127.

The invention claimed is:

1. A compound, or a pharmaceutically acceptable salt or solvate thereof, having the structural formula (II) shown below, or a pharmaceutically acceptable salt or solvate thereof:

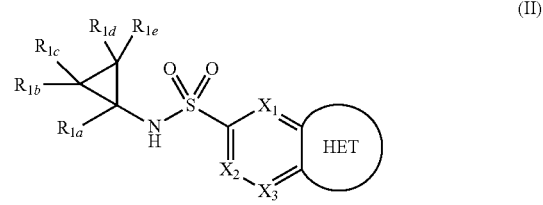

wherein:

$R_{1a}$ is selected from fluoro, chloro, cyano, formyl, (1-2C)alkyl, (1-2C) haloalkyl, (2C)alkenyl, or (2C)alkynyl;

$R_{1b}$, $R_{1c}$, $R_{1d}$, and $R_{1e}$ are each independently selected from H, fluoro or methyl;

$X_1$ is selected from $CR_2$ or N; wherein $R_2$ is H or fluoro;

$X_2$ is selected from $CR_3$ or N; wherein $R_3$ is H or fluoro;

$X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or $R_4$ is selected from a group of the formula:

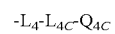

wherein $L_4$ is absent or a (1-3C)alkylene, (2-4C)alkenylene, or (2-4C)alkynylene, each of which is optionally substituted by (1-2C)alkyl or oxo;

$L_{4C}$ is absent or selected from O, S, SO, $SO_2$, $N(R_{4b})$, C(O), C(O)O, OC(O), C(O)N($R_{4b}$), N($R_{4b}$)C(O), N($R_{4b}$)C(O)O, C(O)N($R_{4b}$)O, N($R_{4b}$)C(O)N($R_{4C}$), S(O)₂N(R₄ᵦ), or N(R₄ᵦ)SO₂, wherein R₄ᵦ and R₄c are each independently selected from hydrogen or (1-2C)alkyl; and Q₄c is hydrogen, (1-6C)alkyl, (3-6C)cycloalkyl, aryl, heterocyclyl or heteroaryl; and wherein Q₆C is optionally substituted by one or more substituents selected from halo, trifluoromethyl, trifluoromethoxy, amino, cyano, hydroxy, amino, carboxy, carbamoyl, sulphamoyl, (1-4C)alkyl, NR₄𝒹R₄ₑ, OR₄𝒹, C(O)R₄𝒹, C(O)OR₄𝒹, OC(O)R₄𝒹, C(O)N(R₄ₑ)R₄𝒹, N(R₄ₑ)C(O)R₄𝒹, S(O)ᵧR₄𝒹 (where y is 0, 1 or 2), SO₂N(R₄ₑ)R₄𝒹, N(R₄ₑ)SO₂R₄𝒹 or (CH₂)ᵤNR₄ₑR₄𝒹 (where z is 1, 2 or 3), wherein R₄𝒹 and R₄ₑ are each independently selected from H or (1-4C)alkyl;

wherein HET is a structure of Formula (III), (IV), (V), (VI), (VII), (VIII) or (IX):

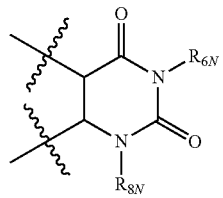
(III)

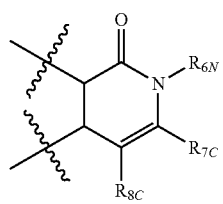
(IV)

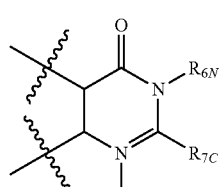
(V)

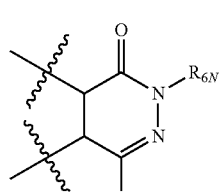
(VI)

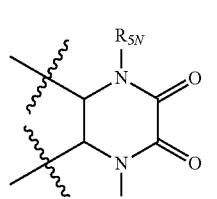
(VII)

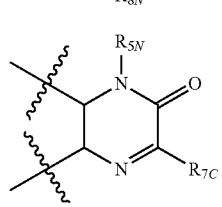
(VIII)

-continued

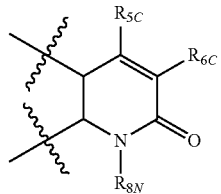
(IX)

R₅c is selected from H, halo, (1-2C)alkyl, (1-2C)alkoxy, amino, (1-2C)alkylamino, (1-2C)dialkylamino, cyano or (2C)alkynyl, wherein said (1-2C)alkyl is optionally substituted by one or more substituents selected from amino or halo;

R₅ₙ is selected from H, (1-2C)alkyl or (1-2C)haloalkyl;

R₆c is selected from hydrogen, cyano, halo or a group of the formula:

-L₆-L₆C-Q₆C wherein

L₆ is absent or (1-3C)alkylene optionally substituted by (1-2C)alkyl or oxo;

L₆C is absent or selected from O, S, SO, SO₂, N(Rᵦ), C(O), C(O)O, OC(O), C(O)N(Rᵦ), N(Rᵦ)C(O), N(Rᵦ)C(O)N(Rc), S(O)₂N(Rᵦ), or N(Rᵦ)SO₂, wherein Rᵦ and Rc are each independently selected from hydrogen or (1-2C)alkyl; and Q₆C is hydrogen, (1-6C)alkyl, (3-6C)cycloalkyl, aryl, heterocyclyl or heteroaryl; and wherein Q₆C is optionally substituted by one or more substituents selected from halo, trifluoromethyl, trifluoromethoxy, amino, cyano, hydroxy, amino, carboxy, carbamoyl, sulphamoyl, (1-4C)alkyl, NR𝒹Rₑ, OR𝒹, C(O)R𝒹, C(O)OR𝒹, OC(O)R𝒹, C(O)N(Rₑ)R𝒹, N(Rₑ)C(O)R𝒹, S(O)ᵧR𝒹 (where y is 0, 1 or 2), SO₂N(Rₑ)R𝒹, N(Rₑ)SO₂R𝒹 or (CH₂)ᵤNRₑR𝒹 (where z is 1, 2 or 3), wherein R𝒹 and Rₑ are each independently selected from H or (1-4C)alkyl;

R₆ₙ is selected from hydrogen, or a group of the formula:

-L₆-L₆N-Q₆N wherein

L₆ is absent or (1-3C)alkylene optionally substituted by (1-2C)alkyl or oxo;

L₆ₙ is absent or selected from O, S, SO, SO₂, N(R𝒻), C(O), C(O)O, OC(O), C(O)N(R𝓰), N(R𝒻)C(O), N(R𝒻)C(O)N(R𝓰), S(O)₂N(R𝒻), or N(R𝒻)SO₂, wherein R𝒻 and R𝓰 are each independently selected from hydrogen or (1-2C)alkyl; and Q₆ₙ is hydrogen, cyano, (1-6C)alkyl, (2C)alkynyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, NRₕRᵢ, ORₕ, C(O)Rₕ, C(O)ORₕ, OC(O)Rₕ, C(O)N(Rₕ)Rᵢ, N(Rₕ)C(O)Rᵢ, N(Rₕ)C(O)ORᵢ, S(O)ᵧRₕ (where y is 0, 1 or 2), SO₂N(Rₕ)Rᵢ, N(Rₕ)SO₂Rᵢ or (CH₂)ᵤNRₕRᵢ (where z is 1, 2 or 3), wherein Rₕ and Rᵢ are each independently selected from H or (1-4C)alkyl; or Q₆ₙ is optionally substituted by a group of formula:

—W₆ₙ—Z₆ₙ wherein

W₆ₙ is absent or (1-3C)alkylene optionally substituted by (1-2C)alkyl or oxo;

$Z_{6N}$ is selected from (3-5C)cycloalkyl, (3-6C)heterocycyl, (2C)alkynyl, phenyl, 5 or 6 membered heteroaryl, carboxy, carbamoyl or cyano, wherein $Z_{6N}$ is substituted by one or more substituents selected from (1-2C)alkyl, (1-2C)alkoxy or halo;

$R_{7C}$ is selected from hydrogen, cyano, halo or a group of the formula:

-$L_7$-$L_{7C}$-$Q_{7C}$ wherein $L_7$ is absent or (1-3C)alkylene optionally substituted by (1-2C)alkyl or oxo;

$L_{7C}$ is absent or selected from O, S, SO, SO$_2$, N($R_j$), C(O), C(O)O, OC(O), C(O)N($R_j$), N($R_j$)C(O), N($R_j$)C(O)N($R_k$), S(O)$_2$N($R_j$), or N($R_j$)SO$_2$, wherein $R_j$ and $R_k$ are each independently selected from hydrogen or (1-2C)alkyl; and $Q_{7C}$ is hydrogen, (1-6C)alkyl, (3-6C)cycloalkyl, aryl, aryl (1-2C)alkyl, heterocyclyl, heterocycyl-(1-2C)-alkyl, heteroaryl or heteroaryl-(1-2C)alkyl; and wherein $Q_7$c is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_l$R$_m$, OR$_l$, C(O)R$_m$, C(O)OR$_l$, OC(O)R$_m$, C(O)N(R$_l$)R$_m$, N(R$_l$)C(O)R$_m$, S(O)$_y$R$_l$ (where y is 0, 1 or 2), SO$_2$N(R$_l$)R$_m$, N(R$_l$)SO$_2$R$_m$ or (CH$_2$)$_z$NR$_l$R$_m$ (where z is 1, 2 or 3), wherein R$_l$ and R$_m$ are each independently selected from H or (1-4C)alkyl;

$R_{8C}$ is selected from hydrogen, cyano, halo or a group of the formula:

-$L_8$-$L_{8C}$-$Q_{8C}$ wherein $L_8$ is absent or (1-3C)alkylene, (3-4C)cycloalkylene, optionally substituted by one or more substituents selected from (1-2C)alkyl, halo, or oxo;

$L_{8C}$ is absent or selected from O, S, SO, SO$_2$, N($R_r$), C(O), C(O)O, OC(O), C(O)N($R_r$), N($R_r$)C(O), N($R_r$)C(O)N($R_s$), S(O)$_2$N($R_r$), or N($R_r$)SO$_2$, wherein $R_r$ and $R_s$ are each independently selected from hydrogen or (1-2C)alkyl; and $Q_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein $Q_{8C}$ is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_t$R$_u$, OR$_t$, C(O)R$_t$, C(O)OR$_t$, OC(O)R$_t$, C(O)N(R$_t$)R$_u$, N(R$_t$)C(O)R$_u$, S(O)$_y$R$_t$ (where y is 0, 1 or 2), SO$_2$N(R$_t$)R$_u$, N(R$_t$)SO$_2$R, or (CH$_2$)$_z$NR$_t$R$_u$ (where z is 1, 2 or 3), wherein R$_t$ and R$_u$ are each independently selected from H or (1-4C)alkyl; or $Q_{8C}$ is optionally substituted by a group of the formula:

—$W_{8C}$-$L_{8'}$-$Z_{8C}$ wherein $W_{8C}$ is absent or (1-3C)alkylene optionally substituted by (1-2C)alkyl or oxo;

$L_{8'}$ is absent or selected from C(O), C(O)O, OC(O), C(O)N($R_v$), N($R_v$)C(O), N($R_v$)C(O)N($R_w$), S(O)$_2$N($R_v$), or N($R_v$)SO$_2$, wherein $R_v$ and $R_w$ are each independently selected from hydrogen or (1-2C)alkyl; and $Z_{8C}$ is phenyl or 5-6 membered heteroaryl; wherein $Z_{8C}$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

$Q_{8C}$ and $R_4$ are linked, such that, together with the carbon atom to which they are attached, they form a group of the formula;

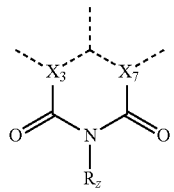

wherein $X_7$ is C;

$R_z$ is selected from (1-4C)alkyl, (1-4C)haloalkyl, or a group of the formula:

-$L_{Rz}$-$Z_{Rz}$ wherein $L_{Rz}$ is absent or (1-3C)alkylene, optionally substituted by one or more substituents selected from (1-2C)alkyl, halo or oxo; and $Z_{Rz}$ is aryl, carbocyclyl, heterocyclyl or heteroaryl, each of which is optionally substituted by one or more substituents selected from (1-4C)alkyl, halo, trifluoromethyl, trifluoromethoxy, haloalkyl, amino, cyano, hydroxyl, carboxy, carbamoyl or sulphamoyl;

$R_{8N}$ is selected from hydrogen or a group of the formula:

-$L_8$-$L_{8N}$-$Q_{8N}$ wherein $L_8$ is absent or (1-3C)alkylene, (3-4C)cycloalkyl optionally substituted by one or more substituents selected from (1-2C)alkyl; halo or oxo;

$L_{8N}$ is absent or selected from O, S, SO, SO$_2$, N($R_x$), C(O), C(O)O, OC(O), C(O)N($R_x$), N($R_x$)C(O), N($R_x$)C(O)N($R_y$), N($R_x$)C(O)O, S(O)$_2$N($R_x$), or N(Rx)SO$_2$, wherein $R_x$ and $R_y$ are each independently selected from hydrogen or (1-2C)alkyl;

$Q_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_{a'}$, OR$_z$, C(O)R$_z$, C(O)OR$_z$, OC(O)R$_z$, C(O)N(R$_z$)R$_{a'}$, N(R$_z$)C(O)R$_{a'}$, S(O)$_y$R$_z$ (where y is 0, 1 or 2), SO$_2$N(R$_z$)R$_{a'}$, N(R$_z$)SO$_2$R$_{a'}$ or (CH$_2$)$_z$NR$_z$R$_{a'}$ (where z is 1, 2 or 3), wherein R$_z$ and R$_{a'}$ are each independently selected from H or (1-4C)alkyl; or $Q_{8N}$ is optionally substituted by a group of the formula:

—$W_{8N}$-$L_{8'}$-$Z_{8N}$ wherein $W_{8N}$ is absent or (1-3C)alkylene optionally substituted by (1-2C)alkyl or oxo;

$L_{8'}$ is absent or selected C(O), C(O)O, OC(O), C(O)N($R_{b'}$), N($R_{b'}$)C(O), N($R_{b'}$)C(O)N($R_{c'}$), S(O)$_2$N($R_{b'}$), or N($R_{b'}$)SO$_2$, wherein $R_{b'}$ and $R_{c'}$ are each independently selected from hydrogen or (1-2C)alkyl; and $Z_{8N}$ is phenyl, (1-4C)alkyl, (4-6C)heterocycyl or a 5-6 membered heteroaryl; wherein $Z_{8N}$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl.

2. A compound according to claim 1, wherein $R_{1a}$ is selected from fluoro, cyano, formyl, (1-2C)alkyl, (1-2C)haloalkyl or (2C)alkynyl.

3. A compound according to claim 2, wherein $R_{1a}$ is selected from cyano, formyl, (1-2C)alkyl or (1-2C)haloalkyl.

4. A compound according to claim 1, wherein $X_1$ is $CR_2$, wherein $R_2$ is H or fluoro.

5. A compound according to claim 4, wherein $X_1$ is C—H.

6. A compound according to claim 1, wherein $X_2$ is $CR_3$, wherein $R_3$ is H or fluoro.

7. A compound according to claim 1, wherein $X_3$ is selected from $CR_4$ or N; wherein $R_4$ is H or halo.

8. A compound according to claim 1, wherein $X_3$ is C—H, C—F or C—C(O)NH$_2$.

9. A compound according to claim 1, wherein $R_{1b}$, $R_{1c}$, $R_{1d}$ and $R_{1e}$ are H.

10. A compound according to claim 1,
wherein
$R_{5c}$ is selected from H, fluoro, (1-2C)alkyl, cyano or (2C)alkynyl;
$R_{5N}$ is selected from H, (1-2C)alkyl or CF$_3$.

11. A compound according to claim 1, wherein HET is a structure of Formula (III), (IV), (V), or (VI).

12. A compound according to claim 1,
wherein
$R_{6N}$ is selected from hydrogen, or a group of the formula:

-L$_6$-L$_{6N}$-Q$_{6N}$ wherein
L$_6$ is absent or (1-3C)alkylene optionally substituted by (1-2C)alkyl or oxo;
L$_{6N}$ is absent or selected from O, S, SO, SO$_2$, N(R$_f$), C(O), C(O)O, OC(O), C(O)N(R$_g$), N(R$_f$)C(O), N(R$_f$)C(O)N(R$_g$), S(O)$_2$N(R$_f$), or N(R$_f$)SO$_2$, wherein R$_f$ and R$_g$ are each independently selected from hydrogen or (1-2C)alkyl; and
Q$_{6N}$ is hydrogen, cyano, (1-6C)alkyl, (2C)alkynyl, (3-6C)cycloalkyl, aryl, heterocyclyl or heteroaryl, each of which is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_h$R$_i$, OR$_h$, C(O)R$_h$, C(O)OR$_h$, OC(O)R$_h$, C(O)N(R$_h$)R$_i$, N(R$_h$)C(O)R$_i$, N(R$_h$)C(O)OR$_i$, S(O)$_y$R$_h$ (where y is 0, 1 or 2), SO$_2$N(R$_h$)R$_i$, N(R$_h$)SO$_2$R$_i$ or (CH$_2$)$_z$NR$_h$R$_i$ (where z is 1, 2 or 3), wherein R$_h$ and R$_i$ are each independently selected from H or (1-4C)alkyl; or
Q$_{6N}$ is optionally substituted by a group of formula:

—W$_{6N}$—Z$_{6N}$ wherein
W$_{6N}$ is absent or (1-3C)alkylene optionally substituted by (1-2C)alkyl or oxo;
Z$_{6N}$ is selected from (3-5C)cycloalkyl, (3-6C)heterocycyl, (2C)alkynyl, phenyl, 5 or 6 membered heteroaryl, carboxy, carbamoyl or cyano, wherein Z$_{6N}$ is substituted by one or more substituents selected from (1-2C)alkyl, (1-2C)alkoxy or halo.

13. A compound according to claim 1,
wherein
$R_{6N}$ is selected from a group of the formula:

-L$_6$-Q$_{6N}$ wherein
L$_6$ is (1-3C)alkylene;
Q$_{6N}$ is hydrogen, cyano or 5- or 6-membered heteroaryl, wherein said heteroaryl is optionally substituted by one or more substituents selected from halo, trifluoromethyl, hydroxy, amino, N(R$_h$)C(O)OR$_i$, or (1-4C)alkyl, wherein R$_h$ and R$_i$ are each independently selected from H or (1-4C)alkyl; or
Q$_{6N}$ is optionally substituted by a group of formula:

—W$_{6N}$—Z$_{6N}$ wherein
W$_{6N}$ is absent or (1-3C)alkylene optionally substituted by (1-2C)alkyl or oxo;
Z$_{6N}$ is selected from (3-5C)cycloalkyl, (2C)alkynyl, phenyl, 5 or 6 membered heteroaryl or cyano, wherein Z$_{6N}$ is substituted by one or more substituents selected from (1-2C)alkyl, (1-2C)alkoxy or halo.

14. A compound according to claim 1,
wherein
$R_{7c}$ is selected from hydrogen, cyano, halo or a group of the formula:

-L$_7$-Q$_{7C}$ wherein
L$_7$ is (1-3C)alkylene optionally substituted by (1-2C)alkyl or oxo; and
Q$_{7C}$ is hydrogen or (1-6C)alkyl, (3-6C)cycloalkyl, aryl, heterocyclyl or heteroaryl; and wherein Q$_7$c is optionally substituted by one or more substituents selected from (1-4C)alkyl or halo.

15. A compound according to claim 1,
wherein
$R_{8c}$ is selected from hydrogen, cyano, halo or a group of the formula:

-L$_8$-L$_{8C}$-Q$_{8C}$ wherein
L$_8$ is absent or (1-3C)alkylene, optionally substituted by or oxo;
L$_{8C}$ is absent or selected from O, S, SO, SO$_2$, N(R$_r$), C(O), C(O)O, OC(O), C(O)N(R$_r$) or N(R$_r$)C(O), wherein R$_r$ is selected from hydrogen or (1-2C)alkyl; and
Q$_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein Q$_{8C}$ is optionally substituted by one or more substituents selected from (1-4C)alkyl, halo, NR$_t$R$_u$, OR$_t$, C(O)R$_t$, C(O)OR$_t$, OC(O)R$_t$, wherein R$_t$ and R$_u$ are each independently selected from H or (1-2C)alkyl; or
$R_{8N}$ is selected from hydrogen or a group of the formula:

-L$_8$-L$_{8N}$-Q$_{8N}$ wherein
L$_8$ is absent or (1-3C)alkylene optionally substituted by one or more substituents selected from (1-2C)alkyl;
L$_{8N}$ is absent or selected from O, S, SO, SO$_2$, N(R$_x$), C(O), C(O)O, OC(O), C(O)N(R$_x$), N(R$_x$)C(O), N(R$_x$)C(O)O, wherein R$_x$ is selected from hydrogen or (1-2C)alkyl;
Q$_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_a'$, OR$_z$, C(O)R$_z$, C(O)OR$_z$, OC(O)R$_z$, C(O)N(R$_z$)R$_{a'}$, N(R$_z$)C(O)R$_{a'}$ or S(O)$_y$R$_z$ (where y is 0, 1 or 2), wherein $R_z$ and $R_{a'}$ are each independently selected from H or (1-2C)alkyl; or $Q_{8N}$ is optionally substituted by a group of the formula:

-L$_{8'}$-Z$_{8N}$ wherein

L$_{8'}$ is absent or selected C(O), C(O)O, OC(O) or C(O)N (R$_{b'}$), wherein R$_{b'}$ and R$_{c'}$ are each independently selected from hydrogen or (1-2C)alkyl; and $Z_{8N}$ is phenyl, (1-4C)alkyl, (4-6C)heterocycyl or a 5-6 membered heteroaryl; wherein $Z_{8N}$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, hydroxyl, carboxy, carbamoyl or sulphamoyl.

16. A compound according to claim 1,
wherein $R_{8c}$ is selected from hydrogen, halo or a group of the formula:

-L$_8$-L$_{8C}$-Q$_{8C}$ wherein

L$_8$ is absent or (1-3C)alkylene, optionally substituted by or oxo;

L$_{8C}$ is absent or selected from O, N(R$_r$), C(O), C(O)O or C(O)N(R$_r$) wherein R$_r$ is selected from hydrogen or (1-2C)alkyl; and $Q_{8C}$ is hydrogen, cyano, (1-6C)alkyl, (3-6C)cycloalkyl, (2-3C)alkenyl, (2-3C)alkynyl, aryl, heterocyclyl or heteroaryl; and wherein $Q_{8C}$ is optionally substituted by one or more substituents selected from (1-4C)alkyl, halo, NR$_t$R$_u$, OR$_t$, wherein R$_t$ and R$_u$ are each independently selected from H or (1-2C)alkyl; or $R_{8N}$ is selected from hydrogen or a group of the formula:

-L$_8$-L$_{8N}$-Q$_{8N}$ wherein

L$_8$ is absent or (1-3C)alkylene optionally substituted by one or more substituents selected from (1-2C)alkyl;

L$_{8N}$ is absent or selected from C(O)N(R$_x$) or N(R$_x$)C(O)O, wherein R$_x$ is selected from hydrogen or (1-2C)alkyl;

$Q_{8N}$ is hydrogen, cyano, (1-6C)alkyl, (3-6C)cycloalkyl, (2-3C)alkenyl, (2-3C)alkynyl, aryl, heterocyclyl or heteroaryl, each of which is optionally substituted by one or more substituents selected from (1-4C)alkyl, halo, trifluoromethyl, trifluoromethoxy, haloalkyl, amino, cyano, aryl, hydroxyl, carboxy, carbamoyl, sulphamoyl, NR$_z$R$_{a'}$, OR$_z$, C(O)N(R$_z$)R$_{a'}$, N(R$_z$)C(O)R$_{a'}$ or S(O)$_y$R$_z$ (where y is 0, 1 or 2), wherein R$_z$ and R$_{a'}$ are each independently selected from H or (1-2C)alkyl; or $Q_{8N}$ is optionally substituted by a group of the formula:

-L$_{8'}$-Z$_{8N}$ wherein

L$_{8'}$ is absent or selected C(O) or C(O)N(R$_{b'}$), wherein R$_{b'}$ and R$_{c'}$ are each independently selected from hydrogen or (1-2C)alkyl; and $Z_{8N}$ is phenyl, (1-4C)alkyl, (4-6C) heterocyclyl or a 5-6 membered heteroaryl; wherein $Z_{8N}$ is optionally substituted by one or more substituents selected from (1-2C)alkyl, halo or hydroxyl.

17. A compound according to claim 1, selected from any one of the following:

N-(1-methylcyclopropyl)-2,4-dioxo-1H-quinazoline-6-sulfonamide;

1,3-dimethyl-N-(1-methylcyclopropyl)-2,4-dioxo-quinazoline-6-sulfonamide;

N-(1-cyanocyclopropyl)-1,3-dimethyl-2,4-dioxo-quinazoline-6-sulfonamide;

1,3-diethyl-N-(1-methylcyclopropyl)-2,4-dioxo-quinazoline-6-sulfonamide;

N-(1-cyanocyclopropyl)-1,3-diethyl-2,4-dioxo-quinazoline-6-sulfonamide;

3-ethyl-N-(1-methylcyclopropyl)-2,4-dioxo-1H-quinazoline-6-sulfonamide;

3-methyl-N-(1-methylcyclopropyl)-2,4-dioxo-1H-quinazoline-6-sulfonamide;

1-benzyl-3-methyl-N-(1-methylcyclopropyl)-2,4-dioxo-quinazoline-6-sulfonamide;

1-ethyl-3-methyl-N-(1-methylcyclopropyl)-2,4-dioxo-quinazoline-6-sulfonamide;

1-benzyl-3-ethyl-N-(1-methylcyclopropyl)-2,4-dioxo-quinazoline-6-sulfonamide;

1-[(2,6-dichlorophenyl)methyl]-3-ethyl-N-(1-methylcyclopropyl)-2,4-dioxo-quinazoline-6-sulfonamide;

3-ethyl-1-methyl-N-(1-methylcyclopropyl)-2,4-dioxo-quinazoline-6-sulfonamide;

1-(cyclohexylmethyl)-3-ethyl-N-(1-methylcyclopropyl)-2,4-dioxo-quinazoline-6-sulfonamide;

1-(cyclopropylmethyl)-3-ethyl-N-(1-methylcyclopropyl)-2,4-dioxo-quinazoline-6-sulfonamide;

3-ethyl-N-(1-methylcyclopropyl)-2,4-dioxo-1-(2-pyrrolidin-1-ylethyl)quinazoline-6-sulfonamide;

3-ethyl-1-(3-methoxypropyl)-N-(1-methylcyclopropyl)-2,4-dioxo-quinazoline-6-sulfonamide;

3-ethyl-1-(2-methoxyethyl)-N-(1-methylcyclopropyl)-2,4-dioxo-quinazoline-6-sulfonamide;

3-ethyl-N-(1-methylcyclopropyl)-1-(2-morpholinoethyl)-2,4-dioxo-quinazoline-6-sulfonamide;

1-methyl-N-(1-methylcyclopropyl)-2,4-dioxo-quinazoline-6-sulfonamide;

3-(cyclopropylmethyl)-1-methyl-N-(1-methylcyclopropyl)-2,4-dioxo-quinazoline-6-sulfonamide;

4-methyl-N-(1-methylcyclopropyl)-2,3-dioxo-1H-quinoxaline-6-sulfonamide;

1-(cyclopropylmethyl)-4-methyl-N-(1-methylcyclopropyl)-2,3-dioxo-quinoxaline-6-sulfonamide;

1-(cyclopropylmethyl)-3-methyl-N-(1-methylcyclopropyl)-2,4-dioxo-quinazoline-6-sulfonamide;

3-ethyl-1-isobutyl-N-(1-methylcyclopropyl)-2,4-dioxo-quinazoline-6-sulfonamide;

1-(2-methoxyethyl)-3-methyl-N-(1-methylcyclopropyl)-2,4-dioxo-quinazoline-6-sulfonamide;

1-[2-(dimethylamino)ethyl]-3-methyl-N-(1-methylcyclopropyl)-2,4-dioxo-quinazoline-6-sulfonamide;

1-isobutyl-3-methyl-N-(1-methylcyclopropyl)-2,4-dioxo-quinazoline-6-sulfonamide;

3-ethyl-2-isobutoxy-N-(1-methylcyclopropyl)-4-oxo-quinazoline-6-sulfonamide;

2-isobutoxy-3-methyl-N-(1-methylcyclopropyl)-4-oxo-quinazoline-6-sulfonamide;

1-methyl-N-(1-methylcyclopropyl)-2,4-dioxo-3-(3-pyridylmethyl)quinazoline-6-sulfonamide;

3-(cyanomethyl)-1-methyl-N-(1-methylcyclopropyl)-2,4-dioxo-quinazoline-6-sulfonamide;

3-methyl-N-(1-methylcyclopropyl)-1-[(1-methylcyclopropyl)methyl]-2,4-dioxo-quinazoline-6-sulfonamide;

3-methyl-N-(1-methylcyclopropyl)-2-[(1-methylcyclopropyl)methoxy]-4-oxo-quinazoline-6-sulfonamide;

1-(cyclohexylmethyl)-3-methyl-N-(1-methylcyclopropyl)-2,4-dioxo-quinazoline-6-sulfonamide;

3-methyl-N-(1-methylcyclopropyl)-1-[(2-methylcyclopropyl)methyl]-2,4-dioxo-quinazoline-6-sulfonamide;

1-[(2,2-difluorocyclopropyl)methyl]-3-methyl-N-(1-methylcyclopropyl)-2,4-dioxo-quinazoline-6-sulfonamide;
3-methyl-N-(1-methylcyclopropyl)-2,4-dioxo-1-(tetrahydrofuran-3-ylmethyl)quinazoline-6-sulfonamide;
3-methyl-N-(1-methylcyclopropyl)-2,4-dioxo-1-(tetrahydropyran-2-ylmethyl)quinazoline-6-sulfonamide;
3-methyl-N-(1-methylcyclopropyl)-2,4-dioxo-1-prop-2-ynyl-quinazoline-6-sulfonamide;
1-benzyl-4-methyl-N-(1-methylcyclopropyl)-2,3-dioxo-quinoxaline-6-sulfonamide;
4-methyl-2-(methylamino)-N-(1-methylcyclopropyl)-3-oxo-quinoxaline-6-sulfonamide;
3-methyl-N-(1-methylcyclopropyl)-1-[(3-methyloxetan-3-yl)methyl]-2,4-dioxo-quinazoline-6-sulfonamide;
1-(2-cyclopropylethyl)-3-methyl-N-(1-methylcyclopropyl)-2,4-dioxo-quinazoline-6-sulfonamide;
2-(2-cyclopropylethoxy)-3-methyl-N-(1-methylcyclopropyl)-4-oxo-quinazoline-6-sulfonamide;
1-allyl-3-methyl-N-(1-methylcyclopropyl)-2,4-dioxo-quinazoline-6-sulfonamide;
1-(cyclopentylmethyl)-3-methyl-N-(1-methylcyclopropyl)-2,4-dioxo-quinazoline-6-sulfonamide;
1-methyl-N-(1-methylcyclopropyl)-2,4-dioxo-3-prop-2-ynyl-quinazoline-6-sulfonamide;
3-methyl-N-(1-methylcyclopropyl)-1-[(1-methylimidazol-2-yl)methyl]-2,4-dioxo-quinazoline-6-sulfonamide;
3-methyl-N-(1-methylcyclopropyl)-2,4-dioxo-1-(tetrahydrofuran-2-ylmethyl)quinazoline-6-sulfonamide;
3-[(2,2-difluorocyclopropyl)methyl]-1-methyl-N-(1-methylcyclopropyl)-2,4-dioxo-quinazoline-6-sulfonamide;
2,3-dimethyl-N-(1-methylcyclopropyl)-4-oxo-quinazoline-6-sulfonamide;
2-methyl-N-(1-methylcyclopropyl)-4-oxo-3H-quinazoline-6-sulfonamide;
1-methyl-N-(1-methylcyclopropyl)-2,4-dioxo-3-(4-pyridylmethyl)quinazoline-6-sulfonamide;
2-cyclopropyl-N-(1-methylcyclopropyl)-4-oxo-3H-quinazoline-6-sulfonamide;
2-isopropyl-N-(1-methylcyclopropyl)-4-oxo-3H-quinazoline-6-sulfonamide;
3-methyl-N-(1-methylcyclopropyl)-1-(o-tolylmethyl)-2,4-dioxo-quinazoline-6-sulfonamide;
3-methyl-N-(1-methylcyclopropyl)-1-(m-tolylmethyl)-2,4-dioxo-quinazoline-6-sulfonamide;
3-methyl-N-(1-methylcyclopropyl)-2,4-dioxo-1-(p-tolylmethyl)quinazoline-6-sulfonamide;
1-[(2-methoxyphenyl)methyl]-3-methyl-N-(1-methylcyclopropyl)-2,4-dioxo-quinazoline-6-sulfonamide;
1-[(3-methoxyphenyl)methyl]-3-methyl-N-(1-methylcyclopropyl)-2,4-dioxo-quinazoline-6-sulfonamide;
1-[(4-methoxyphenyl)methyl]-3-methyl-N-(1-methylcyclopropyl)-2,4-dioxo-quinazoline-6-sulfonamide;
1-[(2-chlorophenyl)methyl]-3-methyl-N-(1-methylcyclopropyl)-2,4-dioxo-quinazoline-6-sulfonamide;
1-[(3-chlorophenyl)methyl]-3-methyl-N-(1-methylcyclopropyl)-2,4-dioxo-quinazoline-6-sulfonamide;
1-[(4-chlorophenyl)methyl]-3-methyl-N-(1-methylcyclopropyl)-2,4-dioxo-quinazoline-6-sulfonamide;
1-[(2-fluorophenyl)methyl]-3-methyl-N-(1-methylcyclopropyl)-2,4-dioxo-quinazoline-6-sulfonamide;
1-[(3-fluorophenyl)methyl]-3-methyl-N-(1-methylcyclopropyl)-2,4-dioxo-quinazoline-6-sulfonamide;
1-[(4-fluorophenyl)methyl]-3-methyl-N-(1-methylcyclopropyl)-2,4-dioxo-quinazoline-6-sulfonamide;
1-[(2-cyanophenyl)methyl]-3-methyl-N-(1-methylcyclopropyl)-2,4-dioxo-quinazoline-6-sulfonamide;
1-[(3-cyanophenyl)methyl]-3-methyl-N-(1-methylcyclopropyl)-2,4-dioxo-quinazoline-6-sulfonamide;
1-[(4-cyanophenyl)methyl]-3-methyl-N-(1-methylcyclopropyl)-2,4-dioxo-quinazoline-6-sulfonamide;
3-methyl-N-(1-methylcyclopropyl)-2,4-dioxo-1-[[2-(trifluoromethyl)phenyl]methyl] quinazoline-6-sulfonamide;
3-methyl-N-(1-methylcyclopropyl)-2,4-dioxo-1-[[3-(trifluoromethyl)phenyl]methyl] quinazoline-6-sulfonamide;
3-methyl-N-(1-methylcyclopropyl)-2,4-dioxo-1-[[4-(trifluoromethyl)phenyl]methyl] quinazoline-6-sulfonamide;
1-[(2,6-dichlorophenyl)methyl]-3-methyl-N-(1-methylcyclopropyl)-2,4-dioxo-quinazoline-6-sulfonamide;
1-[(2,6-difluorophenyl)methyl]-3-methyl-N-(1-methylcyclopropyl)-2,4-dioxo-quinazoline-6-sulfonamide;
1-[(3,5-dichlorophenyl)methyl]-3-methyl-N-(1-methylcyclopropyl)-2,4-dioxo-quinazoline-6-sulfonamide;
1-[(3,5-dimethylphenyl)methyl]-3-methyl-N-(1-methylcyclopropyl)-2,4-dioxo-quinazoline-6-sulfonamide;
1-[(3,5-dimethoxyphenyl)methyl]-3-methyl-N-(1-methylcyclopropyl)-2,4-dioxo-quinazoline-6-sulfonamide;
1-[(3,5-difluorophenyl)methyl]-3-methyl-N-(1-methylcyclopropyl)-2,4-dioxo-quinazoline-6-sulfonamide;
2-cyclopropyl-3-methyl-N-(1-methylcyclopropyl)-4-oxo-quinazoline-6-sulfonamide;
2-isobutyl-3-methyl-N-(1-methylcyclopropyl)-4-oxo-quinazoline-6-sulfonamide;
3-methyl-N-(1-methylcyclopropyl)-2,4-dioxo-1-(2-pyridylmethyl)quinazoline-6-sulfonamide;
3-methyl-N-(1-methylcyclopropyl)-2,4-dioxo-1-(3-pyridylmethyl)quinazoline-6-sulfonamide;
3-methyl-N-(1-methylcyclopropyl)-2,4-dioxo-1-(4-pyridylmethyl)quinazoline-6-sulfonamide;
2-[1-methyl-6-[(1-methylcyclopropyl)sulfamoyl]-2,4-dioxo-quinazolin-3-yl]-N-phenyl-acetamide;
(2S)-1-[2-[1-methyl-6-[(1-methylcyclopropyl)sulfamoyl]-2,4-dioxo-quinazolin-3-yl]acetyl]pyrrolidine-2-carboxamide;
3-[2-(4-aminophenyl)-2-oxo-ethyl]-1-methyl-N-(1-methylcyclopropyl)-2,4-dioxo-quinazoline-6-sulfonamide;
3-[[1-methyl-6-[(1-methylcyclopropyl)sulfamoyl]-2,4-dioxo-quinazolin-3-yl]methyl]-1,2,4-oxadiazole-5-carboxamide;
4-[[1-methyl-6-[(1-methylcyclopropyl)sulfamoyl]-2,4-dioxo-quinazolin-3-yl]methyl]benzamide;
2-[1-methyl-6-[(1-methylcyclopropyl)sulfamoyl]-2,4-dioxo-quinazolin-3-yl]-N-(1-methylpyrazol-4-yl)acetamide;
3-[2-(4-hydroxyphenyl)-2-oxo-ethyl]-1-methyl-N-(1-methylcyclopropyl)-2,4-dioxo-quinazoline-6-sulfonamide;
2-[3-methyl-6-[(1-methylcyclopropyl)sulfamoyl]-2,4-dioxo-quinazolin-1-yl]-N-phenyl-acetamide;
3-[[3-methyl-6-[(1-methylcyclopropyl)sulfamoyl]-2,4-dioxo-quinazolin-1-yl]methyl]benzamide;
1-[[3-(difluoromethyl)phenyl]methyl]-3-methyl-N-(1-methylcyclopropyl)-2,4-dioxo-quinazoline-6-sulfonamide;
3-[[3-methyl-6-[(1-methylcyclopropyl)sulfamoyl]-2,4-dioxo-quinazolin-1-yl]methyl]-1,2,4-oxadiazole-5-carboxamide;
4-[[3-methyl-6-[(1-methylcyclopropyl)sulfamoyl]-2,4-dioxo-quinazolin-1-yl]methyl]benzamide;

3-methyl-N-(1-methylcyclopropyl)-4-oxo-2-phenyl-quinazoline-6-sulfonamide;
N-(1-methylcyclopropyl)-4-oxo-2-pyrrolidin-1-yl-3H-quinazoline-6-sulfonamide;
N-methyl-5-[[1-methyl-6-[(1-methylcyclopropyl)sulfamoyl]-2,4-dioxo-quinazolin-3-yl]methyl]-1,2,4-oxadiazole-3-carboxamide;
1-[(4-cyano-3-fluoro-phenyl)methyl]-3-methyl-N-(1-methylcyclopropyl)-2,4-dioxo-quinazoline-6-sulfonamide;
N-methyl-5-[[3-methyl-6-[(1-methylcyclopropyl)sulfamoyl]-2,4-dioxo-quinazolin-1-yl]methyl]-1,2,4-oxadiazole-3-carboxamide;
3-[2-(4-fluorophenyl)-2-oxo-ethyl]-1-methyl-N-(1-methylcyclopropyl)-2,4-dioxo-quinazoline-6-sulfonamide;
1-methyl-N-(1-methylcyclopropyl)-3-[(5-methylisoxazol-3-yl)methyl]-2,4-dioxo-quinazoline-6-sulfonamide;
3-methyl-N-(1-methylcyclopropyl)-1-[(4-methylsulfonylphenyl)methyl]-2,4-dioxo-quinazoline-6-sulfonamide;
3-methyl-N-(1-methylcyclopropyl)-1-[(5-methylisoxazol-3-yl)methyl]-2,4-dioxo-quinazoline-6-sulfonamide;
2-[3-methyl-6-[(1-methylcyclopropyl)sulfamoyl]-2,4-dioxo-quinazolin-1-yl]-N-(1-methylpyrazol-4-yl)acetamide;
1-[2-(4-hydroxyphenyl)-2-oxo-ethyl]-3-methyl-N-(1-methylcyclopropyl)-2,4-dioxo-quinazoline-6-sulfonamide;
1-methyl-N-(1-methylcyclopropyl)-2,4-dioxo-3-(pyrazin-2-ylmethyl)quinazoline-6-sulfonamide;
1-methyl-N-(1-methylcyclopropyl)-3-[(2-methylthiazol-5-yl)methyl]-2,4-dioxo-quinazoline-6-sulfonamide;
3-[2-[4-(diethylamino)phenyl]-2-oxo-ethyl]-1-methyl-N-(1-methylcyclopropyl)-2,4-dioxo-quinazoline-6-sulfonamide;
1-methyl-N-(1-methylcyclopropyl)-3-[(5-nitro-2-furyl)methyl]-2,4-dioxo-quinazoline-6-sulfonamide;
3-(1H-benzimidazol-2-ylmethyl)-1-methyl-N-(1-methylcyclopropyl)-2,4-dioxo-quinazoline-6-sulfonamide;
1-methyl-N-(1-methylcyclopropyl)-3-[(1-methylimidazol-2-yl)methyl]-2,4-dioxo-quinazoline-6-sulfonamide;
1-methyl-N-(1-methylcyclopropyl)-2,4-dioxo-3-[2-oxo-2-(4-pyrrolidin-1-ylphenyl)ethyl]quinazoline-6-sulfonamide;
3-[(3,5-dimethylisoxazol-4-yl)methyl]-1-methyl-N-(1-methylcyclopropyl)-2,4-dioxo-quinazoline-6-sulfonamide;
1-(1H-benzimidazol-2-ylmethyl)-3-methyl-N-(1-methylcyclopropyl)-2,4-dioxo-quinazoline-6-sulfonamide;
3-methyl-N-(1-methylcyclopropyl)-2,4-dioxo-1-[2-oxo-2-(4-pyrrolidin-1-ylphenyl)ethyl]quinazoline-6-sulfonamide;
N-[4-[[3-methyl-6-[(1-methylcyclopropyl)sulfamoyl]-2,4-dioxo-quinazolin-1-yl]methyl]phenyl]acetamide;
1-[(5-tert-butyl-1,2,4-oxadiazol-3-yl)methyl]-3-methyl-N-(1-methylcyclopropyl)-2,4-dioxo-quinazoline-6-sulfonamide;
3-methyl-N-(1-methylcyclopropyl)-1-[(5-nitro-2-furyl)methyl]-2,4-dioxo-quinazoline-6-sulfonamide;
1-[(3,5-dimethylisoxazol-4-yl)methyl]-3-methyl-N-(1-methylcyclopropyl)-2,4-dioxo-quinazoline-6-sulfonamide;
1-methyl-N-(1-methylcyclopropyl)-3-[(2-methylpyrazol-3-yl)methyl]-2,4-dioxo-quinazoline-6-sulfonamide;
3-[(2,5-dimethylpyrazol-3-yl)methyl]-1-methyl-N-(1-methylcyclopropyl)-2,4-dioxo-quinazoline-6-sulfonamide;
3-methyl-N-(1-methylcyclopropyl)-2,4-dioxo-1-(pyrazin-2-ylmethyl)quinazoline-6-sulfonamide;
3-methyl-N-(1-methylcyclopropyl)-1-[(2-methylpyrazol-3-yl)methyl]-2,4-dioxo-quinazoline-6-sulfonamide;
3-methyl-N-(1-methylcyclopropyl)-1-[(2-methylthiazol-5-yl)methyl]-2,4-dioxo-quinazoline-6-sulfonamide;
1-[(2,5-dimethylpyrazol-3-yl)methyl]-3-methyl-N-(1-methylcyclopropyl)-2,4-dioxo-quinazoline-6-sulfonamide;
1-[(4-fluorophenyl)methyl]-N-(1-methylcyclopropyl)-2,3-dioxo-4H-quinoxaline-6-sulfonamide;
1,3-bis[(3,5-dimethylisoxazol-4-yl)methyl]-N-(1-methylcyclopropyl)-2,4-dioxo-quinazoline-6-sulfonamide;
1-[(4-fluorophenyl)methyl]-4-methyl-N-(1-methylcyclopropyl)-2,3-dioxo-quinoxaline-6-sulfonamide;
N-(3-hydroxypropyl)-4-[[3-methyl-6-[(1-methylcyclopropyl)sulfamoyl]-2,4-dioxo-quinazolin-1-yl]methyl]benzamide;
3-methyl-N-(1-methylcyclopropyl)-2,4-dioxo-1-[(1S)-1-phenylethyl]quinazoline-6-sulfonamide;
1-[(2,4-dimethylthiazol-5-yl)methyl]-3-methyl-N-(1-methylcyclopropyl)-2,4-dioxo-quinazoline-6-sulfonamide;
3-methyl-N-(1-methylcyclopropyl)-1-[(2-methyl-4-phenyl-thiazol-5-yl)methyl]-2,4-dioxo-quinazoline-6-sulfonamide;
1-[(2-bromothiazol-5-yl)methyl]-3-methyl-N-(1-methylcyclopropyl)-2,4-dioxo-quinazoline-6-sulfonamide;
1-but-2-ynyl-3-methyl-N-(1-methylcyclopropyl)-2,4-dioxo-quinazoline-6-sulfonamide;
3-methyl-N-(1-methylcyclopropyl)-2,4-dioxo-1-pent-2-ynyl-quinazoline-6-sulfonamide;
3-methyl-N-(1-methylcyclopropyl)-2,4-dioxo-1-[[4-(piperazine-1-carbonyl)phenyl]methyl]quinazoline-6-sulfonamide;
3-methyl-N-(1-methylcyclopropyl)-1-[(1S)-1-methyl-prop-2-ynyl]-2,4-dioxo-quinazoline-6-sulfonamide;
3-methyl-N-(1-methylcyclopropyl)-1-[(1R)-1-methyl-prop-2-ynyl]-2,4-dioxo-quinazoline-6-sulfonamide;
3-[(2-bromothiazol-5-yl)methyl]-1-methyl-N-(1-methylcyclopropyl)-2,4-dioxo-quinazoline-6-sulfonamide;
3-[(2,4-dimethylthiazol-5-yl)methyl]-1-methyl-N-(1-methylcyclopropyl)-2,4-dioxo-quinazoline-6-sulfonamide;
3-methyl-N-(1-methylcyclopropyl)-2,4-dioxo-1-(thiazol-5-ylmethyl)quinazoline-6-sulfonamide;
3-[(2-chlorothiazol-5-yl)methyl]-1-methyl-N-(1-methylcyclopropyl)-2,4-dioxo-quinazoline-6-sulfonamide;
1-[(2-chlorothiazol-5-yl)methyl]-3-methyl-N-(1-methylcyclopropyl)-2,4-dioxo-quinazoline-6-sulfonamide;
3-methyl-N-(1-methylcyclopropyl)-2,4-dioxo-1-(thiazol-2-ylmethyl)quinazoline-6-sulfonamide;
1-methyl-N-(1-methylcyclopropyl)-2,4-dioxo-3-(thiazol-5-ylmethyl)quinazoline-6-sulfonamide;
3-methyl-N-(1-methylcyclopropyl)-2,4-dioxo-1-(thiazol-4-ylmethyl)quinazoline-6-sulfonamide;
1-[(5-tert-butyl-2-methyl-pyrazol-3-yl)methyl]-3-methyl-N-(1-methylcyclopropyl)-2,4-dioxo-quinazoline-6-sulfonamide;
1-methyl-N-(1-methylcyclopropyl)-3-[(4-methylthiazol-2-yl)methyl]-2,4-dioxo-quinazoline-6-sulfonamide;
3-methyl-N-(1-methylcyclopropyl)-1-[(1-methylpyrazol-3-yl)methyl]-2,4-dioxo-quinazoline-6-sulfonamide;

3-methyl-N-(1-methylcyclopropyl)-1-[(1-methylpyrazol-4-yl)methyl]-2,4-dioxo-quinazoline-6-sulfonamide;

1-methyl-N-(1-methylcyclopropyl)-2,4-dioxo-3-(thiadiazol-4-ylmethyl)quinazoline-6-sulfonamide;

1-methyl-N-(1-methylcyclopropyl)-3-[(3-methylimidazol-4-yl)methyl]-2,4-dioxo-quinazoline-6-sulfonamide;

1-methyl-N-(1-methylcyclopropyl)-3-[(1-methylpyrazol-4-yl)methyl]-2,4-dioxo-quinazoline-6-sulfonamide;

1-(cyclopropylmethyl)-N-(1-methylcyclopropyl)-3-[(2-methylthiazol-5-yl)methyl]-2,4-dioxo-quinazoline-6-sulfonamide;

2-(cyclopropylmethoxy)-N-(1-methylcyclopropyl)-3-[(2-methylthiazol-5-yl)methyl]-4-oxo-quinazoline-6-sulfonamide;

1-(cyclopropylmethyl)-3-[(3,5-dimethylisoxazol-4-yl)methyl]-N-(1-methylcyclopropyl)-2,4-dioxo-quinazoline-6-sulfonamide;

3-[(3,5-dimethylisoxazol-4-yl)methyl]-N-(1-methylcyclopropyl)-2,4-dioxo-1-prop-2-ynyl-quinazoline-6-sulfonamide;

1-methyl-N-(1-methylcyclopropyl)-3-[(5-methyl-1,3,4-oxadiazol-2-yl)methyl]-2,4-dioxo-quinazoline-6-sulfonamide;

N-(1-methylcyclopropyl)-3-[(2-methylthiazol-5-yl)methyl]-2,4-dioxo-1-prop-2-ynyl-quinazoline-6-sulfonamide;

1-[(2,4-dimethylthiazol-5-yl)methyl]-N-(1-methylcyclopropyl)-3-[(2-methylthiazol-5-yl)methyl]-2,4-dioxo-quinazoline-6-sulfonamide;

1-[(2,5-dimethylpyrazol-3-yl)methyl]-N-(1-methylcyclopropyl)-3-[(2-methylthiazol-5-yl)methyl]-2,4-dioxo-quinazoline-6-sulfonamide;

2-[(2,5-dimethylpyrazol-3-yl)methoxy]-N-(1-methylcyclopropyl)-3-[(2-methylthiazol-5-yl)methyl]-4-oxo-quinazoline-6-sulfonamide;

3-[(3,5-dimethylisoxazol-4-yl)methyl]-1-[(2,4-dimethylthiazol-5-yl)methyl]-N-(1-methylcyclopropyl)-2,4-dioxo-quinazoline-6-sulfonamide;

3-[(3,5-dimethylisoxazol-4-yl)methyl]-1-[(2,5-dimethylpyrazol-3-yl)methyl]-N-(1-methylcyclopropyl)-2,4-dioxo-quinazoline-6-sulfonamide;

3-[(3,5-dimethylisoxazol-4-yl)methyl]-2-[(2,5-dimethylpyrazol-3-yl)methoxy]-N-(1-methylcyclopropyl)-4-oxo-quinazoline-6-sulfonamide;

3-[(3,5-dimethylisoxazol-4-yl)methyl]-1-[(4-fluorophenyl)methyl]-N-(1-methylcyclopropyl)-2,4-dioxo-quinazoline-6-sulfonamide;

3-[(3,5-dimethylisoxazol-4-yl)methyl]-1-[(3-methoxyphenyl)methyl]-N-(1-methylcyclopropyl)-2,4-dioxo-quinazoline-6-sulfonamide;

1-[(2,4-dimethylthiazol-5-yl)methyl]-N-(1-methylcyclopropyl)-3-[(1-methylpyrazol-4-yl)methyl]-2,4-dioxo-quinazoline-6-sulfonamide;

1-[(4-fluorophenyl)methyl]-N-(1-methylcyclopropyl)-3-[(1-methylpyrazol-4-yl)methyl]-2,4-dioxo-quinazoline-6-sulfonamide;

1-[(3-methoxyphenyl)methyl]-N-(1-methylcyclopropyl)-3-[(1-methylpyrazol-4-yl)methyl]-2,4-dioxo-quinazoline-6-sulfonamide;

1-[(2,5-dimethylpyrazol-3-yl)methyl]-N-(1-methylcyclopropyl)-3-[(1-methylpyrazol-4-yl)methyl]-2,4-dioxo-quinazoline-6-sulfonamide;

1-(cyclopropylmethyl)-N-(1-methylcyclopropyl)-3-[(1-methylpyrazol-4-yl)methyl]-2,4-dioxo-quinazoline-6-sulfonamide;

1-(cyanomethyl)-3-methyl-N-(1-methylcyclopropyl)-2,4-dioxo-quinazoline-6-sulfonamide;

1-[(4-fluorophenyl)methyl]-N-(1-methylcyclopropyl)-3-[(2-methylthiazol-5-yl)methyl]-2,4-dioxo-quinazoline-6-sulfonamide;

1-[(3-methoxyphenyl)methyl]-N-(1-methylcyclopropyl)-3-[(2-methylthiazol-5-yl)methyl]-2,4-dioxo-quinazoline-6-sulfonamide;

N-(1-methylcyclopropyl)-3-[(1-methylpyrazol-4-yl)methyl]-2,4-dioxo-1-prop-2-ynyl-quinazoline-6-sulfonamide;

1-methyl-N-(1-methylcyclopropyl)-3-[[2-methyl-4-(trifluoromethyl)thiazol-5-yl]methyl]-2,4-dioxo-quinazoline-6-sulfonamide;

1-methyl-N-(1-methylcyclopropyl)-3-[(3-methylisoxazol-5-yl)methyl]-2,4-dioxo-quinazoline-6-sulfonamide;

3-[(1-ethylpyrazol-4-yl)methyl]-1-methyl-N-(1-methylcyclopropyl)-2,4-dioxo-quinazoline-6-sulfonamide;

1-methyl-N-(1-methylcyclopropyl)-3-(2-morpholino-2-oxo-ethyl)-2,4-dioxo-quinazoline-6-sulfonamide;

1-methyl-N-(1-methylcyclopropyl)-2,4-dioxo-3-(1H-pyrazol-4-ylmethyl)quinazoline-6-sulfonamide;

1-methyl-N-(1-methylcyclopropyl)-2,4-dioxo-3-[[(2S)-5-oxopyrrolidin-2-yl]methyl] quinazoline-6-sulfonamide;

1-methyl-N-(1-methylcyclopropyl)-2,4-dioxo-3-[[(2R)-5-oxopyrrolidin-2-yl]methyl] quinazoline-6-sulfonamide;

3-(cyanomethyl)-1-[(4-fluorophenyl)methyl]-N-(1-methylcyclopropyl)-2,4-dioxo-quinazoline-6-sulfonamide;

3-(cyanomethyl)-1-[(3-methoxyphenyl)methyl]-N-(1-methylcyclopropyl)-2,4-dioxo-quinazoline-6-sulfonamide;

1-methyl-N-(1-methylcyclopropyl)-3-[(4-methyloxazol-5-yl)methyl]-2,4-dioxo-quinazoline-6-sulfonamide;

3-[(2,4-dimethyloxazol-5-yl)methyl]-1-methyl-N-(1-methylcyclopropyl)-2,4-dioxo-quinazoline-6-sulfonamide;

1-methyl-N-(1-methylcyclopropyl)-3-[(3-methyl-1,2,4-oxadiazol-5-yl)methyl]-2,4-dioxo-quinazoline-6-sulfonamide;

1-methyl-N-(1-methylcyclopropyl)-3-[(4-methylthiadiazol-5-yl)methyl]-2,4-dioxo-quinazoline-6-sulfonamide;

3-(cyanomethyl)-1-[(2,5-dimethylpyrazol-3-yl)methyl]-N-(1-methylcyclopropyl)-2,4-dioxo-quinazoline-6-sulfonamide;

3-(cyanomethyl)-1-(cyclopropylmethyl)-N-(1-methylcyclopropyl)-2,4-dioxo-quinazoline-6-sulfonamide;

3-(cyanomethyl)-N-(1-methylcyclopropyl)-2,4-dioxo-1-prop-2-ynyl-quinazoline-6-sulfonamide;

1-methyl-N-(1-methylcyclopropyl)-3-[(3-methyl-1H-pyrazol-5-yl)methyl]-2,4-dioxo-quinazoline-6-sulfonamide;

N-[[1-methyl-6-[(1-methylcyclopropyl)sulfamoyl]-2,4-dioxo-quinazolin-3-yl]methyl]acetamide;

1-(cyclopropylmethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-prop-2-ynyl-quinazoline-6-sulfonamide;

1-[(4-fluorophenyl)methyl]-N-(1-methylcyclopropyl)-3-[(3-methylisoxazol-5-yl)methyl]-2,4-dioxo-quinazoline-6-sulfonamide;

1-[(3-methoxyphenyl)methyl]-N-(1-methylcyclopropyl)-3-[(3-methylisoxazol-5-yl)methyl]-2,4-dioxo-quinazoline-6-sulfonamide;
2-[4-[[1-methyl-6-[(1-methylcyclopropyl)sulfamoyl]-2,4-dioxo-quinazolin-3-yl]methyl]pyrazol-1-yl] acetamide;
N-(1-cyanocyclopropyl)-1-[(2,4-dimethylthiazol-5-yl)methyl]-3-methyl-2,4-dioxo-quinazoline-6-sulfonamide;
1-methyl-N-(1-methylcyclopropyl)-3-[(3-methylisoxazol-5-yl)methyl]-2,4-dioxo-pyrido[2,3-d]pyrimidine-6-sulfonamide;
1-[(2,4-dimethylthiazol-5-yl)methyl]-3-methyl-N-(2-methylcyclopropyl)-2,4-dioxo-quinazoline-6-sulfonamide;
1-[(2,5-dimethylpyrazol-3-yl)methyl]-N-(1-methylcyclopropyl)-3-[(3-methylisoxazol-5-yl)methyl]-2,4-dioxo-quinazoline-6-sulfonamide;
N-(1-methylcyclopropyl)-1,3-bis[(3-methylisoxazol-5-yl)methyl]-2,4-dioxo-quinazoline-6-sulfonamide;
4-chloro-N-(1-methylcyclopropyl)-2-[(3-methylisoxazol-5-yl)methyl]-1-oxo-isoquinoline-7-sulfonamide;
N-(1-methylcyclopropyl)-3-[(3-methylisoxazol-5-yl)methyl]-4-oxo-quinazoline-6-sulfonamide;
7-fluoro-3-methyl-N-(1-methylcyclopropyl)-2,4-dioxo-1H-quinazoline-6-sulfonamide;
3-[[1-[(4-methoxyphenyl)methyl]pyrazol-4-yl]methyl]-1-methyl-N-(1-methylcyclopropyl)-2,4-dioxo-quinazoline-6-sulfonamide;
1-[(2,5-dimethylpyrazol-3-yl)methyl]-7-fluoro-3-methyl-N-(1-methylcyclopropyl)-2,4-dioxo-quinazoline-6-sulfonamide;
tert-butyl N-[5-[[1-methyl-6-[(1-methylcyclopropyl)sulfamoyl]-2,4-dioxo-quinazolin-3-yl]methyl]thiazol-2-yl]carbamate;
3-[(1-benzylpyrazol-4-yl)methyl]-1-methyl-N-(1-methylcyclopropyl)-2,4-dioxo-quinazoline-6-sulfonamide;
1-methyl-N-(1-methylcyclopropyl)-2,4-dioxo-3-[(1-prop-2-ynylpyrazol-4-yl)methyl]quinazoline-6-sulfonamide;
3-[[1-(cyanomethyl)pyrazol-4-yl]methyl]-1-methyl-N-(1-methylcyclopropyl)-2,4-dioxo-quinazoline-6-sulfonamide;
3-[[1-(cyclopropylmethyl)pyrazol-4-yl]methyl]-1-methyl-N-(1-methylcyclopropyl)-2,4-dioxo-quinazoline-6-sulfonamide;
3-[[1-[2-(dimethylamino)ethyl]pyrazol-4-yl]methyl]-1-methyl-N-(1-methylcyclopropyl)-2,4-dioxo-quinazoline-6-sulfonamide;
N-(1-methylcyclopropyl)-3-[(2-methylthiazol-5-yl)methyl]-2,4-dioxo-1H-quinazoline-6-sulfonamide;
N-(1-methylcyclopropyl)-3-[(3-methylisoxazol-5-yl)methyl]-2,4-dioxo-1H-quinazoline-6-sulfonamide;
3-(cyanomethyl)-N-(1-methylcyclopropyl)-2,4-dioxo-1H-quinazoline-6-sulfonamide;
2-[6-[(1-methylcyclopropyl)sulfamoyl]-2,4-dioxo-1H-quinazolin-3-yl]acetamide;
7-fluoro-1,3-dimethyl-N-(1-methylcyclopropyl)-2,4-dioxo-quinazoline-6-sulfonamide;
8-fluoro-1,3-dimethyl-N-(1-methylcyclopropyl)-2,4-dioxo-quinazoline-6-sulfonamide;
3-(isoxazol-5-ylmethyl)-1-methyl-N-(1-methylcyclopropyl)-2,4-dioxo-quinazoline-6-sulfonamide;
1-chloro-3-methyl-N-(1-methylcyclopropyl)-4-oxo-phthalazine-6-sulfonamide;
N-(1-cyanocyclopropyl)-3-[(3-methylisoxazol-5-yl)methyl]-2,4-dioxo-1H-quinazoline-6-sulfonamide;
N-(1-cyanocyclopropyl)-1-methyl-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[[2-methyl-5-(trifluoromethyl)pyrazol-3-yl]methyl]-2,4-dioxo-quinazoline-6-sulfonamide;
N-(1-methylcyclopropyl)-3-[(2-methylthiazol-5-yl)methyl]-1-[[2-methyl-5-(trifluoromethyl)pyrazol-3-yl]methyl]-2,4-dioxo-quinazoline-6-sulfonamide;
3-[(2-aminothiazol-5-yl)methyl]-1-methyl-N-(1-methylcyclopropyl)-2,4-dioxo-quinazoline-6-sulfonamide;
3-[(3-aminoisoxazol-5-yl)methyl]-1-methyl-N-(1-methylcyclopropyl)-2,4-dioxo-quinazoline-6-sulfonamide;
3-methyl-1-(methylamino)-N-(1-methylcyclopropyl)-4-oxo-phthalazine-6-sulfonamide;
1-[2-(dimethylamino)ethyl]-N-(1-methylcyclopropyl)-3-[(1-methylpyrazol-4-yl)methyl]-2,4-dioxo-quinazoline-6-sulfonamide;
N-(1-methylcyclopropyl)-1-[(1-methyl-3-piperidyl)methyl]-3-[(1-methylpyrazol-4-yl)methyl]-2,4-dioxo-quinazoline-6-sulfonamide;
1-[3-(dimethylamino)propyl]-N-(1-methylcyclopropyl)-3-[(1-methylpyrazol-4-yl)methyl]-2,4-dioxo-quinazoline-6-sulfonamide;
N-(1-methylcyclopropyl)-1-[(1-methyl-2-piperidyl)methyl]-3-[(1-methylpyrazol-4-yl)methyl]-2,4-dioxo-quinazoline-6-sulfonamide;
1-(3-methoxypropyl)-N-(1-methylcyclopropyl)-3-[(1-methylpyrazol-4-yl)methyl]-2,4-dioxo-quinazoline-6-sulfonamide;
3-cyclopropyl-N-(1-methylcyclopropyl)-2,4-dioxo-1H-quinazoline-6-sulfonamide;
3-cyclopropyl-1-[(2,5-dimethylpyrazol-3-yl)methyl]-N-(1-methylcyclopropyl)-2,4-dioxo-quinazoline-6-sulfonamide;
N-(1-methylcyclopropyl)-2-[(3-methylisoxazol-5-yl)methyl]-1-oxo-isoquinoline-7-sulfonamide;
N-(1-methylcyclopropyl)-3-[(3-methylisoxazol-5-yl)methyl]-1-[(5-methyl-1,2,4-oxadiazol-3-yl)methyl]-2,4-dioxo-quinazoline-6-sulfonamide;
1-(methyl amino)-N-(1-methylcyclopropyl)-3-[(3-methylisoxazol-5-yl)methyl]-4-oxo-phthalazine-6-sulfonamide;
1-methyl-N-(1-methylcyclopropyl)-2,4-dioxo-3-[[3-(trifluoromethyl)isoxazol-5-yl]methyl]quinazoline-6-sulfonamide;
1-[2-(dimethylamino)ethyl]-N-(1-methylcyclopropyl)-3-[(3-methylisoxazol-5-yl)methyl]-2,4-dioxo-quinazoline-6-sulfonamide;
1-[3-(dimethylamino)propyl]-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-2,4-dioxo-1-(2-pyrrolidin-1-yl ethyl)quinazoline-6-sulfonamide;
N-(1-methylcyclopropyl)-3-[(3-methylisoxazol-5-yl)methyl]-1-[(1-methylpyrrolidin-2-yl)methyl]-2,4-dioxo-quinazoline-6-sulfonamide;
1-[3-(methylamino)propyl]-N-(1-methylcyclopropyl)-3-[(3-methylisoxazol-5-yl)methyl]-2,4-dioxo-quinazoline-6-sulfonamide;
1-(3-methoxypropyl)-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[(3-methyl-1,2,4-oxadiazol-5-yl)methyl]-2,4-dioxo-quinazoline-6-sulfonamide;

1-[2-(dimethylamino)ethylamino]-N-(1-methylcyclopropyl)-3-[(3-methylisoxazol-5-yl)methyl]-4-oxo-phthalazine-6-sulfonamide;

tert-butyl N-[2-[6-[(1-methylcyclopropyl)sulfamoyl]-3-[(1-methylpyrazol-4-yl)methyl]-2,4-dioxo-quinazolin-1-yl]ethyl]carbamate;

4-(4-fluorophenyl)-2-methyl-N-(1-methylcyclopropyl)-1-oxo-isoquinoline-7-sulfonamide;

4-methyl-N-(1-methylcyclopropyl)-2-[(3-methylisoxazol-5-yl)methyl]-1-oxo-isoquinoline-7-sulfonamide;

N-(1-methylcyclopropyl)-3-[(1-methylpyrazol-4-yl)methyl]-2,4-dioxo-1-(tetrahydropyran-2-ylmethyl)quinazoline-6-sulfonamide;

N-(1-methylcyclopropyl)-3-[(1-methylpyrazol-4-yl)methyl]-2,4-dioxo-1-(tetrahydrofuran-2-ylmethyl)quinazoline-6-sulfonamide;

N-(1-methylcyclopropyl)-3-[(1-methylpyrazol-4-yl)methyl]-2,4-dioxo-1-(tetrahydrofuran-3-ylmethyl)quinazoline-6-sulfonamide;

N-(1-ethylcyclopropyl)-1-methyl-3-[(3-methylisoxazol-5-yl)methyl]-2,4-dioxo-quinazoline-6-sulfonamide;

1-chloro-N-(1-methylcyclopropyl)-3-[(3-methylisoxazol-5-yl)methyl]-4-oxo-phthalazine-6-sulfonamide;

1-(2-aminoethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-2,4-dioxo-1-[3-(trifluoromethoxy)propyl]quinazoline-6-sulfonamide;

N,N-dimethyl-2-[6-[(1-methylcyclopropyl)sulfamoyl]-3-[(1-methylpyrazol-4-yl)methyl]-2,4-dioxo-quinazolin-1-yl]acetamide;

N-(1-methylcyclopropyl)-3-[(3-methylisoxazol-5-yl)methyl]-2,4-dioxo-1-(tetrahydropyran-2-ylmethyl)quinazoline-6-sulfonamide;

N-(1-methylcyclopropyl)-3-[(3-methylisoxazol-5-yl)methyl]-2,4-dioxo-1-(tetrahydrofuran-2-ylmethyl)quinazoline-6-sulfonamide;

N-(1-methylcyclopropyl)-3-[(3-methylisoxazol-5-yl)methyl]-2,4-dioxo-1-(tetrahydrofuran-3-ylmethyl)quinazoline-6-sulfonamide;

N-(1-methylcyclopropyl)-3-[(1-methylpyrazol-4-yl)methyl]-2,4-dioxo-1-(tetrahydropyran-4-ylmethyl)quinazoline-6-sulfonamide;

1-(2-methoxyethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-1-(2-morpholinoethyl)-2,4-dioxo-quinazoline-6-sulfonamide;

N-(1-methylcyclopropyl)-3-[(1-methylpyrazol-4-yl)methyl]-2,4-dioxo-1-(2-pyrrolidin-1-yl ethyl)quinazoline-6-sulfonamide;

3-[6-[(1-methylcyclopropyl)sulfamoyl]-3-[(1-methylpyrazol-4-yl)methyl]-2,4-dioxo-quinazolin-1-yl]propanamide;

1-(2-methoxyethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-1-[(1-methyl-2-piperidyl)methyl]-2,4-dioxo-quinazoline-6-sulfonamide;

N-(1-methylcyclopropyl)-3-[(3-methylisoxazol-5-yl)methyl]-1-(2-morpholinoethyl)-2,4-dioxo-quinazoline-6-sulfonamide;

3-[6-[(1-methylcyclopropyl)sulfamoyl]-3-[(3-methylisoxazol-5-yl)methyl]-2,4-dioxo-quinazolin-1-yl]propanamide;

N-(1-methylcyclopropyl)-3-[(3-methylisoxazol-5-yl)methyl]-2,4-dioxo-1-[2-(1-piperidyl)ethyl]quinazoline-6-sulfonamide;

1-(cyclopentylmethyl)-N-(1-methylcyclopropyl)-3-[(1-methylpyrazol-4-yl)methyl]-2,4-dioxo-quinazoline-6-sulfonamide;

1-(cyclohexylmethyl)-N-(1-methylcyclopropyl)-3-[(1-methylpyrazol-4-yl)methyl]-2,4-dioxo-quinazoline-6-sulfonamide;

1-(cyclobutylmethyl)-N-(1-methylcyclopropyl)-3-[(1-methylpyrazol-4-yl)methyl]-2,4-dioxo-quinazoline-6-sulfonamide;

1-(dimethylamino)-N-(1-methylcyclopropyl)-3-[(3-methylisoxazol-5-yl)methyl]-4-oxo-phthalazine-6-sulfonamide;

1-[3-(dimethylamino)prop-1-ynyl]-N-(1-methylcyclopropyl)-3-[(3-methylisoxazol-5-yl)methyl]-4-oxo-phthalazine-6-sulfonamide;

1-methyl-N-(1-methylcyclopropyl)-3-[(3-methylisoxazol-5-yl)methyl]-4-oxo-phthalazine-6-sulfonamide;

3-[(3-aminoisoxazol-5-yl)methyl]-1-[(2,5-dimethylpyrazol-3-yl)methyl]-N-(1-methylcyclopropyl)-2,4-dioxo-quinazoline-6-sulfonamide;

4-[3-(dimethylamino)prop-1-ynyl]-N-(1-methylcyclopropyl)-2-[(3-methylisoxazol-5-yl)methyl]-1-oxo-isoquinoline-7-sulfonamide;

4-[3-(dimethylamino)propyl]-N-(1-methylcyclopropyl)-2-[(3-methylisoxazol-5-yl)methyl]-1-oxo-isoquinoline-7-sulfonamide;

1-(cyclobutylmethyl)-N-(1-methylcyclopropyl)-3-[(3-methylisoxazol-5-yl)methyl]-2,4-dioxo-quinazoline-6-sulfonamide;

1-(cyclopentylmethyl)-N-(1-methylcyclopropyl)-3-[(3-methylisoxazol-5-yl)methyl]-2,4-dioxo-quinazoline-6-sulfonamide;

1-(cyclohexylmethyl)-N-(1-methylcyclopropyl)-3-[(3-methylisoxazol-5-yl)methyl]-2,4-dioxo-quinazoline-6-sulfonamide;

1-ethyl-N-(1-methylcyclopropyl)-3-[(1-methylpyrazol-4-yl)methyl]-2,4-dioxo-quinazoline-6-sulfonamide;

1-isopropyl-N-(1-methylcyclopropyl)-3-[(1-methylpyrazol-4-yl)methyl]-2,4-dioxo-quinazoline-6-sulfonamide;

2-isopropoxy-N-(1-methylcyclopropyl)-3-[(1-methylpyrazol-4-yl)methyl]-4-oxo-quinazoline-6-sulfonamide;

N-(1-methylcyclopropyl)-1-[(3-methyloxetan-3-yl)methyl]-3-[(1-methylpyrazol-4-yl)methyl]-2,4-dioxo-quinazoline-6-sulfonamide;

1-isobutyl-N-(1-methylcyclopropyl)-3-[(1-methylpyrazol-4-yl)methyl]-2,4-dioxo-quinazoline-6-sulfonamide;

1-(2-cyclopropylethyl)-N-(1-methylcyclopropyl)-3-[(1-methylpyrazol-4-yl)methyl]-2,4-dioxo-quinazoline-6-sulfonamide;

N-(1-methylcyclopropyl)-3-[(1-methylpyrazol-4-yl)methyl]-1-(oxetan-3-ylmethyl)-2,4-dioxo-quinazoline-6-sulfonamide;

1-benzyl-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl)methyl]-4-oxo-phthalazine-6-sulfonamide;

N-(1-methylcyclopropyl)-3-[(1-methylpyrazol-4-yl) methyl]-2,4-dioxo-1-[(5-oxopyrrolidin-2-yl)methyl] quinazoline-6-sulfonamide;

methyl 6-[(1-methylcyclopropyl)sulfamoyl]-3-[(3-methylisoxazol-5-yl)methyl]-4-oxo-phthalazine-1-carboxylate;

6-[(1-methylcyclopropyl)sulfamoyl]-3-[(3-methylisoxazol-5-yl)methyl]-4-oxo-phthalazine-1-carboxylic acid;

N-methyl-6-[(1-methylcyclopropyl)sulfamoyl]-3-[(3-methylisoxazol-5-yl)methyl]-4-oxo-phthalazine-1-carboxamide;

1-ethyl-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl) methyl]-1-(oxetan-3-ylmethyl)-2,4-dioxo-quinazoline-6-sulfonamide;

N-(1-methylcyclopropyl)-3-[(3-methylisoxazol-5-yl) methyl]-4-oxo-1-(tetrahydropyran-4-ylamino)phthalazine-6-sulfonamide;

4-bromo-N-(1-methylcyclopropyl)-2-[(3-methylisoxazol-5-yl)methyl]-1-oxo-isoquinoline-7-sulfonamide;

N-(1-methylcyclopropyl)-3-[(3-methylisoxazol-5-yl) methyl]-4-oxo-1-(tetrahydropyran-4-ylmethyl)phthalazine-6-sulfonamide;

1-cyclopentyl-N-(1-methylcyclopropyl)-3-[(3-methylisoxazol-5-yl)methyl]-4-oxo-phthalazine-6-sulfonamide;

1-isopropyl-N-(1-methylcyclopropyl)-3-[(3-methylisoxazol-5-yl)methyl]-4-oxo-phthalazine-6-sulfonamide;

4-(cyclopropanecarbonyl)-N-(1-methylcyclopropyl)-2-[(3-methylisoxazol-5-yl)methyl]-1-oxo-isoquinoline-7-sulfonamide;

1-methoxy-N-(1-methylcyclopropyl)-3-[(3-methylisoxazol-5-yl)methyl]-4-oxo-phthalazine-6-sulfonamide;

1-cyclopropyl-N-(1-methylcyclopropyl)-3-[(3-methylisoxazol-5-yl)methyl]-4-oxo-phthalazine-6-sulfonamide;

1-(cyclohexylmethyl)-N-(1-methylcyclopropyl)-3-[(3-methylisoxazol-5-yl)methyl]-4-oxo-phthalazine-6-sulfonamide;

1-[(3-methoxyphenyl)methyl]-N-(1-methylcyclopropyl)-3-[(3-methylisoxazol-5-yl)methyl]-4-oxo-phthalazine-6-sulfonamide;

1-ethoxy-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl) methyl]-1-(oxetan-3-yloxy)-4-oxo-phthalazine-6-sulfonamide;

1-(cyclopropylmethyl)-N-(1-methylcyclopropyl)-3-[(3-methylisoxazol-5-yl)methyl]-4-oxo-phthalazine-6-sulfonamide;

1-(cyclobutoxy)-N-(1-methylcyclopropyl)-3-[(3-methylisoxazol-5-yl)methyl]-4-oxo-phthalazine-6-sulfonamide;

1-(cyclobutylmethyl)-N-(1-methylcyclopropyl)-3-[(3-methylisoxazol-5-yl)methyl]-4-oxo-phthalazine-6-sulfonamide;

N-(1-methylcyclopropyl)-3-[(3-methylisoxazol-5-yl) methyl]-2,4-dioxo-1-(tetrahydropyran-4-ylmethyl)quinazoline-6-sulfonamide;

4-[(4-fluorophenyl)methyl]-N-(1-methylcyclopropyl)-2-[(3-methylisoxazol-5-yl)methyl]-1-oxo-isoquinoline-7-sulfonamide;

1-acetonyl-N-(1-methylcyclopropyl)-3-[(3-methylisoxazol-5-yl)methyl]-2,4-dioxo-quinazoline-6-sulfonamide;

1-(2,2-difluoroethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl) methyl]-2,4-dioxo-1-(2,2,2-trifluoroethyl)quinazoline-6-sulfonamide;

N,N-dimethyl-6-[(1-methylcyclopropyl)sulfamoyl]-3-[(3-methylisoxazol-5-yl)methyl]-4-oxo-phthalazine-1-carboxamide;

6-[(1-methylcyclopropyl)sulfamoyl]-3-[(3-methylisoxazol-5-yl)methyl]-N-(oxetan-3-yl)-4-oxo-phthalazine-1-carboxamide;

N-(1-methylcyclopropyl)-1,3-bis[(1-methylpyrazol-4-yl) methyl]-2,4-dioxo-quinazoline-6-sulfonamide;

1-[(2,2-difluoro-1-methyl-cyclopropyl)methyl]-N-(1-methylcyclopropyl)-3-[(1-methylpyrazol-4-yl) methyl]-2,4-dioxo-quinazoline-6-sulfonamide;

N-(1-methylcyclopropyl)-3-[(3-methylisoxazol-5-yl) methyl]-1-[(1-methylpyrazol-4-yl)methyl]-2,4-dioxo-quinazoline-6-sulfonamide;

6-[(1-methylcyclopropyl)sulfamoyl]-3-[(3-methylisoxazol-5-yl)methyl]-4-oxo-N-(tetrahydropyran-4-ylmethyl)phthalazine-1-carboxamide;

ethyl 2-[6-[(1-methylcyclopropyl)sulfamoyl]-3-[(3-methylisoxazol-5-yl)methyl]-2,4-dioxo-quinazolin-1-yl]acetate;

6-[(1-methylcyclopropyl)sulfamoyl]-3-[(3-methylisoxazol-5-yl)methyl]-N-[(1-methyl-4-piperidyl)methyl]-4-oxo-phthalazine-1-carboxamide;

N-(1-methylcyclopropyl)-3-[(1-methylpyrazol-4-yl) methyl]-2,4-dioxo-1-[2-(2-oxopyrrolidin-1-yl)ethyl] quinazoline-6-sulfonamide;

ethyl 2-fluoro-2-[6-[(1-methylcyclopropyl)sulfamoyl]-3-[(3-methylisoxazol-5-yl)methyl]-2,4-dioxo-quinazolin-1-yl]acetate;

N-(1-cyanocyclopropyl)-3-[(1-methylpyrazol-4-yl) methyl]-2,4-dioxo-1H-quinazoline-6-sulfonamide;

1-(2-hydroxyethyl)-N-(1-methylcyclopropyl)-3-[(3-methylisoxazol-5-yl)methyl]-2,4-dioxo-quinazoline-6-sulfonamide;

1-(2-hydroxypropyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl) methyl]-1-(oxetan-3-yl)-2,4-dioxo-quinazoline-6-sulfonamide;

1-[[3-(hydroxymethyl)oxetan-3-yl]methyl]-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl) methyl]-1-[2-(4-methylpiperazin-1-yl)ethyl]-2,4-dioxo-quinazoline-6-sulfonamide;

N-(1-methylcyclopropyl)-3-[(3-methylisoxazol-5-yl) methyl]-1-[3-(4-methylpiperazin-1-yl)propyl]-2,4-dioxo-quinazoline-6-sulfonamide;

N-(1-methylcyclopropyl)-3-[(1-methylpyrazol-4-yl) methyl]-1-(oxetan-2-ylmethyl)-2,4-dioxo-quinazoline-6-sulfonamide;

N-(1-cyanocyclopropyl)-1-methyl-3-[(1-methylpyrazol-4-yl)methyl]-2,4-dioxo-quinazoline-6-sulfonamide;

N-(1-cyanocyclopropyl)-1-[(2,5-dimethylpyrazol-3-yl) methyl]-3-[(1-methylpyrazol-4-yl)methyl]-2,4-dioxo-quinazoline-6-sulfonamide;

N-(1-cyanocyclopropyl)-1-(cyclopropylmethyl)-3-[(1-methylpyrazol-4-yl)methyl]-2,4-dioxo-quinazoline-6-sulfonamide;

N-(1-cyanocyclopropyl)-1-ethyl-3-[(1-methylpyrazol-4-yl)methyl]-2,4-dioxo-quinazoline-6-sulfonamide;
1-[(3-fluorooxetan-3-yl)methyl]-N-(1-methylcyclopropyl)-3-[(1-methylpyrazol-4-yl)methyl]-2,4-dioxo-quinazoline-6-sulfonamide;
N-(1-methylcyclopropyl)-3-[(3-methylisoxazol-5-yl)methyl]-1-(oxetan-2-ylmethyl)-2,4-dioxo-quinazoline-6-sulfonamide;
1-[(3-fluorooxetan-3-yl)methyl]-N-(1-methylcyclopropyl)-3-[(3-methylisoxazol-5-yl)methyl]-2,4-dioxo-quinazoline-6-sulfonamide;
1-[(4,4-dimethyl oxetan-2-yl)methyl]-N-(1-methylcyclopropyl)-3-[(1-methylpyrazol-4-yl)methyl]-2,4-dioxo-quinazoline-6-sulfonamide;
1-[(4,4-dimethyl oxetan-2-yl)methyl]-N-(1-methylcyclopropyl)-3-[(3-methylisoxazol-5-yl)methyl]-2,4-dioxo-quinazoline-6-sulfonamide;
1-ethyl-N-(1-methylcyclopropyl)-3-[(3-methylisoxazol-5-yl)methyl]-4-oxo-phthalazine-6-sulfonamide;
N-(1-cyanocyclopropyl)-3-[(1-methylpyrazol-4-yl)methyl]-1-(oxetan-3-ylmethyl)-2,4-dioxo-quinazoline-6-sulfonamide;
N-(1-cyanocyclopropyl)-3-[(1-methylpyrazol-4-yl)methyl]-2,4-dioxo-1-prop-2-ynyl-quinazoline-6-sulfonamide;
N-(1-cyanocyclopropyl)-1-(cyanomethyl)-3-[(1-methylpyrazol-4-yl)methyl]-2,4-dioxo-quinazoline-6-sulfonamide;
N-(1-cyanocyclopropyl)-1-(2-methoxyethyl)-3-[(1-methylpyrazol-4-yl)methyl]-2,4-dioxo-quinazoline-6-sulfonamide;
N-(1-cyanocyclopropyl)-1-[(4-fluorophenyl)methyl]-3-[(1-methylpyrazol-4-yl)methyl]-2,4-dioxo-quinazoline-6-sulfonamide;
N-(1-cyanocyclopropyl)-1-[(3-methylisoxazol-5-yl)methyl]-3-[(1-methylpyrazol-4-yl)methyl]-2,4-dioxo-quinazoline-6-sulfonamide;
1-(3-hydroxy-3-methyl-butyl)-N-(1-methylcyclopropyl)-3-[(3-methylisoxazol-5-yl)methyl]-2,4-dioxo-quinazoline-6-sulfonamide;
N-(1-methylcyclopropyl)-3-[(3-methylisoxazol-5-yl)methyl]-1-[(1-methylpyrrolidin-3-yl)methyl]-2,4-dioxo-quinazoline-6-sulfonamide;
N-(1-methylcyclopropyl)-3-[(3-methylisoxazol-5-yl)methyl]-1-(2-methylsulfanylethyl)-2,4-dioxo-quinazoline-6-sulfonamide;
1-[(3,3-difluorocyclobutyl)methyl]-N-(1-methylcyclopropyl)-3-[(3-methylisoxazol-5-yl)methyl]-2,4-dioxo-quinazoline-6-sulfonamide;
1-[(2,2-difluorocyclopropyl)methyl]-N-(1-methylcyclopropyl)-3-[(3-methylisoxazol-5-yl)methyl]-2,4-dioxo-quinazoline-6-sulfonamide;
tert-butyl 3-[[6-[(1-methylcyclopropyl)sulfamoyl]-3-[(1-methylpyrazol-4-yl)methyl]-2,4-dioxo-quinazolin-1-yl]methyl]azetidine-1-carboxylate;
N-(1-methylcyclopropyl)-3-[(1-methylpyrazol-4-yl)methyl]-1-(2-methylsulfanylethyl)-2,4-dioxo-quinazoline-6-sulfonamide;
1-acetonyl-N-(1-methylcyclopropyl)-3-[(1-methylpyrazol-4-yl)methyl]-2,4-dioxo-quinazoline-6-sulfonamide;
1-(3-hydroxy-3-methyl-butyl)-N-(1-methylcyclopropyl)-3-[(1-methylpyrazol-4-yl)methyl]-2,4-dioxo-quinazoline-6-sulfonamide;
N-(1-methylcyclopropyl)-3-[(1-methylpyrazol-4-yl)methyl]-1-(2-methylsulfinylethyl)-2,4-dioxo-quinazoline-6-sulfonamide;
N-(1-methylcyclopropyl)-3-[(1-methylpyrazol-4-yl)methyl]-1-(2-methylsulfonylethyl)-2,4-dioxo-quinazoline-6-sulfonamide;
N-(1-methylcyclopropyl)-3-[(3-methylisoxazol-5-yl)methyl]-1-[(1-methyl-4-piperidyl)methyl]-2,4-dioxo-quinazoline-6-sulfonamide;
N-(1-methylcyclopropyl)-1-[(1-methyl-4-piperidyl)methyl]-3-[(1-methylpyrazol-4-yl)methyl]-2,4-dioxo-quinazoline-6-sulfonamide;
N-(1-methylcyclopropyl)-3-[(3-methylisoxazol-5-yl)methyl]-2,4-dioxo-1-(2-oxo-2-pyrrolidin-1-yl-ethyl)quinazoline-6-sulfonamide;
N-(1-cyanocyclopropyl)-1-[(2,4-dimethylthiazol-5-yl)methyl]-3-[(1-methylpyrazol-4-yl)methyl]-2,4-dioxo-quinazoline-6-sulfonamide;
N-(1-cyanocyclopropyl)-3-[(1-methylpyrazol-4-yl)methyl]-1-[(2-methylthiazol-5-yl)methyl]-2,4-dioxo-quinazoline-6-sulfonamide;
N-(1-cyanocyclopropyl)-1-[(3-methyl oxetan-3-yl)methyl]-3-[(1-methylpyrazol-4-yl)methyl]-2,4-dioxo-quinazoline-6-sulfonamide;
N-(1-cyanocyclopropyl)-3-[(1-methylpyrazol-4-yl)methyl]-2,4-dioxo-1-(tetrahydrofuran-3-ylmethyl)quinazoline-6-sulfonamide;
N-(1-cyanocyclopropyl)-1,3-bis[(1-methylpyrazol-4-yl)methyl]-2,4-dioxo-quinazoline-6-sulfonamide;
N-(1-methylcyclopropyl)-1-[(3-methylisoxazol-5-yl)methyl]-3-[(1-methylpyrazol-4-yl)methyl]-2,4-dioxo-quinazoline-6-sulfonamide;
N-(1-methylcyclopropyl)-3-[(1-methylpyrazol-4-yl)methyl]-2,4-dioxo-1-(tetrahydrothiopyran-4-ylmethyl)quinazoline-6-sulfonamide;
N-(1-methylcyclopropyl)-3-[(3-methylisoxazol-5-yl)methyl]-2,4-dioxo-1-(tetrahydrothiopyran-4-ylmethyl)quinazoline-6-sulfonamide;
1-[(1,1-dioxothian-4-yl)methyl]-N-(1-methylcyclopropyl)-3-[(3-methylisoxazol-5-yl)methyl]-2,4-dioxo-quinazoline-6-sulfonamide;
1-[(1,1-dioxothian-4-yl)methyl]-N-(1-methylcyclopropyl)-3-[(1-methylpyrazol-4-yl)methyl]-2,4-dioxo-quinazoline-6-sulfonamide;
7-fluoro-N-(1-methylcyclopropyl)-3-[(1-methylpyrazol-4-yl)methyl]-2,4-dioxo-1H-quinazoline-6-sulfonamide;
7-fluoro-1-methyl-N-(1-methylcyclopropyl)-3-[(1-methylpyrazol-4-yl)methyl]-2,4-dioxo-quinazoline-6-sulfonamide;
N-(1-cyanocyclopropyl)-3-[(2-methylthiazol-5-yl)methyl]-2,4-dioxo-1H-quinazoline-6-sulfonamide;
N-(1-cyanocyclopropyl)-7-fluoro-3-[(1-methylpyrazol-4-yl)methyl]-2,4-dioxo-1H-quinazoline-6-sulfonamide;
1-(cyclopropylmethyl)-7-fluoro-N-(1-methylcyclopropyl)-3-[(1-methylpyrazol-4-yl)methyl]-2,4-dioxo-quinazoline-6-sulfonamide;
1-ethyl-7-fluoro-N-(1-methylcyclopropyl)-3-[(1-methylpyrazol-4-yl)methyl]-2,4-dioxo-quinazoline-6-sulfonamide;
7-fluoro-1-[(4-fluorophenyl)methyl]-N-(1-methylcyclopropyl)-3-[(1-methylpyrazol-4-yl)methyl]-2,4-dioxo-quinazoline-6-sulfonamide;
7-fluoro-N-(1-methylcyclopropyl)-1-[(3-methylisoxazol-5-yl)methyl]-3-[(1-methylpyrazol-4-yl)methyl]-2,4-dioxo-quinazoline-6-sulfonamide;
1-[(2,5-dimethylpyrazol-3-yl)methyl]-7-fluoro-N-(1-methylcyclopropyl)-3-[(1-methylpyrazol-4-yl)methyl]-2,4-dioxo-quinazoline-6-sulfonamide;

7-fluoro-N-(1-methylcyclopropyl)-1,3-bis[(1-methyl-pyrazol-4-yl)methyl]-2,4-dioxo-quinazoline-6-sulfonamide;

7-fluoro-N-(1-methylcyclopropyl)-3-[(1-methylpyrazol-4-yl)methyl]-1-(oxetan-3-ylmethyl)-2,4-dioxo-quinazoline-6-sulfonamide;

7-fluoro-N-(1-methylcyclopropyl)-3-[(1-methylpyrazol-4-yl)methyl]-2,4-dioxo-1-(tetrahydrofuran-3-ylmethyl)quinazoline-6-sulfonamide;

1-[(2,4-dimethylthiazol-5-yl)methyl]-7-fluoro-N-(1-methylcyclopropyl)-3-[(1-methylpyrazol-4-yl)methyl]-2,4-dioxo-quinazoline-6-sulfonamide;

7-fluoro-N-(1-methylcyclopropyl)-2-[(3-methyloxetan-3-yl)methoxy]-3-[(1-methylpyrazol-4-yl)methyl]-4-oxo-quinazoline-6-sulfonamide;

7-fluoro-N-(1-methylcyclopropyl)-1-[(3-methyloxetan-3-yl)methyl]-3-[(1-methylpyrazol-4-yl)methyl]-2,4-dioxo-quinazoline-6-sulfonamide;

N-(1-cyanocyclopropyl)-1-(cyclopropylmethyl)-3-[(2-methylthiazol-5-yl)methyl]-2,4-dioxo-quinazoline-6-sulfonamide;

N-(1-cyanocyclopropyl)-1-[(3-methylisoxazol-5-yl)methyl]-3-[(2-methylthiazol-5-yl)methyl]-2,4-dioxo-quinazoline-6-sulfonamide;

N-(1-cyanocyclopropyl)-1-[(2,4-dimethylthiazol-5-yl)methyl]-3-[(2-methylthiazol-5-yl)methyl]-2,4-dioxo-quinazoline-6-sulfonamide;

N-(1-cyanocyclopropyl)-1-[(4-fluorophenyl)methyl]-3-[(2-methylthiazol-5-yl)methyl]-2,4-dioxo-quinazoline-6-sulfonamide;

N-(1-cyanocyclopropyl)-3-[(2-methylthiazol-5-yl)methyl]-2,4-dioxo-1-prop-2-ynyl-quinazoline-6-sulfonamide;

N-(1-cyanocyclopropyl)-7-fluoro-1-[(3-methylisoxazol-5-yl)methyl]-3-[(1-methylpyrazol-4-yl)methyl]-2,4-dioxo-quinazoline-6-sulfonamide;

1-[(4,4-difluorocyclohexyl)methyl]-N-(1-methylcyclopropyl)-3-[(3-methylisoxazol-5-yl)methyl]-2,4-dioxo-quinazoline-6-sulfonamide;

N,N-dimethyl-3-[6-[(1-methylcyclopropyl)sulfamoyl]-3-[(3-methylisoxazol-5-yl)methyl]-2,4-dioxo-quinazolin-1-yl]propanamide;

1-(3-hydroxypropyl)-N-(1-methylcyclopropyl)-3-[(3-methylisoxazol-5-yl)methyl]-2,4-dioxo-quinazoline-6-sulfonamide;

N-[1-(fluoromethyl)cyclopropyl]-1-methyl-3-[(1-methylpyrazol-4-yl)methyl]-2,4-dioxo-quinazoline-6-sulfonamide;

tert-butyl 3-[[6-[(1-methylcyclopropyl)sulfamoyl]-3-[(3-methylisoxazol-5-yl)methyl]-2,4-dioxo-quinazolin-1-yl]methyl]azetidine-1-carboxylate;

1-(2-fluoroethyl)-N-(1-methylcyclopropyl)-3-[(1-methylpyrazol-4-yl)methyl]-2,4-dioxo-quinazoline-6-sulfonamide;

1-(2-fluoroethyl)-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-[(3-oxocyclobutyl)methyl]quinazoline-6-sulfonamide;

1-(2-methoxy-2-methyl-propyl)-N-(1-methylcyclopropyl)-3-[(3-methylisoxazol-5-yl)methyl]-2,4-dioxo-quinazoline-6-sulfonamide;

1-[2-(azetidin-1-yl)-2-oxo-ethyl]-N-(1-methylcyclopropyl)-3-[(3-methylisoxazol-5-yl)methyl]-2,4-dioxo-quinazoline-6-sulfonamide;

1-(azetidin-3-ylmethyl)-N-(1-methylcyclopropyl)-3-[(3-methylisoxazol-5-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1H-quinazoline-6-sulfonamide;

1-(cyclopropylmethyl)-N-[1-(fluoromethyl)cyclopropyl]-3-[(1-methylpyrazol-4-yl)methyl]-2,4-dioxo-quinazoline-6-sulfonamide;

1-methyl-N-(1-methylcyclopropyl)-3-[(5-methyl-3-pyridyl)methyl]-2,4-dioxo-quinazoline-6-sulfonamide;

N-[1-(fluoromethyl)cyclopropyl]-1-[(4-fluorophenyl)methyl]-3-[(1-methylpyrazol-4-yl)methyl]-2,4-dioxo-quinazoline-6-sulfonamide;

1-[(1-cyanocyclopropyl)methyl]-N-(1-methylcyclopropyl)-3-[(3-methylisoxazol-5-yl)methyl]-2,4-dioxo-quinazoline-6-sulfonamide;

N-(1-methylcyclopropyl)-3-[(3-methylisoxazol-5-yl)methyl]-2,4-dioxo-1-[(4-oxocyclohexyl)methyl]quinazoline-6-sulfonamide;

8-bromo-N-(1-methylcyclopropyl)-3-[(1-methylpyrazol-4-yl)methyl]-2,4-dioxo-1H-quinazoline-6-sulfonamide;

1-methyl-N-(1-methylcyclopropyl)-3-[(6-methyl-3-pyridyl)methyl]-2,4-dioxo-quinazoline-6-sulfonamide;

6-[(1-methylcyclopropyl)sulfamoyl]-3-[(1-methylpyrazol-4-yl)methyl]-2,4-dioxo-1H-quinazoline-8-carboxamide;

1-[(1-formylazetidin-3-yl)methyl]-N-(1-methylcyclopropyl)-3-[(3-methylisoxazol-5-yl)methyl]-2,4-dioxo-quinazoline-6-sulfonamide;

1-(cyclopropylmethyl)-3-methyl-N-(1-methylcyclopropyl)-2-oxo-quinoline-6-sulfonamide;

N-(1-ethynylcyclopropyl)-1-methyl-3-[(1-methylpyrazol-4-yl)methyl]-2,4-dioxo-quinazoline-6-sulfonamide;

N-[[6-[(1-methylcyclopropyl)sulfamoyl]-3-[(1-methylpyrazol-4-yl)methyl]-2,4-dioxo-1H-quinazolin-8-yl]methyl]acetamide;

8-[3-(dimethylamino)prop-1-ynyl]-N-(1-methylcyclopropyl)-3-[(1-methylpyrazol-4-yl)methyl]-2,4-dioxo-1H-quinazoline-6-sulfonamide;

N-(1-methylcyclopropyl)-3-[(1-methylpyrazol-4-yl)methyl]-2,4-dioxo-1H-quinazoline-6-sulfonamide;

N-(1-ethynylcyclopropyl)-3-[(1-methylpyrazol-4-yl)methyl]-2,4-dioxo-1H-quinazoline-6-sulfonamide;

1-(cyclopropylmethyl)-N-(1-ethynylcyclopropyl)-3-[(1-methylpyrazol-4-yl)methyl]-2,4-dioxo-quinazoline-6-sulfonamide;

1-methyl-N-(1-methylcyclopropyl)-3-[(2-methylpyrimidin-5-yl)methyl]-2,4-dioxo-quinazoline-6-sulfonamide;

1-methyl-N-(1-methylcyclopropyl)-2,4-dioxo-3-(pyrazolo[1,5-a]pyridin-3-ylmethyl)quinazoline-6-sulfonamide;

1-[(2,2-difluorocyclopropyl)methyl]-N-(1-methylcyclopropyl)-3-[(1-methylpyrazol-4-yl)methyl]-2,4-dioxo-quinazoline-6-sulfonamide;

1-[(3,3-difluorocyclobutyl)methyl]-N-(1-methylcyclopropyl)-3-[(1-methylpyrazol-4-yl)methyl]-2,4-dioxo-quinazoline-6-sulfonamide;

1-[(2,5-dimethylpyrazol-3-yl)methyl]-N-[1-(fluoromethyl)cyclopropyl]-3-[(1-methylpyrazol-4-yl)methyl]-2,4-dioxo-quinazoline-6-sulfonamide;

1-ethyl-N-[1-(fluoromethyl)cyclopropyl]-3-[(1-methylpyrazol-4-yl)methyl]-2,4-dioxo-quinazoline-6-sulfonamide;

1-(cyanomethyl)-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-prop-2-ynyl-quinazoline-6-sulfonamide;
N-[1-(fluoromethyl)cyclopropyl]-1-[(3-methylisoxazol-5-yl)methyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-2,4-dioxo-1-(tetrahydropyran-4-ylmethyl)quinazoline-6-sulfonamide;
1-[(2,2-difluorocyclopropyl)methyl]-N-[1-(fluoromethyl)cyclopropyl]-3-[(1-methylpyrazol-4-yl)methyl]-2,4-dioxo-quinazoline-6-sulfonamide;
1-[(3,3-difluorocyclobutyl)methyl]-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-3-[(1-methylpyrazol-4-yl)methyl]-1-(oxetan-3-ylmethyl)-2,4-dioxo-quinazoline-6-sulfonamide;
1-methyl-N-(1-methylcyclopropyl)-2,4-dioxo-3-(pyridazin-4-ylmethyl)quinazoline-6-sulfonamide;
N-(1-methylcyclopropyl)-1,3-dioxo-benzo[de]isoquinoline-5-sulfonamide;
methyl 6-[(1-methylcyclopropyl)sulfamoyl]-3-[(1-methylpyrazol-4-yl)methyl]-2,4-dioxo-1H-quinazoline-8-carboxylate;
N,N-dimethyl-6-[(1-methylcyclopropyl)sulfamoyl]-3-[(1-methylpyrazol-4-yl)methyl]-2,4-dioxo-1H-quinazoline-8-carboxamide;
N-methyl-6-[(1-methylcyclopropyl)sulfamoyl]-3-[(1-methylpyrazol-4-yl)methyl]-2,4-dioxo-1H-quinazoline-8-carboxamide;
N-methoxy-N-methyl-6-[(1-methylcyclopropyl)sulfamoyl]-3-[(1-methylpyrazol-4-yl)methyl]-2,4-dioxo-1H-quinazoline-8-carboxamide;
1-(2-cyano-2-methyl-propyl)-N-(1-methylcyclopropyl)-3-[(3-methylisoxazol-5-yl)methyl]-2,4-dioxo-quinazoline-6-sulfonamide;
1-(2-fluoro-2-methyl-propyl)-N-(1-methylcyclopropyl)-3-[(3-methylisoxazol-5-yl)methyl]-2,4-dioxo-quinazoline-6-sulfonamide;
N-(1-methylcyclopropyl)-2-[(1-methylpyrazol-4-yl)methyl]-1,3-dioxo-benzo[de]isoquinoline-5-sulfonamide;
N-(1-cyanocyclopropyl)-1-ethyl-3-[(2-methylthiazol-5-yl)methyl]-2,4-dioxo-quinazoline-6-sulfonamide;
N-[1-(difluoromethyl)cyclopropyl]-3-[(1-methylpyrazol-4-yl)methyl]-2,4-dioxo-1H-quinazoline-6-sulfonamide;
N-(1-cyanocyclopropyl)-1-[(1-methylpyrazol-4-yl)methyl]-3-[(2-methylthiazol-5-yl)methyl]-2,4-dioxo-quinazoline-6-sulfonamide;
1-(cyclopropylmethyl)-N-[1-(difluoromethyl)cyclopropyl]-3-[(1-methylpyrazol-4-yl)methyl]-2,4-dioxo-quinazoline-6-sulfonamide;
N-[1-(difluoromethyl)cyclopropyl]-1-[(2,5-dimethylpyrazol-3-yl)methyl]-3-[(1-methylpyrazol-4-yl)methyl]-2,4-dioxo-quinazoline-6-sulfonamide;
N-[1-(difluoromethyl)cyclopropyl]-1-[(4-fluorophenyl)methyl]-3-[(1-methylpyrazol-4-yl)methyl]-2,4-dioxo-quinazoline-6-sulfonamide;
1-(cyclobutylmethyl)-N-[1-(fluoromethyl)cyclopropyl]-3-[(1-methylpyrazol-4-yl)methyl]-2,4-dioxo-quinazoline-6-sulfonamide;
N-[1-(fluoromethyl)cyclopropyl]-1-(2-methoxyethyl)-3-[(1-methylpyrazol-4-yl)methyl]-2,4-dioxo-quinazoline-6-sulfonamide;
1-[(2,4-dimethylthiazol-5-yl)methyl]-N-[1-(fluoromethyl)cyclopropyl]-3-[(1-methylpyrazol-4-yl)methyl]-2,4-dioxo-quinazoline-6-sulfonamide;
N-(1-methylcyclopropyl)-2-[(3-methylisoxazol-5-yl)methyl]-1,3-dioxo-benzo[de]isoquinoline-5-sulfonamide;
1-(2,2-dimethylpropyl)-N-(1-methylcyclopropyl)-3-[(3-methylisoxazol-5-yl)methyl]-2,4-dioxo-quinazoline-6-sulfonamide;
1-[(2S)-2-methylbutyl]-N-(1-methylcyclopropyl)-3-[(3-methylisoxazol-5-yl)methyl]-2,4-dioxo-quinazoline-6-sulfonamide;
1-[(1-methylcyclobutyl)methyl]-N-(1-methylcyclopropyl)-3-[(3-methylisoxazol-5-yl)methyl]-2,4-dioxo-quinazoline-6-sulfonamide;
ethyl 2-[1-methyl-6-[(1-methylcyclopropyl)sulfamoyl]-2,4-dioxo-quinazolin-3-yl]acetate;
1-methyl-N-(1-methylcyclopropyl)-2,4-dioxo-3-(2-oxobutyl)quinazoline-6-sulfonamide;
1-(2-ethylbutyl)-N-(1-methylcyclopropyl)-3-[(3-methylisoxazol-5-yl)methyl]-2,4-dioxo-quinazoline-6-sulfonamide;
1-[(1-methoxycyclopentyl)methyl]-N-(1-methylcyclopropyl)-3-[(3-methylisoxazol-5-yl)methyl]-2,4-dioxo-quinazoline-6-sulfonamide;
1-isopentyl-N-(1-methylcyclopropyl)-3-[(3-methylisoxazol-5-yl)methyl]-2,4-dioxo-quinazoline-6-sulfonamide;
1-[(1-isopropylpyrazol-4-yl)methyl]-N-(1-methylcyclopropyl)-3-[(3-methylisoxazol-5-yl)methyl]-2,4-dioxo-quinazoline-6-sulfonamide;
1-isohexyl-N-(1-methylcyclopropyl)-3-[(3-methylisoxazol-5-yl)methyl]-2,4-dioxo-quinazoline-6-sulfonamide;
1-methyl-N-(1-methylcyclopropyl)-2,4-dioxo-3-(2-oxo-2-pyrrolidin-1-yl-ethyl)quinazoline-6-sulfonamide;
N,N-dimethyl-2-[1-methyl-6-[(1-methylcyclopropyl)sulfamoyl]-2,4-dioxo-quinazolin-3-yl]acetamide;
1-[(3,3-dimethylcyclobutyl)methyl]-N-(1-methylcyclopropyl)-3-[(3-methylisoxazol-5-yl)methyl]-2,4-dioxo-quinazoline-6-sulfonamide;
1-[(3,3-dimethylcyclobutyl)methyl]-N-(1-methylcyclopropyl)-3-[(2-methylthiazol-5-yl)methyl]-2,4-dioxo-quinazoline-6-sulfonamide;
N-(1-formylcyclopropyl)-3-[(1-methylpyrazol-4-yl)methyl]-2,4-dioxo-1H-quinazoline-6-sulfonamide;
1-methyl-N-(1-methylcyclopropyl)-3-(oxetan-3-ylmethyl)-2,4-dioxo-quinazoline-6-sulfonamide;
8-bromo-1-methyl-N-(1-methylcyclopropyl)-3-[(3-methylisoxazol-5-yl)methyl]-2,4-dioxo-quinazoline-6-sulfonamide;
1-methyl-N-(1-methylcyclopropyl)-3-[(3-methylisoxazol-5-yl)methyl]-8-(1-methylpyrazol-4-yl)-2,4-dioxo-quinazoline-6-sulfonamide;
1-chloro-N-(1-methylcyclopropyl)isoquinoline-7-sulfonamide;
1-[(2,5-dimethylpyrazol-3-yl)methyl]-3-[(1-methylpyrazol-4-yl)methyl]-2,4-dioxo-N-[1-(trifluoromethyl)cyclopropyl] quinazoline-6-sulfonamide;
N-(1-methylcyclopropyl)-3-[(1-methylpyrazol-4-yl)methyl]-2-oxo-1H-quinoline-6-sulfonamide;
3-bromo-N-(1-methylcyclopropyl)-2-oxo-1H-quinoline-6-sulfonamide;

3-[(1-methylpyrazol-4-yl)methyl]-2,4-dioxo-N-[1-(trideuteriomethyl)cyclopropyl]-1H-quinazoline-6-sulfonamide;

1-methyl-3-[(1-methylpyrazol-4-yl)methyl]-2,4-dioxo-N-[1-(trideuteriomethyl)cyclopropyl]quinazoline-6-sulfonamide;

1-[(2,5-dimethylpyrazol-3-yl)methyl]-3-[(1-methylpyrazol-4-yl)methyl]-2,4-dioxo-N-[1-(trideuteriomethyl)cyclopropyl]quinazoline-6-sulfonamide;

1-methyl-N-(1-methylcyclopropyl)-3-[(1-methylpyrazol-4-yl)methyl]-2-oxo-quinoline-6-sulfonamide;

1-[(2,5-dimethylpyrazol-3-yl)methyl]-N-(1-methylcyclopropyl)-3-[(1-methylpyrazol-4-yl)methyl]-2-oxo-quinoline-6-sulfonamide;

1-methyl-N-(1-methylcyclopropyl)-3-[(3-methylisoxazol-5-yl)methyl]-8-(5-methyl-2-thienyl)-2,4-dioxo-quinazoline-6-sulfonamide;

N-[1-(fluoromethyl)cyclopropyl]-3-(isothiazol-4-ylmethyl)-1-methyl-2,4-dioxo-quinazoline-6-sulfonamide;

N-(1-methylcyclopropyl)-2,4-dioxo-3-[2-(2-pyridyl)ethyl]-1H-quinazoline-6-sulfonamide;

3-(2-cyanoethyl)-N-(1-methylcyclopropyl)-2,4-dioxo-1H-quinazoline-6-sulfonamide;

3-(2-cyanoethyl)-1-methyl-N-(1-methylcyclopropyl)-2,4-dioxo-quinazoline-6-sulfonamide;

1-methyl-N-(1-methylcyclopropyl)-2,4-dioxo-3-[2-(2-pyridyl)ethyl]quinazoline-6-sulfonamide;

1-methyl-N-(1-methylcyclopropyl)-3-[(4-methyl-1,2,4-triazol-3-yl)methyl]-2,4-dioxo-quinazoline-6-sulfonamide;

1-methyl-N-(1-methylcyclopropyl)-3-[(5-methyl-1,3,4-thiadiazol-2-yl)methyl]-2,4-dioxo-quinazoline-6-sulfonamide;

1-methyl-N-(1-methylcyclopropyl)-2,4-dioxo-3-[[5-(trifluoromethyl)-1,3,4-oxadiazol-2-yl]methyl]quinazoline-6-sulfonamide;

1-(cyanomethyl)-N-(1-methylcyclopropyl)-3-[(2-methylthiazol-5-yl)methyl]-2,4-dioxo-quinazoline-6-sulfonamide;

1-(cyanomethyl)-N-(1-methylcyclopropyl)-3-[(3-methylisoxazol-5-yl)methyl]-2,4-dioxo-quinazoline-6-sulfonamide;

3-(3-furylmethyl)-1-methyl-N-(1-methylcyclopropyl)-2,4-dioxo-quinazoline-6-sulfonamide;

3-(1H-imidazol-4-ylmethyl)-1-methyl-N-(1-methylcyclopropyl)-2,4-dioxo-quinazoline-6-sulfonamide;

1-methyl-N-(1-methylcyclopropyl)-3-[(5-methylisoxazol-4-yl)methyl]-2,4-dioxo-quinazoline-6-sulfonamide;

3-[(1-isopropylpyrazol-4-yl)methyl]-1-methyl-N-(1-methylcyclopropyl)-2,4-dioxo-quinazoline-6-sulfonamide;

1-methyl-N-(1-methylcyclopropyl)-3-[(1-methyltetrazol-5-yl)methyl]-2,4-dioxo-quinazoline-6-sulfonamide;

3-[(4-isopropylthiadiazol-5-yl)methyl]-1-methyl-N-(1-methylcyclopropyl)-2,4-dioxo-quinazoline-6-sulfonamide;

3-(isothiazol-5-ylmethyl)-1-methyl-N-(1-methylcyclopropyl)-2,4-dioxo-quinazoline-6-sulfonamide;

1-methyl-N-(1-methylcyclopropyl)-3-[(4-methyl-1,2,5-oxadiazol-3-yl)methyl]-2,4-dioxo-quinazoline-6-sulfonamide;

N-[1-(fluoromethyl)cyclopropyl]-1-methyl-2,4-dioxo-quinazoline-6-sulfonamide;

N-[1-(fluoromethyl)cyclopropyl]-3-(isoxazol-5-ylmethyl)-1-methyl-2,4-dioxo-quinazoline-6-sulfonamide;

N-[1-(fluoromethyl)cyclopropyl]-1-methyl-3-[(3-methylisoxazol-5-yl)methyl]-2,4-dioxo-quinazoline-6-sulfonamide;

N-[1-(fluoromethyl)cyclopropyl]-1-methyl-3-[(5-methyl-1,3,4-thiadiazol-2-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1H-quinazoline-6-sulfonamide;

1-(cyclopropylmethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1-[(4-fluorophenyl)methyl]-3-[(3-methylisoxazol-5-yl)methyl]-2,4-dioxo-quinazoline-6-sulfonamide;

1-[(2,5-dimethylpyrazol-3-yl)methyl]-N-[1-(fluoromethyl)cyclopropyl]-3-[(3-methylisoxazol-5-yl)methyl]-2,4-dioxo-quinazoline-6-sulfonamide;

1-ethyl-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1,3-bis[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-1-(oxetan-3-ylmethyl)-2,4-dioxo-quinazoline-6-sulfonamide;

1-(cyanomethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1-(tetrahydrofuran-3-ylmethyl)quinazoline-6-sulfonamide;

N-[1-(fluoromethyl)cyclopropyl]-1-(3-methoxypropyl)-3-[(3-methylisoxazol-5-yl)methyl]-2,4-dioxo-quinazoline-6-sulfonamide;

1-(2-fluoroethyl)-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-1-(2-methoxyethyl)-3-[(3-methylisoxazol-5-yl)methyl]-2,4-dioxo-quinazoline-6-sulfonamide;

1-methyl-N-(1-methylcyclopropyl)-2,4-dioxo-3-[2-oxo-2-(4-pyridyl)ethyl] quinazoline-6-sulfonamide;

1-methyl-N-(1-methylcyclopropyl)-2,4-dioxo-3-[2-oxo-2-(2-thienyl)ethyl] quinazoline-6-sulfonamide;

1-methyl-N-(1-methylcyclopropyl)-2,4-dioxo-3-phenacyl-quinazoline-6-sulfonamide;

3-[2-(4-cyanophenyl)-2-oxo-ethyl]-1-methyl-N-(1-methylcyclopropyl)-2,4-dioxo-quinazoline-6-sulfonamide;

N-[1-(fluoromethyl)cyclopropyl]-3-[(3-methylisoxazol-5-yl)methyl]-2,4-dioxo-1-prop-2-ynyl-quinazoline-6-sulfonamide;

N-[1-(fluoromethyl)cyclopropyl]-1-methyl-3-[(2-methylthiazol-5-yl)methyl]-2,4-dioxo-quinazoline-6-sulfonamide;

N-[1-(fluoromethyl)cyclopropyl]-1-methyl-2,4-dioxo-3-(thiazol-5-ylmethyl)quinazoline-6-sulfonamide;

N-[1-(fluoromethyl)cyclopropyl]-3-[(3-methylisoxazol-5-yl)methyl]-2,4-dioxo-1-propyl-quinazoline-6-sulfonamide;

1-butyl-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(1-methylpyrazol-4-yl)methyl]-1-[(5-methyl-2-pyridyl)methyl]-2,4-dioxo-quinazoline-6-sulfonamide;

[(6-cyano-2-pyridyl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(5-methyl-3-pyridyl)methyl]-2,4-dioxo-quinazoline-6-sulfonamide;

N-[1-(fluoromethyl)cyclopropyl]-1-[(6-fluoro-2-pyridyl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(2-methyl-4-pyridyl)methyl]-2,4-dioxo-quinazoline-6-sulfonamide;

N-[1-(fluoromethyl)cyclopropyl]-1-[(3-fluoro-2-pyridyl)methyl]-3-[(1-methylpyrazol-4-yl)methyl]-2,4-dioxo-quinazoline-6-sulfonamide;

1-[(4-cyanophenyl)methyl]-N-[1-(fluoromethyl)cyclopropyl]-3-[(1-methylpyrazol-4-yl)methyl]-2,4-dioxo-quinazoline-6-sulfonamide;

1-(2-fluoroethyl)-N-[1-(fluoromethyl)cyclopropyl]-3-[(1-methylpyrazol-4-yl)methyl]-2,4-dioxo-quinazoline-6-sulfonamide;

1-[(3,5-dimethylisoxazol-4-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-[(5-methyl-1,2,4-oxadiazol-3-yl)methyl]-3-[(1-methylpyrazol-4-yl)methyl]-2,4-dioxo-quinazoline-6-sulfonamide;

1-[(2,5-dimethyl-1,2,4-triazol-3-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-[(2-methyl oxazol-5-yl)methyl]-3-[(1-methylpyrazol-4-yl)methyl]-2,4-dioxo-quinazoline-6-sulfonamide;

N-[1-(fluoromethyl)cyclopropyl]-1-isobutyl-3-[(1-methylpyrazol-4-yl)methyl]-2,4-dioxo-quinazoline-6-sulfonamide;

N-[1-(fluoromethyl)cyclopropyl]-3-[(3-methylisoxazol-5-yl)methyl]-1-[(2-methylthiazol-4-yl)methyl]-2,4-dioxo-quinazoline-6-sulfonamide;

N-[1-(fluoromethyl)cyclopropyl]-3-[(3-methylisoxazol-5-yl)methyl]-1-[(4-methyl-1,2,4-triazol-3-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,3,4-thiadiazol-2-yl)methyl]-2,4-dioxo-quinazoline-6-sulfonamide;

N-[1-(fluoromethyl)cyclopropyl]-3-[(3-methylisoxazol-5-yl)methyl]-1-[(1-methyl-1,2,4-triazol-3-yl)methyl]-2,4-dioxo-quinazoline-6-sulfonamide;

1-[(2,5-dimethyl-1,2,4-triazol-3-yl)methyl]-N-[1-(fluoromethyl)cyclopropyl]-3-[(3-methylisoxazol-5-yl)methyl]-2,4-dioxo-quinazoline-6-sulfonamide;

N-[1-(fluoromethyl)cyclopropyl]-3-[(3-methylisoxazol-5-yl)methyl]-1-[(1-methylpyrazol-4-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,3,4-oxadiazol-2-yl)methyl]-2,4-dioxo-quinazoline-6-sulfonamide;

N-[1-(fluoromethyl)cyclopropyl]-3-[(3-methylisoxazol-5-yl)methyl]-1-[(2-methyl-1,2,4-triazol-3-yl)methyl]-2,4-dioxo-quinazoline-6-sulfonamide;

N-[1-(fluoromethyl)cyclopropyl]-3-[(3-methylisoxazol-5-yl)methyl]-1-[(5-methyl-1,2,4-oxadiazol-3-yl)methyl]-2,4-dioxo-quinazoline-6-sulfonamide;

N-[1-(fluoromethyl)cyclopropyl]-3-[(3-methylisoxazol-5-yl)methyl]-1-(oxazol-4-ylmethyl)-2,4-dioxo-quinazoline-6-sulfonamide;

N-[1-(fluoromethyl)cyclopropyl]-3-[(1-methylpyrazol-4-yl)methyl]-2,4-dioxo-1-(2-pyrazol-1-yl ethyl)quinazoline-6-sulfonamide;

N-[1-(fluoromethyl)cyclopropyl]-3-[(1-methylpyrazol-4-yl)methyl]-1-[(3-methyl-1H-pyrazol-5-yl)methyl]-2,4-dioxo-quinazoline-6-sulfonamide;

N-[1-(fluoromethyl)cyclopropyl]-3-[(1-methylpyrazol-4-yl)methyl]-1-[(2-methyl-1,2,4-triazol-3-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(thiazol-5-ylmethyl)quinazoline-6-sulfonamide;

N-[1-(fluoromethyl)cyclopropyl]-3-[(1-methylpyrazol-4-yl)methyl]-1-(oxazol-5-ylmethyl)-2,4-dioxo-quinazoline-6-sulfonamide;

N-[1-(fluoromethyl)cyclopropyl]-1-[(1-methylimidazol-2-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-[2-(2-pyridyl)ethyl] quinazoline-6-sulfonamide;

N-[1-(fluoromethyl)cyclopropyl]-1-[(5-methyl-1,3,4-oxadiazol-2-yl)methyl]-3-[(1-methylpyrazol-4-yl)methyl]-2,4-dioxo-quinazoline-6-sulfonamide;

N-[1-(fluoromethyl)cyclopropyl]-1-[(2-methyl-1H-imidazol-4-yl)methyl]-3-[(1-methylpyrazol-4-yl)methyl]-2,4-dioxo-quinazoline-6-sulfonamide;

N-[1-(fluoromethyl)cyclopropyl]-1-[(5-methylpyrazin-2-yl)methyl]-3-[(1-methylpyrazol-4-yl)methyl]-2,4-dioxo-quinazoline-6-sulfonamide;

N-[1-(fluoromethyl)cyclopropyl]-1-[[1-(hydroxymethyl)cyclopropyl]methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(4-methyl-2-pyridyl)methyl]-2,4-dioxo-quinazoline-6-sulfonamide;

N-[1-(fluoromethyl)cyclopropyl]-3-[(1-methylpyrazol-4-yl)methyl]-1-[(4-methylthiazol-5-yl)methyl]-2,4-dioxo-quinazoline-6-sulfonamide;

N-[1-(fluoromethyl)cyclopropyl]-3-[(1-methylpyrazol-4-yl)methyl]-1-[(6-methyl-3-pyridyl)methyl]-2,4-dioxo-quinazoline-6-sulfonamide;

1-(2-cyanoethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(1H-imidazol-4-ylmethyl)-3-[(1-methylpyrazol-4-yl)methyl]-2,4-dioxo-quinazoline-6-sulfonamide;

1-[(3-ethylimidazol-4-yl)methyl]-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(isothiazol-4-ylmethyl)-3-[(1-methylpyrazol-4-yl)methyl]-2,4-dioxo-quinazoline-6-sulfonamide;

N-[1-(fluoromethyl)cyclopropyl]-1-(isothiazol-5-ylmethyl)-3-[(1-methylpyrazol-4-yl)methyl]-2,4-dioxo-quinazoline-6-sulfonamide;

N-[1-(fluoromethyl)cyclopropyl]-1-[(5-methylisoxazol-4-yl)methyl]-3-[(1-methylpyrazol-4-yl)methyl]-2,4-dioxo-quinazoline-6-sulfonamide;

N-[1-(fluoromethyl)cyclopropyl]-1-[(2-methyloxazol-4-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(thiazol-4-ylmethyl)quinazoline-6-sulfonamide;

N-[1-(fluoromethyl)cyclopropyl]-3-[(1-methylpyrazol-4-yl)methyl]-1-[(2-methylthiazol-4-yl)methyl]-2,4-dioxo-quinazoline-6-sulfonamide;

N-[1-(fluoromethyl)cyclopropyl]-3-[(1-methylpyrazol-4-yl)methyl]-1-[(5-methyl-1,3,4-thiadiazol-2-yl)methyl]-2,4-dioxo-quinazoline-6-sulfonamide;

N-[1-(fluoromethyl)cyclopropyl]-3-[(1-methylpyrazol-4-yl)methyl]-1-[(4-methyl-1,2,4-triazol-3-yl)methyl]-2,4-dioxo-quinazoline-6-sulfonamide;

N-[1-(fluoromethyl)cyclopropyl]-1-(isoxazol-5-ylmethyl)-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(1H-pyrazol-3-ylmethyl)quinazoline-6-sulfonamide;

N-[1-(fluoromethyl)cyclopropyl]-3-[(1-methylpyrazol-4-yl)methyl]-2,4-dioxo-1-(1H-1,2,4-triazol-3-ylmethyl)quinazoline-6-sulfonamide;

N-[1-(fluoromethyl)cyclopropyl]-1-[(3-methylimidazol-4-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(1,3,4-thiadiazol-2-ylmethyl)quinazoline-6-sulfonamide;

N-[1-(fluoromethyl)cyclopropyl]-3-[(1-methylpyrazol-4-yl)methyl]-2,4-dioxo-1-(1H-pyrazol-4-ylmethyl)quinazoline-6-sulfonamide;

N-[1-(fluoromethyl)cyclopropyl]-1-[(3-methylisothiazol-5-yl)methyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(3-methyl-1H-1,2,4-triazol-5-yl)methyl]-2,4-dioxo-quinazoline-6-sulfonamide;

N-[1-(fluoromethyl)cyclopropyl]-3-[(1-methylpyrazol-4-yl)methyl]-1-[(1-methyltriazol-4-yl)methyl]-2,4-dioxo-quinazoline-6-sulfonamide;

N-[1-(fluoromethyl)cyclopropyl]-3-[(1-methylpyrazol-4-yl)methyl]-1-[(2-methylthiazol-5-yl)methyl]-2,4-dioxo-quinazoline-6-sulfonamide;

N-[1-(fluoromethyl)cyclopropyl]-1,3-bis[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-[(2-methyltriazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-propyl-quinazoline-6-sulfonamide;

N-[1-(fluoromethyl)cyclopropyl]-3-[(1-methylpyrazol-4-yl)methyl]-2,4-dioxo-1-(tetrahydrofuran-3-ylmethyl)quinazoline-6-sulfonamide;

1-(2,2-difluoroethyl)-N-(1-methylcyclopropyl)-3-[(1-methylpyrazol-4-yl)methyl]-2,4-dioxo-quinazoline-6-sulfonamide;

1-(2,2-difluoroethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-3-[(5-methyl-1,3,4-thiadiazol-2-yl)methyl]-2,4-dioxo-1H-quinazoline-6-sulfonamide;

1-ethyl-N-[1-(fluoromethyl)cyclopropyl]-3-[(5-methyl-1,3,4-thiadiazol-2-yl)methyl]-2,4-dioxo-quinazoline-6-sulfonamide;

1-[(2,5-dimethylpyrazol-3-yl)methyl]-N-[1-(fluoromethyl)cyclopropyl]-3-[(5-methyl-1,3,4-thiadiazol-2-yl)methyl]-2,4-dioxo-quinazoline-6-sulfonamide;

1-(difluoromethyl)-N-[1-(fluoromethyl)cyclopropyl]-3-[(3-methylisoxazol-5-yl)methyl]-2,4-dioxo-quinazoline-6-sulfonamide;

1-(difluoromethyl)-N-(1-methylcyclopropyl)-3-[(3-methylisoxazol-5-yl)methyl]-2,4-dioxo-quinazoline-6-sulfonamide;

1-(difluoromethyl)-N-(1-methylcyclopropyl)-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-1-(oxazol-4-ylmethyl)-2,4-dioxo-quinazoline-6-sulfonamide;

1-(cyclopentylmethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-(3-methylbut-2-enyl)-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(4-pyridylmethyl)quinazoline-6-sulfonamide;

1-[2-(diethyl amino)ethyl]-N-[1-(fluoromethyl)cyclopropyl]-3-[(1-methylpyrazol-4-yl)methyl]-2,4-dioxo-quinazoline-6-sulfonamide;

1-(2-ethoxyethyl)-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-isopentyl-3-[(1-methylpyrazol-4-yl)methyl]-2,4-dioxo-quinazoline-6-sulfonamide;

1-ethyl-N-(1-methylcyclopropyl)-3-[(5-methyl-1,3,4-thiadiazol-2-yl)methyl]-2,4-dioxo-quinazoline-6-sulfonamide;

1-[(2,5-dimethylpyrazol-3-yl)methyl]-N-(1-methylcyclopropyl)-3-[(5-methyl-1,3,4-thiadiazol-2-yl)methyl]-2,4-dioxo-quinazoline-6-sulfonamide;

1-[(2,4-dimethylthiazol-5-yl)methyl]-N-[1-(fluoromethyl)cyclopropyl]-3-[(3-methylisoxazol-5-yl)methyl]-2,4-dioxo-quinazoline-6-sulfonamide;

1-butyl-N-[1-(fluoromethyl)cyclopropyl]-3-[(1-methylpyrazol-4-yl)methyl]-2,4-dioxo-quinazoline-6-sulfonamide;

N-[1-(fluoromethyl)cyclopropyl]-1-[2-(2-methoxyethoxy)ethyl]-3-[(1-methylpyrazol-4-yl)methyl]-2,4-dioxo-quinazoline-6-sulfonamide;

N-[1-(fluoromethyl)cyclopropyl]-3-[(1-methylpyrazol-4-yl)methyl]-2,4-dioxo-1-(tetrahydrofuran-2-ylmethyl)quinazoline-6-sulfonamide;

N-[1-(fluoromethyl)cyclopropyl]-3-[(1-methylpyrazol-4-yl)methyl]-2,4-dioxo-1-(2-oxobutyl)quinazoline-6-sulfonamide;

N-(1-methylcyclopropyl)-3-[(1-methylpyrazol-4-yl)methyl]-2,4-dioxo-1-(2,2,2-trifluoroethyl)quinazoline-6-sulfonamide;

N-[1-(fluoromethyl)cyclopropyl]-3-[(3-methylisoxazol-5-yl)methyl]-2,4-dioxo-1-(2,2,2-trifluoroethyl)quinazoline-6-sulfonamide;

N-[1-(fluoromethyl)cyclopropyl]-3-[(1-methylpyrazol-4-yl)methyl]-2,4-dioxo-1-(2,2,2-trifluoroethyl)quinazoline-6-sulfonamide;

N-[1-(fluoromethyl)cyclopropyl]-1-methyl-2,4-dioxo-3-(1,3,4-thiadiazol-2-ylmethyl)quinazoline-6-sulfonamide;

N-[1-(fluoromethyl)cyclopropyl]-1-methyl-3-[(3-methylisothiazol-5-yl)methyl]-2,4-dioxo-quinazoline-6-sulfonamide;

N-[1-(fluoromethyl)cyclopropyl]-1-methyl-3-[(2-methyltriazol-4-yl)methyl]-2,4-dioxo-quinazoline-6-sulfonamide;

N-[1-(fluoromethyl)cyclopropyl]-3-[(3-methylisoxazol-5-yl)methyl]-2,4-dioxo-1-(1,3,4-thiadiazol-2-ylmethyl)quinazoline-6-sulfonamide;

3-[(5-ethyl-1,3,4-thiadiazol-2-yl)methyl]-N-[1-(fluoromethyl)cyclopropyl]-1-methyl-2,4-dioxo-quinazoline-6-sulfonamide;

1-(2-fluoroethyl)-N-[1-(fluoromethyl)cyclopropyl]-3-[(5-methyl-1,3,4-thiadiazol-2-yl)methyl]-2,4-dioxo-quinazoline-6-sulfonamide;

N-[1-(fluoromethyl)cyclopropyl]-1-[(1-methylpyrazol-4-yl)methyl]-3-[(5-methyl-1,3,4-thiadiazol-2-yl)methyl]-2,4-dioxo-quinazoline-6-sulfonamide;

N-[1-(fluoromethyl)cyclopropyl]-1-[(5-methyl-1,2,4-oxadiazol-3-yl)methyl]-3-[(5-methyl-1,3,4-thiadiazol-2-yl)methyl]-2,4-dioxo-quinazoline-6-sulfonamide;

or a pharmaceutically acceptable salt or solvate thereof.

18. A pharmaceutical composition comprising a compound according to claim 8, or a pharmaceutically acceptable salt or solvate thereof, in admixture with a pharmaceutically acceptable diluent or carrier.

\* \* \* \* \*